(12) United States Patent
Tsubouchi et al.

(10) Patent No.: US 7,262,212 B2
(45) Date of Patent: Aug. 28, 2007

(54) 2,3-DIHYDRO-6-NITROIMIDAZO[2,1-B]OXAZOLES

(75) Inventors: Hidetsugu Tsubouchi, Tokushima (JP); Hirofumi Sasaki, Kitajima (JP); Hideaki Kuroda, Tokushima (JP); Motohiro Itotani, Tokushima (JP); Takeshi Hasegawa, Aizumi (JP); Yoshikazu Haraguchi, Tokushima (JP); Takeshi Kuroda, Kitajima (JP); Takayuki Matsuzaki, Tokushima (JP); Kuninori Tai, Tokushima (JP); Makoto Komatsu, Matsushige (JP); Makoto Matsumoto, Naruto (JP); Hiroyuki Hashizume, Naruto (JP); Tatsuo Tomishige, Tokushima (JP); Yuji Seike, Naruto (JP); Masanori Kawasaki, Ishii (JP); Takumi Sumida, Naruto (JP); Shin Miyamura, Matsushige (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 135 days.

(21) Appl. No.: 10/530,429

(22) PCT Filed: Oct. 10, 2003

(86) PCT No.: PCT/JP03/13070

§ 371 (c)(1),
(2), (4) Date: Apr. 6, 2005

(87) PCT Pub. No.: WO2004/033463

PCT Pub. Date: Apr. 22, 2004

(65) Prior Publication Data
US 2006/0094767 A1    May 4, 2006

(30) Foreign Application Priority Data
Oct. 11, 2002    (JP)    ................... 2002-298259

(51) Int. Cl.
*A61K 31/424*    (2006.01)
*A61K 31/438*    (2006.01)
*C07D 498/04*    (2006.01)
*C07D 401/14*    (2006.01)

(52) U.S. Cl. .................. 514/375; 514/278; 548/218; 546/17

(58) Field of Classification Search ............. 548/218; 546/17; 514/278, 375

See application file for complete search history.

(56) References Cited

FOREIGN PATENT DOCUMENTS

WO    WO97/01562    1/1997

OTHER PUBLICATIONS

Sehgal et al., "Potential Radiosensitizing Agents. 2. Synthesis and Biological Activity of Derivatives of Dinitroimidazole With Oxiranes"; Journal of Medicinal Chemistry, vol. 24, No. 5, pp. 601-604, (1981).

Ashtekar et al.; "In Vitro and In Vivo Activities of the Nitroimidazole CGI 17341 Against *Mycobacterium tuberculosis*"; Antimicrobial Agents and Chemotherapy, vol. 37, No. 2, pp. 183-186, (1993).

Nagarajan et al.; "Nitroimidazoles XXI 2,3-Dihydro-6-Nitroimidazo [2,1-*b*] Oxazoles With Antitubercular Activity"; European Journal of Medicinal Chemistry, vol. 24, No. 6, pp. 631-633, (1989).

*Primary Examiner*—Kamal A. Saeed
*Assistant Examiner*—Jason M Nolan
(74) *Attorney, Agent, or Firm*—Finnegan, Henderson, Farabow, Garrett & Dunner, L.L.P.

(57) ABSTRACT

The present invention provides a 2,3-dihydro-6-nitroimidazo[2,1-b]oxazole compound represented by the following general formula:

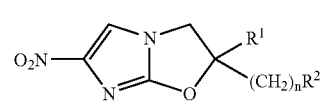

(1)

wherein $R^1$ represents a hydrogen atom or C1-C6 alkyl group, n represents an integer of 0 to 6, $R^2$ represents a group —$OR^3$ or the like, and $R^3$ represents a hydrogen atom, C1-C6 alkyl group or the like, or $R^1$ and —$(CH_2)_nR^2$ may bind to each other together with carbon atoms adjacent thereto through nitrogen atoms so as to form a spiro ring represented by the general formula (H):

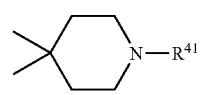

(H)

wherein $R^{41}$ is hydrogen, C1-C6 alkyl group or the like. The present compound has an excellent bactericidal action against *Mycobacterium tuberculosis*, multi-drug-resistant *Mycobacterium tuberculosis*, and atypical acid-fast bacteria.

50 Claims, No Drawings

2,3-DIHYDRO-6-NITROIMIDAZO[2,1-B]OXAZOLES

TECHNICAL FIELD

The present invention relates to a 2,3-dihydroimidazo[2,1-b]oxazole compound.

BACKGROUND ART

From among acid-fast bacteria, human *Mycobacterium tuberculosis* has been widely known. It is said that the one-third of the human population is infected with this bacterium. In addition to the human *Mycobacterium tuberculosis*, *Mycobacterium africanum* and *Mycobacterium bovis* have also been known to belong to the *Mycobacterium tuberoculosis* group. These bacteria are known as Mycobacteria having a strong pathogenicity to humans.

Against these tuberculoses, treatment is carried out using three agents, rifampicin, isoniazid, and ethambutol (or streptomycin) that are regarded as first-line agents, or using four agents such as the above three agents and pyrazinamide.

However, since the treatment of *tuberculosis* requires extremely long-term administration of agents, it might result in poor compliance, and the treatment often ends in failure.

Moreover, in respect of the above agents, it has been reported that: rifampicin causes hepatopathy, flu syndrome, drug allergy, and its concomitant administration with other drugs is contraindicated due to P450-associated enzyme induction; that isoniazid causes peripheral nervous system disorder and induces serious hepatopathy when used in combination with rifampicin; that ethambutol brings on failure of eyesight due to optic nerve disorder; that streptomycin brings on diminution of the hearing faculty due to the 8th cranial nerve disorder; and that pyrazinamide causes adverse reactions such a hepatopathy, gouty attack associated with increase of uric acid level, vomiting (A Clinician's Guide To Tuberculosis, Michael D. Iseman 2000 by Lippincott Williams & Wilkins, printed in the USA, ISBN 0-7817-1749-3, Tuberculosis, 2nd edition, Fumiyuki Kuze and Takahide Izumi, Igaku-Shoin Ltd., 1992).

Actually, it has been reported that cases where the standard chemotherapy could not be carried out due to the adverse reactions to these agents made up 70% (approximately 23%, 52 cases) of the total cases where administration of the agents was discontinued (the total 228 hospitalized patients who were subject to the research) (Kekkaku, Vol. 74, 77-82, 1999).

In particular, hepatotoxicity, which is induced by rifampicin, isoniazid, and ethambutol out of the 5 agents used in combination for the aforementioned first-line treatment, is known as an adverse reaction that is developed most frequently. At the same time, *Mycobacterium tuberculosis* resistant to antitubercular agents, multi-drug-resistant *Mycobacterium tuberculosis*, and the like have been increasing, and the presence of these types of *Mycobacterium tuberculosis* makes the treatment more difficult.

According to the investigation made by WHO (1996 to 1999), the proportion of *Mycobacterium tuberculosis* that is resistant to any of the existing antitubercular agents to the total types of *Mycobacterium tuberculosis* that have been isolated over the world reaches 19%, and it has been published that the proportion of multi-drug-resistant *Mycobacterium tuberculosis* is 5.1%. The number of carriers infected with such multi-drug-resistant *Mycobacterium tuberculosis* is estimated to be 60,000,000, and concerns are still rising that multi-drug-resistant *Mycobacterium tuberculosis* will increase in the future (April 2001 as a supplement to the journal Tuberculosis, the "Scientific Blueprint for TB Drug Development.")

In addition, the major cause of death of AIDS patients is tuberculosis. It has been reported that the number of humans suffering from both tuberculosis and HIV reaches 10,700,000 at the time of year 1997 (Global Alliance for TB drug development). Moreover, it is considered that the mixed infection of tuberculosis and HIV has an at least 30 times higher risk of developing tuberculosis than the ordinary circumstances.

Taking into consideration the aforementioned current situation, the profiles of the desired antitubercular agent is as follows: (1) an agent, which is effective even for multi-drug-resistant *Mycobacterium tuberculosis*, (2) an agent enabling a short-term chemotherapy, (3) an agent with fewer adverse reactions, (4) an agent showing an efficacy to latent infecting *Mycobacterium tuberculosis* (i.e., latent *Mycobacterium tuberculosis*), and (5) an orally administrable agent.

Examples of bacteria known to have a pathogenicity to humans include offending bacteria of recently increasing MAC infection (*Mycobacterium avium*—intracellulare complex infection) such as *Mycobacterium avium* and *Mycobacterium intracellulare*, and atypical acid-fast bacteria such as *Mycobacterium kansasii*, *Mycobacterium marinum*, *Mycobacterium simiae*, *Mycobacterium scrofulaceum*, *Mycobacterium szulgai*, *Mycobacterium xenopi*, *Mycobacterium malmoense*, *Mycobacterium haemophilum*, *Mycobacterium ulcerans*, *Mycobacterium shimoidei*, *Mycobacterium fortuitum*, *Mycobacterium chelonae*, *Mycobacterium smegmatis*, and *Mycobacterium aurum*.

Nowadays, there are few therapeutic agents effective for these atypical acid-fast bacterial infections. Under the presence circumstances, antitubercular agents such as rifampicin, isoniazid, ethambutol, streptomycin and kanamycin, a newquinolone agent that is a therapeutic agent for common bacterial infections, macrolide antibiotics, aminoglycoside antibiotics, and tetracycline antibiotics are used in combination.

However, when compared with the treatment of common bacterial infections, the treatment of atypical acid-fast bacterial infections requires a long-term administration-of agents, and there have been reported cases where the infection is changed to an intractable one, finally leading to death. To break the afore-mentioned current situation, the development of an agent having a stronger efficacy is desired.

For example, National Publication of International Patent Application No. 11-508270 (WO97/01562) discloses that a 6-nitro-1,2,3,4-tetrahydro[2,1-b]-imidazopyran compound has a bactericidal action in vitro to *Mycobacterium tuberculosis* (H37Rv strain) and multi-drug-resistant *Mycobacterium tuberculosis*, and that the above compound has a therapeutic effect to a tuberculosis-infected animal model when it is orally administered and thus useful as antitubercular agent.

However, the compound described in the above publication differs from the compound of the present invention in terms of the basic skeleton, and it is considered to be a compound nonsimilar to the inventive compound.

Kuppsuwamy Nagarajan et al. have reported on European Journal of Medicinal Chemistry, 1989, Vol. 24, pp. 631-633 that compounds represented by the following general formula (I):

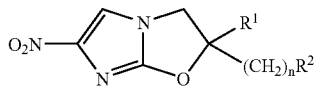

wherein $R^1$ represents a hydrogen atom or methyl group and $-(CH_2)_nR^2$ represents a chloromethyl group, C1-C7 alkyl group, isopropoxymethyl group, 3-propenyloxy-methyl group, or unsubstituted phenoxymethyl group, and compounds represented by the same above general formula (I), wherein $R^1$ and $-(CH_2)_nR^2$ bind to each other to form a cyclopentane or cyclohexane ring (16 types of compounds in total) have a bactericidal action to *Mycobacterium tuberculosis* (H37Rv strain).

However, the above publication describes that only the 4 types of compounds out of the above compounds are effective when they are orally administered. It also describes that the compound having the highest activity, that is, the compound (CGI-17341) represented by the above general formula (I) wherein $R^1$ represents a hydrogen atom and $-(CH_2)_nR^2$ represents ethyl, was found to have mutagenicity, and that accordingly, the development of these series of compounds as agents were abandoned.

In addition, Dilip R. Astekar et al. have reported on Antimicrobial Agents and Chemotherapy, February 1993, pp. 183-186 about the antimicrobial profile of the above compound CGI-17341. According to the report, the compound CGI-17341 has a bactericidal action to *Mycobacterium tuberculosis* (H37Rv strain) and multi-drug-resistant *Mycobacterium tuberculosis*, but it does not have the activity to atypical acid-fast bacteria, *M. avium*, *M. intracellulare*, and *M. fortuitum* when it is used at 250 µg/ml or less.

DISCLOSURE OF THE INVENTION

It is an object of the present invention to provide a compound having an excellent bactericidal action to *Mycobacterium tuberculosis* and multi-drug-resistant *Mycobacterium tuberculosis*.

It is another object of the present invention to provide a compound having an excellent bactericidal action to atypical acid-fast bacteria.

As a result of intensive studies, the present inventors have succeeded in synthesizing a novel 2,3-dihydroimidazo[2,1-b]oxazole compound, which has an excellent bactericidal action to *Mycobacterium tuberculosis*, multi-drug-resistant *Mycobacterium tuberculosis*, and atypical acid-fast bacteria. The present invention have completed based on such findings.

The present invention provides a 2,3-dihydro-6-nitroimidazo[2,1-b]oxazole compound represented by the following general formula (1), optically active form thereof, or pharmaceutically acceptable salt thereof:

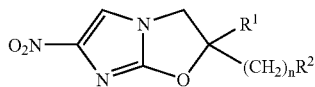

wherein $R^1$ represents a hydrogen atom or C1-6 alkyl group, n represents an integer of 0 to 6, and $R^2$ represents a group represented by general formula (A), (B), (C), (D), (E), (F) or (G) indicated below, and further, $R^1$ and $-(CH_2)_nR^2$ may bind to each other together with carbon atoms adjacent thereto through nitrogen atoms, so as to form a spiro ring represented by general formula (H) indicated below.

General formulas (A)-(H) will be described as follows:

a group represented by the following general formula (A):

$$-OR^3 \quad (A)$$

wherein $R^3$ represents:

A1) hydrogen atom;
A2) C1-6 alkyl group;
A3) C1-6 alkoxy-C1-6 alkyl group
A4) phenyl C1-6 alkyl group (which may be substituted on the phenyl ring by at least one group selected from the group consisting of a phenyl C1-6 alkoxy group, a halogen-substituted or unsubstituted C1-6 alkyl group, a halogen-substituted or unsubstituted C1-6 alkoxy group, and a phenoxy group which may have, as a substituent, at least one halogen-substituted or unsubstituted C1-6 alkoxy group on the phenyl ring);
A5) biphenylyl C1-6 alkyl group;
A6) phenyl C2-6 alkenyl group:
A7) C1-6 alkylsulfonyl group;
A8) benzenesulfonyl group which may be substituted by a C1-6 alkyl group;
A9) C1-6 alkanoyl group;
A10) a group represented by the following general formula (Aa):

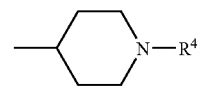

wherein $R^4$ represents a C1-6 alkoxycarbonyl group; phenyl C1-6 alkoxycarbonyl group (which may be substituted on the phenyl ring by at least one group selected from the group consisting of a phenyl C1-6 alkoxy group, a halogen-substituted or unsubstituted C1-6 alkyl group, and a halogen-substituted or unsubstituted C1-6 alkoxy group); or phenyl C1-6 alkyl group (which may be substituted on the phenyl ring by at least one group selected from the group consisting of a phenyl C1-6 alkoxy group, a halogen-substituted or unsubstituted C1-6 alkyl group, and a halogen-substituted or unsubstituted C1-6 alkoxy group);
A11) biphenylyl C1-6 alkoxycarbonyl group;
A12) benzoxazolyl C1-6 alkyl group (which may be substituted on the benzoxazole ring by at least one oxo group as a substituent);
A13) benzoxazolyl group; or
A14) oxazolyl C1-6 alkyl group (which may be substituted on the oxazole ring by at least one group selected from the group consisting of a phenyl group and C1-6 alkyl group as a substituent), a group represented by the following general formula (B):

$$-SR^5 \quad (B)$$

wherein $R^5$ represents a tetrazolyl group (which may be substituted on the tetrazole ring by a C1-6 alkyl group or phenyl group which may have a halogen atom as a substituent), or benzoxazolyl group, a group represented by the following general formula (C):

$$-COOR^6 \quad (C)$$

wherein $R^6$ represents a C1-6 alkyl group, a carbamoyloxy group represented by the following general formula (D):

$$-OOCNR^7R^8 \quad (D)$$

wherein $R^7$ and $R^8$ each identically or differently represent any one of:

D1) hydrogen atom;
D2) C1-8 alkyl group;
D3) halogen-substituted C1-6 alkyl group;
D4) C1-6 alkoxycarbonyl-C1-6 alkyl group;
D5) C3-8 cycloalkyl group;
D6) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
D7) phenyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, a C1-6 alkanoyl group, a carboxyl group, a C1-6 alkoxycarbonyl group, a phenyl C1-6 alkoxycarbonyl group, a carbamoyl group, a C1-6 alkylcarbamoyl group, an aminosulfonyl group, and a morpholino group);
D8) naphthyl group;
D9) pyridyl group; and
D10) $R^7$ and $R^8$ may bind to each other together with nitrogen atoms adjacent thereto directly or through other hetero atoms or carbon atoms, so as to form a saturated heterocyclic group shown in any one of (D10-1) to (D10-3) indicated below, or benzene condensed heterocyclic group shown in any one of (D10-4) to (D10-7) indicated below:

(D10-1) piperazinyl group represented by the following general formula (Da):

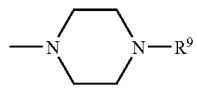

wherein $R^9$ represents:

(Da1) hydrogen atom;
(Da2) C1-6 alkyl group;
(Da3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da4) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da5) C1-6 alkoxycarbonyl group;
(Da6) phenyl C1-6 alkoxycarbonyl group (which may be substituted on the phenyl ring by at least one group selected from the group consisting of a halogen atom, a halogen-substituted or unsubstituted C1-6 alkyl group and a halogen-substituted or unsubstituted C1-6 alkoxy group);
(Da7) phenyl C3-6 alkenyloxycarbonyl group (which may have at least one halogen-substituted or unsubstituted C1-6 alkyl group on the phenyl ring); or
(Da8) phenyl C1-6 alkylidene substituted amino group (which may be substituted on the phenyl ring by at least one halogen-substituted or unsubstituted C1-6 alkyl group as a substituent), (D10-2) a group represented by the following general formula (Db):

wherein the dotted line represents that the bond may be a double bond, and $R^{10}$ represents:

(Db1) hydrogen atom;
(Db2) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Db3) phenoxy group (which may be substituted on the phenyl ring by at least one halogen-substituted or unsubstituted C1-6 alkyl group); or
(Db4) phenylamino group (which may be substituted on the phenyl ring by at least one halogen-substituted or unsubstituted C1-6 alkyl group), (D10-3) morpholino group;
(D10-4) indolinyl group (which may be substituted on the indoline ring by at least one halogen atom as a substituent);
(D10-5) isoindolinyl group (which may be substituted on the isoindoline ring by at least one halogen atom as a substituent);
(D10-6) 1,2,3,4-tetrahydroquinolyl group, (which may be substituted on the 1,2,3,4-tetrahydro-quinoline ring by at least one halogen atom as a substituent); and
(D10-7) 1,2,3,4-tetrahydroisoquinolyl group, (which may be substituted on the 1,2,3,4-tetrahydro-isoquinoline ring by at least one halogen atom as a substituent), a phenoxy group represented by the following general formula (E):

wherein X represents a halogen atom or amino substituted C1-6 alkyl group which may have a C1-6 alkyl group as a substituent, m represents an integer of 0 to 3, and $R^{11}$ represents:

E1) hydrogen atom;
E2) halogen-substituted or unsubstituted C1-6 alkyl group;
E3) halogen-substituted or unsubstituted C1-6 alkoxy group;
E4) a group represented by the following general formula (Ea):

$$-(W)o-NR^{12}R^{13} \quad (Ea)$$

wherein W represents a group —CO— or a C1-6 alkylene group, o represents an integer of 0 or 1, and $R^{12}$ and $R^{13}$ each identically or differently represent any one of:
(Ea1) hydrogen atom;
(Ea2) C1-6 alkyl group;

(Ea3) C1-6 alkanoyl group;

(Ea4) C1-6 alkoxycarbonyl group;

(Ea5) phenyl C1-6 alkyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group as a substituent), and the alkyl portion may be substituted by a C1-6 alkoxyimino group);

(Ea6) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Ea7) benzoyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group);

(Ea8) pyridyl group (which may be substituted on the pyridine ring by at least one halogen atom as a substituent);

(Ea9) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Ea10) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and (Ea11) benzoyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), E5) imidazolyl group;

E6) triazolyl group;

E7) morpholino group;

E8) thiomorpholino group;

E9) s-oxide thiomorpholino group;

E10) piperidyl group represented by the following general formula (Eaa):

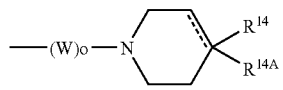

(Eaa)

wherein W and o are the same as above, $R^{14A}$ represents a hydrogen atom, hydroxyl group, C1-6 alkoxy group, or phenyl group (which may be substituted by halogen on the phenyl ring); the dotted line represents that the bond may be a double bond, and when the dotted line represents a double bond, it means that only $R^{14}$ is substituted; $R^{14}$ and $R^{14A}$ may bind to each other together with carbon atoms adjacent thereto to form a C1-4 alkylenedioxy group, and $R^{14}$ represents:

(Eaa1) hydrogen atom;

(Eaa2) C1-6 alkoxycarbonyl group;

(Eaa3) phenoxy group (which may be substituted on the phenyl ring by at least one group selected from the group consisting of a halogen atom; a halogen-substituted or unsubstituted C1-6 alkyl group; a halogen-substituted or unsubstituted C1-6 alkoxy group; a C1-4 alkylenedioxy group; a C1-6 alkoxycarbonyl group; a cyano group; a C2-6 alkenyl group; a nitro group; a phenyl group; an amino group which may have, as a substituent, a group selected from the group consisting of a phenyl group, a C1-6 alkyl group, a carbamoyl group and a C1-6 alkanoyl group; a C1-6 alkanoyl-substituted C1-6 alkyl group; a hydroxyl group; a C1-6 alkoxycarbonyl-substituted C1-6 alkyl group; a phenyl C1-6 alkyl group; a C1-6 alkanoyl group; a C1-6 alkylthio group; a 1,2,4-triazolyl group; an isoxazolyl group; an imidazolyl group; a benzothiazolyl group; a 2H-benzotriazolyl group; a pyrrolyl group; a benzoxazolyl group; a piperazinyl group (which may be substituted on the piperazine ring by at least one group selected from the group consisting of a C1-6 alkoxycarbonyl group and a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent); a piperidinyl group (which may be substituted on the piperidine ring by at least one group selected from the group consisting of an amino group (which may be substituted on the amino group by at least one group selected from the group consisting of a C1-6 alkyl group and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent); and a carbamoyl group));

(Eaa4) hydroxyl group;

(Eaa5) carboxy group;

(Eaa6) phenyl group (which may be substituted on the phenyl ring by at least one group selected from the group consisting of a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group as a substituent), a halogen atom, a halogen-substituted or unsubstituted C1-6 alkyl group, and a halogen-substituted or unsubstituted C1-6 alkoxy group as a substituent);

(Eaa7) C1-6 alkoxy group;

(Eaa8) C3-8 cycloalkyl-C1-6 alkoxy group;

(Eaa9) phenylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eaa10) tetrahydropyranyloxy group;

(Eaa11) 1,3-dioxolanyl group;

(Eaa12) oxo group;

(Eaa13) naphthyloxy group (which may be substituted on the naphthalene ring by at least one C1-6 alkyl group as a substituent);

(Eaa14) 2,3-dihydrobenzofuryloxy group (which may be substituted on the 2,3-dihydrobenzofuran ring by at least one group selected from the group consisting of a C1-6 alkyl group and an oxo group);

(Eaa15) benzothiazolyloxy group (which may be substituted on the benzothiazole ring by at least one C1-6 alkyl group);

(Eaa16) 1,2,3,4-tetrahydronaphthyloxy group (which may be substituted on the 1,2,3,4-tetrahydro-naphthalene ring by at least one oxo group as a substituent);

(Eaa17) 1,3-benzoxathiolanyloxy group (which may be substituted on the 1,3-benzoxathiolan ring by at least one oxo group as a substituent);

(Eaa18) isoquinolyloxy group;

(Eaa19) pyridyloxy group;

(Eaa20) quinolyloxy group (which may be substituted on the quinoline ring by at least one C1-6 alkyl group as a substituent);

(Eaa21) dibenzofuryloxy group;

(Eaa22) 2H-chromenyloxy group (which may be substituted on the 2H-chromen ring by at least one oxo group as a substituent);

(Eaa23) benzisoxazolyloxy group;

(Eaa24) quinoxalyloxy group;

(Eaa25) 2,3-dihydro-1H-indenyloxy group (which may be substituted on the 2,3-dihydro-1H-indene ring by at least one oxo group as a substituent);

(Eaa26) benzofurazanyloxy group; or (Eaa27) phenyl C2-6 alkenyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group), E11) a group represented by the following general formula (Eab):

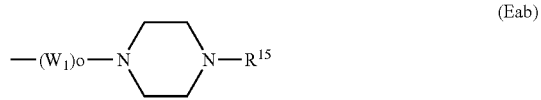

(Eab)

wherein o is the same as above, $W_1$ represents a C1-C6 alkylene group and $R^{15}$ represents:

(Eab1) hydrogen atom;

(Eab2) C1-6 alkyl group (wherein the alkyl group may be substituted by a morpholino group, benzoyl group, carbamoyl group which may have a C1-6 alkyl group as a substituent, or cyano group);

(Eab3) C3-8 cycloalkyl group;

(Eab4) phenyl C1-6 alkyl group (which may be substituted on the phenyl ring by at least one group selected from the group consisting of a halogen atom, a cyano group, a phenyl group, a nitro group, a C1-6 alkylthio group, a C1-6 alkylsulfonyl group, a phenyl C1-6 alkoxy group, a C2-6 alkanoyloxy group, a halogen-substituted or unsubstituted C1-6 alkyl group, a halogen-substituted or unsubstituted C1-6 alkoxy group, and a 1,2,3-thiadiazolyl group);

(Eab5) C2-6 alkenyl group;

(Eab6) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Eab7) C1-6 alkanoyl group;

(Eab8) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eab9) benzoyl group (which may be substituted on the benzene ring by at least one group selected from the group consisting of a halogen atom, a halogen-substituted or unsubstituted C1-6 alkyl group, and a halogen-substituted or unsubstituted C1-6 alkoxy group);

(Eab10) C1-20 alkoxycarbonyl group (which may be substituted on the alkoxy group by at least one group selected from the group consisting of a halogen atom, an amino group which may have a C1-6 alkyl group as a substituent, and a C1-6 alkoxy-substituted C1-6 alkoxy group);

(Eab11) phenyl C1-6 alkoxycarbonyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, a nitro group, a halogen-substituted or unsubstituted C1-6 alkylthio group, an amino group which may have a C1-6 alkanoyl group, a phenyl C1-6 alkoxy group, a C1-6 alkoxycarbonyl group, and a 1,2,3-thiadiazolyl group);

(Eab12) a phenyl C3-6 alkenyloxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eab13) phenoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eab14) phenyl C1-6 alkylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eab15) phenylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eab16) benzofuryl-substituted C1-6 alkoxycarbonyl group which may be substituted by at least one halogen atom on the benzofuran ring;

(Eab17) benzothienyl C1-6 alkoxycarbonyl group (which may be substituted on the benzothiophene ring by at least one group selected from the group consisting of a halogen atom and a halogen-substituted or unsubstituted C1-6 alkoxy group as a substituent);

(Eab18) naphthyl-substituted C1-6 alkoxycarbonyl group;

(Eab19) pyridyl-substituted C1-6 alkoxycarbonyl group (which may be substituted on the pyridine ring by at least one halogen atom as a substituent);

(Eab20) furyl-substituted C1-6 alkoxycarbonyl group (which may be substituted on the furan ring by at least one nitro group as a substituent);

(Eab21) thienyl-substituted C1-6 alkoxycarbonyl group (which may have at least one halogen atom as a substituent on the thiophene ring);

(Eab22) thiazolyl-substituted C1-6 alkoxycarbonyl group (which may be substituted on the thiazole ring by at least one group selected from the group consisting of a C1-6 alkyl group and a phenyl group (which may be substituted on the phenyl ring by at least one halogen-substituted or unsubstituted C1-6 alkyl group));

(Eab23) tetrazolyl-substituted C1-6 alkoxycarbonyl group (which may be substituted on the tetrazole ring by at least one group selected from the group consisting of a C1-6 alkyl group and a phenyl group (which may have at least one halogen atom as a substituent on the phenyl ring) as a substituent);

(Eab24) 2,3-dihydro-1H-indenyloxycarbonyl group;
(Eab25) adamantane-substituted C1-6 alkoxycarbonyl group;
(Eab26) phenyl C3-6 alkynyloxycarbonyl group;
(Eab27) phenylthio C1-6 alkoxycarbonyl group;
(Eab28) phenyl C1-6 alkoxy-substituted C1-6 alkoxycarbonyl group;
(Eab29) C2-6 alkenyloxycarbonyl group;
(Eab30) C2-6 alkynyloxycarbonyl group;
(Eab31) C3-8 cycloalkyl-substituted C1-6 alkoxycarbonyl group; or
(Eab32) benzoyl-substituted C1-6 alkoxycarbonyl group, E12) a group represented by the following general formula (Eb):

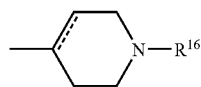
(Eb)

wherein the dotted line represents that the bond may be a double bond, and $R^{16}$ is defined as the same as $R^{15}$;

E13) a group represented by the following general formula (Ec):

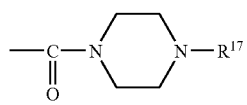
(Ec)

wherein $R^{17}$ represents:
(Ec1) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Ec2) C1-6 alkoxycarbonyl group; or
(Ec3) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), E14) pyridyl group;
E15) a group represented by the following general formula (Ee):

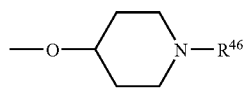
(Ee)

wherein $R^{46}$ represents a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group as a substituent); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or C1-6 alkoxycarbonyl group, E16) phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

E17) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

E18) 8-azabicyclo[3,2,1]octyl group (which may be substituted on the 8-azabicyclo[3,2,1]octane ring by at least one phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent);

E19) a group represented by the following general formula (Ef):

(Ef)

wherein $R^{47}$ and $R^{48}$ each identically or differently represent any one of a hydrogen atom, a C1-6 alkyl group, a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), or a pyridyl group (which may be substituted on the pyridine ring by at least one halogen-substituted or unsubstituted C1-6 alkyl group as a substituent); and further, $R^{47}$ and $R^{48}$ may bind to each other together with nitrogen atoms adjacent thereto directly or through other hetero atoms, so as to form a 5-7 membered saturated heterocyclic ring, which may be substituted on the heterocyclic ring by at least one phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent;

E20) phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

E21) amino substituted C2-6 alkenyl group (which may be substituted on the amino group by at least one group selected from the group consisting of a C1-6 alkyl group and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group)); or E22) oxazolidinyl group (which may be substituted on the oxazolidine ring by at least one oxo group as a substituent), a group represented by the following general formula (F):

(F)

wherein $R^{19}$ and $R^{20}$ each identically or differently represent any one of:

F1) hydrogen atom;

F2) C1-6 alkyl group;

F3) phenyl C1-6 alkyl group (which may be substituted on the phenyl ring by at least one group selected from the group consisting of: a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a halogen atom; a halogen-substituted or unsubstituted C1-6 alkyl group; a halogen-substituted or unsubstituted C1-6 alkoxy group; an amino group which may have at least one group selected from the group consisting of a C1-6 alkyl group, and a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a piperazinyl group (which may be substituted on the piperazine ring by at least one phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent); and a piperidyl group (which may be substituted on the piperidine ring by at least one amino group which may have a group selected from the group consisting of a phenyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group) and a C1-6 alkyl group as a substituent));

F4) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

F5) amino C1-6 alkyl group (which may be substituted on the amino group by at least one group selected from the group consisting of a C1-6 alkyl group, a C1-6 alkoxycarbonyl group, and a phenyl group which may be substituted on the phenyl group by at least one group selected from a group consisting of a halogen atom and a halogen-substituted or unsubstituted C1-6 alkyl group);

F6) phenyl group (which may be substituted on the phenyl ring by at least one group selected from the group consisting of a halogen atom, a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), and a C1-6 alkoxycarbonyl group);

F7) C1-6 alkoxycarbonyl group;

F8) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

F9) a group represented by the following general formula (Fa):

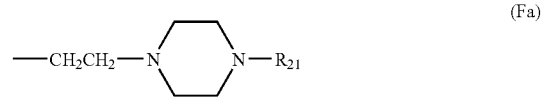

wherein $R^{21}$ represents a C1-6 alkoxycarbonyl group; phenyl C1-6 alkoxycarbonyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom and a halogen-substituted or unsubstituted C1-6 alkyl group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

F10) 1-substituted-4-piperidyl group represented by the following formula (Fb):

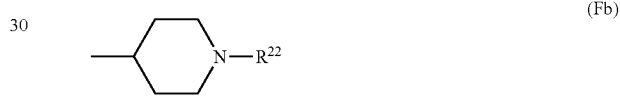

wherein $R^{22}$ represents a C1-6 alkoxycarbonyl group; phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

F11) piperidyl C1-6 alkyl group (which may have at least one phenoxy group (which may have at least one halogen-substituted or unsubstituted C1-6 alkyl group as a substituent) as a substituent);

F12) in addition, $R^{19}$ and $R^{20}$ may bind to each other together with nitrogen atoms adjacent thereto directly or through other hetero atoms or carbon atoms, so as to form a heterocyclic ring shown in any one of (F12-1) to (F12-10) indicated below:

(F12-1) a group represented by the following formula (Fc):

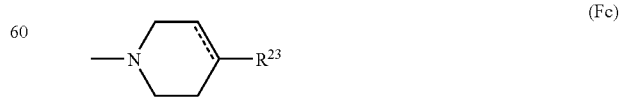

wherein the dotted line represents that the bond may be a double bond, and $R^{23}$ represents:

(Fc1) C1-6 alkyl group;

(Fc2) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc3) phenyl group (which may be substituted on the phenyl ring by at least one group selected from the group consisting of: a halogen atom; a halogen-substituted or unsubstituted C1-6 alkyl group; a halogen-substituted or unsubstituted C1-6 alkoxy group; an amino group which may have, as a substituent, a group selected from the group consisting of a C1-6 alkyl group and a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and a piperidyl group (which may have, on the piperidine ring, as a substituent, at least one amino group that may have a group selected from the group consisting of a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) and a C1-6 alkyl group));

(Fc4) phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc5) biphenylyl C1-6 alkoxy group;

(Fc6) phenyl C3-6 alkenyloxy group which may be substituted on the phenyl ring by at least one halogen atom;

(Fc7) phenoxy group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Fc8) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc9) C1-6 alkoxycarbonyl group;

(Fc10) phenyl C1-6 alkoxycarbonyl group (which may be substituted on the phenyl ring by at least one halogen-substituted or unsubstituted C1-6 alkoxy group);

(Fc11) phenyl C1-6 alkylcarbamoyl group wherein at least one halogen may be substituted on the phenyl ring;

(Fc12) phenylcarbamoyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group);

(Fc13) phenylthio group (which may be substituted on the phenyl ring by at least one halogen-substituted or unsubstituted C1-6 alkoxy group);

(Fc14) phenyl sulfoxide (which may be substituted on the phenyl ring by at least one halogen-substituted or unsubstituted C1-6 alkoxy group);

(Fc15) pyridyl C1-6 alkoxy group; or (Fc16) a group represented by the following general formula (Fca):

$$-(C=O)o-NR^{24}R^{25} \qquad (Fca)$$

wherein o is the same as above, and each of $R^{24}$ and $R^{25}$ represents:

(Fca1) hydrogen atom;

(Fca2) C1-6 alkyl group;

(Fca3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca4) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Fca5) C1-6 alkanoyl group;

(Fca6) phenyl C2-6 alkanoyl group that may be substituted on the phenyl ring by at least one halogen atom;

(Fca7) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca8) C1-6 alkoxycarbonyl group;

(Fca9) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca10) phenylcarbamoyl group (which may be substituted on the phenyl ring by at least one halogen-substituted or unsubstituted C1-6 alkyl group);

(Fca11) piperidyloxycarbonyl group (which may be substituted on the piperidine ring by at least one phenyl group (which may be substituted on the phenyl ring by at least one halogen-substituted or unsubstituted C1-6 alkyl group) as a substituent); or (Fca12) $R^{24}$ and $R^{25}$ may form a 5-6 membered saturated heterocyclic ring through nitrogen atoms adjacent thereto, which may be substituted on the heterocyclic ring by at least one group selected from the group consisting of a C1-6 alkoxycarbonyl group; a benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (F12-2) 4-substituted-1-piperazinyl group represented by the following general formula (Fd):

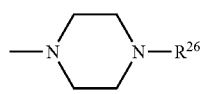

(Fd)

wherein $R^{26}$ represents:

(Fd1) hydrogen atom;

(Fd2) C1-6 alkyl group;

(Fd3) C3-8 cycloalkyl group;

(Fd4) C3-8 cycloalkyl C1-6 alkyl group;

(Fd5) C1-6 alkoxycarbonyl C1-6 alkyl group;

(Fd6) phenyl C2-6 alkenyl group;

(Fd7) phenyl C1-6 alkyl group (which may be substituted on the phenyl ring by 1 to 3 groups selected from the group consisting of: a halogen atom; a cyano group; a halogen-substituted or unsubstituted C1-6 alkyl group; C3-8 cycloalkyl group; a halogen-substituted or unsubstituted C1-6 alkoxy group; an amino group which may have a C1-6 alkyl group as a substituent; a C1-6 alkoxycarbonyl group; a phenoxy group; a phenyl C1-6 alkyl group; a phenyl C2-6 alkenyl group; a pyridyl group; an imidazolyl group; and a piperidyl group);

(Fd8) biphenylyl C1-6 alkyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and an amino group which may have a C1-6 alkyl group as a substituent);

(Fd9) naphthyl C1-6 alkyl group;

(Fd10) phenyl group (which may be substituted on the phenyl ring by at least one group selected from the group consisting of: a halogen atom; a cyano group; an amino group that may have a C1-6 alkyl group as a substituent; a halogen-substituted or unsubstituted C1-6 alkyl group; a halogen-substituted or unsubstituted C1-6 alkoxy group; a C1-6 alkoxycarbonyl group; a carboxyl group, a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); an amino C1-6 alkyl group (which may have on the amino group at least one group selected from the group consisting of a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) and a C1-6 alkyl group)); and a phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group));

(Fd11) biphenylyl group (which may be substituted on the phenyl ring by at least one halogen-substituted or unsubstituted C1-6 alkyl groups);

(Fd12) amino group, amino group which is substituted by a C1-6 alkoxycarbonyl group, phenyl C1-6 alkylamino group (which may be substituted on the phenyl ring by at least one halogen-substituted or unsubstituted C1-6 alkyl group), or phenylamino group (which may be substituted on the phenyl ring by at least one group selected from the group consisting of a halogen-substituted or unsubstituted C1-6 alkyl group and a halogen atom);

(Fd13) benzoyl C1-6 alkyl group (which may have on the phenyl ring at least one halogen atom as a substituent);

(Fd14) phenylcarbamoyl C1-6 alkyl group (which may be substituted on the phenyl ring by at least one halogen-substituted or unsubstituted C1-6 alkyl group);

(Fd15) thiazolyl C1-6 alkyl group (which may be substituted on the thiazole ring by at least one group selected from the group consisting of a halogen-substituted or unsubstituted phenyl group and a C1-6 alkyl group);

(Fd16) oxazolyl C1-6 alkyl group (which may be substituted on the oxazole ring by at least one group selected from the group consisting of a halogen-substituted or unsubstituted phenyl group and a C1-6 alkyl group);

(Fd17) indolyl C1-6 alkyl group;

(Fd18) furyl C1-6 alkyl group (which may be substituted on the furan ring by at least one halogen-substituted or unsubstituted phenyl group);

(Fd19) imidazolyl C1-6 alkyl group (which may be substituted on the imidazole ring by a phenyl group);

(Fd20) quinolyl C1-6 alkyl group;

(Fd21) tetrazolyl group (which may be substituted on the tetrazole ring by a phenyl group);

(Fd22) pyrimidyl group which may be substituted by a phenyl group;

(Fd23) pyridyl group;

(Fd24) benzoxazolyl group;

(Fd25) benzothiazolyl group;

(Fd26) benzoxazolyl C1-6 alkyl group (which may have on the benzoxazole ring at least one oxo group as a substituent);

(Fd27) phenoxy C2-6 alkanoyl group which may be substituted on the phenyl ring by a halogen atom;

(Fd28) phenylthio C2-6 alkanoyl group which may be substituted on the phenyl ring by a halogen atom;

(Fd29) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fd30) benzoyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and an amino group which may have a C1-6 alkyl group as a substituent);

(Fd31) biphenylylcarbonyl group;

(Fd32) pyridylcarbonyl group;

(Fd33) phenyl C2-6 alkenylcarbonyl group wherein a halogen atom may be substituted on the phenyl ring;

(Fd34) phenyl C1-6 alkylsulfonyl group wherein a halogen atom may be substituted on the phenyl ring;

(Fd35) benzenesulfonyl group (which may be substituted on the benzene ring by at least one group selected from the group consisting of a halogen atom and a C1-6 alkyl group);

(Fd36) a group represented by the following general formula (Fda):

—COOR²⁷                   (Fda)

wherein $R^{27}$ represents:

(Fda1) halogen-substituted or unsubstituted C1-8 alkyl group;

(Fda2) C3-8 cycloalkyl group;

(Fda3) C3-8 cycloalkyl-C1-6 alkyl group;

(Fda4) C1-6 alkoxy-C1-6 alkyl group;

(Fda5) amino-C1-6 alkyl group which may have a C1-6 alkyl group;

(Fda6) a group represented by the following general formula (Fdb):

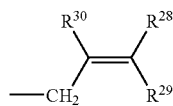

wherein $R^{28}$, $R^{29}$, and $R^{30}$ represent a hydrogen atom, a C1-6 alkyl group, or a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), respectively;

(Fda7) phenyl C1-6 alkyl group (which may be substituted on the phenyl ring by 1 to 5 groups selected from the group consisting of: a halogen atom; a halogen-substituted or unsubstituted C1-6 alkyl group; a halogen-substituted or unsubstituted C1-6 alkoxy group; a halogen-substituted or unsubstituted C1-6 alkylthio group; a phenyl C1-6 alkoxy group; a hydroxy group; a C1-6 alkylsulfinyl group; a C1-6 alkylsulfonyl group; C1-6 alkylsulfonyloxy group; a cyano group; a C1-6 alkanoyl group; a benzoyl group; a phenyl C1-6 alkyl group which may have a C1-6 alkoxy group in the alkyl portion; an amino group; a nitro group; a carbamoyl group; a C1-6 alkanoylamino group; a C1-6 alkoxycarbonyl group; a C1-6 alkylaminocarbonyl group; a C1-6 alkoxycarbonylamino group; a tri-C1-6-alkylsiloxy group; a pyrrolyl group; a tetrahydropyranyloxy group; and an imidazolyl group);

(Fda8) biphenylyl C1-6 alkyl group;

(Fda9) benzhydryl group (which may be substituted on the benzene ring by at least one group selected from the group consisting of a halogen atom, a trifluoromethyl group, and a trifluoromethoxy group);

(Fda10) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fda11) phenyl C2-6 alkynyl group (which may be substituted on the phenyl ring by at least one halogen-substituted or unsubstituted C1-6 alkyl group as a substituent);

(Fda12) pyridyl C1-6 alkyl group;

(Fda13) a group represented by the following general formula (Fdc):

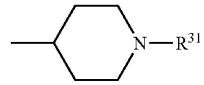

wherein $R^{31}$ represents a phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (Fda14) piperidino C1-6 alkyl group (which may be substituted on the piperidine ring by a phenoxy group which may have at least one halogen-substituted or unsubstituted alkyl group as a substituent on the phenyl ring);

(Fda15) amino C1-6 alkyl group which may have, as a substituent, at least one group selected from the group consisting of a C1-6 alkyl group and a phenyl group which may have, as a substituent, a halogen-substituted or unsubstituted C1-6 alkoxy group on the phenyl ring;

(Fda16) 1,2,3,6-tetrahydropyridyl C1-6 alkyl group (which may be substituted on the 1,2,3,6-tetrahydropyridine ring by at least one phenyl group which may have, as a substituent, at least one halogen-substituted or unsubstituted C1-6 alkoxy group on the phenyl ring);

(Fda17) naphthyl C1-6 alkyl group;

(Fda18) fluorenyl C1-6 alkyl group;

(Fda19) pyridyl C1-6 alkyl group;

(Fda20) furyl C1-6 alkyl group (which may be substituted on the furan ring by a halogen-substituted or unsubstituted phenyl group);

(Fda21) thienyl C1-6 alkyl group;

(Fda22) oxazolyl C1-6 alkyl group (which may be substituted on the oxazole ring by a halogen atom or a halogen-substituted or unsubstituted phenyl group);

(Fda23) oxadiazolyl C1-6 alkyl group (which may be substituted on the oxadiazole ring by a halogen-substituted or unsubstituted phenyl group);

(Fda24) pyrazolyl C1-6 alkyl group (which may be substituted on the pyrazole ring by a halogen-substituted or unsubstituted phenyl group);

(Fda25) benzothienyl C1-6 alkyl group (which may be substituted on the benzothiophene ring by at least one group selected from the group consisting of a halogen atom and a halogen-substituted or unsubstituted C1-6 alkoxy group);

(Fda26) thienyl C1-6 alkyl group that may be substituted on the thiophene ring by a halogen atom;

(Fda27) benzothiazolyl C1-6 alkyl group;

(Fda28) benzofuryl C1-6 alkyl group which may be substituted on the benzofuran ring by a halogen atom;

(Fda29) indolinyl C1-6 alkyl group (which may be substituted on the indoline ring by at least one group selected from the group consisting of a C1-6 alkyl group and an oxo group);

(Fda30) benzoxazolyl C1-6 alkyl group (which may be substituted on the benzoxazole ring by at least one group selected from a group consisting of a halogen atom, a C1-6 alkyl group, and an oxo group);

(Fda31) chromenyl C1-6 alkyl group;

(Fda32) 1,2,3,4-tetrahydroquinolyl C1-6 alkyl group (which may be substituted on the quinoline ring by at least one group selected from the group consisting of a C1-6 alkyl group and an oxo group);

(Fda33) thiazolyl C1-6 alkyl group (which may be substituted on the thiazole ring by at least one group selected from the group consisting of a halogen atom, a halogen-substituted or unsubstituted phenyl group, and a C1-6 alkyl group); or (Fda34) tetrazolyl C1-6 alkyl group (which may be substituted on the tetrazole ring by a group selected from the group consisting of a halogen-substituted or unsubstituted phenyl group and a C1-6 alkyl group);

(Fd37) a group represented by the following general formula (Fe):

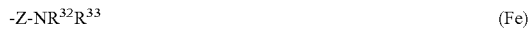

wherein Z repreesents —C=O or —C=S, and $R^{32}$ and $R^{33}$ each identically or differently represent any one of:

(Fe1) hydrogen atom;

(Fe2) C1-6 alkyl group;

(Fe3) C3-8 cycloalkyl group;

(Fe4) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fe5) phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fe6) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and (Fe7) $R^{32}$ and $R^{33}$ may bind to each other together with nitrogen atoms adjacent thereto through other carbon atoms, so as to form a piperidine ring or 1,2,3,6-tetrahydropyridine ring, which may be substituted on the piperidine or 1,2,3,6-tetrahydropyridine ring by a phenyl group, which may be substituted at least one group selected from the group consisting of a halogen atom and a halogen-substituted or unsubstituted C1-6 alkyl group, (Fd38) a group represented by the following general formula (Ff):

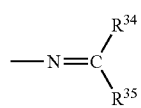

wherein $R^{34}$ represents a hydrogen atom or C1-6 lower alkyl group, and $R^{35}$ represents:

(Ff1) C3-8 cycloalkyl group;

(Ff2) C3-8 cycloalkenyl group;

(Ff3) a group represented by the following general formula (Ffa):

wherein each of $R^{36}$, $R^{37}$, and $R^{38}$ represents: a hydrogen atom; C1-6 alkyl group; phenyl group (which may be substituted on the phenyl ring by at least one 1 to 5 groups selected from the group consisting of a halogen atom, a halogen-substituted or unsubstituted C1-6 alkyl group, a halogen-substituted or unsubstituted C1-6 alkoxy group, a C1-4 alkylenedioxy group, a C1-6 alkylsulfonyl group, a halogen-substituted or unsubstituted C1-6 alkylthio group, a nitro group, and an amino group which may have a C1-6 alkanoyl group as a substituent); benzofuryl group (which may be substituted on the benzofuran ring by at least one group selected from the group consisting of a halogen atom, a halogen-substituted or unsubstituted C1-6 alkyl group, and a halogen-substituted or unsubstituted C1-6 alkoxy group); biphenylyl group; furyl group (which may be substituted on the furan ring by a phenyl group which may have a halogen atom as a substituent); or thiazolyl group (which may be substituted on the thiazole ring by at least one phenyl group which may have a halogen atom as a substituent), (Ff4) phenyl group (which may be substituted on the phenyl ring by at least one group selected from the group consisting of: a halogen atom; a halogen-substituted or unsubstituted C1-6 alkyl group; a C3-8 cycloalkyl group; a hydroxyl group; a halogen-substituted or unsubstituted C1-8 alkoxy group; a C3-8 cycloalkoxy group; a C1-4 alkylenedioxy group; a cyano group; a nitro group; a phenyl C2-6 alkenyl group; a C2-6 alkanoyloxy group; an amino group which may have a C1-6 alkanoyl group as a substituent; a C1-6 alkyl-sulfonylamino group; a phenyl C1-6 alkoxy group; a phenoxy group; an amino group which has at least one C1-6 alkyl group as a substituent; an amino group which has at least one phenyl group as a substituent; an amino C1-6 alkoxy group which may have at least one C1-6 alkyl group as a substituent; a C1-6 alkoxycarbonyl group; a C1-6 alkoxycarbonyl C1-6 alkoxy group; a C1-6 alkylthio group; a pyrrolyl group; an imidazolyl group; a piperidyl group; a morpholino group; a pyrrolidinyl group; a thienyl group; a benzofuryl group; a piperazinyl group (which may be substituted on the piperazine ring by at least one group selected from the group consisting of a C1-6 alkyl group, a phenyl C1-6 alkyl group, and a benzoyl group which may have at least one C1-6 alkyl group as a substituent); a quinolyl group which may be substituted on the quinoline ring by at least one group selected from the group consisting of a C1-6 alkoxy group and an oxo group; a piperidylcarbonyl group which may be substituted on the piperidine ring by a carbostyril group; and a triazolyl group);

(Ff5) naphthyl group which may be substituted on the naphthalene ring by at least one group selected from the group consisting of a halogen atom, a halogen-substituted or unsubstituted C1-6 alkoxy group, and an amino group which may have a C1-6 alkyl group as a substituent;

(Ff6) biphenylyl group (which may be substituted on the biphenylyl ring by at least one group selected from the group consisting of a halogen atom, a halogen-substituted or unsubstituted C1-9 alkyl group, and a halogen-substituted or unsubstituted C1-6 alkoxy group);

(Ff7) fluorenyl group; pyrenyl group;

(Ff8) benzofuryl group (which may be substituted on the benzofuran ring by at least one group selected from the group consisting of a halogen atom, a halogen-substituted or unsubstituted C1-6 alkyl group, and a halogen-substituted or unsubstituted C1-6 alkoxy group);

(Ff9) benzothienyl group (which may be substituted on the benzothiophene ring by at least one group selected from the group consisting of a halogen atom, a halogen-substituted or unsubstituted C1-6 alkyl group, and a halogen-substituted or unsubstituted C1-6 alkoxy group);

(Ff10) pyridyl group (which may be substituted on the pyridine ring by at least one group selected from the group consisting of a halogen atom, a halogen-substituted or unsubstituted C1-6 alkyl group, a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), a furyl group, and a thienyl group);

(Ff11) furyl group (which may be substituted on the furan ring by 1 to 3 groups selected from the group consisting of a C1-6 alkyl group, a nitro group, and a phenyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a nitro group));

(Ff12) benzothiazole group (which may have, on the benzothiazole ring, at least one phenyl group that may have, as a substituent, a C1-6 alkoxy group on the phenyl ring);

(Ff13) thienyl group (which may have, on the thiophene ring, at least one group selected from the group consisting of a halogen atom, a nitro group, a C1-6 alkyl group, a pyrazolyl group which may be substituted on the pyrazole ring by at least one halogen-substituted or unsubstituted C1-6 alkyl group as a substituent, and a thienyl group which may have a halogen atom on the thiophene ring);

(Ff14) indolyl group (which may be substituted on the indole ring by at least one group selected from the group consisting of a phenylsulfonyl group which may have a C1-6 alkyl group as a substituent, a phenyl C1-6 alkyl group, a C1-6 alkoxycarbonyl group, and a phenyl group);

(Ff15) pyrrolyl group (which may be substituted on the pyrrole ring by at least one group selected from the group consisting of a phenyl group which may be substituted by at least one halogen-substituted or unsubstituted C1-6 alkyl group, and a C1-6 alkyl group);

(Ff16) coumaryl group;

(Ff17) benzimidazolyl group (which may be substituted on the benzimidazole ring by at least one thienyl group as a substituent);

(Ff18) oxazolyl group (which may be substituted on the oxazole ring by at least one phenyl group that may have a halogen atom as a substituent);

(Ff19) thiazolyl group (which may be substituted on the thiazole ring by at least one phenyl group, wherein at least one group selected from the group consisting of a halogen atom, a nitro group, and a phenyl group);

(Ff20) quinolyl group;

(Ff21) 3,4-dihydrocarbostyril group (which may be substituted on the 3,4-dihydrocarbostyril ring by at least one group selected from the group consisting of a C1-6 alkoxy group, a C1-6 alkyl group, and a phenyl C1-6 alkoxy group), or carbostyril group (which may be substituted on the carbostyril ring by at least one group selected from the group consisting of a C1-6 alkoxy group, a C1-6 alkyl group, and a phenyl C1-6 alkoxy group);

(Ff22) imidazo[2,1-b]thiazolyl group;

(Ff23) imidazo[2,1-a]pyridyl group;

(Ff24) chromanyl group (which may be substituted on the chroman ring by at least one C1-6 alkyl group); or (Ff25) 2,3-dihydrobenzofuryl group, or (Fd39) a group represented by the following general formula (Ffb):

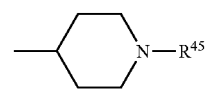

(Ffb)

wherein $R^{45}$ represents: a C1-6 alkoxycarbonyl group; phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); amino substituted C1-6 alkyl group which may have, on the amino group, a group selected from a group consisting of a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) and a C1-6 alkyl group as a substituent; benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (F12-3) morpholino group;

(F12-4) imidazolyl group;

(F12-5) 1,4-dioxaazaspiro[4,5]decyl group (which may be substituted on the 1,4-dioxaazaspiro-[4,5]decane ring by at least one oxo group as a substituent);

(F12-6) homopiperazinyl group (which may be substituted on the homopiperazine ring by at least one group selected from the group consisting of a C1-6 alkoxycarbonyl group, a phenyl C1-6 alkoxycarbonyl group, and a phenyl-substituted or unsubstituted phenyl group as a substituent);

(F12-7) piperazinyl group (which may be substituted on the piperazine ring by at least one group selected from the group consisting of an oxo group, a C1-6 alkyl group, and a phenyl C1-6 alkyl group (which may be substituted on the phenyl ring by at least one halogen-substituted or unsubstituted C1-6 alkyl group));

(F12-8) piperidyl group (which may be substituted on the piperidine ring by at least one oxo group as a substituent);

(F12-9) pyrrolidinyl group (which may be substituted on the pyrrolidine ring by at least one phenoxy C1-6 alkyl group that may have a halogen-substituted or unsubstituted C1-6 alkoxy group as a substituent);

(F12-10) isoindolinyl group, and

F13) moreover, $R^{19}$ and $R^{20}$ may bind to each other together with nitrogen atoms adjacent thereto directly or through hetero atoms, so as to form a cyclic imide or amide shown in any one of (F13-1) to (F13-11) indicated below:

(F13-1) succinimide group;

(F13-2) oxazolidinyl group (which may be substituted on the oxazolidine ring by at least one oxo group as a substituent);

(F13-3) benzo-1,3-oxazolidinyl group (which may be substituted on the benzo-1,3-oxazolidine ring by at least one group selected from the group consisting of an oxo group, a halogen atom, and a phenyl group as a substituent);

(F13-4) imidazolidinyl group (which may be substituted on the imidazolidine ring by at least one group selected from the group consisting of an oxo group, a phenyl C1-6 alkyl group (which may be substituted on the phenyl ring by 1 to 3 groups selected from the group consisting of a halogen atom and a C1-6 alkoxy group), and a phenyl group);

(F13-5) benzimidazolidinyl group (which may be substituted on the benzimidazolidine ring by at least one group selected from the group consisting of: an oxo group; a halogen atom; a halogen-substituted or unsubstituted C1-6 alkyl group; an amino group which may have a C1-6 alkyl group as a substituent; a C1-6 alkoxycarbonyl group; and a piperidyl group (which may be substituted on the piperidine ring by at least one group selected from the group consisting of a C1-6 alkyl group, a phenyl group wherein 1 to 3 halogen atoms may be substituted on the phenyl ring, a C1-6 alkoxycarbonyl group, and a phenyl C1-6 alkoxycarbonyl group as a substituent));

(F13-6) phthalimide group;

(F13-7) indolinyl group (which may have on the indoline ring at least one group selected from the group consisting of a C1-6 alkyl group, a halogen atom, and an oxo group as a substituent);

(F13-8) 2,3-dihydrobenzothiazolyl group (which may have at least one oxo group on the 2,3-dihydrobenzothiazole ring);

(F13-9) 1H-2,4-benzoxazinyl group (which may be substituted on the 1H-2,4-benzoxazine ring by at least one oxo group as a substituent);

(F13-10) a group represented by the following general formula (Fga):

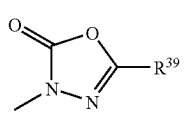

wherein $R^{39}$ represents: a hydrogen atom; a phenyl C1-6 alkyl group which may have, as a substituent, a halogen atom on the phenyl ring; phenoxy C1-6 alkyl group which may have, as a substituent, a halogen atom on the phenyl ring; phenyl C2-6 alkenyl group which may have, as a substituent, a halogen atom on the phenyl ring; phenyl group which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a phenyl group as a substituent; pyridyl group; or pyrazinyl group, and (F13-11) 1,3-thiazolidinyl group (which may be substituted on the 1,3-thiazolidine ring by at least one group selected from a group consisting of an oxo group and a phenyl C1-6 alkylidene group which may have a halogen-substituted or unsubstituted C1-6 alkyl group on the phenyl ring as a substituent), a group represented by the following general formula (G):

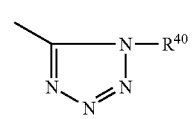

wherein $R^{40}$ represents a C1-6 alkyl group, or halogen-substituted or unsubstituted phenyl group, a spiro ring group represented by the following general formula (H):

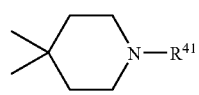

wherein $R^{41}$ represents:

H1) hydrogen atom;

H2) C1-6 alkyl group;

H3) phenyl C1-6 alkyl group that may have a phenyl group as a substituent on the phenyl ring;

H4) phenyl group (which may be substituted on the phenyl ring by at least one group selected from the group consisting of: a halogen atom; a halogen-substituted or unsubstituted C1-6 alkyl group; a halogen-substituted or unsubstituted C1-6 alkoxy group; an amino group (which may be substituted on the amino group by at least one group selected from the group consisting of a C1-6 alkyl group and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group)); an phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and piperidyl group (which may be substituted on the piperidine ring by at least one group selected from the group consisting of phenoxy groups (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent));

H5) piperazinyl C1-6 alkyl group (which may be substituted on the piperazine ring by at least one group selected from the group consisting of a C1-6 alkoxycarbonyl group and a phenyl C1-6 alkoxycarbonyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, and a phenyl group);

H6) piperazinylcarbonyl C1-6 alkyl group (which may be substituted on the piperazine ring by at least one group selected from the group consisting of: a C1-6 alkoxycarbonyl group; a phenyl C1-6 alkoxycarbonyl group which may have, as a substituent, a halogen-substituted or unsubstituted C1-6 alkyl group on the phenyl ring; and a phenyl C1-6 alkyl group which may have, as a substituent, at least one group selected from the group consisting of a halogen-substituted or unsubstituted C1-6 alkyl group and a phenyl group on the phenyl ring);

H7) phenylcarbamoyl C1-6 alkyl group which may have at least one halogen-substituted or unsubstituted C1-6 alkyl group as a substituent on the phenyl ring;

H8) benzoxazolyl C1-6 alkyl group (which may have at least one oxo group as a substituent on the benzoxazole ring);

H9) benzothiazolyl group;

H10) tetrazolyl group (which may have at least one phenyl group as a substituent on the tetrazole ring);

H11) C1-6 alkylsulfonyl group;

H12) phenylsulfonyl group which may have at least one C1-6 alkyl group as a substituent on the phenyl ring;

H13) phenylthiocarbamoyl group which may be substituted on the phenyl ring by at least one halogen atom as a substituent;

H14) C1-8 alkoxycarbonyl group;

H15) phenyl C1-6 alkoxycarbonyl group (which may be substituted on the phenyl ring by at least one group selected from the group consisting of a halogen atom, a C1-6 alkoxycarbonyl group, an amino group which may have a C1-6 alkoxycarbonyl group as a substituent, a halogen-substituted or unsubstituted C1-6 alkyl group, a halogen-substituted or unsubstituted C1-6 alkoxy group, a nitro group, and a C1-6 alkylthio group);

H16) benzhydryloxycarbonyl group (which may be substituted on the phenyl ring by at least one halogen atom);

H17) C1-6 alkoxycarbonyl group which may have a phenyl-substituted or unsubstituted phenyl group;

H18) naphthyl C1-6 alkoxycarbonyl group;

H19) pyridyl C1-6 alkoxycarbonyl group;

H20) C1-6 alkoxy-substituted C1-6 alkoxycarbonyl group;

H21) piperazinyl C1-6 alkoxycarbonyl group (which may be substituted on the piperazine ring by at least one group selected from the group consisting of a C1-6 alkoxycarbonyl group and a phenyl C1-6 alkyl group (which may have at least one halogen atom as a substituent on the phenyl ring) as a substituent);

H22) phenoxycarbonyl group (which may be substituted on the phenyl ring by at least one group selected from the group consisting of a C1-6 alkyl group and a C1-6 alkoxy group);

H23) C1-6 alkanoyl group;

H24) benzoyl group (which may be substituted on the phenyl ring by at least one halogen-substituted or unsubstituted C1-6 alkyl group);

H25) phenyl C1-6 alkanoyl group (which may be substituted on the phenyl ring by at least one halogen-substituted or unsubstituted C1-6 alkyl group);

H26) phenoxy C1-6 alkanoyl group (wherein 1 to 3 halogen atoms may be substituted on the phenyl ring);

H27) piperazinyl C2-6 alkanoyl group (which may be substituted on the piperazine ring by at least one group selected from a group consisting of: a C1-6 alkanoyl group; a phenyl C1-6 alkyl group which may have, as a substituent, at least one group selected from the group consisting of a phenyl group, a halogen atom, a halogen-substituted or unsubstituted C1-6 alkyl group, and a halogen-substituted or unsubstituted C1-6 alkoxy group, on the phenyl ring; a phenyl C1-6 alkoxycarbonyl group which may have, as a substituent, at least one group selected from the group consisting of a halogen atom, a halogen-substituted or unsubstituted C1-6 alkyl group, and a halogen-substituted or unsubstituted C1-6 alkoxy group, on the phenyl ring; a phenylcarbamoyl C1-6 alkyl group which may have, as a substituent, at least one group selected from the group consisting of a halogen atom, a halogen-substituted or unsubstituted C1-6 alkyl group, and a halogen-substituted or unsubstituted C1-6 alkoxy group, on the phenyl ring; a phenylcarbamoyl group which may have, as a substituent, at least one group selected from the group consisting of a halogen atom, a halogen-substituted or unsubstituted C1-6 alkyl group, and a halogen-substituted or unsubstituted C1-6 alkoxy group, on the phenyl ring; and a benzoxazolyl group);

H28) phenylcarbamoyl group (which may be substituted on the phenyl ring by 1 to 3 groups selected from the group consisting of a halogen atom, an amino group which may have a C1-6 alkyl group as a substituent, a carboxyl group, a C1-6 alkoxycarbonyl group, a halogen-substituted or unsubstituted C1-6 alkyl group, a halogen-substituted or unsubstituted C1-6 alkoxy group, a piperazinyl group which may have a C1-6 alkyl group as a substituent on the piperazine ring, and a morpholino group);

H29) phenyl C1-6 alkylcarbamoyl group (which may be substituted on the phenyl ring by at least one group selected from the group consisting of a halogen-substituted or unsubstituted C1-6 alkyl group and a halogen-substituted or unsubstituted C1-6 alkoxy group); or H30) piperazinylcarbonyl group (which may be substituted on the piperazine ring by at least one group selected from the group consisting of a C1-6 alkoxycarbonyl group, a phenyl C1-6 alkoxycarbonyl group which may have at least one halogen-substituted or unsubstituted C1-6 alkyl group on the phenyl ring, and a phenyl C1-6 alkyl group which may have a halogen-substituted or unsubstituted C1-6 alkyl group on the phenyl ring), provided that, in the above general formula (1), when $R^1$ represents a hydrogen atom and $R^2$ represents a group represented by the above general formula (A), then $R^3$ cannot be an isopropyl group; when $R^1$ represents a hydrogen atom, $R^2$ represents a group represented by the above general formula (E), and m is 0, then $R^{11}$ cannot be a hydrogen atom; and further, when $R^1$ represents a hydrogen atom and $R^2$ represents a group represented by the above general formula (F), then it is not possible that $R^{19}$ represents a hydrogen atom and $R^{20}$ represents a tert-butoxycarbonyl group.

Further, the present invention provides a 2,3-dihydro-6-nitroimidazo[2,1-b]oxazole compound represented by the following general formula (1'), optically active form thereof, or pharmaceutically acceptable salt thereof:

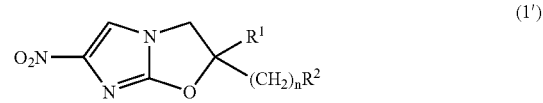

(1')

wherein $R^1$ represents a hydrogen atom or C1-6 alkyl group, n represents an integer of 0 to 6, and $R^2$ represents a group represented by general formula (A'), (B'), (C'), (D'), (E'), (F') or (G') indicated below, and further, $R^1$ and $—(CH_2)_nR^2$ may bind to each other together with carbon atoms adjacent thereto through nitrogen atoms, so as to form a spiro ring represented by general formula (H') indicated below.

General formulas (A')-(H') will be described as follows: a group represented by the following general formula (A'):

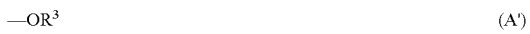 —OR³ (A')

wherein R³ represents:
A1) hydrogen atom;
A2) C1-6 alkyl group;
A3) C1-6 alkoxy-C1-6 alkyl group
A4) phenyl C1-6 alkyl group (which may be substituted on the phenyl ring by at least one group selected from the group consisting of a benzyloxy group, a halogen-substituted or unsubstituted C1-6 alkyl group, and a halogen-substituted or unsubstituted C1-6 alkoxy group);
A5) biphenylyl C1-6 alkyl group;
A6) cinnamyl group:
A7) methanesulfonyl group;
A8) benzenesulfonyl group that may be substituted by a methyl group;
A9) C1-6 alkanoyl group;
A10) a group represented by the following general formula (Aa'):

 (Aa')

wherein R⁴ represents a C1-6 alkoxycarbonyl group, phenyl C1-6 alkoxycarbonyl group (which may be substituted on the phenyl ring by at least one group selected from the group consisting of a benzyloxy group, a halogen-substituted or unsubstituted C1-6 alkyl group, and a halogen-substituted or unsubstituted C1-6 alkoxy group), or phenyl C1-6 alkyl group (which may be substituted on the phenyl ring by at least one group selected from the group consisting of a benzyloxy group, a halogen-substituted or unsubstituted C1-6 alkyl group, and a halogen-substituted or unsubstituted C1-6 alkoxy group);
A11) biphenylyl C1-6 alkoxycarbonyl group;
A12) 2-(2-oxo-3-benzoxazolyl)ethyl group;
A13) 2-benzoxazolyl group; or
A14) 2-phenyl-5-methyl-4-oxazolylmethyl group, a group represented by the following general formula (B'):

 —SR⁵ (B')

wherein R⁵ represents a 5-(1H)-tetrazolyl group (wherein position 1 may be substituted by a C1-6 alkyl group, or halogen-substituted or unsubstituted phenyl group), or 2-benzoxazolyl group, a group represented by the following general formula (C'):

 —COOR⁶ (C')

wherein R⁶ represents a C1-6 alkyl group, a carbamoyloxy group represented by the following general formula (D'):

 —OOCNR⁷R⁸ (D')

wherein R⁷ and R⁸ each identically or differently represent any one of:
D1) hydrogen atom;
D2) C1-8 alkyl group;
D3) halogen-substituted C1-6 alkyl group;
D4) C1-6 alkoxycarbonyl-C1-6 alkyl group;
D5) C5-8 cycloalkyl group;
D6) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
D7) phenyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, a C1-6 alkanoyl group, a carboxyl group, a C1-6 alkoxycarbonyl group, a benzyloxycarbonyl group, a carbamoyl group, a C1-6 alkylcarbamoyl group, an aminosulfonyl group, and a morpholino group);
D8) 1-naphthyl group;
D9) 4-pyridyl group; and
D10) R⁷ and R⁸ may bind to each other together with nitrogen atoms adjacent thereto directly or through other hetero atoms or carbon atoms, so as to form a saturated heterocyclic group shown in any one of (D10-1) to (D10-3) indicated below, or benzene condensed heterocyclic group shown in any one of (D10-4) to (D10-7) indicated below:

(D10-1) a piperazinyl group represented by the following general formula (Da'):

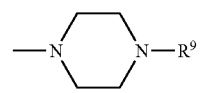 (Da')

wherein R⁹ represents:
(Da1) hydrogen atom;
(Da2) C1-6 alkyl group;
(Da3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da4) phenyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group);
(Da5) C1-6 alkoxycarbonyl group;
(Da6) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da7) 4-trifluoromethylcinnamyloxycarbonyl group; or
(Da8) 4-trifluoromethylbenzylideneamino group, (D10-2) a group represented by the following general formula (Db'):

 (Db')

wherein the dotted line represents that the bond may be a double bond, and R¹⁰ represents:
(Db1) hydrogen atom;
(Db2) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Db3) phenoxy group (which may be substituted on the phenyl ring by at least one halogen-substituted or unsubstituted C1-6 alkyl group); or (Db4) phenylamino group (which may be substituted on the phenyl ring by at least one halogen-substituted or unsubstituted C1-6 alkyl group), and (D10-3) a morpholino group;

(D10-4) halogen-substituted or unsubstituted 1-indolinyl group;

(D10-5) halogen-substituted or unsubstituted 2-isoindolinyl group;

(D10-6) halogen-substituted or unsubstituted 1,2,3,4-tetrahydro-1-quinolinyl group; and (D10-7) halogen-substituted or unsubstituted 1,2,3,4-tetrahydro-2-isoquinolinyl group, a phenoxy group represented by the following general formula (E'):

wherein X represents a halogen atom, m represents an integer of 0 to 3, and $R^{11}$ represents:

E1) hydrogen atom;

E2) halogen-substituted or unsubstituted C1-6 alkyl group;

E3) halogen-substituted or unsubstituted C1-6 alkoxy group;

E4) morpholino group;

E5) thiomorpholino group;

E6) S-oxide thiomorpholino group;

E7) 1-imidazolyl group;

E8) 1-triazolyl group;

E9) piperidinyl group represented by the following general formula (Ea'):

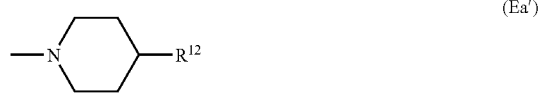

wherein $R^{12}$ represents:

(Ea1) hydrogen atom;

(Ea2) C1-6 alkoxycarbonyl group; or (Ea3) phenoxy group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group), E10) a group represented by the following formula (Eb'):

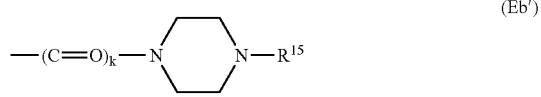

wherein k represents an integer of 0 or 1, and $R^{15}$ represents:

(Eb1) hydrogen atom;

(Eb2) C1-6 alkyl group;

(Eb3) phenyl C1-6 alkyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Eb4) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Eb5) C1-6 alkanoyl group;

(Eb6) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eb7) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eb8) C1-8 alkoxycarbonyl group (which may be substituted on the alkoxy group by at least one group selected from the group consisting of a halogen atom, a di(C1-6 alkyl) amino group, and a C1-6 alkoxy group);

(Eb9) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eb10) phenyl C3-6 alkenyloxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eb11) phenoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eb12) phenyl C1-6 alkylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eb13) phenylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or (Eb14) 2-benzofuranylmethyloxycarbonyl group which may be substituted by a halogen atom on the benzene ring, E11) a group represented by the following general formula (Ec'):

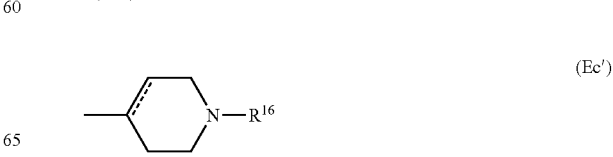

wherein the dotted line represents that the bond may be a double bond, and $R^{16}$ represents:

(Ec1) hydrogen atom;
(Ec2) C1-6 alkyl group;
(Ec3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Ec4) C1-8 alkoxycarbonyl group; or
(Ec5) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), a group represented by the following general formula (F'):

$$-NR^{19}R^{20} \quad (F')$$

wherein $R^{19}$ and $R^{20}$ each identically or differently represent any one of:

F1) hydrogen atom;
F2) C1-6 alkyl group;
F3) phenyl C1-6 alkyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a dimethylamino group);
F4) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
F5) N-methylamino C1-6 alkyl group (wherein, the position N may be substituted by a C1-6 alkoxycarbonyl group, or phenyl group that may be substituted on the phenyl ring by at least one group selected from the group consisting of a halogen atom and a halogen-substituted or unsubstituted C1-6 alkyl group);
F6) phenyl group (which may be substituted on the phenyl ring by at least one group selected from the group consisting of a halogen atom and a C1-6 alkoxycarbonyl group);
F7) C1-6 alkoxycarbonyl group;
F8) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
F9) 4-substituted-1-piperazinylethyl group represented by the following general formula (Fa'):

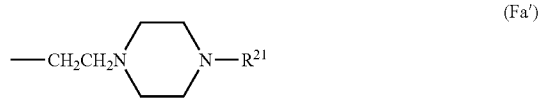

wherein $R^{21}$ represents a C1-6 alkoxycarbonyl group; phenyl C1-6 alkoxycarbonyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom and a halogen-substituted or unsubstituted C1-6 alkyl group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group), F10) 1-substituted-4-piperidinyl group represented by the following formula (Fb'):

wherein $R^{22}$ represents a C1-6 alkoxycarbonyl group; phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group), F11) 2-[4-(4-trifluoromethylphenoxy)-1-piperidinyl]ethyl group;

F12) in addition, $R^{19}$ and $R^{20}$ may bind to each other together with nitrogen atoms adjacent thereto directly or through other hetero atoms or carbon atoms, so as to form a heterocyclic ring shown in any one of (F12-1) to (F12-10) indicated below:

(F12-1) a group represented by the following formula (Fc'):

wherein the dotted line represents that the bond may be a double bond, and $R^{23}$ represents:

(Fc1) C1-6 alkyl group;
(Fc2) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Fc3) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Fc4) phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Fc5) 4-biphenylyl C1-6 alkoxy group;
(Fc6) phenyl C3-6 alkenyloxy group which may be substituted on the phenyl ring by a halogen atom;
(Fc7) phenoxy group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Fc8) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc9) C1-6 alkoxycarbonyl group;

(Fc10) phenyl C1-6 alkoxycarbonyl group (which may be substituted on the phenyl ring by at least one halogen-substituted or unsubstituted C1-6 alkoxy group);

(Fc11) phenyl C1-6 alkylcarbamoyl group wherein a halogen atom may be substituted on the phenyl ring;

(Fc12) phenylcarbamoyl group wherein a halogen atom may be substituted on the phenyl ring;

(Fc13) phenylthio group (which may be substituted on the phenyl ring by at least one halogen-substituted or unsubstituted C1-6 alkoxy group);

(Fc14) phenyl sulfoxide group (which may be substituted on the phenyl ring by at least one halogen-substituted or unsubstituted C1-6 alkoxy group);

(Fc15) pyridylmethoxy group; or (Fc16) a group represented by the following general formula (Fca'):

$$—NR^{24}R^{25} \quad \text{(Fca')}$$

wherein each of $R^{24}$ and $R^{25}$ represents:

(Fca1) hydrogen atom;

(Fca2) C1-6 alkyl group;

(Fca3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca4) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Fca5) C1-6 alkanoyl group;

(Fca6) phenylacetyl group which may be substituted on the phenyl ring by a halogen atom;

(Fca7) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca8) C1-6 alkoxycarbonyl group;

(Fca9) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca10) phenylcarbamoyl group (which may be substituted by at least one halogen-substituted or unsubstituted C1-6 alkoxy group on the phenyl ring);

(Fca11) 1-(4-trifluoromethylphenyl)-4-piperidinyloxycarbonyl group; or (Fca12) $R^{24}$ and $R^{25}$ may form a piperidine ring through nitrogen adjacent thereto, (F12-2) 4-substituted-1-piperazinyl group represented by the following general formula (Fd'):

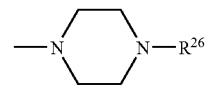

(Fd')

wherein $R^{26}$ represents:

(Fd1) hydrogen atom;

(Fd2) C1-6 alkyl group;

(Fd3) C5-8 cycloalkyl group;

(Fd4) C5-8 cycloalkyl-C1-6 alkyl group;

(Fd5) C1-6 alkoxycarbonyl-C1-6 alkyl group;

(Fd6) cinnamyl group;

(Fd7) phenyl C1-6 alkyl group (which may be substituted on the phenyl ring by 1 to 3 groups selected from the group consisting of a halogen atom; a cyano group; a halogen-substituted or unsubstituted C1-6 alkyl group; a cyclohexyl group; a halogen-substituted or unsubstituted C1-6 alkoxy group; a dimethylamino group; a C1-6 alkoxycarbonyl group; a phenoxy group; a phenyl C1-6 alkyl group; a styryl group; a 3-pyridyl group; a 1-imidazolyl group; and a 1-piperidino group);

(Fd8) biphenylylmethyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a dimethylamino group);

(Fd9) 1- or 2-naphthylmethyl group;

(Fd10) phenyl group (which may be substituted on the phenyl ring by at least one group selected from the group consisting of: a halogen atom; a cyano group; a dimethylamino group; a halogen-substituted or unsubstituted C1-6 alkyl group; a halogen-substituted or unsubstituted C1-6 alkoxy group; a C1-6 alkoxycarbonyl group, and a carboxyl group);

(Fd11) biphenylyl group (which may be substituted on the phenyl ring by at least one group selected from the group consisting of halogen-substituted or unsubstituted C1-6 alkyl groups);

(Fd12) amino group, amino group substituted by a C1-6 alkoxycarbonyl group, benzylamino group, trifluoromethylbenzylamino group, or phenylamino group (which may be substituted on the phenyl ring by at least one group selected from the group consisting of a halogen-substituted or unsubstituted C1-6 alkyl group and a halogen atom);

(Fd13) 4-chlorobenzoylmethyl group;

(Fd14) phenylcarbamoylmethyl group (which may be substituted on the phenyl ring by at least one halogen-substituted or unsubstituted C1-6 alkyl group);

(Fd15) 4- or 5-thiazolylmethyl group (which may be substituted on the thiazole ring by at least one group selected from the group consisting of a halogen-substituted or unsubstituted phenyl group and a C1-6 alkyl group);

(Fd16) 4-oxazolylmethyl group (which may be substituted on the oxazole ring by at least one group selected from the group consisting of a halogen-substituted or unsubstituted phenyl group and a C1-6 alkyl group);

(Fd17) 2-indolylmethyl group;

(Fd18) 2-furylmethyl group (which may be substituted on the furan ring by at least one halogen-substituted or unsubstituted phenyl group);

(Fd19) 4- or 5-imidazolylmethyl group (which may be substituted on the imidazole ring by a phenyl group);

(Fd20) 2-quinolylmethyl group;

(Fd21) 5-(1H)-tetrazolyl group (wherein the position-1 of the tetrazole ring may be substituted by a phenyl group);

(Fd22) 2- or 4-pyrimidyl group that may be substituted by a phenyl group;

(Fd23) 2-, 3-, or 4-pyridyl group;

(Fd24) 2-benzoxazolyl group;

(Fd25) 2-benzothiazolyl group;

(Fd26) 2-oxo-3-benzoxazolyl-C1-6 alkyl group;

(Fd27) phenoxy C2-6 alkanoyl group which may be substituted on the phenyl ring by a halogen atom;

(Fd28) phenylthio C2-6 alkanoyl group that may be substituted on the phenyl ring by a halogen atom;

(Fd29) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fd30) benzoyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a C1-6 alkylamino group);

(Fd31) 4-biphenylylcarbonyl group;

(Fd32) 2-, 3-, or 4-pyridylcarbonyl group;

(Fd33) cinnamoyl group wherein a halogen atom may be substituted on the phenyl ring;

(Fd34) phenyl C1-6 alkylsulfonyl group which may be substituted by a halogen atom on the phenyl ring;

(Fd35) benzenesulfonyl group (which may be substituted on the benzene ring by at least one group selected from the group consisting of a chlorine atom and a methyl group);

(Fd36) a group represented by the following general formula (Fda'):

—COOR$^{27}$ (Fda')

wherein R$^{27}$ represents:

(Fda1) halogen-substituted or unsubstituted C1-8 alkyl group;

(Fda2) C5-8 cycloalkyl group;

(Fda3) C5-8 cycloalkyl-C1-6 alkyl group;

(Fda4) C1-6 alkoxy-C1-6 alkyl group;

(Fda5) C1-6 alkylamino-C1-6 alkyl group;

(Fda6) a group represented by the following general formula (Fdb'):

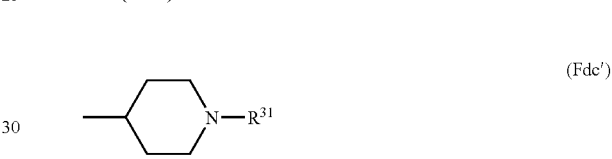

wherein R$^{28}$, R$^{29}$, or R$^{30}$ represent a hydrogen atom, a C1-6 alkyl group, or a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), respectively;

(Fda7) phenyl C1-6 alkyl group (which may be substituted on the phenyl ring by 1 to 5 groups selected from the group consisting of a halogen atom; a halogen-substituted or unsubstituted C1-6 alkyl group; a halogen-substituted or unsubstituted C1-6 alkoxy group; a halogen-substituted or unsubstituted C1-6 alkylthio group; a phenyl C1-6 alkoxy group; a hydroxy group; a methylsulfinyl group; a methanesulfonyl group; methanesulfonyloxy group; a cyano group; an acetyl group; a benzoyl group; an α,α-dimethoxybenzyl group, an amino group, a nitro group; a carbamoyl group; an acetylamino group; a C1-6 alkoxycarbonyl group; a C1-6 alkylaminocarbonyl group; a C1-6 alkoxycarbonylamino group; a tri-C1-6-alkylsiloxy group; a pyrrolyl group; a tetrahydropyranyloxy group; and an 1-imidazolyl group);

(Fda8) biphenylyl C1-6 alkyl group;

(Fda9) benzhydryl group (which may be substituted on the benzene ring by at least one group selected from the group consisting of a halogen atom, a trifluoromethyl group, and a trifluoromethoxy group);

(Fda10) phenoxy C1-6 alkyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group);

(Fda11) 3-(4-trifluoromethyl)phenyl-2-propynyl group;

(Fda12) 2-, 3-, or 4-pyridylmethyl group;

(Fda13) a group represented by the following general formula (Fdc'):

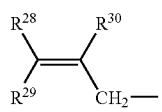

wherein R$^{31}$ represents a phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (Fda14) 1-piperidinoethyl group (wherein the position-4 of the piperidine ring may be substituted by a 4-trifluoromethylphenoxy group);

(Fda15) N-methyl-N-(4-trifluoromethoxy)-phenylaminoethyl group;

(Fda16) 4-(4-trifluoromethoxyphenyl)-1,2,3,6-tetrahydro-1-pyridinylethyl group;

(Fda17) 1- or 2-naphthylmethyl group;

(Fda18) 1-, 2-, 3-, 4-, or 9-fluorenylmethyl group;

(Fda19) 2-, 3-, or 4-pyridylmethyl group;

(Fda20) 2-furylmethyl group (wherein the position-4 of the furan ring may be substituted by a halogen-substituted or unsubstituted phenyl group);

(Fda21) 3-thienylmethyl group;

(Fda22) 4-oxazolylmethyl group (wherein the position-2 of the oxazoline ring may be substituted by a halogen atom or chlorophenyl group);

(Fda23) 4-thiazolylmethyl group which may be substituted by a halogen atom;

(Fda24) 5-oxadiazolylmethyl group wherein the position-2 of the oxadiazoline ring may be substituted by a halogen-substituted or unsubstituted phenyl group;

(Fda25) 3-pyrazolylmethyl group wherein the position-1 of the pyrazoline ring may be substituted by a halogen-substituted or unsubstituted phenyl group;

(Fda26) 2- or 3-benzothiophenylmethyl group (which may be substituted on the benzene ring by at least one group selected from the group consisting of a halogen atom and a halogen-substituted or unsubstituted C1-6 alkoxy group);

(Fda27) benzoxazol-2-ylmethyl group which may be substituted by a halogen atom on the benzene ring;

(Fda28) 2-thienylmethyl group which may be substituted by a halogen atom;

(Fda29) 2-benzothiazolylmethyl group;

(Fda30) 2-(5-chloro)benzofuranylmethyl group;

(Fda31) 3,3-dimethyl-2-oxo-5-indolinylmethyl group (wherein the position-1 of the indoline ring may be substituted by a C1-6 alkyl group);

(Fda32) 2-oxo-6-benzoxazolylmethyl group (wherein the position-1 of the benzoxazoline ring may be substituted by a C1-6 alkyl group);

(Fda33) 7-chromenylmethyl group;

(Fda34) 2-oxo-1,2,3,4-tetrahydro-6-quinolylmethyl group (wherein the position-1 of the quinoline ring may be substituted by a C1-6 alkyl group);

(Fda35) 5-thiazolylmethyl group (which may be substituted on the thiazole ring by at least one group selected from the group consisting of a halogen-substituted or unsubstituted phenyl group and a C1-6 alkyl group); or (Fda36) 5-(1H)-tetrazolyl C1-6 alkyl group (wherein the position-1 of the tetrazole ring may be substituted by a group selected from the group consisting of a halogen-substituted or unsubstituted phenyl group and a C1-6 alkyl group), (Fd37) a group represented by the following general formula (Fe'):

wherein Z represents —C=O or —C=S, and $R^{32}$ and $R^{33}$ each identically or differently represent any one of:

(Fe1) hydrogen atom;

(Fe2) C1-6 alkyl group;

(Fe3) C5-8 cycloalkyl group;

(Fe4) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fe5) phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fe6) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and (Fe7) $R^{32}$ and $R^{33}$ may bind to each other together with nitrogen atoms adjacent thereto through other carbon atoms, so as to form a piperidine ring or 1,2,3,6-tetrahydropyridine ring, wherein the position-4 of the piperidine ring or 1,2,3,6-tetrahydropyridine ring may be substituted by a phenyl group, and the phenyl group may be substituted by at least one group selected from the group consisting of a halogen atom and a halogen-substituted or unsubstituted C1-6 alkyl group, or (Fd38) a group represented by the following general formula (Ff'):

wherein $R^{34}$ represents a hydrogen atom or C1-6 lower alkyl group, and $R^{35}$ represents:

(Ff1) C5-8 cycloalkyl group;

(Ff2) C5-8 cycloalkenyl group;

(Ff3) a group represented by the following general formula (Ffa'):

wherein each of $R^{36}$, $R^{37}$, and $R^{38}$ represents: a hydrogen atom; C1-6 alkyl group; phenyl group (which may be substituted on the phenyl ring by at least one 1 to 5 groups selected from the group consisting of a halogen atom, a halogen-substituted or unsubstituted C1-6 alkyl group, a halogen-substituted or unsubstituted C1-6 alkoxy group, a methylenedioxy group, a methanesulfonyl group, a halogen-substituted or unsubstituted C1-6 alkylthio group, a nitro group, and an acetylamino group); 2-benzofuranyl group (which may be substituted on the benzene ring by at least one group selected from the group consisting of a halogen atom, a halogen-substituted or unsubstituted C1-6 alkyl group, and a halogen-substituted or unsubstituted C1-6 alkoxy group); 4-biphenylyl group; 2-furyl group which may be substituted by a 4-chlorophenyl group; or 2-(4-chlorophenyl)-4-thiazolyl group, (Ff4) phenyl group (which may be substituted on the phenyl ring by at least one group selected from the group consisting of: a halogen atom; a halogen-substituted or unsubstituted C1-6 alkyl group; a C5-8 cycloalkyl group; a hydroxy group; a halogen-substituted or unsubstituted C1-8 alkoxy group; a C5-8 cycloalkoxy group; a methylenedioxy group; an ethylenedioxy group; a cyano group; a nitro group; a cinnamyl group; a C1-6 alkanoyloxy group; a C1-6 alkanoylamino group; a methanesulfonylamino group; a phenyl C1-6 alkoxy group; a phenoxy group; a di(C1-6 alkyl)amino group; a diphenylamino group; a di(C1-6 alkyl) amino C1-6 alkoxy group; a methoxycarbonyl group; a C1-6 alkoxycarbonyl C1-6 alkoxy group; a C1-6 alkylthio group; a pyrrolyl group; a 1-imidazolyl group; a piperidino group; a morpholino group; pyrrolidinyl group; a 2-thienyl group; a 2-benzofuranyl group; a 4-piperazinyl group wherein the position-1 may be substituted by a group selected from the group consisting of a C1-6 alkyl group, a phenyl C1-6 alkyl group, a benzoyl group, and a C1-6 alkyl group substituted benzoyl group; a 2-oxo-3-quinolyl group which may be substituted on the benzene ring by a C1-6 alkoxy group; a 4-(carbostyril-1-yl)piperidinyl-1-carbonyl group; and a triazolyl group);

(Ff5) 1- or 2-naphthyl group substituted by a halogen atom, halogen-substituted or unsubstituted C1-6 alkoxy group, or dimethylamino group;

(Ff6) 3- or 4-biphenylyl group (which may be substituted on the biphenyl ring by at least one group selected from the group consisting of a halogen atom, a halogen-substituted or unsubstituted C1-9 alkyl group, and a halogen-substituted or unsubstituted C1-6 alkoxy group);

(Ff7) 2-fluorenyl group; 3-pyrenyl group;

(Ff8) 2-benzofuranyl group (which may be substituted on the benzene ring by at least one group selected from the group consisting of a halogen atom, a halogen-substituted or unsubstituted C1-6 alkyl group, and a halogen-substituted or unsubstituted C1-6 alkoxy group);

(Ff9) 2- or 3-benzothiophenyl group (which may be substituted on the benzene ring by at least one group selected from the group consisting of a halogen atom, a halogen-substituted or unsubstituted C1-6 alkyl group, and a halogen-substituted or unsubstituted C1-6 alkoxy group; or the position-3 or -2 of the thiophene ring may be substituted by a C1-6 alkyl group);

(Ff10) 2-, 3-, or 4-pyridyl group (which may be substituted on the pyridyl group by at least one group selected from the group consisting of a halogen atom, a halogen-substituted or unsubstituted C1-6 alkyl group, a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), a 2-furyl group, a 3-furyl group, a 2-thienyl group, and a 3-thienyl group);

(Ff11) 2- or 3-furyl group (which may be substituted on the furan ring by 1 to 3 groups selected from the group consisting of a C1-6 alkyl group, a nitro group, and a phenyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, and a nitro group));

(Ff12) 2-(2-methoxyphenyl)benzothiazol-5-yl group;

(Ff13) 2-thienyl group; 3-thienyl group; 4-bromo-2-thienyl group; 5-chloro-2-thienyl group; 5-ethyl-2-thienyl group; 3-methyl-2-thienyl group; 5-nitro-2-thienyl group; 5-(1-methyl-3-trifluoromethyl-5-pyrazolyl)-2-thienyl group; 5-(1-methyl-5-trifluoromethyl-3-pyrazolyl)-2-thienyl group; 2,2'-bithien-5-yl group; 5'-bromo-2,2'-bithien-5-yl group;

(Ff14) 1-(4-methylbenzenesulfonyl)indol-3-yl group; 1-benzylindol-3-yl group; 6-methoxy-carbonylindol-3-yl group; 2-phenylindol-3-yl group;

(Ff15) 1-(3-trifluoromethyl)phenyl-2,5-dimethyl-3-pyrrolyl group;

(Ff16) 6-coumaryl group;

(Ff17) 2-(2-thienyl)-5-benzimidazolyl group; 6-benzimidazolyl group;

(Ff18) 2-(4-chlorophenyl)-4-oxazolyl group;

(Ff19) 2-phenyl-4-thiazolyl group; 2-(4-chlorophenyl)-4-thiazolyl group; 2-(4-nitrophenyl)-4-thiazolyl group; 2-(4-biphenylyl)-4-thiazolyl group;

(Ff20) 2-thiazolyl group;

(Ff21) 2- or 4-quinolinyl group;

(Ff22) 8-methoxy-3,4-dihydrocarbostyril-5-yl group; 8-methoxy-1-methyl-3,4-dihydrocarbostyril-5-yl group; 8-benzyloxy-3,4-dihydrocarbostyril-5-yl group; 8-methoxycarbostyril-5-yl group; 8-methoxy-1-methylcarbostyril-5-yl group; 8-benzyloxycarbostyril-5-yl group; 8-methoxy-3,4-dihydrocarbostyril-6-yl group; 8-methoxy-1-methyl-3,4-dihydrocarbostyril-6-yl group; 8-benzyloxy-3,4-dihydrocarbostyril-6-yl group; 8-methoxycarbostyril-6-yl group; 8-methoxy-1-methylcarbostyril-6-yl group; 8-benzyloxycarbostyril-6-yl group;

(Ff23) 6-imidazo[2,1-b]thiazolyl group;

(Ff24) 2-imidazo[2,1-a]pyridyl group;

(Ff25) 2,2-dimethyl-6-chromanyl group; or (Ff26) 2,3-dihydro-5-benzofuranyl group, (F12-3) morpholino group;

(F12-4) 1-imidazolyl group;

(F12-5) 1,4-dioxa-8-azaspiro[4,5]-8-decyl group;

(F12-6) 4-tert-butoxycarbonyl-1-homopiperazinyl group; 4-benzyloxycarbonyl-1-homopiperazinyl group; 4-(4-biphenylyl)-1-homopiperazinyl group, (F12-7) 1-tert-butyl-2-piperazinon-4-yl group; 1-(4-trifluoromethylbenzyl)-2-piperazinon-4-yl group, (F12-8) 4-oxo-1-piperidinyl group;

(F12-9) 2-(4-trifluoromethoxyphenoxymethyl)-pyrrolidin-1-yl group; and (F12-10) 2-isoindolinyl group, and F13) moreover, $R^{19}$ and $R^{20}$ may bind to each other together with nitrogen atoms adjacent thereto directly or through hetero atoms, so as to form a cyclic imide or amide shown in any one of (F13-1) to (F13-11) indicated below:

(F13-1) 2-succinimide group;

(F13-2) 2-oxooxazolin-3-yl group;

(F13-3) 2-oxobenzo-1,3-oxazolidin-3-yl group; 5-bromo-2-oxobenzo-1,3-oxazolidin-3-yl group; 5-chloro-2-oxobenzo-1,3-oxazolidin-3-yl group; 5-phenyl-2-oxobenzo-1,3-oxazolidin-3-yl group;

(F13-4) 2-oxoimidazolidin-1-yl group (wherein the position-3 of 2-oxoimidazolidin-1-yl group may be substituted by a phenyl C1-6 alkyl group (which may be substituted on the phenyl ring by 1 to 3 groups selected from the group consisting of a halogen atom and a methoxy group), or a phenyl group);

(F13-5) 2-oxobenzimidazolidin-1-yl group (which may be substituted on the benzene ring by a halogen atom, halogen-substituted or unsubstituted C1-6 alkyl group, dimethylamino group, or ethoxycarbonyl group; or the position-3 of the imidazolidine ring may be substituted by a 4-piperidinyl group, which may be substituted by a group selected from the group consisting of a C1-6 alkyl group, a phenyl group wherein 1 to 3 halogen atoms may be substituted on the phenyl ring, a tert-butoxycarbonyl group, and a benzyloxycarbonyl group);

(F13-6) phthalimid-2-yl group;

(F13-7) oxyindol-1-yl group, wherein the position-3 may be substituted by 2 methyl groups or fluorine atoms;

(F13-8) benzoic sulfimid-2-yl group;

(F13-9) 1H-2,4-benzoxazin-3(4H)-on-4-yl group;

(F13-10) a group represented by the following general formula (Fga'):

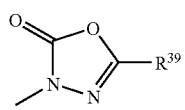

(Fga')

wherein $R^{39}$ represents: a hydrogen atom; halogen-substituted or unsubstituted phenyl C1-6 alkyl group; halogen-substituted or unsubstituted phenoxymethyl group; halogen-substituted or unsubstituted styryl group; phenyl group which may be substituted by at least one group selected from a group consisting of a halogen atom, a halogen-substituted or unsubstituted C1-6 alkyl group, and a halogen-substituted or unsubstituted C1-6 alkoxy group; biphenylyl group; 4-pyridyl group; or 2-pyrazinyl group, and (F13-11) 5-(4-trifluoromethylbenzylidene)-1,3-thiazolidine-2,4-dion-3-yl group;

a group represented by the following general formula (G'):

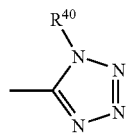

wherein $R^{40}$ represents a C1-6 alkyl group, or halogen-substituted or unsubstituted phenyl group, a spiro ring group represented by the following general formula (H'):

wherein $R^{41}$ represents:

H1) hydrogen atom;
H2) C1-6 alkyl group;
H3) phenyl C1-6 alkyl group or 4-biphenylyl C1-6 alkyl group;
H4) phenyl group (which may be substituted by a halogen-substituted or unsubstituted C1-6 alkyl group);
H5) 4-substituted-1-piperazinyl C1-6 alkyl group (wherein the substituent at the position-4 is a C1-6 alkoxycarbonyl group, 4-biphenylylmethoxycarbonyl group or benzyloxycarbonyl group, and the benzyloxycarbonyl group may be substituted by 1 to 3 groups selected from the group consisting of a halogen atom, a halogen-substituted or unsubstituted C1-6 alkyl group, and a halogen-substituted or unsubstituted C1-6 alkoxy group on the benzene ring);
H6) 4-substituted-1-piperazinylcarbonyl C1-6 alkyl group, wherein the position-4 is substituted with a C1-6 alkylcarbonyl group, 4-trifluoromethylbenzyloxycarbonyl group, 4-trifluoromethylbenzyl group, or biphenylylmethyl group;
H7) 4-trifluoromethylphenylcarbamoyl C1-6 alkyl group;
H8) 2-benzoxazolon-1-ylpropyl group;
H9) 2-benzothiazolyl group;
H10) 1-phenyl-5-tetrazolyl group;
H11) methanesulfonyl group;
H12) benzenesulfonyl or p-toluenesulfonyl group;
H13) phenylthiocarbamoyl group, wherein the position-4 of the phenyl ring may be substituted by a halogen atom;
H14) C1-8 alkoxycarbonyl group;
H15) phenyl C1-6 alkoxycarbonyl group (which may be substituted on the phenyl ring by at least one group selected from the group consisting of a halogen atom, a C1-6 alkoxycarbonyl group, a C1-6 alkoxycarbonylamino group, a halogen-substituted or unsubstituted C1-6 alkyl group, a halogen-substituted or unsubstituted C1-6 alkoxy group, a nitro group, and a methylthio group);
H16) benzhydryloxycarbonyl group (which may be substituted on the phenyl ring by 1 to 4 halogen atoms);
H17) 4-biphenylylmethoxcarbonyl group;
H18) naphthylmethoxycarbonyl group;
H19) pyridylmethoxycarbonyl group;
H20) methoxyethoxycarbonyl group;
H21) 2-(1-piperazinyl)ethoxycarbonyl group wherein the position-4 may be substituted by a C1-6 alkoxycarbonyl group, or halogen-substituted or unsubstituted phenyl C1-6 alkoxycarbonyl group;
H22) phenoxycarbonyl group (which may be substituted on the phenyl ring by at least one group selected from the group consisting of a C1-6 alkyl group and a C1-6 alkoxy group);
H23) C1-6 alkanoyl group;
H24) benzoyl group (which may be substituted on the phenyl ring by at least one halogen-substituted or unsubstituted C1-6 alkyl group);
H25) phenyl C2-6 alkanoyl group (which may be substituted on the phenyl ring by at least one halogen-substituted or unsubstituted C1-6 alkyl group);
H26) phenoxy C2-6 alkanoyl group (which may be substituted by 1 to 3 halogen atoms on the phenyl ring);
H27) 4-substituted-1-piperazinyl C2-6 alkanoyl group (wherein the substituent at the position-4 is a C1-6 alkanoyl group, phenyl C1-6 alkyl group, 4-biphenylylmethyl group, phenyl C1-6 alkoxycarbonyl group, phenylcarbamoylmethyl group, phenyl carbamoyl group, or 2-benzoxazolyl group; and the phenyl ring of each of these phenyl C1-6 alkyl group, phenyl C1-6 alkoxycarbonyl group, phenylcarbamoylmethyl group and phenyl carbamoyl group, may be substituted by 1 to 3 groups selected from the group consisting of a halogen atom, a halogen-substituted or unsubstituted C1-6 alkyl group, and a halogen-substituted or unsubstituted C1-6 alkoxy group);
H28) phenylcarbamoyl group (which may be substituted on the phenyl ring by 1 to 3 groups selected from the group consisting of a halogen atom, a dimethylamino group, a carboxyl group, a C1-6 alkoxycarbonyl group, a halogen-substituted or unsubstituted C1-6 alkyl group, a halogen-substituted or unsubstituted C1-6 alkoxy group, a 4-methyl-1-piperazinyl group, and a morpholino group);
H29) benzylcarbamoyl group (which may be substituted on the phenyl ring by at least one group selected from the group consisting of a halogen-substituted or unsubstituted C1-6 alkyl group and a halogen-substituted or unsubstituted C1-6 alkoxy group); or
H30) 4-substituted-1-piperazinylcarbonyl group, wherein the position-4 is substituted with a tert-butoxycarbonyl group, 4-trifluoromethylbenzyloxycarbonyl group, or 4-trifluoromethylbenzyl group, provided that, in the above general formula (1') when $R^1$ represents a hydrogen atom and $R^2$ represents a group represented by the above general formula (A'), then $R^3$ cannot be an isopropyl group; when $R^1$ represents a hydrogen atom, $R^2$ represents a group represented by the above general formula (E'), and m is 0, then $R^{11}$ cannot be a hydrogen atom; and further, when $R^1$ represents a hydrogen atom and $R^2$ represents a group represented by the above general formula (F'), then it is not possible that $R^{19}$ represents a hydrogen atom and $R^{20}$ represents a tert-butoxycarbonyl group.

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (A).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (B).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (C).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (D).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (G).

The present invention provides 2,3-dihydro-6-nitroimidazo[2,1-b]oxazole compound, optically active form thereof, or pharmaceutically acceptable salt thereof according to the above general formula (1), wherein $R^1$ and $-(CH_2)_n R^2$ may bind to each other together with carbon atoms adjacent thereto through nitrogen atoms, so as to form a spiro ring represented by general formula (H).

The present invention provides 2,3-dihydro-6-nitroimidazo[2,1-b]oxazole compound, optically active form thereof, or pharmaceutically acceptable salt thereof according to the above general formula (1), wherein n is 0 and $R^2$ represents a group represented by any one of the formula (A) to (G) or $R^1$ and $-(CH_2)_n R^2$ may bind to each other together with carbon atoms adjacent thereto through nitrogen atoms, so as to form a spiro ring represented by general formula (H).

The present invention provides 2,3-dihydro-6-nitroimidazo[2,1-b]oxazole compound, optically active form thereof, or pharmaceutically acceptable salt thereof according to the above general formula (1), wherein n represents an integer of 1 to 6 and $R^2$ represents a group represented by any one of the formula (A) to (G) or $R^1$ and $-(CH_2)_n R^2$ may bind to each other together with carbon atoms adjacent thereto through nitrogen atoms, so as to form a spiro ring represented by general formula (H).

The present invention provides 2,3-dihydro-6-nitroimidazo[2,1-b]oxazole compound, optically active form thereof, or pharmaceutically acceptable salt thereof according to the above general formula (1), wherein $R^1$ represents a hydrogen atom and $R^2$ represents a group represented by any one of the formula (A) to (G) or $R^1$ and $-(CH_2)_n R^2$ may bind to each other together with carbon atoms adjacent thereto through nitrogen atoms, so as to form a spiro ring represented by general formula (H).

The present invention provides 2,3-dihydro-6-nitroimidazo[2,1-b]oxazole compound, optically active form thereof, or pharmaceutically acceptable salt thereof according to the above general formula (1), wherein $R^1$ represents a C1-6 alkyl group and $R^2$ represents a group represented by any one of the formula (A) to (G) or $R^1$ and $-(CH_2)_n R^2$ may bind to each other together with carbon atoms adjacent thereto through nitrogen atoms, so as to form a spiro ring represented by general formula (H).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E) and $R^{11}$ represents any one of (E1) to (E3).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E) and $R^{11}$ represents (E4).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E) and $R^{11}$ represents any one of (E5) to (E9).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E) and $R^{11}$ represents (E10).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E) and $R^{11}$ represents (E11).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E) and $R^{11}$ represents (E12).

The present invention provides 2,3-dihydro-6-nitroimidazo[2,1-b]oxazole compound, optically active form thereof, or pharmaceutically acceptable salt thereof according to the above general formula, wherein $R^2$ represents a group represented by general formula (E) and $R^{11}$ represents (E13).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E) and $R^{11}$ represents any one of (E14) to (E17) and (E19) to (E22).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E) and $R^{11}$ represents (E18).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F) and $R^{19}$ and $R^{20}$ each identically or differently represent any one of (F1) to (F11).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F) and $R^{19}$ and $R^{20}$, together with nitrogen atoms adjacent thereto, form a heterocyclic ring shown in any one of (F12-3) to (F12-10) and (F13) directly or through other hetero atoms or carbon atoms.

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F) and $R^{19}$ and $R^{20}$, together with nitrogen atoms adjacent thereto, form a heterocyclic ring shown in (F12-1) directly or through other hetero atoms or carbon atoms.

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F) and $R^{19}$ and $R^{20}$, together with nitrogen atoms adjacent thereto, form a heterocyclic ring shown in (F12-2) directly or through other hetero atoms or carbon atoms.

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E), $R^{11}$ represents (E10), and o is 0.

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E), $R^{11}$ represents (E10), o is 1, and W represents a group —CO—.

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E), $R^{11}$ represents (E10), o is 1, and W represents a C1-6 alkylene group.

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E), $R^{11}$ represents (E10), and $R^{14}$ is any one of (Eaa1) to (Eaa2) and (Eaa4) to (Eaa27).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E), $R^{11}$ represents (E10), and $R^{14}$ is (Eaa3).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (E), $R^{11}$ represents (E11), and o is 0.

The present invention provides 2,3-dihydro-6-nitroimidazo[2,1-b]oxazole compound, optically active form thereof, or pharmaceutically acceptable salt thereof according to the above general formula (1), wherein R represents a group represented by general formula (E), $R^{11}$ represents (E11), and o is 1.

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F), $R^{19}$ and $R^{20}$, together with nitrogen atoms adjacent thereto, form a heterocyclic ring shown in (F12-2) directly or through other hetero atoms or carbon atoms and $R^{26}$ is any one of (Fd1) to (Fd35), (Fd37) and (Fd39).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F), $R^{19}$ and $R^{20}$, together with nitrogen atoms adjacent thereto, form a heterocyclic ring shown in (F12-2) directly or through other hetero atoms or carbon atoms and $R^{26}$ is (Fd36).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F), $R^{19}$ and $R^{20}$, together with nitrogen atoms adjacent thereto, form a heterocyclic ring shown in (F12-2) directly or through other hetero atoms or carbon atoms and $R^{26}$ is (Fd38).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F), $R^{19}$ and $R^{20}$, together with nitrogen atoms adjacent thereto, form a heterocyclic ring shown in (F12-2) directly or through other hetero atoms or carbon atoms, $R^{26}$ is (Fd36) and $R^{27}$ is any one of (Fda1) to (Fda5) and (Fda7) to (Fda34).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F), $R^{19}$ and $R^{20}$, together with nitrogen atoms adjacent thereto, form a heterocyclic ring shown in (F12-2) directly or through other hetero atoms or carbon atoms, $R^{26}$ is (Fd36) and $R^{27}$ is (Fda6).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F), $R^{19}$ and $R^{20}$, together with nitrogen atoms adjacent thereto, form a heterocyclic ring shown in (F12-2) directly or through other hetero atoms or carbon atoms, $R^{26}$ is (Fd38) and $R^{35}$ is any one of (Ff1) to (Ff3), (Ff5) to (Ff7), and (Ff9) to (Ff26).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F), $R^{19}$ and $R^{20}$, together with nitrogen atoms adjacent thereto, form a heterocyclic ring shown in (F12-2) directly or through other hetero atoms or carbon atoms, $R^{26}$ is (Fd38) and $R^{35}$ is (Ff4).

The present invention provides 2,3-dihydro-6-nitroimidazo[2,1-b]oxazole compound, optically active form thereof, or pharmaceutically acceptable salt thereof according to the above general formula (1), wherein $R^2$ represents a group represented by general formula (F), $R^{19}$ and $R^{20}$, together with nitrogen atoms adjacent thereto, form a heterocyclic ring shown in (F12-2) directly or through other hetero atoms or carbon atoms, $R^{26}$ is (Fd38) and $R^{35}$ is (Ff8).

In the compounds represented by general formula (1) or (1') of the present invention, particularly preferred are as follows:

3-(4-Trifluoromethylphenyl)-2-propenyl 4-(2-methyl-6-nitro-2,3-dihydroimidazo[2,1-b]oxazol-2-ylmethyl)piperazin-1-carboxylate, 3-(4-trifluoromethylphenyl)-2-propenyl (S)-4-(2-methyl-6-nitro-2,3-dihydroimidazo[2,1-b]oxazol-2-ylmethyl)-piperazin-1-carboxyate, 3-(4-trifluoromethylphenyl)-2-propenyl (R)-4-(2-methyl-6-nitro-2,3-dihydroimidazo[2,1-b]oxazol-2-ylmethyl)-piperazin-1-carboxylate, 2-methyl-6-nitro-2-{4-[4-(4-trifluoromethoxyphenoxy)-piperidin-1-yl]phenoxymethyl}-2,3-dihydroimidazo[2,1-b]oxazole, (S)-2-methyl-6-nitro-2-{4-[4-(4-trifluoromethoxyphenoxy) piperidin-1-yl]phenoxymethyl}-2,3-dihydroimidazo[2,1-b]oxazole, (R)-2-methyl-6-nitro-2-{4-[4-(4-trifluoromethoxyphenoxy) piperidin-1-yl]phenoxymethyl}-2,3-dihydroimidazo[2,1-b]oxazole, 2-methyl-6-nitro-2-{4-[1-(4-trifluoromethoxybenzyl)-piperidin-4-yl]phenoxymethyl}-2,3-dihydroimidazo[2,1-b]oxazole, (S)-2-methyl-6-nitro-2-{4-[1-(4-trifluoromethoxybenzyl)piperidin-4-yl]phenoxymethyl}-2,3-dihydroimidazo[2,1-b]oxazole, (R)-2-methyl-6-nitro-2-{4-[1-(4-trifluoromethoxybenzyl) piperidin-4-yl]phenoxymethyl}-2,3-dihydroimidazo[2,1-b]oxazole, 6-nitro-2-{4-[4-(4-trifluoromethoxyphenoxy)piperidin-1-yl]phenoxymethyl}-2,3-dihydroimidazo[2,1-b]oxazole, (S)-6-nitro-2-{4-[4-(4-trifluoromethoxyphenoxy)-piperidin-1-yl]phenoxymethyl}-2,3-dihydroimidazo[2,1-b]oxazole, (R)-6-nitro-2-{4-[4-(4-trifluoromethoxyphenoxy)-piperidin-1-yl]phenoxymethyl}-2,3-dihydroimidazo[2,1-b]oxazole, 2-methyl-6-nitro-2-{4-[3-(4-trifluoromethoxyphenoxy)-8-azabicyclo[3.2.1]octan-8-yl]phenoxymethyl}-2,3-dihydroimidazo[2,1-b]oxazole, (S)-2-methyl-6-nitro-2-{4-[3-(4-trifluoromethoxyphenoxy)-8-azabicyclo[3.2.1]octan-8-yl]phenoxymethyl}-2,3-dihydroimidazo[2,1-b]oxazole, (R)-2-methyl-6-nitro-2-{4-[3-(4-trifluoromethoxyphenoxy)-8-azabicyclo[3.2.1]octan-8-yl]phenoxymethyl}-2,3-dihydroimidazo[2,1-b]oxazole, (R)-2-methyl-6-nitro-2-{4-[3-(4-trifluoromethoxyphenoxy)-8-azabicyclo[3.2.1]octan-8-yl]phenoxymethyl}-2,3-dihydroimidazo[2,1-b]oxazole 4-toluene sulfonate, 2-methyl-6-nitro-2-[4-(4-trifluoromethylbenzylideneamino)piperazin-1-yl]-2,3-dihydroimidazo[2,1-b]oxazole, (S)-2-methyl-6-nitro-2-[4-(4-trifluoromethylbenzylideneamino)piperazin-1-yl]-2,3-dihydroimidazo-[2,1-b]oxazole, (R)-2-methyl-6-nitro-2-[4-(4-trifluoromethylbenzylideneamino)piperazin-1-yl]-2,3-dihydroimidazo-[2,1-b]oxazole, 2-[4-(5-chlorobenzofuran-2-ylmethyleneamino)piperazin-1-yl]-2-methyl-6-nitro-2,3-dihydroimidazo[2,1-b]oxazole, (S)-2-[4-(5-chlorobenzofuran-2-ylmethyleneamino)-piperazin-1-yl]-2-methyl-6-nitro-2,3-dihydroimidazo-[2,1-b]oxazole, (R)-2-[4-(5-chlorobenzofuran-2-ylmethyleneamino)-piperazin-1-yl]-2-methyl-6-nitro-2,3-dihydroimidazo-[2,1-b]oxazole, 2-[4-(5-trifluoromethylbenzofuran-2-ylmethyleneamino)-piperazin-1-yl]-2-methyl-6-nitro-2,3-dihydroimidazo-[2,1-b] oxazole, (S)-2-[4-(5-trifluoromethylbenzofuran-2-ylmethyleneamino)piperazin-1-yl]-2-methyl-6-nitro-2,3-dihydroimidazo[2,1-b]oxazole, (R)-2-[4-(5-trifluoromethylbenzofuran-2-ylmethyleneamino)piperazin-1-yl]-2-methyl-6-nitro-2,3-dihydroimidazo[2,1-b]oxazole, 2-methyl-6-nitro-2-{4-[4-(4-trifluoromethylbenzyl)-piperazin-1-yl]phenoxymethyl}-2,3-dihydroimidazo[2,1-b]oxazole, (S)-2-methyl-6-nitro-2-{4-[4-(4-trifluoromethylbenzyl)piperazin-1-yl]phenoxymethyl}-2,3-dihydroimidazo[2,1-b] oxazole, (R)-2-methyl-6-nitro-2-{4-[4-(4-trifluoromethylbenzyl)piperazin-1-yl]phenoxymethyl}-2,3-dihydroimidazo[2,1-b] oxazole, 2-methyl-6-nitro-2-{4-[4-(4-trifluoromethoxybenzyl)-piperazin-1-yl]phenoxymethyl}-2,3-dihydroimidazo[2,1-b] oxazole, (S)-2-methyl-6-nitro-2-{4-[4-(4-trifluoromethoxybenzyl) piperazin-1-yl]phenoxymethyl}-2,3-dihydroimidazo[2,1-b]oxazole, (R)-2-methyl-6-nitro-2-{4-[4-(4-trifluoromethoxybenzyl) piperazin-1-yl]phenoxymethyl}-2,3-dihydroimidazo[2,1-b]oxazole, 2-methyl-6-nitro-2-[4-(4-trifluoromethylphenoxy)-piperidin-1-ylmethyl]-2,3-dihydroimidazo[2,1-b]oxazole, (S)-2-methyl-6-nitro-2-[4-(4-trifluoromethylphenoxy)-piperidin-1-ylmethyl]-2,3-dihydroimidazo[2,1-b]oxazole, (R)-2-methyl-6-nitro-2-[4-(4-trifluoromethylphenoxy)piperidin-1-ylmethyl]-2,3-dihydroimidazo[2,1-b]oxazole, 2-[4-(4-trifluoromethoxyphenyl)piperazin-1-ylmethyl]-2-methyl-6-nitro-2,3-dihydroimidazo[2,1-b]oxazole, (S)-2-[4-(4-trifluoromethoxyphenyl)piperazin-1-ylmethyl]-2-methyl-6-nitro-2,3-dihydroimidazo[2,1-b]oxazole, (R)-2-[4-(4-trifluoromethoxyphenyl)piperazin-1-ylmethyl]-2-methyl-6-nitro-2,3-dihydroimidazo[2,1-b]oxazole, 2-[4-(4-chlorophenyl)piperazin-1-ylmethyl]-2-methyl-6-nitro-2,3-dihydroimidazo[2,1-b]oxazole, (S)-2-[4-(4-chlorophenyl)piperazin-1-ylmethyl]-2-methyl-6-nitro-2,3-dihydroimidazo[2,1-b]oxazole, (R)-2-[4-(4-chlorophenyl)piperazin-1-ylmethyl]-2-methyl-6-nitro-2,3-dihydroimidazo[2,1-b]oxazole, 2-methyl-6-nitro-2-[4-(4'-trifluoromethylbiphenyl-4-ylmethyl)piperazin-1-ylmethyl]-2,3-dihydroimidazo[2,1-b] oxazole, (S)-2-methyl-6-nitro-2-[4-(4'-trifluoromethylbiphenyl-4-ylmethyl)piperazin-1-ylmethyl]-2,3-dihydroimidazo-[2,1-b]oxazole, (R)-2-methyl-6-nitro-2-[4-(4'-trifluoromethylbiphenyl-4-ylmethyl)piperazin-1-ylmethyl]-2,3-dihydroimidazo[2,1-b] oxazole, 2-methyl-6-nitro-2-{4-[4-(4-trifluoromethylphenyl)-piperazin-1-yl]phenoxymethyl}-2,3-dihydroimidazo[2,1-b]oxazole, (S)-2-methyl-6-nitro-2-{4-[4-(4-trifluoromethylphenyl)-piperazin-1-yl]phenoxymethyl}-2,3-dihydroimidazo[2,1-b]oxazole, (R)-2-methyl-6-nitro-2-{4-[4-(4-trifluoromethylphenyl)-piperazin-1-yl]phenoxymethyl}-2,3-dihydroimidazo[2,1-b]oxazole, 2-methyl-6-nitro-2-{4-[4-(4-chlorobenzyl)piperazin-1-yl] phenoxymethyl)-2,3-dihydroimidazo[2,1-b]oxazole, (S)-2-methyl-6-nitro-2-{4-[4-(4-chlorobenzyl)piperazin-1-yl]phenoxymethyl}-2,3-dihydroimidazo[2,1-b]oxazole, (R)-2-methyl-6-nitro-2-{4-[4-(4-chlorobenzyl)piperazin-1-yl]phenoxymethyl}-2,3-dihydroimidazo[2,1-b]oxazole,
2-methyl-6-nitro-2-{4-[4-(4-chlorophenyl)piperazin-1-yl]phenoxymethyl}-2,3-dihydroimidazo[2,1-b]oxazole,
(S)-2-methyl-6-nitro-2-{4-[4-(4-chlorophenyl)piperazin-1-yl]phenoxymethyl}-2,3-dihydroimidazo[2,1-b]oxazole,
(R)-2-methyl-6-nitro-2-{4-[4-(4-chlorophenyl)piperazin-1-yl]phenoxymethyl}-2,3-dihydroimidazo[2,1-b]oxazole,
2-methyl-6-nitro-2-{4-[4-(4-trifluoromethoxybenzylcarbonyl)piperazin-1-yl]phenoxymethyl}-2,3-dihydroimidazo[2,1-b]oxazole,
(S)-2-methyl-6-nitro-2-{4-[4-(4-trifluoromethoxybenzyloxycarbonyl)piperazin-1-yl]phenoxymethyl}-2,3-dihydroimidazo[2,1-b]oxazole,
(R)-2-methyl-6-nitro-2-{4-[4-(4-trifluoromethoxybenzyloxycarbonyl)piperazin-1-yl]phenoxymethyl}-2,3-dihydroimidazo[2,1-b]oxazole,
2-methyl-6-nitro-2-{4-[4-(3,4-dichlorobenzyloxycarbonyl)piperazin-1-yl]phenoxymethyl}-2,3-dihydroimidazo[2,1-b]oxazole,
(S)-2-methyl-6-nitro-2-{4-[4-(3,4-dichlorobenzyloxycarbonyl)piperazin-1-yl]phenoxymethyl}-2,3-dihydroimidazo[2,1-b]oxazole,
(R)-2-methyl-6-nitro-2-{4-[4-(3,4-dichlorobenzyloxycarbonyl)piperazin-1-yl]phenoxymethyl}-2,3-dihydroimidazo[2,1-b]oxazole,
2-methyl-6-nitro-2-[4-(4-trifluoromethoxyphenoxy)-piperidin-1-ylmethyl]-2,3-dihydroimidazo[2,1-b]oxazole,
(S)-2-methyl-6-nitro-2-[4-(4-trifluoromethoxyphenoxy)-piperidin-1-ylmethyl]-2,3-dihydroimidazo[2,1-b]oxazole,
(R)-2-methyl-6-nitro-2-[4-(4-trifluoromethoxyphenoxy)-piperidin-1-ylmethyl]-2,3-dihydroimidazo[2,1-b]oxazole,
2-methyl-6-nitro-2-[4-(4-trifluoromethylphenyl)-piperazin-1-ylmethyl]-2,3-dihydroimidazo[2,1-b]oxazole,
(S)-2-methyl-6-nitro-2-[4-(4-trifluoromethylphenyl)-piperazin-1-ylmethyl]-2,3-dihydroimidazo[2,1-b]oxazole,
(R)-2-methyl-6-nitro-2-[4-(4-trifluoromethylphenyl)-piperazin-1-ylmethyl]-2,3-dihydroimidazo[2,1-b]oxazole,
2-methyl-6-nitro-2-[4-(5-trifluoromethoxylbenzofuran-2-ylmethyleneamino)piperazin-1-ylmethyl]-2,3-dihydroimidazo[2,1-b]oxazole,
(S)-2-methyl-6-nitro-2-[4-(5-trifluoromethoxylbenzofuran-2-ylmethyleneamino)piperazin-1-ylmethyl]-2,3-dihydroimidazo[2,1-b]oxazole,
(R)-2-methyl-6-nitro-2-[4-(5-trifluoromethoxylbenzofuran-2-ylmethyleneamino)piperazin-1-ylmethyl]-2,3-dihydroimidazo[2,1-b]oxazole,
2-methyl-6-nitro-2-[4-(5-trifluoromethylbenzofuran-2-ylmethyleneamino)piperazin-1-ylmethyl]-2,3-dihydroimidazo[2,1-b]oxazole,
(S)-2-methyl-6-nitro-2-[4-(5-trifluoromethylbenzofuran-2-ylmethyleneamino)piperazin-1-ylmethyl]-2,3-dihydroimidazo[2,1-b]oxazole,
(R)-2-methyl-6-nitro-2-[4-(5-trifluoromethylbenzofuran-2-ylmethyleneamino)piperazin-1-ylmethyl]-2,3-dihydroimidazo[2,1-b]oxazole,
2-methyl-6-nitro-2-{4-[4-(4-chlorophenoxy)piperidin-1-yl]phenoxymethyl}-2,3-dihydroimidazo[2,1-b]oxazole,
(S)-2-methyl-6-nitro-2-{4-[4-(4-chlorophenoxy)-piperidin-1-yl]phenoxymethyl}-2,3-dihydroimidazo[2,1-b]oxazole,
(R)-2-methyl-6-nitro-2-{4-[4-(4-chlorophenoxy)-piperidin-1-yl]phenoxymethyl}-2,3-dihydroimidazo[2,1-b]oxazole,
2-methyl-6-nitro-2-{4-[4-(4-trifluoromethylphenoxy)-piperidin-1-yl]phenoxymethyl}-2,3-dihydroimidazo[2,1-b]oxazole,
(S)-2-methyl-6-nitro-2-{4-[4-(4-trifluoromethylphenoxy)piperidin-1-yl]phenoxymethyl}-2,3-dihydroimidazo[2,1-b]oxazole,
(R)-2-methyl-6-nitro-2-{4-[4-(4-trifluoromethylphenoxy)piperidin-1-yl]phenoxymethyl}-2,3-dihydroimidazo[2,1-b]oxazole,
2-methyl-6-nitro-2-{4-[1-(4-chlorobenzyl)piperidin-4-yl]phenoxymethyl}-2,3-dihydroimidazo[2,1-b]oxazole,
(S)-2-methyl-6-nitro-2-{4-[1-(4-chlorobenzyl)piperidin-4-yl]phenoxymethyl}-2,3-dihydroimidazo[2,1-b]oxazole, or
(R)-2-methyl-6-nitro-2-{4-[1-(4-chlorobenzyl)piperidin-4-yl]phenoxymethyl}-2,3-dihydroimidazo[2,1-b]oxazole.

The present invention provides a pharmaceutical composition which is an antitubercular agent comprising, as an active ingredient, the 2,3-dihydro-6-nitroimidazo[2,1-b]oxazole compound, optically active form thereof, or pharmacologically acceptable salt thereof represented by general formula (1) or (1').

In particular, the present invention provides a pharmaceutical composition which is an antitubercular agent comprising, as an active ingredient, at least one compound selected from the 2,3-dihydro-6-nitroimidazo-[2,1-b]oxazole compounds that are preferred compound listed above.

The present invention provides a method for producing a compound represented by the following general formula (1a):

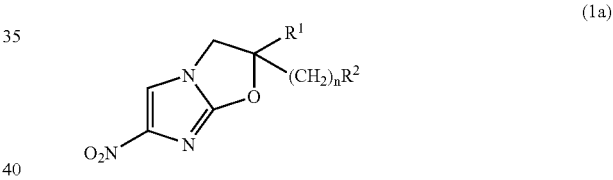

wherein $R^1$, $R^2$ and n are defined as the same as in claim 1, said production method comprising: the reaction of a 4-nitroimidazole compound represented by the following general formula (2):

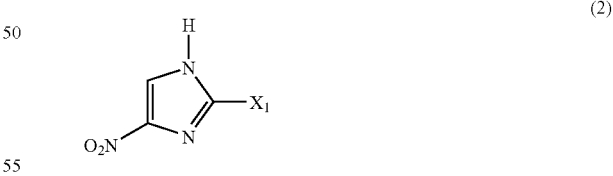

wherein $X_1$ represents a halogen atom or nitro group, with an epoxy compound represented by the following general formula (3a):

wherein $R^1$, $R^2$ and n are defined as the same as in claim 1, so as to obtain a compound represented by the following general formula (4a):

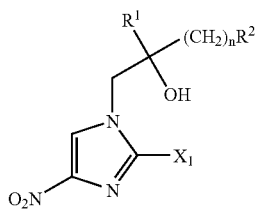

(4a)

wherein $R^1$, $R^2$ and n are defined as the same as in claim 1, and $X_1$ represents a halogen atom or nitro group; and the following ring closure of the obtained compound represented by the above general formula (4a).

The present invention provides a method for producing a compound represented by the following general formula (1b):

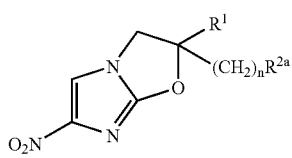

(1b)

wherein $R^1$ is as defined in claim 1, and $R^{2a}$ represents a group represented by the general formula (A), (B), (E) or (F) according to claim 1, said production method comprising: the reaction of a compound represented by the following general formula (3b):

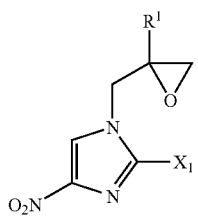

(3b)

wherein $R^1$ is as defined in claim 1, and $X_1$ represents a halogen atom or nitro group, with a compound (5) represented by the following general formula $R^{2a}H$ (5) or a salt thereof, wherein $R^{2a}$ represents the group represented by the general formula (A), (B), (E) or (F) according to claim 1, so as to obtain a compound represented by the following general formula (4b):

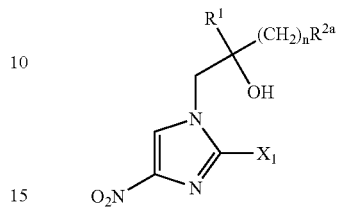

(4b)

wherein $R^1$ is as defined in claim 1, $R^{2a}$ represents the group represented by the general formula (A), (B), (E) or (F) according to claim 1, and $X_1$ represents a halogen atom or nitro group; and the following ring closure of the obtained compound represented by the above general formula (4b).

The present invention provides a method for producing a compound represented by the following general formula (1c):

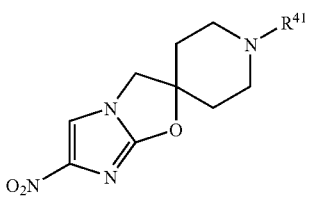

(1c)

wherein $R^{41}$ is as defined in claim 1, said production method comprising: the reaction of a compound represented by the following general formula (2):

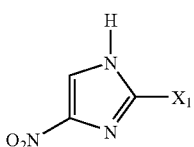

(2)

wherein $X_1$ represents a halogen atom or nitro group, with a compound represented by the following general formula (3c):

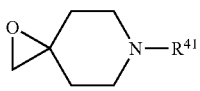

(3c)

wherein R⁴¹ is as defined in claim 1, so as to obtain a compound represented by the following general formula (4c):

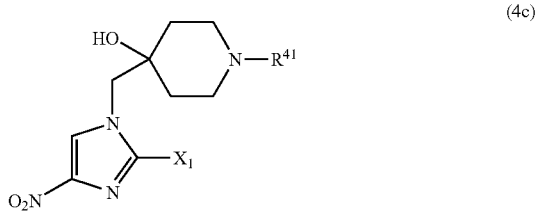

wherein R⁴¹ is as defined in claim 1, and $X_1$ represents a halogen atom or nitro group; and the following ring closure of the obtained compound represented by the above general formula (4c).

BEST MODE FOR CARRYING OUT THE INVENTION

In this specification, each group represented by $R^1$, $R^2$, $R^3$ or the like is specifically as follows:

Examples of halogen atoms are, for example, fluorine atom, chlorine atom, bromine atom and iodine atom.

A C1-6 alkyl group is a straight or branched alkyl group containing 1 to 6 carbon atoms, examples of which include a methyl group, ethyl group, n-propyl group, isopropyl group, n-butyl group, isobutyl group, tert-butyl group, sec-butyl group, n-pentyl group, neopentyl group, n-hexyl group, isohexyl group, 3-methylpentyl group or the like.

A C1-6 alkylene group is a straight or branched alkylene group containing 1 to 6 carbon atoms, examples of which include a methylene group, ethylene group, trimethylene group, 2-methyltrimethylene group, 2,2-dimethyltrimethylene group, 1-methyltrimethylene group, methylmethylene group, ethylmethylene group, tetramethylene group, pentamethylene group, hexamethylene group or the like.

A C1-6 alkoxy group is a group containing a C1-6 alkyl group, as defined above, and an oxygen atom, examples of which include a methoxy group, ethoxy group, n-propoxy group, isopropoxy group, n-butoxy group, isobutoxy group, tert-butoxy group, sec-butoxy group, n-pentoxy group, neopentoxy group, n-hexyloxy group, isohexyloxy group, 3-methylpentoxy group or the like.

A C1-6 alkoxy-C1-6 alkyl group is a group containing a C1-6 alkyl group and C1-6 alkoxy group described above, examples of which include a methoxymethyl group, 2-methoxyethyl group, 3-methoxypropyl group, 4-methoxybutyl group, 5-methoxypentyl group, 6-methoxyhexyl group, ethoxymethyl group, 2-ethoxyethyl group, 3-ethoxypropyl group, 2-isopropoxyethyl group, tert-butoxymethyl group, 2-(tert-butoxy)ethyl group, 3-(tert-butoxy)propyl group, 6-(tert-butoxy)hexyl group, 4-(tert-butoxy)butyl group or the like.

A halogen-substituted or unsubstituted C1-6 alkyl group is a straight or branched alkyl group containing 1 to 6 carbon atoms, as defined above, and optionally substituted by 1 to 7 halogen atoms, examples of which include a methyl group, ethyl group, n-propyl group, isopropyl group, n-butyl group, isobutyl group, tert-butyl group, sec-butyl group, n-pentyl group, neopentyl group, n-hexyl group, isohexyl group, 3-methylpentyl group, fluoromethyl group, difluoromethyl group, trifluoromethyl group, chloromethyl group, dichloromethyl group, trichloromethyl group, bromomethyl group, dibromomethyl group, dichlorofluoromethyl group, 2,2,2-trifluoroethyl group, pentafluoroethyl group, 2-chloroethyl group, 3,3,3-trifluoropropyl group, heptafluoropropyl group, heptafluoroisopropyl group, 3-chloropropyl group, 2-chloropropyl group, 3-bromopropyl group, 4,4,4-trifluorobutyl group, 4,4,4,3,3-pentafluorobutyl group, 4-chlorobutyl group, 4-bromobutyl group, 2-chlorobutyl group, 5,5,5-trifluoropentyl group, 5-chloropentyl group, 6,6,6-trifluorohexyl group, 6-chlorohexyl group or the like.

A halogen-substituted or unsubstituted C1-6 alkoxy group is a C1-6 alkoxy group, as defined above, and an alkoxy group substituted by 1 to 7 halogen atoms, examples of which include a methoxy group, ethoxy group, n-propoxy group, isopropoxy group, n-butoxy group, isobutoxy group, tert-butoxy group, sec-butoxy group, n-pentoxy group, neopentoxy group, n-hexyloxy group, isohexyloxy group, 3-methylpentoxy group, fluoromethoxy group, difluoromethoxy group, trifluoromethoxy group, chloromethoxy group, dichloromethoxy group, trichloromethoxy group, bromomethoxy group, dibromomethoxy group, dichlorofluoromethoxy group, 2,2,2-trifluoroethoxy group, pentafluoroethoxy group, 2-chloroethoxy group, 3,3,3-trifluoropropoxy group, heptafluoropropoxy group, heptafluoroisopropoxy group, 3-chloropropoxy group, 2-chloropropoxy group, 3-bromopropoxy group, 4,4,4-trifluorobutoxy group, 4,4,4,3,3-pentafluorobutoxy group, 4-chlorobutoxy group, 4-bromobutoxy group, 2-chlorobutoxy group, 5,5,5-trifluoropentoxy group, 5-chloropentoxy group, 6,6,6-trifluorohexyloxy group, 6-chlorohexyloxy group or the like.

Examples of a phenyl C1-6 alkyl group (which may be substituted on the phenyl ring by at least one group selected from a group consisting of a phenyl C1-6 alkoxy group; a halogen-substituted or unsubstituted C1-6 alkyl group; a halogen-substituted or unsubstituted C1-6 alkoxy group; and phenoxy group which may have at least one halogen-substituted or unsubstituted C1-6 alkoxy group as a substituent on the phenyl ring) include a phenyl C1-6 alkyl group (which may be substituted on the phenyl ring by 1 to 3 groups selected from a group consisting of a phenyl C1-6 alkoxy group, a halogen-substituted or unsubstituted C1-6 alkyl group, a halogen-substituted or unsubstituted C1-6 alkoxy group, and a phenoxy group which may have 1 to 3 a halogen-substituted or unsubstituted C1-6 alkoxy groups as a substituent on the phenyl ring), for example, a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-benzyloxybenzyl group, 3-benzyloxybenzyl group, 4-benzyloxybenzyl group, 2,4-dibenzyloxybenzyl group, 2,4,6-tribenzyloxybenzyl group, 2-(2-phenethyloxy)benzyl group, 3-(2-phenethyloxy)benzyl group, 4-(2-phenethyloxy) benzyl group, 2-(3-phenylpropoxy)benzyl group, 3-(3-phenylpropoxy)benzyl group, 4-(3-phenylpropoxy)benzyl group, 2-(4-phenylbutoxy)benzyl group, 3-(4-phenylbutoxy)benzyl group, 4-(4-phenylbutoxy)benzyl group, 2-(5-phenylpentyloxy)benzyl group, 3-(5-phenylpentyloxy)benzyl group, 4-(5-phenylpentyloxy)benzyl group, 2-(6-phenylhexyloxy)benzyl group, 3-(6-phenylhexyloxy)benzyl group, 4-(6-phenylhexyloxy)benzyl group, 2-methybenzyl group, 2,3-dimethybenzyl group, 3,4-dimethybenzyl group, 3,5-dimethybenzyl group, 2,6-dimethybenzyl group, 2,4-dimethybenzyl group, 2,5-dimethybehzyl group, 2,4,6-trimethybenzyl group, 3,5-ditrifluoromethylbenzyl group, 2,4,6-trifluoromethylbenzyl group, 2-trifluoromethylbenzyl group, 3-trifluoromethylbenzyl group, 4-trifluoromethylbenzyl group, 2-trifluoromethoxybenzyl group, 3-trifluoromethoxybenzyl group, 4-trifluoromethoxybenzyl group, 3-methoxybenzyl group, 2,3-dimethoxybenzyl group, 3,4-dimethoxybenzyl group, 3,5-dimethoxybenzyl group, 2,6-dimethoxybenzyl group, 2,4-dimethoxybenzyl group, 2,5-dimethoxybenzyl group, 2,4,6-trimethoxybenzyl group, 2,6-ditrifluoromethoxybenzyl group, 2,3,4-trifluoromethoxybenzyl group, 1-(4-benzyloxyphenyl)ethyl group, 1-(3-benzyloxyphenyl)ethyl group, 1-(2-benzyloxyphenyl)ethyl group, 1-(2-trifluoromethylphenyl)ethyl group, 1-(3-trifluoromethylphenyl)ethyl group, 1-(4-trifluoromethylphenyl)ethyl group, 1-(2-trifluoromethoxyphenyl)ethyl group, 1-(3-trifluoromethoxyphenyl)ethyl group, 1-(4-trifluoromethoxyphenyl)ethyl group, 2-(4-benzyloxyphenyl)ethyl group, 2-(3-benzyloxyphenyl)ethyl group, 2-(2-benzyloxyphenyl)ethyl group, 2-(2-trifluoromethylphenyl)ethyl group, 2- (3-trifluoromethylphenyl)ethyl group, 2-(4-trifluoromethylphenyl)ethyl group, 2-(2-trifluoromethoxyphenyl)ethyl group, 2-(3-trifluoromethoxyphenyl)ethyl group, 2-(4-trifluoromethoxyphenyl)ethyl group, 3-(4-benzyloxyphenyl)propyl group, 3-(3-benzyloxyphenyl)propyl group, 3-(2-benzyloxyphenyl)propyl group, 3-(2-trifluoromethylphenyl)propyl group, 3-(3-trifluoromethylphenyl)propyl group, 3-(4-trifluoromethylphenyl)propyl group, 3-(2-trifluoromethoxyphenyl)propyl group, 3-(3-trifluoromethoxyphenyl)propyl group, 3-(4-trifluoromethoxyphenyl)propyl group, 4-(3-trifluoromethylphenyl)butyl group, 5-(4-trifluoromethylphenyl)pentyl group, 4-(4-trifluoromethylphenyl)pentyl group, 4-(4-trifluoromethoxyphenyl)pentyl group, 6-(3-trifluoromethylphenyl)hexyl group, 6-(4-trifluoromethylphenyl)hexyl group, 6-(4-trifluoromethoxyphenyl)hexyl group, 2-phenoxybenzyl group, 3-phenoxybenzyl group, 4-phenoxybenzyl group, 2,5-diphenoxybenzyl group, 2,4,6-triphenoxybenzyl group, 1-(4-phenoxyphenyl)ethyl group, 1-(3-phenoxyphenyl)ethyl group, 1-(2-phenoxyphenyl)ethyl group, 3-(4-phenoxyphenyl)propyl group, 3-(3-phenoxyphenyl)propyl group, 3-(2-phenoxyphenyl)propyl group, 2-(4-trifluoromethoxyphenoxy)benzyl group, 3-(4-trifluoromethoxyphenoxy)benzyl group, 4-(4-trifluoromethoxyphenoxy)benzyl group, 1-(4-(4-trifluoromethoxyphenoxy)phenyl)ethyl group, 1-(3-(4-trifluoromethoxyphenoxy)phenyl)ethyl group, 1-(2-(4-trifluoromethoxyphenoxy)phenyl)ethyl group, 3-(4-(4-trifluoromethoxyphenoxy)phenyl)propyl group, 3-(3-(4-trifluoromethoxyphenoxy)phenyl)propyl group, 3-(2-(4-trifluoromethoxyphenoxy)phenyl)propyl group, 2-trifluoromethyl-3-trifluoromethoxybenzyl group, 2-benzyloxy-3-trifluoromethoxybenzyl group, 3-phenoxy-4-trifluoromethylbenzyl group or the like.

Examples of a biphenylyl C1-6 alkyl group include the phenyl C1-6 alkyl group (which may be substituted on the phenyl ring by 1 to 3 groups selected from a group consisting of a phenyl C1-6 alkoxy group, a halogen-substituted or unsubstituted C1-6 alkyl group, a halogen-substituted or unsubstituted C1-6 alkoxy group and a phenoxy group which may have at least one halogen-substituted or unsubstituted C1-6 alkoxy group as a substituent on the phenyl ring), for example, a 2-biphenylylmethyl group, 2-(2-biphenylyl)ethyl group, 3-(2-biphenylyl)propyl group, 4-(2-biphenylyl)butyl group, 5-(2-biphenylyl)pentyl group, 6-(2-biphenylyl)hexyl group, 3-biphenylylmethyl group, 2-(3-biphenylyl)ethyl group, 3-(3-biphenylyl)propyl group, 4-(3-biphenylyl)butyl group, 5-(3-biphenylyl)pentyl group, 6-(3-biphenylyl)hexyl group, 4-biphenylylmethyl group, 2-(4-biphenylyl)ethyl group, 3-(4-biphenylyl)propyl group, 4-(4-biphenylyl)butyl group, 5-(4-biphenylyl)pentyl group, 6-(4-biphenylyl)hexyl group or the like.

A phenyl C2-6 alkenyl group is a group containing a phenyl group and an alkenyl group having 2 to 6 carbon atoms and 1 to 3 double bonds. These groups may be either in trans or cis form and both forms are included as a matter of course. For example, included is a 3-phenyl-2-propenyl group (trivial name: cinnamyl group), 4-phenyl-2-butenyl group, 4-phenyl-3-butenyl group, 5-phenyl-4-pentenyl group, 5-phenyl-3-pentenyl group, 6-phenyl-5-hexenyl group, 6-phenyl-4-hexenyl group, 6-phenyl-3-hexenyl group, 4-phenyl-1,3-butadienyl group, 6-phenyl-1,3,5-hexatrienyl group or the like.

A C1-6 alkylsulfonyl group is a group containing an alkyl group containing 1 to 6 carbon atoms and a sulfonyl group, examples of which include a methanesulfonyl group, ethanesulfonyl group, propanesulfonyl group, butanesulfonyl group, pentanesulfonyl group, hexanesulfonyl group or the like.

Examples of a benzene sulfonyl group which may be substituted by a C1-6 alkyl group include a benzenesulfonyl group which may be substituted by 1 to 3 C1-6 alkyl groups, for example, a benzene sulfonyl group, o-toluenesulfonyl group, m-toluenesulfonyl group, p-toluenesulfonyl group, 2-ethylbenzenesulfonyl group, 3-ethylbenzenesulfonyl group, 4-ethylbenzenesulfonyl group, 2-propylbenzenesulfonyl group, 3-propylbenzenesulfonyl group, 4-propylbenzenesulfonyl group, 2,3-dimethylbenzenesulfonyl group, 2,4-dimethylbenzenesulfonyl group, 2,4,6-trimethylbenzenesulfonyl group or the like.

A C1-6 alkanoyl group is a group derived from an aliphatic carboxylic acid containing 1 to 6 carbon atoms, examples of which include a formyl group, acetyl group, propionyl group, butyryl group, pentanoyl group, hexanoyl group or the like.

A C1-6 alkoxycarbonyl group is a group containing a C1-6 alkoxy group, as defined above, and a carbonyl group, examples of which include a methoxycarbonyl group, ethoxycarbonyl group, propoxycarbonyl group, isopropoxycarbonyl group, n-butoxycarbonyl group, isobutoxycarbonyl group, tert-butoxycarbonyl group, sec-butoxycarbonyl group, n-pentoxycarbonyl group, neopentoxycarbonyl group, n-hexyloxycarbonyl group, isohexyloxycarbonyl group, 3-methylpentoxycarbonyl group or the like.

A phenyl C1-6 alkoxycarbonyl group (which may be substituted on the phenyl ring by at least one group selected from a group consisting of a phenyl C1-6 alkoxy group, a halogen-substituted or unsubstituted C1-6 alkyl group, and a halogen-substituted or unsubstituted C1-6 alkoxy group) is a group containing a phenyl C1-6 alkoxy group which may be substituted on the phenyl ring, as defined above, by 1 to 3 groups selected from a group consisting of a phenyl C1-6 alkoxy group, a halogen-substituted or unsubstituted C1-6 alkyl group, and a halogen-substituted or unsubstituted C1-6 alkoxy group and a carbonyl group, examples of which include a benzyloxycarbonyl group, 1-phenylethoxycarbonyl group, 2-phenylethoxycarbonyl group, 3-phenylpropoxycarbonyl group, 2-phenylpropoxycarbonyl group, 4-phenylbutoxycarbonyl group, 5-phenylpentoxycarbonyl group, 4-phenylpentoxycarbonyl group, 6-phenylhexyloxycarbonyl group, 2-benzyloxybenzyloxycarbonyl group, 3-benzyloxybenzyloxycarbonyl group, 4-benzyloxybenzyloxycarbonyl group, 2,4-dibenzyloxybenzyloxycarbonyl group, 3,4,5-benzyloxybenzyloxycarbonyl group, 2-trifluoromethylbenzyloxycarbonyl group, 2-methybenzyloxycarbonyl group, 3-methybenzyloxycarbonyl group, 4-methybenzyloxycarbonyl group, 2,6-dimethybenzyloxycarbonyl group, 2,4,6-trimethybenzyloxycarbonyl group, 2,3-ditrifluoromethylbenzyloxycarbonyl group, 2,4,6-tri(trifluoromethyl)benzyloxycarbonyl group, 2-methoxybenzyloxycarbonyl group, 3-methoxybenzyloxycarbonyl group, 4-methoxybenzyloxycarbonyl group, 2,4-dimethoxybenzyloxycarbonyl group, 3,4,5-trimethoxybenzyloxycarbonyl group, 2,5-ditrifluoromethoxybenzyloxycarbonyl group, 2,4,6-tri(trifluoromethoxy)benzyloxycarbonyl group, 3-trifluoromethylbenzyloxycarbonyl group, 4-trifluoromethylbenzyloxycarbonyl group, 2-trifluoromethoxybenzyloxycarbonyl group, 3-trifluoromethoxybenzyloxycarbonyl group, 4-trifluoromethoxybenzyloxycarbonyl group, 2-(2-trifluoromethylphenyl)ethoxycarbonyl group, 2-(3-trifluoromethylphenyl)ethoxycarbonyl group, 2-(4-trifluoromethylphenyl)ethoxycarbonyl group, 2-(2-trifluoromethoxyphenyl)ethoxycarbonyl group, 2-(3-trifluoromethoxyphenyl)ethoxycarbonyl group, 2-(4-trifluoromethoxyphenyl)ethoxycarbonyl group, 3-(4-benzyloxyphenyl)propoxycarbonyl group, 3-(3-benzyloxyphenyl)propoxycarbonyl group, 3-(2-benzyloxyphenyl)propoxycarbonyl group, 3-(2-trifluoromethylphenyl)propoxycarbonyl group, 3-(3-trifluoromethylphenyl)propoxycarbonyl group, 3-(4-trifluoromethylphenyl)propoxycarbonyl group, 3-(2-trifluoromethoxyphenyl)propoxycarbonyl group, 3-(3-trifluoromethoxyphenyl)propoxycarbonyl group, 3-(4-trifluoromethoxyphenyl)propoxycarbonyl group, 4-(3-benzyloxyphenyl)butoxycarbonyl group, 4-(4-benzyloxyphenyl)butoxycarbonyl group, 4-(3-trifluoromethylphenyl)butoxycarbonyl group, 4-(4-trifluoromethylphenyl)butoxycarbonyl group, 5-(3-benzyloxyphenyl)pentoxycarbonyl group, 5-(4-benzyloxyphenyl)pentoxycarbonyl group, 5-(4-trifluoromethylphenyl)pentoxycarbonyl group, 4-(4-trifluoromethylphenyl)pentoxycarbonyl group, 4-(4-trifluoromethoxyphenyl)pentoxycarbonyl group, 6-(3-benzyloxyphenyl)hexyloxycarbonyl group, 6-(4-benzyloxyphenyl)hexyloxycarbonyl group, 6-[3-(2-phenethyloxy)phenyl]hexyloxycarbonyl group, 6-[4-(2-phenethyloxy)phenyl]hexyloxycarbonyl group, 6-[3-(3-phenylpropoxy)phenyl]hexyloxycarbonyl group, 6-[4-(4-phenylbutoxy)phenyl]hexyloxycarbonyl group, 6-[4-(5-phenylpentyloxy)phenyl]hexyloxycarbonyl group, 6-[4-(6-phenylhexyloxy)phenyl]hexyloxycarbonyl group, 6-(3-trifluoromethylphenyl)hexyloxycarbonyl group, 6-(4-trifluoromethylphenyl)hexyloxycarbonyl group, 6-(4-trifluoromethoxyphenyl)hexyloxycarbonyl group, 2-trifluoromethyl-4-benzyloxybenzyloxycarbonyl group, 3-trifluoromethoxy-5-benzyloxybenzyloxycarbonyl group, 2-trifluoromethyl-3-trifluoromethoxybenzyloxycarbonyl group or the like.

Examples of a phenyl C1-6 alkyl group (which may be substituted on the phenyl ring by at least one group selected from a group consisting of a phenyl C1-6 alkoxy group, halogen-substituted or unsubstituted C1-6 alkyl group and halogen-substituted or unsubstituted C1-6 alkoxy group) include a phenyl C1-6 alkyl group (which may be substituted on the phenyl ring by 1 to 3 groups selected from a group consisting of a phenyl C1-6 alkoxy group, halogen-substituted or unsubstituted C1-6 alkyl group and halogen-substituted or unsubstituted C1-6 alkoxy group), for example, a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-benzyloxybenzyl group, 3-benzyloxybenzyl group, 4-benzyloxybenzyl group, 2,4-dibenzyloxybenzyl group, 2,4,6-tribenzyloxybenzyl group, 2-(2-phenethyloxy)benzyl group, 3-(2-phenethyloxy)benzyl group, 4-(2-phenethyloxy)benzyl group, 2-(3-phenylpropoxy)benzyl group, 3-(3-phenylpropoxy)benzyl group, 4-(3-phenylpropoxy)benzyl group, 2-(4-phenylbutoxy)benzyl group, 3-(4-phenylbutoxy)benzyl group, 4-(4-phenylbutoxy)benzyl group, 2-(5-phenylpentyloxy)benzyl group, 3-(5-phenylpentyloxy)benzyl group, 4-(5-phenylpentyloxy)-benzyl group, 2-(6-phenylhexyloxy)benzyl group, 3-(6-phenylhexyloxy)benzyl group, 4-(6-phenylhexyloxy)benzyl group, 2-methybenzyl group, 2,3-dimethybenzyl group, 3,4-dimethybenzyl group, 3,5-dimethybenzyl group, 2,6-dimethybenzyl group, 2,4-dimethybenzyl group, 2,5-dimethybenzyl group, 2,4,6-trimethybenzyl group, 3,5-ditrifluoromethylbenzyl group, 2,4,6-trifluoromethylbenzyl group, 2-trifluoromethylbenzyl group, 3-trifluoromethylbenzyl group, 4-trifluoromethylbenzyl group, 2-trifluoromethoxybenzyl group, 3-trifluoromethoxybenzyl group, 4-trifluoromethoxybenzyl group, 3-methoxybenzyl group, 2,3-dimethoxybenzyl group, 3,4-dimethoxybenzyl group, 3,5-dimethoxybenzyl group, 2,6-dimethoxybenzyl group, 2,4-dimethoxybenzyl group, 2,5-dimethoxybenzyl group, 2,4,6-trimethoxybenzyl group, 2,6-ditrifluoromethoxybenzyl group, 2,3,4-trifluoromethoxybenzyl group, 1-(4-benzyloxyphenyl)ethyl group, 1-(3-benzyloxyphenyl)ethyl group, 1-(2-benzyloxyphenyl)ethyl group, 1-(2-trifluoromethylphenyl)ethyl group, 1-(3-trifluoromethylphenyl)ethyl group, 1-(4-trifluoromethylphenyl)ethyl group, 1-(2-trifluoromethoxyphenyl)ethyl group, 1-(3-trifluoromethoxyphenyl)ethyl group, 1-(4-trifluoromethoxyphenyl)ethyl group, 2-(4-benzyloxyphenyl)ethyl group, 2-(3-benzyloxyphenyl)ethyl group, 2-(2-benzyloxyphenyl)ethyl group, 2-(2-trifluoromethylphenyl)ethyl group, 2-(3-trifluoromethylphenyl)ethyl group, 2-(4-trifluoromethylphenyl)ethyl group, 2-(2-trifluoromethoxyphenyl)ethyl group, 2-(3-trifluoromethoxyphenyl)ethyl group, 2-(4-trifluoromethoxyphenyl)ethyl group, 3-(4-benzyloxyphenyl)propyl group, 3-(3-benzyloxyphenyl)propyl group, 3-(2-benzyloxyphenyl)propyl group, 3-(2-trifluoromethylphenyl)propyl group, 3-(3-trifluoromethylphenyl)propyl group, 3-(4-trifluoromethylphenyl)propyl group, 3-(2-trifluoromethylphenyl)propyl group, 3-(3-trifluoromethoxyphenyl)propyl group, 3-(4-trifluoromethoxyphenyl)propyl group, 4-(3-trifluoromethylphenyl)butyl group, 5-(4-trifluoromethylphenyl)pentyl group, 4-(4-trifluoromethylphenyl)pentyl group, 4-(4-trifluoromethoxyphenyl)pentyl group, 6-(3-trifluoromethylphenyl)hexyl group, 6-(4-trifluoromethylphenyl)hexyl group, $^6$-(4-trifluoromethoxyphenyl)hexyl group, 2-trifluoromethyl-3-trifluoromethoxybenzyl group, $^2$-benzyloxy-3-trifluoromethoxybenzyl group, 3-phenoxy-4-trifluoromethylbenzyl group or the like.

A biphenylyl C1-6 alkoxycarbonyl group includes, for example, a 2-biphenylylmethoxycarbonyl group, 2-(2-biphenylyl)ethoxycarbonyl group, 3-(2-biphenylyl)propoxycarbonyl group, 4-(2-biphenylyl)butoxycarbonyl group, 5-(2-biphenylyl)pentoxycarbonyl group, 6-(2-biphenylyl)hexyloxycarbonyl group, 3-biphenylylmethoxycarbonyl group, 2-(3-biphenylyl)ethoxycarbonyl group, 3-(3-biphenylyl)propoxycarbonyl group, 4-(3-biphenylyl)butoxycarbonyl group, 5-(3-biphenylyl)pentoxycarbonyl group, 6-(3-biphenylyl)hexyloxycarbonyl group, 4-biphenylylmethoxycarbonyl group, 2-(4-biphenylyl)ethoxycarbonyl group, 3-(4-biphenylyl)propoxycarbonyl group, 4-(4-biphenylyl)butoxycarbonyl group, 5-(4-biphenylyl)pentoxycarbonyl group, 6-(4-biphenylyl)hexyloxycarbonyl group or the like.

Examples of a benzoxazolyl C1-6 alkyl group (which may be substituted on the benzoxazole ring by at least one oxo group as a substituent) include, for example, a benzoxazol-2-ylmethyl group, benzoxazol-4-ylmethyl group, benzoxazol-5-ylmethyl group, benzoxazol-6-ylmethyl group, benzoxazol-7-ylmethyl group, 2-(benzoxazol-4-yl)ethyl group, 1-(benzoxazol-5-yl)ethyl group, 3-(benzoxazol-6-yl)propyl group, 4-(benzoxazol-7-yl)butyl group, 5-(benzoxazol-2-yl)pentyl group, 6-(benzoxazol-4-yl)hexyl group, 2-methyl-3-(benzoxazol-5-yl)propyl group, 1,1-dimethyl-2-(benzoxazol-2-yl)ethyl group, (2,3-dihydro-2-oxo-benzoxazol-3-yl)methyl group, (2,3-dihydro-2-oxo-benzoxazol-4-yl)methyl group, (2,3-dihydro-2-oxo-benzoxazol-5-yl)methyl group, (2,3-dihydro-2-oxo-benzoxazol-6-yl)methyl group, (2,3-dihydro-2-oxo-benzoxazol-7-yl)methyl group, 2-(benzoxazol-6-yl)ethyl group, 2-(benzoxazol-7-yl)ethyl group, 2-(2,3-dihydro-2-oxo-benzoxazol-3-yl)ethyl group, 2-(2,3-dihydro-2-oxo-benzoxazol-4-yl)ethyl group, 2-(2,3-dihydro-2-oxo-benzoxazol-5-yl)ethyl group, 2-(2,3-dihydro-2-oxo-benzoxazol-6-yl)ethyl group, 2-(2,3-dihydro-2-oxo-benzoxazol-7-yl)ethyl group, 3-(benzoxazol-2-yl)propyl group, 3-(benzoxazol-4-yl)propyl group, 3-(benzoxazol-5-yl)propyl group, 3-(benzoxazol-7-yl)propyl group, 3-(2,3-dihydro-2-oxo-benzoxazol-3-yl)propyl group, 3-(2,3-dihydro-2-oxo-benzoxazol-4-yl)propyl group, 3-(2,3-dihydro-2-oxo-benzoxazol-5-yl)propyl group, 3-(2,3-dihydro-2-oxo-benzoxazol-6-yl)propyl group, 3-(2,3-dihydro-2-oxo-benzoxazol-7-yl)propyl group, 4-(benzoxazol-2-yl)butyl group, 4-(benzoxazol-4-yl)butyl group, 4-(benzoxazol-5-yl)butyl group, 4-(benzoxazol-6-yl)butyl group, 4-(2,3-dihydro-2-oxo-benzoxazol-3-yl)butyl group, 4-(2,3-dihydro-2-oxo-benzoxazol-4-yl)butyl group, 4-(2,3-dihydro-2-oxo-benzoxazol-5-yl)butyl group, 4-(2,3-dihydro-2-oxo-benzoxazol-6-yl)butyl group, 4-(2,3-dihydro-2-oxo-benzoxazol-7-yl)butyl group, 5-(benzoxazol-4-yl)pentyl group, 5-(benzoxazol-5-yl)pentyl group, 5-(benzoxazol-6-yl)pentyl group, 5-(benzoxazol-7-yl)pentyl group, 5-(2,3-dihydro-2-oxo-benzoxazol-3-yl)pentyl group, 5-(2,3-dihydro-2-oxo-benzoxazol-4-yl)pentyl group, 5-(2,3-dihydro-2-oxo-benzoxazol-5-yl)pentyl group, 5-(2,3-dihydro-2-oxo-benzoxazol-6-yl)pentyl group, 5-(2,3-dihydro-2-oxo-benzoxazol-7-yl)pentyl group, 6-(benzoxazol-2-yl)hexyl group, 6-(benzoxazol-5-yl)hexyl group, 6-(benzoxazol-6-yl)hexyl group, 6-(benzoxazol-7-yl)hexyl group, 6-(2,3-dihydro-2-oxo-benzoxazol-3-yl)hexyl group, 6-(2,3-dihydro-2-oxo-benzoxazol-4-yl)hexyl group, 6-(2,3-dihydro-2-oxo-benzoxazol-5-yl)hexyl group, 6-(2,3-dihydro-2-oxo-benzoxazol-6-yl)hexyl group, 6-(2,3-dihydro-2-oxo-benzoxazol-7-yl)hexyl group or the like.

A benzoxazolyl group includes, for example, a benzoxazol-2-yl group, benzoxazol-4-yl group, benzoxazol-5-yl group, benzoxazol-6-yl group, benzoxazol-7-yl group or the like.

Examples of an oxazolyl C1-6 alkyl group (which may be substituted on the oxazole ring by at least one group selected from a group consisting of a phenyl group and a C1-6 alkyl group as a substituent) include an oxazolyl C1-6 alkyl group (which may be substituted on the oxazole ring by 1 to 3 groups selected from a group consisting of a phenyl group and a C1-6 alkyl group as a substituent), for example, an oxazol-2-ylmethyl group, oxazol-4-ylmethyl group, oxazol-5-ylmethyl group, 2-(oxazol-2-yl)ethyl group, 1-(oxazol-4-yl)ethyl group, 3-(oxazol-5-yl)propyl group, 4-(oxazol-2-yl)butyl group, 5-(oxazol-4-yl)pentyl group, 6-(oxazol-5-yl)hexyl group, 2-methyl-3-(oxazol-2-yl)propyl group, 1,1-dimethyl-2-(oxazol-5-yl)ethyl group, (4-methyloxazol-2-yl)methyl group, (5-methyloxazol-2-yl)methyl group, (4-ethyloxazol-2-yl)methyl group, (5-ethyloxazol-2-yl)methyl group, (4-n-propyloxazol-2-yl)methyl group, (5-n-propyloxazol-2-yl)methyl group, (4-n-butyloxazol-2-yl)methyl group, (5-n-butyloxazol-2-yl)methyl group, (4-n-pentyloxazol-2-yl)methyl group, (5-n-pentyloxazol-2-yl)methyl group, (4-n-hexyloxazol-2-yl)methyl group, (5-n-hexyloxazol-2-yl)methyl group, 2-(oxazol-4-yl)ethyl group, 2-(oxazol-5-yl)ethyl group, 2-(4-methyloxazol-2-yl)ethyl group, 2-(5-methyloxazol-2-yl)ethyl group, 2-(4-ethyloxazol-2-yl)ethyl group, 2-(5-ethyloxazol-2-yl)ethyl group, 2-(4-n-propyloxazol-2-yl)ethyl group, 2-(5-n-propyloxazol-2-yl)ethyl group, 2-(4-n-butyloxazol-2-yl)ethyl group, 2-(5-n-butyloxazol-2-yl)ethyl group, 2-(4-n-pentyloxazol-2-yl)ethyl group, 2-(5-n-pentyloxazol-2-yl)ethyl group, 2-(4-n-hexyloxazol-2-yl)ethyl group, 2-(5-n-hexyloxazol-2-yl)ethyl group, 3-(oxazol-2-yl)propyl group, 3-(oxazol-4-yl)propyl group, 3-(4-methyloxazol-2-yl)propyl group, 3-(5-methyloxazol-2-yl)propyl group, 3-(4-ethyloxazol-2-yl)propyl group, 3-(5-ethyloxazol-2-yl)propyl group, 3-(4-n-propyloxazol-2-yl)propyl group, 3-(5-n-propyloxazol-2-yl)propyl group, 3-(4-n-butyloxazol-2-yl)propyl group, 3-(5-n-butyloxazol-2-yl)propyl group, 3-(4-n-pentyloxazol-2-yl)propyl group, 3-(5-n-pentyloxazol-2-yl)propyl group, 3-(4-n-hexyloxazol-2-yl)propyl group, 3-(5-n-hexyloxazol-2-yl)propyl group, 4-(oxazol-4-yl)butyl group, 4-(oxazol-5-yl)butyl group, 4-(4-methyloxazol-2-yl)butyl group, 4-(5-methyloxazol-2-yl)butyl group, 4-(4-ethyloxazol-2-yl)butyl group, 4-(5-ethyloxazol-2-yl)butyl group, 4-(4-n-propyloxazol-2-yl)butyl group, 4-(5-n-propyloxazol-2-yl)butyl group, 4-(4-n-butyloxazol-2-yl)butyl group, 4-(5-n-butyloxazol-2-yl)butyl group, 4-(4-n-pentyloxazol-2-yl)butyl group, 4-(5-n-pentyloxazol-2-yl)butyl group, 4-(4-n-hexyloxazol-2-yl)butyl group, 4-(5-n-hexyloxazol-2-yl)butyl group, 5-(oxazol-2-yl)pentyl group, 5-(oxazol-5-yl)pentyl group, 6-(oxazol-2-yl)hexyl group, 6-(oxazol-4-yl)hexyl group, (5-phenyloxazol-2-yl)methyl group, (2-phenyloxazol-4-yl)methyl group, (2-phenyloxazol-5-yl)methyl group, 2-(5-phenyloxazol-2-yl)ethyl group, 2-(2-phenyloxazol-4-yl)ethyl group, 2-(2-phenyloxazol-5-yl)ethyl group, 3-(5-phenyloxazol-2-yl)propyl group, 3-(2-phenyloxazol-4-yl)propyl group, 3-(2-phenyloxazol-5-yl)propyl group, 4-(5-phenyloxazol-2-yl)butyl group, 4-(2-phenyloxazol-4-yl)butyl group, 4-(2-phenyloxazol-5-yl)butyl group, 5-(5-phenyloxazol-2-yl)pentyl group, 5-(2-phenyloxazol-4-yl)pentyl group, 5-(2-phenyloxazol-5-yl)pentyl group, (2-phenyl-4-methyloxazol-5-yl)methyl group, (2,4-dimethyloxazol-5-yl)methyl group, (2,5-diphenyloxazol-4-yl)methyl group or the like.

Examples of a tetrazolyl group (which may be substituted on the tetrazole ring by a phenyl group which may have C1-6 alkyl group(s) or halogen atom(s) as a substituent) include a tetrazolyl group (which may be substituted on the tetrazole ring by a phenyl group which may have 1 to 3 C1-6 alkyl groups or halogen atoms as substituent(s)), for example, a 5-(1H)-tetrazolyl group, 1-methyl-5-(1H)-tetrazolyl group, 1-ethyl-5-(1H)-tetrazolyl group, 1-n-propyl-5-(1H)-tetrazolyl group, 1-isopropyl-5-(1H)-tetrazolyl group, 1-n-butyl-5-(1H)-tetrazolyl group, 1-(2-methylpropyl)-5-(1H)-tetrazolyl group, 1-n-pentyl-5-(1H)-tetrazolyl group, 1-n-hexyl-5-(1H)-tetrazolyl group, 1-phenyl-5-(1H)-tetrazolyl group, 1-(4-chlorophenyl)-5-(1H)-tetrazolyl group, 1-(4-fluorophenyl)-5-(1H)-tetrazolyl group, 1-(4-bromophenyl)-5-(1H)-tetrazolyl group, 1-(3,4-difluorophenyl)-5-(1H)-tetrazolyl group, 1-(3,4-dichlorophenyl)-5-(1H)-tetrazolyl group, 1-(3,4,5-trichlorophenyl)-5-(1H)-tetrazolyl group or the like.

A C1-8 alkyl group is a straight or branched alkyl group containing 1 to 8 carbon atoms, examples of which include a methyl group, ethyl group, n-propyl group, isopropyl group, n-butyl group, isobutyl group, tert-butyl group, sec-group, n-pentyl group, neopentyl group, n-hexyl group, isohexyl group, 3-methylpentyl group, n-heptyl group, 6-methylheptyl group, n-octyl group, 3,5-dimethylhexyl group or the like.

Examples of a C1-6 alkyl group substituted by halogen atom(s) include a C1-6 alkyl group substituted by 1 to 7 halogens, for example, a fluoromethyl group, difluoromethyl group, trifluoromethyl group, chloromethyl group, dichloromethyl group, trichloromethyl group, bromomethyl group, dibromomethyl group, dichlorofluoromethyl group, 2,2,2-trifluoroethyl group, pentafluoroethyl group, 2-chloroethyl group, 3,3,3-trifluoropropyl group, heptafluoropropyl group, heptafluoroisopropyl group, 3-chloropropyl group, 2-chloropropyl group, 3-bromopropyl group, 4,4,4-trifluorobutyl group, 4,4,4,3,3-pentafluorobutyl group, 4-chlorobutyl group, 4-bromobutyl group, 2-chlorobutyl group, 5,5,5-trifluoropentyl group, 5-chloropentyl group, 6,6,6-trifluorohexyl group, 6-chlorohexyl group or the like.

A C1-6 alkoxycarbonyl-C1-6 alkyl group is a C1-6 alkyl group defined above substituted by the C1-6 alkoxycarbonyl group defined above, examples of which include a methoxycarbonylmethyl group, ethoxycarbonylmethyl group, propoxycarbonylmethyl group, isopropoxycarbonylmethyl group, n-butoxycarbonylmethyl group, tert-butoxycarbonylmethyl group, pentoxycarbonylmethyl group, n-hexyloxycarbonylmethyl group, 2-(methoxycarbonyl)ethyl group, 2-(ethoxycarbonyl)ethyl group, 2-(1-propoxycarbonyl)ethyl group, 2-(isopropoxycarbonyl)ethyl group, 2-(n-butoxycarbonyl)ethyl group, 2-(tert-butoxycarbonyl)ethyl group, 2-(2-pentoxycarbonyl)ethyl group, 2-(n-hexyloxycarbonyl)ethyl group, 3-(methoxycarbonyl)propyl group, 3-(ethoxycarbonyl)propyl group, 3-(1-propoxycarbonyl)propyl group, 3-(isopropoxycarbonyl)propyl group, 3-(n-butoxycarbonyl)propyl group, 3-(tert-butoxycarbonyl)propyl group, 3-(3-pentoxycarbonyl)propyl group, 3-(n-hexyloxycarbonyl)-propyl group, 4-(methoxycarbonyl)butyl group, 4-(ethoxycarbonyl)butyl group, 4-(1-propoxycarbonyl)butyl group, 4-(isopropoxycarbonyl)butyl group, 4-(n-butoxycarbonyl)butyl group, 4-(tert-butoxycarbonyl)-butyl group, 5-(methoxycarbonyl)pentyl group, 5-(ethoxycarbonyl)pentyl group, 5-(propoxycarbonyl)pentyl group, 5-(isopropoxycarbonyl)pentyl group, 5-(n-butoxycarbonyl)pentyl group, 5-(tert-butoxycarbonyl)-pentyl group, 6-(methoxycarbonyl)hexyl group, 6-(ethoxycarbonyl)hexyl group, 6-(propoxycarbonyl)hexyl group, 6-(isopropoxycarbonyl)hexyl group, 6-(n-butoxycarbonyl)hexyl group, 6-(tert-butoxycarbonyl)-hexyl group or the like.

A C3-8 cycloalkyl group is a 3-membered, 4-membered, 5-membered, 6-membered, 7-membered or 8-membered cyclic alkyl group containing 3 to 8 carbon atoms, examples of which include a cyclopropyl group, cyclobutyl group, cyclopentyl group, cyclohexyl group, cycloheptyl group, cyclooctyl group, 3,4-dimethylcyclopentyl group, 3,3-dimethylcyclohexyl group or the like.

A phenyl C1-6 alkyl group (which may be substituted on the phenyl ring by at least one group selected from a group consisting of a halogen atom, a halogen-substituted or unsubstituted C1-6 alkyl group or a halogen-substituted or unsubstituted C1-6 alkoxy group) is a phenyl C1-6 alkyl group unsubstituted or substituted on the phenyl ring by 1 to 5 groups, preferably 1 to 3 groups selected from a group consisting of a halogen atom, a halogen-substituted or unsubstituted C1-6 alkyl group and a halogen-substituted or unsubstituted C1-6 alkoxy group, examples of which include a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2,3-difluorobenzyl group, 3,4-difluorobenzyl group, 3,5-difluorobenzyl group, 2,4-difluorobenzyl group, 2,6-difluorobenzyl group, 2,3-dichlorobenzyl group, 3,4-dichlorobenzyl group, 3,5-dichlorobenzyl group, 2,4-dichlorobenzyl group, 2,6-dichlorobenzyl group, 2-fluoro-4-bromobenzyl group, 4-chloro-3-fluorobenzyl group, 2,3,4-trichlorobenzyl group, 3,4,5-trifluorobenzyl group, 2,4,6-trichlorobenzyl group, 4-isopropylbenzyl group, 4-n-butylbenzyl group, 4-methylbenzyl group, 2-methylbenzyl group, 3-methylbenzyl group, 2,4-dimethylbenzyl group, 2,3-dimethylbenzyl group, 2,6-dimethylbenzyl group, 3,5-dimethylbenzyl group, 2,5-dimethylbenzyl group, 2,4,6-trimethylbenzyl group, 3,5-ditrifluoromethylbenzyl group, 2,3,4,5,6-pentafluorobenzyl group, 4-isopropoxybenzyl group, 4-n-butoxybenzyl group, 4-methoxybenzyl group, 2-methoxybenzyl group, 3-methoxybenzyl group, 2,4-dimethoxybenzyl group, 2,3-dimethoxybenzyl group, 2,6-dimethoxybenzyl group, 3,5-dimethoxybenzyl group, 2,5-dimethoxybenzyl group, 2,4,6-trimethoxybenzyl group, 3,5-ditrifluoromethoxybenzyl group, 2-isopropoxybenzyl group, 3-chloro-4-methoxybenzyl group, 2-chloro-4-trifluoromethoxybenzyl group, 3-methyl-4-fluorobenzyl group, 4-bromo-3-trifluoromethylbenzyl group, 2-trifluoromethylbenzyl group, 3-trifluoromethylbenzyl group, 4-trifluoromethylbenzyl group, 2-pentafluoroethylbenzyl group, 3-pentafluoroethylbenzyl group, 4-pentafluoroethylbenzyl group, 2-trifluoromethoxybenzyl group, 3-trifluoromethoxybenzyl group, 4-trifluoromethoxybenzyl group, 2-pentafluoroethoxybenzyl group, 3-pentafluoroethoxybenzyl group, 4-pentafluoroethoxybenzyl group, 2-(2-trifluoromethylphenyl)ethyl group, 2-(3-trifluoromethylphenyl)ethyl group, 2-(4-trifluoromethylphenyl)-ethyl group, 2-(2-trifluoromethoxyphenyl)ethyl group, 3-(trifluoromethoxyphenyl)ethyl group, 2-(4-trifluoromethoxyphenyl)ethyl group, 2-(2-pentafluoroethoxyphenyl)ethyl group, 2-(3-pentafluoroethoxyphenyl)ethyl group, 2-(4-pentafluoroethoxyphenyl)ethyl group, 3-(2-trifluoromethylphenyl)propyl group, 3-(3-trifluoromethylphenyl)propyl group, 3-(4-trifluoromethylphenyl)propyl group, 3-(2-trifluoromethoxyphenyl)propyl group, 3-(3-trifluoromethoxyphenyl)propyl group, 3-(4-trifluoromethoxyphenyl)propyl group, 3-(3-pentafluoroethoxyphenyl)propyl group, 3-(4-pentafluoroethoxyphenyl)propyl group, 4-(3-pentafluoroethoxyphenyl)butyl group, 5-(4-trifluoromethylphenyl)pentyl group, 4-(4-trifluoromethylphenyl)pentyl group, 4-(4-trifluoromethoxyphenyl)pentyl group, 6-(3-trifluoromethylphenyl)hexyl group, 6-(4-trifluoromethylphenyl)hexyl group, 6-(4-trifluoromethoxyphenyl)hexyl group or the like.

A phenyl group (which may be substituted on the phenyl ring by 1 to 3 groups selected from a group consisting of halogen atom(s), a C1-6 alkyl group substituted or unsubstituted with halogen atom(s), halogen-substituted or unsubstituted C1-6 alkoxy group, C1-6 alkanoyl group, carboxyl group, C1-6 alkoxycarbonyl group, phenyl C1-6 alkoxycarbonyl group, carbamoyl group, C1-6 alkylcarbamoyl group, aminosulfonyl group and morpholino group) includes, for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 3,4,5-trichlorophenyl group, 2,4,6-trifluorophenyl group, 2,4,6-trichlorophenyl group, 2-fluoro-4-bromophenyl group, 4-chloro-3-fluorophenyl group, 2,3,4-trichlorophenyl group, 4-isopropylphenyl group, 4-n-butylphenyl group, 2,4-dimethylphenyl group, 2,3-dimethylphenyl group, 2,6-dimethylphenyl group, 3,5-dimethylphenyl group, 2,5-dimethylphenyl group, 2,4,6-trimethylphenyl group, 3,5-ditrifluoromethylphenyl group, 4-n-butoxyphenyl group, 2,4-dimethoxyphenyl group, 2,3-dimethoxyphenyl group, 2,6-dimethoxyphenyl group, 3,5-dimethoxyphenyl group, 2,5-dimethoxyphenyl group, 3,5-ditrifluoromethoxyphenyl group, 3-chloro-4-methoxyphenyl group, 2-chloro-4-trifluoromethoxyphenyl group, 3-methyl-4-fluorophenyl group, 4-bromo-3-trifluoromethylphenyl group, 2-methylphenyl group, 3-methylphenyl group, 4-methylphenyl group, 2-trifluoromethylphenyl group, 3-trifluoromethylphenyl group, 4-trifluoromethylphenyl group, 2-pentafluoroethylphenyl group, 3-pentafluoroethylphenyl group, 4-pentafluoroethylphenyl group, 2-isopropylphenyl group, 3-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoropropylphenyl group, 4-n-pentylphenyl group, 4-n-hexylphenyl group, 2-methoxyphenyl group, 3-methoxyphenyl group, 4-methoxyphenyl group, 2,3-dimethoxyphenyl group, 3-fluoro-2-methoxyphenyl group, 2-fluoro-3-methoxyphenyl group, 2-chloro-4-methoxyphenyl group, 2,3,4-trimethoxyphenyl group, 3,4,5-trimethoxyphenyl group, 2,4,6-trimethoxyphenyl group, 2-trifluoromethoxyphenyl group, 3-trifluoromethoxyphenyl group, 4-trifluoromethoxyphenyl group, 2-pentafluoroethoxyphenyl group, 3-pentafluoroethoxyphenyl group, 4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropropoxyphenyl group, 3-n-heptafluoropropoxyphenyl group, 4-n-heptafluoropropoxyphenyl group, 4-pentoxyphenyl group, 4-hexyloxyphenyl group, 2-formylphenyl group, 3-formylphenyl group, 4-formylphenyl group, 2-acetylphenyl group, 3-acetylphenyl group, 4-acetylphenyl group, 2-propionylphenyl group, 3-propionylphenyl group, 4-propionylphenyl group, 2-butyrylphenyl group, 3-butyrylphenyl group, 4-butyrylphenyl group, 2-pentanoylphenyl group, 3-pentanoylphenyl group, 4-pentanoylphenyl group, 2-hexanoylphenyl group, 3-hexanoylphenyl group, 4-hexanoylphenyl group, 2-methoxycarbonylphenyl group, 3-methoxycarbonylphenyl group, 4-methoxycarbonylphenyl group, 2-ethoxycarbonylphenyl group, 3-ethoxycarbonylphenyl group, 4-ethoxycarbonylphenyl group, 2-propoxycarbonylphenyl group, 3-propoxycarbonylphenyl group, 4-propoxycarbonylphenyl group, 2-butoxycarbonylphenyl group, 3-butoxycarbonylphenyl group, 4-butoxycarbonylphenyl group, 2-tert-butoxycarbonylphenyl group, 3-tert-butoxycarbonylphenyl group, 4-tert-butoxycarbonylphenyl group, 2-pentoxycarbonylphenyl group, 3-pentoxycarbonylphenyl group, 4-pentoxycarbonylphenyl group, 2-hexyloxycarbonylphenyl group, 3-hexyloxycarbonylphenyl group, 4-hexyloxycarbonylphenyl group, 2-benzyloxycarbonylphenyl group, 3-benzyloxycarbonylphenyl group, 4-benzyloxycarbonylphenyl group, 2-carboxylphenyl group, 3-carboxylphenyl group, 4-carboxylphenyl group, 2-aminosulfonylphenyl group, 3-aminosulfonylphenyl group, 4-aminosulfonylphenyl group, 2-carbamoylphenyl group, 3-carbamoylphenyl group, 4-carbamoylphenyl group, 2-methylcarbamoylphenyl group, 3-methylcarbamoylphenyl group, 4-methylcarbamoylphenyl group, 2-ethylcarbamoylphenyl group, 3-ethylcarbamoylphenyl group, 4-ethylcarbamoylphenyl group, 2-dimethylcarbamoylphenyl group, 3-dimethylcarbamoylphenyl group, 4-dimethylcarbamoylphenyl group, 2-diethylcarbamoylphenyl group, 3-diethylcarbamoylphenyl group, 4-diethylcarbamoylphenyl group, 4-morpholinophenyl group, 3-morpholinophenyl group, 4-morpholinophenyl group or the like.

A C1-6 alkyl carbamoyl group is a group in which one or two hydrogens on the carbamoyl (—CONH$_2$) group are substituted by the C1-6 alkyl group defined above, examples of which include an N-methylcarbamoyl group, N,N-dimethylcarbamoyl group, N-ethylcarbamoyl group, N-n-propylcarbamoyl group, N-isopropylcarbamoyl group, N-n-butylcarbamoyl group, N-tert-butylcarbamoyl group, N-n-pentylcarbamoyl group, N-n-hexylcarbamoyl group, N-methyl-N-ethylcarbamoyl group, N-methyl-N-n-propylcarbamoyl group, N-methyl-N-isopropylcarbamoyl group, N-methyl-N-n-butylcarbamoyl group, N-methyl-N-tert-butylcarbamoyl group, N-methyl-N-n-pentylcarbamoyl group, N-methyl-N-n-hexylcarbamoyl group, N-ethyl-N-isopropylcarbamoyl group, N-ethyl-N-tert-butylcarbamoyl group, N-propyl-N-tert-butylcarbamoyl group, N-isopropyl-N-tert-butylcarbamoyl group or the like.

A phenyl group (which may be substituted on the phenyl ring by at least one group selected from a group consisting of a halogen atom, a halogen-substituted or unsubstituted C1-6 alkyl group and halogen-substituted or unsubstituted C1-6 alkoxy group) is a phenyl group unsubstituted or substituted by 1 to 5, preferably 1 to 3 substituents selected from a group consisting of halogen(s), a halogen-substituted or unsubstituted C1-6 alkyl group and a halogen-substituted or unsubstituted C1-6 alkoxy group as defined above, examples of which include a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 3,4,5-trichlorophenyl group, 2,4,6-trifluorophenyl group, 2,4,6-trichlorophenyl group, 2-fluoro-4-bromophenyl group, 4-chloro-3-fluorophenyl group, 2,3,4-trichlorophenyl group, 2,3,4-trifluorophenyl group, 2,3,4,5,6-pentafluorophenyl group, 2,4,6-trimethylphenyl group, 4-n-butylphenyl group, 2,4-dimethylphenyl group, 2,3-dimethylphenyl group, 2,6-dimethylphenyl group, 3,5-dimethylphenyl group, 2,5-dimethylphenyl group, 3,5-ditrifluoromethylphenyl group, 4-n-butoxyphenyl group, 2,4-dimethoxyphenyl group, 2,3-dimethoxyphenyl group, 2,6-dimethoxyphenyl group, 3,5-dimethoxyphenyl group, 2,5-dimethoxyphenyl group, 2,4,6-trimethoxyphenyl group, 3,5-ditrifluoromethoxyphenyl group, 3-chloro-4-methoxyphenyl group, 2-chloro-4-trifluoromethoxyphenyl group, 3-methyl-4-fluorophenyl group, 4-bromo-3-trifluoromethylphenyl group, 2-methylphenyl group, 3-methylphenyl group, 4-methylphenyl group, 2-methyl-3-chlorophenyl group, 3-methyl-4-chlorophenyl group, 2-chloro-4-methylphenyl group, 2-methyl-3-fluorophenyl group, 2-trifluoromethylphenyl group, 3-trifluoromethylphenyl group, 4-trifluoromethylphenyl group, 2-pentafluoroethylphenyl group, 3-pentafluoroethylphenyl group, 4-pentafluoroethylphenyl group, 2-isopropylphenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoropropylphenyl group, 4-pentylphenyl group, 4-hexylphenyl group, 2-methoxyphenyl group, 3-methoxyphenyl group, 4-methoxyphenyl group, 3-chloro-2-methoxyphenyl group, 2-fluoro-3-methoxyphenyl group, 2-fluoro-4-methoxyphenyl group, 3,4-dimethoxyphenyl group, 2-trifluoromethoxyphenyl group, 3-trifluoromethoxyphenyl group, 4-trifluoromethoxyphenyl group, 3-fluoro-2-trifluoromethoxyphenyl group, 2-fluoro-3-trifluoromethoxyphenyl group, 3-fluoro-4-trifluoromethoxyphenyl group, 3-chloro-2-trifluoromethoxyphenyl group, 2-chloro-3-trifluoromethoxyphenyl group, 3-chloro-4-trifluoromethoxyphenyl group, 2-pentafluoroethoxyphenyl group, 3-pentafluoroethoxyphenyl group, 4-pentafluoroethoxyphenyl group, 3-chloro-2-pentafluoroethoxyphenyl group, 2-chloro-3-pentafluoroethoxyphenyl group, 3-chloro-4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropropoxyphenyl group, 3-n-heptafluoropropoxyphenyl group, 4-n-heptafluoropropoxyphenyl group, 4-n-pentoxyphenyl group, 4-n-hexyloxyphenyl group or the like.

A phenyl C1-6 alkoxycarbonyl group (which may be substituted on the phenyl ring by at least one group selected from a group consisting of halogen atom(s), a halogen-substituted or a unsubstituted C1-6 alkyl group and a halogen-substituted or unsubstituted C1-6 alkoxy group) is a group containing a phenyl C1-6 alkoxy group which may be substituted by 1 to 5, preferably 1 to 3 groups selected from a group consisting of halogen(s), a halogen-substituted or unsubstituted C1-6 alkyl group and halogen-substituted or unsubstituted C1-6 alkoxy group defined above and a carbonyl group, examples of which include a benzyloxycarbonyl group, 2-phenylethoxycarbonyl group, 3-phenylpropoxycarbonyl group, 2-phenylpropoxycarbonyl group, 4-phenylbutoxycarbonyl group, 5-phenylpentoxycarbonyl group, 4-phenylpentoxycarbonyl group, 6-phenylhexyloxycarbonyl group, 2-fluorobenzyloxycarbonyl group, 3-fluorobenzyloxycarbonyl group, 4-fluorobenzyloxycarbonyl group, 2-(2-fluorophenyl)ethoxycarbonyl group, 2-(3-fluorophenyl)ethoxycarbonyl group, 2-(4-fluorophenyl)ethoxycarbonyl group, 2-chlorobenzyloxycarbonyl group, 3-chlorobenzyloxycarbonyl group, 4-chlorobenzyloxycarbonyl group, 2-fluoro-4-bromobenzyloxycarbonyl group, 4-chloro-3-fluorobenzyloxycarbonyl group, 2,3,4-trichlorobenzyloxycarbonyl group, 3,4,5-trifluorobenzyloxycarbonyl group, 2,3,4,5,6-pentafluorobenzyloxycarbonyl group, 2,4,6-trichlorobenzyloxycarbonyl group, 4-isopropoxybenzyloxycarbonyl group, 4-n-butylbenzyloxycarbonyl group, 4-methybenzyloxycarbonyl group, 2-methybenzyloxycarbonyl group, 3-methybenzyloxycarbonyl group, 2,4-dimethybenzyloxycarbonyl group, 2,3-dimethybenzyloxycarbonyl group, 2,6-dimethybenzyloxycarbonyl group, 3,5-dimethybenzyloxycarbonyl group, 2,5-dimethybenzyloxycarbonyl group, 2,4,6-trimethybenzyloxycarbonyl group, 3,5-ditrifluoromethylbenzyloxycarbonyl group, 4-isopropoxybenzyloxycarbonyl group, 4-n-butoxybenzyloxycarbonyl group, 4-methoxybenzyloxycarbonyl group, 2-methoxybenzyloxycarbonyl group, 3-methoxybenzyloxycarbonyl group, 2,4-dimethoxybenzyloxycarbonyl group, 2,3-dimethoxybenzyloxycarbonyl group, 2,6-dimethoxybenzyloxycarbonyl group, 3,5-dimethoxybenzyloxycarbonyl group, 2,5-dimethoxybenzyloxycarbonyl group, 2,4,6-trimethoxybenzyloxycarbonyl group, 3,5-ditrifluoromethoxybenzyloxycarbonyl group, 2-isopropoxybenzyloxycarbonyl group, 3-chloro-4-methoxybenzyloxycarbonyl group, 2-chloro-4-trifluoromethoxybenzyloxycarbonyl group, 3-methyl-4-fluorobenzyloxycarbonyl group, 4-bromo-3-trifluoromethylbenzyloxycarbonyl group, 2-(2-chlorophenyl)ethyloxycarbonyl group, 2-(3-chlorophenyl)ethoxycarbonyl group, 2-(4-chlorophenyl)ethoxycarbonyl group, 2-trifluoromethylbenzyloxycarbonyl group, 3-trifluoromethylbenzyloxycarbonyl group, 4-trifluoromethylbenzyloxycarbonyl group, 2-trifluoromethoxybenzyloxycarbonyl group, 3-trifluoromethoxybenzyloxycarbonyl group, 4-trifluoromethoxybenzyloxycarbonyl group, 2-(2-trifluoromethylphenyl)ethoxycarbonyl group, 2-(3-trifluoromethylphenyl)ethoxycarbonyl group, 2-(4-trifluoromethylphenyl)ethoxycarbonyl group, 2-(2-trifluoromethoxyphenyl)ethoxycarbonyl group, 2-(3-trifluoromethoxyphenyl)ethoxycarbonyl group, 2-(4-trifluoromethoxyphenyl)ethoxycarbonyl group, 3-(2-trifluoromethylphenyl)propoxycarbonyl group, 3-(3-trifluoromethylphenyl)propoxycarbonyl group, 3-(4-trifluoromethylphenyl)propoxycarbonyl group, 3-(2-trifluoromethoxyphenyl)propoxycarbonyl group, 3-(3-trifluoromethoxyphenyl)propoxycarbonyl group, 3-(4-trifluoromethoxyphenyl)propoxycarbonyl group, 4-(3-trifluoromethylphenyl)butoxycarbonyl group, 5-(4-trifluoromethylphenyl)pentoxycarbonyl group, 4-(4-trifluoromethylphenyl)pentoxycarbonyl group, 4-(4-trifluoromethoxyphenyl)pentoxycarbonyl group, 6-(3-trifluoromethylphenyl)hexyloxycarbonyl group, 6-(4-trifluoromethylphenyl)hexyloxycarbonyl group, 6-(4-trifluoromethoxyphenyl)hexyloxycarbonyl group or the like.

A phenyl C3-6 alkenyloxycarbonyl group (which may be substituted on the phenyl ring by at least one halogen-substituted or unsubstituted C1-6 alkyl group) is a group containing a phenyl group unsubstituted or substituted by 1 to 3 groups selected from a group consisting of C1-6 alkyl groups substituted or unsubstituted with halogen(s), an alkenyloxy group having 1 to 3 double bonds comprising 3 to 6 carbons and a carbonyl group. These groups can be a trans-form and cis-form, and both forms are included as a matter of course. The examples include a 3-phenyl-2-propenyloxycarbonyl group (trivial name: cinnamyloxycarbonyl group), 4-phenyl-2-butenyloxycarbonyl group, 4-phenyl-3-butenyloxycarbonyl group, 5-phenyl-2-pentenyloxycarbonyl group, 5-phenyl-4-pentenyloxycarbonyl group, 5-phenyl-3-pentenyloxycarbonyl group, 6-phenyl-5-hexenyloxycarbonyl group, 6-phenyl-4-hexenyloxycarbonyl group, 6-phenyl-3-hexenyloxycarbonyl group, 6-phenyl-3-hexenyloxycarbonyl group, 4-phenyl-1,3- butadienyloxycarbonyl group, 6-phenyl-1,3,5-hexatrienyloxycarbonyl group, 3-(2-methylphenyl)-2-propenyloxycarbonyl group, 3-(3-methylphenyl)-2-propenyloxycarbonyl group, 3-(4-methylphenyl)-2-propenyloxycarbonyl group, 3-(2-trifluoromethylphenyl)-2-propenyloxycarbonyl group, 3-(3-trifluoromethylphenyl)-2-propenyloxycarbonyl group, 3-(4-trifluoromethylphenyl)-2-propenyloxycarbonyl group, 4-(2-trifluoromethylphenyl)-3-butenyloxycarbonyl group, 4-(3-trifluoromethylphenyl)-3-butenyloxycarbonyl group, 4-(4-trifluoromethylphenyl)-3-butenyloxycarbonyl group, 3-(3,5-ditrifluoromethylphenyl)-2-propenyloxycarbonyl group, 3-[2,4,6-tri(trifluoromethyl)phenyl]-2-propenyloxycarbonyl group, 3-(2,4-dimethylphenyl)-2-propenyloxycarbonyl group or the like.

A phenyl C1-6 alkylidene-substituted amino group (which may be substituted by at least one halogen-substituted or unsubstituted C1-6 alkyl group as a substituent) is a C1-6 alkylidene-substituted amino group substituted by a phenyl group which may be substituted by 1 to 3 halogen-substituted or unsubstituted C1-6 alkyl groups, examples of which include a benzylidene amino group, 2-phenylethylidene amino group, 3-phenylpropylidene amino group, 4-phenylbutylidene amino group, 5-phenylpentylidene amino group, 6-phenylhexylidene amino group, 2-methylbenzylidene amino group, 2-trifluoromethylbenzylidene amino group, 3-methylbenzylidene amino group, 3-trifluoromethylbenzylidene amino group, 4-methylbenzylidene amino group, 4-trifluoromethylbenzylidene amino group, 3,4-dimethylbenzylidene amino group, 3,4,5-trimethylbenzylidene amino group, 3,5-ditrifluoromethylbenzylidene amino group or the like.

A phenoxy group (which may be substituted on the phenyl ring by at least one halogen-substituted or unsubstituted C1-6 alkyl group) is a phenoxy group unsubstituted or substituted by 1 to 3 C1-6 alkyl groups substituted or unsubstituted with halogen(s) as defined above, examples of which include a phenoxy group, 2-methylphenoxy group, 3-methylphenoxy group, 4-methylphenoxy group, 2-ethylphenoxy group, 3-ethylphenoxy group, 4-ethylphenoxy group, 4-n-propylphenoxy group, 4-tert-butylphenoxy group, 4-n-butylphenoxy group, 2-trifluoromethylphenoxy group, 3-trifluoromethylphenoxy group, 4-trifluoromethylphenoxy group, 2-pentafluoroethylphenoxy group, 3-pentafluoroethylphenoxy group, 2,3-dimethylphenoxy group, 3,4,5-trimethylphenoxy group, 4-n-pentylphenoxy group, 4-n-hexylphenoxy group, 3,5-ditrifluoromethylphenoxy group or the like.

A phenylamino group (which may be substituted on the phenyl ring by at least one halogen-substituted or unsubstituted C1-6 alkyl group) is a phenylamino group unsubstituted (another name: anilino group) or a phenylamino group substituted by 1 to 3 C1-6 alkyl groups substituted or unsubstituted with halogen(s) defined above, examples of which include a phenylamino group, 2-methylphenylamino group, 3-methylphenylamino group, 4-methylphenylamino group, 2-ethylphenylamino group, 3-ethylphenylamino group, 4-ethylphenylamino group, 4-propylphenylamino group, 4-tert-butylphenylamino group, 4-butylphenylamino group, 2-trifluoromethylphenylamino group, 3-trifluoromethylphenylamino group, 4-trifluoromethylphenylamino group, 2-pentafluoroethylphenylamino group, 3-pentafluoroethylphenylamino group, 2,3-dimethylphenylamino group, 3,4,5-trimethylphenylamino group, 4-n-pentylphenylamino group, 4-n-hexylphenylamino group, 3,5-ditrifluoromethylphenylamino group or the like.

An indolinyl group which may be substituted by at least one halogen atom is an indolinyl group unsubstituted or substituted by 1 to 3 fluorine, chlorine, bromine or iodine atoms at 2, 3, 4, 5, 6 or 7, position, examples of which include a 1-indolinyl group, 2-fluoro-1-indolinyl group, 3-bromo-1-indolinyl group, 4,5-dichloro-1-indolinyl group, 4-fluoro-1-indolinyl group, 4,5,6-trifluoro-1-indolinyl group, 5-fluoro-1-indolinyl group, 6-fluoro-1-indolinyl group, 7-fluoro-1-indolinyl group, 4-chloro-1-indolinyl group, 5-chloro-1-indolinyl group, 6-chloro-1-indolinyl group, 7-chloro-1-indolinyl group, 4-bromo-1-indolinyl group, 5-bromo-1-indolinyl group, 6-bromo-1-indolinyl group, 7-bromo-1-indolinyl group, 4-iodo-1-indolinyl group, 5-iodo-1-indolinyl group, 6-iodo-1-indolinyl group, 7-iodo-1-indolinyl group or the like.

An isoindolinyl group which may be substituted by at least one halogen atom is the indolinyl group unsubstituted or substituted by 1 to 3 fluorine, chlorine, bromine or iodine atoms at 1, 3, 4, 5, 6 or 7 position, examples of which include a 2-isoindolinyl group, 1-fluoro-2-isoindolinyl group, 3-bromo-2-isoindolinyl group, 4,5-dichloro-2-isoindolinyl group, 4,5,6-trifluoro-2-isoindolinyl group, 4-fluoro-2-isoindolinyl group, 5-fluoro-2-isoindolinyl group, 6-fluoro-2-isoindolinyl group, 7-fluoro-2-isoindolinyl group, 4-chloro-2-isoindolinyl group, 5-chloro-2-isoindolinyl group, 6-chloro-2-isoindolinyl group, 7-chloro-2-isoindolinyl group, 4-bromo-2-isoindolinyl group, 5-bromo-2-isoindolinyl group, 6-bromo-2-isoindolinyl group, 7-bromo-2-isoindolinyl group, 4-iodo-2-isoindolinyl group, 5-iodo-2-isoindolinyl group, 6-iodo-2-isoindolinyl group, 7-iodo-2-isoindolinyl group or the like.

A 1,2,3,4-tetrahydroquinolyl group which may be substituted by at least one halogen atom is a 1,2,3,4-tetrahydroquinolyl group unsubstituted or substituted by 1 to 3 fluorine, chlorine, bromine or iodine atoms at 2, 3, 4, 5, 6, 7 or 8 position, examples of which include a 1,2,3,4-tetrahydro-1-quinolyl group, 5-fluoro-1,2,3,4-tetrahydro-1-quinolyl group, 2-bromo-1,2,3,4-tetrahydro-1-quinolyl group, 3-iodo-1,2,3,4-tetrahydro-1-quinolyl group, 4-chloro-1,2,3,4-tetrahydro-1-quinolyl group, 3,4-dichloro-1,2,3,4-tetrahydro-1-quinolyl group, 4,5,6-trichloro-1,2,3,4-tetrahydro-1-quinolyl group, 6-fluoro-1,2,3,4-tetrahydro-1-quinolyl group, 7-fluoro-1,2,3,4-tetrahydro-1-quinolyl group, 8-fluoro-1,2,3,4-tetrahydro-1-quinolyl group, 5-chloro-1,2,3,4-tetrahydro-1-quinolyl group, 6-chloro-1,2,3,4-tetrahydro-1-quinolyl group, 7-chloro-1,2,3,4-tetrahydro-1-quinolyl group, 8-chloro-1,2,3,4-tetrahydro-1-quinolyl group, 5-bromo-1,2,3,4-tetrahydro-1-quinolyl group, 6-bromo-1,2,3,4-tetrahydro-1-quinolyl group, 7-bromo-1,2,3,4-tetrahydro-1-quinolyl group, 8-bromo-1,2,3,4-tetrahydro-1-quinolyl group, 5-iodo-1,2,3,4-tetrahydro-1-quinolyl group, 6-iodo-1,2,3,4-tetrahydro-1-quinolyl group, 7-iodo-1,2,3,4-tetrahydro-1-quinolyl group, 8-iodo-1,2,3,4-tetrahydro-1-quinolyl group or the like.

A 1,2,3,4-tetrahydroisoquinolyl group which may be substituted by at least one halogen atom is a 1,2,3,4-tetrahydroisoquinolyl group unsubstituted or substituted by 1 to 3 fluorine, chlorine, bromine or iodine atoms at 1, 3, 4, 5, 6, 7 or 8 position, examples of which include a 1,2,3,4-tetrahydro-2-isoquinolyl group, 1-bromo-1,2,3,4-tetrahydro-2-isoquinolyl group, 3-iodo-1,2,3,4-tetrahydro-2-isoquinolyl group, 4-chloro-1,2,3,4-tetrahydro-2-isoquinolyl group, 3,4-dichloro-1,2,3,4-tetrahydro-2-isoquinolyl group, 4,5,6-trichloro-1,2,3,4-tetrahydro-2-isoquinolyl group, 5-fluoro-1,2,3,4-tetrahydro-2-isoquinolyl group, 6-fluoro-1,2,3,4-tetrahydro-2-isoquinolyl group, 7-fluoro-1,2,3,4-tetrahydro-2-isoquinolyl group, 8-fluoro-1,2,3,4-tetrahydro-2- isoquinolyl group, 5-chloro-1,2,3,4-tetrahydro-2-isoquinolyl group, 6-chloro-1,2,3,4-tetrahydro-2-isoquinolyl group, 7-chloro-1,2,3,4-tetrahydro-2-isoquinolyl group, 8-chloro-1,2,3,4-tetrahydro-2-isoquinolyl group, 5-bromo-1,2,3,4-tetrahydro-2-isoquinolyl group, 6-bromo-1,2,3,4-tetrahydro-2-isoquinolyl group, 7-bromo-1,2,3,4-tetrahydro-2-isoquinolyl group, 8-bromo-1,2,3,4-tetrahydro-2-isoquinolyl group, 5-iodo-1,2,3,4-tetrahydro-2-isoquinolyl group, 6-iodo-1,2,3,4-tetrahydro-2-isoquinolyl group, 7-iodo-1,2,3,4-tetrahydro-2-isoquinolyl group, 8-iodo-1,2,3,4-tetrahydro-2-isoquinolyl group, or the like.

A phenyl C1-6 alkyl group (which may be substituted on the phenyl ring by at least one group selected from a group consisting of halogen atom(s), a halogen-substituted or unsubstituted C1-6 alkyl group or a halogen-substituted, unsubstituted C1-6 alkoxy group and a phenoxy group (which may be substituted on the phenyl ring by at least one group selected from a group consisting of halogen atom(s), a halogen-substituted or unsubstituted C1-6 alkyl group and a halogen-substituted or unsubstituted C1-6 alkoxy group as a substituent), and also, the C1-6 alkyl moiety is substituted by a C1-6 alkoxyimino group) is a group containing an unsubstituted phenyl group or a phenyl group substituted by 1 to 5 groups, preferably 1 to 3 groups selected from a group consisting of a halogen atom, a C1-6 alkyl group substituted or unsubstituted with halogen(s), a halogen-substituted or unsubstituted C1-6 alkoxy group and a phenoxy group (which may be substituted on the phenyl ring by 1 to 3 groups selected from a group consisting of a halogen atom, a halogen-substituted or unsubstituted C1-6 alkyl group or a halogen-substituted or unsubstituted C1-6 alkoxy group as a substituent) and containing an alkyl group of 1 to 6 carbons, examples of which include a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2,3-difluorobenzyl group, 3,4-difluorobenzyl group, 3,5-difluorobenzyl group, 2,4-difluorobenzyl group, 2,6-difluorobenzyl group, 2,3-dichlorobenzyl group, 3,4-dichlorobenzyl group, 3,5-dichlorobenzyl group, 2,4-dichlorobenzyl group, 2,6-dichlorobenzyl group, 2-fluoro-4-bromobenzyl group, 4-chloro-3-fluorobenzyl group, 2,3,4-trichlorobenzyl group, 3,4,5-trifluorobenzyl group, 2,3,4,5,6-pentafluorobenzyl group, 2,4,6-trichlotobenzyl group, 4-isopropylbenzyl group, 4-n-butylbenzyl group, 4-methylbenzyl group, 2-methylbenzyl group, 3-methylbenzyl group, 2,4-dimethylbenzyl group, 2,3-dimethylbenzyl group, 2,6-dimethylbenzyl group, 3,5-dimethylbenzyl group, 2,5-dimethylbenzyl group, 2,4,6-trimethylbenzyl group, 3,5-ditrifluoromethylbenzyl group, 4-isopropoxybenzyl group, 4-n-butoxybenzyl group, 4-methoxybenzyl group, 2-methoxybenzyl group, 3-methoxybenzyl group, 2,4-dimethoxybenzyl group, 2,3-dimethoxybenzyl group, 2,6-dimethoxybenzyl group, 3,5-dimethoxybenzyl group, 2,5-dimethoxybenzyl group, 2,4,6-trimethoxybenzyl group, 3,5-ditrifluoromethoxybenzyl group, 2-isopropoxybenzyl group, 3-chloro-4-methoxybenzyl group, 2-chloro-4-trifluoromethoxybenzyl group, 3-methyl-4-fluorobenzyl group, 4-bromo-3-trifluoromethylbenzyl group, 2-trifluoromethylbenzyl group, 3-trifluoromethylbenzyl group, 4-trifluoromethylbenzyl group, 2-pentafluoroethylbenzyl group, 3-pentafluoroethylbenzyl group, 4-pentafluoroethylbenzyl group, 2-trifluoromethoxybenzyl group, 3-trifluoromethoxybenzyl group, 4-trifluoromethoxybenzyl group, 2-pentafluoroethoxybenzyl group, 3-pentafluoroethoxybenzyl group, 4-pentafluoroethoxybenzyl group, 2-(2-trifluoromethylphenyl)ethyl group, 2-(3-trifluoromethylphenyl)ethyl group, 2-(4-trifluoromethylphenyl)ethyl group, 2-(2-trifluoromethoxyphenyl)ethyl group, 2-(3-trifluoromethoxyphenyl)ethyl group, 2-(4-trifluoromethoxyphenyl)ethyl group, 2-(2-pentafluoroethoxyphenyl)ethyl group, 2-(3-pentafluoroethoxyphenyl)ethyl group, 2-(4-pentafluoroethoxyphenyl)ethyl group, 3-(2-trifluoromethylphenyl)-propyl group, 3-(3-trifluoromethylphenyl)propyl group, 3-(4-trifluoromethylphenyl)propyl group, 3-(2-trifluoromethoxyphenyl)propyl group, 3-(3-trifluoromethoxyphenyl)propyl group, 3-(4-trifluoromethoxyphenyl)propyl group, 3-(3-pentafluoroethoxyphenyl)-propyl group, 3-(4-pentafluoroethoxyphenyl)propyl group, 4-(3-pentafluoroethoxyphenyl)butyl group, 5-(4-trifluoromethylphenyl)pentyl group, 4-(4-trifluoromethylphenyl)pentyl group, 4-(4-trifluoromethoxyphenyl)pentyl group, 6-(3-trifluoromethylphenyl)hexyl group, 6-(4-trifluoromethylphenyl)hexyl group, 6-(4-trifluoromethoxyphenyl)hexyl group, (4-pentafluoroethoxyphenyl)propyl group, 4-(3-pentafluoroethoxyphenyl)butyl group, 5-(4-trifluoromethylphenyl)pentyl group, 4-(4-trifluoromethylphenyl)pentyl group, 4-(4-trifluoromethoxyphenyl)pentyl group, 6-(3-trifluoromethylphenyl)hexyl group, 6-(4-trifluoromethylphenyl)-hexyl group, 6-(4-trifluoromethoxyphenyl)hexyl group, 3-phenoxybenzyl group, 4-phenoxybenzyl group, 2-(4-phenoxyphenyl)ethyl group, 3-(4-phenoxyphenyl)propyl group, 2-(4-phenoxyphenyl)propyl group, 4-(4-phenoxyphenyl)butyl group, 5-(4-phenoxyphenyl)pentyl group, 4-(4-phenoxyphenyl)pentyl group, 6-(4-phenoxyphenyl)hexyl group, 2-phenoxybenzyl group, 2-(3-phenoxyphenyl)ethyl group, 3-(2-phenoxyphenyl)propyl group, 2-(2-phenoxyphenyl)propyl group, 4-(3-phenoxyphenyl)butyl group, 5-(2-phenoxyphenyl)pentyl group, 4-(3-phenoxyphenyl)pentyl group, 6-(3-phenoxyphenyl)hexyl group, 4-(2-chlorophenoxy)benzyl group, 4-(3-chlorophenoxy)benzyl group, 4-(4-chlorophenoxy)benzyl group, 4-(2-trifluoromethylphenoxy)benzyl group, 4-(3-trifluoromethylphenoxy)benzyl group, 4-(4-trifluoromethylphenoxy)benzyl group, 4-(2-trifluoromethoxyphenoxy)benzyl group, 4-(3-trifluoromethoxyphenoxy)benzyl group, 4-(4-trifluoromethoxyphenoxy)benzyl group, 2-[4-(4-chlorophenoxy)phenyl]ethyl group, 2-[4-(4-trifluoromethylphenoxy)phenyl]ethyl group, 3-[4-(4-chlorophenoxy)phenyl]propyl group, 3-[4-(4-trifluoromethylphenoxy)phenyl]propyl group, 3-[4-(4-trifluoromethoxyphenoxy)phenyl]propyl group, 2-[4-(4-chlorophenoxy)phenyl]propyl group, 4-[4-(4-chlorophenoxy)phenyl]butyl group, 4-[4-(4-trifluoromethylphenoxy)phenyl]butyl group, 4-[4-(4-trifluoromethoxyphenoxy)phenyl]butyl group, 5-[4-(4-chlorophenoxy)-phenyl]pentyl group, 4-[4-(4-chlorophenoxy)phenyl]-pentyl group, 6-[4-(4-chlorophenoxy)phenyl]hexyl group, 6-[4-(4-trifluoromethylphenoxy)phenyl]hexyl group, 6-[4-(4-trifluoromethoxyphenoxy)phenyl]hexyl group, (2-fluoro-4-bromophenoxy)benzyl group, (4-chloro-3-fluorophenoxy)benzyl group, (2,3,4-trichlorophenoxy)-benzyl group, (3,4,5-trifluorophenoxy)benzyl group, (2,4,6-trichlorophenoxy)benzyl group, (4-isopropylphenoxy)benzyl group, (4-n-butylphenoxy)benzyl group, (4-methylphenoxy)benzyl group, (2-methylphenoxy)benzyl group, (3-methylphenoxy)benzyl group, (2,4-dimethylphenoxy)benzyl group, (2,3-dimethylphenoxy)benzyl group, (2,6-dimethylphenoxy)benzyl group, (3,5-dimethylphenoxy)benzyl group, (2,5-dimethylphenoxy)-benzyl group, (2,4,6-trimethylphenoxy)benzyl group, (3,5-ditrifluoromethylphenoxy)

benzyl group, (4-isopropoxyphenoxy)benzyl group, (4-n-butoxyphenoxy)-benzyl group, (4-methoxyphenoxy)benzyl group, (2-methoxyphenoxy)benzyl group, (3-methoxyphenoxy)benzyl group, (2,4-dimethoxyphenoxy)benzyl group, (2,3-dimethoxyphenoxy)benzyl group, (2,6-dimethoxyphenoxy)benzyl group, (3,5-dimethoxyphenoxy)benzyl group, (2,5-dimethoxyphenoxy)benzyl group, (2,4,6-trimethoxyphenoxy)benzyl group, (3,5-ditrifluoromethoxyphenoxy) benzyl group, (2-isopropoxyphenoxy)-benzyl group, (3-chloro-4-methoxyphenoxy)benzyl group, (2-chloro-4-trifluoromethoxyphenoxy)benzyl group, (3-methyl-4-fluorophenoxy)benzyl group, (4-bromo-3-trifluoromethylphenoxy)benzyl or the like.

A benzoyl group (which may be substituted on the phenyl ring by at least one group selected from a group consisting of a halogen atom, a halogen-substituted or unsubstituted C1-6 alkyl group and a halogen-substituted or unsubstituted C1-6 alkoxy group) include the benzoyl group (which may be substituted on the phenyl ring by 1 to 5, preferably 1 to 3 groups selected from a group consisting of halogen atom(s), a halogen-substituted or unsubstituted C1-6 alkyl group and a halogen-substituted or unsubstituted C1-6 alkoxy group), for example, benzoyl group, 2-fluorobenzoyl group, 3-fluorobenzoyl group, 4-fluorobenzoyl group, 2,3-difluorobenzoyl group, 2,3,4,5,6-pentafluorobenzoyl group, 3,4-difluorobenzoyl group, 2-chlorobenzoyl group, 3-chlorobenzoyl group, 4-chlorobenzoyl group, 2,3-dichlorobenzoyl group, 3,4-dichlorobenzoyl group, 2-bromobenzoyl group, 3-bromobenzoyl group, 4-bromobenzoyl group, 2,3-dibromobenzoyl group, 3,4-dibromobenzoyl group, 2-fluoro-4-bromobenzoyl group, 4-chloro-3-fluorobenzoyl group, 2,3,4-trifluorobenzoyl group, 2,4,6-trichlorobenzoyl group, 4-isopropylbenzoyl group, 4-n-butylbenzoyl group, 2,4-dimethylbenzoyl group, 2,3-dimethylbenzoyl group, 2,6-dimethylbenzoyl group, 3,5-dimethylbenzoyl group, 2,5-dimethylbenzoyl group, 2,4,6-trimethylbenzoyl group, 3,5-ditrifluoromethylbenzoyl group, 4-n-butoxybenzoyl group, 2,4-dimethoxybenzoyl group, 2,3-dimethoxybenzoyl group, 2,6-dimethoxybenzoyl group, 3,5-dimethoxybenzoyl group, 2,5-dimethoxybenzoyl group, 3,5-ditrifluoromethoxybenzoyl group, 3-chloro-4-methoxybenzoyl group, 2-chloro-4-trifluoromethoxybenzoyl group, 3-methyl-4-fluorobenzoyl group, 4-bromo-3-trifluoromethylbenzoyl group, 2-methylbenzoyl group, 3-methylbenzoyl group, 4-methylbenzoyl group, 3,4-dimethylbenzoyl group, 2-iodobenzoyl group, 3-iodobenzoyl group, 4-iodobenzoyl group, 2-trifluoromethylbenzoyl group, 3-trifluoromethylbenzoyl group, 4-trifluoromethylbenzoyl group, 2,3-ditrifluoromethylbenzoyl group, 3,4-ditrifluoromethylbenzoyl group, 2-methoxybenzoyl group, 3-methoxybenzoyl group, 4-methoxybenzoyl group, 2-trifluoromethoxybenzoyl group, 3-trifluoromethoxybenzoyl group, 4-trifluoromethoxybenzoyl group or the like.

Examples of a pyridyl group (which may be substituted on the pyridine ring by at least one halogen atom as a substituent) include a pyridyl group (which may be substituted on the pyridine ring by 1 to 3 halogen atoms as a substituent), for example, 2-pyridyl group, 3-pyridyl group, 4-pyridyl group, a 2-chloropyridin-3-yl group, 2-chloropyridin-4-yl group, 2-chloropyridin-5-yl group, 5-chloropyridin-2-yl group, 4-chloropyridin-2-yl group, 3-chloropyridin-2-yl group, 2-fluoropyridin-3-yl group, 2-fluoropyridin-4-yl group, 2-fluoropyridin-5-yl group, 5-fluoropyridin-2-yl group, 4-fluoropyridin-2-yl group, 3-fluoropyridin-2-yl group, 2-bromopyridin-3-yl group, 2-bromopyridin-4-yl group, 2-bromopyridin-5-yl group, 5-bromopyridin-2-yl group, 4-bromopyridin-2-yl group, 3-bromopyridin-2-yl group, 2-bromo-4-chloropyridin-4-yl group, 2,6-dichloropyridin-4-yl group, 2,4,6-trichloropyridin-3-yl group or the like.

A phenoxy C1-6 alkyl group (which may be substituted on the phenyl ring by at least one group selected from a group consisting of halogen atom(s), a halogen-substituted or unsubstituted C1-6 alkyl group and a halogen-substituted or unsubstituted C1-6 alkoxy group) is a group containing a phenoxy group unsubstituted or substituted by 1 to 5, preferably 1 to 3 groups selected from a group consisting of a halogen-substituted or unsubstituted C1-6 alkyl group and a halogen-substituted or unsubstituted C1-6 alkoxy group defined above and a C1-6 alkyl group, examples of which include a phenoxymethyl group, 2-phenoxyethyl group, 3-phenoxypropyl group, 4-phenoxybutyl group, 5-phenoxypentyl group, 6-phenoxyhexyl group, 4-fluorophenoxymethyl group, 2-fluoro-4-bromophenoxymethyl group, 4-chloro-3-fluorophenoxymethyl group, 2,3,4-trichlorophenoxymethyl group, 3,4,5-trichlorophenoxymethyl group, 2,4,6-trichlorophenoxymethyl group, 4-isopropylphenoxymethyl group, 4-n-butylphenoxymethyl group, 4-methylphenoxymethyl group, 2-methylphenoxymethyl group, 3-methylphenoxymethyl group, 2,4-dimethylphenoxymethyl group, 2,3-dimethylphenoxymethyl group, 2,6-dimethylphenoxymethyl group, 3,5-dimethylphenoxymethyl group, 2,5-dimethylphenoxymethyl group, 2,4,6-trimethylphenoxymethyl group, 3,5-ditrifluoromethylphenoxymethyl group, 2,3,4,5,6-pentafluorophenoxymethyl group, 4-isopropoxyphenoxymethyl group, 4-n-butoxyphenoxymethyl group, 4-methoxyphenoxymethyl group, 2-methoxyphenoxymethyl group, 3-methoxyphenoxymethyl group, 2,4-dimethoxyphenoxymethyl group, 2,3-dimethoxyphenoxymethyl group, 2,6-dimethoxyphenoxymethyl group, 3,5-dimethoxyphenoxymethyl group, 2,5-dimethoxyphenoxymethyl group, 2,4,6-trimethoxyphenoxymethyl group, 3,5-ditrifluoromethoxyphenoxymethyl group, 2-isopropoxyphenoxymethyl group, 3-chloro-4-methoxyphenoxymethyl group, 2-chloro-4-trifluoromethoxyphenoxymethyl group, 3-methyl-4-fluorophenoxymethyl group, 4-bromo-3-trifluoromethylphenoxymethyl group, 2-(4-fluorophenoxy)ethyl group, 3-(4-fluorophenoxy)propyl group, 4-(4-fluorophenoxy)butyl group, 5-(4-fluorophenoxy)pentyl group, 6-(4-fluorophenoxy)hexyl group, 4-chlorophenoxymethyl group, 2-(4-chlorophenoxy)ethyl group, 3-(4-chlorophenoxy)-propyl group, 4-(4-chlorophenoxy)butyl group, 5-(4-chlorophenoxy)pentyl group, 6-(4-chlorophenoxy)hexyl group, 4-methylphenoxymethyl group, 2-(4-methylphenoxy)ethyl group, 3-(4-methylphenoxy)propyl group, 4-(4-methylphenoxy)butyl group, 5-(4-methylphenoxy)-pentyl group, 6-(4-methylphenoxy)hexyl group, 4-trifluoromethylphenoxymethyl group, 2-(4-trifluoromethylphenoxy)ethyl group, 3-(4-trifluoromethylphenoxy)propyl group, 4-(4-trifluoromethylphenoxy)butyl group, 5-(4-trifluoromethylphenoxy)pentyl group, 6-(4-trifluoromethylphenoxy)hexyl group, 4-trifluoromethoxyphenoxymethyl group, 2-(4-trifluoromethoxyphenoxy)ethyl group, 3-(4-trifluoromethoxyphenoxy)propyl group, 4-(4-trifluoromethoxyphenoxy)butyl group, 5-(4-trifluoromethoxyphenoxy)pentyl group, 6-(4-trifluoromethoxyphenoxy)hexyl group, 2-(4-methoxyphenoxy)ethyl group, 3-(4-methoxyphenoxy)propyl group, 4-(4-methoxyphenoxy)butyl group, 5-(4-methoxyphenoxy) pentyl group, 6-(4-methoxyphenoxy)hexyl group or the like.

A benzoyl C1-6 alkyl group (which may be substituted on the phenyl ring by at least one group selected from a group consisting of a halogen atom, a halogen-substituted or unsubstituted C1-6 alkyl group and a halogen-substituted or unsubstituted C1-6 alkoxy group) includes a benzoyl C1-6 alkyl group (which may be substituted on the phenyl ring by 1 to 5, preferably 1 to 3 groups selected from a group consisting of a halogen atom, a halogen-substituted or unsubstituted C1-6 alkyl group and a halogen-substituted or unsubstituted C1-6 alkoxy group), for example, a benzoylmethyl group, 2-benzoylethyl group, 1-benzoylethyl group, 3-benzoylpropyl group, 4-benzoylbutyl group, 5-benzoylpentyl group, 6-benzoylhexyl group, 2-methyl-3-benzoylpropyl group, 1,1-dimethyl-2-benzoylethyl group, 2-fluorobenzoylmethyl group, 3-fluorobenzoylmethyl group, 4-fluorobenzoylmethyl group, 2-chlorobenzoylmethyl group, 3-chlorobenzoylmethyl group, 4-chlorobenzoylmethyl group, 2-bromobenzoylmethyl group, 3-bromobenzoylmethyl group, 4-bromobenzoylmethyl group, 2-fluoro-4-bromobenzoylmethyl group, 4-chloro-3-fluorobenzoylmethyl group, 2,3,4-trichlorobenzoylmethyl group, 2,4,6-trichlorobenzoylmethyl group, 4-isopropylbenzoylmethyl group, 4-n-butylbenzoylmethyl group, 2,4-dimethylbenzoylmethyl group, 2,3-dimethylbenzoylmethyl group, 2,6-dimethylbenzoylmethyl group, 3,5-dimethylbenzoylmethyl group, 2,5-dimethylbenzoylmethyl group, 2,4,6-trimethylbenzoylmethyl group, 3,5-ditrifluoromethylbenzoylmethyl group, 2,3,4,5,6-pentafluorobenzoylmethyl group, 4-n-butoxybenzoylmethyl group, 2,4-dimethoxybenzoylmethyl group, 2,3-dimethoxybenzoylmethyl group, 2,6-dimethoxybenzoylmethyl group, 3,5-dimethoxybenzoylmethyl group, 2,5-dimethoxybenzoylmethyl group, 3,5-ditrifluoromethoxybenzoylmethyl group, 3-chloro-4-methoxybenzoylmethyl group, 2-chloro-4-trifluoromethoxybenzoylmethyl group, 3-methyl-4-fluorobenzoylmethyl group, 4-bromo-3-trifluoromethylbenzoylmethyl group, 2-trifluoromethylbenzoylmethyl group, 3-trifluoromethylbenzoylmethyl group, 4-trifluoromethylbenzoylmethyl group, 2-trifluoromethoxybenzoylmethyl group, 3-trifluoromethoxybenzoylmethyl group, 4-trifluoromethoxybenzoylmethyl group, 2-(2-fluorobenzoyl)ethyl group, 2-(3-fluorobenzoyl)ethyl group, 2-(4-fluorobenzoyl)ethyl group, 2-(2-chlorobenzoyl)ethyl group, 2-(3-chlorobenzoyl)ethyl group, 2-(4-chlorobenzoyl)ethyl group, 2-(2-bromobenzoyl)ethyl group, 2-(3-bromobenzoyl)ethyl group, 2-(4-bromobenzoyl)ethyl group, 2-(2-trifluoromethylbenzoyl)ethyl group, 2-(3-trifluoromethylbenzoyl)ethyl group, 2-(4-trifluoromethylbenzoyl)ethyl group, 2-(2-trifluoromethoxybenzoyl)ethyl group, 2-(3-trifluoromethoxybenzoyl)ethyl group, 2-(4-trifluoromethoxybenzoyl)ethyl group, 3-(2-chlorobenzoyl)propyl group, 3-(3-chlorobenzoyl)propyl group, 3-(4-chlorobenzoyl)propyl group, 3-(2-trifluoromethylbenzoyl)propyl group, 3-(3-trifluoromethylbenzoyl)propyl group, 3-(4-trifluoromethylbenzoyl)propyl group, 3-(2-trifluoromethoxybenzoyl)-propyl group, 3-(3-trifluoromethoxybenzoyl)propyl group, 3-(4-trifluoromethoxybenzoyl)propyl group, 4-(2-chlorobenzoyl)butyl group, 4-(3-chlorobenzoyl)butyl group, 4-(4-chlorobenzoyl)butyl group, 4-(2-trifluoromethylbenzoyl)butyl group, 4-(3-trifluoromethylbenzoyl)butyl group, 4-(4-trifluoromethylbenzoyl)butyl group, 4-(2-trifluoromethoxybenzoyl)butyl group, 4-(3-trifluoromethoxybenzoyl)butyl group, 4-(4-trifluoromethoxybenzoyl)butyl group, 5-(2-chlorobenzoyl)pentyl group, 5-(3-chlorobenzoyl)pentyl group, 5-(4-chlorobenzoyl)pentyl group, 5-(2-trifluoromethylbenzoyl)pentyl group, 5-(3-trifluoromethylbenzoyl)-pentyl group, 5-(4-trifluoromethylbenzoyl)pentyl group, 5-(2-trifluoromethoxylbenzoyl)pentyl group, 5-(3-trifluoromethoxybenzoyl)pentyl group, 5-(4-trifluoromethoxybenzoyl)pentyl group, 6-(2-chlorobenzoyl)hexyl group, 6-(3-chlorobenzoyl)hexyl group, 6-(4-chlorobenzoyl)hexyl group, 6-(2-trifluoromethylbenzoyl)hexyl group, 6-(3-trifluoromethylbenzoyl)hexyl group, 6-(4-trifluoromethylbenzoyl)hexyl group, 6-(2-trifluoromethoxybenzoyl)hexyl group, 6-(3-trifluoromethoxybenzoyl)hexyl group, 6-(4-trifluoromethoxybenzoyl)hexyl group or the like.

A phenoxy group (which may be substituted on the phenyl ring by at least one group selected from a group consisting of a halogen atom; halogen-substituted or unsubstituted C1-6 alkyl group; halogen-substituted or unsubstituted C1-6 alkoxy group; C1-4 alkylenedioxy group; C1-6 alkoxycarbonyl group; cyano group; C2-6 alkenyl group; nitro group; phenyl group; an amino group which may have a group selected from a group consisting of a phenyl group, C1-6 alkyl group, carbamoyl group and C1-6 alkanoyl group as a substituent; C1-6 alkyl group substituted by a C1-6 alkanoyl group; hydroxyl group; C1-6 alkyl group substituted by a C1-6 alkoxycarbonyl group; phenyl C1-6 alkyl group; C1-6 alkanoyl group; C1-6 alkylthio group; 1,2,4-triazolyl group; isoxazolyl group; imidazolyl group; benzothiazolyl group; 2H-benzotriazolyl group; pyrolyl group; benzoxazolyl group; piperazinyl group (which may be substituted on the piperazin ring by at least one group selected from a group consisting of a C1-6 alkoxycarbonyl group and a phenyl C1-6 alkyl group (which may be substituted on the phenyl ring by at least one group selected from a group consisting of a halogen atom, a halogen-substituted or unsubstituted C1-6 alkyl group and a halogen-substituted or unsubstituted C1-6 alkoxy group) as a substituent); piperidyl group (which may be substituted on the piperidine ring by at least one amino group (which may be substituted on the amino group by at least one group selected from a group consisting of a C1-6 alkyl and phenyl group (which may be substituted on the phenyl ring with at least one group from a group consisting of a halogen atom, a halogen-substituted or unsubstituted C1-6 alkyl group and a halogen-substituted or unsubstituted C1-6 alkoxy group) as a substituent); and carbamoyl group)) includes a phenoxy group (which may be substituted on the phenyl ring by 1 to 5, preferably 1 to 3 groups selected from a group consisting of a halogen atom; a halogen-substituted or unsubstituted C1-6 alkyl group; halogen-substituted or unsubstituted C1-6 alkoxy group; C1-4 alkylenedioxy group; C1-6 alkoxycarbonyl group; cyano group; C2-6 alkenyl group; nitro group; phenyl group; an amino group which may have 1 to 2 groups selected from a group consisting of phenyl group, C1-6 alkyl group, carbamoyl group and C1-6 alkanoyl group as a substituent; C1-6 alkyl group substituted by a C1-6 alkanoyl group; hydroxyl group; C1-6 alkyl group substituted by a C1-6 alkoxycarbonyl group; phenyl C1-6 alkyl group; C1-6 alkanoyl group; C1-6 alkylthio group; 1,2,4-triazolyl group; isoxazolyl group; imidazolyl group; benzothiazolyl group; 2H-benzotriazolyl group; pyrolyl group; benzoxazolyl group; piperazinyl group (which may be substituted on the piperazin ring by 1 to 3 groups selected from a group consisting of a C1-6 alkoxycarbonyl group and phenyl C1-6 alkyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group) as a substituent); piperidyl group (which may be substituted on the piperidine ring by 1 to 3 groups selected from a group consisting of an amino group (which may be substituted on the amino group by 1 to 5, preferably 1 to 3 groups selected from a group consisting of a C1-6 alkyl and phenyl group (which may be substituted on the phenyl ring by 1 to 5, preferably 1 to 3 groups from a group consisting of a halogen atom, halogen-substituted or unsubstituted C1-6 alkyl group and halogen-substituted or unsubstituted C1-6 alkoxy group) as a substituent) and carbamoyl group), for example, a phenoxy group, 2-fluorophenoxy group, 3-fluorophenoxy group, 4-fluorophenoxy group, 2-chlorophenoxy group, 3-chlorophenoxy group, 4-chlorophenoxy group, 2-bromophenoxy group, 3-bromophenoxy group, 4-bromophenoxy group, 2-iodophenoxy group, 3-iodophenoxy group, 4-iodophenoxy group, 2,3-difluorophenoxy group, 3,4-difluorophenoxy group, 3,5-difluorophenoxy group, 2,4-difluorophenoxy group, 2,6-difluorophenoxy group, 2,3-dichlorophenoxy group, 3,4-dichlorophenoxy group, 3,5-dichlorophenoxy group, 2,4-dichlorophenoxy group, 2,6-dichlorophenoxy group, 2,3,4-trifluorophenoxy group, 3,4,5-trifluorophenoxy group, 3,4,5-trichlorophenoxy group, 2,4,6-trifluorophenoxy group, 2,3,4,5,6-pentafluorophenoxy group, 2,4,6-trichlorophenoxy group, 2-fluoro-4-chlorophenoxy group, 2-fluoro-4-bromophenoxy group, 3-fluoro-4-chlorophenoxy group, 2-methylphenoxy group, 3-methylphenoxy group, 4-methylphenoxy group, 2,6-dimethylphenoxy group, 2,4,6-trimethylphenoxy group, 2-methyl-3-chlorophenoxy group, 3-methyl-4-chlorophenoxy group, 2-chloro-4-methylphenoxy group, 2-methyl-3-fluorophenoxy group, 2-trifluoromethylphenoxy group, 3-trifluoromethylphenoxy group, 4-trifluoromethylphenoxy group, 3,5-di(trifluoromethyl) phenoxy group, 3,4-di(trifluoromethyl)phenoxy group, 2,4-di(trifluoromethyl)phenoxy group, 2-pentafluoroethylphenoxy group, 3-pentafluoroethylphenoxy group, 4-pentafluoroethyl phenoxy group, 2-isopropylphenoxy group, 3-isopropylphenoxy group, 4-isopropylphenoxy group, 2-tert-butylphenoxy group, 3-tert-butylphenoxy group, 4-tert-butylphenoxy group, 2-sec-butylphenoxy group, 3-sec-butylphenoxy group, 4-sec-butylphenoxy group, 4-n-butylphenoxy group, 4-n-pentylphenoxy group, 4-n-hexylphenoxy group, 2-n-heptafluoropropylphenoxy group, 3-n-heptafluoropropylphenoxy group, 4-n-heptafluoropropylphenoxy group, 4-pentylphenoxy group, 4-hexylphenoxy group, 2-methoxyphenoxy group, 3-methoxyphenoxy group, 4-methoxyphenoxy group, 2-methoxy-3-chlorophenoxy group, 2-fluoro-3-methoxyphenoxy group, 2-fluoro-4-methoxyphenoxy group, 2-fluoro-4-bromophenoxy group, 2,4-dimethylphenoxy group, 2,3-dimethylphenoxy group, 3,5-dimethylphenoxy group, 2,5-dimethylphenoxy group, 4-isopropoxyphenoxy group, 4-n-butoxyphenoxy group, 2,4-dimethoxyphenoxy group, 2,3-dimethoxyphenoxy group, 3,5-dimethoxyphenoxy group, 2,5-dimethoxyphenoxy group, 2,4,6-trimethoxyphenoxy group, 3,5-ditrifluoromethoxyphenoxy group, 2-isopropoxyphenoxy group, 3-chloro-4-methoxyphenoxy group, 2-chloro-4-trifluoromethoxyphenoxy group, 3-methyl-4-fluorophenoxy group, 4-bromo-3-trifluoromethylphenoxy group, 2,6-dimethoxyphenoxy group, 2-trifluoromethoxyphenoxy group, 3-trifluoromethoxyphenoxy group, 4-trifluoromethoxyphenoxy group, 2,3-di(trifluoromethoxy)phenoxy group, 3,5-di(trifluoromethoxy)phenoxy group, 2,4-di(trifluoromethoxy)phenoxy group, 2-pentafluoroethoxyphenoxy group, 3-pentafluoroethoxyphenoxy group, 4-pentafluoroethoxyphenoxy group, 3-isopropoxyphenoxy group, 2-tert-butoxyphenoxy group, 3-tert-butoxyphenoxy group, 4-tert-butoxyphenoxy group, 2-sec-butoxyphenoxy group, 3-sec-butoxyphenoxy group, 4-sec-butoxyphenoxy group, 4-n-hexyloxyphenoxy group, 2-n-heptafluoropropoxyphenoxy group, 3-n-heptafluoropropoxyphenoxy group, 4-n-heptafluoropropoxyphenoxy group, 2,3-methylenedioxyphenoxy group, 3,4-methylenedioxyphenoxy group, 2,3-ethylenedioxyphenoxy group, 3,4-ethylenedioxyphenoxy group, 2-methoxycarbonylphenoxy group, 3-methoxycarbonylphenoxy group, 4-methoxycarbonylphenoxy group, 2-ethoxycarbonylphenoxy group, 3-ethoxycarbonylphenoxy group, 4-ethoxycarbonylphenoxy group, 4-propoxycarbonylphenoxy group, 4-butoxycarbonylphenoxy group, 4-pentoxycarbonylphenoxy group, 4-hexyloxycarbonylphenoxy group, 2-cyanophenoxy group, 3-cyanophenoxy group, 4-cyanophenoxy group, 2,3-dicyanophenoxy group, 2,4,6-tricyanophenoxy group, 2-vinylphenoxy group, 3-vinylphenoxy group, 4-vinylphenoxy group, 2-allylphenoxy group, 3-allylphenoxy group, 4-allylphenoxy group, 2-(3-butenyl)phenoxy group, 3-(3-butenyl)phenoxy group, 4-(3-butenyl)phenoxy group, 2-(4-pentenyl)phenoxy group, 3-(4-pentenyl)phenoxy group, 4-(4-pentenyl)phenoxy group, 2-(5-hexenyl)phenoxy group, 3-(5-hexenyl)phenoxy group, 4-(5-hexenyl)phenoxy group, 2-nitrophenoxy group, 3-nitrophenoxy group, 4-nitrophenoxy group, 2,3-dinitrophenoxy group, 2,4-dinitrophenoxy group, 2,4,6-trinitrophenoxy group, 2-biphenylyloxy group, 3-biphenylyloxy group, 4-biphenylyloxy group, 2-dimethylaminophenoxy group, 3-dimethylaminophenoxy group, 4-dimethylaminophenoxy group, 2-diethylaminophenoxy group, 3-diethylaminophenoxy group, 4-diethylaminophenoxy group, 2-di-(n-propyl)aminophenoxy group, 3-di-(n-propyl)aminophenoxy group, 4-di-(n-propyl)aminophenoxy group, 2-diphenylaminophenoxy group, 3-diphenylaminophenoxy group, 4-diphenylaminophenoxy group, 2-acetylaminophenoxy group, 3-acetylaminophenoxy group, 4-acetylaminophenoxy group, 2-propionylaminophenoxy group, 3-propionylaminophenoxy group, 4-propionylaminophenoxy group, 2-butyrylaminophenoxy group, 3-butyrylaminophenoxy group, 4-butyrylaminophenoxy group, 4-pentanoylaminophenoxy group, 4-hexanoylaminophenoxy group, 3-(N-methyl-N-phenylamino)phenoxy group, 2-(N-acetyl-N-methylamino)phenoxy group, 2-carbamoylaminophenoxy group, 3-carbamoylaminophenoxy group, 4-carbamoylaminophenoxy group, 4-(N-acetyl-N-phenylamino)phenoxy group, 4-acetylmethylphenoxy group, 4-propionylmethylphenoxy group, 4-n-butyrylmethylphenoxy group, 4-(2-acetylethyl)phenoxy group, 4-(3-acetylpropyl)phenoxy group, 4-(4-acetylbutyl)phenoxy group, 4-(5-acetylpentyl)phenoxy group, 4-(6-acetylhexyl)phenoxy group, 2-hydroxyphenoxy group, 3-hydroxyphenoxy group, 4-hydroxyphenoxy group, 2,4-dihydroxyphenoxy group, 2,4,6-trihydroxyphenoxy group, 2-hydroxy-3-chlorophenoxy group, 2-fluoro-3-hydroxyphenoxy group, 2-fluoro-4-hydroxyphenoxy group, 4-methoxycarbonylmethylphenoxy group, 4-ethoxycarbonylmethylphenoxy group, 4-n-propoxycarbonylmethylphenoxy group, 4-(2-ethoxycarbonylethyl)phenoxy group, 4-(3-ethoxycarbonylpropyl)phenoxy group, 4-(4-ethoxycarbonylbutyl)phenoxy group, 4-(5-ethoxycarbonylpentyl)phenoxy group, 4-(6-ethoxycarbonylhexyl)phenoxy group, 2-benzylphenoxy group, 3-benzylphenoxy group, 4-benzylphenoxy group, 2-(2-phenylethyl)phenoxy group, 3-(2-phenylethyl)phenoxy group, 4-(2-phenylethyl)phenoxy group, 2-(3-phenylpropyl)phenoxy group, 3-(3-phenylpropyl)phenoxy group, 4-(3-phenylpropyl)phenoxy group, 2-(4-phenylbutyl)phenoxy group, 3-(4-phenylbutyl)phenoxy group, 4-(4-phenylbutyl)phenoxy group, 2-(5-phenylpentyl)phenoxy group, 3-(5-phenylpentyl)phenoxy group, 4-(5-phenylpentyl)phenoxy group, 2-(6-phenylhexyl)phenoxy group, 3-(6-phenylhexyl)phenoxy group, 4-(6-phenylhexyl)phenoxy group, 2-acetylphenoxy group, 3-acetylphenoxy group, 4-acetylphenoxy group, 4-n-propionylphenoxy group, 4-n- butyrylphenoxy group, 4-n-pentanoylphenoxy group, 4-n-hexanoylphenoxy group, 2-methylthiophenoxy group, 3-methylthiophenoxy group, 4-methylthiophenoxy group, 4-ethylthiophenoxy group, 4-n-propylthiophenoxy group, 4-isopropylthiophenoxy group, 4-n-butylthiophenoxy group, 4-tert-butylthiophenoxy group, 4-n-pentylthiophenoxy group, 4-n-hexylthiophenoxy group, 2,4-dimethylthiophenoxy group, 3,4,5-dimethylthiophenoxy group, 2-(1,2,4-triazol-1-yl)phenoxy group, 3-(1,2,4-triazolyl-1-yl)phenoxy group, 4-(1,2,4-triazol-1-yl)phenoxy group, 2-(3-isoxazolyl)phenoxy group, 3-(4-isoxazolyl)phenoxy group, 4-(5-isoxazolyl)phenoxy group, 2-(1-imidazolyl)phenoxy group, 3-(1-imidazolyl)phenoxy group, 4-(1-imidazolyl)phenoxy group, 2-(2-benzothiazolyl)phenoxy group, 3-(2-benzothiazolyl)phenoxy group, 4-(2-benzothiazolyl)phenoxy group, 2-(2H-benzotriazol-2-yl)phenoxy group, 3-(2H-benzotriazol-2-yl)phenoxy group, 4-(2H-benzotriazol-2-yl)phenoxy group, 2-(1-pyrrolyl)phenoxy group, 3-(1-pyrrolyl)phenoxy group, 4-(1-pyrrolyl)phenoxy group, 2-(2-benzoxazolyl)phenoxy group, 3-(2-benzoxazolyl)phenoxy group, 4-(2-benzoxazolyl)phenoxy group, 2-(1-piperazinyl)phenoxy group, 3-(1-piperazinyl)phenoxy group, 4-(1-piperazinyl)phenoxy group, 4-(4-methoxycarbonyl-1-piperazinyl)phenoxy group, 4-(4-ethoxycarbonyl-1-piperazinyl)phenoxy group, 4-(4-n-propoxycarbonyl-1-piperazinyl)phenoxy group, 4-(4-n-butoxycarbonyl-1-piperazinyl)phenoxy group, 4-(4-n-pentyloxycarbonyl-1-piperazinyl)phenoxy group, 4-(4-n-hexyloxycarbonyl-1-piperazinyl)phenoxy group, 4-(4-benzyl-1-piperazinyl)phenoxy group, 4-(4-(2-phenethyl)-1-piperazinyl)phenoxy group, 4-(4-(3-phenylpropyl)-1-piperazinyl)phenoxy group, 4-(4-(4-phenylbutyl)-1-piperazinyl)phenoxy group, 4-(4-(5-phenylpentyl)-1-piperazinyl)phenoxy group, 4-(4-(6-phenylhexyl)-1-piperazinyl)phenoxy group, 4-[4-(2-fluorobenzyl)-1-piperazinyl]phenoxy group, 4-[4-(3-fluorobenzyl)-1-piperazinyl]phenoxy group, 4-[4-(4-fluorobenzyl)-1-piperazinyl]phenoxy group, 4-[4-(2-chlorobenzyl)-1-piperazinyl]phenoxy group, 4-[4-(3-chlorobenzyl)-1-piperazinyl]phenoxy group, 4-[4-(4-chlorobenzyl)-1-piperazinyl]phenoxy group, 4-[4-(2,3-dichlorobenzyl)-1-piperazinyl]phenoxy group, 4-[4-(2,4-dichlorobenzyl)-1-piperazinyl]phenoxy group, 4-[4-(3,4-dichlorobenzyl)-1-piperazinyl]phenoxy group, 4-[4-(3,5-dichlorobenzyl)-1-piperazinyl]phenoxy group, 4-[4-(3,4,5-trichlorobenzyl)-1-piperazinyl]phenoxy group, 4-[4-(2-trifluoromethylbenzyl)-1-piperazinyl]phenoxy group, 4-[4-(3-trifluoromethylbenzyl)-1-piperazinyl]phenoxy group, 4-[4-(4-trifluoromethylbenzyl)-1-piperazinyl]-phenoxy group, 4-[4-(4-methylbenzyl)-1-piperazinyl]-phenoxy group, 4-[4-(3,4-dimethylbenzyl)-1-piperazinyl]phenoxy group, 4-[4-(2,4,6-trimethylbenzyl)-1-piperazinyl]phenoxy group, 4-[4-(2-pentafluoroethylbenzyl)-1-piperazinyl]phenoxy group, 4-[4-(3-pentafluoroethylbenzyl)-1-piperazinyl]phenoxy group, 4-[4-(4-pentafluoroethylbenzyl)-1-piperazinyl]-phenoxy group, 4-[4-(2-trifluoromethoxybenzyl)-1-piperazinyl]phenoxy group, 4-[4-(3-trifluoromethoxybenzyl)-1-piperazinyl]phenoxy group, 4-[4-(4-trifluoromethoxybenzyl)-1-piperazinyl]phenoxy group, 4-[4-(4-methoxybenzyl)-1-piperazinyl]phenoxy group, 4-[4-(3,4-dimethoxybenzyl)-1-piperazinyl]phenoxy group, 4-[4-(2,4,6-trimethoxybenzyl)-1-piperazinyl]phenoxy group, 4-[4-(2-pentafluoroethoxybenzyl)-1-piperazinyl]phenoxy group, 4-[4-(3-pentafluoroethoxybenzyl)-1-piperazinyl]phenoxy group, 4-[4-(4-pentafluoroethoxybenzyl)-1-piperazinyl]phenoxy group, 4-{4-[2-(4-trifluoromethoxyphenyl)ethyl]-1-piperazinyl}phenoxy group, 4-{4-[3-(4-trifluoromethoxyphenyl)propyl]-1-piperazinyl}phenoxy group, 4-{4-[4-(4-trifluoromethoxyphenyl)butyl]-1-piperazinyl}phenoxy group, 4-{4-[5-(4-trifluoromethoxyphenyl)pentyl]-1-piperazinyl}phenoxy group, 4-{4-[6-(4-trifluoromethoxyphenyl)hexyl]-1-piperazinyl}phenoxy group, 4-{4-[2-(4-trifluoromethylphenyl)ethyl]-1-piperazinyl}phenoxy group, 4-{4-[3-(4-trifluoromethylphenyl)propyl]-1-piperazinyl}phenoxy group, 4-{4-[4-(4-trifluoromethylphenyl)butyl]-1-piperazinyl}phenoxy group, 4-{4-[5-(4-trifluoromethylphenyl)pentyl]-1-piperazinyl}phenoxy group, 4-{4-[6-(4-trifluoromethylphenyl)hexyl]-1-piperazinyl}phenoxy group, 2-piperidinophenoxy group, 3-piperidinophenoxy group, 4-piperidinophenoxy group, 2-(4-amino-1-piperidyl)phenoxy group, 3-(4-amino-1-piperidyl)phenoxy group, 4-(4-amino-1-piperidyl)phenoxy group, 4-(4-methylamino-1-piperidyl)phenoxy group, 4-(4-ethylamino-1-piperidyl)phenoxy group, 4-(4-n-propylamino-1-piperidyl)phenoxy group, 4-(4-dimethylamino-1-piperidyl)phenoxy group, 4-(4-diethylamino-1-piperidyl)phenoxy group, 4-(4-di-n-propylamino-1-piperidyl)phenoxy group, 4-(4-phenylamino-1-piperidyl)phenoxy group, 4-[4-(N-phenyl-N-methylamino)-1-piperidyl]phenoxy group, 4-[4-(2-fluorophenylamino)-1-piperidyl]phenoxy group, 4-[4-(3-fluorophenylamino)-1-piperidyl]phenoxy group, 4-[4-(4-fluorophenylamino)-1-piperidyl]phenoxy group, 4-[4-(2-chlorophenylamino)-1-piperidyl]phenoxy group, 4-[4-(3-chlorophenylamino)-1-piperidyl)]phenoxy group, 4-[4-(4-chlorophenylamino)-1-piperidyl]phenoxy group, 4-[4-(2,3-dichlorophenylamino)-1-piperidyl]phenoxy group, 4-[4-(2,4-dichlorophenylamino)-1-piperidyl]phenoxy group, 4-[4-(3,4-dichlorophenylamino)-1-piperidyl]phenoxy group, 4-[4-(3,5-dichlorophenylamino)-1-piperidyl]-phenoxy group, 4-[4-(2-trifluoromethylphenylamino)-1-piperidyl]phenoxy group, 4-[4-(2-methylphenylamino)-1-piperidyl]phenoxy group, 4-[4-(2,3-dimethylphenylamino)-1-piperidyl]phenoxy group, 4-[4-(2-trifluoromethylphenylamino)-1-piperidyl]phenoxy group, 4-[4-(2,4,6-trimethylphenylamino)-1-piperidyl]phenoxy group, 4-[4-(4-trifluoromethylphenylamino)-1-piperidyl]phenoxy group, 4-[4-(2-pentafluoroethylphenylamino)-1-piperidyl]phenoxy group, 4-[4-(3-pentafluoroethylphenylamino)-1-piperidyl]phenoxy group, 4-[4-(4-pentafluoroethylphenylamino)-1-piperidyl]phenoxy group, 4-[4-(2-trifluoromethoxyphenylamino)-1-piperidyl]-phenoxy group, 4-[4-(2-methoxyphenylamino)-1-piperidyl]phenoxy group, 4-[4-(2,3-dimethoxyphenylamino)-1-piperidyl]phenoxy group, 4-[4-(2,4,6-trimethoxyphenylamino)-1-piperidyl]phenoxy group, 4-{4-[N-methyl-N-(2,4,6-trimethoxyphenylamino)]-1-piperidyl}phenoxy group, 4-{4-[N-methyl-N-(3,4-dimethylphenylamino)]-1-piperidyl}phenoxy group, 4-[4-(3-trifluoromethoxyphenylamino)-1-piperidyl]phenoxy group, 4-[4-(4-trifluoromethoxyphenylamino)-1-piperidyl]phenoxy group, 4-[4-(2-pentafluoroethoxyphenylamino)-1-piperidyl]phenoxy group, 4-[4-(3-pentafluoroethoxyphenylamino)-1-piperidyl]phenoxy group, 4-(4-(4-pentafluoroethoxyphenylamino)-1-piperidyl]phenoxy group, 2-carbamoylphenoxy group, 3-carbamoylphenoxy group, 4-carbamoylphenoxy group or the like.

Examples of a phenyl group (which may be substituted on the phenyl ring by at least one group selected from a group consisting of a phenoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group as a substituent), halogen atom, halogen-substituted or unsubstituted C1-6 alkyl group and halogen-substituted or unsubstituted C1-6 alkoxy group)

include a phenyl group (which may be substituted on the phenyl ring by 1 to 5, preferably 1 to 3 groups selected from a group consisting of a phenoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group as a substituent), halogen atom, halogen-substituted or unsubstituted C1-6 alkyl group and halogen-substituted or unsubstituted C1-6 alkoxy group as a substituent), for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 2,3,4-trifluorophenyl group, 3,4,5-trifluorophenyl group, 3,4,5-trichlorophenyl group, 2,4,6-trifluorophenyl group, 2,3,4,5,6-pentafluorophenyl group, 2,4,6-trichlorophenyl group, 2-fluoro-4-chlorophenyl group, 2-fluoro-4-bromophenyl group, 3-fluoro-4-chlorophenyl group, 2-methylphenyl group, 3-methylphenyl group, 4-methylphenyl group, 2-methyl-3-chlorophenyl group, 3-methyl-4-chlorophenyl group, 2-chloro-4-methylphenyl group, 2-methyl-3-fluorophenyl group, 2-trifluoromethylphenyl group, 3-trifluoromethylphenyl group, 4-trifluoromethylphenyl group, 2-pentafluoroethylphenyl group, 3-pentafluoroethylphenyl group, 4-pentafluoroethylphenyl group, 2-isopropylphenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoropropylphenyl group, 4-pentylphenyl group, 4-hexylphenyl group, 2-fluoro-4-bromophenyl group, 4-chloro-3-fluorophenyl group, 2,3,4-trichlorophenyl group, 4-n-butylphenyl group, 2,4-dimethylphenyl group, 2,3-dimethylphenyl group, 2,4-dimethylphenyl group, 2,6-dimethylphenyl group, 3,5-dimethylphenyl group, 2,5-dimethylphenyl group, 2,4,6-trimethylphenyl group, 3,5-ditrifluoromethylphenyl group, 4-n-butoxyphenyl group, 2,4-dimethoxyphenyl group, 2,3-dimethoxyphenyl group, 2,6-dimethoxyphenyl group, 3,5-dimethoxyphenyl group, 2,5-dimethoxyphenyl group, 3,5-ditrifluoromethoxyphenyl group, 2,4,6-trimethoxyphenyl group, 3-chloro-4-methoxyphenyl group, 2-chloro-4-trifluoromethoxyphenyl group, 3-methyl-4-fluorophenyl group, 4-bromo-3-trifluoromethylphenyl group, 2-methylphenyl group, 3-methylphenyl group, 4-methoxyphenyl group, 2-methoxy-3-chlorophenyl group, 2-fluoro-3-methoxyphenyl group, 2-fluoro-4-methoxyphenyl group, 2,6-dimethoxyphenyl group, 2-trifluoromethoxyphenyl group, 3-trifluoromethoxyphenyl group, 4-trifluoromethoxyphenyl group, 2-pentafluoroethoxyphenyl group, 3-pentafluoroethoxyphenyl group, 4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropropoxyphenyl group, 3-n-heptafluoropropoxyphenyl group, 4-n-heptafluoropropoxyphenyl group, 4-pentyloxyphenyl group, 4-hexyloxyphenyl group, 2-phenoxyphenyl group, 3-phenoxyphenyl group, 4-phenoxyphenyl group, 2-(2-chlorophenoxy)phenyl group, 2-(3-chlorophenoxy)phenyl group, 2-(4-chlorophenoxy)phenyl group, 3-(2-chlorophenoxy)phenyl group, 3-(3-chlorophenoxy)phenyl group, 3-(4-chlorophenoxy)phenyl group, 4-(2-chlorophenoxy)phenyl group, 4-(3-chlorophenoxy)phenyl group, 4-(4-chlorophenoxy)phenyl group, 2-(2-trifluoromethylphenoxy)phenyl group, 2-(2-methylphenoxy)phenyl group, 2-(3-trifluoromethylphenoxy)phenyl group, 2-(4-trifluoromethylphenoxy)phenyl group, 3-(2-trifluoromethylphenoxy)phenyl group, 3-(3-trifluoromethylphenoxy)phenyl group, 3-(4-trifluoromethylphenoxy)phenyl group, 4-(2-trifluoromethylphenoxy)phenyl group, 4-(3-trifluoromethylphenoxy)-phenyl group, 4-(4-trifluoromethylphenoxy)phenyl group, 2-(2-trifluoromethoxyphenoxy)phenyl group, 2-(3-trifluoromethoxyphenoxy)phenyl group, 2-(4-trifluoromethoxyphenoxy)phenyl group, 2-(4-methoxyphenoxy)phenyl group, 2-(2,4-dimethylphenoxy)phenyl group, 2-(2,4,6-trimethylphenoxy)phenyl group, 2-(3,4-dimethoxyphenoxy)phenyl group, 2-(3,4,5-trimethoxyphenoxy)phenyl group, 3-(2-trifluoromethoxyphenoxy)phenyl group, 3-(3-trifluoromethoxyphenoxy)phenyl group, 3-(4-trifluoromethoxyphenoxy)phenyl group, 4-(2-trifluoromethoxyphenoxy)phenyl group, 4-(3-trifluoromethoxyphenoxy)-phenyl group, 4-(4-trifluoromethoxyphenoxy)phenyl group or the like.

A C3-8 cycloalkyl-C1-6 alkoxy group is a group containing a cyclic alkyl group having 3 to 8 carbon atoms and an alkoxy group having 1 to 6 carbon atoms, examples of which include a cyclopropylmethoxy group, 2-cyclopropylethoxy group, 3-cyclopropylpropoxy group, 4-cyclopropylbutoxy group, 5-cyclopropylpentyloxy group, 6-cyclopropylhexyloxy group, cyclobutylmethoxy group, 2-cyclobutylethoxy group, 3-cyclobutylpropoxy group, 4-cyclobutylbutoxy group, 5-cyclobutylpentyloxy group, 6-cyclobutylhexyloxy group, cyclopentylmethoxy group, 2-cyclopentylethoxy group, 3-cyclopentylpropoxy group, 4-cyclopentylbutoxy group, 5-cyclopentylpentyloxy group, 6-cyclopentylhexyloxy group, cyclohexylmethoxy group, 2-cyclohexylethoxy group, 3-cyclohexylpropoxy group, 4-cyclohexylbutoxy group, 5-cyclohexylpentyloxy group, 6-cyclohexylhexyloxy group, cycloheptylmethoxy group, 2-cycloheptylethoxy group, 3-cycloheptylpropoxy group, 4-cycloheptylbutoxy group, 5-cycloheptylpentyloxy group, 6-cycloheptylhexyloxy group, cyclooctylmethoxy group, 2-cyclooctylethoxy group, 3-cyclooctylpropoxy group, 4-cyclooctylbutoxy group, 5-cyclooctylpentyloxy group, 6-cyclooctylhexyloxy group or the like.

A phenylcarbamoyl group (which may be substituted on the phenyl ring by at least one group selected from a group consisting of a halogen atom, a halogen-substituted or unsubstituted C1-6 alkyl group and a halogen-substituted or unsubstituted C1-6 alkoxy group) is a group containing aniline, N-C1-6 alkylaniline or N-phenyl C1-6 alkylaniline which may be substituted on the phenyl ring by 1 to 5, preferably 1 to 3 groups selected from a group consisting of a halogen, a halogen-substituted or unsubstituted C1-6 alkyl group and a halogen-substituted or unsubstituted C1-6 alkoxy group, and a carbonyl group, examples of which include a phenylcarbamoyl group, 2-fluorophenylcarbamoyl group, 3-fluorophenylcarbamoyl group, 4-fluorophenylcarbamoyl group, 2-chlorophenylcarbamoyl group, 3-chlorophenylcarbamoyl group, 4-chlorophenylcarbamoyl group, 2-bromophenylcarbamoyl group, 3-bromophenylcarbamoyl group, 4-bromophenylcarbamoyl group, 2-iodophenylcarbamoyl group, 3-iodophenylcarbamoyl group, 4-iodophenylcarbamoyl group, 2,3-difluorophenylcarbamoyl group, 3,4-difluorophenylcarbamoyl group, 3,5-difluorophenylcarbamoyl group, 2,4-difluorophenylcarbamoyl group, 2,6-difluorophenylcarbamoyl group, 2,3-dichlorophenylcarbamoyl group, 3,4-dichlorophenylcarbamoyl group, 3,5-dichlorophenylcarbamoyl group, 2,4-dichlorophenylcarbamoyl group, 2,6-dichlorophenylcarbamoyl group, 3,4,5-trifluorophenylcarbamoyl group, 2,3,4,5,6-pentafluorophenylcarbamoyl group, 3,4,5-trichlorophenylcarbamoyl group, 2,4,6-trifluorophenylcarbamoyl group, 2,4,6-trichlorophenylcarbamoyl group, 2-methylphenylcarbamoyl group, 3-methylphenylcarbamoyl group, 4-methylphenylcarbamoyl group, 2-methyl-3-chlorophenylcarbamoyl group, 3-methyl-4-chlorophenylcarbamoyl group, 2-chloro-4-methylphenylcarbamoyl group, 2-methyl-3-fluorophenylcarbamoyl group, 2-trifluoromethylphenylcarbamoyl group, 3-trifluoromethylphenylcarbamoyl group, N-methyl-N-phenylcarbamoyl group, N-(2-fluorophenyl)-N-methylcarbamoyl group, N-(3-fluorophenyl)-N-methylcarbamoyl group, N-(4-fluorophenyl)-N-methylcarbamoyl group, N-(2-chlorophenyl)-N-methyl-carbamoyl group, N-(3-chlorophenyl)-N-methylcarbamoyl group, N-(4-chlorophenyl)-N-methylcarbamoyl group, N-(4-bromophenyl)-N-methylcarbamoyl group, N-(2-iodophenyl)-N-methylcarbamoyl group, N-(3-iodophenyl)-N-methylcarbamoyl group, N-(4-iodophenyl)-N-methylcarbamoyl group, N-(2,3-difluorophenyl)-N-methylcarbamoyl group, N-(3,4-difluorophenyl)-N-methylcarbamoyl group, N-(3,5-difluorophenyl)-N-methylcarbamoyl group, N-(2,4-difluorophenyl)-N-methylcarbamoyl group, N-(2,6-difluorophenyl)-N-methylcarbamoyl group, N-(2,3-dichlorophenyl)-N-methylcarbamoyl group, N-(3,4-dichlorophenyl)-N-methylcarbamoyl group, N-(3,5-dichlorophenyl)-N-methylcarbamoyl group, N-(2,4-dichlorophenyl)-N-methylcarbamoyl group, N-(2,6-dichlorophenyl)-N-methylcarbamoyl group, N-(3,4,5-trifluorophenyl)-N-methylcarbamoyl group, N-(3,4,5-trichlorophenyl)-N-methylcarbamoyl group, N-(2,4,6-trifluorophenyl)-N-methylcarbamoyl group, N-(2,4,6-trichlorophenyl)-N-methylcarbamoyl group, N-(2-methylphenyl)-N-methylcarbamoyl group, N-(3-methylphenyl)-N-methylcarbamoyl group, N-(4-methylphenyl)-N-methylcarbamoyl group, N-(2-methyl-3-chlorophenyl)-N-methylcarbamoyl group, N-(3-methyl-4-chlorophenyl)-N-methylcarbamoyl group, N-(2-chloro-4-methylphenyl)-N-methylcarbamoyl group, N-(2-methyl-3-fluorophenyl)-N-methylcarbamoyl group, N-(2-trifluoromethylphenyl)-N-methylcarbamoyl group, N-(4-trifluoromethylphenyl)-N-methylcarbamoyl group, N-benzyl-N-phenylcarbamoyl group, N-benzyl-N-(2-fluorophenyl)carbamoyl group, N-benzyl-N-(3-fluorophenyl)-carbamoyl group, N-benzyl-N-(4-fluorophenyl)carbamoyl group, N-benzyl-N-(2-chlorophenyl)carbamoyl group, N-benzyl-N-(3-chlorophenyl)carbamoyl group, N-benzyl-N-(4-chlorophenyl)carbamoyl group, N-benzyl-N-(2-bromophenyl)carbamoyl group, N-benzyl-N-(3-bromophenyl)carbamoyl group, N-benzyl-N-(4-bromophenyl)carbamoyl group, N-benzyl-N-(2-iodophenyl)-carbamoyl group, N-benzyl-N-(3-iodophenyl)carbamoyl group, N-benzyl-N-(4-iodophenyl)carbamoyl group, N-benzyl-N-(2,3-difluorophenyl)carbamoyl group, N-benzyl-N-(3,4-difluorophenyl)carbamoyl group, N-benzyl-N-(3,5-difluorophenyl)carbamoyl group, N-benzyl-N-(2,4-difluorophenyl)carbamoyl group, N-benzyl-N-(2,6-difluorophenyl)carbamoyl group, N-benzyl-N-(2,3-dichlorophenyl)carbamoyl group, N-benzyl-N-(3,4-dichlorophenyl)carbamoyl group, N-benzyl-N-(3,5-dichlorophenyl)carbamoyl group, N-benzyl-N-(2,4-dichlorophenyl)carbamoyl group, N-benzyl-N-(2,6-dichlorophenyl)carbamoyl group, N-benzyl-N-(3,4,5-trifluorophenyl)carbamoyl group, N-benzyl-N-(3,4,5-trichlorophenyl)carbamoyl group, N-benzyl-N-(2,4,6-trifluorophenyl)carbamoyl group, N-benzyl-N-(2,4,6-trichlorophenyl)carbamoyl group, N-benzyl-N-(2-methylphenyl)carbamoyl group, N-benzyl-N-(3-methyl-phenyl)carbamoyl group, N-benzyl-N-(4-methylphenyl)-carbamoyl group, N-benzyl-N-(2-methyl-3-chlorophenyl)-carbamoyl group, N-benzyl-N-(3-methyl-4-chlorophenyl)-carbamoyl group, N-benzyl-N-(2-chloro-4-methylphenyl)-carbamoyl group, N-benzyl-N-(2-methyl-3-fluorophenyl)-carbamoyl group, N-benzyl-N-(2-trifluoromethylphenyl)carbamoyl group, N-benzyl-N-(3-trifluoromethylphenyl)carbamoyl group, N-benzyl-N-(4-trifluoromethylphenyl)carbamoyl group, 2-pentafluoroethylphenylcarbamoyl group, 3-pentafluoroethylphenylcarbamoyl group, 4-pentafluoroethylphenylcarbamoyl group, 2-isopropylphenylcarbamoyl group, 3-isopropylphenylcarbamoyl group, 4-isopropylphenylcarbamoyl group, 2-tert-butylphenylcarbamoyl group, 3-tert-butylphenylcarbamoyl group, 4-tert-butylphenylcarbamoyl group, 2-sec-butylphenylcarbamoyl group, 3-sec-butylphenylcarbamoyl group, 4-sec-butylphenylcarbamoyl group, 2-n-heptafluoropropylphenylcarbamoyl group, 3-n-heptafluoropropylphenylcarbamoyl group, 4-n-heptafluoropropylphenylcarbamoyl group, 4-pentylphenylcarbamoyl group, 4-hexylphenylcarbamoyl group, 2,4-dimethylphenylcarbamoyl group, 2,4,6-trimethylphenylcarbamoyl group, 3,4-dimethoxyphenylcarbamoyl group, 3,4,5-trimethoxyphenylcarbamoyl group, 2-methoxyphenylcarbamoyl group, 3-methoxyphenylcarbamoyl group, 4-methoxyphenylcarbamoyl group, 2-methoxy-3-chlorophenylcarbamoyl group, 2-fluoro-3-methoxyphenylcarbamoyl group, 2-fluoro-4-methoxyphenylcarbamoyl group, 2,6-dimethoxyphenylcarbamoyl group, 2,3,4-trifluorophenylcarbamoyl group, 3,4,5-trifluorophenylcarbamoyl group, 2-trifluoromethoxyphenylcarbamoyl group, 3-trifluoromethoxyphenylcarbamoyl group, 4-trifluoromethoxyphenylcarbamoyl group, 2-pentafluoroethoxyphenylcarbamoyl group, 3-pentafluoroethoxyphenylcarbamoyl group, 4-pentafluoroethoxyphenylcarbamoyl group, 2-isopropoxyphenylcarbamoyl group, 3-isopropoxyphenylcarbamoyl group, 4-isopropoxyphenylcarbamoyl group, 2-tert-butoxyphenylcarbamoyl group, 3-tert-butoxyphenylcarbamoyl group, 4-tert-butoxyphenylcarbamoyl group, 2-sec-butoxyphenylcarbamoyl group, 3-sec-butoxyphenylcarbamoyl group, 4-sec-butoxyphenylcarbamoyl group, 2-n-heptafluoropropoxyphenylcarbamoyl group, 3-n-heptafluoropropoxyphenylcarbamoyl group, 4-n-heptafluoropropoxyphenylcarbamoyl group, 4-n-pentyloxyphenylcarbamoyl group, 4-n-hexyloxyphenylcarbamoyl group or the like.

Examples of a naphthyloxy group (which may be substituted on the naphthalene ring by at least one C1-6 alkyl group as a substituent) include a naphthyloxy group (which may be substituted on the naphthalene ring by 1 to 3 C1-6 alkyl groups as a substituent), for example, a 1-naphthyloxy group, 2-naphthyloxy group, 2-methyl-1-naphthyloxy group, 3-methyl-1-naphthyloxy group, 4-methyl-1-naphthyloxy group, 5-methyl-1-naphthyloxy group, 6-methyl-1-naphthyloxy group, 7-methyl-1-naphthyloxy group, 8-methyl-1-naphthyloxy group, 1-methyl-2-naphthyloxy group, 5-methyl-2-naphthyloxy group, 4-ethyl-1-naphthyloxy group, 5-ethyl-1-naphthyloxy group, 6-ethyl-1-naphthyloxy group, 1-ethyl-2-naphthyloxy group, 5-ethyl-2-naphthyloxy group, 5-n-propyl-1-naphthyloxy group, 6-n-propyl-1-naphthyloxy group, 1-n-propyl-2-naphthyloxy group, 5-n-propyl-2-naphthyloxy group, 5-n-butyl-1-naphthyloxy group, 6-n-butyl-1-naphthyloxy group, 1-n-butyl-2-naphthyloxy group, 5-n-butyl-1-naphthyloxy group, 5-n-pentyl-1-naphthyloxy group, 6-n-pentyl-1-naphthyloxy group, 1-n-pentyl-2-naphthyloxy group, 5-n-pentyl-2-naphthyloxy group, 5-n-hexyl-1-naphthyloxy group, 6-n-hexyl-1-naphthyloxy group, 1-n-hexyl-2-naphthyloxy group, 5-n-hexyl-2-naphthyloxy group, 2,4-dimethyl-1-naphthyloxy group, 4,6,7-trimethyl-2-naphthyloxy group or the like.

Examples of a 2,3-dihydrobenzofuryloxy group (which may be substituted on the 2,3-dihydrobenzofuran ring by at least one selected from a group consisting of a C1-6 alkyl group and an oxo group) include a 2,3-dihydrobenzofuryloxy group (which may be substituted on the 2,3- dihydrobenzofuran ring by 1 to 3 groups selected from a group consisting of a C1-6 alkyl group and an oxo group), for example, a 2,3-dihydrobenzofuran-3-yloxy group, 2,3-dihydrobenzofuran-4-yloxy group, 2,3-dihydrobenzofuran-5-yloxy group, 2,3-dihydrobenzofuran-6-yloxy group, 2,3-dihydrobenzofuran-7-yloxy group, 2-oxo-2,3-dihydrobenzofuran-3-yloxy group, 2-oxo-2,3-dihydrobenzofuran-4-yloxy group, 2-oxo-2,3-dihydrobenzofuran-5-yloxy group, 2-oxo-2,3-dihydrobenzofuran-6-yloxy group, 2-oxo-2,3-dihydrobenzofuran-7-yloxy group, 3-oxo-2,3-dihydrobenzofuran-2-yloxy group, 3-oxo-2,3-dihydrobenzofuran-4-yloxy group, 3-oxo-2,3-dihydrobenzofuran-5-yloxy group, 3-oxo-2,3-dihydrobenzofuran-6-yloxy group, 3-oxo-2,3-dihydrobenzofuran-7-yloxy group, 2-methyl-2,3-dihydrobenzofuran-3-yloxy group, 2-methyl-2,3-dihydrobenzofuran-4-yloxy group, 2-methyl-2,3-dihydrobenzofuran-5-yloxy group, 2-methyl-2,3-dihydrobenzofuran-6-yloxy group, 2-methyl-2,3-dihydrobenzofuran-7-yloxy group, 2-ethyl-2,3-dihydrobenzofuran-3-yloxy group, 2-ethyl-2,3-dihydrobenzofuran-4-yloxy group, 2-ethyl-2,3-dihydrobenzofuran-5-yloxy group, 2-ethyl-2,3-dihydrobenzofuran-6-yloxy group, 2-ethyl-2,3-dihydrobenzofuran-7-yloxy group, 4-methyl-2,3-dihydrobenzofuran-3-yloxy group, 5-methyl-2,3-dihydrobenzofuran-4-yloxy group, 4-methyl-2,3-dihydrobenzofuran-5-yloxy group, 4-methyl-2,3-dihydrobenzofuran-6-yloxy group, 4-methyl-2,3-dihydrobenzofuran-7-yloxy group, 6-methyl-2,3-dihydrobenzofuran-3-yloxy group, 6-methyl-2,3-dihydrobenzofuran-4-yloxy group, 6-methyl-2,3-dihydrobenzofuran-5-yloxy group, 6-methyl-2,3-dihydrobenzofuran-7-yloxy group, 7-methyl-2,3-dihydrobenzofuran-3-yloxy group, 7-methyl-2,3-dihydrobenzofuran-4-yloxy group, 7-methyl-2,3-dihydrobenzofuran-5-yloxy group, 7-methyl-2,3-dihydrobenzofuran-6-yloxy group, 2-n-propyl-2,3-dihydrobenzofuran-5-yloxy group, 2-n-propyl-2,3-dihydrobenzofuran-6-yloxy group, 2-n-butyl-2,3-dihydrobenzofuran-5-yloxy group, 2-n-butyl-2,3-dihydrobenzofuran-6-yloxy group, 2-n-pentyl-2,3-dihydrobenzofuran-5-yloxy group, 2-n-pentyl-2,3-dihydrobenzofuran-6-yloxy group, 2-n-hexyl-2,3-dihydrobenzofuran-5-yloxy group, 2-n-hexyl-2,3-dihydrobenzofuran-6-yloxy group, 2,2-dimethyl-2,3-dihydrobenzofuran-5-yloxy group, 2,2,4-trimethyl-2,3-dihydrobenzofuran-5-yloxy group, 3-oxo-4-methyl-2,3-dihydrobenzofuran-5-yloxy group, 2,2-dimethyl-3-oxo-2,3-dihydrobenzofuran-5-yloxy group or the like.

Examples of a benzothiazolyloxy group (which may be substituted on the benzothiazole ring by at least one C1-6 alkyl group) include a benzothiazolyloxy group (which may be substituted on the benzothiazole ring by 1 to 3 C1-6 alkyl groups), for example, a 2-benzothiazolyloxy group, 4-benzothiazolyloxy group, 5-benzothiazolyloxy group, 6-benzothiazolyloxy group, 7-benzothiazolyloxy group, 2-methyl-5-benzothiazolyloxy group, 4-methyl-5-benzothiazolyloxy group, 6-methyl-5-benzothiazolyloxy group, 7-methyl-5-benzothiazolyloxy group, 4-ethyl-2-benzothiazolyloxy group, 5-ethyl-2-benzothiazolyloxy group, 6-ethyl-4-benzothiazolyloxy group, 7-ethyl-6-benzothiazolyloxy group, 4-n-propyl-7-benzothiazolyloxy group, 5-n-propyl-2-benzothiazolyloxy group, 6-n-propyl-2-benzothiazolyloxy group, 7-n-propyl-5-benzothiazolyloxy group, 4-n-butyl-5-benzothiazolyloxy group, 5-n-butyl-2-benzothiazolyloxy group, 6-n-butyl-2-benzothiazolyloxy group, 7-n-butyl-4-benzothiazolyloxy group, 4-n-pentyl-6-benzothiazolyloxy group, 5-n-pentyl-7-benzothiazolyloxy group, 6-n-pentyl-2-benzothiazolyloxy group, 7-n-pentyl-2-benzothiazolyloxy group, 4-n-hexyl-2-benzothiazolyloxy group, 5-n-hexyl-2-benzothiazolyloxy group, 6-n-hexyl-2-benzothiazolyloxy group, 7-n-hexyl-2-benzothiazolyloxy group, 2,4-dimethyl-5-benzothiazolyloxy group, 2,4,6-trimethyl-5-benzothiazolyloxy group or the like.

Examples of a 1,2,3,4-tetrahydronaphthyloxy group (which may be substituted on the 1,2,3,4-tetrahydronaphthalene ring by at least one oxo group as a substituent) include a 1,2,3,4-tetrahydro-1-naphthyloxy group, 1,2,3,4-tetrahydro-2-naphthyloxy group, 1,2,3,4-tetrahydro-6-naphthyloxy group, 1,2,3,4-tetrahydro-5-naphthyloxy group, 1,2,3,4-tetrahydro-1-oxo-5-naphthyloxy group, 1,2,3,4-tetrahydro-2-oxo-3-naphthyloxy group, 1,2,3,4-tetrahydro-1-oxo-6-naphthyloxy group, 1,2,3,4-tetrahydro-3-oxo-5-naphthyloxy group, 1,2,3,4-tetrahydro-4-oxo-6-naphthyloxy group, 1,2,3,4-tetrahydro-2-oxo-7-naphthyloxy group, 1,2,3,4-tetrahydro-1-oxo-8-naphthyloxy group or the like.

Examples of a 1,3-benzoxathiolanyloxy group (which may be substituted on the 1,3-benzoxathiolane ring by at least one oxo group as a substituent) include a 1,3-benzoxathiolane-4-yloxy group, 1,3-benzoxathiolane-5-yloxy group, 1,3-benzoxathiolane-6-yloxy group, 1,3-benzoxathiolane-7-yloxy group, 2-oxo-1,3-benzoxathiolane-5-yloxy group, 2-oxo-1,3-benzoxathiolane-6-yloxy group, 2-oxo-1,3-benzoxathiolane-7-yloxy group or the like.

Examples of an isoquinolyloxy group include an isoquinoline-1-yloxy group, isoquinoline-3-yloxy group, isoquinoline-4-yloxy group, isoquinoline-5-yloxy group, isoquinoline-6-yloxy group, isoquinoline-7-yloxy group, isoquinoline-8-yloxy group or the like.

Examples of a pyridyloxy group include 2-pyridyloxy group, 3-pyridyloxy group or 4-pyridyloxy group.

Examples of a quinolyloxy group (which may be substituted on the quinoline ring by at least one C1-6 alkyl group as a substituent) include a quinolyloxy group (which may be substituted on the quinoline ring by 1 to 3 C1-6 alkyl groups as a substituent), for example, a 2-quinolyloxy group, 3-quinolyloxy group, 4-quinolyloxy group, 5-quinolyloxy group, 6-quinolyloxy group, 7-quinolyloxy group, 8-quinolyloxy group, 3-methyl-2-quinolyloxy group, 4-methyl-2-quinolyloxy group, 5-methyl-2-quinolyloxy group, 6-methyl-2-quinolyloxy group, 7-methyl-2-quinolyloxy group, 2-methyl-3-quinolyloxy group, 4-methyl-3-quinolyloxy group, 5-methyl-3-quinolyloxy group, 6-methyl-3-quinolyloxy group, 7-methyl-3-quinolyloxy group, 8-methyl-3-quinolyloxy group, 2-methyl-4-quinolyloxy group, 3-methyl-4-quinolyloxy group, 5-methyl-4-quinolyloxy group, 6-methyl-4-quinolyloxy group, 7-methyl-4-quinolyloxy group, 8-methyl-4-quinolyloxy group, 2-methyl-5-quinolyloxy group, 4-methyl-5-quinolyloxy group, 3-methyl-5-quinolyloxy group, 6-methyl-5-quinolyloxy group, 7-methyl-5-quinolyloxy group, 8-methyl-5-quinolyloxy group, 2-methyl-6-quinolyloxy group, 4-methyl-6-quinolyloxy group, 5-methyl-6-quinolyloxy group, 3-methyl-6-quinolyloxy group, 7-methyl-6-quinolyloxy group, 8-methyl-6-quinolyloxy group, 2-methyl-7-quinolyloxy group, 4-methyl-7-quinolyloxy group, 5-methyl-7-quinolyloxy group, 6-methyl-7-quinolyloxy group, 3-methyl-7-quinolyloxy group, 8-methyl-7-quinolyloxy group, 2-methyl-8-quinolyloxy group, 4-methyl-8-quinolyloxy group, 5-methyl-8-quinolyloxy group, 6-methyl-8-quinolyloxy group, 7-methyl-8-quinolyloxy group, 3-methyl-8-quinolyloxy group, 2,5-dimethyl-8-quinolyloxy group, 6,7-dimethyl-4-quinolyloxy group, 4,6,7-trimethyl-5-quinolyloxy group, compounds substituted by an ethyl group, n-propyl group, n-butyl group, n-pentyl group or n-hexyl group in place of the methyl group of these compounds or the like.

Examples of a dibenzofuryloxy group include a 1-dibenzofuryloxy group, 2-dibenzofuryloxy group, 3-dibenzofuryloxy group, 4-dibenzofuryloxy group, 5-dibenzofuryloxy group, 6-dibenzofuryloxy group, 7-dibenzofuryloxy group, 8-dibenzofuryloxy group or 9-dibenzofuryloxy group.

Examples of a 2H-chromenyloxy group (which may be substituted on the 2H-chromene ring by at least one oxo group as a substituent) include a 4-(2H)chromenyloxy group, 5-(2H)chromenyloxy group, 6-(2H)chromenyloxy group, 7-(2H)chromenyloxy group, 8-(2H)chromenyloxy group, 2-oxo-4-(2H)chromenyloxy group, 2-oxo-5-(2H)chromenyloxy group, 2-oxo-6-(2H)chromenyloxy group, 2-oxo-7-(2H)chromenyloxy group, 2-oxo-8-(2H)chromenyloxy group or the like.

Examples of a benzisoxazolyloxy group include a 3-benzisoxazolyloxy group, 4-benzisoxazolyloxy group, 5-benzisoxazolyloxy group, 6-benzisoxazolyloxy group, 7-benzisoxazolyloxy group or the like.

Examples of a quinoxalyloxy group include a 2-quinoxalyloxy group, 5-quinoxalyloxy group, 6-quinoxalyloxy group or the like.

Examples of a 2,3-dihydro-1H-indenyloxy group (which may be substituted on the 2,3-dihydro-1H-indene ring by at least one oxo group as a substituent) include a 2,3-dihydro-1H-inden-1-yloxy group, 2,3-dihydro-1H-inden-2-yloxy group, 2,3-dihydro-1H-inden-3-yloxy group, 2,3-dihydro-1H-inden-4-yloxy group, 2,3-dihydro-1H-inden-5-yloxy group, 2,3-dihydro-1H-inden-6-yloxy group, 2,3-dihydro-1H-inden-7-yloxy group, 2,3-dihydro-1-oxo-1H-inden-2-yloxy group, 2,3-dihydro-1-oxo-1H-inden-3-yloxy group, 2,3-dihydro-1-oxo-1H-inden-4-yloxy group, 2,3-dihydro-1-oxo-1H-inden-5-yloxy group, 2,3-dihydro-1-oxo-1H-inden-6-yloxy group, 2,3-dihydro-1-oxo-1H-inden-7-yloxy group or the like.

Examples of a benzofurazanyloxy group include, for example, a 4-benzofurazanyloxy group, 5-benzofurazanyloxy group or the like.

A phenyl C2-6 alkenyl group (which may be substituted on the phenyl ring by at least one group selected from a group consisting of a halogen atom, a halogen-substituted or unsubstituted C1-6 alkyl group and a halogen-substituted or unsubstituted C1-6 alkoxy group) is a group containing a phenyl group unsubstituted or substituted by 1 to 5, preferably 1 to 3 groups selected from a group consisting of a halogen atom, a halogen-substituted or unsubstituted C1-6 alkyl group and a halogen-substituted or unsubstituted C1-6 alkoxy group, and an alkenyl group containing 2 to 6 carbon atoms and having at least one double bond. These groups may be either in trans or cis form and both forms are included as a matter of course. These phenyl C2-6 alkenyl groups include, for example, a 3-(2-fluorophenyl)-2-propenyl group, 3-(3-fluorophenyl)-2-propenyl group, 3-(4-fluorophenyl)-2-propenyl group, 3-(2,3-difluorophenyl)-2-propenyl group, 3-(2,3,4,5,6-pentafluorophenyl)-2-propenyl group, 3-(2,4-difluorophenyl)-2-propenyl group, 3-(3,4-difluorophenyl)-2-propenyl group, 3-(3,5-difluorophenyl)-2-propenyl group, 3-(2-chlorophenyl)-2-propenyl group, 3-(3-chlorophenyl)-2-propenyl group, 3-(4-chlorophenyl)-2-propenyl group, 3-(2,3-dichlorophenyl)-2-propenyl group, 3-(2,4-dichlorophenyl)-2-propenyl group, 3-(3,4-dichlorophenyl)-2-propenyl group, 3-(3,5-dichlorophenyl)-2-propenyl group, 3-(2-bromophenyl)-2-propenyl group, 3-(3-bromophenyl)-2-propenyl group, 3-(4-bromophenyl)-2-propenyl group, 3-(2-methylphenyl)-2-propenyl group, 3-(3-methylphenyl)-2-propenyl group, 3-(4-methylphenyl)-2-propenyl group, 3-(2-trifluoromethylphenyl)-2-propenyl group, 3-(2-fluoro-4-bromophenyl)-2-propenyl group, 3-(4-chloro-3-fluorophenyl)-2-propenyl group, 3-(2,3,4-trichlorophenyl)-2-propenyl group, 3-(2,4,6-trichlorophenyl)-2-propenyl group, 3-(4-isopropylphenyl)-2-propenyl group, 3-(4-n-butylphenyl)-2-propenyl group, 3-(2,4-dimethylphenyl)-2-propenyl group, 3-(2,3-dimethylphenyl)-2-propenyl group, 3-(2,6-dimethylphenyl)-2-propenyl group, 3-(3,5-dimethylphenyl)-2-propenyl group, 3-(2,5-dimethylphenyl)-2-propenyl group, 3-(2,4,6-trimethylphenyl)-2-propenyl group, 3-(3,5-ditrifluoromethylphenyl)-2-propenyl group, 3-(4-n-butoxyphenyl)-2-propenyl group, 3-(2,4-dimethoxyphenyl)-2-propenyl group, 3-(2,3-dimethoxyphenyl)-2-propenyl group, 3-(2,6-dimethoxyphenyl)-2-propenyl group, 3-(3,5-dimethoxyphenyl)-2-propenyl group, 3-(2,5-dimethoxyphenyl)-2-propenyl group, 3-(3,5-ditrifluoromethoxyphenyl)-2-propenyl group, 3-(3-chloro-4-methoxyphenyl)-2-propenyl group, 3-(2-chloro-4-trifluoromethoxyphenyl)-2-propenyl group, 3-(3-methyl-4-fluorophenyl)-2-propenyl group, 3-(4-bromo-3-trifluoromethylphenyl)-2-propenyl group, 3-(3-trifluoromethylphenyl)-2-propenyl group, 3-(4-trifluoromethylphenyl)-2-propenyl group, 3-(2-trifluoromethoxyphenyl)-2-propenyl group, 3-(3-trifluoromethoxyphenyl)-2-propenyl group, 3-(4-trifluoromethoxyphenyl)-2-propenyl group, 3-(2-methoxyphenyl)-2-propenyl group, 3-(3-methoxyphenyl)-2-propenyl group, 3-(4-methoxyphenyl)-2-propenyl group, 3-(3,4-dimethoxyphenyl)-2-propenyl group, 4-(4-chlorophenyl)-2-butenyl group, 4-(4-chlorophenyl)-3-butenyl group, 5-(4-chlorophenyl)-2-pentenyl group, 5-(4-chlorophenyl)-4-pentenyl group, 5-(4-chlorophenyl)-3-pentenyl group, 6-(4-chlorophenyl)-5-hexenyl group, 6-(4-chlorophenyl)-4-hexenyl group, 6-(4-chlorophenyl)-3-hexenyl group, 6-(4-chlorophenyl)-3-hexenyl group or the like.

Examples of a C1-6 alkyl group (the alkyl group may be substituted by a morpholino group, benzoyl group and carbamoyl group which may have a C1-6 alkyl group as a substituent or cyano group) include a methyl group, ethyl group, n-propyl group, n-butyl group, n-pentyl group, n-hexyl group, morpholinomethyl group, 2-morpholinoethyl group, 3-morpholinopropyl group, 4-morpholinobutyl group, 5-morpholinopentyl group, 6-morpholinohexyl group, benzoylmethyl group, 2-benzoylethyl group, 1-benzoylethyl group, 3-benzoylpropyl group, 4-benzoylbutyl group, 5-benzoylpentyl group, 6-benzoylhexyl group, carbamoylmethyl group, 2-carbamoylethyl group, 1-carbamoylethyl group, 3-carbamoylpropyl group, 4-carbamoylbutyl, 5-carbamoylpentyl group, 6-carbamoylhexyl group, 2-methyl-3-carbamoylpropyl group, 1,1-dimethyl-2-carbamoylethyl group, methylcarbamoylmethyl group, 2-methylcarbamoylethyl group, 3-methylcarbamoylpropyl group, 4-methylcarbamoylbutyl group, 5-methylcarbamoylpentyl group, 6-methylcarbamoylhexyl group, dimethylcarbamoylmethyl group, 2-dimethylcarbamoylethyl group, 3-dimethylcarbamoylpropyl group, 4-dimethylcarbamoylbutyl group, 5-dimethylcarbamoylpentyl group, 6-dimethylcarbamoylhexyl group, diethylcarbamoylmethyl group, 2-diethylcarbamoylethyl group, 3-diethylcarbamoylpropyl group, 4-diethylcarbamoylbutyl group, 5-diethylcarbamoylpentyl group, 6-diethylcarbamoylhexyl group, n-propylcarbamoylmethyl group, 2-n-propylcarbamoylethyl group, 3-n-propylcarbamoylpropyl group, 4-n-propylcarbamoylbutyl group, 5-n-propylcarbamoylpentyl group, 6-n-propylcarbamoylhexyl group, n-butylcarbamoylmethyl group, 2-n-butylcarbamoylethyl group, 3-n-butylcarbamoylpropyl group, 4-n-butylcarbamoylbutyl group, 5-n-butylcarbamoylpentyl group, 6-n-butylcarbamoylhexyl group, n-hexylcarbamoylmethyl group, 2-n-hexylcarbamoylethyl group, 3-n-hexylcarbamoylpropyl group, 4-n-hexylcarbamoylbutyl group, 5-n-hexylcarbamoylpentyl group, 6-n-hexylcarbamoylhexyl group, cyanomethyl group, 2-cyanoethyl group, 1-cyanoethyl group, 3-cyanopropyl group, 4-cyanobutyl group, 5-cyanopentyl group, 6-cyanohexyl group or the like.

Examples of a phenyl C1-6 alkyl group (which may be substituted on the phenyl ring by at least one group selected from a group consisting of a halogen atom, cyano group, phenyl group, nitro group, C1-6 alkylthio group, C1-6 alkylsulfonyl group, phenyl C1-6 alkoxy group, C2-6 alkanoyloxy group, halogen-substituted or unsubstituted C1-6 alkyl group, halogen-substituted or unsubstituted C1-6 alkoxy group and 1,2,3-thiadiazolyl group) include a phenyl C1-6 alkyl group (which may be substituted on the phenyl ring by 1 to 5, preferably 1 to 3 groups selected from a group consisting of a halogen atom, a cyano group, phenyl group, nitro group, C1-6 alkylthio group, C1-6 alkylsulfonyl group, phenyl C1-6 alkoxy group, C2-6 alkanoyloxy group, halogen-substituted or unsubstituted C1-6 alkyl group, halogen-substituted or unsubstituted C1-6 alkoxy group and 1,2,3-thiadiazolyl group), for example, a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 4-biphenylylmethyl group, 2-(4-biphenylyl)ethyl group, 3-(4-biphenylyl)propyl group, 2-(4-biphenylyl)propyl group, 4-(4-biphenylyl)-butyl group, 5-(4-biphenylyl)pentyl group, 4-(4-biphenylyl)pentyl group, 6-(4-biphenylyl)hexyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2,3-difluorobenzyl group, 3,4-difluorobenzyl group, 3,5-difluorobenzyl group, 2,4-difluorobenzyl group, 2,6-difluorobenzyl group, 2,4,6-trifluorobenzyl group, 3,4,5-trifluorobenzyl group, 2,3-dichlorobenzyl group, 3,4-dichlorobenzyl group, 3,5-dichlorobenzyl group, 2,4-dichlorobenzyl group, 2,6-dichlorobenzyl group, 2,4,6-trichlorobenzyl group, 3,4,5-trichlorobenzyl group, 2-difluoromethylbenzyl group, 3-difluoromethylbenzyl group, 4-difluoromethylbenzyl group, 4-chloro-3-difluoromethylbenzyl group, 3-chloro-4-difluoromethylbenzyl group, 3-bromo-4-difluoromethylbenzyl group, 3,5-difluoro-4-difluoromethylbenzyl group, 2-fluoro-4-bromobenzyl group, 4-chloro-3-fluorobenzyl group, 2,3,4-trichlorobenzyl group, 4-isopropylbenzyl group, 4-n-butylbenzyl group, 4-methylbenzyl group, 2-methylbenzyl group, 3-methylbenzyl group, 2,4-dimethylbenzyl group, 2,3-dimethylbenzyl group, 2,6-dimethylbenzyl group, 3,5-dimethylbenzyl group, 2,5-dimethylbenzyl group, 2,4,6-trimethylbenzyl group, 3,5-ditrifluoromethylbenzyl group, 4-isopropoxybenzyl group, 4-n-butoxybenzyl group, 4-methoxybenzyl group, 2-methoxybenzyl group, 3-methoxybenzyl group, 2,4-dimethoxybenzyl group, 2,3-dimethoxybenzyl group, 2,6-dimethoxybenzyl group, 3,5-dimethoxybenzyl group, 2,5-dimethoxybenzyl group, 2,4,6-trimethoxybenzyl group, 3,5-ditrifluoromethoxybenzyl group, 2,3,4,5,6-pentafluorobenzyl group, 2-isopropoxybenzyl group, 3-chloro-4-methoxybenzyl group, 2-chloro-4-trifluoromethoxybenzyl group, 3-methyl-4-fluorobenzyl group, 4-bromo-3-trifluoromethylbenzyl group, 2-trifluoromethylbenzyl group, 3-trifluoromethylbenzyl group, 4-trifluoromethylbenzyl group, 4-fluoro-3-trifluoromethylbenzyl group, 3-fluoro-4-trifluoromethylbenzyl group, 4-chloro-3-pentafluoroethylbenzyl group, 3-chloro-4-pentafluoroethylbenzyl group, 2-pentafluoroethylbenzyl group, 3-pentafluoroethylbenzyl group, 4-pentafluoroethylbenzyl group, 2-trifluoromethoxybenzyl group, 3-trifluoromethoxybenzyl group, 4-trifluoromethoxybenzyl group, 4-fluoro-3-trifluoromethyoxybenzyl group, 3-fluoro-4-trifluoromethoxybenzyl group, 2-pentafluoroethoxybenzyl group, 3-pentafluoroethoxybenzyl group, 4-pentafluoroethoxybenzyl group, 3-chloro-4-trifluoromethoxybenzyl group, 3-chloro-4-pentafluoroethoxybenzyl group, 2-(2-trifluoromethylphenyl)ethyl group, 2-(3-trifluoromethylphenyl)ethyl group, 2-(4-trifluoromethylphenyl)ethyl group, 2-(2-trifluoromethoxyphenyl)ethyl group, 2-(3-trifluoromethoxyphenyl)ethyl group, 2-(4-trifluoromethoxyphenyl)ethyl group, 2-(2-pentafluoroethoxyphenyl)ethyl group, 2-(3-pentafluoroethoxyphenyl)ethyl group, 2-(4-pentafluoroethoxyphenyl)ethyl group, 3-(2-trifluoromethylphenyl)propyl group, 3-(3-trifluoromethylphenyl)propyl group, 3-(4-trifluoromethylphenyl)propyl group, 3-(2-trifluoromethoxyphenyl)propyl group, 3-(3-trifluoromethoxyphenyl)propyl group, 3-(4-trifluoromethoxyphenyl)propyl group, 3-(3-pentafluoroethoxyphenyl)propyl group, 3-(4-pentafluoroethoxyphenyl)propyl group, 4-(3-pentafluoroethoxyphenyl)butyl group, 5-(4-trifluoromethylphenyl)pentyl group, 4-(4-trifluoromethylphenyl)pentyl group, 4-(4-trifluoromethoxyphenyl)pentyl group, 6-(3-trifluoromethylphenyl)hexyl group, 6-(4-trifluoromethylphenyl)hexyl group, 6-(4-trifluoromethoxyphenyl)hexyl group, 2-methylthiobenzyl group, 3-methylthiobenzyl group, 4-methylthiobenzyl group, 2,3-dimethylthiobenzyl group, 2,4,6-trimethylthiobenzyl group, 2-(2-methylthiophenyl)ethyl group, 2-(3-methylthiophenyl)ethyl group, 2-(4-methylthiophenyl)ethyl group, 3-(4-methylthiophenyl)propyl group, 4-(4-methylthiophenyl)-butyl group, 5-(4-methylthiophenyl)pentyl group, 6-(4-methylthiophenyl)hexyl group, 2-benzyloxybenzyl group, 3-benzyloxybenzyl group, 4-benzyloxybenzyl group, 2-(2-benzyloxyphenyl)ethyl group, 2-(3-benzyloxyphenyl)ethyl group, 2-(4-benzyloxyphenyl)ethyl group, 3-(4-benzyloxyphenyl)propyl group, 4-(4-benzyloxyphenyl)-butyl group, 5-(4-benzyloxyphenyl)pentyl group, 6-(4-benzyloxyphenyl)hexyl group, 2-(2-phenylethoxy)benzyl group, 3-(2-phenylethoxy)benzyl group, 4-(2-phenylethoxy)benzyl group, 2-(2-(2-phenylethoxy)-phenyl)ethyl group, 2-(3-(2-phenylethoxy)phenyl)ethyl group, 2-(4-(2-phenylethoxy)phenyl)ethyl group, 3-(4-(2-phenylethoxy)phenyl)propyl group, 4-(4-(2-phenylethoxy)phenyl)butyl group, 5-(4-(2-phenylethoxy)-phenyl)pentyl group, 6-(4-(2-phenylethoxy)

phenyl)hexyl group, 2-(3-phenylpropoxy)benzyl group, 3-(3-phenylpropoxy)benzyl group, 4-(3-phenylpropoxy)benzyl group, 2-(4-phenylbutoxy)benzyl group, 3-(4-phenylbutoxy)-benzyl group, 4-(4-phenylbutoxy)benzyl group, 2-acetyloxybenzyl group, 3-acetyloxybenzyl group, 4-acetyloxybenzyl group, 2-(2-acetyloxyphenyl)ethyl group, 2-(3-acetyloxyphenyl)ethyl group, 2-(4-acetyloxyphenyl)ethyl group, 3-(4-acetyloxyphenyl)-propyl group, 4-(4-acetyloxyphenyl)butyl group, 5-(4-acetyloxyphenyl)pentyl group, 6-(4-acetyloxyphenyl)-hexyl group, 2-methanesulfonylbenzyl group, 3-methanesulfonylbenzyl group, 4-methanesulfonylbenzyl group, 3,4-dimethanesulfonylbenzyl group, 3,4,5-trimethanesulfonylbenzyl group, 2-(2-methanesulfonylphenyl)ethyl group, 2-(3-methanesulfonylphenyl)ethyl group, 2-(4-methanesulfonylphenyl)ethyl group, 3-(4-methanesulfonylphenyl)propyl group, 4-(4-methanesulfonylphenyl)butyl group, 5-(4-methanesulfonylphenyl)pentyl group, 6-(4-methanesulfonylphenyl)hexyl group, 2-cyanobenzyl group, 3-cyanobenzyl group, 4-cyanobenzyl group, 2,4-dicyanobenzyl group, 3,4,5-tricyanobenzyl group, 2-(2-cyanophenyl)ethyl group, 2-(3-cyanophenyl)ethyl group, 2-(4-cyanophenyl)ethyl group, 3-(4-cyanophenyl)propyl group, 4-(4-cyanophenyl)butyl group, 5-(4-cyanophenyl)pentyl group, 6-(4-cyanophenyl)hexyl group, 2-nitrobenzyl group, 3-nitrobenzyl group, 4-nitrobenzyl group, 2,6-dinitrobenzyl group, 3,4,5-trinitrobenzyl group, 2-(2-nitrophenyl)ethyl group, 2-(3-nitrophenyl)ethyl group, 2-(4-nitrophenyl)ethyl group, 3-(4-nitrophenyl)propyl group, 4-(4-nitrophenyl)butyl group, 5-(4-nitrophenyl)-pentyl group, 6-(4-nitrophenyl)hexyl group, 2-(1,2,3-thiadiazol-4-yl)benzyl group, 3-(1,2,3-thiadiazol-4-yl)benzyl group, 4-(1,2,3-thiadiazol-4-yl)benzyl group or the like.

Examples of a C2-6 alkenyl group includes a vinyl group, 2-propenyl group, 3-butenyl group, 2-butenyl group, 4-pentenyl group, 3-pentenyl group, 5-hexenyl group, 4-hexenyl group, 3-hexenyl group or the like.

A phenyl group (which may be substituted on the phenyl ring with at least one group selected from a group consisting of a halogen atom, cyano group, halogen-substituted or unsubstituted C1-6 alkyl group and halogen-substituted or unsubstituted C1-6 alkoxy group), include a phenyl group unsubstituted or substituted by 1 to 5, preferably 1 to 3 substituents selected from a group consisting of a halogen atom, cyano group, halogen-substituted or unsubstituted C1-6 alkyl group and halogen-substituted or unsubstituted C1-6 alkoxy group, as defined above, examples of which include a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,3,4,5,6-pentafluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 3,4,5-trichlorophenyl group, 2,4,6-trifluorophenyl group, 2,4,6-trichlorophenyl group, 2-methylphenyl group, 3-methylphenyl group, 4-methylphenyl group, 2-methyl-3-chlorophenyl group, 3-methyl-4-chlorophenyl group, 2-chloro-4-methylphenyl group, 2-methyl-3-fluorophenyl group, 2-trifluoromethylphenyl group, 3-trifluoromethylphenyl group, 4-trifluoromethylphenyl group, 2-pentafluoroethylphenyl group, 3-pentafluoroethylphenyl group, 4-pentafluoroethylphenyl group, 2-isopropylphenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoropropylphenyl group, 4-pentylphenyl group, 4-hexylphenyl group, 2-methoxyphenyl group, 3-methoxyphenyl group, 4-methoxyphenyl group, 3-chloro-2-methoxyphenyl group, 2-fluoro-3-methoxyphenyl group, 2-fluoro-4-methoxyphenyl group, 2,6-dimethoxyphenyl group, 2,3,4-trifluorophenyl group, 2-fluoro-4-bromophenyl group, 4-chloro-3-fluorophenyl group, 2,3,4-trichlorophenyl group, 4-n-butylphenyl group, 2,4-dimethylphenyl group, 2,3-dimethylphenyl group, 2,6-dimethylphenyl group, 3,5-dimethylphenyl group, 2,5-dimethylphenyl group, 2,4,6-trimethylphenyl group, 2,4,6-trimethoxyphenyl group, 3,5-ditrifluoromethylphenyl group, 4-n-butoxyphenyl group, 2,4-dimethoxyphenyl group, 2,3-dimethoxyphenyl group, 3,5-dimethoxyphenyl group, 2,5-dimethoxyphenyl group, 3,5-ditrifluoromethoxyphenyl group, 3-chloro-4-methoxyphenyl group, 2-chloro-4-trifluoromethoxyphenyl group, 3-methyl-4-fluorophenyl group, 4-bromo-3-trifluoromethylphenyl group, 2-cyanophenyl group, 3-cyanophenyl group, 4-cyanophenyl group, 2-trifluoromethoxyphenyl group, 3-trifluoromethoxyphenyl group, 4-trifluoromethoxyphenyl group, 3-fluoro-2-trifluoromethoxyphenyl group, 2-fluoro-3-trifluoromethoxyphenyl group, 3-fluoro-4-trifluoromethoxyphenyl group, 3-chloro-2-trifluoromethoxyphenyl group, 2-chloro-3-trifluoromethoxyphenyl group, 3-chloro-4-trifluoro-methoxyphenyl group, 2-pentafluoroethoxyphenyl group, 3-pentafluoroethoxyphenyl group, 4-pentafluoroethoxyphenyl group, 3-chloro-2-pentafluoroethoxyphenyl group, 2-chloro-3-pentafluoroethoxyphenyl group, 3-chloro-4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropropoxyphenyl group, 3-n-heptafluoropropoxyphenyl group, 4-n-heptafluoropropoxyphenyl group, 4-n-pentoxyphenyl group, 4-n-hexyloxyphenyl group or the like.

A phenyl C2-6 alkanoyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) includes a phenyl C2-6 alkanoyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group), for example, a phenylacetyl group, 3-phenylpropionyl group, 4-phenylbutyryl group, 5-phenylpentanoyl group, 6-phenylhexanoyl group, 4-fluorophenylacetyl group, 3-(4-fluorophenyl)propionyl group, 4-(4-fluorophenyl)butyryl group, 5-(4-fluorophenyl)pentanoyl group, 6-(4-fluorophenyl)-hexanoyl group, 2-chlorophenylacetyl group, 2,3,4,5,6-pentafluorophenylacetyl group, 3-(2-chlorophenyl)propionyl group, 4-(2-chlorophenyl)butyryl group, 5-(2-chlorophenyl)pentanoyl group, 6-(2-chlorophenyl)-hexanoyl group, 3-chlorophenylacetyl group, 3-(3-chlorophenyl)-propionyl group, 4-(3-chlorophenyl)butyryl group, 5-(3-chlorophenyl)pentanoyl group, 6-(3-chlorophenyl)hexanoyl group, 4-chlorophenylacetyl group, 3-(4-chlorophenyl)propionyl group, 4-(4-chlorophenyl)butyryl group, 5-(4-chlorophenyl)pentanoyl group, 6-(4-chlorophenyl)hexanoyl group, 3,4-dichlorophenylacetyl group, 3-(3,4-dichlorophenyl)propionyl group, 4-(3,4-dichlorophenyl)butyryl group, 5-(3,4-dichlorophenyl)pentanoyl group, 6-(3,4-dichlorophenyl)-hexanoyl group, 2-methylphenylacetyl group, 3-methylphenylacetyl group, 4-methylphenylacetyl group, (2,4,6-trimethylphenyl)-acetyl group, (2,6-dimethoxyphenyl)acetyl group, (2,4,5-trimethoxyphenyl)acetyl group, (3,5-ditrifluoromethylphenyl)acetyl group, (3,5-ditrifluoromethoxyphenyl)acetyl group, 2-trifluoro-methylphenylacetyl group, 3-trifluoromethylphenylacetyl group, 4-trifluoromethylphenylacetyl group, 2-phenylpropionyl group, 3-(2-methylphenyl)propionyl group, 3-(3-methylphenyl)propionyl group, 3-(4-methylphenyl)-propionyl group, 3-(2-trifluoromethylphenyl)propionyl group, 3-(3-trifluoromethylphenyl)propionyl group, 3-(4-trifluoromethylphenyl)propionyl group, 3-(3,5-dimethylphenyl)propionyl group, 4-(4-trifluoromethylphenyl)butyryl group, 5-(4-trifluoromethylphenyl)pentanoyl group, 6-(4-trifluoromethylphenyl)hexanoyl group, 4-(4-pentafluoroethylphenyl)butyryl group, 5-(4-pentafluoroethylphenyl)pentanoyl group, 6-(4-pentafluoroethylphenyl)hexanoyl group, 2-methoxyphenylacetyl group, 3-methoxyphenylacetyl group, 4-methoxyphenylacetyl group, 2-trifluoromethoxyphenylacetyl group, 3-trifluoromethoxyphenylacetyl group, 4-trifluoromethoxyphenylacetyl group, 3-(2-methoxyphenyl)propionyl group, 3-(3-methoxyphenyl)-propionyl group, 3-(4-methoxyphenyl)propionyl group, 3-(2-trifluoromethoxyphenyl)propionyl group, 3-(3-trifluoromethoxyphenyl)propionyl group, 3-(4-trifluoromethoxyphenyl)propionyl group, 3-(3,5-dimethoxyphenyl)propionyl group, 4-(4-trifluoromethoxyphenyl)butyryl group, 5-(4-trifluoromethoxyphenyl)-pentanoyl group, 6-(4-trifluoromethoxyphenyl)hexanoyl group, 4-(4-trifluoromethoxyphenyl)butyryl group, 5-(4-pentafluoroethoxyphenyl)pentanoyl group, 6-(4-pentafluoroethoxyphenyl)hexanoyl group or the like.

A C1-20 alkoxycarbonyl group (which may be substituted on the alkoxy group by at least one group selected from a group consisting of a halogen atom, amino group which may have a C1-6 alkyl group as a substituent and C1-6 alkoxy group substituted by the C1-6 alkoxy group) is a group containing an alkoxy group having 1 to 20 carbon atoms which may have 1 to 7 groups selected from a group consisting of a halogen atom, amino group which may have the C1-6 alkyl group and C1-6 alkoxy group substituted by the C1-6 alkoxy group as a substituent and a carbonyl group, examples of which include a methoxycarbonyl group, ethoxycarbonyl group, n-propoxycarbonyl group, n-butoxycarbonyl group, n-pentyloxycarbonyl group, n-hexyloxycarbonyl group, n-heptyloxycarbonyl group, n-octyloxycarbonyl group, n-nonyloxycarbonyl group, n-decyloxycarbonyl group, n-undecyloxycarbonyl group, n-dodecyloxycarbonyl group, n-tridecyloxycarbonyl group, n-tetradecyloxycarbonyl group, n-pentadecyloxycarbonyl group, n-hexadecyloxycarbonyl group, n-heptadecyloxycarbonyl group, n-octadecyloxycarbonyl group, n-nonadecyloxycarbonyl group, n-icosyloxycarbonyl group, chloromethoxycarbonyl group, trichloromethoxycarbonyl group, 2-bromoethoxyoxycarbonyl group, 2,2-bromoethoxycarbonyl group, 3-fluoropropoxycarbonyl group, 4-iodobutoxycarbonyl group, 5,5,5,4,4,3,3-heptafluoropentyloxycarbonyl group, 4,4,4,3,3,2,2-heptafluorobutoxycarbonyl group, 5-chloropentyloxycarbonyl group, 6-bromohexyloxycarbonyl group, 7-chloroheptyloxycarbonyl group, 8-iodooctyloxyxycarbonyl group, 9-chlorononyloxycarbonyl group, 10-bromodecyloxycarbonyl group, 11-fluoroundecyloxycarbonyl group, 12-iodododecyloxycarbonyl group, 12-chlorododecyloxycarbonyl group, 13-fluorotridecyloxycarbonyl group, 14-bromotetradecyloxycarbonyl group, 15-iodopentadecyloxycarbonyl group, 16-chlorohexadecyloxycarbonyl group, 17-bromoheptadecyloxycarbonyl group, 18-fluorooctadecyloxycarbonyl group, 19-chlorononadecyloxy carbonyl group, 20-chloroicosyloxycarbonyl group, aminomethoxycarbonyl group, diethylaminomethoxycarbonyl group, 2-diethylaminoethoxycarbonyl group, 3-diethylaminopropoxycarbonyl group, 4-diethylaminobutoxycarbonyl group, 5-diethylaminopentyloxycarbonyl group, 6-diethylaminohexyloxycarbonyl group, 7-diethylaminoheptyloxycarbonyl group, 8-diethylaminooctyloxycarbonyl group, 9-diethylaminononyloxycarbonyl group, 10-diethylaminodecyloxycarbonyl group, 11-diethylaminoundecyloxycarbonyl group, 12-diethylaminododecyloxycarbonyl group, 13-diethylaminotridecyloxycarbonyl group, 14-diethylaminotetradecyloxycarbonyl group, 15-diethylaminopentadecyloxycarbonyl group, 16-diethylaminohexadecyloxycarbonyl group, 17-diethylaminoheptadecyloxycarbonyl group, 18-diethylaminooctadecyloxycarbonyl group, 19-diethylaminononadecyloxycarbonyl group, 20-diethylaminoicosyloxycarbonyl group, methoxyethoxymethoxycarbonyl group, 2-(2-ethoxyethoxy)ethoxycarbonyl group, 2-(2-propoxyethoxy)ethoxycarbonyl group, 2-(2-butoxyethoxy)ethoxycarbonyl group, 2-(2-pentyloxyethoxy)ethoxycarbonyl group, 2-(2-hexyloxyethoxy)-ethoxycarbonyl group, 2-methoxyethoxyethoxycarbonyl group, 3-(3-methoxypropoxy)propoxycarbonyl group, 4-(4-methoxybutoxy)butoxycarbonyl group, 5-(5-methoxypentyloxy)pentyloxycarbonyl group, 6-(6-methoxyhexyloxy)hexyloxycarbonyl group, 7-(2-methoxyethoxy)-heptyloxycarbonyl group, 8-(1-methoxyethoxy)-octyloxycarbonyl group, 9-(1-methoxyethoxy) nonyloxycarbonyl group, 10-(2-methoxyethoxy) decyloxycarbonyl group, 11-(2-methoxyethoxy) undecyloxyxycarbonyl group, 12-(2-methoxyethoxy) dodecyloxycarbonyl group, 12-(1-methoxyethoxy) dodecyloxycarbonyl group, 13-(2-methoxyethoxy) tridecyloxycarbonyl group, 14-(1-methoxyethoxy) tetradecyloxycarbonyl group, 15-(2-methoxyethoxy) pentadecyloxycarbonyl group, 16-(1-methoxyethoxy) hexadecyloxycarbonyl group, 17-(2-methoxyethoxy) heptadecyloxycarbonyl group, 18-(1-methoxyethoxy) octadecyloxycarbonyl group, 19-(2-methoxyethoxy) nonadecyloxycarbonyl group, 20-(1-methoxyethoxy) icosyloxycarbonyl group, dimethylaminomethoxycarbonyl group, 2-methylaminoethoxycarbonyl group, 3-(N-methyl-N-butylamino)propoxycarbonyl group, 4-propylaminobutoxycarbonyl group, 5-hexylaminopentyloxycarbonyl group, 6-pentylaminohexyloxycarbonyl group, 7-(N-ethyl-N-propylamino)heptyloxycarbonyl group, 8-(N-propyl-N-hexyl)aminooctyloxycarbonyl group, 9-(N-pentyl-N-methylamino)-nonyloxycarbonyl group, 10-dipropylaminodecyloxycarbonyl group, 11-dipentylaminoundecyloxycarbonyl group, 12-dihexylaminododecyloxycarbonyl group, 12-dibutylaminododecyloxycarbonyl group, 13-(N-ethyl-N-butylamino)tridecyloxycarbonyl group, 14-(N-methyl-N-hexylamino)tetradecyloxycarbonyl group, 15-dimethylaminopentadecyloxycarbonyl group, 16-dimethylaminohexadecyloxycarbonyl group, 17-dimethylaminoheptadecyloxycarbonyl group, 18-dimethylaminooctadecyloxycarbonyl group, 19-dimethylaminononadecyloxycarbonyl group, 20-dimethylaminoicosyloxycarbonyl group or the like.

Examples of a phenyl C1-6 alkoxycarbonyl group (which may be substituted on the phenyl ring by at least one group selected from a group consisting of a halogen atom, halogen-substituted or unsubstituted C1-6 alkyl group, halogen-substituted or unsubstituted C1-6 alkoxy group, nitro group, halogen-substituted or unsubstituted C1-6 alkylthio group, amino group which may have a C1-6 alkanoyl group, phenyl C1-6 alkoxy group, C1-6 alkoxycarbonyl group and 1,2,3-thiadiazolyl group) include a phenyl C1-6 alkoxycarbonyl group (which may be substituted on the phenyl ring by 1 to 5, preferably 1 to 3 groups selected from a group consisting of a halogen atom, halogen-substituted or unsubstituted C1-6 alkyl group, halogen-substituted or unsubstituted C1-6 alkoxy group, nitro group, halogen-substituted or unsubstituted C1-6 alkylthio group, amino group which may have 1 to 2 alkanoyl group, phenyl C1-6 alkoxy group, C1-6 alkoxycarbonyl group and 1,2,3-thiadiazolyl group), for example, a benzyloxycarbonyl group, 1-phenethyloxycarbonyl group, 2-phenethyloxycarbonyl group, 3-phenylpropoxycarbonyl group, 2-phenylpropoxycarbonyl group, 4-phenylbutoxycarbonyl group, 5-phenylpentyloxycarbonyl group, 4-phenylpentyloxycarbonyl group, 6-phenylhexyloxycarbonyl group, 2-fluorobenzyloxycarbonyl group, 3-fluorobenzyloxycarbonyl group, 4-fluorobenzyloxycarbonyl group, 2-chlorobenzyloxycarbonyl group, 3-chlorobenzyloxycarbonyl group, 4-chlorobenzyloxycarbonyl group, 2-bromobenzyloxycarbonyl group, 3-bromobenzyloxycarbonyl group, 4-bromobenzyloxycarbonyl group, 2-iodobenzyloxycarbonyl group, 3-iodobenzyloxycarbonyl group, 4-iodobenzyloxycarbonyl group, 2,3-difluorobenzyloxycarbonyl group, 3,4-difluorobenzyloxycarbonyl group, 3,5-difluorobenzyloxycarbonyl group, 2,4-difluorobenzyloxycarbonyl group, 2,6-difluorobenzyloxycarbonyl group, 2,4,6-trifluorobenzyloxycarbonyl group, 3,4,5-trifluorobenzyloxycarbonyl group, 2,3-dichlorobenzyloxycarbonyl group, 3,4-dichlorobenzyloxycarbonyl group, 3,5-dichlorobenzyloxycarbonyl group, 2,4-dichlorobenzyloxycarbonyl group, 2,6-dichlorobenzyloxycarbonyl group, 2,4,6-trichlorobenzyloxycarbonyl group, 3,4,5-trichlorobenzyloxycarbonyl group, 2,3,4,5,6-pentafluorobenzyloxycarbonyl group, 2-difluoromethylbenzyloxycarbonyl group, 3-difluoromethylbenzyloxycarbonyl group, 4-difluoromethylbenzyloxycarbonyl group, 4-chloro-3-difluoromethylbenzyloxycarbonyl group, 3-chloro-4-difluoromethylbenzyloxycarbonyl group, 3-bromo-4-difluoromethylbenzyloxycarbonyl group, 3,5-difluoro-4-difluoromethylbenzyloxycarbonyl group, 2-trifluoromethylbenzyloxycarbonyl group, 2-fluoro-4-bromobenzyloxycarbonyl group, 4-chloro-3-fluorobenzyloxycarbonyl group, 2,3,4-trichlorobenzyloxycarbonyl group, 4-isopropylbenzyloxycarbonyl group, 4-n-butylbenzyloxycarbonyl group, 4-methylbenzyloxycarbonyl group, 2-methylbenzyloxycarbonyl group, 3-methylbenzyloxycarbonyl group, 2,4-dimethylbenzyloxycarbonyl group, 2,3-dimethylbenzyloxycarbonyl group, 2,6-dimethylbenzyloxycarbonyl group, 3,5-dimethylbenzyloxycarbonyl group, 2,5-dimethylbenzyloxycarbonyl group, 2,4,6-trimethylbenzyloxycarbonyl group, 3,5-ditrifluoromethylbenzyloxycarbonyl group, 4-isopropoxybenzyloxycarbonyl group, 4-n-butoxybenzyloxycarbonyl group, 4-methoxybenzyloxycarbonyl group, 2-methoxybenzyloxycarbonyl group, 3-methoxybenzyloxycarbonyl group, 2,4-dimethoxybenzyloxycarbonyl group, 2,3-dimethoxybenzyloxycarbonyl group, 2,6-dimethoxybenzyloxycarbonyl group, 3,5-dimethoxybenzyloxycarbonyl group, 2,5-dimethoxybenzyloxycarbonyl group, 2,4,6-trimethoxybenzyloxycarbonyl group, 3,5-ditrifluoromethoxybenzyloxycarbonyl group, 2-isopropoxybenzyloxycarbonyl group, 3-chloro-4-methoxybenzyloxycarbonyl group, 2-chloro-4-fluoromethoxybenzyloxycarbonyl group, 3-methyl-4-fluorobenzyloxycarbonyl group, 4-bromo-3-trifluoromethylbenzyloxycarbonyl group, 3-trifluoromethylbenzyloxycarbonyl group, 4-trifluoromethylbenzyloxycarbonyl group, 4-fluoro-3-trifluoromethylbenzyloxycarbonyl group, 3-fluoro-4-trifluoromethylbenzyloxycarbonyl group, 2-pentafluoroethylbenzyloxycarbonyl group, 4-chloro-3-pentafluoroethylbenzyloxycarbonyl group, 3-chloro-4-pentafluoroethylbenzyloxycarbonyl group, 3-pentafluoroethylbenzyloxycarbonyl group, 4-pentafluoroethylbenzyloxycarbonyl group, 2-trifluoromethoxybenzyloxycarbonyl group, 3-trifluoromethoxybenzyloxycarbonyl group, 4-trifluoromethoxybenzyloxycarbonyl group, 4-fluoro-3-trifluoromethoxybenzyloxycarbonyl group, 3-fluoro-4-trifluoromethoxybenzyloxycarbonyl group, 2-pentafluoroethoxybenzyloxycarbonyl group, 3-pentafluoroethoxybenzyloxycarbonyl group, 4-pentafluoroethoxybenzyloxycarbonyl group, 3-chloro-4-trifluoromethoxybenzyloxycarbonyl group, 3-chloro-4-pentafluoroethoxybenzyloxycarbonyl group, 2-(2-trifluoromethylphenyl)ethoxycarbonyl group, 2-(3-trifluoromethylphenyl)ethoxycarbonyl group, 2-(4-trifluoromethylphenyl)ethoxycarbonyl group, (2-trifluoromethoxyphenyl)methoxycarbonyl group, (3-trifluoromethoxyphenyl)methoxycarbonyl group, 2-(4-trifluoromethoxyphenyl)ethoxycarbonyl group, 2-(2-pentafluoroethoxyphenyl)ethoxycarbonyl group, 2-(3-pentafluoroethoxyphenyl)ethoxycarbonyl group, 2-(4-pentafluoroethoxyphenyl)ethoxycarbonyl group, 3-(2-trifluoromethylphenyl)propoxycarbonyl group, 3-(3-trifluoromethylphenyl)propoxycarbonyl group, 3-(4-trifluoromethylphenyl)propoxycarbonyl group, 3-(2-trifluoromethoxyphenyl)propoxycarbonyl group, 3-(3-trifluoromethoxyphenyl)propoxycarbonyl group, 3-(4-trifluoromethoxyphenyl)propoxycarbonyl group, 3-(3-pentafluoroethoxyphenyl)propoxycarbonyl group, 3-(4-pentafluoroethoxyphenyl)propoxycarbonyl group, 4-(3-pentafluoroethoxyphenyl)butoxycarbonyl group, 5-(4-trifluoromethylphenyl)pentyloxycarbonyl group, 4-(4-trifluoromethylphenyl)pentyloxycarbonyl group, 4-(4-trifluoromethoxyphenyl)pentyloxycarbonyl group, 6-(3-trifluoromethylphenyl)hexyloxycarbonyl group, 6-(4-trifluoromethylphenyl)hexyloxycarbonyl group, 6-(4-trifluoromethoxyphenyl)hexyloxycarbonyl group, 2-methylthiobenzyloxycarbonyl group, 3-methylthiobenzyloxycarbonyl group, 4-methylthiobenzyloxycarbonyl group, 2-(2-methylthiophenyl)ethoxycarbonyl group, 2-(3-methylthiophenyl)ethoxycarbonyl group, 2-(4-methylthiophenyl)ethoxycarbonyl group, 3-(4-methylthiophenyl)propoxycarbonyl group, 4-(4-methylthiophenyl)butoxycarbonyl group, 5-(4-methylthiophenyl)-pentyloxycarbonyl group, 6-(4-methylthiophenyl)-hexyloxycarbonyl group, 2-trifluoromethylthiobenzyloxycarbonyl group, 3-trifluoromethylthiobenzyloxycarbonyl group, 4-trifluoromethylthiobenzyloxycarbonyl group, 2-(2-trifluoromethylthiophenyl)ethoxycarbonyl group, 2-(3-trifluoromethylthiophenyl)ethoxycarbonyl group, 2-(4-trifluoromethylthiophenyl)ethoxycarbonyl group, 3-(4-trifluoromethylthiophenyl)propoxycarbonyl group, 4-(4-trifluoromethylthiophenyl)butoxycarbonyl group, 5-(4-trifluoromethylthiophenyl)pentyloxycarbonyl group, 6-(4-trifluoromethylthiophenyl)hexyloxycarbonyl group, 2-benzyloxybenzyloxycarbonyl group, 3-benzyloxybenzyloxycarbonyl group, 4-benzyloxybenzyloxycarbonyl group, 2-(2-benzyloxyphenyl)ethoxycarbonyl group, 2-(3-benzyloxyphenyl)ethoxycarbonyl group, 2-(4-benzyloxyphenyl)ethoxycarbonyl group, 3-(4-benzyloxyphenyl)propoxycarbonyl group, 4-(4-benzyloxyphenyl)butoxycarbonyl group, 5-(4-benzyloxyphenyl)pentyloxycarbonyl group, 6-(4-benzyloxyphenyl)hexyloxycarbonyl group, 2-(2-phenylethoxy)benzyloxycarbonyl group, 3-(2-phenylethoxy)benzyloxycarbonyl group, 4-(2-phenylethoxy)benzyloxycarbonyl group, 2-[2-(2-phenylethoxy)phenyl]ethoxycarbonyl group, 2-[3-(2-phenylethoxy)phenyl]ethoxycarbonyl group, 2-[4-(2-phenylethoxy)phenyl]ethoxycarbonyl group, 3-(4-(2-phenylethoxyphenyl))propoxycarbonyl group, 4-(4-(2-phenylethoxyphenyl))butoxycarbonyl group, 5-(4-(2-phenylethoxyphenyl))pentyloxycarbonyl group, 6-(4-(2-phenylethoxyphenyl))hexyloxycarbonyl group, 2-(3-phenylpropoxy)benzyloxycarbonyl group, 3-(3-phenylpropoxy)benzyloxycarbonyl group, 4-(3-phenylpropoxy)benzyloxycarbonyl group, 2-(4-phenylbutoxy)benzyloxycarbonyl group, 3-(4-phenylbutoxy)benzyloxycarbonyl group, 4-(4-phenylbutoxy)benzyloxycarbonyl group, 2-methoxycarbonylbenzyloxycarbonyl group, 3-methoxycarbonylbenzyloxycarbonyl group, 4-methoxycarbonylbenzyloxycarbonyl group, 2-(2-methoxycarbonylphenyl)-ethoxycarbonyl group, 2-(3-methoxycarbonylphenyl)-ethoxycarbonyl group, 2-(4-methoxycarbonylphenyl)-ethoxycarbonyl group, 3-(4-methoxycarbonylphenyl)-propoxycarbonyl group, 4-(4-methoxycarbonylphenyl)-butoxycarbonyl group, 5-(4-methoxycarbonylphenyl)-pentyloxycarbonyl group, 6-(4-methoxycarbonylphenyl)-hexyloxycarbonyl group, 2-butyrylaminobenzyloxycarbonyl group, 3-butyrylaminobenzyloxycarbonyl group, 4-butyrylaminobenzyloxycarbonyl group, 2-(2-butyrylaminophenyl)ethoxycarbonyl group, 2-(3-butyrylaminophenyl)ethoxycarbonyl group, 2-(4-butyrylaminophenyl)ethoxycarbonyl group, 3-(4-butyrylaminophenyl)propoxycarbonyl group, 4-(4-butyrylaminophenyl)butoxycarbonyl group, 5-(4-butyrylaminophenyl)pentyloxycarbonyl group, 6-(4-butyrylaminophenyl)hexyloxycarbonyl group, 2-nitrobenzyloxycarbonyl group, 3-nitrobenzyloxycarbonyl group, 4-nitrobenzyloxycarbonyl group, 2-(2-nitrophenyl)ethoxycarbonyl group, 2-(3-nitrophenyl)ethoxycarbonyl group, 2-(2,4-dinitrophenyl)ethoxycarbonyl group, 2-(2,4,6-trinitrophenyl)methoxycarbonyl group, 2-(4-nitrophenyl)ethoxycarbonyl group, 3-(4-nitrophenyl)-propoxycarbonyl group, 4-(4-nitrophenyl)butoxycarbonyl group, 5-(4-nitrophenyl)pentyloxycarbonyl group, 6-(4-nitrophenyl)hexyloxycarbonyl group, 2-aminobenzyloxycarbonyl group, 3-aminobenzyloxycarbonyl group, 4-aminobenzyloxycarbonyl group, 2-(2-aminophenyl)ethoxycarbonyl group, 2-(3-aminophenyl)ethoxycarbonyl group, 2-(4-aminophenyl)ethoxycarbonyl group, 3-(4-aminophenyl)propoxycarbonyl group, 4-(4-aminophenyl)butoxycarbonyl group, 5-(4-aminophenyl)pentyloxycarbonyl group, 6-(4-aminophenyl)-hexyloxycarbonyl group, 2-acetylaminobenzyloxycarbonyl group, 3-propionylaminobenzyloxycarbonyl group, 4-pentanoylaminobenzyloxycarbonyl group, 2-(2-hexanoylaminophenyl)ethoxycarbonyl group, 2-(3-acetylaminophenyl)ethoxycarbonyl group, 2-(4-acetylaminophenyl)-ethoxycarbonyl group, 3-(4-acetylaminophenyl)propoxycarbonyl group, 4-(4-acetylaminophenyl)butoxycarbonyl group, 5-(4-acetylaminophenyl)pentyloxycarbonyl group, 6-(4-acetylaminophenyl)hexyloxycarbonyl group, 2-ethoxycarbonylbenzyloxycarbonyl group, 3-ethoxycarbonylbenzyloxycarbonyl group, 4-ethoxycarbonylbenzyloxycarbonyl group, 2-(2-ethoxycarbonylphenyl)-ethoxycarbonyl group, 2-(3-butoxycarbonylphenyl)-ethoxycarbonyl group, 2-(4-propoxycarbonylphenyl)-ethoxycarbonyl group, 3-(4-ethoxycarbonylphenyl)-propoxycarbonyl group, 4-(4-pentyloxycarbonylphenyl)-butoxycarbonyl group, 5-(4-hexyloxycarbonylphenyl)-pentyloxycarbonyl group, 6-(4-ethoxycarbonylphenyl)-hexyloxycarbonyl group, 2-(1,2,3-thiadiazol-4-yl)benzyloxycarbonyl group, 3-(1,2,3-thiadiazol-4-yl)benzyloxycarbonyl group, 4-(1,2,3-thiadiazol-4-yl)benzyloxycarbonyl group or the like.

A phenyl C3-6 alkenyloxycarbonyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) is a group containing a phenyl group unsubstituted or substituted by 1 to 5, preferably 1 to 3 groups selected from a group consisting of a halogen atom, a halogen C1-6 alkyl group and a halogen-substituted or unsubstituted C1-6 alkoxy group, an alkenyloxy group having 3 to 6 carbon atoms and 1 to 3 double bonds, and a carbonyl group. These groups may be either in trans or cis form and both forms are included as a matter of course. For example, included is an unsubstituted 3-phenyl-2-propenyloxycarbonyl group (trivial name: cinnamyloxycarbonyl group), 4-phenyl-2-butenyloxycarbonyl group, 4-phenyl-3-butenyloxycarbonyl group, 5-phenyl-2-pentenyloxycarbonyl group, 5-phenyl-4-pentenyloxycarbonyl group, 5-phenyl-3-pentenyloxycarbonyl group, 6-phenyl-5-hexenyloxycarbonyl group, 6-phenyl-4-hexenyloxycarbonyl group, 6-phenyl-3-hexenyloxycarbonyl group, 4-phenyl-1,3-butadienyloxycarbonyl group, 6-phenyl-1,3,5-hexatrienyloxycarbonyl group, 6-phenyl-3-hexenyloxycarbonyl group, 3-(2-fluorophenyl)-2-propenyloxycarbonyl group, 3-(3-fluorophenyl)-2-propenyloxycarbonyl group, 3-(4-fluorophenyl)-2-propenyloxycarbonyl group, 3-(2,3-difluorophenyl)-2-propenyloxycarbonyl group, 3-(2,4-difluorophenyl)-2-propenyloxycarbonyl group, 3-(3,4-difluorophenyl)-2-propenyloxycarbonyl group, 3-(3,5-difluorophenyl)-2-propenyloxycarbonyl group, 3-(2-chlorophenyl)-2-propenyloxycarbonyl group, 3-(3-chlorophenyl)-2-propenyloxycarbonyl group, 3-(4-chlorophenyl)-2-propenyloxycarbonyl group, 3-(2,3-dichlorophenyl)-2-propenyloxycarbonyl group, 3-(2,4-dichlorophenyl)-2-propenyloxycarbonyl group, 3-(3,4-dichlorophenyl)-2-propenyloxycarbonyl group, 3-(3,5-dichlorophenyl)-2-propenyloxycarbonyl group, 3-(2-bromophenyl)-2-propenyloxycarbonyl group, 3-(3-bromophenyl)-2-propenyloxycarbonyl group, 3-(4-bromophenyl)-2-propenyloxycarbonyl group, 3-(2-fluoro-4-bromophenyl)-2-propenyloxycarbonyl group, 3-(2,3,4,5,6-pentafluorophenyl)-2-propenyloxycarbonyl group, 3-(4-chloro-3-fluorophenyl)-2-propenyloxycarbonyl group, 3-(2,3,4-trichlorophenyl)-2-propenyloxycarbonyl group, 3-(2,4,6-trichlorophenyl)-2-propenyloxycarbonyl group, 3-(4-isopropylphenyl)-2-propenyloxycarbonyl group, 3-(4-n-butylphenyl)-2-propenyloxycarbonyl group, 3-(2,4-dimethylphenyl)-2-propenyloxycarbonyl group, 3-(2,3-dimethylphenyl)-2-propenyloxycarbonyl group, 3-(2,6-dimethylphenyl)-2-propenyloxycarbonyl group, 3-(3,5-dimethylphenyl)-2-propenyloxycarbonyl group, 3-(2,5-dimethylphenyl)-2-propenyloxycarbonyl group, 3-(2,4,6-trimethylphenyl)-2-propenyloxycarbonyl group, 3-(3,5-ditrifluoromethylphenyl)-2-propenyloxycarbonyl group, 3-(4-n-butoxyphenyl)-2-propenyloxycarbonyl group, 3-(2,4-dimethoxyphenyl)-2-propenyloxycarbonyl group, 3-(2,3-dimethoxyphenyl)-2-propenyloxycarbonyl group, 3-(2,6-dimethoxyphenyl)-2-propenyloxycarbonyl group, 3-(3,5- dimethoxyphenyl)-2-propenyloxycarbonyl group, 3-(2,5-dimethoxyphenyl)-2-propenyloxycarbonyl group, 3-(3,5-ditrifluoromethoxyphenyl)-2-propenyloxycarbonyl group, 3-(3-chloro-4-methoxyphenyl)-2-propenyloxycarbonyl group, 3-(2-chloro-4-trifluoromethoxyphenyl)-2-propenyloxycarbonyl group, 3-(3-methyl-4-fluorophenyl)-2-propenyloxycarbonyl group, 3-(4-bromo-3-trifluoromethylphenyl)-2-propenyloxycarbonyl group, 3-(2-methylphenyl)-2-propenyloxycarbonyl group, 3-(3-methylphenyl)-2-propenyloxycarbonyl group, 3-(4-methylphenyl)-2-propenyloxycarbonyl group, 3-(2-trifluoromethylphenyl)-2-propenyloxycarbonyl group, 3-(3-trifluoromethylphenyl)-2-propenyloxycarbonyl group, 3-(4-trifluoromethylphenyl)-2-propenyloxycarbonyl group, 3-(2-trifluoromethoxyphenyl)-2-propenyloxycarbonyl group, 3-(3-trifluoromethoxyphenyl)-2-propenyloxycarbonyl group, 3-(4-trifluoromethoxyphenyl)-2-propenyloxycarbonyl group, 3-(2-methoxyphenyl)-2-propenyloxycarbonyl group, 3-(3-methoxyphenyl)-2-propenyloxycarbonyl group, 3-(4-methoxyphenyl)-2-propenyloxycarbonyl group, 3-(3,4-dimethoxyphenyl)-2-propenyloxycarbonyl group, 4-(4-chlorophenyl)-2-butenyloxycarbonyl group, 4-(4-chlorophenyl)-3-butenyloxycarbonyl group, 5-(4-chlorophenyl)-2-pentenyloxycarbonyl group, 5-(4-chlorophenyl)-4-pentenyloxycarbonyl group, 5-(4-chlorophenyl)-3-pentenyloxycarbonyl group, 6-(4-chlorophenyl)-5-hexenyloxycarbonyl group, 6-(4-chlorophenyl)-4-hexenyloxycarbonyl group, 6-(4-chlorophenyl)-3-hexenyloxycarbonyl group, 6-(4-chlorophenyl)-2-hexenyloxycarbonyl group or the like.

A phenoxycarbonyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) includes, a phenoxycarbonyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group), for example, a phenoxycarbonyl group, 2-fluorophenoxycarbonyl group, 3-fluorophenoxycarbonyl group, 2,3,4,5,6-pentafluorophenoxycarbonyl group, 4-fluorophenoxycarbonyl group, 2-chlorophenoxycarbonyl group, 3-chlorophenoxycarbonyl group, 4-chlorophenoxycarbonyl group, 2,3-dichlorophenoxycarbonyl group, 3,4-dichlorophenoxycarbonyl group, 3,5-dichlorophenoxycarbonyl group, 2-bromophenoxycarbonyl group, 3-bromophenoxycarbonyl group, 4-bromophenoxycarbonyl group, 2-methylphenoxycarbonyl group, 3-methylphenoxycarbonyl group, 4-methylphenoxycarbonyl group, 2-ethylphenoxycarbonyl group, 3-ethylphenoxycarbonyl group, 4-ethylphenoxycarbonyl group, 4-propylphenoxycarbonyl group, 4-tert-butylphenoxycarbonyl group, 4-butylphenoxycarbonyl group, 2,3-dimethylphenoxycarbonyl group, 3,4,5-trimethylphenoxycarbonyl group, 4-pentylphenoxycarbonyl group, 4-hexylphenoxycarbonyl group, 2-fluoro-4-bromophenoxycarbonyl group, 4-chloro-3-fluorophenoxycarbonyl group, 2,3,4-trichlorophenoxycarbonyl group, 2,4,6-trichlorophenoxycarbonyl group, 4-isopropylphenoxycarbonyl group, 4-n-butylphenoxycarbonyl group, 2,4-dimethylphenoxycarbonyl group, 2,6-dimethylphenoxycarbonyl group, 3,5-dimethylphenoxycarbonyl group, 2,5-dimethylphenoxycarbonyl group, 2,4,6-trimethylphenoxycarbonyl group, 3,5-ditrifluoromethylphenoxycarbonyl group, 4-n-butoxyphenoxycarbonyl group, 2,4-dimethoxyphenoxycarbonyl group, 2,3-dimethoxyphenoxycarbonyl group, 2,6-dimethoxyphenoxycarbonyl group, 3,5-dimethoxyphenoxycarbonyl group, 2,5-dimethoxyphenoxycarbonyl group, 3,5-ditrifluoromethoxyphenoxycarbonyl group, 3-chloro-4-methoxyphenoxycarbonyl group, 2-chloro-4-trifluoromethoxyphenoxycarbonyl group, 3-methyl-4-fluorophenoxycarbonyl group, 4-bromo-3-trifluoromethylphenoxycarbonyl group, 2-trifluoromethylphenoxycarbonyl group, 3-trifluoromethylphenoxycarbonyl group, 4-trifluoromethylphenoxycarbonyl group, 2-pentafluoroethylphenoxycarbonyl group, 3-pentafluoroethylphenoxycarbonyl group, 4-pentafluoroethylphenoxycarbonyl group, 2-methoxyphenoxycarbonyl group, 3-methoxyphenoxycarbonyl group, 4-methoxyphenoxycarbonyl group, 2-ethoxyphenoxycarbonyl group, 3-ethoxyphenoxycarbonyl group, 4-ethoxyphenoxycarbonyl group, 4-propoxyphenoxycarbonyl group, 4-tert-butoxyphenoxycarbonyl group, 4-n-butoxyphenoxycarbonyl group, 3,4,5-trimethoxyphenoxycarbonyl group, 4-pentoxyphenoxycarbonyl group, 4-hexyloxyphenoxycarbonyl group, 2-trifluoromethoxyphenoxycarbonyl group, 3-trifluoromethoxyphenoxycarbonyl group, 4-trifluoromethoxyphenoxycarbonyl group, 2-pentafluoroethoxyphenoxycarbonyl group, 3-pentafluoroethoxyphenoxycarbonyl group, 4-pentafluoroethoxyphenoxycarbonyl group or the like.

A phenyl C1-6 alkylcarbamoyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) includes a phenyl C1-6 alkylcarbamoyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group), for example, a benzylcarbamoyl group, 2-phenethylcarbamoyl group, 3-phenylpropylcarbamoyl group, 2-phenylpropylcarbamoyl group, 4-phenylbutylcarbamoyl group, 5-phenylpentycarbamoyl group, 4-phenylpentylcarbamoyl group, 6-phenylhexylcarbamoyl group, 2-fluorobenzylcarbamoyl group, 3-fluorobenzylcarbamoyl group, 4-fluorobenzylcarbamoyl group, 2-chlorobenzylcarbamoyl group, 3-chlorobenzylcarbamoyl group, 4-chlorobenzylcarbamoyl group, 2-bromobenzylcarbamoyl group, 3-bromobenzylcarbamoyl group, 4-bromobenzylcarbamoyl group, 2-iodobenzylcarbamoyl group, 3-iodobenzylcarbamoyl group, 4-iodobenzylcarbamoyl group, N-benzyl-N-methylcarbamoyl group, N-methyl-N-(2-phenethyl)carbamoyl group, N-methyl-N-(3-phenylpropyl)carbamoyl group, N-methyl-N-(2-phenylpropyl)carbamoyl group, N-methyl-N-(4-phenylbutyl)carbamoyl group, N-methyl-N-(5-phenylpentyl)carbamoyl group, N-methyl-N-(4-phenylpentyl)carbamoyl group, N-methyl-N-(6-phenylhexyl)carbamoyl group, N-(2-fluorobenzyl)-N-methylcarbamoyl group, N-(3-fluorobenzyl)-N-methylcarbamoyl group, N-(4-fluorobenzyl)-N-methylcarbamoyl group, N-(2-chlorobenzyl)-N-methylcarbamoyl group, N-(3-chlorobenzyl)-N-methylcarbamoyl group, N-(4-chlorobenzyl)-N-methylcarbamoyl group, N-(2-bromobenzyl)-N-methylcarbamoyl group, N-(3-bromobenzyl)-N-methylcarbamoyl group, N-(4-bromobenzyl)-N-methylcarbamoyl group, N,N-dibenzylcarbamoyl group, N-benzyl-N-(2-phenethyl)carbamoyl group, N-benzyl-(3-phenylpropyl)carbamoyl group, N-benzyl-N-(2-phenylpropyl)carbamoyl group, N-benzyl-N-(4-phenylbutyl)carbamoyl group, N-benzyl-N-(5-phenylpentyl)carbamoyl group, N-benzyl-N-(4-phenylpentyl)carbamoyl group, N-benzyl-N-(6- phenylhexyl)-carbamoyl group, N-benzyl-N-(2-fluorobenzyl)carbamoyl group, N-benzyl-N-(3-fluorobenzyl)carbamoyl group, N-benzyl-N-(4-fluorobenzyl)carbamoyl group, N-benzyl-N-(2-chlorobenzyl)carbamoyl group, N-benzyl-N-(3-chloro-benzyl)carbamoyl group, N-benzyl-N-(4-chlorobenzyl)-carbamoyl group, N-benzyl-N-(2-bromobenzyl)carbamoyl group, N-benzyl-N-(3-bromobenzyl)carbamoyl group, N-benzyl-N-(4-bromobenzyl)carbamoyl group, 2,3-difluorobenzylcarbamoyl group, 3,4-difluorobenzylcarbamoyl group, 3,5-difluorobenzylcarbamoyl group, 2,4-difluorobenzylcarbamoyl group, 2,6-difluorobenzylcarbamoyl group, 2,3-dichlorobenzylcarbamoyl group, 3,4-dichlorobenzylcarbamoyl group, 3,5-dichlorobenzylcarbamoyl group, 2,4-dichlorobenzylcarbamoyl group, 2,6-dichlorobenzylcarbamoyl group, 2-fluoro-4-bromobenzylcarbamoyl group, 4-chloro-3-fluorobenzylcarbamoyl group, 2,3,4-trichlorobenzylcarbamoyl group, 3,4,5-trifluorobenzylcarbamoyl group, 2,4,6-trichloro benzylcarbamoyl group, 4-isopropylbenzylcarbamoyl group, 4-n-butylbenzylcarbamoyl group, 4-methylbenzylcarbamoyl group, 2-methylbenzylcarbamoyl group, 3-methylbenzylcarbamoyl group, 2,4-dimethylbenzylcarbamoyl group, 2,3-dimethylbenzylcarbamoyl group, 2,6-dimethylbenzylcarbamoyl group, 3,5-dimethylbenzylcarbamoyl group, 2,5-dimethylbenzylcarbamoyl group, 2,4,6-trimethylbenzylcarbamoyl group, 3,5-ditrifluoromethylbenzylcarbamoyl group, 4-isopropylbenzylcarbamoyl group, 4-n-butoxybenzylcarbamoyl group, 4-methoxy-benzylcarbamoyl group, 2-methoxybenzylcarbamoyl group, 3-methoxybenzylcarbamoyl group, 2,4-dimethoxybenzylcarbamoyl group, 2,3-dimethoxybenzylcarbamoyl group, 2,6-dimethoxybenzylcarbamoyl group, 3,5-dimethoxybenzylcarbamoyl group, 2,5-dimethoxybenzylcarbamoyl group, 2,4,6-trimethoxybenzylcarbamoyl group, 3,5-ditrifluoromethoxybenzylcarbamoyl group, 2-isopropoxybenzylcarbamoyl group, 3-chloro-4-methoxybenzylcarbamoyl group, 2-chloro-4-trifluoromethoxybenzylcarbamoyl group, 3-methyl-4-fluorobenzylcarbamoyl group, 4-bromo-3-trifluoromethylbenzylcarbamoyl group, 2-trifluoromethoxybenzylcarbamoyl group, 3-trifluoromethylbenzylcarbamoyl group, 4-trifluoromethylbenzylcarbamoyl group, 2-pentafluoroethylbenzylcarbamoyl group, 3-pentafluoroethylbenzylcarbamoyl group, 4-pentafluoroethylbenzylcarbamoyl group, 2-trifluoromethoxybenzylcarbamoyl group, 3-trifluoromethoxybenzylcarbamoyl group, 4-trifluoromethoxybenzylcarbamoyl group, 2-pentafluoroethoxybenzylcarbamoyl group, 3-pentafluoroethoxybenzylcarbamoyl group, 4-pentafluoroethoxybenzylcarbamoyl group, 2-(2-trifluoromethylphenyl)ethylcarbamoyl group, 2-(3-trifluoromethylphenyl)ethylcarbamoyl group, 2-(4-trifluoromethylphenyl)ethylcarbamoyl group, 2-(2-trifluoromethoxyphenyl)ethylcarbamoyl group, 2-(3-trifluoromethoxyphenyl)ethylcarbamoyl group, 2-(4-trifluoromethoxyphenyl)ethylcarbamoyl group, 2-(2-pentafluoroethoxyphenyl)ethylcarbamoyl group, 2-(3-pentafluoroethoxyphenyl)ethylcarbamoyl group, 2-(4-pentafluoroethoxyphenyl)ethylcarbamoyl group, 3-(2-trifluoromethylphenyl)propylcarbamoyl group, 3-(3-trifluoromethylphenyl)propylcarbamoyl group, 3-(4-trifluoromethylphenyl)propylcarbamoyl group, 3-(2-trifluoromethoxyphenyl)propylcarbamoyl group, 3-(3-trifluoromethoxyphenyl)propylcarbamoyl group, 3-(4-trifluoromethoxyphenyl)propylcarbamoyl group, 3-(3-pentafluoroethoxyphenyl)propylcarbamoyl group, 3-(4-pentafluoroethoxyphenyl)propylcarbamoyl group, 4-(3-pentafluoroethoxyphenyl)butylcarbamoyl group, 5-(4-trifluoromethylphenyl)pentylcarbamoyl group, 4-(4-trifluoromethylphenyl)pentylcarbamoyl group, 4-(4-trifluoromethoxyphenyl)pentylcarbamoyl group, 6-(3-trifluoromethylphenyl)hexylcarbamoyl group, 6-(4-trifluoromethylphenyl)hexylcarbamoyl group, 6-(4-trifluoromethoxyphenyl)hexylcarbamoyl group or the like.

A benzofuryl-substituted C1-6 alkoxycarbonyl group which may be substituted on the benzofuran ring by at least one halogen atom includes a benzofuryl-substituted C1-6 alkoxycarbonyl group which may be substituted on the benzofuran ring by 1 to 3 halogen atoms, for example, a 2-benzofurylmethoxycarbonyl group, 1-(2-benzofuryl)ethoxycarbonyl group, 2-(4-benzofuryl)ethoxycarbonyl group, 3-(5-benzofuryl)propoxycarbonyl group, 4-(6-benzofuryl)butoxycarbonyl group, 5-(7-benzofuryl)pentyloxycarbonyl group, 6-(2-benzofuryl)hexyloxycarbonyl group, 4-fluoro-2-benzofurylmethoxycarbonyl group, 5-fluoro-2-benzofurylmethoxycarbonyl group, 6-fluoro-2-benzofurylmethoxycarbonyl group, 7-fluoro-2-benzofurylmethoxycarbonyl group, 4-chlororo-2-benzofurylmethoxycarbonyl group, 5-chlororo-2-benzofurylmethoxycarbonyl group, 6-chlororo-2-benzofurylmethoxycarbonyl group, 7-chlororo-2-benzofurylmethoxycarbonyl group, 4-bromo-2-benzofurylmethoxycarbonyl group, 5-bromo-2-benzofurylmethoxycarbonyl group, 6-bromo-2-benzofurylmethoxycarbonyl group, 7-bromo-2-benzofurylmethoxycarbonyl group, 4-iodo-2-benzofurylmethoxycarbonyl group, 5-iodo-2-benzofurylmethoxycarbonyl group, 6-iodo-2-benzofurylmethoxycarbonyl group, 7-iodo-2-benzofurylmethoxycarbonyl group, 4-fluoro-3-benzofurylmethoxycarbonyl group, 5-fluoro-3-benzofurylmethoxycarbonyl group, 6-fluoro-3-benzofurylmethoxycarbonyl group, 7-fluoro-3-benzofurylmethoxycarbonyl group, 4-chlororo-3-benzofurylmethoxycarbonyl group, 5-chlororo-3-benzofurylmethoxycarbonyl group, 6-chlororo-3-benzofurylmethoxycarbonyl group, 7-chlororo-3-benzofurylmethoxycarbonyl group, 4-bromo-3-benzofurylmethoxycarbonyl group, 5-bromo-3-benzofurylmethoxycarbonyl group, 6-bromo-3-benzofurylmethoxycarbonyl group, 7-bromo-3-benzofurylmethoxycarbonyl group, 4-iodo-3-benzofurylmethoxycarbonyl group, 5-iodo-3-benzofurylmethoxycarbonyl group, 6-iodo-3-benzofurylmethoxycarbonyl group, 7-iodo-3-benzofurylmethoxycarbonyl group, 2-(4-fluoro-2-benzofuryl)ethoxycarbonyl group, 2-(5-fluoro-2-benzofuryl)ethoxycarbonyl group, 2-(6-fluoro-2-benzofuryl)ethoxycarbonyl group, 2-(7-fluoro-2-benzofuryl)ethoxycarbonyl group, 2-(4-chloro-2-benzofuryl)ethoxycarbonyl group, 2-(5-chloro-2-benzofuryl)ethoxycarbonyl group, 2-(6-chloro-2-benzofuryl)ethoxycarbonyl group, 2-(7-chloro-2-benzofuryl)ethoxycarbonyl group, 2-(4-fluoro-3-benzofuryl)ethoxycarbonyl group, 2-(5-fluoro-3-benzofuryl)ethoxycarbonyl group, 2-(6-fluoro-3-benzofuryl)ethoxycarbonyl group, 2-(7-fluoro-3-benzofuryl)ethoxycarbonyl group, 2-(4-chloro-3-benzofuryl)ethoxycarbonyl group, 2-(5-chloro-3-benzofuryl)ethoxycarbonyl group, 2-(6-chloro-3-benzofuryl)ethoxycarbonyl group, 2-(7-chloro-3-benzofuryl)ethoxycarbonyl group, 6-(4-fluoro-2-benzofuryl)hexyloxycarbonyl group, 6-(5-fluoro-2-benzofuryl)hexyloxycarbonyl group, 6-(6-fluoro-2-benzofuryl)hexyloxycarbonyl group, 6-(7-fluoro-2-benzofuryl)hexyloxycarbonyl group, 6-(4-chloro-2- benzofuryl)hexyloxycarbonyl group, 6-(5-chloro-2-benzofuryl)hexyloxycarbonyl group, 6-(6-chloro-2-benzofuryl)hexyloxycarbonyl group, 6-(7-chloro-2-benzofuryl)hexyloxycarbonyl group, 6-(4-fluoro-2-benzofuryl)ethoxycarbonyl group, 6-(5-fluoro-3-benzofuryl)hexyloxycarbonyl group, 6-(6-fluoro-3-benzofuryl)hexyloxycarbonyl group, 6-(7-fluoro-3-benzofuryl)hexyloxycarbonyl group, 6-(4-chloro-3-benzofuryl)hexyloxycarbonyl group, 6-(5-chloro-3-benzofuryl)hexyloxycarbonyl group, 6-(6-chloro-3-benzofuryl)hexyloxycarbonyl group, 6-(7-chloro-3-benzofuryl)hexyloxycarbonyl group, (2,4-dibromo-3-benzofuryl)methoxycarbonyl group, (4,5,6-trichloro-3-benzofuryl)methoxycarbonyl group or the like.

A benzothienyl C1-6 alkoxycarbonyl group (which may be substituted on the benzothiophene ring by at least one group selected from a group consisting of a halogen atom and halogen-substituted or unsubstituted C1-6 alkoxy group as a substituent) includes a benzothienyl C1-6 alkoxycarbonyl group (which may be substituted on the benzothiophene ring by 1 to 3 groups selected from a group consisting of a halogen atom and halogen-substituted or unsubstituted C1-6 alkoxy group as a substituent), for example, a 2-benzothienylmethoxycarbonyl group, 3-benzothienylmethoxycarbonyl group, 4-benzothienylmethoxycarbonyl group, 5-benzothienylmethoxycarbonyl group, 6-benzothienylmethoxycarbonyl group, 7-benzothienylmethoxycarbonyl group, 2-(2-benzothienyl)ethoxycarbonyl group, 3-(2-benzothienyl)propoxycarbonyl group, 4-(2-benzothienyl)-butoxycarbonyl group, 5-(2-benzothienyl)pentyloxycarbonyl group, 6-(2-benzothienyl)hexyloxycarbonyl group, 5-trifluoromethoxy-2-benzothienylmethoxycarbonyl group, 5-trifluoromethoxy-3-benzothienylmethoxycarbonyl group, 5-trifluoromethoxy-4-benzothienylmethoxycarbonyl group, 4-trifluoromethoxy-5-benzothienylmethoxycarbonyl group, 3-trifluoromethoxy-6-benzothienylmethoxycarbonyl group, 2-trifluoromethoxy-7-benzothienylmethoxycarbonyl group, 2-methoxy-7-benzothienylmethoxycarbonyl group, 5,6-dimethoxy-3-benzothienylmethoxycarbonyl group, 2,5,6-trimethoxy-3-benzothienylmethoxycarbonyl group, 5-chloro-6-methoxy-3-benzothienylmethoxycarbonyl group, 2-(4-ethoxy-2-benzothienyl)ethoxycarbonyl group, 5-chloro-3-benzothienylmethoxycarbonyl group, 3,4-dibromo-2-benzothienylmethoxycarbonyl group, 4,5,6-trichloro-2-benzothienylmethoxycarbonyl group, 5-trifluoromethoxy-2-chloro-7-benzothienylmethoxycarbonyl group or the like.

Examples of a naphthyl-substituted C1-6 alkoxycarbonyl group include a 1-naphthylmethoxycarbonyl group, 2-naphthylmethoxycarbonyl group, 2-(1-naphthyl)ethoxycarbonyl group, 2-(2-naphthyl)ethoxycarbonyl group, 3-(1-naphthyl)propoxycarbonyl group, 3-(2-naphthyl)propoxycarbonyl group, 4-(1-naphthyl)-butoxycarbonyl group, 4-(2-naphthyl)butoxycarbonyl group, 5-(1-naphthyl)pentoxycarbonyl group, 5-(2-naphthyl)pentoxycarbonyl group, 6-(1-naphthyl)hexyloxycarbonyl group, 6-(2-naphthyl)hexyloxycarbonyl group or the like.

A pyridyl-substituted C1-6 alkoxycarbonyl group (which may be substituted on the pyridine ring by at least one halogen atom as a substituent) includes a pyridyl-substituted C1-6 alkoxycarbonyl group (which may be substituted on the pyridine ring by 1 to 3 halogen atoms as a substituent), for example, a 2-pyridylmethoxycarbonyl group, 3-pyridylmethoxycarbonyl group, 4-pyridylmethoxycarbonyl group, 2-(2-pyridyl)ethoxycarbonyl group, 2-(3-pyridyl)ethoxycarbonyl group, 2-(4-pyridyl)ethoxycarbonyl group, 3-(2-pyridyl)propoxycarbonyl group, 3-(3-pyridyl)propoxycarbonyl group, 3-(4-pyridyl)propoxycarbonyl group, 4-(2-pyridyl)butoxycarbonyl group, 4-(3-pyridyl)butoxycarbonyl group, 4-(4-pyridyl)butoxycarbonyl group, 5-(2-pyridyl)pentyloxycarbonyl group, 5-(3-pyridyl)-pentyloxycarbonyl group, 5-(4-pyridyl)pentyloxycarbonyl group, 6-(2-pyridyl)hexyloxycarbonyl group, 6-(3-pyridyl)hexyloxycarbonyl group, 6-(4-pyridyl)hexyloxycarbonyl group, 2-chloro-3-pyridylmethoxycarbonyl group, 3-bromo-2-pyridylmethoxycarbonyl group, 4-fluoro-2-pyridylmethoxycarbonyl group, 2-(2-chloro-4-pyridyl)ethoxycarbonyl group, 2-(3-chloro-5-pyridyl)-ethoxycarbonyl group, 2-(4-iodo-3-pyridyl)ethoxycarbonyl group, 3-(2-bromo-5-pyridyl)propoxycarbonyl group, 3-(3-fluoro-4-pyridyl)propoxycarbonyl group, 3-(4-chloro-2-pyridyl)propoxycarbonyl group, 4-(2-iodo-5-pyridyl)butoxycarbonyl group, 4-(3-bromo-5-pyridyl)-butoxycarbonyl group, 4-(4-chloro-5-pyridyl)butoxycarbonyl group, 5-(2-chloro-5-pyridyl)pentyloxycarbonyl group, 5-(3-fluoro-2-pyridyl)pentyloxycarbonyl group, 5-(4-bromo-2-pyridyl)pentyloxycarbonyl group, 6-(2-chloro-5-pyridyl)hexyloxycarbonyl group, 6-(3-fluoro-4-pyridyl)hexyloxycarbonyl group, 6-(4-bromo-2-pyridyl)hexyloxycarbonyl group, (2,6-dichloro-4-pyridyl)methoxycarbonyl group, (2,3,4-trichloro-6-pyridyl)methoxycarbonyl group or the like.

A furyl-substituted C1-6 alkoxycarbonyl group (which may be substituted on the furan ring by at least one nitro group as a substituent) includes a furyl-substituted C1-6 alkoxycarbonyl group (which may be substituted on the furan ring by 1 to 3 nitro groups as a substituent), for example, a 2-furylmethoxycarbonyl group, 3-furylmethoxycarbonyl group, 2-(2-furyl)ethoxycarbonyl group, 3-(2-furyl)propoxycarbonyl group, 3-(3-furyl)propoxycarbonyl group, 4-(2-furyl)butoxycarbonyl group, 4-(3-furyl)butoxycarbonyl group, 5-(2-furyl)pentyloxycarbonyl group, 5-(3-furyl)pentyloxycarbonyl group, 6-(2-furyl)hexyloxycarbonyl group, 6-(3-furyl)hexyloxycarbonyl group, 5-nitro-2-furylmethoxycarbonyl group, 5-nitro-3-furylmethoxycarbonyl group, 2-(5-nitro-2-furyl)ethoxycarbonyl group, 3-(5-nitro-2-furyl)propoxycarbonyl group, 4-(5-nitro-2-furyl)butoxycarbonyl group, 4-(5-nitro-3-furyl)butoxycarbonyl group, 5-(5-nitro-2-furyl)pentyloxycarbonyl group, 5-(5-nitro-3-furyl)pentyloxycarbonyl group, 6-(5-nitro-2-furyl)hexyloxycarbonyl group, 6-(5-nitro-3-furyl)hexyloxycarbonyl group, (4,5-dinitro-2-furyl)methoxycarbonyl group, (2,4,5-trinitro-3-furyl)methoxycarbonyl group or the like.

A thienyl-substituted C1-6 alkoxycarbonyl group (which may be substituted on the thiophene ring by at least one halogen atom as a substituent) includes a thienyl-substituted C1-6 alkoxycarbonyl group (which may be substituted on the thiophene ring by 1 to 3 halogen atoms as a substituent), for example, a 2-thienylmethoxycarbonyl group, 3-thienylmethoxycarbonyl group, 2-(2-thienyl)ethoxycarbonyl group, 3-(2-thienyl)propoxycarbonyl group, 3-(3-thienyl)propoxycarbonyl group, 4-(2-thienyl)butoxycarbonyl group, 4-(3-thienyl)butoxycarbonyl group, 5-(2-thienyl)-pentyloxycarbonyl group, 5-(3-thienyl)pentyloxycarbonyl group, 6-(2-thienyl)hexyloxycarbonyl group, 6-(3-thienyl)hexyloxycarbonyl group, 5-chloro-2-thienylmethoxycarbonyl group, 5-chloro-3-thienylmethoxycarbonyl group, 2-(4-bromo-2-thienyl)ethoxycarbonyl group, 3-(3-fluoro-2-thienyl)propoxycarbonyl group, 4-(5-iodo-2-thienyl)butoxycarbonyl group, 4-(4-chloro-3-thienyl)butoxycarbonyl group, 5-(3-chloro-2-thienyl)pentyloxycarbonyl group, 5-(2-chloro-3-thienyl)pentyloxycarbonyl group, 6-(3-chloro-2-thienyl)hexyloxycarbonyl group, 6-(5-chloro-3-thienyl)hexyloxycarbonyl group, (4,5-dichloro-2-thienyl)

methoxycarbonyl group, (2,4,5-trichloro-3-thienyl)methoxycarbonyl group or the like.

A thiazolyl-substituted C1-6 alkoxycarbonyl group (which may be substituted on the thiazole ring by at least one group selected from a group consisting of a C1-6 alkyl group and a phenyl group (which may be substituted on the phenyl ring by a halogen-substituted or unsubstituted C1-6 alkyl group)) includes a thiazolyl-substituted C1-6 alkoxycarbonyl group (which may be substituted on the thiazole ring by 1 to 2 groups selected from a group consisting of a C1-6 alkyl group and a phenyl group (which may be substituted on the phenyl ring by 1 to 5, preferably 1 to 3 halogen-substituted or unsubstituted C1-6 alkyl groups)), for example, a 2-thiazolylmethoxycarbonyl group, 2-(2-thiazolyl)ethoxycarbonyl group, 3-(2-thiazolyl)propoxycarbonyl group, 4-(2-thiazolyl)butoxycarbonyl group, 5-(2-thiazolyl)pentyloxycarbonyl group, 6-(2-thiazolyl)-hexyloxycarbonyl group, 4-thiazolylmethoxycarbonyl group, 5-thiazolylmethoxycarbonyl group, 2-methyl-4-thiazolylmethoxycarbonyl group, 2-methyl-5-thiazolyl-methoxycarbonyl group, 5-methyl-2-thiazolylmethoxycarbonyl group, 4-methyl-2-thiazolylmethoxycarbonyl group, 5-methyl-4-thiazolylmethoxycarbonyl group, 4-methyl-5-thiazolylmethoxycarbonyl group, 2-ethyl-4-thiazolylmethoxycarbonyl group, 2-ethyl-5-thiazolylmethoxycarbonyl group, 5-ethyl-2-thiazolylmethoxycarbonyl group, 5-propyl-2-thiazolylmethoxycarbonyl group, 4-n-butyl-2-thiazolylmethoxycarbonyl group, 5-ethyl-4-thiazolylmethoxycarbonyl group, 4-n-pentyl-5-thiazolylmethoxycarbonyl group, 2-n-hexyl-4-thiazolylmethoxycarbonyl group, 2-n-hexyl-5-thiazolylmethoxycarbonyl group, 4-n-pentyl-2-thiazolylmethoxycarbonyl group, 5-n-hexyl-2-thiazolylmethoxycarbonyl group, 4-n-hexyl-2-thiazolylmethoxycarbonyl group, 5-n-hexyl-4-thiazolylmethoxycarbonyl group, 4-n-hexyl-5-thiazolylmethoxycarbonyl group, 2-phenyl-4-thiazolylmethoxycarbonyl group, 2-phenyl-5-thiazolylmethoxycarbonyl group, 2-phenyl-4-thiazolylmethoxycarbonyl group, 4-phenyl-2-thiazolylmethoxycarbonyl group, 5-phenyl-2-thiazolylmethoxycarbonyl group, 2-(4-phenyl-2-thiazolyl)ethoxycarbonyl group, 5-phenyl-4-thiazolylmethoxycarbonyl group, 4-phenyl-5-thiazolylmethoxycarbonyl group, 5-(2-fluorophenyl)-2-thiazolylmethoxycarbonyl group, 5-(2-fluorophenyl)-4-thiazolylmethoxycarbonyl group, 4-(2-fluorophenyl)-5-thiazolylmethoxycarbonyl group, 2-(2-bromophenyl)-4-thiazolylmethoxycarbonyl group, 2-(2-fluorophenyl)-5-thiazolylmethoxycarbonyl group, 2-(3-chlorophenyl)-4-thiazolylmethoxycarbonyl group, 2-(2,3-difluorophenyl)-5-thiazolylmethoxycarbonyl group, 2-(2,4-dibromophenyl)-4-thiazolylmethoxycarbonyl group, 4-(2,5-dichlorophenyl)-5-thiazolylmethoxycarbonyl group, 2-(2-chlorophenyl)-4-thiazolylmethoxycarbonyl group, 2-(2,4,6-trichlorophenyl)-5-thiazolylmethoxycarbonyl group, 2-(4-chlorophenyl)-4-thiazolylmethoxycarbonyl group, 2-(2-fluorophenyl)-5-thiazolylmethoxycarbonyl group, 2-(4-chlorophenyl)-5-thiazolylmethoxycarbonyl group, 2-(2,4-dichlorophenyl)-5-thiazolylmethoxycarbonyl group, 4-(2-methylphenyl)-5-thiazolylmethoxycarbonyl group, 2-(2-ethylphenyl)-4-thiazolylmethoxycarbonyl group, 2-(2-n-propylphenyl)-5-thiazolylmethoxycarbonyl group, 2-(3-isopropylphenyl)-4-thiazolylmethoxycarbonyl group, 2-(3-n-butylphenyl)-5-thiazolylmethoxycarbonyl group, 2-(4-n-pentylphenyl)-4-thiazolylmethoxycarbonyl group, 4-(2-n-hexylphenyl)-5-thiazolylmethoxycarbonyl group, 2-(2,4-dimethylphenyl)-4-thiazolylmethoxycarbonyl group, 2-(2,3-dimethylphenyl)-5-thiazolylmethoxycarbonyl group, 2-(2,4,6-trimethylphenyl)-4-thiazolylmethoxycarbonyl group, 2-(2-methylphenyl)-4-methyl-5-thiazolylmethoxycarbonyl group, 2-(4-chlorophenyl)-5-methyl-4-thiazolylmethoxycarbonyl group, 2,4-dimethyl-5-thiazolylmethoxycarbonyl group, 5-(2-trifluoromethylphenyl)-2-thiazolylmethoxycarbonyl group, 5-(2-trifluoromethylphenyl)-4-thiazolylmethoxycarbonyl group, 4-(2-trifluoromethylphenyl)-5-thiazolylmethoxycarbonyl group, 2-(2-trifluoromethylphenyl)-4-thiazolylmethoxycarbonyl group, 2-(2-trifluoromethylphenyl)-5-thiazolylmethoxycarbonyl group, 2-(3-trifluoromethylphenyl)-4-thiazolylmethoxycarbonyl group, 2-(3-trifluoromethylphenyl)-5-thiazolylmethoxycarbonyl group, 2-(4-trifluoromethylphenyl)-4-thiazolylmethoxycarbonyl group or the like.

A tetrazolyl-substituted C1-6 alkoxycarbonyl group (which may be substituted on the tetrazole ring by at least one group selected from a group consisting of a C1-6 alkyl group and a phenyl group which may have at least one halogen atom as a substituent on the phenyl ring as a substituent) includes a tetrazolyl-substituted C1-6 alkoxycarbonyl group (which may be substituted on the tetrazole ring by a group selected from a group consisting of a C1-6 alkyl group and a phenyl group which may have 1 to 5, preferably 1 to 3 halogen atoms as a substituent on the phenyl ring, as a substituent), for example, a 5-(1H)-tetrazolylmethoxycarbonyl group, 2-(5-(1H)-tetrazolyl)ethoxycarbonyl group, 3-(5-(1H)-tetrazolyl)propoxycarbonyl group, 4-(5-(1H)-tetrazolyl)butoxycarbonyl group, 5-(5-(1H)-tetrazolyl)pentyloxycarbonyl group, 6-(5-(1H)-tetrazolyl)hexyloxycarbonyl group, 1-methyl-5-(1H)-tetrazolylmethoxycarbonyl group, 1-ethyl-5-(1H)-tetrazolylmethoxycarbonyl group, 1-n-propyl-5-(1H)-tetrazolylmethoxycarbonyl group, 1-n-butyl-5-(1H)-tetrazolylmethoxycarbonyl group, 1-n-pentyl-5-(1H)-tetrazolylmethoxycarbonyl group, 1-n-hexyl-5-(1H)-tetrazolylmethoxycarbonyl group, 1-phenyl-5-(1H)-tetrazolylmethoxycarbonyl group, 1-(2-fluorophenyl)-5-(1H)-tetrazolylmethoxycarbonyl group, 1-(3-fluorophenyl)-5-(1H)-tetrazolylmethoxycarbonyl group, 1-(4-fluorophenyl)-5-(1H)-tetrazolylmethoxycarbonyl group, 1-(2-chlorophenyl)-5-(1H)-tetrazolylmethoxycarbonyl group, 1-(3-chlorophenyl)-5-(1H)-tetrazolylmethoxycarbonyl group, 1-(4-chlorophenyl)-5-(1H)-tetrazolylmethoxycarbonyl group, 1-(2-bromophenyl)-5-(1H)-tetrazolylmethoxycarbonyl group, 1-(3-bromophenyl)-5-(1H)-tetrazolylmethoxycarbonyl group, 1-(4-bromophenyl)-5-(1H)-tetrazolylmethoxycarbonyl group, 2-(1-methyl-5-(1H)-tetrazolyl)ethoxycarbonyl group, 2-(1-ethyl-5-(1H)-tetrazolyl)ethoxycarbonyl group, 2-(1-propyl-5-(1H)-tetrazolyl)ethoxycarbonyl group, 2-(1-butyl-5-(1H)-tetrazolyl)ethoxycarbonyl group, 2-(1-pentyl-5-(1H)-tetrazolyl)ethoxycarbonyl group, 2-(1-hexyl-5-(1H)-tetrazolyl)ethoxycarbonyl group, 2-(1-phenyl-5-(1H)-tetrazolyl)ethoxycarbonyl group, 2-(1-(2,4-difluorophenyl)-5-(1H)-tetrazolyl)ethoxycarbonyl group, 2-(1-(3-fluorophenyl)-5-(1H)-tetrazolyl)ethoxycarbonyl group, 2-(1-(4-fluorophenyl)-5-(1H)-tetrazolyl)ethoxycarbonyl group, 2-(1-(2,4,6-trichlorophenyl)-5-(1H)-tetrazolyl)ethoxycarbonyl group, 2-(1-(3-chlorophenyl)-5-(1H)-tetrazolyl)-ethoxycarbonyl group, 2-(1-(4-chlorophenyl)-5-(1H)-tetrazolyl)ethoxycarbonyl group, 2-(1-(2-bromophenyl)-5-(1H)-tetrazolyl)ethoxycarbonyl group, 2-(1-(3-bromophenyl)-5-(1H)-tetrazolyl)ethoxycarbonyl group, 2-(1-(4-bromophenyl)-5-(1H)-tetrazolyl)ethoxycarbonyl group or the like.

Examples of a 2,3-dihydro-1H-indenyloxycarbonyl group include a 2,3-dihydro-1H-inden-1-yloxycarbonyl group, 2,3-dihydro-1H-inden-2-yloxycarbonyl group or the like.

Examples of an adamantane-substituted C1-6 alkoxycarbonyl group include an adamantane-1-ylmethoxycarbonyl group, 2-(adamantane-1-yl)ethoxycarbonyl group, 3-(adamantane-1-yl)propoxycarbonyl group, 4-(adamantane-1-yl)butoxycarbonyl group, 5-(adamantane-1-yl)pentyloxycarbonyl group, 6-(adamantane-1-yl)hexyloxycarbonyl group or the like.

Examples of a phenyl C3-6 alkynyloxycarbonyl group include a 2-phenylethynyloxycarbonyl group, 3-phenyl-2-propynyloxycarbonyl group, 4-phenyl-3-butyne-1-yloxycarbonyl group, 4-phenyl-3-butyne-2-yloxycarbonyl group, 5-phenyl-4-pentyne-1-yloxycarbonyl group, 6-phenyl-5-hexyne-1-yloxycarbonyl group or the like.

Examples of a phenylthio C1-6 alkoxycarbonyl group include a phenylthiomethoxycarbonyl group, 2-phenylthioethoxycarbonyl group, 1-phenylthioethoxycarbonyl group, 3-(phenylthio)propoxycarbonyl group, 4-(phenylthio)butoxycarbonyl group, 5-(phenylthio)pentyloxycarbonyl group, 6-(phenylthio)hexyloxycarbonyl group or the like.

Examples of a phenyl C1-6 alkoxy-substituted C1-6 alkoxycarbonyl group include a benzyloxymethoxycarbonyl group, 2-benzyloxyethoxycarbonyl group, 3-(benzyloxy)propoxycarbonyl group, 4-(benzyloxy)butoxycarbonyl group, 5-(benzyloxy)pentyloxycarbonyl group, 6-(benzyloxy)hexyloxycarbonyl group, 2-phenylethoxymethoxycarbonyl group, 2-phenylethoxyethoxycarbonyl group, 3-(2-phenylethoxy)propoxycarbonyl group, 4-(2-phenylethoxy)butoxycarbonyl group, 5-(2-phenylethoxy)pentyloxycarbonyl group, 6-(2-phenylethoxy)hexyloxycarbonyl group, 3-phenylpropoxymethoxycarbonyl group, 3-phenylpropoxyethoxycarbonyl group, 3-(3-phenylpropoxy)propoxycarbonyl group, 4-(3-phenylpropoxy)-butoxycarbonyl group, 5-(3-phenylpropoxy)pentyloxycarbonyl group, 6-(3-phenylpropoxy)hexyloxycarbonyl group, 4-phenylbutoxymethoxycarbonyl group, 4-phenylbutoxyethoxycarbonyl group, 3-(4-phenylbutoxy)-propoxycarbonyl group, 4-(4-phenylbutoxy)butoxycarbonyl group, 5-(4-phenylbutoxy)pentyloxycarbonyl group, 6-(4-phenylbutoxy)hexyloxycarbonyl group, 5-phenylpentyloxymethoxycarbonyl group, 5-phenylpentyloxyethoxycarbonyl group, 3-(5-phenylpentyloxy)propoxycarbonyl group, 4-(5-phenylpentyloxy)butoxycarbonyl group, 5-(5-phenylpentyloxy)pentyloxycarbonyl group, 6-(5-phenylpentyloxy)hexyloxycarbonyl group, 6-phenylhexyloxymethoxycarbonyl group, 6-phenylhexyloxyethoxycarbonyl group, 3-(6-phenylhexyloxy)propoxycarbonyl group, 4-(6-phenylhexyloxy)butoxycarbonyl group, 5-(6-phenylhexyloxy)pentyloxycarbonyl group, 6-(6-phenylhexyloxy)hexyloxycarbonyl group or the like.

Examples of a C2-6 alkenyloxycarbonyl group include a vinyl oxycarbonyl group, 2-propenyloxycarbonyl group (trivial name: allyloxycarbonyl group), 2-butene-1-yloxycarbonyl group, 3-butene-1-yloxycarbonyl group, 4-pentene-1-yloxycarbonyl group, 3-pentene-1-yloxycarbonyl group, 5-hexene-1-yloxycarbonyl group, 4-hexene-1-yloxycarbonyl group, 3-hexene-1-yloxycarbonyl group or the like.

Examples of a C2-6 alkynyloxycarbonyl group include an acetyleneoxycarbonyl group, 2-propynyloxycarbonyl group, 2-butyne-1-yloxycarbonyl group, 3-butyne-1-yloxycarbonyl group, 4-pentyne-1-yloxycarbonyl group, 3-pentyne-1-yloxycarbonyl group, 5-hexyne-1-yloxycarbonyl group, 4-hexyne-1-yloxycarbonyl group, 3-hexyne-1-yloxycarbonyl group or the like.

Examples of a C3-8 cycloalkyl-substituted C1-6 alkoxycarbonyl group include a cyclopropylmethoxycarbonyl group, cyclobutylmethoxycarbonyl group, cyclopentylmethoxycarbonyl group, cyclohexylmethoxycarbonyl group, cycloheptylmethoxycarbonyl group, cyclooctylmethoxycarbonyl group, 2-cyclopropylethoxycarbonyl group, 2-cyclobutylethoxycarbonyl group, 2-cyclopentylethoxycarbonyl group, 2-cyclohexylethoxycarbonyl group, 2-cycloheptylethoxycarbonyl group, 3-cyclopropylpropoxycarbonyl group, 3-cyclobutylpropoxycarbonyl group, 3-cyclopentylpropoxycarbonyl group, 3-cyclohexylpropoxycarbonyl group, 3-cycloheptylpropoxycarbonyl group, 3-cyclooctylpropoxycarbonyl group, 4-cyclopropylbutoxycarbonyl group, 4-cyclobutylbutoxycarbonyl group, 4-cyclohexylbutoxycarbonyl group, 5-cyclohexylpentyloxycarbonyl group, 6-cyclohexylhexyloxycarbonyl group or the like.

Examples of a benzoyl-substituted C1-6 alkoxycarbonyl group include a benzoylmethoxycarbonyl group, 2-benzoylethoxycarbonyl group, 1-benzoylethoxycarbonyl group, 3-(benzoyl)propoxycarbonyl group, 4-(benzoyl)butoxycarbonyl group, 5-(benzoyl)pentyloxycarbonyl group, 6-(benzoyl)hexyloxycarbonyl group or the like.

Examples of a phenoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group) include a phenoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group), for example, a phenoxy group, 2-fluorophenoxy group, 3-fluorophenoxy group, 4-fluorophenoxy group, 2-chlorophenoxy group, 3-chlorophenoxy group, 4-chlorophenoxy group, 2-bromophenoxy group, 3-bromophenoxy group, 4-bromophenoxy phenoxy group, 2-iodophenoxy group, 3-iodophenoxy group, 4-iodophenoxy group, 2,3-difluorophenoxy group, 3,4-difluorophenoxy group, 3,5-difluorophenoxy group, 2,4-difluorophenoxy group, 2,6-difluorophenoxy group, 2,3-dichlorophenoxy group, 3,4-dichlorophenoxy group, 3,5-dichlorophenoxy group, 2,4-dichlorophenoxy group, 2,6-dichlorophenoxy group, 2,3,4-trifluorophenoxy group, 3,4,5-trifluorophenoxy group, 3,4,5-trichlorophenoxy group, 2,4,6-trifluorophenoxy group, 2,3,4,5,6-pentafluorophenoxy group, 2,4,6-trichlorophenoxy group, 2-fluoro-4-chlorophenoxy group, 2-fluoro-4-bromophenoxy group, 3-fluoro-4-chlorophenoxy group, 2-methylphenoxy group, 3-methylphenoxy group, 4-methylphenoxy group, 2,6-dimethylphenoxy group, 2,4,6-trimethylphenoxy group, 2-methyl-3-chlorophenoxy group, 3-methyl-4-chlorophenoxy group, 2-chloro-4-methylphenoxy group, 2-methyl-3-fluorophenoxy group, 2-trifluoromethylphenoxy group, 3-trifluoromethylphenoxy group, 4-trifluoromethylphenoxy group, 3,5-di(trifluoromethyl)phenoxy group, 3,4-di(trifluoromethyl)phenoxy group, 2,4-di(trifluoromethyl)phenoxy group, 2-pentafluoroethylphenoxy group, 3-pentafluoroethylphenoxy group, 4-pentafluoroethylphenoxy group, 2-isopropylphenoxy group, 3-isopropylphenoxy group, 4-isopropylphenoxy group, 2-tert-butylphenoxy group, 3-tert-butylphenoxy group, 4-tert-butylphenoxy group, 2-sec-butylphenoxy group, 3-sec-butylphenoxy group, 4-sec-butylphenoxy group, 4-n-butylphenoxy group, 4-n-pentylphenoxy group, 4-n-hexylphenoxy group, 2-n-heptafluoropropylphenoxy group, 3-n-heptafluoropropylphenoxy group, 4-n-heptafluoropropylphenoxy group, 4-pentylphenoxy group, 4-hexylphenoxy group, 2-methoxyphenoxy group, 3-methoxyphenoxy group, 4-methoxyphenoxy group, 2-methoxy-3-chlorophenoxy group, 2-fluoro-3-methoxyphenoxy group, 2-fluoro-4-methoxyphenoxy group, 2-fluoro-4-bromophenoxy group, 4-chloro-3-fluorophenoxy group, 2,3,4-trichlorophenoxy group, 3,4,5-trifluorophenoxy group, 2,4,6-trichlorophenoxy group, 2,4-dimethylphenoxy group, 2,3-dimethylphenoxy group, 3,5-dimethylphenoxy group, 2,5-dimethylphenoxy group, 4-isopropoxyphenoxy group, 4-n-butoxyphenoxy group, 2,4-dimethoxyphenoxy group, 2,3-dimethoxyphenoxy group, 3,5-dimethoxyphenoxy group, 2,5-dimethoxyphenoxy group, 2,4,6-trimethoxyphenoxy group, 3,5-di(trifluoromethoxy)phenoxy group, 3-chloro-4-methoxyphenoxy group, 2-chloro-4-trifluoromethoxyphenoxy group, 3-methyl-4-fluorophenoxy group, 4-bromo-3-trifluoromethylphenoxy group, 2,6-dimethoxyphenoxy group, 2-trifluoromethoxyphenoxy group, 3-trifluoromethoxyphenoxy group, 4-trifluoromethoxyphenoxy group, 2,3-di(trifluoromethoxy)phenoxy group, 2,4-di(trifluoromethoxy)phenoxy group, 2-pentafluoroethoxyphenoxy group, 3-pentafluoroethoxyphenoxy group, 4-pentafluoroethoxyphenoxy group, 2-isopropoxyphenoxy group, 3-isopropoxyphenoxy group, 4-isopropoxyphenoxy group, 2-tert-butoxyphenoxy group, 3-tert-butoxyphenoxy group, 4-tert-butoxyphenoxy group, 2-sec-butoxyphenoxy group, 3-sec-butoxyphenoxy group, 4-sec-butoxyphenoxy group, 4-n-hexyloxyphenoxy group, 2-n-heptafluoropropoxyphenoxy group, 3-n-heptafluoropropoxyphenoxy group, 4-n-heptafluoropropoxyphenoxy group or the like.

Examples of an 8-azabicyclo[3,2, l]octyl group (which may be substituted on the 8-azabicyclo[3,2,1]-octane ring by at least one phenoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group)) include an 8-azabicyclo[3,2,1] octyl group (which may be substituted on the 8-azabicyclo[3,2,1]-octane ring by at least one phenoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group)), for example, an 8-azabicyclo-[3,2,1]octan-8-yl group, 3-phenoxy-8-azabicyclo[3,2,1]-octan-8-yl group, 3-(3-chlorophenoxy)-8-azabicyclo-[3,2,1]octan-1-yl group, 3-(4-bromophenoxy)-8-azabicyclo[3,2,1]octan-8-yl group, 3-(2-fluorophenoxy)-8-azabicyclo[3,2,1]octan-8-yl group, 3-(3-iodophenoxy)-8-azabicyclo[3,2,1]octan-8-yl group, 3-(3-trifluoromethylphenoxy)-8-azabicyclo[3,2,1]octan-1-yl group, 3-(3-methylphenoxy)-8-azabicyclo[3,2,1]octan-1-yl group, 3-(4-methoxyphenoxy)-8-azabicyclo[3,2,1]octan-1-yl group, 3-(3,5-ditrifluoromethylphenoxy)-8-azabicyclo[3,2,1]octan-1-yl group, 3-(3-trifluoromethyl-4-fluorophenoxy)-8-azabicyclo[3,2,1]octan-1-yl group, 3-(2-trifluoromethoxy-3-chlorophenoxy)-8-azabicyclo-[3,2,1]octan-1-yl group, 3-(2,4-difluorophenoxy)-8-azabicyclo[3,2,1]octan-1-yl group, 3-(2,4,6-trichlorophenoxy)-8-azabicyclo[3,2,1]octan-1-yl group, 3-(4-trifluoromethylphenoxy)-8-azabicyclo[3,2,1]octan-1-yl group, 3-(3-trifluoromethoxyphenoxy)-8-azabicyclo[3,2,1]octan-1-yl group, 3-(4-trifluoromethoxyphenoxy)-8-azabicyclo[3,2,1]octan-1-yl group or the like.

Examples of a group represented by a pyridyl group (which may be substituted on the pyridine ring by at least one halogen-substituted or unsubstituted C1-6 alkyl group as a substituent) include a pyridyl group (which may be substituted on the pyridine ring by 1 to 3 halogen-substituted or unsubstituted C1-6 alkyl groups as a substituent), for example, a pyridin-3-yl group, pyridin-2-yl group, pyridin-4-yl group, 4-trifluoromethylpyridin-2-yl group, 4-trifluoromethylpyridin-3-yl group, 5-trifluoromethylpyridin-2-yl group, 5-trifluoromethylpyridin-3-yl group, 2-trifluoromethylpyridin-3-yl group, 2,4-dimethylpyridin-3-yl group, 3,4,5-trimethylpyridin-2-yl group, 4-ethylpyridin-2-yl group, 3-n-butylpyridin-2-yl group, 5-n-pentylpyridin-2-yl group, 4-n-hexylpyridin-2-yl group or the like.

$R^{47}$ and $R^{48}$ may form a 5-membered to 7-membered saturated heterocycle by bonding to each other through or not through other hetero atoms together with the adjacent nitrogen atom. The heterocycle may be substituted by at least one phenyl group (which may be substituted on the phenyl ring by at least one group selected from a group consisting of a halogen atom, halogen-substituted or unsubstituted C1-6 alkyl group or halogen-substituted or unsubstituted C1-6 alkoxy group) as a substituent) and include the heterocycle (which may be substituted on the heterocycle by 1 to 3 phenyl groups (which may be substituted on the phenyl ring by 1 to 5, preferably 1 to 3 groups selected from a group consisting of a halogen atom, halogen-substituted or unsubstituted C1-6 alkyl group or halogen-substituted or unsubstituted C1-6 alkoxy group) as a substituent), examples of which include a pyrrolidinyl group, morpholino group, thiomorpholino group, piperazyl group, piperidyl group, homopiperazyl group, 4-phenylpiperazin-1-yl group, 4-phenylpiperidin-1-yl group, 4-(3-chlorophenyl)piperazin-1-yl group, 4-(4-chlorophenyl)piperazin-1-yl group, 4-(3,4-dichlorophenyl)piperazin-1-yl group, 4-(3-trifluoromethylphenyl)piperazin-1-yl group, 4-(4-trifluoromethylphenyl)piperazin-1-yl group, 4-(3-trifluoromethoxyphenyl)piperazin-1-yl group, 4-(4-trifluoromethoxyphenyl)piperazin-1-yl group, 4-phenylpiperidin-1-yl group, 4-(3-chlorophenyl)piperidin-1-yl group, 4-(4-chlorophenyl)piperidin-1-yl group, 4-(3,4-dichlorophenyl)piperidin-1-yl group, 4-(3-trifluoromethylphenyl)piperidin-1-yl group, 4-(4-trifluoromethylphenyl)piperidin-1-yl group, 4-(3-trifluoromethoxyphenyl)piperidin-1-yl group, 4-(4-trifluoromethoxyphenyl)piperidin-1-yl group, 4-(2,4,6-trifluorophenyl)piperazin-1-yl group, 4-(4-methylphenyl) piperazin-1-yl group, 4-(3-methoxyphenyl)-piperazin-1-yl group, 4-(3,4-dimethoxyphenyl)piperazin-1-yl group, 4-(2,4-dimethylphenyl)piperazin-1-yl group, 4-(2,4,6-trimethoxyphenyl)piperazin-1-yl group, 4-(3,4,5-trimethylphenyl)piperazin-1-yl group, 4-(2,4,6-trifluorophenyl)piperidin-1-yl group, 4-(2,3,4,5,6-pentafluorophenyl)piperidin-1-yl group, 4-(4-methylphenyl)piperidin-1-yl group, 4-(3-methoxyphenyl)-piperidin-1-yl group, 4-(3,4-dimethoxyphenyl) piperidin-1-yl group, 4-(2,4-dimethylphenyl)piperidin-1-yl group, 4-(2,4,6-trimethoxyphenyl)piperidin-1-yl group, 4-(3,4,5-trimethylphenyl)piperidin-1-yl group, 3-(4-methylphenyl)morpholino group, 3-(3-methoxyphenyl)-pyrrolidinyl-1-yl group, 2-(4-methylphenyl)-pyrrolidinyl-1-yl group, 4-(2,4,6-trimethoxyphenyl)-homopiperazin-1-yl group, 4-(3,4,5-trimethylphenyl)-thiomorpholino group, 2,4-diphenylpiperazin-1-yl group, 2,4,6-triphenylpiperazin-1-yl group, 4-phenylpiperazin-1-yl group, 4-phenylpiperidin-1-yl group, 3-(3-chlorophenyl)pyrrolidin-1-yl group, 3-(4-chlorophenyl)-morpholino group, 4-(3,4-dichlorophenyl)homopiperazin-1-yl group, 3-(3-trifluoromethylphenyl) thiomorpholino group, 2-(4-trifluoromethylphenyl)pyrrolidin-1-yl group, 2-(3-trifluoromethoxyphenyl)morpholino group, 3-(4-trifluoromethoxyphenyl)homopiperazin-1-yl group, 3-phenylpyrrolidin-1-yl group, 4-(3-chlorophenyl) morpholino group, 4-(4-chlorophenyl)homopiperidin-1-yl group, 3-(3,4-dichlorophenyl)thiomorpholino group, 3-(3-trifluoromethylphenyl)pyrrolidin-1-yl group, 4-(4-trifluoromethylphenyl)homopiperazin-1-yl group, 3-phenylthiomorpholino group, 4-phenylmorpholino group or the like.

Examples of an amino-substituted C2-6 alkenyl group (which may be substituted on the amino group by at least one group selected from a group consisting of a C1-6 alkyl group and a phenyl group (which may be substituted on the phenyl ring by at least one group selected from a group consisting of a halogen atom, halogen-substituted or unsubstituted C1-6 alkyl group and halogen-substituted or unsubstituted C1-6 alkoxy group)) include an amino-substituted C2-6 alkenyl group (which may be substituted on the amino group by 1 to 2 groups selected from a group consisting of a C1-6 alkyl group and a phenyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group)), for example, an aminovinyl group, 3-amino-2-propenyl group, 3-amino-1-propenyl group, 4-amino-3-butenyl group, 4-amino-3-butenyl group, 5-amino-4-pentenyl group, 6-amino-5-hexenyl group, methylaminovinyl group, 3-methylamino-2-propenyl group, 3-methylamino-1-propenyl group, 4-methylamino-3-butenyl group, 4-methylamino-3-butenyl group, 5-methylamino-4-pentenyl group, 6-methylamino-5-hexenyl group, methylaminovinyl group, 3-methylamino-2-propenyl group, 3-dimethylamino-2-propenyl group, 3-ethylamino-1-propenyl group, 3-diethylamino-1-propenyl group, 4-ethylamino-3-butenyl group, 4-dimethylamino-3-butenyl group, 4-diethylamino-3-butenyl group, 5-ethylamino-4-pentenyl group, 6-ethylamino-5-hexenyl group, n-propylaminovinyl group, 3-n-propylamino-2-propenyl group, 3-n-propylamino-1-propenyl group, 4-n-propylamino-3-butenyl group, 4-n-propylamino-3-butenyl group, 5-n-propylamino-4-pentenyl group, 6-n-propylamino-5-hexenyl group, n-butylaminovinyl group, 3-n-butylamino-2-propenyl group, 3-n-butylamino-1-propenyl group, 4-n-butylamino-3-butenyl group, 4-n-butylamino-3-butenyl group, 5-n-butylamino-4-pentenyl group, 6-n-butylamino-5-hexenyl group, n-pentylaminovinyl group, 3-n-pentylamino-2-propenyl group, 3-n-hexylamino-1-propenyl group, 4-n-hexylamino-3-butenyl group, 4-n-hexylamino-3-butenyl group, 5-n-hexylamino-4-pentenyl group, 6-n-pentylamino-5-hexenyl group, phenylaminovinyl group, 3-phenylamino-2-propenyl group, 3-phenylamino-1-propenyl group, 4-phenylamino-3-butenyl group, 4-phenylamino-3-butenyl group, 5-phenylamino-4-pentenyl group, 6-phenylamino-5-hexenyl group, 4-chlorophenylaminovinyl group, 3-(4-bromophenyl)amino-2-propenyl group, 3-(2,4-dichlorophenyl)amino-1-propenyl group, 4-(2,4,6-trichlorophenyl)amino-3-butenyl group, 4-(2,3,4,5,6-pentafluorophenyl)amino-3-butenyl group, 4-(4-fluorophenyl)amino-3-butenyl group, 5-(4-iodophenyl)amino-4-pentenyl group, 6-(4-chlorophenyl)-amino-5-hexenyl group, (3-methylphenyl)aminovinyl group, (4-trifluoromethylphenyl)aminovinyl group, 3-(4-trifluoromethylphenyl)amino-2-propenyl group, 3-(4-trifluoromethylphenyl)amino-1-propenyl group, 4-(4-trifluoromethylphenyl)amino-3-butenyl group, 5-(3,4-dimethylphenyl)amino-4-pentenyl group, 6-(3,4,5-trimethylphenyl)amino-5-hexenyl group, (2-methoxyphenyl)aminovinyl group, (4-trifluoromethoxyphenyl)aminovinyl group, 3-(4-trifluoromethoxyphenyl)-amino-2-propenyl group, 3-(3,5-dimethoxyphenyl)amino-1-propenyl group, 4-(2,5-dimethoxyphenyl)amino-3-butenyl group, 4-(2,4,6-trimethoxyphenyl)amino-3-butenyl group, 5-[N-methyl-N-(4-trifluoromethylphenyl)amino]-4-pentenyl group, 6-[N-ethyl-N-(4-trifluoromethoxyphenyl)amino]-5-hexenyl group or the like.

Examples of an oxazolidinyl group (which may be substituted on the oxazolidine ring by at least one oxo group as a substituent) include an oxazolidin-4-yl group, oxazolidin-5-yl group, 2-oxazolidin-4-yl group, 2-oxo-oxazolidin-5-yl group or the like.

Examples of a phenyl C1-6 alkyl group (which may be substituted on the phenyl ring by at least one group selected from a group consisting of a phenoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group); halogen atom; halogen-substituted or unsubstituted C1-6 alkyl group; halogen-substituted or unsubstituted C1-6 alkoxy group; amino group which may have at least one group selected from a group consisting of a C1-6 alkyl group and a phenyl C1-6 alkyl group (which may be substituted on the phenyl ring by at least one group selected from a group consisting of a halogen atom; a halogen-substituted or unsubstituted C1-6 alkyl group and a halogen-substituted or unsubstituted C1-6 alkoxy group); a piperazinyl group (which may be substituted on the piperazine ring by at least one phenyl C1-6 alkyl group (which may be substituted on the phenyl ring by at least one group selected from a group consisting of a halogen atom, a halogen-substituted or unsubstituted C1-6 alkyl group and a halogen-substituted or unsubstituted C1-6 alkoxy group) as a substituent); and a piperidyl group (which may have at least one amino group which may have a group selected from a group consisting of a C1-6 alkyl group and a phenyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) as a substituent on the piperidine ring) include a phenyl C1-6 alkyl group (which may be substituted on the phenyl ring by 1 to 5, preferably 1 to 3 groups selected from a group consisting of a phenoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group); halogen atom; halogen-substituted or unsubstituted C1-6 alkyl group; halogen-substituted or unsubstituted C1-6 alkoxy group; amino group which may have 1 to 2 groups selected from a group consisting of a C1-6 alkyl group and a phenyl C1-6 alkyl group (which may be substituted on the phenyl ring by 1 to 5, preferably 1 to 3 groups selected from a group consisting of a halogen atom, a halogen-substituted or unsubstituted C1-6 alkyl group and a halogen-substituted or unsubstituted C1-6 alkoxy group); a piperazinyl group (which may be substituted on the piperazine ring by 1 to 3 groups selected from a group consisting of a phenyl C1-6 alkyl group (which may be substituted on the phenyl ring by 1 to 5, preferably 1 to 3 groups selected from a group consisting of a halogen atom, a halogen-substituted or unsubstituted C1-6 alkyl group and a halogen-substituted or unsubstituted C1-6 alkoxy group) as a substituent); and a piperidyl group (which may have 1 to 3 amino groups which may have 1 to 2 groups selected from a group consisting of the C1-6 alkyl group and a phenyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group) as a substituent on the piperidine ring), for example, a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2,3-difluorobenzyl group, 3,4-difluorobenzyl group, 3,5-difluorobenzyl group, 2,3,4,5,6-pentafluorobenzyl group, 2,4-difluorobenzyl group, 2,6-difluorobenzyl group, 2,3-dichlorobenzyl group, 3,4-dichlorobenzyl group, 3,5-dichlorobenzyl group, 2,4-dichlorobenzyl group, 2,6-dichlorobenzyl group, 2-fluoro-4-bromobenzyl group, 4-chloro-3-fluorobenzyl group, 2,3,4-trichlorobenzyl group, 3,4,5-trifluorobenzyl group, 2,4,6-trichlorobenzyl group, 4-isopropylbenzyl group, 4-n-butylbenzyl group, 4-methylbenzyl group, 2-methylbenzyl group, 3-methylbenzyl group, 2,4-dimethylbenzyl group, 2,3-dimethylbenzyl group, 2,6-dimethylbenzyl group, 3,5-dimethylbenzyl group, 2,5-dimethylbenzyl group, 2,4,6-trimethylbenzyl group, 3,5-ditrifluoromethylbenzyl group, 2,3,4,5,6-penta-fluorobenzyl group, 4-isopropoxybenzyl group, 4-n-butoxybenzyl group, 4-methoxybenzyl group, 2-methoxybenzyl group, 3-methoxybenzyl group, 2,4-dimethoxybenzyl group, 2,3-dimethoxybenzyl group, 2,6-dimethoxybenzyl group, 3,5-dimethoxybenzyl group, 2,5-dimethoxybenzyl group, 2,4,6-trimethoxybenzyl group, 3,5-ditrifluoromethoxybenzyl group, 2-isopropoxybenzyl group, 3-chloro-4-methoxybenzyl group, 2-chloro-4-trifluoromethoxybenzyl group, 3-methyl-4-fluorobenzyl group, 4-bromo-3-trifluoromethylbenzyl group, 2-trifluoromethylbenzyl group, 3-trifluoromethylbenzyl group, 4-trifluoromethylbenzyl group, 2-pentafluoroethylbenzyl group, 3-pentafluoroethylbenzyl group, 4-pentafluoroethylbenzyl group, 2-trifluoromethoxybenzyl group, 3-trifluoromethoxybenzyl group, 4-trifluoromethoxybenzyl group, 2-pentafluoroethoxybenzyl group, 3-pentafluoroethoxybenzyl group, 4-pentafluoroethoxybenzyl group, 2-(2-trifluoromethylphenyl)ethyl group, 2-(3-trifluoromethylphenyl)ethyl group, 2-(4-trifluoromethylphenyl)ethyl group, 2-(2-trifluoromethoxyphenyl)ethyl group, 2-(3-(trifluoromethoxyphenyl)ethyl group, 2-(4-trifluoromethoxyphenyl)ethyl group, 2-(2-pentafluoroethoxyphenyl)ethyl group, 2-(3-pentafluoroethoxyphenyl)ethyl group, 2-(4-pentafluoroethoxyphenyl)ethyl group, 3-(2-trifluoromethylphenyl)propyl group, 3-(3-trifluoromethylphenyl)propyl group, 3-(4-trifluoromethylphenyl)propyl group, 3-(2-trifluoromethoxyphenyl)propyl group, 3-(3-trifluoromethoxyphenyl)propyl group, 3-(4-trifluoromethoxyphenyl)propyl group, 3-(3-pentafluoroethoxyphenyl)propyl group, 3-(4-pentafluoroethoxyphenyl)propyl group, 4-(3-pentafluoroethoxyphenyl)butyl group, 5-(4-trifluoromethylphenyl)-pentyl group, 4-(4-trifluoromethylphenyl)pentyl group, 4-(4-trifluoromethoxyphenyl)pentyl group, 6-(3-trifluoromethylphenyl)hexyl group, 6-(4-trifluoromethylphenyl)hexyl group, 6-(4-trifluoromethoxyphenyl)hexyl group, 2-aminobenzyl group, 2,4-diaminobenzyl group, 2,4,6-triaminobenzyl group, 2-methylaminobenzyl group, 2-benzylaminobenzyl group, 2-fluorobenzylaminobenzyl group, 3-fluorobenzylaminobenzyl group, 4-fluorobenzylaminobenzyl group, 2-chlorobenzylaminobenzyl group, 3-chlorobenzylaminobenzyl group, 4-chlorobenzylaminobenzyl group, 2-bromobenzylaminobenzyl group, 3-bromobenzylaminobenzyl group, 4-bromobenzylaminobenzyl group, 2-iodobenzylaminobenzyl group, 3-iodobenzylaminobenzyl group, 4-iodobenzylaminobenzyl group, 2,3-difluorobenzylaminobenzyl group, 3,4-difluorobenzylaminobenzyl group, 3,5-difluorobenzylaminobenzyl group, 2,3,4,5,6-pentafluorobenzylaminobenzyl group, 2,4-difluorobenzylaminobenzyl group, 2,6-difluorobenzylaminobenzyl group, 2,3-dichlorobenzylaminobenzyl group, 3,4-dichlorobenzylaminobenzyl group, 3,5-dichlorobenzylaminobenzyl group, 2,4-dichlorobenzylaminobenzyl group, 2,6-dichlorobenzylaminobenzyl group, 2-fluoro-4-bromobenzylaminobenzyl group, 4-chloro-3-fluorobenzylaminobenzyl group, 2,3,4-trichlorobenzylaminobenzyl group, 3,4,5-trifluorobenzylaminobenzyl group, 2,4,6-trichlorobenzylaminobenzyl group, 4-isopropylbenzylaminobenzyl group, 4-n-butylbenzylaminobenzyl group, 4-methylbenzylaminobenzyl group, 2-methylbenzylaminobenzyl group, 3-methylbenzylaminobenzyl group, 2,4-dimethylbenzylaminobenzyl group, 2,3-dimethylbenzylaminobenzyl group, 2,6-dimethylbenzylaminobenzyl group, 3,5-dimethylbenzylaminobenzyl group, 2,5-dimethylbenzylaminobenzyl group, 2,4,6-trimethylbenzylaminobenzyl group, 3,5-ditrifluoromethylbenzylaminobenzyl group, 2,3,4,5,6-pentafluorobenzylaminobenzyl group, 4-isopropoxybenzylaminobenzyl group, 4-n-butoxybenzylaminobenzyl group, 4-methoxybenzylaminobenzyl group, 2-methoxybenzylaminobenzyl group, 3-methoxybenzylaminobenzyl group, 2,4-dimethoxybenzylaminobenzyl group, 2,3-dimethoxybenzylaminobenzyl group, 2,6-dimethoxybenzylaminobenzyl group, 3,5-dimethoxybenzylaminobenzyl group, 2,5-dimethoxybenzylaminobenzyl group, 2,4,6-trimethoxybenzylaminobenzyl group, 3,5-ditrifluoromethoxybenzylaminobenzyl group, 2-isopropoxybenzylaminobenzyl group, 3-chloro-4-methoxybenzylaminobenzyl group, 2-chloro-4-trifluoromethoxybenzylaminobenzyl group, 3-methyl-4-fluorobenzylaminobenzyl group, 4-bromo-3-trifluoromethylbenzylaminobenzyl group, 2-trifluoromethylbenzylaminobenzyl group, 3-trifluoromethylbenzylaminobenzyl group, 4-trifluoromethylbenzylaminobenzyl group, 2-pentafluoroethoxybenzylaminobenzyl group, 3-pentafluoroethoxybenzylaminobenzyl group, 4-pentafluoroethoxybenzylaminobenzyl group, 2-trifluoromethoxybenzylaminobenzyl group, 3-trifluoromethoxybenzylaminobenzyl group, 4-trifluoromethoxybenzylaminobenzyl group, 2-pentafluoroethoxybenzylaminobenzyl group, 3-pentafluoroethoxybenzylaminobenzyl group, 4-pentafluoroethoxybenzylaminobenzyl group, 3-(N-methyl-N-benzylamino)benzyl group, 4-(dibenzylamino)benzyl group, 2-dimethylaminobenzyl group, 3-dimethylaminobenzyl group, 4-dimethylaminobenzyl group, 2-(2-dimethylaminophenyl)ethyl group, 2-(3-dimethylaminophenyl)ethyl group, 2-(4-dimethylaminophenyl)ethyl group, 3-(2-dimethylaminophenyl)propyl group, 3-(3-dimethylaminophenyl)propyl group, 3-(4-dimethylaminophenyl)propyl group, 2-phenoxybenzyl group, 2,3-diphenoxybenzyl group, 2,4,6-triphenoxybenzyl group, 2-(2-fluorophenoxy)benzyl group, 3-(3-fluorophenoxy)benzyl group, 4-(4-fluorophenoxy)benzyl group, 2-(2-chlorophenoxy)benzyl group, 3-(3-chlorophenoxy)benzyl group, 4-(4-chlorophenoxy)benzyl group, 2-(2-bromophenoxy)benzyl group, 3-(3-bromophenoxy)benzyl group, 4-(4-bromophenoxy)benzyl group, 2-(2-iodophenoxy)benzyl group, 3-(3-iodophenoxy)benzyl group, 4-(4-iodophenoxy)benzyl group, 3-(2,3-difluorophenoxy)benzyl group, 4-(3,4-difluorophenoxy)benzyl group, 2-(3,5-difluorophenoxy)benzyl group, 4-(2,3,4,5,6-pentafluorophenoxy)benzyl group, 2-(2,4-difluorophenoxy) benzyl group, 4-(2,6-difluorophenoxy)benzyl group, 3-(2,3-dichlorophenoxy)benzyl group, 2-(3,4-dichlorophenoxy) benzyl group, 4-(3,5-dichlorophenoxy)benzyl group, 3-(2,4-dichlorophenoxy)benzyl group, 4-(2,6-dichlorophenoxy)benzyl group, 4-(2-fluoro-4-bromophenoxy)benzyl group, 3-(4-chloro-3-fluorophenoxy)benzyl group, 4-(2,3,4-trichlorophenoxy)benzyl group, 4-(3,4,5-trifluorophenoxy)benzyl group, 4-(2,4,6-trichlorophenoxy)benzyl group, 2-(4-isopropylphenoxy)benzyl group, 3-(4-n-butylphenoxy)benzyl group, 4-(4-methylphenoxy)benzyl group, 3-(2-methylphenoxy)benzyl group, 2-(3-methylphenoxy)benzyl group, 2-(2,4-dimethylphenoxy)benzyl group, 3-(2,3-dimethylphenoxy)benzyl group, 4-(2,6-dimethylphenoxy)benzyl group, 2-(3,5-dimethylphenoxy)benzyl group, 3-(2,5-dimethylphenoxy)benzyl group, 2-(2,4,6-trimethylphenoxy)benzyl group, 3-(3,5-ditrifluoromethylphenoxy)benzyl group, 4-(2,3,4,5,6-pentafluorophenoxy)benzyl group, 2-(4-isopropoxyphenoxy)benzyl group, 2-(4-n-butoxyphenoxy)benzyl group, 2-(4-methoxyphenoxy)benzyl group, 3-(2-methoxyphenoxy)benzyl group, 4-(3-methoxyphenoxy)benzyl group, 2-(2,4-dimethoxyphenoxy)benzyl group, 3-(2,3-dimethoxyphenoxy)benzyl group, 4-(2,6-dimethoxyphenoxy)benzyl group, 2-(3,5-dimethoxyphenoxy)benzyl group, 3-(2,5-dimethoxyphenoxy)benzyl group, 4-(2,4,6-trimethoxyphenoxy)benzyl group, 2-(3,5-ditrifluoromethoxyphenoxy)benzyl group, 3-(2-isopropoxyphenoxy)-benzyl group, 4-(3-chloro-4-methoxyphenoxy)benzyl group, 3-(2-chloro-4-trifluoromethoxyphenoxy)benzyl group, 2-(3-methyl-4-fluorophenoxy)benzyl group, 3-(4-bromo-3-trifluoromethylphenoxy)benzyl group, 4-(2-trifluoromethylphenoxy)benzyl group, 2-(3-trifluoromethylphenoxy)benzyl group, 3-(4-trifluoromethylphenoxy)benzyl group, 4-(2-pentafluoromethylphenoxy)-benzyl group, 2-(3-pentafluoroethylphenoxy)benzyl group, 3-(4-pentafluoroethylphenoxy)benzyl group, 4-(2-trifluoromethoxyphenoxy)benzyl group, 2-(3-trifluoromethoxyphenoxy)benzyl group, 3-(4-trifluoromethoxyphenoxy)benzyl group, 4-(2-pentafluoroethoxyphenoxy)-benzyl group, 2-(3-pentafluoroethoxyphenoxy)benzyl group, 3-(4-pentafluoroethoxyphenoxy)benzyl group, 2-[3-(2-trifluoromethylphenoxy)phenyl]ethyl group, 2-[3-(3-trifluoromethylphenoxy)phenyl]ethyl group, 2-[4-(4-trifluoromethylphenoxy)phenyl]ethyl group, 3-[4-(2-trifluoromethylphenoxy)phenyl]propyl group, 4-[3-(3-pentafluoroethoxyphenoxy)phenyl]butyl group, 5-[4-(4-trifluoromethylphenoxy)phenyl]pentyl group, 6-[2-(3-trifluoromethylphenoxy)phenyl]hexyl group, 4-(1-piperazinyl)benzyl group, 4-(1-piperidinyl)benzyl group, 4-(4-benzyl-1-piperanzinyl)benzyl group, 4-(4-(3-chlorobenzyl)-1-piperanzinyl)benzyl group, 4-(4-(2,4-dimethylbenzyl)-1-piperanzinyl)benzyl group, 4-(4-(2,4-dimethylbenzyl)-1-piperanzinyl)benzyl group, 4-(2,4-dibenzyl-1-piperanzinyl)benzyl group, 4-(2,3,4-tribenzyl-1-piperanzinyl)benzyl group, 4-(4-(4-trifluoromethylbenzyl)-1-piperanzinyl)benzyl group, 4-(4-anilino-1-piperidinyl)benzyl group, 4-(4-(3-trifluoromethylbenzyl)-1-piperanzinyl)benzyl group, 4-[4-(N-methylanilino)-1-piperidinyl]benzyl group, 4-[4-(N-methyl-3-chloroanilino)-1-piperidinyl]benzyl group, 4-[4-(2,4-dimethylanilino)-1-piperidinyl]benzyl group, 4-[4-(N-methyl-2,4,6-trimethoxyanilino)-1-piperidinyl]-benzyl group, 4-[4-(4-trifluoromethoxyanilino)-1-piperidinyl]benzyl group, 4-[4-(N-methyl-3-trifluoromethylanilino)-1-piperidinyl]benzyl group, 4-(3,4-dianilino-1-piperidinyl)benzyl group, 4-(3,4,5-trianilino-1-piperidinyl)benzyl group or the like.

Examples of an amino C1-6 alkyl group (which may be substituted on the amino group by at least one group selected from a group consisting of C1-6 alkyl group, C1-6 alkoxycarbonyl group and phenyl group which may be substituted on the phenyl ring by at least one group selected from a group consisting of a halogen atom or a halogen-substituted or unsubstituted C1-6 alkyl group) include an amino C1-6 alkyl group (which may be substituted on the amino group by 1 to 2 groups selected from a group consisting of C1-6 alkyl groups, C1-6 alkoxycarbonyl group and phenyl groups which may be substituted on the phenyl group by 1 to 5, preferably 1 to 3 groups selected from a group consisting of a halogen atom or a halogen-substituted or unsubstituted C1-6 alkyl group), for example, an aminomethyl group, 2-aminoethyl group, 1-aminoethyl group, 3-aminopropyl group, 4-aminobutyl group, 5-aminopentyl group, 6-aminohexyl group, 2-methyl-3-aminopropyl group, 1,1-dimethyl-2-aminoethyl group, 2-(methylamino)ethyl group, 3-(methylamino)propyl group, 4-(methylamino)butyl group, 5-(methylamino)pentyl group, 6-(methylamino)hexyl group,-2-(N-methyl-N-methoxycarbonylamino)ethyl group, 3-(N-methyl-N-methoxycarbonylamino)propyl group, 4-(N-methyl-N-methoxycarbonylamino)butyl group, 5-(N-methyl-N-methoxycarbonylamino)pentyl group, 6-(N-methyl-N-methoxycarbonylamino)hexyl group, 2-(N-ethoxycarbonyl-N-methylamino)ethyl group, 3-(N-ethoxycarbonyl-N-methylamino)propyl group, 4-(N-ethoxycarbonyl-N-methylamino)butyl group, 5-(N-ethoxycarbonyl-N-methylamino)pentyl group, 6-(N-ethoxycarbonyl-N-methylamino)hexyl group, 2-[N-methyl-N-(n-propoxycarbonylamino)]ethyl group, 3-[N-methyl-N-(n-propoxycarbonylamino)]propyl group, 4-[N-methyl-N-(n-propoxycarbonylamino)]butyl group, 5-[N-methyl-N-(n-propoxycarbonylamino)]pentyl group, 6-[N-methyl-N-(n-propoxycarbonylamino)]hexyl group, 2-[N-(tert-butoxycarbonyl)-N-methylamino)]ethyl group, 3-[N-(tert-butoxycarbonyl)-N-methylamino)]propyl group, 4-[N-(tert-butoxycarbonyl-N-methylamino)]butyl group, 5-[N-(tert-butoxycarbonyl)-N-methylamino)]pentyl group, 6-[N-(tert-butoxycarbonyl)-N-methylamino)]hexyl group, 2-[N-methyl-N-(n-pentoxycarbonyl)amino]ethyl group, 2-[N-methyl-N-(n-hexyloxycarbonyl)amino]ethyl group, 2-(N-methylanilino)ethyl group, 3-(N-methylanilino)propyl group, 4-(N-methylanilino)butyl group, 2-(N-methyl-4-chloroanilino)ethyl group, 3-(N-methyl-4-chloroanilino)propyl group, 4-(N-methyl-4-chloroanilino)butyl group, 2-(4-fluoro-N-methylanilino)ethyl group, 3-(4-fluoro-N-methylanilino)propyl group, 2-(3-fluoro-N-methylanilino)ethyl group, 3-(3-fluoro-N-methyl-anilino)propyl group, 4-(3-fluoro-N-methylanilino)butyl group, 2-(2-fluoro-N-methylanilino)ethyl group, 3-(2-fluoro-N-methylanilino)propyl group, 4-(2-fluoro-N-methylanilino)butyl group, 2-(2-chloro-N-methyl-anilino)ethyl group, 3-(2-chloro-N-methylanilino)propyl group, 4-(2-chloro-N-methylanilino)butyl group, 2-(3-chloro-N-methylanilino)ethyl group, 3-(3-chloro-N-methylanilino)propyl group, 4-(3-chloro-N-methyl-anilino)butyl group, 2-(4-trifluoromethyl-N-methyl-anilino)ethyl group, 2-(4-methylanilino)ethyl group, 2-(3,5-ditrifluoromethyl-N-ethoxycarbonylanilino)ethyl group, 2-(3,5-ditrifluoromethyl-N-methylanilino)ethyl group, 2-(2,4-dimethyl-N-methylanilino)ethyl group, 2-(3,5-dimethoxy-N-methylanilino)ethyl group, 2-(2,4,6-trimethylanilino)ethyl group, 2-(3,4,5-trimethoxyanilino)ethyl group, 3-(4-trifluoromethyl-N-methylanilino)propyl group, 4-(4-trifluoromethyl-N-methylanilino)butyl group, 2-(3-trifluoromethyl-N-methylanilino)ethyl group, 3-(3-trifluoromethyl-N-methylanilino)propyl group, 2-(2-trifluoromethyl-N-methylanilino)ethyl group, 3-(2-trifluoromethyl-N-methylanilino)propyl group, 4-(2-trifluoromethyl-N-methylanilino)butyl group, 2-(4-trifluoromethoxy-N-methylanilino)ethyl group, 3-(4-trifluoromethoxy-N-methylanilino)propyl group, 4-(4-trifluoromethoxy-N-methylanilino)butyl group, 2-(3-trifluoromethoxy-N-methylanilino)ethyl group, 3-(3-trifluoromethoxy-N-methylanilino)propyl group, 4-(3-trifluoromethoxy-N-methylanilino)butyl group, 2-(2-trifluoromethoxy-N-methylanilino)ethyl group, 3-(2-trifluoromethoxy-N-methylanilino)propyl group, 4-(2-trifluoromethoxy-N-methylanilino)butyl group, 2-(4-methoxy-N-methylanilino)ethyl group, 3-(4-methoxy-N-methylanilino)propyl group, 4-(4-methoxy-N-methylanilino)butyl group, 2-(3-methoxy-N-methylanilino)ethyl group, 3-(3-methoxy-N-methylanilino)propyl group, 4-(3-methoxy-N-methylanilino)butyl group, 2-(2-methoxy-N-methylanilino)ethyl group, 3-(2-methoxy-N-methylanilino)propyl group, 4-(2-methoxy-N-methylanilino)butyl group or the like.

Examples of a phenyl group (which may be substituted on the phenyl ring by at least one group selected from a group consisting of a halogen atom, a phenoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group) and a C1-6 alkoxycarbonyl group) include a phenyl group (which may be substituted on the phenyl ring by 1 to 5, preferably 1 to 3 groups selected from a group consisting of a halogen atom, a phenoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group) and a C1-6 alkoxycarbonyl group), for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 2,3,4-trifluorophenyl group, 3,4,5-trifluorophenyl group, 3,4,5-trichlorophenyl group, 2,4,6-trifluorophenyl group, 2,3,4,5,6-pentafluorophenyl group, 2,4,6-trichlorophenyl group, 2-fluoro-4-chlorophenyl group, 2-fluoro-4-bromophenyl group, 3-fluoro-4-chlorophenyl group, 2-methoxycarbonylphenyl group, 3-methoxycarbonylphenyl group, 4-methoxycarbonylphenyl group, 2,4-dimethoxycarbonylphenyl group, 2,4,6-trimethoxycarbonylphenyl group, 2-ethoxycarbonylphenyl group, 3-ethoxycarbonylphenyl group, 4-ethoxycarbonylphenyl group, 2-propoxycarbonylphenyl group, 3-propoxycarbonylphenyl group, 4-propoxycarbonylphenyl group, 2-butoxycarbonylphenyl group, 3-butoxycarbonylphenyl group, 4-butoxycarbonylphenyl group, 4-pentoxycarbonylphenyl group, 4-hexyloxycarbonylphenyl group, 2-phenoxyphenyl group, 3-phenoxyphenyl group, 4-phenoxyphenyl group, 2-(2-chlorophenoxy)phenyl group, 2-(3-chlorophenoxy)phenyl group, 2-(4-chlorophenoxy)phenyl group, 3-(2-chlorophenoxy)phenyl group, 3-(3-chlorophenoxy)phenyl group, 3-(4-chlorophenoxy)phenyl group, 4-(2-chlorophenoxy)phenyl group, 4-(2,4-dichlorophenoxy)phenyl group, 4-(2,4,6-trichlorophenoxy)phenyl group, 4-(3-chlorophenoxy)phenyl group, 4-(4-chlorophenoxy)phenyl group, 2-(2-trifluoromethylphenoxy)phenyl group, 2-(3-trifluoromethylphenoxy)phenyl group, 2-(4-trifluoromethylphenoxy)phenyl group, 3-(2-trifluoromethylphenoxy)phenyl group, 3-(2-methylphenoxy)phenyl group, 3-(2,4-dimethylphenoxy)phenyl group, 3-(2,4,6-trimethylphenoxy)phenyl group, 3-(2-methoxyphenoxy)-phenyl group, 3-(2,4-dimethoxyphenoxy)phenyl group, 3-(2,4,6-trimethoxyphenoxy)phenyl group, 2-(3,5-ditrifluoromethylphenoxy)phenyl group, 2-(3,5-ditrifluoromethoxyphenoxy)phenyl group, 3-(3-trifluoromethylphenoxy)phenyl trifluoromethylphenoxy)phenyl group, 3-(4-trifluoromethylphenoxy)phenyl group, 4-(2-trifluoromethylphenoxy)phenyl group, 4-(3-trifluoromethylphenoxy)phenyl group, 4-(4-trifluoromethylphenoxy)phenyl group, 2-(2-trifluoromethoxyphenoxy)phenyl group, 2-(3-trifluoromethoxyphenoxy)phenyl group, 2-(4-trifluoromethoxyphenoxy)phenyl group, 3-(2-trifluoromethoxyphenoxy)phenyl group, 3-(3-trifluoromethoxyphenoxy)phenyl group, 3-(4-trifluoromethoxyphenoxy)phenyl group, 4-(2-trifluoromethoxyphenoxy)phenyl group, 4-(3-trifluoromethoxyphenoxy)phenyl group, 4-(4-trifluoromethoxyphenoxy)phenyl group or the like.

A phenyl C1-6 alkoxycarbonyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) includes a phenyl C1-6 alkoxycarbonyl group (which may be substituted on the phenyl ring by 1 to 5, preferably 1 to 3 groups selected from a group consisting of a halogen atom, a halogen-substituted or unsubstituted C1-6 alkyl group and halogen-substituted or unsubstituted C1-6 alkoxy group), for example, a benzyloxycarbonyl group, 1-phenethyloxycarbonyl group, 2-phenethyloxycarbonyl group, 3-phenylpropoxycarbonyl group, 2-phenylpropoxycarbonyl group, 4-phenylbutoxycarbonyl group, 5-phenylpentyloxycarbonyl group, 4-phenylpentyloxycarbonyl group, 6-phenylhexyloxycarbonyl group, 2-fluorobenzyloxycarbonyl group, 3-fluorobenzyloxycarbonyl group, 4-fluorobenzyloxycarbonyl group, 2-chlorobenzyloxycarbonyl group, 3-chlorobenzyloxycarbonyl group, 4-chlorobenzyloxycarbonyl group, 2-bromobenzyloxycarbonyl group, 3-bromobenzyloxycarbonyl group, 4-bromobenzyloxycarbonyl group, 2-iodobenzyloxycarbonyl group, 3-iodobenzyloxycarbonyl group, 4-iodobenzyloxycarbonyl group, 2,3-difluorobenzyloxycarbonyl group, 3,4-difluorobenzyloxycarbonyl group, 3,5-difluorobenzyloxycarbonyl group, 2,4-difluorobenzyloxycarbonyl group, 2,6-difluorobenzyloxycarbonyl group, 2,4,6-trifluorobenzyloxycarbonyl group, 2,3,4,5,6-pentafluorobenzyloxycarbonyl group, 3,4,5-trifluorobenzyloxycarbonyl group, 2,3-dichlorobenzyloxycarbonyl group, 3,4-dichlorobenzyloxycarbonyl group, 3,5-dichlorobenzyloxycarbonyl group, 2,4-dichlorobenzyloxycarbonyl group, 2,6-dichlorobenzyloxycarbonyl group, 2,4,6-trichlorobenzyloxycarbonyl group, 3,4,5-trichlorobenzyloxycarbonyl group, perfluorobenzyloxycarbonyl group, 2-difluoromethylbenzyloxycarbonyl group, 3-methylbenzyloxycarbonyl group, 3,5-dimethylbenzyloxycarbonyl group, 2,4,6-trimethylbenzyloxycarbonyl group, 3-methoxybenzyloxycarbonyl group, 3,5-dimethoxybenzyloxycarbonyl group, 2,4,6-trimethoxybenzyloxycarbonyl group, 3-difluoromethylbenzyloxycarbonyl group, 4-difluoromethylbenzyloxycarbonyl group, 4-chloro-3-difluoromethylbenzyloxycarbonyl group, 3-chloro-4-difluoromethylbenzyloxycarbonyl group, 3-bromo-4-difluoromethylbenzyloxycarbonyl group, 3,5-difluoro-4-difluoromethylbenzyloxycarbonyl group, 2-trifluoromethylbenzyloxycarbonyl group, 3-trifluoromethylbenzyloxycarbonyl group, 4-trifluoromethylbenzyloxycarbonyl group, 4-fluoro-3-trifluoromethylbenzyloxycarbonyl group, 3-fluoro-4-trifluoromethylbenzyloxycarbonyl group, 4-chloro-3-pentafluoroethylbenzyloxycarbonyl group, 3-chloro-4-pentafluoroethylbenzyloxycarbonyl group, 2-pentafluoroethylbenzyloxycarbonyl group, 3-pentafluoroethylbenzyloxycarbonyl group, 4-pentafluoroethylbenzyloxycarbonyl group, 2-trifluoromethoxybenzyloxycarbonyl group, 3-trifluoromethoxybenzyloxycarbonyl group, 4-trifluoromethoxybenzyloxycarbonyl group, 4-fluoro-3-trifluoromethoxybenzyloxycarbonyl group, 3-fluoro-4-trifluoromethoxybenzyloxycarbonyl group, 2-pentafluoroethoxybenzyloxycarbonyl group, 3-pentafluoroethoxybenzyloxycarbonyl group, 4-pentafluoroethoxybenzyloxycarbonyl group, 3-chloro-4-trifluoromethoxybenzyloxycarbonyl group, 3-chloro-4-pentafluoroethoxybenzyloxycarbonyl group, 2-(2-trifluoromethylphenyl)ethoxycarbonyl group, 2-(3-trifluoromethylphenyl)ethoxycarbonyl group, 2-(4-trifluoromethylphenyl)ethoxycarbonyl group, (2-trifluoromethoxyphenyl)methoxycarbonyl group, (3-trifluoromethoxyphenyl)methoxycarbonyl group, 2-(4-trifluoromethoxyphenyl)ethoxycarbonyl group, 2-(2-pentafluoroethoxyphenyl)ethoxycarbonyl group, 2-(3-pentafluoroethoxyphenyl)ethoxycarbonyl group, 2-(4-pentafluoroethoxyphenyl)ethoxycarbonyl group, 3-(2-trifluoromethylphenyl)propoxycarbonyl group, 3-(3-trifluoromethylphenyl)propoxycarbonyl group, 3-(4-trifluoromethylphenyl)propoxycarbonyl group, 3-(2-trifluoromethylphenyl)propoxycarbonyl group, 3-(3-trifluoromethoxyphenyl)propoxycarbonyl group, 3-(4-trifluoromethoxyphenyl)propoxycarbonyl group, 3-(3-pentafluoroethoxyphenyl)propoxycarbonyl group, 3-(4-pentafluoroethoxyphenyl)propoxycarbonyl group, 4-(3-pentafluoroethoxyphenyl)butoxycarbonyl group, 5-(4-trifluoromethylphenyl)pentyloxycarbonyl group, 4-(4-trifluoromethylphenyl)pentyloxycarbonyl group, 4-(4-trifluoromethoxyphenyl)pentyloxycarbonyl group, 6-(3-trifluoromethylphenyl)hexyloxycarbonyl group, 6-(4-trifluoromethylphenyl)hexyloxycarbonyl group, 6-(4-trifluoromethoxyphenyl)hexyloxycarbonyl group or the like.

A phenyl C1-6 alkoxycarbonyl group (which may be substituted on the phenyl ring by at least one group selected from a group consisting of a halogen atom, cyano group, halogen-substituted or unsubstituted C1-6 alkyl group and halogen-substituted or unsubstituted C1-6 alkoxy group) includes a phenyl C1-6 alkoxycarbonyl group (which may be substituted on the phenyl ring by 1 to 5, preferably 1 to 3 groups selected from a group consisting of a halogen atom, cyano group, halogen-substituted or unsubstituted C1-6 alkyl group and halogen-substituted or unsubstituted C1-6 alkoxy group), for example, a benzyloxycarbonyl group, phenylethoxycarbonyl group, 3-phenylpropoxycarbonyl group, 2-phenylpropoxycarbonyl group, 4-phenylbutoxycarbonyl group, 5-phenylpentoxycarbonyl group, 4-phenylpentoxycarbonyl group, 6-phenylhexyloxycarbonyl group, 2-fluorobenzyloxycarbonyl group, 3-fluorobenzyloxycarbonyl group, 4-fluorobenzyloxycarbonyl group, 2-(2-fluorophenyl)ethoxycarbonyl group, 1-(3-fluorophenyl)ethoxycarbonyl group, 2-(4-fluorophenyl)-ethoxycarbonyl group, 2-chlorobenzyloxycarbonyl group, 3-chlorobenzyloxycarbonyl group, 4-chlorobenzyloxycarbonyl group, 2-(2-bromophenyl)ethoxycarbonyl group, 1-(3-chlorophenyl)ethoxycarbonyl group, 2-(4-iodophenyl)ethoxycarbonyl group, 2-(2,3-dichlorophenyl)ethoxycarbonyl group, (2,4,6-trichlorophenyl)-methoxycarbonyl group, (2,3,4,5,6-pentafluorophenyl)-methoxycarbonyl group, 2-cyanobenzyloxycarbonyl group, 3-cyanobenzyloxycarbonyl group, 4-cyanobenzyloxycarbonyl group, 2,4-dicyanobenzyloxycarbonyl group, 3,4,5-tricyanobenzyloxycarbonyl group, 2-cyanophenylethoxycarbonyl group, 3-cyanophenylethoxycarbonyl group, 4-cyanophenylethoxycarbonyl group, 2-methylbenzyloxycarbonyl group, 2,4-dimethylbenzyloxycarbonyl group, 2,4,6-trimethylbenzyloxycarbonyl group, 2-trifluoromethylbenzyloxycarbonyl group, 3-trifluoromethylbenzyloxycarbonyl group, 4-trifluoromethylbenzyloxycarbonyl group, 2-methoxybenzyloxycarbonyl group, 2,4-dimethoxybenzyloxycarbonyl group, 2,4,6-trimethoxybenzyloxycarbonyl group, 2-trifluoromethoxybenzyloxycarbonyl group, 3-trifluoromethoxybenzyloxycarbonyl group, 4-trifluoromethoxybenzyloxycarbonyl group, 2-(2-trifluoromethylphenyl)ethoxycarbonyl group, 2-(3-trifluoromethylphenyl)ethoxycarbonyl group, 2-(4-trifluoromethylphenyl)ethoxycarbonyl group, 2-(2-trifluoromethoxyphenyl)ethoxycarbonyl group, 2-(3-trifluoromethoxyphenyl)ethoxycarbonyl group, 2-(4-trifluoromethoxyphenyl)ethoxycarbonyl group, 3-(2-trifluoromethylphenyl)propoxycarbonyl group, 3-(3-trifluoromethylphenyl)propoxycarbonyl group, 3-(4-trifluoromethylphenyl)propoxycarbonyl group, 3-(2-trifluoromethoxyphenyl)propoxycarbonyl group, 3-(3-trifluoromethoxyphenyl)propoxycarbonyl group, 3-(4-trifluoromethoxyphenyl)propoxycarbonyl group, 3-(4-biphenylyl)propoxycarbonyl group, 4-(4-biphenylyl)butoxycarbonyl group, 5-(4-biphenylyl)pentoxycarbonyl group, 4-(3-trifluoromethylphenyl)butoxycarbonyl group, 5-(4-trifluoromethylphenyl)pentyloxycarbonyl group, 4-(4-trifluoromethylphenyl)pentoxycarbonyl group, 4-(4-trifluoromethoxylphenyl)pentoxycarbonyl group, 6-(3-trifluoromethylphenyl)hexyloxycarbonyl group, 6-(4-trifluoromethylphenyl)hexyloxycarbonyl group, 6-(4-trifluoromethoxyphenyl)hexyloxycarbonyl group or the like.

A phenyl C1-6 alkyl group (which may be substituted on the phenyl ring by at least one group selected from a group consisting of a halogen atom and a halogen-substituted or unsubstituted C1-6 alkyl group) is a phenyl C1-6 alkyl group unsubstituted or substituted on the phenyl ring by 1 to 5, preferably 1 to 3 groups selected from a group consisting of a halogen atom and a halogen-substituted or unsubstituted C1-6 alkyl group, examples of which include a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2,3-difluorobenzyl group, 3,4-difluorobenzyl group, 3,5-difluorobenzyl group, 2,4-difluorobenzyl group, 2,6-difluorobenzyl group, 2,3,4,5,6-pentafluorobenzyl group, 2,3-dichlorobenzyl group, 3,4-dichlorobenzyl group, 3,5-dichlorobenzyl group, 2,4-dichlorobenzyl group, 2,6-dichlorobenzyl group, 2-trifluoromethyl benzyl group, 3-trifluoromethyl benzyl group, 4-trifluoromethylbenzyl group, 2-methylbenzyl group, 2,3-dimethylbenzyl group, 2,4,6-trimethylbenzyl group, 3,5-ditrifluoromethylbenzyl group, 2-(2-trifluoromethylphenyl)ethyl group, 2-(3-trifluoromethylphenyl)ethyl group, 2-(4-trifluoromethylphenyl)ethyl group, 3-(2-trifluoromethylphenyl)propyl group, 3-(3-trifluoromethylphenyl)

propyl group, 3-(4-trifluoromethylphenyl)-propyl group, 3-(2-trifluoromethylphenyl)propyl group, 5-(4-trifluoromethylphenyl)pentyl group, 4-(4-trifluoromethylphenyl)pentyl group, 6-(3-trifluoromethylphenyl)hexyl group, 6-(4-trifluoromethylphenyl)-hexyl group or the like.

A piperidinyl C1-6 alkyl group (which may be substituted on the piperidine ring by at least one phenoxy group (which may have at least one halogen-substituted or unsubstituted C1-6 alkyl group on the phenyl ring as a substituent) as a substituent) includes a piperidinyl C1-6 alkyl group (which may be substituted on the piperidine ring by at least one phenoxy group (which may have 1 to 5, preferably 1 to 3 halogen-substituted or unsubstituted C1-6 alkyl groups on the phenyl ring as a substituent) as a substituent), for example, piperidin-1-ylmethyl group, piperidin-2-ylethyl group, piperidin-3-ylpropyl group, piperidin-4-ylbutyl group, piperidin-1-ylpentyl group, piperidin-2-yl-n-hexyl group, 4-phenoxypiperidin-1-ylmethyl group, 2-(4-phenoxypiperidin-1-yl)ethyl group, 3-(4-phenoxy-piperidin-1-yl)propyl group, 4-(4-phenoxypiperidin-1-yl)butyl group, 5-(4-phenoxypiperidin-1-yl)pentyl group, 6-(4-phenoxypiperidin-1-yl)hexyl group, 4-(3-methylphenoxy)piperidin-1-ylmethyl group, 4-(2,5-dimethylphenoxy)piperidin-1-ylmethyl group, 4-(2,4,6-trimethylphenoxy)piperidin-1-ylmethyl group, 4-(3,5-ditrifluoromethylphenoxy)piperidin-1-ylmethyl group, 4-(2-trifluoromethylphenoxy)piperidin-1-ylmethyl group, 2-[4-(2-trifluoromethylphenoxy)piperidin-1-yl]ethyl group, 3-[4-(2-trifluoromethylphenoxy)piperidin-1-yl]propyl group, 4-[4-(2-trifluoromethylphenoxy)-piperidin-1-yl]butyl group, 5-[4-(2-trifluoromethylphenoxy)piperidin-1-yl]pentyl group, 6-[4-(2-trifluoromethylphenoxy)piperidin-1-yl]hexyl group, 4-(3-trifluoromethylphenoxy)piperidin-1-ylmethyl group, 2-[4-(3-trifluoromethylphenoxy)piperidin-1-yl]ethyl group, 3-[4-(3-trifluoromethylphenoxy)piperidin-1-yl]propyl group, 4-[4-(3-trifluoromethylphenoxy)-piperidin-1-yl]butyl group, 5-[4-(3-trifluoromethylphenoxy)piperidin-1-yl]pentyl group, 6-[4-(3-trifluoromethylphenoxy)piperidin-1-yl]hexyl group, 4-(4-trifluoromethylphenoxy)piperidin-1-ylmethyl group, 2-[4-(4-trifluoromethylphenoxy)piperidin-1-yl]ethyl group, 3-[4-(4-trifluoromethylphenoxy)piperidin-1-yl]propyl group, 4-[4-(4-trifluoromethylphenoxy)piperidin-1-yl]butyl group, 5-[4-(4-trifluoromethylphenoxy)piperidin-1-yl]pentyl group, 6-[4-(4-trifluoromethylphenoxy)piperidin-1-yl]hexyl group or the like.

A phenyl group (which may be substituted on the phenyl ring by at least one group selected from a group consisting of a halogen atom; a halogen-substituted or unsubstituted C1-6 alkyl group; a halogen-substituted or unsubstituted C1-6 alkoxy group; an amino group which may have a group selected from a group consisting of a C1-6 alkyl group and a phenyl C1-6 alkyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) as a substituent; a phenoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group); a phenyl C1-6 alkoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group); and a piperidyl group (which may have at least one amino group on the piperidine ring which may have at least one group selected from a group consisting of a phenyl C1-6 alkyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) and C1-6 alkyl group)) includes a phenyl group (which may be substituted on the phenyl ring by 1 to 5, preferably 1 to 3 groups selected from a group consisting of a halogen atom; a halogen-substituted or unsubstituted C1-6 alkyl group; a halogen-substituted or unsubstituted C1-6 alkoxy group; an amino group which may have 1 to 2 groups selected from a group consisting of a C1-6 alkyl group and a phenyl C1-6 alkyl group (which may be substituted on the phenyl ring by 1 to 5, preferably 1 to 3 groups selected from a group consisting of a halogen atom; halogen-substituted or unsubstituted C1-6 alkyl group; and halogen-substituted or unsubstituted C1-6 alkoxy group) as a substituent; a phenoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group); a phenyl C1-6 alkoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group); and a piperidyl group (which may have at least one amino group on the piperidine ring which may have 1 to 2 groups selected from a group consisting of a phenyl C1-6 alkyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group) and C1-6 alkyl group)), for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 3,4,5-trichlorophenyl group, 2,4,6-trifluorophenyl group, 2,3,4,5,6-pentafluorophenyl group, 2,4,6-trichlorophenyl group, 2-methylphenyl group, 3-methylphenyl group, 4-methylphenyl group, 2,4-dimethylphenyl group, 3,4,5-trimethylphenyl group, 3,5-ditrifluoromethylphenyl group, 2-methyl-3-chlorophenyl group, 3-methyl-4-chlorophenyl group, 2-chloro-4-methylphenyl group, 2-methyl-3-fluorophenyl group, 2-trifluoromethylphenyl group, 3-trifluoromethylphenyl group, 4-trifluoromethylphenyl group, 2-pentafluoroethylphenyl group, 3-pentafluoroethylphenyl group, 4-pentafluoroethylphenyl group, 2-isopropylphenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoropropylphenyl group, 4-pentylphenyl group, 4-hexylphenyl group, 2-methoxyphenyl group, 3-methoxyphenyl group, 4-methoxyphenyl group, 2-methoxy-3-chlorophenyl group, 2-fluoro-3-methoxyphenyl group, 2-fluoro-4-methoxyphenyl group, 2,6-dimethoxyphenyl group, 2,4,6-trimethoxyphenyl group, 3,5- difluoromethoxyphenyl group, 2-trifluoromethoxyphenyl group, 3-trifluoromethoxyphenyl group, 4-trifluoromethoxyphenyl group, 2-pentafluoroethoxyphenyl group, 3-pentafluoroethoxyphenyl group, 4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropropoxyphenyl group, 3-n-heptafluoropropoxyphenyl group, 4-n-heptafluoropropoxyphenyl group, 4-pentyloxyphenyl group, 4-hexyloxyphenyl group, 3-aminophenyl, 3-methylaminophenyl group, 3-dimethylaminophenyl group, 4-methylaminophenyl group, 4-dimethylaminophenyl group, 4-ethylaminophenyl group, 4-diethylaminophenyl group, 4-n-propylaminophenyl group, 4-di-n-propylaminophenyl group, 4-n-butylaminophenyl group, 4-di-n-butylaminophenyl group, 4-n-pentylaminophenyl group, 4-di-n-pentylaminophenyl group, 4-n-hexylaminophenyl group, 4-di-n-hexylaminophenyl group, 4-benzylaminophenyl group, 4-(2-fluorobenzylamino)phenyl group, 4-(3-fluorobenzylamino)phenyl group, 4-(4-fluorobenzylamino)phenyl group, 4-(2,3-difluorobenzylamino)phenyl group, 4-(2,4-difluorobenzylamino)phenyl group, 4-(3,4-difluorobenzylamino)phenyl group, 4-(3,5-difluorobenzylamino)-phenyl group, 4-(2-chlorobenzylamino)phenyl group, 4-(3-chlorobenzylamino)phenyl group, 4-(4-chlorobenzylamino)phenyl group, 4-(2-bromobenzylamino)phenyl group, 4-(3-bromobenzylamino)phenyl group, 4-(4-bromobenzylamino)phenyl group, 4-(2,3-dichlorobenzylamino)phenyl group, 4-(2,4-dichlorobenzylamino)phenyl group, 4-(3,4-dichlorobenzylamino)phenyl group, 4-(3,5-dichlorobenzylamino)phenyl group, 4-(2-methylbenzylamino)phenyl group, 4-(3-methylbenzylamino)phenyl group, 4-(4-methylbenzylamino)phenyl group, 4-(2-ethylbenzylamino)-phenyl group, 4-(3-ethylbenzylamino)phenyl group, 4-(4-ethylbenzylamino)phenyl group, 4-(4-n-propylbenzylamino)phenyl group, 4-(4-tert-butylbenzylamino)phenyl group, 4-(4-n-butylbenzylamino)phenyl group, 4-(2-trifluoromethylbenzylamino)phenyl group, 4-(3-trifluoromethylbenzylamino)phenyl group, 4-(4-trifluoromethylbenzylamino)phenyl group, 4-(2-pentafluoroethylbenzylamino)phenyl group, 4-(3-pentafluoroethylbenzylamino)phenyl group, 4-(2,3-dimethylbenzylamino)phenyl group, 4-(3,4,5-trimethylbenzylamino)phenyl group, 4-(4-pentylbenzylamino)phenyl group, 4-(4-hexylbenzylamino)phenyl group, 4-(3-methoxybenzylamino)phenyl group, 4-(3,5-dimethoxybenzylamino)phenyl group, 4-(2,4,6-trimethoxybenzylamino)phenyl group, 4-(2-trifluoromethoxybenzylamino)phenyl group, 4-(3-trifluoromethoxybenzylamino)phenyl group, 4-(4-trifluoromethoxybenzylamino)phenyl group, 4-(2-pentafluoroethoxybenzylamino)phenyl group, 4-(3-pentafluoroethoxybenzylamino)phenyl group, 4-(4-pentafluoroethoxybenzylamino)phenyl group, (phenethylamino)phenyl group, 4-(2-fluorophenethylamino)phenyl group, 4-(3-fluorophenethylamino)phenyl group, 4-(4-fluorophenethylamino)phenyl group, 4-(2,3-difluorophenethylamino)phenyl group, 4-(2,4-difluorophenethylamino)phenyl group, 4-(3,4-difluorophenethylamino)phenyl group, 4-(3,5-difluorophenethylamino)phenyl group, 4-(2-chlorophenethylamino)phenyl group, 4-(3-chlorophenethylamino)phenyl group, 4-(4-chlorophenethylamino)phenyl group, 4-(2-bromophenethylamino)phenyl group, 4-(3-bromophenethylamino)phenyl group, 4-(4-bromophenethylamino)phenyl group, 4-(2,3-dichlorophenethylamino)phenyl group, 4-(2,4-dichlorophenethylamino)phenyl group, 4-(3,4-dichlorophenethylamino)-phenyl group, 4-(3,5-dichlorophenethylamino)phenyl group, 4-(2-methylphenethylamino)phenyl group, 4-(3-methylphenethylamino)phenyl group, 4-(4-methylphenethylamino)phenyl group, 4-(4-ethylphenethylamino)phenyl group, 4-(4-propylphenethylamino)phenyl group, 4-(4-tert-butylphenethylamino)phenyl group, 4-(2-trifluoromethylphenethylamino)phenyl group, 4-(3-trifluoromethylphenethylamino)phenyl group, 4-(4-trifluoromethylphenethylamino)phenyl group, 4-(2-pentafluoroethylphenethylamino)phenyl group, 4-(3-pentafluoroethylphenethylamino)phenyl group, 4-(2,3-dimethylphenethylamino)phenyl group, 4-(2-trifluoromethoxyphenethylamino)phenyl group, 4-(3-trifluoromethoxyphenethylamino)phenyl group, 4-(4-trifluoromethoxyphenethylamino)phenyl group, 4-(2-pentafluoroethoxyphenethylamino)phenyl group, 4-(3-pentafluoroethoxyphenethylamino)phenyl group, 4-(4-pentafluoroethoxyphenethylamino)phenyl group, 4-(3-phenylpropylamino)phenyl group, 4-[3-(2-fluorophenyl)propylamino]-phenyl group, 4-[3-(3-fluorophenyl)propylamino]phenyl group, 4-[3-(4-fluorophenyl)propylamino]phenyl group, 4-[3-(2,3-difluorophenyl)propylamino]phenyl group, 4-[3-(2,4-difluorophenyl)propylamino]phenyl group, 4-[3-(3,4-difluorophenyl)propylamino]phenyl group, 4-[3-(3,5-difluorophenyl)propylamino]phenyl group, 4-[3-(2-chlorophenyl)propylamino]phenyl group, 4-[3-(3-chlorophenyl)propylamino]phenyl group, 4-[3-(4-chlorophenyl)propylamino]phenyl group, 4-[3-(2-bromophenyl)propylamino]phenyl group, 4-[3-(3-bromophenyl)propylamino]phenyl group, 4-[3-(4-bromophenyl)propylamino]phenyl group, 4-[3-(2,3-dichlorophenyl)propylamino]phenyl group, 4-[3-(2,4-dichlorophenyl)propylamino]phenyl group, 4-[3-(3,4-dichlorophenyl)propylamino]phenyl group, 4-[3-(3,5-dichlorophenyl)propylamino]phenyl group, 4-[3-(2-methylphenyl)propylamino]phenyl group, 4-[3-(3-methylphenyl)propylamino]phenyl group, 4-[3-(4-methylphenyl)propylamino]phenyl group, 4-[3-(2-ethylphenyl)propylamino]phenyl group, 4-[3-(3-ethylphenyl)-propylamino]phenyl group, 4-[3-(4-ethylphenyl)propylamino]phenyl group, 4-[3-(4-propylphenyl)propylamino]-phenyl group, 4-[3-(4-tert-butylphenyl)propylamino]-phenyl group, 4-[3-(4-butylphenyl)propylamino]phenyl group, 4-[3-(2-trifluoromethylphenyl)propylamino]phenyl group, 4-[3-(3-trifluoromethylphenyl)propylamino]phenyl group, 4-[3-(4-trifluoromethylphenyl)propylamino]phenyl group, 4-[3-(2-pentafluoroethylphenyl)propylamino]-phenyl group, 4-[3-(3-pentafluoroethylphenyl)propylamino]phenyl group, 4-[3-(2,3-dimethylphenyl)propylamino]phenyl group, 4-[3-(3,4,5-timethylphenyl)propylamino]phenyl group, 4-[3-(4-pentylphenyl)propylamino]-phenyl group, 4-[3-(4-hexylphenyl)propylamino]phenyl group, 4-[3-(2-trifluoromethoxyphenyl)propylamino]-phenyl group, 4-[3-(3-trifluoromethoxyphenyl)propylamino]-phenyl group, 4-[3-(4-trifluoromethoxyphenyl)propylamino]phenyl group, 4-[3-(2-pentafluoroethoxyphenyl)-propylamino]phenyl group, 4-[3-(3-pentafluoroethoxyphenyl)propylamino]phenyl group, 4-[3-(4-pentafluoroethoxyphenyl)propylamino]phenyl group, 2-phenoxyphenyl group, 3-phenoxyphenyl group, 4-phenoxyphenyl group, 2-(2-chlorophenoxy)phenyl group, 2-(3-chlorophenoxy)-phenyl group, 2-(4-chlorophenoxy)phenyl group, 3-(2-chlorophenoxy)phenyl group, 3-(3-chlorophenoxy)phenyl group, 3-(4-chlorophenoxy)phenyl group, 4-(2-chlorophenoxy)phenyl group, 4-(3-chlorophenoxy)phenyl group, 4-(4-chlorophenoxy)phenyl group, 3-(4-methylphenoxy)phenyl group, 3-(3,4-dimethylphenoxy)-phenyl group, 4-(2,4,6-trimethylphenoxy)phenyl group, 2-(2-trifluoromethylphenoxy)phenyl group, 2-(3-trifluoromethylphenoxy)phenyl group, 2-(4-trifluoromethylphenoxy)phenyl group, 3-(2-trifluoromethylphenoxy)phenyl group, 3-(3-trifluoromethylphenoxy)-phenyl group, 3-(4-trifluoromethylphenoxy)phenyl group, 4-(2-trifluoromethylphenoxy)phenyl group, 4-(3-trifluoromethylphenoxy)phenyl group, 4-(4-trifluoromethylphenoxy)phenyl group, 3-(4-methoxyphenoxy)phenyl group, 2-(3,4-dimethoxyphenoxy)phenyl group, 4-(2,4,6-trimethoxyphenoxy)phenyl group, 2-(2-trifluoromethoxyphenoxy)phenyl group, 2-(3-trifluoromethoxyphenoxy)phenyl group, 2-(4-trifluoromethoxyphenoxy)phenyl group, 3-(2-trifluoromethoxyphenoxy) phenyl group, 3-(3-trifluoromethoxyphenoxy)phenyl group, 3-(4-trifluoromethoxyphenoxy)phenyl group, 4-(2-trifluoromethoxyphenoxy)phenyl group, 4-(3-trifluoromethoxyphenoxy)phenyl group, 4-(4-trifluoromethoxyphenoxy) phenyl group, 4-benzyloxyphenyl group, 4-(2-phenylethoxy)phenyl group, 4-(3-phenylpropoxy)phenyl group, 4-(4-phenylbutoxy)phenyl group, 4-(5-phenylpentoxy)phenyl group, 4-(6-phenylhexyloxy)phenyl group, 4-(4-fluorobenzyloxy)phenyl group, 4-(3-fluorobenzyloxy) phenyl group, 4-(2-fluorobenzyloxy)phenyl group, 4-(4-chlorobenzyloxy)phenyl group, 4-(3-chlorobenzyloxy)phenyl group, 4-(2-chlorobenzyloxy)phenyl group, 3-(4-methylbenzyloxy)phenyl group, 2-(2,4-dimethylbenzyloxy)phenyl group, 4-(2,4,6-trimethylbenzyloxy)-phenyl group, 4-(2-trifluoromethylbenzyloxy)phenyl group, 4-(3-trifluoromethylbenzyloxy)phenyl group, 4-(4-trifluoromethylbenzyloxy)phenyl group, 3-(4-methoxybenzyloxy) phenyl group, 2-(2,4-dimethoxy-benzyloxy)phenyl group, 4-(2,4,6-trimethoxybenzyloxy)phenyl group, 4-(2-trifluoromethoxybenzyloxy)phenyl group, 4-(3-trifluoromethoxybenzyloxy)phenyl group, 4-(4-trifluoromethoxybenzyloxy) phenyl group, 4-(4-fluorophenylethoxy)phenyl group, 4-(3-fluorophenyl-ethoxy)phenyl group, 4-(2-fluorophenylethoxy)phenyl group, 4-(4-chlorophenylethoxy)phenyl group, 4-(3-chlorophenylethoxy)phenyl group, 4-(2-chlorophenylethoxy)phenyl group, 4-(2-trifluoromethylphenylethoxy)-phenyl group, 4-(3-trifluoromethylphenylethoxyl)phenyl group, 4-(4-trifluoromethylphenylethoxyl)phenyl group, 4-(2-trifluoromethoxyphenylethoxyl)phenyl group, 4-(3-trifluoromethoxyphenylethoxyl)phenyl group, 4-(4-trifluoromethoxyphenylethoxyl)phenyl group, 4-(3-trifluoromethoxyphenylethoxyl)phenyl group, 4-(4-trifluoromethoxyphenylethoxyl)phenyl group, 4-[3-(4-fluorophenyl)propoxy]phenyl group, 4-[3-(3-fluoro-phenyl)propoxy]phenyl group, 4-[3-(2-fluorophenyl)propoxy]phenyl group, 4-[3-(2-trifluoromethylphenyl)propoxy]phenyl group, 4-[3-(3-trifluoromethylphenyl)propoxy]phenyl group, 4-[3-(4-trifluoromethylphenyl)propoxy]phenyl group, 4-[3-(2-trifluoromethylphenyl)-propoxy]phenyl group, 4-[3-(3-trifluoromethoxyphenyl)-propoxy]phenyl group, 4-[3-(4-trifluoromethoxyphenyl)-propoxy]phenyl group, 4-[4-(3-trifluoromethylphenyl)-butoxy]phenyl group, 4-[5-(4-trifluoromethylphenyl)-pentoxy]phenyl group, 4-[4-(4-trifluoromethoxyphenyl)-pentoxy]phenyl group, 4-[6-(3-trifluoromethylphenyl)-hexyloxy]phenyl group, 4-[6-(4-trifluoromethylphenyl)-hexyloxy]phenyl group, 4-[6-(4-trifluoromethoxyphenyl)-hexyloxy]phenyl group, 3-(piperidin-1-yl)phenyl group, 2-(4-benzylaminopiperidin-1-yl)phenyl group, 2-(3-benzylaminopiperidin-1-yl)phenyl group, 2-(4-benzylaminopiperidin-1-yl)phenyl group, 2-(4-benzylaminopiperidin-1-yl)phenyl group, 2-(4-benzylaminopiperidin-1-yl)phenyl group, 2-[4-(4-chlorobenzyl)aminopiperidin-1-yl]phenyl group, 2-[2-(2,4-dichlorobenzyl)aminopiperidin-1-yl]phenyl group, 2-[4-(2,4,6-trichlorobenzyl)aminopiperidin-1-yl]phenyl group, 2-[4-(4-methylbenzyl)aminopiperidin-1-yl]phenyl group, 2-[4-(2,4-dimethylbenzyl)aminopiperidin-1-yl]phenyl group, 2-[4-(2,4,6-trimethylbenzyl)aminopiperidin-1-yl] phenyl group, 2-[4-(4-trifluoromethylbenzyl)aminopiperidin-1-yl]phenyl group, 2-{4-[2,4-di(trifluoromethyl)benzyl]piperidin-1-yl}phenyl group, 2-{4-[2,4,6-tri(trifluoromethyl)benzyl]aminopiperidin-1-yl}phenyl group, 2-[4-(4-methoxybenzyl)aminopiperidin-1-yl]phenyl group, 2-[4-(2,4-dimethoxybenzyl)aminopyridin-1-yl]phenyl group, 2-[4-(2,4,6-trimethoxybenzyl)aminopeperidin-1-yl] phenyl group, 2-[4-(4-trifluoromethoxybenzyl)aminopiperidin-1-yl]phenyl group, 2-{4-[2,4,6-tri(trifluoromethoxy)benzyl]-aminopiperidin-1-yl}phenyl group, 2-{4-[3,5-di(trifluoromethoxy)benzyl]aminopiperidin-1-yl}phenyl group, 4-(4-methylaminopiperidin-1-yl)phenyl group, 4-(4-dimethylaminopiperidin-1-yl)phenyl group, 4-(4-ethylaminopiperidin-1-yl)phenyl group, 4-(4-diethylaminopiperidin-1-yl)phenyl group, 4-(4-n-propylaminopiperidin-1-yl) phenyl group, 4-(4-(din-propylamino)piperidin-1-yl group, 4-(4-n-butylaminopiperidin-1-yl)phenyl group, 4-[4-(N-ethyl-N-methylamino)piperidin-1-yl]phenyl group, 4-[4-(N-benzyl-N-methylamino)piperidin-1-yl]phenyl group, 4-(4-n-pentylaminopiperidin-1-yl)phenyl group, 4-(4-n-hexylaminopiperidin-1-yl)phenyl group or the like.

Examples of a biphenylyl C1-6 alkoxy group include 1,1'-biphenyl-4-ylmethoxy group, 2-(1,1'-biphenyl-4-yl)ethoxy group, 3-(1,1'-biphenyl-4-yl)propoxy group, 4-(1,1'-biphenyl-4-yl)butoxy group, 5-(1,1'-biphenyl-4-yl)pentyloxy group, 6-(1,1'-biphenyl-4-yl)hexyloxy group or the like.

A phenyl C3-6 alkenyloxy group which may be substituted on the phenyl ring by at least one halogen atom includes a phenyl C3-6 alkenyloxy group which may be substituted on the phenyl ring by 1 to 5, preferably 1 to 3 halogen atoms, for example, a 3-phenyl-2-propenyloxy group (trivial name: cinnamyloxy group), 4-phenyl-2-butenyloxy group, 4-phenyl-3-butenyloxy group, 3-(2-fluorophenyl)-2-propenyloxy group, 3-(3-fluorophenyl)-2-propenyloxy group, 3-(4-fluorophenyl)-2-propenyloxy group, 3-(2,3-difluorophenyl)-2-propenyloxy group, 3-(2,4-difluorophenyl)-2-propenyloxy group, 3-(3,4-difluorophenyl)-2-propenyloxy group, 3-(3,5-difluorophenyl)-2-propenyloxy group, 3-(2-chlorophenyl)-2-propenyloxy group, 3-(3-chlorophenyl)-2-propenyloxy group, 3-(4-chlorophenyl)-2-propenyloxy group, 3-(2,4,6-trichlorophenyl)-2-propenyloxy group, 3-(2,3,4,5,6-pentafluorophenyl)-2-propenyloxy group, 3-(2,3-dichlorophenyl)-2-propenyloxy group, 3-(2,4-dichlorophenyl)-2-propenyloxy group, 3-(3,4-dichlorophenyl)-2-propenyloxy group, 3-(3,5-dichlorophenyl)-2-propenyloxy group, 3-(2-bromophenyl)-2-propenyloxy group, 3-(3-bromophenyl)-2-propenyloxy group, 3-(4-bromophenyl)-2-propenyloxy group, 4-(4-chlorophenyl)-3-butenyloxy group, 4-(2,3-dichlorophenyl)-3-butenyloxy group, 4-(2,4-dichlorophenyl)-3-butenyloxy group, 4-(3,4-dichlorophenyl)-3-butenyloxy group, 4-(3,5-dichlorophenyl)-3-butenyloxy group, 5-(4-chlorophenyl)-4-pentenyloxy group, 5-(2,3-dichlorophenyl)-4-pentenyloxy group, 5-(2,4-dichlorophenyl)-4-pentenyloxy group, 5-(3,4-dichlorophenyl)-4-pentenyloxy group, 5-(3,5-dichlorophenyl)-4-pentenyloxy group, 6-(4-chlorophenyl)-5-hexenyloxy group, 6-(2,3-dichlorophenyl)-5-hexenyloxy group, 6-(2,4-dichlorophenyl)-5-hexenyloxy group, 6-(3,4-dichlorophenyl)-5-hexenyloxy group, 6-(3,5-dichlorophenyl)-5-hexenyloxy group or the like.

A phenoxy group (which may be substituted on the phenyl ring by at least one group selected from a group consisting of a halogen atom, cyano group, halogen-substituted or unsubstituted C1-6 alkyl group and halogen-substituted or unsubstituted C1-6 alkoxy group) includes a phenoxy group (which may be substituted on the phenyl ring by 1 to 5, preferably 1 to 3 groups selected from a group consisting of a halogen atom, cyano group, halogen-substituted or unsubstituted C1-6 alkyl group and halogen-substituted or unsubstituted C1-6 alkoxy group), for example, a phenoxy group, 2-fluorophenoxy group, 3-fluorophenoxy group, 4-fluorophenoxy group, 2-chlorophenoxy group, 3-chlorophenoxy group, 4-chlorophenoxy group, 2-bromophenoxy group, 3-bromophenoxy group, 4-bromophenoxy group, 2,3-dichlorophenoxy group, 3,4-dichlorophenoxy group, 2,4-dichlorophenoxy group, 3,4,5-trichlorophenoxy group, 2,4,6-trichlorophenoxy group, 2,3,4,5,6-pentafluorophenoxy group, 2-cyanophenoxy group, 3-cyanophenoxy group, 4-cyanophenoxy group, 2-methylphenoxy group, 2,4,6-tricyanophenoxy group, 2,3-dicyanophenoxy group, 3-methylphenoxy group, 4-methylphenoxy group, 2-ethylphenoxy group, 3-ethylphenoxy group, 4-ethylphenoxy group, 4-n-propylphenoxy group, 4-tert-butylphenoxy group, 4-n-butylphenoxy group, 2-trifluoromethylphenoxy group, 3-trifluoromethylphenoxy group, 4-trifluoromethylphenoxy group, 2-pentafluoroethylphenoxy group, 3-pentafluoroethylphenoxy group, 2,3-dimethylphenoxy group, 3,4,5-trimethylphenoxy group, 4-n-pentylphenoxy group, 4-n-hexylphenoxy group, 2-methoxyphenoxy group, 3-methoxyphenoxy group, 4-methoxyphenoxy group, 2-ethoxyphenoxy group, 3-ethoxyphenoxy group, 4-ethoxyphenoxy group, 4-n-propoxyphenoxy group, 4-tert-butoxyphenoxy group, 4-n-butoxyphenoxy group, 2-trifluoromethoxyphenoxy group, 3-trifluoromethoxyphenoxy group, 4-trifluoromethoxyphenoxy group, 2-pentafluoroethoxyphenoxy group, 3-pentafluoroethoxy-phenoxy group, 2,3-dimethoxyphenoxy group, 3,4,5-trimethoxyphenoxy group, 4-n-pentyloxyphenoxy group, 4-n-hexyloxyphenoxy group or the like.

A phenyl C1-6 alkoxycarbonyl group (which may be substituted on the phenyl ring by at least one halogen-substituted or unsubstituted C1-6 alkoxy group) includes a phenyl C1-6 alkoxycarbonyl group (which may be substituted on the phenyl ring by 1 to 3 halogen-substituted or unsubstituted C1-6 alkoxy groups), for example, a benzyloxycarbonyl group, phenylethoxyoxycarbonyl group, 3-phenylpropoxycarbonyl group, 2-phenylpropoxycarbonyl group, 4-phenylbutoxycarbonyl group, 5-phenylpentoxycarbonyl group, 4-phenylpentoxycarbonyl group, 6-phenylhexyloxycarbonyl group, 2-methoxybenzyloxycarbonyl group, 2,4-dimethoxybenzyloxycarbonyl group, 2,4,6-trimethoxybenzyloxycarbonyl group, 2-trifluoromethoxybenzyloxycarbonyl group, 3-trifluoromethoxybenzyloxycarbonyl group, 4-trifluoromethoxybenzyloxycarbonyl group, 2-(2-trifluoromethoxyphenyl)ethoxycarbonyl group, 2-(3-trifluoromethoxyphenyl)ethoxycarbonyl group, 2-(4-trifluoromethoxyphenyl)ethoxycarbonyl group, 3-(3-trifluoromethoxyphenyl)propoxycarbonyl group, 3-(4-trifluoromethoxyphenyl)propoxycarbonyl group, 4-(4-trifluoromethoxyphenyl)pentoxycarbonyl group, 6-(4-trifluoromethoxyphenyl)hexyloxycarbonyl group or the like.

A phenyl C1-6 alkylcarbamoyl group which may be substituted on the phenyl ring by at least one halogen atom includes a phenyl C1-6 alkylcarbamoyl group which may be substituted on the phenyl ring by 1 to 5 halogen atoms, for example, a benzylcarbamoyl group, 2-phenethylcarbamoyl group, 3-phenylpropylcarbamoyl group, 2-phenylpropylcarbamoyl group, 4-phenylbutylcarbamoyl group, 5-phenylpentylcarbamoyl group, 4-phenylpentylcarbamoyl group, 6-phenylhexylcarbamoyl group, 2-fluorobenzylcarbamoyl group, 3-fluorobenzylcarbamoyl group, 2,4,6-trichlorobenzylcarbamoyl group, 2,3,4,5,6-pentafluorobenzylcarbamoyl group, 4-fluorobenzylcarbamoyl group, 2-chlorobenzylcarbamoyl group, 3-chlorobenzylcarbamoyl group, 4-chlorobenzylcarbamoyl group, 2-bromobenzylcarbamoyl group, 3-bromobenzylcarbamoyl group, 4-bromobenzylcarbamoyl group, 2-iodobenzylcarbamoyl group, 3-iodobenzylcarbamoyl group, 4-iodobenzylcarbamoyl group, 2,3-difluorobenzylcarbamoyl group, 3,4-difluorobenzylcarbamoyl group, 3,5-difluorobenzylcarbamoyl group, 2,4-difluorobenzylcarbamoyl group, 2,6-difluorobenzylcarbamoyl group, 2,3-dichlorobenzylcarbamoyl group, 3,4-dichlorobenzylcarbamoyl group, 3,5-dichlorobenzylcarbamoyl group, 2,4-dichlorobenzylcarbamoyl group, 2,6-dichlorobenzylcarbamoyl group or the like.

A phenylthio group (which may be substituted on the phenyl ring by at least one halogen-substituted or unsubstituted C1-6 alkoxy group) includes a phenylthio group (which may be substituted on the phenyl ring by 1 to 3 halogen-substituted or unsubstituted C1-6 alkoxy groups), for example, a phenylthio group, 2-methoxyphenylthio group, 3-methoxyphenylthio group, 4-methoxyphenylthio group, 2,4-dimethoxyphenylthio group, 2,4,6-trimethoxyphenylthio group, 3,5-ditrifluoromethoxyphenylthio group, 2-trifluoromethoxyphenylthio group, 3-trifluoromethoxyphenylthio group, 4-trifluoromethoxyphenylthio group, 4-ethoxyphenylthio group, 4-pentafluoroethoxyphenylthio group, 4-propoxyphenylthio group, 4-butoxyphenylthio group, 4-pentyloxyphenylthio group, 4-hexyloxyphenylthio group or the like.

A phenylsulfoxide group (which may be substituted on the phenyl ring by at least one halogen-substituted or unsubstituted C1-6 alkoxy group) includes a phenylsulfoxide group (which may be substituted on the phenyl ring by 1 to 3 halogen-substituted or unsubstituted C1-6 alkoxy groups), for example, a phenylsulfoxide group, 2-methoxyphenyl-sulfoxide group, 3-methoxyphenylsulfoxide group, 4-methoxyphenylsulfoxide group, 2,4-dimethoxyphenylsulfoxide group, 2,4,6-trimethoxyphenylsulfoxide group, 3,5-ditrifluoromethoxyphenylsulfoxide group, 2-trifluoromethoxyphenylsulfoxide group, 3-trifluoromethoxyphenylsulfoxide group, 4-trifluoromethoxyphenylsulfoxide group or the like.

A pyridyl C1-6 alkoxy group includes, for example, 2-pyridylmethoxy group, 3-pyridylmethoxy group, 4-pyridylmethoxy group, 2-(2-pyridyl)ethoxy group, 2-(3-pyridyl)ethoxy group, 2-(4-pyridyl)ethoxy group, 3-(2-pyridyl)propoxy group, 3-(3-pyridyl)propoxy group, 3-(4-pyridyl)propoxy group, 4-(2-pyridyl)butoxy group, 4-(3-pyridyl)butoxy group, 4-(4-pyridyl)butoxy group, 5-(2-pyridyl)pentyloxy group, 5-(3-pyridyl)pentyloxy group, 5-(4-pyridyl)pentyloxy group, 6-(2-pyridyl)hexyoxy group, 6-(3-pyridyl)hexyloxy group, 6-(4-pyridyl)hexyloxy group or the like.

A phenyl C2-6 alkanoyl group which may be substituted on the phenyl ring by at least one halogen atom includes a phenyl C2-6 alkanoyl group which may be substituted on the phenyl ring by 1 to 5 halogen atoms, for example, a phenylacetyl group, 3-phenylpropionyl group, 4-phenylbutyryl group, 5-phenylpentanoyl group, 6-phenylhexanoyl group, 2-fluorophenylacetyl group, 3-fluorophenylacetyl group, 4-fluorophenylacetyl group, 2-chlorophenylacetyl group, 3-chlorophenylacetyl group, 4-chlorophenylacetyl group, 2-bromophenylacetyl group, 3-bromophenylacetyl group, 4-bromophenylacetyl group, 2,3-dichlorophenylacetyl group, 2,4,6-trichlorophenylacetyl group, 2,3,4,5,6-pentafluorophenylacetyl group, 3-(2-fluorophenyl)propionyl group, 3-(3-fluorophenyl)-propionyl group, 3-(4-fluorophenyl)propionyl group, 3-(2-chlorophenyl)propionyl group, 3-(3-chlorophenyl)propionyl group, 3-(4-chlorophenyl)propionyl group, 3-(2-bromophenyl)propionyl group, 3-(3-bromophenyl)-propionyl group, 3-(4-bromophenyl)propionyl group, 4-(4-fluorophenyl)butyryl group, 4-(3-chlorophenyl)-butyryl group, 4-(4-chlorophenyl)butyryl group, 5-(4-fluorophenyl)pentanoyl group, 5-(3-chlorophenyl)-pentanoyl group, 5-(4-chlorophenyl)pentanoyl group, 6-(4-fluorophenyl)hexanoyl group, 5-(3-chlorophenyl)-hexanoyl group, 6-(4-chlorophenyl)hexanoyl group or the like.

A phenylcarbamoyl group (which may be substituted on the phenyl ring by at least one halogen-substituted or unsubstituted C1-6 alkyl group) includes a phenylcarbamoyl group (which may be substituted on the phenyl ring by 1 to 3 halogen-substituted or unsubstituted C1-6 alkyl groups) wherein the amino moiety of the carbamoyl group may be substituted further by a C1-6 alkyl group or a phenyl C1-6 alkyl group, for example, a phenylcarbamoyl group, 2-methylphenylcarbamoyl group, 3-methylphenylcarbamoyl group, 4-methylphenylcarbamoyl group, 3,4-dimethyl-phenylcarbamoyl group, 2,4,6-trimethylphenylcarbamoyl group, 4-n-propylphenylcarbamoyl group, 4-n-butylphenylcarbamoyl group, 3-n-pentylphenylcarbamoyl group, 2-n-hexylphenylcarbamoyl group, 2-trifluoromethylphenylcarbamoyl group, 3-trifluoromethylphenylcarbamoyl group, 4-trifluoromethylphenylcarbamoyl group, N-methyl-N-phenylcarbamoyl group, N-(2-methylphenyl)-N-methylcarbamoyl group, N-(3-ethylphenyl)-N-methylcarbamoyl group, N-(4-n-hexylphenyl)-N-methylcarbamoyl group, N-(2-isopropylphenyl)-N-methylcarbamoyl group, N-(3-n-butylphenyl)-N-methylcarbamoyl group, N-(4-tert-butylphenyl)-N-methylcarbamoyl group, N-(4-n-pentylphenyl)-N-methylcarbamoyl group, N-benzyl-N-phenylcarbamoyl group, N-benzyl-N-(2-trifluoromethylphenyl)carbamoyl group, N-benzyl-N-(2,3-dimethylphenyl)carbamoyl group, N-benzyl-N-(2,4,6-trimethylphenyl)carbamoyl group, N-benzyl-N-(3,5-ditrifluoromethylphenyl)carbamoyl group, N-benzyl-N-(3-methylphenyl)carbamoyl group, N-benzyl-N-(4-tert-butylphenyl)carbamoyl group, N-benzyl-N-(2-isopropylphenyl)-carbamoyl group, N-benzyl-N-(3-n-propylphenyl)carbamoyl group, N-benzyl-N-(4-ethylphenyl)carbamoyl group or the like.

A piperidinyloxycarbonyl group (which may be substituted on the piperidine ring by at least one phenyl group (which may be substituted on the phenyl ring by at least one halogen-substituted or unsubstituted C1-6 alkyl group) as a substituent) includes a piperidinyloxycarbonyl group (which may be substituted on the piperidine ring by 1 to 3 phenyl groups (which may be substituted on the phenyl ring by 1 to 3 halogen-substituted or unsubstituted C1-6 alkyl groups) as a substituent), for example, piperidin-1-yloxycarbonyl group, piperidin-2-yloxycarbonyl group, piperidin-3-yloxycarbonyl group, piperidin-4-yloxycarbonyl group, 1-phenylpiperidin-4-yloxycarbonyl group, 1,2-diphenylpiperidin-4-yloxycarbonyl group, 1,3,4-triphenylpiperidin-4-yloxycarbonyl group, 1-(2-methylphenyl)piperidin-4-yloxycarbonyl group, 1-(3-methylphenyl)piperidin-4-yloxycarbonyl group, 1-(4-methylphenyl)piperidin-4-yloxycarbonyl group, 1-(2,4-dimethylphenyl)piperidin-4-yloxycarbonyl group, 1-(2,4,6-trimethylphenyl)piperidin-4-yloxycarbonyl group, 1-(2-trifluoromethylphenyl)piperidin-4-yloxycarbonyl group, 1-(3-trifluoromethylphenyl)piperidin-4-yloxycarbonyl group, 1-(3,5-ditrifluoromethylphenyl)-piperidin-4-yloxycarbonyl group, 1-(4-trifluoromethylphenyl)piperidin-4-yloxycarbonyl group, 1-(2-pentafluoroethylphenyl)piperidin-4-yloxycarbonyl group, 1-(3-pentafluoroethylphenyl)piperidin-4-yloxycarbonyl group, 1-(4-pentafluoroethylphenyl)piperidin-4-yloxycarbonyl group, 1-(2-n-propylphenyl)piperidin-4-yloxycarbonyl group, 1-(3-n-propylphenyl)piperidin-4-yloxycarbonyl group, 1-(4-n-propylphenyl)piperidin-4-yloxycarbonyl group or the like.

A 5-membered to 6-membered saturated heterocycle formed by bonding $R^{24}$ and $R^{25}$ to each other through the adjacent nitrogen atom is a heterocycle by bonding $R^{24}$ and $R^{25}$ to each other through or not through a nitrogen atom, oxygen atom or sulfur atom together with the adjacent nitrogen atom, examples of which include a pyrrolidinyl group, piperazyl group, piperidyl group, morpholino group, thiomorpholino group or the like.

A C3-8 cycloalkyl-C1-6 alkyl group includes, for example, a cyclopropylmethyl group, 2-cyclopropyethyl group, 3-cyclopropylpropyl group, 4-cyclopropylbutyl group, 4-cyclopropylpentyl group, 6-cyclopropylhexyl group, cyclobutylmethyl group, 2-cyclobutylethyl group, 3-cyclobutylpropyl group, 4-cyclobutylbutyl group, 4-cyclobutylpentyl group, 6-cyclobutylhexyl group, cyclopentylmethyl group, 2-cyclopentylethyl group, 3-cyclopentylpropyl group, 4-cyclopentylbutyl group, 4-cyclopentylpentyl group, 6-cyclopentylhexyl group, cyclohexylmethyl group, 2-cyclohexylethyl group, 3-cyclohexylpropyl group, 4-cyclohexylbutyl group, 4-cyclohexylpentyl group, 6-cyclohexylhexyl group, cycloheptylmethyl group, 2-cycloheptylethyl group, 3-cycloheptylpropyl group, 4-cycloheptylbutyl group, 4-cycloheptylpentyl group, 6-cycloheptylhexyl group, cyclooctylmethyl group, 2-cyclooctylethyl group, 3-cyclooctylpropyl group, 4-cyclooctylbutyl group, 4-cyclooctylpentyl group, 6-cyclooctylhexyl group or the like.

A phenyl C1-6 alkyl group (which may be substituted on the phenyl ring by 1 to 3 groups selected from a group consisting of a halogen atom; cyano group; halogen-substituted or unsubstituted C1-6 alkyl group; C3-8 cycloalkyl group; halogen-substituted or unsubstituted C1-6 alkoxy group; amino group which may have a C1-6 alkyl group as a substituent; C1-6 alkoxycarbonyl group; phenoxy group; phenyl C1-6 alkyl group; phenyl C2-6 alkenyl group; pyridyl group; imidazolyl group; and piperizynyl group) includes, for example, a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 4-cyanobenzyl group, 2,3-dicyanobenzyl group, 2,4,6-tricyanobenzyl group, 2-(4-cyanophenyl)ethyl group, 3-(4-cyanophenyl)propyl group, 2-(4-cyanophenyl)propyl group, 4-(4-cyanophenyl)butyl group, 5-(4-cyanophenyl)pentyl group, 4-(4-cyanophenyl)pentyl group, 6-(4-cyanophenyl)hexyl group, 2-cyanobenzyl group, 2-(3-cyanophenyl)ethyl group, 3-(2-cyanophenyl)propyl group, 2-(2-cyanophenyl)propyl group, 4-(3-cyanophenyl)butyl group, 5-(2-cyanophenyl)- pentyl group, 4-(3-cyanophenyl)pentyl group, 6-(3-cyanophenyl)hexyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2,3-difluorobenzyl group, 3,4-difluorobenzyl group, 3,5-difluorobenzyl group, 2,4-difluorobenzyl group, 2,6-difluorobenzyl group, 2,3-dichlorobenzyl group, 3,4-dichlorobenzyl group, 3,5-dichlorobenzyl group, 2,4,6-trichlorobenzyl group, 2,4-dichlorobenzyl group, 2,6-dichlorobenzyl group, 2-trifluorobenzyl group, 2-methylbenzyl group, 2,4-dimethylbenzyl group, 2,4,6-trimethylbenzyl group, 3,5-ditrifluoromethylbenzyl group, 3-trifluoromethylbenzyl group, 4-trifluoromethylbenzyl group, 2-pentafluoroethylbenzyl group, 3-pentafluoroethylbenzyl group, 4-pentafluoroethylbenzyl group, 2-trifluoromethoxybenzyl group, 3-trifluoromethoxybenzyl group, 4-trifluoromethoxybenzyl group, 2-pentafluoroethoxybenzyl group, 3-pentafluoroethoxybenzyl group, 4-pentafluoroethoxybenzyl group, 2-(2-trifluoromethylphenyl)ethyl group, 2-(3-trifluoromethylphenyl)ethyl group, 2-(4-trifluoromethylphenyl)ethyl group, 2-methoxybenzyl group, 2,4-dimethoxybenzyl group, 2,4,6-trimethoxybenzyl group, 3,5-ditrifluoromethoxybenzyl group, 2-chloro-4-trifluoromethylbenzyl group, 3-fluoro-4-trichloromethoxybenzyl group, 2-(2-trifluoromethoxyphenyl)ethyl group, 2-(3-trifluoromethoxyphenyl)ethyl group, 2-(4-trifluoromethoxyphenyl)ethyl group, 2-(2-pentafluoroethoxyphenyl)ethyl group, 2-(3-pentafluoroethoxyphenyl)ethyl group, 2-(4-pentafluoroethoxyphenyl)ethyl group, 3-(2-trifluoromethylphenyl)propyl group, 3-(3-trifluoromethylphenyl)propyl group, 3-(4-trifluoromethylphenyl)propyl group, 3-(2-trifluoromethoxyphenyl)propyl group, 3-(3-trifluoromethoxyphenyl)propyl group, 3-(4-trifluoromethoxyphenyl)propyl group, 3-(3-pentafluoroethoxyphenyl)propyl group, 3-(4-pentafluoroethoxyphenyl)propyl group, 4-(3-pentafluoroethoxyphenyl)butyl group, 5-(4-trifluoromethylphenyl)-pentyl group, 4-(4-trifluoromethylphenyl)pentyl group, 4-(4-trifluoromethoxyphenyl)pentyl group, 6-(3-trifluoromethylphenyl)hexyl group, 6-(4-trifluoromethylphenyl)hexyl group, 6-(4-trifluoromethoxyphenyl)hexyl group, 2-cyclohexylbenzyl group, 3-cyclohexylbenzyl group, 4-cyclohexylbenzyl group, 2-(2-cyclohexylphenyl)ethyl group, 2-(3-cyclohexylphenyl)-ethyl group, 2-(4-cyclohexylphenyl)ethyl group, 3-(2-cyclohexylphenyl)propyl group, 3-(3-cyclohexylphenyl)-propyl group, 3-(4-cyclohexylphenyl)propyl group, 3-aminobenzyl group, 2,4-diaminobenzyl group, 2,4,6-triaminobenzyl group, 2-dimethylaminobenzyl group, 3-dimethylaminobenzyl group, 4-dimethylaminobenzyl group, 2-(2-dimethylaminophenyl)ethyl group, 2-(3-dimethylaminophenyl)ethyl group, 2-(4-dimethylaminophenyl)ethyl group, 3-(2-dimethylaminophenyl)propyl group, 3-(3-dimethylaminophenyl)propyl group, 3-(4-dimethylaminophenyl)propyl group, 2-methoxycarbonylbenzyl group, 3-methoxycarbonylbenzyl group, 4-methoxycarbonylbenzyl group, 2-(2-methoxycarbonylphenyl)ethyl group, 2-(3-methoxycarbonylphenyl)ethyl group, 2-(4-methoxycarbonylphenyl)ethyl group, 3-(2-methoxycarbonylphenyl)propyl group, 3-(3-methoxycarbonylphenyl)propyl group, 3-(4-methoxycarbonylphenyl)propyl group, 2-ethoxycarbonylbenzyl group, 3-ethoxycarbonylbenzyl group, 4-ethoxycarbonylbenzyl group, 2-(2-ethoxycarbonylphenyl)ethyl group, 2-(3-ethoxycarbonylphenyl)ethyl group, 2-(4-ethoxycarbonylphenyl)ethyl group, 3-(2-ethoxycarbonylphenyl)propyl group, 3-(3-ethoxycarbonylphenyl)propyl group, 3-(4-ethoxycarbonylphenyl)propyl group, 2-phenoxybenzyl group, 3-phenoxybenzyl group, 4-phenoxybenzyl group, 2-styrylbenzyl group, 3-styrylbenzyl group, 4-styrylbenzyl group, 2-(2-phenoxyphenyl)ethyl group, 2-(3-phenoxyphenyl)ethyl group, 2-(4-phenoxyphenyl)ethyl group, 3-(2-phenoxyphenyl)propyl group, 3-(3-phenoxyphenyl)propyl group, 3-(4-phenoxyphenyl)propyl group, 2-benzylbenzyl group, 3-benzylbenzyl group, 4-benzylbenzyl group, 2-(2-benzylphenyl)ethyl group, 2-(3-benzylphenyl)ethyl group, 2-(4-benzylphenyl)ethyl group, 3-(2-benzylphenyl)propyl group, 3-(3-benzylphenyl)propyl group, 3-(4-benzylphenyl)propyl group, 2-(2-phenethyl)benzyl group, 3-(2-phenethyl)benzyl group, 4-(2-phenethyl)benzyl group, 2-(2-(1-phenethyl)phenyl)ethyl group, 2-(3-(2-phenethyl)phenyl)ethyl group, 2-(4-(2-phenethyl)-phenyl)ethyl group, 2-(3-(2-phenethyl)phenyl)propyl group, 3-(2-(2-phenethyl)phenyl)propyl group, 3-(4-(1-phenethyl)phenyl)propyl group, 2-(3-pyridyl)benzyl group, 3-(3-pyridyl)benzyl group, 4-(3-pyridyl)benzyl group, 2-(1-imidazolyl)benzyl group, 3-(1-imidazolyl)benzyl group, 4-(1-imidazolyl)benzyl group, 2-(1-piperidino)benzyl group, 3-(1-piperidino)benzyl group, 4-(1-piperidino)benzyl group or the like.

A biphenylyl C1-6 alkyl group (which may be substituted on the phenyl ring by at least one group selected from a group consisting of a halogen atom, a halogen-substituted or unsubstituted C1-6 alkyl group, a halogen-substituted or unsubstituted C1-6 alkoxy group and an amino group which may have a C1-6 alkyl group as a substituent) includes a biphenylyl C1-6 alkyl group (which may be substituted on the phenyl ring by 1 to 5, preferably 1 to 3 groups selected from a group consisting of a halogen atom, a halogen-substituted or unsubstituted C1-6 alkyl group, a halogen-substituted or unsubstituted C1-6 alkoxy group and an amino group which may have 1 to 2 C1-6 alkyl groups as a substituent), for example, a 2-biphenylylmethyl group, 3-biphenylylmethyl group, 4-biphenylylmethyl group, 2-(2-biphenylyl)ethyl group, 2-(3-biphenylyl)ethyl group, 2-(4-biphenylyl)ethyl group, 3-(2-biphenylyl)propyl group, 3-(3-biphenylyl)propyl group, 3-(4-biphenylyl)propyl group, 4-(4-biphenylyl)-butyl group, 5-(4-biphenylyl)pentyl group, 6-(4-biphenylyl)hexyl group, 2'-fluoro-2-biphenylylmethyl group, 2'-fluoro-3-biphenylylmethyl group, 2'-fluoro-4-biphenylylmethyl group, 3'-fluoro-2-biphenylylmethyl group, 3¹-fluoro-3-biphenylylmethyl group, 3'-fluoro-4-biphenylylmethyl group, 4'-fluoro-2-biphenylylmethyl group, 4'-fluoro-3-biphenylylmethyl group, 4'-fluoro-4-biphenylylmethyl group, 2'-chloro-2-biphenylylmethyl group, 2'-chloro-3-biphenylylmethyl group, 2'-chloro-4-biphenylylmethyl group, 3'-chloro-2-biphenylylmethyl group, 3'-chloro-3-biphenylylmethyl group, 3'-chloro-4-biphenylylmethyl group, 4'-chloro-2-biphenylylmethyl group, 4'-chloro-3-biphenylylmethyl group, 4'-chloro-4-biphenylylmethyl group, 2',4'-dichloro-4-biphenylylmethyl group, 2',4',6'-trichloro-3-biphenylylmethyl group, 3',5'-ditritrifluoromethyl-4-biphenylylmethyl group, 2',3',4',5',6'-pentafluoro-3-biphenylylmethyl group, 2'-methyl-2-biphenylylmethyl group, 2'-methyl-3-biphenylylmethyl group, 2'-methyl-4-biphenylylmethyl group, 3'-methyl-2-biphenylylmethyl group, 3'-methyl-3-biphenylylmethyl group, 3'-methyl-4-biphenylylmethyl group, 4'-methyl-2-biphenylylmethyl group, 4'-methyl-3-biphenylylmethyl group, 4'-methyl-4-biphenylylmethyl group, 2'-trifluoromethyl-2- biphenylylmethyl group, 2'-trifluoromethyl-3-biphenylylmethyl group, 2'-trifluoromethyl-4-biphenylylmethyl group, 3'-trifluoromethyl-2-biphenylylmethyl group, 3'-trifluoromethyl-3-biphenylylmethyl group, 3'-trifluoromethyl-4-biphenylylmethyl group, 4'-trifluoromethyl-2-biphenylylmethyl group, 4'-trifluoromethyl-3-biphenylylmethyl group, 4'-trifluoromethyl-4-biphenylylmethyl group, 2'-methoxy-2-biphenylylmethyl group, 2'-methoxy-3-biphenylylmethyl group, 2'-methoxy-4-biphenylylmethyl group, 3'-methoxy-2-biphenylylmethyl group, 3'-methoxy-3-biphenylylmethyl group, 2',4'-dimethoxy-3-biphenylylmethyl group, 2',4',6'-trimethoxy-4-biphenylylmethyl group, 2'-methoxy-4'-trifluoromethyl-2-biphenylylmethyl group, 3'-methyl-4'-trifluoromethoxy-2-biphenylylmethyl group, 2'-chloro-4'-trifluoromethoxy-3-biphenylylmethyl group, 3'-methoxy-4-biphenylylmethyl group, 4'-methoxy-2-biphenylylmethyl group, 4'-methoxy-3-biphenylylmethyl group, 4'-methoxy-4-biphenylylmethyl group, 2'-trifluoromethoxy-2-biphenylylmethyl group, 2'-trifluoromethoxy-3-biphenylylmethyl group, 2'-trifluoromethoxy-4-biphenylylmethyl group, 3'-trifluoromethoxy-2-biphenylylmethyl group, 3'-trifluoromethoxy-3-biphenylylmethyl group, 3'-trifluoromethoxy-4-biphenylylmethyl group, 4'-trifluoromethoxy-2-biphenylylmethyl group, 4'-trifluoromethoxy-3-biphenylylmethyl group, 4'-trifluoromethoxy-4-biphenylylmethyl group, 2-(4'-trifluoromethoxy-4-biphenylyl)ethyl group, 3-(4'-trifluoromethoxy-4-biphenylyl)propyl group, 3-(4'-trifluoromethoxy-4-biphenylyl)propyl group, 4-(4'-trifluoromethoxy-4-biphenylyl)butyl group, 5-(4'-trifluoromethoxy-4-biphenylyl)pentyl group, 6-(4'-trifluoromethoxy-4-biphenylyl)hexyl group, 4'-dimethylamino-3-biphenylylmethyl group, 4'-dimethylamino-4-biphenylylmethyl group or the like.

A naphthyl C1-6 alkyl group includes, for example, 1-naphthylmethyl group, 2-naphthylmethyl group, 2-(1-naphthyl)ethyl group, 1-(2-naphthyl)ethyl group, 3-(1-naphthyl)propyl group, 3-(2-naphthyl)propyl group, 4-(1-naphthyl)butyl group, 4-(2-naphthyl)butyl group, 5-(1-naphthyl)pentyl group, 5-(2-naphthyl)pentyl group, 6-(1-naphthyl)hexyl group, 6-(2-naphthyl)hexyl group or the like.

A phenyl group (which may be substituted on the phenyl ring by at least one group selected from a group consisting of a halogen atom; cyano group; amino group which may have a C1-6 alkyl group as a substituent; halogen-substituted or unsubstituted C1-6 alkyl group; halogen-substituted or unsubstituted C1-6 alkoxy group; C1-6 alkoxycarbonyl group; carboxyl group; phenoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group); amino C1-6 alkyl group (which may have on the amino group at least one group selected from a group consisting of a phenyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) and a C1-6 alkyl group); and a phenyl C1-6 alkoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group) includes a phenyl group (which may be substituted on the phenyl ring by 1 to 5, preferably 1 to 3 groups selected from a group consisting of a halogen atom; cyano group; amino group which may have a C1-6 alkyl group as a substituent; halogen-substituted or unsubstituted C1-6 alkyl group; halogen-substituted or unsubstituted C1-6 alkoxy group; C1-6 alkoxycarbonyl group; carboxyl group; phenoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group); amino C1-6 alkyl group (which may have 1 to 2 groups on the amino group selected from a group consisting of a phenyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group) and a C1-6 alkyl group); and a phenyl C1-6 alkoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group), for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 2,3,4,5,6-pentafluorophenyl group, 3,4,5-trichlorophenyl group, 2,4,6-trifluorophenyl group, 2,4,6-trichlorophenyl group, 2-cyanophenyl group, 3-cyanophenyl group, 4-cyanophenyl group, 2,4-dicyanophenyl group, 2,4,6-tricyanophenyl group, 2-methylphenyl group, 3-methylphenyl group, 4-methylphenyl group, 2,3-dimethylphenyl group, 2,4,6-trimethylphenyl group, 2-methyl-3-chlorophenyl group, 3-methyl-4-chlorophenyl group, 2-chloro-4-methylphenyl group, 2-methyl-3-fluorophenyl group, 2-trifluoro-methylphenyl group, 3-trifluoromethylphenyl group, 4-trifluoromethylphenyl group, 2-pentafluoroethylphenyl group, 3-pentafluoroethylphenyl group, 4-pentafluoroethylphenyl group, 2-isopropylphenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoropropylphenyl group, 4-pentylphenyl group, 4-hexylphenyl group, 2-methoxyphenyl group, 3-methoxyphenyl group, 4-methoxyphenyl group, 2,4-dimethoxyphenyl group, 2,4,6-trimethoxyphenyl group, 2-methoxy-3-chlorophenyl group, 2-fluoro-3-methoxyphenyl group, 2-fluoro-4-methoxyphenyl group, 2,6-dimethoxyphenyl group, 2,3,4-trifluorophenyl group, 2-trifluoromethoxyphenyl group, 3-trifluoromethoxyphenyl group, 4-trifluoromethoxyphenyl group, 2-pentafluoroethoxyphenyl group, 3-pentafluoroethoxyphenyl group, 4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropoxyphenyl group, 3-n-heptafluoropropoxyphenyl group, 4-n-heptafluoropropoxyphenyl group, 4-pentyloxyphenyl group, 4-hexyloxyphenyl group, 3-aminophenyl group, 4-methylaminophenyl group, 2-dimethylaminophenyl group, 3-dimethylaminophenyl group, 4-dimethylaminophenyl group, 2-methoxycarbonylphenyl group, 3-methoxycarbonylphenyl group, 4-methoxycarbonylphenyl group, 2-carboxyphenyl group, 3-carboxyphenyl group, 4-carboxyphenyl group, 2,3-dicarboxyphenyl group, 2,4,6-tricarboxyphenyl group, 2-ethoxycarbonylphenyl group, 3-ethoxycarbonylphenyl group, 4-ethoxycarbonylphenyl group, 2,3-diethoxycarbonylphenyl group, 2,4,6-trimethoxycarbonylphenyl group, 2-phenoxyphenyl group, 3-phenoxyphenyl group, 4-phenoxyphenyl group, 2-(2-chlorophenoxy)phenyl group, 2-(3-chlorophenoxy)phenyl group, 2-(4-chlorophenoxy)phenyl group, 3-(2-chlorophenoxy)phenyl group, 3-(3-chlorophenoxy)phenyl group, 3-(4-chlorophenoxy)phenyl group, 4-(2-chlorophenoxy)phenyl group, 4-(3-chlorophenoxy)phenyl group, 4-(4-chlorophenoxy)phenyl group, 2-(2-trifluoromethylphenoxy)phenyl group, 2-(3-trifluoromethylphenoxy)phenyl group, 2-(3-methylphenoxy)phenyl group, 2-(2,3-dimethylphenoxy)phenyl group, 2-(3,4,5-trimethylphenoxy)phenyl group, 2-(4-trifluoromethylphenoxy)-phenyl group, 3-(2-trifluoromethylphenoxy)phenyl group, 3-(3-trifluoromethylphenoxy)phenyl group, 3-(4-trifluoromethylphenoxy)phenyl group, 4-(2-trifluoromethylphenoxy)phenyl group, 4-(3-trifluoromethylphenoxy)phenyl group, 4-(4-trifluoromethylphenoxy)-phenyl group, 2-(3-methoxyphenoxy)phenyl group, 2-(2,3-dimethoxyphenoxy)phenyl group, 2-(3,4,5-trimethoxyphenoxy)phenyl group, 2-(2-trifluoromethoxyphenoxy)-phenyl group, 2-(3-trifluoromethoxyphenoxy)phenyl group, 2-(4-trifluoromethoxyphenoxy)phenyl group, 3-(2-trifluoromethoxyphenoxy)phenyl group, 3-(3-trifluoromethoxyphenoxy)phenyl group, 3-(4-trifluoromethoxyphenoxy)phenyl group, 4-(2-trifluoromethoxyphenoxy)-phenyl group, 4-(3-trifluoromethoxyphenoxy)phenyl group, 4-(4-trifluoromethoxyphenoxy)phenyl group, 4-aminomethylphenyl group, 4-methylaminomethylphenyl group, 4-dimethylaminomethylphenyl group, 4-diethylaminomethylphenyl group, 4-di(n-propyl)aminomethylphenyl group, 4-(phenylaminomethyl)phenyl group, 4-(2-phenylaminoethyl)phenyl group, 4-(3-phenylaminopropyl)phenyl group, 4-(N-methyl-N-phenylaminomethyl)-phenyl group, 4-(2-N-methyl-N-phenylaminoethyl)phenyl group, 4-(3-N-ethyl-N-phenylaminopropyl)phenyl group, 4-(4-chlorophenylaminomethyl)phenyl group, 4-[2-(4-chlorophenylamino)ethyl]phenyl group, 4-[3-(4-chlorophenylamino)propyl]phenyl group, 4-[N-methyl-N-4-chlorophenylamino]methyl]phenyl group, 4-[2-(N-methyl-N-4-chlorophenylamino)ethyl]phenyl group, 4-[3-(N-ethyl-N-4-chlorophenylamino)propyl] phenyl group, 4-(4-trifluoromethylphenylaminomethyl)phenyl group, 4-[2-(4-trifluoromethylphenylamino)ethyl] phenyl group, 4-[2-(4-methylphenylamino)methyl]phenyl group, 4-[2-(2,4-dimethylphenylamino)methyl]phenyl group, 4-[2-(2,4,6-trimethylphenylamino)methyl]phenyl group, 4-[3-(3,5-ditrifluoromethylphenylamino)propyl]phenyl group, 4-[N-methyl-N-4-trifluoromethylphenylamino] methyl]phenyl group, 4-[2-(N-methyl-N-4-trifluoromethylphenylamino)-ethyl]phenyl group, 4-[3-(N-ethyl-N-4-trifluoromethylphenylamino)propyl]phenyl group, 4-[2-(3-methoxyphenylamino)methyl]phenyl group, 4-[2-(2,4-dimethoxyphenylamino)methyl]phenyl group, 4-[2-(2,4,6-trimethoxyphenylamino)methyl]phenyl group, 4-(4-trifluoromethoxy-phenylaminomethyl)phenyl group, 4-[2-(3,5-ditrifluoromethoxyphenylamino)ethyl]phenyl group, 4-[3-(4-trifluoromethoxyphenylamino)propyl]phenyl group, 4-[N-methyl-N-4-trifluoromethoxyphenylamino]methyl] phenyl group, 4-[2-(N-methyl-N-4-trifluoromethoxyphenylamino)ethyl]phenyl group, 4-[3-(N-ethyl-N-4-trifluoromethoxyphenylamino)propyl] group, 4-benzyloxyphenyl group, 4-(4-chlorobenzyloxy)phenyl group, 4-[2-(2,3-dichlorophenyl)ethoxy]phenyl group, 4-[3-(4-chlorophenyl)propoxy]phenyl group, 4-[4-(2,4,6-trichlorophenyl)butoxy]phenyl group, 4-(4-methylbenzyloxy)phenyl group, 4-(3,4-dimethylbenzyloxy)phenyl group, 4-(2,4,6-trimethylbenzyloxy)phenyl group, 4-(4-trifluoromethylbenzyloxy)-phenyl group, 4-[2-(4-trifluoromethylphenyl)ethoxy]phenyl group, 4-[3-(4-trifluoromethylphenyl)propoxy]phenyl group, 4-[4-(4-trifluoromethylphenyl)butoxy]phenyl group, 4-(4-trifluoromethoxybenzyloxy)phenyl group, 4-(4-methoxybenzyloxy)phenyl group, 4-(3,4-dimethoxybenzyloxy)phenyl group, 4-(2,4,6-trimethoxybenzyloxy)-phenyl group, 4-[2-(4-trifluoromethoxyphenyl)ethoxy]-phenyl group, 4-[3-(4-trifluoromethoxyphenyl)propoxy]-phenyl group, 4-[4-(4-trifluoromethoxyphenyl)butoxy]-phenyl group or the like.

A biphenylyl group (which may be substituted on the phenyl ring by at least one halogen-substituted or unsubstituted C1-6 alkyl group) includes a biphenylyl group (which may be substituted on the phenyl ring by 1 to 3 halogen-substituted or unsubstituted C1-6 alkyl group), for example, a 2-biphenylyl group, 3-biphenylyl group, 4-biphenylyl group, 2'-methyl-2-biphenylyl group, 2'-methyl-3-biphenylyl group, 2'-methyl-4-biphenylyl group, 3'-methyl-2-biphenylyl group, 3'-methyl-3-biphenylyl group, 3'-methyl-4-biphenylyl group, 4'-methyl-2-biphenylyl group, 4'-methyl-3-biphenylyl group, 4'-methyl-4-biphenylyl group, 3',4'-dimethyl-2-biphenylyl group, 2',4',6'-trimethyl-3-biphenylyl group, 2'-trifluoromethyl-4',6'-dimethyl-3-biphenylyl group, 2'-trifluoromethyl-2-biphenylyl group, 2'-trifluoromethyl-3-biphenylyl group, 2'-trifluoromethyl-4-biphenylyl group, 3'-trifluoromethyl-2-biphenylyl group, 3'-trifluoromethyl-3-biphenylyl group, 3'-trifluoromethyl-4-biphenylyl group, 4'-trifluoromethyl-2-biphenylyl group, 4'-trifluoroethyl-3-biphenylyl group, 4'-trifluoromethyl-4-biphenylyl group or the like.

An amino group substituted by a C1-6 alkoxycarbonyl group includes an amino group which is substituted by a C1-6 alkoxycarbonyl group and may have a C1-6 alkyl group as another substituent on the amino group, for example, a methoxycarbonylamino group, ethoxycarbonylamino group, n-propoxycarbonylamino group, isopropoxycarbonylamino group, tert-butoxycarbonylamino group, n-pentoxycarbonylamino group, n-hexyloxycarbonylamino group, N-methyl-N-methoxycarbonylamino group, N-ethoxycarbonyl-N-methylamino group, N-methyl-N-(n-propoxycarbonyl)amino group, N-methyl-N-(isopropoxycarbonyl)amino group, N-(tert-butoxycarbonyl)-N-methylamino group, N-methyl-N-(n-pentoxycarbonyl)amino group, N-(n-hexyloxycarbonyl)-N-methylamino group, N-ethyl-N-methoxycarbonylamino group, N-ethyl-N-ethoxycarbonylamino group, N-ethyl-N-(n-propoxycarbonyl)amino group, N-ethyl-N-isopropoxycarbonylamino group, N-(tert-butoxycarbonyl)-N-ethylamino group, N-ethyl-N-(n-pentoxycarbonyl)amino group, N-ethyl-N-(n-hexyloxycarbonyl)amino group or the like.

A phenylamino group (which may be substituted on the phenyl ring by at least one group selected from a group consisting of a halogen atom and a halogen-substituted or unsubstituted C1-6 alkyl group) includes an amino group having 1 to 2 phenyl groups (which may be substituted on the phenyl ring by 1 to 5, preferably 1 to 3 groups selected from a group consisting of a halogen atom and a halogen-substituted or unsubstituted C1-6 alkyl group), for example, a phenylamino group, 2-methylphenylamino group, 3-methylphenylamino group, 4-methylphenylamino group, 2-ethylphenylamino group, 3-ethylphenylamino group, 4-ethylphenylamino group, 4-propylphenylamino group, 4-tertbutylphenylamino group, 4-butylphenylamino group, 2-trifluoromethylphenylamino group, 3-trifluoromethylphenylamino group, 4-trifluoromethylphenylamino group, 2-pentafluoroethylphenylamino group, 3-pentafluoroethylphenylamino group, 2,3-dimethylphenylamino group, 3,4,5-trimethylphenylamino group, 4-pentylphenylamino group, 4-hexylphenylamino group, N-phenyl-N-(2-fluorophenyl)amino group, 2-fluorophenylamino group, 3-fluorophenylamino group, 4-fluorophenylamino group, 2-chlorophenylamino group, 3-chlorophenylamino group, 4-chlorophenylamino group, 2-bromophenylamino group, 3-bromophenylamino group, 4-bromophenylamino group, 2-iodophenylamino group, 3-iodophenylamino group, 4-iodophenylamino group, 2,3-difluorophenylamino group, 3,4-difluorophenylamino group, 3,5-difluorophenylamino group, 2,4-difluorophenylamino group, 2,6-difluorophenylamino group, 2,3-dichlorophenylamino group, 3,4-dichlorophenylamino group, 3,5-dichlorophenylamino group, 2,4-dichlorophenylamino group, 2,6-dichlorophenylamino group, 3,4,5-trifluorophenylamino group, 2,3,4,5,6-pentafluorophenylamino group, 3,4,5-trichlorophenylamino group, 2,4,6-trifluorophenylamino group, 2,4,6-trichlorophenylamino group or the like.

A benzoyl C1-6 alkyl group (which may be substituted on the phenyl ring by at least one halogen atom as a substituent) includes a benzoyl C1-6 alkyl group (which may have 1 to 5 halogen atoms as a substituent on the phenyl ring), for example, a benzoylmethyl group, 2-fluorobenzoylmethyl group, 3-fluorobenzoylmethyl group, 4-fluorobenzoylmethyl group, 2-chlorobenzoylmethyl group, (2,3-dichlorobenzoyl)-methyl group, (2,4,6-trichlorobenzoyl)methyl group, (2,3,4,5,6-pentafluorobenzoyl)methyl group, 3-chlorobenzoylmethyl group, 4-chlorobenzoylmethyl group, 2-bromobenzoylmethyl group, 3-bromobenzoylmethyl group, 4-bromobenzoylmethyl group, 2-benzoylethyl group, 2-(2-fluorobenzoyl)ethyl group, 2-(3-fluorobenzoyl)ethyl group, 2-(4-fluorobenzoyl)ethyl group, 2-(2-chlorobenzoyl)ethyl group, 2-(3-chlorobenzoyl)ethyl group, 2-(4-chlorobenzoyl)ethyl group, 3-(2-chlorobenzoyl)propyl group, 3-(3-chlorobenzoyl)propyl group, 3-(4-chlorobenzoyl)propyl group, 4-(2-chlorobenzoyl)butyl group, 4-(3-chlorobenzoyl)butyl group, 4-(4-chlorobenzoyl)butyl group, 5-(2-chlorobenzoyl)pentyl group, 5-(3-chlorobenzoyl)pentyl group, 5-(4-chlorobenzoyl)pentyl group, 6-(2-chlorobenzoyl)hexyl group, 6-(3-chlorobenzoyl)hexyl group, 6-(4-chlorobenzoyl)hexyl group or the like.

A phenylcarbamoyl C1-6 alkyl group (which may be substituted on the phenyl ring by at least one of halogen-substituted or unsubstituted C1-6 alkyl groups) includes a phenylcarbamoyl C1-6 alkyl group (which may be substituted on the phenyl ring by 1 to 3 groups of halogen-substituted or unsubstituted C1-6 alkyl groups), for example, a phenylcarbamoylmethyl group, 2-methylphenylcarbamoylmethyl group, 3-methylphenylcarbamoylmethyl group, 4-methylphenylcarbamoylmethyl group, 2,3-dimethylphenylcarbamoylmethyl group, 2,4-dimethylphenylcarbamoylmethyl group, 2,6-dimethylphenylcarbamoylmethyl group, 2,4,6-trimethylphenylcarbamoylmethyl group, 2-trifluoromethylphenylcarbamoylmethyl group, 3-trifluoromethylphenylcarbamoylmethyl group, 4-trifluoromethylphenylcarbamoylmethyl group, 2,3-ditrifluoromethylphenylcarbamoylmethyl group, 2,4-ditrifluoromethylphenylcarbamoylmethyl group, 2,6-ditrifluoromethylphenylcarbamoylmethyl group, 2-pentafluoroethylphenylcarbamoylmethyl group, 3-pentafluoroethylphenylcarbamoylmethyl group, 4-pentafluoroethylphenylcarbamoylmethyl group, 2-(n-propylphenyl)carbamoylmethyl group, 3-(n-propylphenyl)carbamoylmethyl group, 4-(n-propylphenyl)carbamoylmethyl group, 2-(phenylcarbamoyl)ethyl group, 2-(3-trifluoromethylphenylcarbamoyl)ethyl group, 2-(4-trifluoromethylphenylcarbamoyl)ethyl group, 2-(2,3-ditrifluoromethylphenylcarbamoyl)ethyl group, 2-(2,4-ditrifluoromethylphenylcarbamoyl)ethyl group, 2-(2,6-ditrifluoromethylphenylcarbamoyl)ethyl group, 2-(2-pentafluoroethylphenylcarbamoyl)ethyl group, 2-(3-pentafluoroethylphenylcarbamoyl)ethyl group, 2-(4-pentafluoroethylphenylcarbamoyl)ethyl group, 3-(phenylcarbamoyl)propyl group, 3-(3-trifluoromethylphenylcarbamoyl)propyl group, 3-(4-trifluoromethylphenylcarbamoyl)propyl group, 3-(2,3-ditrifluoromethylphenylcarbamoyl)propyl group, 3-(2,4-ditrifluoromethylphenylcarbamoyl)propyl group, 3-(2,6-ditrifluoromethylphenylcarbamoyl)propyl group, 3-(2-pentafluoroethylphenylcarbamoyl)propyl group, 3-(3-pentafluoroethylphenylcarbamoyl)propyl group, 3-(4-pentafluoroethylphenylcarbamoyl)propyl group, 4-(4-trifluoromethylphenylcarbamoyl)butyl group, 5-(4-trifluoromethylphenylcarbamoyl)pentyl group, 6-(4-trifluoromethylphenylcarbamoyl)hexyl group or the like.

A thiazolyl C1-6 alkyl group (which may be substituted on the thiazole ring by at least one group selected from a group consisting of a halogen-substituted or unsubstituted phenyl group and a C1-6 alkyl group) includes a thiazolyl C1-6 alkyl group (which may be substituted on the thiazole ring by 1 to 2 groups selected from a group consisting of a halogen-substituted or unsubstituted phenyl group and a C1-6 alkyl group), for example, 4-thiazolylmethyl group, 5-thiazolylmethyl group, 2-methyl-4-thiazolylmethyl group, 2-methyl-5-thiazolylmethyl group, 2,5-dimethyl-4-thiazolylmethyl group, 2,4-dimethyl-5-thiazolylmethyl group, 2-methyl-5-phenyl-4-thiazolylmethyl group, 2-methyl-4-phenyl-5-thiazolylmethyl group, 2-phenyl-4-thiazolylmethyl group, 2-phenyl-5-thiazolylmethyl group, 2-phenyl-5-methyl-4-thiazolylmethyl group, 2-phenyl-4-methyl-5-thiazolylmethyl group, 2-methyl-5-(2-fluorophenyl)-4-thiazolylmethyl group, 2-methyl-4-(2-fluorophenyl)-5-thiazolylmethyl group, 2-(2-chlorophenyl)-4-thiazolylmethyl group, 2-(2-bromophenyl)-5-thiazolylmethyl group, 2-(2-fluorophenyl)-5-methyl-4-thiazolylmethyl group, 2-(2-fluorophenyl)-4-methyl-5-thiazolylmethyl group, 2-methyl-5-(3-iodophenyl)-4-thiazolylmethyl group, 2-methyl-4-(3-fluorophenyl)-5-thiazolylmethyl group, 2-(2,3-difluorophenyl)-5-thiazolylmethyl group, 2-(3-fluorophenyl)-5-thiazolylmethyl group, 2-(3-fluorophenyl)-5-methyl-4-thiazolylmethyl group, 2-(3-fluorophenyl)-4-methyl-5-thiazolylmethyl group, 2-methyl-5-(2,4,6-trichloro-phenyl)-4-thiazolylmethyl group, 2-methyl-4-(2,3,4,5,6-pentafluorophenyl)-5-thiazolylmethyl group, 2-(4-fluorophenyl)-4-thiazolylmethyl group, 4-(2-fluorophenyl)-5-thiazolylmethyl group, 2-(4-fluorophenyl)-5-methyl-4-thiazolylmethyl group, 2-(4-fluorophenyl)-4-methyl-5-thiazolylmethyl group, 2-methyl-5-(2-chlorophenyl)-4-thiazolylmethyl group, 2-methyl-4-(2-chlorophenyl)-5-thiazolylmethyl group, 2-(2-chlorophenyl)-4-thiazolylmethyl group, 2-(2-chlorophenyl)-5-thiazolylmethyl group, 2-(2-chlorophenyl)-5-methyl-4-thiazolylmethyl group, 2-(2-chlorophenyl)-4-methyl-5-thiazolylmethyl group, 2-methyl-5-(3-chlorophenyl)-4-thiazolylmethyl group, 2-methyl-4-(3-chlorophenyl)-5-thiazolylmethyl group, 2-(3-chlorophenyl)-4-thiazolylmethyl group, 2-(3-fluorophenyl)-5-thiazolylmethyl group, 2-(3-chlorophenyl)-5-methyl-4-thiazolylmethyl group, 2-(3-chlorophenyl)-4-methyl-5- thiazolylmethyl group, 2-methyl-5-(4-chlorophenyl)-4-thiazolylmethyl group, 2-methyl-4-(4-chlorophenyl)-5-thiazolylmethyl group, 2-(4-chlorophenyl)-4-thiazolylmethyl group, 2-(4-chlorophenyl)-5-thiazolylmethyl group, 2-(4-chlorophenyl)-S-methyl-4-thiazolylmethyl group, 2-(4-chlorophenyl)-4-methyl-5-thiazolylmethyl group, 2-(2-thiazolyl)ethyl group, 2-(4-thiazolyl)ethyl group, 2-(5-thiazolyl)ethyl group, 2-(2-methyl-4-thiazolyl)ethyl group, 2-(2-methyl-5-thiazolyl)ethyl group, 2-(2,5-dimethyl-4-thiazolyl)ethyl group, 2-(2,4-dimethyl-5-thiazolyl)ethyl group, 2-(2-methyl-5-phenyl-4-thiazolyl)ethyl group, 2-(2-methyl-4-phenyl-5-thiazolyl)ethyl group, 2-(2-phenyl-4-thiazolyl)ethyl group, 2-(2-phenyl-5-thiazolyl)ethyl group, 2-(2-phenyl-5-methyl-4-thiazolyl)ethyl group, 3-(2-thiazolyl)-propyl group, 2-(4-thiazolyl)propyl group, 3-(5-thiazolyl)propyl group, 3-(2-methyl-4-thiazolyl)propyl group, 2-(2-methyl-5-thiazolyl)propyl group, 3-(2,5-dimethyl-4-thiazolyl)propyl group, 3-(2,4-dimethyl-5-thiazolyl)propyl group, 3-(2-methyl-5-phenyl-4-thiazolyl)propyl group, 3-(2-methyl-4-phenyl-5-thiazolyl)propyl group, 2-(2-phenyl-4-thiazolyl)-propyl group, 3-(3-phenyl-5-thiazolyl)propyl group, 3-(2-phenyl-5-methyl-4-thiazolyl)propyl group, 4-(2-thiazolyl)butyl group, 4-(4-thiazolyl)butyl group, 3-(5-thiazolyl)butyl group, 4-(2-methyl-4-thiazolyl)butyl group, 4-(2-methyl-5-thiazolyl)butyl group, 4-(2,5-dimethyl-4-thiazolyl)butyl group, 4-(2,4-dimethyl-5-thiazolyl)butyl group, 4-(2-methyl-5-phenyl-4-thiazolyl)butyl group, 4-(2-methyl-4-phenyl-5-thiazolyl)butyl group, 4-(2-phenyl-4-thiazolyl)butyl group, 4-phenyl-5-thiazolyl)butyl group, 4-(2-phenyl-5-methyl-4-thiazolyl)butyl group, 5-(2-thiazolyl)pentyl group, 5-(4-thiazolyl)pentyl group, 5-(5-thiazolyl)-pentyl group, 5-(2-methyl-4-thiazolyl)pentyl group, 5-(2-methyl-5-thiazolyl)pentyl group, 5-(2,5-dimethyl-4-thiazolyl)pentyl group, 5-(2,4-dimethyl-5-thiazolyl)-pentyl group, 5-(2-methyl-5-phenyl-4-thiazolyl)pentyl group, 5-(2-methyl-4-phenyl-5-thiazolyl)pentyl group, 5-(2-phenyl-4-thiazolyl)pentyl group, 5-(4-phenyl-5-thiazolyl)pentyl group, 5-(2-phenyl-5-methyl-4-thiazolyl)pentyl group, 5-(2-thiazolyl)hexyl group, 5-(4-thiazolyl)hexyl group, 5-(5-thiazolyl)hexyl group, 5-(2-methyl-4-thiazolyl)hexyl group, 5-(2-methyl-5-thiazolyl)hexyl group, 5-(2,5-dimethyl-4-thiazolyl)-hexyl group, 5-(2,4-dimethyl-5-thiazolyl)hexyl group, 5-(2-methyl-5-phenyl-4-thiazolyl)hexyl group, 5-(2-methyl-4-phenyl-5-thiazolyl)hexyl group, 5-(2-phenyl-4-thiazolyl)hexyl group, 5-(4-phenyl-5-thiazolyl)hexyl group, 5-(2-phenyl-5-methyl-4-thiazolyl)hexyl group or the like.

An oxazolyl C1-6 alkyl group (which may be substituted on the oxazole ring by at least one group selected from a group consisting of a halogen-substituted or unsubstituted phenyl group and a C1-6 alkyl group) includes an oxazolyl C1-6 alkyl group (which may be substituted on the oxazole ring by 1 to 2 groups selected from a group consisting of a halogen-substituted or unsubstituted phenyl group and a C1-6 alkyl group), for example, a 4-oxazolylmethyl group, 5-oxazolylmethyl group, 2-methyl-4-oxazolylmethyl group, 2-methyl-5-oxazolylmethyl group, 2,5-dimethyl-4-oxazolylmethyl group, 2,5-diphenyl-4-oxazolylmethyl group, 2,4-dimethyl-5-oxazolylmethyl group, 2-methyl-5-phenyl-4-oxazolylmethyl group, 2-methyl-4-phenyl-5-oxazolylmethyl group, 2-phenyl-4-oxazolylmethyl group, 2-phenyl-5-oxazolylmethyl group, 2-phenyl-5-methyl-4-oxazolylmethyl group, 2-phenyl-4-methyl-5-oxazolylmethyl group, 2-methyl-5-(2,3,4,5,6-pentafluorophenyl)-4-oxazolylmethyl group, 2-methyl-4-(2-fluorophenyl)-5-oxazolylmethyl group, 2-(2,4-difluorophenyl)-4-oxazolylmethyl group, 2-(2-fluorophenyl)-5-oxazolylmethyl group, 2-(2-fluorophenyl)-5-methyl-4-oxazolylmethyl group, 2-(2-fluorophenyl)-4-methyl-5-oxazolylmethyl group, 2-methyl-5-(3-fluorophenyl)-4-oxazolylmethyl group, 2-methyl-4-(3-fluorophenyl)-5-oxazolylmethyl group, 2-(3-fluorophenyl)-4-oxazolylmethyl group, 2-(3-fluorophenyl)-5-oxazolylmethyl group, 2-(3-fluorophenyl)-5-methyl-4-oxazolylmethyl group, 2-(3-fluorophenyl)-4-methyl-5-oxazolylmethyl group, 2-methyl-5-(4-fluorophenyl)-4-oxazolylmethyl group, 2-methyl-4-(4-fluorophenyl)-5-oxazolylmethyl group, 2-(4-fluorophenyl)-4-oxazolylmethyl group, 2-(4-fluorophenyl)-5-oxazolylmethyl group, 2-(4-fluorophenyl)-5-methyl-4-oxazolylmethyl group, 2-(4-bromophenyl)-4-methyl-5-oxazolylmethyl group, 2-methyl-5-(2-chlorophenyl)-4-oxazolylmethyl group, 2-methyl-4-(2-chlorophenyl)-5-oxazolylmethyl group, 2-(2-chlorophenyl)-4-oxazolylmethyl group, 2-(2-iodophenyl)-5-oxazolylmethyl group, 2-(2-chlorophenyl)-5-methyl-4-oxazolylmethyl group, 2-(2-chlorophenyl)-4-methyl-5-oxazolylmethyl group, 2-methyl-5-(3-chlorophenyl)-4-oxazolylmethyl group, 2-methyl-4-(3-chlorophenyl)-5-oxazolylmethyl group, 2-(3-chlorophenyl)-4-oxazolylmethyl group, 2-(2,4,6-trichlorophenyl)-5-oxazolylmethyl group, 2-(3-chlorophenyl)-5-methyl-4-oxazolylmethyl group, 2-(3-chlorophenyl)-4-methyl-5-oxazolylmethyl group, 2-methyl-5-(4-chlorophenyl)-4-oxazolylmethyl group, 2-methyl-4-(4-chlorophenyl)-5-oxazolylmethyl group, 2-(4-chlorophenyl)-4-oxazolylmethyl group, 2-(4-chloro-phenyl)-5-oxazolylmethyl group, 2-(4-chlorophenyl)-5-methyl-4-oxazolylmethyl group, 2-(4-chlorophenyl)-4-methyl-5-oxazolylmethyl group, 2-(4-oxazolyl)ethyl group, 2-(5-oxazolyl)ethyl group, 2-(2-methyl-4-oxazolyl)ethyl group, 2-(2-methyl-5-oxazolyl)ethyl group, 2-(2-phenyl-5-methyl-4-oxazolyl)ethyl group, 2-[2-(4-chlorophenyl)-5-methyl-4-oxazolyl]ethyl group, 3-(4-oxazolyl)propyl group, 3-(5-oxazolyl)propyl group, 3-(2-methyl-4-oxazolyl)propyl group, 3-(2-methyl-5-oxazolyl)propyl group, 3-(2-phenyl-5-methyl-4-oxazolyl)propyl group, 3-[2-(4-chlorophenyl)-5-methyl-4-oxazolyl]propyl group, 4-(4-oxazolyl)butyl group, 4-(5-oxazolyl)butyl group, 4-(2-methyl-4-oxazolyl)butyl group, 4-(2-methyl-5-oxazolyl)butyl group, 4-(2-phenyl-5-methyl-4-oxazolyl)butyl group, 4-[2-(4-chlorophenyl)-5-methyl-4-oxazolyl]butyl group, 5-(4-oxazolyl)pentyl group, 5-(5-oxazolyl)pentyl group, 5-(2-methyl-4-oxazolyl)pentyl group, 5-(2-methyl-5-oxazolyl)pentyl group, 5-(2-phenyl-5-methyl-4-oxazolyl)pentyl group, 5-[2-(4-chlorophenyl)-5-methyl-4-oxazolyl]pentyl group, 6-(4-oxazolyl)hexyl group, 6-(5-oxazolyl)hexyl group, 6-(2-methyl-4-oxazolyl)hexyl group, 6-(2-methyl-5-oxazolyl)hexyl group, 6-(2-phenyl-5-methyl-4-oxazolyl)-hexyl group, 6-[2-(4-chlorophenyl)-6-methyl-4-oxazolyl]hexyl group or the like.

Examples of an indolyl C1-6 alkyl group include an indolin-1-ylmethyl group, indolin-2-ylmethyl group, indolin-3-ylmethyl group, indolin-4-ylmethyl group, indolin-5-ylmethyl group, indolin-6-ylmethyl group, indolin-7-ylmethyl group, 2-(indolin-3-yl)ethyl group, 3-(indolin-3-yl)propyl group, 4-(indolin-3-yl)butyl group, 5-(indolin-3-yl)pentyl group, 6-(indolin-3-yl)hexyl group, 2-(indolin-4-yl)ethyl group, 3-(indolin-4-yl)propyl group, 4-(indolin-4-yl)butyl group, 5-(indolin-4-yl)pentyl group, 6-(indolin-4-yl)hexyl group, 2-(indolin-5-yl)ethyl group, 3-(indolin-5-yl)propyl group, 4-(indolin-5-yl)butyl group, 5-(indolin-5-yl)pentyl group, 6-(indolin-5-yl)hexyl group, 2-(indolin-6-yl)ethyl group, 3-(indolin-6-yl)propyl group, 4-(indolin-6-yl)butyl group, 5-(indolin-6-yl)pentyl group, 6-(indolin-6-yl)hexyl group, 2-(indolin-7-yl)ethyl group, 3-(indolin-7-yl)

propyl group, 4-(indolin-7-yl)butyl group, 5-(indolin-7-yl) pentyl group, 6-(indolin-7-yl)hexyl group or the like.

A furyl C1-6 alkyl group (which may be substituted on the furan ring by at least one halogen-substituted or unsubstituted phenyl group) includes a furyl C1-6 alkyl group (which may be substituted on the furan ring by 1 to 3 halogen-substituted or unsubstituted phenyl groups), for example, a 2-furylmethyl group, 1-(3-furyl)ethyl group, 2-(2-furyl)ethyl group, 3-(3-furyl)propyl group, 4-(3-furyl) butyl group, 5-(2-furyl)pentyl group, 6-(2-furyl)hexyl group, 2-methyl-3-(3-furyl)propyl group, 1,1-dimethyl-2-(2-furyl)ethyl group, 3,4-diphenyl-2-furylmethyl group, 3,4,5-triphenyl-2-furylmethyl group, 5-phenyl-2-furylmethyl group, 5-(2-fluorophenyl)-2-furylmethyl group, 5-(3-fluorophenyl)-2-furylmethyl group, 5-(4-fluorophenyl)-2-furylmethyl group, 5-(2-chlorophenyl)-2-furylmethyl group, 5-(3-chlorophenyl)-2-furylmethyl group, 5-(4-chlorophenyl)-2-furylmethyl group, 5-(2-bromophenyl)-2-furylmethyl group, 5-(3-bromophenyl)-2-furylmethyl group, 5-(4-bromophenyl)-2-furylmethyl group, 4-phenyl-2-furylmethyl group, 4-(2,3,4,5,6-pentafluorophenyl)-2-furylmethyl group, 4-(3,4-difluorophenyl)-2-furylmethyl group, 4-(4-iodophenyl)-2-furylmethyl group, 4-(2,3-dichlorophenyl)-2-furylmethyl group, 4-(3-chlorophenyl)-2-furylmethyl group, 4-(2,4,6-trichlorophenyl)-2-furylmethyl group, 4-(2-bromophenyl-2-furylmethyl group, 4-(3-bromophenyl)-2-furylmethyl group, 4-(4-bromophenyl)-2-furylmethyl group, 5-phenyl-2-furylmethyl group, 2-(2-furyl)ethyl group, 3-(2-furyl)propyl group, 4-(2-furyl)butyl group, 5-(2-furyl)pentyl group, 6-(2-furyl)hexyl group, 2-[5-(4-chlorophenyl)-2-furyl]ethyl group, 3-[5-(4-chlorophenyl)-2-furyl]propyl group, 4-[5-(4-chlorophenyl)-2-furyl]butyl group, 5-(2-furyl)pentyl group, 6-[5-(4-chlorophenyl)-2-furyl]hexyl group or the like.

An imidazolyl C1-6 alkyl group (which may be substituted on the imidazole ring by a phenyl group) includes an imidazolyl C1-6 alkyl group (which may be substituted on the imidazole ring by 1 to 2 phenyl groups), for example, a 4-imidazolylmethyl group, 2-(4-imidazolyl)ethyl group, 3-(2-imidazolyl)propyl group, 4-(1-imidazolyl)butyl group, 5-(5-imidazolyl)pentyl group, 6-(4-imidazolyl)hexyl group, 2,5-diphenyl-1-imidazolylmethyl group, 2-phenyl-4-imidazolylmethyl group, 2-(2-phenyl-4-imidazolyl)ethyl group, 3-(2-phenyl-4-imidazolyl)propyl group, 4-(2-phenyl-5-imidazolyl)butyl group, 5-(2-phenyl-4-imidazolyl)pentyl group, 6-(2-phenyl-4-imidazolyl)hexyl group or the like.

Examples of a quinolyl C1-6 alkyl group include a 4-quinolylmethyl group, 2-(4-quinolyl)ethyl group, 3-(4-quinolyl)propyl group, 4-(4-quinolyl)butyl group, 5-(4-quinolyl)pentyl group, 6-(4-quinolyl)hexyl group, 5-quinolylmethyl group, 2-(5-quinolyl)ethyl group, 3-(5-quinolyl)propyl group, 4-(5-quinolyl)butyl group, 5-(5-quinolyl)pentyl group, 6-(5-quinolyl)hexyl group, 6-quinolylmethyl group, 2-(6-quinolyl)ethyl group, 3-(6-quinolyl)propyl group, 4-(6-quinolyl)butyl group, 5-(6-quinolyl)pentyl group, 6-(6-quinolyl)hexyl group, 7-quinolylmethyl group, 2-(7-quinolyl)ethyl group, 3-(7-quinolyl)propyl group, 4-(7-quinolyl)butyl group, 5-(7-quinolyl)pentyl group, 6-(7-quinolyl)hexyl group, 8-quinolylmethyl group, 2-(8-quinolyl)ethyl group, 3-(8-quinolyl)propyl group, 4-(8-quinolyl)butyl group, 5-(8-quinolyl)pentyl group, 6-(8-quinolyl)hexyl group or the like.

Examples of a tetrazolyl group (which may be substituted on the tetrazole ring by a phenyl group) include a 5-(1H)-tetrazolyl group and a 1-phenyl-5-(1H)-tetrazolyl group.

Examples of a pyrimidyl group which may be substituted by a phenyl group include a 2-pyrimidyl group, 3-pyrimidyl group, 4-pyrimidyl group, 4-phenyl-2-pyrimidyl group, 2-phenyl-4-pyrimidyl group, 4,6-diphenyl-2-pyrimidyl group or the like.

Examples of a benzoxazolyl group include a 2-benzoxazolyl group, 4-benzoxazolyl group, 5-benzoxazolyl group, 6-benzoxazolyl group, 7-benzoxazolyl group or the like.

Examples of a benzothiazolyl group include a benzothiazol-2-yl group, benzothiazol-4-yl group, benzothiazol-5-yl group, benzothiazol-6-yl group, benzothiazol-7-yl group or the like.

A phenoxy C2-6 alkanoyl group which may be substituted on the phenyl ring by a halogen atom includes a phenoxy C2-6 alkanoyl group which may be substituted on the phenyl ring by 1 to 5 halogen atoms, for example, a phenoxyacetyl group, 3-phenoxypropionyl group, 4-phenoxybutyryl group, 5-phenoxypentanoyl group, 6-phenoxyhexanoyl group, 4-(4-chlorophenoxy)-butyryl group, 5-(4-chlorophenoxy) pentanoyl group, 6-(4-chlorophenoxy)hexanoyl group, 2-fluorophenoxyacetyl group, 3-fluorophenoxyacetyl group, 4-fluorophenoxyacetyl group, 2-chlorophenoxyacetyl group, 3-chlorophenoxyacetyl group, 4-chlorophenoxyacetyl group, 4-bromophenoxyacetyl group, 2,3-difluorophenoxyacetyl group, 2-fluoro-4-chlorophenoxyacetyl group, 3,5-difluorophenoxyacetyl group, 2,3,4,5,6-pentafluorophenoxyacetyl group, 2,4,6-trichlorophenoxyacetyl group, 3-(2-fluorophenoxy)propionyl group, 3-(3-fluorophenoxy)propionyl group, 3-(4-fluorophenoxy)-propionyl group, 3-(2-chlorophenoxy)propionyl group, 3-(3-chlorophenoxy)propionyl group, 3-(4-chlorophenoxy)-propionyl group, 3-(4-bromophenoxy)propionyl group, 3-(2,3-difluorophenoxy)propionyl group, 3-(2-fluoro-4-chlorophenoxy)propionyl group, 3-(3,5-difluorophenoxy)-propionyl group or the like.

A phenylthio C2-6 alkanoyl group which may be substituted by a halogen atom is a group containing 1 to 5 halogen-substituted or unsubstituted phenylthio groups and a C1-6 alkanoyl group, examples of which include a phenylthioacetyl group, 3-phenylthiopropionyl group, 4-phenylthiobutyryl group, 5-phenylthiopentanoyl group, 6-phenylthiohexanoyl group, 4-(4-chlorophenyl)-thiobutyryl group, 5-(4-chlorophenyl)thiopentanoyl group, 6-(4-chlorophenyl)thiohexanoyl group, 2-fluorophenylthioacetyl group, 3-fluorophenylthioacetyl group, 4-fluorophenylthioacetyl group, 2-chlorophenylthioacetyl group, 2,4-dichlorophenylthioacetyl group, 2,4,6-trichlorophenylthioacetyl group, 2,3,4,5,6-pentafluorophenylthioacetyl group, 3-chlorophenylthioacetyl group, 4-chlorophenylthioacetyl group, 4-bromophenylthioacetyl group, 2,3-difluorophenylthioacetyl group, 2-fluoro-4-chlorophenylthioacetyl group, 3,5-difluorophenylthioacetyl group, 3-(2-fluorophenyl)thiopropionyl group, 3-(3-fluorophenyl)thiopropionyl group, 3-(4-fluorophenyl)thiopropionyl group, 3-(2-chlorophenyl)thiopropionyl group, 3-(3-chlorophenyl)thiopropionyl group, 3-(4-chlorophenyl)thiopropionyl group, 3-(4-bromophenyl)thiopropionyl group, 3-(2,3-difluorophenyl)thiopropionyl group, 3-(2-fluoro-4-chlorophenyl)thiopropionyl group, 3-(3,5-difluorophenyl)thiopropionyl group or the like.

A benzoyl group (which may be substituted on the phenyl ring by at least one group selected from a group consisting of a halogen atom, halogen-substituted or unsubstituted C1-6 alkyl group, halogen-substituted or unsubstituted C1-6 alkoxy group and amino group which may have a C1-6 alkyl group as a substituent) include a benzoyl group (which may be substituted on the phenyl ring by 1 to 5, preferably 1 to 3 groups selected from a group consisting of a halogen atom, halogen-substituted or unsubstituted C1-6 alkyl group, halogen-substituted or unsubstituted C1-6 alkoxy group and amino group which may have 1 to 2 C1-6 alkyl groups as a substituent), for example, a benzoyl group, 2-fluorobenzoyl group, 3-fluorobenzoyl group, 4-fluorobenzoyl group, 2,3-difluorobenzoyl group, 3,4-difluorobenzoyl group, 2-chlorobenzoyl group, 3-chlorobenzoyl group, 4-chlorobenzoyl group, 2,3-dichlorobenzoyl group, 3,4-dichlorobenzoyl group, 2,4,6-trichlorobenzoyl group, 4-iodobenzoyl group, 2,3,4,5,6-pentafluorobenzoyl group, 2-bromobenzoyl group, 3-bromobenzoyl group, 4-bromobenzoyl group, 2,3-dibromobenzoyl group, 3,4-dibromobenzoyl group, 2-methylbenzoyl group, 3-methylbenzoyl group, 4-methylbenzoyl group, 2,3-dimethylbenzoyl group, 3,4-dimethylbenzoyl group, 3,4,5-trimethylbenzoyl group, 2-trifluoromethylbenzoyl group, 3-trifluoromethylbenzoyl group, 4-trifluoromethylbenzoyl group, 2,3-ditrifluoromethylbenzoyl group, 3,4-ditrifluoromethylbenzoyl group, 2-methoxybenzoyl group, 3-methoxybenzoyl group, 4-methoxybenzoyl group, 3,4-dimethoxybenzoyl group, 2,4,6-trimethoxybenzoyl group, 2-trifluoromethoxybenzoyl group, 3-trifluoromethoxybenzoyl group, 4-trifluoromethoxybenzoyl group, 2-aminobenzoyl group, 3-aminobenzoyl group, 4-aminobenzoyl group, 2-methylaminobenzoyl group, 3-methylaminobenzoyl group, 4-methylaminobenzoyl group, 2-ethylaminobenzoyl group, 3-ethylaminobenzoyl group, 4-ethylaminobenzoyl group, 2-propylaminobenzoyl group, 3-propylaminobenzoyl group, 4-propylaminobenzoyl group, 4-butylaminobenzoyl group, 4-pentylaminobenzoyl group, 4-hexylaminobenzoyl group, 2-dimethylaminobenzoyl group, 3-dimethylaminobenzoyl group, 4-dimethylaminobenzoyl group, 2-diethylaminobenzoyl group, 3-diethylaminobenzoyl group, 4-diethylaminobenzoyl group, 2-dipropylaminobenzoyl group, 3-dipropylaminobenzoyl group, 4-dipropylaminobenzoyl group, 4-dibutylaminobenzoyl group, 4-dipentylaminobenzoyl group, 4-dihexylaminobenzoyl group or the like.

Examples of a biphenylylcaronyl group include a 2-biphenylylcaronyl group, 3-biphenylylcaronyl group, 4-biphenylylcaronyl group or the like.

Examples of a pyridylcarbonyl group include a 2-pyridylcarbonyl group, 3-pyridylcarbonyl group, 4-pyridylcarbonyl group or the like.

Examples of a phenyl C2-6 alkenyloxycarbonyl group which may be substituted on the phenyl ring by a halogen atom include a phenyl C2-6 alkenyloxycarbonyl group which may be substituted on the phenyl ring by 1 to 5 halogen atoms, for example, a 3-phenyl-2-propenylcarbonyl group (trivial name: cinnamoyl group), 4-phenyl-2-butenylcarbonyl group, 4-phenyl-3-butenylcarbonyl group, 5-phenyl-2-pentenylcarbonyl group, 5-phenyl-4-pentenylcarbonyl group, 5-phenyl-3-pentenylcarbonyl group, 6-phenyl-5-hexenylcarbonyl group, 6-phenyl-4-pentenylcarbonyl group, 6-phenyl-3-hexenylcarbonyl group, 4-phenyl-1,3-butadienylcarbonyl group, 6-phenyl-1,3,5-hexatrienylcarbonyl group, 3-(2-fluorophenyl)-2-propenylcarbonyl group (which also referred to as 2-fluorocinnamoyl group of a trivial name), 3-(3-fluorophenyl)-2-propenylcarbonyl group, 3-(4-fluorophenyl)-2-propenylcarbonyl group, 2,4-difluorocinnamoyl group, 3-(2,5-difluorophenyl)-2-propenylcarbonyl group, 3-(3,5-difluorophenyl)-2-propenylcarbonyl group, 3-(3,4-difluorophenyl)-2-propenylcarbonyl group, 3-(2,3,4,5,6-pentafluorophenyl)-2-propenylcarbonyl group, 3-(2-chlorophenyl)-2-propenylcarbonyl group, 3-(3-chlorophenyl)-2-propenylcarbonyl group, 3-(4-chlorophenyl)-2-propenylcarbonyl group, 3-(2,4-dichlorophenyl)-2-propenylcarbonyl group, 3-(2,5-dichlorophenyl)-2-propenylcarbonyl group, 3-(3,5-dichlorophenyl)-2-propenylcarbonyl group, 3-(3,4-dichlorophenyl)-2-propenylcarbonyl group, 3-(2,4,6-trichlorophenyl)-2-propenylcarbonyl group, 3-(2-bromophenyl)-2-propenylcarbonyl group, 3-(3-bromophenyl)-2-propenylcarbonyl group, 3-(4-bromophenyl)-2-propenylcarbonyl group, 3-(2,4-dibromophenyl)-2-propenylcarbonyl group, 3-(2,5-dibromophenyl)-2-propenylcarbonyl group, 3-(3,5-dibromophenyl)-2-propenylcarbonyl group, 3-(3,4-dibromophenyl)-2-propenylcarbonyl group or the like.

A phenyl C1-6 alkylsulfonyl group which may be substituted on the phenyl ring by halogen atoms is a group containing a phenyl C1-6 alkyl group which may be substituted on the phenyl ring by 1 to 5 halogen atoms, as defined above, and a sulfonyl group, examples of which include a benzylsulfonyl group, phenethylsulfonyl group, 3-phenylpropylsulfonyl group, 4-phenylbutylsulfonyl group, 5-phenylpentylsulfonyl group, 6-phenylhexylsulfonyl group, 2-fluorobenzylsulfonyl group, 3-fluorobenzylsulfonyl group, 4-fluorobenzylsulfonyl group, 2-chlorobenzylsulfonyl group, 3-chlorobenzylsulfonyl group, 4-chlorobenzylsulfonyl group, 2,3-dichlorobenzylsulfonyl group, 3,4-dichlorobenzylsulfonyl group, 3,5-dichlorobenzylsulfonyl group, 2,4-dichlorobenzylsulfonyl group, 3,4,5-trifluorobenzylsulfonyl group, 2,3,4,5,6-pentafluorobenzylsulfonyl group, 2-(2-fluoro)phenethylsulfonyl group, 2-(3-fluoro)phenethylsulfonyl group, 2-(4-fluoro)phenethylsulfonyl group, 2-(2-chloro)-phenethylsulfonyl group, 2-(3-chloro)phenethylsulfonyl group, 2-(4-chloro)phenethylsulfonyl group, 2-(2,3-dichloro)phenethylsulfonyl group, 2-(3,4-dichloro)-phenethylsulfonyl group, 2-(3,5-dichloro)phenethylsulfonyl group, 2-(2,4-dichloro)phenethylsulfonyl group, 2-(3,4,5-trifluoro)phenethylsulfonyl group, 3-(2-fluorophenyl)propylsulfonyl group, 3-(3-fluorophenyl)propylsulfonyl group, 3-(4-fluorophenyl)propylsulfonyl group, 3-(2-chlorophenyl)propylsulfonyl group, 3-(3-chlorophenyl)propylsulfonyl group, 3-(4-chlorophenyl)propylsulfonyl group, 2-(2,3-dichlorophenyl)propylsulfonyl group, 3-(3,4-dichlorophenyl)-propylsulfonyl group, 3-(3,5-dichlorophenyl)propylsulfonyl group, 3-(2,4-dichlorophenyl)propylsulfonyl group, 3-(3,4,5-trifluorophenyl)propylsulfonyl group or the like.

A halogen-substituted or unsubstituted C1-8 alkyl group include a C1-8 alkyl group unsubstituted or substituted by 1-7 halogen atoms, for example, a methyl group, ethyl group, n-propyl group, isopropyl group, n-butyl group, isobutyl group, tert-butyl group, sec-group, n-pentyl group, neopentyl group, 3-methylpentyl group, n-hexyl group, isohexyl group, 1,3,5-trimethylhexyl group, n-heptyl group, 6-methylheptyl group, 1-methylheptyl group, n-octyl group, fluoromethyl group, difluoromethyl group, trifluoromethyl group, chloromethyl group, dichloromethyl group, trichloromethyl group, bromomethyl group, dibromomethyl group, dichlorofluoromethyl group, 2,2,2-trifluoroethyl group, pentafluoroethyl group, 2-chloroethyl group, 3,3,3-trifluoropropyl group, heptafluoropropyl group, heptafluoroisopropyl group, 3-chloropropyl group, 2-chloropropyl group, 3-bromopropyl group, 4,4,4-trifluorobutyl group, 4,4,4,3,3-pentafluorobutyl group, 4-chlorobutyl group, 4-bromobutyl group, 2-chlorobutyl group, 5,5,5-trifluoropentyl group, 5-chloropentyl group, 6,6,6-trifluorohexyl group, 6-chlorohexyl group, 7-chloroheptyl group, 8-chlorooctyl group or the like.

An amino-C1-6 alkyl group which may have a C1-6 alkyl group include an amino-C1-6 alkyl group which may have 1 to 2 C1-6 alkyl groups, for example, an aminomethyl group, 2-aminoethyl group, 1-aminoethyl group, 3-aminopropyl group, 4-aminobutyl group, 5-aminopentyl group, 6-aminohexyl group, 2-methyl-3-aminopropyl group, 1,1-dimethyl-2-aminoethyl group, ethylaminomethyl group, 1-(propylamino)ethyl group, 2-(methylamino)ethyl group, 3-(isopropylamino)propyl group, 4-(n-butylamino)butyl group, 5-(n-pentylamino)-pentyl group, 6-(n-hexylamino) hexyl group, dimethylaminomethyl group, (N-methyl-N-propylamino)-methyl group, 2-(N-methyl-N-hexylamino) ethyl group or the like.

Examples of a phenyl C1-6 alkyl group (which may be substituted on the phenyl ring by 1 to 5 groups selected from a group consisting of a halogen atom, halogen-substituted or unsubstituted C1-6 alkyl group, halogen-substituted or unsubstituted C1-6 alkoxy group, halogen-substituted or unsubstituted C1-6 alkylthio group, phenyl C1-6 alkoxy group, hydroxy group, C1-6 alkylsulfinyl group, C1-6 alkyl sulfonyl group, C1-6 alkyl sulfonyloxy group, cyano group, C1-6 alkanoyl group, benzoyl group, phenyl C1-6 alkyl group (which may have a C1-6 alkoxy group on the alkyl moiety), amino group, nitro group, carbamoyl group, C1-6 alkanoylamino group, C1-6 alkoxycarbonyl group, C1-6 alkylaminocarbonyl group, C1-6 alkoxycarbonylamino group, tri C1-6 alkylsiloxy group, pyrrolyl group, tetrahydropyranyloxy group and imidazolyl group) include a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2,3-difluorobenzyl group, 3,4-difluorobenzyl group, 3,5-difluorobenzyl group, 2,3,4,5,6-pentafluorobenzyl group, 2,4-difluorobenzyl group, 2,6-difluorobenzyl group, 2,4,6-trifluorobenzyl group, 3,4,5-trifluorobenzyl group, 2,3-dichlorobenzyl group, 3,4-dichlorobenzyl group, 3,5-dichlorobenzyl group, 2,4-dichlorobenzyl group, 2,6-dichlorobenzyl group, 2,4,6-trichlorobenzyl group, 3,4,5-trichlorobenzyl group, perfluorobenzyl group, 2-difluoromethylbenzyl group, 3-difluoromethylbenzyl group, 4-difluoromethylbenzyl group, 4-chloro-3-difluoromethylbenzyl group, 3-chloro-4-difluoromethylbenzyl group, 3-bromo-4-difluoromethylbenzyl group, 3,5-difluoro-4-difluoromethylbenzyl group, 2-methylbenzyl group, 3-methylbenzyl group, 4-methylbenzyl group, 2,3-dimethylbenzyl group, 2,4,6-trimethylbenzyl group, 3,5-ditrifluoromethylbenzyl group, 2-trifluoromethylbenzyl group, 3-trifluoromethylbenzyl group, 4-trifluoromethylbenzyl group, 4-fluoro-3-trifluoromethylbenzyl group, 3-fluoro-4-trifluoromethylbenzyl group, 2-pentafluoroethylbenzyl group, 4-chloro-3-pentafluoroethylbenzyl group, 3-chloro-4-pentafluoroethylbenzyl group, 2-pentafluoroethylbenzyl group, 3-pentafluoroethylbenzyl group, 4-pentafluoroethylbenzyl group, 2-methoxybenzyl group, 3-methoxybenzyl group, 4-methoxybenzyl group, 2,3-dimethoxybenzyl group, 2,4,6-trimethoxybenzyl group, 3,5-ditrifluoromethoxybenzyl group, 2-trifluoromethoxybenzyl group, 3-trifluoromethoxybenzyl group, 4-trifluoromethoxybenzyl group, 4-fluoro-3-trifluoromethoxybenzyl group, 3-fluoro-4-trifluoromethoxybenzyl group, 2-pentafluoroethoxybenzyl group, 3-pentafluoroethoxybenzyl group, 4-pentafluoroethoxybenzyl group, 3-chloro-4-trifluoromethoxybenzyl group, 3-chloro-4-pentafluoroethoxybenzyl group, 2-(2-trifluoromethylphenyl)ethyl group, 2-(3-trifluoromethylphenyl)ethyl group, 2-(4-trifluoromethylphenyl)ethyl group, 2-trifluoromethoxyphenyl)ethyl group, 3-trifluoromethoxyphenyl)ethyl group, 2-(4-trifluoromethoxyphenyl)ethyl group, 2-(2-pentafluoroethoxyphenyl)ethyl group, 2-(3-pentafluoroethoxyphenyl)ethyl group, 2-(4-pentafluoroethoxyphenyl)ethyl group, 3-(2-trifluoromethylphenyl)propyl group, 3-(3-trifluoromethylphenyl)propyl group, 3-(4-trifluoromethylphenyl)propyl group, 3-(2-trifluoromethoxyphenyl)propyl group, 3-(3-trifluoromethoxyphenyl)propyl group, 3-(4-trifluoromethoxyphenyl)propyl group, 3-(3-pentafluoroethoxyphenyl)propyl group, 3-(4-pentafluoroethoxyphenyl)propyl group, 4-(3-pentafluoroethoxyphenyl)butyl group, 5-(4-trifluoromethylphenyl)pentyl group, 4-(4-trifluoromethylphenyl)pentyl group, 4-(4-trifluoromethoxyphenyl)pentyl group, 6-(3-trifluoromethylphenyl)hexyl group, 6-(4-trifluoromethylphenyl)-hexyl group, 6-(4-trifluoromethoxyphenyl)hexyl group, 2-methylthiobenzyl group, 3-methylthiobenzyl group, 4-methylthiobenzyl group, 2,3-dimethylthiobenzyl group, 2,4,6-trimethylthiobenzyl group, 2-(2-methylthiophenyl)ethyl group, 2-(3-methylthiophenyl)ethyl group, 2-(4-methylthiophenyl)ethyl group, 3-(4-methylthiophenyl)propyl group, 4-(4-methylthiophenyl)butyl group, 5-(4-methylthiophenyl)pentyl group, 6-(4-methylthiophenyl)hexyl group, 2-trifluoromethylthiobenzyl group, 3-trifluoromethylthiobenzyl group, 4-trifluoromethylthiobenzyl group, 2-(2-trifluoromethylthiophenyl)ethyl group, 2-(3-trifluoromethylthiophenyl)ethyl group, 2-(4-trifluoromethylthiophenyl)ethyl group, 3-(4-trifluoromethylthiophenyl)propyl group, 4-(4-trifluoromethylthiophenyl)butyl group, 5-(4-trifluoromethylthiophenyl)pentyl group, 6-(4-trifluoromethylthiophenyl)-hexyl group, 2-benzyloxybenzyl group, 3-benzyloxybenzyl group, 4-benzyloxybenzyl group, 2-(2-benzyloxyphenyl)-ethyl group, 2-(3-benzyloxyphenyl)ethyl group, 2-(4-benzyloxyphenyl) ethyl group, 3-(4-benzyloxyphenyl)-propyl group, 4-(4-benzyloxyphenyl)butyl group, 5-(4-benzyloxyphenyl)pentyl group, 6-(4-benzyloxyphenyl)-hexyl group, 2-(2-phenylethoxy)benzyl group, 3-(2-phenylethoxy)benzyl group, 4-(2-phenylethoxy)benzyl group, 2-[2-(2-phenylethoxyphenyl)]ethyl group, 2-[3-(2-phenylethoxyphenyl)]ethyl group, 2-[4-(2-phenylethoxyphenyl)]ethyl group, 3-[4-(2-phenylethoxyphenyl)]propyl group, 4-[4-(2-phenylethoxyphenyl)]butyl group, 5-[4-(2-phenylethoxyphenyl)]pentyl group, 6-[4-(2-phenylethoxyphenyl)]hexyl group, 2-(3-phenylpropoxy)benzyl group, 3-(3-phenylpropoxy)benzyl group, 4-(3-phenylpropoxy)benzyl group, 2-(4-phenylbutoxy)-benzyl group, 3-(4-phenylbutoxy)benzyl group, 4-(4-phenylbutoxy)benzyl group, 2-methoxycarbonylbenzyl group, 3-methoxycarbonylbenzyl group, 4-methoxycarbonylbenzyl group, 2-(2-methoxycarbonylphenyl)ethyl group, 2-(3-methoxycarbonylphenyl)ethyl group, 2-(4-methoxycarbonylphenyl)ethyl group, 3-(4-methoxycarbonylphenyl) propyl group, 4-(4-methoxycarbonylphenyl)butyl group, 5-(4-methoxycarbonylphenyl)pentyl group, 6-(4-methoxycarbonylphenyl)hexyl group, 2-hydroxybenzyl group, 3-hydroxybenzyl group, 4-hydroxybenzyl group, 2,3-dihydroxybenzyl group, 2,4,6-trihydroxybenzyl group, 2-(2-hydroxyphenyl)ethyl group, 2-(3-hydroxyphenyl)ethyl group, 2-(4-hydroxyphenyl)-ethyl group, 3-(4-hydroxyphenyl)propyl group, 4-(4-hydroxyphenyl)butyl group, 5-(4-hydroxyphenyl)pentyl group, 6-(4-hydroxyphenyl)hexyl group, 2-methylsulfinylbenzyl group, 3-methylsulfinylbenzyl group, 4-methylsulfinylbenzyl group, 2,3-dimethylsulfinylbenzyl group, 2,4,6-trimethylsulfinylbenzyl group, 2-(2-methylsulfinylphenyl)ethyl group, 2-(3-methylsulfinylphenyl)ethyl group, 2-(4-methylsulfinylphenyl)ethyl group, 3-(4-methylsulfinylphenyl)propyl group, 4-(4-methylsulfinylphenyl)butyl group, 5-(4- methylsulfinylphenyl)pentyl group, 6-(4-methylsulfinylphenyl)hexyl group, 2-methanesulfonylbenzyl group, 3-methanesulfonylbenzyl group, 4-methanesulfonylbenzyl group, 2,3-dimethanesulfonylbenzyl group, 2,4,6-trimethanesulfonylbenzyl group, 2-(2-methanesulfonylphenyl)ethyl group, 2-(3-methanesulfonylphenyl)ethyl group, 2-(4-methanesulfonylphenyl)ethyl group, 3-(4-methanesulfonylphenyl)propyl group, 4-(4-methanesulfonylphenyl)butyl group, 5-(4-methanesulfonylphenyl)pentyl group, 6-(4-methanesulfonylphenyl)hexyl group, 2-methanesulfonyloxybenzyl group, 3-methanesulfonyloxybenzyl group, 4-methanesulfonyloxybenzyl group, 2,3-dimethanesulfonyloxybenzyl group, 2,4,6-trimethanesulfonyloxybenzyl group, 2-(2-methanesulfonyloxyphenyl)ethyl group, 2-(3-methanesulfonyloxyphenyl)ethyl group, 2-(4-methanesulfonyloxyphenyl)ethyl group, 3-(4-methanesulfonyloxyphenyl)propyl group, 4-(4-methanesulfonyloxyphenyl)butyl group, 5-(4-methanesulfonyloxyphenyl)pentyl group, 6-(4-methanesulfonyloxyphenyl)hexyl group, 2-cyanobenzyl group, 3-cyanobenzyl group, 4-cyanobenzyl group, 2,3-dicyanobenzyl group, 2,4,6-tricyanobenzyl group, 2-(2-cyanophenyl)ethyl group, 2-(3-cyanophenyl)ethyl group, 2-(4-cyanophenyl)ethyl group, 3-(4-cyanophenyl)propyl group, 4-(4-cyanophenyl)butyl group, 5-(4-cyanophenyl)-pentyl group, 6-(4-cyanophenyl)hexyl group, 2-acetylbenzyl group, 3-acetylbenzyl group, 4-acetylbenzyl group, 2-(2-acetylphenyl)ethyl group, 2-(3-acetylphenyl)ethyl group, 2-(4-acetylphenyl)ethyl group, 3-(4-acetylphenyl)propyl group, 4-(4-acetylphenyl)butyl group, 5-(4-acetylphenyl)pentyl group, 6-(4-acetylphenyl)hexyl group, 2-benzoylbenzyl group, 3-benzoylbenzyl group, 4-benzoylbenzyl group, 2-(2-benzoylphenyl)ethyl group, 2-(3-benzoylphenyl)ethyl group, 2-(4-benzoylphenyl)ethyl group, 3-(4-benzoylphenyl)propyl group, 4-(4-benzoylphenyl)butyl group, 5-(4-benzoylphenyl)pentyl group, 6-(4-benzoylphenyl)hexyl group, 2-α,α-dimethoxybenzylbenzyl group, 3-α,α-dimethoxybenzylbenzyl group, 4-α,α-dimethoxybenzylbenzyl group, 2-(2-α,α-dimethoxybenzylphenyl)ethyl group, 2-(3-(α,α-dimethoxybenzyl)phenyl)-ethyl group, 2-(4-(α,α-dimethoxybenzyl)phenyl)ethyl group, 3-(4-(α,α-dimethoxybenzyl)phenyl)propyl group, 4-(4-(α,α-dimethoxybenzyl)phenyl)butyl group, 5-(4-(α,α-dimethoxybenzyl)phenyl)pentyl group, 6-(4-(α,α-dimethoxybenzyl)phenyl)hexyl group, 2-aminobenzyl group, 3-aminobenzyl group, 4-aminobenzyl group, 2,3-diaminobenzyl group, 2,4,6-triaminobenzyl group, 2-(2-aminophenyl)ethyl group, 2-(3-aminophenyl)ethyl group, 2-(4-aminophenyl)ethyl group, 3-(4-aminophenyl)propyl group, 4-(4-aminophenyl)butyl group, 5-(4-aminophenyl)pentyl group, 6-(4-aminophenyl)hexyl group, 2-nitrobenzyl group, 3-nitrobenzyl group, 4-nitrobenzyl group, 2,4-dinitrobenzyl group, 2,4,6-trinitrobenzyl group, 2-(2-nitrophenyl)ethyl group, 2-(3-nitrophenyl)ethyl group, 2-(4-nitrophenyl)ethyl group, 3-(4-nitrophenyl)-propyl group, 4-(4-nitrophenyl)butyl group, 5-(4-nitrophenyl)pentyl group, 6-(4-nitrophenyl)hexyl group, 2-carbamoylbenzyl group, 3-carbamoylbenzyl group, 4-carbamoylbenzyl group, 2-(2-carbamoylphenyl)ethyl group, 2-(3-carbamoylphenyl)ethyl group, 2-(4-carbamoylphenyl)ethyl group, 3-(4-carbamoylphenyl)-propyl group, 4-(4-carbamoylphenyl)butyl group, 5-(4-carbamoylphenyl)pentyl group, 6-(4-carbamoylphenyl)-hexyl group, 2-acetylaminobenzyl group, 3-acetylaminobenzyl group, 4-acetylaminobenzyl group, 2-(2-acetylaminophenyl)ethyl group, 2-(3-acetylaminophenyl)-ethyl group, 2-(4-acetylaminophenyl)ethyl group, 3-(4-acetylaminophenyl)propyl group, 4-(4-acetylaminophenyl)butyl group, 5-(4-acetylaminophenyl)pentyl group, 6-(4-acetylaminophenyl)hexyl group, 2-ethoxycarbonylbenzyl group, 3-ethoxycarbonylbenzyl group, 4-ethoxycarbonylbenzyl group, 2-(2-ethoxycarbonylphenyl)ethyl group, 2-(3-ethoxycarbonylphenyl)-ethyl group, 2-(4-ethoxycarbonylphenyl)ethyl group, 3-(4-ethoxycarbonylphenyl)propyl group, 4-(4-ethoxycarbonylphenyl)butyl group, 5-(4-ethoxycarbonylphenyl)-pentyl group, 6-(4-ethoxycarbonylphenyl)hexyl group, 2-methylaminocarbonylbenzyl group, 3-methylaminocarbonylbenzyl group, 4-methylaminocarbonylbenzyl group, 2-dimethylaminocarbonylbenzyl group, 3-dimethylaminocarbonylbenzyl group, 2-ethylaminocarbonylbenzyl group, 3-ethylaminocarbonylbenzyl group, 4-ethylaminocarbonylbenzyl group, 4-dimethylaminocarbonylbenzyl group, 2-diethylaminocarbonylbenzyl group, 3-diethylaminocarbonylbenzyl group, 4-diethylaminocarbonylbenzyl group, 2-(di-n-propylaminocarbonyl)benzyl group, 3-(di-n-propylaminocarbonyl)benzyl group, 4-(di-n-propylaminocarbonyl)benzyl group, 2-methoxycarbonylaminobenzyl group, 3-methoxycarbonylaminobenzyl group, 4-methoxycarbonylaminobenzyl group, 2-ethoxycarbonylaminobenzyl group, 3-ethoxycarbonylaminobenzyl group, 4-ethoxycarbonylaminobenzyl group, 2-(tert-butoxycarbonylamino)benzyl group, 3-(tert-butoxycarbonylamino)benzyl group, 4-(tert-butoxycarbonylamino)benzyl group, 4-trimethylsiloxybenzyl group, 4-triethylsiloxybenzyl group, 2-pyrrolylbenzyl group, 3-pyrrolylbenzyl group, 4-pyrrolylbenzyl group, 2-(1-imidazolyl)benzyl group, 3-(1-imidazolyl)benzyl group, 4-(1-imidazolyl)-benzyl group, 2-(2-tetrahydropyranyloxy)benzyl group, 3-(2-tetrahydropyranyloxy)benzyl group, 4-(2-tetrahydropyranyloxy)benzyl group or the like.

Example of a benzhydryl group (which may be substituted on the benzene ring by at least one group selected from a group consisting of a halogen atom, trifluoromethyl group and trifluoromethoxy group) include a benzhydryl group, 4,4'-dichlorobenzhydryl group, 4,4'-difluorobenzhydryl group, 4,4'-ditrifluoromethylbenzhydryl group, 4,4'-ditrifluoromethoxybenzhydryl group or the like.

A phenyl C2-6 alkynyl group (which may have at least one halogen-substituted or unsubstituted C1-6 alkyl group as a substituent on the phenyl ring) includes a phenyl C2-6 alkynyl group (which may have 1 to 3 halogen-substituted or unsubstituted C1-6 alkyl groups as a substituent on the phenyl ring), for example, 2-phenylethynyl group, 3-phenyl-2-propynyl group, 4-phenyl-3-butynyl group, 4-phenyl-2-butynyl group, 5-phenyl-4-pentynyl group, 6-phenyl-5-hexynyl group, 2-methylphenyl-2-propynyl group, 3-methylphenyl-3-butynyl group, 4-methylphenyl-2-butynyl group, 2,4-dimethylphenyl-4-pentynyl group, 2,4,6-trimethylphenyl-5-hexynyl group, 3,5-ditrifluoromethylphenyl-2-propynyl group, 2-trifluoromethylphenyl-3-butynyl group, 3-trifluoromethylphenyl-2-butynyl group, 4-trifluoromethylphenyl-2-propynyl group or the like.

A phenyl C2-6 alkynyl group (which may have at least one halogen-substituted or unsubstituted C1-6 alkyl group as a substituent on the phenyl ring) includes a phenyl C2-6 alkynyl group (which may have 1 to 3 halogen-substituted or unsubstituted C1-6 alkyl groups as a substituent on the phenyl ring), for example, 2-phenylethynyl group, 3-phenyl-2-propynyl group, 4-phenyl-3-butynyl group, 4-phenyl-2-butynyl group, 5-phenyl-4-pentynyl group, 6-phenyl-5-hexynyl group, 2-methylphenyl-2-propynyl group, 3-methylphenyl-3-butynyl group, 4-methylphenyl-2-butynyl group, 2,4-dimethylphenyl-4-pentynyl group, 2,4,6-trimethylphenyl-5-hexynyl group, 3,5-ditrifluoromethylphenyl-2-propynyl group, 2-trifluoromethylphenyl-3-butynyl group, 3-trifluoromethylphenyl-2-butynyl group, 4-trifluoromethylphenyl-2-propynyl group or the like.

Examples of a pyridyl C1-6 alkyl group include a 2-pyridylmethyl group, 2-(3-pyridyl)ethyl group, 1-(4-pyridyl)ethyl group, 3-(2-pyridyl)propyl group, 4-(3-pyridyl)butyl group, 5-(4-pyridyl)pentyl group, 6-(2-pyridyl)hexyl group, 2-methyl-3-(3-pyridyl)propyl group, 1,1-dimethyl-2-(2-pyridyl)ethyl group or the like.

A piperidino C1-6 alkyl group (which may be substituted on the piperidine ring by at least one phenoxy group which may have at least one halogen-substituted or unsubstituted alkyl group as a substituent on the phenyl ring) includes a piperidino C1-6 alkyl group (which may be substituted on the piperidine ring by a phenoxy group which may have 1 to 3 halogen-substituted or unsubstituted alkyl groups as a substituent on the phenyl ring), for example, piperidin-1-ylmethyl group, 2-(piperidin-2-yl)ethyl group, 3-(piperidin-3-yl)propyl group, 4-(piperidin-4-yl)butyl group, 5-(piperidin-1-yl)pentyl group, 6-(piperidin-1-yl)hexyl group, 4-(4-trifluoromethylphenoxy)piperidin-1-ylmethyl group, 4-phenoxypiperidin-1-ylmethyl group, 4-(4-methylphenoxy)piperidin-1-ylmethyl group, 4-(2,4-dimethylphenoxy)piperidin-1-ylmethyl group, 4-(2,4,6-trimethylphenoxy)piperidin-1-ylmethyl group, 2-[4-(4-trifluoromethylphenoxy)-piperidin-1-yl]ethyl group, 3-[4-(4-trifluoromethylphenoxy)piperidin-1-yl]propyl group, 4-[4-(4-trifluoromethylphenoxy)piperidin-1-yl]butyl group, 5-[4-(4-trifluoromethylphenoxy)piperidin-1-yl]pentyl group, 6-[4-(4-trifluoromethylphenoxy)piperidin-1-yl]hexyl group or the like.

An amino C1-6 alkyl group which may have as a substituent at least one group selected from a group consisting of a C1-6 alkyl group and a phenyl group which may have a halogen-substituted or unsubstituted a C1-6 alkoxy group as a substituent on the phenyl ring includes an amino C1-6 alkyl group which may have as a substituent 1 to 2 groups selected from a group consisting of a C1-6 alkyl group and a phenyl group which may have 1 to 3 halogen-substituted or unsubstituted C1-6 alkoky groups as a substituent on the phenyl ring, for example, an aminomethyl group, 2-aminoethyl group, 2-aminopropyl group, 3-aminopropyl group, 3-aminobutyl group, 4-aminobutyl group, 5-aminopentyl group, 6-aminohexyl group, 2-methylaminoethyl group, 2-methylaminopropyl group, 3-methylaminopropyl group, 3-methylaminobutyl group, 4-methylaminobutyl group, 5-methylaminopentyl group, 6-methylaminohexyl group, 2-(ethylamino)ethyl group, 3-(ethylamino)propyl group, 4-(ethylamino)butyl group, 5-(ethylamino)pentyl group, 6-(ethylamino)hexyl group, 2-(n-propylamino)ethyl group, 3-(n-propylamino)propyl group, 4-(n-propylamino)butyl group, 5-(n-propylamino)pentyl group, 6-(n-propylamino)hexyl group, 2-(n-butylamino)ethyl group, 3-(n-butylamino)propyl group, 2-(n-pentylamino)ethyl group, 3-(n-pentylamino)propyl group, 2-(n-hexylamino)ethyl group, 3-(n-hexylamino)propyl group, 2-dimethylaminoethyl group, 2-dimethylaminopropyl group, 3-dimethylaminopropyl group, 3-dimethylaminobutyl group, 4-dimethylaminobutyl group, 5-dimethylaminopentyl group, 6-dimethylaminohexyl group, 2-(diethylamino)ethyl group, 3-(diethylamino)propyl group, 4-(diethylamino)butyl group, 5-(diethylamino)-pentyl group, 6-(diethylamino)hexyl group, 2-(di-n-propylamino)ethyl group, 3-(di-n-propylamino)propyl group, 4-(di-n-propylamino)butyl group, 5-(di-n-propylamino)pentyl group, 6-(di-n-propylamino)hexyl group, 2-(phenylamino)ethyl group, 3-(phenylamino)-propyl group, 4-(phenylamino)butyl group, 5-(phenylamino)pentyl group, 6-(phenylamino)hexyl group, 2-(N-methyl-N-phenylamino)ethyl group, 3-(N-methyl-N-phenylamino)proyyl group, 4-(N-methyl-N-phenylamino)-butyl group, 5-(N-methyl-N-phenylamino)pentyl group, 6-(N-methyl-N-phenylamino)hexyl group, (4-methoxyphenyl)-aminomethyl group, (3,4-dimethoxyphenyl)aminomethyl group, (2,4,6-trimethoxyphenyl)aminomethyl group, 2-(4-trifluoromethoxyphenylamino)ethyl group, 3-(4-trifluoromethoxyphenylamino)propyl group, 4-(4-trifluoromethoxyphenylamino)butyl group, 5-(4-trifluoromethoxyphenylamino)pentyl group, 6-(4-trifluoromethoxyphenylamino)hexyl group, 2-(N-methyl-N-4-trifluoromethoxyphenylamino)ethyl group, 3-(N-methyl-N-4-trifluoromethoxyphenylamino)propyl group, 4-(N-methyl-N-4-trifluoromethoxyphenylamino)butyl group, 5-(N-methyl-N-4-trifluoromethoxyphenylamino)pentyl group, 6-(N-methyl-N-4-trifluoromethoxyphenylamino) hexyl group or the like.

A 1,2,3,6-tetrahydropyridyl C1-6 alkyl group (which may be substituted on the 1,2,3,6-tetrahydropyridine ring by at least one phenyl group which may have at least one halogen-substituted or unsubstituted C1-6 alkoxy group as a substituent on the phenyl ring) includes a 1,2,3,6-tetrahydropyridyl C1-6 alkyl group (which may be substituted on the 1,2,3,6-tetrahydropyridine ring by 1 to 3 phenyl groups which may have 1 to 3 halogen-substituted or unsubstituted C1-6 alkoxy group as a substituent on the phenyl ring), for example, (1,2,3,6-tetrahydropyridin-1-yl)methyl group, 1-(1,2,3,6-tetrahydropyridin-2-yl)ethyl group, 2-(1,2,3,6-tetrahydropyridin-3-yl)ethyl group, 3-(1,2,3,6-tetrahydropyridin-4-yl)propyl group, 4-(1,2,3,6-tetrahydropyridin-1-yl)butyl group, 5-(1,2,3,6-tetrahydropyridin-2-yl)pentyl group, 6-(1,2,3,6-tetrahydropyridin-3-yl)hexyl group, 2-methyl-3-(1,2,3,6-tetrahydropyridin-1-yl)propyl group, 1,1-dimethyl-2-(1,2,3,6-tetrahydropyridin-4-yl)ethyl group, 4-phenyl-1,2,3,6-tetrahydropyridin-1-ylmethyl group, 3,4,5-triphenyl-1,2,3,6-tetrahydropyridin-1-ylmethyl group, 3,4-diphenyl-1,2,3,6-tetrahydropyridin-1-ylmethyl group, 4-(2-methoxyphenyl)-1,2,3,6-tetrahydropyridin-1-ylmethyl group, 4-(3-methoxyphenyl)-1,2,3,6-tetrahydropyridin-1-ylmethyl group, 4-(4-methoxyphenyl)-1,2,3,6-tetrahydropyridin-1-ylmethyl group, 4-(2,4-dimethoxyphenyl)-1,2,3,6-tetrahydropyridin-1-ylmethyl group, 3-(2,4,6-trimethoxyphenyl)-1,2,3,6-tetrahydropyridin-1-ylmethyl group, 4-(2-trifluoromethoxyphenyl)-1,2,3,6-tetrahydropyridin-1-ylmethyl group, 4-(3-trifluoromethoxyphenyl)-1,2,3,6-tetrahydropyridin-1-ylmethyl group, 4-(3,5-ditrifluoromethoxyphenyl)-1,2,3,6-tetrahydropyridin-1-ylmethyl group, 4-(4-trifluoromethoxyphenyl)-1,2,3,6-tetrahydropyridin-1-ylmethyl group, 2-(4-phenyl-1,2,3,6-tetrahydropyridin-1-yl)ethyl group, 2-[4-(4-methoxyphenyl)-1,2,3,6-tetrahydropyridin-1-yl]ethyl group, 2-[4-(4-trifluoromethoxyphenyl)-1,2,3,6-tetrahydropyridin-1-yl]ethyl group, 3-(4-phenyl-1,2,3,6-tetrahydropyridin-1-yl)propyl group, 3-[4-(4-methoxyphenyl)-1,2,3,6-tetrahydropyridin-1-yl]propyl group, 3-[4-(4-trifluoromethoxyphenyl)-1,2,3,6-tetrahydropyridin-1-yl]propyl group, 4-(4-phenyl-1,2,3,6-tetrahydropyridin-1-yl)butyl group, 4-[4-(4-methoxyphenyl)-1,2,3,6-tetrahydropyridin-1-yl]butyl group, 4-[4-(4-trifluoromethoxyphenyl)-1,2,3,6-tetrahydropyridin-1-yl]butyl group, 5-(4-phenyl-1,2,3,6-tetrahydropyridin-1-yl)pentyl group, 5-[4-(4-methoxyphenyl)-1,2,3,6-tetrahydropyridin-1-yl]pentyl group, 5-[4-(4-trifluoromethoxyphenyl)-1,2,3,6-tetrahydropyridin-1-yl]pentyl group, 6-(4-phenyl-1,2,3,6-tetrahydropyridin-1-yl)hexyl group, 6-[4-(4-methoxyphenyl)-1,2,3,6- tetrahydropyridin-1-yl]hexyl group, 6-[4-(4-trifluoromethoxyphenyl)-1,2,3,6-tetrahydropyridin-1-yl]hexyl group or the like.

Examples of a fluorenyl C1-6 alkyl group include a 1-fluorenylmethyl group, 2-fluorenylmethyl group, 3-fluorenylmethyl group, 4-fluorenylmethyl group, 9-fluorenylmethyl group, 2-(1-fluorenyl)ethyl group, 2-(2-fluorenyl)ethyl group, 2-(3-fluorenyl)ethyl group, 2-(4-fluorenyl)ethyl group, 2-(9-fluorenyl)ethyl group, 3-(1-fluorenyl)propyl group, 3-(2-fluorenyl)-propyl group, 3-(3-fluorenyl)propyl group, 3-(4-fluorenyl)propyl group, 3-(9-fluorenyl)propyl group, 4-(1-fluorenyl)butyl group, 4-(2-fluorenyl)butyl group, 5-(1-fluorenyl)pentyl group, 5-(2-fluorenyl)pentyl group, 6-(1-fluorenyl)hexyl group, 6-(2-fluorenyl)hexyl group or the like.

A furyl C1-6 alkyl group (which may be substituted on the furan ring by a halogen-substituted or unsubstituted phenyl group) includes a furyl C1-6 alkyl group (which may be substituted on the furan ring by a phenyl group unsubstituted or substituted by 1 to 5 halogen atom, for example, a 2-furylmethyl group, 3-furylmethyl group, 2-(2-furyl)ethyl group, 1-(3-furyl)ethyl group, 3-(2-furyl)propyl group, 3-(3-furyl)propyl group, 4-(2-furyl)butyl group, 4-(3-furyl)butyl group, 5-(2-furyl)pentyl group, 5-(3-furyl)pentyl group, 6-(2-furyl)hexyl group, 6-(3-furyl)hexyl group, 4-phenyl-2-furylmethyl group, 4-(2-fluorophenyl)-2-furylmethyl group, 4-(3-fluorophenyl)-2-furylmethyl group, 4-(4-fluorophenyl)-2-furylmethyl group, 4-(2,3,4,5,6-pentafluorophenyl)-2-furylmethyl group, 4-(2-chlorophenyl)-2-furylmethyl group, 4-(3-chlorophenyl)-2-furylmethyl group, 4-(4-chlorophenyl)-2-furylmethyl group, 4-(2-bromophenyl)-2-furylmethyl group, 4-(3-bromophenyl)-2-furylmethyl group, 4-(4-bromophenyl)-2-furylmethyl group, 4-phenyl-3-furylmethyl group, 4-(2,3-dichlorophenyl)-3-furylmethyl group, 4-(4-chlorophenyl)-3-furylmethyl group, 4-(2-bromophenyl)-3-furylmethyl group, 4-(3-bromophenyl)-3-furylmethyl group, 4-(4-bromophenyl)-3-furylmethyl group, 4-phenyl-3-furylethyl group, 2-[4-(3-chlorophenyl)-3-furyl]ethyl group, 2-[4-(4-chlorophenyl)-3-furyl]ethyl group, 2-[4-(2-bromophenyl)-3-furyl]ethyl group, 2-[4-(3-bromophenyl)-3-furyl]ethyl group, 2-[4-(2,4-dibromophenyl)-3-furyl]ethyl group, 2-(4-phenyl-2-furyl)ethyl group, 2-[4-(3-chlorophenyl)-2-furyl]ethyl group, 2-[4-(4-chlorophenyl)-2-furyl]ethyl group, 2-[4-(4-bromophenyl)-2-furyl]ethyl group, 3-(4-phenyl-3-furyl)propyl group, 3-[4-(3-chlorophenyl)-3-furyl]-propyl group, 3-[4-(2,4,6-trichlorophenyl)-3-furyl]propyl group, 3-[4-(4-bromophenyl)-3-furyl]propyl group, 3-(4-phenyl-2-furyl)propyl group, 3-[4-(3-chlorophenyl)-2-furyl]propyl group, 3-[4-(4-chlorophenyl)-2-furyl]propyl group, 3-[4-(4-bromophenyl)-2-furyl]propyl group, 4-(4-phenyl-3-furyl)butyl group, 4-[4-(3-chlorophenyl)-3-furyl]butyl group, 4-[4-(4-chlorophenyl)-3-furyl]butyl group, 4-[4-(4-bromophenyl)-3-furyl]butyl group, 4-(4-phenyl-2-furyl)butyl group, 4-[4-(3-chlorophenyl)-2-furyl]butyl group, 4-[4-(4-chlorophenyl)-2-furyl]butyl group, 4-[4-(4-bromophenyl)-2-furyl]butyl group, 5-(4-phenyl-3-furyl)pentyl group, 5-[4-(3-chlorophenyl)-3-furyl]-pentyl group, 5-[4-(4-chlorophenyl)-3-furyl]pentyl group, 5-[4-(4-bromophenyl)-3-furyl]pentyl group, 5-(4-phenyl-2-furyl)pentyl group, 5-[4-(3-chlorophenyl)-2-furyl]pentyl group, 5-[4-(4-chlorophenyl)-2-furyl]pentyl group, 5-[4-(4-bromophenyl)-2-furyl]pentyl group, 6-(4-phenyl-3-furyl)hexyl group, 6-[4-(3-chlorophenyl)-3-furyl]hexyl group, 6-[4-(4-chlorophenyl)-3-furyl]hexyl group, 6-[4-(4-bromophenyl)-3-furyl]hexyl group, 6-(4-phenyl-2-furyl)hexyl group, 6-[4-(3-chlorophenyl)-2-furyl]hexyl group, 6-[4-(4-chlorophenyl)-2-furyl]hexyl group, 6-[4-(4-bromophenyl)-2-furyl]hexyl group or the like.

Examples of a thienyl-substituted C1-6 alkyl group include a 2-thienylmethyl group, 3-thienylmethyl group, 2-(2-thienyl)ethyl group, 1-(3-thienyl)ethyl group, 4-(2-thienyl)butyl group, 4-(3-thienyl)butyl group, 5-(2-thienyl)pentyl group, 5-(3-thienyl)pentyl group, 6-(2-thienyl)hexyl group, 6-(3-thienyl)hexyl group or the like.

An oxazolyl C1-6 alkyl group (which may be substituted on the oxazole ring by a halogen atom or a halogen-substituted or unsubstituted phenyl group) includes an oxazolyl C1-6 alkyl group (which may be substituted on the oxazole ring by a halogen atom or 1 to 2 phenyl groups which may be substituted on the phenyl ring by 1 to 5 halogen atoms), for example, a 2-oxazolylmethyl group, 4-oxazolylmethyl group, 5-oxazolylmethyl group, 2-(2-oxazolyl)ethyl group, 1-(4-oxazolyl)ethyl group, 3-(2-oxazolyl)propyl group, 4-(2-oxazolyl)butyl group, 5-(2-oxazolyl)pentyl group, 6-(2-oxazolyl)hexyl group, 2-(4-oxazolyl)ethyl group, 3-(4-oxazolyl)propyl group, 4-(4-oxazolyl)butyl group, 5-(4-oxazolyl)pentyl group, 6-(4-oxazolyl)hexyl group, 2-chloro-4-oxazolylmethyl group, 2,5-dichloro-4-oxazolylmethyl group, 2,5-diphenyl-4-oxazolylmethyl group, 2-(2-chloro-4-oxazolyl)ethyl group, 3-(2-chloro-4-oxazolyl)propyl group, 4-(2-iodo-4-oxazolyl)butyl group, 5-(2-bromo-4-oxazolyl)pentyl group, 6-(2-fluoro-4-oxazolyl)hexyl group, 2-(4-chlorophenyl)-4-oxazolylmethyl group, 2-(2,3,4,5,6-pentafluorophenyl)-4-oxazolylmethyl group, 2-[2-(4-chlorophenyl)-4-oxazoly]ethyl group, 3-[2-(4-chlorophenyl)-4-oxazolyl]propyl group, 4-[2-(2,4,6-trichlorophenyl)-4-oxazolyl]butyl group, 5-[2-(4-chlorophenyl)-4-oxazolyl]pentyl group, 6-[2-(4-chlorophenyl)-4-oxazolyl]hexyl group, [2-chloro-4-(3-chlorophenyl)-5-oxazolyl]methyl group or the like.

An oxadiazolyl C1-6 alkyl group (which may be substituted on the oxadiazol ring by a halogen-substituted or unsubstituted phenyl group) includes an oxadiazolyl C1-6 alkyl group (which may be substituted on the oxadiazol ring by a phenyl group unsubstituted or substituted by 1 to 5 halogen atoms), for example, a 5-oxadiazolylmethyl group, 2-(5-oxadiazolyl)ethyl group, 1-(2-oxadiazolyl)ethyl group, 3-(5-oxadiazolyl)-propyl group, 4-(2-oxadiazolyl)butyl group, 5-(5-oxadiazolyl)pentyl group, 6-(2-oxadiazolyl)hexyl group, 2-methyl-3-(2-oxadiazolyl)propyl group, 1,1-dimethyl-2-(5-oxadiazolyl)ethyl group, 2-phenyl-5-oxadiazolylmethyl group, 2-(2-fluorophenyl)-5-oxadiazolylmethyl group, 2-(3-fluorophenyl)-5-oxadiazolylmethyl group, 2-(2,3,4,5,6-pentafluorophenyl)-5-oxadiazolylmethyl group, 2-(2,4-dichlorophenyl)-5-oxadiazolylmethyl group, 2-(3-chlorophenyl)-5-oxadiazolylmethyl group, 2-(4-chlorophenyl)-5-oxadiazolylmethyl group, 2-(2-bromophenyl)-5-oxadiazolylmethyl group, 2-(2,4,6-tribromophenyl)-5-oxadiazolylmethyl group, 2-(4-bromophenyl)-5-oxadiazolylmethyl group, 2-(5-oxadiazolyl)ethyl group, 3-(5-oxadiazolyl)propyl group, 4-(5-oxadiazolyl)butyl group, 5-(5-oxadiazolyl)pentyl group, 6-(5-oxadiazolyl)hexyl group, 2-(2-phenyl-5-oxadiazolyl)ethyl group, 3-(2-phenyl-5-oxadiazolyl)-propyl group, 4-(2-phenyl-5-oxadiazolyl)butyl group, 5-(2-phenyl-5-oxadiazolyl)pentyl group, 6-(2-phenyl-5-oxadiazolyl)hexyl group, 2-[2-(4-chlorophenyl)-5-oxadiazolyl]ethyl group, 3-[2-(4-chlorophenyl)-5-oxadiazolyl]propyl group, 4-[2-(4-chlorophenyl)-5-oxadiazolyl]butyl group, 5-[2-(4-chlorophenyl)-5-oxadiazolyl]pentyl group, 6-[2-(4-chlorophenyl)-5-oxadiazolyl]hexyl group or the like.

A pyrazolyl C1-6 alkyl group (which may be substituted on the pyrazole ring by a halogen-substituted or unsubstituted phenyl group) includes a pyrazolyl C1-6 alkyl group (which may be substituted on the pyrazole ring by 1 to 3 phenyl groups unsubstituted or substituted by 1 to 5 halogen atoms), for example, a 3-pyrazolylmethyl group, 2-(4-pyrazolyl)ethyl group, 1-(5-pyrazolyl)ethyl group, 3-(3-pyrazolyl)propyl group, 4-(4-pyrazolyl)butyl group, 5-(1-pyrazolyl)pentyl group, 6-(5-pyrazolyl)hexyl group, 2-methyl-3-(1-pyrazolyl)propyl group, 1,1-dimethyl-2-(3-pyrazolyl)ethyl group, 1-(1-phenyl-3-pyrazolylmethyl group, 1-(2-fluorophenyl)-4-pyrazolylmethyl group, 1-(3-fluorophenyl)-3-pyrazolylmethyl group, 3-phenyl-1-pyrazolylmethyl group, 3,4,5-triphenyl-1-pyrazolylmethyl group, 3,4-diphenyl-1-pyrazolylmethyl group, 1-(4-fluorophenyl)-3-pyrazolylmethyl group, 1-(2,3,4,5,6-pentafluorophenyl)-3-pyrazolylmethyl group, 1-(2-chlorophenyl)-5-pyrazolylmethyl group, 1-(3-chlorophenyl)-3-pyrazolylmethyl group, 1-(4-chlorophenyl)-3-pyrazolylmethyl group, 1-(2-bromophenyl)-3-pyrazolylmethyl group, 1-(3-bromophenyl)-3-pyrazolylmethyl group, 1-(4-bromophenyl)-3-pyrazolylmethyl group, 2-(3-pyrazolyl)ethyl group, 3-(3-pyrazolyl)propyl group, 4-(3-pyrazolyl)butyl group, 5-(3-pyrazolyl)pentyl group, 6-(3-pyrazolyl)hexyl group, 2-[1-(4-chlorophenyl)-3-pyrazolyl]ethyl group, 3-[1-(2,4-dichlorophenyl)-3-pyrazolyl]propyl group, 4-[1-(4-chlorophenyl)-3-pyrazolyl]butyl group, 5-[1-(4-chlorophenyl)-3-pyrazolyl]pentyl group, 6-[1-(2,4,6-trichlorophenyl)-3-pyrazolyl]hexyl group or the like.

A benzothienyl C1-6 alkyl group (which may be substituted on the benzothiophene ring by at least one group selected from a group consisting of a halogen atom and a halogen-substituted or unsubstituted C1-6 alkoxy group) includes a benzothienyl C1-6 alkyl group (which may be substituted on the benzothiophene ring by 1 to 3 groups selected from a group of a halogen atom and a halogen-substituted or unsubstituted C1-6 alkoxy group), for example, a 2-benzothienylmethyl group, 2-(3-benzothienyl)ethyl group, 1-(4-benzothienyl)ethyl group, 3-(5-benzothienyl)propyl group, 4-(6-benzothienyl)butyl group, 5-(7-benzothienyl)pentyl group, 6-(2-benzothienyl)hexyl group, 2-methyl-3-(3-benzothienyl)propyl group, 1,1-dimethyl-2-(2-benzothienyl)ethyl group, 4-fluoro-2-benzothienylmethyl group, 5-fluoro-2-benzothienylmethyl group, 6-fluoro-2-benzothienylmethyl group, 7-fluoro-2-benzothienylmethyl group, 4-chloro-2-benzothienylmethyl group, 5-chloro-2-benzothienylmethyl group, 6-chloro-2-benzothienylmethyl group, 7-chloro-2-benzothienylmethyl group, 4-bromo-2-benzothienylmethyl group, 5-bromo-2-benzothienylmethyl group, 6-bromo-2-benzothienylmethyl group, 7-bromo-2-benzothienylmethyl group, 4-methoxy-2-benzothienylmethyl group, 5-methoxy-2-benzothienylmethyl group, 6-methoxy-2-benzothienylmethyl group, 6,7-dimethoxy-2-benzothienylmethyl group, 3,6,7-trimethoxy-2-benzothienylmethyl group, 7-methoxy-2-benzothienylmethyl group, 4-trifluoromethoxy-2-benzothienylmethyl group, 5-trifluoromethoxy-2-benzothienylmethyl group, 6-trifluoromethoxy-2-benzothienylmethyl group, 7-trifluoromethoxy-2-benzothienylmethyl group, 4-ethoxy-2-benzothienylmethyl group, 5-ethoxy-2-benzothienylmethyl group, 6-ethoxy-2-benzothienylmethyl group, 7-ethoxy-2-benzothienylmethyl group, 4-chloro-5-trifluoromethoxy-2-benzothienylmethyl group, 6-chloro-5-trifluoromethoxy-2-benzothienylmethyl group, 7-chloro-5-trifluoromethoxy-2-benzothienylmethyl group, 3-benzothienylmethyl group, 4-fluoro-3-benzothienylmethyl group, 5-fluoro-3-benzothienylmethyl group, 6-fluoro-3-benzothienylmethyl group, 7-fluoro-3-benzothienylmethyl group, 4-chloro-3-benzothienylmethyl group, 5-chloro-3-benzothienylmethyl group, 6-chloro-3-benzothienylmethyl group, 7-chloro-3-benzothienylmethyl group, 4-bromo-3-benzothienylmethyl group, 5-bromo-3-benzothienylmethyl group, 6-bromo-3-benzothienylmethyl group, 7-bromo-3-benzothienylmethyl group, 4-methoxy-3-benzothienylmethyl group, 5-methoxy-3-benzothienylmethyl group, 6-methoxy-3-benzothienylmethyl group, 7-methoxy-3-benzothienylmethyl group, 4-trifluoromethoxy-3-benzothienylmethyl group, 5-trifluoromethoxy-3-benzothienylmethyl group, 6-trifluoromethoxy-3-benzothienylmethyl group, 7-trifluoromethoxy-3-benzothienylmethyl group, 4-ethoxy-3-benzothienylmethyl group, 5-ethoxy-3-benzothienylmethyl group, 6-ethoxy-3-benzothienylmethyl group, 7-ethoxy-3-benzothienylmethyl group, 4-chloro-5-trifluoromethoxy-3-benzothienylmethyl group, 6-chloro-5-trifluoromethoxy-3-benzothienylmethyl group, 7-chloro-5-trifluoromethoxy-3-benzothienylmethyl group, 2-(2-benzothienyl)ethyl group, 3-(2-benzothienyl)propyl group, 4-(2-benzothienyl)butyl group, 5-(2-benzothienyl)pentyl group, 6-(2-benzothienyl)hexyl group, 2-(3-benzothienyl)ethyl group, 3-(3-benzothienyl)propyl group, 4-(3-benzothienyl)butyl group, 5-(3-benzothienyl)pentyl group, 6-(3-benzothienyl)hexyl group, 2-(5-chloro-2-benzothienyl)ethyl group, 3-(5-chloro-2-benzothienyl)propyl group, 4-(5-chloro-2-benzothienyl)butyl group, 5-(5-chloro-2-benzothienyl)-pentyl group, 6-(5-chloro-2-benzothienyl)hexyl group, 2-(5-chloro-3-benzothienyl)ethyl group, 3-(5-chloro-3-benzothienyl)propyl group, 4-(5-chloro-3-benzothienyl)-butyl group, 5-(5-chloro-3-benzothienyl)pentyl group, 6-(5-chloro-3-benzothienyl)hexyl group or the like.

A thienyl C1-6 alkyl group which may be substituted on the thiophene ring by a halogen atom includes a thienyl C1-6 alkyl group (which may be substituted on the thiophene ring by 1 to 3 halogen atoms, for example, a 2-thienylmethyl group, 2-(3-thienyl)ethyl group, 1-(2-thienyl)ethyl group, 3-(2-thienyl)propyl group, 4-(3-thienyl)butyl group, 5-(2-thienyl)pentyl group, 6-(2-thienyl)hexyl group, 2-methyl-3-(3-thienyl)propyl group, 1,1-dimethyl-2-(2-thienyl)ethyl group, 3-fluoro-2-thienylmethyl group, 4-fluoro-2-thienylmethyl group, 3,4-difluoro-2-thienylmethyl group, 3,4,5-trichloro-2-thienylmethyl group, 5-fluoro-2-thienylmethyl group, 3-chloro-2-thienylmethyl group, 4-chloro-2-thienylmethyl group, 5-chloro-2-thienylmethyl group, 3-bromo-2-thienylmethyl group, 4-bromo-2-thienylmethyl group, 5-bromo-2-thienylmethyl group, 3-thienylmethyl group, 2-fluoro-3-thienylmethyl group, 4-fluoro-3-thienylmethyl group, 5-fluoro-3-thienylmethyl group, 2-chloro-3-thienylmethyl group, 4-chloro-3-thienylmethyl group, 5-chloro-3-thienylmethyl group, 2-bromo-3-thienylmethyl group, 4-bromo-3-thienylmethyl group, 5-iodo-3-thienylmethyl group, 2-(5-chloro-2-thienyl)ethyl group, 3-(5-chloro-2-thienyl)propyl group, 4-(5-chloro-2-thienyl)butyl group, 5-(5-chloro-2-thienyl)pentyl group, 6-(5-chloro-2-thienyl)hexyl group, 2-(5-chloro-3-thienyl)ethyl group, 3-(5-chloro-3-thienyl)propyl group, 4-(5-chloro-3-thienyl)butyl group, 5-(5-chloro-3-thienyl)pentyl group, 6-(5-chloro-3-thienyl)hexyl group or the like.

Examples of a benzothiazolyl C1-6 alkyl group include a benzothiazol-2-ylmethyl group, benzothiazol-4-ylmethyl group, benzothiazol-5-ylmethyl group, benzothiazol-6-ylmethyl group, benzothiazol-7-ylmethyl group, 2-(benzothiazol-4-yl)ethyl group, (benzothiazol-5-yl)methyl group, 2-(benzothiazol-6-yl)ethyl group, 2-(benzothiazol-7-yl)ethyl group, 3-(benzothiazol-4-yl)propyl group, 3-(benzothiazol-5-yl)propyl group, 3-(benzothiazol-6-yl)propyl group, 3-(benzothiazol-7-yl)propyl group, 4-(benzothiazol-2-yl)butyl group, 4-(benzothiazol-4-yl)butyl group, 4-(benzothiazol-5-yl)butyl group, 4-(benzothiazol-6-yl)butyl group, 4-(benzothiazol-7-yl)butyl group, 5-(benzothiazol-2-yl)pentyl group, 5-(benzothiazol-4-yl)pentyl group, 5-(benzothiazol-5-yl)pentyl group, 5-(benzothiazol-6-yl)pentyl group, 5-(benzothiazol-7-yl)pentyl group, 6-(benzothiazol-2-yl)hexyl group, 6-(benzothiazol-4-yl)hexyl group, 6-(benzothiazol-5-yl)hexyl group, 6-(benzothiazol-6-yl)hexyl group, 6-(benzothiazol-7-yl)hexyl group or the like.

A benzofuryl C1-6 alkyl group which may be substituted on the benzofuran ring by a halogen atom as a substituent includes a benzofuryl C1-6 alkyl group which may be substituted on the benzofuran ring by 1 to 3 halogen atoms as a substituent, for example, a 2-benzofurylmethyl group, 2-(3-benzofuryl)ethyl group, 1-(4-benzofuryl)ethyl group, 3-(5-benzofuryl)propyl group, 4-(6-benzofuryl)butyl group, 5-(7-benzofuryl)-pentyl group, 6-(2-benzofuryl)hexyl group, 2-methyl-3-(3-benzofuryl)propyl group, 1,1-dimethyl-2-(2-benzofuryl)ethyl group, 4-fluoro-2-benzofurylmethyl group, 5-fluoro-2-benzofurylmethyl group, 6-fluoro-2-benzofurylmethyl group, 7-fluoro-2-benzofurylmethyl group, 4-chloro-2-benzofurylmethyl group, 5-chloro-2-benzofurylmethyl group, 6-chloro-2-benzofurylmethyl group, 7-chloro-2-benzofurylmethyl group, 4-bromo-2-benzofurylmethyl group, 5-bromo-2-benzofurylmethyl group, 6-bromo-2-benzofurylmethyl group, 7-bromo-2-benzofurylmethyl group, 4-iodo-2-benzofurylmethyl group, 5-iodo-2-benzofurylmethyl group, 6-iodo-2-benzofurylmethyl group, 7-iodo-2-benzofurylmethyl group, 4-fluoro-3-benzofurylmethyl group, 5-fluoro-3-benzofurylmethyl group, 5,6-difluoro-2-benzofurylmethyl group, 7-fluoro-3-benzofurylmethyl group, 4-chloro-3-benzofurylmethyl group, 3,5,6-trichloro-3-benzofurylmethyl group, 6-chloro-3-benzofurylmethyl group, 7-chloro-3-benzofurylmethyl group, 4-bromo-3-benzofurylmethyl group, 5-bromo-3-benzofurylmethyl group, 6-bromo-3-benzofurylmethyl group, 7-bromo-3-benzofurylmethyl group, 4-iodo-3-benzofurylmethyl group, 5-iodo-3-benzofurylmethyl group, 6-iodo-3-benzofurylmethyl group, 7-iodo-3-benzofurylmethyl group or the like.

An indolinyl C1-6 alkyl group (which may be substituted on the indoline ring by at least one group selected from a group consisting of a C1-6 alkyl group and an oxo group) includes an indolinyl C1-6 alkyl group (which may be substituted on the indoline ring by 1 to 5 groups selected from a group consisting of a C1-6 alkyl group and an oxo group), for example, a 2-indolinylmethyl group, 2-(3-indolinyl)ethyl group, 1-(4-indolinyl)ethyl group, 3-(5-indolinyl)propyl group, 4-(6-indolinyl)butyl group, 5-(7-indolinyl)pentyl group, 6-(1-indolinyl)hexyl group, 2-methyl-3-(3-indolinyl)propyl group, 1,1-dimethyl-2-(2-indolinyl)-ethyl group, 3,3-dimethyl-5-indolinylmethyl group, 1,3,3-trimethyl-5-indolinylmethyl group, 1-ethyl-3,3-dimethyl-5-indolinylmethyl group, 1-methyl-5-indolinylmethyl group, 1,3-dimethyl-5-indolinylmethyl group, 1,3,3,6,7-pentamethyl-5-indolinylmethyl group, 3,3-dimethyl-1-(n-propyl)-5-indolinylmethyl group, 3,3-dimethyl-1-(isopropyl)-5-indolinylmethyl group, 1-(n-butyl)-3,3-dimethyl-5-indolinylmethyl group, 1-(sec-butyl)-3,3-dimethyl-5-indolinylmethyl group, 1-(tert-butyl)-3,3-dimethyl-5-indolinylmethyl group, 1-(n-pentyl)-3,3-dimethyl-5-indolinylmethyl group, 1-(n-hexyl)-3,3-dimethyl-5-indolinylmethyl group, 3,3-dimethyl-2-oxo-5-indolinylmethyl group, 1,3,3-trimethyl-2-oxo-5-indolinylmethyl group, 1-ethyl-3,3-dimethyl-2-oxo-5-indolinylmethyl group, 3,3-dimethyl-2-oxo-1-(n-propyl)-5-indolinylmethyl group, 3,3-dimethyl-2-oxo-1-(isopropyl)-5-indolinylmethyl group, 1-(n-butyl)-3,3-dimethyl-2-oxo-5-indolinylmethyl group, 1-(sec-butyl)-3,3-dimethyl-2-oxo-5-indolinylmethyl group, 1-(tert-butyl)-3,3-dimethyl-2-oxo-5-indolinylmethyl group, 1-(n-pentyl)-3,3-dimethyl-2-oxo-5-indolinylmethyl group, 1-(n-hexyl)-3,3-dimethyl-2-oxo-5-indolinylmethyl group, 2-oxo-5-indolinylmethyl group or the like.

A benzoxazolyl C1-6 alkyl group (which may be substituted on the benzoxazole ring by at least one group selected from a group consisting of a halogen atom, C1-6 alkyl group and oxo group) includes benzoxazoyl C1-6 alkyl group (which may be substituted on the benzoxazole ring by 1 to 3 groups selected from a group consisting of a halogen atom, C1-6 alkyl group and oxo group), for example, a benzoxazol-2-ylmethyl group, benzoxazol-4-ylmethyl group, benzoxazol-5-ylmethyl group, benzoxazol-6-ylmethyl group, benzoxazol-7-ylmethyl group, 2-(benzoxazol-2-yl)ethyl group, 1-(benzoxazol-4-yl)ethyl group, 3-(benzoxazol-5-yl)propyl group, 4-(benzoxazol-6-yl)butyl group, 5-(benzoxazol-7-yl)pentyl group, 6-(benzoxazol-2-yl)hexyl group, 2-methyl-3-(benzoxazol-4-yl)propyl group, 1,1-dimethyl-2-(benzoxazol-5-yl)ethyl group, 2,5-dimethylbenzoxazol-4-ylmethyl group, 2,5,6-trimethylbenzoxazol-4-ylmethyl group, 4,5-dichlorobenzoxazol-4-ylmethyl group, 2,4,5-trichlorobenzoxazol-4-ylmethyl group, (2,3-dihydro-2-oxo-benzoxazol-3-yl)methyl group, (2,3-dihydro-2-oxo-benzoxazol-4-yl)methyl group, (2,3-dihydro-2-oxo-benzoxazol-5-yl)methyl group, (2,3-dihydro-2-oxo-benzoxazol-6-yl)methyl group, (2,3-dihydro-2-oxo-benzoxazol-7-yl)methyl group, 2-(benzoxazol-4-yl)ethyl group, (benzoxazol-5-yl)methyl group, 2-(benzoxazol-6-yl)ethyl group, 2-(benzoxazol-7-yl)ethyl group, 2-(2,3-dihydro-2-oxo-benzoxazol-3-yl)ethyl group, 2-(2,3-dihydro-2-oxo-benzoxazol-4-yl)ethyl group, 2-(2,3-dihydro-2-oxo-benzoxazol-5-yl)ethyl group, 2-(2,3-dihydro-2-oxo-benzoxazol-6-yl)ethyl group, 2-(2,3-dihydro-2-oxo-benzoxazol-7-yl)ethyl group, 3-(benzoxazol-2-yl)propyl group, 3-(benzoxazol-4-yl)propyl group, 3-(benzoxazol-6-yl)propyl group, 3-(benzoxazol-7-yl)propyl group, 3-(2,3-dihydro-2-oxo-benzoxazol-3-yl)propyl group, 3-(2,3-dihydro-2-oxo-benzoxazol-4-yl)propyl group, 3-(2,3-dihydro-2-oxo-benzoxazol-5-yl)propyl group, 3-(2,3-dihydro-2-oxo-benzoxazol-6-yl)propyl group, 3-(2,3-dihydro-2-oxo-benzoxazol-7-yl)propyl group, 4-(benzoxazol-2-yl)butyl group, 4-(benzoxazol-4-yl)butyl group, 4-(benzoxazol-5-yl)butyl group, 4-(benzoxazol-7-yl)butyl group, 4-(2,3-dihydro-2-oxo-benzoxazol-3-yl)butyl group, 4-(2,3-dihydro-2-oxo-benzoxazol-4-yl)butyl group, 4-(2,3-dihydro-2-oxo-benzoxazol-5-yl)butyl group, 4-(2,3-dihydro-2-oxo-benzoxazol-6-yl)butyl group, 4-(2,3-dihydro-2-oxo-benzoxazol-7-yl)butyl group, 5-(benzoxazol-2-yl)pentyl group, 5-(benzoxazol-4-yl)pentyl group, 5-(benzoxazol-5-yl)pentyl group, 5-(benzoxazol-6-yl)pentyl group, 5-(2,3-dihydro-2-oxo-benzoxazol-3-yl)pentyl group, 5-(2,3-dihydro-2-oxo-benzoxazol-4-yl)pentyl group, 5-(2,3-dihydro-2-oxo-benzoxazol-5-yl)pentyl group, 5-(2,3-dihydro-2-oxo-benzoxazol-6-yl)pentyl group, 5-(2,3-dihydro-2-oxo-benzoxazol-7-yl)pentyl group, 6-(benzoxazol-4-yl)hexyl group, 6-(benzoxazol-5-yl)hexyl group, 6-(benzoxazol-6-yl)hexyl group, 6-(benzoxazol-7-yl)hexyl group, 6-(2,3-dihydro-2-oxo-benzoxazol-3-yl)hexyl group, 6-(2,3-dihydro-2-oxo-benzoxazol-4-yl)hexyl group, 6-(2,3-dihydro-2-oxo-benzoxazol-5-yl)hexyl group, 6-(2,3-dihydro-2-oxo-benzoxazol-6-yl)hexyl group, 6-(2,3-dihydro-2-oxo-benzoxazol-7-yl)hexyl group, 2-methylbenzoxazol-4-ylmethyl group, 2-methylbenzoxazol-5-ylmethyl group, 2-methylbenzoxazol-6-ylmethyl group, 4-methylbenzoxazol-2-ylmethyl group, 5-methylbenzoxazol-2-ylmethyl group, 6-methylbenzoxazol-2-ylmethyl group, 7-methylbenzoxazol-2-ylmethyl group, 2-ethylbenzoxazol-4-ylmethyl group, 2-ethylbenzoxazol-5-ylmethyl group, 2-ethylbenzoxazol-6-ylmethyl group, 2-n-propylbenzoxazol-4-ylmethyl group, 2-n-propylbenzoxazol-5-ylmethyl group, 2-n-propylbenzoxazol-6-ylmethyl group, 4-fluorobenzoxazol-2-ylmethyl group, 5-fluoro-2-benzoxazolylmethyl group, 6-fluoro-2-benzoxazolylmethyl group, 7-fluorobenzoxazol-2-ylmethyl group, 4-chlorobenzoxazol-2-ylmethyl group, 5-chloro-2-benzoxazol-2-ylmethyl group, 6-chloro-2-benzoxazol-2-ylmethyl group, 7-chloro-2-benzoxazol-2-ylmethyl group, 4-bromo-2-benzoxazol-2-ylmethyl group, 5-bromo-2-benzoxazol-2-ylmethyl group, 6-bromo-2-benzoxazol-2-ylmethyl group, 7-bromo-2-benzoxazol-2-ylmethyl group, 4-fluoro-2-oxo-2,3-dihydrobenzoxazol-3-ylmethyl group, 5-fluoro-2-oxo-2,3-dihydrobenzoxazol-3-ylmethyl group, 6-fluoro-2-oxo-2,3-dihydrobenzoxazol-3-ylmethyl group, 7-fluoro-2-oxo-2,3-dihydrobenzoxazol-3-ylmethyl group, 4-chloro-2-oxo-2,3-dihydrobenzoxazol-3-ylmethyl group, 5-chloro-2-oxo-2,3-dihydrobenzoxazol-3-ylmethyl group, 6-chloro-2-oxo-2,3-dihydrobenzoxazol-3-ylmethyl group, 7-chloro-2-oxo-2,3-dihydrobenzoxazol-3-ylmethyl group, 4-bromo-2-oxo-2,3-dihydrobenzoxazol-3-ylmethyl group, 5-bromo-2-oxo-2,3-dihydrobenzoxazol-3-ylmethyl group, 6-bromo-2-oxo-2,3-dihydrobenzoxazol-3-ylmethyl group, 7-bromo-2-oxo-2,3-dihydrobenzoxazol-3-ylmethyl group, 4-fluoro-2-oxo-2,3-dihydrobenzoxazol-5-ylmethyl group, 5-fluoro-2-oxo-2,3-dihydrobenzoxazol-5-ylmethyl group, 6-fluoro-2-oxo-2,3-dihydrobenzoxazol-5-ylmethyl group, 7-fluoro-2-oxo-2,3-dihydrobenzoxazol-5-ylmethyl group, 4-chloro-2-oxo-2,3-dihydrobenzoxazol-5-ylmethyl group, 5-chloro-2-oxo-2,3-dihydrobenzoxazol-5-ylmethyl group, 6-chloro-2-oxo-2,3-dihydrobenzoxazol-5-ylmethyl group, 7-chloro-2-oxo-2,3-dihydrobenzoxazol-5-ylmethyl group, 4-bromo-2-oxo-2,3-dihydrobenzoxazol-5-ylmethyl group, 5-bromo-2-oxo-2,3-dihydrobenzoxazol-5-ylmethyl group, 6-bromo-2-oxo-2,3-dihydrobenzoxazol-5-ylmethyl group, 7-bromo-2-oxo-2,3-dihydrobenzoxazol-5-ylmethyl group, 4-fluoro-2-oxo-2,3-dihydrobenzoxazol-6-ylmethyl group, 5-fluoro-2-oxo-2,3-dihydrobenzoxazol-6-ylmethyl group, 6-fluoro-2-oxo-2,3-dihydrobenzoxazol-6-ylmethyl group, 7-fluoro-2-oxo-2,3-dihydrobenzoxazol-6-ylmethyl group, 4-chloro-2-oxo-2,3-dihydrobenzoxazol-6-ylmethyl group, 5-chloro-2-oxo-2,3-dihydrobenzoxazol-6-ylmethyl group, 6-chloro-2-oxo-2,3-dihydrobenzoxazol-6-ylmethyl group, 7-chloro-2-oxo-2,3-dihydrobenzoxazol-6-ylmethyl group, 4-bromo-2-oxo-2,3-dihydrobenzoxazol-6-ylmethyl group, 5-bromo-2-oxo-2,3-dihydrobenzoxazol-6-ylmethyl group, 6-bromo-2-oxo-2,3-dihydrobenzoxazol-6-ylmethyl group, 7-bromo-2-oxo-2,3-dihydrobenzoxazol-6-ylmethyl group or the like.

Examples of a chromenyl C1-6 alkyl group include 2-chromenylmethyl group, 3-chromenylmethyl group, 4-chromenylmethyl group, 5-chromenylmethyl group, 6-chromenylmethyl group, 7-chromenylmethyl group, 8-chromenylmethyl group, 2-(2-chromenyl)ethyl group, 1-(3-chromenyl)ethyl group, 3-(4-chromenyl)-propyl group, 4-(5-chromenyl)butyl group, 5-(6-chromenyl)pentyl group, 6-(7-chromenyl)hexyl group, 2-methyl-3-(8-chromenyl) propyl group, 1,1-dimethyl-2-(6-chromenyl)ethyl group or the like.

Examples of a 1,2,3,4-tetrahydroquinolyl C1-6 alkyl group (which may be substituted on the quinoline ring by at least one group selected from a group consisting of a C1-6 alkyl group and an oxo group) includes a 1,2,3,4-tetrahydroquinolyl C1-6 alkyl group (which may be substituted on the quinoline ring by 1 to 3 groups selected from a group consisting of a C1-6 alkyl group and an oxo group), for example, a (1,2,3,4-tetrahydro-6-quinolyl)methyl group, 2-(1,2,3,4-tetrahydro-2-quinolyl)ethyl group, 1-(1,2,3,4-tetrahydro-1-quinolyl)ethyl group, 3-(1,2,3,4-tetrahydro-3-quinolyl)propyl group, 4-(1,2,3,4-tetrahydro-4-quinolyl)butyl group, 5-(1,2,3,4-tetrahydro-5-quinolyl)pentyl group, 6-(1,2,3,4-tetrahydro-6-quinolyl)hexyl group, 2-methyl-3-(1,2,3,4-tetrahydro-7-quinolyl)propyl group, 1,1-dimethyl-2-(1,2,3,4-tetrahydro-8-quinolyl)ethyl group, 2-oxo-1,2,3,4-tetrahydro-6-quinolylmethyl group, 4-methyl-1,2,3,4-tetrahydro-6-quinolylmethyl group, 4-oxo-1,2,3,4-tetrahydro-6-quinolylmethyl group, 4,6-dimethyl-1,2,3,4-tetrahydro-5-quinolylmethyl group, 1,4,8-trimethyl-1,2,3,4-tetrahydro-6-quinolylmethyl group, 1-methyl-2-oxo-1,2,3,4-tetrahydro-6-quinolylmethyl group, 1-ethyl-2-oxo-1,2,3,4-tetrahydro-6-quinolylmethyl group, 2-oxo-1-(n-propyl)-1,2,3,4-tetrahydro-6-quinolylmethyl group, 2-oxo-1-(isopropyl)-1,2,3,4-tetrahydro-6-quinolylmethyl group, 1-(n-butyl)-2-oxo-1,2,3,4-tetrahydro-6-quinolylmethyl group, 1-(sec-butyl)-2-oxo-1,2,3,4-tetrahydro-6-quinolylmethyl group, 1-(tert-butyl)-2-oxo-1,2,3,4-tetrahydro-6-quinolylmethyl group, 1-(n-pentyl)-2-oxo-1,2,3,4-tetrahydro-6-quinolylmethyl group, 1-(n-hexyl)-2-oxo-1,2,3,4-tetrahydro-6-quinolylmethyl group, 2-(2-oxo-1,2,3,4-tetrahydro-6-quinolyl)ethyl group, 3-(2-oxo-1,2,3,4-tetrahydro-6-quinolyl)propyl group, 4-(2-oxo-1,2,3,4-tetrahydro-6-quinolyl)butyl group, 5-(2-oxo-1,2,3,4-tetrahydro-6-quinolyl)pentyl group, 6-(2-oxo-1,2,3,4-tetrahydro-6-quinolyl)hexyl group, 2-(1-methyl-2-oxo-1,2,3,4-tetrahydro-6-quinolyl)ethyl group, 3-(1-methyl-2-oxo-1,2,3,4-tetrahydro-6-quinolyl)propyl group, 4-(1-methyl-2-oxo-1,2,3,4-tetrahydro-6-quinolyl)butyl group, 5-(1-methyl-2-oxo-1,2,3,4-tetrahydro-6-quinolyl)pentyl group, 6-(1-methyl-2-oxo-1,2,3,4-tetrahydro-6-quinolyl)hexyl group or the like.

A thiazolyl C1-6 alkyl group (which may be substituted on the thiazole ring by at least one group selected from a group consisting of a halogen atom, a halogen-substituted or unsubstituted phenyl group and a C1-6 alkyl group) includes a thiazolyl C1-6 alkyl group (which may be substituted on the thiazole ring by 1 to 2 groups selected from a group consisting of a halogen atom, 1 to 5 halogen-substituted or unsubstituted phenyl group and a C1-6 alkyl group), for example, a 2-thiazolylmethyl group, 4-thiazolylmethyl group, 5-thiazolylmethyl group, 2-(2-thiazolyl)ethyl group, 1-(4-thiazolyl)ethyl group, 3-(5-thiazolyl)propyl group, 4-(2-thiazolyl)butyl group, 5-(4-thiazolyl)pentyl group, 6-(5-thiazolyl)hexyl group, 2-methyl-3-(2-thiazolyl)propyl group, 1,1-dimethyl-2-(4-thiazolyl)-ethyl group, 2-chloro-4-thiazolylmethyl group, 2,5-dichloro-4-thiazolylmethyl group, 2-chloro-5-thiazolylmethyl group, 2-chloro-6-thiazolylmethyl group, 6-chloro-2-thiazolylmethyl group, 5-chloro-2-thiazolylmethyl group, 4-chloro-2-thiazolylmethyl group, 5-chloro-4-thiazolylmethyl group, 4-chloro-5-thiazolylmethyl group, 2-ethyl-4-thiazolylmethyl group, 2,5-dimethyl-4-thiazolylmethyl group, 2-methyl-4-thiazolylmethyl group, 2-methyl-5-thiazolylmethyl group, 2-methyl-6-thiazolylmethyl group, 6-methyl-2-thiazolylmethyl group, 5-methyl-2-thiazolylmethyl group, 4-methyl-2-thiazolylmethyl group, 5-methyl-4-thiazolylmethyl group, 4-methyl-5-thiazolylmethyl group, 2-ethyl-4-thiazolylmethyl group, 2-ethyl-5-thiazolylmethyl group, 2-ethyl-6-thiazolylmethyl group, 6-ethyl-2-thiazolylmethyl group, 5-ethyl-2-thiazolylmethyl group, 4-ethyl-2-thiazolylmethyl group, 5-ethyl-4-thiazolylmethyl group, 4-ethyl-5-thiazolylmethyl group, 2-phenyl-4-thiazolylmethyl group, 2-phenyl- 5-thiazolylmethyl group, 2-phenyl-6-thiazolylmethyl group, 6-phenyl-2-thiazolylmethyl group, 5-phenyl-2-thiazolylmethyl group, 4-phenyl-2-thiazolylmethyl group, 5-phenyl-4-thiazolylmethyl group, 4-phenyl-5-thiazolylmethyl group, 5-(2-fluorophenyl)-2-thiazolylmethyl group, 5-(2,4-difluorophenyl)-4-thiazolylmethyl group, 4-(2-fluorophenyl)-5-thiazolylmethyl group, 2-(2-fluorophenyl)-4-thiazolylmethyl group, 2-(2-fluorophenyl)-5-thiazolylmethyl group, 2-(3-fluorophenyl)-4-thiazolylmethyl group, 2-(3-fluorophenyl)-5-thiazolylmethyl group, 2-(4-fluorophenyl)-4-thiazolylmethyl group, 4-(2-fluorophenyl)-5-thiazolylmethyl group, 2-(2-chlorophenyl)-4-thiazolylmethyl group, 2-(2-chlorophenyl)-5-thiazolylmethyl group, 2-(3-chlorophenyl)-4-thiazolylmethyl group, 2-(2-fluorophenyl)-5-thiazolylmethyl group, 2-(4-chlorophenyl)-4-thiazolylmethyl group, 2-(4-chlorophenyl)-5-thiazolylmethyl group or the like.

A tetrazolyl C1-6 alkyl group (which may be substituted on the tetrazole ring by a group selected from a group consisting of a halogen-substituted or unsubstituted phenyl group and a C1-6 alkyl group) includes a tetrazolyl C1-6 alkyl group (which may be substituted on the tetrazole ring by a group selected from a group consisting of a phenyl group unsubstituted or substituted by 1 to 5 halogen atoms and a C1-6 alkyl group), for example, a 5-(1H)-tetrazolylmethyl group, 2-(5-(1H)-tetrazolyl)ethyl group, 1-(5-(1H)-tetrazolyl)ethyl group, 3-(5-(1H)-tetrazolyl)propyl group, 4-(5-(1H)-tetrazolyl)butyl group, 5-(5-(1H)-tetrazolyl)pentyl group, 6-(5-(1H)-tetrazolyl)hexyl group, 2-methyl-3-(5-(1H)-tetrazolyl)propyl group, 1,1-dimethyl-2-(5-(1H)-tetrazolyl)ethyl group, 1-methyl-5-(1H)-tetrazolylmethyl group, 1-ethyl-5-(1H)-tetrazolylmethyl group, 1-propyl-5-(1H)-tetrazolylmethyl group, 1-butyl-5-(1H)-tetrazolylmethyl group, 1-pentyl-5-(1H)-tetrazolylmethyl group, 1-hexyl-5-(1H)-tetrazolylmethyl group, 1-phenyl-5-(1H)-tetrazolylmethyl group, 1-(2-fluorophenyl)-5-(1H)-tetrazolylmethyl group, 1-(3-fluorophenyl)-5-(1H)-tetrazolylmethyl group, 1-(2,3,4,5,6-pentafluorophenyl)-5-(1H)-tetrazolylmethyl group, 1-(2-chlorophenyl)-5-(1H)-tetrazolylmethyl group, 1-(3-chlorophenyl)-5-(1H)-tetrazolylmethyl group, 1-(2,4,6-trichlorophenyl)-5-(1H)-tetrazolylmethyl group, 1-(2-bromophenyl)-5-(1H)-tetrazolylmethyl group, 1-(2,3-dibromophenyl)-5-(1H)-tetrazolylmethyl group, 1-(4-bromophenyl)-5-(1H)-tetrazolylmethyl group, 2-(1-methyl-5-(1H)-tetrazolyl)-ethyl group, 2-(1-ethyl-5-(1H)-tetrazolyl)ethyl group, 2-(1-prpopyl-5-(1H)-tetrazolyl)ethyl group, 2-(1-butyl-5-(1H)-tetrazolyl)ethyl group, 2-(1-pentyl-5-(1H)-tetrazolyl)ethyl group, 2-(1-hexyl-5-(1H)-tetrazolyl)ethyl group, 2-(1-phenyl-5-(1H)-tetrazolyl)ethyl group, 2-(1-(2-fluorophenyl)-5-(1H)-tetrazolyl)ethyl group, 2-(1-(3-fluorophenyl)-5-(1H)-tetrazolyl)ethyl group, 2-(1-(4-fluorophenyl)-5-(1H)-tetrazolyl)ethyl group, 2-(1-(2-chlorophenyl)-5-(1H)-tetrazolyl)ethyl group, 2-(1-(3-chlorophenyl)-5-(1H)-tetrazolyl)ethyl group, 2-(1-(4-chlorophenyl)-5-(1H)-tetrazolyl)ethyl group, 2-(1-(2-bromophenyl)-5-(1H)-tetrazolyl)ethyl group, 2-(1-(3-bromophenyl)-5-(1H)-tetrazolyl)ethyl group, 2-(1-(4-bromophenyl)-5-(1H)-tetrazolyl)ethyl group or the like.

A piperidine ring or a 1,2,3,6-tetrahydropyridine ring which is formed by combining $R^{32}$ and $R^{33}$ together with the adjacent nitrogen atom through the other carbon atom (the piperidine ring or a 1,2,3,6-tetrahydropyridine ring may have a phenyl group as a substituent, and the phenyl group may have at least one substituent selected from a group consisting of a halogen atom and a halogen-substituted or unsubstituted C1-6 alkyl group as a substituent) include a piperidine ring and a 1,2,3,6-tetrahydropyridine ring which may be substituted a phenyl group on the ring which may be substituted by 1 to 5, preferably 1 to 3 groups s-elected from a group consisting of a halogen atom and a halogen-substituted or unsubstituted C1-6 alkyl group as a substituent, for example, a piperidine group, 4-phenylpiperidine group, 4-(2-fluorophenyl)piperidine group, 4-(3-fluorophenyl)piperidine group, 4-(3-fluoro-4-trifluoromethylphenyl)piperidine group, 4-(3,4,5-trichlorophenyl)piperidine group, 4-(2,3,4,5,6-pentafluorophenyl)piperidine group, 4-(2,4-dimethylphenyl)piperidine group, 4-(2,4,6-trimethylphenyl)-piperidine group, 4-(2-trifluoromethyl-4-methylphenyl)-piperidine group, 4-(4-fluorophenyl)piperidine group, 4-(3,4-difluorophenyl)piperidine group, 4-(2-chlorophenyl)piperidine group, 4-(3-chlorophenyl)-piperidine group, 4-(4-chlorophenyl)piperidine group, 4-(3,4-dichlorophenyl)piperidine group, 4-(2-methylphenyl)piperidine group, 4-(3-methylphenyl)-piperidine group, 4-(4-methylphenyl)piperidine group, 4-(2-trifluoromethylphenyl)piperidine group, 4-(3-trifluoromethylphenyl)piperidine group, 4-(4-trifluoromethylphenyl)piperidine group, 4-phenyl-1,2,3,6-tetrahydropyridine group, 4-(2-fluorophenyl)-1,2,3,6-tetrahydropyridine group, 4-(3-fluorophenyl)-1,2,3,6-tetrahydropyridine group, 4-(4-fluorophenyl)-1,2,3,6-tetrahydropyridine group, 4-(3,4-difluorophenyl)-1,2,3,6-tetrahydropyridine group, 4-(2-chlorophenyl)-1,2,3,6-tetrahydropyridine group, 4-(3-chlorophenyl)-1,2,3,6-tetrahydropyridine group, 4-(4-chlorophenyl)-1,2,3,6-tetrahydropyridine group, 4-(3,4-dichlorophenyl)-1,2,3,6-tetrahydropyridine group, 4-(2-methylphenyl)-1,2,3,6-tetrahydropyridine group, 4-(3-methylphenyl)-1,2,3,6-tetrahydropyridine group, 4-(4-methylphenyl)-1,2,3,6-tetrahydropyridine group, 4-(2-trifluoromethylphenyl)-1,2,3,6-tetrahydropyridine group, 4-(3-trifluoromethylphenyl)-1,2,3,6-tetrahydropyridine group, 4-(4-trifluoromethylphenyl)-1,2,3,6-tetrahydropyridine group, 4-(3-fluoro-4-trifluoromethylphenyl)-1,2,3,6-tetrahydropyridine group, 4-(3,4,5-trichlorophenyl)-1,2,3,6-tetrahydropyridine group, 4-(2,3,4,5,6-pentafluorophenyl)-1,2,3,6-tetrahydropyridine group, 4-(2,4-dimethylphenyl)-1,2,3,6-tetrahydropyridine group, 4-(2,4,6-trimethylphenyl)-1,2,3,6-tetrahydropyridine group, 4-(2-trifluoromethyl-4-methylphenyl)-1,2,3,6-tetrahydropyridine group or the like.

Examples of a C3-8 cycloalkenyl group include a cyclopropenyl group, cyclobutenyl group, cyclopentenyl group, cyclohexenyl group, cycloheptenyl group, cyclooctenyl group or the like.

A phenyl group (which may be substituted on the phenyl ring by 1 to 5 groups selected from a group consisting of a halogen atom, halogen-substituted or unsubstituted C1-6 alkyl group, halogen-substituted or unsubstituted C1-6 alkoxy group, C1-4 alkylenedioxy group, C1-6 alkylsulfonyl group, halogen-substituted or unsubstituted C1-6 alkylthio group, nitro group and amino group which may have a C1-6 alkanoyl group as a substituent) includes a phenyl group (which may be substituted on the phenyl ring by 1 to 5, preferably 1 to 3 groups selected from a group consisting of a halogen atom, halogen-substituted or unsubstituted C1-6 alkyl group, halogen-substituted or unsubstituted C1-6 alkoxy group, C1-4 alkylenedioxy group, C1-6 alkylsulfonyl group, halogen-substituted or unsubstituted C1-6 alkylthio group, nitro group and amino group which may have 1 to 2 C1-6 alkanoyl group as a substituent (in case of a C1-4 alkylenedioxy group as a substituent, 1 to 3 substituents are preferable)), for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 3,4,5-dichlorophenyl group, 2,4,6-trifluorophenyl group, 2,3,4,5,6-pentafluorophenyl group, 2,4,6-trichlorophenyl group, 2-methylphenyl group, 3-methylphenyl group, 4-methylphenyl group, 2,4-dimethylphenyl group, 2,4,6-trimethylphenyl group, 2-methyl-3-chlorophenyl group, 3-methyl-4-chlorophenyl group, 2-chloro-4-methylphenyl group, 2-methyl-3-fluorophenyl group, 2-trifluoromethylphenyl group, 3-trifluoromethylphenyl group, 4-trifluoromethylphenyl group, 2-pentafluoroethylphenyl group, 3-pentafluoroethylphenyl group, 4-pentafluoroethylphenyl group, 2-isopropylphenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoropropylphenyl group, 4-pentylphenyl group, 4-hexylphenyl group, 2-methoxyphenyl group, 3-methoxyphenyl group, 4-methoxyphenyl group, 2-methoxy-3-chlorophenyl group, 2-fluoro-3-methoxyphenyl group, 2-fluoro-4-methoxyphenyl group, 2,6-dimethoxyphenyl group, 2,4,6-trimethoxyphenyl group, 2,3,4-trifluorophenyl group, 3,4,5-trifluorophenyl group, 2-trifluoromethoxyphenyl group, 3-trifluoromethoxyphenyl group, 4-trifluoromethoxyphenyl group, 2-pentafluoroethoxyphenyl group, 3-pentafluoroethoxyphenyl group, 4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropropoxyphenyl group, 3-n-heptafluoropropoxyphenyl group, 4-n-heptafluoropropoxyphenyl group, 4-pentoxyphenyl group, 4-hexyloxyphenyl group, 2,3-methylenedioxyphenyl group, 3,4-methylenedioxyphenyl group, 3-nitrophenyl group, 2,3-dinitrophenyl group, 2,4,6-trinitrophenyl group, 4-nitrophenyl group, 3-methylthiophenyl group, 4-methylthiophenyl group, 3-trifluoromethylthiophenyl group, 4-trifluoromethylthiophenyl group, 3-methanesulfonylphenyl group, 4-methanesulfonylphenyl group, 2-methanesulfonylphenyl group, 2-aminophenyl, 2,4-diaminophenyl, 2,4,6-triaminophenyl, 2-acetylaminophenyl group, 3-acetylaminophenyl group, 4-acetylaminophenyl group or the like.

A benzofuryl group (which may be substituted on the benzofuran ring by at least one group selected from a group consisting of a halogen atom, a halogen-substituted or unsubstituted C1-6 alkyl group and a halogen-substituted or unsubstituted C1-6 alkoxy group) includes a benzofuryl group (which may be substituted on the benzofuran ring by 1 to 3 groups selected from a group consisting of a halogen atom, a halogen-substituted or unsubstituted C1-6 alkyl group and a halogen-substituted or unsubstituted C1-6 alkoxy group), for example, an unsubstituted 2-benzofuryl group, 4-fluoro-2-benzofuryl group, 5-fluoro-2-benzofuryl group, 6-fluoro-2-benzofuryl group, 7-fluoro-2-benzofuryl group, 4-chloro-2-benzofuryl group, 5-chloro-2-benzofuryl group, 6-chloro-2-benzofuryl group, 7-chloro-2-benzofuryl group, 4-bromo-2-benzofuryl group, 5-bromo-2-benzofuryl group, 6-bromo-2-benzofuryl group, 7-bromo-2-benzofuryl group, 4-methyl-2-benzofuryl group, 5-methyl-2-benzofuryl group, 6-methyl-2-benzofuryl group, 7-methyl-2-benzofuryl group, 4-trifluoromethyl-2-benzofuryl group, 5-trifluoromethyl-2-benzofuryl group, 6-trifluoromethyl-2-benzofuryl group, 7-trifluoromethyl-2-benzofuryl group, 4-ethyl-2-benzofuryl group, 5-ethyl-2-benzofuryl group, 6-ethyl-2-benzofuryl group, 7-ethyl-2-benzofuryl group, 4-pentafluoroethyl-2-benzofuryl group, 5-pentafluoroethyl-2-benzofuryl group, 6-pentafluoroethyl-2-benzofuryl group, 7-pentafluoroethyl-2-benzofuryl group, 4-methoxy-2-benzofuryl group, 5-methoxy-2-benzofuryl group, 6-methoxy-2-benzofuryl group, 7-methoxy-2-benzofuryl group, 4-trifluoromethoxy-2-benzofuryl group, 5-trifluoromethoxy-2-benzofuryl group, 6-trifluoromethoxy-2-benzofuryl group, 7-trifluoromethoxy-2-benzofuryl group, 4-isopropyl-2-benzofuryl group, 5-isopropyl-2-benzofuryl group, 6-isopropyl-2-benzofuryl group, 7-isopropyl-2-benzofuryl group, 4-hexyl-2-benzofuryl group, 5-hexyl-2-benzofuryl group, 6-hexyl-2-benzofuryl group, 7-hexyl-2-benzofuryl group, 4-ethoxy-2-benzofuryl group, 5-ethoxy-2-benzofuryl group, 6-ethoxy-2-benzofuryl group, 7-ethoxy-2-benzofuryl group, 4-fluoro-5-trifluoromethyl-2-benzofuryl group, 6-fluoro-5-trifluoromethyl-2-benzofuryl group, 7-fluoro-5-trifluoromethyl-2-benzofuryl group, 4-chloro-5-trifluoromethyl-2-benzofuryl group, 6-chloro-5-trifluoromethyl-2-benzofuryl group, 7-chloro-5-trifluoromethyl-2-benzofuryl group, 4-chloro-5-trifluoromethoxy-2-benzofuryl group, 6-chloro-5-trifluoromethoxy-2-benzofuryl group, 7-chloro-5-trifluoromethoxy-2-benzofuryl group, 3-benzofuryl group, 4-fluoro-3-benzofuryl group, 5-fluoro-3-benzofuryl group, 6-fluoro-3-benzofuryl group, 7-fluoro-3-benzofuryl group, 4-chloro-3-benzofuryl group, 5-chloro-3-benzofuryl group, 6-chloro-3-benzofuryl group, 7-chloro-3-benzofuryl group, 4-bromo-3-benzofuryl group, 5-bromo-3-benzofuryl group, 6-bromo-3-benzofuryl group, 7-bromo-3-benzofuryl group, 4-methyl-3-benzofuryl group, 5-methyl-3-benzofuryl group, 6-methyl-3-benzofuryl group, 7-methyl-3-benzofuryl group, 4-trifluoromethyl-3-benzofuryl group, 5-trifluoromethyl-3-benzofuryl group, 6-trifluoromethyl-3-benzofuryl group, 7-trifluoromethyl-3-benzofuryl group, 4-ethyl-3-benzofuryl group, 5-ethyl-3-benzofuryl group, 6-ethyl-3-benzofuryl group, 7-ethyl-3-benzofuryl group, 4-pentafluoroethyl-3-benzofuryl group, 5-pentafluoroethyl-3-benzofuryl group, 6-pentafluoroethyl-3-benzofuryl group, 7-pentafluoroethyl-3-benzofuryl group, 4-methoxy-3-benzofuryl group, 5-methoxy-3-benzofuryl group, 6-methoxy-3-benzofuryl group, 7-methoxy-3-benzofuryl group, 4-trifluoromethoxy-3-benzofuryl group, 5-trifluoromethoxy-3-benzofuryl group, 6-trifluoromethoxy-3-benzofuryl group, 7-trifluoromethoxy-3-benzofuryl group, 4-isopropyl-3-benzofuryl group, 5-isopropyl-3-benzofuryl group, 6-isopropyl-3-benzofuryl group, 7-isopropyl-3-benzofuryl group, 4-hexyl-3-benzofuryl group, 5-hexyl-3-benzofuryl group, 6-hexyl-3-benzofuryl group, 7-hexyl-3-benzofuryl group, 4-ethoxy-3-benzofuryl group, 5-ethoxy-3-benzofuryl group, 6-ethoxy-3-benzofuryl group, 7-ethoxy-3-benzofuryl group, 4-fluoro-5-trifluoromethyl-3-benzofuryl group, 6-fluoro-5-trifluoromethyl-3-benzofuryl group, 7-fluoro-5-trifluoromethyl-3-benzofuryl group, 4-chloro-5-trifluoromethyl-3-benzofuryl group, 6-chloro-5-trifluoromethyl-3-benzofuryl group, 7-chloro-5-trifluoromethyl-3-benzofuryl group, 4-chloro-5-trifluoromethoxy-3-benzofuryl group, 6-chloro-5-trifluoromethoxy-3-benzofuryl group, 6,7-dichloro-5-trifluoromethoxy-3-benzofuryl group, 5,6,7-trichloro-2-benzofuryl group, 7-chloro-5-trifluoromethoxy-3-benzofuryl group or the like.

A furyl group (which may be substituted on the furan ring by a phenyl group which may have a halogen atom as a substituent) includes a furyl group (which may be substituted on the furan ring by 1 to 3 phenyl groups which may have 1 to 5 halogen atoms as a substituent), for example, a 2-furyl group, 3,5-diphenyl-2-furyl group, 2,4,5-triphenyl-3-furyl group, 5-(4-chlorophenyl)-2-furyl group, 4-(4-fluorophenyl)-2-furyl furyl group, 4-(2,3,4,5,6-pentafluorophenyl)-2-furyl group, 3-(4-bromophenyl)-2-furyl group, 3-furyl group, 5-(2,4-dichlorophenyl)-3-furyl group, 4-(2,4,6-trichlorophenyl)-3-furyl group, 3-(4-iodophenyl)-3-furyl group or the like.

A phenyl group (which may be substituted on the phenyl ring by at least one group selected from a group consisting of a halogen atom; halogen-substituted or unsubstituted C1-6 alkyl group; C3-8 cycloalkoxy group; hydroxyl group; halogen-substituted or unsubstituted C1-8 alkoxy group; C3-8 cycloalkoxy group; C1-4 alkylenedioxy group; cyano group; nitro group; phenyl C2-6 alkenyl group; C2-6 alkanoyloxy group; amino group having a C1-6 alkanoyl group as a substituent; C1-6 alkylsulfonylamino group; phenyl C1-6 alkoxy group; phenoxy group; amino group having at least one C1-6 alkyl group as a substituent; amino group which may have at least one phenyl group as a substituent; amino C1-6 alkoxy group which may have at least one C1-6 alkyl group on the amino group as a substituent; C1-6 alkoxycarbonyl group; C1-6 alkoxycarbonyl C1-6 alkoxy group; C1-6 alkylthio group; pyrrolyl group; imidazolyl group; piperidyl group; morpholino group; pyrrolidinyl group; thienyl group; benzofuryl group; piperazinyl group (which may be substituted on the piperazine ring by at least one group selected from a group consisting of a C1-6 alkyl group, phenyl C1-6 alkyl group and benzoyl group which may have at least one C1-6 alkyl group as a substituent); quinolyl group which may be substituted on the quinoline ring by at least one group selected from a group consisting of a C1-6 alkoxy group and an oxo group; a piperidylcarbonyl group which may be substituted on the piperidine ring by a carbostyryl group; and a triazolyl group) includes a phenyl group (which may be substituted on the phenyl ring by 1 to 5, preferably 1 to 3 groups selected from a group consisting of a halogen atom; halogen-substituted or unsubstituted C1-6 alkyl group; C3-8 cycloalkoxy group; hydroxyl group; halogen-substituted or unsubstituted C1-8 alkoxy group; C3-8 cycloalkoxy group; C1-4 alkylenedioxy group; cyano group; nitro group; phenyl C2-6 alkenyl group; C2-6 alkanoyloxy group; amino group which may have 1 to 2 C1-6 alkanoyl groups as a substituent; C1-6 alkylsulfonylamino group; phenyl C1-6 alkoxy group; phenoxy group; amino group having 1 to 2 C1-6 alkyl groups as a substituent; amino group having 1 to 2 phenyl groups as a substituent; amino C1-6 alkoxy group which may have 1 to 2 C1-6 alkyl groups on the amino group as a substituent; C1-6 alkoxycarbonyl group; C1-6 alkoxycarbonyl C1-6 alkoxy group; C1-6 alkylthio group; pyrrolyl group; imidazolyl group; piperidinyl group; morpholino group; pyrrolidinyl group; thienyl group; benzofuryl group; piperazinyl group (which may be substituted on the piperazine ring by at least one group selected from a group consisting of a C1-6 alkyl group, phenyl C1-6 alkyl group and benzoyl group which may have 1 to 3 C1-6 alkyl group as a substituent); quinolyl group which may be substituted on the quinoline ring by at least one group selected from a group consisting of a C1-6 alkoxy group and an oxo group; a piperidylcarbonyl group which may be substituted on the piperidine ring by a carbostyril group; and a triazolyl group (in case of a 1 to 3 C1-4 alkylenedioxy group as a substituent, 1 to 3 substituents are preferable)), for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 2,3,4-trifluorophenyl group, 3,4,5-trifluorophenyl group, 3,4,5-trichlorophenyl group, 2,4,6-trifluorophenyl group, 2,3,4,5,6-pentafluorophenyl group, 2,4,6-trichlorophenyl group, 2-fluoro-4-chlorophenyl group, 2-fluoro-4-bromophenyl group, 3-fluoro-4-chlorophenyl group, 2-methylphenyl group, 3-methylphenyl group, 4-methylphenyl group, 2,6-dimethylphenyl group, 2,4,6-trimethylphenyl group, 2-methyl-3-chlorophenyl group, 3-methyl-4-chlorophenyl group, 2-chloro-4-methylphenyl group, 2-methyl-3-fluorophenyl group, 2-trifluoromethylphenyl group, 3-trifluoromethylphenyl group, 4-trifluoromethylphenyl group, 3,5-di(trifluoromethyl)phenyl group, 3,4-di(trifluoromethyl)phenyl group, 2,4-di(trifluoromethyl)phenyl group, 2-pentafluoroethylphenyl group, 3-pentafluoroethylphenyl group, 4-pentafluoroethylphenyl group, 2-isopropylphenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 4-n-butylphenyl group, 4-n-pentylphenyl group, 4-n-hexylphenyl group, 2-n-heptafluoropropylphenyl group, 3-n-heptafluoropropylphenyl group, 4-n-heptafluoropropylphenyl group, 4-pentylphenyl group, 4-hexylphenyl group, 2-methoxyphenyl group, 3-methoxyphenyl group, 4-methoxyphenyl group, 2-methoxy-3-chlorophenyl group, 2-fluoro-3-methoxyphenyl group, 2-fluoro-4-methoxyphenyl group, 4-cyclopropylphenyl group, 4-cyclobutylphenyl group, 4-cyclopentylphenyl group, 4-cyclohexylphenyl group, 4-cycloheptylphenyl group, 4-cyclooctylphenyl group, 2,6-dimethoxyphenyl group, 2-trifluoromethoxyphenyl group, 3-trifluoromethoxyphenyl group, 4-trifluoromethoxyphenyl group, 2,3-di(trifluoromethoxy)phenyl group, 3,5-di(trifluoromethoxy)phenyl group, 2,4-di(trifluoromethoxy)phenyl group, 2-pentafluoroethoxyphenyl group, 3-pentafluoroethoxyphenyl group, 4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 4-n-hexyloxyphenyl group, 4-n-heptyloxyphenyl group, 4-n-octyloxyphenyl group, 2-n-heptafluoropropoxyphenyl group, 3-n-heptafluoropropoxyphenyl group, 4-n-heptafluoropropoxyphenyl group, 4-cyclopropoxyphenyl group, 4-cyclobutoxyphenyl group, 4-cyclopentoxyphenyl group, 4-cyclohexyloxyphenyl group, 4-cycloheptyloxyphenyl group, 4-cyclooctyloxyphenyl group, 4-pentoxyphenyl group, 4-hexyloxyphenyl group, 2-hydroxyphenyl group, 3-hydroxyphenyl group, 4-hydroxyphenyl group, 2,4-dihydroxyphenyl group, 2,4,6-trihydroxyphenyl group, 2-methoxy-3-chlorophenyl group, 2-fluoro-3-hydroxyphenyl group, 2-fluoro-4-hydroxyphenyl group, 2,3-methylenedioxyphenyl group, 3,4-methylenedioxyphenyl group, 2,3-ethylenedioxyphenyl group, 3,4-ethylenedioxyphenyl group, 2-cyanophenyl group, 3-cyanophenyl group, 4-cyanophenyl group, 2,3-dicyanophenyl group, 2,4,6-tricyanophenyl group, 2-nitrophenyl group, 3-nitrophenyl group, 4-nitrophenyl group, 2,4-dinitrophenyl group, 2,4,6-trinitrophenyl group, 2-cinnamylphenyl group, 3-cinnamylphenyl group, 4-cinnamylphenyl group, 2-acetyloxyphenyl group, 3-acetyloxyphenyl group, 2-aminophenyl group, 2,4-diaminophenyl group, 2,4,6-triaminophenyl group, 4-acetyloxyphenyl group, 2-propionyloxyphenyl group, 3-propionyloxyphenyl group, 4-propionyloxyphenyl group, 2-butyryloxyphenyl group, 3-butyryloxyphenyl group, 4-butyryloxyphenyl group, 4-pentanoyloxyphenyl group, 4-hexanoyloxyphenyl group, 2-acetylaminophenyl group, 3-acetylaminophenyl group, 4-acetylaminophenyl group, 2-propionylaminophenyl group, 3-propionylaminophenyl group, 4-propionylaminophenyl group, 2-butyrylaminophenyl group, 3-butyrylaminophenyl group, 4-butyrylaminophenyl group, 4-pentanoylaminophenyl group, 4-hexanoylaminophenyl group, 2-methanesulfonylaminophenyl group, 3-methanesulfonylaminophenyl group, 4-methanesulfonylaminophenyl group, 2-benzyloxyphenyl group, 3-benzyloxyphenyl group, 4-benzyloxyphenyl group, 2-(2-phenylethoxy)phenyl group, 3-(2-phenylethoxy)phenyl group, 4-(2-phenylethoxy)phenyl group, 2-(3-phenylpropoxy)phenyl group, 3-(3-phenylpropoxy)phenyl group, 4-(3-phenylpropoxy)phenyl group, 2-(4-phenylbutoxy)phenyl group, 3-(4-phenylbutoxy)phenyl group, 4-(4-phenylbutoxy)phenyl group, 2-(5-phenylpentoxy)phenyl group, 3-(5-phenylpentoxy)phenyl group, 4-(5-phenylpentoxy)phenyl group, 2-(6-phenylhexloxy)phenyl group, 3-(6-phenylhexloxy)phenyl group, 4-(6-phenylhexloxy)phenyl group, 2-phenoxyphenyl group, 3-phenoxyphenyl group, 4-phenoxyphenyl group, 2-methylaminophenyl group, 3-ethylaminophenyl group, 4-propylaminophenyl group, 2-n-butylaminophenyl group, 3-n-pentylaminophenyl group, 4-n-hexylaminophenyl group, 2-dimethylaminophenyl group, 3-dimethylaminophenyl group, 4-dimethylaminophenyl group, 2-diethylaminophenyl group, 3-diethylaminophenyl group, 4-diethylaminophenyl group, 2-di-(n-propyl)-aminophenyl group, 3-di-(n-propyl)aminophenyl group, 4-di-(n-propyl)aminophenyl group, 3-phenylaminophenyl group, 2-diphenylaminophenyl group, 3-diphenylaminophenyl group, 4-diphenylaminophenyl group, 2-(2-methylaminoethoxy)phenyl group, 3-ethylaminomethoxyphenyl group, 2-(2-dimethylaminoethoxy)phenyl group, 3-(2-dimethylaminoethoxy)phenyl group, 4-(2-dimethylaminoethoxy)phenyl group, 2-(3-dimethylaminopropoxy)-phenyl group, 3-(3-dimethylaminopropoxy)phenyl group, 4-(3-dimethylaminopropoxy)phenyl group, 4-(4-dimethylaminobutoxy)phenyl group, 4-(5-dimethylaminopentoxy)phenyl group, 4-(6-dimethylaminohexyloxy)phenyl group, 2-(2-diethylaminoethoxy)phenyl group, 3-(2-diethylaminoethoxy)phenyl group, 4-(2-diethylaminoethoxy)phenyl group, 2-(3-diethylaminopropoxy)phenyl group, 3-(3-diethylaminopropoxy)phenyl group, 4-(3-diethylaminopropoxy)phenyl group, 4-(4-diethylaminobutoxy)phenyl group, 4-(5-diethylaminopentoxy)phenyl group, 4-(6-diethylaminohexyloxy)phenyl group, 2-methoxycarbonylphenyl group, 3-methoxycarbonylphenyl group, 4-methoxycarbonylphenyl group, 2-ethoxycarbonylphenyl group, 3-ethoxycarbonylphenyl group, 4-ethoxycarbonylphenyl group, 4-(3-propoxycarbonyl)phenyl group, 4-(4-butoxycarbonyl)phenyl group, 4-(5-pentoxycarbonyl)phenyl group, 4-(6-hexyloxycarbonyl)-phenyl group, 2-methoxycarbonylmethoxyphenyl group, 3-methoxycarbonylmethoxyphenyl group, 4-methoxycarbonylmethoxyphenyl group, 2-ethoxycarbonylmethoxyphenyl group, 3-ethoxycarbonylmethoxyphenyl group, 4-ethoxycarbonylmethoxyphenyl group, 4-(3-propoxycarbonyl)methoxyphenyl group, 4-(4-butoxycarbonyl)-methoxyphenyl group, 4-(5-pentoxycarbonyl)methoxyphenyl group, 4-(6-hexyloxycarbonyl)methoxyphenyl group, 4-(2-methoxycarbonylethoxy)phenyl group, 4-(2-ethoxycarbonyl)ethoxyphenyl group, 4-(2-(3-propoxycarbonyl)ethoxy)phenyl group, 4-(2-(4-butoxycarbonyl)ethoxy)-phenyl group, 4-(2-(5-pentoxycarbonyl)ethoxy)phenyl group, 4-(2-(6-hexyloxycarbonyl)ethoxy)phenyl group, 4-(3-methoxycarbonylpropoxy)phenyl group, 4-(3-(2-ethoxycarbonyl)propoxy)phenyl group, 4-(3-(3-propoxycarbonyl)propoxy)phenyl group, 4-(3-(4-butoxycarbonyl)-propxy)phenyl group, 4-(3-(5-pentoxycarbonyl)propoxy)-phenyl group, 4-(3-(6-hexyloxycarbonyl)propoxy)phenyl group, 4-(4-methoxycarbonylbutoxy)phenyl group, 4-(4-(2-ethoxycarbonyl)butoxy)phenyl group, 4-(5-methoxycarbonylpentoxy)phenyl group, 4-(5-(2-ethoxycarbonyl)-pentoxy)phenyl group, 4-(6-(2-ethoxycarbonyl)hexyloxy)-phenyl group, 2-methylthiophenyl group, 3-methylthiophenyl group, 4-methylthiophenyl group, 4-ethylthiophenyl group, 4-n-propylthiophenyl group, 4-isopropylthiophenyl group, 4-n-butylthiophenyl group, 4-tert-butylthiophenyl group, 4-n-pentylthiophenyl group, 4-n-hexylthiophenyl group, 2-(1-pyrrolyl)phenyl group, 3-(1-pyrrolyl)phenyl group, 4-(1-pyrrolyl)phenyl group, 2-(1-imidazolyl)phenyl group, 3-(1-imidazolyl)-phenyl group, 4-(1-imidazolyl)phenyl group, 2-piperidinophenyl group, 3-piperidinophenyl group, 4-piperidinophenyl group, 4-morpholinophenyl group, 3-morpholinophenyl group, 2-morpholinophenyl group, 2-(1-pyrrolidinyl)phenyl group, 3-(1-pyrrolidinyl)phenyl group, 4-(1-pyrrolidinyl) phenyl group, 2-(2-thienyl)-phenyl group, 3-(2-thienyl)phenyl group, 4-(2-thienyl)phenyl group, 2-(2-benzofuryl)phenyl group, 3-(2-benzofuryl)phenyl group, 4-(2-benzofuryl) phenyl group, 2-(1-piperazinyl)phenyl group, 3-(1-piperazinyl)phenyl group, 4-(1-piperazinyl)phenyl group, 2-(4-methyl-1-piperazinyl)phenyl group, 3-(4-methyl-1-piperazinyl)phenyl group, 4-(4-methyl-1-piperazinyl)phenyl group, 4-(4-ethyl-1-piperazinyl)-phenyl group, 4-(4-n-propyl-1-piperazinyl)phenyl group, 4-(4-isopropyl-1-piperazinyl)phenyl group, 4-(4-n-butyl-1-piperazinyl) phenyl group, 4-(4-tert-butyl-1-piperazinyl)phenyl group, 4-(4-n-pentyl-1-piperazinyl)-phenyl group, 4-(4-n-hexyl-1-piperazinyl)phenyl group, 4-(4-benzyl-1-piperazinyl)phenyl group, 4-(4-(2-phenethyl)-1-piperazinyl)phenyl group, 4-(4-(3-phenylpropyl)-1-piperazinyl)phenyl group, 4-(4-(4-phenylbutyl)-1-piperazinyl)phenyl group, 4-(4-(5-phenylpentyl)-1-piperazinyl)phenyl group, 4-(4-(6-phenylhexyl)-1-piperazinyl)phenyl group, 4-(4-benzoyl-1-piperazinyl) phenyl group, 4-(4-(2-methylbenzoyl)-1-piperazinyl) group, 4-(4-(2,3-dimethylbenzoyl)-1-piperazinyl)phenyl group, 4-(4-(2,4,6-trimethylbenzoyl)-1-piperazinyl)phenyl group, 4-(4-(3-methylbenzoyl)-1-piperazinyl)phenyl group, 4-(4-(4-methylbenzoyl)-1-piperazinyl)phenyl group, 4-(4-(4-ethylbenzoyl)-1-piperazinyl)phenyl group, 4-(4-(4-isopropylbenzoyl)-1-piperazinyl)phenyl group, 4-(4-(4-n-butylbenzoyl)-1-piperazinyl)phenyl group, 4-(4-(4-n-pentylbenzoyl)-1-piperazinyl)phenyl group, 4-(4-(4-n-hexylbenzoyl)-1-piperazinyl)phenyl group, 3-(2-quinolyl) phenyl, 4-(4,5,6-trimethoxy-3-quinolyl)phenyl group, 4-(6-methoxy-2-quinolyl)phenyl group, 2-(5,6-dimethoxy-4-quinolyl)phenyl group, 3-(2-oxo-3-quinolyl)phenyl group, 4-(2-oxo-3-quinolyl)phenyl group, 3-(5-methoxy-2-oxo-3-quinolyl)phenyl group, 4-(5-methoxy-2-oxo-3-quinolyl) phenyl group, 3-(6-methoxy-2-oxo-7-quinolyl)phenyl group, 4-(6-methoxy-2-oxo-3-quinolyl)phenyl group, 3-(7-methoxy-2-oxo-6-quinolyl)-phenyl group, 4-(7-methoxy-2-oxo-8-quinolyl)phenyl group, 3-(8-methoxy-2-oxo-3-quinolyl)phenyl group, 4-(8-methoxy-2-oxo-3-quinolyl) phenyl group, 3-(5,6-diethoxy-2-oxo-4-quinolyl)phenyl group, 4-(5-ethoxy-2-oxo-3-quinolyl)phenyl group, 3-(6-ethoxy-2-oxo-5-quinolyl)phenyl group, 4-(6-ethoxy-2-oxo-3-quinolyl)-phenyl group, 3-(7-ethoxy-2-oxo-3-quinolyl)phenyl group, 4-(7-ethoxy-2-oxo-3-quinolyl)phenyl group, 3-(8-ethoxy-2-oxo-3-quinolyl)phenyl group, 4-(8-ethoxy-2-oxo-3-quinolyl)phenyl group, 3-(1-piperidinylcarbonyl)phenyl group, 4-(4-(carbostyril-1-yl)piperidinyl-1-carbonyl) phenyl group, 4-(1,2,4-triazol-1-yl)phenyl group or the like.

A naphthyl group which may be substituted on the naphthalne ring by a group selected from a group consisting of a halogen atom, a halogen-substituted or unsubstituted C1-6 alkoxy group and an amino group which may have a C1-6 alkyl group as a substituent includes a naphthyl group which may be substituted on the naphthalne ring by 1 to 3 groups selected from a group consisting of a halogen atom, a halogen-substituted or unsubstituted C1-6 alkoxy group and an amino group which may have 1 to 2 C1-6 alkyl groups as a substituent, for example, a 1-naphthylmethyl group, 2-(2-naphthyl)ethyl group, 1-(3-naphthyl)ethyl group, 3-(4-naphthyl)propyl group, 4-(5-naphthyl)butyl group, 5-(6-naphthyl)pentyl group, 6-(7-naphthyl)hexyl group, 2-methyl-3-(8-naphthyl)propyl group, 1,1-dimethyl-2-(3-naphthyl)ethyl group, 2-fluoro-1-naphthyl group, 2-chloro-1-naphthyl group, 2-bromo-1-naphthyl group, 3-fluoro-1-naphthyl group, 3-chloro-1-naphthyl group, 3-bromo-1-naphthyl group, 4-fluoro-1-naphthyl group, 4-chloro-1-naphthyl group, 4-bromo-1-naphthyl group, 5-fluoro-1-naphthyl group, 5-chloro-1-naphthyl group, 5-bromo-1-naphthyl group, 6-fluoro-1-naphthyl group, 6-chloro-1-naphthyl group, 6-bromo-1-naphthyl group, 7-fluoro-1-naphthyl group, 7-chloro-1-naphthyl group, 7-bromo-1-naphthyl group, 1-fluoro-2-naphthyl group, 8-fluoro-1-naphthyl group, 8-chloro-1-naphthyl group, 8-bromo-1-naphthyl group, 1-fluoro-2-naphthyl group, 1-chloro-2-naphthyl group, 1-bromo-2-naphthyl group, 3-fluoro-2-naphthyl group, 3-chloro-2-naphthyl group, 3-bromo-2-naphthyl group, 4-fluoro-2-naphthyl group, 4-chloro-2-naphthyl group, 4-bromo-2-naphthyl group, 4-dimethylamino-1-naphthyl group, 2-methoxy-1-naphthyl group, 3-methoxy-1-naphthyl group, 4-methoxy-1-naphthyl group, 5-methoxy-1-naphthyl group, 6-methoxy-1-naphthyl group, 7-methoxy-1-naphthyl group, 8-methoxy-1-naphthyl group, 2-trifluoromethoxy-1-naphthyl group, 3-trifluoromethoxy-1-naphthyl group, 4-trifluoromethoxy-1-naphthyl group, 5-trifluoromethoxy-1-naphthyl group, 6-trifluoromethoxy-1-naphthyl group, 7-trifluoromethoxy-1-naphthyl group, 8-trifluoromethoxy-1-naphthyl group, 3-amino-2-naphthyl group, 2-methylamino-1-naphthyl group, 4-ethylamino-2-naphthyl group, 5-propylamino-1-naphthyl group, 6-n-butylamino-2-naphthyl group, 7-n-pentylamino-1-naphthyl group, 8-hexylamino-2-naphthyl group, 2,3-dichloro-1-naphthyl group, 2,4,6-trichloro-1-naphthyl group, 2-chloro-4-trifluoromethoxy-1-naphthyl group, 2-chloro-6-dimethylamino-1-naphthyl group, 2-dimethylamino-1-naphthyl group, 3-dimethylamino-1-naphthyl group, 4-dimethylamino-1-naphthyl group, 5-dimethylamino-1-naphthyl group, 6-dimethylamino-1-naphthyl group, 7-dimethylamino-1-naphthyl group, 8-dimethylamino-1-naphthyl group, 1-methoxy-2-naphthyl group, 3-methoxy-2-naphthyl group, 4-methoxy-2-naphthyl group, 5-methoxy-2-naphthyl group, 6-methoxy-2-naphthyl group, 7-methoxy-2-naphthyl group, 8-methoxy-2-naphthyl group, 1-trifluoromethoxy-2-naphthyl group, 3-trifluoromethoxy-2-naphthyl group, 4-trifluoromethoxy-2-naphthyl group, 5-trifluoromethoxy-2-naphthyl group, 6-trifluoromethoxy-2-naphthyl group, 7-trifluoromethoxy-2-naphthyl group, 8-trifluoromethoxy-2-naphthyl group, 1-dimethylamino-2-naphthyl group, 3-dimethylamino-2-naphthyl group, 4-dimethylamino-2-naphthyl group, 5-dimethylamino-2-naphthyl group, 6-dimethylamino-2-naphthyl group, 7-dimethylamino-2-naphthyl group, 8-dimethylamino-2-naphthyl group or the like.

A biphenylyl group (which may be substituted on the biphenylyl ring by at least one group selected from a group consisting of a halogen atom, a halogen-substituted or unsubstituted C1-9 alkyl group and a halogen-substituted or unsubstituted C1-6 alkoxy group) includes a biphenylyl group (which may be substituted on the biphenylyl ring by 1 to 5, preferably 1 to 3 groups selected from a group consisting of a halogen atom, a halogen-substituted or unsubstituted C1-9 alkyl group and a halogen-substituted or unsubstituted C1-6 alkoxy group), for example, a 3-biphenylyl group, 4-biphenylyl group, 2'-fluoro-3-biphenylyl group, 3'-fluoro-3-biphenylyl group, 4'-fluoro-3-biphenylyl group, 3',4'-difluoro-3-biphenylyl group, 3',4',5'-trichloro-3-biphenylyl group, 2',3',4',5',6'-pentafluoro-4-biphenylyl group, 2'-fluoro-3',4'-ditrifluoromethyl-3-biphenylyl group, 2',4'-ditrifluoro-3-biphenylyl group, 3',5'-fluoro-3-biphenylyl group, 2'-chloro-3-biphenylyl group, 3'-chloro-3-biphenylyl group, 4'-chloro-3-biphenylyl group, 3',4'-dichloro-3-biphenylyl group, 2',4'-dichloro-3-biphenylyl group, 3',5'-dichloro-3-biphenylyl group, 2'-methyl-3-biphenylyl group, 3'-methyl-3-biphenylyl group, 4'-methyl-3-biphenylyl group, 3',4'-dimethyl-3-biphenylyl group, 2',4'-dimethyl-3-biphenylyl group, 3',5'-dimethyl-3-biphenylyl group, 2'-trifluoromethyl-3-biphenylyl group, 3'-trifluoromethyl-3-biphenylyl group, 4'-trifluoromethyl-3-biphenylyl group, 3',4'-ditrifluoromethyl-3-biphenylyl group, 2',4'-ditrifluoromethyl-3-biphenylyl group, 3',5'-ditrifluoromethyl-3-biphenylyl group, 2'-methoxy-3-biphenylyl group, 3'-methoxy-3-biphenylyl group, 4'-methoxy-3-biphenylyl group, 3',4'-dimethoxy-3-biphenylyl group, 2',4'-dimethoxy-3-biphenylyl group, 3',4',5'-trimethoxy-3-biphenylyl group, 3',5'-dimethoxy-3-biphenylyl group, 2'-trifluoromethoxy-3-biphenylyl group, 3'-trifluoromethoxy-3-biphenylyl group, 4'-trifluoromethoxy-3-biphenylyl group, 3',4'-ditrifluoromethoxy-3-biphenylyl group, 2',4'-ditrifluoromethoxy-3-biphenylyl group, 3',5'-ditrifluoromethoxy-3-biphenylyl group, 2'-fluoro-4-biphenylyl group, 3'-fluoro-4-biphenylyl group, 4'-fluoro-4-biphenylyl group, 3',4'-difluoro-4-biphenylyl group, 2',4'-difluoro-4-biphenylyl group, 3',5'-difluoro-4-biphenylyl group, 2'-chloro-4-biphenylyl group, 3'-chloro-4-biphenylyl group, 4'-chloro-4-biphenylyl group, 3',4'-dichloro-4-biphenylyl group, 2',4'-dichloro-4-biphenylyl group, 3',5'-dichloro-4-biphenylyl group, 2'-methyl-4-biphenylyl group, 3'-methyl-4-biphenylyl group, 4'-methyl-4-biphenylyl group, 4'-ethyl-4-biphenylyl group, 4'-n-propyl-4-biphenylyl group, 4'-n-butyl-4-biphenylyl group, 4'-n-pentyl-4-biphenylyl group, 4'-n-hexyl-4-biphenylyl group, 4'-n-heptyl-4-biphenylyl group, 4'-n-octyl-4-biphenylyl group, 4'-n-nonyl-4-biphenylyl group, 3',4'-dimethyl-4-biphenylyl group, 2',4'-dimethyl-4-biphenylyl group, 3',5'-dimethyl-4-biphenylyl group, 3',4',5'-trimethyl-4-biphenylyl group, 2'-trifluoromethyl-4-biphenylyl group, 3'-trifluoromethyl-4-biphenylyl group, 4'-trifluoromethyl-4-biphenylyl group, 3',4'-ditrifluoromethyl-4-biphenylyl group, 2',4'-ditrifluoromethyl-4-biphenylyl group, 3',5'-ditrifluoromethyl-4-biphenylyl group, 2'-methoxy-4-biphenylyl group, 3'-methoxy-4-biphenylyl group, 4'-methoxy-4-biphenylyl group, 3',4'-dimethoxy-4-biphenylyl group, 2',4'-dimethoxy-4-biphenylyl group, 3',4'-dimethoxy-2'-chloro-4-biphenylyl group, 3',5'-dimethoxy-4-biphenylyl group, 2'-trifluoromethoxy-4-biphenylyl group, 3'-trifluoromethoxy-4-biphenylyl group, 4'-trifluoromethoxy-4-biphenylyl group, 3',4'-ditrifluoromethoxy-4-biphenylyl group, 2',4'-ditrifluoromethoxy-4-biphenylyl group, 3',5'-ditrifluoromethoxy-4-biphenylyl group or the like.

A benzothienyl group (which may be substituted on the benzothiophene ring by at least one group selected from a group of a halogen atom, a halogen-substituted or unsubstituted C1-6 alkyl group and a halogen-substituted or unsubstituted C1-6 alkoxy group) includes a benzothienyl group (which may be substituted on the benzothiophene ring by 1 to 3 groups selected from a group of a halogen atom, a halogen-substituted or unsubstituted C1-6 alkyl group and a halogen-substituted or unsubstituted C1-6 alkoxy group), for example, a 2-benzothienyl group, 3-benzothienyl group, 3-methyl-2-benzothienyl group, 2-methyl-3-benzothienyl group, 4-fluoro-2-benzothienyl group, 5-fluoro-2-benzothienyl group, 4,5,6-trichloro-2-benzothienyl group, 6-fluoro-2-benzothienyl group, 7-fluoro-2-benzothienyl group, 4-chloro-2-benzothienyl group, 5-chloro-2-benzothienyl group, 6-chloro-2-benzothienyl group, 7-chloro-2-benzothienyl group, 4-bromo-2-benzothienyl group, 5-bromo-2-benzothienyl group, 6-bromo-2-benzothienyl group, 7-bromo-2-benzothienyl group, 5-methyl-2-benzothienyl group, 6-methyl-2-benzothienyl group, 7-methyl-2-benzothienyl group, 4-trifluoromethyl-2-benzothienyl group, 5-trifluoromethyl-2-benzothienyl group, 6-trifluoromethyl-2-benzothienyl group, 7-trifluoromethyl-2-benzothienyl group, 4-ethyl-2-benzothienyl group, 5-ethyl-2-benzothienyl group, 6-ethyl-2-benzothienyl group, 7-ethyl-2-benzothienyl group, 4-pentafluoroethyl-2-benzothienyl group, 5-pentafluoroethyl-2-benzothienyl group, 6-pentafluoroethyl-2-benzothienyl group, 7-pentafluoroethyl-2-benzothienyl group, 4-methoxy-2-benzothienyl group, 5-methoxy-2-benzothienyl group, 6-methoxy-2-benzothienyl group, 7-methoxy-2-benzothienyl group, 4-trifluoromethoxy-2-benzothienyl group, 5-trifluoromethoxy-2-benzothienyl group, 6-trifluoromethoxy-2-benzothienyl group, 7-trifluoromethoxy-2-benzothienyl group, 4-fluoro-3-methyl-2-benzothienyl group, 5-fluoro-3-methyl-2-benzothienyl group, 6-fluoro-3-methyl-2-benzothienyl group, 7-fluoro-3-methyl-2-benzothienyl group, 4-chloro-3-methyl-2-benzothienyl group, 5-chloro-3-methyl-2-benzothienyl group, 6-chloro-3-methyl-2-benzothienyl group, 7-chloro-3-methyl-2-benzothienyl group, 4-bromo-3-methyl-2-benzothienyl group, 5-bromo-3-methyl-2-benzothienyl group, 6-bromo-3-methyl-2-benzothienyl group, 7-bromo-3-methyl-2-benzothienyl group, 5-methyl-3-methyl-2-benzothienyl group, 6-methyl-3-methyl-2-benzothienyl group, 7-methyl-3-methyl-2-benzothienyl group, 3,4,6-trimethyl-2-benzothienyl group, 4,5,6-trimethoxy-2-benzothienyl group, 4-trifluoromethyl-3-methyl-2-benzothienyl group, 5-trifluoromethyl-3-methyl-2-benzothienyl group, 6-trifluoromethyl-3-methyl-2-benzothienyl group, 7-trifluoromethyl-3-methyl-2-benzothienyl group, 4-ethyl-3-methyl-2-benzothienyl group, 5-ethyl-3-methyl-2-benzothienyl group, 6-ethyl-3-methyl-2-benzothienyl group, 7-ethyl-3-methyl-2-benzothienyl group, 4-pentafluoroethyl-3-methyl-2-benzothienyl group, 5-pentafluoroethyl-3-methyl-2-benzothienyl group, 6-pentafluoroethyl-3-methyl-2-benzothienyl group, 7-pentafluoroethyl-3-methyl-2-benzothienyl group, 4-methoxy-3-methyl-2-benzothienyl group, 5-methoxy-3-methyl-2-benzothienyl group, 6-methoxy-3-methyl-2-benzothienyl group, 7-methoxy-3-methyl-2-benzothienyl group, 4-trifluoromethoxy-3-methyl-2-benzothienyl group, 5-trifluoromethoxy-3-methyl-2-benzothienyl group, 6-trifluoromethoxy-3-methyl-2-benzothienyl group, 7-trifluoromethoxy-3-methyl-2-benzothienyl group, 4-isopropyl-2-benzothienyl group, 5-isopropyl-3-methyl-2-benzothienyl group, 6-isopropyl-2-benzothienyl group, 7-isopropyl-2-benzothienyl group, 4-hexyl-2-benzothienyl group, 5-hexyl-2-benzothienyl group, 6-hexyl-2-benzothienyl group, 7-hexyl-2-benzothienyl group, 4-ethoxy-2-benzothienyl group, 5-ethoxy-2-benzothienyl group, 6-ethoxy-2-benzothienyl group, 7-ethoxy-2-benzothienyl group, 4-fluoro-5-trifluoromethyl-2-benzothienyl group, 6-fluoro-5-trifluoromethyl-2-benzothienyl group, 7-fluoro-5-trifluoromethyl-2-benzothienyl group, 4-chloro-5-trifluoromethyl-2-benzothienyl group, 6-chloro-5-trifluoromethyl-2-benzothienyl group, 7-chloro-5-trifluoromethyl-2-benzothienyl group, 4-chloro-5-trifluoromethoxy-2-benzothienyl group, 6-chloro-5-trifluoromethoxy-2-benzothienyl group, 7-chloro-5-trifluoromethoxy-2-benzothienyl group, 4-fluoro-3-benzothienyl group, 5-fluoro-3-benzothienyl group, 6-fluoro-3-benzothienyl group, 7-fluoro-3-benzothienyl group, 4-chloro-3-benzothienyl group, 5-chloro-3-benzothienyl group, 6-chloro-3-benzothienyl group, 7-chloro-3-benzothienyl group, 4-bromo-3-benzothienyl group, 5-bromo-3-benzothienyl group, 6-bromo-3-benzothienyl group, 7-bromo-3-benzothienyl group, 4-fluoro-3-benzothienyl group, 5-methyl-3-benzothienyl group, 6-methyl-3-benzothienyl group, 7-methyl-3-benzothienyl group, 4-trifluoromethyl-3-benzothienyl group, 5-trifluoromethyl-3-benzothienyl group, 6-trifluoromethyl-3-benzothienyl group, 7-trifluoromethyl-3-benzothienyl group, 4-fluoro-2-methyl-3-benzothienyl group, 5-fluoro-2-methyl-3-benzothienyl group, 6-fluoro-2-methyl-3-benzothienyl group, 7-fluoro-2-methyl-3-benzothienyl group, 4-chloro-2-methyl-3-benzothienyl group, 5-chloro-2-methyl-3-benzothienyl group, 6-chloro-2-methyl-3-benzothienyl group, 7-chloro-2-methyl-3-benzothienyl group, 4-bromo-2-methyl-3-benzothienyl group, 5-bromo-2-methyl-3-benzothienyl group, 6-bromo-2-methyl-3-benzothienyl group, 7-bromo-2-methyl-3-benzothienyl group, 4-fluoro-2-methyl-3-benzothienyl group, 5-methyl-2-methyl-3-benzothienyl group, 6-methyl-2-methyl-3-benzothienyl group, 7-methyl-2-methyl-3-benzothienyl group, 4-trifluoromethyl-2-methyl-3-benzothienyl group, 5-trifluoromethyl-2-methyl-3-benzothienyl group, 6-trifluoromethyl-2-methyl-3-benzothienyl group, 7-trifluoromethyl-2-methyl-3-benzothienyl group, 4-ethyl-3-benzothienyl group, 5-ethyl-3-benzothienyl group, 6-ethyl-3-benzothienyl group, 7-ethyl-3-benzothienyl group, 4-pentafluoroethyl-3-benzothienyl group, 5-pentafluoroethyl-3-benzothienyl group, 6-pentafluoroethyl-3-benzothienyl group, 7-pentafluoroethyl-3-benzothienyl group, 4-methoxy-3-benzothienyl group, 5-methoxy-3-benzothienyl group, 6-methoxy-3-benzothienyl group, 7-methoxy-3-benzothienyl group, 4-trifluoromethoxy-3-benzothienyl group, 5-trifluoromethoxy-3-benzothienyl group, 6-trifluoromethoxy-3-benzothienyl group, 7-trifluoromethoxy-3-benzothienyl group, 4-isoprpyl-3-benzothienyl group, 5-isoprpyl-3-benzothienyl group, 6-isoprpyl-3-benzothienyl group, 7-isoprpyl-3-benzothienyl group, 4-hexyl-3-benzothienyl group, 5-hexyl-3-benzothienyl group, 6-hexyl-3-benzothienyl group, 7-hexyl-3-benzothienyl group, 4-ethoxy-3-benzothienyl group, 5-ethoxy-3-benzothienyl group, 6-ethoxy-3-benzothienyl group, 7-ethoxy-3-benzothienyl group, 4-fluoro-5-trifluoromethyl-3-benzothienyl group, 6-fluoro-5-trifluoromethyl-3-benzothienyl group, 7-fluoro-5-trifluoromethyl-3-benzothienyl group, 4-chloro-5-trifluoromethyl-3-benzothienyl group, 6-chloro-5-trifluoromethyl-3-benzothienyl group, 7-chloro-5-trifluoromethyl-3-benzothienyl group, 4-chloro-5-trifluoromethoxy-3-benzothienyl group, 6-chloro-5-trifluoromethoxy-3- benzothienyl group, 7-chloro-5-trifluoromethoxy-3-benzothienyl group or the like.

A pyridyl group (which may be substituted on the pyridine ring by at least one group selected from a group consisting of a halogen atom, halogen-substituted or unsubstituted C1-6 alkyl group, phenyl group (which may be substituted on the phenyl ring by at least one group selected from a group consisting of a halogen atom, halogen-substituted or unsubstituted C1-6 alkyl group and halogen-substituted or unsubstituted C1-6 alkoxy group), furyl group and thienyl group) includes a pyridyl group (which may be substituted on the pyridine ring by 1 to 3 groups selected from a group consisting of a halogen atom, halogen-substituted or unsubstituted C1-6 alkyl group, phenyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group), furyl group and thienyl group), for example, an unsubstituted 2-pyridyl group, 3-pyridyl group, 4-pyridyl group, 3-fluoro-2-pyridyl group, 4-fluoro-2-pyridyl group, 5-fluoro-2-pyridyl group, 6-fluoro-2-pyridyl group, 3-chloro-2-pyridyl group, 4-chloro-2-pyridyl group, 5-chloro-2-pyridyl group, 6-chloro-2-pyridyl group, 6-chloro-4-methyl-2-pyridyl group, 3,4,5-trichloro-2-pyridyl group, 3-methyl-2-pyridyl group, 4-methyl-2-pyridyl group, 5-methyl-2-pyridyl group, 6-methyl-2-pyridyl group, 3-ethyl-2-pyridyl group, 4-ethyl-2-pyridyl group, 5-ethyl-2-pyridyl group, 6-ethyl-2-pyridyl group, 3-n-propyl-2-pyridyl group, 4-n-propyl-2-pyridyl group, 5-n-propyl-2-pyridyl group, 6-n-propyl-2-pyridyl group, 5-tert-butyl-2-pyridyl group, 4-n-pentyl-2-pyridyl group, 5-n-hexyl-2-pyridyl group, 6-n-hexyl-2-pyridyl group, 2-chloro-3-pyridyl group, 4-chloro-3-pyridyl group, 5-chloro-3-pyridyl group, 6-chloro-3-pyridyl group, 3-pyridyl group, 4-pyridyl group, 3-methyl-3-pyridyl group, 4-methyl-3-pyridyl group, 5-methyl-3-pyridyl group, 6-methyl-3-pyridyl group, 2-ethyl-3-pyridyl group, 4-ethyl-3-pyridyl group, 5-ethyl-3-pyridyl group, 6-ethyl-3-pyridyl group, 2-propyl-3-pyridyl group, 4-propyl-3-pyridyl group, 5-propyl-3-pyridyl group, 6-propyl-3-pyridyl group, 5-tert-butyl-3-pyridyl group, 4-pentyl-3-pyridyl group, 5-hexyl-3-pyridyl group, 6-hexyl-3-pyridyl group, 3-chloro-4-pyridyl group, 2-chloro-4-pyridyl group, 3-methyl-4-pyridyl group, 2-methyl-4-pyridyl group, 3-trifluoromethyl-4-pyridyl group, 3-ethyl-4-pyridyl group, 2-ethyl-4-pyridyl group, 3-propyl-4-pyridyl group, 6-n-propyl-4-pyridyl group, 5-tert-butyl-4-pyridyl group, 2-n-hexyl-4-pyridyl group, 3-phenyl-2-pyridyl group, 4-phenyl-2-pyridyl group, 5-phenyl-2-pyridyl group, 6-phenyl-2-pyridyl group, 2-phenyl-3-pyridyl group, 2-phenyl-4-pyridyl group, 2-phenyl-5-pyridyl group, 3-(4-fluorophenyl)-2-pyridyl group, 3-(3-fluoro-4-chlorophenyl)-2-pyridyl group, 3-(3-fluorophenyl)-2-pyridyl group, 3-(4-bromophenyl)-4-pyridyl group, 3-(3-fluorophenyl)-4-pyridyl group, 4-(2,3,4,5,6-pentafluorophenyl)-2-pyridyl group, 4-(3-fluoro-4-chlorophenyl)-2-pyridyl group, 4-(3-fluorophenyl)-2-pyridyl group, 3-(4-chlorophenyl)-2-pyridyl group, 4-(4-chlorophenyl)-2-pyridyl group, 5-(4-chlorophenyl)-2-pyridyl group, 6-(2,4,6-trichlorophenyl)-2-pyridyl group, 2-(4-chlorophenyl)-3-pyridyl group, 2-(4-chlorophenyl)-4-pyridyl group, 6-(4-chlorophenyl)-3-pyridyl group, 4-(3-fluoro-4-chlorophenyl)-2-pyridyl group, 5-(4-iodo-3-chlorophenyl)-2-pyridyl group, 6-(4-fluoro-3-chlorophenyl)-2-pyridyl group, 2-(4-fluoro-3-chlorophenyl)-3-pyridyl group, 2-(4-fluoro-3-chlorophenyl)-4-pyridyl group, 6-(4-fluoro-3-chlorophenyl)-3-pyridyl group, 5-(4-trifluoromethylphenyl)-2-pyridyl group, 6-(4-trifluoromethylphenyl)-2-pyridyl group, 2-(4-trifluoromethylphenyl)-3-pyridyl group, 2-(4-trifluoromethylphenyl)-4-pyridyl group, 6-(4-trifluoromethylphenyl)-3-pyridyl group, 5-(4-methylphenyl)-2-pyridyl group, 6-(4-methylphenyl)-2-pyridyl group, 2-(4-methylphenyl)-3-pyridyl group, 2-(4-methylphenyl)-4-pyridyl group, 6-(4-methylphenyl)-3-pyridyl group, 4-fluoro-2-(4-methoxyphenyl)-3-pyridyl group, 4-methyl-5-phenyl-3-chloro-2-pyridyl group, 5-(4-methoxyphenyl)-2-pyridyl group, 6-(4-methoxyphenyl)-2-pyridyl group, 2-(4-methoxyphenyl)-3-pyridyl group, 2-(4-methoxyphenyl)-4-pyridyl group, 6-(4-methoxyphenyl)-3-pyridyl group, 5-(4-trifluoromethoxyphenyl)-2-pyridyl group, 6-(4-trifluoromethoxyphenyl)-2-pyridyl group, 2-(4-trifluoromethoxyphenyl)-3-pyridyl group, 2-(4-trifluoromethoxyphenyl)-4-pyridyl group, 6-(4-trifluoromethoxyphenyl)-3-pyridyl group, 5-(3-chloro-4-trifluoromethoxyphenyl)-2-pyridyl group, 6-(3-chloro-4-trifluoromethoxyphenyl)-2-pyridyl group, 2-(3-chloro-4-trifluoromethoxyphenyl)-3-pyridyl group, 2-(3-chloro-4-trifluoromethoxyphenyl)-4-pyridyl group, 6-(3-chloro-4-trifluoromethoxyphenyl)-3-pyridyl group, 5-(3-fluoro-4-trifluoromethoxyphenyl)-2-pyridyl group, 6-(3-fluoro-4-trifluoromethoxyphenyl)-2-pyridyl group, 2-(3-fluoro-4-trifluoromethoxyphenyl)-3-pyridyl group, 2-(3-fluoro-4-trifluoromethoxyphenyl)-4-pyridyl group, 6-(3-fluoro-4-trifluoromethoxyphenyl)-3-pyridyl group, 5-(3,4-dimethoxyphenyl)-2-pyridyl group, 6-(3,4-dimethoxyphenyl)-2-pyridyl group, 2-(3,4-dimethoxyphenyl)-3-pyridyl group, 2-(3,4-dimethoxyphenyl)-4-pyridyl group, 6-(3,4-dimethoxyphenyl)-3-pyridyl group, 5-(3,4-difluorophenyl)-2-pyridyl group, 6-(3,4-difluorophenyl)-2-pyridyl group, 2-(3,4-difluorophenyl)-3-pyridyl group, 2-(3,4-difluorophenyl)-4-pyridyl group, 6-(3,4-difluorophenyl)-3-pyridyl group, 5-(3,4-dichlorophenyl)-2-pyridyl group, 6-(3,4-dichlorophenyl)-2-pyridyl group, 2-(3,4-dichlorophenyl)-3-pyridyl group, 2-(3,4-dichlorophenyl)-4-pyridyl group, 6-(3,4-dichlorophenyl)-3-pyridyl group, 5-(2-furyl)-2-pyridyl group, 6-(2-furyl)-2-pyridyl group, 5-(2-furyl)-3-pyridyl group, 6-(2-furyl)-3-pyridyl group, 5-(3-furyl)-2-pyridyl group, 6-(3-furyl)-2-pyridyl group, 5-(3-furyl)-3-pyridyl group, 6-(3-furyl)-3-pyridyl group, 5-(2-thienyl)-2-pyridyl group, 6-(2-thienyl)-2-pyridyl group, 5-(2-thienyl)-3-pyridyl group, 6-(2-thienyl)-3-pyridyl group, 5-(3-thienyl)-2-pyridyl group, 6-(3-thienyl)-2-pyridyl group, 5-(3-thienyl)-3-pyridyl group, 6-(3-thienyl)-3-pyridyl group or the like.

A furyl group (which may be substituted on the furan ring by 1 to 3 groups selected from a group consisting of a C1-6 alkyl group, nitro group and phenyl group (which may be substituted on the phenyl ring by at least one group selected from a group consisting of a halogen atom, a halogen-substituted or unsubstituted C1-6 alkyl group, a halogen-substituted or unsubstituted C1-6 alkoxy group and a nitro group)) includes a furyl group (which may be substituted on the furan ring by 1 to 3 groups selected from a group consisting of a C1-6 alkyl group, nitro group and phenyl group (which may be substituted on the phenyl ring by 1 to 5, preferably 1 to 3 groups selected from a group consisting of a halogen atom, a halogen-substituted or unsubstituted C1-6 alkyl group, a halogen-substituted or unsubstituted C1-6 alkoxy group and a nitro group)), for example, a 2-furyl group, 3-furyl group, 3-methyl-2-furyl group, 3,4-dimethyl-2-furyl group, 3,4,5-trimethyl-2-furyl group, 4-methyl-2-furyl group, 5-methyl-2-furyl group, 3-ethyl-2-furyl group, 4-ethyl-2-furyl group, 5-ethyl-2-furyl group, 3-n-propyl-2-furyl group, 4-n-propyl-2-furyl group, 5-n-propyl-2-furyl group, 3-n-butyl-2-furyl group, 4-n-butyl-2-furyl group, 5-n-butyl-2-furyl group, 3-n-pentyl-2-furyl group, 4-n-pentyl-2-furyl group, 5-n-pentyl-2-furyl group, 3-n-hexyl-2-furyl group, 4-n-hexyl-2-furyl group, 5-n-hexyl-2-furyl group, 2-methyl-3-furyl group, 4-methyl-3-furyl group, 5-methyl-3-furyl group, 2-ethyl-3-furyl group, 4-ethyl-3-furyl group, 5-ethyl-3-furyl group, 2-n-propyl-3-furyl group, 4-n-propyl-3-furyl group, 5-n-propyl-3-furyl group, 2-n-butyl-3-furyl group, 4-n-butyl-3-furyl group, 5-n-butyl-3-furyl group, 2-n-pentyl-3-furyl group, 4-n-pentyl-3-furyl group, 5-n-pentyl-3-furyl group, 2-n-hexyl-3-furyl group, 4-n-hexyl-3-furyl group, 5-n-hexyl-3-furyl group, 3-nitro-2-furyl group, 4-nitro-2-furyl group, 5-nitro-2-furyl group, 2-nitro-3-furyl group, 4-nitro-3-furyl group, 3-phenyl-2-furyl group, 4-phenyl-2-furyl group, 5-phenyl-2-furyl group, 3-phenyl-4-furyl group, 4-phenyl-3-furyl group, 3-(3-fluorophenyl)-2-furyl group, 4-(3-fluorophenyl)-2-furyl group, 5-(3-fluorophenyl)-2-furyl group, 2-(3-fluorophenyl)-3-furyl group, 3-(2-fluorophenyl)-2-furyl group, 4-(2-fluorophenyl)-2-furyl group, 5-(2-fluorophenyl)-2-furyl group, 2-(2-fluorophenyl)-3-furyl group, 4-nitro-3-furyl group, 3-(4-fluorophenyl)-2-furyl group, 4-(4-fluorophenyl)-2-furyl group, 5-(4-fluorophenyl)-2-furyl group, 2-(4-fluorophenyl)-3-furyl group, 4-(4-fluorophenyl)-3-furyl group, 3-(3,4-difluorophenyl)-2-furyl group, 4-(2,3,4,5,6-pentafluorophenyl)-2-furyl group, 5-(3,4-difluorophenyl)-2-furyl group, 2-(3,4-difluorophenyl)-3-furyl group, 4-(3,4-difluorophenyl)-3-furyl group, 3-(4-chlorophenyl)-2-furyl group, 4-(4-chlorophenyl)-2-furyl group, 5-(4-chlorophenyl)-2-furyl group, 2-(4-chlorophenyl)-3-furyl group, 4-(4-chlorophenyl)-3-furyl group, 3-(2-chlorophenyl)-2-furyl group, 4-(2-chlorophenyl)-2-furyl group, 5-(2-chlorophenyl)-2-furyl group, 2-(2-chlorophenyl)-3-furyl group, 4-(2-chlorophenyl)-3-furyl group, 5-(2-chlorophenyl)-3-furyl group, 3-(3-chlorophenyl)-2-furyl group, 4-(3-chlorophenyl)-2-furyl group, 5-(3-chlorophenyl)-2-furyl group, 2-(3-chlorophenyl)-3-furyl group, 4-(3-chlorophenyl)-3-furyl group, 3-(3,4,5-trichlorophenyl)-2-furyl group, 4-(3,4-dichlorophenyl)-2-furyl group, 5-(3,4-dichlorophenyl)-2-furyl group, 2-(3,4-chlorophenyl)-3-furyl group, 4-(3,4-dichlorophenyl)-3-furyl group, 3-(4-methylphenyl)-2-furyl group, 4-(4-methylphenyl)-2-furyl group, 5-(4-methylphenyl)-2-furyl group, 2-(4-methylphenyl)-3-furyl group, 4-(4-methylphenyl)-3-furyl group, 3-(4-trifluoromethylphenyl)-2-furyl group, 4-(4-trifluoromethylphenyl)-2-furyl group, 5-(4-trifluoromethylphenyl)-2-furyl group, 2-(4-trifluoromethylphenyl)-3-furyl group, 4-(4-trifluoromethylphenyl)-3-furyl group, 3-(2-trifluoromethylphenyl)-2-furyl group, 4-(2-trifluoromethylphenyl)-2-furyl group, 5-(2-trifluoromethylphenyl)-2-furyl group, 2-(2-trifluoromethylphenyl)-3-furyl group, 4-(2-trifluoromethylphenyl)-3-furyl group, 3-(3-trifluoromethylphenyl)-2-furyl group, 4-(3-trifluoromethylphenyl)-2-furyl group, 5-(4-trifluoromethylphenyl)-2-furyl group, 2-(3-trifluoromethylphenyl)-3-furyl group, 4-(3-trifluoromethylphenyl)-3-furyl group, 3-(2-chloro-5-trifluoromethylphenyl)-2-furyl group, 4-(2-chloro-5-trifluoromethylphenyl)-2-furyl group, 5-(2-chloro-5-trifluoromethylphenyl)-2-furyl group, 2-(2-chloro-5-trifluoromethylphenyl)-3-furyl group, 4-(2-chloro-5-trifluoromethylphenyl)-3-furyl group, 3-(4-methoxyphenyl)-2-furyl group, 4-(4-methoxyphenyl)-2-furyl group, 5-(4-methoxyphenyl)-2-furyl group, 3-(4-methoxyphenyl)-4-furyl group, 4-(4-methoxyphenyl)-3-furyl group, 3-(2-methoxyphenyl)-2-furyl group, 4-(2-methoxyphenyl)-2-furyl group, 5-(2-methoxyphenyl)-2-furyl group, 2-(2-methoxyphenyl)-3-furyl group, 4-(2-methoxyphenyl)-3-furyl group, 3-(2-trifluoromethoxyphenyl)-2-furyl group, 4-(2-trifluoromethoxyphenyl)-2-furyl group, 5-(2-trifluoromethoxyphenyl)-2-furyl group, 3-(4-trifluoromethoxyphenyl)-2-furyl group, 4-(4-trifluoromethoxyphenyl)-2-furyl group, 5-(4-trifluoromethoxyphenyl)-2-furyl group, 2-(4-trifluoromethoxyphenyl)-3-furyl group, 4-(4-trifluoromethoxyphenyl)-3-furyl group, 3-(3,4-dimethoxyphenyl)-2-furyl group, 4-(3,4-dimethoxyphenyl)-2-furyl group, 5-(3,4-dimethoxyphenyl)-2-furyl group, 3-(3,4-dimethoxyphenyl)-3-furyl group, 4-(3,4-dimethoxyphenyl)-3-furyl group, 3-(4-nitrophenyl)-2-furyl group, 4-(4-nitrophenyl)-2-furyl group, 5-(4-nitrophenyl)-2-furyl group, 2-(4-nitrophenyl)-3-furyl group, 4-(4-nitrophenyl)-3-furyl group, 3-(3-nitrophenyl)-2-furyl group, 4-(3-nitrophenyl)-2-furyl group, 5-(3-nitrophenyl)-2-furyl group, 2-(3-nitrophenyl)-3-furyl group, 4-(3-nitrophenyl)-3-furyl group, 4-methyl-5-nitro-2-furyl group, 4-phenyl-3,5-dimethyl-2-furyl group or the like.

A benzothiazole group (which may have on the benzothiazole ring at least one phenyl group which may have a C1-6 alkoxy group as a substituent on the phenyl ring) includes a benzothiazole group (which may have on the benzothiazole ring 1 to 3 phenyl groups which may have 1 to 3 C1-6 alkoxy groups as a substituent on the phenyl ring), for example, a benzothiazol-2-yl group, benzothiazol-4-yl group, benzothiazol-5-yl group, benzothiazol-6-yl group, benzothiazol-7-yl group, 2-phenylbenzothiazol-4-yl group, 2,5-diphenylbenzothiazol-4-yl group, 4,5,6-triphenylbenzothiazol-2-yl group, 2-phenylbenzothiazol-5-yl group, 2-phenylbenzothiazol-6-yl group, 2-phenylbenzothiazol-7-yl group, 2-(3-ethoxyphenyl)benzothiazol-7-yl group, 2-(4-propoxyphenyl)benzothiazol-4-yl group, 2-(4-n-butoxyphenyl)-benzothiazol-5-yl group, 2-(4-n-hexyloxyphenyl)-benzothiazol-6-yl group, 2-(4-n-pentyloxyphenyl)-benzothiazol-7-yl group, 4-phenylbenzothiazol-2-yl group, 5-phenylbenzothiazol-2-yl group, 6-phenylbenzothiazol-2-yl group, 7-phenylbenzothiazol-2-yl group, 4-(3,4-dimethoxyphenyl)benzothiazol-2-yl group, 5-(3,4,5-trimethoxyphenyl)benzothiazol-2-yl group, 7-(3-methoxyphenyl)benzothiazol-2-yl group, 4-(4-methoxyphenyl)benzothiazol-2-yl group, 5-(4-methoxyphenyl)benzothiazol-2-yl group, 6-(4-methoxyphenyl)-benzothiazol-2-yl group, 7-(4-methoxyphenyl)-benzothiazol-2-yl group or the like.

A thienyl group (which may have on the thiophene ring at least one group selected from a group consisting of a halogen atom, nitro group, C1-6 alkyl group, pyrazolyl group which may be substituted on the pyrazole ring by at least one halogen-substituted or unsubstituted C1-6 alkyl group as a substituent and thienyl group which may have a halogen atom on the thiophene ring) includes a thienyl group (which may have on the thiophene ring 1 to 3 groups selected from a group consisting of a halogen atom, nitro group, C1-6 alkyl group, pyrazolyl group which may be substituted on the pyrazole ring by 1 to 3 halogen-substituted or unsubstituted C1-6 alkyl groups as a substituent and thienyl group which may have 1 to 3 halogen atoms on the thiophene ring), for example, a 2-thienyl group, 3-fluoro-2-thienyl group, 4-fluoro-2-thienyl group, 5-fluoro-2-thienyl group, 3-chloro-2-thienyl group, 4-chloro-2-thienyl group, 5-chloro-2-thienyl group, 3-bromo-2-thienyl group, 4-bromo-2-thienyl group, 5-bromo-2-thienyl group, 3-thienyl group, 2-fluoro-3-thienyl group, 4-fluoro-3-thienyl group, 5-fluoro-3-thienyl group, 2-chloro-3-thienyl group, 4-chloro-3-thienyl group, 5-chloro-3-thienyl group, 2-bromo-3-thienyl group, 4-bromo-3-thienyl group, 5-bromo-3-thienyl group, 3-nitro-2-thienyl group, 4-nitro-2-thienyl group, 5-nitro-2-thienyl group, 2-nitro-3-thienyl group, 4-nitro-3-thienyl group, 5-nitro-3-thienyl group, 3-methyl-2-thienyl group, 4-methyl-2-thienyl group, 5-methyl-2-thienyl group, 5-ethyl-2-thienyl group, 2-methyl-3-thienyl group, 4-methyl-3-thienyl group, 5-methyl-3-thienyl group, 2,5-dimethyl-3-thienyl group, 2,4,5-trimethyl-3-thienyl group, 2,4-dimethyl-3-thienyl group, 3-(pyrazol-1-yl)-2-thienyl group, 4-(pyrazol-1-yl)-2-thienyl group, 5-(pyrazol-1-yl)-2-thienyl group, 2-(pyrazol-1-yl)-3-thienyl group, 4-(pyrazol-1-yl)-3-thienyl group, 5-(pyrazol-1-yl)-3-thienyl group, 3-(3-trifluoromethylpyrazol-1-yl)-2-thienyl group, 4-(3-trifluoromethylpyrazol-1-yl)-2-thienyl group, 5-(1-methyl-3-trifluoromethylpyrazol-5-yl)-2-thienyl group, 2-(1,4,5-trimethylpyrazol-3-yl)-3-thienyl group, 4-(1,5-dimethylpyrazol-3-yl)-3-thienyl group, 5-(1-methyl-pyrazol-3-yl)-3-thienyl group, 5-(1-n-pentyl-pyrazol-5-yl)-2-thienyl group, 5-(1-n-hexyl-pyrazol-5-yl)-2-thienyl group, 3-(5-trifluoromethylpyrazol-1-yl)-2-thienyl group, 4-(5-n-propyl-pyrazol-1-yl)-2-thienyl group, 5-(5-n-butyl-pyrazol-1-yl)-2-thienyl group, 2-(5-trifluoromethylpyrazol-1-yl)-3-thienyl group, 4-(5-ethyl-pyrazol-1-yl)-3-thienyl group, 5-(5-trifluoromethylpyrazol-1-yl)-3-thienyl group, 3-(2-thienyl)-2-thienyl group, 4-(2-thienyl)-2-thienyl group, 3-chloro-4-(2-thienyl)-2-thienyl group, 5-(2-thienyl)-2-thienyl group, 2-(2-thienyl)-3-thienyl group, 4-(2-thienyl)-3-thienyl group, 5-(2-thienyl)-3-thienyl group, 3-(5-chloro-2-thienyl)-2-thienyl group, 4-(5-bromo-2-thienyl)-2-thienyl group, 5-(5-chloro-2-thienyl)-2-thienyl group, 2-(5-chloro-2-thienyl)-3-thienyl group, 4-(5-chloro-2-thienyl)-3-thienyl group, 5-(5-chloro-2-thienyl)-3-thienyl group, 3-(4-chloro-2-thienyl)-2-thienyl group, 4-(3,4-dichloro-2-thienyl)-2-thienyl group, 5-(3,4,5-trichloro-2-thienyl)-2-thienyl group, 2-(4-bromo-2-thienyl)-3-thienyl group, 4-(4-chloro-2-thienyl)-3-thienyl group, 5-(4-bromo-2-thienyl)-3-thienyl group or the like.

An indolyl group (which may be substituted on the indole ring by at least one group selected from a group consisting of a phenylsulfonyl group which may have a C1-6 alkyl group as a substituent, phenyl C1-6 alkyl group, C1-6 alkoxycarbonyl group and phenyl group) includes an indolyl group (which may be substituted on the indole ring by 1 to 3 groups selected from a group consisting of a phenylsulfonyl group which may have 1 to 3 C1-6 alkyl groups as a substituent, phenyl C1-6 alkyl group, C1-6 alkoxycarbonyl group and phenyl group), for example, an indol-1-yl, indol-2-yl, indol-3-yl, indol-4-yl, indol-5-yl, indol-6-yl, indol-7-yl, 1-(benzenesulfonyl)indol-3-yl group, 1-(4-methylbenzenesulfonyl)indol-3-yl group, 1-(3,4-dimethylbenzenesulfonyl)indol-3-yl group, 1-(3,4,6-trimethylbenzenesulfonyl)indol-3-yl group, 1-benzylindol-3-yl group, 1-(2-phenethyl)indol-3-yl group, 1-(1-phenethyl)indol-3-yl group, 1-(3-phenylpropyl)indol-3-yl group, 1-(4-phenylbutyl)indol-3-yl group, 1-(5-phenylpentyl)indol-3-yl group, 1-(6-phenylhexyl)indol-3-yl group, 6-methoxycarbonylindol-3-yl group, 6-ethoxycarbonylindol-3-yl group, 6-n-propoxycarbonylindol-3-yl group, 6-n-butoxy-carbonylindol-3-yl group, 6-n-pentyloxycarbonylindol-3-yl group, 6-n-hexyloxycarbonylindol-3-yl group, 2-phenylindol-3-yl group, 1-benzyl-6-phenyl-6-methoxycarbonylindol-3-yl group, 1-benzyl-6-methoxycarbonylindol-3-yl group, 2-phenyl-1-(4-methylbenzenesulfonyl)indol-3-yl group or the like.

A pyrrolyl group (which may be substituted on the pyrrole ring by at least one group selected from a group consisting of a phenyl group which may be substituted by at least one halogen-substituted or unsubstituted C1-6 alkyl group and C1-6 alkyl group) includes a pyrrolyl group (which may be substituted on the pyrrole ring by 1 to 3 groups selected from a group consisting of a phenyl group which may be substituted by 1 to 3 halogen-substituted or unsubstituted C1-6 alkyl groups and C1-6 alkyl group), for example, a 2-pyrrolyl group, 1-methyl-2-pyrrolyl group, 1-ethyl-2-pyrrolyl group, 1-n-propyl-2-pyrrolyl group, 1-n-butyl-2-pyrrolyl group, 1-n-pentyl-2-pyrrolyl group, 1-n-hexyl-2-pyrrolyl group, 3-pyrrolyl group, 1-methyl-3-pyrrolyl group, 1-ethyl-3-pyrrolyl group, 1-n-propyl-3-pyrrolyl group, 1-n-butyl-3-pyrrolyl group, 1-n-pentyl-3-pyrrolyl group, 1-n-hexyl-3-pyrrolyl group, 2,5-dimethyl-3-pyrrolyl group, 1-(3-methylphenyl)-2,5-dimethyl-3-pyrrolyl group, 1-(4-methylphenyl)-2,5-dimethyl-3-pyrrolyl group, 1-(3-trifluoromethylphenyl)-2,5-dimethyl-3-pyrrolyl group, 1-(4-trifluoromethylphenyl)-2,5-dimethyl-3-pyrrolyl group, 1-(2,3-dimethylphenyl)-3-pyrrolyl group, 1-(4-methylphenyl)-3-pyrrolyl group, 1-(3-trifluoromethylphenyl)-3-pyrrolyl group, 1-(4-trifluoromethylphenyl)-3-pyrrolyl group, 1-(3-methylphenyl)-3,5-dimethyl-2-pyrrolyl group, 1-(4-methylphenyl)-3,5-dimethyl-2-pyrrolyl group, 1-(3-trifluoromethylphenyl)-3,5-dimethyl-2-pyrrolyl group, 1-(4-trifluoromethylphenyl)-3,5-dimethyl-2-pyrrolyl group, 1-(3-methylphenyl)-2-pyrrolyl group, 1-(2,4,6-trimethylphenyl)-2-pyrrolyl group, 1-(3,5-ditrifluoromethylphenyl)-2-pyrrolyl group, 1-(4-trifluoromethylphenyl)-2-pyrrolyl group or the like.

A coumaryl group includes a 4-coumaryl group, 5-coumaryl group, 6-coumaryl group, 7-coumaryl group or 8-coumaryl group.

Examples of a benzimidazolyl group (which may be substituted on the benzimidazole ring by at least one thienyl group as a substituent) include a 2-benzimidazolyl group, 4-benzimidazolyl group, 5-benzimidazolyl group, 6-benzimidazolyl group, 2-(2-thienyl)-4-benzimidazolyl group, 2-(2-thienyl)-5-benzimidazolyl group, 2-(2-thienyl)-6-benzimidazolyl group, 2-(2-thienyl)-7-benzimidazolyl group, 2-(3-thienyl)-4-benzimidazolyl group, 2-(3-thienyl)-5-benzimidazolyl group, 2-(3-thienyl)-6-benzimidazolyl group, 2-(3-thienyl)-7-benzimidazolyl group or the like.

An oxazolyl group (which may be substituted on the oxazole ring by at least one phenyl group, as a substituent, which may have a halogen atom) includes an oxazolyl group (which may be substituted on the oxazole ring by 1 to 2 phenyl groups, as a substituent, which may have 1 to 5 halogen atoms), for example, a 2-oxazolyl group, 4-oxazolyl group, 5-oxazolyl group, 2-phenyl-4-oxazolyl group, 2-(4-fluorophenyl)-4-oxazolyl group, 2,4-di(4-chlorophenyl)-5-oxazolyl group, 2-(4-chlorophenyl)-4-oxazolyl group, 2-(4-bromophenyl)-4-oxazolyl group, 2-(4-iodophenyl)-4-oxazolyl group, 2-(4-fluorophenyl)-5-oxazolyl group, 2-(4-chlorophenyl)-5-oxazolyl group, 2-(4-bromophenyl)-5-oxazolyl group, 2-(4-iodophenyl)-5-oxazolyl group, 2-(4-fluorophenyl)-4-oxazolyl group, 2-(3,4-chlorophenyl)-4-oxazolyl group, 2-(4-bromophenyl)-5-oxazolyl group, 2-(4-iodophenyl)-5-oxazolyl group, 2-(2,3,4,5,6-pentafluorophenyl)-4-oxazolyl group, 2-(2,4,6-trichlorophenyl)-4-oxazolyl group, 2-(4-bromophenyl)-5-oxazolyl group, 2-(4-iodophenyl)-5-oxazolyl group or the like.

A thiazolyl group (which may be substituted on the thiazole ring by at least one phenyl group which may be substituted by at least one group selected from a group consisting of a halogen atom, nitro group and phenyl group) includes a thiazolyl group (which may be substituted on the thiazole ring by 1 to 2 phenyl groups which may be substituted by 1 to 5, preferably 1 to 3 groups selected from a group consisting of a halogen atom, nitro group and phenyl group), for example, a 2-thiazolyl group, 4-thiazolyl group, 5-thiazolyl group, 2-phenyl-4-thiazolyl group, 2-phenyl-5-thiazolyl group, 2,4-diphenyl-5-thiazolyl group, 2,5-diphenyl-4-thiazolyl group, 2-(4-chlorophenyl)-4-thiazolyl group, 2-(4-fluorophenyl)-5-thiazolyl group, 2-(2,3,4,5,6-pentafluorophenyl)-4-thiazolyl group, 2-(4-bromophenyl)-4-thiazolyl group, 2-(3,4-dichlorophenyl)-4-thiazolyl group, 2-(3,4-dichlorophenyl)-5-thiazolyl group, 2-(3,4-difluorophenyl)-5-thiazolyl group, 2-(2,4,6-trichlorophenyl)-4-thiazolyl group, 2-(3-chloro-4-nitrophenyl)-4-thiazolyl group, 2-(4-phenyl-3-bromophenyl)-4-thiazolyl group, 2-(4-nitrophenyl)-4-thiazolyl group, 2-(4-nitrophenyl)-5-thiazolyl group, 2-(2,4,6-trinitrophenyl)-5-thiazolyl group, 2-(2,4-dinitrophenyl)-4-thiazolyl group, 2-(4-biphenylyl)-4-thiazolyl group, 2-(4-biphenylyl)-5-thiazolyl group, 4-(4-biphenylyl)-2-thiazolyl group, 2-(4-biphenylyl)-4-thiazolyl group or the like.

Examples of a quinolyl group include 2-quinolyl group, 3-quinolyl group, 4-quinolyl group, 5-quinolyl group, 6-quinolyl group, 7-quinolyl group or 8-quinolyl group.

Examples of a 3,4-dihydrocarbostyril group (which may be substituted on the 3,4-dihydrocarbostyril ring by at least one group selected from a group consisting of a C1-6 alkoxy group, C1-6 alkyl group, and phenyl C1-6 alkoxy group) or carbostyril group (which may be substituted on the carbostyril ring by at least one group selected from a group consisting of a C1-6 alkoxy group, C1-6 alkyl group, and phenyl C1-6 alkoxy group) include a 3,4-dihydrocarbostyril group (which may be substituted on the 3,4-dihydrocarbostyril ring by 1 to 3 groups selected from a group consisting of a C1-6 alkoxy group, C1-6 alkyl group, and phenyl C1-6 alkoxy group) or carbostyril group (which may be substituted on the carbostyril ring by 1 to 3 groups selected from a group consisting of a C1-6 alkoxy group, C1-6 alkyl group, and phenyl C1-6 alkoxy group), for example, a 3,4-dihydrocarbostyril-1-yl group, 3,4-dihydrocarbostyril-3-yl group, 3,4-dihydrocarbostyril-4-yl group, 3,4-dihydrocarbostyril-5-yl group, 3,4-dihydrocarbostyril-6-yl group, 3,4-dihydrocarbostyril-7-yl group, 3,4-dihydrocarbostyril-8-yl group, carbostyril-1-yl group, carbostyril-3-yl group, carbostyril-4-yl group, carbostyril-5-yl group, carbostyril-6-yl group, carbostyril-7-yl group, carbostyril-8-yl group, 6-methoxy-3,4-dihydrocarbostyril-5-yl group, 7-methoxy-3,4-dihydrocarbostyril-5-yl group, 8-methoxy-3,4-dihydrocarbostyril-5-yl group, 8-methoxy-1-methyl-3,4-dihydrocarbostyril-5-yl group, 8-benzyloxy-3,4-dihydrocarbostyril-5-yl group, 8-methoxycarbostyril-5-yl group, 8-methoxy-1-methylcarbostyryl-5-yl group, 8-benzyloxycarbostyril-5-yl group, 8-methoxy-3,4-dihydrocarbostyril-6-yl group, 6-methyl-3,4-dihydrocarbostyril-5-yl group, 6,7-dimethyl-3,4-dihydrocarbostyril-5-yl group, 1,5,6-trimethyl-3,4-dihydrocarbostyril-7-yl group, 6-methylcarbostyril-5-yl group, 6,7-dimethylcarbostyril-5-yl group, 1,5,6-trimethylcarbostyril-7-yl group, 8-methoxy-1-methyl-3,4-dihydrocarbostyril-6-yl group, 8-benzyloxy-3,4-dihydrocarbostyril-6-yl group, 8-methoxycarbostyril-6-yl group, 8-methoxy-1-methylcarbostyril-6-yl group, 8-benzyloxy-carbostyril-6-yl group, 8-methoxy-3,4-dihydrocarbostyril-7-yl group, 8-methoxy-1-methyl-3,4-dihydrocarbostyril-7-yl group, 8-benzyloxy-3,4-dihydrocarbostyril-7-yl group, 8-ethoxycarbostyril-7-yl group, 8-methoxy-1-propyl-carbostyryl-7-yl group, 8-(2-phenylethoxy)carbostyril-7-yl group or the like.

Examples of an imidazo[2,1-b]thiazolyl group include such as a 6-imidazo[2,1-b]thiazolyl group, 5-imidazo[2,1-b]thiazolyl group, 3-imidazo[2,1-b]thiazolyl group and 2-imidazo[2,1-b]thiazolyl group or the like.

Examples of an imidazo[2,1-a]pyridyl group include a 2-imidazo[2,1-a]pyridyl group, 3-imidazo[2,1-a]pyridyl group, 5-imidazo[2,1-a]pyridyl group, 6-imidazo[2,1-a]pyridyl group, 7-imidazo[2,1-a]pyridyl group or the like.

A chromanyl group (which may be substituted on the chroman ring by at least one C1-6 alkyl group) includes a chromanyl group (which may be substituted on the chroman ring by 1 to 3 C1-6 alkyl groups), for example, a 2-methyl-5-chromanyl group, 2,2-dimethyl-5-chromanyl group, 2-methyl-6-chromanyl group, 2-ethyl-6-chromanyl group, 2-n-propyl-6-chromanyl group, 2-n-butyl-6-chromanyl group, 2-n-pentyl-6-chromanyl group, 2-n-hexyl-6-chromanyl group, 2,2-dimethyl-6-chromanyl group, 2,2-diethyl-6-chromanyl group, 2-methyl-7-chromanyl group, 2,2-dimethyl-7-chromanyl group, 2,2,4-trimethyl-6-chromanyl group, 2-methyl-8-chromanyl group, 2,2-dimethyl-8-chromanyl group or the like.

Examples of a 2,3-dihydrobenzofuryl group include a 2,3-dihydro-4-benzofuryl group, 2,3-dihydro-5-benzofuryl group, 2,3-dihydro-6-benzofuryl group, 2,3-dihydro-7-benzofuryl group or the like.

An amino-substituted C1-6 alkyl group (which may have at least one group selected from a group consisting of a phenyl group (which may be substituted on the phenyl ring by at least one group selected from a group consisting of a halogen atom, halogen-substituted or unsubstituted C1-6 alkyl group and halogen-substituted or unsubstituted C1-6 alkoxy group) and C1-6 alkyl group as a substituent) includes an amino-substituted C1-6 alkyl group (which may have 1 to 2 groups selected from a group consisting of a phenyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group) and C1-6 alkyl group as a substituent), for example, an aminomethyl group, 2-aminoethyl group, 1-aminoethyl group, 3-aminopropyl group, 4-aminobutyl group, 5-aminopentyl group, 6-aminohexyl group, 2-methyl-3-aminopropyl group, 1,1-dimethyl-2-aminoethyl group, 2-(methylamino)ethyl group, 3-(methylamino)propyl group, 4-(methylamino)butyl group, 5-(methylamino)pentyl group, 6-(methylamino)hexyl group, dimethylaminomethyl group, 2-(diethylamino)ethyl group, 3-(di-n-propylamino)propyl group, 4-(di-n-butylamino)butyl group, 5-(di-n-pentylamino)pentyl group, 2-(di-n-hexylamino)hexyl group, anilinomethyl group, 2-(N-methylanilino)ethyl group, 3-(N-methylanilino)propyl group, 4-anilinobutyl group, 2-(N-methyl-4-chloroanilino)ethyl group, 3-(N-methyl-4-chloroanilino)propyl group, 4-(N-methyl-4-chloroanilino)butyl group, 2-(N-methyl-4-fluoroanilino)ethyl group, 3-(N-methyl-2,3,4,5,6-pentafluoroanilino)propyl group, 2-(3-fluoroanilino)-ethyl group, 3-(N-methyl-3-fluoroanilino)propyl group, 4-(3-fluoroanilino)butyl group, 2-(N-methyl-2-fluoroanilino)ethyl group, 3-(2-fluoro-anilino)propyl group, 4-(N-methyl-2-fluoroanilino)butyl group, 2-(N-methyl-2-chloroanilino)ethyl group, 3-(N-methyl-2-chloroanilino)propyl group, 4-(N-methyl-2-chloroanilino)butyl group, 2-(N-methyl-2,3-dichloroanilino)-ethyl group, 3-(N-methyl-2,4,6-trichloroanilino)propyl group, 4-(N-methyl-3-chloroanilino)butyl group, 2-(N-methyl-4-trifluoromethylanilino)ethyl group, 2-(4-methylanilino)ethyl group, 2-(N-ethyl-3,5-ditrifluoromethylanilino)ethyl group, 2-(N-methyl-3,5-ditrifluoromethylanilino)ethyl group, 2-(N-methyl-2,4-dimethylanilino)ethyl group, 2-(N-methyl-3,5-dimethoxyanilino)ethyl group, 2-(2,4,6-trimethylanilino)ethyl group, 2-(3,4,5-trimethoxyanilino)ethyl group, 3-(N-methyl-4-trifluoromethylanilino)propyl group, 4-(N-methyl-4-trifluoromethylanilino)butyl group, 2-(N-methyl-3-trifluoromethylanilino)ethyl group, 3-(N-methyl-3-trifluoromethylanilino)propyl group, 2-(N-methyl-2- trifluoromethylanilino)ethyl group, 3-(N-methyl-2-trifluoromethylanilino)propyl group, 4-(N-methyl-2-trifluoromethylanilino)butyl group, 2-(N-methyl-4-trifluoromethoxyanilino)ethyl group, 3-(N-methyl-4-trifluoromethoxyanilino)propyl group, 4-(4-trifluoromethoxyanilino)butyl group, 2-(N-methyl-3-trifluoromethoxyanilino)ethyl group, 3-(N-methyl-3-trifluoromethoxyanilino)propyl group, 4-(N-methy-3-trifluoromethoxylanilino)butyl group, 2-(N-methyl-2-trifluoromethoxyanilino)ethyl group, 3-(N-methyl-2-trifluoromethoxyanilino)propyl group, 4-(N-methyl-2-trifluoromethoxyanilino)butyl group, 2-(N-methyl-4-methoxyanilino)ethyl group, 3-(N-methyl-4-methoxyanilino)propyl group, 4-(N-methyl-4-methoxyanilino)butyl group, 2-(N-methyl-3-methoxyanilino)ethyl group, 3-(N-methyl-3-methoxyanilino)propyl group, 4-(3-methoxyanilino)butyl group, 2-(2-methoxyanilino)ethyl group, 3-(N-methyl-2-methoxyanilino)propyl group, 4-(N-methyl-2-methoxyanilino)butyl group or the like.

Examples of a 1,4-dioxaazaspiro[4,5]decyl group (which may be substituted on the 1,4-dioxa-azaspiro[4,5]decane ring by at least one oxo group as a substituent) include a 1,4-dioxa-8-azaspiro[4,5]dec-8-yl group, 7-oxo-1,4-dioxa-8-azaspiro[4,5]dec-8-yl group, 6-oxo-1,4-dioxa-8-azaspiro[4,5]dec-8-yl group or the like.

A homopiperazinyl group (which may be substituted on the homopiperazine ring by at least one group selected from a group consisting of a C1-6 alkoxycarbonyl group, phenyl C1-6 alkoxycarbonyl group and phenyl-substituted or unsubstituted phenyl group) includes a homopiperazinyl group (which may be substituted on the homopiperazine ring by 1 to 3 groups selected from a group consisting of a C1-6 alkoxycarbonyl group, phenyl C1-6 alkoxycarbonyl group and phenyl-substituted or unsubstituted phenyl group), for example, a 1-homopiperazinyl group, 2-homopiperazinyl group, 3-homopiperazinyl group, 4-homopiperazinyl group, 5-homopiperazinyl group, 6-homopiperazinyl group, 7-homopiperazinyl group, 4-methoxycarbonyl-1-homopiperazinyl group, 4-ethoxycarbonyl-1-homopiperazinyl group, 4-n-propoxycarbonyl-1-homopiperazinyl group, 4-tert-butoxycarbonyl-1-homopiperazinyl group, 4-n-pentyloxycarbonyl-1-homopiperazinyl group, 4-n-hexyloxycarbonyl-1-homopiperazinyl group, 4-benzyloxyoxycarbonyl-1-homopiperazinyl group, 4-(2-phenylethoxycarbonyl)-1-homopiperazinyl group, 4-(3-phenylpropoxycarbonyl)-1-homopiperazinyl group, 4-(4-phenylbutoxycarbonyl)-1-homopiperazinyl group, 4-(5-phenylpentyloxycarbonyl)-1-homopiperazinyl group, 4-(6-phenylhexyloxycarbonyl)-1-homopiperazinyl group, 4-(4-biphenylyl)-1-homopiperazinyl group, 3,4-diphenyl-1-homopiperazinyl group, 3,4,5-triphenyl-1-homopiperazinyl group, 3-phenyl-4-methoxycarbonyl-1-homopiperazinyl group or the like.

A piperazinyl group (which may be substituted on the piperazine ring by at least one group selected from a group consisting of an oxo group, C1-6 alkyl group and phenyl C1-6 alkyl group (which may be substituted on the phenyl ring by at least one halogen-substituted or unsubstitued C1-6 alkyl group)) includes a piperazinyl group (which may be substituted on the piperazine ring by 1 to 3 groups selected from a group consisting of an oxo group, C1-6 alkyl group and phenyl C1-6 alkyl group (which may be substituted on the phenyl ring by 1 to 3 halogen-substituted or unsubstitued C1-6 alkyl groups)), for example, a piperazin-1-yl group, piperazin-2-yl group, piperazin-3-yl group, piperazin-4-yl group, 1-methyl-piperazin-4-yl group, 1-benzyl-piperazin-4-yl group, 1,2-dimethyl-piperazin-4-yl group, 1-benzyl-2,6-dimethyl-piperazin-4-yl group, 1-ethyl-2-oxopiperazin-4-yl group, 1-n-propyl-2-oxopiperazin-4-yl group, 1-isopropyl-2-oxopiperazin-4-yl group, 1-n-butyl-2-oxopiperazin-4-yl group, 1-tert-butyl-2-oxopiperazin-4-yl group, 1-n-pentyl-2-oxopiperazin-4-yl group, 1-n-hexyl-2-oxopiperazin-4-yl group, 1-(4-benzyl)-2-oxopiperazin-4-yl group, 1-(2,4-dimethylbenzyl)piperazin-4-yl group, 1-(2,4,6-trimethylbenzyl)piperazin-4-yl group, 1-(3,5-ditrifluoromethylbenzyl)piperazin-4-yl group, 1-(4-methylbenzyl)-2-oxopiperazin-4-yl group, 1-(4-trifluoromethylbenzyl)-2-oxopiperazin-4-yl group, 1-[2-(4-trifluoromethylphenyl)ethyl]-2-oxopiperazin-4-yl group, 1-[3-(4-trifluoromethylphenyl)propyl]-2-oxopiperazin-4-yl group, 1-[4-(4-trifluoromethyl-phenyl)butyl]-2-oxopiperazin-4-yl group, 1-[5-(4-trifluoromethylphenyl)pentyl]-2-oxopiperazin-4-yl group, 1-[6-(4-trifluoromethylphenyl)hexyl]-2-oxopiperazin-4-yl group or the like.

Examples of a piperidyl group (which may be substituted on the piperidine ring by at least one oxo group as a substituent) includes a 1-piperidyl group, 2-piperidyl group, 3-piperidyl group, 4-piperidyl group, 2-oxo-1-piperidyl group, 3-oxo-1-piperidyl group, 4-oxo-1-piperidyl group or the like.

A pyrrolidinyl group (which may be substituted on the pyrrolidine ring by at least one phenoxy C1-6 alkyl group which may have a halogen-substituted or unsubstitued C1-6 alkoxy group as a substituent) includes a pyrrolidinyl group (which may be substituted on the pyrrolidine ring by 1 to 3 phenoxy C1-6 alkyl groups which may have 1 to 3 halogen-substituted or unsubstitued C1-6 alkoxy groups as a substituent), for example, a pyrrolidin-1-yl group, pyrrolidin-2-yl group, pyrrolidin-3-yl group, 2-phenoxymethylpyrrolidin-1-yl group, 3-phenoxymethylpyrrolidin-1-yl group, 2-(2,4-dimethoxyphenoxymethyl)pyrrolidin-1-yl group, 2-(2,4,6-trimethoxyphenoxymethyl)pyrrolidin-1-yl group, 2,3-diphenoxymethylpyrrolidin-1-yl group, 1,3,4-phenoxymethylpyrrolidin-2-yl group, 2-(4-methoxyphenoxymethyl)pyrrolidin-1-yl group, 2-(4-trifluoromethoxyphenoxymethyl)pyrrolidin-1-yl group, 2-[2-(3-trifluoromethoxyphenoxy)ethyl]pyrrolidin-1-yl group, 2-[3-(4-trifluoromethoxyphenoxy)propyl]-pyrrolidin-1-yl group, 2-[4-(4-trifluoromethoxyphenoxy)butyl]pyrrolidin-1-yl group, 2-[5-(4-trifluoromethoxyphenoxy)pentyl]pyrrolidin-1-yl group, 2-[6-(4-trifluoromethoxyphenoxy)hexyl]pyrrolidin-1-yl group, 3-(4-methoxyphenoxymethyl)pyrrolidin-1-yl group, 3-(3-trifluoromethoxyphenoxymethyl)pyrrolidin-1-yl group, 3-(4-trifluoromethoxyphenoxymethyl)pyrrolidin-1-yl group or the like.

Examples of an isoindolinyl group include a 2-isoindolinyl group, 1-isoindolinyl group, 3-isoindolinyl group, 4-isoindolinyl group, 5-isoindolinyl group, 6-isoindolinyl group or the like.

Examples of an oxazolidinyl group (which may be substituted on the oxazolidine ring by at least one oxo group as a substituent) include a 2-oxazolidinyl group, 3-oxazolidinyl group, 4-oxazolidinyl group, 5-oxazolidinyl group, 2-oxo-3-oxazolidinyl group or the like.

A benzo-1,3-oxazolidinyl group (which may be substituted on the benzo-1,3-oxazolidine ring by at least one group selected from a group consisting of an oxo group, halogen atom and phenyl group as a substituent) includes a benzo-1,3-oxazolidinyl group (which may be substituted on the benzo-1,3-oxazolidine ring by 1 to 3 groups selected from a group consisting of an oxo group, halogen atom and phenyl group as a substituent), for example, a benzo-1,3-oxazolidin-2-yl group, benzo-1,3-oxazolidin-3-yl group, benzo-1, 3-oxazolidin-4-yl group, benzo-1,3-oxazolidin-5-yl group, benzo-1,3-oxazolidin-6-yl group, benzo-1,3-oxazolidin-7-yl group, 2-oxobenzo-1,3-oxazolidin-3-yl group, 4-chloro-2-oxobenzo-1,3-oxazolidin-3-yl group, 5-chloro-2-oxobenzo-1,3-oxazolidin-3-yl group, 5-bromo-2-oxobenzo-1,3-oxazolidin-3-yl group, 5-fluoro-benzo-1,3-oxazolidin-3-yl group, 6-phenyl-benzo-1,3-oxazolidin-3-yl group, 5-bromo-6-phenyl-2-oxobenzo-1,3-oxazolidin-3-yl group, 6-chloro-2-oxobenzo-1,3-oxazolidin-3-yl group, 7-chloro-2-oxobenzo-1,3-oxazolidin-3-yl group, 5-bromo-2-oxobenzo-1,3-oxazolidin-3-yl group, 4-phenyl-2-oxobenzo-1,3-oxazolidin-3-yl group, 5-phenyl-2-oxobenzo-1,3-oxazolidin-3-yl group, 6-phenyl-2-oxobenzo-1,3-oxazolidin-3-yl group, 7-phenyl-2-oxobenzo-1,3-oxazolidin-3-yl group or the like.

An imidazolidinyl group (which may be substituted on the imidazolidine ring by at least one group selected from a group consisting of an oxo group, phenyl C1-6 alkyl group (which may be substituted on the phenyl ring by 1 to 3 groups selected from a group consisting of a halogen atom and C1-6 alkoxy group) and phenyl group) includes an imidazolidinyl group (which may be substituted on the imidazolidine ring by 1 to 3 groups selected from a group consisting of an oxo group, phenyl C1-6 alkyl group (which may be substituted on the phenyl ring by 1 to 3 groups selected from a group consisting of a halogen atom and a C1-6 alkoxy group) and phenyl group), for example, an imidazolidin-1-yl group, imidazolidin-2-yl group, imidazolidin-3-yl group, imidazolidin-4-yl group, imidazolidin-5-yl group, 3-benzyl-imidazolidin-1-yl group, 3,4-dibenzyl-2-oxoimidazolidin-1-yl group, 2-oxoimidazolidin-1-yl group, 3-benzyl-2-oxoimidazolidin-1-yl group, 3-(2-fluorobenzyl)-2-oxoimidazolidin-1-yl group, 3-(3-fluorobenzyl)-2-oxoimidazolidin-1-yl group, 3-(4-fluorobenzyl)-2-oxoimidazolidin-1-yl group, 3-phenyl-2-oxoimidazolidin-1-yl group, 3-(3,4-difluorobenzyl)-2-oxoimidazolidin-1-yl group, 3-(3,5-difluorobenzyl)-2-oxoimidazolidin-1-yl group, 3-(3,4,5-trifluorobenzyl)-2-oxoimidazolidin-1-yl group, 3-(2-chlorobenzyl)-2-oxoimidazolidin-1-yl group, 3-(3-chlorobenzyl)-2-oxoimidazolidin-1-yl group, 3-(4-chlorobenzyl)-2-oxoimidazolidin-1-yl group, 3-(2,3-dichlorobenzyl)-2-oxoimidazolidin-1-yl group, 3-(3,4-dichlorobenzyl)-2-oxoimidazolidin-1-yl group, 3-(3,5-dichlorobenzyl)-2-oxoimidazolidin-1-yl group, 3-(3,4,5-trichlorobenzyl)-2-oxoimidazolidin-1-yl group, 3-(2-bromobenzyl)-2-oxoimidazolidin-1-yl group, 3-(3-bromobenzyl)-2-oxoimidazolidin-1-yl group, 3-(4-bromobenzyl)-2-oxoimidazolidin-1-yl group, 3-(2-methoxybenzyl)-2-oxoimidazolidin-1-yl group, 3-(3-methoxybenzyl)-2-oxoimidazolidin-1-yl group, 3-(4-methoxybenzyl)-2-oxoimidazolidin-1-yl group, 3-(2,4-dimethoxybenzyl)-2-oxoimidazolidin-1-yl group, 3-(2,4,6-trimethoxybenzyl)-2-oxoimidazolidin-1-yl group, 3-(3,5-dimethoxybenzyl)-2-oxoimidazolidin-1-yl group, 3-(4-ethoxybenzyl)-2-oxoimidazolidin-1-yl group, 3-(4-isopropoxybenzyl)-2-oxoimidazolidin-1-yl group, 3-(4-n-butoxybenzyl)-2-oxoimidazolidin-1-yl group, 3-(4-n-pentyloxybenzyl)-2-oxoimidazolidin-1-yl group, 3-(4-hexyloxybenzyl)-2-oxoimidazolidin-1-yl group, 3-[2-(3-methoxy-4-chlorophenyl)ethyl]-2-oxoimidazolidin-1-yl group, 3-[3-(4-chlorophenyl)propyl]-2-oxoimidazolidin-1-yl group, 3-[4-(4-chlorophenyl)butyl]-2-oxoimidazolidin-1-yl group, 3-[5-(4-chlorophenyl)-pentyl]-2-oxoimidazolidin-1-yl group, 3-[6-(4-chlorophenyl)hexyl]-2-oxoimidazolidin-1-yl group, 2-phenylidazolidine-1-yl group, 3-phenyl-2-benzylidazolidine-1-yl group, 3-phenyl-4-benzyl-2-oxoidazolidine-1-yl group, 3-phenyl-5-benzyl-2-oxoidazolidine-1-yl group, 4-phenyl-2-oxoidazolidine-1-yl group or the like.

A benzimidazolidinyl group (which may be substituted on the benzimidazolidine ring by at least one group selected from a group consisting of an oxo group, halogen atom, halogen-substituted or unsubstituted C1-6 alkyl group, amino group which may have a C1-6 alkyl group as a substituent, C1-6 alkoxycarbonyl group and, piperidyl group which may be substituted on the piperidine ring by at least one group selected from a group consisting of a C1-6 alkyl group, phenyl group which may be substituted on the phenyl ring by 1 to 3 halogen atoms, C1-6 alkoxycarbonyl group and phenyl C1-6 alkoxycarbonyl group as a substituent) includes a benzimidazolidinyl group (which may be substituted on the benzimidazolidine ring by 1 to 3 groups selected from a group consisting of an oxo group, halogen atom, halogen-substituted or unsubstituted C1-6 alkyl group, amino group which may have 1 to 2 C1-6 alkyl groups as a substituent, C1-6 alkoxycarbonyl group, and piperidyl group which may be substituted on the piperidine ring by 1 to 3 groups selected from a group consisting of a C1-6 alkyl group, phenyl group which may be substituted on the phenyl ring by 1 to 3 halogen atoms, C1-6 alkoxycarbonyl group and phenyl C1-6 alkoxycarbonyl group as a substituent), for example, a benzimidazolidin-1-yl group, benzimidazolidin-2-yl group, benzimidazolidin-3-yl group, benzimidazolidin-4-yl group, benzimidazolidin-5-yl group, benzimidazolidin-6-yl group, benzimidazolidin-7-yl group, 2-oxobenzimidazolidin-1-yl group, 3-methyl-2-oxobenzimidazolidin-1-yl group, 3-methylbenzimidazolidin-1-yl group, 6-dimethylaminobenzimidazolidin-1-yl group, 6-ethoxycarbonylbenzimidazolidin-1-yl group, 3-(4-phenylpiperidin-4-yl)benzimidazolidin-1-yl group, 4-fluorobenzimidazolidin-1-yl group, 3-ethyl-2-oxobenzimidazolidin-1-yl group, 3-n-propyl-2-oxobenzimidazolidin-1-yl group, 3-n-butyl-2-oxobenzimidazolidin-1-yl group, 3-n-pentyl-2-oxobenzimidazolidin-1-yl group, 3-n-hexyl-2-oxobenzimidazolidin-1-yl group, 3-methyl-6-fluoro-2-oxobenzimidazolidin-1-yl group, 3-methyl-4-fluoro-2-oxobenzimidazolidin-1-yl group, 3-methyl-5-fluoro-2-oxobenzimidazolidin-1-yl group, 3-methyl-7-fluoro-2-oxobenzimidazolidin-1-yl group, 3-methyl-6-chloro-2-oxobenzimidazolidin-1-yl group, 3-methyl-5-chloro-2-oxobenzimidazolidin-1-yl group, 3-methyl-4-chloro-2-oxobenzimidazolidin-1-yl group, 3-methyl-5-chloro-2-oxobenzimidazolidin-1-yl group, 3-methyl-7-chloro-2-oxobenzimidazolidin-1-yl group, 3-methyl-6-bromo-2-oxobenzimidazolidin-1-yl group, 3-methyl-4-bromo-2-oxobenzimidazolidin-1-yl group, 3-methyl-5-bromo-2-oxobenzimidazolidin-1-yl group, 3-methyl-7-bromo-2-oxobenzimidazolidin-1-yl group, 3-ethyl-6-fluoro-2-oxobenzimidazolidin-1-yl group, 3-isopropyl-6-fluoro-2-oxobenzimidazolidin-1-yl group, 3-n-hexyl-6-fluoro-2-oxobenzimidazolidin-1-yl group, 3-ethyl-6-chloro-2-oxobenzimidazolidin-1-yl group, 3-isopropyl-6-chloro-2-oxobenzimidazolidin-1-yl group, 3-n-hexyl-6-chloro-2-oxobenzimidazolidin-1-yl group, 3-ethyl-5-chloro-2-oxobenzimidazolidin-1-yl group, 3-isopropyl-5-chloro-2-oxobenzimidazolidin-1-yl group, 3-tert-butyl-5-chloro-2-oxobenzimidazolidin-1-yl group, 3-methyl-6-ethoxycarbonyl-2-oxobenzimidazolidin-1-yl group, 3-isopropyl-6-ethoxycarbonyl-2-oxobenzimidazolidin-1-yl group, 3-n-propyl-6-ethoxycarbonyl-2-oxobenzimidazolidin-1-yl group, 3-methyl-6-trifluoromethyl-2-oxobenzimidazolidin-1-yl group, 5-trifluoromethyl-2-oxobenzimidazolidin-1-yl group, 3-methyl-5-trifluoromethyl-2- oxobenzimidazolidin-1-yl group, 3-isopropyl-5-trifluoromethyl-2-oxobenzimidazolidin-1-yl group, 3-(4-phenylpiperidin-1-yl)-2-oxobenzimidazolidin-1-yl group, 3-(4-phenylpiperidin-1-yl)-5-trifluoromethyl-2-oxobenzimidazolidin-1-yl group, 3-(4-phenylpiperidin-1-yl)-6-trifluoromethyl-2-oxobenzimidazolidin-1-yl group, 3-methyl-6-dimethylamino-2-oxobenzimidazolidin-1-yl group, 3-ethyl-6-dimethylamino-2-oxobenzimidazolidin-1-yl group, 3-methyl-6-amino-2-oxobenzimidazolidin-1-yl group, 3-isopropyl-6-dimethylamino-2-oxobenzimidazolidin-1-yl group, 3-[4-(3-fluorophenyl)-piperidin-1-yl]-2-oxobenzimidazolidin-1-yl group, 3-[4-(4-fluorophenyl)piperidin-1-yl]-2-oxobenzimidazolidin-1-yl group, 3-[4-(3-chlorophenyl)piperidin-1-yl]-2-oxobenzimidazolidin-1-yl group, 3-[4-(4-chlorophenyl)-piperidin-1-yl]-2-oxobenzimidazolidin-1-yl group, 3-[4-(2,3-difluorophenyl)piperidin-1-yl]-5-chloro-2-oxobenzimidazolidin-1-yl group, 3-[4-(4-fluorophenyl)-piperidin-1-yl]-5-chloro-2-oxobenzimidazolidin-1-yl group, 3-[4-(2,4,6-trichlorophenyl)piperidin-1-yl]-5-chloro-2-oxobenzimidazolidin-1-yl group, 3-[4-(4-chlorophenyl)piperidin-1-yl]-5-chloro-2-oxobenzimidazolidin-1-yl group, 3-[4-(3-fluorophenyl)-piperidin-1-yl]-6-chloro-2-oxobenzimidazolidin-1-yl group, 3-[4-(4-iodophenyl)piperidin-1-yl]-6-chloro-2-oxobenzimidazolidin-1-yl group, 3-[4-(3-bromophenyl)-piperidin-1-yl]-6-chloro-2-oxobenzimidazolidin-1-yl group, 3-[1-methylpiperidin-4-yl]-6-chloro-2-oxobenzimidazolidin-1-yl group, 3-(piperidin-4-yl)-2-oxobenzimidazolidin-1-yl group, 3-(1-tert-butoxycarbonylpiperidin-4-yl)-2-oxobenzimidazolidin-1-yl group, 3-(benzyloxycarbonylpiperidin-4-yl)-2-oxobenzimidazolidin-1-yl group, 3-(piperidin-4-yl)-6-fluoro-2-oxobenzimidazolidin-1-yl group, 3-(1-tert-butoxycarbonylpiperidin-4-yl)-6-fluoro-2-oxobenzimidazolidin-1-yl group, 3-(1-benzyloxycarbonylpiperidin-4-yl)-6-fluoro-2-oxobenzimidazolidin-1-yl group, 3-(piperidin-4-yl)-6-chloro-2-oxobenzimidazolidin-1-yl group, 3-(1-tert-butoxycarbonylpiperidin-4-yl)-6-chloro-2-oxobenzimidazolidin-1-yl group, 3-(1-benzyloxycarbonyl-4-piperidin-4-yl)-6-chloro-2-oxobenzimidazolidin-1-yl group, 3-(1,2-dimethylpiperidin-4-yl)benzimidazolidin-1-yl group, 3-(1-benzyloxycarbonyl-2-methylpiperidin-4-yl)benzimidazolidin-1-yl group, 3-(1,2,6-trimethyl-piperidin-4-yl)benzimidazolidin-1-yl group or the like.

A phthalimide group includes, for example, a phthalimid-2-yl group or the like.

An indolinyl group (which may be substituted by at least one group selected from a group consisting of a C1-6 alkyl group, halogen atom and oxo group as a substituent on the indoline ring) includes an indolinyl group (which may have 1 to 3 groups selected from a group consisting of a C1-6 alkyl group, halogen atom and oxo group as a substituent on the indoline ring), for example, an indolinin-1-yl group, indolinin-2-yl group, indolinin-3-yl group, indolinin-4-yl group, indolinin-5-yl group, indolinin-6-yl group, indolinin-7-yl group, 3-methyl-indolin-1-yl group, 3,8-dibromoindolin-1-yl group, 2-oxoindolin-1-yl group (another name: oxyindol-1-yl group), 3-methyl-2-oxoindolin-1-yl group, 3,3-dimethyl-2-oxoindolin-1-yl group, 3-ethyl-2-oxoindolin-1-yl group, 3-n-propyl-2-oxoindolin-1-yl group, 3-n-butyyl-2-oxoindolin-1-yl group, 3-n-pentyl-2-oxoindolin-1-yl group, 3-fluoro-2-oxoindolin-1-yl group, 3,3-difluoro-2-oxoindolin-1-yl group, 3-chloro-2-oxoindolin-1-yl group, 3,3-dichloro-2-oxoindolin-1-yl group or the like.

An example of a 2,3-dihydrobenzisothiazolyl group (which may have at least one oxo group as a substituent on the 2,3-dihydrobenzisothiazole ring) includes a 3-benzisothiazolydinon-1,1-dioxide-2-yl group or the like.

Examples of a 1H-2,4-benzoxazinyl group (which may have at least one oxo group as a substituent on the 1H-2,4-benzoxazine ring) include a 1H-2,4-benzoxazin-3(4H)-on-4-yl group, 1H-2,4-benzoxazin-1,3(4H)-dion-4-yl group or the like.

A phenoxy C1-6 alkyl group which may have a halogen atom as a substituent on the phenyl ring includes a phenoxy C1-6 alkyl group which may have 1 to 5 halogen atoms, for example, a phenoxymethyl group, 2-fluorophenoxymethyl group, 3-fluorophenoxymethyl group, 3,4-difluorophenoxymethyl group, 3,5-difluorophenoxymethyl group, 2,3,4,5,6-pentafluorophenoxymethyl group, 2-chlorophenoxymethyl group, 3-chlorophenoxymethyl group, 4-chlorophenoxymethyl group, 3,4-dichlorophenoxymethyl group, 3,5-dichlorophenoxymethyl group, 2-phenoxyethy group, 1-phenoxyethy group, 3-phenoxypropyl group, 4-phenoxybutyl group, 5-phenoxypentyl group, 6-phenoxy group, 2-(2,4,6-chlorophenoxy)ethyl group, 3-(4-iodophenoxy)propyl group, 4-(4-bronophenoxy)butyl group, 5-(4-chlorophenoxy)pentyl group, 6-(4-chlorophenoxy)hexyl group or the like.

A phenyl C2-6 alkenyl group which may have a halogen atom as a substituent on the phenyl ring includes a phenyl C2-6 alkenyl group which has 1 to 2 double bonds and may have 1 to 5 halogen atoms as a substituent on the phenyl ring, for example, a 3-phenyl-2-propenyl group (trivial name: cinnamyl group), 4-phenyl-2-butenyl group, 4-phenyl-3-butenyl group, 4-phenyl-1,3-butadienyl group, 5-phenyl-1,3,5-hexatrienyl group, 3-(2-fluorophenyl)-2-propenyl group, 3-(3-fluorophenyl)-2-propenyl group, 3-(4-fluorophenyl)-2-propenyl group, 3-(2,3-difluorophenyl)-2-propenyl group, 3-(2,3,4,5,6-pentafluorophenyl)-2-propenyl group, 3-(3,4-difluorophenyl)-2-propenyl group, 3-(3,5-difluorophenyl)-2-propenyl group, 3-(2,4,6-trichlorophenyl)-2-propenyl group, 3-(3-chlorophenyl)-2-propenyl group, 3-(4-chlorophenyl)-2-propenyl group, 3-(2,3-dichlorophenyl)-2-propenyl group, 3-(2,4-dichlorophenyl)-2-propenyl group, 3-(3,4-dichlorophenyl)-2-propenyl group, 3-(3,5-dichlorophenyl)-2-propenyl group, 3-(2-bromophenyl)-2-propenyl group, 3-(3-bromophenyl)-2-propenyl group, 3-(4-bromophenyl)-2-propenyl group, 4-(4-chlorophenyl)-2-butenyl group, 4-(4-chlorophenyl)-3-butenyl group, 5-(4-chlorophenyl)-2-pentenyl group, 5-(4-chlorophenyl)-4-pentenyl group, 5-(4-chlorophenyl)-3-pentenyl group, 6-(4-chlorophenyl)-5-hexenyl group, 6-(4-chlorophenyl)-4-hexenyl group, 6-(4-chlorophenyl)-3-hexenyl group, 6-(4-chlorophenyl)-3-hexenyl group or the like.

A phenyl group which may be substituted on the phenyl ring by at least one group selected from a group consisting of a halogen atom, halogen-substituted or unsubstituted C1-6 alkyl group, halogen-substituted or unsubstituted C1-6 alkoxy group and phenyl group as a substituent includes a phenyl group which may be substituted on the phenyl ring by 1 to 5, preferably 1 to 3 groups selected from a group consisting of a halogen atom, halogen-substituted or unsubstituted C1-6 alkyl group, halogen-substituted or unsubstituted C1-6 alkoxy group and phenyl group as a substituent, for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3,4-difluorophenyl group, 3,5-difluorophenyl group, 2,4-difluorophenyl group, 2,6-difluorophenyl group, 2,3-dichlorophenyl group, 3,4- dichlorophenyl group, 3,5-dichlorophenyl group, 2,4-dichlorophenyl group, 2,6-dichlorophenyl group, 3,4,5-trifluorophenyl group, 3,4,5-trichlorophenyl group, 2,4,6-trifluorophenyl group, 2,4,6-trichlorophenyl group, 2-fluoro-4-bromophenyl group, 4-chloro-3-fluorophenyl group, 2,3,4-trichlorophenyl group, 3,4,5-trifluorophenyl group, 2,4,6-triburomophenyl group, 4-n-butylphenyl group, 2,4-dimethylphenyl group, 2,3-dimethylphenyl group, 2,6-dimethylphenyl group, 3,5-dimethylphenyl group, 2,5-dimethylphenyl group, 2,4,6-trimethylphenyl group, 3,5-ditrifluoromethylphenyl group, 4-n-butoxyphenyl group, 2,4-dimethoxyphenyl group, 2,3-dimethoxyphenyl group, 2,6-dimethoxyphenyl group, 3,5-dimethoxyphenyl group, 2,5-dimethoxyphenyl group, 2,4,6-trimethoxyphenyl group, 3,5-ditrifluoromethoxyphenyl group, 3-chloro-4-methoxyphenyl group, 2-chloro-4-trifluoromethoxyphenyl group, 3-methyl-4-fluorophenyl group, 4-bromo-3-trifluoromethylphenyl group, 2-methylphenyl group, 3-methylphenyl group, 4-methylphenyl group, 2-methyl-3-chlorophenyl group, 3-methyl-4-chlorophenyl group, 2-chloro-4-methylphenyl group, 2-methyl-3-fluorophenyl group, 2-trifluoromethylphenyl group, 3-trifluoromethylphenyl group, 4-trifluoromethylphenyl group, 2-pentafluoroethylphenyl group, 3-pentafluoroethylphenyl group, 4-pentafluoroethylphenyl group, 2-isopropylphenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoropropylphenyl group, 4-pentylphenyl group, 4-hexylphenyl group, 2-methoxyphenyl group, 3-methoxyphenyl group, 4-methoxyphenyl group, 3-chloro-2-methoxyphenyl group, 2-fluoro-3-methoxyphenyl group, 2-fluoro-4-methoxyphenyl group, 2,6-dimethoxyphenyl group, 2,3,4-trifluorophenyl group, 2,3,4,5,6-pentafluorophenyl group, 2-trifluoromethoxyphenyl group, 3-trifluoromethoxyphenyl group, 4-trifluoromethoxyphenyl group, 3-fluoro-2-trifluoromethoxyphenyl group, 2-fluoro-3-trifluoromethoxyphenyl group, 3-fluoro-4-trifluoromethoxyphenyl group, 3-chloro-2-trifluoromethoxyphenyl group, 2-chloro-3-trifluoromethoxyphenyl group, 3-chloro-4-trifluoromethoxyphenyl group, 2-pentafluoroethoxyphenyl group, 3-pentafluoroethoxyphenyl group, 4-pentafluoroethoxyphenyl group, 3-chloro-2-pentafluoroethoxyphenyl group, 2-chloro-3-pentafluoroethoxyphenyl group, 3-chloro-4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropropoxyphenyl group, 3-n-heptafluoropropoxyphenyl group, 4-n-heptafluoropropoxyphenyl group, 4-n-pentoxyphenyl group, 4-n-hexyloxyphenyl group, 4-biphenylyl group, 3-biphenylyl group, 2-biphenylyl or the like.

A 1,3-thiazolidinyl group (which may be substituted on the 1,3-thiazolidine ring by at least one group selected from a group consisting of an oxo group and phenyl C1-6 alkylidene group which may have a halogen-substituted or unsubstituted C1-6 alkyl group on the phenyl group as a substituent) includes a 1,3-thiazolidinyl (which may be substituted on the 1,3-thiazolidine ring by 1 to 3 groups selected from a group consisting of an oxo group and phenyl C1-6 alkylidene group which may 1 to 3 halogen-substituted or unsubstituted C1-6 alkyl groups as a substituent on the phenyl group), for example, a 1,3-thiazolidine-2-yl group, 1,3-thiazolidine-3-yl group, 1,3-thiazolidine-4-yl group, 1,3-thiazolidine-5-yl group, 1,3-thiazolidine-2,4-dion-3-yl group, 5-benzylidene-1,3-thiazolidine-3-yl group, 5-benzylidene-1,3-thiazolidine-2-on-3-yl group, 5-benzylidene-1,3-thiazolidine-4-on-3-yl group, 5-(2-methylbenzylidene)-1,3-thiazolidine-3-yl group, 5-(2,4-dimethylbenzylidene)-1,3-thiazolidine-3-yl group, 5-(2,4,6-trimethylbenzylidene)-1,3-thiazolidine-3-yl group, 5-benzylidene-1,3-thiazolidine-2,4-dion-3-yl group, 5-(2-trifluoromethylbenzylidene)-1,3-thiazolidine-2,4-dion-3-yl group, 5-(3,5-ditrifluoromethylbenzylidene)-1,3-thiazolidine-2,4-dion-3-yl group, 5-(4-tritrifluoromethylbenzylidene)-1,3-thiazolidine-2,4-dion-3-yl group, 5-[2-(4-tritrifluoromethylphenyl)ethylidene]-1,3-thiazolidine-2,4-dion-3-yl group, 5-[3-(4-tritrifluoromethylphenyl)propylidene]-1,3-thiazolidine-2,4-dion-3-yl group, 5-[4-(4-tritrifluoromethylphenyl)-butylidene]-1,3-thiazolidine-2,4-dion-3-yl group, 5-[5-(4-tritrifluoromethylphenyl)pentylidene]-1,3-thiazolidine-2,4-dion-3-yl group, 5-[6-(4-trifluoromethylphenyl)hexylidene]-1,3-thiazolidine-2,4-dion-3-yl group or the like.

A halogen-substituted or unsubstituted phenyl group includes a phenyl group which may be substituted by 1 to 5 halogen atoms, for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 3, 4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 3,4,5-trichlorophenyl group, 2,4,6-trifluorophenyl group, 2,4,6-trichlorophenyl group, 2-fluoro-4-bromophenyl group, 4-chloro-3-fluorophenyl group, 2,3,4-trichlorophenyl group, 3,4,5-trifluorophenyl group, 2,4,6-trifluorophenyl group, 2,3,4,5,6-pentafluorophenyl group or the like.

A phenyl C1-6 alkyl group which may have a phenyl group as a substituent on the phenyl ring includes a phenyl C1-6 alkyl group which may have 1 to 3 phenyl groups as a substituent on the phenyl ring, for example, a benzyl group, 2-phenylethyl group, 1-phenylethyl group, 3-phenylpropyl group, 4-phenylbutyl group, 5-phenylpentyl group, 6-phenylhexyl group, 2-methyl-3-phenylpropyl group, 1,1-dimethyl 2-phenylethyl group, 3-phenylbenzyl group, 2-phenylbenzyl group, 4-phenylbenzyl group, 2,4-diphenylbenzyl group, 2,4,6-triphenylbenzyl group or the like.

A phenyl group (which may be substituted on the phenyl ring by at least one group selected from a group consisting of a halogen atom, halogen-substituted or unsubstituted C1-6 alkyl group and halogen-substituted or unsubstituted C1-6 alkoxy group, amino group (which may be substituted on the amino group by at least one group selected from a group consisting of a C1-6 alkyl group and phenyl group (which may be substituted on the phenyl ring by at least one group selected from a group consisting of a halogen atom, halogen-substituted or unsubstituted C1-6 alkyl group and halogen-substituted or unsubstituted C1-6 alkoxy group), phenoxy group (which may be substituted on the phenyl ring by at least one group selected from a group consisting of a halogen atom, halogen-substituted or unsubstituted C1-6 alkyl group and halogen-substituted or unsubstituted C1-6 alkoxy group) and piperidyl group (which may be substituted on the piperidine ring by at least one phenoxy group as a substituent (which may be substituted by at least one group selected from a group consisting of a halogen atom, halogen-substituted or unsubstituted C1-6 alkyl group and halogen-substituted or unsubstituted C1-6 alkoxy group))) includes a phenyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group, amino group (which may be substituted on the amino group by 1 to 2 groups selected from a group consisting of a C1-6 alkyl group and a phenyl group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group), phenoxy group (which may be substituted on the phenyl ring by 1 to 5, preferably 1 to 3 groups selected from a group consisting of a halogen atom, halogen-substituted or unsubstituted C1-6 alkyl group and halogen-substituted or unsubstituted C1-6 alkoxy group) and piperidyl group (which may be substituted on the piperidine ring by 1 to 3 phenoxy groups, as a substituent, (which may be substituted by 1 to 5, preferably 1 to 3 groups selected from a group consisting of a halogen atom, halogen-substituted or unsubstituted C1-6 alkyl group and halogen-substituted or unsubstituted C1-6 alkoxy group))), for example, a phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 2,3,4,5,6-pentafluorophenyl group, 3,4-difluorophenyl group, 3,5-difluorophenyl group, 2,4-difluorophenyl group, 2,6-difluorophenyl group, 2,3-dichlorophenyl group, 3,4-dichlorophenyl group, 3,5-dichlorophenyl group, 2,4-dichlorophenyl group, 2,6-dichlorophenyl group, 3,4,5-trifluorophenyl group, 3,4,5-trichlorophenyl group, 2,4,6-trifluorophenyl group, 2,4,6-trichlorophenyl group, 2-methylphenyl group, 3-methylphenyl group, 4-methylphenyl group, 2,4-dimethylphenyl group, 2,4,6-trimethylphenyl group, 2-methyl-3-chlorophenyl group, 3-methyl-4-chlorophenyl group, 2-chloro-4-methylphenyl group, 2-methyl-3-fluorophenyl group, 2-trifluoromethylphenyl group, 3-trifluoromethylphenyl group, 3,5-di(trifluoromethyl)phenyl group, 4-trifluoromethylphenyl group, 2-pentafluoroethylphenyl group, 3-pentafluoroethylphenyl group, 4-pentafluoroethylphenyl group, 2-isopropylphenyl group, 3-isopropylphenyl group, 4-isopropylphenyl group, 2-tert-butylphenyl group, 3-tert-butylphenyl group, 4-tert-butylphenyl group, 2-sec-butylphenyl group, 3-sec-butylphenyl group, 4-sec-butylphenyl group, 2-n-heptafluoropropylphenyl group, 3-n-heptafluoropropylphenyl group, 4-n-heptafluoropropylphenyl group, 4-pentylphenyl group, 4-hexylphenyl group, 2-methoxyphenyl group, 3-methoxyphenyl group, 4-methoxyphenyl group, 2-methoxy-3-chlorophenyl group, 2-fluoro-3-methoxyphenyl group, 2-fluoro-4-methoxyphenyl group, 2,6-dimethoxyphenyl group, 2,4,6-trimethoxyphenyl group, 2-trifluoromethoxyphenyl group, 3-trifluoromethoxyphenyl group, 4-trifluoromethoxyphenyl group, 3,5-ditrifluoromethoxyphenyl group, 4-trifluoromethoxyphenyl group, 2-pentafluoroethoxyphenyl group, 3-pentafluoroethoxyphenyl group, 4-pentafluoroethoxyphenyl group, 2-isopropoxyphenyl group, 3-isopropoxyphenyl group, 4-isopropoxyphenyl group, 2-tert-butoxyphenyl group, 3-tert-butoxyphenyl group, 4-tert-butoxyphenyl group, 2-sec-butoxyphenyl group, 3-sec-butoxyphenyl group, 4-sec-butoxyphenyl group, 2-n-heptafluoropropoxyphenyl group, 3-n-heptafluoropropoxyphenyl group, 4-n-heptafluoropropoxyphenyl group, 4-pentyloxyphenyl group, 4-hexyloxyphenyl group, 2-aminophenyl group, 3-aminophenyl group, 4-aminophenyl group, 3-methylaminophenyl group, 3-dimethylaminophenyl group, 4-ethylaminophenyl group, 4-dimethylaminophenyl group, 4-ethylaminophenyl group, 4-diethylaminophenyl group, 4-di-n-propylaminophenyl group, 4-n-propylaminophenyl group, 4-n-butylaminophenyl group, 4-di-n-butylaminophenyl group, 4-n-pentylaminophenyl group, 4-di-n-pentylaminophenyl group, 4-n-hexylaminophenyl group, 4-di-n-hexylaminophenyl group, 4-phenylaminophenyl group, 4-(2-fluorophenylamino)phenyl group, 4-(3-fluorophenylamino)phenyl group, 4-(4-fluorophenylamino)phenyl group, 4-(2,3,4,5,6-pentafluorophenylamino)phenyl group, 4-(2,4-difluorophenylamino)phenyl group, 4-(3,4-difluorophenylamino)phenyl group, 4-(3,5-difluorophenylamino)phenyl group, 4-(2-chlorophenylamino)phenyl group, 4-(3-chlorophenylamino)phenyl group, 4-(4-chlorophenylamino)phenyl group, 4-(2-bromophenylamino)phenyl group, 4-(3-bromophenylamino)phenyl group, 4-(4-bromophenylamino)phenyl group, 4-(2,3-dichlorophenylamino)phenyl group, 4-(2,4-dichlorophenylamino)-phenyl group, 4-(2,4,6-trichlorophenylamino)phenyl group, 4-(3,5-dichlorophenylamino)phenyl group, 4-(2-methylphenylamino)phenyl group, 4-(3-methylphenylamino)phenyl group, 4-(4-methylphenylamino)phenyl group, 4-(2-ethylphenylamino)phenyl group, 4-(3-ethylphenylamino)phenyl group, 4-(4-ethylphenylamino)-phenyl group, 4-(4-n-propylphenylamino)phenyl group, 4-(4-tert-butylphenylamino)phenyl group, 4-(4-n-butylphenylamino)phenyl group, 4-(2-trifluoromethylphenylamino)phenyl group, 4-(3-trifluoromethylphenylamino)phenyl group, 4-(4-trifluoromethylphenylamino)-phenyl group, 4-(2-pentafluoroethylphenylamino)phenyl group, 4-(3-pentafluoroethylphenylamino)phenyl group, 4-(2,3-dimethylphenylamino)phenyl group, 4-(3,4,5-trimethylphenylamino)phenyl group, 4-(4-pentylphenylamino)phenyl group, 4-(4-hexylphenylamino)phenyl group, 4-(2-trifluoromethoxyphenylamino)phenyl group, 4-(3-trifluoromethoxyphenylamino)phenyl group, 4-(3-methoxyphenylamino)phenyl group, 4-(2,4-dimethoxyphenylamino)phenyl group, 4-(2,4,6-trimethoxyphenylamino)phenyl group, 4-(4-trifluoromethoxyphenylamino)phenyl group, 4-(2-pentafluoroethoxyphenylamino)-phenyl group, 4-(3-pentafluoroethoxyphenylamino)phenyl group, 4-(4-pentafluoroethoxyphenylamino)phenyl group, 3-(N-methyl-N-phenylamino)phenyl group, 2-phenoxyphenyl group, 3-phenoxyphenyl group, 4-phenoxyphenyl group, 2-(2-chlorophenoxy)phenyl group, 2,4-diphenoxyphenyl group, 2-(3-chlorophenoxy)phenyl group, 2-(4-chlorophenoxy)phenyl group, 3-(2-chlorophenoxy)phenyl group, 3-(3-chlorophenoxy)phenyl group, 3-(4-chlorophenoxy)-phenyl group, 4-(2-chlorophenoxy)phenyl group, 4-(2,3-dichlorophenoxy)phenyl group, 4-(2,4,6-trichlorophenoxy)phenyl group, 2-(2-trifluoromethylphenoxy)-phenyl group, 2-(3-trifluoromethylphenoxy)phenyl group, 2-(4-trifluoromethylphenoxy)phenyl group, 3-(2-trifluoromethylphenoxy)phenyl group, 3-(3-trifluoromethylphenoxy)phenyl group, 3-(2,3,4,5,6-pentafluoromethylphenoxy)phenyl group, 4-(2-trifluoromethylphenoxy)phenyl group, 4-(3- trifluoromethylphenoxy)-phenyl group, 4-(2,4-dimethylphenoxy)phenyl group, 4-(2,4,6-trimethylphenoxy)phenyl group, 4-(3-trifluoromethylphenoxy)phenyl group, 4-(4-trifluoromethylphenoxy)phenyl group, 2-(2-trifluoromethoxyphenoxy)-phenyl group, 2-(3-trifluoromethoxyphenoxy)phenyl group, 2-(4-trifluoromethoxyphenoxy)phenyl group, 2-(4-methoxyphenoxy)phenyl group, 2-(2,4-dimethoxyphenoxy)-phenyl group, 2-(2,4,6-trimethoxyphenoxy)phenyl group, 3-(2-trifluoromethoxyphenoxy)phenyl group, 3-(3-trifluoromethoxyphenoxy)phenyl group, 3-(4-trifluoromethoxyphenoxy)phenyl group, 4-(2-trifluoromethoxyphenoxy)phenyl group, 4-(3-trifluoromethoxyphenoxy)-phenyl group, 4-(4-trifluoromethoxyphenoxy)phenyl group, 2-(4-phenoxypiperidin-1-yl)phenyl group, 3-(4-phenoxypiperidin-1-yl)phenyl group, 4-(4-phenoxypiperidin-1-yl)phenyl group, 2-[4-(4-chlorophenoxy)-piperidin-1-yl]phenyl group, 4-[4-(4-chlorophenoxy)-piperidin-1-yl]phenyl group, 3-[4-(2,4,6-trichlorophenoxy)piperidin-1-yl]phenyl group, 4-[4-(3,4-dichlorophenoxy)piperidin-1-yl]phenyl group, 4-[4-(2,3,4,5,6-pentafluorophenoxy)piperidin-1-yl]phenyl group, 4-[4-(4-bromophenoxy)piperidin-1-yl]phenyl group, 3-[4-(4-chlorophenoxy)piperidin-1-yl]phenyl group, 2-[4-(4-methylphenoxy)piperidin-1-yl]phenyl group, 2-[4-(3,4-dimethylphenoxy)piperidin-1-yl]phenyl group, 2-[4-(3,4,5-trimethylphenoxy)piperidin-1-yl]phenyl group, 3-[4-(4-trifluoromethylphenoxy)-piperidin-1-yl]phenyl group, 4-[4-(4-trifluoromethylphenoxy)piperidin-1-yl]phenyl group, 3-[4-(4-pentafluoroethylphenoxy)piperidin-1-yl]phenyl group, 4-[4-(4-pentafluoroethylphenoxy)piperidin-1-yl]phenyl group, 2-[4-(4-trifluoromethoxyphenoxy)piperidin-1-yl]phenyl group, 3-[4-(4-trifluoromethoxyphenoxy)piperidin-1-yl]phenyl group, 4-[4-(4-methoxyphenoxy)piperidin-1-yl]phenyl group, 4-[4-(2,4-dimethoxyphenoxy)piperidin-1-yl]phenyl group, 4-[4-(2,4,6-trimethoxyphenoxy)piperidin-1-yl]phenyl group, 4-[4-(4-trifluoromethoxyphenoxy)piperidin-1-yl]phenyl group, 2-[4-(4-pentafluoroethoxyphenoxy)piperidin-1-yl]phenyl group, 4-[4-(4-pentafluoroethoxyphenoxy)piperidin-1-yl]phenyl group, (3,4-diphenoxypiperidin-1-yl)phenyl group, piperidin-1-ylphenyl group, (3,4,5-triphenoxypiperidin-1-yl)phenyl group, piperidin-4-ylphenyl group or the like.

A piperazinyl C1-6 alkyl group (which may be substituted on the piperazine ring by at least one group selected from a group consisting of a C1-6 alkoxycarbonyl group and phenyl C1-6 alkoxycarbonyl group which may be substituted on the phenyl ring by 1 to 3 groups selected from a group consisting of a halogen atom, halogen-substituted or unsubstituted C1-6 alkyl group or halogen-substituted or unsubstituted C1-6 alkoxy group and phenyl group) includes a piperazinyl C1-6 alkyl group (which may be substituted on the piperazin ring by 1 to 3 groups selected from a group consisting of a C1-6 alkoxycarbonyl group and a phenyl C1-6 alkoxycarbonyl group which may be substituted on the phenyl ring by 1 to 3 groups selected from a group consisting of a halogen atom, halogen-substituted or unsubstituted C1-6 alkyl group or halogen-substituted or unsubstituted C1-6 alkoxy group and phenyl group), for example, a 1-piperazinylmethyl group, 2-(2-piperazinyl)ethyl group, 1-(3-piperazinyl)ethyl group, 3-(4-piperazinyl)propyl group, 4-(1-piperazinyl)butyl group, 5-(2-piperazinyl)pentyl group, 6-(3-piperazinyl)hexyl group, 4-methoxycarbonyl-1-piperazinylmethyl group, 2-(4-methoxycarbonyl-1-piperazinyl)ethyl group, 3-(4-methoxycarbonyl-1-piperazinyl)propyl group, 4-(4-methoxycarbonyl-1-piperazinyl)butyl group, 5-(4-methoxycarbonyl-1-piperazinyl)pentyl group, 6-(4-methoxycarbonyl-1-piperazinyl)hexyl group, 4-ethoxycarbonyl-1-piperazinylmethyl group, 2-(4-ethoxycarbonyl-1-piperazinyl)ethyl group, 3-(4-ethoxycarbonyl-1-piperazinyl)propyl group, 4-(4-ethoxycarbonyl-1-piperazinyl)butyl group, 5-(4-ethoxycarbonyl-1-piperazinyl)pentyl group, 6-(4-ethoxycarbonyl-1-piperazinyl)hexyl group, 4-tert-butoxycarbonyl-1-piperazinylmethyl group, 2-(4-tert-butoxycarbonyl-1-piperazinyl)ethyl group, 3-(4-tert-butoxycarbonyl-1-piperazinyl)propyl group, 4-(4-tert-butoxycarbonyl-1-piperazinyl)butyl group, 5-(4-tert-butoxycarbonyl-1-piperazinyl)pentyl group, 6-(4-tert-butoxycarbonyl-1-piperazinyl)hexyl group, 2-(4-biphenylylmethoxycarbonyl-1-piperazinyl)ethyl group, 3-(4-biphenylylmethoxycarbonyl-1-piperazinyl)propyl group, 4-(4-biphenylylmethoxycarbonyl-1-piperazinyl)butyl group, 5-(4-biphenylylmethoxycarbonyl-1-piperazinyl)pentyl group, 6-(4-biphenylylmethoxycarbonyl-1-piperazinyl)hexyl group, 2-(4-benzyloxycarbonyl-1-piperazinyl)ethyl group, 3-(4-benzyloxycarbonyl-1-piperazinyl)propyl group, 4-(4-benzyloxycarbonyl-1-piperazinyl)butyl group, 5-(4-benzyloxycarbonyl-1-piperazinyl)pentyl group, 6-4-(4-benzyloxycarbonyl)-1-piperazinyl)hexyl group, 2-(4-(2-fluorobenzyloxycarbonyl)-1-piperazinyl)ethyl group, 3-(4-(2-fluorobenzyloxycarbonyl)-1-piperazinyl)propyl group, 4-(4-(2,3-difluorobenzyloxycarbonyl)-1-piperazinyl)butyl group, 5-(4-(2-fluorobenzyloxycarbonyl)-1-piperazinyl)pentyl group, 6-(4-(4-fluorobenzyloxycarbonyl)-1-piperazinyl)hexyl group, 3-(4-(3-fluorobenzyloxycarbonyl)-1-piperazinyl)propyl group, 4-(4-(3-fluorobenzyloxycarbonyl)-1-piperazinyl)butyl group, 5-(4-(3-fluorobenzyloxycarbonyl)-1-piperazinyl)pentyl group, 3-(4-(4-fluorobenzyloxycarbonyl)-1-piperazinyl)propyl group, 4-(4-(4-fluorobenzyloxycarbonyl)-1-piperazinyl)butyl group, 5-(4-(4-fluorobenzyloxycarbonyl)-1-piperazinyl)pentyl group, 6-(4-(4-fluorobenzyloxycarbonyl)-1-piperazinyl)hexyl group, 2-(4-(2,3-dichlorobenzyloxycarbonyl)-1-piperazinyl)ethyl group, 3-(4-(2-chlorobenzyloxycarbonyl)-1-piperazinyl)propyl group, 4-(4-(2-chlorobenzyloxycarbonyl)-1-piperazinyl)butyl group, 5-(4-(2,4,6-trichlorobenzyloxycarbonyl)-1-piperazinyl)pentyl group, 6-(4-(2-chlorobenzyloxycarbonyl)-1-piperazinyl)hexyl group, 2-(4-(3-chlorobenzyloxycarbonyl)-1-piperazinyl)ethyl group, 3-(4-(3-chlorobenzyloxycarbonyl)-1-piperazinyl)propyl group, 4-(4-(3-trichlorobenzyloxycarbonyl)-1-piperazinyl)butyl group, 5-(4-(3-chlorobenzyloxycarbonyl)-1-piperazinyl)pentyl group, 6-(3-chloro-4-methylbenzyloxycarbonyl-1-piperazinyl)hexyl group, 2-(4-(4-chlorobenzyloxycarbonyl)-1-piperazinyl)ethyl group, 3-(4-(4-chlorobenzyloxycarbonyl)-1-piperazinyl)propyl group, 4-(4-(4-chloro-3-methoxybenzyloxycarbonyl)-1-piperazinyl)butyl group, 5-(4-(4-chlorobenzyloxycarbonyl)-1-piperazinyl)pentyl group, 6-(4-chlorobenzyloxycarbonyl-1-piperazinyl)hexyl group, 2-(4-(2-methylbenzyloxycarbonyl)-1-piperazinyl)methyl group, 2-(4-(2,4-dimethylbenzyloxycarbonyl)-1-piperazinyl)methyl group, 2-(4-(2,4,6-trimethylbenzyloxycarbonyl)-1-piperazinyl)methyl group, 2-(4-(2-trifluoromethylbenzyloxycarbonyl)-1-piperazinyl)ethyl group, 3-(4-(3,5-ditrifluoromethylbenzyloxycarbonyl)-1-piperazinyl)propyl group, 4-(4-(2-trifluoromethylbenzyloxycarbonyl)-1-piperazinyl)butyl group, 5-(4-(2-trifluoromethylbenzyloxycarbonyl)-1-piperazinyl)pentyl group, 6-(4-(2-trifluoromethylbenzyloxycarbonyl)-1-piperazinyl)hexyl group, 3-(4-(3-trifluoromethylbenzyloxycarbonyl)-1-piperazinyl)propyl group, 4-(4-(3-trifluoromethylbenzyloxycarbonyl)-1-piperazinyl)butyl group, 5-(4-(3-trifluoromethylbenzyloxycarbonyl)-1-piperazinyl)pentyl group, 3-(4-(4-trifluoromethylbenzyloxycarbonyl)-1-piperazinyl)propyl group, 4-(4-(4-trifluoromethylbenzyloxycarbonyl)-1-piperazinyl)butyl group, 5-(4-(4-trifluoromethylbenzyloxycarbonyl)-1-piperazinyl)pentyl group, 6-(4-(4-trifluoromethylbenzyloxycarbonyl)-1-piperazinyl)hexyl group, 2-(4-(3,5-ditrifluoromethylbenzyloxycarbonyl)-1-piperazinyl)ethyl group, 2-(4-(2-methoxybenzyloxycarbonyl)-1-piperazinyl)methyl group, 2-(4-(2,4-dimethoxybenzyloxycarbonyl)-1-piperazinyl)methyl group, 2-(4-(2,4,6-trimethoxybenzyloxycarbonyl)-1-piperazinyl)methyl group, 3-(4-(2-trifluoromethoxybenzyloxycarbonyl)-1-piperazinyl)propyl group, 4-(4-(2-trifluoromethoxybenzyloxycarbonyl)-1-piperazinyl)butyl group, 5-(4-(2-trifluoromethoxybenzyloxycarbonyl)-1-piperazinyl)pentyl group, 6-(4-(2-trifluoromethoxybenzyloxycarbonyl)-1-piperazinyl)hexyl group, 3-(4-(3-trifluoromethoxybenzyloxycarbonyl)-1-piperazinyl)propyl group, 4-(4-(3-trifluoromethoxybenzyloxycarbonyl)-1-piperazinyl)butyl group, 5-(4-(3-trifluoromethoxybenzyloxycarbonyl)-1-piperazinyl)pentyl group, 3-(4-(4-trifluoromethoxybenzyloxycarbonyl)-1-piperazinyl)propyl group, 4-(4-(4-trifluoromethoxybenzyloxycarbonyl)-1-piperazinyl)butyl group, 5-(4-(4-trifluoromethoxybenzyloxycarbonyl)-1-piperazinyl)pentyl group, 6-(4-(4-trifluoromethoxybenzyloxycarbonyl)-1-piperazinyl)hexyl group, (3,4-diethoxycarbonyl-1-piperazinyl)methyl group, 4-phenylmethoxycarbonyl-2,5-dimethoxycarbonyl-1-piperazinyl)methyl group or the like.

A piperazinylcarbonyl C1-6 alkyl group (which may be substituted on the piperazine ring by at least one group selected from a group consisting of a C1-6 alkoxycarbonyl group, phenyl C1-6 alkoxycarbonyl group which may have a halogen-substituted or unsubstituted C1-6 alkyl group as a substituent on the phenyl ring and phenyl C1-6 alkyl group which may have at least one group selected from a group consisting of a halogen-substituted or unsubstituted C1-6 alkyl group and phenyl group as a substituent on the phenyl ring) includes a piperazinylcarbonyl C1-6 alkyl group (which may be substituted on the piperazine ring by 1 to 3 groups selected from a group consisting of a C1-6 alkoxycarbonyl group, phenyl C1-6 alkoxycarbonyl group which may have 1 to 3 groups halogen-substituted or unsubstituted C1-6 alkyl groups as a substituent on the phenyl ring and phenyl C1-6 alkyl group which may have 1 to 3 groups selected from a group consisting of a halogen-substituted or unsubstituted C1-6 alkyl group and phenyl group as a substituent on the phenyl ring), for example, a 1-piperazinylcarbonylmethyl group, 2-(2-piperazinylcarbonyl)ethyl group, 1-(3-piperazinylcarbonyl)ethyl group, 3-(4-piperazinylcarbonyl)propyl group, 4-(1-piperazinylcarbonyl)butyl group, 5-(2-piperazinylcarbonyl)pentyl group, 6-(3-piperazinylcarbonyl)hexyl group, 4-tert-butoxycarbonyl-1-piperazinylcarbonylmethyl group, 2-(4-tert-butoxycarbonyl-1-piperazinylcarbonyl)ethyl group, 3-(4-tert-butoxycarbonyl-1-piperazinylcarbonyl)propyl group, 4-(4-tert-butoxycarbonyl-1-piperazinylcarbonyl)butyl group, 5-(4-tert-butoxycarbonyl-1-piperazinyl-carbonyl)pentyl group, 6-(4-tert-butoxycarbonyl-1-piperazinylcarbonyl)hexyl group, 4-ethoxycarbonyl-1-piperazinylcarbonylmethyl group, 2-(4-ethoxycarbonyl-1-piperazinylcarbonyl)ethyl group, 3-(4-n-propoxycarbonyl-1-piperazinylcarbonyl)propyl group, 4-(4-ethoxycarbonyl-1-piperazinylcarbonyl)butyl group, 5-(4-n-pentyloxycarbonyl-1-piperazinylcarbonyl)pentyl group, 6-(4-n-hexyloxycarbonyl-1-piperazinylcarbonyl)hexyl group, 4-(benzyloxycarbonyl)-1-piperazinylcarbonylmethyl group, 2-(4-benzyloxycarbonyl)-1-piperazinylcarbonyl)ethyl group, 3-(4-(benzyloxycarbonyl)-1-piperazinylcarbonyl)propyl group, 4-(4-(benzyloxycarbonyl)-1-piperazinylcarbonyl)butyl group, 5-(4-benzyloxycarbonyl)-1-piperazinylcarbonyl)pentyl group, 6-(4-(benzyloxycarbonyl)-1-piperazinylcarbonyl)hexyl group, 4-(4-methylbenzyloxycarbonyl)-1-piperazinylcarbonyl)methyl group, 4-(2,4-dimethylbenzyloxycarbonyl)-1-piperazinylcarbonyl)methyl group, 4-(2,4,6-trimethylbenzyloxycarbonyl)-1-piperazinylcarbonyl)methyl group, 4-(4-trifluoromethylbenzyloxycarbonyl)-1-piperazinylcarbonylmethyl group, 2-(4-(3,5-ditrifluoromethylbenzyloxycarbonyl)-1-piperazinylcarbonyl)ethyl group, 3-(4-(4-trifluoromethylbenzyloxycarbonyl)-1-piperazinylcarbonyl)propyl group, 4-(4-(4-trifluoromethylbenzyloxycarbonyl)-1-piperazinylcarbonyl)butyl group, 5-(4-(4-trifluoromethylbenzyloxycarbonyl)-1-piperazinylcarbonyl)pentyl group, 6-(4-(4-trifluoromethylbenzyloxycarbonyl)-1-piperazinylcarbonyl)hexyl group, 4-(2-phenylethoxycarbonyl)-1-piperazinylcarbonyl)methyl group, 2-{4-[2-(4-trifluoromethylphenyl)ethoxycarbonyl]-1-piperazinylcarbonyl}ethyl group, 3-{4-[2-(4-trifluoromethylphenyl)-ethoxycarbonyl]-1-piperazinylcarbonyl}propyl group, 4-{4-[2-(4-methylphenyl)ethoxycarbonyl]-1-piperazinylcarbonyl}butyl group, 5-{4-[2-(2,4,6-trimethylphenyl)ethoxycarbonyl]-1-piperazinylcarbonyl}pentyl group, 6-{4-[2-(4-trifluoromethylphenyl)ethoxycarbonyl]-1-piperazinylcarbonyl}hexyl group, 4-benzyl-1-piperazinylcarbonylmethyl group, 4-(4-trifluoromethylbenzyl)-1-piperazinylcarbonylmethyl group, 2-(4-(4-trifluoromethylbenzyl)-1-piperazinylcarbonyl)ethyl group, 3-(4-(4-trifluoromethylbenzyl)-1-piperazinylcarbonyl)propyl group, 4-(4-methylbenzyl)-1-piperazinylcarbonylmethyl group, 4-(2,4-dimethylbenzyl)-1-piperazinylcarbonylmethyl group, 4-(2,4,6-trimethylbenzyl)-1-piperazinylcarbonylmethyl group, 4-(4-(4-trifluoromethylbenzyl)-1-piperazinylcarbonyl)-butyl group, 5-(4-(3,5-ditrifluoromethylbenzyl)-1-piperazinylcarbonyl)pentyl group, 6-(4-(4-trifluoromethylbenzyl)-1-piperazinylcarbonyl)hexyl group, 4-(4-biphenylylmethyl)-1-piperazinylcarbonylmethyl group, 2-(4-(4-biphenylylmethyl)-1-piperazinylcarbonyl)ethyl group, 3-(4-(4-biphenylylmethyl)-1-piperazinylcarbonyl)propyl group, 4-(4-(4-biphenylylmethyl)-1-piperazinylcarbonyl)butyl group, 5-(4-(4-biphenylylmethyl)-1-piperazinylcarbonyl)pentyl group, 6-(4-(4-biphenylylmethyl)-1-piperazinylcarbonyl)hexyl group, 2,4-dibenzyl-1-piperazinylcarbonylmethyl group, 4-benzyloxycarbonyl-3-benzyl-1-piperazinylcarbonylmethyl group, 4-ethoxycarbonyl-2,6-dibenzyl-1-piperazinylcarbonylmethyl group or the like.

A phenylcarbamoyl C1-6 alkyl group which may have at least one halogen-substituted or unsubstituted C1-6 alkyl group as a substituent on the phenyl ring includes a phenylcarbamoyl C1-6 alkyl group which may have 1 to 3 halogen-substituted or unsubstituted C1-6 alkyl groups as a substituent on the phenyl ring, for example, a 4-methylphenylcarbamoylmethyl group, 2,4-dimethylphenylcarbamoylmethyl group, 2,4,6-trimethylphenylcarbamoylmethyl group, 3-ethylphenylcarbamoylmethyl group, 2-n-propylphenylcarbamoylmethyl group, 4-n-butylphenylcarbamoylmethyl group, 4-n-pentylphenylcarbamoylmethyl group, 4-n-hexylphenylcarbamoylmethyl group, 4-trifluoromethylphenylcarbamoylmethyl group, 2-(4-trifluoromethylphenylcarbamoyl)ethyl group, 3-(3,5-ditrifluoromethylphenylcarbamoyl)propyl group, 4-(4- trifluoromethylphenylcarbamoyl)butyl group, 5-(4-trifluoromethylphenylcarbamoyl)pentyl group, 6-(4-trifluoromethylphenylcarbamoyl)hexyl group or the like.

Examples of a benzoxazolyl C1-6 alkyl group (which may have at least one oxo group as a substituent on the benzoxazole ring) include a benzoxazol-2-ylmethyl group, benzoxazol-4-ylmethyl group, benzoxazol-5-ylmethyl group, benzoxazol-6-ylmethyl group, benzoxazol-7-ylmethyl group, 2-(benzoxazol-2-yl)ethyl group, 1-(benzoxazol-4-yl)ethyl group, 3-(benzoxazol-5-yl)propyl group, 4-(benzoxazol-6-yl)butyl group, 5-(benzoxazol-7-yl)pentyl group, 6-(benzoxazol-2-yl)hexyl group, 2-methyl-3-(benzoxazol-4-yl)propyl group, 1,1-dimethyl-2-(benzoxazol-5-yl)ethyl group, (2,3-dihydro-2-oxo-benzoxazol-3-yl)methyl group, (2,3-dihydro-2-oxo-benzoxazol-4-yl)methyl group, (2,3-dihydro-2-oxo-benzoxazol-5-yl)methyl group, (2,3-dihydro-2-oxo-benzoxazol-6-yl)methyl group, (2,3-dihydro-2-oxo-benzoxazol-7-yl)methyl group or the like.

A phenylthiocarbamoyl group which may be substituted on the phenyl ring by at least one halogen atom as a substituent includes a phenylthiocarbamoyl group which may be substituted on the phenyl ring by 1 to 5 halogen atoms as a substituent, for example, a phenylthiocarbamoyl group, 4-fluorophenylthiocarbamoyl group, 4-chlorophenylthiocarbamoyl group, 4-bromophenylthiocarbamoyl group, 3,4-dichlorophenylthiocarbamoyl group, 3,4,6-trichlorophenylthiocarbamoyl group, 2,3,4,5,6-pentafluorophenylthiocarbamoyl group or the like.

Examples of a C1-8 alkoxycarbonyl group include a methoxycarbonyl group, ethoxycarbonyl group, n-propoxycarbonyl group, n-pentyloxycarbonyl group, n-hexyloxycarbonyl group, n-heptyloxycarbonyl group, n-octyloxycarbonyl group or the like.

A phenyl C1-6 alkoxycarbonyl group (which may be substituted on the phenyl ring by at least one group selected from a group consisting of a halogen atom, C1-6 alkoxycarbonyl group, amino group which may have a C1-6 alkoxycarbonyl group as a substituent, halogen-substituted or unsubstituted C1-6 alkyl group, halogen-substituted or unsubstituted C1-6 alkoxy group, nitro group and C1-6 alkylthio group) includes a phenyl C1-6 alkoxycarbonyl group (which may be substituted on the phenyl ring by 1 to 5, preferably 1 to 3 groups selected from a group consisting of a halogen atom, C1-6 alkoxycarbonyl group, amino group which may have a C1-6 alkoxycarbonyl group as a substituent, halogen-substituted or unsubstituted C1-6 alkyl group, halogen-substituted or unsubstituted C1-6 alkoxy group, nitro group and C1-6 alkylthio group), for example, a benzyloxycarbonyl group, 1-phenethyloxyoxycarbonyl group, 2-phenethyloxyoxycarbonyl group, 3-phenylpropoxycarbonyl group, 2-phenylpropoxycarbonyl group, 4-phenylbutoxycarbonyl group, 5-phenylpentyloxycarbonyl group, 4-phenylpentyloxycarbonyl group, 6-phenylhexyloxycarbonyl group, 2-fluorobenzyloxycarbonyl group, 3-fluorobenzyloxycarbonyl group, 4-fluorobenzyloxycarbonyl group, 2-chlorobenzyloxycarbonyl group, 3-chlorobenzyloxycarbonyl group, 4-chlorobenzyloxycarbonyl group, 2-bromobenzyloxycarbonyl group, 3-bromobenzyloxycarbonyl group, 4-bromobenzyloxycarbonyl group, 2-iodobenzyloxycarbonyl group, 3-iodobenzyloxycarbonyl group, 4-iodobenzyloxycarbonyl group, 2,3-difluorobenzyloxycarbonyl group, 3,4-difluorobenzyloxycarbonyl group, 3,5-difluorobenzyloxycarbonyl group, 2,4-difluorobenzyloxycarbonyl group, 2,6-difluorobenzyloxycarbonyl group, 2,4,6-trifluorobenzyloxycarbonyl group, 2,3,4,5,6-pentafluorobenzyloxycarbonyl group, 3,4,5-trifluorobenzyloxycarbonyl group, 2,3-dichlorobenzyloxycarbonyl group, 3,4-dichlorobenzyloxycarbonyl group, 3,5-dichlorobenzyloxycarbonyl group, 2,4-dichlorobenzyloxycarbonyl group, 2,6-dichlorobenzyloxycarbonyl group, 2,4,6-trichlorobenzyloxycarbonyl group, 3,4,5-trichlorobenzyloxycarbonyl group, 2-trifluoromethylbenzyloxycarbonyl group, 3-methylbenzyloxycarbonyl group, 2,4-dimethylbenzyloxycarbonyl group, 2,4,6-trimethylbenzyloxycarbonyl group, 3-difluoromethylbenzyloxycarbonyl group, 4-difluoromethylbenzyloxycarbonyl group, 4-chloro-3-difluoromethylbenzyloxycarbonyl group, 3-chloro-4-difluoromethylbenzyloxycarbonyl group, 3-bromo-4-difluoromethylbenzyloxycarbonyl group, 3,5-difluoro-4-difluoromethylbenzyloxycarbonyl group, 3,5-ditrifluoromethylbenzyloxycarbonyl group, 3-trifluoromethylbenzyloxycarbonyl group, 4-trifluoromethylbenzyloxycarbonyl group, 4-fluoro-3-trifluoromethylbenzyloxycarbonyl group, 3-fluoro-4-trifluoromethylbenzyloxycarbonyl group, 2-pentafluoroethylbenzyloxycarbonyl group, 4-chloro-3-pentafluoroethylbenzyloxycarbonyl group, 3-chloro-4-pentafluoroethylbenzyloxycarbonyl group, 2-pentafluoroethylbenzyloxycarbonyl group, 3-pentafluoroethylbenzyloxycarbonyl group, 4-pentafluoroethylbenzyloxycarbonyl group, 3-methoxybenzyloxycarbonyl group, 2,4-dimethoxybenzyloxycarbonyl group, 2,4,6-trimethoxybenzyloxycarbonyl group, 2-trifluoromethoxybenzyloxycarbonyl group, 3-trifluoromethoxybenzyloxycarbonyl group, 4-trifluoromethoxybenzyloxycarbonyl group, 4-fluoro-3-trifluoromethoxybenzyloxycarbonyl group, 3-fluoro-4-trifluoromethoxybenzyloxycarbonyl group, 2-pentafluoroethoxybenzyloxycarbonyl group, 3-pentafluoroethoxybenzyloxycarbonyl group, 4-pentafluoroethoxybenzyloxycarbonyl group, 3-chloro-4-trifluoromethoxybenzyloxycarbonyl group, 3-chloro-4-pentafluoroethoxybenzyloxycarbonyl group, 2-(2-trifluoromethylphenyl)ethoxycarbonyl group, 2-(3-trifluoromethylphenyl)ethoxycarbonyl group, 2-(4-trifluoromethylphenyl)ethoxycarbonyl group, 2-(4-trifluoromethoxyphenyl)ethoxycarbonyl group, 2-(2-pentafluoroethoxyphenyl)ethoxycarbonyl group, 2-(3-pentafluoroethoxyphenyl)ethoxycarbonyl group, 2-(4-pentafluoroethoxyphenyl)ethoxycarbonyl group, 3-(2-trifluoromethylphenyl)propoxycarbonyl group, 3-(3-trifluoromethylphenyl)propoxycarbonyl group, 3-(4-trifluoromethylphenyl)propoxycarbonyl group, 3-(2-trifluoromethylphenyl)propoxycarbonyl group, 3-(3-trifluoromethylphenyl)propoxycarbonyl group, 3-(4-trifluoromethoxyphenyl)propoxycarbonyl group, 3-(3-trifluoromethoxyphenyl)propoxycarbonyl group, 3-(4-pentafluoroethoxyphenyl)propoxycarbonyl group, 4-(3-pentafluoroethoxyphenyl)propoxycarbonyl group, 4-(3-pentafluoroethoxyphenyl)butoxycarbonyl group, 5-(4-trifluoromethylphenyl)pentyloxycarbonyl group, 4-(4-trifluoromethylphenyl)pentyloxycarbonyl group, 4-(4-trifluoromethoxyphenyl)pentyloxycarbonyl group, 6-(3-trifluoromethylphenyl)hexyloxycarbonyl group, 6-(4-trifluoromethylphenyl)hexyloxycarbonyl group, 6-(4-trifluoromethoxyphenyl)hexyloxycarbonyl group, 2-methylthiobenzyloxycarbonyl group, 3-methylthiobenzyloxycarbonyl group, 4-methylthiobenzyloxycarbonyl group, 2-($^2$-methylthiophenyl)ethoxycarbonyl group, 2-(3-methylthiophenyl)ethoxycarbonyl group, 2-(4-methylthiophenyl)ethoxycarbonyl group, 3-(4-methylthiophenyl)propoxycarbonyl group, 4-(4-methylthiophenyl)butoxycarbonyl group, 5-(4-methylthiophenyl)pentyloxycarbonyl group, 6-(4-methylthiophenyl)hexyloxycarbonyl group, 2-methoxycarbonylbenzyloxycarbonyl group, 3-methoxycarbonylbenzyloxycarbonyl group, 4-methoxycarbonylbenzyloxycarbonyl group, 2-(2-methoxycarbonylphenyl)ethoxycarbonyl group, 2-(3-methoxycarbonylphenyl)ethoxycarbonyl group, 2-(4-methoxycarbonylphenyl)ethoxycarbonyl group, 3-(4-methoxycarbonylphenyl)propoxycarbonyl group, 4-(4-methoxycarbonylphenyl)butoxycarbonyl group, 5-(4-methoxycarbonylphenyl)pentyloxycarbonyl group, 6-(4-methoxycarbonylphenyl)hexyloxycarbonyl group, 4-n-pentyloxycarbonylaminobenzyloxycarbonyl group, 4-ethoxycarbonylaminobenzyloxycarbonyl group, 4-propoxycarbonylaminobenzyloxycarbonyl group, 4-tert-butoxycarbonylaminobenzyloxycarbonyl group, 2-(n-hexyloxycarbonylaminophenyl)ethoxycarbonyl group, 3-(4-tert-butoxycarbonylaminophenyl)propoxycarbonyl group, 4-(4-tert-butoxycarbonylaminophenyl)butoxycarbonyl group, 5-(4-tert-butoxycarbonylaminophenyl)pentyloxycarbonyl group, 6-(4-tert-butoxycarbonylaminophenyl)-hexyloxycarbonyl group, 2-nitrobenzyloxycarbonyl group, 3-nitrobenzyloxycarbonyl group, 4-nitrobenzyloxycarbonyl group, 2-(2-nitrophenyl)ethoxycarbonyl group, 2-(3-nitrophenyl)ethoxycarbonyl group, 2-(4-nitrophenyl)ethoxycarbonyl group, 3-(2,4-dinitrophenyl)-propoxycarbonyl group, 4-(4-nitrophenyl)butoxycarbonyl group, 5-(4-nitrophenyl)pentyloxycarbonyl group, 6-(2,4,6-trinitrophenyl)hexyloxycarbonyl group, 2-aminobenzyloxycarbonyl group, 3-aminobenzyloxycarbonyl group, 4-aminobenzyloxycarbonyl group, 2-(2-aminophenyl)ethoxycarbonyl group, 2-(2,3-diaminophenyl)-ethoxycarbonyl group, 2-(4-aminophenyl)ethoxycarbonyl group, 3-(2,4,6-triaminophenyl) propoxycarbonyl group, 4-(4-aminophenyl)butoxycarbonyl group, 5-(4-aminophenyl)pentyloxycarbonyl group, 6-(4-aminophenyl)-hexyloxycarbonyl group, 2-ethoxycarbonylbenzyloxycarbonyl group, 3-ethoxycarbonylbenzyloxycarbonyl group, 4-methoxycarbonylbenzyloxycarbonyl group, 2-(2-ethoxycarbonylphenyl)ethoxycarbonyl group, 2-(3-ethoxycarbonylphenyl)ethoxycarbonyl group, 2-(4-ethoxycarbonylphenyl)ethoxycarbonyl group, 3-(4-n-butoxycarbonylphenyl)propoxycarbonyl group, 4-(4-n-pentyloxycarbonylphenyl)butoxycarbonyl group, 5-(4-n-hexyloxycarbonylphenyl)pentyloxycarbonyl group, 6-(4-n-ethoxycarbonylphenyl)hexyloxycarbonyl group or the like.

A benzhydryloxycarbonyl group (which may be substituted on the phenyl ring by at least one halogen atom) includes a benzhydryloxycarbonyl group (which may be substituted on the phenyl ring by 1 to 4 halogen atoms), for example, a benzhydryloxycarbonyl group, 3-fluorobenzhydryloxycarbonyl group, 4-fluorobenzhydryloxycarbonyl group, 3,3'-difluorobenzhydryloxycarbonyl group, 3,4'-difluorobenzhydryloxycarbonyl group, 4,4'-difluorobenzhydryloxycarbonyl group, 3,4,4'-trifluorobenzhydryloxycarbonyl group, 3,3',4,4'-tetrafluorobenzhydryloxycarbonyl group, 2,2',4,4'-tetrafluorobenzhydryloxycarbonyl group, 3,3',5,5'-tetrafluorobenzhydryloxycarbonyl group, 3-chlorobenzhydryloxycarbonyl group, 4-chlorobenzhydryloxycarbonyl group, 3,3'-dichlorobenzhydryloxycarbonyl group, 3,4'-dichlorobenzhydryloxycarbonyl group, 4,4'-dichlorobenzhydryloxycarbonyl group, 3,4,4'-trichlorobenzhydryloxycarbonyl group, 3,3',4,4'-tetrachlorobenzhydryloxycarbonyl group, 2,2',4,4'-tetrachlorobenzhydryloxycarbonyl group, 3,3',5,5'-tetrachlorobenzhydryloxycarbonyl group or the like.

Examples of a phenyl-substituted or unsubstituted phenyl C1-6 alkoxycarbonyl group include a benzyloxycarbonyl group, 1-phenylethoxycarbonyl group, 2-phenylethoxycarbonyl group, 3-phenylethoxycarbonyl group, 2-phenylpropoxycarbonyl group, 4-phenylbutoxycarbonyl group, 5-phenylpentoxycarbonyl group, 4-phenylpentoxycarbonyl group, 6-phenylhexyloxycarbonyl group, 2-biphenylylmethoxycarbonyl group, 2-(2-biphenylyl)ethoxycarbonyl group, 3-(2-biphenylyl)-propoxycarbonyl group, 4-(2-biphenylyl)butoxycarbonyl group, 5-(2-biphenylyl)pentoxycarbonyl group, 6-(2-biphenylyl)hexyloxycarbonyl group, 3-biphenylylmethoxycarbonyl group, 2-(3-biphenylyl)ethoxycarbonyl group, 3-(3-biphenylyl)propoxycarbonyl group, 4-(3-biphenylyl)butoxycarbonyl group, 5-(3-biphenylyl)-pentoxycarbonyl group, 6-(3-biphenylyl)hexyloxycarbonyl group, 4-biphenylylmethoxycarbonyl group, 2-(4-biphenylyl)ethoxycarbonyl group, 3-(4-biphenylyl)-propoxycarbonyl group, 4-(4-biphenylyl)butoxycarbonyl group, 5-(4-biphenylyl)pentoxycarbonyl group, 6-(4-biphenylyl)hexyloxycarbonyl group or the like.

Examples of a pyridyl C1-6 alkoxycarbonyl group include a 2-pyridylmethoxycarbonyl group, 3-pyridylmethoxycarbonyl group, 4-pyridylmethoxycarbonyl group, 2-(2-pyridyl)ethoxycarbonyl group, 2-(3-pyridyl)ethoxycarbonyl group, 2-(4-pyridyl)ethoxycarbonyl group, 3-(2-pyridyl)propoxycarbonyl group, 3-(3-pyridyl)propoxycarbonyl group, 3-(4-pyridyl)propoxycarbonyl group, 4-(2-pyridyl)butoxycarbonyl group, 4-(3-pyridyl)butoxycarbonyl group, 4-(4-pyridyl)butoxycarbonyl group, 5-(2-pyridyl)pentyloxycarbonyl group, 5-(3-pyridyl)pentyloxycarbonyl group, 5-(4-pyridyl)-pentyloxycarbonyl group, 6-(2-pyridyl)hexyloxycarbonyl group, 6-(3-pyridyl)hexyloxycarbonyl group, 6-(4-pyridyl)hexyloxycarbonyl group or the like.

Examples of a C1-6 alkoxy-substituted C1-6 alkoxycarbonyl group include a methoxymethoxycarbonyl group, methoxyethoxycarbonyl group, 1-ethoxyethoxycarbonyl group, n-propoxymethoxycarbonyl group, n-butoxymethoxycarbonyl group, n-pentyloxymethoxycarbonyl group, n-hexyloxymethoxycarbonyl group, 1-methoxyethoxycarbonyl group, 2-ethoxyethoxycarbonyl group, 2-n-propoxyethoxycarbonyl group, n-butoxymethoxycarbonyl group, n-pentyloxymethoxycarbonyl group, n-hexyloxymethoxycarbonyl group, 3-methoxypropoxycarbonyl group, 4-methoxybutoxycarbonyl group, 5-methoxypentyloxycarbonyl group, 6-methoxyhexyloxycarbonyl group or the like.

A piperazinyl C1-6 alkoxycarbonyl group (which may be substituted on the piperazin ring by at least one group selected from a group consisting of a C1-6 alkoxycarbonyl group and phenyl C1-6 alkoxycarbonyl group which may have as a substitutent at least one halogen atom on the phenyl ring, as a substitutent) includes a piperazinyl C1-6 alkoxycarbonyl group (which may be substituted on the piperazin ring by 1 to 3 groups selected from a group consisting of a C1-6 alkoxycarbonyl group and phenyl C1-6 alkoxycarbonyl group which may have as a substitutent 1 to 5 halogen atom on the phenyl ring, as a substitutent), for example, a (1-piperazinyl)methoxycarbonyl group, 2-(2-piperazinyl)ethoxycarbonyl group, 1-(3-piperazinyl)ethoxycarbonyl group, 3-(4-piperazinyl)propoxycarbonyl group, 4-(1-piperazinyl)-butoxycarbonyl group, 5-(2-piperazinyl) pentyloxycarbonyl group, 6-(3-piperazinyl)hexyloxycarbonyl group, 2-methyl-3-(1-piperazinyl)propoxycarbonyl group, 1,1-dimethyl-2-(4-piperazinyl)ethoxycarbonyl group, 2-(1-piperazinyl)ethoxycarbonyl group, 2-(4-methoxycarbonyl-1-piperazinyl)ethoxycarbonyl group, 2-(4-ethoxycarbonyl-1-piperazinyl)ethoxycarbonyl group, 2-(4-n-propoxycarbonyl-1-piperazinyl)ethoxycarbonyl group, 2-(4-tert-butopoxycarbonyl-1-piperazinyl)-ethoxycarbonyl group, 2-(4-sec-butopoxycarbonyl-1-piperazinyl)ethoxycarbonyl group, 2-(4-n-pentyloxycarbonyl-1-piperazinyl) ethoxycarbonyl group, 2-(4-n-hexyloxycarbonyl-1-piperazinyl)ethoxycarbonyl group, 2-(4-benzyloxycarbonyl-1-piperazinyl)ethoxycarbonyl group, 2-(4-phenylethoxycarbonyl-1-piperazinyl)-ethoxycarbonyl group, 2-(4-(3-phenylpropoxycarbonyl-1-piperazinyl) ethoxycarbonyl group, 2-(4-(2-fluorobenzyloxycarbonyl-1-piperazinyl)ethoxycarbonyl group, 2-(4-(4-fluorobenzyloxycarbonyl-1-piperazinyl)ethoxycarbonyl group, 2-(4-(4-chlorobenzyloxycarbonyl-1-piperazinyl)ethoxycarbonyl group, 2-(4-(3-chlorobenzyloxycarbonyl-1-piperazinyl) ethoxycarbonyl group, 2-(4-(2-bromobenzyloxycarbonyl-1-piperazinyl)-ethoxycarbonyl group, 2-(4-(2-chlorobenzyloxycarbonyl-1-piperazinyl)ethoxycarbonyl group, 2-(4-(3,4-difluorobenzyloxycarbonyl-1-piperazinyl)ethoxycarbonyl group, 2-(4-(2,3,4,5,6-pentafluorobenzyloxycarbonyl-1-piperazinyl)methoxycarbonyl group, 2-(4-(2,4-dichlorobenzyloxycarbonyl-1-piperazinyl)ethoxycarbonyl group, 2-(4-(2,4,6-trichlorobenzyloxycarbonyl-1-piperazinyl) ethoxycarbonyl group, (3,4-methoxycarbonyl-1-piperazinyl)thoxycarbonyl group, (2,5-methoxy-carbonyl-4-benzyloxycarbonyl-1-piperazinyl)methoxy-carbonyl group or the like.

A phenoxycarbonyl group (which may be substituted on the phenyl ring by at least one group selected from a group consisting of a C1-6 alkyl group and C1-6 alkoxy group) includes a phenoxycarbonyl group (which may be substituted on the phenyl ring by 1 to 3 groups selected from a group consisting of a C1-6 alkyl group and a C1-6 alkoxy group), for example, a phenoxycarbonyl group, 2-methylphenoxycarbonyl group, 3-methylphenoxycarbonyl group, 4-methylphenoxycarbonyl group, 2-ethylphenoxycarbonyl group, 3-ethylphenoxycarbonyl group, 4-ethylphenoxycarbonyl group, 4-propylphenoxycarbonyl group, 4-tert-butylphenoxycarbonyl group, 4-butylphenoxycarbonyl group, 2,3-dimethylphenoxycarbonyl group, 3,4,5-trimethylphenoxycarbonyl group, 4-pentylphenoxycarbonyl group, 4-hexylphenoxycarbonyl group, 2-methoxyphenoxycarbonyl group, 3-methoxyphenoxycarbonyl group, 4-methoxyphenoxycarbonyl group, 2-ethoxyphenoxycarbonyl group, 3-ethoxyphenoxycarbonyl group, 4-ethoxyphenoxycarbonyl group, 4-propoxyphenoxycarbonyl group, 4-tert-butoxyphenoxycarbonyl group, 4-n-butoxyphenoxycarbonyl group, 2,3-dimethoxyphenoxycarbonyl group, 3,4,5-trimethoxyphenoxycarbonyl group, 4-pentoxyphenoxycarbonyl group, 4-hexyloxyphenoxycarbonyl group, 2-methyl-4-methoxyphenoxycarbonyl group or the like.

A benzoyl group (which may be substituted on the phenyl ring by at least one halogen-substituted or unsubstituted C1-6 alkyl group) includes a benzoyl group (which may be substituted on the phenyl ring by 1 to 3 halogen-substituted or unsubstituted C1-6 alkyl groups), for example, a benzoyl group, 2-methylbenzoyl group, 3-methylbenzoyl group, 4-methylbenzoyl group, 2-ethylbenzoyl group, 3-ethylbenzoyl group, 4-ethylbenzoyl group, 4-n-propylbenzoyl group, 4-tert-butylbenzoyl group, 4-n-pentylbenzoyl group, 4-n-hexylbenzoyl group, 2,3-dimethylbenzoyl group, 3,4-dimethylbenzoyl group, 2,4,6-trimethylbenzoyl group, 2-trifluoromethylbenzoyl group, 3-trifluoromethylbenzoyl group, 4-trifluoromethylbenzoyl group, 4-pentafluoroethylbenzoyl group, 2,3-difluoromethylbenzoyl group, 3,4-trifluoromethylbenzoyl group or the like.

A phenyl C2-6 alkanoyl group (which may be substituted on the phenyl ring by at least one halogen-substituted or unsubstituted C1-6 alkyl group) includes a phenyl C2-6 alkanoyl group (which may be substituted on the phenyl ring by 1 to 3 halogen-substituted or unsubstituted C1-6 alkyl groups), for example, a phenylacetyl group, 3-phenylpropionyl group, 4-phenylbutyryl group, 5-phenylpentanoyl group, 6-phenylhexanoyl group, 2-methylphenylacetyl group, 3-methylphenylacetyl group, 4-methylphenylacetyl group, 2-trifluoromethylphenylacetyl group, 3-trifluoromethylphenylacetyl group, 4-trifluoromethylphenylacetyl group, 3-(2,4-dimethylphenyl)propionyl group, (2,4,6-trimethylphenyl)acetyl group, 3-(2-methylphenyl)propionyl group, 3-(3-methylphenyl)propionyl group, 3-(4-methylphenyl)propionyl group, 3-(2-trifluoromethylphenyl)propionyl group, 3-(3-trifluoromethylphenyl)-propionyl group, 3-(4-trifluoromethylphenyl)propionyl group, 3-(3,5-dimethylphenyl)propionyl group, 4-(4-trifluoromethylphenyl)butyryl group, 5-(4-trifluoromethylphenyl)pentanoyl group, 6-(3,5-ditrifluoromethylphenyl)hexanoyl group, 4-(4-trifluoromethylphenyl)-butyryl group, 5-(4-pentafluoroethylphenyl)pentanoyl group, 6-(4-pentafluoroethylphenyl) hexanoyl group or the like.

Examples of a phenoxy C2-6 alkanoyl group (which may be substituted on the phenyl ring by 1 to 3 halogen atoms) include a phenoxyacetyl group, 3-phenoxypropionyl group, 4-phenoxypropionyl group, 5-phenoxypropionyl group, 6-phenoxypropionyl group, 4-(4-chlorophenoxy)butyryl group, 5-(4-chlorophenoxy)-pentanoyl group, 6-(4-chlorophenoxy)hexanoyl group, 2-fluorophenoxyacetyl group, 3-fluorophenoxyacetyl group, 4-fluorophenoxyacetyl group, 2-chlorophenoxyacetyl group, 3-chlorophenoxyacetyl group, 4-chlorophenoxyacetyl group, 4-bromophenoxyacetyl group, 2,3-difluorophenoxyacetyl group, 2-fluoro-4-chlorophenoxyacetyl group, 3,5-difluorophenoxyacetyl group, 2,4,6-trichlorophenoxyacetyl group, 3-(2-fluorophenoxy)-propionyl group, 3-(3-fluorophenoxy)propionyl group, 3-(4-fluorophenoxy)propionyl group, 3-(2-chlorophenoxy)-propionyl group, 3-(3-chlorophenoxy)propionyl group, 3-(4-chlorophenoxy)propionyl group, 3-(4-bromophenoxy)-propionyl group, 3-(2,3-difluorophenoxy) propionyl group, 3-(2-fluoro-4-chlorophenoxy)propionyl group, 3-(3,5-difluorophenoxy)propionyl group, 4-(4-fluorophenoxy)butyryl group, 5-(4-boromophenoxy)pentanoyl group, 6-(4-chlorophenoxy)hexanoyl group, 4-(4-chlorophenoxy)butyryl group, 5-(4-iodophenoxy)pentanoyl group, 6-(4-chlorophenoxy)hexanoyl group or the like.

A piperazinyl C2-6 alkanoyl group (which may be substituted on the piperazin ring by at least one group selected from a group consisting of a C1-6 alkanoyl group; phenyl C1-6 alkyl group which may have on the phenyl ring at least one group, as a substitutent, selected from a group consisting of a halogen atom, halogen-substituted or unsubstituted C1-6 alkyl group and halogen-substituted or unsubstituted C1-6 alkoxy group; phenyl C1-6 alkoxycarbonyl group which may have on the phenyl ring at least one group, as a substitutent, selected from a group consisting of a halogen atom, halogen-substituted or unsubstituted C1-6 alkyl group and a halogen-substituted or unsubstituted C1-6 alkoxy group; phenylcarbamoyl C1-6 alkyl group which may have on the phenyl ring at least one group, as a substitutent, selected from a group consisting of a halogen atom, halogen-substituted or unsubstituted C1-6 alkyl group and halogen-substituted or unsubstituted C1-6 alkoxy group; phenylcarbamoyl which may have on the phenyl ring at least one group, as a substitutent, selected from a group consisting of a halogen atom, halogen-substituted or unsubstituted C1-6 alkyl group and halogen-substituted or unsubstituted C1-6 alkoxy group; and benzoxazolyl group) includes a piperazinyl C2-6 alkanoyl group (which may be substituted on the piperazin ring by 1 to 3 groups selected from a group consisting of a C1-6 alkanoyl group; phenyl C1-6 alkyl group which may have on the phenyl ring 1 to 5, preferably 1 to 3 groups, as a substitutent, selected from a group consisting of a halogen atom, halogen-substituted or unsubstituted C1-6 alkyl group and halogen-substituted or unsubstituted C1-6 alkoxy group; phenyl C1-6 alkoxycarbonyl group which may have on the phenyl ring 1 to 5, preferably 1 to 3 groups, as a substitutent, selected from a group consisting of a halogen atom, halogen-substituted or unsubstituted C1-6 alkyl group and halogen-substituted or unsubstituted C1-6 alkoxy group; phenylcarbamoyl C1-6 alkyl group which may have on the phenyl ring 1 to 5, preferably 1 to 3 groups, as a substitutent, selected from a group consisting of a halogen atom, halogen-substituted or unsubstituted C1-6 alkyl group and halogen-substituted or unsubstituted C1-6 alkoxy group; phenylcarbamoyl which may have on the phenyl ring 1 to 5, preferably 1 to 3 groups, as a substitutent, selected from a group consisting of a halogen atom, halogen-substituted or unsubstituted C1-6 alkyl group and a halogen-substituted or unsubstituted C1-6 alkoxy group; and benzoxazolyl group), for example, a 1-piperazinylacetyl group, 3-(2-piperazinyl)propanoyl group, 4-(3-piperazinyl)butyryl group, 4-(4-piperazinyl)pentanoyl group, 5-(1-piperazinyl)pentanoyl group, 6-(2-piperazinyl)hexanoyl group, 4-acetyl-1-piperazinylacetyl group, 3-(4-propionyl-1-piperazinyl)propionyl group, 3-(4-butyryl-1-piperazinyl)butyryl group, 4-(4-pentanoyl-1-piperazinyl)butyryl group, 5-(4-hexanoyl-1-piperazinyl)pentanoyl group, 6-(4-acetyl-1-piperazinyl)hexanoyl group, 4-benzyl-1-piperazinylacetyl group, 3-[(4-(2-phenyethyl)-1-piperazinyl]propionyl group, (4-acetyl-3-benzyl-1-piperazinyl)acetyl group, (4-benzyloxycarbonyl-2-benzyl-1-piperazinyl)acetyl group, (4-phenylcarbamoyl-2,6-dibenzyl-1-piperazinyl)acetyl group, 4-[4-(1-phenylethyl)-1-piperazinyl]butyryl group, [4-(3-phenylpropyl)-1-piperazinyl]butyryl group, 5-[4-(5-phenylpentyl)-1-piperazinyl]pentanoyl group, 6-[4-(6-phenylhexyl)-1-piperazinyl]hexanoyl group, 4-(4-phenylbenzyl)-1-piperazinylacetyl group, 3-[4-(3-fluorobenzyl)-1-piperazinyl]propionyl group, 4-[4-(2,3,4,5,6-pentafluorobenzyl)-1-piperazinyl]butyryl group, 4-[4-(2,4-dichlorobenzyl)-1-piperazinyl]butyryl group, 5-[4-(2,4,6-trichlorobenzyl)-1-piperazinyl]-pentanoyl group, 6-[4-(4-methylbenzyl)-1-piperazinyl]-hexanoyl group, [4-(4-trifluoromethylbenzyl)-1-piperazinyl]acetyl group, [4-(3,5-ditrifluoromethylbenzyl)-1-piperazinyl]acetyl group, [4-(2,3-dimethylbenzyl)-1-piperazinyl]acetyl group, [4-(2,4,6-trimethylbenzyl)-1-piperazinyl]acetyl group, 6-[4-(4-methoxybenzyl)-1-piperazinyl]hexanoyl group, [4-(4-trifluoromethoxybenzyl)-1-piperazinyl]acetyl group, [4-(3,5-ditrifluoromethoxybenzyl)-1-piperazinyl]acetyl group, [4-(2,3-dimethoxybenzyl)-1-piperazinyl]acetyl group, [4-(2,4,6-trimethoxybenzyl)-1-piperazinyl]acetyl group, 3-(4-benzyloxycarbonyl-1-piperazinyl)propionyl group, 4-(2,4-dichlorobenzyloxycarbonyl-1-piperazinyl)-acetyl group, 3-(4-benzyloxycarbonyl-1-piperazinyl)-butyryl group, 4-(4-benzyloxycarbonyl-1-piperazinyl)-butyryl group, 5-(4-benzyloxycarbonyl-1-piperazinyl)-pentanoyl group, 6-(4-benzyloxycarbonyl-1-piperazinyl)-hexanoyl group, 3-(4-(2-fluorobenzyloxycarbonyl)-1-piperazinyl)propionyl group, 3-(4-(2-fluorobenzyloxycarbonyl)-1-piperazinyl)butyryl group, 4-(4-(2-fluorobenzyloxycarbonyl)-1-piperazinyl)butyryl group, 5-(4-(2,3,4,5,6-pentafluorobenzyloxycarbonyl)-1-piperazinyl)pentanoyl group, 6-(4-fluorobenzyloxycarbonyl)-1-piperazinyl)hexanoyl group, 3-(4-(2,3-difluorobenzyloxycarbonyl-1-piperazinyl)butyryl group, 4-(4-(3-fluorobenzyloxycarbonyl-1-piperazinyl)butyryl group, 5-(4-(3-fluorobenzyloxycarbonyl-1-piperazinyl)-pentanoyl group, 3-(4-(4-fluorobenzyloxycarbonyl-1-piperazinyl)butyryl group, 4-(4-(4-fluorobenzyloxycarbonyl-1-piperazinyl)butyryl group, 5-(4-(4-fluorobenzyloxycarbonyl-1-piperazinyl)pentanoyl group, 6-(4-(4-fluorobenzyloxycarbonyl)-1-piperazinyl)hexanoyl group, 3-(4-(2-chlorobenzyloxycarbonyl)-1-piperazinyl)-propionyl group, 3-(4-(2-chlorobenzyloxycarbonyl)-1-piperazinyl)butyryl group, 4-(4-(2-chlorobenzyloxycarbonyl)-1-piperazinyl)butyryl group, 5-(4-(2-chlorobenzyloxycarbonyl)-1-piperazinyl)pentanoyl group, 6-(2,4,6-trichlorobenzyloxycarbonyl)-1-piperazinyl)hexanoyl group, 3-(4-(3-chlorobenzyloxycarbonyl)-1-piperazinyl)-propionyl group, 3-(4-(3-chlorobenzyloxycarbonyl)-1-piperazinyl)butyryl group, 4-(4-(3-chlorobenzyloxycarbonyl)-1-piperazinyl)butyryl group, 5-(4-(3-chlorobenzyloxycarbonyl)-1-piperazinyl)pentanoyl group, 6-(3-chlorobenzyloxycarbonyl-1-piperazinyl)hexanoyl group, 2-(4-(4-chlorobenzyloxycarbonyl)-1-piperazinyl)-propionyl group, 3-(4-(4-chlorobenzyloxycarbonyl)-1-piperazinyl)butyryl group, 4-(4-(4-chlorobenzyloxycarbonyl)-1-piperazinyl)butyryl group, 5-(4-(4-chlorobenzyloxycarbonyl)-1-piperazinyl)pentanoyl group, 6-(4-chlorobenzyloxycarbonyl-1-piperazinyl)hexanoyl group, (4-(2-methylbenzyloxycarbonyl)-1-piperazinyl)-acetyl group, (4-(2,4-dimethylbenzyloxycarbonyl)-1-piperazinyl)acetyl group, (4-(2,4,6-trimethylbenzyloxycarbonyl)-1-piperazinyl)acetyl group, 4-(2-methoxybenzyloxycarbonyl)-1-piperazinyl)acetyl group, (4-(2,4-dimethoxybenzyloxycarbonyl)-1-piperazinyl)acetyl group, (4-(2,4,6-trimethoxybenzyloxycarbonyl)-1-piperazinyl)-acetyl group, (4-(3,5-ditrifluoromethylbenzyloxycarbonyl)-1-piperazinyl)acetyl group, (4-(3,5-ditrifluoromethoxybenzyloxycarbonyl)-1-piperazinyl)-acetyl group, 3-(4-(2-trifluoromethylbenzyloxycarbonyl)-1-piperazinyl)propionyl group, 3-(4-(2-trifluoromethylbenzyloxycarbonyl)-1-piperazinyl)butyryl group, 4-(4-(2-trifluoromethylbenzyloxycarbonyl)-1-piperazinyl)butyryl group, 5-(4-(2-trifluoromethylbenzyloxycarbonyl)-1-piperazinyl)pentanoyl group, 6-(4-trifluoromethylbenzyloxycarbonyl-1-piperazinyl)hexanoyl group, 3-(4-(3-trifluoromethylbenzyloxycarbonyl)-1-piperazinyl)butyryl group, 4-(4-(3-trifluoromethylbenzyloxycarbonyl)-1-piperazinyl)butyryl group, 5-(4-(3-trifluoromethylbenzyloxycarbonyl)-1-piperazinyl)-pentanoyl group, 3-(4-(4-trifluoromethylbenzyloxycarbonyl)-1-piperazinyl)butyryl group, 4-(4-(4-trifluoromethylbenzyloxycarbonyl)-1-piperazinyl) butyryl group, 5-(4-(4-trifluoromethylbenzyloxycarbonyl)-1-piperazinyl)pentanoyl group, 6-(4-(4-trifluoromethylbenzyloxycarbonyl)-1-piperazinyl)hexanoyl group, 2-(4-(2-trifluoromethoxybenzyloxycarbonyl)-1-piperazinyl)-propionyl group, 3-(4-(2-trifluoromethoxybenzyloxycarbonyl)-1-piperazinyl)butyryl group, 4-(4-(2-trifluoromethoxybenzyloxycarbonyl)-1-piperazinyl)-butyryl group, 5-(4-(2-trifluoromethoxybenzyloxycarbonyl)-1-piperazinyl)pentanoyl group, 6-(4-trifluoromethoxybenzyloxycarbonyl-1-piperazinyl)-hexanoyl group, 3-(4-(3-trifluoromethoxybenzyloxycarbonyl)-1-piperazinyl)butyryl group, 4-(4-(3-trifluoromethoxybenzyloxycarbonyl)-1-piperazinyl)-butyryl group, 5-(4-(3-trifluoromethoxybenzyloxycarbonyl)-1-piperazinyl)pentanoyl group, 3-(4-(4-trifluoromethoxybenzyloxycarbonyl)-1-piperazinyl)-butyryl group, 4-(4-(4-trifluoromethoxybenzyloxycarbonyl)-1-piperazinyl)butyryl group, 5-(4-(4-trifluoromethoxybenzyloxycarbonyl)-1-piperazinyl)-pentanoyl group, 6-(4-(4-trifluoromethoxybenzyloxycarbonyl)-1-piperazinyl)hexanoyl group, 4-phenylcarbamoylmethyl-1-piperazinylacetyl group, 3-(4-phenylcarbamoylmethyl-1-piperazinyl)propionyl group, 4-(4-fluorophenylcarbamoylmethyl-1-piperazinyl)acetyl group, 3-(4-(2,3,4,5,6-pentafluorophenylcarbamoylmethyl)-1-piperazinyl)propionyl group, 4-(4-chlorophenylcarbamoylmethyl-1-piperazinylacetyl group, 3-(4-(3,4-dichlorophenylcarbamoylmethyl)-1-piperazinyl) propionyl group, 4-(4-methylphenylcarbamoylmethyl)-1-piperazinylacetyl group, 3-(4-(2,4-dimethylphenylcarbamoylmethyl)-1-piperazinyl)propionyl group, 4-(4-methoxyphenylcarbamoylmethyl)-1-piperazinylacetyl group, 3-(4-(2,4,6-trimethoxyphenylcarbamoylmethyl)-1-piperazinyl)propionyl group, 3-(4-(4-trifluoromethylphenylcarbamoylmethyl)-1-piperazinyl)propionyl group, 4-(4-trifluoromethoxyphenylcarbamoylmethyl)-1-piperazinylacetyl group, 3-(4-(4-trifluoromethoxyphenylcarbamoylmethyl)-1-piperazinyl) propionyl group, 4-phenylcarbamoyl-1-piperazinylacetyl group, 3-(4-phenylcarbamoyl-1-piperazinyl)propionyl group, 4-(4-fluorophenylcarbamoyl-1-piperazinyl)acetyl group, 3-(4-(2,3,4,5,6-pentafluorophenylcarbamoyl)-1-piperazinyl]propionyl group, 4-(4-chlorophenylcarbamoyl-1-piperazinylacetyl group, 4-(2,4-dichlorophenylcarbamoyl-1-piperazinylacetyl group, 4-(2,6-dichlorophenylcarbamoyl-1-piperazinylacetyl group, 3-(4-(4-chlorophenylcarbamoyl)-1-piperazinyl)propionyl group, 4-(4-methylphenylcarbamoyl-1-piperazinylacetyl group, 3-(4-(3,4-dimethylphenylcarbamoyl)-1-piperazinyl)propionyl group, 4-(4-methoxyphenylcarbamoyl-1-piperazinylacetyl group, 3-[4-(2,4,6-trimethoxyphenylcarbamoyl)-1-piperazinyl]propionyl group, 3-(4-(4-trifluoromethylphenylcarbamoyl)-1-piperazinyl)propionyl group, 4-(3,5-ditrifluoromethoxyphenylcarbamoyl)-1-piperazinylacetyl group, 3-(4-(4-trifluoromethoxyphenylcarbamoyl)-1-piperazinyl)propionyl group, 3-(4-(4-fluorophenylcarbamoyl)-1-piperazinyl)propionyl group, 3-(4-(4-methylphenylcarbamoyl)-1-piperazinyl)-propionyl group, 3-(4-(4-methoxyphenylcarbamoyl)-1-piperazinyl)propionyl group, 4-(2-benzoxazolinyl)-1-piperazinylacetyl group, 3-(4-(2-benzoxazolinyl)-1-piperazinyl)propionyl group, 4-(4-(2-benzoxazolinyl)-1-piperazinyl)butyryl group, 5-(4-(2-benzoxazolinyl)-1-piperazinyl)pentanoyl group, 6-(4-(2-benzoxazolinyl)-1-piperazinyl)hexanoyl group or the like.

A phenylcarbamoyl group (which may be substituted on the phenyl ring by 1 to 3 groups selected from a group consisting of a halogen atom, amino group which may have a C1-6 alkyl group as a substitutent, carboxyl group, C1-6 alkoxycarbonyl group, halogen-substituted or unsubstituted C1-6 alkyl group, halogen-substituted or unsubstituted C1-6 alkoxy group, piperazinyl group which may have a C1-6 alkyl group as a substituent on the piperazin ring and morpholino group) includes a phenylcarbamoyl group (which may be substituted on the phenyl ring by 1 to 3 groups selected from a group consisting of a halogen atom, amino group which may have 1 to 2 C1-6 alkyl groups as a substitutent, carboxyl group, C1-6 alkoxycarbonyl group, halogen-substituted or unsubstituted C1-6 alkyl group, halogen-substituted or unsubstituted C1-6 alkoxy group, piperazinyl group which may have 1 to 3 C1-6 alkyl groups as a substituent on the piperazin ring and morpholono group, and an amino group moiety may be substituted by another C1-6 alkyl group or phenyl C1-6 alkyl group), for example, a phenylcarbamoyl group, 2-fluorophenylcarbamoyl group, 3-fluorophenylcarbamoyl group, 4-fluorophenylcarbamoyl group, 2-chlorophenylcarbamoyl group, 3-chlorophenylcarbamoyl group, 4-chlorophenylcarbamoyl group, 2-bromophenylcarbamoyl group, 3-bromophenylcarbamoyl group, 4-bromophenylcarbamoyl group, 2-iodophenylcarbamoyl group, 3-iodophenylcarbamoyl group, 4-iodophenylcarbamoyl group, 2,3-difluorophenylcarbamoyl group, 3,4-difluorophenylcarbamoyl group, 3,5-difluorophenylcarbamoyl group, 2,4-difluorophenylcarbamoyl group, 2,6-difluorophenylcarbamoyl group, 2,3-dichlorophenylcarbamoyl group, 3,4-dichlorophenylcarbamoyl group, 3,5-dichlorophenylcarbamoyl group, 2,4-dichlorophenylcarbamoyl group, 2,6-dichlorophenylcarbamoyl group, 3,4,5-trifluorophenylcarbamoyl group, 2,3-difluorophenylcarbamoyl group, 3,4,5-trichlorophenylcarbamoyl group, 2,4,6-trifluorophenylcarbamoyl group, 2,4,6-trichlorophenylcarbamoyl group, 2-methylphenylcarbamoyl group, 3-methylphenylcarbamoyl group, 4-methylphenylcarbamoyl group, 2-methyl-3-chlorophenylcarbamoyl group, 3-methyl-4-chlorophenylcarbamoyl group, 2-chloro-4-methylphenylcarbamoyl group, 2-methyl-3-fluorophenylcarbamoyl group, 2-trifluoromethylphenylcarbamoyl group, 3-trifluoromethylphenylcarbamoyl group, 4-trifluoromethylphenylcarbamoyl group, N-methyl-N-phenylcarbamoyl group, N-(2-fluorophenyl)-N-methylcarbamoyl group, N-(3-fluorophenyl)-N-methylcarbamoyl group, N-(4-fluorophenyl)-N-methylcarbamoyl group, N-(2-chlorophenyl)-N-methylcarbamoyl group, N-(3-chlorophenyl)-N-methylcarbamoyl group, N-(4-chlorophenyl)-N-methylcarbamoyl group, N-(4-bromophenyl)-N-methylcarbamoyl group, N-(2-iodophenyl)-N-methylcarbamoyl group, N-(3-iodophenyl)-N-methylcarbamoyl group, N-(4-iodophenyl)-N-methylcarbamoyl group, N-(2,3-difluorophenyl)-N-methylcarbamoyl group, N-(3,4-difluorophenyl)-N-methylcarbamoyl group, N-(3,5-difluorophenyl)-N-methylcarbamoyl group, N-(2,4-difluorophenyl)-N-methylcarbamoyl group, N-(2,6-difluorophenyl)-N-methylcarbamoyl group, N-(2,3-dichlorophenyl)-N-methylcarbamoyl group, N-(3,4-dichlorophenyl)-N-methylcarbamoyl group, N-(3,5-dichlorophenyl)-N-methylcarbamoyl group, N-(2,4-dichlorophenyl)-N-methylcarbamoyl group, N-(2,6-dichlorophenyl)-N-methylcarbamoyl group, N-(3,4,5-trifluorophenyl)-N-methylcarbamoyl group, N-(3,4,5-trichlorophenyl)-N-methylcarbamoyl group, N-(2,4,6-trifluorophenyl)-N-methylcarbamoyl group, N-(2,4,6-trichlorophenyl)-N-methylcarbamoyl group, N-(2-methylphenyl)-N-methylcarbamoyl group, N-(3-methylphenyl)-N-methylcarbamoyl group, N-(4-methylphenyl)-N-methylcarbamoyl group, N-(2-methyl-3-chlorophenyl)-N-methylcarbamoyl group, N-(3-methyl-4-chlorophenyl)-N-methylcarbamoyl group, N-(2-chloro-4-methylphenyl)-N-methylcarbamoyl group, N-(2-methyl-3-fluorophenyl)-N-methylcarbamoyl group, N-(2-trifluoromethylphenyl)-N-methylcarbamoyl group, N-(4-trifluoromethylphenyl)-N-methylcarbamoyl group, N-benzyl-N-phenylcarbamoyl group, N-benzyl-N-(2-fluorophenyl)-carbamoyl group, N-benzyl-N-(3-fluorophenyl)carbamoyl group, N-benzyl-N-(4-fluorophenyl)carbamoyl group, N-benzyl-N-(2-chlorophenyl)carbamoyl group, N-benzyl-N-(3-chlorophenyl)carbamoyl group, N-benzyl-N-(4-chlorophenyl)carbamoyl group, N-benzyl-N-(2-bromophenyl)-carbamoyl group, N-benzyl-N-(3-bromophenyl)carbamoyl group, N-benzyl-N-(4-bromophenyl)carbamoyl group, N-benzyl-N-(2-iodophenyl)carbamoyl group, N-benzyl-N-(3-iodophenyl)carbamoyl group, N-benzyl-N-(4-iodophenyl)-carbamoyl group, N-benzyl-N-(2,3-difluorophenyl)-carbamoyl group, N-benzyl-N-(3,4-difluorophenyl)-carbamoyl group, N-benzyl-N-(3,5-difluorophenyl)-carbamoyl group, N-benzyl-N-(2,4-difluorophenyl)-carbamoyl group, N-benzyl-N-(2,6-difluorophenyl)-carbamoyl group, N-benzyl-N-(2,3-dichlorophenyl)-carbamoyl group, N-benzyl-N-(3,4- dichlorophenyl)-carbamoyl group, N-benzyl-N-(3,5-dichlorophenyl)-carbamoyl group, N-benzyl-N-(2,4-dichlorophenyl)-carbamoyl group, N-benzyl-N-(2,6-dichlorophenyl)-carbamoyl group, N-benzyl-N-(3,4,5-triifluorophenyl)-carbamoyl group, N-benzyl-N-(3,4,5-trichlorophenyl)-carbamoyl group, N-benzyl-N-(2,3-difluorophenyl)-carbamoyl group, N-benzyl-N-(2,4,6-trichlorophenyl)-carbamoyl group, N-benzyl-N-(2-methylphenyl)carbamoyl group, N-benzyl-N-(3-methylphenyl)carbamoyl group, N-benzyl-N-(4-methylphenyl)carbamoyl group, N-benzyl-N-(2-methyl-3-chlorophenyl)carbamoyl group, N-benzyl-N-(3-methyl-4-chlorophenyl)carbamoyl group, N-benzyl-N-(2-chloro-4-methylphenyl)carbamoyl group, N-benzyl-N-(2-methyl-3-fluorophenyl)carbamoyl group, N-benzyl-N-(2-trifluoromethylphenyl)carbamoyl group, N-benzyl-N-(3-trifluoromethylphenyl)carbamoyl group, N-benzyl-N-(4-trifluoromethylphenyl)carbamoyl group, 2-pentafluoroethylphenylcarbamoyl group, 3-pentafluoroethylphenylcarbamoyl group, 4-pentafluoroethylphenylcarbamoyl group, 2-isopropylphenylcarbamoyl group, 3-isopropylphenylcarbamoyl group, 4-isopropylphenylcarbamoyl group, 2-tert-butylphenylcarbamoyl group, 3-tert-butylphenylcarbamoyl group, 4-tert-butylphenylcarbamoyl group, 2-sec-butylphenylcarbamoyl group, 3-sec-butylphenylcarbamoyl group, 4-sec-butylphenylcarbamoyl group, 2-n-heptafluoropropylphenylcarbamoyl group, 3-n-heptafluoropropylphenylcarbamoyl group, 4-n-heptafluoropropylphenylcarbamoyl group, 4-pentylphenylcarbamoyl group, 4-hexylphenylcarbamoyl group, 2-methoxyphenylcarbamoyl group, 3-methoxyphenylcarbamoyl group, 4-methoxyphenylcarbamoyl group, 2-methoxy-3-chlorophenylcarbamoyl group, 2-fluoro-3-methoxyphenylcarbamoyl group, 2-fluoro-4-methoxyphenylcarbamoyl group, 2,6-dimethoxyphenylcarbamoyl group, 2,3,4-trifluorophenylcarbamoyl group, 3,4,5-trifluorophenylcarbamoyl group, 2-trifluoromethoxyphenylcarbamoyl group, 3-trifluoromethoxyphenylcarbamoyl group, 4-trifluoromethoxyphenylcarbamoyl group, 2-pentafluoroethoxyphenylcarbamoyl group, 3-pentafluoroethoxyphenylcarbamoyl group, 4-pentafluoroethoxyphenylcarbamoyl group, 2-isopropoxyphenylcarbamoyl group, 3-isopropoxyphenylcarbamoyl group, 4-isopropoxyphenylcarbamoyl group, 2-tert-butoxyphenylcarbamoyl group, 3-tert-butoxyphenylcarbamoyl group, 4-tert-butoxyphenylcarbamoyl group, 2-sec-butoxyphenylcarbamoyl group, 3-sec-butoxyphenylcarbamoyl group, 4-sec-butoxyphenylcarbamoyl group, 2-n-heptafluoropropoxyphenylcarbamoyl group, 3-n-heptafluoropropoxyphenylcarbamoyl group, 4-n-heptafluoropropoxyphenylcarbamoyl group, 4-pentyloxyphenylcarbamoyl group, 4-hexyloxyphenylcarbamoyl group, 2-dimethylaminophenylcarbamoyl group, 2,4-dimethylaminophenylcarbamoyl group, 2,4,6-trimethylaminophenylcarbamoyl group, 3-dimethylaminophenylcarbamoyl group, 4-methylaminophenylcarbamoyl group, 2-carboxyphenylcarbamoyl group, 3-carboxyphenylcarbamoyl group, 4-carboxyphenylcarbamoyl group, 2,3-dicarboxyphenylcarbamoyl group, 2,4,6-tricarboxyphenylcarbamoyl group, 2-methoxycarbonylphenylcarbamoyl group, 3-methoxycarbonylphenylcarbamoyl group, 4-methoxycarbonylphenylcarbamoyl group, 2-ethoxycarbonylphenylcarbamoyl group, 3-ethoxycarbonylphenylcarbamoyl group, 4-ethoxycarbonylphenylcarbamoyl group, 2-propoxycarbonylphenylcarbamoyl group, 3-propoxycarbonylphenylcarbamoyl group, 4-propoxycarbonylphenylcarbamoyl group, 2-(1-piperazinyl)phenylcarbamoyl group, 2-(2,4-dimethyl-1-piperazinyl)phenylcarbamoyl group, 2-(2,3,4-trimethyl-1-piperazinyl)phenylcarbamoyl group, 2-(4-methyl-1-piperazinyl)phenylcarbamoyl group, 3-(4-methyl-1-piperazinyl)phenylcarbamoyl group, 4-(4-methyl-1-piperazinyl)phenylcarbamoyl group, 2-morpholinophenylcarbamoyl group, 3-morpholinophenylcarbamoyl group, 4-morpholinophenylcarbamoyl group or the like.

A phenyl C1-6 alkylcarbamoyl group (which may be substituted on the phenyl ring by at least one group selected from a group consisting of a halogen-substituted or unsubstituted C1-6 alkyl group and halogen-substituted or unsubstituted C1-6 alkoxy group) includes a phenyl C1-6 alkylcarbamoyl group (which may be substituted on the phenyl ring by 1 to 3 groups selected from a group consisting of a halogen-substituted or unsubstituted C1-6 alkyl group and halogen-substituted or unsubstituted C1-6 alkoxy group), for example, a benzylcarbamoyl group, 1-phenylethylcarbamoyl group, 2-phenylethylcarbamoyl group, 3-phenylpropylcarbamoyl group, 4-phenylbutyl-carbamoyl group, 5-phenylpentylcarbamoyl group, 6-phenylhexylcarbamoyl group, 2-methyl-3-phenylpropylcarbamoyl group, 1,1-dimethyl-2-phenylethylcarbamoyl group, 2-methylbenzylcarbamoyl group, 3-methylbenzylcarbamoyl group, 4-methylbenzylcarbamoyl group, 2,4-dimethylbenzylcarbamoyl group, 2,4,6-trimethylbenzylcarbamoyl group, 4-trifluoromethyl-3-methoxybenzylcarbamoyl group, 2-ethylbenzylcarbamoyl group, 3-ethylbenzylcarbamoyl group, 4-ethylbenzylcarbamoyl group, 2-isopropylbenzylcarbamoyl group, 3-isopropylbenzylcarbamoyl group, 4-isopropylbenzylcarbamoyl group, 2,4-dimethoxybenzylcarbamoyl group, 2,4,6-trimethoxybenzylcarbamoyl group, 4-trifluoromethoxy-3-methylbenzylcarbamoyl group, 4-methoxybenzylcarbamoyl group, 2-ethoxybenzylcarbamoyl group, 3-ethoxybenzylcarbamoyl group, 4-ethoxybenzylcarbamoyl group, 2-isopropoxybenzylcarbamoyl group, 3-isopropoxybenzylcarbamoyl group, 4-isopropoxybenzylcarbamoyl group, 4-trifluoromethylbenzylcarbamoyl group, 4-pentafluoroethylbenzylcarbamoyl group, 4-n-heptafluoropropylbenzylcarbamoyl group, 4-trifluoromethoxybenzylcarbamoyl group, 4-pentafluoroethoxybenzylcarbamoyl group, 4-n-heptafluoropropoxybenzylcarbamoyl group or the like.

A piperazinylcarbonyl group (which may be substituted on the piperazine ring by at least one group selected from a group consisting of a C1-6 alkoxycarbonyl group, phenyl C1-6 alkoxycarbonyl group which may have at least one halogen-substituted or unsubstituted C1-6 alkyl group on the phenyl ring and phenyl C1-6 alkyl group which may have at least one halogen-substituted or unsubstituted C1-6 alkyl group on the phenyl ring) includes a piperazinylcarbonyl group (which may be substituted on the piperazine ring by 1 to 3 groups selected from a group consisting of a C1-6 alkoxycarbonyl group, phenyl C1-6 alkoxycarbonyl group which may have 1 to 3 halogen-substituted or unsubstituted C1-6 alkyl groups on the phenyl ring and phenyl C1-6 alkyl group which may have 1 to 3 halogen-substituted or unsubstituted C1-6 alkyl groups on the phenyl ring), for example, a 1-piperazinylcarbonyl group, 2-piperazinylcarbonyl group, 3-piperazinylcarbonyl group, 4-piperazinylcarbonyl group, 4-tert-butoxycarbonyl-1-piperazinylcarbonyl group, 4-(4-methylbenzyloxycarbonyl)-1-piperazinylcarbonyl group, 4-(2,4-dimethylbenzyloxycarbonyl)-1-piperazinylcarbonyl group, 4-(2,4,6-trimethylbenzyloxycarbonyl)-1-piperazinylcarbonyl group, 4-(4-trifluoromethylbenzyloxycarbonyl)-1-piperazinylcarbonyl group, 4-(4-methylbenzyl)-1-piperazinylcarbonyl group, 4-(3,4-dimethylbenzyl)-1-piperazinylcarbonyl group, 4-(3,4,5-trimethylbenzyl)-1-piperazinylcarbonyl group, 4-(4-trifluoromethylbenzyl)-1-piperazinylcarbonyl group, 4-methoxycarbonyl-3-benzyl-1-piperazinylcarbonyl group, 4-benzyloxycarbonyl-3,5-dimethoxycarbonyl-1-piperazinylcarbonyl group or the like.

A phenyl C1-6 alkoxy group (the phenyl group may have at least one group selected from a group consisting of a halogen atom, halogen-substituted or unsubstituted C1-6 alkyl group and halogen-substituted or unsubstituted C1-6 alkoxyl group, as a substituent on the phenyl ring) is a phenyl C1-6 alkoxy group which may be substituted by 1 to 5, preferably 1 to 3 groups selected from a group consisting of a halogen atom, halogen-substituted or unsubstituted C1-6 alkyl group and halogen-substituted or unsubstituted C1-6 alkoxyl group, as defined above, examples of which include a benzyloxy group, 2-phenylethoxy group, 3-phenylpropoxy group, 2-phenylpropoxy group, 4-phenylbutoxy group, 5-phenylpentoxy group, 4-phenylpentoxy group, 6-phenylhexyloxy group, 2-fluorobenzyloxy group, 3-fluorobenzyloxy group, 4-fluorobenzyloxy group, 2-(2-fluorophenyl)ethoxy group, 2-(3-fluorophenyl)ethoxy group, 2-(4-fluorophenyl)ethoxy group, 2-chlorobenzyloxy group, 3-chlorobenzyloxy group, 4-chlorobenzyloxy group, 2-fluoro-4-bromobenzyloxy group, 4-chloro-3-fluorobenzyloxy group, 2,3,4-trichlorobenzyloxy group, 3,4,5-trifluorobenzyloxy group, 2,3,4,5,6-pentafluorobenzyloxy group, 2,4,6-trichlorobenzyloxy group, 4-isopropylbenzyloxy group, 4-n-butylbenzyloxy group, 4-methylbenzyloxy group, 2-methylbenzyloxy group, 3-methylbenzyloxy group, 2,4-dimethylbenzyloxy group, 2,3-dimethylbenzyloxy group, 2,6-dimethylbenzyloxy group, 3,5-dimethylbenzyloxy group, 2,5-dimethylbenzyloxy group, 2,4,6-trimethylbenzyloxy group, 3,5-di(trifluoromethyl)benzyloxy group, 4-isopropoxybenzyloxy group, 4-n-butoxybenzyloxy group, 4-methoxybenzyloxy group, 2-methoxybenzyloxy group, 3-methoxybenzyloxy group, 2,4-dimethoxybenzyloxy group, 2,3-dimethoxybenzyloxy group, 2,6-dimethoxybenzyloxy group, 3,5-dimethoxybenzyloxy group, 2,5-dimethoxybenzyloxy group, 2,4,6-trimethoxybenzyloxy group, 3,5-di(trifluoromethoxy)benzyloxy group, 2-isopropoxybenzloxy group, 3-chloro-4-methoxybenzyloxy group, 2-chloro-4-trifluoromethoxybenzyloxy group, 3-methyl-4-fluorobenzyloxy group, 4-bromo-3-trifluoromethylbenzyloxy group, 2-(2-chlorophenyl)-ethoxy group, 2-(3-chlorophenyl)ethoxy group, 2-(4-chlorophenyl)ethoxy group, 2-trifluoromethylbenzyloxy group, 3-trifluoromethylbenzyloxy group, 4-trifluoromethylbenzyloxy group, 2-trifluoromethoxybenzyloxy group, 3-trifluoromethoxybenzyloxy group, 4-trifluoromethoxybenzyloxy group, 2-(2-trifluoromethyl-phenyl)ethoxy group, 2-(3-trifluoromethylphenyl)ethoxy group, 2-(4-trifluoromethylphenyl)ethoxy group, 2-(2-trifluoromethoxyphenyl)ethoxy group, 2-(3-trifluoromethoxyphenyl)ethoxy group, 2-(4-trifluoromethoxyphenyl)ethoxy group, 3-(2-trifluoromethylphenyl)propoxy group, 3-(3-trifluoromethylphenyl)propoxy group, 3-(4-trifluoromethylphenyl)propoxy group, 3-(2-trifluoro-methylphenyl)propoxy group, 3-(3-trifluoromethoxy-phenyl) propoxy group, 3-(4-trifluoromethoxyphenyl)-propoxy group, 4-(3-trifluoromethylphenyl)butoxy group, 5-(4-trifluoromethylphenyl)pentoxy group, 4-(4-trifluoromethylphenyl)pentoxy group, 4-(4-trifluoromethoxyphenyl)pentoxy group, 6-(3-trifluoromethylphenyl)hexyloxy group, 6-(4-trifluoromethylphenyl)-hexyloxy group, 6-(4-trifluoromethoxyphenyl)hexyloxy group, or the like.

A C3-8 cycloalkyl-C1-6 alkyl group is a group consisting of a cyclic alkyl group having 3 to 8 carbon atoms and an alkyl group having 1 to 6 carbon atoms, examples of which include a cyclopropylmethyl group, 2-cyclopropylethyl group, 3-cyclopropylpropyl group, 4-cyclopropylbutyl group, 5-cyclopropylpentyl group, 6-cyclopropylhexyl group, cyclobutylmethyl group, 2-cyclobutylethyl group, 3-cyclobutylpropyl group, 4-cyclobutylbutyl group, 5-cyclobutylpentyl group, 6-cyclobutylhexyl group, cyclopentylmethyl group, 2-cyclopentylethyl group, 3-cyclopentylpropyl group, 4-cyclopentylbutyl group, 5-cyclopentylpentyl group, 6-cyclopentylhexyl group, cyclohexylmethyl group, 2-cyclohexylethyl group, 3-cyclohexylpropyl group, 4-cyclohexylbutyl group, 5-cyclohexylpentyl group, 6-cyclohexylhexyl group, cycloheptylmethyl group, 2-cycloheptylethyl group, 3-cycloheptylpropyl group, 4-cycloheptylbutyl group, 5-cycloheptylpentyl group, 6-cycloheptylhexyl group, cyclooctylmethyl group, 2-cyclooctylethyl group, 3-cyclooctylpropyl group, 4-cyclooctylbutyl group, 5-cyclooctylpentyl group, 6-cyclooctylhexyl group or the like.

The methods for producing the compounds of the present invention are explained below.

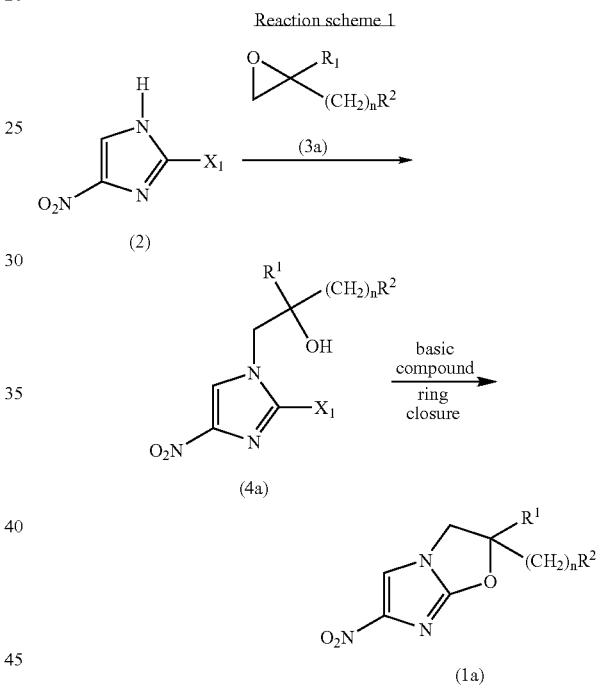

Reaction scheme 1 wherein $R^1$, $R^2$ and n are the same as above, and $X_1$ represents a halogen atom or nitro group.

According to reaction scheme 1, the compound of the present invention represented by general formula (1a) is produced by reacting a 4-nitroimidazole compound represented by general formula (2) with an epoxy compound represented by general formula (3a) in the presence or absence of a basic compound to obtain a compound represented by general formula (4a), and then subjecting the obtained compound to a ring closure reaction.

The molar ratio of the compound of general formula (2) to the compound of general formula (3a) may be generally between 1:0.5 and 1:5, and preferably between 1:0.5 and 1:3.

Known compounds can be widely used as a basic compound herein. Examples of such a basic compound include inorganic basic compounds such as a metal hydride, metal alcoholate, hydroxide, carbonate or hydrogencarbonate, and organic basic compounds such as acetate.

Specific examples of a metal hydride include sodium hydride and potassium hydride. Specific examples of a metal alcoholate include sodium methoxide, sodium ethoxide and potassium tert-butoxide. Specific examples of a hydroxide include sodium hydroxide and potassium hydroxide. Specific examples of a carbonate include sodium carbonate and potassium carbonate. Specific examples of a hydrogencarbonate include sodium hydrogencarbonate and potassium hydrogencarbonate. In addition to the above compounds, sodium amide and the like may also be included in the inorganic basic compounds.

Specific examples of acetate include sodium acetate and potassium acetate. In addition to these compounds, specific examples of organic basic compounds include triethylamine, trimethylamine, diisopropylethylamine, pyridine, dimethylaniline, 1-methylpyrrolidine, N-methylmorpholine, 1,5-diazabicyclo-[4.3.0]nonene-5(DBN), 1,8-diazabicyclo[5.4.0]undecene-7(DBU), and 1,4-diazabicyclo[2.2.2]octane (DABCO).

The molar ratio of the above basic compound to the compound of general formula (2) may be generally between 0.1:1 and 2:1, preferably between 0.1:1 and 1:1, and more preferably between 0.1:1 and 0.5:1.

The reaction of the compound of general formula (2) with the compound of general formula (3a) is generally carried out in an appropriate solvent.

Common solvents can be widely used as the above solvent, as long as it does not inhibit the reaction. Examples of such a solvent include aprotic polar solvents such as dimethylformamide (DMF), dimethylsulfoxide (DMSO) or acetonitrile, ketone solvents such as acetone or methylethylketone, hydrocarbon solvents such as benzene, toluene, xylene, tetralin or liquid paraffin, alcohol solvents such as methanol, ethanol, isopropanol, n-butanol or tert-butanol, ether solvents such as tetrahydrofuran (THF), dioxane, dipropyl ether, diethyl ether or diglyme, ester solvents such as ethyl acetate or methyl acetate, and mixed solvents thereof. Water may be contained in these solvents.

The reaction of the compound of general formula (2) with the compound of general formula (3a) is carried out, for example, as follows: The compound of general formula (2) is dissolved in a reaction solvent, and while stirring, a basic compound is added to the mixture cooled on ice or at up to room temperature (30° C.). Thereafter, the mixture is stirred at room temperature to 80° C. for 30 minutes to 1 hour, and the compound of general formula (3a) is then added thereto. Thereafter, the mixture is further stirred generally at room temperature to 100° C., and preferably 50° C. to 80° C., generally for 30 minutes to 60 hours, and preferably for 1 to 50 hours.

The compound (2) used as a starting material is known. The compound (3a) includes a novel compound, and a method for producing the compound will be explained later.

The thus obtained reaction mixture is, for example, cooled, and then its crude reaction product is separated therefrom by an isolation operation such as filtration, concentration or extraction. Thereafter, a compound of general formula (4a) can be isolated and purified from the reaction mixture by a common purification operation such as column chromatography or recrystallization.

The compound of the present invention represented by general formula (1a) is produced by subjecting the compound represented by general formula (4a) to a ring closure reaction. The ring closure reaction is carried out by dissolving the above obtained compound represented by general formula (4a) in a reaction solvent and then adding a basic compound thereto followed by stirring.

Herein, as a reaction solvent and a basic compound, there can be used the same reaction solvent and the same basic compound as used in the above reaction of the compound of general formula (2) with the compound of general formula (3a).

The molar ratio of the basic compound to the compound of general formula (4a) is generally equal to 1:1 or higher, preferably between 1:1 and 5:1, and more preferably between 1:1 and 2:1.

The reaction temperature for the ring closure reaction is generally 0° C. to 150° C., preferably room temperature to 120° C., and more preferably 50° C. to 100° C. The reaction time is generally 30 minutes to 48 hours, preferably 1 to 24 hours, and more preferably 1 to 12 hours.

The thus obtained reaction mixture is, for example, cooled, and then its crude reaction product is separated therefrom by an isolation operation such as filtration, concentration or extraction. Thereafter, the compound of general formula (1a) can be isolated and purified from the reaction mixture by a common purification operation such as column chromatography or recrystallization.

In the present invention, the reaction mixture can be directly subjected to the following ring closure reaction without isolating the compound of general formula (4a) generated as a result of the reaction of the compound of general formula (2) with the compound of general formula (3a). For example, the compound of general formula (2) is reacted with the compound of general formula (3a) at room temperature to 80° C., and thereafter, a basic compound is added to the obtained reaction mixture followed by stirring at 50° C. to 100° C. Otherwise, after the compound of general formula (2) is reacted with the compound of general formula (3a) at room temperature to 80° C., the obtained reaction mixture is concentrated, and the residue is dissolved in a high boiling solvent. Thereafter, a basic compound is added to the obtained solution followed by stirring at 50° C. to 100° C., so as to produce a compound of interest represented by general formula (1a).

Alternatively, in the reaction of the compound of general formula (2) with the compound of general formula (3a), a basic compound is used at a molar ratio of the basic compound to the compound (2) that is between 0.9:1 and 2:1. The stirring is carried out at 50° C. to 100° C., so that the reaction of the compound of general formula (2) with the compound of general formula (3a) is carried out in a single process to produce a compound of interest represented by general formula (1a).

Reaction scheme 2

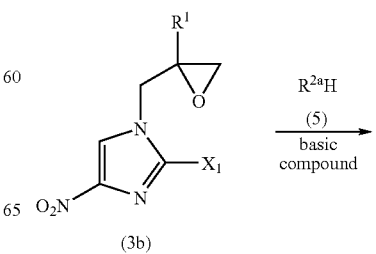

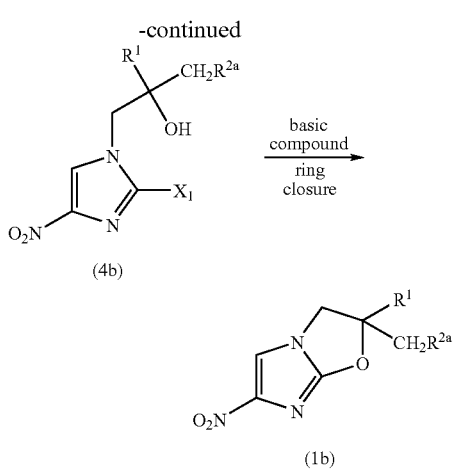

wherein R$^1$ and X$_1$ are the same as above, and R$^{2a}$ represents a group represented by general formula (A), (B), (E) or (F).

According to reaction scheme 2, the compound of the present invention represented by general formula (1b) is produced by-reacting a compound represented by general formula (3b) with a compound represented by general formula (5) or a salt thereof, so as to obtain a compound represented by general formula (4b), and then subjecting the obtained compound to a ring closure reaction, in the presence of a basic compound.

The compound (3b) is novel, and a method for producing the compound will be explained later (reaction scheme 13). The compound (5), in which R$^{2a}$ represents a group represented by general formula (E), includes a novel compound. An example of methods for producing the above compound will be described later in Reference Examples 182, 186 to 188, and 192.

The molar ratio of the compound of general formula (3b) to the compound of general formula (5) may be generally between 1:0.5 and 1:5, and preferably between 1:0.5 and 1:2.

The reaction of the compound of general formula (3b) with the compound of general formula (5) is carried out in the presence of a basic compound in an appropriate solvent.

As a basic compound and a reaction solvent, there can be used the same basic compound and the same reaction solvent as used in the above reaction of the compound of general formula (2) with the compound of general formula (3a). The molar ratio of the basic compound to the compound of general formula (3b) is generally a catalytic amount, preferably between 0.1:1 and 3:1, and more preferably between 0.1:1 and 2:1.

In the case of the compound (5) in which R$^{2a}$ represents a group represented by general formula (B) or (E), the salt of the compound (5) can be used instead of using the compound (5) and a basic compound. Examples of such a salt include alkali metal salts such as a sodium salt or a potassium salt of the compound (5).

The reaction of the compound of general formula (3b) with the compound of general formula (5) is carried out, generally at room temperature to 150° C., preferably at room temperature to 120° C., and more preferably at room temperature to 80° C. The reaction time is generally 10 minutes to 48 hours, preferably 10 minutes to 24 hours, and more preferably 10 minutes to 2 hours.

The thus obtained reaction mixture is, for example, cooled, and then its crude reaction product is separated therefrom by an isolation operation such as filtration, concentration or extraction. Thereafter, the compound of general formula (4b) can be isolated and purified from the reaction mixture by a common purification operation such as column chromatography or recrystallization.

The compound of the present invention represented by general formula (1b) is produced by subjecting the compound represented by general formula (4b) to a ring closure reaction. The ring closure reaction is carried out by dissolving the above obtained compound represented by general formula (4b) in a reaction solvent and then adding a basic compound thereto followed by stirring at a certain temperature.

Herein, as a reaction solvent and a basic compound, there can be used the same reaction solvent and the same basic compound as used in the above reaction of the compound of general formula (3b) with the compound of general formula (5).

The molar ratio of the basic compound to the compound of general formula (4b) is generally equal to 1:1 or higher, preferably between 1:1 and 5:1, and more preferably between 1:1 and 2:1.

The reaction temperature for the ring closure reaction is generally 0° C. to 150° C., preferably room temperature to 120° C., and more preferably 50° C. to 100° C. The reaction time is generally 10 minutes to 48 hours, preferably 10 minutes to 24 hours, and more preferably 20 minutes to 4 hours.

The thus obtained reaction mixture is, for example, cooled, and then its crude reaction product is separated therefrom by an isolation operation such as filtration, concentration or extraction. Thereafter, the compound of general formula (1b) can be isolated and purified from the reaction mixture by a common purification operation such as column chromatography or recrystallization.

In the present invention, the reaction mixture can be directly subjected to the following ring closure reaction without isolating the compound of general formula (4b) produced as a result of the reaction of the compound of general formula (3b) with the compound of general formula (5), so as to produce a compound of interest that is the compound of the present invention represented by general formula (1b).

Particularly, in the case of the compound (5) in which R$^{2a}$ represents a group represented by general formula (B) or (E), if a basic compound is used to the compound (5) at a molar ratio of equal to 1:1 or higher, and if the reaction is carried out at 50° C. to 100° C., the compound of the present invention represented by general formula (1b) can be produced in a single process without isolating an intermediate (4). In the case of using the alkali metal salt (e.g., a sodium salt or a potassium salt) of the compound (5) in which R$^{2a}$ represents a group represented by general formula (B) or (E), the same thing can be said.

Reaction scheme 3

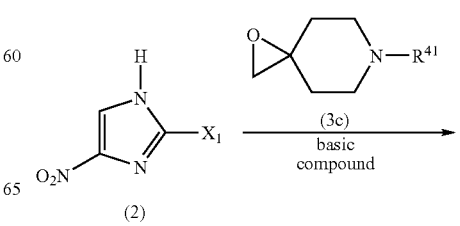

-continued

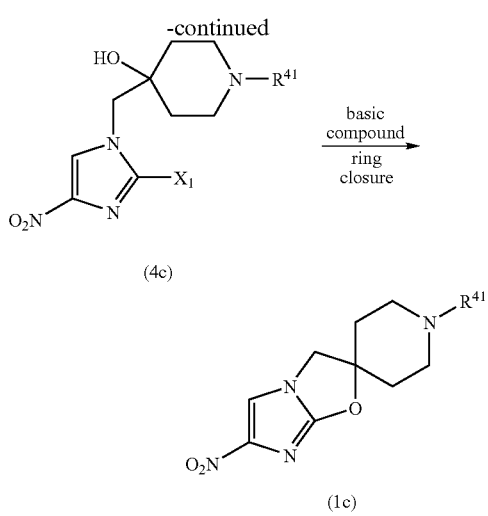

(4c)

(1c)

wherein $R^{41}$ and $X_1$ are the same as above.

According to reaction scheme 3, the compound of the present invention represented by general formula (1c) is produced by reacting the compound represented by general formula (2) with a compound represented by general formula (3c) so as to obtain a compound represented by general formula (4c), and then subjecting the obtained compound to a ring closure reaction, in the presence of a basic compound.

The compound (3c) includes a novel compound, and a method for producing the compound will be explained later (reaction scheme 14).

The molar ratio of the compound of general formula (2) to the compound of general formula (3c) may be generally between 0.1:1 and 2:1, preferably between 0.1:1 and 1:1, and more preferably between 0.1:1 and 0.5:1.

The reaction of the compound of general formula (2) with the compound of general formula (3c) is carried out in the presence of a basic compound in an appropriate solvent.

As a basic compound and a reaction solvent, there can be used the same basic compound and the same reaction solvent as used in the above reaction of the compound of general formula (2) with the compound of general formula (3a). The molar ratio of the basic compound to the compound of general formula (2) is generally 0.1:1 or higher, preferably between 1:1 and 5:1, and more preferably between 1:1 and 2:1.

The reaction of the compound of general formula (2) with the compound of general formula (3c) is carried out, for example, as follows: The compound of general formula (2) is dissolved in a reaction solvent, and while stirring, a basic compound is added to the mixture cooled on ice or at up to room temperature (30° C.). Thereafter, the mixture is stirred at room temperature to 80° C. for 30 minutes to 1 hour, and the compound of general formula (3c) is then added thereto. Thereafter, the mixture is further stirred generally at room temperature to 100° C., and preferably 50° C. to 80° C., generally for 30 minutes to 24 hours, preferably for 1 to 12 hours, and more preferably for 1 to 8 hours.

The thus obtained reaction mixture is, for example, cooled, and then its crude reaction product is separated therefrom by an isolation operation such as filtration, concentration or extraction. Thereafter, the compound of general formula (4c) can be isolated and purified from the reaction mixture by a common purification operation such as column chromatography or recrystallization.

The compound of the present invention represented by general formula (1c) is produced by subjecting the compound represented by general formula (4c) to a ring closure reaction. The ring closure reaction is carried out by dissolving the above obtained compound represented by general formula (4c) in a reaction solvent and then adding a basic compound thereto followed by stirring at a certain temperature.

Herein, as a reaction solvent and a basic compound, there can be used the same reaction solvent and the same basic compound as used in the above reaction of the compound of general formula (2) with the compound of general formula (3c).

The molar ratio of the basic compound to the compound of general formula (4c) is generally equal to 1:1 or higher, preferably between 1:1 and 5:1, and more preferably between 1:1 and 2:1.

The reaction temperature for the ring closure reaction is generally 0° C. to 150° C., preferably room temperature to 120° C., and more preferably 50° C. to 100° C. The reaction time is generally 30 minutes to 48 hours, preferably 1 to 24 hours, and more preferably 1 to 12 hours.

The thus obtained reaction mixture is, for example, cooled, and then its crude reaction product is separated therefrom by an isolation operation such as filtration, concentration or extraction. Thereafter, the compound of general formula (1c) can be isolated and purified from the reaction mixture by a common purification operation such as column chromatography or recrystallization.

In the present invention, the reaction mixture can be directly subjected to the following ring closure reaction without isolating the compound of general formula (4c) generated as a result of the reaction of the compound of general formula (2) with the compound of general formula (3c), so that the compound of interest of the present invention represented by general formula (1c) can be produced.

Reaction scheme 4

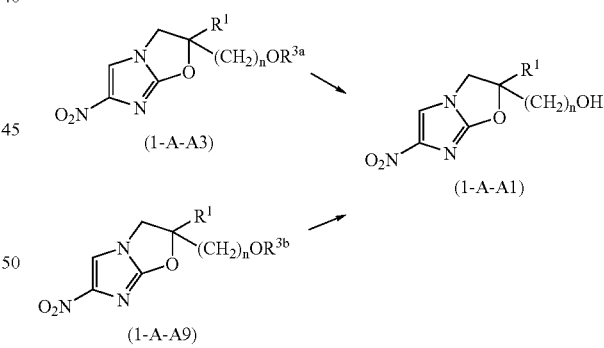

wherein $R^1$ and n are the same as above, $R^{3a}$ represents a C1-C6 alkoxy-C1-C6 alkyl group, and $R^{3b}$ represents a C1-C6 alkanoyl group.

A compound wherein, in general formula (1), $R^2$ represents a group represented by general formula (A) and $R^3$ represents A1) a hydrogen atom (hereinafter referred to as a compound (1-A-A1)), is produced by the hydrolysis of a corresponding compound in which $R^3$ represents A3) a C1-C6 alkoxy-C1-C6 alkyl group (hereinafter referred to as a compound (1-A-A3)), or a corresponding compound wherein $R^3$ represents A9) a C1-C6 alkanoyl group (hereinafter referred to as a compound (1-A-A9)).

Hydrolysis of the compound (1-A-A3) is carried out under acidic conditions. The hydrolysis is carried out, for example, by suspending or dissolving the compound (1-A-A3) in an appropriate solvent, and adding acid to the obtained solution followed by stirring at 0° C. to 120° C. Example of the used solvent may include water, alcohol solvents such as methanol, ethanol, isopropanol or ethylene glycol, acetonitrile, acetone, toluene, DMF, DMSO, acetic acid, trifluoroacetic acid, and mixed solvents thereof. Examples of the used acid may include organic acids such as trifluoroacetic acid or acetic acid, and inorganic acids such as hydrochloric acid, bromic acid, hydrobromic acid or sulfuric acid. Organic acids such as trifluoroacetic acid or acetic acid can also be used as reaction solvents. The reaction temperature is generally 0° C. to 120° C., preferably room temperature to 100° C., and more preferably room temperature to 80° C. The reaction time is generally 30 minutes to 24 hours, preferably 30 minutes to 12 hours, and more preferably 1 to 8 hours.

Hydrolysis of the compound (1-A-A9) is carried out under basic condition. The hydrolysis is carried out, for example, by suspending or dissolving the compound (1-A-A9) in an appropriate solvent, and adding base to the obtained solution followed by stirring at 0° C. to 120° C. Example of the used solvent may include water, alcohol solvents such as methanol, ethanol, isopropanol or ethylene glycol, and mixed solvents thereof. Examples of the used base may include alkali metal hydroxides such as sodium hydroxide or potassium hydroxide, alkali metal carbonates such as sodium carbonate or potassium carbonate, and acetates such as sodium acetate. The reaction temperature is generally 0° C. to 120° C., preferably room temperature to 100° C., and more preferably room temperature to 80° C. The reaction time is generally 30 minutes to 24 hours, preferably 30 minutes to 12 hours, and more preferably 1 to 8 hours.

The thus obtained reaction mixture is, for example, cooled, and then its crude reaction product is separated therefrom by an isolation operation such as filtration, concentration or extraction. Thereafter, the compound (1-A-A1) can be isolated and purified from the reaction mixture by a common purification operation such as column chromatography or recrystallization.

Reaction scheme 5

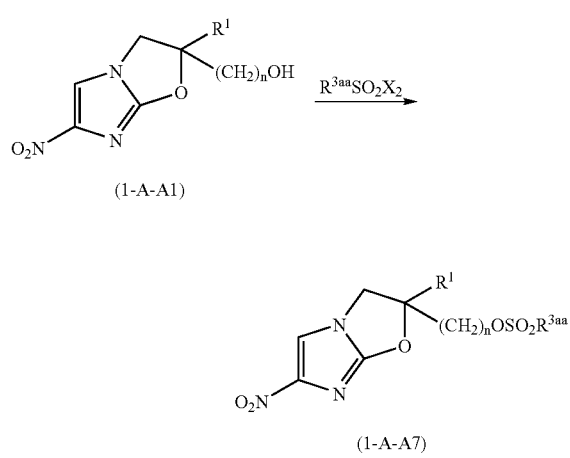

wherein $R^1$ and n are the same as above, $X_2$ represents a halogen atom, and $R^{3aa}$ represents a C1-C6 alkyl group or phenyl group which may be substituted by the C1-C6 alkyl group.

A compound wherein, in general formula (1), $R^2$ represents a group represented by general formula (A) and $R^3$ represents a sulfonyl group of the definitions A7) or A8) (hereinafter referred to as a compound (1-A-A7)), is produced by the sulfonylation of a corresponding compound wherein $R^3$ represents A1) a hydrogen atom (the compound (1-A-A1)).

For the sulfonylation of the compound (1-A-A1), reaction conditions for the common sulfonylation reaction of alcohol can be widely applied. For example, the compound (1-A-A1) is dissolved in an appropriate solvent, and the compound represented by general formula $R^{3aa}SO_2X_2$ is added to the obtained solution in the presence of a basic compound followed by stirring at 0° C. to 150° C., so that the compound (1-A-A7) can be obtained.

Any solvent can be used herein, as long as it does not inhibit the sulfonylation reaction. Examples of such a solvent include halogenated hydrocarbon solvents such as methylene chloride or chloroform, aprotic polar solvents such as DMF, DMSO or acetonitrile, aromatic hydrocarbon solvents such as benzene, toluene or xylene, hydrocarbon solvents such as tetralin, liquid paraffin or cyclohexane, ether solvents such as THF, dioxane, dipropyl ether, diethyl ether or diglyme, ethyl acetate, acetone, and mixed solvents thereof.

The compound represented by general formula $R^{3aa}SO_2X_2$ is used to the compound (1-A-A1) at a molar ratio of generally equal to 1:1 or higher, preferably between 1:1 and 2:1, and more preferably between 1:1 and 1.1:1.

As a basic compound, there can be used the same basic compound as used in the above reaction of the compound of general formula (2) with the compound of general formula (3a).

The molar ratio of the basic compound to the compound represented by general formula $R^{3aa}SO_2X_2$ is generally equal to 1:1 or higher, preferably between 1:1 and 5:1, and more preferably between 1:1 and 2:1.

In the present sulfonylation reaction, 4-dimethylaminopyridine, 4-(1-pyrrolidinyl)pyridine or the like can be used as a catalyst.

The reaction temperature is generally 0° C. to 150° C., preferably 0° C. to 100° C., and more preferably 0° C. to 60° C. The reaction time is generally 30 minutes to 48 hours, preferably 1 to 24 hours, and more preferably 1 to 4 hours.

The thus obtained reaction mixture is, for example, cooled, and then its crude reaction product is separated therefrom by an isolation operation such as filtration, concentration or extraction. Thereafter, the compound (1-A-A7) can be isolated and purified from the reaction mixture by a common purification operation such as column chromatography or recrystallization.

Reaction scheme 6

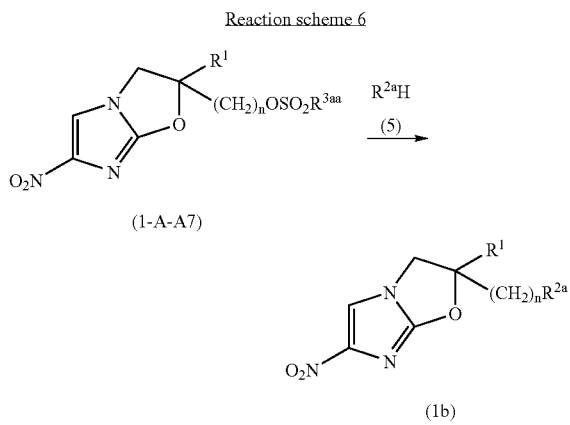

(1b)

Reaction scheme 7

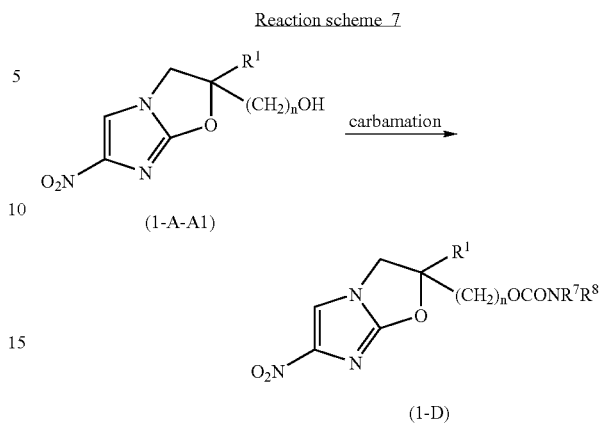

wherein $R^1$, $R^{2a}$, $R^{3aa}$ and n are the same as above.

A compound wherein, in general formula (1), $R^2$ represents a group represented by general formula (A), (B), (E) or (F) (hereinafter referred to as a compound (1b)), is also produced by the reaction of a corresponding compound wherein $R^2$ represents a group represented by general formula (A) and $R^3$ represents a sulfonyl group of the definitions A7) or A8) (a compound (1-A-A7)) with a compound represented by general formula (5).

The reaction of the compound (1-A-A7) with the compound represented by general formula (5) is carried out in an appropriate solvent in the presence of a basic compound.

Any solvent can be used herein, as long as it does not inhibit the present reaction. Examples of such a solvent include water, aprotic polar solvents such as DMF, DMSO or acetonitrile, hydrocarbon solvents such as benzene, toluene, xylene, tetralin, liquid paraffin or cyclohexane, alcohol solvents such as ethanol, isopropanol, n-butanol or tert-butanol, ether solvents such as THF, dioxane, dipropyl ether, diethyl ether or diglyme, ethyl acetate, acetone, and mixed solvents thereof.

As a basic compound, there can be used the same basic compound as used in the above reaction of the compound of general formula (2) with the compound of general formula (3a).

The molar ratio of the basic compound to the compound (1-A-A7) is generally equal to 1:1 or higher, preferably between 1:1 and 5:1, and more preferably between 1:1 and 2:1.

The molar ratio of the compound represented by general formula (5) to the compound (1-A-A7) may be generally equal to 1:1 or higher, preferably between 0.9:1 and 2:1, and more preferably between 0.9:1 and 1.5:1.

The reaction temperature is generally room temperature to 150° C., preferably room temperature to 100° C., and more preferably 60° C. to 100° C. The reaction time is generally 10 minutes to 24 hours, preferably 10 minutes to 12 hours, and more preferably 20 minutes to 7 hours.

The thus obtained reaction mixture is, for example, cooled, and then its crude reaction product is separated therefrom by an isolation operation such as filtration, concentration or extraction. Thereafter, a compound of interest can be isolated and purified from the reaction mixture by a common purification operation such as column chromatography or recrystallization.

wherein $R^1$, n, $R^7$ and $R^8$ are the same as above.

A compound wherein, in general formula (1), $R^2$ represents a group represented by general formula (D) (hereinafter referred to as a compound (1-D)), is produced by the carbamation of a compound wherein $R^2$ represents a group represented by general formula (A) and $R^3$ represents A1) a hydrogen atom (the compound (1-A-A1)).

For the carbamation of the compound (1-A-A1), reaction conditions for the common carbamation reaction of alcohol can be widely applied. Examples of such a method include: (1) a method using amine represented by a general formula $R^7R^8NH$ (wherein $R^7$ and $R^8$ are the same as above) and triphosgene, (2) a reaction of using amine represented by a general formula $R^7R^8NH$ (wherein $R^7$ and $R^8$ are the same as above) and carbodiimidazole, and (3) a method using an isocyanate compound.

(1) Method Using Amine and Triphosgene

Amine represented by the general formula $R^7R^8NH$ (wherein $R^7$ and $R^8$ are the same as above) is reacted with triphosgene, so as to generate carbamoyl chloride represented by a general formula $ClCONR^7R^8$ (wherein $R^7$ and $R^8$ are the same as above). Carbamoyl chloride may be isolated. However, since it is generally unstable, it is immediately used in the following step without isolation.

A basic compound and the above amine are added to a methylene chloride solution containing triphosgene, while the solution is cooled and stirred. Thereafter, the mixture is stirred at 0° C. to 30° C. for 30 minutes to 4 hours, so as to generate carbamoyl chloride. The molar ratio of triphosgene to amine is generally between 0.3:1 and 1.5:1, preferably between 0.3:1 and 0.6:1, and more preferably between 0.3:1 and 0.4:1.

Examples of a basic compound used in the reaction between amine and triphosgene include triethylamine, N-ethyldiisopropylamine, and N-methylmorpholine. The molar ratio of a basic compound to triphosgene is generally 3:1 or higher, preferably between 3:1 and 4.5:1, and more preferably between 3:1 and 3.3:1.

The reaction temperature is generally 0° C. to 60° C., and preferably 0° C. to room temperature (30° C.) The reaction time is generally 30 minutes to 8 hours, preferably 1 to 4 hours, and more preferably 1 to 2 hours.

The thus obtained reaction solution of carbamoyl chloride can be directly used. However, it is more advantageous to eliminate insoluble products by filtration prior to concentration of the filtrate.

Subsequently, the compound (1-A-A1) is dissolved in an appropriate reaction solvent, and the carbamoyl chloride produced above is added thereto, while stirring on ice cooling. Thereafter, copper chloride is further added thereto, and the mixture is stirred at a certain temperature for a certain time, so as to produce the compound (1-D).

Any reaction solvent can be widely used herein, as long as it does not inhibit the reaction. Examples of such a solvent may include aprotic polar solvents such as DMF, DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

The molar ratio of carbamoyl chloride to the compound (1-A-A1) may be generally between 1:1 and 5:1, preferably between 1:1 and 3:1, and more preferably between 1:1 and 2:1.

Moreover, the molar ratio of copper chloride to the compound (1-A-A1) may be generally between 0.1 1 and 5:1, preferably between 0.5:1 and 2:1, and more preferably between 0.5:1 and 1:1.

The reaction temperature is generally 0° C. to 60° C., preferably 10° C. to 50° C., and more preferably 20° C. to 35° C. The reaction time is generally 30 minutes to 48 hours, preferably 1 to 30 hours, and more preferably 2 to 24 hours.

(2) Reaction of Using Amine and Carbodiimidazole

Amine represented by the general formula $R^7R^8NH$ (wherein $R^7$ and $R^8$ are the same as above) is dissolved in an appropriate reaction solvent. 1,1'-carbonyldiimidazole is added to the obtained solution, while stirring on ice. The obtained mixture is stirred at a certain temperature for a certain time, so as to obtain an amino carbonylimidazole derivative.

The molar ratio of 1,1'-carbonyldiimidazole to amine is generally between 0.9:1 and 2:1, preferably between 1:1 and 1.5:1, and more preferably between 1:1 and 1.2:1.

Examples of the used solvent may include aprotic polar solvents such as acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

The reaction temperature is generally 0° C. to 60° C., and preferably 0° C. to room temperature (30° C.) The reaction time is generally 30 minutes to 8 hours, preferably 1 to 4 hours, and more preferably 1 to 2 hours.

The compound (1-A-A1) is dissolved in an appropriate solvent in advance. Then, the above obtained amino carbonylimidazole derivative is added to the solution, while stirring on ice. Thereafter, copper chloride is further added thereto, and the mixture is stirred at a certain temperature for a certain time, so as to produce the compound (1-D).

Any solvent can be widely used herein as a reaction solvent, as long as it does not inhibit the reaction. Examples of such a solvent may include aprotic polar solvents such as DMF, DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

The molar ratio of the amino carbonylimidazole derivative to the compound (1-A-A1) may be generally between 1:1 and 5:1, preferably between 1:1 and 3:1, and more preferably between 1:1 and 2:1.

Moreover, the molar ratio of the copper chloride to the compound (1-A-A1) may be generally between 0.9:1 and 5:1, preferably between 1:1 and 2:1, and more preferably between 1:1 and 1.2:1.

The reaction temperature is generally 0° C. to 60° C., preferably 10° C. to 50° C., and more preferably 20° C. to 35° C. The reaction time is generally 30 minutes to 48 hours, preferably 1 to 30 hours, and more preferably 1 to 3 hours.

(3) Method Using Isocyanate

The compound (1-A-A1) is dissolved in an appropriate reaction solvent. Then, isocyanate is added to the solution, while stirring on ice. Thereafter, copper chloride is further added thereto, and the mixture is stirred at a certain temperature for a certain time, so as to produce a compound (1-D) in which $R^7$ or $R^8$ represents a hydrogen atom.

Any solvent can be widely used herein as a reaction solvent, as long as it does not inhibit the reaction. Examples of such a solvent may include aprotic polar solvents such as DMF, DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

The molar ratio of the isocyanates to the compound (1-A-A1) may be generally between 1:1 and 5:1, preferably between 1:1 and 3:1, and more preferably between 1:1 and 2:1.

Moreover, the molar ratio of the copper chloride to the compound (1-A-A1) may be generally between 0.9:1 and 5:1, preferably between 1:1 and 2:1, and more preferably between 1:1 and 1.2:1.

The reaction temperature is generally 0° C. to 60° C., preferably 10° C. to 50° C., and more preferably 20° C. to 35° C. The reaction time is generally 30 minutes to 48 hours, preferably 1 to 30 hours, and more preferably 1 to 3 hours.

The reaction mixture obtained by the above method (1), (2) or (3) is, for example, cooled, and then its crude reaction product is separated therefrom by an isolation operation such as filtration, concentration or extraction. Thereafter, the compound (1-D) can be isolated and purified from the reaction mixture by a common purification operation such as column chromatography or recrystallization.

A compound having a heterocycle containing a nitrogen atom in a molecule thereof and comprising a C1-C6 alkoxycarbonyl group substituted on the nitrogen atom of the above heterocycle selected from among the compounds of the present invention represented by general formula (1) can be converted by deprotection into a compound having a hydrogen atom that is substituted on the nitrogen atom of the corresponding heterocycle.

According to this method, for example, a starting material to be deprotected is dissolved in an appropriate reaction solvent followed by hydrolysis using acid, so as to obtain a compound of interest.

Any solvent can be widely used herein as a reaction solvent, as long as it does not inhibit the reaction. Examples of such a solvent may include water, alcohol solvents such as methanol or ethanol, aprotic polar solvents such as DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

Examples of acid include inorganic acids such as hydrochloric acid, bromic acid or hydrobromic acid, and organic acids such as acetic acid, trifluoroacetic acid or trichloroacetic acid. Of these, the use of trifluoroacetic acid is advantageous.

The molar ratio of such acid to the starting material is generally equal to 1:1 or higher, and preferably between 2:1 and 10:1. However, such acid may also be used a large excess amount as a reaction solvent. The reaction temperature is generally room temperature to 100° C., but it may be appropriately adjusted depending on the type of the used acid. When trifluoroacetic acid is used, it is enough to set at room temperature. The reaction time is generally 1 to 24 hours, and preferably 1 to 12 hours.

The thus obtained reaction mixture is concentrated, and if necessary, acid such as hydrochloric acid is added thereto for crystallization, so that a compound of interest can be isolated in a form of hydrochloride or trifluoroacetate by recrystallization or the like.

The deprotected compound of interest can be isolated as described above. Alternatively, a basic compound such as triethylamine is added thereto without isolation, so that the compound of interest is converted into a free compound, which can be used in the following reaction.

For example, the above free base compound of interest is reacted with an acid halide, acid anhydride or mixed acid anhydride, so that the corresponding amide or carbamate can be produced. The reaction of the above free base compound of interest with sulfonyl chloride enables the production of the corresponding sulfon amide. Moreover, the ureation of the above free base compound of interest with amine enables the production of the corresponding urea. Furthermore, the reductive amination of the above free base compound of interest with aldehyde or the alkylation of the same above compound with alkyl halide enables the production of the N-alkylated derivative of the above compound of interest.

A compound having a heterocycle containing a nitrogen atom in a molecule thereof and comprising a hydrogen atom substituted on the nitrogen atom of the above heterocycle selected from among the compounds of the present invention represented by general formula (1) can be converted by carbamation into a compound having —$COOR^{27}$ (wherein $R^{27}$ is the same as above) substituted on the nitrogen atom of the corresponding heterocycle.

Examples of a method for carbamation include (1) a method using various types of halogenated formates and (2) a method using an active intermediate obtained by reacting alcohol with carbonyldiimidazole.

(1) Method Using Halogenated Formate

A starting material is reacted with halogenated formate in a reaction solvent in the presence of a basic compound, so as to produce a compound of interest.

Any solvent can be widely used herein as a reaction solvent, as long as it does not inhibit the reaction. Examples of such a solvent may include aprotic polar solvents such as DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

Known compounds can be widely used as a basic compound herein. Examples of such a basic compound include inorganic basic compounds such as hydroxide, carbonate or hydrogencarbonate, and organic basic compounds such as acetate.

Specific examples of hydroxide include sodium hydroxide, potassium hydroxide, cesium hydroxide and lithium hydroxide. Specific examples of carbonate include sodium carbonate, potassium carbonate, cesium carbonate and lithium carbonate. Specific examples of hydrogencarbonate include sodium hydrogencarbonate, potassium hydrogencarbonate, cesium hydrogencarbonate and lithium hydrogencarbonate.

Specific examples of acetate include sodium acetate and potassium acetate. In addition to these compounds, specific examples of other organic basic compounds include triethylamine, trimethylamine, diisopropylethylamine, pyridine, dimethylaniline, 1-methylpyrrolidine, N-methylmorpholine, DBN, DBU, and DABCO.

The molar ratio of such a basic compound to the starting material may be generally between 1:1 and 4:1, preferably between 1:1 and 1.5:1, and more preferably between 1:1 and 1.1:1.

The molar ratio of such halogenated formate to the starting material may be generally equal to 1:1 or higher, preferably between 1:1 and 1.5:1, and more preferably between 1:1 and 1.1:1.

The reaction temperature is generally 0° C. to 100° C., preferably 0° C. to 60° C., and more preferably 10° C. to 30° C. The reaction time is generally 30 minutes to 12 hours, preferably 1 to 6 hours, and more preferably 1 to 2 hours.

(2) Method Using Active Intermediate

Alcohol represented by a general formula $R^{27}OH$ ($R^{27}$ is the same as above) is reacted with 1,1'-carbonyldiimidazole in an appropriate solvent to obtain an active intermediate (the first step), and then the obtained active intermediate is reacted with a starting material (the second step), so that a compound of interest can be produced.

Any solvent can be widely used herein as a reaction solvent, as long as it does not inhibit the reaction. Examples of such a solvent may include aprotic polar solvents such as DMF, DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

The molar ratio of the 1,1'-carbonyldiimidazole to the alcohol represented by the above general formula may be generally equal to 1:1 or higher, preferably between 1:1 and 1.5:1, and more preferably between 1:1 and 1.1:1.

In the first step, the reaction temperature is generally 0° C. to 100° C., preferably 0° C. to 60° C., and more preferably 10° C. to 30° C. The reaction time is generally 30 minutes to 12 hours, preferably 1 to 6 hours, and more preferably 1 to 2 hours.

The molar ratio of the active intermediate to the starting material may be generally equal to 1:1 or higher, preferably between 1:1 and 1.5:1, and more preferably between 1:1 and 1.1:1.

In the second step, the reaction temperature is generally 0° C. to 100° C., preferably 0° C. to 60° C., and more preferably 10° C. to 30° C. The reaction time is generally 30 minutes to 12 hours, preferably 1 to 6 hours, and more preferably 1 to 2 hours.

The reaction mixture obtained by the above method (1) or (2) is, for example, cooled, and then its crude reaction product is separated therefrom by an isolation operation such as filtration, concentration or extraction. Thereafter, the carbamate of interest can be isolated and purified from the reaction mixture by a common purification operation such as column chromatography or recrystallization.

A compound having a heterocycle containing a nitrogen atom in a molecule thereof and comprising an $R^{32}R^{33}NCO$-group (wherein $R^{32}$ and $R^{33}$ are the same as above) substituted on the nitrogen atom of the above heterocycle selected from among the compounds of the present invention represented by general formula (1) can be produced by the reaction of a compound having a hydrogen atom substituted on the nitrogen atom of the corresponding heterocycle.

For such a urea formation, for example, (1) a method using amine represented by a general formula $R^{32}R^{33}NH$ (wherein $R^{32}$ and $R^{33}$ are the same as above) and triphosgene, (2) a reaction of using amine represented by the general formula $R^{32}R^{33}NH$ (wherein $R^{32}$ and $R^{33}$ are the same as above) and carbodiimidazole, and (3) a method using an isocyanate compound.

These reactions (1), (2) and (3) are carried out, for example, under the same reaction conditions for the reactions with the compound (1-A-A1) as described in (1), (2) and (3) above.

The reaction mixture obtained by the above method (1), (2) or (3) is, for example, cooled, and then its crude reaction product is separated therefrom by an isolation operation such as filtration, concentration or extraction. Thereafter, a compound of interest can be isolated and purified from the reaction mixture by a common purification operation such as column chromatography or recrystallization.

As for the compounds of the present invention represented by general formula (1), a compound having a heterocycle containing a nitrogen atom in a molecule thereof and comprising an $R^{38a}$-group substituted on the nitrogen atom of the above heterocycle (wherein $R^{38a}$ represents a C1-C6 alkanoyl group, phenyl C2-C6 alkanoyl group (wherein, on the phenyl ring, at least one type of group selected from a group consisting of halogen atom, a halogen substituted or unsubstituted C1-C6 alkyl group and a halogen substituted or unsubstituted C1-C6 alkoxy group may be substituted), phenoxy C2-C6 alkanoyl group wherein halogen atom may be substituted on the phenyl ring, phenylthio C2-C6 alkanoyl group wherein halogen may be substituted on the phenyl ring, benzoyl group (wherein, on the phenyl ring, at least one type of group selected from a group consisting of halogen, a halogen substituted or unsubstituted C1-C6 alkyl group, a halogen substituted or unsubstituted C1-C6 alkoxy group, and a C1-C6 alkylamino group may be substituted), 4-biphenylcarbonyl group, pyridinylcarbonyl group, or phenyl C2-C6 alkenylcarbonyl group wherein halogen atom may be substituted on the phenyl ring), can be produced by reacting a compound comprising a hydrogen atom substituted on the nitrogen atom of the corresponding heterocycle, with carboxylic acid represented by a general formula $R^{38a}OH$ (wherein $R^{38a}OH$ is the same as above).

The above reaction can be carried out under the same conditions for the reaction of a compound (Ea-2) with a compound (18) represented by reaction scheme 19, which will be described later.

The reaction mixture obtained by the above method is, for example, cooled, and then its crude reaction product is separated therefrom by an isolation operation such as filtration, concentration or extraction. Thereafter, a compound of interest can be isolated and purified from the reaction mixture by a common purification operation such as column chromatography or recrystallization.

A compound having a heterocycle containing a nitrogen atom in a molecule thereof and comprising $R^{39a}SO_2$-substituted on the nitrogen atom of the above heterocycle (wherein $R^{39a}$ represents a phenyl group which may be substituted by at least one group selected from a group consisting of a halogen atom and C1-C6 alkyl groups), selected from the compounds of the present invention represented by general formula (1), can be produced by reacting a compound having a hydrogen atom substituted on the nitrogen atom of the corresponding heterocycle, with sulfonyl halide represented by a general formula $R^{39a}SO_2X_2$ (wherein $R^{39a}$ and $X_2$ are the same as above).

The above reaction can be carried out under the same conditions for the reaction of the compound (Fd-1) with a compound (15) represented by reaction scheme 18, which will be described later.

The reaction mixture obtained by the above method is, for example, cooled, and then its crude reaction product is separated therefrom by an isolation operation such as filtration, concentration or extraction. Thereafter, a compound of interest can be isolated and purified from the reaction mixture by a common purification operation such as column chromatography or recrystallization.

As for the compounds of the present invention represented by general formula (1), a compound having a heterocycle containing a nitrogen atom in a molecule thereof and comprising an $R^{40a}$—CH—$R^{52}$ group substituted on the nitrogen atom of the above heterocycle (wherein $R^{52}$ is the same as described later, and $R^{40a}$ represents a phenyl group (wherein, on the phenyl ring, at least one group selected from a group consisting of halogen atom, a cyano group, a halogen substituted or unsubstituted C1-C6 alkyl group, a cyclohexyl group, an amino group which may have a C1-C6 alkyl group as a substituent, a C1-C6 alkoxycarbonyl group, a phenoxy group, a phenyl C1-C6 alkyl group, a phenyl C2-C6 alkenyl group, a pyridyl group, an imidazolyl group, a halogen substituted or unsubstituted C1-C6 alkoxy group, and a piperidinyl group may be substituted), 4-biphenylyl group (wherein, on the phenyl ring, at least one group selected from a group consisting of halogen atom, a cyano group, a halogen substituted or unsubstituted C1-C6 alkyl group, a halogen substituted or unsubstituted C1-C6 alkoxy group, and an amino group which may have a C1-C6 alkyl group as a substituent may be substituted), naphthyl group, furyl group, or thienyl group), can be produced by subjecting a compound comprising a hydrogen atom substituted on the nitrogen atom of the corresponding heterocycle to a reductive alkylation reaction.

This reductive alkylation reaction is carried out, for example, by reacting a starting material with aldehyde or ketone represented by a general formula

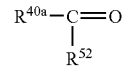

($R^{40a}$ is the same as described above, and $R^{52}$ is a hydrogen atom or C1-C6 alkyl group) in an appropriate solvent in the presence of the reducing agent.

This reaction can be carried out under the same condition for the reaction of a compound (E-2) with a compound (13) represented by reaction scheme 16, which will be described later.

The reaction mixture obtained by the above described method is, for example, cooled, and then its crude reaction product is separated therefrom by an isolation operation such as filtration, concentration or extraction. Thereafter, a compound of interest can be isolated and purified from the reaction mixture by a common purification operation such as column chromatography or recrystallization.

crystallization, so that a compound of interest can be isolated in a form of hydrochloride or trifluoroacetate by recrystallization or the like.

A compound (1-F-Fc16c) is produced by reacting the compound (1-F-Fc16b) with $R^{42c}X_2$. This reaction can be

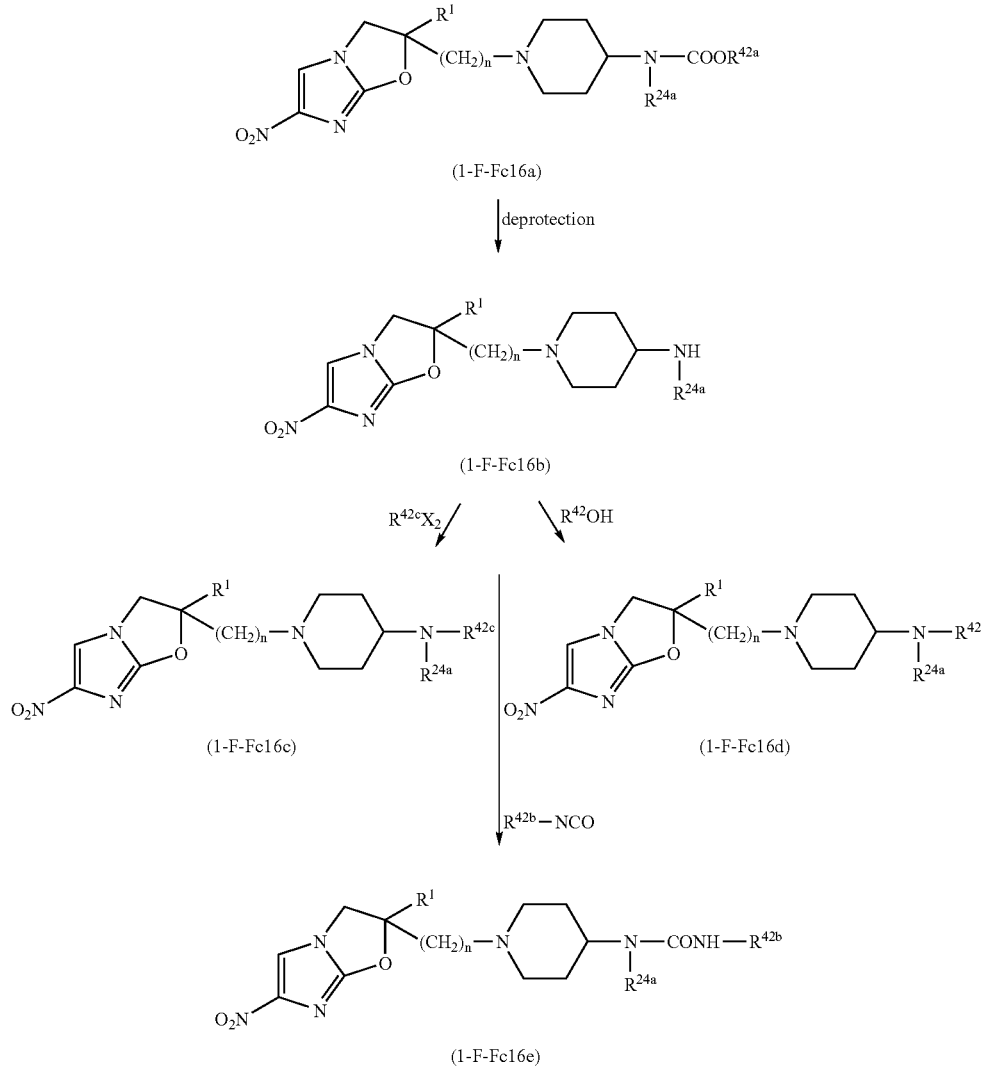

Reaction scheme 8 wherein $R^1$, $X_2$ and n are the same as above, $R^{24a}$ represents a group represented by each of (Fca1) to (Fca11), $R^{42a}$ represents a C1-C6 alkyl group, $R^{42}$ represents a group represented by (Fca5), (Fca6) or (Fca7), $R^{42c}$ represents a group represented by (Fca2), (Fca3), (Fca4), (Fca8) or (Fca9), and $R^{42b}$ represents a phenyl group (wherein at least one selected from halogen substituted or unsubstituted C1-C6 alkyl groups may be substituted on the phenyl ring).

The reaction of converting a compound (1-F-Fc16a) into a compound (1-F-Fc16b) can be carried out under the same conditions for the reaction of converting a compound (E-1) into a compound (E-2) represented by reaction scheme 16, which is described later.

The thus obtained reaction mixture is concentrated, and if necessary, acid such as hydrochloric acid is added thereto for carried out under the same condition for the reaction of the compound (Fd-1) with the compound (15) represented by reaction scheme 18, which is described later.

A compound (1-F-Fc16d) is produced by reacting the compound (1-F-Fc16b) with $R^{42c}OH$. This reaction can be carried out under the same condition for the reaction of the compound (Ea-2) with the compound (18) represented by reaction scheme 19, which is described later.

The reaction mixture obtained by the above method is, for example, cooled, and then its crude reaction product is separated therefrom by an isolation operation such as filtration, concentration or extraction. Thereafter, a compound of interest can be isolated and purified from the reaction mixture by a common purification operation such as column chromatography or recrystallization.

A compound (1-F-Fc16e) is produced by reacting the compound (1-F-Fc16b) with $R^{42b}$—NCO. This reaction can be carried out in the presence or absence of, preferably in the absence of, a basic compound, in an appropriate inert solvent or without solvent. Herein, as a solvent and a basic compound, there can be used the solvent and basic compound as follows. Examples of such a basic compound include: organic bases such as triethylamine, trimethylamine, pyridine, dimethylaniline, N-ethyldiisopropylamine, dimethylaminopyridine, N-methylmorpholine, 1,5-diazabicyclo-[4.3.0]nonene-5 (DBN), 1,8-diazabicyclo[5.4.0]undecene-7 (DBU) or 1,4-diazabicyclo[2.2.2]octane (DABCO); inorganic bases including carbonates such as sodium carbonate, potassium carbonate, sodium hydrogencarbonate or potassium hydrogencarbonate, metal hydroxides such as sodium hydroxide, potassium hydroxide or calcium hydroxide, potassium hydride, sodium hydride, potassium, sodium, sodium amide, and metal alcoholates such as sodium methylate or sodium ethylate. Further, examples of a solvent include halogenated hydrocarbons such as chloroform, dichloromethane, dichloroethane or carbon tetrachloride, aromatic hydrocarbons such as benzene, toluene or xylene, ethers such as diethyl ether, diisopropyl ether, tetrahydrofuran or dimethoxyethane, esters such as methyl acetate, ethyl acetate or isopropyl acetate, alcohols such as methanol, ethanol, isopropanol, propanol, butanol, 3-methoxy-1-butanol, ethyl cellosolve or methyl cellosolve, acetonitrile, pyridine, acetone, water, aprotic polar solvents such as N,N-dimethylacetamide, N,N-dimethylformamide, dimethylsulfoxide or hexamethylphosphoric acid triamide, and mixed solvents thereof. The molar ratio of the compound $R^{42b}$—NCO to the compound (1-F-Fc16b) may be generally between 1:1 and 5:1, and preferably equal to 1:1 and 3:1. The reaction is carried out generally at 0° C. to 200° C., and preferably at room temperature to 150° C., generally for 5 minutes to 30 hours. In the reaction, a boron compound such as boron trifluoride diethyl ether complex, or a halogenated copper compound such as cuprous chloride may be added.

The thus obtained reaction mixture is, for example, cooled, and then its crude reaction product is separated therefrom by an isolation operation such as filtration, concentration or extraction. Thereafter, a compound of interest can be isolated and purified from the reaction mixture by a common purification operation such as column chromatography or recrystallization.

Reaction scheme 9

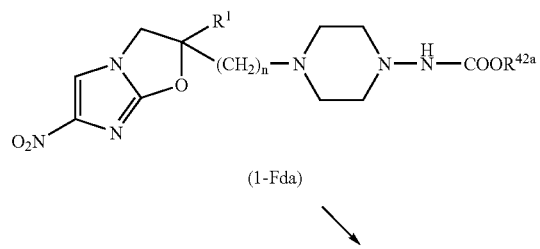

(1-Fda)

-continued

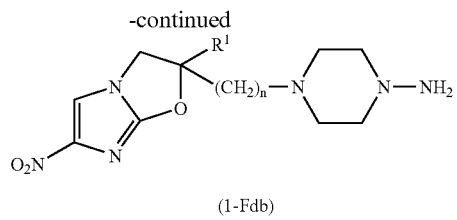

(1-Fdb)

wherein $R^{42a}$, $R^1$ and n are the same as above.

A compound (1-Fdb) is produced by deprotecting a compound (1-Fda). For example, the compound (1-Fda) is dissolved in an appropriate reaction solvent followed by hydrolysis with acid, so as to obtain the compound (1-Fdb).

Any reaction solvent can be widely used herein, as long as it does not inhibit the reaction. Examples of such a solvent include water, alcohol solvents such as methanol or ethanol, aprotic polar solvents such as DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

Examples of acid include inorganic acids such as hydrochloric acid, hydrobromic acid or bromic acid, and organic acids such as acetic acid, trifluoroacetic acid or trichloroacetic acid. Of these, trifluoroacetic acid is advantageously used.

The molar ratio of such acid to the compound (1-Fda) is generally equal to 1:1 or higher, and preferably between 2:1 and 10:1. However, such acid may also be used a large excess amount as a reaction solvent. The reaction temperature is generally room temperature to 100° C., but it may be appropriately adjusted depending on the type of the used acid. When trifluoroacetic acid is used, it is enough to set at room temperature. The reaction time is generally 1 to 24 hours, and preferably 1 to 12 hours.

The thus obtained reaction mixture is concentrated, and if necessary, acid such as hydrochloric acid is added thereto for crystallization, so that the compound (1-Fdb) can be isolated in a form of hydrochloride or trifluoroacetate by recrystallization or the like.

Reaction scheme 10

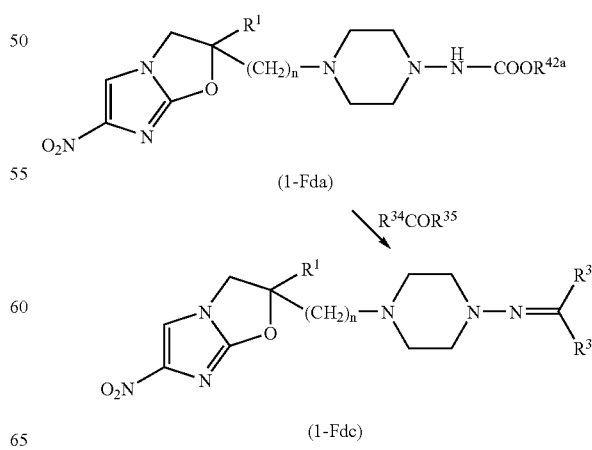

(1-Fda)

(1-Fdc)

wherein $R^{42a}$, $R^1$, n, $R^{34}$ and $R^{35}$ are the same as above.

A compound (1-Fdc) is produced by reacting the compound (1-Fda) with aldehyde or ketone represented by a general formula $R^{34}COR^{35}$ (wherein $R^{34}$ and $R^{35}$ are the same as above).

This reaction is carried out in the presence of acid in an appropriate solvent.

Any reaction solvent can be widely used herein, as long as it does not inhibit the reaction. Examples of such a solvent include water, alcohol solvents such as methanol or ethanol, aprotic polar solvents such as DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

Examples of acid include inorganic acids such as hydrochloric acid, hydrobromic acid or bromic acid, and organic acids such as acetic acid, trifluoroacetic acid or trichloroacetic acid. Of these, trifluoroacetic acid is advantageously used.

The molar ratio of such acid to the compound (1-Fda) is generally 0.5:1 or higher, and preferably between 0.5:1 and 1.5:1. However, such acid may also be used a large excess amount as a reaction solvent.

The molar ratio of aldehyde or ketone to the compound (1-Fda) is generally between 0.9:1 and 3:1, preferably between 1:1 and 1.5:1, and more preferably between 1:1 and 1.3:1.

The reaction temperature is generally room temperature to 100° C., but it may be appropriately adjusted depending on the type of the used acid. The reaction time is generally 1 to 12 hours, and preferably 1 to 3 hours.

The thus obtained reaction mixture is concentrated, and if necessary, acid such as hydrochloric acid is added thereto for crystallization, so that the compound (1-Fdc) can be isolated in a form of hydrochloride or trifluoroacetate by recrystallization or the like.

Next, a method for producing a starting material and an intermediate used for production of the compound of the present invention will be explained.

Reaction scheme 11

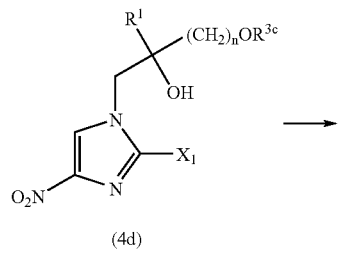

(4d)

-continued (4e)

(4f)

wherein $R^1$, $R^7$, $R^8$, $X_1$ and n are the same as above, and $R^{3c}$ represents a C1-C6 alkoxy-C1-C6 alkyl group, a C1-C6 alkanoyl group or a p-nitrobenzoyl group.

A reaction to lead from a compound (4d) into a compound (4e) is carried out, for example, under the same reaction conditions for the reaction to lead from the compound (1-A-A3) or compound (1-A-A9) into the compound (1-A-A1) as shown in reaction scheme 4. For example, in the case of the compound (4d) in which $R^{3c}$ represents a C1-C6 alkoxy-C1-C6 alkyl group, it may be adequate to carry out the reaction under the same conditions for the reaction to lead from the compound (1-A-A3) into the compound (1-A-A1). In the case of the compound (4d) in which $R^{3c}$ represents a C1-C6 alkanoyl or p-nitrobenzoyl group, it may be adequate to carry out the reaction under the same conditions for the reaction to lead from the compound (1-A-A9) into the compound (1-A-A1).

A reaction to lead from a compound (4e) into a compound (4f) is carried out, for example, under the same reaction conditions for the reaction to lead from the compound (1-A-A1) into the compound (1-D) as shown in reaction scheme 7.

Reaction scheme 12

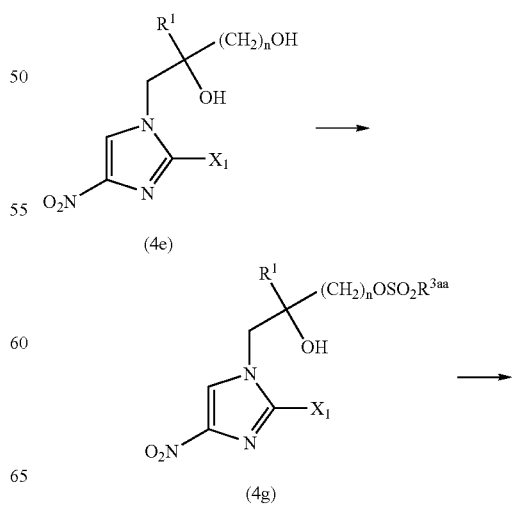

(4e)

(4g)

-continued

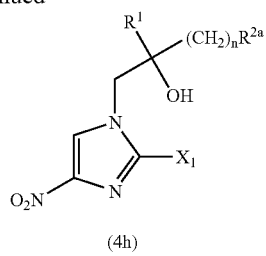

(4h)

wherein $R^1$, $R^{2a}$, $R^{3aa}$, $X_1$ and n are the same as above.

A reaction to lead from the compound (4e) into a compound (4g) is carried out, for example, under the same reaction conditions for the reaction to lead from the compound (1-A-A1) into the compound (1-A-A7) as shown in reaction scheme 5.

A reaction to lead from the compound (4g) into a compound (4h) is carried out, for example, under the same reaction conditions for the reaction to lead from the compound (1-A-A7) into the compound (1b) as shown in reaction scheme 6.

Reaction scheme 13

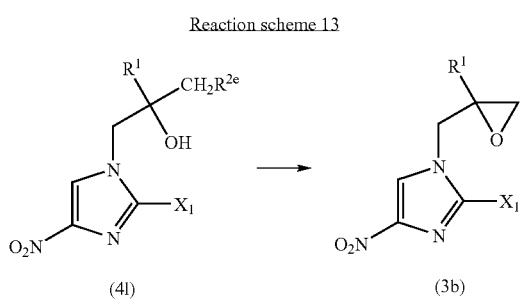

wherein $R^1$ and $X_1$ are the same as above, and $R^{2e}$ represents a halogen atom, a C1-C6 alkylsulfonyloxy group or a phenylsulfonyloxy group which may have a C1-C6 alkyl group as a substituent on the phenyl ring.

A reaction to lead from a compound (4l) into a compound (3b) is carried out in an appropriate solvent in the presence of a basic compound.

Any solvent can be widely used herein, as long as it does not inhibit the reaction. Examples of such a solvent may include aprotic polar solvents such as DMSO or acetonitrile, hydrocarbon solvents such as benzene, toluene, xylene, tetralin or liquid paraffin, halogenated hydrocarbon solvents such as methylene chloride, chloroform or dichloroethane, ether solvents such as THF, dioxane, dipropyl ether, diethyl ether or diglyme, acetone, ethyl acetate, and mixed solvents thereof.

The same basic compound as used in the reaction of the compound represented by the above general formula (2) with the compound represented by the above general formula (3a) can be used herein.

The molar ratio of such a basic compound to the compound (4l) may be generally equal to 1:1 or higher, preferably between 1:1 and 5:1, and more preferably between 1:1 and 2:1.

The reaction temperature for this reaction is generally 0° C. to 150° C., preferably 0° C. to 100° C., and more preferably 0° C. to 60° C. The reaction time is generally 30 minutes to 48 hours, preferably 1 to 24 hours, and more preferably 1 to 4 hours.

The reaction mixture obtained by the above method is, for example, cooled, and then its crude reaction product is separated therefrom by an isolation operation such as filtration, concentration or extraction. Thereafter, the compound (3b) can be isolated and purified from the reaction mixture by a common purification operation such as column chromatography or recrystallization.

Reaction scheme 14

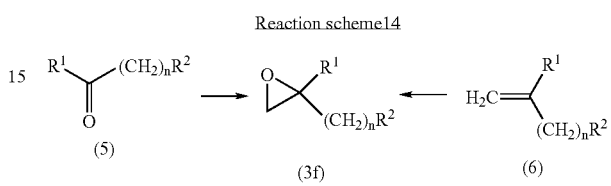

wherein $R^1$, $R^2$ and n are the same as above.

A reaction to lead from a compound (5) into a compound (3f) is carried out, for example, by treating the compound (5) with trimethylsulfoxonium iodide in an appropriate solvent in the presence of a basic compound.

Any solvent can be widely used herein, as long as it does not inhibit the reaction. Examples of such a solvent may include aprotic polar solvents such as DMSO or acetonitrile, hydrocarbon solvents such as benzene, toluene, xylene, tetralin or liquid paraffin, ether solvents such as THF, dioxane, dipropyl ether, diethyl ether or diglyme, and mixed solvents thereof.

Examples of a basic compound may include sodium hydride, sodium amide, metal alcoholates such as sodium methoxide, sodium ethoxide or potassium tert-butoxide.

The molar ratio of such a basic compound to the compound (5) may be generally equal to 1:1 or higher, preferably between 1:1 and 3:1, and more preferably between 1:1 and 1.5:1.

Moreover, the molar ratio of trimethylsulfoxonium iodide to the compound (5) may be generally equal to 1:1 or higher, preferably between 1:1 and 3:1, and more preferably between 1:1 and 1.5:1.

The reaction temperature for this reaction is generally 0° C. to 80° C., preferably 10° C. to 50° C., and more preferably 20° C. to 35° C. The reaction time is generally 1 to 24 hours, preferably 1 to 12 hours, and more preferably 1 to 4 hours.

The reaction mixture obtained by the above method is, for example, cooled, and then its crude reaction product is separated therefrom by an isolation operation such as filtration, concentration or extraction. Thereafter, the compound (3f) can be isolated and purified from the reaction mixture by a common purification operation such as column chromatography or recrystallization.

A reaction to lead from a compound (6) into the compound (3f) is carried out, for example, by treating the compound (6) with peroxide in an appropriate solvent.

Any reaction solvent can be widely used herein, as long as it does not inhibit the reaction. Examples of such a solvent may include water, alcohol solvents such as methanol or ethanol, aprotic polar solvents such as DMF, DMSO or acetonitrile, hydrocarbon solvents such as benzene, toluene, xylene, tetralin, liquid paraffin or cyclohexane, halogenated hydrocarbon solvents such as methylene chloride, chloroform or dichloroethane, ether solvents such as THF, dioxane, dipropyl ether, diethyl ether or diglyme, and mixed solvents thereof.

Examples of peroxide include metachloroperbenzoic acid (mCPBA), perbenzoic acid, peracetic acid and hydrogen peroxide.

The molar ratio of such peroxide to the compound (6) may be generally between 1:1 and 2:1, preferably between 1:1 and 1.5:1, and more preferably between 1:1 and 1.3:1.

The reaction temperature for this reaction is generally 0° C. to 80° C., preferably 0° C. to 50° C., and more preferably 20° C. to 35° C. The reaction time is generally 10 minutes to 24 hours, preferably 1 to 12 hours, and more preferably 1 to 8 hours.

The reaction mixture obtained by the above method is, for example, cooled, and then its crude reaction product is separated therefrom by an isolation operation such as filtration, concentration or extraction. Thereafter, the compound (3f) can be isolated and purified from the reaction mixture by a common purification operation such as column chromatography or recrystallization.

For example, one type of the compounds (3f) that is optically active is produced from the compound (6) as follows.

Such an optically active compound (3f) can be produced by what is called Sharpless epoxidation. This is to say, the compound can be produced by epoxidation with cumene hydroperoxide or tert-butyl hydroperoxide, in the coexistence of Ti (O-iso-$C_3H_7$)$_4$ and optically active C1-C6 alkyl tartarate such as diethyl tartarate (D- or L-form) as catalysts, in the above reaction to lead from the compound (6) into the compound (3f).

Any solvent can be widely used herein, as long as it does not inhibit the reaction. Examples of such a solvent may include aprotic polar solvents such as acetonitrile, hydrocarbon solvents such as benzene, toluene, xylene, tetralin, liquid paraffin or cyclohexane, halogenated hydrocarbon solvents such as methylene chloride, chloroform or dichloroethane, ether solvents such as THF, dioxane, dipropyl ether, diethyl ether or diglyme, and mixed solvents thereof.

The molar ratio of cumene hydroperoxide or tert-butyl hydroperoxide to the compound (6) may be generally between 0.1:1 and 2:1, preferably between 0.1:1 and 1.5:1, and more preferably between 0.1:1 and 1:1.

The molar ratio of Ti (O-iso-$C_3H_7$)$_4$ to the compound (6) may be generally between 0.1:1 and 2:1, preferably between 0.1:1 and 1.5:1, and more preferably between 0.1:1 and 1:1.

The molar ratio of optically active C1-C6 tartarates (D- or L-form) to the compound (6) may be generally between 1:1 and 2:1, preferably between 1:1 and 1.5:1, and more preferably between 1:1 and 1.3:1.

The reaction temperature for this reaction is generally −50° C. to 30° C., preferably −20° C. to 20° C., and more preferably −20° C. to 5° C. The reaction time is generally 1 to 48 hours, preferably 4 to 24 hours, and more preferably 4 to 12 hours.

The compound (5) or (6), wherein $R^1$ and —$(CH_2)_nR^{2a}$, together with carbon atoms adjacent thereto, are bound with each other via nitrogen atoms to form a piperidine ring, is converted in the same manner as stated above into a compound (compound (3c)), wherein $R^1$ and —$(CH_2)_nR^{2a}$, together with carbon atoms adjacent thereto, are bound with each other via nitrogen atoms to form a piperidine ring, in the compound (3f).

The reaction mixture obtained by the above method is, for example, cooled, and then its crude reaction product is separated therefrom by an isolation operation such as filtration, concentration or extraction. Thereafter, the optically active compound (3f) can be isolated and purified from the reaction mixture by a common purification operation such as column chromatography or recrystallization.

2,3-Dihydro-6-nitroimidazo[2,1-b]oxazole represented by the compound (1) of the present invention and its intermediates represented by above various reaction formulas include stereoisomers and optical isomers.

Reaction scheme 15

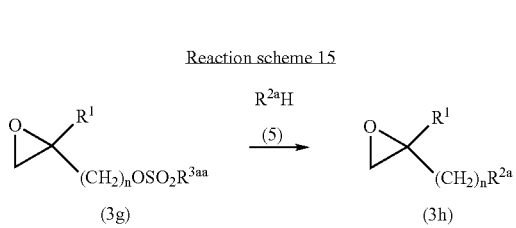

wherein $R^{3aa}$, $R^1$, $R^{2a}$ and n are the same as above.

A reaction to lead from a compound (3g) into a compound (3h) is carried out, for example, under the same reaction conditions for the reaction to lead from the compound (1-A-A7) into the compound (1b) as shown in reaction scheme 6.

Reaction scheme 16

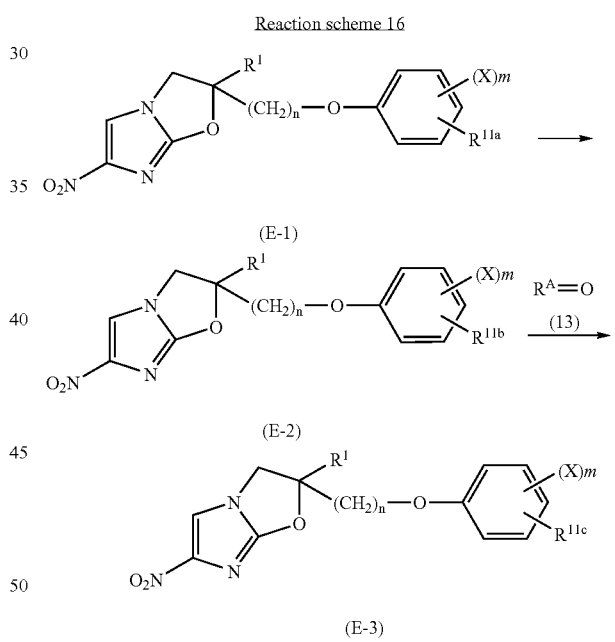

wherein $R^1$, X, n and m are the same as above, $R^{11a}$ represents the group

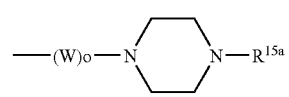

(wherein W and o are the same as above, $R^{15a}$ represents a C1-C20 alkoxycarbonyl group, with the exception that when W represents the group C=O, $R^{15a}$ represents a C1-C6 alkoxycarbonyl group), or the group

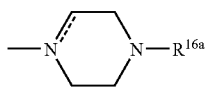

(wherein $R^{16a}$ represents a C1-C8 alkoxycarbonyl group), $R^{11b}$ represents the group

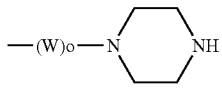

or group

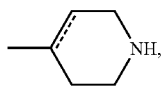

$R^{11c}$ represents the group

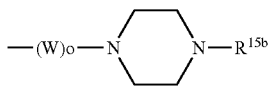

or the group

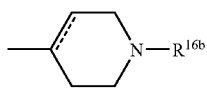

(wherein each of $R^{15b}$ and $R^{16b}$ represents a C3-C8 cycloalkyl group), and $R^4$ represents a C3-C8 cycloalkyl group.

The reaction to lead the compound (E-1) into the compound (E-2) can be carried out by the hydrolysis of the compound (E-1).

This hydrolysis reaction can be carried out in an appropriate solvent or without solvent in the presence of acid or a basic compound. Examples of the used solvent may include water, lower alcohols such as methanol, ethanol, isopropanol or tert-butanol, ketones such as acetone or methylethylketone, ethers such as diethyl ether, dioxane, tetrahydrofuran, monoglyme or diglyme, fatty acids such as acetic acid or formic acid, esters such as methyl acetate or ethyl acetate, halogenated hydrocarbons such as chloroform, dichloromethane, dichloroethane or carbon tetrachloride, dimethyl sulfoxide, N,N-dimethylformamide, hexamethylphosphoric acid triamide, and mixed solvents thereof. Examples of acid may include inorganic acids such as hydrochloric acid, sulfuric acid or hydrobromic acid, and organic acids including formic acid, acetic acid, trifluoroacetic acid or sulfonic acids such as p-toluenesulfonic acid. Examples of a basic compound may include carbonates such as sodium carbonate, potassium carbonate, sodium hydrogencarbonate or potassium hydrogencarbonate, and metal hydroxides such as sodium hydroxide, potassium hydroxide, calcium hydroxide or lithium hydroxide. This reaction is carried out generally at 0° C. to 200° C., and preferably at 0° C. to 150° C., generally for 10 minutes to 30 hours.

The molar ratio of acid or basic compound to the compound (E-1) may be at least equal to 1:1, and preferably between 1:1 and 10:1. However, acid may also be used a much higher amount as a reaction solvent.

After completion of the hydrolysis, the reaction may further be carried out in an appropriate solvent in the presence of a basic compound, generally at 0° C. to 100° C., and preferably at room temperature to 70° C., approximately for 1 to 30 minutes, so as to complete the reaction. Herein, as a solvent and a basic compound, there can be used the solvent and basic compound as follows. Examples of such a basic compound include: organic bases such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU) or 1,4-diazabicyclo[2.2.2]octane (DABCO); inorganic bases including carbonates such as sodium carbonate, potassium carbonate, sodium hydrogencarbonate or potassium hydrogencarbonate, metal hydroxides such as sodium hydroxide, potassium hydroxide or calcium hydroxide, potassium hydride, sodium hydride, potassium, sodium, sodium amide, and metal alcoholates such as sodium methylate or sodium ethylate. Further, examples of a solvent include halogenated hydrocarbons such as chloroform, dichloromethane, dichloroethane or carbon tetrachloride, aromatic hydrocarbons such as benzene, toluene or xylene, ethers such as diethyl ether, diisopropyl ether, tetrahydrofuran or dimethoxyethane, esters such as methyl acetate, ethyl acetate or isopropyl acetate, alcohols such as methanol, ethanol, isopropanol, propanol, butanol, 3-methoxy-1-butanol, ethyl cellosolve or methyl cellosolve, acetonitrile, pyridine, acetone, water, aprotic polar solvents such as N,N-dimethylacetamide, N,N-dimethylformamide, dimethylsulfoxide or hexamethylphosphoric acid triamide, and mixed solvents thereof.

The reaction of the compound (E-2) with the compound (13) is carried out without solvent or in an appropriate solvent, in the presence of a reducing agent.

Examples of a solvent used herein may include water, lower alcohols such as methanol, ethanol, isopropanol butanol, tert-butanol or ethylene glycol, acetonitrile, fatty acids such as formic acid, acetic acid or trifluoroacetic acid, ethers such as diethyl ether, tetrahydrofuran, dioxane, monoglyme or diglyme, aromatic hydrocarbons such as benzene, toluene or xylene, halogenated hydrocarbons such as dichloromethane, dichloroethane, chloroform or carbon tetrachloride, and mixed solvents thereof. Examples of a reducing agent include formic acid, fatty acid alkali metal salts such as sodium formate or sodium acetate, and metal hydride reducing agents such as sodium borohydride, sodium cyanoborohydride, sodium triacetyloxy borohydride, lithium aluminum hydride or a mixture thereof, and catalytic hydrogenation reducing agents such as palladium-black, palladium-carbon, platinum oxide, platinum black or Raney nickel.

When formic acid is used as a reducing agent, the reaction temperature is generally room temperature to 200° C., and preferably 50° C. to 150° C. The reaction is carried out for 10 minutes to 10 hours. It may be preferable to use a much higher amount of formic acid to the compound (E-2).

When a hydrogenation reducing agent is used, the reaction temperature is generally −80° C. to 100° C., and preferably −80° C. to 70° C. The reaction is carried out for 30 minutes to 100 hours. The hydrogenation reducing agent is used to the compound (E-2) at a molar ratio of generally between 1:1 and 20:1, and preferably between 1:1 and 6:1. In particular, when lithium aluminum hydride is used as a reducing agent, it is preferable to use, as a solvent, ethers such as diethyl ether, tetrahydrofuran, dioxane, monoglyme or diglyme, or aromatic hydrocarbons such as benzene, toluene or xylene. Moreover, amines such as trimethylamine, triethylamine, N-ethyldiisopropylamine may also be added for the reaction. Furthermore, molecular sieves such as molecular sieves 3A (MS-3A) or molecular sieves 4A (MS-4A) may also be added.

When a catalytic hydrogenation reducing agent is used, the reaction is carried out in hydrogen atmosphere, generally at normal atmospheric pressure to 20 atmospheric pressure, preferably at normal atmospheric pressure to 10 atmospheric pressure, in the presence of a hydrogen provider such as formic acid, ammonium formate, cyclohexene or hydrated hydrazine, at a temperature of generally −30° C. to 100° C., and preferably 0° C. to 60° C. The reaction is generally carried out for 1 to 12 hours. Generally 0.1 to 40% by weight, and preferably 1 to 20% by weight of the catalytic hydrogenation reducing agent is used to the compound (E-2).

The compound (13) is used to the compound (E-2) at a molar ratio of generally at least equal to 1:1, and preferably equal to 1:1 or much higher.

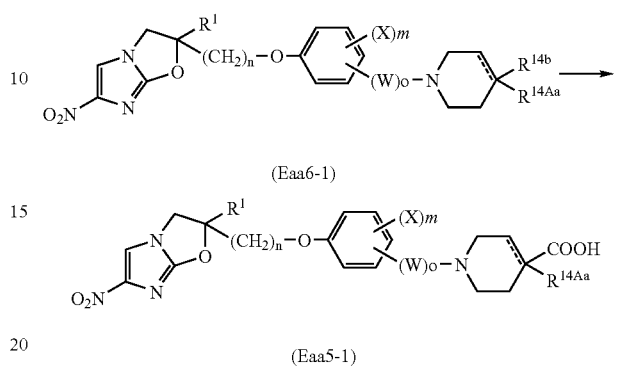

wherein $R^1$, X, n, m, W and o are the same as above, $R^{14b}$ represents a C1-C6 alkoxycarbonyl group, and $R^{14Aa}$ is a hydrogen atom, a C1-C6 alkoxy group, a hydroxyl group or a phenyl group (phenyl group may have halogen atoms on the phenyl ring).

The reaction to lead the compound (Eaa 6-1) into the compound (Eaa 5-1) can be carried out under the same conditions for the reaction to lead the compound (E-1) into the compound (E-2) represented by the above reaction scheme 16.

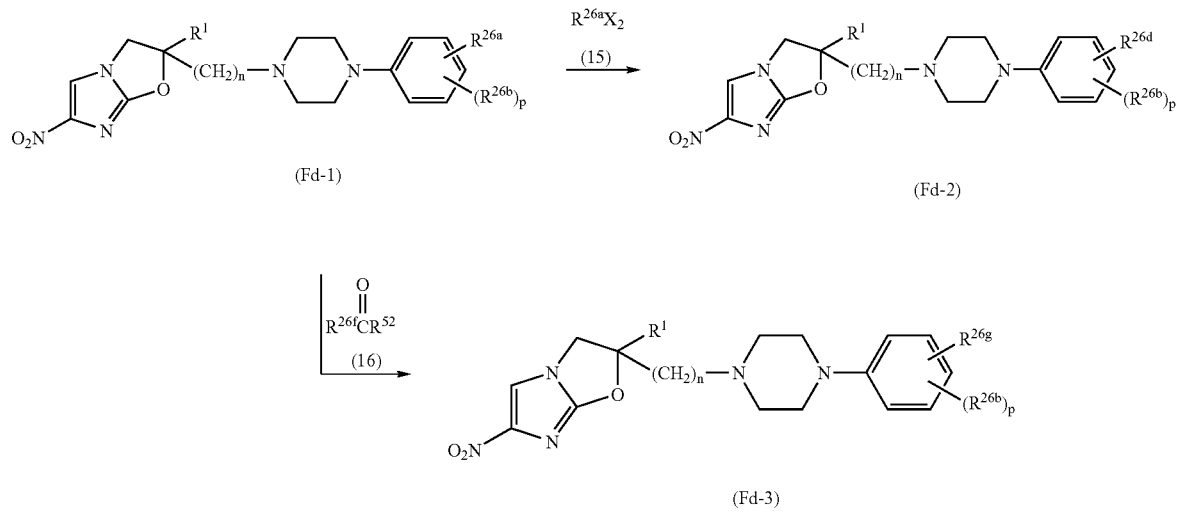

wherein $R^1$, n and $X_2$ are the same as above, $R^{52}$ is a hydrogen atom or C1-C6 alkyl group.

$R^{26b}$ represents a halogen atom, a cyano group, amino group which may have a C1-C6 alkyl group as a substituent, a halogen substituted or unsubstituted C1-C6 alkyl group, a halogen substituted or unsubstituted C1-C6 alkoxy group, a C1-C6 alkoxycarbonyl group, a carboxyl group, a phenoxy group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), an amino C1-C6 alkyl group (wherein, on the amino group, at least one group selected from a group consisting of a C1-C6 alkyl group and a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent) may be substituted as a substituent), or a phenyl C1-C6 alkoxy group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), p represents an integer of 0 to 4, $R^{26a}$ represents the group $-NHR^{26h}$ (wherein $R^{26h}$ represents a hydrogen atom or a C1-C6 alkyl group), or the group $-W_1-NHR^{26c}$ (wherein $W_1$ is a C1-C6 alkylene group, $R^{26c}$ represents a hydrogen atom, a C1-C6 alkyl group or a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent)), $R^{26d}$ represents the group $-N(R^{26e1})R^{26h}$ or the group $-W_1-N(R^{26c})R^{26e}$, $R^{26e}$ represents a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent) or a C1-C6 alkyl group, $R^{26e1}$ represents a C1-C6 alkyl group, $R^{26f}$ represents a C1-C6 alkyl group, and $R^{26g}$ represents the group $-N(R^{26h})\underline{CH(R^{52})R^{26f}}$ or the group $-W_1-N(R^{26c})\underline{CH(R^{52})R^{26f}}$, provided that the total number of carbon atoms of the underlined portions is not greater than 6.

The reaction of the compound (Fd-1) with the compound (15) is generally carried out in an appropriate solvent in the presence or absence of a basic compound.

Examples of an inert solvent used herein may include aromatic hydrocarbons such as benzene, toluene or xylene, ethers such as diethyl ether, tetrahydrofuran, dioxane, monoglyme or diglyme, halogenated hydrocarbons such as dichloromethane, dichloroethane, chloroform or carbon tetrachloride, lower alcohols such as methanol, ethanol, isopropanol, butanol, tert-butanol or ethylene glycol, fatty acids such as acetic acid, esters such as ethyl acetate or methyl acetate, ketones such as acetone or methylethylketone, acetonitrile, pyridine, dimethylsulfoxide, N,N-dimethylformamide or hexamethylphosphoric acid triamide, and mixed solvents thereof. Examples of a basic compound may include carbonates such as sodium carbonate, potassium carbonate, sodium hydrogencarbonate, potassium hydrogencarbonate or cesium carbonate, metal hydroxides such as sodium hydroxide, potassium hydroxide or calcium hydroxide, sodium hydride, potassium hydride, potassium, sodium, sodium amide, metal alcoholates such as sodium methylate, sodium ethylate, sodium n-butoxide, organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo-[5.4.0]undecene-7 (DBU) or 1,4-diazabicyclo[2.2.2]-octane (DABCO), and mixtures thereof. The compound (15) may be used to the compound (Fd-1) at a molar ratio of at least equal to 1:1, and preferably between 1:1 and 10:1. The basic compound may be used to the compound (Fd-1) at a molar ratio of at least equal to 1:1, and preferably between 1:1 and 10:1. The reaction is carried out generally at 0° C. to 200° C., and preferably at 0° C. to 150° C. The reaction is generally carried out for 5 minutes to 80 hours.

Alkali metal halides such as sodium iodide or potassium iodide may be added to the reaction system, or a phase-transfer catalyst may also be added thereto. Examples of such a phase-transfer catalyst include: quaternary ammonium salts, in which a group selected from a group consisting of a linear or branched alkyl group containing 1 to 18 carbon atoms, a phenyl C1-C6 alkyl group, and a phenyl group is substituted, such as tetrabutylammonium chloride, tetrabutylammonium bromide, tetrabutylammonium fluoride, tetrabutylammonium iodide, tetrabutylammonium hydroxide, tetrabutylammonium bisulfite, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride, or tetramethylammonium chloride; phosphonium salts such as tetrabutylphosphonium chloride, in which a linear or branched alkyl group containing 1 to 18 carbon atoms is substituted; and pyridinium salts such as 1-dodecanylpyridinium chloride, in which a linear or branched alkyl group containing 1 to 18 carbon atoms is substituted. The phase-transfer catalyst may be used to the compound (Fd-1) at a molar ratio of generally between 0.1:1 and 1:1, and preferably between 0.1:1 and 0.5:1.

The reaction of the compound (Fd-1) with the compound (16) can be carried out under the same conditions for the above reaction of the compound (E-2) with the compound (13) represented by the above reaction scheme 16.

Reaction scheme 19

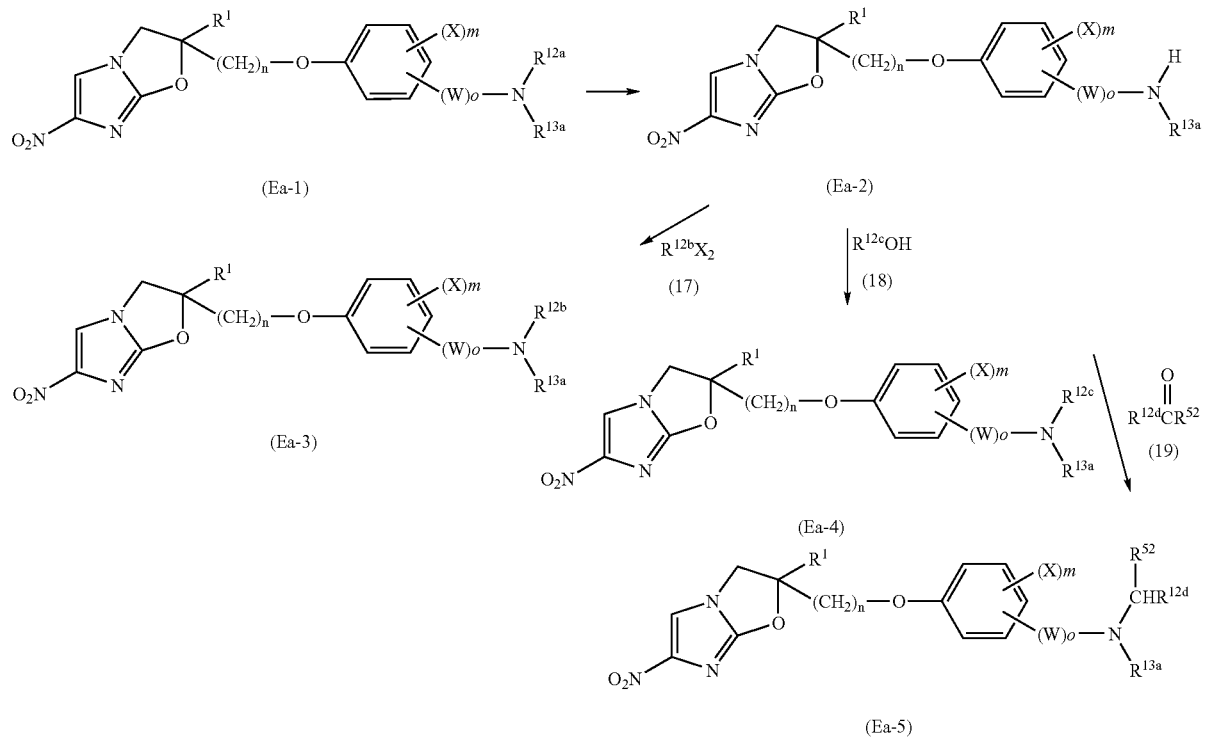

wherein $R^1$, n, W, X, m, o, $R^{52}$ and $X_2$ are the same as above, $R^{12a}$ represents a C1-C6 alkoxycarbonyl group, $R^{13a}$ represents a hydrogen atom, a C1-C6 alkyl group, a C1-C6 alkanoyl group, a C1-C6 alkoxycarbonyl group, a phenyl C1-C6 alkyl group (wherein, on the phenyl ring, at least one of group selected from a group consisting of a halogen atom, a halogen substituted or unsubstituted C1-C6 alkyl group, a halogen substituted or unsubstituted C1-C6 alkoxy group, and a phenoxy group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent) may be substituted, and a C1-C6 alkoxyimino group may be substituted for the alkyl portion), a phenyl group (wherein, on the phenyl ring, at least one of group selected from a group consisting of a halogen atom, a halogen substituted or unsubstituted C1-C6 alkyl group, and a halogen substituted or unsubstituted C1-C6 alkoxy group may be substituted as a substituent), a benzoyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), a pyridyl group (wherein, on the pyridine ring, at least one of halogen atom may be substituted as a substituent), phenoxy C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), or a benzoyl C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), $R^{12b}$ represents a C1-C6 alkyl group, a C1-C6 alkoxycarbonyl group, a phenyl C1-C6 alkyl group (wherein, on the phenyl ring, at least one group selected from a group consisting of a halogen atom, a halogen substituted or unsubstituted C1-C6 alkyl group, a halogen substituted or unsubstituted C1-C6 alkoxy group, and a phenoxy group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), may be substituted as a substituent, and a C1-C6 alkoxyimino group may be substituted for the alkyl portion), a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), a pyridyl group (wherein, on the pyridine ring, at least one of halogen atom may be substituted as a substituent), a phenoxy C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), or a benzoyl C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), $R^{12c}$ represents a C1-C6 alkanoyl group, or a benzoyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), $R^{12d}$ represents a hydrogen atom, a C1-C6 alkyl group, a phenyl C1-C6 alkyl group (wherein, on the phenyl ring, at least one group selected from a group consisting of a halogen atom, a halogen substituted or unsubstituted C1-C6 alkyl group, a halogen substituted or unsubstituted C1-C6 alkoxy group, and a phenoxy group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent) may be substituted), a phenyl group (wherein, on the phenyl ring, at least one group selected from a group consisting of a halogen atom, a halogen substituted or unsubstituted C1-C6 alkyl group, a halogen substituted or unsubstituted C1-C6 alkoxy group, and a phenoxy group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent) may be substituted), a phenoxy C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), or a benzoyl C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), and in the group —(W)o-N($R^{13a}$)CH($R^{52}$)$R^{12d}$ in general formula (Ea-5), the total number of carbon atoms of the underlined portion is not greater than 6.

The reaction to lead the compound (Ea-1) into the compound (Ea-2) can be carried out under the same conditions for the reaction to lead the compound (E-1) into the compound (E-2) represented by the above reaction scheme 16.

The reaction of the compound (Ea-2) with the compound (17) can be carried out under the same conditions for the reaction of the compound (Fd-1) with the compound (15) represented by the above reaction scheme 18.

The reaction of the compound (Ea-2) with the compound (18) is carried out by reacting the compound (Ea-2) with carboxylic acid of the compound (18) by a common amide bond formation reaction. Conditions for a known amide bond formation reaction can be easily applied herein. Examples of such an amide bond formation reaction include (a) mixed acid anhydride method, that is, a method of reacting carboxylic acid (18) with alkyl haloformate to obtain a mixed acid anhydride and reacting the mixed acid anhydride with amine (Ea-2), (b) active ester method, that is, a method of converting carboxylic acid (18) into active ester such as phenyl, p-nitrophenyl ester, N-hydroxy succinic acid imide ester or 1-hydroxybenzotriazole ester, or into active amide such as benzoxazoline-2-thione, and then reacting this with amine (Ea-2), (c) carbodiimide method, that is, a method of carrying out the condensation reaction of carboxylic acid (18) with amine (Ea-2) in the presence of an activator such as dicyclohexylcarbodiimide, 1-(3-dimethylaminopropyl)-3-ethylcarbodiimide (WSC) or carbonyldiimidazole, and (d) other methods including a method of converting carboxylic acid (18) into carboxylic anhydride by using a dehydrator such as acetic anhydride and reacting the carboxylic anhydride with amine (Ea-2), a method of reacting ester of carboxylic acid (18) and lower alcohol with amine (Ea-2) at high pressure and high temperature, and a method of reacting acid halide of carboxylic acid (18), i.e., carboxylic acid halide, with amine (Ea-2).

The mixed acid anhydride used in (a) mixed acid anhydride method as described above is obtained by a common Schotten-Baumann reaction. The mixed acid anhydride is reacted with amine (Ea-2) generally without subjecting to isolation, so as to produce the compound of the present invention represented by general formula (Ea-4). The above Schotten-Baumann reaction is carried out in the presence of a basic compound. Compounds that are commonly used for the Schotten-Baumann reaction can be used herein as basic compounds. Examples of such a basic compound include: organic bases such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU) or 1,4-diazabicyclo[2.2.2]octane (DABCO); inorganic bases including carbonates such as sodium carbonate, potassium carbonate, sodium hydrogencarbonate or potassium hydrogencarbonate, metal hydroxides such as sodium hydroxide, potassium hydroxide or calcium hydroxide, potassium hydride, sodium hydride, potassium, sodium, sodium amide, and metal alcoholates such as sodium methylate or sodium ethylate. The reaction is carried out generally at −20° C. to 100° C., and preferably at 0° C. to 50° C. The reaction time is generally 5 minutes to 10 hours, and preferably 5 minutes to 2 hours. The reaction of the obtained mixed acid anhydride with amine (Ea-2) is carried out generally at −20° C. to 150° C., and preferably at 10° C. to 50° C. The reaction time is generally 5 minutes to 10 hours, and preferably 5 minutes to 5 hours. The mixed acid anhydride method is generally carried out in a solvent. Any solvent that is commonly used for the mixed acid anhydride method can be used herein. Examples of such a solvent include halogenated hydrocarbons such as chloroform, dichloromethane, dichloroethane or carbon tetrachloride, aromatic hydrocarbons such as benzene, toluene or xylene, ethers such as diethyl ether, diisopropyl ether, tetrahydrofuran or dimethoxyethane, esters such as methyl acetate, ethyl acetate or isopropyl acetate, aprotic polar solvents such as N,N-dimethylacetamide, N,N-dimethylformamide, dimethylsulfoxide or hexamethylphosphoric acid triamide, and mixed solvents thereof. Examples of alkyl haloformate used for the mixed acid anhydride method include methyl chloroformate, methyl bromoformate, ethyl chloroformate, ethyl bromoformate, and isobutyl chloroformate. The molar ratio among carboxylic acid (18), alkyl haloformate and amine (Ea-2) may be generally equal to 1:1. Each of alkyl haloformate and carboxylic acid (18) can also be used to amine (Ea-2) within the molar range between 1:1 and 1.5:1.

The above method (c) involving the condensation reaction in the presence of the above activator can be carried out in an appropriate solvent in the presence or absence of a basic compound. As a solvent and a basic compound used herein, any solvent used in the reaction of carboxylic acid halide with amine (Ea-2) described as above in (d) other methods can be used. The molar ratio of the activator to the compound (Ea-2) may be at least equal to 1:1, and preferably between 1:1 and 5:1. When WSC is used as an activator, the reaction advantageously proceeds if 1-hydroxybenzotriazole is added into the reaction system. The reaction is carried out generally at −20° C. to 180° C., and preferably at 0° C. to 150° C. The reaction time is generally 5 minutes to 90 hours.

When the method of reacting carboxylic acid halide with amine (Ea-2) is adopted from (d) other methods described above, the reaction is carried out in the presence of a basic compound in an appropriate solvent. Known basic compounds can be widely used herein. For example, any basic compound used in the above Schotten-Baumann reaction can be used. Examples of the used solvent may include alcohols such as methanol, ethanol, isopropanol, propanol, butanol, 3-methoxy-1-butanol, ethyl cellosolve or methyl cellosolve, acetonitrile, pyridine, acetone, water, as well as solvents used for the above mixed acid anhydride method. The molar ratio of amine (Ea-2) to carboxylic acid halide is not particularly limited, but it may be appropriately selected from a wide range. The molar ratio of these compounds may be generally at least equal to 1:1, and preferably between 1:1 and 1:5. The reaction is carried out generally at −20° C. to 180° C., and preferably at 0° C. to 150° C. The reaction time is generally 5 minutes to 50 hours.

The amide bond formation reaction represented by the above reaction scheme-19 can also be carried out by reacting carboxylic acid (18) with amine (Ea-2) in the presence of a phosphorus condensing agent such as diphenylphosphinic chloride, phenyl-N-phenyl phosphoramide chloridate, diethyl chlorophosphate, diethyl cyanophosphate, azide diphenyl phosphate, or bis(2-oxo-3-oxazolidinyl)phophinic chloride.

This reaction is carried out in the presence of a solvent and a basic compound that are used for the above method of reacting carboxylic acid halide with amine (Ea-2), generally at −20° C. to 150° C., and preferably at 0° C. to 100° C. The reaction time is generally 5 minutes to 30 hours. Each of the condensing agent and the carboxylic acid (18) is used to amine (Ea-2) at a molar ratio of at least equal to 1:1, and preferably between 1:1 and 2:1.

The reaction of the compound (Ea-2) with the compound (19) can be carried out under the same conditions for the reaction of the compound (E-2) with the compound (13) represented by the above reaction scheme 16.

wherein $R^1$, n, $R^{52}$, p, $W_1$ and $X_2$ are the same as above, $R^{19a}$ represents a group represented by each of (F1) to (F11).

$R^{53}$ represents a phenoxy group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), a halogen atom, a halogen substituted or unsubstituted C1-C6 alkyl group, a halogen substituted or unsubstituted C1-C6 alkoxy group, an amino group which may have, as a substituent, a group selected from a group consisting of a C1-C6 alkyl group and a phenyl C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), a piperazinyl group (wherein, on the piperazine ring, at least one group selected from a group consisting of a phenyl C1-C6 alkyl group (wherein, on the phenyl ring, at least one group selected from a group consisting of a halogen atom, a halogen substituted or unsubstituted C1-C6 alkyl group and a halogen substituted or unsubstituted C1-C6 alkoxy group) may be substituted as a substituent or a piperidinyl group (wherein, on the piperidine ring, at least one amino group may be substituted, as a substituent, and on the amino group, at least one group selected from a group consisting of a phenyl group (wherein, on the phenyl ring, at least one group selected from a group consisting of a halogen atom, a halogen substituted or unsubstituted C1-C6 alkyl group, and a halogen substituted unsubstituted C1-C6 alkoxy group may be substituted as a substituent) and a C1-C6 alkyl group may be substituted), $R^{54}$ represents a phenyl C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent),

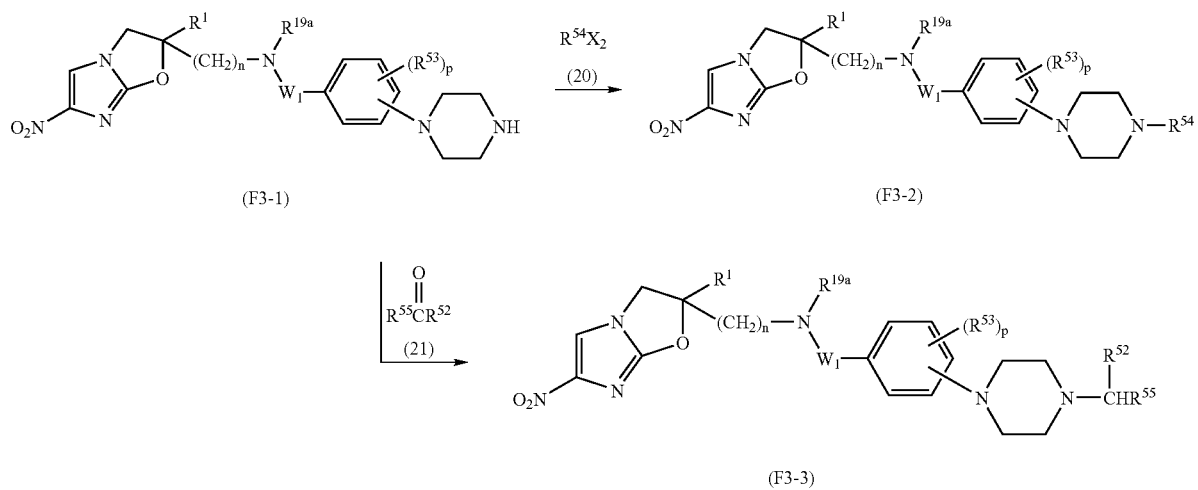

$R^{55}$ represents a phenyl C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), or phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), and the total number of carbon atoms of the group $CH(R^{52})$ $R^{55}$ in general formula (F3-3) is not greater than 6.

The reaction of the compound (F3-1) with the compound (20) can be carried out under the same conditions for the reaction of the compound (Fd-1) with the compound (15) represented by the above reaction scheme 18.

The reaction of the compound (F3-1) with the compound (21) can be carried out under the same conditions for the reaction of the compound (E-2) with the compound (13) represented by the above reaction scheme 16.

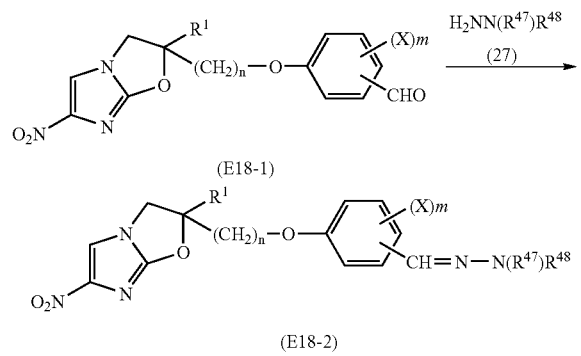

wherein $R^1$, n, X, $R^{47}$, $R^{48}$ and m are the same as above.

The reaction of the compound (27) with the compound (E18-1) can be carried out in an appropriate inert solvent in the presence or absence of a basic compound.

Examples of the used basic compound may include inorganic basic compounds such as sodium hydroxide, potassium hydroxide, calcium hydroxide, sodium carbonate or potassium carbonate, fatty acid alkali metal salts such as sodium acetate, and organic bases such as piperidine, triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo-[5.4.0]undecene-7 (DBU) or 1,4-diazabicyclo[2.2.2]-octane (DABCO). Any inert solvent can be used herein, as long as it does not affect the reaction. Examples of such a solvent include water, aromatic hydrocarbons such as benzene, toluene or xylene, ethers such as diethyl ether, tetrahydrofuran, dioxane, monoglyme or diglyme, halogenated hydrocarbons such as dichloromethane, dichloroethane, chloroform or carbon tetrachloride, lower alcohols such as methanol, ethanol, isopropanol, butanol, tert-butanol or ethylene glycol, fatty acids such as acetic acid, esters such as ethyl acetate or methyl acetate, ketones such as acetone or methylethylketone, acetonitrile, pyridine, dimethylsulfoxide, N,N-dimethylformamide, hexamethylphosphoric acid triamide, and mixed solvents thereof. The molar ratio of the compound (27) to the compound (E18-1) may be generally at least equal to 1:1, and preferably between 1:1 and 5:1. The reaction temperature is generally room temperature to 200° C., and preferably room temperature to 150° C. The reaction time is generally 5 minutes to 30 hours.

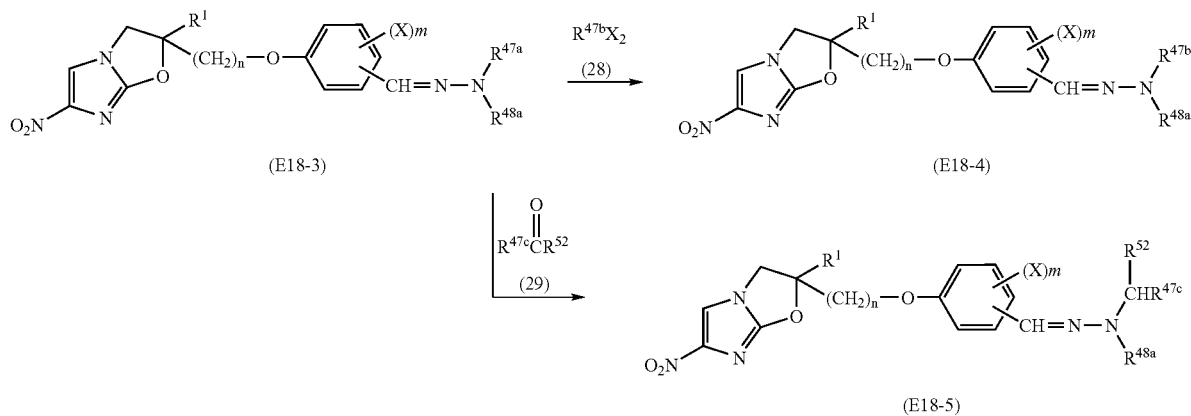

wherein $R^1$, n, X, m, $X_2$ and $R^{52}$ are the same as above, $R^{47a}$ represents a hydrogen atom, $R^{48a}$ represents a hydrogen atom, a C1-C6 alkyl group, a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), or a pyridyl group (wherein, on the pyridine ring, at least one halogen substituted or unsubstituted C1-C6 alkyl group may be substituted as a substituent), $R^{47b}$ represents a C1-C6 alkyl group; a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent); or a pyridyl group (wherein, on the pyridine ring, at least one halogen substituted or unsubstituted C1-C6 alkyl group may be substituted as a substituent), and $R^{47c}$ represents a hydrogen atom or a C1-C6 alkyl group, provided that, in the group —CH═N—N($R^{48a}$) $\underline{CH(R^{52})R^{47c}}$ in general formula (Ea 18-5), the total number of carbon atoms of the underlined portion is not greater than 6.

The reaction of the compound (E18-3) with the compound (28) can be carried out under the same conditions for the reaction of the compound (Fd-1) with the compound (15) represented by the above reaction scheme 18.

The reaction of the compound (E18-3) with the compound (29) can be carried out under the same conditions for the reaction of the compound (E-2) with the compound (13) represented by the above reaction scheme 16.

wherein $R^1$, n, X, m, W, o and $R^{14Aa}$ are the same as above, the dotted line on the piperidine ring represents that the bond may be a double bond, and when the dotted line represents a double bond, it means that the hydroxyl group is substituted, $R^{57}$ represents a phenyl group (wherein, on the phenyl ring, at least one group selected from a group consisting of a halogen atom, a halogen substituted or unsubstituted C1-C6 alkyl group, a halogen substituted or unsubstituted C1-C6 alkoxy group, a C1-C4 alkylenedioxy group, a C1-C6 alkoxycarbonyl group, a cyano group, a C2-C6 alkenyl group, a nitro group, a phenyl group, an amino group which may have, as a substituent, a group selected from a group consisting of a phenyl group, a C1-C6 alkyl group, a carbomoyl group and a C1-C6 alkanoyl group, a C1-C6 alkanoyl substituted C1-C6 alkyl group, a hydroxyl group, a C1-C6 alkoxycarbonyl substituted C1-C6 alkyl group, phenyl C1-C6 alkyl group, a C1-C6 alkanoyl group, a C1-C6 alkylthio group, a 1,2,4-triazolyl group, an isoxazolyl group, an imidazolyl group, a benzothiazolyl group, a 2H-benzotriazolyl group, a pyrrolyl group, a benzoxazolyl group, a piperazinyl group (wherein, on the piperazine ring, at least one group selected from a group consisting of a C1-C6 alkoxycarbonyl group and a phenyl C1-C6 alkyl group (wherein, on the phenyl ring, at least one of group selected from a group consisting of a halogen atom, a halogen substituted or unsubstituted C1-C6 alkyl group, and a halogen substituted or unsubstituted C1-C6 alkoxy group may be Reaction scheme 23

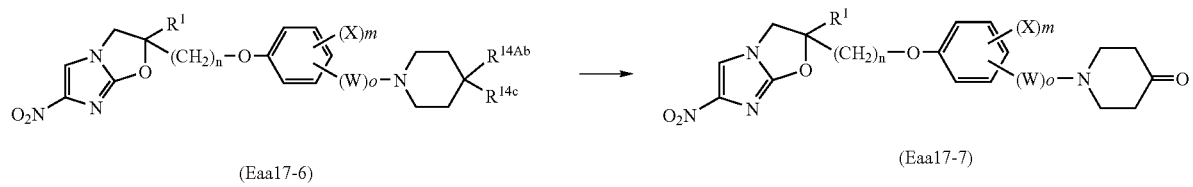

(Eaa17-6) (Eaa17-7)

wherein $R^1$, n, X, m, W and o are the same as above, each of $R^{14Ab}$ and $R^{14c}$ represents a C1-C6 alkoxy group.

The reaction to lead the compound (Eaa 17-6) into the compound (Eaa 17-7) can be carried out under the same conditions for the reaction to lead the compound (E-1) into the compound (E-2) represented by the above reaction scheme 16.

substituted as a substituent) may be substituted as a substituent), a piperidinyl group (wherein, on the piperidine ring, at least one amino group may be substituted as a substituent, and on the amino group, at least one group selected from a group consisting of a C1-C6 alkyl group and a phenyl group (wherein, on the phenyl ring, at least one group selected from a group consisting of a halogen atom, Reaction scheme 24

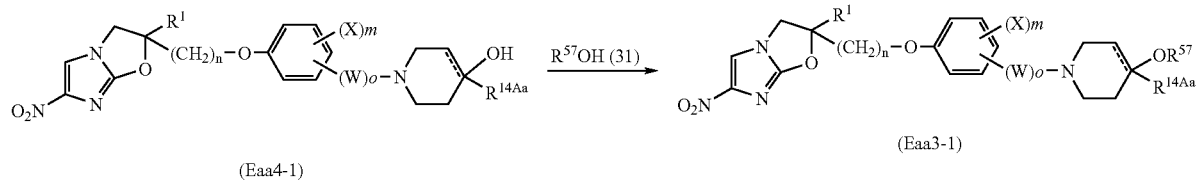

(Eaa4-1) (Eaa3-1)

a halogen substituted or unsubstituted C1-C6 alkyl group, and a halogen substituted or unsubstituted C1-C6 alkoxy group may be substituted as a substituent) may be substituted as a substituent) and a carbamoyl group may be substituted as a substituent).

ratio of the condensing agent to the compound (Eaa 4-1) may be at least equal to 1:1, and preferably between 1:1 and 3:1. The molar ratio of the compound (31) to the compound (Eaa 4-1) may be at least equal to 1:1, and preferably between 1:1 and 2:1.

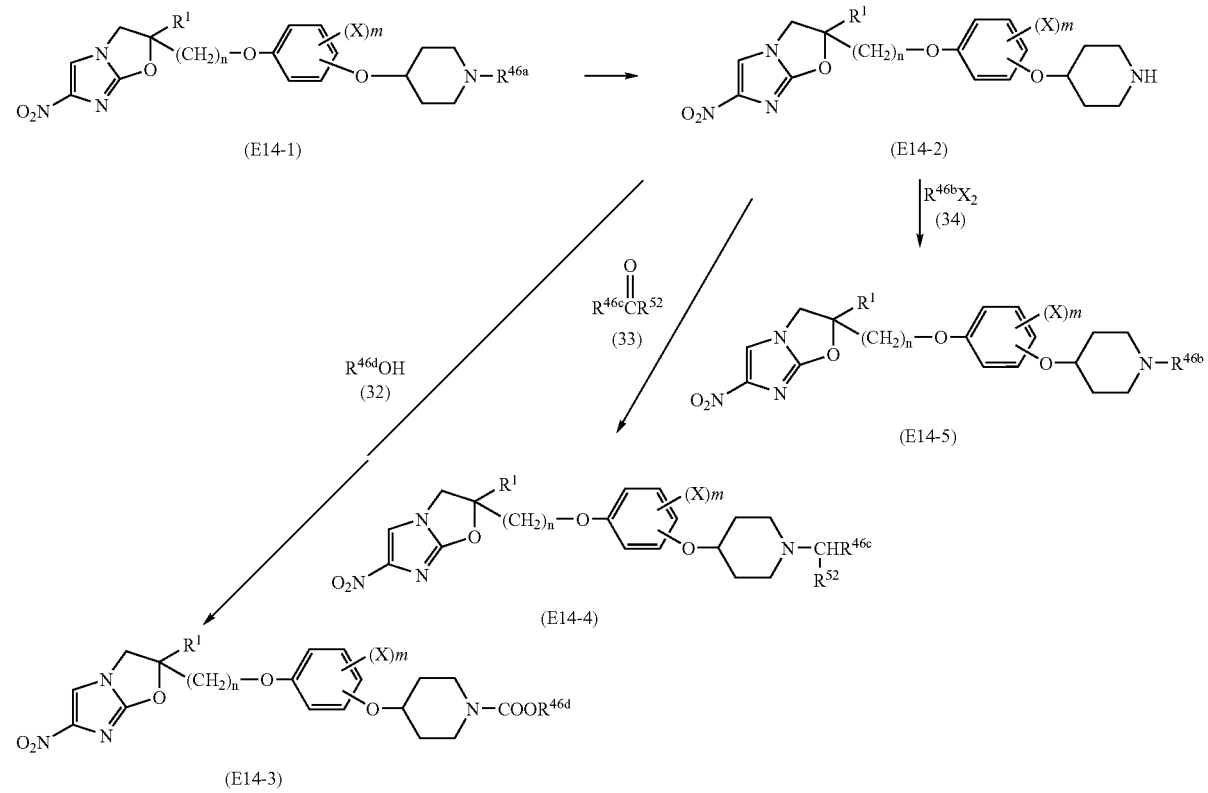

The reaction of the compound (Eaa 4-1) with the compound (31) can be carried out in an appropriate solvent in the presence of a condensing agent.

Herein, there can be used the solvent mentioned below. Examples of such a solvent include halogenated hydrocarbons such as chloroform, dichloromethane, dichloroethane or carbon tetrachloride, aromatic hydrocarbons such as benzene, toluene or xylene, ethers such as diethyl ether, diisopropyl ether, tetrahydrofuran or dimethoxyethane, esters such as methyl acetate, ethyl acetate or isopropyl acetate, alcohols such as methanol, ethanol, isopropanol, propanol, butanol, 3-methoxy-1-butanol, ethyl cellosolve or methyl cellosolve, acetonitrile, pyridine, acetone, water, aprotic polar solvents such as N,N-dimethylacetamide, N,N-dimethylformamide, dimethylsulfoxide or hexamethylphosphoric acid triamide, and mixed solvents thereof.

Examples of the condensing agent used herein may include azocarboxylates such as diethyl azodicarboxylate or tert-butyl azodicarboxylate, and phosphorus compound mixtures such as triphenylphosphine or triphenylphosphine polymer supported. This reaction is carried out generally at 0° C. to 200° C., and preferably at 0° C. to 150° C. The reaction is generally carried out for 1 to 10 hours. The molar wherein $R^1$, n, X, m, $X_2$ and $R^{52}$ are the same as above, $R^{46a}$ represents a C1-C6 alkoxycarbonyl group, $R^{46b}$ represents a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), a phenyl C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), a phenyl C1-C6 alkoxycarbonyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), or a C1-C6 alkoxycarbonyl group, $R^{46c}$ represents a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), or a phenyl C1-C6 alkyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), and $R^{46d}$ represents a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), or a C1-C6 alkyl group.

The reaction to lead the compound (E14-1) into the compound (E14-2) can be carried out under the same conditions for the reaction to lead the compound (E-1) into the compound (E-2) represented by the above reaction scheme 16.

The reaction of the compound (E14-2) with the compound (34) can be carried out under the same conditions for the reaction of the compound (Fd-1) with the compound (15) represented by the above reaction scheme 18.

The reaction of the compound (E14-2) with the compound (33) can be carried out under the same conditions for the reaction of the compound (E-2) with the compound (13) represented by the above reaction scheme 16.

The reaction of the compound (E14-2) with the compound (32) can be carried out in an appropriate solvent in the presence of a condensing agent. Any solvent can be used herein, which is used in the method of the reactions of the compound (Eaa 4-1) with the compound (31) represented by the above reaction scheme 24. N,N'-carbonyldiimidazole is an example of the condensing agent used herein. Each of the compound (32) and the condensing agent is used to the compound (E14-2) at a molar ratio of at least equal to 1:1, and preferably between 1:1 and 2:1. This reaction is carried out generally at 0° C. to 150° C., and preferably at 0° C. to 100° C., approximately for 1 to 30 hours.

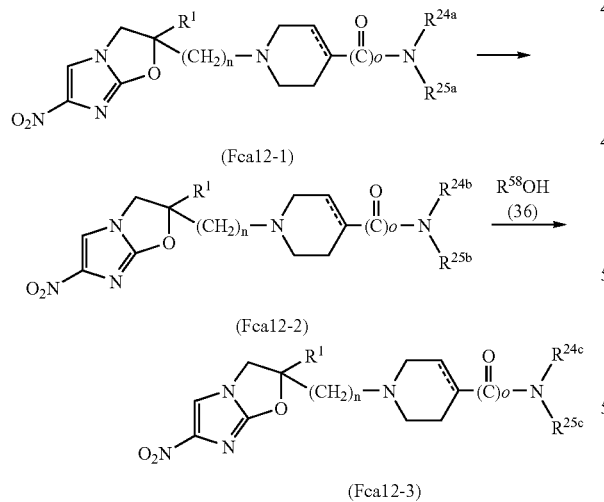

(Fca12-1)

(Fca12-2)

(Fca12-3)

wherein $R^1$, n and o are the same as above, $R^{24a}$ and $R^{25a}$ form a piperazine ring through a nitrogen atom adjacent thereto, and the piperazine ring, which $R^{24a}$ and $R^{25a}$ form, may have, as a substituent, at least one substituent described as above, for the substituents of the 5 to 6-membered saturated heterocycle that $R^{24}$ and $R^{25}$ form through nitrogen atoms adjacent thereto, and the piperazine ring that $R^{24a}$ and $R^{25a}$ form has a C1-C6 alkoxycarbonyl group on the nitrogen atom on the piperazine ring, $R^{58}$ represents a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent), $R^{24b}$ and $R^{25b}$ form a piperazine ring through a nitrogen atom adjacent thereto, and the piperazine ring, which $R^{24b}$ and $R^{25b}$ form, may have, as a substituent at least one substituent described as above, for the substituent of the 5 to 6-membered saturated heterocycle that $R^{24}$ and $R^{25}$ form through nitrogen atoms adjacent thereto, and the piperazine ring that $R^{24b}$ and $R^{25b}$ form has a hydrogen atom on the nitrogen atom on the piperazine ring, and $R^{24c}$ and $R^{25c}$ form a piperazine ring through a nitrogen atom adjacent thereto, and the piperazine ring, which $R^{24c}$ and $R^{25c}$ form, may have, as a substituent, at least one substituent described as above, for the substituents of the 5 to 6-membered saturated heterocycle that $R^{24}$ and $R^{25}$ form through nitrogen atoms adjacent thereto, and the piperazine ring that $R^{24c}$ and $R^{25c}$ form has a phenyl C1-C6 alkoxycarbonyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent) on the nitrogen atom on the piperazine ring.

The reaction to lead the compound (Fca 12-1) into the compound (Fca 12-2) can be carried out under the same conditions for the reaction to lead the compound (E-1) into the compound (E-2) represented by the above reaction scheme 16.

The reaction of the compound (Fca 12-2) with the compound (36) can be carried out under the same conditions for the reaction of the compound (E14-2) with the compound (32) represented by the above reaction scheme 25.

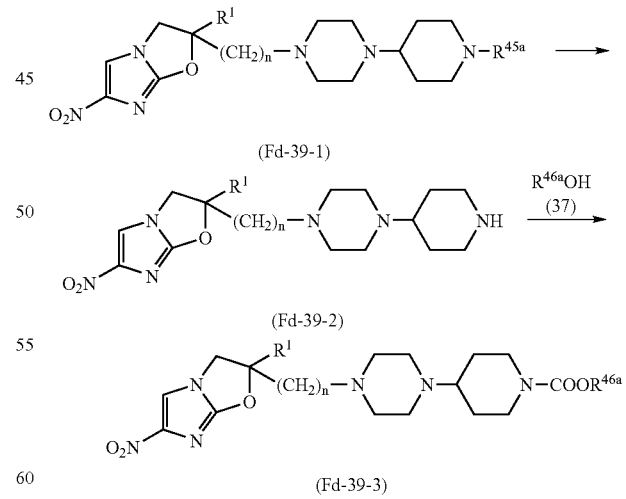

(Fd-39-1)

(Fd-39-2)

(Fd-39-3)

wherein $R^1$ and n are the same as above, $R^{45a}$ represents a C1-C6 alkoxycarbonyl group, and $R^{46a}$ represents a phenyl group (wherein, on the phenyl ring, at least one group selected from a group consisting of a halogen atom, a halogen substituted or unsubstituted C1-C6 alkyl group, and a halogen substituted or unsubstituted C1-C6 alkoxy group may be substituted as a substituent).

The reaction to lead the compound (Fd-39-1) into the compound (Fd-39-2) can be carried out under the same conditions for the reaction to lead the compound (E-1) into the compound (E-2) represented by the above reaction scheme 16.

The reaction of the compound (Fd-39-2) with the compound (37) can be carried out under the same conditions for the reaction of the compound (E14-2) with the compound (32) represented by the above reaction scheme 25.

The compound of the present invention includes a pharmaceutically acceptable salt. Examples of such a salt include inorganic salts such as hydrochloride, hydrobromide, nitrate, sulfate or phosphate, and organic salts such as methanesulfonate, p-toluenesufonate, acetate, citrate, tartrate, maleate, fumarate, malate or lactate.

Next, a medical preparation containing the compound of the present invention as an active ingredient will be explained.

The above medical preparation is obtained by preparing the compound of the present invention in the form of a common medical preparation. It is prepared using commonly used diluents or excipients such as a filler, expander, binder, wetting agent, disintegrator, surfactant or lubricant.

Such a medical preparation can be selected from among various forms, depending on therapeutic purposes. Typical examples of a preparation form include a tablet, pill, powder, liquid, suspension, emulsion, granule, capsule, suppository, and injection (liquid, suspension, etc.)

Known carriers can be widely used in making the medical preparation in a tablet form. Examples of such a carrier include excipients such as lactose, sucrose, sodium chloride, glucose, urea, starch, calcium carbonate, kaoline or crystalline cellulose; binders such as water, ethanol, propanol, simple syrup, glucose solution, starch solution, gelatin solution, carboxymethylcellulose, shellac, methylcellulose, potassium phosphate or polyvinylpyrrolidone; disintegrators such as dry starch, sodium alginate, agar powder, laminaran powder, sodium hydrogen-carbonate, calcium carbonate, polyoxyethylene sorbitan fatty acid esters, sodium lauryl sulfate, monoglyceride stearate, starch or lactose; disintegration controllers such as sucrose, stearin, cacao butter or hydrogenated oil; absorption enhancers such as quaternary ammonium base or sodium lauryl sulfate, humectants such as glycerin or starch, adsorbents such as starch, lactose, kaoline, bentonite or colloidal silica, and lubricants such as purified talc, stearate, boric acid powder or polyethylene glycol.

Moreover, such tablets can be prepared as tablets with common tablet coating, such as a sugar coated tablet, gelatin coated tablet, enteric coated tablet, film coated tablet, double coated tablet, or multi-coated tablet.

Known carriers can be widely used in making the medical preparation in a pill form. Examples of such a carrier include excipients such as glucose, lactose, starch, cacao butter, hydrogenated vegetable oil, kaoline or talc, binders such as gum arabic powder, tragacanth powder, gelatin or ethanol, and disintegrators such as laminaran or agar.

Known carriers can be widely used in making the medical preparation in a suppository form. Examples of such a carrier include polyethylene glycol, cacao butter, higher alcohol, higher alcohol esters, gelatin, and semisynthetic glyceride.

In a case where the medical preparation is prepared as an injection such as a liquid, emulsion or suspension, these solutions are preferably sterilized and prepared to be isotonic to blood. Known diluents can be widely used in making the medical preparation in such a liquid, emulsion or suspension form. Examples of such a diluent include water, ethanol, propylene glycol, ethoxylated isostearyl alcohol, polyoxylated isostearyl alcohol, and polyoxyethylene sorbitan fatty acid esters. Moreover, in the case of using the medical preparation as an injection, a certain amount of common salts, glucose or glycerin that is sufficient to prepare an isotonic solution may be added to the medical preparation. Otherwise, a common solubilizing agent, buffer, soothing agent or the like may also be added to the medical preparation. Further, a coloring agent, preservative, perfume, flavor, sweetening agent or other pharmaceuticals may also be added thereto, if necessary.

The amount of the compound of the present invention contained in the medical preparation is not particularly limited, but it can be appropriately selected from a wide range. Generally, 1 to 70% by weight of the compound of the present invention is preferably contained in the medical preparation.

The method of administering the medical preparation of the present invention is not particularly limited. It is administered depending on various preparation forms, patients' age, sex, conditions of disease, or other conditions. For example, where the medical preparation adopts a tablet, pill, liquid, suspension, emulsion, granule or capsule form, it is administered orally. In the case of an injection, it can be administered intravenously, singly or in combination with a common auxiliary fluid such as glucose or amino acid. Moreover, if necessary, it can be singly administered intramuscularly, intradermally, subcutaneously or intraperitoneally. In the case of a suppository, it can be administered intrarectally.

The dose of the above medical preparation may be appropriately selected depending on usage, patients' age, sex, level of disease, or other conditions. Generally 0.01 to 100 mg, preferably 0.1 to 50 mg per kg of body weight of the medical preparation is administered once or divided into several times per day.

Since the above dose is altered depending on various conditions, the dose smaller than the above range may be sufficient in some cases, or the dose greater than the above range may be required in other cases.

The compound of the present invention has a specific effect against *Mycobacterium tuberculosis* such as acid-fast bacteria (*Mycobacterium*, atypical acid-fast bacteria). The compound of the present invention has an excellent effect against multi-drug-resistant *Mycobacterium tuberculosis*. The compound of the present invention has an antimicrobial action against anaerobic bacteria.

The compound of the present invention does not only show the above described activities in vitro, but it also expresses the above activities in oral administration.

The compound of the present invention does not induce diarrhea, which is induced by known antimicrobial agents having a wide spectrum for common bacteria such as Gram-positive bacteria or Gram-negative bacteria. In addition, it has lesser adverse reactions than existing agents. Accordingly, it can be a medical preparation, which can be administered for a long time.

The compound of the present invention can be distributed well in the tissues of the lung, the main organ that is infected by acid-fast bacteria, and it has properties such as sustained efficacy or excellent safety. Accordingly, a high therapeutic effect can be expected from the compound.

When compared with existing antitubercular agents, the compound of the present invention shows a strong bactericidal action even towards cytozoic bacteria such as *Mycobacterium tuberculosis* present in a human macrophage. Accordingly, it enables a reduction of reoccurrence rate of tuberculosis and the realization of a short-term chemotherapy. It is therefore expected that the compound of the present invention will also be used as a main preventive agent administered for a mixed infection by HIV and tuberculosis, which is considered to be a serious problem.

EXAMPLES

Formulation Example, Reference Examples, Examples and Test Examples will be Described Below Formulation Example 1

100 g of a compound of the invention, 40 g of Avicel (trade name, manufactured by Asahi Kasei Corporation), 30 g of corn starch and 2 g of magnesium stearate were mixed and ground, and then formed into tablets with a pestle of sugarcoat R10 mm.

A film coating agent containing 10 g of TC-5 (trade name, hydroxypropyl methylcellulose, manufactured by Shin-Etsu Chemical Co., Ltd.), 3 g of polyethylene glycol-6000, 40 g of castor oil and an appropriate amount of ethanol was used to coat the obtained tablets, producing a film-coated tablet having the composition described above.

Reference Example 1

Preparation of benzyl 4-(2-oxopropyl)piperazine-1-carboxylate

Potassium carbonate (1.27 g, 9.22 mmol), N-ethyldiisopropylamine (0.80 ml, 4.61 mmol), and chloroacetone (1.22 ml, 13.83 mmol) were added to a solution of benzyl piperazine-1-carboxylate (2.03 g, 90.22 mmol) in acetonitrile (20 ml), and the mixture was heated under reflux for 2 hours. The insoluble substances were removed by filtration and washed with ethyl acetate. The filtrate was concentrated under reduced pressure. The residue was purified by silica gel column chromatography(methylene chloride/methanol=100/1) to afford benzyl 4-(2-oxopropyl)piperazine-1-carboxylate (2.24 g, yield 88%) as a pale yellow oil.

$^1$H-NMR (CDCl$_3$) δppm: 2.15 (3H, s), 2.35-2.50 (4H, m), 3.21 (2H, s), 3.50-3.62 (4H, m), 5.13 (2H, s), 7.27-7.42 (5H, m).

Reference Example 2

Preparation of tert-butyl 4-(3-oxobutyl)piperazine-1-carboxylate

A solution of tert-butyl piperazine-1-carboxylate (6 g, 32.3 mmol) in THF (50 ml) was gradually added dropwise to a solution of methyl vinyl ketone (2.3 g, 32.9 mmol) in THF (25 ml) while cooling in an ice-bath, and the mixture was stirred at room temperature for 3 days. The reaction mixture was concentrated under reduced pressure, and the residue was purified by silica gel column chromatography (methylene chloride/methanol=20/1) to afford tert-butyl 4-(3-oxobutyl)piperazine-1-carboxylate (7.2 g, yield 87%) as a pale yellow oil.

$^1$H-NMR (CDCl$_3$) δppm: 1.46 (9H, s), 2.17 (3H, s), 2.30-2.42 (4H, m), 2.53-2.70 (4H, m), 3.33-3.47 (4H, m).

Using corresponding starting materials, compounds of Reference Examples 3 to 10 were prepared in the same manner as described in Reference Example 1.

Reference Example 3

1-[4-(4-trifluoromethylphenyl)piperazin-1-yl]propan-2-one yield 99% $^1$H-NMR (CDCl$_3$) δppm: 2.18 (3H, s), 2.63-2.68 (4H, m), 3.27 (2H, s), 3.30-3.45 (4H, m), 6.92 (2H, d, J=8.7 Hz), 7.48 (2H, d, J=8.7 Hz).

Reference Example 4

1-(4-phenylpiperazin-1-yl)propan-2-one yield 95% $^1$H-NMR (CDCl$_3$) δppm: 2.19 (3H, s), 2.65-2.70 (4H, m), 3.27-3.32 (6H, m), 6.97-7.01 (2H, m), 7.24-7.31 (1H, m), 7.37-7.43 (2H, m).

Reference Example 5

1-[4-(4-chlorophenyl)piperazin-1-yl]propan-2-one yield 99% $^1$H-NMR (CDCl$_3$) δppm: 2.17 (3H, s), 2.63-2.67 (4H, m), 3.18-3.23 (4H, m), 3.26 (2H, s), 6.80-6.87 (2H, m), 7.17-7.23 (2H, m).

Reference Example 6

1-[4-(4-trifluoromethoxyphenyl)piperazin-1-yl]propan-2-one yield 100% $^1$H-NMR (CDCl$_3$) δppm: 2.18 (3H, s), 2.63-2.68 (4H, m), 3.20-3.25 (4H, m), 3.26 (2H, s), 6.85-6.92 (2H, m), 7.09-7.13 (2H, m).

Reference Example 7

1-[4-(2-pyridyl)piperazin-1-yl]propan-2-one yield 97% $^1$H-NMR (CDCl$_3$) δppm: 2.19 (3H, s), 2.58-2.63 (4H, m), 3.25 (2H, s), 3.57-3.62 (4H, m), 6.60-6.66 (2H, m), 7.44-7.51 (1H, m), 8.17-8.20 (1H, m).

Reference Example 8

1-[4-(2-pyrimidyl)piperazin-1-yl]propan-2-one yield 88% $^1$H-NMR (CDCl$_3$) δppm: 2.19 (3H, s), 2.53-2.57 (4H, m), 3.25 (2H, s), 3.86-3.90 (4H, m), 6.49 (1H, t, J=4.8 Hz), 8.30 (2H, d, J=4.8 Hz).

Reference Example 9 tert-butyl N-methyl-[1-(2-oxopropyl)piperidin-4-yl]carbamate yield 79% $^1$H-NMR (CDCl$_3$) δppm: 1.46 (9H, s), 1.57-1.63 (2H, m), 1.70-1.91 (2H, m), 2.04-2.18 (2H, m), 2.14 (3H, s), 2.71-2.74 (1H, m), 2.74 (3H, s), 2.90-2.95 (2H, m), 3.19 (2H, s).

Reference Example 10 tert-butyl 4-(2-oxopropyl)homopiperazine-1-carboxylate yield 58% $^1$H-NMR (CDCl$_3$) δppm: 1.46 (9H, s), 1.75-1.93 (2H, m), 2.14 (3H, s), 2.64-2.76 (4H, m), 3.32 (2H, s), 3.38-3.58 (4H, m).

Reference Example 11

Preparation of 1-(4-trifluoromethylbenzoyl)-4-hydroxypiperidine 4-(Trifluoromethyl)benzoyl chloride (1.5 ml, 9.89 mmol) was added to a solution of 4-hydroxypiperidine (1 g, 9.89 mmol) and triethylamine (1.7 ml, 11.9 mmol) in methylene chloride (20 ml) while cooling in an ice-bath, and the mixture was stirred at room temperature for 30 minutes. The reaction mixture was washed with water, saturated sodium bicarbonate aqueous solution and brine, and dried over magnesium sulfate. After filtration, the filtrate was concentrated under reduced pressure. The residue was purified by silica gel column chromatography (n-hexane/acetone=2/1) to afford 1-(4-trifluoromethylbenzoyl)-4-hydroxypiperidine (2.07 g, yield 77%) as a colorless crystalline powder.

$^1$H-NMR (CDCl$_3$) δppm: 1.36-2.07 (4H, m), 3.07-3.70 (3H, m), 3.91-4.32 (2H, m), 7.51 (2H, d, J=8.0 Hz), 7.68 (2H, d, J=8.0 Hz).

Using a corresponding starting material, a compound of Reference Example 12 was prepared in the same manner as described in Reference Example 11.

Reference Example 12

1-(4-trifluoromethoxybenzoyl)-4-hydroxypiperidine a colorless crystalline powder, yield 100% $^1$H-NMR (CDCl$_3$) δppm: 1.34-2.07 (4H, m), 3.09-3.80 (3H, m), 3.91-4.32 (2H, m), 7.25 (2H, d, J=7.9 Hz), 7.45 (2H, d, J=7.9 Hz).

Reference Example 13

Preparation of 1-[2-(tetrahydropyran-2-yloxy)ethyl]-4-(4-trifluoromethylphenoxy)piperidine A mixture of 4-(4-trifluoromethylphenoxy)-piperidine (1.87 g, 7.63 mmol), 2-(2-bromoethoxy)-tetrahydropyran (1.75 g, 8.4 mmol), potassium carbonate (1.16 g, 8.38 mmol), sodium iodide (1.2 g, 8.01 mmol) in DMF (30 ml) was stirred at 100° C. for 1 hour. The reaction mixture was allowed to return to room temperature, poured into water and extracted with ethyl acetate twice. The extract was washed with water twice and brine, and dried over magnesium sulfate. After filtration, the filtrate was concentrated under reduced pressure. The residue was purified by silica gel column chromatography (methylene chloride/methanol=50/1) to afford 1-[2-(tetrahydropyran-2-yloxy)ethyl]-4-(4-trifluoromethylphenoxy)piperidine (1.69 g, yield 59%) as a colorless oil.

$^1$H-NMR (CDCl$_3$) δppm: 1.39-2.12 (10H, m), 2.36-2.53 (2H, m), 2.68 (2H, t, J=6.1 Hz), 2.71-2.92 (2H, m), 3.43-3.63 (2H, m), 3.78-3.94 (2H, m), 4.31-4.47 (1H, m), 4.57-4.67 (1H, m), 6.96 (2H, d, J=8.7 Hz), 7.52 (2H, d, J=8.7 Hz).

Reference Example 14

Preparation of 2-[4-(4-trifluoromethylphenoxy)piperidin-1-yl]ethanol

A mixture of 1-[2-(tetrahydropyran-2-yloxy)ethyl]-4-(4-trifluoromethylphenoxy)piperidine (1.69 g, 4.53 mmol) prepared in Reference Example 13 and pyridinium p-toluenesulfonate (114 mg, 0.45 mmol) in ethanol (50 ml) was stirred at 60 to 70° C. for 6 hours. The reaction mixture was allowed to return to room temperature and concentrated under reduced pressure. To the residue, 10% sodium hydroxide aqueous solution was added, and the mixture was extracted with methylene chloride. The extract was washed with brine and dried over magnesium sulfate. After filtration, the filtrate was concentrated under reduced pressure. The residue was purified by silica gel column chromatography (methylene chloride/methanol=50/1) to afford 2-[4-(4-trifluoromethylphenoxy)piperidin-1-yl]ethanol (1.19 g, yield 91%) as a colorless oil.

$^1$H-NMR (CDCl$_3$) δppm: 1.73-2.10 (4H, m), 2.31-2.47 (2H, m), 2.58 (2H, t, J=5.5 Hz), 2.69-3.00 (3H, m), 3.63 (2H, t, J=5.5 Hz), 4.33-4.48 (1H, m), 6.95 (2H, d, J=8.6 Hz), 7.53 (2H, d, J=8.6 Hz).

Reference Example 15

Preparation of 2-[2-(4-trifluoromethylphenoxy)ethoxy]-tetrahydropyran

A mixture of 4-hydroxybenzotrifluoride (2.08 g, 12.83 mmol), 2-(2-bromoethoxy)tetrahydropyran (3 g, 14.11 mmol), potassium carbonate (1.95 g, 14.11 mmol), and sodium iodide (2 g, 13.47 mmol) in DMF (15 ml) was stirred at 100° C. for 3 hours. The reaction mixture was allowed to return to room temperature, poured into water, and extracted with ethyl acetate twice. The extract was washed with water twice and brine, and dried over magnesium sulfate. After filtration, the filtrate was concentrated under reduced pressure. The residue was purified by silica gel column chromatography (n-hexane/ethyl acetate=1/1) to afford 2-[2-(4-trifluoromethylphenoxy)ethoxy]tetrahydropyran (2.47 g, yield 66%) as a colorless oil.

$^1$H-NMR (CDCl$_3$) δppm: 1.41-1.90 (6H, m), 3.45-3.66 (1H, m), 3.76-3.96 (2H, m), 4.02-4.24 (3H, m), 4.63-4.76 (1H, m), 6.98 (2H, d, J=8.6 Hz), 7.53 (2H, d, J=8.6 Hz).

Reference Example 16

Preparation of 2-(4-trifluoromethylphenoxy)ethanol

Using 2-[2-(4-trifluoromethylphenoxy)ethoxy]-tetrahydropyran (2.47 g, 8.51 mmol) prepared in Reference Example 15, 2-(4-trifluoromethylphenoxy)-ethanol (1.32 g, yield 79%) as a colorless crystalline powder was prepared in the same manner as described in Reference Example 14.

$^1$H-NMR (CDCl$_3$) δppm: 3.88-4.14 (4H, m), 6.98 (2H, d, J=8.6 Hz), 7.55 (2H, d, J=8.6 Hz).

Reference Example 17

Preparation of 1-[2-(tetrahydropyran-2-yloxy)ethyl]-4-(4-trifluoromethoxyphenyl)-1,2,3,6-tetrahydropyridine Using 4-(4-trifluoromethoxyphenyl)-1,2,3,6-tetrahydropyridine monohydrochloride (680 mg, 2.43 mmol) and 2-(2-bromoethoxy)tetrahydropyran (610 mg, 2.92 mmol), 1-[2-(tetrahydropyran-2-yloxy)ethyl]-4-(4-trifluoromethoxyphenyl)-1,2,3,6-tetrahydropyridine (425 mg, yield 47%) as a pale brown oil was prepared in the same manner as described in Reference Example 15.

$^1$H-NMR (CDCl$_3$) δppm: 1.41-1.92 (6H, m), 2.45-2.59 (2H, m), 2.67-2.86 (4H, m), 3.18-3.31 (2H, m), 3.43-3.65 (2H, m), 3.80-4.00 (2H, m), 4.55-4.65 (1H, m), 5.98-6.10 (1H, m), 7.15 (2H, dd, J=2.1 Hz, 8.8 Hz), 7.38 (2H, dd, J=2.1 Hz, 8.8 Hz).

Reference Example 18

Preparation of 2-[4-(4-trifluoromethoxyphenyl)-1,2,3,6-tetrahydropyridin-1-yl]ethanol Using 1-[2-(tetrahydropyran-2-yloxy)ethyl]-4-(4-trifluoromethoxyphenyl)-1,2,3,6-tetrahydropyridine (425 mg, 1.14 mmol) prepared in Reference Example 17, 2-[4-(4-trifluoromethoxyphenyl)-1,2,3,6-tetrahydropyridin-1-yl]ethanol (222 mg, yield 68%) as a pale brown oil was prepared in the same manner as described in Reference Example 14.

$^1$H-NMR (CDCl$_3$) δppm: 2.47-2.59 (2H, m), 2.68 (2H, t, J=5.5 Hz), 2.79 (2H, t, J=5.5 Hz), 3.16-3.25 (2H, m), 3.70 (2H, t, J=5.5 Hz), 6.00-6.10 (1H, m), 7.17 (2H, dd, J=2.1 Hz, 6.7 Hz), 7.40 (2H, dd, J=2.1 Hz, 6.7 Hz).

Reference Example 19

Preparation of 3-(4-trifluoromethylphenyl)-2-propyn-1-ol

A mixture of 4-bromobenzotrifluoride (6.5 g, 28.89 mmol), propargyl alcohol (2.35 ml, 40.45 mmol), triethylamine (5.64 ml, 40.45 mmol), triphenylphosphine (230 mg, 0.87 mmol), cuprous iodide (110 mg, 0.58 mmol), and dichlorobis(triphenylphosphine)palladium (210 mg, 0.29 mmol) in toluene (100 ml) was stirred at 100° C. under a nitrogen atmosphere for 2 hours. The reaction mixture was allowed to return to room temperature and filtered through Celite. The filtrate was concentrated under reduced pressure, and the residue was purified by silica gel column chromatography (methylene chloride/ethyl acetate =9/1) to afford 3-(4-trifluoromethylphenyl)-2-propyn-1-ol (3.47 g, yield 60%) as a pale brown oil.

$^1$H-NMR (CDCl$_3$) δppm: 4.52 (2H, d, J=6.2 Hz), 7.53 (2H, d, J=8.7 Hz), 7.58 (2H, d, J=8.7 Hz).

Reference Example 20

Preparation of 2-[N-methyl-(4-trifluoromethoxyphenyl)-amino]ethanol

A mixture of N-methyl-(4-trifluoromethoxyphenyl)amine (4.83 g, 24.24 mmol), 2-(2-bromoethoxy)-tetrahydropyran (6.1 g, 29.03 mmol), and potassium carbonate (3.84 g, 27.76 mmol) in DMF (20 ml) was stirred at 100° C. for 5 hours. The reaction mixture was allowed to return to room temperature, poured into water, and extracted with ethyl acetate twice. The extract was washed with water twice and brine, and dried over magnesium sulfate. After filtration, the filtrate was concentrated under reduced pressure. The residue was purified by silica gel column chromatography (methylene chloride/ethyl acetate=20/1) to afford 2-[N-methyl-(4-trifluoromethoxyphenyl)-amino]ethanol (3.1 g, yield 53%) as a pale yellow oil.

$^1$H-NMR (CDCl$_3$) δppm: 2.96 (3H, s), 3.46 (2H, t, J=5.7 Hz), 3.81 (2H, q, J=5.7 Hz), 6.74 (2H, d, J=8.7 Hz), 7.08 (2H, d, J=8.7 Hz).

Reference Example 21

Preparation of 8-(4-trifluoromethoxyphenyl)-1,4-dioxa-8-azaspiro[4.5]decane

A mixture of 1-bromo-4-(trifluoromethoxy)-benzene (6.3 g, 26.14 mmol), 1,4-dioxa-8-azaspiro-[4,5]decane (3.35 ml, 26.14 mmol), palladium acetate (60 mg, 0.26 mmol), (S)-(−)-2,2'-bis(diphenylphosphino)-1,1'-binaphthyl (BINAP) (244 mg, 0.39 mmol), and sodium tert-butoxide (3.77 g, 39.23 mmol) in toluene (50 ml) was stirred at 80° C. for 1 hour. The reaction mixture was allowed to return to room temperature, to which ethyl acetate (50 ml) was added, and the resulting mixture was then filtered. The filtrate was washed with water and brine, and dried over magnesium sulfate. After filtration, the filtrate was concentrated under reduced pressure. The residue was purified by silica gel column chromatography (methylene chloride/methanol=50/1) to afford 8-(4-trifluoromethoxyphenyl)-1,4-dioxa-8-azaspiro[4,5]decane (6.54 g, yield 83%) as a pale yellow powder.

$^1$H-NMR (CDCl$_3$) δppm: 1.83 (4H, t, J=5.8 Hz), 3.31 (4H, t, J=5.8 Hz), 3.99 (4H, s), 6.90 (2H, d, J=8.8 Hz), 7.09 (2H, d, J=8.8 Hz).

Reference Example 22

Preparation of 1-(4-trifluoromethoxyphenyl)piperidin-4-one

A mixture of 8-(4-trifluoromethoxyphenyl)-1,4-dioxa-8-azaspiro[4.5]decane (1.23 g, 4.06 mmol) prepared in Reference Example 21, concentrated hydrochloric acid (5 ml), water (10 ml), and ethanol (30 ml) was heated under reflux for 5 hours. The reaction mixture was allowed to return to room temperature and concentrated under reduced pressure. To the residue, 10% sodium hydroxide aqueous solution was added, and the mixture was extracted with methylene chloride. The extract was washed with water and brine, and dried over magnesium sulfate. After filtration, the filtrate was concentrated under reduced pressure. The residue was purified by silica gel column chromatography (n-hexane/ethyl acetate=3/1) to afford 1-(4-trifluoromethoxyphenyl)piperidin-4-one (848 mg, yield 81%) as a colorless oil.

$^1$H-NMR (CDCl$_3$) δppm: 2.56 (4H, t, J=6.2 Hz), 3.59 (4H, t, J=6.2 Hz), 6.94 (2H, d, J=8.5 Hz), 7.14 (2H, d, J=8.5 Hz).

Reference Example 23

Preparation of 1-(4-trifluoromethoxyphenyl)piperidin-4-ol

Sodium borohydride (324 mg, 8.56 mmol) was added to a solution of 1-(4-trifluoromethoxyphenyl) piperidin-4-one (1.11 g, 4.28 mmol) prepared in Reference Example 22 in methanol (30 ml) while cooling in an ice-bath, and the mixture was stirred for 30 minutes. To which 10% hydrochloric acid was added, and the resulting mixture was concentrated under reduced pressure. To the residue saturated sodium bicarbonate aqueous solution was added, and the mixture was extracted with methylene chloride. The extract was washed with water and brine, and dried over magnesium sulfate. After filtration, the filtrate was concentrated under reduced pressure. The residue was purified by silica gel column chromatography (n-hexane/ethyl acetate=3/1) to afford 1-(4-trifluoromethoxyphenyl)piperidin-4-ol (1.08 g, yield 97%) as a white powder.

$^1$H-NMR (CDCl$_3$) δppm: 1.59-1.76 (2H, m), 1.90-2.06 (2H, m), 2.82-2.98 (2H, m), 3.43-3.57 (2H, m), 3.75-3.91 (1H, m), 6.89 (2H, d, J=7.1 Hz), 7.09 (2H, d, J=7.1 Hz).

Compounds of Reference Examples 24 and 25 were prepared in the same manner as described in Example 23.

Reference Example 24

1-(4-trifluoromethylphenyl)piperidin-4-ol a white powder, yield 76%

$^1$H-NMR (CDCl$_3$) δppm: 1.53-1.71 (2H, m), 1.89-2.04 (2H, m), 2.91-3.11 (2H, m), 3.56-3.71 (2H, m), 3.80-4.00 (1H, m), 6.93 (2H, d, J=8.7 Hz), 7.46 (2H, d, J=8.7 Hz).

Reference Example 25

1-(4-methoxyphenyl)piperidin-4-ol a white powder, yield 5%

$^1$H-NMR (CDCl$_3$) δppm: 1.64-1.79 (2H, m), 1.92-2.08 (2H, m), 2.74-2.88 (2H, m), 3.32-3.47 (2H, m), 3.70-3.85 (4H, m), 6.84 (2H, dd, J=2.4 Hz, 6.8 Hz), 6.93 (2H, dd, J=2.4 Hz, 6.8 Hz).

Reference Example 26

Preparation of 1-(4-chlorophenyl)piperidin-4-ol

A mixture of 8-(4-chlorophenyl)-1,4-dioxa-8-azaspiro[4.5]decane (2.6 g, 10.25 mmol), concentrated hydrochloric acid (12 ml), water (10 ml), and ethanol (50 ml) was heated under reflux for 5 hours. The reaction mixture was allowed to return to room temperature and concentrated under reduced pressure. To the residue 10% sodium hydroxide aqueous solution was added, and the mixture was extracted with methylene chloride. The extract was washed with water and brine, and dried over magnesium sulfate. After filtration, the filtrate was concentrated under reduced pressure. The residue was dissolved in methanol (50 ml), to which sodium borohydride (388 mg, 10.25 mmol) was added while cooling in an ice-bath, and the mixture was stirred for 30 minutes. To the reaction mixture, 10% hydrochloric acid was added, and the mixture was concentrated under reduced pressure. Saturated sodium bicarbonate aqueous solution was added to the residue, and the mixture was extracted with methylene chloride. The extract was washed with water and brine, and was dried over magnesium sulfate. After filtration, the filtrate was concentrated under reduced pressure. The residue was purified by silica gel column chromatography (n-hexane/ethyl acetate=3/1) to afford 1-(4-chlorophenyl)piperidin-4-ol (1.73 g, yield 80%) as a pale yellow crystalline powder.

$^1$H-NMR (CDCl$_3$) δppm: 1.55-1.74 (2H, m), 1.89-2.08 (2H, m), 2.79-3.00 (2H, m), 3.43-3.57 (2H, m), 3.75-3.92 (1H, br), 6.89 (2H, d, J=7.1 Hz), 7.09 (2H, d, J=7.1 Hz).

Using a corresponding starting material, a compound of Reference Example 27 was prepared in the same manner as described in Reference Example 26.

Reference Example 27

1-(4-fluorophenyl)piperidin-4-ol a white powder, yield 66% $^1$H-NMR (CDCl$_3$) δppm: 1.57-1.79 (2H, m), 1.92-2.08 (2H, m), 2.75-2.92 (2H, m), 3.36-3.50 (2H, m), 3.74-3.89 (1H, m), 6.77-7.00 (4H, m).

Reference Example 28

Preparation of 4-[4-(tert-butyldimethylsiloxy)piperidin-1-yl]benzonitrile

A mixture of 4-bromobenzonitrile (2.76 g, 15.16 mmol), 4-(tert-butyldimethylsiloxy)piperidine (2.9 g, 13.79 mmol), palladium acetate (62 mg, 0.28 mmol), (S)-(−)-2,2'-bis(diphenylphosphino)-1,1'-binaphthyl (BINAP) (258 mg, 0.41 mmol), and sodium tert-butoxide (1.99 g, 20.68 mmol) in toluene (60 ml) was stirred at 80° C. for 1 hour. The reaction mixture was allowed to return to room temperature, to which ethyl acetate (60 ml) was added, and the mixture was filtered. The filtration was washed with water and brine, and dried over magnesium sulfate. After filtration, the filtrate was concentrated under reduced pressure. The residue was purified by silica gel column chromatography (n-hexane/methylene chloride=1/1) to afford 4-[4-(tert-butyldimethylsiloxy)piperidin-1-yl]benzonitrile (2.8 g, yield 66%) as a pale yellow crystalline powder.

$^1$H-NMR (CDCl$_3$) δppm: 0.90 (9H, s), 1.50-1.69 (8H, m), 1.73-1.90 (2H, m), 3.18-3.31 (2H, m), 3.50-3.65 (2H, m), 3.90-4.04 (1H, m), 6.85 (2H, d, J=7.0 Hz), 7.47 (2H, d, J=7.0 Hz).

Reference Example 29

Preparation of 4-(4-hydroxypiperidin-1-yl)benzonitrile

Tetra-n-butylammonium fluoride (1M) THF solution (10.6 ml, 10.2 mmol) was added to a mixture of 4-[4-(tert-butyldimethylsiloxy)piperidin-1-yl]benzonitrile (2.8 g, 8.85 mmol) prepared in Reference Example 28 in THF (30 ml) while cooling in an ice-bath, and the mixture was stirred at room temperature for 16 hours. The reaction mixture was concentrated under reduced pressure. Water was added to the residue, and the mixture was extracted with ethyl acetate twice. The extract was washed with water and brine, and dried over magnesium sulfate. After filtration, the filtrate was concentrated under reduced pressure. The residue was purified by silica gel column chromatography (n-hexane/ethyl acetate=1/2) to afford 4-(4-hydroxypiperidin-1-yl)benzonitrile (1.52 g, yield 85%) as a colorless crystalline powder.

$^1$H-NMR (CDCl$_3$) δppm: 1.50-1.73 (2H, m), 1.90-2.04 (2H, m), 3.00-3.20 (2H, m), 3.59-3.76 (2H, m), 3.84-4.04 (1H, m), 6.86 (2H, dd, J=2.0 Hz, 7.1 Hz), 7.48 (2H, dd, J=2.0 Hz, 7.1 Hz).

Reference Example 30

Preparation of ethyl 1-(4-trifluoromethylphenyl)-piperidine-4-carboxylate

Using 4-bromobenzotrifluoride (3.15 g, 13.99 mmol) and ethyl isonipecotate (2.2 g, 13.99 mmol), ethyl 1-(4-trifluoromethylphenyl)piperidine-4-carboxylate (3.18 g, yield 74%) as a pale brown crystalline powder was prepared in the same manner as described in Reference Example 21.

$^1$H-NMR (CDCl$_3$) δppm: 1.27 (3H, t, J=7.2 Hz), 1.71-2.10 (4H, m), 2.41-2.55 (1H, m), 2.82-2.98 (2H, m), 3.65-3.80 (2H, m), 4.16 (2H, q, J=7.2 Hz), 6.92 (2H, d, J=6.9 Hz), 7.63 (2H, d, J=6.9 Hz).

Reference Example 31

Preparation of [1-(4-trifluoromethylphenyl)piperidin-4-yl]methanol

Lithium aluminum hydride (1.58 g, 41.64 mmol) was suspended in THF (30 ml), to which absolution of ethyl 1-(4-trifluoromethylphenyl)piperidine-4-carboxylate prepared in Reference Example 30 (3.18 g, 10.41 mmol) in THF (10 ml) was added dropwise therein while cooling in an ice-bath under a nitrogen atmosphere. The mixture was stirred for 30 minutes. Water and 10% sodium hydroxide aqueous solution were added to the reaction mixture, which was filtered through Celite. The filtrate was extracted with ethyl acetate twice. The extract was washed with water and brine, and dried over magnesium sulfate. After filtration, the filtrate was concentrated under reduced pressure to afford [1-(4-trifluoromethylphenyl)-piperidin-4-yl]methanol (2.64 g, yield 98%) as a pale yellow oil.

$^1$H-NMR (CDCl$_3$) δppm: 1.31-1.47 (2H, m), 1.61-1.90 (3H, m), 2.74-2.90 (2H, m), 3.45-3.61 (2H, m), 3.83 (2H, d, J=12.6 Hz), 6.92 (2H, d, J=8.8 Hz), 7.46 (2H, d, J=8.8 Hz).

Reference Example 32

Preparation of 1-(4-trifluoromethoxybenzyl)piperidin-4-ol

Sodium triacetoxyborohydride (1.67 g, 7.89 mmol) was added to a solution of 4-(trifluoromethoxy)-benzaldehyde (1 g, 5.26 mmol) and 4-hydroxy piperidine (798 mg, 7.89 mmol) in acetonitrile (2 ml) while cooling in an ice-bath, and the mixture was stirred for 30 minutes, and then at room temperature overnight. The reaction mixture was poured into 7.5% sodium bicarbonate aqueous solution and extracted with ethyl acetate twice. The extract was washed with water and brine, and dried over magnesium sulfate. After filtration, the filtrate was concentrated under reduced pressure. The residue was purified by silica gel column chromatography (methylene chloride/methanol 10/1) to afford 1-(4-trifluoromethoxybenzyl)piperidin-4-ol (1.21 g, yield 84%) as a pale yellow oil.

$^1$H-NMR (CDCl$_3$) δppm: 1.50-1.74 (2H, m), 1.80-1.98 (2H, m), 2.08-2.24 (2H, m), 2.63-2.84 (2H, m), 3.49 (2H, s), 3.61-3.80 (1H, m), 7.15 (2H, d, J=8.5 Hz), 7.34 (2H, d, J=8.5 Hz).

Compounds of Reference Examples 33 and 34 were prepared in the same manner as described in Reference Example 32.

Reference Example 33

1-(4-chlorobenzyl)piperidin-4-ol a white powder, yield 87% $^1$H-NMR (CDCl$_3$) δppm: 1.48-1.63 (2H, m), 1.76-1.91 (2H, m), 2.04-2.20 (2H, m), 2.61-2.76 (2H, m), 3.45 (2H, s), 3.57-3.72 (1H, m), 7.24 (2H, d, J=8.8 Hz), 7.28 (2H, d, J=8.8 Hz).

Reference Example 34

1-(4-trifluoromethylbenzyl)piperidin-4-ol a white powder, yield 83% $^1$H-NMR (CDCl$_3$) δppm: 1.43-1.67 (2H, m), 1.80-1.94 (2H, m), 2.06-2.24 (2H, m), 2.63-2.78 (2H, m), 3.67 (2H, s), 3.61-3.72 (1H, m), 7.44 (2H, d, J=8.0 Hz), 7.57 (2H, d, J=8.0 Hz).

Reference Example 35

Preparation of tert-butyl(4-benzylpiperazin-1-yl)carbamate

4-Benzylpiperazin-1-yl-amine (36.03 g, 188 mmol) was dissolved in methanol (260 ml) and the solution was cooled in an ice-bath, to which a solution of di-tert-butyl dicarbonate (61.66 g, 283 mmol) in methanol (100 ml) was added dropwise over 20 minutes. The mixture was allowed to return to room temperature and stirred overnight. The reaction mixture was concentrated under reduced pressure, and the residue was purified by silica gel column chromatography (n-hexane/acetone=3/1). Isopropyl ether (IPE) (60 ml) and n-hexane (20 ml) were added to thus obtained solid, and the mixture was stirred and then filtered to afford primary crystals. The filtrate was concentrated under reduced pressure, isopropyl ether (10 ml) and n-hexane (10 ml) were added to the residue, and the mixture was stirred and then filtered to afford secondary crystals. These crystals were combined and dried under reduced pressure to afford tert-butyl(4-benzylpiperazin-1-yl)carbamate (42.22 g, yield 77%) as a colorless crystalline powder.

$^1$H-NMR (CDCl$_3$) δppm: 1.45 (9H, s), 2.55-2.58 (4H, m), 2.80 (4H, br), 3.51 (2H, s), 5.35 (1H, br), 7.24-7.31 (5H, m).

Reference Example 36

Preparation of tert-butyl piperazin-1-yl-carbamate

Tert-butyl(4-benzylpiperazin-1-yl)carbamate (42.22 g, 145 mmol) prepared in Reference Example 35 was dissolved in ethanol (300 ml). To which 20% palladium hydroxide/carbon (6.0 g) was added, and the mixture was stirred at room temperature under an atmospheric pressure of hydrogen for 20 minutes, and then at 50° C. for 30 minutes. The catalyst was removed by filtration, and the filtrate was concentrated under reduced pressure. Thus obtained solid was washed with IPE, collected by filtration, and dried under reduced pressure to afford tert-butyl piperazin-1-yl-carbamate (28.9 g, yield 99%) as a colorless crystalline powder.

$^1$H-NMR (CDCl$_3$) δppm: 1.46 (9H, s), 2.74-2.77 (4H, m), 2.95-2.99 (4H, m), 5.45 (1H, br).

Reference Example 37

Preparation of tert-butyl 4-(4-trifluoromethyl phenoxy)piperidine-1-carboxylate

Tert-butyl 4-hydroxypiperidine-1-carboxylate (2.22 g, 10.0 mmol), 4-hydroxybenzotrifluoride (1.21 g, 7.45 mmol), tri-n-butylphosphine (2.26 g, 11.2 mmol) and 1,1'-(azodicarbonyl)dipiperidine (2.82 g, 11.2 mmol) were dissolved in benzene (20 ml), and the mixture was stirred at room temperature for 2 days. To which water was added, and the mixture was extracted with ethyl acetate. The extract was dried over magnesium sulfate and thereafter filtered, and the filtrate was concentrated under reduced pressure. The residue was purified by silica gel column chromatography (n-hexane/ethyl acetate=5/1) ro afford tert-butyl 4-(4-trifluoromethylphenoxy)piperidine-1-carboxylate (1.13 g, yield 44%) as a colorless oil.

$^1$H-NMR (CDCl$_3$) δppm: 1.48 (9H, s), 1.65-1.82. (2H, m), 1.87-1.97 (2H, m), 3.34-3.44 (2H, m), 3.63-3.74 (2H, m), 4.47-4.58 (1H, m), 6.89-6.97 (2H, m), 7.47-7.55 (2H, m).

Reference Example 38

Preparation of 4-(4-trifluoromethylphenoxy)piperidine

Tert-butyl 4-(4-trifluoromethylphenoxy)piperidine-1-carboxylate (1.13 g, 3.27 mmol) prepared in Reference Example 37 was dissolved in methylene chloride (10 ml). To which trifluoroacetic acid (10 ml) was added dropwise and the mixture was stirred at room temperature for 5 hours. After the reaction mixture was concentrated under reduced pressure, the residue was again dissolved in methylene chloride. The solution was neutralized with a sodium hydroxide aqueous solution, and the mixture was extracted with methylene chloride. The extract was washed with brine, dried over magnesium sulfate, and then filtered. The filtrate was concentrated under reduced pressure to afford 4-(4-trifluoromethylphenoxy)piperidine (727 mg, yield 91%) as a white powder.

$^1$H-NMR (CDCl$_3$) δppm: 1.63-1.75 (2H, m), 1.97-2.06 (2H, m), 2.69-2.80 (2H, m), 3.10-3.20 (2H, m), 4.38-4.49 (1H, m), 6.94-6.98 (2H, m), 7.50-7.55 (2H, m).

Using corresponding starting materials, compounds of Reference Examples 39 to 43 were prepared in the same manner as described in Reference Example 38.

Reference Example 39

4-(4-fluorophenoxy)piperidine a white powder, yield 76% $^1$H-NMR (CDCl$_3$) δppm: 1.61-1.74 (2H, m), 1.96-2.06 (2H, m), 2.50 (1H, bs), 2.70-2.80 (2H, m), 3.11-3.20 (2H, m), 4.23-4.33 (1H, m), 6.80-6.89 (2H, m), 6.91-7.00 (2H, m).

Reference Example 40

4-(3-trifluoromethylphenoxy)piperidine a white powder, yield 48% $^1$H-NMR (CDCl$_3$) δppm: 1.62-1.76 (2H, m), 1.80 (1H, bs), 1.97-2.08 (2H, m), 2.71-2.81 (2H, m), 3.11-3.20 (2H, m), 4.37-4.47 (1H, m), 7.05-7.20 (3H, m), 7.34-7.41 (1H, m).

Reference Example 41

4-(4-trifluoromethoxyphenoxy)piperidine a white powder, yield 88% $^1$H-NMR (CDCl$_3$) δppm: 1.59-1.73 (3H, m), 1.97-2.04 (2H, m), 2.68-2.78 (2H, m), 3.10-3.19 (2H, m), 4.29-4.36 (1H, m), 6.85-6.92 (2H, m), 7.10-7.14 (2H, m).

Reference Example 42

4-(4-cyanophenoxy)piperidine a white powder, yield 83% $^1$H-NMR (CDCl$_3$) δppm: 1.63-1.77 (3H, m), 1.98-2.08 (2H, m), 2.72-2.82 (2H, m), 3.12-3.21 (2H, m), 4.42-4.51 (1H, m), 6.92-6.98 (2H, m), 7.55-7.61 (2H, m).

Reference Example 43

4-(4-chlorophenoxy)piperidine a white powder, yield 62% $^1$H-NMR (CDCl$_3$) δppm: 1.50 (1H, bs), 1.56-1.71 (2H, m), 1.94-2.04 (2H, m), 2.66-2.76 (2H, m), 3.08-3.18 (2H, m), 4.25-4.35 (1H, m), 6.80-6.86 (2H, m), 7.18-7.25 (2H, m).

Reference Example 44

Preparation of 1-ethyl-5-(3-methyl-3-butenyl)-1H-tetrazole n-Butyl lithium (1.53 M) hexane solution (6.5 ml, 9.98 mmol) was added dropwise to a solution of 1-ethyl-5-methyl-1H-tetrazole (0.80 g, 7.13 mmol) in THF (15 ml) while stirring at −70° C., and the mixture was further stirred for 1.5 hours. A solution of 3-chloro-2-methyl-1-propene (0.77 ml, 7.84 mmol) in THF (5 ml) was added to the mixture, and the resulting mixture was stirred for 2 hours. Water was added to the reaction mixture, the resulting mixture was extracted with ethyl acetate, and the extract was dried over magnesium sulfate, and then concentrated under reduced pressure to afford 1-ethyl-5-(3-methyl-3-butenyl)-1H-tetrazole (0.95 g, yield 80%) as a brown oil.

$^1$H-NMR (CDCl$_3$) δppm: 1.56 (3H, t, J=7.3 Hz), 1.80 (3H, s), 2.44-2.67 (2H, m), 2.90-3.06 (2H, m), 4.32 (2H, q, J=7.3 Hz), 4.65-4, 77 (1H, m), 4.77-4.87 (1H, m).

Using corresponding starting materials, compounds of Reference Examples 45, and 46 were prepared in the same manner as described in Reference Example 44.

Reference Example 45

1-phenyl-5-(3-methyl-3-butenyl)-1H-tetrazole a white powder, yield 45% $^1$H-NMR (CDCl$_3$) δppm: 1.67 (3H, s), 2.49 (2H, t, J=8.1 Hz), 3.04 (2H, t, J=8.1 Hz), 4.58-4.65 (1H, m), 4.71-4.77 (1H, m), 7.43-7.47 (2H, m), 7.59-7.62 (3H, m).

Reference Example 46

1-(4-chlorophenyl)-5-(3-methyl-3-butenyl)-1H-tetrazole a white powder, yield 55% $^1$H-NMR (CDCl$_3$) δppm: 1.68 (3H, s), 2.50 (2H, t, J=8.1 Hz), 3.03 (2H, t, J=8.1 Hz), 4.58-4.63 (1H, m), 4.71-4.77 (1H, m), 7.38-7.44 (2H, m), 7.56-7.62 (2H, m).

Reference Example 47

Preparation of
3-(4-methyl-4-pentenyl)-3H-benzoxazol-2-one

Potassium tert-butoxide (3.5 g, 31.2 mmol) was gradually added to a mixture of methyltriphenylphosphonium bromide (11 g, 30.8 mmol) in THF (100 ml) while cooling in an ice-bath, and the mixture was stirred for 20 minutes. To which a solution of 3-(4-oxopentyl)-3H-benzoxazol-2-one (5.6 g, 25.6 mmol) in THF (10 ml) was gradually added dropwise. The resulting mixture was stirred at room temperature for 2 hours. The reaction mixture was poured into ice water, and extracted with ethyl acetate twice. The extract was washed with water and brine, and dried over sodium sulfate. After filtration, the filtrate was concentrated under reduced pressure. The residue was purified by silica gel column chromatography (n-hexane/ethyl acetate=3/1) to afford 3-(4-methyl-4-pentenyl)-3H-benzoxazol-2-one (3.4 g, yield 61%) as a colorless oil.

$^1$H-NMR (CDCl$_3$) δppm: 1.73 (3H, s), 1.84-2.16 (4H, m), 3.83 (2H, t, J=7.3 Hz), 4.75 (2H, d, J=12.7 Hz), 6.97 (1H, d, J=8.2 Hz), 7.02-7.28 (3H, m).

Reference Example 48

Preparation of
3-(5-methyl-5-hexenyl)-3H-benzoxazol-2-one

Using 3-(5-oxohexyl)-3H-benzoxazol-2-one (1.4 g, 6 mmol), 3-(5-methyl-5-hexenyl)-3H-benzoxazol-2-one (1.1 g, yield 79%) as a colorless oil was prepared in the same manner as described in Reference Example 47.

$^1$H-NMR (CDCl$_3$) δppm: 1.42-1.60 (2H, m), 1.65-1.83 (5H, m), 2.00-2.16 (2H, m), 3.84 (2H, t, J=6.9 Hz), 4.69 (2H, d, J=11.7 Hz), 6.97 (1H, d, J=7.9 Hz), 7.02-7.23 (3H, m).

Reference Example 49

Preparation of 5-(4-trifluoromethoxyphenyl)-3H-[1,3,4]oxadiazol-2-one

Triethylamine (3.52 ml, 25.28 mmol) and 1,1'-carbonyldiimidazole (4.84 g, 29.87 mmol) were added to a solution of 4-trifluoromethoxybenzoic hydrazide (5.06 g, 22.98 mmol) in THF (150 ml) while cooling in an ice-bath and the mixture was stirred at room temperature for 2 hours. The reaction mixture was concentrated under reduced pressure, to which water was added. The mixture was extracted with ethyl acetate, and the extract was dried over magnesium sulfate and then concentrated under reduced pressure to afford 5-(4-trifluoromethoxyphenyl)-3H-[1,3,4]oxadiazol-2-one (5.34 g, yield 94%) as a colorless crystalline powder.

$^1$H-NMR (DMSO-d$_6$) δppm: 7.01 (1H, s), 7.47-7.59 (2H, m), 7.86-7.98 (2H, m).

Using corresponding starting materials, compounds of Reference Examples 50 to 61 were prepared in the same manner as described in Reference Example 49.

Reference Example 50

5-(4-trifluoromethylphenyl)-3H-[1,3,4]oxadiazol-2-one a white powder, yield 97% $^1$H-NMR (DMSO-d$_6$) δppm: 7.90 (2H, d, J=8.5 Hz), 7.99 (2H, d, J=8.5 Hz).

Reference Example 51

5-(4-biphenylyl)-3H-[1,3,4]oxadiazol-2-one a white powder, yield 97% $^1$H-NMR (DMSO-d$_6$) δppm: 7.35-7.52 (3H, m), 7.68-7.73 (2H, m), 7.76-7.87 (4H, m).

Reference Example 52

5-phenyl-3H-[1,3,4]oxadiazol-2-one a white powder, yield 92% $^1$H-NMR (CDCl$_3$) δppm: 7.40-7.58 (3H, m), 7.77-7.91 (2H, m).

Reference Example 53

5-(4-chlorophenyl)-3H-[1,3,4]oxadiazol-2-one a white powder, yield 80% $^1$H-NMR (DMSO-d$_6$) δppm: 7.61 (2H, dd, J=1.9 Hz, 6.6 Hz), 7.80 (2H, dd, J=1.9 Hz, 6.6 Hz).

Reference Example 54

5-(4-fluorophenyl)-3H-[1,3,4]oxadiazol-2-one a white powder, yield 74% $^1$H-NMR (DMSO-d$_6$) δppm: 7.30-7.49 (2H, m), 7.78-7.92 (2H, m).

Reference Example 55

5-(4-bromophenyl)-3H-[1,3,4]oxadiazol-2-one a white powder, yield 87% $^1$H-NMR (DMSO-d$_6$) δppm: 7.65-7.78 (4H, m).

Reference Example 56

5-(4-chlorobenzyl)-3H-[1,3,4]oxadiazol-2-one a white powder, yield 83% $^1$H-NMR (DMSO-d$_6$) δppm: 3.94 (2H, s), 7.31 (2H, dd, J=2.1 Hz, 6.4 Hz), 7.41 (2H, dd, J=2.1 Hz, 6.4 Hz).

Reference Example 57

5-[2-(4-chlorophenyl)ethyl]-3H-[1,3,4]oxadiazol-2-one a white powder, yield 78% $^1$H-NMR (DMSO-d$_6$) δppm: 2.76-3.00 (4H, m), 7.27 (2H, d, J=8.5 Hz), 7.35 (2H, d, J=8.5 Hz), 12.03 (1H, s).

Reference Example 58

5-(4-chlorostyryl)-3H-[1,3,4]oxadiazol-2-one a white powder, yield 88% $^1$H-NMR (DMSO-d$_6$) δppm: 6.99 (1H, d, J=16.5 Hz), 7.32 (1H, d, J=16.5 Hz), 7.47 (2H, d, J=8.6 Hz), 7.75 (2H, d, J=8.6 Hz), 12.06 (1H, s).

Reference Example 59

5-(4-chlorophenoxymethyl)-3H-[1,3,4]oxadiazol-2-one a white powder, yield 68% $^1$H-NMR (DMSO-$d_6$) δppm: 5.07 (2H, s), 7.07 (2H, d, J=6.8 Hz), 7.37 (2H, d, J=6.8 Hz), 12.41 (1H, br).

Reference Example 60

5-(4-pyridyl)-3H-[1,3,4]oxadiazol-2-one a white powder, yield 40% $^1$H-NMR (DMSO-$d_6$) δppm: 7.72 (2H, dd, J=1.6 Hz, 4.6 Hz), 8.76 (2H, dd, J=1.6 Hz, 4.6 Hz), 12.90 (1H, s).

Reference Example 61

5-(2-pyrimidyl)-3H-[1,3,4]oxadiazol-2-one a white powder, yield 70% $^1$H-NMR (DMSO-$d_6$) δppm: 8.68-8.86 (2H, m), 9.12 (1H, d, J=1.4 Hz), 12.97 (1H, s).

Reference Example 62

Preparation of tert-butyl (S)-2-(4-trifluoromethoxyphenoxymethyl)pyrrolidine-1-carboxylate A mixture of 4-(trifluoromethoxy)phenol (2.1 g, 11.8 mmol), tert-butyl (S)-2-hydroxymethyl pyrrolidine-1-carboxylate (2 g, 9.8 mmol), diethyl azodicarboxylate (2.3 ml, 14.7 mmol), and triphenylphosphine (3.86 g, 14.7 mmol) in THF (30 ml) was heated under reflux for 1 hour. The reaction mixture was allowed to return to room temperature and concentrated under reduced pressure. The residue was purified by silica gel column chromatography (n-hexane/ethyl acetate=10/1) to afford tert-butyl (S)-2-(4-trifluoromethoxyphenoxymethyl)pyrrolidine-1-carboxylate (2.96 g, yield 65%) as a pale yellow oil.

$^1$H-NMR (CDCl$_3$) δppm: 1.48 (9H, s), 1.78-2.10 (4H, m), 3.27-3.49 (2H, m), 3.73-3.98 (1H, m), 4.04-4.20 (2H, m), 6.90 (2H, dd, J=2.2 Hz, 7.0 Hz), 7.12 (2H, dd, J=2.2 Hz, 7.0 Hz).

Reference Example 63

Preparation of (S)-2-(4-trifluoromethoxyphenoxymethyl)-pyrrolidine

A mixture of tert-butyl (S)-2-(4-trifluoromethoxyphenoxymethyl)pyrrolidine-1-carboxylate (2.31 g, 6.39 mmol) prepared in Reference Example 62, trifluoroacetic acid (20 ml), and methylene chloride (20 ml) was stirred at room temperature for 4 hours. The reaction mixture was concentrated under reduced pressure. The residue was neutralized with 10% sodium hydroxide aqueous solution and the mixture was extracted with methylene chloride, and the extract was dried over magnesium sulfate. After filtration, the filtrate was concentrated under reduced pressure to afford (S)-2-(4-trifluoromethoxyphenoxymethyl)-pyrrolidine (1.65 g, yield 99%) as a pale brown oil.

$^1$H-NMR (CDCl$_3$) δppm: 1.45-1.63 (1H, m), 1.65-2.04 (3H, m), 2.70 (1H, bs), 2.88-3.08 (2H, m), 3.43-3.59 (1H, m), 3.78-3.96 (2H, m), 6.88 (2H, dd, J=2.3 Hz, 8.4 Hz), 7.11 (2H, dd, J=2.3 Hz, 8.4 Hz).

Reference Example 64

Preparation of tert-butyl 3-oxo-4-(4-trifluoromethylbenzyl)piperazine-1-carboxylate Sodium hydride (840 mg, 24.5 mmol) was gradually added to a solution of tert-butyl 3-oxopiperazine-1-carboxylate (4.1 g, 20.4 mmol) in DMF (30 ml) while cooling in an ice-bath, and the mixture was stirred at room temperature for 30 minutes. A solution of 4-trifluoromethylbenzyl chloride (5 g, 20.9 mmol) in DMF (5 ml) was added dropwise to the mixture while cooling in an ice-bath, which was stirred at room temperature for 2 hours. The reaction mixture was poured into ice water, and extracted with ethyl acetate twice. The extract was washed with water twice and brine, and dried over sodium sulfate. After filtration, the filtrate was concentrated under reduced pressure. The residue was purified by silica gel column chromatography (methylene chloride) to afford tert-butyl 3-oxo-4-(4-trifluoromethylbenzyl)piperazine-1-carboxylate (6.7 g, yield 91%) as a colorless crystalline powder.

$^1$H-NMR (CDCl$_3$) δppm: 1.47 (9H, s), 3.27 (2H, t, J=5.7 Hz), 3.62 (2H, t, J=5.7 Hz), 4.18 (2H, s), 4.67 (2H, s), 7.39 (2H, d, J=8.1 Hz), 7.61 (2H, d, J=8.1 Hz).

Reference Example 65

Preparation of 1-(4-trifluoromethylbenzyl)piperazin-2-one

Using tert-butyl 3-oxo-4-(4-trifluoromethylbenzyl)piperazine-1-carboxylate (6.7 g, 18.7 mmol) prepared in Reference Example 64, 1-(4-trifluoromethylbenzyl)piperazin-2-one (4.5 g, yield 93%) as a pale yellow powder was prepared in the same manner as described in Reference Example 63.

$^1$H-NMR (CDCl$_3$) δppm: 3.06 (2H, t, J=5.2 Hz), 3.24 (2H, t, J=5.2 Hz), 3.62 (2H, s), 4.60 (2H, s), 7.39 (2H, d, J=8.1 Hz), 7.59 (2H, d, J=8.1 Hz).

Reference Example 66

Preparation of 4'-trifluoromethoxybiphenyl-4-carbaldehyde

A mixture of 1-bromo-4-(trifluoromethoxy)-benzene (1.53 g, 6.35 mmol), 4-formylbenzeneboronic acid (1 g, 6.67 mmol), tetrakis(triphenylphosphine)-palladium (147 mg, 0.13 mmol), and potassium phosphate (2.02 g, 9.53 mmol) in DMF (10 ml) was stirred at 100° C. for 5 hours. The reaction mixture was poured into water, and extracted with ethyl acetate, and the extract was washed with water three times and brine, and dried over magnesium sulfate. After filtration, the filtrate was concentrated under reduced pressure, and the residue was purified by silica gel column chromatography (n-hexane/methylene chloride=3/1) to afford 4'-trifluoromethoxybiphenyl-4-carbaldehyde (1.56 g, yield 92%) as a white powder.

$^1$H-NMR (CDCl$_3$) δppm: 7.33 (2H, d, J=8.8 Hz), 7.60-7.80 (4H, m), 7.97 (2H, d, J=8.2 Hz), 10.07 (1H, s).

Compounds of Reference Examples 67 to 73 were prepared from corresponding iodobenzene or bromobenzene compounds and formylbenzeneboronic acids in the same manner as described in Reference Example 66.

Reference Example 67

4'-trifluoromethylbiphenyl-4-carbaldehyde a colorless crystalline powder, yield 27% $^1$H-NMR (CDCl$_3$) δppm: 7.68-7.81 (6H, m), 7.99 (2H, dd, J=1.7 Hz, 6.5 Hz), 10.09 (1H, s).

Reference Example 68

4'-trifluoromethylbiphenyl-3-carbaldehyde a yellow oil, yield 83% $^1$H-NMR (CDCl$_3$) δppm: 7.33 (2H, d, J=8.8 Hz), 7.60-7.80 (4H, m), 7.97 (2H, d, J=8.2 Hz), 10.07 (1H, s).

Reference Example 69

4'-dimethylaminobiphenyl-4-carbaldehyde a yellow powder, yield 46% $^1$H-NMR (CDCl$_3$) δppm: 3.03 (6H, s), 6.81 (2H, dd, J=2.1 Hz, 6.8 Hz), 7.58 (2H, dd, J=2.1 Hz, 6.8 Hz), 7.71 (2H, dd, J=1.8 Hz, 6.6 Hz), 7.90 (2H, dd, J=1.8 Hz, 6.6 Hz), 10.00 (1H, s).

Reference Example 70

4'-chlorobiphenyl-4-carbaldehyde a pale yellow crystalline powder, yield 47% $^1$H-NMR (CDCl$_3$) δppm: 7.45 (2H, d, J=8.6 Hz), 7.57 (2H, d, J=8.6 Hz), 7.73 (2H, d, J=8.4 Hz), 7.96 (2H, d, J=8.4 Hz), 10.06 (1H, s).

Reference Example 71

2'-chlorobiphenyl-4-carbaldehyde

A colorless crystalline powder, yield 46% $^1$H-NMR (CDCl$_3$) δppm: 7.30-7.40 (3H, m), 7.38-7.58 (1H, m), 7.63 (2H, d, J=8.1 Hz), 7.96 (2H, d, J=8.1 Hz), 10.08 (1H, s).

Reference Example 72

3',4'-dichlorobiphenyl-4-carbaldehyde

A colorless crystalline powder, yield 24% $^1$H-NMR (CDCl$_3$) δppm: 7.46 (1H, dd, J=2.1 Hz, 8.4 Hz), 7.56 (1H, d, J=8.4 Hz), 7.70-7.80 (3H, m), 7.97 (2H, dd, J=1.8 Hz, 6.6 Hz), 10.07 (1H, s).

Reference Example 73

4'-methoxybiphenyl-4-carbaldehyde

A colorless crystalline powder, yield 45% $^1$H-NMR (CDCl$_3$) δppm: 3.87 (3H, s), 7.01 (2H, d, J=6.8 Hz), 7.59 (2H, d, J=6.8 Hz), 7.72 (2H, d, J=8.3 Hz), 7.93 (2H, d, J=8.3 Hz), 10.04 (1H, s).

Reference Example 74

Preparation of 4-(pyridin-3-yl)benzaldehyde

A mixture of 4-bromobenzaldehyde (2 g, 10.8 mmol), diethyl(3-pyridyl)borane (1.75 g, 11.9 mmol), tetrakis(triphenylphosphine)palladium (375 mg, 0.32 mmol), and 2N sodium carbonate aqueous solution(10.8 ml, 21.6 mmol) in toluene (40 ml) was heated under reflux under a nitrogen atmosphere overnight. The reaction mixture was allowed to return to room temperature and diluted with ethyl acetate. The mixture was washed with water and brine, and dried over sodium sulfate. After filtration, the filtrate was concentrated under reduced pressure, and the residue was purified by silica gel column chromatography (n-hexane/ethyl acetate=1/1) to afford 4-(pyridin-3-yl)benzaldehyde (1.43 g, yield 72%) as a pale yellow crystalline powder.

$^1$H-NMR (CDCl$_3$) δppm: 7.33-7.50 (1H, m), 7.76 (2H, dd, J=1.8 Hz, 6.6 Hz), 7.89-8.06 (3H, m), 8.56-8.69 (1H, m), 8.90 (1H, dd, J=0.7 Hz, 1.7 Hz), 10.09 (1H, s).

Reference Example 75

Preparation of 4-(imidazol-1-yl)benzaldehyde

A mixture of 4-fluorobenzaldehyde (4.96 g, 40 mmol), imidazole (2.86 g, 42 mmol), and potassium carbonate (6.08 g, 44 mmol) in DMSO (40 ml) was stirred at 110° C. overnight. The reaction mixture was allowed to return to room temperature, and poured into ice water (100 ml). The resulting precipitates were collected by filtration and washed with water and then with ethyl acetate to afford 4-(imidazol-1-yl)benzaldehyde (2.33 g, yield 34%) as a pale yellow crystalline powder.

$^1$H-NMR (CDCl$_3$) δppm: 7.20-7.30 (1H, m), 7.38 (1H, dd, J=1.3 Hz, 1.4 Hz), 7.58 (2H, dd, J=1.8 Hz, 6.8 Hz), 7.98-8.10 (3H, m), 10.05 (1H, s).

Using a corresponding starting material, a compound of Reference Example 76 was prepared in the same manner as described in Reference Example 75.

Reference Example 76

4-(piperidin-1-yl)benzaldehyde a yellow crystalline powder, yield 46% $^1$H-NMR (CDCl$_3$) δppm: 1.58-1.75 (6H, m), 3.33-3.50 (4H, m), 6.89 (2H, dd, J=1.9 Hz, 7.0 Hz), 7.73 (2H, dd, J=1.9 Hz, 7.0 Hz), 9.75 (1H, s).

Reference Example 77

Preparation of tert-butyl 4-(4-trifluoromethylphenyl)-piperazine-1-carboxylate

A mixture of 4-bromobenzotrifluoride (3.0 g, 13.3 mmol), tert-butyl piperazine-1-carboxylate (2.9 g, 15.3 mmol), bis(dibenzylideneacetone)palladium (306 mg, 0.53 mmol), tri-o-tolylphosphine (162 mg, 0.53 mmol), and sodium tert-butoxide (2.2 g, 22.7 mmol) in toluene (60 ml) was refluxed under a nitrogen atmosphere for 4 hours. Ethyl acetate and water were added to the reaction mixture, which was stirred for a while, and the insoluble substances were removed by filtration through Celite, and the filtrate was then extracted with ethyl acetate. The extract was washed with brine, dried over magnesium sulfate, and then filtered. The filtrate was concentrated under reduced pressure, and the residue was purified by silica gel column chromatography (n-hexane/methylene chloride=2/1) to afford tert-butyl 4-(4-trifluoromethylphenyl)-piperazine-1-carboxylate (3.8 g, yield 87%) as a white powder.

$^1$H-NMR (CDCl$_3$) δppm: 1.49 (9H, s), 3.21-3.26 (4H, m), 3.56-3.61 (4H, m), 6.90-6.93 (2H, m), 7.47-7.51 (2H, m).

Using corresponding starting materials, compounds of Reference Examples 78 to 84 were prepared in the same manner as described in Reference Example 77.

Reference Example 78 tert-butyl 4-(4-trifluoromethoxyphenyl)piperazine-1-carboxylate a white powder, yield 95% $^1$H-NMR (CDCl$_3$) δppm: 1.48 (9H, s), 3.09-3.13 (4H, m), 3.55-3.60 (4H, m), 6.87-6.91 (2H, m), 7.10-7.14 (2H, m).

Reference Example 79 tert-butyl 4-(4-biphenylyl)piperazine-1-carboxylate a white powder, yield 95% $^1$H-NMR (CDCl$_3$) δppm: 1.49 (9H, s), 3.16-3.21 (4H, m), 3.58-3.62 (4H, m), 6.97-7.01 (2H, m), 7.27-7.32 (1H, m), 7.37-7.44 (2H, m), 7.50-7.58 (4H, m).

Reference Example 80 tert-butyl 4-(4-dimethylaminophenyl)piperazine-1-carboxylate a white powder, yield 79% $^1$H-NMR (CDCl$_3$) δppm: 1.48 (9H, s), 2.87 (6H, s), 2.96-3.00 (4H, m), 3.54-3.59 (4H, m), 6.72-6.77 (2H, m), 6.87-6.92 (2H, m).

Reference Example 81 tert-butyl 4-(3-pyridyl)piperazine-1-carboxylate a white powder, yield 99% $^1$H-NMR (CDCl$_3$) δppm: 1.49 (9H, s), 3.14-3.19 (4H, m), 3.57-3.62 (4H, m), 7.17-7.19 (2H, m), 8.12-8.14 (1H, m), 8.31-8.33 (1H, m).

Reference Example 82 tert-butyl 4-(4-ethoxycarbonylphenyl)piperazine-1-carboxylate a white powder, yield 42% $^1$H-NMR (CDCl$_3$) δppm: 1.37 (3H, t, J=7.1 Hz), 1.48 (9H, s), 3.27-3.32 (4H, m), 3.56-3.60 (4H, m), 4.33 (2H, q, J=7.1 Hz), 6.84-6.88 (2H, m), 7.92-7.96 (2H, m).

Reference Example 83 tert-butyl 4-(4-methylphenyl)piperazine-1-carboxylate a white powder, yield 55% $^1$H-NMR (CDCl$_3$) δppm: 1.48 (9H, s), 2.27 (3H, s), 3.04-3.09 (4H, m), 3.55-3.59 (4H, m), 6.82-6.87 (2H, m), 7.06-7.10 (2H, m).

Reference Example 84 tert-butyl 4-(4-cyanophenyl)piperazine-1-carboxylate a white powder, yield 86% $^1$H-NMR (CDCl$_3$) δppm: 1.49 (9H, s), 3.28-3.33 (4H, m), 3.56-3.60 (4H, m), 6.83-6.87 (2H, m), 7.49-7.53 (2H, m).

Reference Example 85

Preparation of 1-(4-trifluoromethylphenyl)piperazine

Tert-butyl 4-(4-trifluoromethylphenyl)-piperazine-1-carboxylate (3.8 g, 11.5 mmol) prepared in Reference Example 77 was dissolved in methylene chloride (40 ml), to which trifluoroacetic acid (10 ml) was added dropwise, and the mixture was stirred at room temperature overnight. The reaction mixture was concentrated under reduced pressure, and the residue was neutralized with saturated sodium hydrogencarbonate aqueous solution and the mixture was extracted with methylene chloride. The extract was dried over magnesium sulfate, and then filtered. The filtrate was concentrated under reduced pressure to afford 1-(4-trifluoromethylphenyl)piperazine (2.5 g, yield 96%) as a white powder.

$^1$H-NMR (CDCl$_3$) δppm: 3.01-3.06 (4H, m), 3.21-3.26 (4H, m), 6.92 (2H, d, J=8.6 Hz), 7.48 (2H, d, J=8.6 Hz).

Using corresponding starting materials, compounds of Reference Examples 86 to 89 were prepared in the same manner as described in Reference Example 85.

Reference Example 86

1-(4-trifluoromethoxyphenyl)piperazine a white powder, yield 100% $^1$H-NMR (CDCl$_3$) δppm: 1.61 (1H, s), 3.00-3.05 (4H, m), 3.10-3.15 (4H, m), 6.85-6.92 (2H, m), 7.08-7.13 (2H, m).

Reference Example 87

1-(4-dimethylaminophenyl)piperazine a white powder, yield 99% $^1$H-NMR (CDCl$_3$) δppm: 1.60 (1H, br), 2.86 (6H, s), 3.01 (8H, br), 6.71-6.78 (2H, m), 6.87-6.92 (2H, m).

Reference Example 88

1-(3-pyridyl)piperazine a white powder, yield 100% $^1$H-NMR (CDCl$_3$) δppm: 2.09 (1H, s), 3.03-3.09 (4H, m), 3.14-3.20 (4H, m), 7.16-7.18 (2H, m), 8.09-8.11 (1H, m), 8.31 (1H, s).

Reference Example 89

1-(4-ethoxycarbonylphenyl)piperazine a white powder, yield 95% $^1$H-NMR (CDCl$_3$) δppm: 1.37 (3H, t, J=7.1 Hz), 1.84 (1H, s), 3.00-3.04. (4H, m), 3.26-3.31 (4H, m), 4.33 (2H, q, J=7.1 Hz), 6.83-6.89 (2H, m), 7.89-7.96 (2H, m).

Reference Example 90

Preparation of tert-butyl 4-(piperazin-1-yl)benzoate

A mixture of tert-butyl 4-bromobenzoate (4.8 g, 18.8 mmol), piperazine (9.7 g, 0.11 mol), palladium acetate (85 mg, 0.38 mmol), (S)-(–)-BINAP (352 mg, 0.57 mmol), and sodium tert-butoxide (2.7 g, 28.2 mmol) in toluene (50 ml) was refluxed under a nitrogen atmosphere for 2 hours. Ethyl acetate and water were added to the reaction mixture and the insoluble substances were removed by filtration though Celite, and the filtrate was extracted with ethyl acetate. The extract was washed with brine, dried over magnesium sulfate, and then filtered. The filtrate was concentrated under reduced pressure, and the residue was purified by silica gel column chromatography (methylene chloride/methanol=5/1) to afford tert-butyl 4-(piperazin-1-yl)benzoate (3.8 g, yield 77%) as a gray powder.

$^1$H-NMR (CDCl$_3$) δppm: 1.57 (9H, s), 3.00-3.04 (4H, m), 3.24-3.29 (4H, m), 6.83-6.87 (2H, m), 7.85-7.89 (2H, m).

Reference Example 91

Preparation of 4-trifluoromethoxybenzyl piperazine-1-carboxylate

To a solution of 4-trifluoromethoxybenzyl alcohol (25 g, 130.11 mmol) and phenyl chloroformate (20.37 g, 130.11 mmol) in ethyl acetate (125 ml), a solution of pyridine (11.6 ml, 143.12 mmol) in ethyl acetate (50 ml) was added dropwise below 15° C. over 35 minutes. The mixture was stirred for 30 minutes. The reaction mixture was washed with water, 3 N hydrochloric acid, 10% potassium carbonate aqueous solution and brine, and dried over sodium sulfate. After filtration, the filtrate was concentrated under reduced pressure to afford a carbonate compound as a colorless oil. To a solution of piperazine (33.62 g, 390.34 mmol) in methanol (125 ml), a solution of the carbonate compound in ethyl acetate (50 ml) was added dropwise below 10° C. over 25 minutes. The resulting mixture was stirred for 1 hour. The reaction mixture was concentrated under reduced pressure, and the residue was purified by silica gel column chromatography (methylene chloride/methanol=10/1) to afford 4-trifluoromethoxybenzyl piperazine-1-carboxylate (35.33 g, yield 89%) as a colorless oil.

$^1$H-NMR (CDCl$_3$) δppm: 2.57-2.96 (4H, m), 3.42-3.63 (4H, m), 5.13 (2H, s), 7.21 (2H, d, J=8.5 Hz), 7.39 (2H, d, J=8.5 Hz).

Reference Example 92

Preparation of 3-(4-trifluoromethylphenyl)-2-propenyl piperazine-1-carboxylate

A solution of pyridine (0.5 ml, 6.18 mmol) in ethyl acetate (2 ml) was gradually added dropwise to a solution of 3-(4-trifluoromethylphenyl)-2-propen-1-ol (1 g, 4.95 mmol) and phenyl chloroformate (0.72 ml, 5.69 mmol) in ethyl acetate (5 ml) while cooling in an ice-bath. The mixture was stirred at room temperature for 1 hour. The reaction mixture was washed with water, 3 N hydrochloric acid, 10% potassium carbonate aqueous solution and brine in this order, and dried over sodium sulfate. After filtration, the filtrate was concentrated under reduced pressure to afford a carbonate compound as a colorless oil. To a solution of piperazine (1.28 g, 14.84 mmol) in methanol (5 ml), a solution of the carbonate compound in ethyl acetate (5 ml) was gradually added dropwise while cooling in an ice-bath. The mixture was stirred at room temperature for 2.5 hours. The reaction mixture was concentrated under reduced pressure, and the residue was purified by silica gel column chromatography (methylene chloride/methanol=10/1) to afford 3-(4-trifluoromethylphenyl)-2-propenyl piperazine-1-carboxylate (1.4 g, yield 90%) as a colorless oil.

$^1$H-NMR (CDCl$_3$) δppm: 2.75-2.95 (4H, m), 3.43-3.57 (4H, m), 4.78 (2H, dd, J=1.2 Hz, 6.0 Hz), 6.33-6.43 (1H, m), 6.66 (1H, d, 16.0 Hz), 7.48 (2H, d, J=8.4 Hz), 7.57 (2H, d, J=8.4 Hz).

Using a corresponding starting material, a compound of Reference Example 93 was prepared in the same manner as described in Reference Example 92.

Reference Example 93

3-(4-Trifluoromethoxyphenyl)-2-propenyl piperazine-1-carboxylate a colorless oil, yield 90% $^1$H-NMR (CDCl$_3$) δppm: 2.75-2.88 (4H, m), 3.44-3.52 (4H, m), 4.75 (2H, dd, J=1.3 Hz, 6.2 Hz); 6.29 (1H, dt, J=6.2 Hz, 15.9 Hz), 6.62 (1H, d, J=15.9 Hz), 7.15-7.18 (2H, m), 7.38-7.42 (2H, m).

Reference Example 94

Preparation of 4-(4-chlorophenyl)-1,2,3,6-tetrahydropyridine-1-carbonylchloride

A mixture of 4-(4-chlorophenyl)-1,2,3,6-tetrahydropyridine hydrochloride (1 g, 4.3 mmol), pyridine (680 mg, 8.6 mmol), and triphosgene (430 mg, 1.45 mmol) in toluene (20 ml) was heated under reflux for 3 hours. The reaction mixture was allowed to return to room temperature and diluted with diethyl ether. The mixture was washed with 10% hydrochloric acid, water and brine in this order, and dried over magnesium sulfate. After filtration, the filtrate was concentrated under reduced pressure to afford 4-(4-chlorophenyl)-1,2,3,6-tetrahydropyridine-1-carbonylchloride (1 g, yield 90%) as a yellow oil.

$^1$H-NMR (CDCl$_3$) δppm: 2.51-2.72 (2H, m), 3.81-4.00 (2H, m), 4.26-4.40 (2H, m), 5.93-6.09 (1H, m), 7.16-7.35 (4H, m).

Reference Example 95

Preparation of 1-benzyl-4-(4-trifluoromethylphenyl)piperidin-4-ol

4-Bromobenzotrifluoride (1 g, 4.44 mmol) was dissolved in THF (15 ml), to which n-butyllithium (1.5 M) hexane solution (3.1 ml, 4.67 mmol) was added dropwise at −70° C. Then a solution of 1-benzyl-4-piperidone in THF (15 ml) was added dropwise to the mixture, and the resulting mixture was stirred for 2 hours and then at room temperature for 2 hours. The reaction mixture was diluted with ethyl acetate, washed with water and brine, and dried over sodium sulfate. After filtration, the filtrate was concentrated under reduced pressure. The residue was purified by silica gel column chromatography (n-hexane/acetone=2/1) to afford 1-benzyl-4-(4-trifluoromethylphenyl)piperidin-4-ol (692 mg, yield 46%) as a colorless crystalline powder.

$^1$H-NMR (CDCl$_3$) δppm: 1.60-1.78 (2H, m), 2.07-2.25 (2H, m), 2.38-2.54 (2H, m), 2.74-2.87 (2H, m), 3.59 (2H, s), 7.20-7.38 (5H, m), 7.51-7.67 (4H, m).

Reference Example 96

Preparation of 1-benzyl-4-(4-trifluoromethylphenyl)-1,2,3,6-tetrahydropyridine

A mixture of 1-benzyl-4-(4-trifluoromethylphenyl)piperidin-4-ol (692 mg, 2.06 mmol) prepared in Reference Example 95, concentrated hydrochloric acid (4.5 ml) and acetic acid (10 ml) was heated under reflux overnight. The reaction mixture was allowed to return to room temperature, and diluted with methylene chloride. The mixture was washed with water, 10% sodium hydroxide aqueous solution and brine, and dried over sodium sulfate. After filtration, the filtrate was concentrated under reduced pressure. The residue was purified by silica gel column chromatography (n-hexane/acetone=4/1) to afford 1-benzyl-4-(4-trifluoromethylphenyl)-1,2,3,6-tetrahydropyridine (528 mg, yield 80%) as a pale yellow crystalline powder.

$^1$H-NMR (CDCl$_3$) δppm: 2.50-2.60 (2H, m), 2.62-2.76 (2H, m), 3.11-3.22 (2H, m), 3.65 (2H, s), 6.10-6.20 (1H, m), 7.20-7.54 (9H, m).

Reference Example 97

Preparation of 4-(4-trifluoromethylphenyl)-1,2,3,6-tetrahydropyridine hydrochloride 1-Benzyl-4-(4-trifluoromethylphenyl)-1,2,3,6-tetrahydropyridine (2 g, 6.3 mmol) prepared in Reference Example 96 was dissolved in methylene chloride (20 ml), to which 2-chloroethyl chloroformate (1.67 g, 11.68 mmol) was added dropwise under a nitrogen atmosphere while cooling in an ice-bath, and the mixture was stirred at the same temperature for 3 hours. Methanol (20 ml) was added to the mixture, which was heated under reflux for 1 hour. The reaction mixture was allowed to return to room temperature, to which diethyl ether was added, and the resulting precipitates were collected by filtration to afford 4-(4-trifluoromethylphenyl)-1,2,3,6-tetrahydropyridine hydrochloride (1.44 g, yield 87%) as a colorless crystalline powder.

$^1$H-NMR (DMSO-d$_6$) δppm: 2.64-2.80 (2H, m), 3.18-3.34 (2H, m), 3.68-3.80 (2H, m), 6.25-6.39 (1H, m), 7.61-7.80 (4H, m).

Reference Example 98

Preparation of 4-(4-trifluoromethylphenyl)-1,2,3,6-tetrahydropyridine-1-carbonylchloride Using 4-(4-trifluoromethylphenyl)-1,2,3,6-tetrahydropyridine hydrochloride (300 mg, 1.14 mmol) prepared in Reference Example 97, pyridine (0.18 ml, 2.28 mmol) and triphosgene (112 mg, 0.38 mmol), 4-(4-trifluoromethylphenyl)-1,2,3,6-tetrahydropyridine-1-carbonylchloride (220 mg, yield 67%) as a yellow oil was prepared in the same manner as described in Reference Example 94.

$^1$H-NMR (CDCl$_3$) δppm: 2.57-2.75 (2H, m), 3.82-4.00 (2H, m), 4.25-4.40 (2H, m), 6.05-6.16 (1H, m), 7.47 (2H, d, J=8.2 Hz), 7.59 (2H, d, J=8.2 Hz).

Reference Example 99

Preparation of 4-(4-chlorophenyl)piperidine hydrochloride

A mixture of 4-(4-chlorophenyl)-1,2,3,6-tetrahydropyridine hydrochloride (2 g, 8.7 mmol) and platinum oxide (100 mg) in ethanol (100 ml) was stirred at room temperature under an atmospheric pressure of hydrogen. The reaction mixture was filtered through Celite, and the filtrate was concentrated under reduced pressure. The resulting precipitates by treating the residue with diethyl ether were collected by filtration to afford 4-(4-chlorophenyl)piperidine hydrochloride (1.9 g, yield 94%) as a pale gray powder.

$^1$H-NMR (DMSO-d$_6$) δppm: 1.75-1.95 (4H, m), 2.74-3.05 (3H, m), 3.25-3.44 (2H, m), 7.25 (2H, d, J=8.5 Hz), 7.38 (2H, d, J=8.5 Hz).

Reference Example 100

Preparation of 4-(4-trifluoromethylphenyl)piperidine

A mixture of 1-benzyl-4-(4-trifluoromethylphenyl)-1,2,3,6-tetrahydropyridine (528 mg, 1.66 mmol) prepared in Reference Example 96 and 10% palladium/carbon (50 mg) in acetic acid (5 ml) was stirred at room temperature under an atmospheric pressure of hydrogen. The reaction mixture was filtered through Celite, and the filtrate was concentrated under reduced pressure. The residue was dissolved in methylene chloride, and the mixture was washed with water, 10% sodium hydroxide aqueous solution and brine, and dried over sodium sulfate. After filtration, the filtrate was concentrated under reduced pressure to afford 4-(4-trifluoromethylphenyl)piperidine (400 mg, quantitative) as a yellow oil.

$^1$H-NMR (CDCl$_3$) δppm: 1.72-2.00 (4H, m), 2.61-2.84 (3H, m), 3.07-3.27 (2H, m), 7.32 (2H, d, J=8.2 Hz), 7.56 (2H, d, J=8.2 Hz).

Reference Example 101

Preparation of 4-(4-trifluoromethylphenyl)piperidine-1-carbonylchloride

Using 4-(4-trifluoromethylphenyl)piperidine (760 mg, 3.32 mmol) prepared in Reference Example 100, 4-(4-trifluoromethylphenyl)piperidine-1-carbonylchloride (crude product) a pale brown oil was prepared in the same manner as described in Reference Example 94.

$^1$H-NMR (CDCl$_3$) δppm: 1.65-1.84 (2H, m), 1.86-2.02 (2H, m), 2.77-3.28 (3H, m), 4.42-4.60 (2H, m), 7.32 (2H, d, J=8.1 Hz), 7.59 (2H, d, J=8.1 Hz).

Reference Example 102

Preparation of 2-[3-(4-trifluoromethylphenyl)-2-propenyl]phthalimide 4-(Trifluoromethyl)cinnamyl alcohol (3 g, 14.84 mmol) was dissolved in THF (60 ml), and phthalimide (2.84 g, 19.29 mmol) and triphenylphosphine (5.84 g, 22.26 mmol) were added to the solution, to which a solution of diethyl azodicarboxylate (3.87 g, 22.26 mmol) in THF (20 ml) was gradually added dropwise. The mixture was stirred at room temperature for 3 hours. The reaction mixture was concentrated under reduced pressure, and the residue was purified by silica gel column chromatography (n-hexane/methylene chloride=1/1) to afford 2-[3-(4-trifluoromethylphenyl)-2-propenyl]phthalimide (4.57 g, yield 93%) as a white powder.

$^1$H-NMR (CDCl$_3$) δppm: 4.47 (2H, dd, J=1.2 Hz, 6.3 Hz), 6.27-6.41 (1H, m), 6.68 (1H, d, J=15.9 Hz), 7.44 (2H, d, J=8.4 Hz), 7.54 (2H, d, J=8.4 Hz), 7.74 (2H, dd, J=2.0 Hz, 7.0 Hz), 7.85 (2H, dd, J=2.0 Hz, 7.0 Hz).

Reference Example 103

Preparation of 3-(4-trifluoromethylphenyl)-2-propenylamine

A mixture of 2-[3-(4-trifluoromethylphenyl)-2-propenyl]phthalimide (4.57 g, 13.79 mmol) prepared in Reference Example 102 and hydrazine hydrate (897 mg, 17.93 mmol)

in ethanol (80 ml) was heated under reflux for 3 hours. The reaction mixture was allowed to return to room temperature and filtered, and the filtrate was concentrated under reduced pressure. To the residue, ethyl acetate was added, and the resulting mixture was washed with 1 N sodium hydroxide aqueous solution and brine, and dried over magnesium sulfate. After filtration, the filtrate was concentrated under reduced pressure to afford 3-(4-trifluoromethylphenyl)-2-propenylamine (2.78 g, quantitative) as a pale brown crystalline powder.

$^1$H-NMR (CDCl$_3$) δppm: 3.51 (2H, d, J=4.7 Hz), 6.31-6.47 (1H, m), 6.55 (1H, d, J=16.0 Hz), 7.45 (2H, d, J=8.3 Hz), 7.55 (2H, d, J=8.3 Hz).

Reference Example 104

Preparation of piperazin-1-yl-(5-chlorobenzofuran-2-yl methylene)amine

1-Aminopiperazine (29 g, 287 mmol) was dissolved in isopropyl alcohol (173 ml), to which 5-chlorobenzofuran-2-aldehyde (34.52 g, 191 mmol) was added, and the mixture was stirred at room temperature for 16 hours. The reaction mixture was concentrated under reduced pressure, and the residue was purified by silica gel column chromatography to afford piperazin-1-yl-(5-chlorobenzofuran-2-yl methylene)amine (49.49 g, yield 98%) as a yellow crystalline powder.

$^1$H-NMR (CDCl$_3$) δppm: 2.95-3.10 (4H, m), 3.17-3.29 (4H, m), 6.70 (1H, s), 7.20 (1H, dd, J=2.1 Hz, 8.7 Hz), 7.38-7.52 (3H, m).

Reference Example 105

Preparation of piperazin-1-yl-(4-trifluoromethyl benzylidene)amine

Tert-butyl piperazin-1-yl-carbamate (403 mg, 2.0 mmol) was suspended in methylene chloride (4 ml), to which trifluoroacetic acid (1.6 ml) was added, and the mixture was stirred at room temperature for 5 minutes. To which 4-(trifluoromethyl)benzaldehyde (0.3 ml, 2.2 mmol) was added, and the resulting mixture was stirred at room temperature for 1 hour. The reaction mixture was poured into sodium hydrogencarbonate aqueous solution, and extracted with ethyl acetate. The extract was washed with brine, dried over sodium sulfate, and then concentrated under reduced pressure. The residue was purified by silica gel column chromatography (methylene chloride/methanol=9/1) to afford piperazin-1-yl-(4-trifluoromethylbenzylidene)-amine (432 mg, yield 84%) as a colorless crystalline powder.

$^1$H-NMR (CDCl$_3$) δppm: 3.00-3.29 (8H, m), 7.43-7.62 (3H, m), 7.68 (2H, d, J=8.2 Hz).

Reference Example 106

Preparation of piperazin-1-yl-(4-trifluoromethoxy benzylidene)amine

To a solution of 4-benzylpiperazin-1-yl-amine (43.18 g, 225 mmol) in etanol (400 ml), a suspension of 20% palladium hydroxide/carbon (6.50 g) in etanol (30 ml) was added, and the mixture was stirred at room temperature under an atmospheric pressure of hydrogen for 3 hours and then at 50° C. for 2 hours. The reaction mixture was filtered through Celite, 4-(trifluoromethoxy)benzaldehyde (42.92 g, 225 mmol) was added to the filtrate, and the mixture was stirred at room temperature for 1.5 hours. The reaction mixture was concentrated under reduced pressure, and the residue was purified by silica gel column chromatography (methylene chloride/methanol=10/1) to afford piperazin-1-yl-(4-trifluoromethoxybenzylidene)amine (56.88 g, yield 93%) as a pale yellow crystalline powder.

$^1$H-NMR (CDCl$_3$) δppm: 3.00-3.23 (8H, m), 7.18 (2H, d, J=8.7 Hz), 7.58 (1H, s), 7.62 (2H, d, J=8.7 Hz).

Using a corresponding starting material, a compound of Reference Example 107 was prepared in the same manner as described in Reference Example 106.

Reference Example 107 piperazin-1-yl-(5-trifluoromethylbenzofuran-2-yl methylene)amine a pale yellow crystalline powder, yield 77% $^1$H-NMR (CDCl$_3$) δppm: 3.00-3.14 (4H, m), 3.23-3.32 (4H, m), 6.79 (1H, s), 7.41-7.59 (3H, m), 7.82 (1H, s).

Reference Example 108

Preparation of (4-benzylpiperazin-1-yl)-(4-trifluoromethylphenyl)amine

A mixture of 4-bromobenzotrifluoride (3.00 g, 13.3 mmol), 4-benzylpiperazin-1-yl-amine (3.06 g, 16.0 mmol), palladium acetate (60 mg, 0.267 mmol), (S)-(−)-BINAP (174 mg, 0.280 mmol) and sodium tert-butoxide (1.92 g, 20.0 mmol) in toluene (60 ml) was refluxed under a nitrogen atmosphere for 7 hours. Water was added to the reaction mixture, and the mixture was extracted with ethyl acetate. The extract was washed with brine, dried over sodium sulfate, and then filtered. The filtrate was concentrated under reduced pressure, and the residue was then purified by silica gel column chromatography (n-hexane/acetone=4/1) to afford (4-benzylpiperazin-1-yl)-(4-trifluoromethylphenyl) amine (2.666 g, yield 59%) as a pale yellow oil.

$^1$H-NMR (CDCl$_3$) δppm: 2.58 (4H, br), 2.76 (4H, br), 3.55 (2H, s), 4.65 (1H, br), 6.90 (2H, d, J=8.6 Hz), 7.23-7.35 (5H, m), 7.41 (2H, d, J=8.6 Hz).

Reference Example 109

Preparation of piperazin-1-yl-(4-trifluoromethylphenyl)amine

A mixture of (4-benzylpiperazin-1-yl)-(4-trifluoromethylphenyl)amine prepared in Reference Example 108 and 10% palladium/carbon (0.53 g) in ethanol (50 ml) was stirred at room temperature under an atmospheric pressure of hydrogen for 6 hours, and then at 60° C. for 10 hours. After the catalyst was removed by filtration through Celite, 10% palladium/carbon (0.53 g) was added to the filtrate, and the mixture was stirred at 60° C. under an atmospheric pressure of hydrogen for 8 hours. After the catalyst was removed by filtration through Celite, the filtrate was concentrated under reduced pressure. The resulting solid was dried in vacuo to afford piperazin-1-yl-(4-trifluoromethylphenyl)amine (1.76 g, yield 90%) as a colorless crystalline powder.

$^1$H-NMR (CDCl$_3$) δppm: 2.71 (4H, br), 3.00 (4H, t, J=4.8 Hz), 4.71 (1H, br), 6.92 (2H, d, J=8.5 Hz), 7.42 (2H, d, J=8.5 Hz).

Reference Example 110

Preparation of tert-butyl 4-(3-phenyl-2-propenyloxy)-piperidine-1-carboxylate

Tert-butyl 4-hydroxypiperidine-1-carboxylate (0.396 g, 1.97 mmol) was dissolved in DMF (5 ml), to which sodium hydride (0.086 g, 2.16 mmol) was added, and the mixture was stirred at room temperature for 1 hour. Cinnamyl chloride (0.300 g, 1.97 mmol) was added to the mixture while cooling in an ice-bath, and the resulting mixture was stirred overnight. The reaction mixture was diluted with ethyl acetate, and the mixture was washed with water and brine. The organic layer was dried over magnesium sulfate, and then filtered, and the filtrate was concentrated under reduced pressure. The residue was purified by silica gel column chromatography (n-hexane/ethyl acetate=6/1) to afford tert-butyl 4-(3-phenyl-2-propenyloxy)piperidine-1-carboxylate (0.314 g, yield 50%) as a yellow oil.
$^1$H-NMR (CDCl$_3$) δppm: 1.46 (9H, s), 1.48-1.59 (2H, m), 1.81-1.93 (2H, m), 3.01-3.15 (2H, m), 3.50-3.61 (1H, m), 3.74-3.87 (2H, m), 4.19 (2H, d, J=5.9 Hz), 6.29 (1H, ddd, J=5.9 Hz, 5.9 Hz, 15.9 Hz), 6.61 (1H, d, J=15.9 Hz), 7.18-7.43 (5H, m).

Reference Example 111

Preparation of 4-(3-phenyl-2-propenyloxy)piperidine

Tert-butyl 4-(3-phenyl-2-propenyloxy)-piperidine-1-carboxylate (0.314 g, 0.989 mmol) prepared in Reference Example 110 was dissolved in ethanol (10 ml), to which 6N hydrochloric acid aqueous solution (3 ml, 18 mmol) was added, and the mixture was stirred at 60° C. for 1 hour. The reaction mixture was neutralized with sodium hydroxide aqueous solution, and the mixture was extracted with methylene chloride. The extract was washed with brine, dried over sodium sulfate, and then filtered. The filtrate was concentrated under reduced pressure, and the residue was dried in vacuo to afford 4-(3-phenyl-2-propenyloxy)piperidine (0.198 g, yield 92%) as a yellow oil.
$^1$H-NMR (CDCl$_3$) δppm: 1.40-1.57 (2H, m), 1.91-2.02 (2H, m), 2.56-2.70 (2H, m), 3.12 (2H, ddd, J=4.2 Hz, 4.2 Hz, 12.8 Hz), 3.42-3.52 (1H, m), 4.19 (2H, d, J=5.9 Hz), 6.30 (1H, ddd, J=5.9 Hz, 5.9 Hz, 15.9 Hz), 6.57 (1H, d, J=15.9 Hz), 7.20-7.43 (5H, m).

Reference Example 112

Preparation of tert-butyl 4-[3-(4-chlorophenyl)-2-propenyloxy]piperidine-1-carboxylate Tert-butyl 4-hydroxypiperidine-1-carboxylate (3.58 g, 17.8 mmol) was dissolved in DMF (30 ml), to which sodium hydride (0.71 g, 17.8 mmol) was added, and the mixture was stirred at room temperature for 2 hours.
On the other hand, 4-chlorocinnamyl alcohol (3.00 g, 17.8 mmol) was dissolved in methylene chloride (60 ml), to which triethyl amine (5 ml, 35.6 mmol) and methanesulfonyl chloride (2.1 ml, 26.7 mmol) were added dropwise while cooling in an ice-bath, the mixture was stirred at room temperature for 1.5 hours. Water was added to the mixture, which was extracted with methylene chloride, and the extract was washed with dilute hydrochloric acid solution, sodium bicarbonate aqueous solution and brine. The organic layer was dried over magnesium sulfate, and then filtered, and the filtrate was concentrated under reduced pressure. The residue was dissolved in DMF (10 ml).
Both the DMF solutions were combined while cooling in an ice-bath, and the mixture was stirred overnight. After the reaction mixture was diluted with ethyl acetate, the mixture was washed with water and brine. The organic layer was dried over sodium sulfate, and then filtered, and the filtrate was concentrated under reduced pressure. The residue was purified by silica gel column chromatography (n-hexane/ethyl acetate=6/1) to afford tert-butyl 4-[3-(4-chlorophenyl)-2-propenyloxy]piperidine-1-carboxylate (0.759 g, yield 12%) as a yellow oil.
$^1$H-NMR (CDCl$_3$) δppm: 1.46 (9H, s), 1.50-1.62 (2H, m), 1.83-1.94 (2H, m), 3.03-3.14 (2H, m), 3.53-3.58 (1H, m), 3.77-3.83 (2H, m), 4.17 (1H, d, J=5.7 Hz), 4.18 (1H, d, J=5.7 Hz), 6.27 (1H, ddd, J=5.7 Hz, 5.7 Hz, 15.9 Hz), 6.57 (1H, d, J=15.9 Hz), 7.20-7.33 (4H, m).

Reference Example 113

Preparation of 4-[3-(4-chlorophenyl)-2-propenyloxy]-piperidine

Using tert-butyl 4-[3-(4-chlorophenyl)-2-propenyloxy]piperidine-1-carboxylate (0.350 g, 0.995 mmol) prepared in Reference Example 112, 4-[3-(4-chlorophenyl)-2-propenyloxy]piperidine (0.291 g, quantitative) as a brown oil was prepared in the same manner as described in Reference Example 111.
$^1$H-NMR (CDCl$_3$) δppm: 1.38-1.56 (2H, m), 1.91-2.01 (2H, m), 2.55-2.69 (2H, m), 3.11 (2H, ddd, J=4.0 Hz, 4.0 Hz, 13.0 Hz), 3.39-3.51 (1H, m), 4.18 (2H, d, J=5.8 Hz), 6.28 (1H, ddd, J=5.8 Hz, 5.8 Hz, 15.9 Hz), 6.57 (1H, d, J=15.9 Hz), 7.25-7.35 (4H, m).

Reference Example 114

Preparation of tert-butyl 4-[3-(4-chlorophenyl)propoxy]piperidine-1-carboxylate

A mixture of tert-butyl 4-[3-(4-chlorophenyl)-2-propenyloxy]piperidine-1-carboxylate (0.37 g, 1.05 mmol) prepared in Reference example 112 and platinum oxide (37 mg) in ethanol (10 ml), was stirred at room temperature under atmospheric pressure of hydrogen. The reaction mixture was filtered through Celite, and the filtrate was concentrated under a reduced pressure. The residue was purified by silica gel column chromatography (n-hexane/ethyl acetate=4/1) to afford tert-butyl 4-[3-(4-chlorophenyl)propoxy]piperidine-1-carboxylate (0.151 g, yield 40%) as a yellow oil.
$^1$H-NMR (CDCl$_3$) δppm: 1.40-1.51 (2H, m), 1.46 (9H, s), 1.77-1.90 (4H, m), 2.67 (2H, t, J=7.9 Hz), 3.02-3.12 (2H, m), 3.38-3.45 (3H, m), 3.73-3.79 (2H, m), 7.11 (2H, d, J=8.4 Hz), 7.24 (1H, d, J=8.4 Hz).

Reference Example 115

Preparation of 4-[3-(4-chlorophenyl)propoxy]piperidine

Tert-butyl 4-[3-(4-chlorophenyl)propoxy]-piperidine-1-carboxylate (0.151 g, 0.427 mmol) prepared in Reference example 114 was dissolved in methylene chloride (4 ml), to which trifluoroacetic acid was added, and the mixture was stirred at room temperature overnight. The reaction mixture was neutralized with sodium hydroxide aqueous solution, and the mixture was extracted with methylene chloride twice. The extracts were combined and washed with brine. The organic layer was dried over sodium sulfate, and then filtered. The filtrate was concentrated under reduced pressure, and the residue was dried in vacuo to afford 4-[3-(4-chlorophenyl)propoxy]piperidine (0.109 g, yield 92%) as a brown oil.

$^1$H-NMR (CDCl$_3$) δppm: 1.35-1.51 (2H, m), 1.83-1.94 (4H, m), 2.54-2.70 (4H, m), 3.03-3.14 (2H, m), 3.22-3.38 (1H, m), 3.43 (2H, t, J=6.3 Hz), 7.12 (2H, d, J=8.4 Hz), 7.25 (2H, d, J=8.4 Hz).

Reference Example 116

Preparation of tert-butyl 4-[2-(4-chlorophenyl)ethoxy]piperidine-1-carboxylate (4-Chlorobenzyl)triphenyl phosphonium chloride (1.191 g, 2.81 mmol) was dissolved in DMSO (20 ml), to which sodium hydride (0.118 g, 2.95 mmol) was added while cooling in an ice-bath, and the mixture was stirred at room temperature for 1 hour. Tert-butyl 4-formyloxypiperidine-1-carboxylate (0.500 g, 2.34 mmol) was added to the mixture, and the resulting mixture was stirred at room temperature overnight. After the reaction mixture was diluted with ethyl acetate, the mixture was washed with water and brine. The organic layer was dried over sodium sulfate, and then filtered, and the filtrate was concentrated under reduced pressure. The residue was purified by silica gel column chromatography (methylene chloride/hexane=9/1) to afford a colorless oil.

Using thus obtained oil, tert-butyl 4-[2-(4-chlorophenyl)ethoxy]piperidine-1-carboxylate (0.127 g, yield 16%) as a colorless oil was prepared in the same manner as described in Reference Example 114.

$^1$H-NMR (CDCl$_3$) δppm: 1.40-1.51 (2H, m), 1.45 (9H, s), 1.71-1.79 (2H, m), 2.83 (2H, t, J=6.9 Hz), 3.02-3.13 (2H, m), 3.38-3.44 (1H, m), 3.62-3.75 (4H, m), 7.15 (2H, d, J=8.5 Hz), 7.25 (2H, d, J=8.5 Hz).

Reference Example 117

Preparation of 4-[2-(4-chlorophenyl)ethoxy]piperidine

Using tert-butyl 4-[2-(4-chlorophenyl)ethoxy]piperidine-1-carboxylate (0.127 g, 0.374 mmol) prepared in Reference Example 116, 4-[2-(4-chlorophenyl)ethoxy]piperidine (0.080 g, yield 89%) as a colorless oil was prepared in the same manner as described in Reference Example 115.

$^1$H-NMR (CDCl$_3$) δppm: 1.37-1.48 (2H, m), 1.84-1.91 (2H, m), 2.53-2.63 (2H, m), 2.83 (2H, t, J=7.0 Hz), 3.01-3.09 (2H, m), 3.25-3.41 (1H, m), 3.64 (2H, t, J=7.0 Hz), 7.15 (2H, d, J=8.4 Hz), 7.25 (2H, d, J=8.4 Hz).

Reference Example 118

Preparation of 1-(2-nitrovinyl)-4-trifluoromethylbenzene

4-Trifluoromethylbenzaldehyde (3.00 g, 17.2 mmol) was dissolved in nitromethane (10 ml), to which ammonium acetate (1.341 g, 17.4 mmol) was added, and the mixture was heated under reflux for 2 hours. Water was added to the mixture, which was extracted with methylene chloride twice, and the extracts were combined and washed with brine, and dried over magnesium sulfate, and then filtered. The filtrate was concentrated under reduced pressure. The residue was purified by silica gel column chromatography (n-hexane/ethyl acetate=9/1) to afford 1-(2-nitrovinyl)-4-trifluoromethylbenzene (1.596 g, yield 43%) as a pale yellow crystalline powder.

$^1$H-NMR (CDCl$_3$) δppm: 7.58-7.74 (5H, m), 8.02 (1H, d, J=13.8 Hz).

Reference Example 119

Preparation of 2-(4-trifluoromethylphenyl)ethylamine

Lithium aluminum hydride (0.558 g, 14.7 mmol) was suspended in THF (10 ml), to which a solution of 1-(2-nitrovinyl)-4-trifluoromethylbenzene (1.596 g, 7.35 mmol) prepared in Reference Example 118 in THF (10 ml) was added dropwise while cooling in an ice-bath, and the mixture was heated under reflux for 2 hours. Methanol was slowly added to the mixture until it no longer foamed. Water (0.6 ml), 15% sodium hydroxide aqueous solution (0.6 ml) and water (1.8 ml) were added in this order, and the insoluble substances were removed by filtration. The filtrate was concentrated under reduced pressure, and the residue was purified by column chromatography on silica gel with an amine-treated surface (Fuji Silysia; NH-DM1020, solvent; methylene chloride/n-hexane=4/1) to afford 2-(4-trifluoromethylphenyl)ethylamine (0.431 g, yield 31%) as an orange-colored oil.

$^1$H-NMR (CDCl$_3$) δppm: 2.81 (2H, t, J=6.9 Hz), 3.03 (2H, t, J=6.9 Hz), 7.32 (2H, d, J=8.0 Hz), 7.56 (2H, d, J=8.0 Hz).

Reference Example 120

Preparation of tert-butyl N-(1-benzylpiperidin-4-yl)-N-[2-(4-trifluoromethylphenyl)ethyl]carbamate 2-(4-Trifluoromethylphenyl)ethylamine (0.431 g, 2.28 mmol) prepared in Reference Example 119 and 1-benzyl-4-piperidone (0.517 g, 2.73 mmol) were dissolved in methanol (15 ml), to which sodium cyanoborohydride (0.429 g, 6.83 mmol) and acetic acid (0.52 ml, 9.11 mmol) were added, and the mixture was stirred at room temperature overnight. The reaction mixture was concentrated under reduced pressure, and the residue was dissolved in ethyl acetate. The mixture was washed with saturated sodium bicarbonate aqueous solution and brine. The organic layer was dried over sodium sulfate, and then filtered, and the filtrate was concentrated under reduced pressure. The residue was dissolved in methanol (5 ml), to which di-tert-butyl dicarbonate (0.597 g, 2.74 mmol) was added, and the mixture was stirred at room temperature overnight. The reaction mixture was diluted with ethyl acetate, and the mixture was washed with brine. The organic layer was dried over sodium sulfate, and then filtered, and the filtrate was concentrated under reduced pressure. The residue was purified by silica gel column chromatography (n-hexane/ethyl acetate=3/1) to afford tert-butyl N-(1-benzylpiperidin-4-yl)-N-[2-(4-trifluoromethylphenyl)ethyl]carbamate (0.437 g, yield 41%) as a colorless oil.

$^1$H-NMR (CDCl$_3$) δppm: 1.55 (9H, s), 1.59-1.73 (4H, m), 1.90-2.10 (2H, m), 2.82-2.96 (4H, m), 3.24-3.28 (2H, m), 3.49 (2H, s), 4.00 (1H, bs), 7.26-7.31 (7H, m), 7.54 (2H, d, J=8.0 Hz).

Reference Example 121

Preparation of tert-butyl N-(piperidin-4-yl)-N-[2-(4-trifluoromethylphenyl)ethyl]carbamate A mixture of tert-butyl N-(1-benzylpiperidin-4-yl)-N-[2-(4-trifluoromethylphenyl)ethyl]carbamate (0.437 g, 0.944 mmol) prepared in Reference Example 120 and 20% palladium hydroxide/carbon (100 mg) in ethanol (20 ml) was stirred at room temperature under an atmospheric pressure of hydrogen. The reaction mixture was filtered through Celite, and the filtrate was concentrated under reduced pressure to afford tert-butyl N-(piperidin-4-yl)-N-[2-(4-trifluoromethylphenyl)ethyl]carbamate (0.332 g, yield 94%) as a colorless oil.

$^1$H-NMR (CDCl$_3$) δppm: 1.49 (9H, s), 1.51-1.80 (4H, m), 2.62-3.49 (9H, m), 7.28-7.31 (2H, m), 7.54 (2H, d, J=8.0 Hz).

Reference Example 122

Preparation of tert-butyl 4-(4-trifluoromethylbenzyloxy)piperidine-1-carboxylate Tert-butyl 4-hydroxypiperidine-1-carboxylate (1.88 g, 9.34 mmol) was dissolved in THF (20 ml). Sodium hydride (411 mg, 10.3 mmol) was added to this solution while cooling in an ice-bath, and the mixture was stirred for 1 hour. 4-(Trifluoromethyl) benzylbromide (2.23 g, 9.34 mmol) was added to the mixture, which was stirred at room temperature for 2 hours. Water was added to the reaction mixture, which was extracted with methylene chloride. The extract was dried over magnesium sulfate, and then filtered, and the filtrate was concentrated under reduced pressure. The residue was purified by silica gel column chromatography (methylene chloride/methanol=100/1) to afford tert-butyl 4-(4-trifluoromethylbenzyloxy)piperidine-1-carboxylate (2.56 g, yield 76%) as a pale yellow oil.

$^1$H-NMR (CDCl$_3$) δppm: 1.46 (9H, s), 1.51-1.67 (2H, m), 1.83-1.91 (2H, m), 3.07-3.18 (2H, m), 3.52-3.63 (1H, m), 3.73-3.83 (2H, m), 4.61 (2H, m), 7.46 (2H, d, J=8.2 Hz), 7.60 (2H, d, J=8.2 Hz).

Using a corresponding starting material, a compound of Reference Example 123 was prepared in the same manner as described in Reference Example 122.

Reference Example 123 tert-butyl 4-(4-trifluoromethoxybenzyloxy)piperidine-1-carboxylate a pale yellow oil, yield 74% $^1$H-NMR (CDCl$_3$) δppm: 1.46 (9H, s), 1.51-1.65 (2H, m), 1.82-1.90 (2H, m), 3.06-3.17 (2H, m), 3.52-3.62 (1H, m), 3.73-3.83 (2H, m), 4.54 (2H, s), 7.17-7.20 (2H, m), 7.35-7.38 (2H, m).

Reference Example 124

Preparation of 4-(4-trifluoromethylbenzyloxy)piperidine

Tert-butyl 4-(4-trifluoromethylbenzyloxy)-piperidine-1-carboxylate (2.56 g, 7.12 mmol) prepared in Reference Example 122 was dissolved in methylene chloride (20 ml), to which trifluoroacetic acid (10 ml) was added dropwise, and the mixture was stirred at room temperature for 5 hours. The reaction mixture was concentrated under reduced pressure, and the residue was then dissolved in methylene chloride. This solution was neutralized with sodium hydroxide aqueous solution and the mixture was extracted with methylene chloride. The extract was washed with brine, dried over magnesium sulfate, and then filtered. The filtrate was concentrated under reduced pressure to afford 4-(4-trifluoromethylbenzyloxy)piperidine (1.85 g, yield 99%) as a white powder.

$^1$H-NMR (CDCl$_3$) δppm: 1.46-1.60 (2H, m), 1.87 (1H, s), 1.93-2.01 (2H, m), 2.58-2.69 (2H, m), 3.07-3.16 (2H, m), 3.43-3.54 (1H, m), 4.61 (2H, s), 7.44-7.48 (2H, m), 7.57-7.61 (2H, m).

Using corresponding starting materials, compounds of Reference Examples 125 to 128 were prepared in the same manner as described in Reference Example 124.

Reference Example 125

4-(4-trifluoromethoxybenzyloxy)piperidine a white powder, yield 74% $^1$H-NMR (CDCl$_3$) δppm: 1.45-1.60 (2H, m), 1.92-2.02 (2H, m), 2.11 (1H, s), 2.59-2.70 (2H, m), 3.07-3.17 (2H, m), 3.43-3.54 (1H, m), 4.55 (2H, s), 7.17-7.20 (2H, m), 7.35-7.40 (2H, m).

Reference Example 126

4-(4-chlorobenzyloxy)piperidine a white powder, yield 94% $^1$H-NMR (CDCl$_3$) δppm: 1.39-1.56 (3H, m), 1.90-1.99 (2H, m), 2.55-2.66 (2H, m), 3.06-3.11 (2H, m), 3.39-3.51 (1H, m), 4.52 (2H, s), 7.25-7.33 (4H, m).

Reference Example 127

4-(3,4-dichlorobenzyloxy)piperidine a white powder, yield 99% $^1$H-NMR (CDCl$_3$) δppm: 1.45-1.60 (2H, m), 1.91-2.01 (2H, m), 2.19 (1H, s), 2.59-2.70 (2H, m), 3.07-3.16 (2H, m), 3.42-3.52 (1H, m), 4.50 (2H, s), 7.17 (1H, dd, J=1.9 Hz, 8.2 Hz), 7.40 (1H, d, J=8.2 Hz), 7.45 (1H, d, J=1.9 Hz).

Reference Example 128

4-(4-phenylbenzyloxy)piperidine a white powder, yield 16% $^1$H-NMR (CDCl$_3$) δppm: 1.45-1.60 (2H, m), 1.72 (1H, s), 1.95-2.02 (2H, m), 2.57-2.68 (2H, m), 3.07-3.16 (2H, m), 3.45-3.56 (1H, m), 4.60 (2H, s), 7.25-7.60 (9H, m).

Reference Example 129

Preparation of (1-benzylpiperidin-4-yl)-(4-trifluoromethoxyphenyl)amine

A mixture of 1-bromo-4-trifluoromethoxybenzene (2.0 g, 8.3 mmol), 4-amino-1-benzylpiperidine (1.73 g, 9.13 mmol), palladium acetate (37 mg, 0.17 mmol), (R)-(+)-BINAP (155 mg, 0.25 mmol) and sodium tert-butoxide (1.2 g, 11.6 mmol) in toluene (30 ml) was refluxed under a nitrogen atmosphere for 5 hours. Ethyl acetate and water were added to the reaction mixture while stirring, the insoluble substances were removed by filtration through Celite, and the filtrate was extracted with ethylacetate. The extract was washed with brine, dried over magnesium sulfate, and then filtered. The filtrate was concentrated under reduced pressure, and the residue was purified by silica gel column chromatography (methylene chloride/methanol=100/1) to afford (1-benzylpiperidin-4-yl)-(4-trifluoromethoxyphenyl)amine (3.0 g, yield 99%) as a dark oil.

$^1$H-NMR (CDCl$_3$) δppm: 1.39-1.55 (2H, m), 1.98-2.05 (2H, m), 2.09-2.20 (2H, m), 2.80-2.89 (2H, m), 3.21-3.28 (1H, m), 3.52 (2H, s), 3.52-3.59 (1H, m), 6.48-6.55 (2H, m), 6.98-7.02 (2H, m), 7.22-7.33 (5H, m).

Reference Example 130

Preparation of piperidin-4-yl-(4-trifluoromethoxyphenyl)amine

A mixture of (1-benzylpiperidin-4-yl)-(4-trifluoromethoxyphenyl)amine (3.0 g, 8.3 mmol) prepared in Reference Example 129 and a catalytic amount of 10% palladium/carbon in ethanol (30 ml) was refluxed under an atmospheric pressure of hydrogen for 20 hours. The reaction mixture was filtered through Celite, and the filtrate was concentrated under reduced pressure. The residue was purified by silica gel column chromatography (methylene chloride/methanol=10/1) to afford piperidin-4-yl-(4-trifluoromethoxyphenyl)amine (2.02 g, yield 94%) as a colorless crystalline powder.

$^1$H-NMR (CDCl$_3$) δppm: 1.24-1.39 (2H, m), 2.03-2.08 (2H, m), 2.65-2.77 (2H, m), 3.08-2.16 (2H, m), 3.24-3.41 (1H, m), 3.59 (1H, br), 6.50-6.58 (2H, m), 6.99-7.03 (2H, m).

Reference Example 131

Preparation of tert-butyl 4-(4-chlorophenylamino)-piperidine-1-carboxylate

A mixture of p-bromochlorobenzene (1.91 g, 9.99 mmol), tert-butyl 4-aminopiperidine-1-carboxylate (2.0 g, 9.99 mmol), palladium acetate (45 mg, 0.2 mmol), (R)-(+)-BINAP (187 mg, 0.3 mmol) and sodium tert-butoxide (1.35 g, 14.0 mmol) in toluene (20 ml) was refluxed under a nitrogen atmosphere for 1 hour. Ethyl acetate and water were added to the reaction mixture while stirring, the insoluble substances were removed by filtration through Celite, and the filtrate was then extracted with ethyl acetate. The extract was washed with brine, dried over magnesium sulfate, and then filtered. The filtrate was concentrated under reduced pressure, and the residue was purified by silica gel column chromatography (methylene chloride/methanol=100/1) to afford tert-butyl 4-(4-chlorophenylamino)piperidine-1-carboxylate (2.67 g, yield 86%) as a yellow powder.

$^1$H-NMR (CDCl$_3$) δppm: 1.21-1.54 (2H, m) 1.46 (9H, s), 1.99-2.05 (2H, m), 2.85-2.97 (2H, m), 3.37 (1H, br), 3.51 (1H, br), 4.01-4.07 (2H, m), 6.48-6.54 (2H, m), 7.07-7.14 (2H, m).

Using corresponding starting materials, compounds of Reference Examples 132 to 133 were prepared in the same manner as described in Reference Example 131.

Reference Example 132 tert-butyl 4-(4-trifluoromethylphenylamino)piperidine-1-carboxylate a yellow powder, yield 93% $^1$H-NMR (CDCl$_3$) δppm: 1.21-1.58 (2H, m), 1.47 (9H, s), 2.00-2.06 (2H, m), 2.88-2.99 (2H, m), 3.47 (1H, br), 3.88 (1H, bs), 4.03-4.09 (1H, m), 6.56 (2H, d, J=8.6 Hz), 7.39 (2H, d, J=8.6 Hz).

Reference Example 133 tert-butyl 4-(4-cyanophenylamino)piperidine-1-carboxylate a yellow powder, yield 92% $^1$H-NMR (CDCl$_3$) δppm: 1.26-1.54 (2H, m), 1.47 (9H, s), 1.99-2.05 (2H, m), 2.87-2.99 (2H, m), 3.41-3.53 (1H, br), 4.02-4.14 (3H, m), 6.52-6.58 (2H, m), 7.39-7.45 (2H, m).

Reference Example 134

Preparation of 4-(4-chlorophenylamino)piperidine

Tert-butyl 4-(4-chlorophenylamino)piperidine-1-carboxylate (2.67 g, 8.59 mmol) prepared in Reference Example 131 was dissolved in methylene chloride (20 ml), to which trifluoroacetic acid (15 ml) was added dropwise, and the mixture was stirred at room temperature for 5 hours. The reaction mixture was concentrated under reduced pressure, and the residue was then dissolved in methylene chloride. This solution was neutralized with sodium hydroxide aqueous solution, and the mixture was extracted with methylene chloride. The extract was washed with brine, dried over magnesium sulfate, and then filtered. The filtrate was concentrated under reduced pressure to afford 4-(4-chlorophenylamino)piperidine as a pale yellow powder.

$^1$H-NMR (CDCl$_3$) δppm: 1.22-1.38 (2H, m), 2.02-2.07 (2H, m), 2.65-2.76 (2H, m), 3.08-3.16 (2H, m), 3.25-3.38 (1H, m), 3.50-3.54 (1H, m), 6.48-6.55 (2H, m), 7.06-7.26 (2H, m).

Using corresponding starting materials, compounds of Reference Examples 135 to 136 were prepared in the same manner as described in Reference Example 134.

Reference Example 135

4-(4-trifluoromethylphenylamino)piperidine a yellow powder, yield 97% $^1$H-NMR (CDCl$_3$) δppm: 1.26-1.42 (2H, m), 2.04-2.09 (2H, m), 2.67-2.78 (2H, m), 3.09-3.17 (2H, m), 3.34-3.46 (1H, m), 3.86-3.90 (1H, m), 6.59 (2H, d, J=8.6 Hz), 7.38 (2H, d, J=8.6 Hz).

Reference Example 136

4-(4-cyanophenylamino)piperidine a yellow powder, yield 98% $^1$H-NMR (CDCl$_3$) δppm: 1.27-1.45 (2H, m), 2.02-2.07 (2H, m), 2.67-2.78 (2H, m), 3.09-3.17 (2H, m), 3.34-3.46 (1H, m), 4.09-4.13 (1H, m), 6.51-6.57 (2H, m), 7.38-7.44 (2H, m).

Reference Example 137

Preparation of tert-butyl 4-(toluene-4-sulfonyloxy)piperidine-1-carboxylate

Tert-butyl 4-hydroxypiperidine-1-carboxylate (2.22 g, 10.0 mmol) was dissolved in acetonitrile (40 ml), to which triethylamine (2.74 ml, 19.7 mmol) and N,N,N',N'-tetramethyl-1,6-diaminohexane (0.57 ml, 2.64 mmol) were added, and the mixture was cooled in an ice-bath. p-Toluenesulfonyl chloride (2.75 g, 14.4 mmol) was added to this mixture, which was allowed to return to room temperature and stirred overnight. Water was poured into the reaction mixture, and the mixture was extracted with diethyl ether. The extract was washed with brine, dried over magnesium sulfate, and then filtered. The filtrate was concentrated under reduced pressure. The residue was purified by silica gel column chromatography (methylene chloride/methanol=100/1) to afford tert-butyl 4-(toluene-4-sulfonyloxy)piperidine-1-carboxylate (4.16 g, yield 89%) as a pale yellow powder.

$^1$H-NMR (CDCl$_3$) δppm: 1.44 (9H, s), 1.64-1.82 (4H, m), 2.44 (3H, s), 3.19-3.30 (2H, m), 3.54-3.64 (2H, m), 4.63-4.72 (1H, m), 7.31-7.37 (2H, m), 7.78-7.82 (2H, m).

Reference Example 138

Preparation of tert-butyl 4-(4-trifluoromethoxyphenylsulfanyl)piperidine-1-carboxylate 4-(Trifluoromethoxy)thiophenol (2.0 g, 10.3 mmol) was dissolved in THF (30 ml), and this solution was cooled in an ice-bath. To which sodium hydride (453 mg, 11.3 mmol) was added, and the mixture was stirred for 30 minutes. To which tert-butyl 4-(toluene-4-sulfonyloxy)piperidine-1-carboxylate (3.66 g, 10.3 mmol) prepared in Reference Example 137 was added, and the resulting mixture was stirred at room temperature for 30 minutes, and then heated under reflux for 1 hour. Water was added to the reaction mixture, and the mixture was extracted with methylene chloride. The extract was dried over magnesium sulfate, and then filtered, and the filtrate was concentrated under reduced pressure. The residue was purified by silica gel column chromatography (n-hexane/ethyl chloride=20/1) to afford tert-butyl 4-(4-trifluoromethoxyphenylsulfanyl)piperidine-1-carboxylate (3.12 g, yield 80%) as a colorless oil.

$^1$H-NMR (CDCl$_3$) δppm: 1.45 (9H, s), 1.46-1.60 (2H, m), 1.87-1.95 (2H, m), 2.86-2.98 (2H, m), 3.14-3.23 (1H, m), 3.94-4.00 (2H, m), 7.13-7.17 (2H, m), 7.40-7.47 (2H, m).

Reference Example 139

Preparation of 4-(4-trifluoromethoxyphenylsulfanyl)piperidine

Using tert-butyl 4-(4-trifluoromethoxy-phenylsulfanyl)piperidine-1-carboxylate prepared in Reference Example 138, 4-(4-trifluoromethoxyphenylsulfanyl)piperidine (yield 92%) as a colorless oil was prepared in the same manner as described in Reference Example 134.

$^1$H-NMR (CDCl$_3$) δppm: 1.43-1.59 (2H, m), 1.91-1.98 (2H, m), 2.59-2.70 (2H, m), 3.06-3.20 (3H, m), 7.12-7.16 (2H, m), 7.40-7.46 (2H, m).

Reference Example 140

Preparation of tert-butyl 4-(4-trifluoromethoxybenzyl)piperidine-1-carboxylate

Triphenyl-(4-trifluoromethoxybenzyl)-phosphonium bromide (2.0 g, 3.87 mmol) was dissolved in DMSO (20 ml), to which sodium hydride (168 mg, 4.2 mmol) was added, and the mixture was stirred for 30 minutes. Tert-butyl 4-oxopiperidine-1-carboxylate (700 mg, 3.51 mmol) was added to the mixture, and the resulting mixture was stirred at 60° C. for 2 hours. The reaction mixture was poured into water, and extracted with diethyl ether. The extract was washed with brine, dried over magnesium sulfate, and then filtered. The filtrate was concentrated under reduced pressure. The residue was purified by silica gel column chromatography (methylene chloride/methanol=100/1) to afford a colorless crystalline powder.

A mixture of this intermediate and a catalytic amount of 10% Pd/C in methanol (30 ml) was stirred at room temperature under an atmospheric pressure of hydrogen for 3 hours. The reaction mixture was filtered, and the filtrate was concentrated under reduced pressure to afford tert-butyl 4-(4-trifluoromethoxybenzyl)piperidine-1-carboxylate (1.28 g, yield 60%) as a colorless oil.

$^1$H-NMR (CDCl$_3$) δppm: 1.06-1.21 (2H, m), 1.45 (9H, s), 1.57-1.70 (3H, m), 2.52-2.69 (4H, m), 4.08 (2H, br), 7.09-7.17 (4H, m).

Reference Example 141

Preparation of 4-(4-trifluoromethoxybenzyl)piperidine

Using tert-butyl 4-(4-trifluoromethoxybenzyl)piperidine-1-carboxylate prepared in Reference Example 140, 4-(4-trifluoromethoxybenzyl)piperidine was prepared in the same manner as described in Reference Example 134.

Colorless solid, yield 99% $^1$H-NMR (CDCl$_3$) δppm: 1.06-1.22 (2H, m), 1.50 (1H, s), 1.53-1.68 (3H, m), 2.48-2.60 (4H, m), 3.02-3.08 (2H, m), 7.09-7.17 (4H, m).

Reference Example 142

Preparation of 1-benzyl-4-(4-trifluoromethoxybenzylidene)piperidine

Triphenyl-(4-trifluoromethoxybenzyl) phosphonium bromide (21.6 g, 41.75 mmol) was dissolved in DMSO (110 ml), to which sodium hydride (1.82 g, 45.52 mmol) was added, and the mixture was stirred for 30 minutes. 1-Benzyl-4-piperidone (7.18 g, 37.96 mmol) was added to the mixture, and the resulting mixture was stirred at 60° C. for 2 hours. The reaction mixture was poured into ice water, and extracted with ethyl acetate. The extract was washed with brine, dried over magnesium sulfate, and then filtered. The filtrate was concentrated under reduced pressure. The residue was purified by silica gel column chromatography (methylene chloride/ethyl acetate=10/1) to afford 1-benzyl-4-(4-trifluoromethoxybenzylidene)piperidine (9.75 g, yield 74%) as a yellow oil.

$^1$H-NMR (CDCl$_3$) δppm: 2.36-2.55 (8H, m), 3.53 (2H, s), 6.23 (1H, s), 7.11-7.34 (9H, m).

Using a corresponding starting material, a compound of Reference Example 143 was prepared in the same manner as described in Reference Example 142.

Reference Example 143

1-benzyl-4-(4-trifluoromethylbenzylidene)piperidine a yellow oil, yield 52% $^1$H-NMR (CDCl$_3$) δppm: 2.38-2.57 (8H, m), 3.53 (2H, s), 6.28 (1H, m), 7.24-7.56 (9H, m).

Reference Example 144

Preparation of 4-(4-trifluoromethoxybenzyl)piperidine (an alternative method for synthesis of the compound in Reference Example 141)

A mixture of 1-benzyl-4-(4-trifluoromethylbenzylidene)piperidine (9.7 g, 27.92 mmol) prepared in Reference Example 142, 6 N hydrochloric acid (9.3 ml), and 10% palladium/carbon (970 mg) in ethanol (100 ml) was stirred at 50° C. under an atmospheric pressure of hydrogen for 5 hours. The reaction mixture was filtered through Celite, and the filtrate was concentrated under reduced pressure. Water and 10% sodium hydroxide aqueous solution were added to the residue, and the mixture was extracted with methylene chloride. The extract was washed with brine, dried over magnesium sulfate, and then filtered. The filtrate was concentrated under reduced pressure to afford 4-(4-trifluoromethoxybenzyl)piperidine (6.77 g, yield 94%) as a colorless crystalline powder.

$^1$H-NMR (CDCl$_3$) δppm: 1.06-1.22 (2H, m), 1.50 (1H, s), 1.53-1.68 (3H, m), 2.48-2.60 (4H, m), 3.02-3.08 (2H, m), 7.09-7.17 (4H, m)

Using corresponding starting materials, compounds of Reference Examples 145 and 146 were prepared in the same manner as described in Reference Example 144.

Reference Example 145

4-(4-trifluoromethylbenzyl)piperidine a colorless crystalline powder, yield 94% $^1$H-NMR (CDCl$_3$) δppm: 1.06-1.29 (2H, m), 1.50-1.69 (4H, m), 2.48-2.60 (4H, m), 3.02-3.09 (2H, m), 7.23-7.29 (2H, m), 7.51-7.54 (2H, m).

Reference Example 146

4-(4-chlorobenzyl)piperidine a colorless crystalline powder, yield 94% $^1$H-NMR (CDCl$_3$) δppm: 1.07-1.21 (2H, m), 1.53-1.82 (4H, m), 2.47-2.59 (4H, m), 3.02-3.08 (2H, m), 7.04-7.08 (2H, m), 7.22-7.27 (2H, m).

Reference Example 147

Preparation of 1-benzylpiperidine-4-carboxylic acid N-methyl-N-methoxyamide 1-benzylpiperidine-4-carboxylic acid hydrochloride (21 g, 82.3 mmol) was suspended in chloroform, to which DMF (1 ml) and thionyl chloride (30 ml) were added at room temperature, and the mixture was heated under reflux for 2 hours. The mixture was concentrated under reduced pressure to prepare an acid chloride compound.

In another vessel, N,O-dimethylhydroxylamine hydrochloride (12 g, 0.12 mol) was dissolved in acetone (200 ml)-water (20 ml), to which potassium carbonate (34.12 g, 246.9 mmol) was added, and the mixture was stirred while cooling in an ice-bath. A solution of the previously prepared acid chloride compound in acetone (120 ml) was added dropwise to this mixture, which was stirred at room temperature for 2 hours. The reaction mixture was concentrated under reduced pressure, to which water was added, and the mixture was extracted with methylene chloride. The extract was washed with brine, dried over magnesium sulfate, and then filtered. The filtrate was concentrated under reduced pressure to afford 1-benzylpiperidine-4-carboxylic acid N-methyl-N-methoxyamide (16.8 g, yield 78%) as a brown oil.

$^1$H-NMR (CDCl$_3$) δppm: 1.65-1.92 (4H, m), 1.97-2.07 (2H, m), 2.62-2.68 (1H, m), 2.91-2.96 (2H, m), 3.17 (3H, s), 3.51 (2H, s), 3.69 (3H, s), 7.20-7.32 (5H, m)

Reference Example 148

Preparation of 1-benzyl-4-(4-trifluoromethoxybenzoyl)piperidine

1-Bromo-4-trifluoromethoxybenzene (5.3 g, 22.0 mmol) was dissolved in dry THF (70 ml) under a nitrogen atmosphere, and this solution was cooled to −60° C. n-Butyllithium (1.6 M) hexane solution (15 ml, 24.0 mmol) was added dropwise to the solution, and the mixture was allowed to reach a temperature of −30° C. and stirred for 1 hour. This mixture was cooled to −60° C. again, to which a solution of 1-benzylpiperidine-4-carboxylic acid N-methyl-N-methoxyamide (4.1 g, 15.6 mmol) prepared in Reference Example 147 in THF (10 ml) was added dropwise, and the mixture was stirred for 1 hour and then at 0° C. for 3 hours. The reaction mixture was poured into saturated ammonium chloride aqueous solution, and extracted with diethyl ether. The extract was washed with water and brine, dried over magnesium sulfate, and then filtered. The filtrate was concentrated under reduced pressure. The residue was purified by silica gel column chromatography (n-hexane/ethyl acetate=4/1) to afford 1-benzyl-4-(4-trifluoromethoxybenzoyl)piperidine (4.8 g, yield 85%) as a pale yellow oil.

$^1$H-NMR (CDCl$_3$) δppm: 1.80-1.89 (4H, m), 2.04-2.18 (2H, m), 2.94-3.01 (2H, m), 3.15-3.24 (1H, m), 3.55 (2H, s), 7.19-7.34 (7H, m), 7.95-8.01 (2H, m).

Using a corresponding starting material, a compound of Reference Example 149 was prepared in the same manner as described in Reference Example 148.

Reference Example 149

1-benzyl-4-(4-trifluoromethylbenzoyl)piperidine a pale yellow oil, yield 66% $^1$H-NMR (CDCl$_3$) δppm: 1.78-1.89 (4H, m), 2.09-2.19 (2H, m), 2.94-3.02 (2H, m), 3.16-3.29 (1H, m), 3.55 (2H, m), 7.26-7.34 (5H, m), 7.70-7.74 (2H, m), 8.00-8.04 (2H, m).

Reference Example 150

Preparation of 4-(4-trifluoromethoxybenzoyl)piperidine

1-Benzyl-4-(4-trifluoromethoxybenzoyl)piperidine (4.8 g, 13.2.2 mmol) prepared in Reference Example 148 was dissolved in methylene chloride (60 ml), and this solution was cooled in an ice-bath. 2-Chloroethyl chloroformate (2.9 ml, 26.4 mmol) was added dropwise to the solution, and the mixture was stirred at the same temperature for 30 minutes. The reaction mixture was concentrated under reduced pressure, methanol (100 ml) was added to the residue, and the resulting mixture was heated under reflux for 15 minutes. Water was added to the reaction mixture, which was stirred for 30 minutes, and neutralized with sodium hydroxide aqueous solution. The mixture was extracted with methylene chloride. The extract was washed with brine, dried over magnesium sulfate, and then filtered. The filtrate was concentrated under reduced pressure, and the residue was purified by silica gel column chromatography(n-hexane/ethyl acetate=1/1) to afford 4-(4-trifluoromethoxybenzoyl)piperidine (1.3 g, yield 36%) as a pale orange-colored crystalline powder.

$^1$H-NMR (CDCl$_3$) δppm: 1.57-1.88 (5H, m), 2.71-2.81 (2H, m), 3.15-3.23 (2H, m), 3.29-3.42 (1H, m), 7.27-7.28 (2H, m), 7.95-8.05 (2H, m).

Using corresponding starting materials, compounds of Reference Examples 151 and 152 were prepared in the same manner as described in Reference Example 150.

Reference Example 151

4-(4-trifluoromethylbenzoyl)piperidine a colorless crystalline powder, yield 68% $^1$H-NMR (CDCl$_3$) δppm: 1.61-1.76 (3H, m), 1.82-1.89 (2H, m), 2.72-2.83 (2H, m), 3.16-3.24 (2H, m), 3.32-3.44 (1H, m), 7.72-7.76 (2H, m), 8.01-8.05 (2H, m).

Reference Example 152

4-(4-chlorobenzoyl)piperidine a colorless crystalline powder, yield 100% $^1$H-NMR (CDCl$_3$) δppm: 1.60-1.84 (5H, m), 2.72-2.83 (2H, m), 3.16-3.24 (2H, m), 3.30-3.40 (1H, m), 7.41-7.47 (2H, m), 7.85-7.91 (2H, m).

Reference Example 153

Preparation of N-{2-[4-(4-trifluoromethylphenyl)piperazin-1-yl]ethyl}phthalimide A mixture of 1-(4-trifluoromethylphenyl)piperazine (5.2 g, 22.59 mmol), N-(2-bromoethyl)phthalimide (5.22 g, 20.53 mmol) and potassium carbonate (3.36 g, 24.28 mmol) in DMF (30 ml) was stirred at 100° C. for 2 hours. The reaction mixture was allowed to return to room temperature, to which water was added, and the mixture was extracted with ethyl acetate. The extract was washed with brine, dried over magnesium sulfate, and then filtered. The filtrate was concentrated under reduced pressure. The residue was purified by silica gel column chromatography (methylene chloride/ethyl acetate=50/1), and the resulting solid was washed with methanol, and then dried in vacuo to afford N-{2-[4-(4-trifluoromethylphenyl)piperazin-1-yl]ethyl}phthalimide (4.85 g, yield 53%) as a white powder.

$^1$H-NMR (CDCl$_3$) δppm: 2.64-2.72 (6H, m), 3.18-3.23 (4H, m), 3.86 (2H, t, J=6.4 Hz), 6.89 (2H, d, J=8.7 Hz), 7.45 (2H, d, J=8.7 Hz), 7.70-7.75 (2H, m), 7.81-7.86 (2H, m).

Reference Example 154

Preparation of 2-[4-(4-trifluoromethylphenyl)piperazin-1-yl]ethylamine

N-{2-[4-(4-trifluoromethylphenyl)piperazin-1-yl]ethyl}phthalimide (4 g, 9.92 mmol) prepared in Reference Example 153 was suspended in ethanol (30 ml), to which hydrazine monohydrate (0.53 ml, 10.91 mmol) was added, and the mixture was heated under reflux for 5 hours. The reaction mixture was allowed to return to room temperature, and the resulting precipitates were collected by filtration. This was purified by silica gel column chromatography (methylene chloride/ethyl acetate=100/1) to afford 2-[4-(4-trifluoromethylphenyl)piperazin-1-yl]ethylamine (2.87 g, yield 100%) as a colorless crystalline powder.

$^1$H-NMR (CDCl$_3$) δppm: 1.33 (2H, bs), 2.49 (2H, t, J=6.1 Hz), 2.59-2.63 (4H, m), 2.84 (2H, t, J=6.1 Hz), 3.26-3.31 (4H, m), 6.92 (2H, d, J=8.7 Hz), 7.48 (2H, d, J=8.7 Hz).

Reference Example 155

Preparation of N-{2-[4-(4-trifluoromethylphenyl)piperazin-1-yl]ethyl}formamide

A mixture of 2-[4-(4-trifluoromethylphenyl)piperazin-1-yl]ethylamine (906 mg, 3.32 mmol) prepared in Reference Example 154 and ethyl formate (10 ml) was heated under reflux for 5 hours. The reaction mixture was concentrated under reduced pressure, and the residue was purified by silica gel column chromatography (methylene chloride/methanol=100/1) to afford N-{2-[4-(4-trifluoromethylphenyl)piperazin-1-yl]ethyl}formamide (942 mg, yield 94%) as a white powder.

$^1$H-NMR (CDCl$_3$) δppm: 2.53-2.65 (6H, m), 3.26-3.31 (4H, m), 3.42-3.49 (2H, m), 6.05 (1H, bs), 6.92 (2H, d, J=8.7 Hz), 7.49 (2H, d, J=8.7 Hz), 8.21 (1H, s).

Reference Example 156

Preparation of N-methyl-{2-[4-(4-trifluoromethylphenyl)piperazin-1-yl]ethyl}amine Lithium aluminum hydride (237 mg, 6.25 mmol) was suspended in THF (20 ml), which was stirred while cooling in an ice-bath. To which a solution of N-{2-[4-(4-trifluoromethylphenyl)piperazin-1-yl]ethyl}-formamide (942 mg, 3.13 mmol) prepared in Reference Example 155 in THF (10 ml) was added dropwise, and the mixture was stirred at room temperature for 2 hours and then heated under reflux for 2 hours. The reaction mixture was allowed to return to room temperature, to which water and a 15% sodium hydroxide aqueous solution were added carefully. To the mixture, sodium sulfate was added, and the resulting mixture was vigorously stirred and filtered through Celite. The filtrate was concentrated under reduced pressure to afford N-methyl-{2-[4-(4-trifluoromethylphenyl)piperazin-1-yl]ethyl}-amine (900 mg, yield 100%) as a yellow oil.

$^1$H-NMR (CDCl$_3$) δppm: 2.47 (3H, s), 2.52-2.74 (8H, m), 3.26-3.30 (4H, m), 3.71-3.77 (1H, m), 6.91 (2H, d, J=8.7 Hz), 7.47 (2H, d, J=8.7 Hz).

Reference Example 157

Preparation of tert-butyl 4-(2-methylaminoethyl)piperazine-1-carboxylate

Tert-butyl 4-(2-chloroethyl)piperazine-1-carboxylate (3.13 g, 12.58 mmol) was dissolved in methanol (20 ml), to which 40% methylamine methanol solution (30 ml) was added, and the mixture was heated under reflux for 5 hours. The reaction mixture was concentrated under reduced pressure, and the residue was dissolved in methylene chloride. The mixture was washed with saturated sodium hydrogencarbonate aqueous solution. The organic layer was dried over magnesium sulfate, and then filtered, and the filtrate was concentrated under reduced pressure to afford tert-butyl 4-(2-methylaminoethyl)piperazine-1-carboxylate (3.0 g, yield 98%) as a pale yellow oil.

¹H-NMR (CDCl₃) δppm: 1.46 (9H, m), 1.66 (1H, s), 2.36-2.41 (4H, m), 2.45 (3H, s), 2.46-2.53 (2H, m), 2.65-2.70 (2H, m), 3.40-3.44 (4H, m).

Reference Example 158

Preparation of N-[2-(4-trifluoromethylphenoxy)ethyl]phthalimide

A mixture of N-(2-hydroxyethyl)phthalimide (3.59 g, 18.75 mmol), 4-hydroxybenzotrifluoride (3.04 g, 18.75 mmol), diethyl azodicarboxylate (4.37 ml, 28.13 mmol) and triphenylphosphine (7.38 g, 28.13 mmol) in THF (50 ml) was stirred at room temperature overnight. The reaction mixture was concentrated under reduced pressure, and the residue was purified by silica gel column chromatography (n-hexane/ethyl acetate=5/1) to afford N-[2-(4-trifluoromethylphenoxy)ethyl]phthalimide (4.05 g, yield 69%) as a colorless crystalline powder.

1H-NMR (CDCl₃) δppm: 4.11-4.16 (2H, m), 4.25-4.30 (2H, m), 6.92-6.96 (2H, m), 7.48-7.52 (2H, m), 7.72-7.77 (2H, m), 7.83-7.89 (2H, m).

Reference Example 159

Preparation of 2-(4-trifluoromethylphenoxy)ethylamine

Using N-[2-(4-trifluoromethylphenoxy)ethyl]phthalimide prepared in Reference Example 158, 2-(4-trifluoromethylphenoxy)ethylamine was prepared in the same manner as described in Reference Example 154.

a colorless oil, yield 95% ¹H-NMR (CDCl₃) δppm: 1.36 (2H, s), 3.11 (2H, t, J=5.1 Hz), 4.03 (2H, t, J=5.1 Hz), 6.97 (2H, d, J=8.6 Hz), 7.54 (2H, d, J=8.6 Hz).

Reference Example 160

Preparation of N-[2-(4-trifluoromethylphenoxy)ethyl]-formamide

A mixture of 2-(4-trifluoromethylphenoxy)ethylamine (1.38 g, 6.72 mmol) prepared in Reference Example 159 and ethyl formate (10 ml) was heated under reflux for 5 hours. The reaction mixture was concentrated under reduced pressure, and the residue was purified by silica gel column chromatography (methylene chloride/methanol=100/1) to afford N-[2-(4-trifluoromethylphenoxy)ethyl]formamide (1.51 g, yield 97%) as a white powder.

¹H-NMR (CDCl₃) δppm: 3.72-3.78 (2H, m), 4.09-4.13 (2H, m), 6.02 (1H, bs), 6.96 (2H, d, J=8.6 Hz), 7.56 (2H, d, J=8.6 Hz), 8.24 (1H, s).

Reference Example 161

Preparation of N-methyl-N-[2-(4-trifluoromethylphenoxy)ethyl]amine

N-[2-(4-trifluoromethylphenoxy)ethyl]-formamide (2.02 g, 8.66 mmol) prepared in Reference Example 160 was dissolved in THF (20 ml). Borane-THF complex (1 M) THF solution (21.7 ml, 21.7 mmol) was added dropwise to this solution while cooling in an ice-bath, and the mixture was stirred overnight. The reaction mixture was cooled, to which water and 6N hydrochloric acid were added, and the mixture was stirred for 20 minutes. The reaction mixture was neutralized with a sodium hydroxide aqueous solution, and the mixture extracted with methylene chloride. The extract was dried over magnesium sulfate, and then filtered. The filtrate was concentrated under reduced pressure. The residue was purified by silica gel column chromatography (methylene chloride/methanol=200/1) to afford N-methyl-N-[2-(4-trifluoromethylphenoxy)ethyl]amine (1.05 g, yield 55%) as a white powder.

¹H-NMR (CDCl₃) δppm: 2.68 (3H, d, J=5.8 Hz), 3.05-3.28 (2H, m), 4.06 (1H, br), 4.10-4.18 (1H, m), 4.45-4.54 (1H, m), 6.98 (2H, d, J=8.5 Hz), 7.58 (2H, d, J=8.5 Hz).

Reference Example 162

Preparation of N-methyl-N-[2-(4-trifluoromethoxyphenoxy)ethyl]amine 1-(2-Bromoethoxy)-4-(trifluoromethoxy)benzene (2.2 g, 7.72 mmol) was dissolved in methanol (20 ml), to which 40% methylamine methanol solution (20 ml) was added, and the mixture was heated under reflux for 5 hours. The reaction mixture was concentrated under reduced pressure, and the residue was dissolved in methylene chloride, and the mixture was washed with saturated sodium hydrogencarbonate aqueous solution. The organic layer was dried over magnesium sulfate, and filtered, and the filtrate was concentrated under reduced pressure to afford N-methyl-N-[2-(4-trifluoromethoxyphenoxy)ethyl]amine (1.44 g, yield 79%) as a pale yellow oil.

¹H-NMR (CDCl₃) δppm: 1.54 (1H, s), 2.51 (3H, s), 2.97 (2H, t, J=5.1 Hz), 4.06 (2H, t, J=5.1 Hz), 6.85-6.92 (2H, m), 7.10-7.17 (2H, m).

Reference Example 163

Preparation of N-methyl-N-[2-(4-trifluoromethylphenoxy)ethyl]amine

Using 1-(2-bromoethoxy)-4-(trifluoromethyl)benzene, N-methyl-N-[2-(4-trifluoromethylphenoxy)ethyl]amine was prepared in the same manner as described in Reference Example 162.

a white powder, yield 82% ¹H-NMR (CDCl₃) δppm: 2.68 (3H, d, J=5.8 Hz), 3.02-3.28 (2H, m), 3.92-4.18 (2H, m), 4.41-4.54 (1H, m), 6.98 (2H, d, J=8.5 Hz), 7.58 (2H, d, J=8.5 Hz)

Reference Example 164

Preparation of N,N'-dimethyl-N-[4-(trifluoromethyl)phenyl]-1,2-ethylenediamine

A mixture of 4-bromobenzotrifluoride (3.0 g, 13.3 mmol), N,N'-dimethylethylenediamine (9.4 g, 0.11 mol), palladium acetate (60 mg, 0.27 mmol), BINAP (250 mg, 0.40 mmol) and sodium tert-butoxide (1.80 g, 18.7 mmol) in toluene (20 ml) was refluxed under a nitrogen atmosphere for 3 hours. Ethyl acetate and water were added to the reaction mixture, and the mixture was stirred for a while. The insoluble substances were removed by filtration through Celite, and the filtrate was then extracted with ethyl acetate. The extract was washed with brine, dried over magnesium sulfate, and then filtered. The filtrate was concentrated under reduced pressure, and the residue was purified by silica gel column chromatography (methylene chloride/methanol=10/1) to afford N,N'-dimethyl-N-[4-(trifluoromethyl)phenyl]-1,2-ethylenediamine (650 mg, yield 21%) as a pale yellow oil.

$^1$H-NMR (CDCl$_3$) δppm: 1.53 (1H, s), 2.47 (3H, s), 2.82 (2H, t, J=6.7 Hz), 3.02 (3H, s), 3.52 (2H, t, J=6.7 Hz), 6.74 (2H, d, J=8.8 Hz), 7.43 (2H, d, J=8.8 Hz).

Reference Example 165

Preparation of tert-butyl N-[1-(4-chlorophenyl)piperidin-4-yl]-N-methylcarbamate A mixture of p-bromochlorobenzene (3.13 g, 16.3 mmol), tert-butyl (piperidin-4-yl)-N-methylcarbamate (3.5 g, 10.8 mmol), palladium acetate (73 mg, 0.33 mmol), (S)-(–)-BINAP (305 mg, 0.49 mmol) and sodium tert-butoxide (2.2 g, 22.9 mmol) in toluene (30 ml) was refluxed under a nitrogen atmosphere for 3 hours. Ethyl acetate and water were added to the reaction mixture, the mixture was stirred for a while. The insoluble substances were removed by filtration through Celite, and the filtrate was extracted with ethyl acetate. The extract was washed with brine, dried over magnesium sulfate, and then filtered. The filtrate was concentrated under reduced pressure, and the residue was purified by silica gel column chromatography (methylene chloride/ethyl acetate=10/1) to afford tert-butyl N-[1-(4-chlorophenyl)piperidin-4-yl]-N-methylcarbamate (4.7 g, yield 89%) as a yellow powder.

$^1$H-NMR (CDCl$_3$) δppm: 1.47 (9H, s), 1.70-1.90 (4H, m), 2.73-2.82 (2H, m), 2.74 (3H, s), 3.64-3.71 (2H, m), 4.08 (1H, br), 6.81-6.87 (2H, m), 7.15-7.22 (2H, m).

Using corresponding starting materials, compounds of Reference Examples 166 to 168 were prepared in the same manner as described in Reference Example 165.

Reference Example 166 tert-butyl N-[1-(4-trifluoromethoxyphenyl)piperidin-4-yl]-N-methylcarbamate yield 88% $^1$H-NMR (CDCl$_3$) δppm: 1.48 (9H, s), 1.72-1.91 (4H, m), 2.76 (3H, s), 2.79-2.85 (2H, m), 3.67-3.73 (2H, m), 4.10 (1H, br), 6.86-6.93 (2H, m), 7.07-7.11 (2H, m).

Reference Example 167 tert-butyl N-[1-(4-trifluoromethylphenyl)piperidin-4-yl]-N-methylcarbamate yield 91% $^1$H-NMR (CDCl$_3$) δppm: 1.47 (9H, s), 1.72-1.87 (4H, m), 2.74 (3H, s), 2.82-2.94 (2H, m), 3.83-3.89 (2H, m), 4.12 (1H, br), 6.92 (2H, d, J=8.7 Hz), 7.46 (2H, d, J=8.7 Hz).

Reference Example 168 tert-butyl N-[1-(4-cyanophenyl)piperidin-4-yl]-N-methylcarbamate yield 73% $^1$H-NMR (CDCl$_3$) δppm: 1.47 (9H, s), 1.69-1.77 (4H, m), 2.73 (3H, s), 2.87-3.00 (2H, m), 3.89-3.97 (2H, m), 4.16 (1H, br), 6.84-6.89-(2H, m), 7.45-7.51 (2H, m).

Reference Example 169

Preparation of N-[1-(4-chlorophenyl)piperidin-4-yl]-N-methylamine

Tert-butyl N-[1-(4-chlorophenyl)piperidin-4-yl]-N-methylcarbamate (4.71 g, 14.5 mmol) prepared in Reference Example 165 was dissolved in methylene chloride (30 ml), to which trifluoroacetic acid (20 ml) was added dropwise, and the mixture was stirred at room temperature for 5 hours. The reaction mixture was concentrated under reduced pressure, and the residue was then dissolved in methylene chloride. The solution was neutralized with sodium hydroxide aqueous solution, and the mixture was extracted with methylene chloride. The extract was washed with brine, dried over magnesium sulfate, and then filtered. The filtrate was concentrated under reduced pressure to afford N-[1-(4-chlorophenyl)piperidin-4-yl]-N-methylamine (3.1 g, yield 95%) as a pale brown oil.

$^1$H-NMR (CDCl$_3$) δppm: 0.99 (1H, s), 1.38-1.54 (2H, m), 1.95-2.00 (2H, m), 2.44-2.54 (1H, m), 2.46 (3H, s), 2.71-2.82 (2H, m), 3.55-3.63 (2H, m), 6.81-6.87 (2H, m), 7.14-7.21 (2H, m).

Using corresponding starting materials, compounds of Reference Examples 170 to 172 were prepared in the same manner as described in Reference Example 169.

Reference Example 170

N-[1-(4-trifluoromethoxyphenyl)piperidin-4-yl]-N-methylamine a pale brown powder, yield 100% $^1$H-NMR (CDCl$_3$) δppm: 0.96 (1H, s), 1.39-1.55 (2H, m), 1.96-2.02 (2H, m), 2.44-2.57 (1H, m), 2.47 (3H, s), 2.73-2.84 (2H, m), 3.58-3.66 (2H, m), 6.86-6.92 (2H, m), 7.05-7.10 (2H, m).

Reference Example 171

N-[1-(4-trifluoromethylphenyl)piperidin-4-yl]-N-methylamine a pale brown powder, yield 100% $^1$H-NMR (CDCl$_3$) δppm: 0.96 (1H, s), 1.36-1.52 (2H, m), 1.96-2.02 (2H, m), 2.47 (3H, s), 2.50-2.62 (1H, m), 2.82-2.94 (2H, m), 3.72-3.80 (2H, m), 6.92 (2H, d, J=8.8 Hz), 7.45 (2H, d, J=8.8 Hz).

Reference Example 172

N-[1-(4-cyanophenyl)piperidin-4-yl]-N-methylamine a pale brown powder, yield 99% $^1$H-NMR (CDCl$_3$) δppm: 1.05 (1H, s), 1.34-1.49 (2H, m), 1.95-2.02 (2H, m), 2.47 (3H, s), 2.55-2.67 (1H, m), 2.90-3.01 (2H, m), 3.76-3.84 (2H, m), 6.82-6.90 (2H, m), 7.43-7.50 (2H, m).

Reference Example 173

Preparation of benzyl N-(2-methyl-2-propenyl)carbamate

2-Methallylamine hydrochloride (21.52 g, 0.2 mol) was dissolved in water (200 ml), to which benzyl chloroformate (37.53 g, 0.22 mol) was added, and the mixture was cooled in an ice-bath. Sodium carbonate (46.63 g, 0.44 mol) was gradually added to this mixture, which was stirred at room temperature for 3 hours. After the reaction mixture was extracted with methylene chloride twice, the extracts were combined, dried over sodium sulfate, and then filtered, and the filtrate was concentrated under reduced pressure. The residue was purified by silica gel column chromatography (n-hexane/ethyl acetate=7/1) to afford benzyl N-(2-methyl-2-propenyl)carbamate (41.58 g, quantitative) as a colorless oil.

$^1$H-NMR (CDCl$_3$) δppm: 1.74 (3H, s), 3.75 (2H, d, J=6.2 Hz), 4.69-4.94 (2H, m), 5.13 (2H, s), 7.26-7.39 (5H, m).

Reference Example 174

Production of 4-chlorobenzyl N-(2-methyl-2-propenyl)-carbamate 4-chlorobenzyl alcohol (3.00 g, 21.0 mmol) and triphosgene (3.12 g, 10.5 mmol) were dissolved in toluene (15 ml), to which N-ethyldiisopropylamine (3.6 ml, 21.0 mmol) was added while cooling in an ice-bath, and the mixture was stirred for 1 hour. The reaction mixture was poured into water, and extracted with methylene chloride twice. The extracts were combined and dried over magnesium sulfate, and then filtered. The filtrate was concentrated under a reduced pressure. A solution of 2-methallylamine hydrochloride (2.49 g, 23.1 mmol) in water (40 ml) were added to the residue, to which sodium carbonate (5.15 g, 48.6 mmol) was added under while cooling in an ice-bath, and the mixture was stirred for 15 minutes. The reaction mixture was extracted with methylene chloride twice, and the extracts were combined, dried over magnesium sulfate, and then filtered, and the filtrate was concentrated under a reduced pressure. The residue was purified by silica gel column chromatography (n-hexane/ethyl acetate=10/1) to afford 4-chlorobenzyl N-(2-methyl-2-propenyl)carbamate (4.06 g, yield 80%) as a colorless liquid.

$^1$H-NMR (CDCl$_3$) δppm: 1.74 (3H, s), 3.74 (2H, d, J=5.8 Hz), 4.73-4.91 (2H, m), 5.08 (2H, s), 7.26-7.41 (4H, m).

Reference Example 175

Preparation of 4-fluorobenzyl N-(2-methyl-2-propenyl)-carbamate

4-Fluorobenzyl alcohol (3.00 g, 23.8 mmol) was dissolved in THF (60 ml), to which 1,1'-carbonyldiimidazole (4.05 g, 25.0 mmol) was added while cooling in an ice-bath, and the mixture was stirred for 30 minutes. 2-Methallylamine hydrochloride (2.81 g, 26.2 mmol) and triethylamine (3.98 g, 28.5 mmol) were added to the mixture, which was stirred for 2 hours. After the reaction mixture was concentrated under reduced pressure, water were added to the residue, and the mixture was extracted with methylene chloride twice. The extracts were combined, dried over sodium sulfate and then filtered. The filtrate was concentrated under reduced pressure. The residue was purified by silica gel column chromatography (n-hexane/ethyl acetate=10/1) to afford 4-fluorobenzyl N-(2-methyl-2-propenyl)carbamate (4.69 g, yield 88%) as a colorless oil.

$^1$H-NMR (CDCl$_3$) δppm: 1.73 (3H, s), 3.74 (2H, d, J=5.8 Hz), 4.55-4.95 (3H, m), 5.08 (2H, s), 6.95-7.14 (2H, m), 7.27-7.41 (2H, m).

Reference Example 176

Preparation of 3-methoxymethoxy-2-methyl-1-propene

Chloromethyl methyl ether (105 ml, 1386 mmol) and N-ethyldiisopropylamine (265 ml, 1525 mmol) were added to a solution of 2-methyl-2-propen-1-ol (50 g, 693 mmol) in THF (500 ml) while cooling in an ice-bath, and the mixture was stirred at room temperature for 2 hours. The reaction mixture was filtered and washed with diethyl ether, and the filtrate was concentrated under a reduced pressure. The residue was dissolved in diethyl ether, washed with water, a saturated sodium hydrogencarbonate solution and then water, dried over magnesium sulfate. After filtration, the filtrate was concentrated under a reduced pressure to afford 3-methoxymethoxy-2-methylpropene (9.7 g, yield 12%) as colorless liquid.

$^1$H-NMR (CDCl$_3$) δppm: 1.76 (3H, s), 3.39 (3H, s), 3.97 (2H, s), 4.65 (2H, s), 4.85-4.94 (1H, m), 4.98-5.06 (1H, m).

Reference Example 177

Preparation of 2-methoxymethoxymethyl-2-methyloxirane m-Chloroperbenzoic acid (22.7 g, 92 mmol) was gradually added to a solution of 3-methoxymethoxy-2-methyl-1-propene (9.7 g, 84 mmol) prepared in Reference Example 176 in methylene chloride (200 ml) while cooling in an ice-bath and the mixture was stirred at room temperature for 6 hours. Sodium hydrogencarbonate (14.1 g, 168 mmol), water and methylene chloride were added to the reaction mixture, which was stirred for a while. The organic layer was separated, washed with sodium hydrogencarbonate aqueous solution, sodium thiosulfate aqueous solution and then sodium hydrogencarbonate aqueous solution, and dried over magnesium sulfate. After filtration, the filtrate was concentrated under reduced pressure to afford 2-methoxymethoxymethyl-2-methyloxirane (6.8 g, yield 62%) as a green-colored oil.

$^1$H-NMR (CDCl$_3$) δppm: 1.40 (3H, S), 2.65 (1H, d, J=4.9 Hz), 2.78 (1H, d, J=4.9 Hz), 3.38 (3H, s), 3.53 (1H, d, J=11.1 Hz), 3.62 (1H, d, J=11.1 Hz), 4.65 (2H, s).

Reference Example 178

Preparation of tert-butyl 4-(4-chlorobenzyl)piperazine-1-carboxylate

Potassium carbonate (1.45 g, 10.47 mmol) and 4-chlorobenzyl chloride (1.82 g, 8.86 mmol) were added to a solution of tert-butyl piperazine-1-carboxylate (1.5 g, 8.05 mmol) in DMF (10 ml), and the mixture was stirred at 50° C. for 1 hour. The reaction mixture was diluted with ethyl acetate, and the mixture was washed with water, and dried over magnesium sulfate. After filtration, the filtrate was concentrated under reduced pressure. The residue was purified by silica gel column chromatography (methylene chloride/ethyl acetate=9/1) to afford tert-butyl 4-(4-chlorobenzyl)piperazine-1-carboxylate (2.50 g, quantitative) as a colorless oil.

$^1$H-NMR (CDCl$_3$) δppm: 1.45 (9H, s), 2.36 (4H, t, J=5.0 Hz), 3.42 (4H, t, J=5.0 Hz), 3.46 (2H, s), 7.23-7.31 (4H, m).

Reference Example 179

Preparation of 1-(4-chlorobenzyl)piperazine

Trifluoroacetic acid (8 ml) was added to a solution of tert-butyl 4-(4-chlorobenzyl)piperazine-1-carboxylate (2.50 g, 8.05 mmol) prepared in Reference Example 178 in methylene chloride (16 ml), and the mixture was stirred at room temperature for 5 hours. The reaction mixture was concentrated under reduced pressure. Sodium hydroxide aqueous solution was added to the residue, and the mixture was extracted with methylene chloride. The extract was dried over sodium sulfate, and then filtered. The filtrate was concentrated under reduced pressure to afford 1-(4-chlorobenzyl)piperazine (1.70 g, quantitative) as a colorless oil.
$^1$H-NMR (DMSO-$d_6$) δppm: 2.55-2.74 (4H, m), 3.57-3.76 (6H, m), 7.35-7.45 (4H, m), 8.55-8.88 (1H, br).

Reference Example 180

Preparation of 1-(4-trifluoromethylbenzyl)piperazine

Using tert-butyl 4-(4-trifluoromethylbenzyl)-piperazine-1-carboxylate, 1-(4-trifluoromethylbenzyl)-piperazine was prepared in the same manner as described in Reference Example 179.
yield 100% $^1$H-NMR (CDCl$_3$) δppm: 2.72 (4H, t, J=4.9 Hz), 3.16-3.26 (4H, m), 3.62 (2H, s), 7.44 (2H, d, J=8.1 Hz), 7.59 (2H, d, J=8.1 Hz).

Reference Example 181

Preparation of 1-(4-trifluoromethoxybenzyl)piperazine

Using tert-butyl 4-(4-trifluoromethoxy-benzyl)piperazine-1-carboxylate, 1-(4-trifluoro-methoxybenzyl)piperazine was prepared in the same manner as described in Reference Example 179.
yield 100% $^1$H-NMR (CDCl$_3$) δppm: 2.70 (4H, t, J=4.9 Hz), 3.19 (4H, t, J=4.9 Hz), 3.56 (2H, s), 7.17 (2H, d, J=7.9 Hz), 7.33 (2H, d, J=7.9 Hz).

Reference Example 182

Preparation of 4-[4-(4-trifluoromethoxybenzyl)piperazin-1-yl]phenol 4-(4-hydroxyphenyl)piperazine (3 g, 16.8 mmol) and 4-trifluoromethoxy benzaldehyde (3.36 g, 17.7 mmol) were dissolved in methanol (60 ml) and methylene chloride (15 ml). Sodium cyanoborohydride (1.59 g, 25.3 mmol) and acetic acid (1.6 ml) were added to this solution while cooling in an ice-bath, and the mixture was stirred for 2 hours. Saturated sodium hydrogencarbonate aqueous solution and methylene chloride were added to the reaction mixture, which was extracted with methylene chloride. The extract was washed with brine, dried over magnesium sulfate, and then filtered. The filtrate was concentrated under reduced pressure. The residue was purified by silica gel column chromatography (methylene chloride/methanol=100/1) to afford 4-[4-(4-trifluoromethoxybenzyl)piperazin-1-yl]phenol (3.36 g, yield 57%) as a colorless crystalline powder.
$^1$H-NMR (CDCl$_3$) δppm: 2.59-2.64 (4H, m), 3.05-3.10 (4H, m), 3.56 (2H, s), 4.90-5.40 (1H, br), 6.69-6.75 (2H, m), 6.79-6.85 (2H, m), 7.16 (2H, d, J=8.4 Hz), 7.37 (2H, d, J=8.4 Hz).

Reference Example 183

Preparation of 1-[4-(tetrahydropyran-2-yloxy)phenyl]-4-(4-trifluoromethoxyphenyl)piperazine A mixture of 1-(4-trifluoromethoxyphenyl)-piperazine (4.4 g, 17.8 mmol), 2-(4-bromophenoxy)-tetrahydropyran (4.6 g, 17.8 mmol), palladium acetate (159 mg, 0.71 mmol), BINAP (666 mg, 1.07 mmol) and sodium tert-butoxide (2.2 g, 23.1 mmol) in toluene (40 ml) was refluxed under a nitrogen atmosphere for 5 hours. Ethyl acetate and water were added to the reaction mixture, which was stirred for a while. The insoluble substances were removed by filtration through Celite, and the filtrate was then extracted with ethyl acetate. The extract was washed with brine, dried over magnesium sulfate, and then filtered. The filtrate was concentrated under reduced pressure, and the residue was purified by silica gel column chromatography (n-hexane/ethyl acetate=20/1) to afford 1-[4-(tetrahydropyran-2-yloxy)phenyl]-4-(4-trifluoromethoxyphenyl)piperazine (2.7 g, yield 35%) as a white powder.
$^1$H-NMR (CDCl$_3$) δppm: 1.54-2.05 (6H, m), 3.21-3.34 (8H, m), 3.55-3.64 (1H, m), 3.89-3.99 (1H, m), 5.31-5.34 (1H, m), 6.90-7.03 (6H, m), 7.11-7.16 (2H, m).
This title compound was also prepared by the method described in Reference Example 185.

Reference Example 184

Preparation of 1-[4-(tetrahydropyran-2-yloxy)phenyl]-piperazine

A mixture of 2-(4-bromophenoxy)-tetrahydropyran (7.8 g, 30.3 mmol), piperazine (15.7 g, 180 mmol), palladium acetate (136 mg, 0.61 mmol), BINAP (567 mg, 0.91 mmol) and sodium tert-butoxide (3.8 g, 39.4 mmol) in toluene (50 ml) was refluxed under a nitrogen atmosphere for 2 hours. Ethyl acetate and water were added to the reaction mixture, which was stirred for a while. The insoluble substances were removed by filtration through Celite, and the filtrate was extracted with ethyl acetate. The extract was washed with brine, dried over magnesium sulfate, and then filtered. The filtrate was concentrated under reduced pressure, and the residue was purified by silica gel column chromatography (n-hexane/ethyl acetate=20/1) to afford 1-[4-(tetrahydropyran-2-yloxy)phenyl]piperazine (6.8 g, yield 85%) as a pale gray powder.
$^1$H-NMR (CDCl$_3$) δppm: 1.57-2.04 (6H, m), 3.00-3.06 (8H, m), 3.53-3.66 (1H, m), 3.89-3.99 (1H, m), 5.29-5.32 (1H, m), 6.84-6.90 (2H, m), 6.95-7.02 (2H, m).

Reference Example 185

Preparation of 1-[4-(tetrahydropyran-2-yloxy)phenyl]-4-(4-trifluoromethoxyphenyl)piperazine (an alternative method for synthesis of the compound in Reference Example 183)

A mixture of 1-[4-(tetrahydropyran-2-yloxy)phenyl]piperazine (2.1 g, 8.05 mmol) prepared in Reference Example 184, 4-trifluoromethoxy-1-bromobenzene (1.9 g, 8.05 mmol), palladium acetate (72 mg, 0.32 mmol), BINAP (300 mg, 0.48 mmol) and sodium tert-butoxide (1.0 g, 10.5 mmol) in toluene (30 ml) was refluxed under a nitrogen atmosphere for 5 hours. Ethyl acetate and water were added to the reaction mixture, which was stirred for a while. The insoluble substances were removed by filtration through Celite, and the filtrate was extracted with ethyl acetate. The extract was washed with brine, dried over magnesium sulfate, and then filtered. The filtrate was concentrated under reduced pressure, and the residue was purified by silica gel column chromatography (n-hexane/ethyl acetate=20/1) to afford 1-[4-(tetrahydropyran-2-yloxy)phenyl]-4-(4-trifluoromethoxyphenyl)piperazine (3.1 g, yield 90%) as a white powder.

Reference Example 186

Preparation of 4-[4-(4-trifluoromethoxyphenyl)piperazin-1-yl]phenol

A mixture of 1-[4-(tetrahydropyran-2-yloxy)phenyl]-4-(4-trifluoromethoxyphenyl)piperazine (2.65 g, 6.27 mmol) prepared in Reference Example 185 and pyridinium p-toluene sulfonate (473 mg, 1.88 mmol) in ethanol (50 ml) was stirred at 70° C. for 5 hours. The reaction mixture was concentrated under reduced pressure, and methylene chloride and a saturated sodium hydrogencarbonate aqueous solution were added to the residue, which was stirred for a while. The mixture was extracted with methylene chloride, and the extract was dried over magnesium sulfate, and then filtered. The filtrate was concentrated under reduced pressure, and the residue was purified by silica gel column chromatography (methylene chloride/ethyl acetate=10/1) to afford 4-[4-(4-trifluoromethoxyphenyl)-piperazin-1-yl]phenol (1.95 g, yield 92%) as a white powder.

$^1$H-NMR (CDCl$_3$) δppm: 3.19-3.24 (4H, m), 3.29-3.34 (4H, m), 4.50 (1H, s), 6.76-6.80 (2H, m), 6.87-6.97 (4H, m), 7.11-7.15 (2H, m).

Using corresponding starting materials, compounds of Reference Examples 187 and 188 were prepared in the same manner as described in Reference Example 186.

Reference Example 187

4-[4-(4-trifluoromethylphenyl)piperazin-1-yl]phenol a white powder, yield 82% $^1$H-NMR (CDCl$_3$) δppm: 3.18-3.23 (4H, m), 3.41-3.45 (4H, m), 4.47 (1H, s), 6.76-6.82 (2H, m), 6.87-7.00 (4H, m), 7.48-7.52 (2H, m).

Reference Example 188

4-[4-(4-chlorophenyl)piperazin-1-yl]phenol a white powder, yield 23% $^1$H-NMR (CDCl$_3$) δppm: 3.18-3.23 (4H, m), 3.28-3.32 (4H, m), 4.45 (1H, s), 6.77-6.81 (2H, m), 6.87-6.92 (4H, m), 7.21-7.24 (2H, m).

Reference Example 189

Preparation of tert-butyl 4-(4-trifluoromethoxyphenoxy)piperidine-1-carboxylate

Tert-butyl 4-hydroxypiperidine-1-carboxylate (56.5 g, 0.28 mol), 4-trifluoromethoxyphenol (50 g, 0.28 mol) and triphenylphosphine (108 g, 0.42 mol) were dissolved in THF (500 ml). Diethyl azodicarboxylate (65 ml, 0.42 mol) was added dropwise to this solution under reflux, and the mixture was refluxed for 5 hours. The reaction mixture was concentrated under reduced pressure, and the residue was purified by silica gel column chromatography (n-hexane/ethyl acetate=5/1) to afford tert-butyl 4-(4-trifluoromethoxyphenoxy)-piperidine-1-carboxylate (92 g, yield 91%) as a colorless oil.

$^1$H-NMR (CDCl$_3$) δppm: 1.47 (9H, s), 1.69-1.80 (2H, m), 1.85-1.96 (2H, m), 3.28-3.39 (2H, m), 3.64-3.75 (2H, m), 4.40-4.46 (1H, m), 6.85-6.92 (2H, m), 7.11-7.15 (2H, m).

Reference Example 190

Preparation of 4-(4-trifluoromethoxyphenoxy)-piperidine

Tert-butyl 4-(4-trifluoromethoxyphenoxy)-piperidine-1-carboxylate (92 g, 254.59 mmol) prepared in Reference Example 189 was dissolved in methylene chloride (100 ml). Trifluoroacetic acid (200 ml) was added dropwise to this solution at room temperature, and the mixture was stirred overnight. The reaction mixture was concentrated under reduced pressure, and the residue was then dissolved in methylene chloride, which was neutralized with a sodium hydroxide aqueous solution. The mixture was extracted with methylene chloride. The extract was washed with brine, dried over sodium sulfate, and then filtered. The filtrate was concentrated under reduced pressure, and the residue was then purified by silica gel column chromatography (methylene chloride/methanol=5/1) to afford 4-(4-trifluoromethoxyphenoxy)piperidine (55 g, yield 83%) as a white powder.

$^1$H-NMR (CDCl$_3$) δppm: 1.65-1.78 (2H, m), 2.00-2.07 (2H, m), 2.73-2.83 (2H, m), 3.12-3.21 (2H, m), 4.32-4.38 (2H, m), 6.85-6.92 (2H, m), 7.10-7.15 (2H, m).

Reference Example 191

Preparation of 1-[4-(tetrahydropyran-2-yloxy)phenyl]-4-(4-trifluoromethoxyphenoxy)piperidine A mixture of 4-(4-trifluoromethoxyphenoxy)piperidine (30.3 g, 0.116 mol) prepared in Reference Example 190, 2-(4-bromophenoxy)tetrahydropyran (30 g, 0.116 mol), palladium acetate (1.0 g, 4.64 mmol), BINAP (4.3 g, 6.96 mmol) and cesium carbonate (49 g, 0.151 mol) in toluene (300 ml) was refluxed under a nitrogen atmosphere for 30 hours. Ethyl acetate and water were added to the reaction mixture, which was stirred for a while. The insoluble substances were removed by filtration through Celite, and the filtrate was then extracted with ethyl acetate. The extract was washed with brine, dried over magnesium sulfate, and then filtered. The filtrate was concentrated under reduced pressure, and the residue was purified by silica gel column chromatography (n-hexane/ethyl acetate=20/1) to afford 1-[4-(tetrahydropyran-2-yloxy)phenyl]-4-(4-trifluoromethoxyphenoxy)piperidine (32.6 g, yield 64%) as a yellow powder.

$^1$H-NMR (CDCl$_3$) δppm: 1.55-1.75 (3H, m), 1.81-2.20 (7H, m), 2.95-3.04 (2H, m), 3.38-3.42 (2H, m), 3.55-3.66 (1H, m), 3.87-3.99 (1H, m), 4.36-4.45 (1H, m), 5.29-5.32 (1H, m), 6.89-7.01 (6H, m), 7.11-7.16 (2H, m).

Reference Example 192

Preparation of 4-[4-(4-trifluoromethoxyphenoxy)-piperidin-1-yl]phenol

A mixture of 1-[4-(tetrahydropyran-2-yloxy)phenyl]-4-(4-trifluoromethoxyphenoxy)piperidine (30.1 g, 68.8 mmol) prepared in Reference Example 191 and pyridinium p-toluene sulfonate (5.2 g, 20.6 mmol) in ethanol (450 ml) was stirred at 70° C. for 24 hours. The reaction mixture was concentrated under reduced pressure, and methylene chloride and a saturated sodium hydrogencarbonate aqueous solution were added to the residue, which was stirred for a while. The mixture was extracted with methylene chloride, and the extract was dried over magnesium sulfate, and then filtered. The filtrate was concentrated under reduced pressure, and the residue was purified by silica gel column chromatography (methylene chloride/ethyl acetate=10/1) to afford 4-[4-(4-trifluoromethoxyphenoxy)-piperidin-1-yl]phenol (22.9 g, yield 94%) as a a pale brown powder.

$^1$H-NMR (CDCl$_3$) δppm: 1.88-2.02 (2H, m), 2.06-2.16 (2H, m), 2.92-3.02 (2H, m), 3.30-3.39 (2H, m), 4.36-4.44 (1H, m), 4.74 (1H, s), 6.71-6.78 (2H, m), 6.85-6.94 (4H, m), 7.10-7.16 (2H, m).

Reference Example 193

Preparation of tert-butyl 4-[2-chloro-4-(tetrahydropyran-2-yloxy)phenyl]piperazine-1-carboxylate A mixture of tert-butyl piperazine-1-carboxylate (3.94 g, 21.6 mmol), 2-(4-bromo-3-chlorophenoxy)tetrahydropyran (5.61 g, 19.2 mol), palladium acetate (86.4 mg, 0.39 mmol), BINAP (172 mg, 0.58 mmol) and sodium tert-butoxide (2.4 g, 25.0 mmol) in toluene (40 ml) was refluxed under a nitrogen atmosphere for 2 hours. Ethyl acetate and water were added to the reaction mixture, which was stirred for a while. The insoluble substances were removed by filtration through Celite, and the filtrate was extracted with ethyl acetate. The extract was washed with brine, dried over magnesium sulfate, and then filtered. The filtrate was concentrated under reduced pressure, and the residue was purified by silica gel column chromatography (n-hexane/ethyl acetate=20/1) to afford tert-butyl 4-[2-chloro-4-(tetrahydropyran-2-yloxy)phenyl]piperazine-1-carboxylate (4.72 g, yield 62%) as a yellow oil.

$^1$H-NMR (CDCl$_3$) δppm: 1.48 (9H, s), 1.51-2.04 (6H, m), 2.88-2.93 (4H, m), 3.56-3.63. (5H, m), 3.83-3.94 (1H, m), 5.31-5.34 (1H, m), 6.88-6.96 (2H, m), 7.10-7.13 (1H, m)

Reference Example 194

Preparation of tert-butyl 4-(2-chloro-4-hydroxyphenyl)-piperazine-1-carboxylate

A mixture of tert-butyl 4-[2-chloro-4-(tetrahydropyran-2-yloxy)phenyl]piperazine-1-carboxylate (4.73 g, 11.9 mmol) prepared in Reference Example 193 and a catalytic amount of pyridinium p-toluene sulfonate in ethanol (50 ml) was stirred at 70° C. for 1 hour. The reaction mixture was concentrated under reduced pressure, and methylene chloride and saturated sodium hydrogencarbonate aqueous solution were added to the residue, which was stirred for a while. The resulting precipitates were collected by filtration, and dried in vacuo to afford tert-butyl 4-(2-chloro-4-hydroxyphenyl)piperazine-1-carboxylate (2.68 g, yield 72%) as a white powder.

$^1$H-NMR (CDCl$_3$) δppm: 1.49 (9H, s), 2.87-2.91 (4H, m), 3.55-3.60 (4H, m), 5.19 (1H, br), 6.68-6.74 (1H, m), 6.88-6.93 (2H, m).

Reference Example 195

Preparation of tert-butyl 4-(4-acetoxybenzoyl)-piperazine-1-carboxylate p-Acetoxybenzoic acid (11 g, 61.1 mmol) was dissolved in methylene chloride (100 ml), to which DMF (3 drops) and thionyl chloride (5.54 ml, 76.3 mmol) were added, and the mixture was heated under reflux for 2 hours. The mixture was cooled in an ice-bath, to which a solution of tert-butyl piperazine-1-carboxylate (10.3 g, 55.5 mmol) and pyridine (12 ml, 0.15 mol) in methylene chloride (100 ml) was added dropwise, and the mixture was stirred at room temperature for 2 hours. The reaction mixture was diluted with methylene chloride, and the mixture was washed with water, 10% hydrochloric acid, saturated sodium hydrogencarbonate aqueous solution and brine, dried over magnesium sulfate, and then filtered. The filtrate was concentrated under reduced pressure. The residue was purified by silica gel column chromatography (methylene chloride/ethyl acetate=20/1) to afford tert-butyl 4-(4-acetoxybenzoyl)piperazine-1-carboxylate (18.5 g, yield 87%) as a colorless crystalline powder.

$^1$H-NMR (CDCl$_3$) δppm: 1.47 (9H, s), 2.31 (3H, s), 3.46 (8H, br), 7.12-7.18 (2H, m), 7.41-7.46 (2H, m).

Reference Example 196

Preparation of tert-butyl 4-(4-hydroxybenzoyl)-piperazine-1-carboxylate

A mixture of tert-butyl 4-(4-acetoxybenzoyl)piperazine-1-carboxylate (18.5 g, 53.1 mmol) prepared in Reference Example 195 and potassium carbonate (370 mg, 2.65 mmol) in methanol (200 ml) was stirred at room temperature overnight. The reaction mixture was concentrated under reduced pressure, 5% hydrochloric acid and methylene chloride were added to the residue, and the mixture was vigorously stirred. The resulting precipitates were collected by filtration, and washed with water and methylene chloride, and then dried in vacuo to afford tert-butyl 4-(4-hydroxybenzoyl)piperazine-1-carboxylate (14.9 g, yield 92%) as a white powder.

$^1$H-NMR (CDCl$_3$) δppm: 1.48 (9H, s), 3.46 (4H, br), 3.60 (4H, br), 6.75-6.79 (2H, m), 7.22-7.28 (2H, m).

Reference Example 197

Preparation of 1-benzyl-4-[4-(tetrahydropyran-2-yloxy)phenyl]piperidin-4-ol

A solution of 2-(4-bromophenoxy)-tetrahydropyran (7.2 g, 28 mmol) in THF (70 ml) was cooled to −60° C., to which n-butyl lithium (1.53 M) hexane solution (20 ml, 30.8 mmol) was added dropwise, and the mixture was stirred for 30 minutes. Then, a solution of 1-benzyl-4-piperidone (5.3 g, 28 mmol) in THF (20 ml) was added dropwise to this mixture, which was stirred for 3 hours while being allowed to reach a temperature of 0° C. Saturated ammonium chloride aqueous solution was added to the reaction mixture, which was extracted with ethyl acetate. The extract was washed with brine, dried over magnesium sulfate, and then filtered. The filtrate was concentrated under reduced pressure. The residue was purified by silica gel column chromatography (n-hexane/ethyl acetate=20/1) to afford 1-benzyl-4-[4-(tetrahydropyran-2-yloxy)phenyl]piperidin-4-ol (5.27 g, yield 51%) as an orange-colored oil.

$^1$H-NMR (CDCl$_3$) δppm: 1.52-2.21 (11H, m), 2.41-2.52 (2H, m), 2.74-2.78 (2H, m), 3.57 (2H, s), 3.56-3.63 (1H, m), 3.83-3.96 (1H, m), 5.39-5.42 (1H, m), 6.98-7.04 (2H, m), 7.20-7.44 (7H, m).

Reference Example 198

Preparation of tert-butyl 4-(4-hydroxyphenyl)piperidine-1-carboxylate

A solution of 1-benzyl-4-[4-(tetrahydropyran-2-yloxy)phenyl]piperidin-4-ol (1.67 g, 4.55 mmol) prepared in Reference Example 197 in acetonitrile (45 ml) was cooled to −10° C., to which triethylsilane (2.9 ml, 18.2 mmol) and boron trifluoride diethyl ether complex (1.1 ml, 9.1 mmol) were added, and the mixture was stirred at room temperature for 2 days. Water was added to the reaction mixture, and the mixture was extracted with methylene chloride. The extract was dried over magnesium sulfate, and then filtered, and the filtrate was concentrated under reduced pressure. The residue was dissolved in ethanol (50 ml), to which a catalytic amount of 20% palladium hydroxide/carbon was added. The mixture was stirred at room temperature under an atmospheric pressure of hydrogen overnight. The reaction mixture was filtered through Celite, di-tert-butyl dicarbonate (1.1 ml, 4.78 mmol) was added to the filtrate, and the mixture was stirred at room temperature for 30 minutes. The reaction mixture was concentrated under reduced pressure, and the residue was purified by silica gel column chromatography (methylene chloride/methanol=50/1) to afford tert-butyl 4-(4-hydroxyphenyl)piperidine-1-carboxylate (1.07 g, yield 85%) as a colorless crystalline powder.

$^1$H-NMR (CDCl$_3$) δppm: 1.41-1.63 (2H, m), 1.49 (9H, s), 1.73-1.80 (2H, m), 2.50-2.62 (1H, m), 2.73-2.83 (2H, m), 4.19-4.24 (2H, m), 5.87 (1H, bs), 6.76-6.81 (2H, m), 7.02-7.08 (2H, m).

Reference Example 199

Preparation of tert-butyl 4-[3-(tetrahydropyran-2-yloxy)phenyl]piperazine-1-carboxylate A mixturte of tert-butyl piperazine-1-carboxylate (2.94 g, 15.8 mmol), 2-(3-bromophenoxy)tetrahydropyran (3.69 g, 14.4 mmol), palladium acetate (64 mg, 0.29 mmol), BINAP (285 mg, 0.43 mmol) and sodium tert-butoxide (1.8 g, 18.7 mmol) in toluene (40 ml) was refluxed under a nitrogen atmosphere for 2 hours. Ethyl acetate and water were added to the reaction mixture, which was stirred for a while. The insoluble substances were removed by filtration through Celite, and the filtrate was then extracted with ethyl acetate. The extract was washed with brine, dried over magnesium sulfate, and then filtered. The filtrate was concentrated under reduced pressure, and the residue was purified by silica-gel column chromatography (n-hexane/ethyl acetate=20/1) to afford tert-butyl 4-[3-(tetrahydropyran-2-yloxy)phenyl]piperazine-1-carboxylate (5.3 g, yield 99%) as a colorless oil.

$^1$H-NMR (CDCl$_3$) δppm: 1.48 (9H, s), 1.52-2.04 (6H, m), 3.10-3.15 (4H, m), 3.53-3.64 (5H, m), 3.87-3.94 (1H, m), 5.38-5.41 (1H, m), 6.53-6.63 (3H, m), 7.12-7.19 (1H, m).

Reference Example 200

Preparation of tert-butyl 4-(3-hydroxyphenyl)piperazine-1-carboxylate

A mixture of tert-butyl 4-[3-(tetrahydropyran-2-yloxy)phenyl]piperazine-1-carboxylate (5.20 g, 14.4 mmol) prepared in Reference Example 199 and a catalytic amount of pyridinium p-toluene sulfonate in ethanol (100 ml) was stirred at 70° C. for 1.5 hours. The reaction mixture was concentrated under reduced pressure, and methylene chloride and a saturated sodium hydrogencarbonate aqueous solution were added to the residue, which was stirred for a while. The resulting precipitates were collected by filtrasion, and then dried in vacuo to afford tert-butyl 4-(3-hydroxyphenyl)piperazine-1-carboxylate (3.73 g, yield 93%) as a a pale brown powder.

$^1$H-NMR (CDCl$_3$) δppm: 1.49 (9H, s), 3.09-3.14 (4H, m), 3.54-3.59 (4H, m), 5.38 (1H, br), 6.33-6.41 (2H, m), 6.47-6.52 (1H, m), 7.08-7.15 (1H, m)

Reference Example 201

Preparation of 3-methyl-2-methylene butylaldehyde 3-methyl-2-methylene butylaldehyde was prepared according to the method described in Journal of American Chemical Society, 1957, p. 3267 (J. Am. Chem. Soc., 3267, 1957), that is, a mixture of isovaleraldehyde (100 ml, 932 mmol), 37% formalin (83.8 ml, 1120 mmol) and dimethylamine hydrochloride (91.2 g, 1120 mmol) was stirred at 70° C. for 30 hours. The mixture was steam distilled to separate the fraction, and thus obtained aqueous layer was extracted with diethyl ether. The extracts were combined, dried over sodium sulfate, and filtered. The filtrate was concentrated under reduced pressure. The residue was distilled to afford 3-methyl-2-methylene butylaldehyde (65.5 g, yield 72%) as a colorless oil. boiling point: 105-115° C.

$^1$H-NMR (CDCl$_3$) δppm: 1.08 (6H, d, J=6.9 Hz), 2.75-2.89 (1H, m), 5.95 (1H, s), 6.24 (1H, s), 9.53 (1H, s).

Reference Example 202

Preparation of 3-methyl-2-methylene-butan-1-ol

A solution of 3-methyl-2-methylene butylaldehyde (65 g, 668 mmol) prepared in Reference Example 201 in THF (30 ml) was added dropwise to a suspension of lithium aluminum hydride (14.15 g, 373 mmol) in THF (1000 ml) while cooling in an ice-bath, and the mixture was allowed to return to room temperature, and stirred for 2 hours. While cooling, water, 15% sodium hydroxide aqueous solution, and then water were added to the reaction mixture, which was filtered. The filtrate was dried over sodium sulfate. After filtration, the filtrate was concentrated under reduced pressure to afford 3-methyl-2-methylenebutan-1-ol (61.5 g, yield 93%) as a colorless oil.

$^1$H-NMR (CDCl$_3$) δppm: 1.07 (6H, d, J=6.9 Hz), 1.42 (1H, t, J=6.1 Hz), 2.25-2.43 (1H, m), 4.13 (2H, d, J=6.1 Hz), 4.84-4.93 (1H, m), 4.98-5.05 (1H, m).

Reference Example 203

Preparation of 2-methoxymethoxymethyl-3-methyl-1-butene

Chloromethyl methyl ether (98 ml, 1292 mmol) and N-ethyldiisopropylamine (234 ml, 1344 mmol) were added to a solution of 3-methyl-2-methylenebutane-1-ol (61.5 g, 615 mmol) prepared in Reference Example 202 in THF (500 ml) while cooling in an ice-bath, and the mixture was stirred at room temperature for 22 hours. The reaction mixture was filtered, and the filtrate was concentrated under reduced pressure. The residue was dissolved in diethyl ether, and the mixture was washed with water and brine, dried over sodium sulfate. After filtration, the filtrate was concentrated under reduced pressure to afford 2-methoxymethoxymethyl-3-methyl-1-butene (89 g, quantitative) as a colorless oil.

¹H-NMR (CDCl₃) δppm: 1.07 (6H, d, J=6.9 Hz), 2.25-2.41 (1H, m), 3.39 (3H, s), 4.05 (2H, s), 4.65 (2H, s), 4.87-4.95 (1H, m), 5.00-5.05 (1H, m).

Reference Example 204

Preparation of 2-methylenebutylaldehyde

A mixture of butylaldehyde (100 ml, 1110 mmol), 37% formalin (99.8 ml, 1330 mmol) and dimethylamine hydrochloride (108.6 g, 1330 mmol) was stirred at 70° C. for 23 hours. The mixture was steam distilled to separate the fraction, and thus obtained aqueous layer was extracted with diethyl ether. The extracts were combined, dried over sodium sulfate. After filtration, the filtrate was concentrated under reduced pressure. The residue was distilled to afford 2-methylenebutylaldehyde (66.9 g, yield 72%) as a colorless oil.

boiling point: 70-93° C. ¹H-NMR (CDCl₃) δppm: 1.08 (3H, t, J=7.5 Hz), 2.27 (2H, q, J=7.5 Hz), 5.98 (1H, s), 6.25 (1H, s), 9.56 (1H, s).

Reference Example 205

Preparation of 2-methylene-1-butanol

2-Methylenebutylaldehyde (66.9 g, 796 mmol) prepared in Reference Example 204 was added dropwise to a suspension of lithium aluminum hydride (15.1 g, 398 mmol) in THF (1000 ml) while cooling in an ice-bath, and the mixture was stirred for 1 hour. Water, 15% sodium hydroxide aqueous solution and then water were added to the reaction mixture, which was filtered, and the filtrate was dried over sodium sulfate. After filtration, and the filtrate was concentrated under reduced pressure to afford 2-methylene-1-butanol (65.1 g, yield 95%) as a colorless oil.

¹H-NMR (CDCl₃) δppm: 1.07 (3H, t, J=7.5 Hz), 1.44 (1H, t, J=6.0 Hz), 2.13 (2H, q, J=7.5 Hz), 4.09 (2H, d, J=6.0 Hz), 4.82-4.93 (1H, m), 4.98-5.07 (1H, m).

Reference Example 206

Preparation of 2-methoxymethoxymethyl-1-butene

Chloromethyl methyl ether (103.4 ml, 1363 mmol) and N-ethyldiisopropylamine (247.2 ml, 1419 mmol) were added to a solution of 2-methylene-1-butanol (65.1 g, 757 mmol) prepared in Reference Example 205 in THF (750 ml) while cooling in an ice-bath, and the mixture was stirred at room temperature for 3 days. The reaction mixture was filtered, and the filtrate was concentrated under reduced pressure. The residue was dissolved in diethyl ether, and the mixture was washed with water and brine, dried over sodium sulfate, and filtered. The filtrate was concentrated under reduced pressure to afford 2-methoxymethoxymethyl-1-butene (98 g, quantitative) as a colorless oil.

¹H-NMR (CDCl₃) δppm: 1.07 (3H, t, J=7.5 Hz), 2.09 (2H, q, J=7.5 Hz), 3.38 (3H, s), 4.01 (2H, s), 4.64 (2H, s), 4.86-4.95 (1H, m), 5.00-5.05 (1H, m).

Reference Example 207

Preparation of tert-butyl 4-[2-oxo-2-(4-oxopiperidin-1-yl)ethyl]piperazine-1-carboxylate 1-(2-Chloroacetyl)piperidin-4-one (5.17 g, 29.4 mmol) was dissolved in acetonitrile (50 ml). To this solution, tert-butyl piperazine-1-carboxylate (5.48 g, 29.4 mmol) and N-ethyldiisopropylamine (6.2 ml, 35.3 mmol) were added, and the mixture was heated under reflux for 2 hours. The reaction mixture was allowed to return to room temperature, to which water was added, and the mixture was extracted with ethyl acetate. The extract was washed with brine, dried over magnesium sulfate, and then filtered. The filtrate was concentrated under reduced pressure, and the residue was purified by silica gel column chromatography (methylene chloride/methanol=100/1) to afford tert-butyl 4-[2-oxo-2-(4-oxopiperidin-1-yl)ethyl]piperazine-1-carboxylate (6.49 g, yield 68%) as a pale yellow crystalline powder.

¹H-NMR (CDCl₃) δppm: 1.46 (9H, s), 2.44-2.54 (8H, m), 3.28 (2H, s), 3.42-3.47 (4H, m), 3.85-3.90 (4H, m).

Reference Example 208

Preparation of 4-methyl-4-pentenyl acetate

Potassium tert-butoxide (9.4 g, 84 mmol) was added to a mixture of methyltriphenylphosphonium bromide (30 g, 84 mmol) in THF (300 ml), and the mixture was stirred at room temperature for 40 minutes. To the mixture a solution of 4-oxopentyl acetate (9.9 g, 68.8 mmol) in THF (30 ml) was gradually added dropwise while cooling in an ice-bath, and the mixture was stirred at room temperature for 2 hours. The reaction mixture was poured into ice water, and extracted with diethyl ether twice. The extracts were combined, washed with brine, and dried over magnesium sulfate. After filtration, the filtrate was concentrated under reduced pressure. The residue was purified by silica gel column chromatography (n-hexane/ethyl acetate=4/1) to afford 4-methyl-4-pentenyl acetate (5.9 g, yield 60.4%) as a colorless oil.

¹H-NMR (CDCl₃) δppm: 1.70-1.86 (5H, m), 2.00-2.14 (5H, m), 4.07 (2H, t, J=6.7 Hz), 4.69 (1H, s), 4.74 (1H, s).

Reference Example 209

Preparation of benzyl 4-(2-methyl-2-oxiranylmethyl)-piperazine-1-carboxylate

Trimethylsulfoxonium iodide (1.96 g, 8.91 mmol) was added to a suspension of sodium hydride (0.37 g, 9.32 mmol) in DMSO (20 ml) while cooling in an ice-bath, and the mixture was stirred at room temperature for 30 minutes. To the mixture a solution of benzyl 4-(2-oxopropyl)piperazine-1-carboxylate (2.24 g, 8.10 mmol) in DMSO (10 ml) was added, and the mixture was stirred at room temperature for 1 hour. The reaction mixture was poured into ice water, and extracted with diethyl ether. The extract was washed with water, dried over magnesium sulfate, and then concentrated under reduced pressure to afford benzyl 4-(2-methyl-2-oxiranylmethyl)piperazine-1-carboxylate (1.51 g, yield 64%) as a pale yellow oil.

¹H-NMR (CDCl₃) δppm: 1.37 (3H, s), 2.27-2.63 (8H, m), 3.44-3.63 (4H, m), 5.13 (2H, s), 7.29-7.44 (5H, m).

Reference Example 210

Preparation of tert-butyl 4-(2-methyl-2-oxiranylmethyl)homopiperazine-1-carboxylate Trimethylsulfoxonium iodide (22.95 g, 104 mmol) was gradually added to a suspension of sodium hydride (4.3 g, 109 mmol) in DMSO (200 ml), and the mixture was stirred at room temperature for 2 hours. To which a solution tert-butyl 4-(2-oxopropyl)homopiperazine-1-carboxylate (24.3 g, 94.8 mmol) prepared in Reference Example 10 in DMSO (25 ml) was gradually added dropwise, and the mixture was stirred at room temperature for 1 hour. The reaction mixture was poured into ice water, and extracted with diethyl ether. The extract was washed with water, and dried over magnesium sulfate. After filtration, the filtrate was concentrated under reduced pressure. The residue was purified by silica gel column chromatography (methylene chloride/methanol=100/1) to afford tert-butyl 4-(2-methyl-2-oxiranylmethyl)homopiperazine-1-carboxylate (15.38 g, yield 60%) as a pale yellow oil.

$^1$H-NMR (CDCl$_3$) δppm: 1.38 (3H, s), 1.43 (9H, s), 1.69-1.90 (2H, m), 2.40-2.75 (8H, m), 3.36-3.55 (4H, m).

Reference Example 211

Preparation of tert-butyl 4-[2-(2-methyl-2-oxiranyl)-ethyl]piperazine-1-carboxylate Trimethylsulfoxonium iodide (7.8 g, 35 mmol) was gradually added to a suspension of sodium hydride (1.2 g, 35 mmol) in DMSO (120 ml), under a nitrogen atmosphere, and the mixture was stirred at room temperature for 2 hours. To which a solution of tert-butyl 4-(3-oxobutyl)piperazine-1-carboxylate (6.1 g, 23.8 mmol) in DMSO (10 ml) was gradually added dropwise, and the mixture was stirred at room temperature for 1.5 hours, and then at 50 to 60° C. for 1.5 hours. The reaction solution was allowed to return to room temperature, poured into iced water, and extracted with ethyl acetate three times. The extracts were combined, washed with water three times and then washed with a saturated saline solution, and dried over sodium sulfate. After filtration, the filtrate was concentrated under a reduced pressure to afford tert-butyl 4-[2-(2-methyl-2-oxiranyl) ethyl]piperazine-1-carboxylate (5.6 g, 87%) as a light yellow oil.

$^1$H-NMR (CDCl$_3$) δppm: 1.33 (3H, s), 1.46 (9H, s), 1.66-1.85 (2H, m), 2.28-2.50 (6H, m), 2.55-2.66 (2H, m), 3.34-3.47 (4H, m).

Reference Example 212

Preparation of 1-(2-methyl-2-oxiranylmethyl)-4-(4-trifluoromethylphenyl)piperazine Trimethylsulfoxonium iodide (2.5 g, 11.6 mmol) was gradually added to a suspension of sodium hydride (484 mg, 12.1 mmol) in dimethylsulfoxide (30 ml), and the mixture was stirred at room temperature for 1 hour. To which a solution of 1-{4-(4-trifluoromethylphenyl)piperazin-1-yl}propan-2-one (3.4 g, 11.9 mmol) in dimethylsulfoxide (20 ml) was added, and the mixture was stirred at room temperature for 1 hour. The reaction mixture was poured into iced water, and extracted with diethyl ether. The organic phase was washed with a saturated saline solution, dried over magnesium sulfate, and then filtered. The resultant filtrate was concentrated under a reduced pressure, and the residue was purified by silica gel column chromatography (methylene chloride/methanol=100/1) to afford 1-(2-methyl-2-oxiranylmethyl)-4-(4-trifluoromethylphenyl)piperazine (3.2 g, yield 98%)as a light yellow powder.

$^1$H-NMR (CDCl$_3$) δppm: 1.40 (3H, s), 2.33 (1H, d, J=13.0 Hz), 2.53-2.73 (7H, m), 3.26-3.30 (4H, m), 6.91 (2H, d, J=8.7 Hz), 7.47 (2H, d, J=8.7 Hz)

Compounds of Reference Examples 213 to 217 were prepared in the same manner as described in Reference Example 212.

Reference Example 213

1-(2-methyl-2-oxiranylmethyl)-4-(4-biphenylyl)piperazine a pale yellow powder, yield 99% $^1$H-NMR (CDCl$_3$) δppm: 1.41 (3H, s), 2.37 (1H, d, J=12.9 Hz), 2.58-2.76 (7H, m), 3.23-3.28 (4H, m), 6.97-7.01 (2H, m), 7.24-7.30 (1H, m), 7.37-7.43 (2H, m), 7.49-7.58 (4H, m).

Reference Example 214

1-(2-methyl-2-oxiranylmethy)-4-(4-chlorophenyl)-piperazine a pale yellow powder, yield 99% $^1$H-NMR (CDCl$_3$) δppm: 1.39 (3H, s), 2.34 (1H, d, J=12.9 Hz), 2.54-2.73 (7H, m), 3.14-3.18 (4H, m), 6.81-6.87 (2H, m), 7.16-7.22 (2H, m).

Reference Example 215

1-(2-methyl-2-oxiranylmethyl)-4-(4-trifluoromethoxy-phenyl)piperazine a pale yellow powder, yield 99% $^1$H-NMR (CDCl$_3$) δppm: 1.40 (3H, s), 2.34 (1H, d, J=12.9 Hz), 2.54-2.73 (7H, m), 3.16-3.20 (4H, m), 6.85-6.92 (2H, m), 7.08-7.13 (2H, m).

Reference Example 216

1-(2-methyl-2-oxiranylmethyl)-4-(pyridine-2-yl)-piperazine a pale yellow powder, yield 99% $^1$H-NMR (CDCl$_3$) δppm: 1.41 (3H, s), 2.35 (1H, d, J=12.9 Hz), 2.50-2.69 (7H, m), 3.48-3.60 (4H, m), 6.59-6.66 (2H, m), 7.43-7.50 (1H, m), 8.17-8.20 (1H, m).

Reference Example 217

1-(2-methyl-2-oxiranylmethyl)-4-(pyrimidin-2-yl)-piperazine a pale yellow powder, yield 99% $^1$H-NMR (CDCl$_3$) δppm: 1.41 (3H, s), 2.36 (1H, d, J=12.9 Hz), 2.45-2.64 (7H, m), 3.81-3.85 (4H, m), 6.47 (1H, t, J=4.8 Hz), 8.30 (2H, d, J=4.8 Hz).

Reference Example 218

Preparation of tert-butyl N-methyl-[1-(2-methyl-2-oxiranylmethyl)piperidin-4-yl]carbamate Trimethylsulfoxonium iodide (1.96 g, 8.89 mmol) was gradually added to a suspension of sodium hydride (372 mg, 9.32 mmol) in dimethylsulfoxide (20 ml), and the mixture was stirred at room temperature for 1.5 hours. To which a solution of tert-butyl N-methyl-[1-(2-oxopropyl)piperidin-4-yl]carbamate (2.3 g, 8.5 mmol) in dimethylsulfoxide (20 ml) was added, and the mixture was stirred at room temperature for 2 hours. The reaction mixture was poured into iced water, and extracted with diethyl ether. The extract was washed with a saturated saline solution, dried over magnesium sulfate, and then filtered. The resultant filtrate was concentrated under a reduced pressure, and the residue was purified by silica gel column chromatography (methylene chloride/methanol=100/1) to afford tert-butyl N-methyl-[1-(2-methyl-2-oxiranylmethyl)piperidin-4-yl]carbamate (2.1 g, yield 86%) as a light yellow oily material.

$^1$H-NMR (CDCl$_3$) δppm: 1.36 (3H, s), 1.46 (9H, s), 1.55-1.79 (5H, m), 1.97-2.13 (2H, m), 2.30 (1H, d, J=12.9 Hz), 2.49 (1H, d, J=12.9 Hz), 2.59 (2H, s), 2.74 (3H, s), 2.88-3.06 (2H, m).

Reference Example 219

Preparation of 3-(2-methyl-2-oxiranyl)-pyridine

Using 3-acetylpyridine (8 g, 66.1 mmol), a light brown oil of 3-(2-methyl-2-oxiranyl)pyridine (7 g, yield 78.4%) was produced in the same manner as in Reference Example 218.

$^1$H-NMR (CDCl$_3$) δppm: 1.74 (3H, s), 2.82 (1H, d, J=5.2 Hz), 3.02 (1H, d, J=5.2 Hz), 7.21-7.33 (1H, m), 7.58-7.70 (1H, m), 8.54 (1H, dd, 1.6 Hz, 4.8 Hz), 8.65 (1H, d, J=2.3 Hz).

Reference Example 220

Preparation of tert-butyl 1-oxa-6-azaspiro[2,5]octane-6-carboxylate

Trimethylsulfoxonium iodide (70 g, 0.32 mol) was gradually added to a suspension of sodium hydride (13.3 g, 0.33 mol) in dimethylsulfoxide (600 ml), and the mixture was stirred at room temperature for 1 hour. To which tert-butyl 4-oxo-piperidine-1-carboxylate (58 g, 0.291 mol) was gradually added, and the mixture was stirred at 55° C. for 1 hour. The reaction mixture was poured into iced water, and extracted with diethyl ether. The organic phase was washed with a saturated saline solution, dried over magnesium sulfate, and then filtered. The resultant filtrate was concentrated under a reduced pressure, and the residue was crystallized from n-hexane to afford tert-butyl 1-oxa-6-azaspiro[2,5]octane-6-carboxylate (61.7 g, yield 96%) as a white powder.

$^1$H-NMR (CDCl$_3$) δppm: 1.40-1.53 (2H, m), 1.47 (9H, s), 1.72-1.85 (2H, m), 2.69 (2H, s), 3.37-3.48 (2H, m), 3.67-3.77 (2H, m).

Reference Example 221

Preparation of tert-butyl 4-[2-(1-oxa-6-azaspiro[2,5]-octan-6-yl)-2-oxoethyl]piperazine-1-carboxylate Trimethylsulfoxonium iodide (2.02 g, 9.20 mmol) was gradually added to a suspension of sodium hydride (385 mg, 9.64 mmol) in dimethylsulfoxide (50 ml), and the resultant mixture was stirred at room temperature for 1 hour. To which tert-butyl 4-[2-oxo-2-(4-oxopiperidin-1-yl)ethyl]piperazine-1-carboxylate (2.85 g, 8.76 mmol) in DMSO (10 ml) was added, and the mixture was stirred at room temperature for 2 hours, and stirred at 55° C. for 1 hour. The reaction mixture was poured into iced water, and extracted with diethyl ether. The organic phase was washed with a saturated saline solution, dried over magnesium sulfate, and filtered. The resultant filtrate was concentrated under a reduced pressure to afford tert-butyl 4-[2-(1-oxa-6-azaspiro[2,5]octan-6-yl)-2-oxoethyl]piperazine-1-carboxylate (2.97 g, yield 99%) as a white solid.

$^1$H-NMR (CDCl$_3$) δppm: 1.45-1.54 (1H, m), 1.48 (9H, s), 1.78-1.93 (1H, m), 2.44-2.49 (4H, m), 2.62 (2H, s), 2.73 (2H, s), 3.42-3.47 (2H, m), 3.52-3.68 (1H, m), 3.77-3.88 (1H, m).

Reference Example 222

Preparation of 6-(4-trifluoromethylphenyl)-1-oxa-6-azaspiro[2,5]octane

Trimethylsulfoxonium iodide (2.00 g, 9.02 mmol) was gradually added to a suspension of sodium hydride (361 mg, 9.02 mmol) in dimethylsulfoxide (30 ml), and the mixture was stirred at room temperature for 1 hour. To which a solution of 1-(4-trifluoromethylphenyl)piperidin-4-one (2.00 g, 8.2 mmol) in DMSO (10 ml) was added, and the mixture was stirred overnight. The reaction mixture was poured into ice water, and extracted with diethyl ether. The extract was washed with brine, dried over sodium sulfate, and then filtered. The residue was purified by silica gel column chromatography (n-hexane/ethyl acetate=5/1) to afford 6-(4-trifluoromethylphenyl)-1-oxa-6-azaspiro[2,5]octane (1.51 g, yield 72%) as a pale yellow crystalline powder.

$^1$H-NMR (CDCl$_3$) δppm: 1.54-1.65 (2H, m), 1.91-2.04 (2H, m), 2.54-2.59 (2H, m), 2.73 (2H, s), 3.38-3.48 (1H, m), 3.52-3.62 (1H, m), 6.95 (2H, d, J=8.7 Hz), 7.48 (2H, d, J=8.7 Hz).

Reference Example 223

Preparation of 3-(2-methyl-2-oxyranyl)propyl acetate m-Chloroperbenzoic acid (12.3 g, 71.30 mmol) was gradually added to a solution of 4-methyl-4-pentenyl acetate (5.9 g, 41.5 mmol) prepared in Reference Example 208 in methylene chloride (60 ml) while cooling in an ice-bath, and the mixture was stirred at room temperature for 2 hours. Saturated sodium sulfite aqueous solution and saturated sodium carbonate aqueous solution were added to the mixture while cooling in an ice-bath, which was stirred for 30 minutes, and the organic layer was separated. The aqueous layer was extracted with methylene chloride. The extracts were combined, washed with saturated sodium bicarbonate aqueous solution and brine, and dried over sodium sulfate. After filtration, the filtrate was concentrated under reduced pressure to afford 3-(2-methyl-2-oxyranyl)propyl acetate (6.9 g, quantitative) as a colorless oil.

$^1$H-NMR (CDCl$_3$) δppm: 1.33 (3H, s), 1.56-1.79 (4H, m), 2.05 (3H, s), 2.56-2.70 (2H, m), 4.08 (2H, t, J=6.5 Hz).

Reference Example 224

Preparation of 1-ethyl-5-[2-(2-methyl-2-oxiranyl)ethyl]-1H-tetrazole m-Chloroperbenzoic acid (1.97 g, 7.99 mmol) was gradually added to a solution of 1-ethyl-5-(3-methyl-3-butenyl)-1H-tetrazole (0.95 g, 5.71 mmol) in methylene chloride (20 ml) while cooling in an ice-bath, and the mixture was stirred at room temperature for 21 hours. To the reaction mixture, sodium thiosulfate aqueous solution and sodium hydrogencarbonate aqueous solution were added, and the resulting mixture was filtered. The organic layer was separated, washed with sodium hydrogencarbonate aqueous solution, dried over magnesium sulfate. After filtration, the filtrate was concentrated under reduced pressure to afford 1-ethyl-5-[2-(2-methyl-2-oxiranyl)ethyl]-1H-tetrazole (1.2 g, quantitative) as a pale yellow oil.

$^1$H-NMR (CDCl$_3$) δppm: 1.40 (3H, s), 1.55 (3H, t, J=7.3 Hz), 2.00-2.16 (1H, m), 2.20-2.37 (1H, m), 2.66 (2H, s), 2.78-2.98 (2H, m), 4.32 (2H, q, J=7.3 Hz).

Using corresponding starting materials, compounds of Reference Examples 225 and 226 were prepared in the same manner as described in Reference Example 224.

Reference Example 225

1-phenyl-5-[2-(2-methyl-2-oxiranyl)ethyl]-1H-tetrazole yield 100% $^1$H-NMR (CDCl$_3$) δppm: 1.32 (3H, s), 2.01-2.28 (2H, m), 2.59 (2H, s), 2.92-2.99 (2H, m), 7.43-7.47 (2H, m), 7.58-7.63 (3H, m).

Reference Example 226

1-(4-chlorophenyl)-5-[2-(2-methyl-2-oxiranyl)ethyl]-1H-tetrazole yield 100% $^1$H-NMR (CDCl$_3$) δppm: 1.33 (3H, s), 2.00-2.12 (1H, m), 2.19-2.31 (1H, m), 2.60 (2H, s), 2.90-2.97 (2H, m), 7.39-7.45 (2H, m), 7.56-7.62 (2H, m).

Reference Example 227

Preparation of 1-(2-methyl-2-oxiranylmethyl)-1,4-dihydrobenzo[d][1,3]oxazin-2-one m-Chloroperbenzoic acid (13.76 g, 55.81 mmol) was added to a solution of 1-(2-methyl-2-propenyl)-1,4-dihydrobenzo[d][1,3]oxazin-2-one (7.09 g, 34.88 mmol) in methylene chloride (150 ml), and the mixture was stirred at room temperature for 24 hours. To the mixture, sodium thiosulfate aqueous solution and sodium hydrogencarbonate aqueous solution were added, and the resulting mixture was filtered. The organic layer was separated, washed with sodium hydrogencarbonate aqueous solution, dried over magnesium sulfate. After filtration, the filtrate was concentrated under reduced pressure. The residue was purified by silica gel column chromatography (n-hexane/ethyl acetate=4/1) to afford 1-(2-methyl-2-oxiranylmethyl)-1,4-dihydrobenzo[d][1,3]oxazin-2-one (5.13 g, 67%) as a pale yellow oil.

$^1$H-NMR (CDCl$_3$) δppm: 1.39 (3H, s), 2.70 (1H, d, J=4.4 Hz), 2.78 (1H, d, J=4.4 Hz), 3.79 (1H, d, J=15.5 Hz), 4.51 (1H, d, J=15.5 Hz), 5.23 (2H, s), 7.04-7.13 (2H, m), 7.21-7.27 (1H, m), 7.29-7.38 (1H, m).

Reference Example 228

Preparation of 3-(2-methyl-2-oxiranylmethyl)-3H-benzoxazol-2-one m-Chloroperbenzoic acid (1.66 g, 9.65 mmol) was added to a mixture of 3-(2-methyl-2-propenyl)-3H-benzoxazol-2-one (1.66 g, 8.77 mmol) in methylene chloride (30 ml) while cooling in an ice-bath, and the mixture was stirred at room temperature overnight. The reaction mixture was filtered, and the filtrate was washed with a 20% sodium sulfite aqueous solution, saturated sodium bicarbonate aqueous solution and brine, and dried over magnesium sulfate. After filtration, the filtrate was concentrated under reduced pressure. The residue was treated with methylene chloride/n-hexane, and the resulting precipitates were collected by filtration to afford 3-(2-methyl-2-oxiranylmethyl)-3H-benzoxazol-2-one (1.78 g, yield 99%) as a white powder.

$^1$H-NMR (CDCl$_3$) δppm: 1.38 (3H, s), 2.73 (1H, d, J=4.3 Hz), 2.81 (1H, d, J=4.3 Hz), 3.68 (1H, d, J=15.0 Hz), 4.26 (1H, d, J=15.0 Hz), 7.09-7.29 (4H, m).

Using corresponding starting materials, compounds of Reference Examples 229 to 232 were prepared in the same manner as described in Reference Example 228.

Reference Example 229

5-chloro-3-(2-methyl-2-oxiranylmethyl)-3H-benzoxazol-2-one yield 93% $^1$H-NMR (CDCl$_3$) δppm: 1.38 (3H, s), 2.75 (1H, d, J=4.2 Hz), 2.79 (1H, d, J=4.2 Hz), 3.60 (1H, d, J=15.1 Hz), 4.28 (1H, d, J=15.1 Hz), 7.05-7.16 (2H, m), 7.20-7.27 (1H, m).

Reference Example 230

5-fluoro-3-(2-methyl-2-oxiranylmethyl)-3H-benzoxazol-2-one yield 97% $^1$H-NMR (CDCl$_3$) δppm: 1.38 (3H, s), 2.75 (1H, d, J=4.3 Hz), 2.80 (1H, d, J=4.3 Hz), 3.60 (1H, d, J=15.1 Hz), 4.29 (1H, d, J=15.1 Hz), 6.75-6.85 (1H, m), 7.01 (1H, dd, J=2.6 Hz, 7.9 Hz), 7.13 (1H, dd, J=4.2 Hz, 8.8 Hz).

Reference Example 231

5-phenyl-3-(2-metyl-2-oxiranylmethyl)-3H-benzoxazol-2-one yield 92% $^1$H-NMR (CDCl$_3$) δppm: 1.40 (3H, s), 2.74 (1H, d, J=4.3 Hz), 2.82 (1H, d, J=4.3 Hz), 3.70 (1H, d, J=15.0 Hz), 4.32 (1H, d, J=15.0 Hz), 7.25 (1H, d, J=8.4 Hz), 7.29-7.49 (5H, m), 7.57 (2H, dd, J=1.6 Hz, 8.5 Hz).

Reference Example 232

5-bromo-3-(2-methyl-2-oxiranylmethyl)-3H-benzoxazol-2-one yield 80% $^1$H-NMR (CDCl$_3$) δppm: 1.38 (3H, s), 2.75 (1H, d, J=4.2 Hz), 2.79 (1H, d, J=4.2 Hz), 3.61 (1H, d, J=15.1 Hz), 4.27 (1H, d, J=15.1 Hz), 7.08 (1H, d, J=8.5 Hz), 7.18-7.31 (1H, m), 7.38 (1H, d, J=1.9 Hz).

Reference Example 233

Preparation of 1-(2-methyl-2-oxiranylmethyl)-3-phenyl-1,3-dihydrobenzimidazol-2-one Using 1-(2-methyl-2-propenyl)-3-phenyl-1,3-dihydrobenzimidazol-2-one (720 mg, 2.72 mmol), 1-(2-methyl-2-oxiranylmethyl)-3-phenyl-1,3-dihydrobenzimidazol-2-one (758 mg, yield 99%) as a pale yellow oil was prepared in the same manner as described in Reference Example 228.

$^1$H-NMR (CDCl$_3$) δppm: 1.40 (3H, s), 2.73 (1H, d, J=4.5 Hz), 2.86 (1H, d, J=4.5 Hz), 3.82 (1H, d, J=15.0 Hz), 4.38 (1H, d, J=15.0 Hz), 7.02-7.30 (4H, m), 7.34-7.45 (1H, m), 7.50-7.57 (4H, m).

Using corresponding starting materials, compounds of Reference Examples 234 to 245 were prepared in the same manner as described in Reference Example 233.

Reference Example 234

1-(4-fluorophenyl)-3-(2-methyl-2-oxiranylmethyl)-1,3-dihydrobenzimidazol-2-one yield 96% $^1$H-NMR (CDCl$_3$) δppm: 1.40 (3H, s), 2.73 (1H, d, J=4.5 Hz), 2.85 (1H, d, J=4.5 Hz), 3.81 (1H, d, J=15.0 Hz), 4.38 (1H, d, J=15.0 Hz), 7.00-7.30 (6H, m), 7.43-7.57 (2H, m).

Reference Example 235

1-(1-tert-butoxycarbonylpiperidin-4-yl)-3-(2-methyl-2-oxiranylmethyl)-1,3-dihydrobenzimidazol-2-one yield 40% $^1$H-NMR (CDCl$_3$) δppm: 1.34 (3H, s), 1.54 (9H, s), 1.71-1.87 (2H, m), 2.20-2.42 (2H, m), 2.70 (1H, d, J=4.5 Hz), 2.71-2.89 (3H, m), 3.75 (1H, d, J=15.0 Hz), 4.20-4.53 (4H, m), 7.00-7.13 (3H, m), 7.15-7.25 (1H, m)

Reference Example 236

1-methyl-3-(2-methyl-2-oxiranylmethyl)-1,3-dihydrobenzimidazol-2-one yield 68% $^1$H-NMR (CDCl$_3$) δppm: 1.34 (3H, s), 2.69 (1H, d, J=4.5 Hz), 2.78 (1H, d, J=4.5 Hz), 3.44 (3H, s), 3.76 (1H, d, J=15.0 Hz), 4.31 (1H, d, J=15.0 Hz), 6.91-7.00 (1H, m), 7.05-5.25 (3H, m).

Reference Example 237

5-chloro-1-methyl-3-(2-methyl-2-oxiranylmethyl)-1,3-dihydrobenzimidazol-2-one yield 89% $^1$H-NMR (CDCl$_3$) δppm: 1.34 (3H, s), 2.70 (1H, d, J=4.4 Hz), 2.76 (1H, d, J=4.4 Hz), 3.42 (3H, s), 3.69 (1H, d, J=15.1 Hz), 4.28 (1H, d, J=15.1 Hz), 6.88 (1H, d, J=8.3 Hz), 7.09 (1H, dd, J=1.9 Hz, 8.3 Hz), 7.22 (1H, d, J=1.9 Hz).

Reference Example 238

1-methyl-3-(2-methyl-2-oxiranylmethyl)-5-trifluoromethyl-1,3-dihydrobenzimidazol-2-one yield 99% $^1$H-NMR (CDCl$_3$) δppm: 1.36 (3H, s), 2.71 (1H, d, J=4.4 Hz), 2.77 (1H, d, J=4.4 Hz), 3.47 (3H, s), 3.74 (1H, d, J=15.1 Hz), 4.38 (1H, d, J=15.1 Hz), 7.04 (1H, d, J=8.2 Hz), 7.39 (1H, dd, J=1.9 Hz, 8.2 Hz), 7.45 (1H, d, J=1.9 Hz).

Reference Example 239

6-chloro-1-methyl-3-(2-methyl-2-oxiranylmethyl)-1,3-dihydrobenzimidazole-2-one yield 99% $^1$H-NMR (CDCl$_3$) δppm: 1.32 (3H, S), 2.69 (1H, d, J=4.6 Hz), 2.75 (1H, d, J=4.6 Hz), 3.41 (3H, s), 3.68 (1H, d, J=15.1 Hz), 4.33 (1H, d, J=15.1 Hz), 6.97 (1H, d, J=1.9 Hz), 7.07 (1H, dd, J=1.9 Hz, 8.4 Hz), 7.13 (1H, d, J=8.4 Hz)

Reference Example 240

5-fluoro-1-methyl-3-(2-methyl-2-oxiranylmethyl)-1,3-dihydrobenzimidazol-2-one yield 66% $^1$H-NMR (CDCl$_3$) δppm: 1.34 (3H, s), 2.70 (1H, d, J=4.4 Hz), 2.77 (1H, d, J=4.4 Hz), 3.42 (3H, s), 3.77 (1H, d, J=15.0 Hz), 4.33 (1H, d, J=15.0 Hz), 6.74-6.91 (2H, m), 7.00 (1H, dd, J=2.2 Hz, 8.6 Hz).

Reference Example 241

5-chloro-1-ethyl-3-(2-methyl-2-oxiranylmethyl)-1,3-dihydrobenzimidazol-2-one yield 100% $^1$H-NMR (CDCl$_3$) δppm: 1.25-1.39 (6H, m), 2.70 (1H, d, J=4.4 Hz), 2.76 (1H, d, J=4.4 Hz), 3.69 (1H, d, J=15.1 Hz), 3.93 (2H, q, J=7.3 Hz), 4.30 (1H, d, J=15.1 Hz), 6.90 (1H, d, J=8.3 Hz), 7.07 (1H, dd, J=2.0 Hz, 8.3 Hz), 7.23 (1H, d, J=2.0 Hz).

Reference Example 242

5-chloro-1-isopropyl-3-(2-methyl-2-oxiranylmethyl)-1,3-dihydrobenzimidazole-2-one yield 100% $^1$H-NMR (CDCl$_3$) δppm: 1.34 (3H, s), 1.53 (6H, dd, J=2.1 Hz, 6.7 Hz), 2.70 (1H, d, J=4.5 Hz), 2.75 (1H, d, J=4.5 Hz), 3.68 (1H, d, J=15.1 Hz), 4.28 (1H, d, J=15.1 Hz), 4.65-4.79 (1H, m), 7.04 (2H, s), 7.22 (1H, s).

Reference Example 243

5-dimethylamino-1-methyl-3-(2-methyl-2-oxiranylmethyl)-1,3-dihydrobenzimidazol-2-one yield 100% $^1$H-NMR (DMSO-d$_6$) δppm: 1.33 (3H, s), 2.69 (1H, d, J=4.5 Hz), 2.79 (1H, d, J=4.5 Hz), 2.92 (6H, s), 3.39 (3H, s), 3.67 (1H, d, J=15.0 Hz), 4.32 (1H, d, J=15.0 Hz), 6.55 (1H, dd, J=2.4 Hz, 8.6 Hz), 6.71 (1H, d, J=2.4 Hz), 6.85 (1H, d, J=8.6 Hz).

Reference Example 244

5-chloro-1-(n-hexyl)-3-(2-methyl-2-oxiranylmethyl)-1,3-dihydrobenzimidazol-2-one yield 100% $^1$H-NMR (CDCl$_3$) δppm: 0.87 (3H, t, J=6.9 Hz), 1.18-1.43 (9H, m), 1.64-1.80 (2H, m), 2.70 (1H, d, J=4.4 Hz), 2.75 (1H, d, J=4.4 Hz), 3.69 (1H, d, J=15.0 Hz), 3.86 (2H, t, J=7.4 Hz), 4.30 (1H, d, J=15.0 Hz), 6.88 (1H, d, J=8.4 Hz), 7.06 (1H, dd, J=1.9 Hz, 8.4 Hz), 7.22 (1H, d, J=1.9 Hz).

Reference Example 245

5-ethoxycarbonyl-1-methyl-3-(2-methyl-2-oxiranylmethyl)-1,3-dihydrobenzimidazol-2-one yield 100% $^1$H-NMR (CDCl$_3$) δppm: 1.32-1.43 (6H, m), 2.69 (1H, d, J=4.5 Hz), 2.78 (1H, d, J=4.5 Hz), 3.47 (3H, s), 3.87 (1H, d, J=15.0 Hz), 4.28 (1H, d, J=15.0 Hz), 4.39 (2H, q, J=7.2 Hz), 7.00 (1H, d, J=8.2 Hz), 7.85 (1H, d, J=1.5 Hz), 7.90 (1H, dd, J=1.5 Hz, 8.2 Hz).

Reference Example 246

Preparation of 1-benzyl-3-(2-methyl-2-oxiranylmethyl)-imidazolidin-2-one

Using 1-benzyl-3-(2-methyl-2-propenyl)-imidazolidin-2-one (1.63 g, 7.05 mmol), 1-benzyl-3-(2-methyl-2-oxiranylmethyl)imidazolidin-2-one (680 mg, yield 39%) as a pale yellow oil was prepared in the same manner as described in Reference Example 228.

$^1$H-NMR (CDCl$_3$) δppm: 1.35 (3H, s), 2.62 (1H, d, J=4.7 Hz), 2.69 (1H, d, J=4.7 Hz), 3.05-3.25 (3H, m), 3.27-3.49 (2H, m), 3.61 (1H, d, J=14.6 Hz), 4.39 (2H, s), 7.20-7.34 (5H, m).

Using corresponding starting materials, compounds of Reference Examples 247 to 250 were prepared in the same manner as described in Reference Example 246.

Reference Example 247

1-(2-methyl-2-oxiranylmethyl)-3-phenylimidazolidin-2-one yield 58% $^1$H-NMR (CDCl$_3$) δppm: 1.37 (3H, s), 2.65 (1H, d, J=4.6 Hz), 2.72 (1H, d, J=4.6 Hz), 3.18 (1H, d, J=14.7 Hz), 3.48-3.61 (2H, m), 3.64 (1H, d, J=14.7 Hz), 3.77-3.91 (2H, m), 7.03 (1H, t, J=7.3 Hz), 7.25-7.36 (2H, m), 7.56 (2H, d, J=7.9 Hz).

Reference Example 248

1-(4-fluorobenzyl)-3-(2-methyl-2-oxiranylmethyl)-imidazolidin-2-one yield 34% $^1$H-NMR (CDCl$_3$) δppm: 1.35 (3H, s), 2.62 (1H, d, J=4.7 Hz), 2.68 (1H, d, J=4.7 Hz), 3.12 (1H, d, J=14.6 Hz), 3.16-3.20 (2H, m), 3.27-3.45 (2H, m), 3.61 (1H, d, J=14.6 Hz), 4.35 (2H, s), 6.89-7.07 (2H, m), 7.14-7.27 (2H, m).

Reference Example 249

1-(4-bromobenzyl)-3-(2-methyl-2-oxiranylmethyl)-imidazolidin-2-one yield 51% $^1$H-NMR (CDCl$_3$) δppm: 1.34 (3H, s), 2.62 (1H, d, J=4.7 Hz), 2.67 (1H, d, J=4.7 Hz), 3.12 (1H, d, J=14.7 Hz), 3.16-3.25 (2H, m), 3.27-3.50 (2H, m), 3.61 (1H, d, J=14.7 Hz), 4.33 (2H, s), 7.15 (2H, d, J=8.4 Hz), 7.45 (2H, d, J=8.4 Hz).

Reference Example 250

1-(4-methoxybenzyl)-3-(2-methyl-2-oxiranylmethyl)-imidazolidin-2-one yield 43% $^1$H-NMR (CDCl$_3$) δppm: 1.34 (3H, s), 2.61 (1H, d, J=4.7 Hz), 2.67 (1H, d, J=4.7 Hz), 3.07-3.23 (3H, m), 3.27-3.50 (2H, m), 3.58 (1H, d, J=14.6 Hz), 3.80 (3H, s), 4.32 (2H, s), 6.86 (2H, d, J=8.4 Hz), 7.19 (2H, d, J=8.4 Hz).

Reference Example 251

1-(4-chlorobenzyl)-3-(2-methyl-2-oxiranylmethyl)-imidazolidin-2-one

Sodium hydride (99 mg, 2.49 mmol) was added to a solution of 2-methyl-2-oxiranylmethyl toluene-4-sulfonate (500 mg, 2.37 mmol) in DMF (5 ml) while cooling in an ice-bath, and the mixture was stirred at room temperature for 1 hour. To which a solution of 1-(4-chlorobenzyl)imidazolidin-2-one (633 mg, 2.61 mmol) in DMF (5 ml) was added while cooling in an ice-bath, and the mixture was stirred at room temperature overnight. Water was added to the reaction mixture, and the mixture was extracted with diethyl ether twice. The extracts were combined, washed with water twice and then with brine, and dried over sodium sulfate. After filtration, the filtrate was concentrated under reduced pressure. The residue was purified by silica gel column chromatography (n-hexane/acetone=3/1) to afford 1-(4-chlorobenzyl)-3-(2-methyl-2-oxiranylmethyl)imidazolidin-2-one (399 mg, 60%) as a pale yellow oil.

$^1$H-NMR (CDCl$_3$) δppm: 1.35 (3H, s), 2.62 (1H, d, J=4.7 Hz), 2.68 (1H, d, J=4.7 Hz), 3.05-3.25 (3H, m), 3.27-3.49 (2H, m), 3.61 (1H, d, J=14.7 Hz), 4.35 (2H, s), 7.21 (2H, dd, J=2.0 Hz, 6.7 Hz), 7.30 (2H, dd, J=2.0 Hz, 6.7 Hz).

Using corresponding starting materials, compounds of Reference Examples 252 and 253 were prepared in the same manner as described in Reference Example 251.

Reference Example 252

1-(1-benzylpiperidin-4-yl)-3-(2-methyl-2-oxiranylmethyl)imidazolin-2-one yield 54% $^1$H-NMR (CDCl$_3$) δppm: 1.35 (3H, s), 1.59-1.80 (4H, m), 2.00-2.16 (2H, m), 2.60 (1H, d, J=4.7 Hz), 2.66 (1H, d, J=4.7 Hz), 2.84-3.00 (2H, m), 3.07 (1H, d, J=14.7 Hz), 3.22-3.43 (4H, m), 3.50 (2H, s), 3.54 (1H, d, J=14.7 Hz), 3.68-3.86 (1H, m), 7.16-7.34 (5H, m).

Reference Example 253

1-(2,4-dimethoxybenzyl)-3-(2-methyl-2-oxiranylmethyl)-imidazolin-2-one yield 40% $^1$H-NMR (CDCl$_3$) δppm: 1.34 (3H, s), 2.60 (1H, d, J=4.7 Hz), 2.67 (1H, d, J=4.7 Hz), 3.10 (1H, d, J=14.6 Hz), 3.14-3.34 (4H, m), 3.56 (1H, d, J=14.6 Hz), 3.80 (6H, s), 4.35 (2H, s), 6.32-6.43 (2H, m), 7.18 (1H, d, J=8.9 Hz).

Reference Example 254

Preparation of 1-(2-methyl-2-oxiranylmethyl)pyrrolidine-2,5-dione

Using 1-(2-methyl-2-propenyl)pyrrolidine-2,5-dione, 1-(2-methyl-2-oxiranylmethyl)pyrrolidine-2,5-dione was prepared in the same manner as described in Reference Example 228.

yield 86% $^1$H-NMR (DMSO-d$_6$) δppm: 1.34 (3H, s), 2.58 (1H, d, J=4.6 Hz), 2.67-2.79 (5H, m), 3.56 (1H, d, J=13.9 Hz), 3.84 (1H, d, J=13.9 Hz).

Reference Example 255

Preparation of
2-(2-methyl-2-oxiranylmethyl)phthalimide

Using 2-(2-methyl-2-propenyl)phthalimide, 2-(2-methyl-2-oxiranylmethyl)phthalimide was prepared in the same manner as described in Reference Example 228.

yield 98% $^1$H-NMR (DMSO-$d_6$) δppm: 1.38 (3H, s), 2.62 (1H, d, J=4.6 Hz), 2.82 (1H, d, J=4.6 Hz), 3.71 (1H, d, J=14.3 Hz), 4.01 (1H, d, J=14.3 Hz), 7.73 (2H, dd, J=2.9 Hz, 8.6 Hz), 7.87 (2H, dd, J=2.9 Hz, 8.6 Hz).

Reference Example 256

Preparation of
1-(2-methyl-2-oxiranylmethyl)-1H-benzimidazole

Using 1-(2-methyl-2-propenyl)-1H-benzimidazole, 1-(2-methyl-2-oxiranylmethyl)-1H-benzimidazole was prepared in the same manner as described in Reference Example 228.

yield 11% $^1$H-NMR (CDCl$_3$) δppm: 1.32 (3H, s), 2.60 (1H, d, J=4.4 Hz), 2.71 (1H, d, J=4.4 Hz), 4.17 (1H, d, J=15.1 Hz), 4.44 (1H, d, J=15.1 Hz), 7.23-7.41 (2H, m), 7.48 (1H, dd, J=2.2 Hz, 7.8 Hz), 7.80 (1H, dd, J=2.2 Hz, 7.8 Hz), 7.93 (1H, s).

Reference Example 257

Preparation of
1-(2-methyl-2-oxiranylmethyl)-1H-imidazole

Using 1-(2-methyl-2-propenyl)-1H-imidazole, 1-(2-methyl-2-oxiranylmethyl)-1H-imidazole was prepared in the same manner as described in Reference Example 228.

yield 53% $^1$H-NMR (CDCl$_3$) δppm: 1.26 (3H, s), 2.57 (1H, d, J=4.4 Hz), 2.69 (1H, d, J=4.4 Hz), 3.94 (1H, d, J=14.7 Hz), 4.16 (1H, d, J=14.7 Hz), 6.97 (1H, s), 7.08 (1H, s), 7.49 (1H, s).

Reference Example 258

Preparation of 3-[3-(2-methyl-2-oxiranyl)propyl]-3H-benzoxazol-2-one

Using 3-(4-methyl-4-pentenyl)-3H-benzoxazol-2-one (3.4 g, 15.65 mmol), 3-[3-(2-methyl-2-oxiranyl)propyl]-3H-benzoxazol-2-one (3.8 g, quantitative) as a colorless crystalline powder was prepared in the same manner as described in Reference Example 228.

$^1$H-NMR (CDCl$_3$) δppm: 1.33 (3H, s), 1.56-1.77 (2H, m), 1.80-1.95 (2H, m), 2.59 (1H, d, J=4.8 Hz), 2.63 (1H, d, J=4.8 Hz), 3.85 (2H, t, J=7.4 Hz), 6.99 (1H, d, J=7.9 Hz), 7.05-7.23 (3H, m).

Reference Example 259

Preparation of 3-[4-(2-methyl-2-oxiranyl)butyl]-3H-benzoxazol-2-one

Using 3-(5-methyl-5-hexenyl)-3H-benzoxazol-2-one (1.1 g, 4.8 mmol), 3-[4-(2-methyl-2-oxiranyl)butyl]-3H-benzoxazol-2-one (1.2 g, quantitative) as a colorless oil was prepared in the same manner as described in Reference Example 228.

$^1$H-NMR (CDCl$_3$) δppm: 1.30 (3H, s), 1.42-1.67 (4H, m), 1.74-1.88 (2H, m), 2.57 (1H, d, J=4.9 Hz), 2.60 (1H, d, J=4.9 Hz), 3.84 (2H, t, J=7.2 Hz), 6.98 (1H, d, J=8.1 Hz), 7.02-7.30 (3H, m).

Reference Example 260

Preparation of
3-(2-methyl-2-oxiranylmethyl)oxazolidin-2-one

Using 3-(2-methyl-2-propenyl)oxazolidin-2-one (4.28 g, 30.35 mmol), 3-(2-methyl-2-oxiranylmethyl)-oxazolidin-2-one (2.87 g, yield 62%) as a colorless oil was prepared by the method in Reference Example 228.

$^1$H-NMR (CDCl$_3$) δppm: 1.36 (3H, s), 2.66 (1H, d, J=4.5 Hz), 2.70 (1H, d, J=4.5 Hz), 3.15 (1H, d, J=14.7 Hz), 3.57-3.75 (3H, m), 4.25-4.39 (2H, m).

Reference Example 261

Preparation of 3,3-difluoro-1-(2-methyl-2-oxiranylmethyl)-1,3-dihydroindol-2-one Using 3,3-difluoro-1-(2-methyl-2-propenyl)-1,3-dihydroindol-2-one (1.08 g, 4.83 mmol), 3,3-difluoro-1-(2-methyl-2-oxiranylmethyl)-1,3-dihydroindol-2-one (1.14 g, yield 99%) as a pale yellow powder was prepared in the same manner as described in Reference Example 228.

$^1$H-NMR (CDCl$_3$) δppm: 1.35 (3H, s), 2.71 (1H, d, J=4.3 Hz), 2.77 (1H, d, J=4.3 Hz), 3.46 (1H, d, J=15.0 Hz), 4.26 (1H, d, J=15.0 Hz), 7.12-7.24 (2H, m), 7.45-7.61 (2H, m).

Using corresponding starting materials, compounds of Reference Examples 262 and 263 were prepared in the same manner as described in Reference Example 261.

Reference Example 262

3,3-dimethyl-1-(2-methyl-2-oxiranylmethyl)-1,3-dihydroindol-2-one $^1$H-NMR (CDCl$_3$) δppm: 1.31 (3H, s), 1.39 (6H, s), 2.67 (1H, d, J=4.5 Hz), 2.74 (1H, d, J=4.5 Hz), 3.53 (1H, d, J=14.0 Hz), 4.22 (1H, d, J=14.0 Hz), 7.00-7.10 (2H, m), 7.16-7.31 (2H, m).

Reference Example 263

1-(2-methyl-2-oxiranylmethyl)-1,3-dihydroindol-2-one $^1$H-NMR (CDCl$_3$) δppm: 1.34 (3H, s), 2.67 (1H, d, J=4.5 Hz), 2.76 (1H, d, J=4.5 Hz), 3.49-3.61 (3H, m), 4.22 (1H, d, J=14.9 Hz), 7.00-7.10 (2H, m), 7.18-7.35 (2H, m).

Reference Example 264

Preparation of benzyl
(2-methyl-2-oxiranylmethyl)-carbamate

Benzyl N-(2-methyl-2-propenyl)carbamate (3.90 g, 19.0 mmol) prepared in Reference Example 173 was dissolved in methylene chloride (80 ml), to which m-chloroperbenzoic acid (5.15 g, 20.9 mmol) was added, and the mixture was stirred at room temperature overnight. Sodium thiosulfate aqueous solution and saturated sodium hydrogencarbonate aqueous solution were added to the reaction mixture, which was stirred for a while. The organic layer was separated, washed with saturated sodium hydrogencarbonate aqueous solution, dried over sodium sulfate, and then filtered. The filtrate was concentrated under reduced pressure to afford benzyl(2-methyl-2-oxiranylmethyl)carbamate (4.31 g, quantitative) as a colorless oil.

$^1$H-NMR (CDCl$_3$) δppm: 1.35 (3H, s), 2.61 (1H, d, J=4.5 Hz), 2.72 (1H, d, J=4.5 Hz), 3.28-3.53 (2H, m), 4.90 (1H, br), 5.11 (2H, s), 7.26-7.44 (5H, m).

Using corresponding starting materials, compounds of Reference Examples 265 to 276 were prepared in the same manner as described in Reference Example 264.

Reference Example 265 benzyl N-methyl-N-(2-methyl-2-oxiranylmethyl)carbamate yield 42% $^1$H-NMR (CDCl$_3$) δppm: 1.26 (1.5H, s), 1.31 (1.5H, s), 2.57 (1H, s), 2.61 (1H, s), 2.99 (3H, s), 3.24 (1H, d, J=15.1 Hz), 3.62 (0.5H, d, J=15.1 Hz), 3.72 (0.5H, d, J=15.1 Hz), 5.14 (2H, s), 7.27-7.41 (5H, m).

Reference Example 266

4-chlorobenzyl(2-methyl-2-oxiranylmethyl)carbamate yield 98% $^1$H-NMR (CDCl$_3$) δppm: 1.35 (3H, s), 2.62 (1H, d, J=4.4 Hz), 2.71 (1H, d, J=4.4 Hz), 3.27-3.50 (2H, m), 4.88 (1H, br), 5.06 (2H, s), 7.23-7.41 (4H, m).

Reference Example 267

4-fluorobenzyl(2-methyl-2-oxiranylmethyl)carbamate yield 100% $^1$H-NMR (CDCl$_3$) δppm: 1.34 (3H, s), 2.61 (1H, d, J=4.5 Hz), 2.71 (1H, d, J=4.5 Hz), 3.32-3.50 (2H, m), 4.86 (1H, br), 5.06 (2H, s), 6.95-7.09 (2H, m), 7.27-7.41 (2H, m).

Reference Example 268 ethyl(2-methyl-2-oxiranylmethyl)carbamate yield 82% $^1$H-NMR (CDCl$_3$) δppm: 1.24 (3H, t, J=7.1 Hz), 1.35 (3H, s), 2.62 (1H, d, J=4.5 Hz), 2.74 (1H, d, J=4.5 Hz), 3.27-3.50 (2H, m), 4.12 (2H, q, J=7.1 Hz), 4.78 (1H, br).

Reference Example 269

4-trifluoromethoxybenzyl(2-methyl-2-oxiranylmethyl)-carbamate yield 99% $^1$H-NMR (CDCl$_3$) δppm: 1.35 (3H, s), 2.62 (1H, d, J=4.4 Hz), 2.71 (1H, d, J=4.4 Hz), 3.42 (2H, d, J=5.6 Hz), 4.90 (1H, br), 5.10 (2H, s), 7.20 (2H, d, J=8.3 Hz), 7.38 (2H, d, J=8.3 Hz).

Reference Example 270

4-fluorobenzyl N-methyl-N-(2-methyl-2-oxiranylmethyl)-carbamate yield 73% $^1$H-NMR (CDCl$_3$) δppm: 1.25 (1.5H, s), 1.30 (1.5H, s), 2.56 (1H, s), 2.61 (1H, s), 2.97 (3H, s), 3.22 (1H, d, J=14.8 Hz), 3.61 (0.5H, d, J=14.8 Hz), 3.72 (0.5H, d, J=14.8 Hz), 5.10 (2H, s), 6.95-7.09 (2H, m), 7.27-7.41 (2H, m).

Reference Example 271

4-chlorobenzyl oxiranylmethylcarbamate yield 97% $^1$H-NMR (CDCl$_3$) δppm: 2.59 (1H, dd, J=2.6 Hz, 4.6 Hz), 2.79 (1H, t, J=4.3 Hz), 3.11 (1H, br), 3.20-3.32 (1H, m), 3.50-3.73 (1H, m), 4.93 (1H, br), 5.07 (2H, s), 7.23-7.41 (4H, m).

Reference Example 272

4-fluorobenzyl oxiranylmethylcarbamate yield 89% $^1$H-NMR (CDCl$_3$) δppm: 2.59 (1H, dd, J=2.6 Hz, 4.6 Hz), 2.79 (1H, t, J=4.3 Hz), 3.11 (1H, br), 3.21-3.32 (1H, m), 3.45-3.73 (1H, m), 4.92 (1H, br), 5.07 (2H, s), 6.95-7.09 (2H, m), 7.27-7.41 (2H, m).

Reference Example 273

4-fluorobenzyl N-methyl-N-oxiranylmethylcarbamate yield 34% $^1$H-NMR (CDCl$_3$) δppm: 2.51 (1H, br), 2.76 (1H, br), 3.01 (3H, s), 3.02-3.27 (2H, m), 3.55-3.91 (1H, m), 5.10 (2H, s), 6.95-7.09 (2H, m), 7.27-7.41 (2H, m).

Reference Example 274 tert-butyl oxiranylmethylcarbamate yield 83% $^1$H-NMR -(CDCl$_3$) δppm: 1.45 (9H, s), 2.59 (1H, dd, J=2.6 Hz, 4.6 Hz), 2.78 (1H, t, J=4.4 Hz), 3.09 (1H, br), 3.16-3.28 (1H, m), 3.38-3.66 (1H, br), 4.53-4.91 (1H, br).

Reference Example 275 benzyl oxiranylmethylcarbamate yield 72% $^1$H-NMR (DMSO-d$_6$) δppm: 2.67 (1H, t, J=4.5 Hz), 2.91-3.32 (4H, m), 4.91-5.09 (3H, m), 7.23-7.55 (5H, m).

Reference Example 276 phenyl oxiranylmethylcarbamate

Yield 90% $^1$H-NMR (DMSO-d$_6$) δppm: 2.57 (1H, dd, J=2.5 Hz, 5.0 Hz), 2.73 (1H, t, J=4.5 Hz), 3.00-3.45 (3H, m), 7.10 (2H, d, J=7.6 Hz), 7.20 (1H, t, J=7.6 Hz), 7.38 (2H, t, J=7.6 Hz), 7.94 (1H, br).

Reference Example 277

Preparation of (2-methyl-2-oxiranylmethyl)(4-chloro-phenyl)carbamate m-Chloroperbenzoic acid (1.6 g, 6.6 mmol) was added to a solution of 2-methyl-2-propenyl(4-chlorophenyl)carbamate (1.0 g, 4.4 mmol) in methylene chloride (20 ml) while cooling in an ice-bath, and the mixture was stirred at room temperature for 4 hours. To which sodium thiosulfate aqueous solution was added and the mixture was filtered, and sodium hydrogencarbonate aqueous solution was added to the filtrate. The organic layer was separated, dried over magnesium sulfate, and concentrated under reduced pressure to afford (2-methyl-2-oxiranylmethyl)(4-chlorophenyl) carbamate (1.1 g, quantitative) as a pale yellow crystalline powder.

$^1$H-NMR (CDCl$_3$) δppm: 1.42 (3H, s), 2.71 (1H, d, J=4.6 Hz), 2.82 (1H, d, J=4.6 Hz), 4.01 (1H, d, J=11.9 Hz), 4.37 (1H, d, J=11.9 Hz), 6.79 (1H, br), 7.23-7.37 (4H, m).

Reference Example 278

Preparation of (2-methyl-2-oxiranylmethyl) N-(4-chlorophenyl)-N-methylcarbamate m-Chloroperbenzoic acid (2.5 g, 10.1 mmol) was added to a solution of 2-methyl-2-propenyl N-(4-chlorophenyl)-N-methylcarbamate (1.78 g, 6.7 mmol) in methylene chloride (20 ml) while cooling in an ice-bath, and the mixture was stirred at room temperature for 6.5 hours. To which sodium thiosulfate aqueous solution was added and the mixture was filtered, and sodium hydrogencarbonate aqueous solution was added to the filtrate. The organic layer was separated, dried over magnesium sulfate, and filtered. The filtrate was concentrated under reduced pressure. The residue was purified by silica gel column chromatography (methylene chloride/methanol=20/1) to afford (2-methyl-2-oxiranylmethyl) N-(4-chlorophenyl)-N-methylcarbamate (1.7 g, quantitative) as a pale yellow oil.

$^1$H-NMR (CDCl$_3$) δppm: 1.32 (3H, s), 2.62 (1H, d, J=4.6 Hz), 2.69 (1H, d, J=4.6 Hz), 3.30 (3H, s), 3.99 (1H, d, J=11.8 Hz), 4.30 (1H, d, J=11.8 Hz), 7.15-7.25 (2H, m), 7.31-7.38 (2H, m).

Reference Example 279

Preparation of tert-butyl 4-oxiranylmethylpiperazine-1-carboxylate

A mixture of tert-butyl piperazine-1-carboxylate (6.2 g, 33.29 mmol), epibromohydrin (5.4 g, 39.42 mmol) and potassium carbonate (5.5 g, 39.79 mmol) in acetonitrile (70 ml) was heated under reflux for 3 hours. The reaction mixture was concentrated under reduced pressure, and water was added to the residue. The mixture was extracted with methylene chloride. The extract was washed with brine, dried over sodium sulfate, and then filtered, and the filtrate was concentrated under reduced pressure. The residue was purified by silica gel column chromatography (ethyl acetate) to afford tert-butyl 4-oxiranylmethylpiperazine-1-carboxylate (6.2 g, yield 77%) as a colorless oil.

$^1$H-NMR (CDCl$_3$) δppm: 1.46 (9H, s), 2.21-2.60 (6H, m), 2.70-2.81 (2H, m), 3.05-3.12 (1H, m), 3.35-3.56 (4H, m).

Reference Example 280

Preparation of tert-butyl[4-(2-methyl-2-oxiranylmethyl)piperazin-1-yl]carbamate

A mixture of (2-methyl-2-oxiranylmethyl) toluene-4-sufonate (9.75 g, 40.3 mmol), tert-butyl piperazin-1-yl-carbamate (6.75 g, 33.5 mmol) prepared in Reference Example 36, triethylamine (7 ml, 50.3 mmol) and potassium iodide (6.68 g, 33.5 mmol) in DMF (70 ml) was stirred at room temperature overnight. The reaction mixture was poured into water, and extracted with ethyl acetate. The extract was washed with water and brine, dried over sodium sulfate, and filtered. The filtrate was concentrated under reduced pressure. The residue was purified by silica gel column chromatography (hexane/acetone=4/1) to afford tert-butyl[4-(2-methyl-2-oxiranylmethyl)piperazin-1-yl]carbamate (4.66 g, yield 51%) as a colorless crystalline powder.

$^1$H-NMR (CDCl$_3$) δppm: 1.35 (3H, s), 1.46 (9H, s), 2.31 (1H, d, J=12.9 Hz), 2.49-2.84 (11H, m), 5.37 (1H, br).

Reference Example 281

Preparation of 3-(2-methyl-2-oxiranylmethyl)-5-(4-trifluoromethoxyphenyl)-3H-[1,3,4]oxadiazol-2-one A mixture of 5-(4-trifluoromethoxyphenyl)-3H-[1,3,4]oxadiazol-2-one (3.18 g, 12.92 mmol) prepared in Reference Example 49, (2-methyl-2-oxiranylmethyl) toluene-4-sulfonate (4.80 g, 19.38 mmol), potassium carbonate (2.14 g, 15.50 mmol) and sodium iodide (2.90 g, 19.38 mmol) in DMF (30 ml) was stirred at room temperature for 24 hours, and then at 60° C. for 4 hours. The reaction mixture was poured into water, and extracted with ethyl acetate. The extract was washed with water, dried over magnesium sulfate, and filtered. The filtrate was concentrated under reduced pressure. The residue was purified by silica gel column chromatography (hexane/ethyl acetate=9/1) to afford 3-(2-methyl-2-oxiranylmethyl)-5-(4-trifluoromethoxyphenyl)-3H-[1,3,4]oxadiazol-2-one (2.37 g, yield 58%) as a colorless crystalline powder.

$^1$H-NMR (DMSO-d$_6$) δppm: 1.43 (3H, s), 2.72 (1H, d, J=4.4 Hz), 2.86 (1H, d, J=4.4 Hz), 3.93 (2H, dd, J=14.8 Hz, 22.2 Hz), 7.28-7.41 (2H, m), 7.83-7.98 (2H, m).

Using 5-substituted-3H-[1,3,4]oxadiazol-2-one and (2-methyl-2-oxiranylmethyl) toluene-4-sulfonate, compounds of Reference Examples 282 to 289 were prepared in the same manner as described in Reference Example 281.

Reference Example 282

3-(2-methyl-2-oxiranylmethyl)-5-phenyl-3H-[1,3,4]-oxadiazol-2-one yield 41% $^1$H-NMR (CDCl$_3$) δppm: 1.44 (3H, s), 2.72 (1H, d, J=4.5 Hz), 2.88 (1H, d, J=4.5 Hz), 3.87 (1H, d, J=14.7 Hz), 3.99 (1H, d, J=14.7 Hz), 7.40-7.57 (3H, m), 7.79-7.87 (2H, m).

Reference Example 283

3-(2-methyl-2-oxiranylmethyl)-5-(4-trifluoromethylphenyl)-3H-[1,3,4]oxadiazol-2-one Yield 34% $^1$H-NMR (CDCl$_3$) δppm: 1.45 (3H, s), 2.73 (1H, d, J=4.5 Hz), 2.87 (1H, d, J=4.5 Hz), 3.92 (1H, d, J=14.8 Hz), 4.00 (1H, d, J=14.8 Hz), 7.75 (2H, d, J=8.3 Hz), 8.01 (2H, d, J=8.3 Hz)

Reference Example 284

3-(2-methyl-2-oxiranylmethyl)-5-(4-biphenylyl)-3H-[1,3,4]oxadiazol-2-one yield 38% $^1$H-NMR (CDCl$_3$) δppm: 1.45 (3H, s), 2.73 (1H, d, J=4.5 Hz), 2.89 (1H, d, J=4.5 Hz), 3.89 (1H, d, J=14.8 Hz), 4.00 (1H, d, J=14.8 Hz), 7.33-7.50 (3H, m), 7.57-7.75 (4H, m), 7.93 (2H, d, J=8.6 Hz)

Reference Example 285

3-(2-methyl-2-oxiranylmethyl)-5-(4-chlorophenyl)-3H-[1,3,4]oxadiazol-2-one yield 52% $^1$H-NMR (CDCl$_3$) δppm: 1.44 (3H, s), 2.72 (1H, d, J=4.4 Hz), 2.86 (1H, d, J=4.4 Hz), 3.89 (1H, d, J=14.8 Hz), 3.97 (1H, d, J=14.8 Hz), 7.46 (2H, d, J=8.7 Hz), 7.80 (2H, d, J=8.7 Hz).

Reference Example 286

3-(2-methyl-2-oxiranylmethyl)-5-(4-fluorophenyl)-3H-[1,3,4]oxadiazol-2-one yield 72% $^1$H-NMR (CDCl$_3$) δppm: 1.43 (3H, s), 2.72 (1H, d, J=4.5 Hz), 2.87 (1H, d, J=4.5 Hz), 3.88 (1H, d, J=14.7 Hz), 3.96 (1H, d, J=14.7 Hz), 7.11-7.21 (2H, m), 7.74-7.89 (2H, m).

Reference Example 287

3-(2-methyl-2-oxiranylmethyl)-5-[2-(4-chlorophenyl)-ethyl]-3H-[1,3,4]oxadiazol-2-one yield 78% $^1$H-NMR (CDCl$_3$) δppm: 1.32 (3H, s), 2.64 (1H, d, J=4.5 Hz), 2.72 (1H, d, J=4.5 Hz), 2.79-2.90 (2H, m), 2.93-3.04 (2H, m), 3.74 (1H, d, J=14.8 Hz), 3.79 (1H, d, J=14.8 Hz), 7.12 (2H, d, J=8.6 Hz), 7.27 (2H, d, J=8.6 Hz).

Reference Example 288

3-(2-methyl-2-oxiranylmethyl)-5-[2-(4-chlorophenyl)vinyl]-3H-[1,3,4]oxadiazol-2-one yield 100% $^1$H-NMR (CDCl$_3$) δppm: 1.41 (3H, s), 2.71 (1H, d, J=4.4 Hz), 2.83 (1H, d, J=4.4 Hz), 3.88 (2H, s), 6.60 (1H, d, J=16.4 Hz), 7.28-7.47 (5H, m).

Reference Example 289

3-(2-methyl-2-oxiranylmethyl)-5-(4-chlorophenoxymethyl)-3H-[1,3,4]oxadiazol-2-one yield 59% $^1$H-NMR (CDCl$_3$) δppm: 1.37 (3H, s), 2.68 (1H, d, J=4.4 Hz), 2.78 (1H, d, J=4.4 Hz), 3.86 (2H, s), 4.90 (2H, s), 6.91 (2H, dd, J=2.3 Hz, 6.9 Hz), 7.29 (2H, dd, J=2.3 Hz, 6.9 Hz).

Reference Example 290

Preparation of 2-(2-methyl-2-oxiranylmethyl)-1,1-dioxo-1,2-dihydrobenzo[d]isothiazol-3-one Using saccharin and (2-methyl-2-oxiranylmethyl) toluene-4-sulfonate, 2-(2-methyl-2-oxiranylmethyl)-1,1-dioxo-1,2-dihydrobenzo[d]isothiazol-3-one was prepared in the same manner as described in Reference Example 281. a colorless crystalline powder, yield 43%

$^1$H-NMR (CDCl$_3$) δppm: 1.49 (3H, s), 2.74 (1H, d, J=4.5 Hz), 2.96 (1H, d, J=4.5 Hz), 3.73 (1H, d, J=15.5 Hz), 4.04 (1H, d., J=15.5 Hz), 7.81-8.00 (3H, m), 8.09 (1H, dd, J=2.4 Hz, 6.6 Hz).

Reference Example 291

Preparation of 1-(2-methyl-2-oxiranylmethyl)piperidin-4-one

Using 4-piperidone hydrochloride monohydrate-hydrate, 1-(2-methyl-2-oxiranylmethyl)piperidin-4-one was prepared in the same manner as described in Reference Example 281.

a colorless oil, yield 50% $^1$H-NMR (CDCl$_3$) δppm: 1.43 (3H, s), 2.35-2.51 (5H, m), 2.58-2.93 (7H, m).

Reference Example 292

Preparation of 4-(2-methyl-2-oxiranylmethyl)-1-(4-trifluoromethylbenzyl)piperazin-2-one Using 1-(4-trifluoromethylbenzyl)piperazin-2-one, 4-(2-methyl-2-oxiranylmethyl)-1-(4-trifluoro-methylbenzyl)piperazin-2-one was prepared in the same manner as described in Reference Example 281.

a colorless crystalline powder, yield 63% $^1$H-NMR (CDCl$_3$) δppm: 1.37 (3H, s), 2.34 (1H, d, J=12.9 Hz), 2.53-2.67 (4H, m), 2.77-2.91 (1H, m), 3.14-3.37 (4H, m), 4.62 (1H, d, J=15.1 Hz), 4.69 (1H, d, J=15.1 Hz), 7.38 (2H, d, J=8.2 Hz), 7.60 (2H, d, J=8.2 Hz).

Reference Example 293

Preparation of 4-(2-methyl-2-oxiranylmethyl)-1-(tert-butyl)piperazin-2-one

Using 1-(tert-butyl)piperazin-2-one, 4-(2-methyl-2-oxiranylmethyl)-1-(tert-butyl)piperazin-2-one was prepared in the same manner as described in Reference Example 281.

a colorless crystalline powder, yield 39% $^1$H-NMR (CDCl$_3$) δppm: 1.38 (3H, s), 1.45 (9H, s), 2.31 (1H, d, J=12.9 Hz), 2.42-2.55 (4H, m), 2.74-2.88 (1H, m), 3.02 (1H, d, J=16.1 Hz), 3.20 (1H, d, J=16.1 Hz), 3.28-3.37 (2H, m).

Reference Example 294

Preparation of (S)-1-(2-methyl-2-oxiranylmethyl)-4-(4-trifluoromethoxyphenyl)piperazine A solution of (2-methyl-2-oxiranylmethyl) (R)-toluene-4-sulfonate (0.80 g, 3.30 mmol), 1-(4-trifluoromethoxyphenyl)piperazine (0.91 g, 3.36 mmol), and triethylamine (0.55 ml, 3.96 mmol) in DMF (8 ml) was stirred at room temperature for 22 hours. The reaction mixture was poured into water, and extracted with ethyl acetate, washed with water, dried over magnesium sulfate, and then concentrated under reduced pressure. The residue was purified by silica gel column chromatography (methylene chloride/methanol=100/1) to afford (S)-1-(2-methyl-2-oxiranylmethyl)-4-(4-trifluoromethoxyphenyl)piperazine (0.46 g, yield 44%) as a pale yellow oil.

$^1$H-NMR (CDCl$_3$) δppm: 1.40 (3H, s), 2.34 (1H, d, J=12.9 Hz), 2.52-2.77 (7H, m), 3.10-3.27 (4H, m), 6.81-6.94 (2H, m), 7.06-7.17 (2H, m).

Reference Example 295

Preparation of ethyl (S)-1-(2-methyl-2-oxiranylmethyl)piperidine-4-carboxylate

A solution of (2-methyl-2-oxiranylmethyl) (R)-toluene-4-sulfonate (13.5 g, 55.8 mmol), ethyl piperidine 4-carboxylate (8.9 g, 50.9 mmol), and triethylamine (6.5 g, 64.4 mmol) in DMF (70 ml) was stirred at room temperature for 2 days. The reaction mixture was poured into water, and extracted with ethyl acetate. The extract was washed with water and brine, dried over magnesium sulfate, and then filtered. The filtrate was concentrated under reduced pressure. The residue was purified by silica gel column chromatography (n-hexane/ethyl acetate=3/1) to afford ethyl (S)-1-(2-methyl-2-oxiranylmethyl)piperidine-4-carboxylate (5.4 g, yield 47%) as a colorless oil.
$^1$H-NMR (CDCl$_3$) δppm: 1.25 (3H, t, J=7.1 Hz), 1.36 (3H, s), 1.67-1.93 (4H, m), 1.97-2.08 (2H, m), 2.19-2.37 (2H, m), 2.48 (1H, d, J=11.5 Hz), 2.58 (2H, s), 2.78-2.97 (2H, m), 4.13 (2H, q, J=7.1 Hz).

Using corresponding starting materials, compounds of Reference Examples 296 to 299 were prepared in the same manner as described in Reference Example 295.

Reference Example 296

4-trifluoromethylbenzyl (S)-1-(2-methyl-2-oxiranylmethyl)piperidine-4-carboxylate a colorless oil, yield 18% $^1$H-NMR (CDCl$_3$) δppm: 1.35 (3H, s), 1.69-2.10 (6H, m), 2.25-2.37 (1H, m), 2.28 (1H, d, J=12.9 Hz), 2.48 (1H, d, J=12.9 Hz), 2.58 (2H, s), 2.81-3.00 (2H, m), 5.11 (2H, s), 7.20 (2H, d, J=8.0 Hz), 7.38 (2H, d, J=8.0 Hz)

Reference Example 297

4-chlorobenzyl (S)-1-(2-methyl-2-oxiranylmethyl)-piperidine-4-carboxylate a colorless oil, yield 26% $^1$H-NMR (CDCl$_3$) δppm: 1.36 (3H, s), 1.75-2.16 (7H, m), 2.27 (1H, d, J=12.9 Hz), 2.50 (1H, d, J=12.9 Hz), 2.58 (2H, s), 2.87-3.09 (2H, m), 5.13 (2H, s), 7.17-7.21 (2H, m), 7.27-7.31 (2H, m).

Reference Example 298

N-(4-chlorobenzyl) (S)-1-(2-methyl-2-oxiranylmethyl)piperidine-4-carboxamide a colorless oil, yield 26% $^1$H-NMR (CDCl$_3$) δppm: 1.36 (3H, s), 1.75-2.16 (7H, m), 2.27 (1H, d, J=12.9 Hz), 2.50 (1H, d, J=12.9 Hz), 2.58 (2H, s), 2.87-3.09 (2H, m), 4.41 (2H, d, J=5.8 Hz), 5.78 (1H, br), 7.17-7.21 (2H, m), 7.27-7.31 (2H, m).

Reference Example 299

N-(4-chlorophenyl) (S)-1-(2-methyl-2-oxiranyl-methyl)piperidine-4-carboxamide a colorless oil, yield 33% $^1$H-NMR (CDCl$_3$) δppm: 1.37 (3H, s), 1.82-2.08 (6H, m), 2.13-2.27 (1H, m), 2.30 (1H, d, J=13.0 Hz), 2.53 (1H, d, J=13.0 Hz), 2.60 (2H, s), 2.93-3.12 (2H, m), 7.16 (1H, bs), 7.26-7.31 (2H, m), 7.45-7.49 (2H, m).

Reference Example 300

Preparation of 5-(2-methyl-2-oxiranylmethylsulfanyl)-1-phenyl-1H-tetrazole

A mixture of 1-phenyl-5-mercapto-1H-tetrazole (3.5 g, 19.64 mmol), (2-methyl-2-oxiranylmethyl) toluene-4-sulfonate (5 g, 20.64 mmol), potassium carbonate (3 g, 21.71 mmol), and sodium iodide (4.5 g, 30.02 mmol) in DMF (30 ml) was stirred at 60° C. for 6 hours. The reaction mixture was was poured into water, and extracted with ethyl acetate twice. The extracts were combined, washed with 5% sodium hydroxide aqueous solution and then with water three times, and dried over sodium sulfate. After filtration, the filtrate was concentrated under reduced pressure. The residue was purified by silica gel column chromatography (n-hexane/ethyl acetate=2/1) to afford 5-(2-methyl-2-oxiranylmethylsulfanyl)-1-phenyl-1H-tetrazole (1.9 g, yield 39%) as a colorless oil.
$^1$H-NMR (CDCl$_3$) δppm: 1.46 (3H, s), 2.73 (1H, d, J=4.5 Hz), 2.91 (1H, d, J=4.5 Hz), 3.61 (1H, d, J=13.9 Hz), 3.77 (1H, d, J.=13.9 Hz), 7.50-7.65 (5H, m).

Reference Example 301

Preparation of tert-butyl 3-(2-methyl-2-oxiranyl)-propionate

Trimethylsulfoxonium iodide (19.54 g, 88.78 mmol) was added to a suspension of sodium hydride (3.71 g, 92.82 mmol) in DMSO (50 ml) while cooling in an ice-bath, and the mixture was stirred for 2.5 hours. To which a solution of tert-butyl 4-oxopentanoate (13.90 g, 80.71 mmol) in DMSO (20 ml) was added, and the mixture was stirred at room temperature for 15 hours. The mixture was poured into ice water, extracted with diethyl ether. The extract was washed with water, dried over magnesium sulfate, and concentrated under reduced pressure to afford tert-butyl 3-(2-methyl-2-oxiranyl)propionate (10.1 g, yield 67%) as a pale yellow oil.
$^1$H-NMR (CDCl$_3$) δppm: 1.32 (3H, s), 1.44 (9H, s), 1.85-1.94 (2H, m), 2.27-2.33 (2H, m), 2.58 (1H, d, J=4.7 Hz), 2.63 (1H, d, J=4.7 Hz).

Reference Example 302

Preparation of 2-isopropyl-2-methoxymethoxymethyloxirane m-Chloroperbenzoic acid (213 g, 861 mmol) was gradually added to a solution of 2-methoxymethoxymethyl-3-methyl-l-butene (89 g, 615 mmol) in methylene chloride (800 ml) while cooling in an ice-bath, and the mixture was stirred at room temperature for 18 hours. The reaction mixture was washed with 10% potassium sulfide aqueous solution and sodium hydrogencarbonate aqueous solution, dried over sodium sulfate, and then concentrated under reduced pressure to afford 2-isopropyl-2-methoxymethoxymethyloxirane (98 g, quantitative) as a colorless oil.
$^1$H-NMR (CDCl$_3$) δppm: 0.95 (3H, d, J=7.0 Hz), 1.02 (3H, d, J=7.0 Hz), 1.84-2.05 (1H, m), 2.66 (1H, d, J=4.9 Hz), 2.75 (1H, d, J=4.9 Hz), 3.37 (3H, s), 3.63 (1H, d, J=11.3 Hz), 3.70 (1H, d, J=11.3 Hz), 4.62 (2H, s).

Reference Example 303

Preparation of
2-ethyl-2-methoxymethoxymethyloxirane m-Chloroperbenzoic acid (143.7 g, 833 mmol) was gradually added to a solution of 2-methoxymethoxymethyl-1-butene (98 g, 757 mmol) prepared in Reference Example 206 in methylene chloride (8800 ml) while cooling in an ice-bath, and the mixture was stirred at room temperature overnight. The reaction mixture was washed with water, 10% sodium sulfide aqueous solution and sodium hydrogencarbonate aqueous solution, dried over sodium sulfate. After filtration, the filtrate was concentrated under reduced pressure to afford 2-ethyl-2-methoxymethoxymethyloxirane (111 g, quantitative) as a colorless oil.

$^1$H-NMR (CDCl$_3$) δppm: 0.96 (3H, t, J=7.5 Hz), 1.60-1.73 (1H, m), 1.77-1.93 (1H, m), 2.66 (1H, d, J=4.8 Hz), 2.74 (1H, d, J=4.8 Hz), 3.37 (3H, s), 3.56 (1H, d, J=11.2 Hz), 3.65 (1H, d, J=11.2 Hz), 4.64 (2H, s).

Reference Example 304

Preparation of 2-(2-methoxymethoxyethyl)oxirane m-Chloroperbenzoic acid (20.6 g, 95.6 mmol) was gradually added to a solution of 4-methoxymethoxy-1-butene (10.46 g, 90.1 mmol) in methylene chloride (250 ml) while cooling in an ice-bath, the mixture was stirred at room temperature for 6 hours. The reaction mixture was filtered, and the filtrate was washed with a 10% sodium sulfide aqueous solution and sodium hydrogencarbonate aqueous solution, dried over magnesium sulfate. After filtration, the filtrate was concentrated under reduced pressure to afford 2-(2-methoxymethoxyethyl)oxirane (10.3 g, 86%) as a colorless oil.

$^1$H-NMR (CDCl$_3$) δppm: 1.69-1.96 (2H, m), 2.53 (1H, dd, J=2.7 Hz, 4.9 Hz), 2.79 (1H, t, J=4.9 Hz), 3.02-3.08 (1H, m), 3.38 (3H, s), 3.68 (2H, t, J=5.9 Hz), 4.64 (2H, s).

Reference Example 305

Preparation of 4-(4-trifluoromethylphenoxy)piperidine-1-carbonylchloride

A mixture of 4-(4-trifluoromethylphenoxy) piperidine (0.6 g, 2.45 mmol), triphosgene (0.25 g, 0.86 mmol), and pyridine (0.4 ml, 4.90 mmol) in toluene (6 ml) was heated under reflux for 2.5 hours. To which ethyl acetate was added, and the mixture was washed with 10% hydrochloric acid, dried over magnesium sulfate. After filtration, the filtrate was concentrated under reduced pressure to afford 4-(4-trifluoromethylphenoxy)piperidine-1-carbonylchloride (0.72 g, yield 96%) as a pale yellow oil.

$^1$H-NMR (CDCl$_3$) δppm: 1.79-2.10 (4H, m), 3.50-3.96 (4H, m), 4.58-4.75 (1H, m), 6.97 (2H, d, J=8.8 Hz), 7.56 (2H, d, J=8.8 Hz).

Reference Example 306

Preparation of 4-(4-trifluoromethylphenylamino)-piperidine-1-carbonylchloride

A mixture of (4-trifluoromethylphenylamino)-piperidine (1.14 g, 4.67 mmol), triphosgene (0.55 g, 1.87 mmol), and triethylamine (0.98 ml, 7.01 mmol) in methylene chloride (10 ml) was stirred at room temperature for 1.5 hours. The reaction mixture was washed with water, and dried over magnesium sulfate. After filtration, the filtrate was concentrated under reduced pressure to afford 4-(4-trifluoromethylphenylamino)piperidine-1-carbonylchloride (1.43 g, quantitative) as a pale yellow oil.

$^1$H-NMR (CDCl$_3$) δppm: 1.33-1.65 (2H, m), 2.09-2.24 (2H, m), 3.02-3.22 (1H, m), 3.22-3.41 (1H, m), 3.48-3.70 (1H, m), 4.20-4.35 (2H, m), 6.66 (2H, d, J=8.5 Hz), 7.43 (2H, d, J=8.5 Hz).

As shown in Reference Example 305 or 306, amines, cyclic amines, and benzene-condensed heterocyclic compounds were allowed to react in the presence of triphosgene and triethylamine or pyridine to afford compounds of Reference Examples 307 to 324.

Reference Example 307

5-chloro-2,3-dihydroindole-1-carbonylchloride a pale yellow crystalline powder, yield 100% $^1$H-NMR (CDCl$_3$) δppm: 3.19 (2H, t, J=8.3 Hz), 4.28 (2H, t, J=8.3 Hz), 7.18-7.22 (2H, m), 7.80 (1H, d, J=9.5 Hz).

Reference Example 308

6-chloro-3,4-dihydro-1H-isoquinoline-2-carbonylchloride a pale yellow oil, yield 100% $^1$H-NMR (CDCl$_3$) δppm: 2.83-3.00 (2H, m), 3.83 (1H, t, J=6.0 Hz), 3.90 (1H, t, J=6.0 Hz), 4.71 (1H, s), 4.80 (1H, s), 7.06 (1H, d, J=8.0 Hz), 7.13-7.28 (2H, m).

Reference Example 309

6-chloro-3,4-dihydro-2H-quinoline-1-carbonylchloride a yellow oil, yield 100% $^1$H-NMR (CDCl$_3$) δppm: 1.99-2.09 (2H, m), 2.79 (2H, t, J=6.5 Hz), 3.94 (2H, t, J=6.3 Hz), 7.14-7.20 (2H, m), 7.62 (1H, d, J=8.5 Hz).

Reference Example 310

5-chloro-1,3-dihydroisoindole-2-carbonylchloride a yellow oil, yield 100% $^1$H-NMR (CDCl$_3$) δppm: 3.19 (2H, t, J=8.3 Hz), 4.28 (2H, t, J=8.3 Hz), 7.18-7.22 (2H, m), 7.80 (1H, d, J=9.5 Hz).

Reference Example 311 tert-butyl 4-chlorocarbonylpiperazine-1-carboxylate a pale yellow crystalline powder, yield 100% $^1$H-NMR (CDCl$_3$) δppm: 1.47 (9H, s), 3.16-3.29 (2H, m), 3.37-3.55 (4H, m), 3.55-3.78 (2H, m)

Reference Example 312

4-(4-trifluoromethoxybenzyloxycarbonyl)piperazine-1-carbonylchloride

Yield 100% $^1$H-NMR (CDCl$_3$) δppm: 3.43-3.80 (8H, m), 5.15 (2H, s), 7.15-7.25 (2H, m), 7.33-7.45 (2H, m).

Reference Example 313

4-[3-(4-trifluoromethylphenyl)-2-propenyloxycarbonyl]-piperazine-1-carbonylchloride Yield 100% $^1$H-NMR (CDCl$_3$) δppm: 3.54-3.65 (4H, m), 3.65-3.72 (2H, m), 3.72-3.83 (2H, m), 4.80 (2H, dd, J=1.1 Hz, 6.1 Hz), 6.39 (1H, dt, J=6.1 Hz, 15.9 Hz), 6.68 (1H, d, J=15.9 Hz), 7.49 (2H, d, J=8.4 Hz), 7.59 (2H, d, J=8.4 Hz).

Reference Example 314

4-(4-chlorobenzyl)piperazine-1-carbonylchloride a brown oil, yield 100% $^1$H-NMR (CDCl$_3$) δppm: 2.65-2.96 (4H, m), 3.67-4.08 (6H, m), 7.36-7.39 (4H, m).

Reference Example 315

4-(4-trifluoromethylbenzyl)piperazine-1-carbonylchloride a brown oil, yield 100% $^1$H-NMR (CDCl$_3$) δppm: 2.97-3.12 (4H, m), 3.91-4.06 (2H, m), 4.06-4.21 (2H, m), 4.15 (2H, s), 7.58-7.73 (4H, m).

Reference Example 316

4-(4-trifluoromethoxybenzyl)piperazine-1-carbonylchloride a brown oil, yield 100% $^1$H-NMR (CDCl$_3$) δppm: 2.58-2.85 (4H, m), 3.58-3.90 (6H, m), 7.17-7.25 (2H, m), 7.35-7.46 (2H, m).

Reference Example 317

4-(4-trifluoromethoxyphenyl)-1,2,3,6-tetrahydropyridine-1-carbonylchloride a pale brown oil, yield 57% $^1$H-NMR (CDCl$_3$) δppm: 2.54-2.67 (2H, m), 3.85 (1H, t, J=5.7 Hz), 3.94 (1H, t, J=5.7 Hz), 4.28 (1H, d, J=2.7 Hz), 4.36 (1H, d, J=2.7 Hz), 5.94-6.06 (1H, m), 7.16-7.21 (2H, m), 7.36-7.41 (2H, m).

Reference Example 318

4-(4-methoxyphenyl)-1,2,3,6-tetrahydropyridine-1-carbonylchloride a pale brown oil, yield 60% $^1$H-NMR (CDCl$_3$) δppm: 2.54-2.67 (2H, m), 3.51 (1H, t, J=5.6 Hz), 3.81 (3H, s), 3.92-4.02 (1H, m), 4.23-4.31 (1H, m), 4.31-4.37 (1H, m), 5.87-5.96 (1H, m), 6.85-6.90 (2H, m), 7.29-7.35 (2H, m).

Reference Example 319

4-(3-trifluoromethylphenyl)-1,2,3,6-tetrahydropyridine-1-carbonylchloride a pale brown oil, yield 100% $^1$H-NMR (CDCl$_3$) δppm: 2.58-2.71 (2H, m), 3.87 (1H, t, J=5.7 Hz), 3.96 (1H, t, J=5.7 Hz), 4.31 (1H, d, J=2.8 Hz), 4.39 (1H, d, J=2.8 Hz), 6.04-6.15 (1H, m), 7.45-7.63 (4H, m).

Reference Example 320

4-(4-bromophenyl)-1,2,3,6-tetrahydropyridine-1-carbonylchloride a pale brown oil, yield 100% $^1$H-NMR (CDCl$_3$) δppm: 2.52-2.67 (2H, m), 3.84 (1H, t, J=5.7 Hz), 3.93 (1H, t, J=5.7 Hz), 4.27 (1H, d, J=2.6 Hz), 4.35 (1H, d, J=2.6 Hz), 5.94-6.06 (1H, m), 7.21-7.24 (2H, m), 7.43-7.49 (2H, m).

Reference Example 321

4-(4-fluorophenyl)-1,2,3,6-tetrahydropyridine-1-carbonylchloride a pale brown oil, yield 100% $^1$H-NMR (CDCl$_3$) δppm: 2.54-2.67 (2H, m), 3.84 (1H, t, J=5.7 Hz), 3.93 (1H, t, J=5.7 Hz), 4.27 (1H, d, J=2.6 Hz), 4.35 (1H, d, J=2.6 Hz), 5.90-6.00 (1H, m), 7.00-7.07 (2H, m), 7.24-7.35 (2H, m).

Reference Example 322

N-(4-chlorophenyl)-N-cyclohexylcarbamylchloride a pale yellow crystalline powder, yield 100% $^1$H-NMR (CDCl$_3$) δppm: 0.79-1.06 (1H, m), 1.14 (2H, t, J=3.5 Hz, 12.5 Hz), 1.23-1.44 (2H, m), 1.50-65 (1H, m), 1.67-1.81 (2H, m), 1.87-2.00 (2H, m), 4.78 (1H, m), 7.06-7.10 (2H, m), 7.36-7.41 (2H, m).

Reference Example 323

N-methyl-N-(4-trifluoromethoxybenzyl)carbamylchloride a yellow oil, yield 100% $^1$H-NMR (CDCl$_3$) δppm: 3.09 (3H, s), 4.58 (2H, s), 7.16-7.33 (4H, m).

Reference Example 324

4-[(4-trifluoromethylbenzylidene)amino]piperazine-1-carbonylchloride a brown oil, yield 100% $^1$H-NMR (CDCl$_3$) δppm: 3.17-3.39 (4H, m), 3.74-4.02 (4H, m), 7.56 (1H, s), 7.60 (2H, d, J=8.3 Hz), 7.69 (2H, d, J=8.3 Hz).

Reference Example 325

Preparation of 4-(4-trifluoromethoxyphenyl)piperazine-1-carbonylchloride

A mixture of 1-(4-trifluoromethoxyphenyl)piperazine (1.0 g, 4.1 mmol), triphosgene (0.42 g, 1.4 mmol), and pyridine (0.66 ml, 8.2 mmol) in toluene (20 ml) was stirred at 100° C. for 4.5 hours. To which ethyl acetate was added, and the mixture was washed with water, dried over magnesium sulfate. After filtration, the filtrate was concentrated under reduced pressure to afford 4-(4-trifluoromethoxyphenyl)piperazine-1-carbonylchloride (1.3 g, quantitative) as a brown oil.

$^1$H-NMR (CDCl$_3$) δppm: 3.08-3.30 (4H, m), 3.67-4.00 (4H, m), 6.79-6.98 (2H, m), 7.08-7.17 (2H, m).

Using corresponding starting materials, compounds of Reference Examples 326 to 332 were quantitatively prepared in the same manner as described in Reference Example 325.

Reference Example 326

4-(4-trifluoromethylphenyl)piperazine-1-carbonyl-chloride $^1$H-NMR (CDCl$_3$) δppm: 3.26-3.39 (4H, m), 3.76-3.87 (2H, m), 3.87-3.98 (2H, m), 6.87-6.98 (2H, m), 7.48-7.59 (2H, m).

Reference Example 327

4-(4-methoxyphenyl)piperazine-1-carbonylchloride $^1$H-NMR (CDCl$_3$) δppm: 3.04-3.15 (4H, m), 3.52-3.75 (2H, m), 3.75-3.92 (2H, m), 3.78 (3H, s), 6.81-6.98 (4H, m).

Reference Example 328

4-(4-chlorophenyl)piperazine-1-carbonylchloride $^1$H-NMR (CDCl$_3$) δppm: 3.10-3.25 (4H, m), 3.37-3.52 (2H, m), 3.73-3.90 (2H, m), 6.83-6.88 (2H, m), 7.20-7.25 (2H, m).

Reference Example 329

4-(3-chlorophenyl)piperazine-1-carbonylchloride $^1$H-NMR (CDCl$_3$) δppm: 3.15-3.29 (4H, m), 3.73-3.94 (4H, m), 6.77-6.81 (1H, m), 6.88-6.91 (2H, m), 7.20 (1H, t, J=8.3 Hz).

Reference Example 330

4-(3,4-dichlorophenyl)piperazine-1-carbonylchloride $^1$H-NMR (CDCl$_3$) δppm: 3.08-3.27 (4H, m), 3.37-3.48 (2H, m), 3.60-3.73 (1H, m), 3.73-3.90 (1H, m), 6.75 (1H, dd, J=2.9 Hz, 9.0 Hz), 6.96-6.98 (1H, m), 7.30 (1H, dd, J=5.1 Hz, 9.0 Hz)

Reference Example 331

4-(4-fluorophenyl)piperazine-1-carbonylchloride $^1$H-NMR (CDCl$_3$) δppm: 3.04-3.19 (4H, m), 3.40-3.50 (2H, m), 3.62-3.75 (1H, m), 3.75-3.92 (1H, m), 6.86-7.03 (4H, m)

Reference Example 332

4-(3-trifluoromethylphenyl)piperazine-1-carbonyl-chloride $^1$H-NMR (CDCl$_3$) δppm: 3.21-3.35 (4H, m), 3.42-3.54 (2H, m), 3.77-3.96 (2H, m), 7.02-7.19 (3H, m), 7.31-7.46 (1H, m).

Reference Example 333

Preparation of tert-butyl 4-[1-(4-trifluoromethoxyphenyl)piperidin-4-yl]piperazine-1-carboxylate A mixture of tert-butyl 4-piperidin-4-ylpiperazine-1-carboxylate (1.5 g, 5.67 mmol), 4-(trifluoromethoxy)bromobenzene (3.36 g, 13.92 mmol), palladium acetate (25 mg, 0.11 mmol), BINAP (87 mg, 0.14 mmol), and sodium tert-butoxide (1.07 g, 11.14 mmol) in toluene (20 ml) was stirred at 80° C. under a nitrogen atmosphere for 8 hours. The reaction mixture was allowed to return to room temperature, to which ethyl acetate (10 ml) and brine (20 ml) were added, and the mixture was filtered. The organic layer was separated, and dried over sodium sulfate. After filtration, the filtrate was concentrated, and the residue was purified by silica gel column chromatography (methylene chloride/methanol=20/1) to afford tert-butyl 4-[1-(4-trifluoromethoxyphenyl)piperidin-4-yl]piperazine-1-carboxylate (1.01 g, 42%) as a yellow powder.

$^1$H-NMR(CDCl$_3$) δppm 1.49(9H, s), 1.52-1.75(2H, m), 1.83-1.99(2H, m), 2.31-2.52(5H, m), 2.64-2.81(2H, m), 3.36-3.49(4H, m), 3.62-3.75(2H, m), 6.86(2H, d, J=8.5 Hz), 7.09(2H, d, J=8.5 Hz).

Reference Example 334

Preparation of 1-[1-(4-trifluoromethoxyphenyl)piperidin-4-yl]piperazine

Tert-butyl 4-[1-(4-trifluoromethoxyphenyl)-piperidin-4-yl]piperazine-1-carboxylate (1 g, 2.33 mmol) was dissolved in methylene chloride (10 ml), to which trifluoroacetic acid (10 ml) was added while cooling in an ice-bath, and the mixture was stirred at room temperature for 1 hour. The reaction mixture was washed with a 25% sodium hydroxide aqueous solution (40 ml) and brine (10 ml), and dried over sodium sulfate. After filtration, the filtrate was concentrated to afford 1-[1-(4-trifluoromethoxyphenyl)piperidin-4-yl]piperazine (770 mg, quantitative) as a yellow amorphous form.

$^1$H-NMR(CDCl$_3$) δppm 1.52-1.75(2H, m), 1.83-1.99(2H, m), 2.25-2.38(1H, m), 2.48-2.76(6H, m), 2.79-2.99(4H, m), 3.56-3.75(2H, m), 6.89(2H, d, J=8.5 Hz), 7.09(2H, d, J=8.5 Hz).

Following compounds were prepared in the same manner as described in Reference Example 334.

TABLE 1

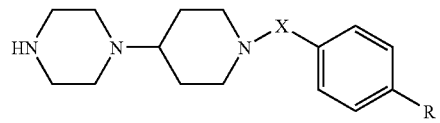

| Reference Example | X | R | $^1$H-NMR (CDCl$_3$) δppm |
|---|---|---|---|
| 335 | none | OCF$_3$ | 1.52-1.75(2H, m), 1.83-1.99(2H, m), 2.25-2.35(1H, m), 2.48-2.76(6H, m), 2.79-2.99(4H, m), 3.56-3.75(2H, m), 6.89(2H, d, J=8.5Hz), 7.09(2H, d, J=8.5Hz) |
| 336 | C=O | Cl | 1.31-1.55(2H, m), 1.69-1.98(2H, m), 2.36-2.60(5H, m), 2.69-3.00(6H, m), |

TABLE 1-continued

Structure: HN-piperazine-N-piperidine-N-X-C6H4-R

| Reference Example | X | R | $^1$H-NMR (CDCl$_3$) δppm |
|---|---|---|---|
| 337 | C=O | OCF$_3$ | 3.69-3.86(1H, m), 4.55-4.79(1H, m), 7.24-7.43(4H, m) 1.31-1.60(2H, m), 1.71-2.00(2H, m), 2.38-2.60(5H, m), 2.67-3.07(6H, m), 3.62-3.86(1H, m), 4.57-4.83(1H, m), 7.25(2H, d, J=2.3Hz, 8.7Hz), 7.45(2H, d, J=2.3H, 8.7Hz). |
| 338 | CH$_2$ | Cl | 1.45-1.60(2H, m), 1.67-1.83(2H, m), 1.86-2.00(2H, m), 2.12-2.24(1H, m), 2.45-2.57(4H, m), 2.79-2.93(6H, m), 3.44(2H, s), 7.14-7.31(4H, m) |
| 339 | CH$_2$ | OCF$_3$ | 1.48-1.81(4H, m), 1.85-2.00(2H, m), 2.12-2.29(1H, m), 2.43-2.57(4H, m), 2.76-2.98(6H, m), 3.46(2H, s), 7.15(2H, d, J=8.5Hz), 7.33(2H, d, J=8.5Hz) |

TABLE 2

Structure: HN-piperidine-N-piperazine-N-X-C6H4-R

| Reference Example | X | R | $^1$H-NMR (CDCl$_3$) δ ppm |
|---|---|---|---|
| 340 | C=O | Cl | 1.29-1.48(2H, m), 1.67-1.86(2H, m), 2.31-2.69(7H, m), 3.07-3.21(2H, m), 3.31-3.50(2H, m), 3.60-3.83(2H, m), 7.26-7.45(4H, m) |
| 341 | C=O | OCF$_3$ | 1.31-1.50(2H, m), 1.64-1.83(2H, m), 2.29-2.69(7H, m), 3.07-3.21(2H, m), 3.31-3.50(2H, m), 3.64-3.83(2H, m), 7.25(2H, d, J=8.7Hz), 7.45(2H, d, J=8.7Hz) |
| 342 | CH$_2$ | OCF$_3$ | 1.25-1.48(2H, m), 1.69-1.86(2H, m), 2.19-2.62(11H, m), 3.00-3.17(2H, m), 3.50(2H, s), 7.15(2H, d, J=8.6Hz), 7.34(2H, d, J=8.6Hz) |
| 343 | CH$_2$ | Cl | 1.24-1.43(2H, m), 1.74-1.86(2H, m), 2.21-2.60(11H, m), 3.02-3.17(2H, m), 3.46(2H, s), 7.19-7.33(4H, m) |
| 344 | none | OCF$_3$ | 1.31-1.51(2H, m), 1.76-1.93(2H, m), 2.29-2.45(1H, m), 2.52-2.79(6H, m), 3.10-3.26(6H, m), 6.88(2H, d, J=8.6Hz), 7.10(2H, d, J=8.6Hz). |
| 345 | none | Cl | 1.33-1.52(2H, m), 1.81-1.98(2H, m), 2.26-2.43(1H, m), 2.52-2.74(6H, m), 3.05-3.21(6H, m), 6.84(2H, d, J=6.9Hz), 7.19(2H, d, J=6.9Hz) |

TABLE 3

Structure: HN-piperazine-N-C6H4-O-R

| Reference Example | R | $^1$H-NMR (CDCl$_3$) δppm |
|---|---|---|
| 346 | 4-ClPh— | 2.98-3.12(8H, m), 6.80-6.94(6H, m), 7.24(2H, d, J=2.3Hz, 6.8Hz) |
| 347 | 4-CF$_3$PhCH$_2$— | 3.04(8H, s), 5.08(2H, s), 6.90(4H, s), 7.54(2H, d, J=8.2Hz), 7.63(2H, d, J=8.2Hz) |
| 348 | 4-ClPhCH$_2$— | 3.03(8H, s), 4.98(2H, s), 6.89(4H, s), 7.35(4H, s). |
| 349 | 4-CF$_3$OPhCH$_2$— | 3.04(8H, s), 5.01(2H, s), 6.90(4H, s), 7.22(2H, d, J=8.5Hz), 7.45(2H, d, J=8.5Hz) |
| 350 | 4-CF$_3$OPh— | 2.96-3.14(8H, m), 6.82-6.98(6H, m), 7.06-7.16(2H, m) |
| 351 | 4-CF$_3$Ph— | 2.96-3.14(8H, m), 6.84-7.00(6H, m), 7.53(2H, d, J=8.6Hz) |

TABLE 4

Structure: HN-piperazine-N-C6H4-CH2-NH-C6H4-R

| Reference Example | R | $^1$H-NMR (CDCl$_3$) δppm |
|---|---|---|
| 352 | Cl— | 2.96-3.16(8H, m), 3.97(1H, br), 4.20(1H, d, J=5.4Hz), 6.55(1H, d, J=8.8Hz), 6.60(1H, d, J=8.8Hz), 6.90(1H, d, J=8.8Hz), 7.00-7.14(4H, m), 7.18-7.25(1H, m) |
| 353 | CF$_3$O— | 2.94-3.20(8H, m), 4.00(1H, br), 4.21(1H, d, J=5.3Hz), 6.57(1H, d, J=6.8Hz), 6.64(1H, d, J=8.8Hz), 6.80-7.12(5H, m), 7.16-7.25(1H, m) |

TABLE 5

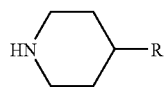

| Reference Example | R | $^1$H-NMR(CDCl$_3$) δppm |
|---|---|---|
| 354 | ![4-methylphenoxy-4-trifluoromethylphenyl] | 1.51-1.73(2H, m), 1.76-1.92(2H, m), 2.51-2.82(3H, m), 3.10-3.27(2H, m), 6.92-7.08(4H, m), 7.12-7.27(2H, m), 7.56(2H, d, J=8.6Hz) |
| 355 | ![N-methylpiperidinyloxy-4-OCF3-phenyl] | 1.33-1.60(4H, m), 1.69-2.02(4H, m), 2.29-2.64(5H, m), 2.76-2.88(2H, m), 3.05-3.17(2H, m), 4.14-4.31(1H, m), 6.85(2H, d, J=8.7Hz), 7.12(2H, d, J=8.7Hz) |
| 356 | ![acetamido-4-OCF3-phenyl] | 1.52-1.98(4H, m), 2.26-2.43(1H, m), 2.55-2.74(2H, m), 3.10-3.26(2H, m), 7.18(2H, d, J=8.4Hz), 7.55(2H, d, J=8.4Hz) |
| 357 | ![acetylpiperazinyl-4-OCF3-phenyl] | 1.60-1.81(4H, m), 2.57-2.74(3H, m), 3.05-3.21(6H, m), 3.60-3.83(4H, m), 6.90(2H, d, J=8.4Hz), 7.13(2H, d, J=8.4Hz) |
| 358 | ![4-phenoxy-4-CF3-phenyl] | 1.56-1.73(2H, m), 1.83-1.89(3H, m), 2.57-2.82(3H, m), 3.18-3.24(2H, m), 6.95-7.05(4H, m), 7.20-7.25(2H, m), 7.53-7.57(2H, m) |
| 359 | ![phenoxymethyl-4-OCF3-phenyl] | 1.57-1.86(4H, m), 2.52-2.81(4H, m), 3.19-3.25(2H, m), 5.03(2H, s), 6.89-6.94(2H, m), 7.11-7.25(4H, m), 7.44-7.48(2H, m) |
| 360 | ![phenoxymethyl-4-CF3-phenyl] | 1.51-1.68(3H, m), 1.78-1.84(2H, m), 2.50-2.64(1H, m), 2.67-2.79(2H, m), 3.15-3.21(2H, m), 5.11(1H, s), 6.87-6.94(2H, m), 7.12-7.18(2H, m), 7.52-7.57(2H, m), 7.62-7.66(2H, m) |
| 361 | ![phenoxymethyl-4-Cl-phenyl] | 1.60-2.12(5H, m), 2.52-2.66(1H, m), 2.71-2.83(2H, m), 3.22-3.28(2H, m), 5.01(2H, s), 6.88-6.93(2H, m), 7.11-7.18(2H, m), 7.30-7.41(4H, m) |
| 362 | ![N-methyl-N-(4-OCF3-benzyl)aniline] | 1.86-2.18(3H, m), 2.35-2.52(1H, m), 2.61-2.69(1H, m), 2.93-3.01(5H, m), 3.24-3.59(3H, m), 4.49(2H, s), 6.67-6.70(2H, m), 7.07-7.17(4H, m), 7.23-7.27(2H, m) |

TABLE 6

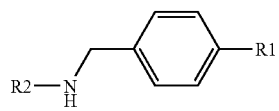

| Reference Example | R1 | R2 | $^1$H-NMR(CDCl$_3$) δppm |
|---|---|---|---|
| 363 | ![Boc-piperazinyl] | CH$_3$ | 1.50(9H, s), 2.44(3H, s), 3.00-3.14(4H, m), 3.49-3.57(4H, m), 3.72(2H, s), 6.89(2H, d, J=7.2Hz), 7.26(2H, d, J=7.2Hz). |

TABLE 6-continued

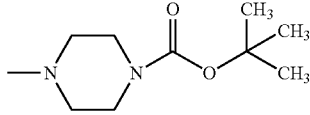

| Reference Example | R1 | R2 | ¹H-NMR(CDCl₃) δppm |
|---|---|---|---|
| 364 | 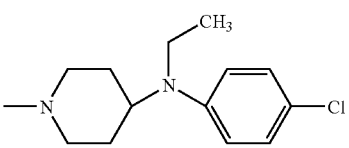 | C₂H₅ | 1.15(3H, t, J=7.1Hz), 1.48(9H, s), 2.18(1H, brs), 2.69(2H, q, J=7.1Hz), 3.09-3.12(4H, m), 3.55-3.59(4H, m), 3.73(2H, s), 6.86-6.92(2H, m), 7.23-7.26(2H, m). |
| 365 | 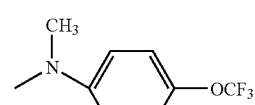 | CH₃ | 1.09-1.16(3H, m), 1.78-1.88(2H, m), 2.49(3H, s), 2.73-2.80(2H, m), 3.17-3.31(3H, m), 3.62-3.79(5H, m), 3.92(2H, s), 6.67-6.70(2H, m), 6.91-6.93(2H, m), 7.13-7.19(2H, m), 7.39-7.42(2H, m). |

TABLE 7

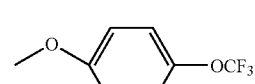

| Reference Example | R | ¹H-NMR(CDCl) δppm |
|---|---|---|
| 366 | —Cl | 1.51-1.67(2H, m), 1.90-2.04(2H, m), 2.72(2H, s), 3.18-3.43(4H, m), 6.89(2H, d, J=8.4Hz), 7.21(2H, d, J=8.4Hz) |
| 367 | —OCF₃ | 1.53-1.67(2H, m), 1.86-2.04(2H, m), 2.73(2H, s), 3.22-3.45(4H, m), 6.93(2H, d, J=8.4Hz), 7.11(2H, d, J=8.4Hz). |
| 368 | 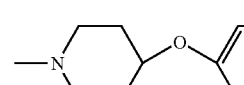 | 1.53-1.63(2H, m), 1.90-2.06(2H, m), 2.73(2H, s), 3.24(3H, s), 3.27-3.45(4H, m), 6.72(2H, d, J=8.4Hz), 6.90-7.10(6H, m). |
| 369 | 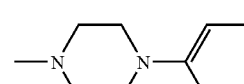 | 1.54-1.69(2H, m), 1.92-2.06(2H, m), 2.73(2H, s), 3.20-3.43(4H, m), 6.84-6.96(6H, m), 7.14(2H, d, J=8.4Hz) |
| 370 | (N-methylpiperidin-4-yl-oxy)-phenyl-OCF₃ | 1.58-1.69(2H, m), 1.88-2.15(6H, m), 2.71(2H, s), 2.90-3.04(2H, m), 3.17-3.44(6H, m), 4.31-4.46(1H, m), 6.85-6.94(6H, m), 7.14(2H, d, J=8.4Hz) |
| 371 | (N-methylpiperazin-1-yl)-phenyl-OCF₃ | 1.55-1.71(2H, m), 1.92-2.04(2H, m), 2.72(2H, s), 3.12-3.35(12H, m), 6.86-7.00(6H, m), 7.14(2H, d, J=8.5Hz) |

Following compounds were prepared in the same manner as described in Reference Example 186.

Reference Example 372

1-(4-Hydroxyphenyl)-4-phenylpiperidin-4-ol

MS: 269(M$^+$)

Reference Example 373

4-(4-chlorophenyl)-1-(4-hydroxyphenyl)piperidin-4-ol

MS: 349(M$^+$−1)

Reference Example 374

1-(4-hydroxyphenyl)-4-(4-trifluoromethoxyphenyl)piperidin-4-ol

MS: 353(M$^+$)

Reference Example 375

(4-hydroxyphenyl)-[4-(4-trifluoromethoxyphenoxy)-piperidin-1-yl]methanone

MS: 381(M$^+$)

Reference Example 376 tert-butyl 1-(4-hydroxyphenyl)piperidine-4-carboxylate $^1$H-NMR(CDCl$_3$) δppm 1.46(9H, s), 1.76-2.05(4H, m), 2.23-2.34(1H, m), 2.62-2.73(2H, m), 3.39-3.48(2H, m), 4.39-4.49(1H, m), 4.78(1H, s), 6.72-6.78(2H, m), 6.82-6.89(2H, m).

Reference Example 377

4-(4-phenylpiperidin-1-yl)phenol

MS: 253(M$^+$)

Reference Example 378

4-(4,4-diethoxypiperidin-1-yl)phenol

MS: 265(M$^+$)

Reference Example 379

2-dimethylaminomethyl-4-[4-(4-trifluoromethoxyphenoxy)piperidin-1-yl]phenol

MS: 410(M$^+$)

Reference Example 380

4-(4-[1,3]dioxolan-2-ylpiperidin-1-yl)phenol $^1$H NMR(CDCl$_3$) δppm 1.51-1.70(2H, m), 1.80-1.92(2H, m), 2.53-2.66(2H, m), 3.48-3.57(2H, m), 3.84-3.92(2H, m), 3.92-4.02(2H, m), 4.63(1H, brs), 4.69(1H, d, J=4.9 Hz), 6.70-6.78(2H, m), 6.83-6.91(2H, m).

Reference Example 381

4-[4-(4-trifluoromethoxyphenyl)piperazin-1-yl]phenol

MS: 337(M$^+$)

Reference Example 382 tert-butyl 4-(4-hydroxyphenoxy)piperidine-1-carboxylate

MS: 293(M$^+$)

Reference Example 383

4-[1-(4-trifluoromethylphenyl)piperidin-4-yloxy]phenol

MS: 337(M$^+$)

Reference Example 384

4-(1,4-dioxa-8-azaspiro[4,5]decan-8-yl)phenol $^1$H NMR(CDCl$_3$) δppm 1.87(4H, t, J=5.7 Hz), 3.18(4H, t, J=5.7 Hz), 3.99(4H, s), 6.74(2H, d, J=8.9 Hz), 6.88(2H, d, J=8.9 Hz).

Reference Example 385

4-(4-phenyl-1,2,3,6-tetrahydropyridin-1-yl)phenol

MS: 251(M$^+$)

Reference Example 386 tert-butyl 4-(4-hydroxyphenyl)piperazine-1-carboxylate $^1$H NMR(CDCl$_3$) δppm 1.49(9H, s), 2.95-3.00(4H, m), 3.55-3.60(4H, m), 5.77(1H, s), 6.74-6.86(4H, m).

Reference Example 387

4-[4-(4-trifluoromethoxyphenyl)piperazin-1-yl]phenol $^1$H NMR(CDCl$_3$) δppm 3.19-3.24(4H, m), 3.29-3.34(4H, m), 4.51(1H, s), 6.76-6.82(2H, m), 6.87-6.97(4H, m), 7.11-7.16(2H, m).

Reference Example 388

4-{4-[(4-trifluoromethoxybenzylidene)amino]piperazin-1-yl}phenol

MS: 349(M$^+$−1)

Reference Example 389

4-[4-(4-chlorobenzyl)piperazin-1-yl]phenol $^1$H NMR(CDCl$_3$) δppm 2.60(4H, t, J=4.8 Hz), 3.08(4H, t, J=4.8 Hz), 3.53(2H, s), 6.71-6.78(2H, m), 6.81-6.89(2H, m), 7.27-7.42(4H, m).

Reference Example 390

3-(4-hydroxyphenyl)oxazolidin-2-one $^1$H NMR(CDCl$_3$) δppm 3.94-4.01(2H, m), 4.35-4.42(2H, m), 6.73-6.80(2H, m), 7.29-7.36(2H, m), 9.34(1H, s).

Reference Example 391

4-(4-pyridyl)phenol $^1$H NMR(CDCl$_3$) δppm 6.87-6.93(2H, m), 7.60-7.70(4H, m), 8.54-8.57(2H, m), 9.85(1H, s).

Reference Example 392

4-hydroxy-N-(4-trifluoromethoxyphenyl)benzamide $^1$H NMR(CDCl$_3$) δppm 6.84-6.87(2H, m), 7.31-7.34(2H, m), 7.83-7.87(4H, m), 10.11(1H, brs), 10.15(1H, brs).

Reference Example 393

(4-hydroxyphenyl)-(4-trifluoromethoxyphenyl)methanone $^1$H NMR(CDCl$_3$) δppm 6.08(1H, s), 6.92-6.96(2H, m), 7.30-7.33(2H, m), 7.76-7.83(4H, m).

Reference Example 394

(4-hydroxyphenyl)-(4-trifluoromethylphenyl)methanone

MS: 266(M$^+$)

Reference Example 395

4-(4-trifluoromethoxyphenoxy)phenol $^1$H NMR(CDCl$_3$) δppm 4.67(1H, brs), 6.81-6.85(2H, m), 6.90-6.96(4H, m), 7.13-7.16(2H, m).

TABLE 8

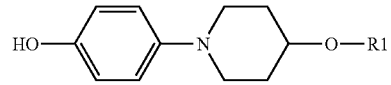

| Reference Example | R1 | NMR or Ms |
|---|---|---|
| 396 | 4-ClPh— | $^1$H NMR(CDCl$_3$) δ 1.87-2.01(2H, m), 2.04-2.16(2H, m), 2.91-3.02(2H, m), 3.29-3.39(2H, m), 4.34-4.44(1H, m), 4.85(1H, s), 6.71-6.78(2H, m), 6.82-6.92(4H, m), 7.20-7.26(2H, m). |
| 397 | 4-CF$_3$Ph— | $^1$H NMR(CDCl$_3$) δ 1.90-2.05(2H, m), 2.08-2.20(2H, m), 2.94-3.05(2H, m), 3.30-3.40(2H, m), 4.46-4.56(1H, m), 4.64(1H, s), 6.72-6.80(2H, m), 6.86-6.93(2H, m), 6.96-7.00(2H, m), 7.52-7.56(2H, m). |
| 398 | 4-FPh— | $^1$H NMR(CDCl$_3$) δ 1.86-2.00(2H, m), 2.04-2.16(2H, m), 2.90-3.00(2H, m), 3.30-3.40(2H, m), 4.29-4.39(1H, m), 4.72(1H, s), 6.71-6.78(2H, m), 6.83-7.01(6H, m). |
| 399 | 4-CH$_3$OPh— | $^1$H NMR(CDCl$_3$) δ 1.86-2.00(2H, m), 2.05-2.13(2H, m), 2.88-2.99(2H, m), 3.31-3.41(2H, m), 3.77(3H, s), 4.25-4.35(1H, m), 4.72(1H, s), 6.72-6.77(2H, m), 6.80-6.92(6H, m). |
| 400 | 4-CH$_3$Ph— | $^1$H NMR(CDCl$_3$) δ 1.87-2.01(2H, m), 2.04-2.16(2H, m), 2.29(3H, s), 2.90-3.00(2H, m), 3.30-3.40(2H, m), 4.33-4.43(1H, m), 4.85(1H, s), 6.71-6.78(2H, m), 6.80-6.92(4H, m), 7.06-7.10(2H, m). |
| 401 | —C$_6$H$_5$ | $^1$H NMR(CDCl$_3$) δ 1.89-2.03(2H, m), 2.04-2.18(2H, m), 2.92-3.02(2H, m), 3.31-3.41(2H, m), 4.39-4.49(1H, m), 4.92(1H, s), 6.70-6.78(2H, m), 6.84-6.98(5H, m), 7.24-7.33(2H, m). |
| 402 | 4-CNPh— | $^1$H NMR(CDCl$_3$) δ 1.90-2.04(2H, m), 2.09-2.18(2H, m), 2.94-3.04(2H, m), 3.29-3.39(2H, m), 4.49-4.55(1H, m), 6.75-6.80(2H, m), 6.86-6.90(2H, m), 6.93-7.00(2H, m), 7.55-7.62(2H, m). |
| 403 | —CH$_2$-cyclo-C$_6$H$_{11}$ | Ms: 289(M+) |
| 404 | (tetrahydropyran-2-ylmethyl) | $^1$H NMR(CDCl$_3$) δ 1.54-2.07(11H, m), 2.74-2.87(2H, m), 3.31-3.43(2H, m), 3.47-3.57(1H, m), 3.72-3.83(1H, m), 3.88-3.98(1H, m), 4.74-4.78(1H, m), 6.69-6.76(2H, m), 6.83-6.88(2H, m). |

TABLE 9

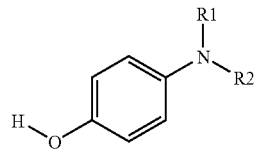

| Reference Example | R1 | R2 | NMR |
|---|---|---|---|
| 405 | —CH₃ | 4-CF₃OPh— | ¹H NMR(CDCl₃) δ 3.23(3H, s), 4.88(1H, s), 6.66-6.73(2H, m), 6.80-6.87(2H, m), 6.99-7.08(4H, m). |
| 406 | —CH₃ | 4-ClPh— | ¹H NMR(CDCl₃) δ 3.22(3H, s), 4.69(1H, brs), 6.66-6.68(2H, m), 6.81-6.84(2H, m), 7.01-7.04(2H, m), 7.10-7.13(2H, m). |
| 407 | —CH₃ | 4-CF₃Ph— | ¹H NMR(CDCl₃) δ 3.28(3H, s), 4.80(1H, brs), 6.68-6.71(2H, m), 6.85-6.88(2H, m), 7.06-7.09(2H, m), 7.37-7.40(2H, m). |
| 408 | —C₂H₅ | 4-CF₃OPh— | ¹H NMR(CDCl₃) δ 1.19(3H, t, J=7.1Hz), 3.66(2H, q, J=7.1Hz), 4.75(1H, brs), 6.62-6.66(2H, m), 6.83-6.87(2H, m), 6.98-7.05(4H, m). |
| 409 | 4-CF₃OPhCH₂— | 4-CF₃OPhCH₂— | ¹H NMR(CDCl₃) δ 4.34(1H, bs), 4.49(4H, brs), 6.61-6.72(4H, m), 7.14-7.16(4H, m), 7.24-7.26(4H, m). |
| 410 | —C₂H₅ | 4-CF₃Ph— | ¹H NMR(CDCl₃) δ 1.21(3H, t, J=7.1Hz), 3.70(2H, q, J=7.1Hz), 4.87(1H, brs), 6.62-6.65(2H, m), 6.85-6.91(2H, m), 7.03-7.09(2H, m), 7.34-7.37(2H, m). |
| 411 | —C₂H₅ | 4-ClPh— | ¹H NMR(CDCl₃) δ 1.17(3H, t, J=7.1Hz), 3.65(2H, q, J=7.1Hz), 4.73(1H, brs), 6.59-6.63(2H, m), 6.82-6.85(2H, m), 6.98-7.03(2H, m), 7.06-7.10(2H, m). |
| 412 | —CH₃ | 4-CF₃OPhCH₂— | ¹H NMR(CDCl₃) δ 2.90(3H, s), 4.33(1H, brs), 4.40(2H, brs), 6.66-6.70(2H, m), 6.72-6.76(2H, m), 7.13-7.16(2H, m), 7.25-7.27(2H, m). |
| 413 | —CH₃ | 4-ClPhCH₂— | ¹H NMR(CDCl₃) δ 2.88(3H, s), 4.34(1H, brs), 4.36(2H, brs), 6.65-6.69(2H, m), 6.71-6.76(2H, m), 7.15-7.18(2H, m), 7.25-7.28(2H, m). |
| 414 | —CH₃ | 4-CF₃PhCH₂— | ¹H NMR(CDCl₃) δ 2.92(3H, s), 4.35(1H, brs), 4.46(2H, brs), 6.65-6.68(2H, m), 6.73-6.76(2H, m), 7.34-7.37(2H, m), 7.55-7.58(2H, m). |
| 415 | —C₂H₅ | 4-CF₃OPhCH₂— | ¹H NMR(CDCl₃) δ 1.14(3H, t, J=7.1Hz), 4.12(2H, q, J=7.1Hz), 4.28(1H, brs), 4.39(2H, brs), 6.50-6.80(4H, m), 7.13-7.15(2H, m), 7.26-7.28(2H, m). |
| 416 | —C₂H₅ | 4-CF₃PhCH₂— | 4.29(1H, brs), 4.45(2H, brs), 6.61-6.70(4H, m), 7.35-7.38(2H, m), 7.54-7.56(2H, m). |
| 417 | —C₂H₅ | 4-ClPhCH₂— | ¹H NMR(CDCl₃) δ 1.14(3H, t, J=7.0Hz), 3.35(2H, brs), 4.28(1H, brs), 4.36(2H, brs), 6.62-6.70(4H, m), 7.17-7.19(2H, m), 7.25-7.28(2H, m). |
| 418 | —COCH₃ | —C₆H₅ | ¹H NMR(CDCl₃) δ 2.06(3H, s), 6.27(1H, brs), 6.69-6.80(2H, m), 7.08-7.33(7H, m). |
| 419 | —COCH₃ | 4-ClPh— | ¹H NMR(CDCl₃) δ 2.06(3H, s), 6.50(1H, brs), 6.63-6.85(2H, m), 7.05-7.08(2H, m), 7.18-7.38(4H, m). |

TABLE 10

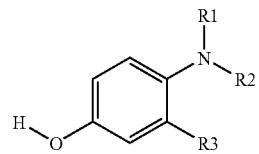

| Reference Example | R1 | R2 | R3 | NMR |
|---|---|---|---|---|
| 420 | —CH₃ | 4-CF₃OPh— | —F | ¹H NMR(CDCl₃) δ 3.22(3H, s), 5.02(1H, brs), 6.57-6.71(4H, m), 7.01-7.14(3H, m). |
| 421 | —CH₃ | 4-ClPh— | —F | ¹H NMR(CDCl₃) δ 3.20(3H, s), 5.02(1H, brs), 6.54-6.70(4H, m), 7.07-7.13(3H, m) |
| 422 | —CO₂CH₃ | —C₆H₅ | —H | ¹H NMR(CDCl₃) δ 3.75(3H, s), 5.86(1H, brs), 6.69-6.72(2H, m), 7.05-7.08(2H, m), 7.18-7.31(5H, m). |
| 423 | —CO₂CH₃ | 4-ClPh— | —H | ¹H NMR(CDCl₃) δ 3.75(3H, s), 5.52(1H, brs), 6.73-6.76(2H, m), 7.04-7.07(2H, m), 7.16-7.18(2H, m), 7.26-7.29(2H, m). |
| 424 | —COCH₃ | 4-CF₃Ph— | —H | ¹H NMR(CDCl₃) δ 2.08(3H, s), 6.04(1H, brs), 6.83-6.86(2H, m), 7.09-7.12(2H, m), 7.37-7.40(2H, m), 7.56-7.59(2H, m). |

TABLE 10-continued

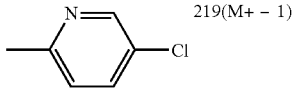

| Reference Example | R1 | R2 | R3 | NMR |
|---|---|---|---|---|
| 425 | —COCH₃ | 4-CF₃OPh— | —H | ¹H NMR(CDCl₃) δ 2.07(3H, s), 6.60-6.92(3H, m), 6.98-7.30(6H, m). |
| 426 | —CH₃ | —C₆H₅ | —H | ¹H NMR(CDCl₃) δ 3.24(3H, s), 4.63(1H, brs), 6.76-6.84(5H, m), 7.01-7.05(2H, m), 7.17-7.22(2H, m). |
| 427 | —COCH₃ | 4-ClPh— | —F | ¹H NMR(CDCl₃) δ 2.07(3H, brs), 6.46-6.61(2H, m), 6.96-7.36(6H, m). |
| 428 | —COCH₃ | 4-CF₃OPh— | —F | ¹H NMR(CDCl₃) δ 2.07(3H, brs), 6.48-6.62(2H, m), 6.90-7.42(6H, m). |

TABLE 11

| Reference Example | R1 | R2 | NMR or Ms |
|---|---|---|---|
| 429 | —C₆H₅ | 4-CF₃OPhCH₂— | ¹H NMR(CDCl₃) δ 4.72(1H, brs), 4.89(2H, brs), 6.75-6.83(5H, m), 7.05-7.18(6H, m), 7.34-7.37(2H, m). |
| 430 | —C₆H₅ | 4-CF₃PhCH₂— | ¹H NMR(CDCl₃) δ 4.67(1H, brs), 4.95(2H, brs), 6.74-6.83(5H, m), 7.06-7.18(4H, m), 7.44-7.47(2H, m), 7.54-7.57(2H, m). |
| 431 | —C₆H₅ | 4-ClPhCH₂— | ¹H NMR(CDCl₃) δ 4.64(1H, brs), 4.86(2H, brs), 6.74-6.82(5H, m), 7.04-7.08(2H, m), 7.12-7.17(2H, m), 7.26(4H, brs). |
| 432 | —COCH₃ | 4-CF₃OPhCH₂— | ¹H NMR(CDCl₃ δ 1.89(3H, s), 4.83(2H, s), 6.54(1H, brs), 6.82(4H, m), 7.09-7.12(2H, m), 7.20-7.26(2H, m). |
| 433 | —CH₃ | 4-CF₃PhCO— | ¹H NMR(CDCl₃) δ 3.46(3H, s), 6.28(1H, brs), 6.68-6.71(2H, m), 6.85-6.92(2H, m), 7.33-7.44(4H, m). |
| 434 | —CH₃ | 4-ClPhCO— | ¹H NMR(CDCl₃) δ 3.44(3H, s), 5.12(1H, brs), 6.67-6.72(2H, m), 6.88-6.91(2H, m), 7.13-7.16(2H, m), 7.21-7.24(2H, m). |
| 435 | —H | 4-CF₃OPhCO— | ¹H NMR(CDCl₃) δ 6.71-6.76(2H, m), 7.48-7.52(4H, m), 8.02-8.05(2H, m), 9.25(1H, s), 10.10(1H, brs). |
| 436 | —CH₃ | 4-CF₃OPhCO— | ¹H NMR(CDCl₃) δ 3.45(3H, s), 6.13(1H, brs), 6.69-6.72(2H, m), 6.87-6.89(2H, m), 6.99-7.02(2H, m), 7.31-7.34(2H, m). |
| 437 | —CH₃ | 4-CF₃OPhO(CH₂)₃— | ¹H NMR(CDCl₃) δ 1.97-2.06(2H, m), 2.85(3H, s), 3.42(2H, t, J=6.9Hz), 3.99(2H, t, J=6.0Hz), 4.28(1H, brs), 6.65-6.75(4H, m), 6.86-6.89(2H, m), 7.11-7.14(2H, m). |
| 438 | —H | [2-pyridyl-5-Cl] | 219(M+ − 1) |

TABLE 12

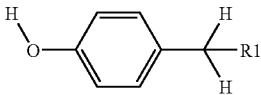

| Reference Example | R1 | NMR or Ms |
|---|---|---|
| 439 | 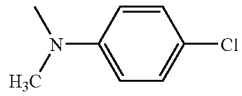 | Ms: 367(M+) |
| 440 | 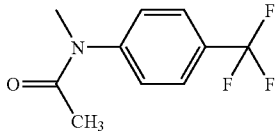 | ¹H NMR(CDCl₃) δ 2.96(3H, s), 4.43(2H, brs), 4.68(1H, s), 6.63-6.66(2H, m), 6.76-6.80(2H, m), 7.05-7.08(2H, m), 7.12-7.15(2H, m). |
| 441 | 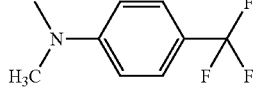 | ¹H NMR(CDCl₃) δ 1.90(3H, brs), 4.83(2H, s), 6.88(1H, brs), 6.74-6.76(2H, m), 7.02-7.06(2H, m), 7.10-7.13(2H, m), 7.60-7.63(2H, m). |
| 442 | 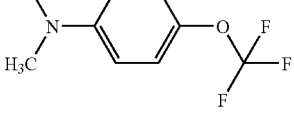 | ¹H NMR(CDCl₃) δ 3.06(3H, s), 4.52(2H, s), 4.70(1H, s), 6.71-6.81(4H, m), 7.05-7.07(2H, m), 7.41-7.44(2H, m). |
| 443 | 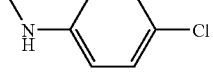 | ¹H NMR(CDCl₃) δ 2.99(3H, s), 4.44(2H, s), 4.68(1H, s), 6.66-6.70(2H, m), 6.77-6.81(2H, m), 7.04-7.10(4H, m). |
| 444 |  | ¹H NMR(CDCl₃) δ 3.95(1H, brs), 4.21(2H, s), 4.69(1H, brs), 6.53-6.56(2H, m), 6.79-6.82(2H, m), 7.09-7.12(2H, m), 7.20-7.23(2H, m). |
| 445 | 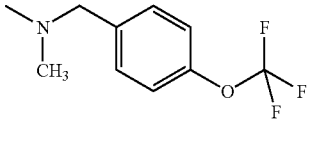 | ¹H NMR(CDCl₃) δ 4.28(3H, brs), 4.71(1H, brs), 6.60-6.63(2H, m), 6.79-6.83(2H, m), 7.21-7.23(2H, m), 7.38-7.40(2H, m). |
| 446 | 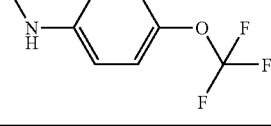 | ¹H NMR(CDCl₃) δ 2.16(3H, s), 3.45(2H, s), 3.48(2H, s), 4.82(1H, brs), 6.76-6.79(2H, m), 7.14-7.22(4H, m), 7.35-7.38(2H, m). |
| 447 | | ¹H NMR(CDCl₃) δ 4.03(1H, brs), 4.22(2H, s), 4.72(1H, brs), 6.56-6.69(2H, m), 6.80-6.83(2H, m), 7.01-7.04(2H, m), 7.21-7.24(2H, m). |

Example 1

Preparation of 2-chloro-1-(3-chloro-2-hydroxypropyl)-4-nitroimidazole

Sodium hydrogencarbonate (1.25 g, 14.91 mmol) was added to a solution of 2-chloro-4-nitro-1H-imidazole (2 g, 13.56 mmol) and epichlorohydrin (1.38 g, 14.91 mmol) in acetonitrile (60 ml), and the resulting mixture was stirred under reflux for 4 hours. The reaction mixture was allowed to return to room temperature, and concentrated under reduced pressure. To the residue, water (20 ml) was added, the resulting mixture was extracted with methylene chloride (15 ml) twice, and the extracts were dried over sodium sulfate, and then filtrated. The filtrate was concentrated under reduced pressure, and the residue was purified by silica gel column chromatography (ethyl acetate/n-hexane=1/1) to afford 2-chloro-1-(3-chloro-2-hydroxypropyl)-4-nitroimidazole (2.04 g, yield 63%) as a light yellow oil.

¹H-NMR (CDCl₃) δppm: 3.51-3.70 (2H, m), 4.02-4.35 (4H, m), 7.92 (1H, s).

Example 2

Preparation of 2-chloro-4-nitro-1-(oxiran-2-ylmethyl)imidazole

2-Chloro-1-(3-chloro-2-hydroxypropyl)-4-nitroimidazole prepared in Example 1 (2.04 g, 8.5 mmol) was dissolved in methylene chloride (20 ml), and 1,8-diazabicyclo[5.4.0]-7-undecene (DBU) (2.04 ml, 13.67 mmol) was added to the solution. The resulting mixture was stirred at room temperature overnight. The reaction mixture was washed with 3N hydrochloric acid (20 ml) and a saturated saline solution (20 ml) in this order, dried over sodium sulfate and then filtered. The filtrate was concentrated under reduced pressure, and the residue was purified by silica gel column chromatography (methylene chloride/ethyl acetate=20/1) to afford 2-chloro-4-nitro-1-(oxiran-2-ylmethyl)imidazole (190 mg, yield 11%) as a colorless oil.

$^1$H-NMR (CDCl$_3$) δppm: 2.55-2.69 (1H, m), 2.97 (1H, t, J=4.2 Hz), 3.26-3.43 (1H, m), 3.94 (1H, dd, J=6.4 Hz, 15.0 Hz), 4.52 (1H, dd, J=2.6 Hz, 15.0 Hz), 7.88 (1H, s).

Example 3

Preparation of 2-chloro-1-(2,3-dihydroxy-2-methylpropyl)-4-nitroimidazole

2-Chloro-4-nitro-1H-imidazole (6.78 g, 46 mmol) and 2-methyloxiran-2-ylmethyl 4-nitrobenzoate (12 g, 51 mmol) were dissolved in ethyl acetate (24 ml), and triethylamine (1.3 ml, 9.2 mmol) was added to the solution. The resulting mixture was stirred under reflux for 14 hours. The reaction mixture was concentrated under reduced pressure, and methylene chloride (40 ml) was added to the residue. The resulting precipitates were filtered off, and dissolved in methanol (120 ml). To the solution, potassium carbonate (318 mg, 2.3 mmol) was added, and the resulting mixture was stirred at room temperature for 1 hour. To the resulting mixture, 6 N hydrochloric acid (0.8 ml) and magnesium sulfate (8 g) were added in this order with cooling on ice-bath, and the resulting mixture was stirred for 30 minutes. Insoluble matters were removed by filtration through Celite, and the filtrate was concentrated under reduced pressure. To the residue, ethyl acetate (6 ml) and toluene (60 ml) were added. The resulting precipitates were filtered off and dried at 50° C. to afford 2-chloro-1-(2,3-dihydroxy-2-methylpropyl)-4-nitroimidazole (7.88 g, yield 72%) as a white powder.

$^1$H-NMR (DMSO-d$_6$) δppm: 1.02 (3H, s), 3.25 (2H, d, J=5.3 Hz), 4.04 (2H, s), 4.98 (1H, s), 5.10 (1H, t, J=5.4 Hz), 8.29 (1H, s).

Example 4

Preparation of 2-chloro-1-(2-hydroxy-3-methanesulfonyloxy-2-methylpropyl)-4-nitroimidazole Methanesulfonyl chloride (2.01 ml, 25.72 mmol) was added to a solution of 2-chloro-1-(2,3-dihydroxy-2-methylpropyl)-4-nitroimidazole prepared in Example 3 (5.05 g, 21.43 mmol) in pyridine (10 ml) with cooling on ice-bath and the resulting mixture was stirred at room temperature for 1.5 hours. 6N hydrochloric acid was added to the mixture, and the resulting mixture was extracted with ethyl acetate. The organic phase was dried over magnesium sulfate, and then concentrated under reduced pressure to afford 2-chloro-1-(2-hydroxy-3-methanesulfonyloxy-2-methylpropyl)-4-nitroimidazole (6.72 g, quantitative) as a yellow oil.

$^1$H-NMR (CDCl$_3$) δppm: 1.31 (3H, s), 2.10 (1H, s), 3.11 (3H, s), 4.08-4.23 (4H, m), 8.02 (1H, s).

Example 5

Preparation of 2-chloro-1-[2-hydroxy-2-methyl-3-(4-methylbenzenesulfonyloxy)propyl]-4-nitroimidazole 2-Chloro-4-nitro-1H-imidazole (1 g, 6.78 mmol), 2-methyloxiran-2-ylmethyl paratoluenesulfonate (2.46 g, 10.15 mmol), benzyl(triethyl) ammonium chloride (1.50 mg, 0.66 mmol) and acetonitrile (10 ml) were stirred under reflux for 8 hours. The reaction mixture was allowed to return to room temperature, diluted with ethyl acetate. The organic phase was washed with a saturated aqueous sodium bicarbonate solution twice, dried over magnesium sulfate and then filtered. The filtrate was concentrated under reduced pressure, and the residue was purified by silica gel column chromatography (methylene chloride/ethyl acetate=6/1) to afford 2-chloro-1-[2-hydroxy-2-methyl-3-(4-methylbenzenesulfonyloxy)propyl]-4-nitroimidazole (1.86 g, yield 70%) as a light yellow oil.

$^1$H-NMR (CDCl$_3$) δppm: 1.25 (3H, s), 2.46 (3H, s), 2.80 (1H, s), 3.91 (1H, d, J=10.4 Hz), 3.95 (1H, d, J=10.4 Hz), 4.04-4.16 (2H, m), 7.38 (2H, d, J=8.0 Hz), 7.76 (2H, d, J=8.0 Hz), 7.93 (1H, s).

Example 6

Preparation of 2-chloro-1-(2-methyloxiran-2-ylmethyl)-4-nitroimidazole

2-Chloro-1-(2-hydroxy-3-methanesulfonyloxy-2-methylpropyl)-4-nitroimidazole prepared in Example 4 (6.72 g, 21.43 mmol) was treated in the same manner as in Example 2 to afford 2-chloro-1-(2-methyloxiran-2-ylmethyl)-4-nitroimidazole (5.6 g, yield 94%) as a white powder.

$^1$H-NMR (CDCl$_3$) δppm: 1.39 (3H, s), 2.62 (2H, d, J=4.0 Hz), 2.78 (1H, d, J=4.0 Hz), 4.00 (1H, d, J=14.9 Hz), 4.38 (1H, d, J=14.9 Hz), 7.87 (1H, s).

Example 7

Preparation of 2-chloro-1-(2-methyloxiran-2-ylmethyl)-4-nitro-1H-imidazole

Using 2-chloro-1-[2-hydroxy-2-methyl-3-(4-methylbenzenesulfonyloxy)propyl]-4-nitroimidazole prepared in Example 5 (1.11 g, 2.84 mmol) gave 2-chloro-1-(2-methyloxiran-2-ylmethyl)-4-nitro-1H-imidazole (523 mg, yield 85%) as a light yellow powder in the same manner as in Example 2.

The properties of the obtained compound were same as those of the compound obtained in Example 6.

Example 8

Preparation of (R)-2-chloro-1-[2-hydroxy-3-(4-methylbenzenesulfonyloxy)propyl]-4-nitroimidazole 2-Chloro-4-nitro-1H-imidazole (10 g, 67.79 mmol) and (R)-(−)-glycidyl tosylate (17.02 g, 74.58 mmol) were dissolved in acetonitrile (50 ml), sodium hydrogencarbonate (6.26 g, 74.15 mmol) was added to the solution, and the resulting mixture was stirred under reflux for 3.5 hours. The reaction mixture was allowed to return to room temperature. After filtration, the filtrate was concentrated under reduced pressure. The residue was purified by silica gel column chromatography (ethyl acetate/n-hexane=1/2) to afford (R)-2-chloro-1-[2-hydroxy-3-(4-methylbenzenesulfonyloxy)propyl]-4-nitroimidazole (16.9 g, yield 66%) as a light yellow oil.

$^1$H-NMR (CDCl$_3$) δppm: 2.47 (3H, s), 3.65 (1H, d, J=5.8 Hz), 3.93-4.33 (5H, m), 7.38 (2H, d, J=8.3 Hz), 7.70 (2H d, J=8.3 Hz), 7.86 (1H, s).

Example 9

Preparation of (R)-2-chloro-4-nitro-1-(oxiran-2-ylmethyl)imidazole

2-Chloro-4-nitro-1H-imidazole (1 g, 6.78 mmol) and (R)-(−)-glycidyl tosylate (1.7 g, 7.45 mmol) were dissolved in tetrahydrofuran (THF) (10 ml), sodium hydrogencarbonate (600 mg, 7.14 mmol) was added to the solution, and the resulting mixture was stirred under reflux for 11 hours. The reaction mixture was concentrated under reduced pressure, water was added to the solution, and the resulting mixture was extracted with ethyl acetate. The organic phase was washed with water and a saturated saline solution in this order, dried over sodium sulfate, and filtered. The filtrate was concentrated, and the residue was purified by silica gel column chromatography (ethyl acetate/n-hexane=1/1) to afford (R)-2-chloro-4-nitro-1-(oxiran-2-ylmethyl)imidazole (1.45 g, yield 57%) as a light yellow oil.

Optical purity 79.2% e.e. $[α]_D^{27}$=42.55° (concentration: 1.262, CHCl$_3$) $^1$H-NMR (CDCl$_3$) δppm: 2.61 (1H, t, J=2.5 Hz, 4.3 Hz), 2.97 (1H, t, J=4.3 Hz), 3.25-3.34 (1H, m), 3.95 (1H, dd, J=6.4 Hz, 15.0 Hz), 4.51 (1H, dd, J=2.6 Hz, 15.0 Hz), 7.88 (1H, s).

Example 10

Preparation of (R)-2-chloro-1-(2,3-dihydroxy-2-methylpropyl)-4-nitroimidazole

2-Chloro-4-nitro-1H-imidazole (600 g, 4.07 mol) and (R)-2-methyloxiran-2-ylmethyl 4-nitrobenzoate (1060 g, 4.47 mol) were dissolved in ethyl acetate (2124 ml), triethylamine (113.64 ml, 0.82 mol) was added to the solution, and the resulting mixture was stirred under reflux for 16 hours. The reaction mixture was concentrated under reduced pressure, and ethyl acetate (530 ml) and toluene (5300 ml) were added to the residue. The resulting precipitates were filtered off and dissolved in methanol (10.6 l). Potassium carbonate (55.4 g, 0.4 mol) was added to the solution, the resulting mixture was stirred at room temperature for 1 hour, concentrated hydrochloric acid (66 ml) and magnesium sulfate (671 g) were added in this order with cooling on ice-bath, and the resulting mixture was stirred for 30 minutes. Insoluble matters were removed by filtration, and the filtrate was concentrated under reduced pressure. To the residue, ethyl acetate (530 ml) and toluene (5300 ml) were added. The resulting precipitates were filtered off and dried at 50° C. to afford (R)-2-chloro-1-(2,3-dihydroxy-2-methylpropyl)-4-nitroimidazole (879.1 g, yield 92%) as a light brown powder.

Optical purity 99.0% e.e. $[α]_D^{27}$=17.38° (concentration: 1.03, DMSO) $^1$H-NMR (DMSO-d$_6$) δppm: 1.01 (3H, s), 3.25 (2H, d, J=5.3 Hz), 4.05 (2H, s), 5.01 (1H, s), 5.11 (1H, t, J=5.4 Hz), 8.32 (1H, s).

Example 11

Preparation of (R)-2-chloro-1-(2-hydroxy-3-methanesulfonyloxy-2-methylpropyl)-4-nitroimidazole (R)-2-Chloro-1-(2,3-dihydroxy-2-methylpropyl)-4-nitroimidazole prepared in Example 10 (879 g, 3.73 mol) was dissolved in pyridine (1778 ml) and cooled to 5° C. To this solution, methanesulfonyl chloride (432.7 ml, 5.59 mol) was added dropwise below 15° C., and the resulting mixture was stirred at the same temperature for 1 hour. To the mixture, 6N hydrochloric acid (5500 ml) was added below 30° C., and the resulting mixture was stirred for 40 minutes with cooling on ice-bath. The precipitates were filtered off and washed with water and toluene in this order to afford primary crystals. In addition, the filtrate was extracted with ethyl acetate (5 liters) twice. The organic phase was washed with water, dried over magnesium sulfate, and filtered to afford a solid. The filtrate was concentrated under reduced pressure. To the residue, toluene was added and the precipitates were filtered off to afford a solid. The solids were combined and dried at 60° C. to afford (R)-2-chloro-1-(2-hydroxy-3-methanesulfonyloxy-2-methylpropyl)-4-nitroimidazole (942.6 g, yield 81%) as a white powder.

$^1$H-NMR (DMSO-d$_6$) δppm: 1.12 (3H, s), 3.23 (3H, s), 4.09 (2H, s), 4.13 (2H, s), 5.60 (1H, br), 8.34 (1H, s).

Example 12

Preparation of (R)-2-chloro-1-(2-methyloxiran-2-ylmethyl)-4-nitroimidazole (R)-2-Chloro-1-(2-hydroxy-3-methanesulfonyloxy-2-methylpropyl)-4-nitroimidazole prepared in Example 11 (942.6 g, 3 mol) was suspended in ethyl acetate (9426 ml). DBU (494 ml, 3.3 mol) was added to the suspension, and the resulting mixture was stirred at room temperature for 1 hour. The reaction mixture was washed with water (5 liters). The water layer was extracted with ethyl acetate (5 liters) twice. The organic phases were combined together, and the mixture was washed with a saturated saline solution (5 liters), dried over magnesium sulfate and then filtered. The filtrate was concentrated under reduced pressure, and the residue was purified by silica gel column chromatography (ethyl acetate/n-hexane=1/2) to afford (R)-2-chloro-1-(2-methyloxiran-2-ylmethyl)-4-nitroimidazole (600.7 g, yield 92%) as a white powder.

Optical purity 98.8% e.e. $[α]_D^{26}$=31.11° (concentration: 2.02, CHCl$_3$) $^1$H-NMR (CDCl$_3$) δppm: 1.38 (3H, s), 2.62 (1H, d, J=4.0 Hz), 2.78 (1H, d, J=4.0 Hz), 4.00 (1H, d, J=14.9 Hz), 4.38 (1H, d, J=14.9 Hz), 7.87 (1H, s).

Example 13

Preparation of (R)-2-chloro-1-[2-hydroxy-2-methyl-3-(4-methylbenzenesulfonyloxy)propyl]-4-nitroimidazole 2-Chloro-4-nitro-1H-imidazole (18.4 g, 125 mmol) and (R)-2-methyloxiran-2-ylmethyl 4-methylbenzene sulfonate (36.2 g, 149 mmol) were suspended in acetonitrile (150 ml). Benzyl(triethyl)ammonium chloride (5.7 g, 25 mmol) was added to the suspension, and the resulting mixture was stirred under reflux for 8 hours. The reaction mixture was concentrated under reduced pressure. The residue was purified by silica gel column chromatography (methylene chloride/ethyl acetate=20/1) to afford (R)-2-chloro-1-[2-hydroxy-2-methyl-3-(4-methylbenzenesulfonyloxy)propyl]-4-nitroimidazole (20.1 g, 43%) as a white amorphous form.

$^1$H-NMR (CDCl$_3$) δppm: 1.24 (3H, s), 2.47 (3H, s), 2.81 (1H, s), 3.90 (1H, d, J=10.4 Hz), 3.95 (1H, d, J=10.4 Hz), 4.04-4.14 (2H, m), 7.39 (2H, d, J=8.0 Hz), 7.76 (2H, d, J=8.0 Hz), 7.91 (1H, s)

Example 14

Preparation of (R)-2-chloro-1-(2-methyloxiran-2-ylmethyl)-4-nitroimidazole (another method for synthesis of the compound of Example 12)

2-Chloro-4-nitro-1H-imidazole (1.51 g, 10.17 mmol) and (R)-2-methyloxiran-2-ylmethyl 4-methylbenzene sulfonate (3.70 g, 15.25 mmol) were suspended in acetonitrile (150 ml). Benzyl(triethyl)ammonium chloride (0.23, 1.02 mmol) was added to this suspension, and the resulting mixture was stirred under reflux for 10 hours. After the reaction mixture was allowed to return to room temperature, ethyl acetate was added to the solution. The resulting mixture was washed with an aqueous sodium hydrogencarbonate, dried over magnesium sulfate and then filtered. The filtrate was concentrated under reduced pressure and dissolved in ethyl acetate (40 ml). DBU (1.57 ml, 10.17 mmol) was added to the solution with cooling on ice-bath, and the resulting mixture was stirred at room temperature for 1.5 hours. The reaction mixture was washed with water, dried over magnesium sulfate, and then concentrated under reduced pressure. The residue was purified by silica gel column chromatography (n-hexane/ethyl acetate=7/3) to afford (R)-2-chloro-1-(2-methyloxiran-2-ylmethyl)-4-nitroimidazole (1.50 g, yield 68%) as a light yellow oil.

Example 15

Preparation of (S)-2-chloro-4-nitro-1-[2-hydroxy-3-(4-nitrobenzoyloxy)-2-methylpropyl]imidazole 2-Chloro-4-nitro-1H-imidazole (3 g, 20.34 mmol) and (S)-2-methyloxiran-2-ylmethyl 4-nitrobenzoate (5.31 g, 22.37 mmol) were dissolved in ethyl acetate (10 ml). Triethylamine (0.57 ml, 4.07 mmol) was added to the solution, and the resulting mixture was stirred at 60-65° C. for 10 hours. The reaction mixture was concentrated under reduced pressure. Ethyl acetate (3 ml) and toluene (30 ml) were added to the residue, and the resulting precipitates were filtered off to afford (S)-2-chloro-4-nitro-1-[2-hydroxy-3-(4-nitrobenzoyloxy)-2-methylpropyl]imidazole (6.82 g, yield 87%) as a yellow powder.

$^1$H-NMR (DMSO-d$_6$) δppm: 1.23 (3H, s), 4.11-4.33 (4H, m), 5.61 (1H, s), 8.25 (2H, d, J=8.9 Hz), 8.31-8.45 (3H, m).

Example 16

Preparation of (S)-2-chloro-1-(2,3-dihydroxy-2-methylpropyl)-4-nitroimidazole (S)-2-Chloro-4-nitro-1-[2-hydroxy-3-(4-nitrobenzoyloxy)-2-methylpropyl]imidazole prepared in Example 15 (6.8 g, 17.67 mmol) was dissolved in methanol (68 ml). Potassium carbonate (122 mg, 0.88 mmol) was added to the solution, and the resulting mixture was stirred at room temperature overnight. The mixture was cooled on ice-bath, 6N hydrochloric acid (0.3 ml) and magnesium sulfate (3 g) were added to the mixture in this order, and the mixture was stirred for 30 minutes. Insoluble matters were removed by filtration, and the filtrate was concentrated under reduced pressure. Ethyl acetate (3.4 ml) and toluene (34 ml) were added to the residue, and the resulting precipitates were filtered off to afford (S)-2-chloro-1-(2,3-dihydroxy-2-methylpropyl)-4-nitroimidazole (4.09 g, yield 97%) as a yellow powder.

$^1$H-NMR (DMSO-d$_6$) δppm: 1.02 (3H, s), 3.25 (2H, d, J=5.3 Hz), 4.05 (2H, s), 4.98 (1H, s), 5.11 (1H, t, J=5.2 Hz), 8.30 (1H, s)

Example 17

Preparation of (S)-2-chloro-1-(2-hydroxy-2-methyl-3-methanesulfonyloxypropyl)-4-nitroimidazole (S)-2-Chloro-1-(2,3-dihydroxy-2-methylpropyl)-4-nitroimidazole prepared in Example 16 (4.05 g, 16.9 mmol) was dissolved in pyridine (8 ml), and this solution was cooled to 4° C. Methanesulfonyl chloride (1.6 ml, 20.28 mmol) was added dropwise to the solution below 15° C. followed by stirring at the same temperature for 1 hour. 6N hydrochloric acid (33 ml) was added to the mixture below 30° C. The reaction mixture was extracted with methylene chloride (20 ml) three times. The organic phases were combined, washed with water (20 ml) and a saturated saline solution (20 ml), dried over sodium sulfate and then filtered. The filtrate was concentrated under reduced pressure. Toluene (10 ml) was added to the residue, and the resulting precipitates were filtered off to afford (S)-2-chloro-1-(2-hydroxy-2-methyl-3-methanesulfonyloxypropyl)-4-nitroimidazole (3.04 g, yield 57%) as a white powder.

$^1$H-NMR (DMSO-d$_6$) δppm: 1.12 (3H, s), 3.24 (3H, s), 4.09 (2H, s), 4.13 (2H, s), 5.62 (1H, br), 8.34 (1H, s).

Example 18

Preparation of (S)-2-chloro-1-(2-methyloxiran-2-ylmethyl)-4-nitroimidazole (S)-2-Chloro-1-(2-hydroxy-2-methyl-3-methanesulfonyloxypropyl)-4-nitroimidazole prepared in Example 17 (3.02 g, 9.51 mmol) was dissolved in methylene chloride (30 ml). DBU (1.7 ml, 11.41 mmol) was added to the solution, and the resulting mixture was stirred at room temperature for 1.5 hours. The reaction mixture was washed with 3N hydrochloric acid (30 ml) and saturated saline solution (20 ml) in this order, dried over magnesium sulfate and then filtered. The filtrate was concentrated and the residue was purified by silica gel column chromatography (methylene chloride/ethyl acetate=20/1) to afford (S)-2-chloro-1-(2-methyloxiran-2-ylmethyl)-4-nitroimidazole (1.89 g, yield 91%) as a light yellow solid.

Optical purity 93.2% e.e. $[\alpha]_D^{27}$=−29.15° (concentration: 1.18, CHCl$_3$) $^1$H-NMR (CDCl$_3$) δppm: 1.39 (3H, s), 2.63 (1H, d, J=4.0 Hz), 2.79 (1H, d, J=4.0 Hz), 4.00 (1H, d, J=14.9 Hz), 4.38 (1H, d, J=14.9 Hz), 7.88 (1H, s)

Example 19

Preparation of 2-tert-butoxymethyl-6-nitro-2,3-dihydroimidazo[2,1-b]oxazole 2,4-Dinitro-1H-imidazole (10 g, 63.3 mmol), 2-tert-butoxymethyloxirane (27 ml, 189 mmol) and sodium acetate (5.19 g, 189 mmol) were suspended in ethanol (100 ml) followed by stirring under reflux for 17 hours. The reaction mixture was allowed to return to room temperature and concentrated under reduced pressure. Water was added to the residue, and the resulting mixture was extracted with methylene chloride. The organic phase was dried over sodium sulfate and then filtered. The filtrate was concentrated under reduced pressure. The residue was purified by silica gel column chromatography (methylene chloride/methanol=50/1) to afford 2-tert-butoxymethyl-6-nitro-2,3-dihydroimidazo[2,1-b]oxazole (3.2 g, yield 21%) as a white powder.

$^1$H-NMR (CDCl$_3$) δppm: 1.18 (9H, s), 3.63-3.80 (2H, m), 4.22-4.36 (2H, m), 5.27-5.42 (1H, m), 7.53 (1H, s).

Using 2-methyl-2-(2-methoxymethoxyethyl) oxirane, 2-ethyl-2-methoxymethoxymethyloxirane or 2-isopropyl-2-methoxymethoxymethyloxirane gave compounds of Examples 20 to 22 in the same manner as in Example 19.

Example 20

2-(2-Methoxymethoxyethyl)-2-methyl-6-nitro-2,3-dihydroimidazo[2,1-b]oxazole

White powder, yield 48%, MS=257

Example 21

2-Ethyl-2-methoxymethoxymethyl-6-nitro-2,3-dihydroimidazo[2,1-b]oxazole

Light yellow powder, yield 49% $^1$H-NMR (DMSO-d$_6$) δppm: 0.91 (3H, t, J=7.5 Hz), 1.91 (2H, q, J=7.5 Hz), 3.24 (3H, s), 3.72 (1H, d, J=11.2 Hz), 3.78 (1H, d, J=11.2 Hz), 4.15 (1H, d, J=11.2 Hz), 4.23 (1H, d, J=11.2 Hz), 4.59 (2H, s), 8.10 (1H, s).

Example 22

2-Isopropyl-2-methoxymethoxymethyl-6-nitro-2,3-dihydroimidazo[2,1-b]oxazole

Light yellow powder, yield 90% $^1$H-NMR (DMSO-d$_6$) δppm: 0.94 (6H, d, J=6.9 Hz), 2.16-2.32 (1H, m), 3.24 (3H, s), 3.76 (1H, d, J=13.0 Hz), 3.82 (1H, d, J=13.0 Hz), 4.18 (1H, d, J=13.0 Hz), 4.25 (1H, d, J=13.0 Hz), 4.59 (2H, s), 8.09 (1H, s).

Example 23

Preparation of 2-chloro-1-(2-hydroxy-4-methoxymethoxybutyl)-4-nitroimidazole

Sodium acetate (3.51 g, 42.82 mmol) and 2-(2-methoxymethoxyethyl)oxirane (10.3 g, 77.86 mmol) were added to 2-chloro-4-nitro-1H-imidazole (5.74 g, 38.93 mmol) in ethanol (60 ml), and the resulting mixture was stirred under reflux for 13.5 hours. The reaction mixture was concentrated under reduced pressure. Water was added to the residue, and the resulting mixture was extracted with methylene chloride. The extract was dried over magnesium sulfate and then concentrated under reduced pressure, and the residue was purified by silica gel column chromatography (methylene chloride/methanol=100/1) and then crystallized from methylene chloride-diisopropyl ether to afford 2-chloro-1-(2-hydroxy-4-methoxymethoxybutyl)-4-nitroimidazole (8.51 g, yield 78%) as a light yellow powder.

$^1$H-NMR (CDCl$_3$) δppm: 1.67 (2H, m), 3.38 (3H, s), 3.46 (1H, d, J=2.4 Hz), 3.78-3.83 (2H, m), 4.00 (1H, dd, J=7.6 Hz, 14.3 Hz), 4.11-4.21 (2H, m), 4.63 (2H, s), 7.96 (1H, s).

Using 2-methyl-2-methoxymethoxymethyloxirane gave a compound of Example 24 in the same manner as in Example 23.

Example 24

2-Chloro-1-(2-hydroxy-3-methoxymethoxypropyl)-4-nitroimidazole

Colorless liquid, yield 63% $^1$H-NMR (CDCl$_3$) δppm: 1.20 (3H, s), 3.08 (1H, s), 3.42 (3H, s), 3.53 (2H, dd, J=10.4 Hz, 13.8 Hz), 4.67 (2H, s), 8.01 (1H, s).

Example 25

Preparation of 2-(2-methoxymethoxyethyl)-6-nitro-2,3-dihydroimidazo[2,1-b]oxazole Sodium hydride (1.33 g, 33.23 mmol) was added to a solution of 2-chloro-1-(2-hydroxy-4-methoxymethoxybutyl)-4-nitroimidazole prepared in Example 23 (8.45 g, 30.21 mmol) in 1,4-dioxane (100 ml) with cooling on ice-bath followed by stirring under reflux for 40 hours. The reaction mixture was concentrated under reduced pressure, and cooled on ice-bath. Water was added to the residue, and the resulting mixture was extracted with methylene chloride. The organic phase was dried over magnesium sulfate and then concentrated under reduced pressure. The residue was purified by silica gel column chromatography (methylene chloride/methanol=100/1) and crystallized from methylene chloride-diisopropyl ether to afford 2-(2-methoxymethoxyethyl)-6-nitro-2,3-dihydroimidazo[2,1-b]oxazole (3.4 g, yield 47%) as a light yellow powder.

$^1$H-NMR (CDCl$_3$) δppm: 2.11-2.35 (2H, m), 3.36 (3H, s), 3.75 (2H, dd, J=4.8 Hz, 6.8 Hz), 4.08 (1H, dd, J=7.6 Hz, 10.3 Hz), 4.40 (1H, dd, J=7.6 Hz, 10.3 Hz), 4.61 (2H, s), 5.43-5.54 (1H, m), 7.53 (1H, s).

Using 2-chloro-1-(2-hydroxy-3-methoxymethoxypropyl)-4-nitroimidazole prepared in Example 24 gave a compound of Example 26 in the same manner as in Example 25.

Example 26

2-Methoxymethoxymethyl-2-methyl-6-nitro-2,3-dihydroimidazo[2,1-b]oxazole

Light yellow powder, yield 38% $^1$H-NMR (CDCl$_3$) δppm: 1.66 (3H, s), 3.34 (3H, s), 3.63 (1H, d, J=11.0 Hz), 3.84 (1H, d, J=11.0 Hz), 3.93 (1H, d, J=9.9 Hz), 4.37 (1H, d, J=9.9 Hz), 4.62 (2H, s), 7.52 (1H, s).

Example 27

Preparation of (R)-2-chloro-1-(2-hydroxy-3-methoxymethoxy-2-methylpropyl)-4-nitroimidazole (R)-2-Chloro-1-(2,3-dihydroxy-2-methylpropyl)-4-nitroimidazole prepared in Example 10 (7.4 g, 31 mmol) was dissolved in methylene chloride (120 ml). N,N-diisopropylethylamine (13.1 ml, 74 mmol) and chloromethylmethyl ether (7.1 ml, 74 mmol) were added to the solution followed by stirring at room temperature for 46 hours. The reaction mixture was washed with water, dried over magnesium sulfate and then concentrated under reduced pressure. The residue was purified by silica gel column chromatography (methylene chloride/ethyl acetate=9/1) to afford (R)-2- chloro-1-(2-hydroxy-3-methoxymethoxy-2-methylpropyl)-4-nitroimidazole (6.0 g, yield 69%) as a light yellow oil.

$^1$H-NMR (CDCl$_3$) δppm: 1.20 (3H, s), 3.08 (1H, s), 3.42 (3H, s), 3.50 (1H, d, J=10.4 Hz), 3.55 (1H, d, J=10.4 Hz), 4.05 (1H, d, J=14.4 Hz), 4.15 (1H, d, J=14.4 Hz), 4.67 (2H, s), 8.01 (1H, s).

Example 28

Preparation of (R)-2-methoxymethoxymethyl-2-methyl-6-nitro-2,3-dihydroimidazo[2,1-b]oxazole Sodium hydride (1.0 g, 25 mmol) was added to a solution of (R)-2-chloro-1-(2-hydroxy-3-methoxymethoxy-2-methylpropyl)-4-nitroimidazole prepared in Example 27 (6.0 g, 21 mmol) in DMF (30 ml) with cooling on ice-bath followed by stirring at room temperature for 1.5 hours. Ice-water was added to the reaction mixture, and the precipitates were filtered off and washed with water to afford (R)-2-methoxymethoxymethyl-2-methyl-6-nitro-2,3-dihydroimidazo[2,1-b]oxazole (3.1 g, yield 59%) as a yellow solid.

$^1$H-NMR (CDCl$_3$) δppm: 1.66 (3H, s), 3.34 (3H, s), 3.63 (1H, d, J=11.0 Hz), 3.84 (1H, d, J=11.0 Hz), 3.93 (1H, d, J=10.0 Hz), 4.42 (1H, d, J=10.0 Hz), 4.63 (2H, s), 7.52 (1H, s).

Example 29

Preparation of 2-chloro-1-(5-acetoxy-2-hydroxy-2-methylpentyl)-4-nitroimidazole

2-Chloro-4-nitro-1H-imidazole (6.8 g, 43 mmol), 2-(3-acetoxypropyl)-2-methyloxirane (5.8 g, 39.3 mmol) and sodium acetate (3.9 g, 47.6 mmol) were suspended in ethanol (60 ml) followed by stirring under reflux overnight. The reaction mixture was allowed to return to room temperature and concentrated under reduced pressure. Water was added to the residue, and the resulting mixture was extracted with methylene chloride twice. The organic phases were combined, washed with a saturated aqueous sodium bicarbonate solution and a saturated saline solution in this order, dried over sodium sulfate and then filtered. The filtrate was concentrated under reduced pressure to afford 2-chloro-1-(5-acetoxy-2-hydroxy-2-methylpentyl)-4-nitroimidazole (9.5 g, yield 79%) as a light brown oil.

$^1$H-NMR (CDCl$_3$) δppm: 1.21 (3H, s), 1.50-1.81 (4H, m), 2.05 (3H, s), 3.91-4.12 (4H, m), 8.02 (1H, s).

Example 30

Preparation of 2-(3-acetoxypropyl)-2-methyl-6-nitro-2,3-dihydroimidazo[2,1-b]oxazole Using 2-chloro-1-(5-acetoxy-2-hydroxy-2-methylpentyl)-4-nitroimidazole (9.5 g, 31.1 mmol) prepared in Example 29 gave 2-(3-acetoxypropyl)-2-methyl-6-nitro-2,3-dihydroimidazo[2,1-b]oxazole (5.2 g, yield 62%) as a light orange-colored powder in the same manner as in Example 25.

$^1$H-NMR (CDCl$_3$) δppm: 1.67 (3H, s), 1.67-2.00 (4H, m), 2.05 (3H, s), 3.91-4.14 (4H, m), 7.52 (1H, s)

Example 31

Preparation of 2-(2-hydroxyethyl)-6-nitro-2,3-dihydroimidazo[2,1-b]oxazole

Trifluoroacetic acid (2 ml) was added to a solution of 2-(2-methoxymethoxyethyl)-6-nitro-2,3-dihydroimidazo[2,1-b]oxazole prepared in Example 25 (0.2 g, 0.822 mmol) in methylene chloride (10 ml) followed by stirring at room temperature overnight. The mixture was concentrated under reduced pressure, and the residue was purified by silica gel column chromatography (methylene chloride/methanol=100/1), and crystallized from methanol-diisopropyl ether to afford 2-(2-hydroxyethyl)-6-nitro-2,3-dihydroimidazo[2,1-b]oxazole (0.11 g, yield 65%) as a light yellow powder.

$^1$H-NMR (DMSO-d$_6$) δppm: 1.92-2.14 (2H, m), 3.52-3.63 (2H, m), 4.05 (1H, dd, J=7.6 Hz, 10.6 Hz), 4.43 (1H, dd, J=7.6 Hz, 10.6 Hz), 4.72 (1H, t, J=2.7 Hz), 5.38-5.53 (1H, m), 8.12 (1H, s).

Example 32

Preparation of 2-hydroxymethyl-6-nitro-2,3-dihydroimidazo[2,1-b]oxazole

Using 2-tert-butoxymethyl-6-nitro-2,3-dihydroimidazo[2,1-b]oxazole prepared in Example 19 (5.82 g, 24.1 mmol) gave 2-hydroxymethyl-6-nitro-2,3-dihydroimidazo[2,1-b]oxazole (4.25 g, yield 95%) as a white powder in the same manner as in Example 31.

$^1$H-NMR (DMSO-d$_6$) δppm: 3.55-3.67 (1H, m), 3.72-3.88 (1H, m), 4.12 (1H, dd, J=6.5 Hz, 10.5 Hz), 4.36 (1H, t, J=10.4 Hz), 5.25-5.50 (2H, m), 8.11 (1H, s)

Example 33

Preparation of 2-hydroxymethyl-2-methyl-6-nitro-2,3-dihydroimidazo[2,1-b]oxazole Using 2-methoxymethoxymethyl-2-methyl-6-nitro-2,3-dihydroimidazo[2,1-b]oxazole prepared in Example 26 (4.14 g, 38 mmol) gave 2-hydroxymethyl-2-methyl-6-nitro-2,3-dihydroimidazo[2,1-b]oxazole (2.17 g, yield 64%) as a light yellow powder in the same manner as in Example 31.

Melting point 166-168° C. $^1$H-NMR (DMSO-d$_6$) δppm: 1.51 (3H, s), 3.53 (1H, d, J=12.1 Hz), 3.64 (1H, d, J=12.1 Hz), 4.03 (1H, d, J=10.6 Hz), 4.24 (1H, d, J=10.6 Hz), 5.40 (1H, br), 8.10 (1H, s).

Example 34

Preparation of 2-(2-hydroxyethyl)-2-methyl-6-nitro-2,3-dihydroimidazo[2,1-b]oxazole Using 2-(2-methoxymethoxyethyl)-2-methyl-6-nitro-2,3-dihydroimidazo[2,1-b]oxazole prepared in Example 20 (13.4 g, 52.1 mmol) gave 2-(2-hydroxyethyl)-2-methyl-6-nitro-2,3-dihydroimidazo[2,1-b]oxazole (2.32 g, yield 21%) as a light yellow powder in the same manner as in Example 31.

$^1$H-NMR (DMSO-d$_6$) δppm: 1.58 (3H, s), 1.93-2.17 (2H, m), 3.59 (2H, t, J=6.4 Hz), 4.04 (1H, d J=10.9 Hz), 4.33 (d, 1H, J=10.9 Hz), 8.11 (1H, s).

Example 35

Preparation of 2-ethyl-2-hydroxymethyl-6-nitro-2,3-dihydroimidazo[2,1-b]oxazole

2-Ethyl-2-methoxymethoxymethyl-6-nitro-2,3-dihydroimidazo[2,1-b]oxazole prepared in Example 21 (21.5 g, 83.7 mmol) was suspended in methanol (430 ml). Concentrated hydrochloric acid (2.15 ml) was added to this suspension followed by stirring under reflux for 5 hours. The reaction mixture was concentrated under reduced pressure, and the precipitates were filtered off to afford 2-ethyl-2-hydroxymethyl-6-nitro-2,3-dihydroimidazo[2,1-b]oxazole (7.14 g, yield 40%) as a light yellow powder.

$^1$H-NMR (DMSO-$d_6$) δppm: 0.89 (3H, t, J=7.4 Hz), 1.95 (2H, q, J=7.4 Hz), 3.53-3.69 (2H, m), 4.08 (1H, d, J=10.8 Hz), 4.21 (1H, d, J=10.8 Hz), 5.39 (t, 1H, J=5.6 Hz), 8.09 (1H, s).

Using corresponding starting materials gave a compound of Example 36 in the same manner as in Example 35.

Example 36

2-Hydroxymethyl-2-isopropyl-6-nitro-2,3-dihydroimidazo[2,1-b]oxazole

Light yellow powder, yield 50% $^1$H-NMR (DMSO-$d_6$) δppm: 0.91 (6H, d, J=6.9 Hz), 2.12-2.23 (1H, m), 3.60-3.77 (2H, m), 4.16 (2H, s), 5.35 (1H, t, J=5.6 Hz), 8.08 (1H, s).

Example 37

Preparation of (R)-2-hydroxymethyl-2-methyl-6-nitro-2,3-dihydroimidazo[2,1-b]oxazole Trifluoroacetic acid (15 ml) was added to a solution of (R)-2-methoxymethoxymethyl-2-methyl-6-nitro-2,3-dihydroimidazo[2,1-b]oxazole prepared in Example 28 (3.1 g, 13 mmol) in methylene chloride (30 ml) followed by stirring at room temperature for 25 hours. The reaction mixture was concentrated under reduced pressure. Methanol was added to the solution, and the resulting mixture was concentrated under reduced pressure. To the residue, 2-propanol was added, and the precipitates were filtered off and washed with 2-propanol to afford (R)-2-hydroxymethyl-2-methyl-6-nitro-2,3-dihydroimidazo[2,1-b]oxazole (1.2 g, yield 46%) as a light yellow powder.

Melting point 162-163° C. Optical purity 97% e.e. $[α]_D^{26}$=−19.01° (concentration: 0.526, DMSO)

Example 38

Preparation of 2-methyl-2-(3-hydroxypropyl)-6-nitro-2,3-dihydroimidazo[2,1-b]oxazole A mixture of 2-(3-acetoxypropyl)-2-methyl-6-nitro-2,3-dihydroimidazo[2,1-b]oxazole prepared in Example 30 (3.2 g, 11.88 mmol), potassium carbonate (320 mg, 2.32 mmol) and methanol (35 ml) was stirred at room temperature for 2 hours. The reaction mixture was concentrated under reduced pressure, and the residue was purified by silica gel column chromatography (methylene chloride/methanol=25/1) to afford 2-methyl-2-(3-hydroxypropyl)-6-nitro-2,3-dihydroimidazo[2,1-b]oxazole (2.1 g, 78%) as a light yellow powder.

$^1$H-NMR (CDCl$_3$) δppm: 1.67-1.72 (5H, m), 1.91-2.07 (2H, m), 3.51-3.65 (2H, m), 4.01 (1H, d, J=10.5 Hz), 4.15 (1H, d, J=10.5 Hz), 7.66 (1H, s).

Example 39

Preparation of 3-(2-methyl-6-nitro-2,3-dihydroimidazo-[2,1-b]oxazol-2-yl)propyl methanesulfonate Methanesulfonyl chloride (1.4 ml, 18.09 mmol) in methylene chloride (10 ml) was added dropwise to a mixture of 2-methyl-2-(3-hydroxypropyl)-6-nitro-2,3-dihydroimidazo[2,1-b]oxazole prepared in Example 38 (2.1 g, 9.24 mmol), triethylamine (2.8 g, 20.09 mmol), 4-dimethylaminopyridine (50 mg, 0.41 mmol) and methylene chloride (80 ml) with cooling on ice-bath followed by stirring at room temperature overnight. The reaction mixture was concentrated. 10% hydrochloric acid was added to the residue, and the resulting mixture was stirred for 30 minutes with cooling on ice-bath. The precipitates were filtered off and washed with water to afford 3-(2-methyl-6-nitro-2,3-dihydroimidazo[2,1-b]oxazol-2-yl)propyl methanesulfonate (2.6 g, yield 92%) as a white powder.

$^1$H-NMR (DMSO-$d_6$) δppm: 1.58 (3H, s), 1.65-2.02 (4H, m), 3.17 (3H, s), 4.05-4.26 (4H, m), 8.12 (1H, s)

Using corresponding starting materials gave compounds of Examples 40 to 42 in the same manner as in Example 39.

Example 40

6-Nitro-2,3-dihydroimidazo[2,1-b]oxazol-2-ylmethyl methanesulfonate

Light yellow powder, yield 82% $^1$H-NMR (DMSO-$d_6$) δppm: 3.25 (3H, s), 4.11 (1H, dd, J=6.6 Hz, 11.0 Hz), 4.47 (1H, t, J=9.1 Hz), 4.55-4.70 (2H, m), 5.60-5.75 (1H, m), 8.14 (1H, s).

Example 41

2-Methyl-6-nitro-2,3-dihydroimidazo[2,1-b]oxazol-2-ylmethyl methanesulfonate

Light yellow powder, yield 87% $^1$H-NMR (DMSO-$d_6$) δppm: 1.64 (3H, s), 3.24 (3H, s), 4.17 (1H, d, J=11.2 Hz), 4.27 (1H, d, J=11.2 Hz), 4.52 (2H, br), 8.14 (1H, s)

Example 42

2-(2-Methyl-6-nitro-2,3-dihydroimidazo[2,1-b]oxazol-2-yl)ethyl methanesulfonate

Light yellow powder, yield 87% $^1$H-NMR (DMSO-$d_6$) δppm: 1.61 (3H, s), 2.38 (2H, t, J=6.5 Hz), 3.19 (3H, s), 4.11 (1H, d, J=11.0 Hz), 4.25 (1H, d, J=11.0 Hz), 4.36 (2H, t, J=6.5Hz), 8.14 (1H, s).

Example 43

Preparation of tert-butyl 5-(2-chloro-4-nitroimidazol-1-yl)-4-hydroxy-4-methylpentanoate Sodium acetate (0.59 g, 7.18 mmol) was added to a suspension of tert-butyl 3-(2-methyloxiran-2-yl)propionate (1.00 g, 5.39 mmol) and 2-chloro-4-nitro-1H-imidazole (0.53 g, 3.59 mmol) in ethanol (5 ml) followed by stirring under reflux for 6 hours. Insoluble matters were removed by filtration, and the filtrate was concentrated under reduced pressure. The residue was purified by silica gel column chromatography (methylene chloride/methanol=100/1) to afford tert-butyl 5-(2-chloro-4-nitroimidazol-1-yl)-4-hydroxy-4-methylpentanoate (0.94 g, yield 78%) as a light yellow oil.

$^1$H-NMR (CDCl$_3$) δppm: 1.17 (3H, s), 1.45 (9H, s), 1.78-1.87 (2H, m), 2.43-2.54 (2H, m), 3.59 (1H, br), 3.99 (2H, s), 8.06 (1H, s)

Example 44

Preparation of tert-butyl 3-(2-methyl-6-nitro-2,3-dihydroimidazo[2,1-b]oxazol-2-yl)propionate Sodium hydride (0.12 g, 3.07 mmol) was added to a solution of tert-butyl 5-(2-chloro-4-nitroimidazol-1-yl)-4-hydroxy-4-methylpentanoate prepared in Example 43 (0.93 g, 2.79 mmol) in 1,4-dioxane (10 ml) with cooling on ice-bath followed by stirring under reflux for 7.5 hours. The reaction mixture was concentrated under reduced pressure. Water was added to the solution, and the resulting mixture was extracted with methylene chloride. The organic phase was dried over magnesium sulfate and then concentrated under reduced pressure. The residue was treated with diethyl ether to afford tert-butyl 3-(2-methyl-6-nitro-2,3-dihydroimidazo[2,1-b]oxazol-2-yl)propionate (0.35 g, 42%) as a white solid.

$^1$H-NMR (CDCl$_3$) δppm: 1.45 (9H, s), 1.65 (3H, s), 2.12-2.25 (2H, m), 2.37-2.46 (2H, m), 3.98 (1H, d, J=10.3 Hz), 4.10 (1H, d, J=10.3 Hz), 7.52 (1H, s).

Example 45

Preparation of 3-(2-methyl-6-nitro-2,3-dihydroimidazo-[2,1-b]oxazol-2-yl)propionic acid Trifluoroacetic acid (2 ml) was added to a solution of tert-butyl 3-(2-methyl-6-nitro-2,3-dihydroimidazo[2,1-b]oxazol-2-yl) propionate prepared in Example 44 (0.72 g, 2.42 mmol) in methylene chloride (14 ml) followed by stirring at room temperature for 30 minutes. The reaction mixture was concentrated under reduced pressure. The residue was crystallized from ethanol-methylene chloride to afford 3-(2-methyl-6-nitro-2,3-dihydroimidazo[2,1-b]oxazol-2-yl)propionic acid (0.30 g, 51%) as a light yellow solid.

$^1$H-NMR (DMSO-d$_6$) δppm: 1.32 (3H, s), 1.91-2.09 (1H, m), 2.12-2.26 (1H, m), 2.41-2.74 (2H, m), 3.89 (2H, s), 7.96 (1H, s), 12.19 (1H, br).

Example 46

Preparation of 2-(2-methyl-6-nitro-2,3-dihydroimidazo-[2,1-b]oxazol-2-ylmethoxy)benzoxazole Sodium hydride (77 mg, 1.9 mmol) was added to a solution of 2-hydroxymethyl-2-methyl-6-nitro-2,3-dihydroimidazo[2,1-b]oxazole prepared in Example 33 (0.32 g, 1.6 mmol) in DMF (3 ml) with cooling on ice-bath followed by stirring at 0° C. for 30 minutes. To the reaction mixture, 2-chlorobenzoxazole (0.30 g, 1.9 mmol) in DMF (3 ml) was added with cooling on ice-bath followed by stirring at room temperature for 44 hours. Ice-water was added to the reaction mixture, and the resulting mixture was extracted with ethyl acetate. The organic phase was washed with water, dried over magnesium sulfate and then concentrated. The residue was purified by silica gel column chromatography (methylene chloride/methanol=100/1) and recrystallized from acetonitrile-isopropanol to afford 2-(2-methyl-6-nitro-2,3-dihydroimidazo[2,1-b]oxazol-2-ylmethoxy)benzoxazole (0.20 g, 39%) as a light yellow solid.

Melting point 200-203° C.

Example 47

Preparation of (R)-2-(2-methyl-6-nitro-2,3-dihydroimidazo[2,1-b]oxazol-2-ylmethoxy)benzoxazole Sodium hydride (0.1 g, 2.4 mmol) was added to a solution of (R)-2-hydroxymethyl-2-methyl-6-nitro-2,3-dihydroimidazo[2,1-b]oxazole prepared in Example 37 (0.40 g, 2.0 mmol) in DMF (4 ml) followed by stirring for 30 minutes with cooling on ice-bath. To the reaction mixture, 2-chlorobenzoxazole (0.38 g, 2.4 mmol) in DMF (4 ml) was added with cooling on ice-bath followed by stirring at room temperature for 48 hours. Ice-water was added to the reaction mixture. The precipitates were filtered off, washed with water, and then recrystallized from acetonitrile-isopropanol to afford (R)-2-(2-methyl-6-nitro-2,3-dihydroimidazo[2,1-b]oxazol-2-ylmethoxy)benzoxazole (0.15 g, yield 24%) as a light yellow solid.

Melting point 232-233° C. Optical purity >99.5% e.e. $[\alpha]_D^{26}$=+11.20° (concentration: 0.518, DMSO)

Example 48

Preparation of 2-(2-methyl-6-nitro-2,3-dihydroimidazo-[2,1-b]oxazol-2-ylmethylthio)benzoxazole Sodium hydride (50 mg, 1.25 mmol) was added to a mixture of 2-mercaptobenzoxazole (200 mg, 1.3 mmol) and DMF (3 ml) followed by stirring at room temperature for 1 hour. To the reaction mixture, 2-methyl-6-nitro-2,3-dihydroimidazo[2,1-b]oxazol-2-ylmethyl methanesulfonate prepared in Example 41 (330 mg, 1.2 mmol) was added, and the resulting mixture was stirred at 60-70° C. for 5 hours. The reaction mixture was allowed to return to room temperature. Water was added to the solution, and the resulting mixture was extracted with ethyl acetate twice. The organic phases were combined, washed with 5% sodium hydroxyde solution and water three times, dried over sodium sulfate and then filtered. The filtrate was concentrated under reduced pressure. The residue was purified by silica gel column chromatography(n-hexane/ethyl acetate=1/1) to afford 2-(2-methyl-6-nitro-2,3-dihydroimidazo[2,1-b]oxazol-2-ylmethylthio)benzoxazole (37 mg, yield 9%) as a white powder.

Melting point 163-166° C.

Example 49

Preparation of 2-[2-(2-methyl-6-nitro-2,3-dihydroimidazo[2,1-b]oxazol-2-yl)ethylthio]benzoxazole Using 2-(2-methyl-6-nitro-2,3-dihydroimidazo-[2,1-b]oxazol-2-yl)ethyl methanesulfonate prepared in Example 42 (300 mg, 1 mmol) gave 2-[2-(2-methyl-6-nitro-2,3-dihydroimidazo[2,1-b]oxazol-2-yl)ethylthio]benzoxazole (296 mg, yield 83%) as a white powder in the same manner as in Example 48.

Melting point 174-175° C.

Example 50

Preparation of 1-(2-chloro-4-nitroimidazol-1-yl)-2-methyl-3-(1-phenyl-1H-tetrazol-5-ylthio)propane-2-ol A mixture of 2-chloro-4-nitro-1H-imidazole (1.2 g, 8.13 mmol), 5-(2-methyloxiran-2-ylmethylthio)-1-phenyl-1H-tetrazole (1.9 g, 7.65 mmol), sodium acetate (700 mg, 8.53 mmol) and ethanol (20 ml) was stirred under reflux overnight. The reaction mixture was allowed to return to room temperature and concentrated under reduced pressure. To the residue, water was added, and the resulting mixture was extracted with ethyl acetate twice. The organic phases were combined, washed with a saturated aqueous sodium bicarbonate solution twice, then washed with water and a saturated saline solution in this order, dried over sodium sulfate and then filtered. The filtrate was concentrated under reduced pressure. The residue was purified by silica gel column chromatography (methylene chloride/methanol=50/1) to afford 1-(2-chloro-4-nitroimidazol-1-yl)-2-methyl-3-(1-phenyl-1H-tetrazol-5-ylthio)propane-2-ol to afford (2.1 g, yield 69%) as a light yellow powder.

$^1$H-NMR (CDCl$_3$) δppm: 1.38 (3H, s), 3.54 (1H, d, J=14.8 Hz), 3.62 (1H, d, J=14.8 Hz), 4.19 (2H, s), 4.58 (1H, s), 7.50-7.67 (5H, m), 8.08 (1H, s).

Example 51

Preparation of 2-methyl-6-nitro-2-(1-phenyl-1H-tetrazol-5-ylthiomethyl)-2,3-dihydroimidazo[2,1-b]oxazole Sodium hydride (220 mg, 5.5 mmol) was added to a mixture of 1-(2-chloro-4-nitroimidazol-1-yl)-2-methyl-3-(1-phenyl-1H-tetrazol-5-ylthio)propane-2-ol prepared in Example 50 (2.1 g, 5.3 mmol) and 1,4-dioxane (40 ml), and the resulting mixture was stirred under reflux for 24 hours. The reaction mixture was allowed to return to room temperature, and concentrated under reduced pressure. Water was added to the residue, and the resulting mixture was extracted with ethyl acetate twice. The organic phases were combined, washed with water and a saturated saline solution in this order, dried over sodium sulfate and then filtered. The filtrate was concentrated under reduced pressure. The residue was purified by silica gel column chromatography (n-hexane/ethyl acetate=1/1) to afford 2-methyl-6-nitro-2-(1-phenyl-1H-tetrazol-5-ylthiomethyl)-2,3-dihydroimidazo[2,1-b]oxazole (500 mg, yield 26%) as a light brown powder.

Melting point 140-147° C.

Example 52

Preparation of tert-butyl(2-methyl-6-nitro-2,3-dihydroimidazo[2,1-b]oxazol-2-ylmethoxycarbonylamino) acetate Glycine tert-butyl ester monohydrochloride (0.52 g, 2.27 mmol) in methylene chloride (5 ml) and N,N-diisopropylethylamine (1.05 ml, 4.53 mmol) were added to a triphosgene (0.30 g, 0.76 mmol) in methylene chloride (10 ml) with cooling on ice-bath followed by stirring at room temperature for 2 hours. Insoluble matters were removed by filtration, and the filtrate was concentrated under reduced pressure. The residue was added to a solution of 2-hydroxymethyl-2-methyl-6-nitro-2,3-dihydroimidazo[2,1-b]oxazole prepared in Example 33 (0.30 g, 1.51 mmol) in DMF (3 ml) with cooling on ice-bath. Then cuprous chloride (75 mg, 0.76 mmol) was added to the resulting mixture followed by stirring at room temperature for 22 hours. Water was added to the reaction mixture, the resulting mixture was extracted with ethyl acetate. The organic phase was washed with water, dried over magnesium sulfate and then concentrated under reduced pressure. The residue was purified by silica gel column chromatography (n-hexane/ethyl acetate=3/2) to afford tert-butyl(2-methyl-6-nitro-2,3-dihydroimidazo[2,1-b]oxazol-2-ylmethoxycarbonylamino)acetate (40 mg, yield 7%) as a white solid.

Melting point 104-106° C.

Example 53

Preparation of 6-nitro-2,3-dihydroimidazo[2,1-b]oxazol-2-ylmethyl (4-morpholinophenyl)carbamate 1,1'-Carbonyldiimidazole (0.44 g, 2.69 mmol) was added to a solution of 4-morpholinoaniline (0.40 g, 2.24 mmol) in THF (4 ml) followed by stirring for 2 hours with cooling on ice-bath. The reaction mixture was filtered and washed with diethyl ether. The filtrate was added to a solution of 2-hydroxymethyl-6-nitro-2,3-dihydroimidazo[2,1-b]oxazole (0.30 g, 1.62 mmol) in DMF (3 ml) with cooling on ice-bath. Then, cuprous chloride (75 mg, 0.76 mmol) was added to the resulting mixture followed by stirring at room temperature for 2 hours. Water was added to the reaction mixture, the resulting mixture was extracted with ethyl acetate, and the extract was washed with water, dried over magnesium sulfate, and then concentrated under reduced pressure. The residue was purified by silica gel column chromatography (methylene chloride/acetone=9/1), and washed with methylene chloride-ethyl acetate to afford 6-nitro-2,3-dihydroimidazo[2,1-b]oxazol-2-ylmethyl (4-morpholinophenyl)carbamate (34 mg, yield 5%) as a white solid.

$^1$H-NMR (DMSO-d$_6$) δppm: 2.93-3.09 (4H, m), 3.64-3.80 (4H, m), 4.13 (1H, dd, J=6.8 Hz, 10.9 Hz), 4.34-4.55 (3H, m), 5.55-5.73 (1H, m), 6.77-6.95 (2H, m), 7.18-7.41 (2H, m), 8.15 (1H, s), 9.52 (1H, br).

Example 54

Preparation of 2-(6-nitro-2,3-dihydroimidazo[2,1-b]oxazol-2-yl)ethyl 4-chlorophenylcarbamate 4-Chlorophenylisocyanate (169 ml, 1.1 mmol) and cuprous chloride (50 mg, 0.5 mmol) was added to a solution of 2-hydroxyethyl-6-nitro-2,3-dihydroimidazo[2,1-b]oxazole prepared in Example 31 (0.2 g, 1.0 mmol) in DMF (5 ml) with cooling on ice-bath followed by stirring at room temperature for 4 hours. The mixture was cooled on ice-bath and added 10% hydrochloric acid. The resulting mixture was extracted with ethyl acetate, and the extract was washed with water, dried over magnesium sulfate, and then concentrated under reduced pressure. The residue was purified by silica gel column chromatography (methylene chloride/methanol=100/1) and crystallized from methylene chloride-isopropyl ether to afford 2-(6-nitro-2,3-dihydroimidazo[2,1-b]oxazol-2-yl)ethyl 4-chlorophenylcarbamate (0.16 g, yield 45%) as a white solid.

$^1$H-NMR (DMSO-d$_6$) δppm: 2.16-2.38 (2H, m), 4.08 (1H, dd, J=7.4 Hz, 10.6 Hz), 4.16-4.36 (2H, m), 4.47 (1H, dd, J=7.4 Hz, 10, 6 Hz), 5.44-5.55 (1H, m), 7.30-7.36 (2H, m), 7.46-7.52 (2H, m), 8.14 (1H, s), 9.83 (1H, br).

Using phenylisocyanate and 2-hydroxyethyl-2-methyl-6-nitro-2,3-dihydroimidazo[2,1-b]oxazole, 2-ethyl-2-hydroxymethyl-6-nitro-2,3-dihydroimidazo[2,1-b]oxazole or 2-hydroxymethyl-2-isopropyl-6-nitro-2,3-dihydroimidazo[2,1-b]oxazole gave compounds of Examples 55 to 57 in the same manner as in Example 54. In addition, using 2-hydroxymethyl-2-methyl-6-nitro-2,3-dihydroimidazo[2,1-b]oxazole and 3-fluorophenylisosyanate or 4-tert-butoxycarbonylphenyl-isocyanate gave compounds of Examples 58 and 59 in the same manner as in Example 54.

Example 55

2-(2-Methyl-6-nitro-2,3-dihydroimidazo[2,1-b]oxazol-2-yl)ethyl phenylcarbamate

Yellow solid, yield 17% $^1$H-NMR (DMSO-$d_6$) δppm: 1.63 (3H, s), 2.30 (2H, t, J=6.9 Hz), 4.13 (1H, d, J=10.9 Hz), 4.21-4.32 (3H, m), 6.96-7.02 (1H, m), 7.24-7.27 (2H, m), 7.43-7.46 (2H, m), 8.12 (1H, s), 9.60 (1H, br).

Example 56

2-Ethyl-6-nitro-2,3-dihydroimidazo[2,1-b]oxazol-2-ylmethyl phenylcarbamate

White solid, yield 60% $^1$H-NMR (DMSO-$d_6$) δppm: 0.93 (3H, t, J=7.4 Hz), 1.89-2.11 (2H, m), 4.19-4.29 (2H, m), 4.39-4.50 (2H, m), 6.99 (1H, t, J=7.2 Hz), 7.23-7.29 (2H, m), 7.34-7.55 (2H, m), 8.14 (1H, s), 9.70 (1H, br).

Example 57

2-Isopropyl-6-nitro-2,3-dihydroimidazo[2,1-b]oxazol-2-ylmethyl phenylcarbamate

White solid, yield 73% $^1$H-NMR (DMSO-$d_6$) δppm: 0.97 (6H, dd, J=2.7 Hz, 6.9 Hz), 2.25-2.39 (1H, m), 4.20 (1H, d, J=11.4 Hz), 4.30 (1H, d, J=11.4 Hz), 4.48 (2H, s), 6.99 (1H, t, J=7.1 Hz), 7.23-7.29 (2H, m), 7.32-7.52 (2H, m), 8.13 (1H, s), 9.67 (1H, br).

Example 58

2-Methyl-6-nitro-2,3-dihydroimidazo[2,1-b]oxazol-2-ylmethyl 3-fluorophenylcarbamate White solid, yield 71% Melting point 168-169° C.

Example 59

Tert-butyl 4-(2-methyl-6-nitro-2,3-dihydroimidazo[2,1-b]oxazol-2-ylmethoxycarbonylamino) benzoate White solid, yield 32% Melting point 177-178° C.

Example 60

Preparation of 4-(2-methyl-6-nitro-2,3-dihydroimidazo-[2,1-b]oxazol-2-ylmethoxycarbonylamino) benzoic acid Trifluoroacetic acid (1 ml) was added to a suspension of tert-butyl 4-(2-methyl-6-nitro-2,2-dihydroimidazo[2,1-b]oxazol-2-ylmethoxycarbonylamino)benzoate prepared in Example 59 (185 ml, 0.44 mmol) in methylene chloride (10 ml) with cooling on ice-bath followed by stirring at room temperature for 2 hours. The reaction mixture was concentrated under reduced pressure. The residue was dissolved in ethyl acetate. The solution was washed with water, dried over magnesium sulfate, and then concentrated under reduced pressure. The residue was washed with ethyl acetate to afford 4-(2-methyl-6-nitro-2,3-dihydromidazo[2,1-b]oxazol-2-ylmethoxycarbonylamino)benzoic acid (50 mg, yield 31%) as a white solid.

Melting point 248° C. (decomposition)

Example 61

Preparation of 2-methyl-6-nitro-2,3-dihydroimidazo[2,1-b]oxazol-2-ylmethyl 4-chlorophenylcarbamate 2-Methyloxiran-2-ylmethyl 4-chlorophenylcarbamate (1.1 g, 4.4 mmol) and 2,4-dinitro-1H-imidazole (0.35 g, 2.2 mmol) were suspended in ethanol (1 ml), and the resulting mixture was stirred at room temperature for 24 hours. Then, sodium acetate (0.36 g, 4.4 mmol) and ethanol (2 ml) were added to the mixture followed by stirring under reflux for 6 hours. The reaction mixture was concentrated under reduced pressure. The residue was added water, and the resulting mixture was extracted with ethyl acetate. The extract was dried over magnesium sulfate and then concentrated under reduced pressure. The residue was crystallized from methylene chloride-diethyl ether to afford 2-methyl-6-nitro-2,3-dihydroimidazo[2,1-b]oxazol-2-ylmethyl 4-chlorophenylcarbamate (0.17 g, yield 22%) as a light yellow solid.

Melting point 179-181° C.

Example 62

Preparation of 3-(2-chloro-4-nitroimidazol-1-yl)-2-hydroxy-2-methylpropyl N-(4-chlorophenyl)-N-methylcarbamate 2-Methyloxiran-2-ylmethyl N-(4-chlorophenyl)-N-methylcarbamate (1.7 g, 6.6 mmol) and 2-chloro-4-nitro-1H-imodazole (0.98 g, 6.6 mmol) were suspended in ethanol (10 ml) added sodium acetate (0.85 g, 10 mmol) followed by stirring under reflux for 4 hours. The reaction mixture was concentrated under reduced pressure. A saturated aqueous sodium hydrogencarbonate was added to the residue, and the resulting mixture was extracted with methylene chloride. The extract was dried over magnesium sulfate and then concentrated under reduced pressure. The residue was purified by silica gel column chromatography (methylene chloride/ethyl acetate=9/1) to afford 3-(2-chloro-4-nitroimidazol-1-yl)-2-hydroxy-2-methylpropyl N-(4-chlorophenyl-N-methylcarbamate (2.7 g, quantitative) as a light yellow oil.

$^1$H-NMR (CDCl$_3$) δppm: 1.15 (3H, br), 3.28 (3H, s), 3.78-4.28 (4H, m), 7.11-7.24 (2H, m), 7.30-7.41 (2H, m), 7.90 (1H, br).

Example 63

Preparation of 2-methyl-6-nitro-2,3-dihydroimidazo[2,1-b]oxazol-2-ylmethyl N-(4-chlorophenyl)-N-methyl-carbamate Sodium hydride (0.32 g, 7.9 mmol) was added to a solution of 3-(2-chloro-4-nitroimidazol-1-yl)-2-hydroxy-2-methylpropyl N-(4-chlorophenyl)-N-methylcarbamate prepared in Example 62 (2.7 g, 6.6 mmol) in 1,4-dioxane (30 ml) with cooling on ice-bath followed by stirring under reflux for 12 hours. The reaction mixture was concentrated under reduced pressure. The residue was cooled on ice-bath and added water, and the resulting solution was extracted with methylene chloride. The extract was dried over magnesium sulfate and then concentrated under reduced pressure. The residue was purified by silica gel column chromatography (ethyl acetate) and crystallized from methylene chloride-ethanol to afford 2-methyl-6-nitro-2,3-dihydroimidazo[2,1-b]oxazol-2-ylmethylN-(4-chlorophenyl)-N-methylcarbamate (0.88 g, yield 36%) as a white solid.

Melting point 146-148° C.

Example 64

Preparation of (R)-3-(2-chloro-4-nitroimidazol-1-yl)-2-hydroxy-2-methylpropyl 4-chlorophenylcarbamate A THF solution (15 ml) of 4-chlorophenylisocyanate (1.3 g, 85 mmol) and triethylamine (0.1 ml) were added to a suspension of (R)-2-chloro-1-(2,3-dihydroxy-2-methylpropyl)-4-nitroimidazole prepared in Example 10 (1.5 g, 6.5 mmol) in THF (30 ml) followed by stirring at room temperature for 19 hours. Insoluble matters were removed by filtration, and the filtrate was concentrated under reduced pressure. The residue was purified by silica gel column chromatography (methylene chloride/ethyl acetate=9/1) to afford (R)-3-(2-chloro-4-nitroimidazol-1-yl)-2-hydroxy-2-methylpropyl 4-chlorophenylcarbamate (2.1 g, yield 83%) as a white solid.

$^1$H-NMR (DMSO-d$_6$) δppm: 1.15 (3H, s), 3.99 (2H, s), 4.07 (2H, s), 7.29-7.39 (2H, m), 7.45-7.58 (2H, m), 8.33 (1H, s), 9.86 (1H, br).

Using various kinds of corresponding phenylisocyanates gave compounds of Examples 65 to 69 in the same manner as in Example 64. In addition, using benzylisocyanate or methylisocyanate gave compounds of Examples 70 and 71 in the same manner as in Example 64.

Example 65

(R)-3-(2-Chloro-4-nitroimidazol-1-yl)-2-hydroxy-2-methylpropyl 3-chlorophenylcarbamate Yield 41% $^1$H-NMR (DMSO-d$_6$) δppm: 1.15 (3H, s), 4.00 (2H, s), 4.13 (2H, s), 5.41 (1H, s), 7.04-7.09 (1H, m), 7.29-7.41 (2H, m), 7.55-7.66 (1H, m), 8.33 (1H, s), 9.93 (1H, br).

Example 66

(R)-3-(2-Chloro-4-nitroimidazol-1-yl)-2-hydroxy-2-methylpropyl 4-bromophenylcarbamate Yield 62% $^1$H-NMR (DMSO-d$_6$) δppm: 1.15 (3H, s), 3.99 (2H, s), 4.13 (2H, s), 5.40 (1H, s), 7.34-7.53 (4H, m), 8.33 (1H, s), 9.86 (1H, br).

Example 67

(R)-3-(2-Chloro-4-nitroimidazol-1-yl)-2-hydroxy-2-methylpropyl 4-trifluoromethylphenylcarbamate Yield 83% $^1$H-NMR (DMSO-d$_6$) δppm: 1.16 (3H, s), 4.02 (2H, s), 4.14 (2H, s), 5.42 (1H, s), 7.58-7.74 (4H, m), 8.34 (1H, s), 10.14 (1H, br).

Example 68

(R)-3-(2-Chloro-4-nitroimidazol-1-yl)-2-hydroxy-2-methylpropyl 4-trifluoromethoxyphenylcarbamate Yield 58% $^1$H-NMR (DMSO-d$_6$) δppm: 1.15 (3H, s), 3.99 (2H, s), 4.13 (2H, s), 5.41 (1H, s), 7.31 (2H, d, J=8.5 Hz), 7.58 (2H, d, J=8.5 Hz), 8.33 (1H, s), 9.92 (1H, br).

Example 69

(R)-3-(2-Chloro-4-nitroimidazol-1-yl)-2-hydroxy-2-methylpropyl 4-fluorophenylcarbamate Yield 95% $^1$H-NMR (DMSO-d$_6$) δppm: 1.15 (3H, s), 3.98 (2H, s), 4.12 (2H, s), 5.39 (1H, s), 7.10-7.17 (2H, m), 7.45-7.51 (2H, m), 8.33 (1H, s), 9.73 (1H, br).

Example 70

(R)-3-(2-Chloro-4-nitroimidazol-1-yl)-2-hydroxy-2-methylpropyl benzylcarbamate

Yield 72% $^1$H-NMR (CDCl$_3$) δppm: 1.20 (3H, s), 3.61 (1H, br), 3.97-4.04 (3H, m), 4.23 (1H, d, J=12.0 Hz), 4.70-4.89 (1H, m), 7.13-7.39 (5H, m), 8.01 (1H, s).

Example 71

(R)-3-(2-Chloro-4-nitroimidazol-1-yl)-2-hydroxy-2-methylpropyl methylcarbamate

Yield 73% $^1$H-NMR (CDCl$_3$) δppm: 1.21 (3H, s), 2.80 (3H, d, J=4.8 Hz), 3.57 (1H, br), 3.98-4.16 (3H, m), 4.24 (1H, d, J=12.3 Hz), 4.72-4.91 (1H, m), 8.03 (1H, s).

Example 72

Preparation of (R)-3-(2-chloro-4-nitroimidazol-1-yl)-2-hydroxy-2-methylpropyl N-methyl-N-(4-trifluoromethoxybenzyl)carbamate (R)-2-Chloro-1-(2,3-dihydroxy-2-methylpropyl)-4-nitroimidazole prepared in Example 10 (2.16 g, 9.18 mmol), N,N-diisopropylethylamine (2.67 ml, 15.30 mmol) and 4-dimethylaminopyridine (0.19 g, 1.53 mmol) were added to a suspension of N-methyl-N-(4-trifluoromethoxybenzyl)carbamoylchloride (2.05 g, 7.65 mmol) in toluene (40 ml) followed by stirring at 100° C. for 3.5 hours. The reaction mixture was diluted with ethyl acetate, and the solution washed with 10% hydrochloric acid, dried over magnesium sulfate and then concentrated under reduced pressure. The residue was purified by silica gel column chromatography (methylene chloride/ethyl acetate=9/1) to afford (R)-3-(2-chloro-4-nitroimidazol-1-yl)-2-hydroxy-2-methylpropyl N-methyl-N-(4-trifluoromethoxybenzyl)carbamate (2.74 g, yield 77%) as a colorless oil.

$^1$H-NMR (CDCl$_3$) δppm: 1.25 (3H, s), 2.83 (3H, s), 3.87-4.17 (4H, m), 4.44 (2H, s), 7.18-7.25 (4H, m), 8.05 (1H, s).

Example 73

Preparation of (R)-2-methyl-6-nitro-2,3-dihydroimidazo[2,1-b]oxazol-2-ylmethyl N-methyl-N-(4-trifluoromethoxybenzyl)carbamate Sodium hydride (0.28 g, 7.04 mmol) was added to a solution of (R)-3-(2-chloro-4-nitroimidazol-1-yl)-2-hydroxy-2-methylpropyl N-methyl-N-(4-trifluoromethoxybenzyl)carbamate prepared in Example 72 (2.74 g, 5.87 mmol) in DMF (20 ml) followed by stirring for 1 hour with cooling on ice-bath. To the reaction mixture, ice-water was added, and the precipitates were filtered off, washed with water and then recrystallized from isopropanol to afford (R)-2-methyl-6-nitro-2,3-dihydroimidazo[2,1-b]oxazol-2-ylmethyl N-methyl-N-(4-trifluoromethoxybenzyl)carbamate (1.40 g, yield 55%) as a white solid.
Melting point 123-124° C.

Example 74

Preparation of (R)-3-(2-chloro-4-nitroimidazol-1-yl)-2-hydroxy-2-methylpropyl N-(4-chlorophenyl)-N-cyclohexylcarbamate (R)-2-Chloro-1-(2,3-dihydroxy-2-methylpropyl)-4-nitroimidazole prepared in Example 10 (0.95 g, 4.03 mmol), N,N-diisopropylethylamine (1.45 ml, 8.06 mmol) and 4-dimethylaminopyridine (0.10 g, 0.81 mmol) were added to a suspension of N-(4-chlorophenyl)-N-cyclohexylcarbamoylchloride (1.56 g, 6.05 mmol) in toluene (10 ml) followed by stirring at 100° C. for 3 hours. The reaction mixture was diluted with ethyl acetate, and the solution was washed with 10% hydrochloric acid, dried over magnesium sulfate and then concentrated under reduced pressure. The residue was purified by silica gel column chromatography (methylene chloride/ethyl acetate=9/1) to afford (R)-3-(2-chloro-4-nitroimidazol-1-yl)-2-hydroxy-2-methylpropyl-N-(4-chlorophenyl)-N-cyclohexylcarbamate (0.75 g, yield 40%) as a white amorphous form.
$^1$H-NMR (CDCl$_3$) δppm: 0.78-1.22 (6H, m), 1.24-1.48 (2H, m), 1.54-1.67 (1H, m), 1.70-1.93 (4H, m), 2.87-3.13 (1H, m), 3.72-3.98 (3H, m), 4.00-4.24 (2H, m), 7.00-7.06 (2H, m), 7.35-7.41 (2H, m), 7.80 (1H, br).

Example 75

Preparation of (R)-2-methyl-6-nitro-2,3-dihydroimidazo[2,1-b]oxazol-2-ylmethyl N-(4-chlorophenyl)-N-cyclohexylcarbamate Sodium hydride (76 mg, 1.91 mmol) was added to a solution of (R)-3-(2-chloro-4-nitroimidazol-1-yl)-2-hydroxy-2-methylpropyl N-(4-chlorophenyl)-N-cyclohexylcarbamate prepared in Example 74 (0.75 g, 1.59 mmol) in DMF (7 ml) followed by stirring for 0.5 hours with cooling on ice-bath. To the reaction mixture, ice-water was added, and the resulting mixture was extracted with ethyl acetate. The extract was washed with water, dried over magnesium sulfate and then concentrated under reduced pressure. The residue was recrystallized from isopropanol to afford (R)-2-methyl-6-nitro-2,3-dihydroimidazo[2,1-b]oxazol-2-ylmethyl N-(4-chlorophenyl)-N-cyclohexylcarbamate (0.53 g, yield 77%) as a white solid.
Melting point 175-177° C.

Example 76

Preparation of (R)-3-(2-chloro-4-nitroimidazol-1-yl)-2-hydroxy-2-methylpropyl N-methyl-N-(4-trifluoromethoxyphenyl)carbamate N-Methyl-N-(4-trifluoromethoxyphenyl)-carbamoyl chloride (1.33 g, 5.23 mmol), N,N-diisopropylethylamine (1.2 ml, 6.97 mmol) and 4-dimethylaminopyridine (85 mg, 0.70 mmol) were added to a suspension of (R)-2-chloro-1-(2,3-dihydroxy-2-methyl)propyl-4-nitroimidazole prepared in Example 10 (0.82 g, 3.48 mmol) in toluene (10 ml) followed by stirring at 100° C. for 5 hours. The reaction mixture was diluted with ethyl acetate, and the solution was washed with water, dried over magnesium sulfate and then concentrated under reduced pressure. The residue was purified by silica gel column chromatography (n-hexane/ethyl acetate=2/1) to afford (R)-3-(2-chloro-4-nitroimidazol-1-yl)-2-hydroxy-2-methylpropyl N-methyl-N-(4-trifluoromethoxyphenyl)carbamate (1.04 g, yield 65%) as a light yellow amorphous form.
$^1$H-NMR (DMSO-d$_6$) δppm: 1.02 (3H, s), 3.26 (3H, s), 3.80-4.00 (4H, m), 5.39 (1H, s), 7.37-7.40 (2H, m), 7.47-7.52 (2H, m), 8.25 (1H, s).

Example 77

Preparation of (R)-2-methyl-6-nitro-2,3-dihydroimidazo[2,1-b]oxazol-2-ylmethyl N-methyl-N-(4-trifluoromethoxyphenyl)carbamate Sodium hydride (0.48 g, 11.9 mmol) was added to a solution of (R)-3-(2-chloro-4-nitroimidazol-1-yl)-2-hydroxy-2-methylpropyl N-methyl-N-(4-trifluoromethoxyphenyl)carbamate prepared in Example 76 (4.50 g, 9.94 mmol) in DMF (13.5 ml) with cooling on ice-bath followed by stirring at room temperature for 1 hour. Water and ethyl acetate were added to the reaction mixture, and the precipitates were filtered off. The precipitates were recrystallized from isopropanol to afford (R)-2-methyl-6-nitro-2,3-dihydroimidazo[2,1-b]oxazol-2-ylmethyl N-methyl-N-(4-trifluoromethoxyphenyl)carbamate (2.95 g, yield 71%) as a light yellow solid.
Melting point 144-145° C. Optical purity 99.8% e.e. $[α]_D^{24}$=7.68° (concentration: 0.938, CHCl$_3$)
Using corresponding starting materials gave compounds of Examples 78 and 79 in the same manner as in Example 77.

Example 78

(R)-2-Methyl-6-nitro-2,3-dihydroimidazo[2,1-b]oxazol-2-ylmethyl methylcarbamate

Yield 26%, melting point 175-178° C.

Example 79

(R)-2-Methyl-6-nitro-2,3-dihydroimidazo[2,1-b]oxazol-2-ylmethyl diethylcarbamate Yield 27%, melting point 196-197° C.

Example 80

Preparation of (R)-2-methyl-6-nitro-2,3-dihydroimidazo[2,1-b]oxazol-2-ylmethyl N-(4-chlorophenyl)-N-methylcarbamate Iodomethane (0.71 ml, 11.4 mmol) and potassium hydroxide (0.64 g, 11.4 mmol) were added to a solution of (R)-3-(2-chloro-4-nitroimidazol-1-yl)-2-hydroxy-2-methylpropyl 4-chlorophenylcarbamate prepared in Example 64 (1.5 g, 3.8 mmol) in DMSO (40 ml) followed by stirring at room temperature for 4 hours. The mixture was cooled on ice-bath and added 10% hydrochloric acid. The resulting

Example 81

Preparation of (R)-2-methyl-6-nitro-2,3-dihydroimidazo[2,1-b]oxazol-2-ylmethyl N-(4-chlorophenyl)-N-methylcarbamate mixture was extracted with ethyl acetate, and the extract was washed with water, dried over magnesium sulfate and then concentrated under reduced pressure. The residue was purified by silica gel column chromatography (n-hexane/ethyl acetate=1/1) and recrystallized from isopropanol to afford (R)-2-methyl-6-nitro-2,3-dihydroimidazo[2,1-b]oxazol-2-ylmethyl N-(4-chlorophenyl)-N-methylcarbamate (0.67 g, 60%) as a white solid.

Melting point 131-133° C. Optical purity 99.8% e.e. $[\alpha]^{D26}$ =22.86° (concentration: 1.028, $CHCl_3$)

Example 81

Preparation of (R)-2-methyl-6-nitro-2,3-dihydroimidazo[2,1-b]oxazol-2-ylmethyl bis(4-chlorophenyl)carbamate Pyridine (0.37 ml, 4.5 mmol) and triphosgene (0.16 g, 0.5 mmol) were added to a suspension of (R)-2-hydroxymethyl-2-methyl-6-nitro-2,3-dihydroimidazo[2,1-b]oxazole prepared in Example 37 (0.30 g, 1.5 mmol) in methylene chloride (15 ml) with cooling on ice-bath followed by stirring at room temperature for 2.5 hours. To the reaction mixture, bis(4-chlorophenyl)amine (0.39 g, 1.6 mmol) was added, and the resulting mixture was stirred at room temperature for 20 hours. The reaction mixture was cooled on ice-bath and added 10% hydrochloric acid. The resulting mixture was extracted with methylene chloride, and the extract was dried over magnesium sulfate and then concentrated under reduced pressure. The residue was purified by silicagel column chromatography (methylene chloride/ethyl acetate=19/1) and recrystallized from isopropanol to afford (R)-2-methyl-6-nitro-2,3-dihydroimidazo[2,1-b]oxazol-2-ylmethyl bis(4-chlorophenyl)carbamate (82 mg, yield 12%) as a white solid.

Melting point 200-201° C.

Example 82

Preparation of 2-methyl-6-nitro-2,3-dihydroimidazo[2,1-b]oxazol-2-ylmethyl piperidine-1-carboxylate Pyridine (0.37 ml, 4.5 mmol) and triphosgene (0.18 g, 0.6 mmol) were added to a suspension of 2-hydroxymethyl-2-methyl-6-nitro-2,3-dihydroimidazo[2,1-b]oxazole prepared in Example 33 (0.3 g, 1.5 mmol) in methylene chloride (15 ml) with cooling on ice-bath followed by stirring at room temperature for 2 hours. The reaction mixture was cooled on ice-bath and added piperidine (0.16 ml, 1.7 mmol). The resulting mixture was stirred at room temperature for 3 hours. The reaction mixture was cooled on ice-bath and added 10% hydrochloric acid, and the insoluble matters were removed by filtration. The filtrate was extracted with methylene chloride, and the organic phase was dried over magnesium sulfate and then concentrated under reduced pressure. The residue was purified by silica gel column chromatography (n-hexane/ethyl acetate=3/2) and recrystallized from methylene chloride-diisopropyl ether to afford 2-methyl-6-nitro-2,3-dihydroimidazo[2,1-b]oxazol-2-ylmethyl piperidine-1-carboxylate (65 mg, yield 14%) as a white solid.

Melting point 152-154° C.

Example 83

Preparation of 3-(2-chloro-4-nitroimidazol-1-yl)-2-hydroxy-2-methylpropyl 4-(4-trifluoromethoxyphenyl)-piperazine-1-carboxylate 4-(4-Trifluoromethoxyphenyl)piperazine-1-carbonylchloride (0.26 g, 0.85 mmol), N,N-diisopropylethylamine (0.30 ml, 1.7 mmol) and 4-dimethylaminopyridine (21 mg, 0.17 mmol) were added to a suspension of 2-chloro-1-(2,3-dihydroxy-2-methylpropyl)-4-nitroimidazol prepared in Example 3 (0.30 g, 1.3 mmol) in toluene (5 ml) followed by stirring at 100° C. for 2.5 hours. The mixture was diluted with ethyl acetate, washed with water, dried over magnesium sulfate and then concentrated under reduced pressure. The residue was purified by silica gel column chromatography (methylene chloride/ethyl acetate=9/1) to afford 3-(2-chloro-4-nitroimidazol-1-yl)-2-hydroxy-2-methylpropyl 4-(4-trifluoromethoxyphenyl)piperazine-1-carboxylate (0.24 g, yield 55%) as a light yellow oil.

$^1$H-NMR ($CDCl_3$) δppm: 1.26 (3H, s), 3.02-3.17 (4H, m), 3.39-3.72 (4H, m), 3.91 (1H, s), 3.99-4.18 (3H, m), 4.34 (1H, d, J=12.3 Hz), 6.85-6.98 (2H, m), 7.09-7.22 (2H, m), 8.05 (1H, s).

Example 84

Preparation of 2-methyl-6-nitro-2,3-dihydroimidazo[2,1-b]oxazol-2-ylmethyl 4-(4-trifluoromethoxyphenyl)-piperazine-1-carboxylate Sodium hydride (23 mg, 0.56 mmol) was added to a solution of 3-(2-chloro-4-nitroimidazol-1-yl)-2-hydroxy-2-methylpropyl 4-(4-trifluoromethoxyphenyl)piperazine-1-carboxylate prepared in Example 83 (0.24 g, 0.47 mmol) in DMF (2 ml) followed by stirring at 0° C. for 1 hour. Ice-water was added to the reaction mixture, and the resulting mixture was extracted with ethyl acetate. The extract was washed with water, dried over magnesium sulfate and then concentrated under reduced pressure. The residue was purified by silica gel column chromatography (ethyl acetate) and then washed with diisopropyl ether to afford 2-methyl-6-nitro-2,3-dihydroimidazo[2,1-b]oxazol-2-ylmethyl 4-(4-trifluoromethoxyphenyl)piperazine-1-carboxylate (0.13 g, yield 58%) as a white solid.

Melting point 138-140° C.

Example 85

Preparation of 3-(2-chloro-4-nitroimidazol-1-yl)-2-hydroxy-2-methylpropyl 4-(4-trifluoromethylphenyl)-1,2,3,6-tetrahydropyridine-1-carboxylate 2-Chloro-1-(2,3-dihydroxy-2-methylpropyl)-4-nitroimidazole prepared in Example 3 (0.13 g, 0.57 mmol), N,N-diisopropylethylamine (0.13 ml, 0.76 mmol) and 4-dimethylaminopyridine (10 mg, 0.08 mmol) were added to a suspension of 4-(4-trifluoromethylphenyl)-1,2,3,6-tetrahydropyridine-1-carbonylchloride (0.10 g, 0.38 mmol) in toluene (3 ml) followed by stirring at 100° C. for 2.5 hours. The reaction mixture was diluted with ethyl acetate, washed with water, dried over magnesium sulfate and then concentrated under reduced pressure. The residue was purified by silica gel column chromatography (methylene chloride/ethyl acetate=9/1) to afford 3-(2-chloro-4-nitroimidazol-1-yl)-2-hydroxy-2-methylpropyl 4-(4-trifluoromethylphenyl)-1,2,3,6-tetrahydropyridine-1-carboxylate (0.11 g, yield 59%) as a colorless oil.

¹H-NMR (CDCl₃) δppm: 1.26 (3H, s), 2.43-2.50 (2H, m), 3.50-3.78 (2H, m), 3.93-4.24 (5H, m), 7.46 (1H, d, J=8.3 Hz), 7.60 (1H, d, J=8.3 Hz), 8.05 (1H, s).

Example 86

Preparation of 2-methyl-6-nitro-2,3-dihydroimidazo[2,1-b]oxazol-2-ylmethyl 4-(4-trifluoromethylphenyl)-1,2,3,6-tetrahydropyridine-1-carboxylate Sodium hydride (11 mg, 0.28 mmol) was added to a solution of 3-(2-chloro-4-nitroimidazol-1-yl)-2-hydroxy-2-methylpropyl 4-(4-trifluoromethylphenyl)-1,2,3,6-tetrahydropyridine-1-carboxylate prepared in Example 85 (0.11 g, 0.23 mmol) in DMF (1 ml) followed by stirring for 1 hour with cooling on ice-bath. Ice-water was added to the reaction mixture, the resulting mixture was extracted with ethyl acetate. The extract was washed with water, dried over magnesium sulfate and then concentrated under reduced pressure. The residue was purified by silica gel column chromatography (methylene chloride/ethyl acetate=4/1) and then washed with diisopropyl ether to afford 2-methyl-6-nitro-2,3-dihydroimidazo[2,1-b]oxazol-2-ylmethyl 4-(4-trifluoromethylphenyl)-1,2,3,6-tetrahydropyridine-1-carboxylate (0.04 g, yield 39%) as a white solid.
Melting point 113-115° C.

Example 87

Preparation of (R)-3-(2-chloro-4-nitroimidazol-1-yl)-2-hydroxy-2-methylpropyl 4-tert-butoxycarbonylpiperazine-1-carboxylate (R)-2-Chloro-1-(2,3-dihydroxy-2-methylpropyl)-4-nitroimidazole prepared in Example 10 (4.43 g, 18.79 mmol), N,N-diisopropylethylamine (4.68 ml, 26.84 mmol) and 4-dimethylaminopyridine (0.33 g, 2.68 mmol) were added to a suspension of tert-butyl 4-chlorocarbonylpiperazine-1-carboxylate (3.34 g, 13.42 mmol) in toluene (70 ml), and the resulting mixture was stirred at 100° C. for 4.5 hours. The reaction mixture was diluted with ethyl acetate, washed with water, dried over magnesium sulfate and then concentrated under reduced pressure. The residue was purified by silica gel column chromatography (n-hexane/methylene chloride/ethyl acetate=45/45/10) to afford (R)-3-(2-chloro-4-nitroimidazol-1-yl)-2-hydroxy-2-methylpropyl 4-tert-butoxycarbonylpiperazine-1-carboxylate (4.12 g, yield 69%) as a colorless oil.
¹H-NMR (CDCl₃) δppm: 1.23 (3H, s), 1.47 (9H, s), 3.33-3.50 (8H, m), 3.91 (1H, s), 3.99-4.16 (3H, m), 4.30 (1H, d, J=12.1 Hz), 8.04 (1H, s).
Using 4-(4-trifluoromethoxybenzyloxycarbonyl)piperazine-1-carbonylchloride or 4-[3-(4-trifluoromethylphenyl)-2-propenyloxycarbonyl]-piperazine-1-carbonylchloride gave compounds of Examples 88 and 89 in the same manner as in Example 87.

Example 88

(R)-2-Chloro-1-{3-[4-(4-trifluoromethoxybenzyloxycarbonyl)piperazin-1-ylcarbonyloxy]-2-hydroxy-2-methylpropyl}-4-nitroimidazole Yield 81% ¹H-NMR (CDCl₃) δppm: 1.24 (3H, s), 3.28-3.61 (8H, m), 3.89 (1H, s), 4.00-4.20 (3H, m), 4.31 (1H, d, J=12.5 Hz), 5.14 (2H, s), 7.22 (2H, d, J=8.7 Hz), 7.39 (2H, d, J=8.7 Hz), 8.04 (1H, s).

Example 89

(R)-2-Chloro-1-{3-[4-[3-(4-trifluoromethylphenyl)-2-propenylcarbonyl]piperazin-1-ylcarbonyloxy]-2-hydroxy-2-methylpropyl}-4-nitroimidazole Yield 95% ¹H-NMR (CDCl₃) δppm: 1.24 (3H, s), 3.33-3.61 (8H, m), 3.90 (1H, s), 3.99-4.17 (3H, m), 4.31 (1H, d, J=12.1 Hz), 4.79 (2H, d, J=6.1 Hz), 6.39 (1H, dt, J=6.1 Hz, 15.9 Hz), 6.67 (1H, d, J=15.9 Hz), 7.39 (2H, d, J=8.3 Hz), 7.49 (2H, d, J=8.3 Hz), 8.04 (1H, s).

Example 90

Preparation of (R)-3-(2-chloro-4-nitroimidazol-1-yl)-2-hydroxy-2-methylpropyl 4-(4-chlorobenzyl)piperazine-1-carboxylate (R)-2-Chloro-1-(2,3-dihydroxy-2-methyl)propyl-4-nitroimidazole prepared in Example 10 (2.28 g, 9.66 mmol), N,N-diisopropylethylamine (2.81 ml, 16.10 mmol) and 4-dimethylaminopyridine (0.20 g, 1.61 mmol) were added to a suspension of 4-(4-chlorobenzyl)piperazine-1-carbonylchloride (2.20 g, 8.05 mmol) in toluene (30 ml) followed by stirring 100° C. for 3 hours. The reaction mixture was diluted with ethyl acetate, washed with water, dried over magnesium sulfate and then concentrated under reduced pressure. The residue was purified by silica gel column chromatography (methylene chloride/ethyl acetate=9/1) to afford (R)-3-(2-chloro-4-nitroimidazol-1-yl)-2-hydroxy-2-methylpropyl 4-(4-chlorobenzyl)piperazine-1-carboxylate (1.82 g, yield 48%) as a yellow oil.
¹H-NMR (CDCl₃) δppm: 1.23 (3H, s), 2.17-2.50 (4H, m), 2.55 (1H, s), 3.26-3.52 (6H, m), 3.98-4.20 (3H, m), 4.30 (1H, d, J=12.4 Hz), 7.23-7.32 (4H, m), 8.05 (1H, s).
Using corresponding starting materials gave compounds of Examples 91 and 92 in the same manner as in Example 90.

Example 91

(R)-2-Chloro-1-{3-[4-(4-trifluoromethylbenzyl)piperazin-1-ylcarbonyloxy]-2-hydroxy-2-methylpropyl}-4-nitroimidazole Yield 31% ¹H-NMR (CDCl₃) δppm: 1.23 (3H, s), 2.24-2.54 (4H, m), 3.24-3.50 (4H, m), 3.56 (2H, s), 3.97-4.20 (3H, m), 4.32 (1H, d, J=12.4 Hz), 7.45 (2H, d, J=8.0 Hz), 7.58 (2H, d, J=8.0 Hz), 8.05 (1H, s).

Example 92

(R)-2-Chloro-1-{3-[4-(4-trifluoromethoxybenzyl)piperazin-1-ylcarbonyloxy]-2-hydroxy-2-methylpropyl}-4-nitroimidazole Yield 47% ¹H-NMR (CDCl₃) δppm: 1.23 (3H, s), 2.22-2.54 (4H, m), 3.30-3.54 (4H, m), 3.50 (2H, s), 3.97-4.16 (3H, m), 4.32 (1H, d, J=12.5 Hz), 7.15-7.18 (2H, m), 7.32-7.36 (2H, m), 8.05 (1H, s).

Example 93

Preparation of (R)-3-(2-chloro-4-nitroimidazol-1-yl)-2-hydroxy-2-methylpropyl 4-(4-trifluoromethoxyphenyl)piperazine-1-carboxylate 4-(4-Trifluoromethoxyphenyl)piperazine-1-carbonylchloride (1.25 g, 4.2 mmol), N,N-diisopropylethylamine (0.96 ml, 5.6 mmol) and 4-dimethylaminopyridine (67 mg, 0.56 mmol) were added to a suspension of (R)-2-chloro-1-(2,3-dihydroxy-2-methylpropyl)-4-nitroimidazole prepared in Example 10 (0.65 g, 2.8 mmol) in toluene (13 ml) followed by stirring at 100° C. for 8.5 hours. The reaction mixture was diluted with ethyl acetate, washed with water, dried over magnesium sulfate and then concentrated under reduced pressure. The residue was purified by silica gel column chromatography (methylene chloride/ethyl acetate=19/1) to afford (R)-3-(2-chloro-4-nitroimidazol-1-yl)-2-hydroxy-2-methylpropyl 4-(4-trifluoromethoxyphenyl)piperazine-1-carboxylate (1.29 g, yield 92%) as a yellow oil.

$^1$H-NMR (CDCl$_3$) δppm: 1.26 (3H, s), 3.02-3.17 (4H, m), 3.39-3.72 (4H, m), 3.91 (1H, s), 3.99-4.18 (3H, m), 4.34 (1H, d, J=12.3 Hz), 6.85-6.98 (2H, m), 7.09-7.22 (2H, m), 8.05 (1H, s).

Using corresponding starting materials gave compounds of Examples 94 to 102 in the same manner as in Example 93.

Example 94

(R)-3-(2-Chloro-4-nitroimidazol-1-yl)-2-hydroxy-2-methylpropyl 4-(4-trifluoromethylphenyl)piperazine-1-carboxylate Yield 48% $^1$H-NMR (CDCl$_3$) δppm: 1.26 (3H, s), 3.13-3,35 (4H, m), 3.48-3.72 (4H, m), 3.94 (1H, s), 4.00-4.18 (3H, m), 4.33 (1H, d, J=12.3 Hz), 6.93 (2H, d, J=8.6 Hz), 7.50 (2H, d, J=8.6 Hz), 8.05 (1H, s).

Example 95

(R)-3-(2-Chloro-4-nitroimidazol-1-yl)-2-hydroxy-2-methylpropyl 4-(4-methoxyphenyl)piperazine-1-carboxylate Yield 54% $^1$H-NMR (CDCl$_3$) δppm: 1.24 (3H, s), 2.93-3.09 (4H, m), 3.52-3.63 (4H, m), 3.77 (3H, s), 3.96 (1H, s), 4.00-4.19 (3H, m), 4.32 (1H, d, J=12.3 Hz), 6.82-6.92 (4H, m), 8.05 (1H, s).

Example 96

(R)-3-(2-Chloro-4-nitroimidazol-1-yl)-2-hydroxy-2-methylpropyl 4-(4-chlorophenyl)piperazine-1-carboxylate Yield 81% $^1$H-NMR (CDCl$_3$) δppm: 1.25 (3H, s), 3.00-3.13 (4H, m), 3.52-3.65 (4H, m), 3.93 (1H, s), 4.00-4.17 (3H, m), 4.33 (1H, d, J=12.5 Hz), 6.82-6.86 (2H, m), 7.20-7.25 (2H, m), 8.05 (1H, s).

Example 97

(R)-3-(2-Chloro-4-nitroimidazol-1-yl)-2-hydroxy-2-methylpropyl 4-(3-chlorophenyl)piperazine-1-carboxylate Yield 87% $^1$H-NMR (CDCl$_3$) δppm: 1.25 (3H, s), 3.04-3.22 (4H, m), 3.43-3.70 (4H, m), 3.89 (1H, s), 4.00-4.17 (3H, m), 4.33 (1H, d, J=12.3 Hz), 6.78 (1H, ddd, J=1.6 Hz, 2.4 Hz, 8.4 Hz), 6.85-6.88 (2H, m), 7.19 (1H, t, J=8.4 Hz), 8.05 (1H, s).

Example 98

(R)-3-(2-Chloro-4-nitroimidazol-1-yl)-2-hydroxy-2-methylpropyl 4-(3,4-dichlorophenyl)piperazine-1-carboxylate Yield 47% $^1$H-NMR (DMSO-d$_6$) δppm: 1.12 (3H, s), 3.15-3.26 (4H, m), 3.39-3.61 (4H, m), 3.88 (1H, d, J=11.0 Hz), 3.93 (1H, d, J=11.0 Hz), 4.07 (1H, d, J=14.7 Hz), 4.15 (1H, d, J=14.7 Hz), 6.96 (1H, dd, J=2.9 Hz, 9.1 Hz), 7.16 (1H, d, J=2.9 Hz), 7.42 (1H, d, J=9.1 Hz), 8.34 (1H, s).

Example 99

(R)-3-(2-Chloro-4-nitroimidazol-1-yl)-2-hydroxy-2-methylpropyl 4-(4-fluorophenyl)piperazine-1-carboxylate Yield 100% $^1$H-NMR (CDCl$_3$) δppm: 1.25 (3H, s), 2.96-3.09 (4H, m), 3.50-3.67 (4H, m), 3.98 (1H, s), 4.05-4.16 (3H, m), 4.33 (1H, d, J=12.3 Hz), 6.85-7.02 (4H, m), 8.05 (1H, s).

Example 100

(R)-3-(2-Chloro-4-nitroimidazol-1-yl)-2-hydroxy-2-methylpropyl 4-(3-trifluoromethylphenyl)piperazine-1-carboxylate Yield 83% $^1$H-NMR (CDCl$_3$) δppm: 1.25 (3H, s), 3.11-3.26 (4H, m), 3, 48-3.70 (4H, m), 3.91 (1H, s), 4.00-4.24 (3H, m), 4.33 (1H, d, J=12.3 Hz), 7.02-7.20 (3H, m), 7.38 (1H, t, J=8.0 Hz), 8.05 (1H, s).

Example 101

(R)-2-Chloro-1-(3-diethylaminocarbonyloxy-2-hydroxy-2-methylpropyl)-4-nitroimidazole Yield 37% $^1$H-NMR (CDCl$_3$) δppm: 1.11 (6H, t, J=7.1 Hz), 1.20 (3H, s), 3, 16 (4H, q, J=7.1 Hz), 3.76 (1H, br), 4.06-4.11 (3H, m), 4.26 (1H, d, J=11.1 Hz), 8.05 (1H, s).

Example 102

2-Chloro-1-(3-morpholinocarbonyloxy-2-hydroxy-2-methylpropyl)-4-nitroimidazole

Yield 100% $^1$H-NMR (CDCl$_3$) δppm: 1.23 (3H, s), 3.35-3.52 (4H, m), 3.61-3.72 (4H, m), 3.99-4.16 (3H, m), 4.31 (1H, d, J=12.3 Hz), 8.05 (1H, s).

Example 103

Preparation of (R)-3-(2-chloro-4-nitroimidazol-1-yl)-2-hydroxy-2-methylpropyl 4-(4-trifluoromethylbenzylideneamino)piperazine-1-carboxylate (R)-2-Chloro-1-(2,3-dihydroxy-2-methylpropyl)-4-nitroimidazole prepared in Example 10 (2.75 g, 11.66 mmol), N,N-diisopropylethylamine (2.71 ml, 15.54 mmol) and 4-dimethylaminopyridine (0.19 g, 1.55 mmol) were added to a suspension of 4-(4-trifluoromethylbenzylideneamino)piperazine-1-carbonylchloride (2.48 g, 7.77 mmol) in toluene (40 ml) followed by stirring at 100° C. for 2.5 hours. The reaction mixture was diluted with ethyl acetate, washed with 10% hydrochloric acid, dried over magnesium sulfate and then concentrated under reduced pressure. The residue was purified by silica gel column chromatography (methylene chloride/ethyl acetate=9/1) to afford (R)-3-(2-chloro-4-nitroimidazol-1-yl)-2-hydroxy-2-methylpropyl 4-(4-trifluoromethylbenzylideneamino)piperazine-1-carboxylate (4.03 g, quantitative) as a yellow oil.

$^1$H-NMR (CDCl$_3$) δppm: 1.25 (3H, s), 3.04-3.33 (4H, m), 3.48-3.76 (4H, m), 3.83 (1H, s), 4.00-4.17 (3H, m), 4.33 (1H, d, J=12.3 Hz), 7.55 (1H, s), 7.59 (2H, d, J=8.4 Hz), 7.69 (2H, d, J=8.4 Hz), 8.04 (1H, s).

Example 104

Preparation of (R)-3-(2-chloro-4-nitroimidazol-1-yl)-2-hydroxy-2-methylpropyl 4-(4-trifluoromethylphenoxy)-piperidine-1-carboxylate (R)-2-Chloro-1-(2,3-dihydroxy-2-methylpropyl)-4-nitroimidazole prepared in Example 10 (1.16 g, 4.68 mmol) and triethylamine (1.63 ml, 11.70 mmol) were added to a suspension of 4-(4-trifluoromethylphenoxy)piperidine-1-carbonylchloride (0.72 g, 2.34 mmol) in toluene (40 ml) followed by stirring at 100° C. for 2.5 hours. The reaction mixture was diluted with ethyl acetate, washed with water, dried over magnesium sulfate and then concentrated under reduced pressure. The residue was purified by silica gel column chromatography (methylene chloride/ethyl acetate=9/1) to afford (R)-3-(2-chloro-4-nitroimidazol-1-yl)-2-hydroxy-2-methylpropyl 4-(4-trifluoromethylphenoxy)-piperidine-1-carboxylate (184 mg, yield 16%) as a colorless oil.

$^1$H-NMR (CDCl$_3$) δppm: 1.24 (3H, s), 1.72-1.98 (4H, m), 3.33-3.67 (4H, m), 3.91-4.20 (3H, m), 4.24-4.39 (1H, m), 4.52-4.65 (1H, m), 6.96 (2H, d, J=8.7 Hz), 7.55 (2H, d, J=8, 7 Hz), 8.05 (1H, s).

Example 105

Preparation of (R)-3-(2-chloro-4-nitroimidazol-1-yl)-2-hydroxy-2-methylpropyl 4-(4-trifluoromethylphenylamino)-piperidine-1-carboxylate (R)-2-Chloro-1-(2,3-dihydroxy-2-methylpropyl)-4-nitroimidazole prepared in Example 10 (1.54 g, 7.01 mmol), N,N-diisopropylethylamine (1.63 ml, 9.34 mmol) and 4-dimethylaminopyridine (0.11 g, 0.93 mmol) were added to a suspension of 4-(4-trifluoromethylphenylamino)piperidine-1-carbonylchloride (1.43 g, 4.67 mmol) in toluene (30 ml) followed by stirring at 100° C. for 2.5 hours. The reaction mixture was diluted with ethyl acetate, washed with water, dried over magnesium sulfate and then concentrated under reduced pressure. The residue was purified by silica gel column chromatography (methylene chloride/ethyl acetate=9/1) to afford (R)-3-(2-chloro-4-nitroimidazol-1-yl)-2-hydroxy-2-methylpropyl 4-(4-trifluoromethylphenylamino)piperidine-1-carboxylate (1.44 g, yield 61%) as a light yellow oil.

$^1$H-NMR (CDCl$_3$) δppm: 1.25 (3H, s), 1.30-1.48 (2H, m), 1.98-2.13 (2H, m), 2.83-3.13 (2H, m), 3.37-3.61 (1H, m), 3.83-3.96 (2H, m), 3.96-4.22 (4H, m), 4.34 (1H, d, J=11.8 Hz), 7.40 (2H, d, J=8.5 Hz), 7.60 (2H, d, J=8.5 Hz), 8.07 (1H, s).

Example 106

Preparation of (R)-3-(2-chloro-4-nitroimidazol-1-yl)-2-hydroxy-2-methylpropyl 4-(4-trifluoromethylphenyl)-1,2,3,6-tetrahydropyridine-1-carboxylate (R)-2-Chloro-1-(2,3-dihydroxy-2-methyl)-propyl-4-nitroimidazole prepared in Example 10 (0.74 g, 3.11 mmol) and triethylamine (1.74 ml, 12.42 mmol) were added to a suspension of 4-(4-trifluoromethylphenyl)-1,2,3,6-tetrahydropyridine-1-carbonylchloride (0.60 g, 2.07 mmol) in toluene (36 ml) followed by stirring at 100° C. for 16 hours. The mixture was diluted with ethyl acetate, washed with water, dried over magnesium sulfate and then concentrated under reduced pressure. The residue was purified by silica gel column chromatography (methylene chloride/ethyl acetate=9/1) to afford (R)-3-(2-chloro-4-nitroimidazol-1-yl)-2-hydroxy-2-methylpropyl 4-(4-trifluoromethylphenyl)-1,2,3,6-tetrahydropyridine-1-carboxylate (0.32 g, yield 31%) as a light yellow oil.

$^1$H-NMR (CDCl$_3$) δppm: 1.26 (3H, s), 2.43-2.50 (2H, m), 3.50-3.78 (2H, m), 3.93-4.24 (5H, m), 7.46 (2H, d, J=8.3 Hz), 7.60 (2H, d, J=8.3 Hz), 8.05 (1H, s).

Using corresponding starting materials gave compounds of Examples 107 to 112 in the same manner as in Example 106.

Example 107

(R)-3-(2-Chloro-4-nitroimidazol-1-yl)-2-hydroxy-2-methylpropyl 4-(4-chlorophenyl)-1,2,3,6-tetrahydropyridine-1-carboxylate Yield 94% $^1$H-NMR (CDCl$_3$) δppm: 1.25 (3H, s), 2.41-2.59 (2H, m), 3.50-3.78 (2H, m), 3.93-4.22 (6H, m), 4.35 (1H, d, J=12.3 Hz), 5.87-6.13 (1H, m), 7.26-7.37 (4H, m), 8.05 (1H, s).

Example 108

(R)-3-(2-Chloro-4-nitroimidazol-1-yl)-2-hydroxy-2-methylpropyl 4-(4-trifluoromethoxyphenyl)-1,2,3,6-tetrahydropyridine-1-carboxylate Yield 92% $^1$H-NMR (CDCl$_3$) δppm: 1.26 (3H, s), 2.46-2.59 (2H, m), 3.13-3.37 (1H, m), 3.50-3.74 (2H, m), 4.00-4.14 (6H, m), 4.36 (1H, d, J=12.4 Hz), 7.19 (2H, d, J=8.0 Hz), 7.37 (2H, d, J=8.0 Hz), 8.05 (1H, s).

Example 109

(R)-3-(2-Chloro-4-nitroimidazol-1-yl)-2-hydroxy-2-methylpropyl 4-(4-methoxyphenyl)-1,2,3,6-tetrahydropyridine-1-carboxylate Yield 63% $^1$H-NMR (CDCl$_3$) δppm: 1.23 (3H, s), 2.43-2.61 (2H, m), 3.52-3.74 (2H, m), 3.82 (3H, s), 4.01-4.16 (5H, m), 4.34 (1H, d, J=12.6 Hz), 5.83-6.00 (1H, m), 6.88 (2H, d, J=8.8 Hz), 7.30 (2H, d, J=8.8 Hz), 8.05 (1H, s).

Example 110

(R)-3-(2-Chloro-4-nitroimidazol-1-yl)-2-hydroxy-2-methylpropyl 4-(3-trifluoromethylphenyl)-1,2,3,6-tetrahydropyridine-1-carboxylate Yield 54% $^1$H-NMR (CDCl$_3$) δppm: 1.25 (3H, s), 2.46-2.70 (2H, m), 3.50-3.78 (2H, m), 4.00-4.32 (6H, m), 4.35 (1H, d, J=12.6 Hz), 5.98-6.22 (1H, m), 7.39-7.67 (4H, m), 8.06 (1H, s).

Example 111

(R)-3-(2-Chloro-4-nitroimidazol-1-yl)-2-hydroxy-2-methylpropyl 4-(4-bromophenyl)-1,2,3,6-tetrahydropyridine-1-carboxylate Yield 80% $^1$H-NMR (CDCl$_3$) δppm: 1.25 (3H, s), 2.41-2.63 (2H, m), 3.50-3.76 (2H, m), 3.96-4.20 (6H, m), 4.35 (1H, d, J=12.3 Hz), 5.87-6.13 (1H, m), 7.15-7.26 (2H, m), 7.43-7.48 (2H, m), 8.05 (1H, s).

Example 112

(R)-3-(2-Chloro-4-nitroimidazol-1-yl)-2-hydroxy-2-methylpropyl 4-(4-fluorophenyl)-1,2,3,6-tetrahydropyridine-1-carboxylate Yield 57% $^1$H-NMR (CDCl$_3$) δppm: 1.25 (3H, s), 2.41-2.63 (2H, m), 3.50-3.76 (2H, m), 3.89-4.22 (6H, m), 4.35 (1H, d, J=12.6 Hz), 5.83-6.04 (1H, m), 6.99-7.06 (2H, m), 7.29-7.35 (2H, m), 8.05 (1H, s).

Using 5-chloro-2,3-dihydroindole-1-carbonylchloride, 5-chloro-1,3-dihydroisoindol-2-carbonylchloride, 6-chloro-3,4-dihydro-1H-isoquinoline-2-carbonylchloride or 6-chloro-3,4-dihydro-2H-quinoline-1-carbonylchloride gave compounds of Examples 113 to 116 in the same manner as in Example 106.

Example 113

(R)-3-(2-Chloro-4-nitroimidazol-1-yl)-2-hydroxy-2-methylpropyl 5-chloroindolinyl-1-carboxylate Light yellow amorphous form, yield 50% $^1$H-NMR (CDCl$_3$) δppm: 1.27 (3H, s), 3.14 (2H, t, J=8.5 Hz), 3.42 (1H, br), 3.91-4.28 (5H, m), 4.37 (1H, d, J=11.8 Hz), 7.04-7.24 (2H, m), 7.73 (1H, d, J=8.3 Hz), 8.04 (1H, s).

Example 114

(R)-3-(2-Chloro-4-nitroimidazol-1-yl)-2-hydroxy-2-methylpropyl 5-chloroisoindolinyl-2-carboxylate Brown solid, yield 19% $^1$H-NMR (CDCl$_3$) δppm: 1.27 (3H, s), 3.93 (1H, d, J=7.8 Hz), 4.04-4.24 (7H, m), 4.32 (1H, d, J=11.8 Hz), 7.16-7.29 (3H, m), 8.07 (1H, s).

Example 115

(R)-3-(2-Chloro-4-nitroimidazol-1-yl)-2-hydroxy-2-methylpropyl 6-chloro-3,4-dihydro-1H-isoquinoline-2-carboxylate Light yellow oil, yield 63% $^1$H-NMR (CDCl$_3$) δppm: 1.24 (3H, s), 2.83 (2H, t, J=5.8 Hz), 3.46-3.76 (2H, m), 3.90 (1H, d, J=5.3 Hz), 4.01-4.15 (3H, m), 4.34 (1H, d, J=12.3 Hz), 4.43-4.65 (2H, m), 6.93-7.09 (1H, m), 7.09-7.22 (2H, m), 8.04 (1H, s).

Example 116

(R)-3-(2-Chloro-4-nitroimidazol-1-yl)-2-hydroxy-2-methylpropyl 6-chloro-3,4-dihydro-2H-quinoline-1-carboxylate Light yellow oil, yield 70% $^1$H-NMR (CDCl$_3$) δppm: 1.26 (3H, s), 1.87-2.00 (2H, m), 2.76 (2H, t, J=6.5 Hz), 3.27 (1H, br), 3.57-3.83 (2H, m), 3.98-4.17 (3H, m), 4.33 (1H, d, J=12.0 Hz), 7.12-7.16 (2H, m), 7.41-7.61 (1H, br), 7.98 (1H, s).

Example 117

Preparation of (R)-2-methyl-6-nitro-2,3-dihydroimidazo[2,1-b]oxazol-2-ylmethyl 4-tertbutoxycarbonylpiperazine-1-carboxylate To the solution of (R)-3-(2-chloro-4-nitroimidazol-1-yl)-2-hydroxy-2-methylpropyl 4-tertbutoxycarbonylpiperazine-1-carboxylate prepared in Example 87 (4.12 g, 9.20 mmol) in DMF (30 ml), sodium hydride (0.44 g, 11.04 mmol) was added followed by stirring for 1 hour with cooling on ice-bath. Ice-water was added to the reaction mixture, and the precipitates were filtered off, purified by silica gel column chromatography (ethyl acetate) and then washed with isopropanol to afford (R)-2-methyl-6-nitro-2,3-dihydroimidazo[2,1-b]oxazol-2-ylmethyl 4-tertbutoxycarbonylpiperazine-1-carboxylate (2.24 g, yield 59%) as a white solid.

Melting point 211-212° C.

Example 118

Preparation of (R)-2-methyl-6-nitro-2,3-dihydroimidazo[2,1-b]oxazol-2-ylmethyl 4-(4-trifluoromethoxyphenyl)piperazine-1-carboxylate To the solution of (R)-3-(2-chloro-4-nitroimidazol-1-yl)-2-hydroxy-2-methylpropyl 4-(4-trifluoromethoxyphenyl)piperazine-1-carboxylate prepared in Example 93 (1.29 g, 2.5 mmol) in DMF (13 ml), sodium hydride (0.12 g, 3 mmol) was added followed by stirring for 1 hour with cooling on ice-bath. To the reaction mixture, ice water was added, and the precipitates were filtered off, washed with water and recrystallized from isopropanol to afford (R)-2-methyl-6-nitro-2,3-dihydroimidazo[2,1-b]oxazol-2-ylmethyl 4-(4-trifluoromethoxyphenyl)piperazine-1-carboxylate (0.70 g, yield 59%) as a white solid.

Optical purity 99.6% e.e. $[\alpha]_D^{25}$=0.99° (concentration: 0.704, CHCl$_3$) Melting point 168-169° C.

Example 119

Preparation of (R)-2-methyl-6-nitro-2,3-dihydroimidazo[2,1-b]oxazol-2-ylmethyl 4-(4-chlorobenzyl)piperazine-1-carboxylate To the solution of (R)-3-(2-chloro-4-nitroimidazol-1-yl)-2-hydroxy-2-methylpropyl 4-(4-chlorobenzyl)piperazine-1-carboxylate prepared in Example 90 (1.82 g, 3.85 mmol) in DMF (10 ml), sodium hydride (0.31 g, 7.70 mmol) was added followed by stirring for 1 hour with cooling on ice-bath. To the reaction mixture, ice-water was added, and the precipitates were filtered off and washed with isopropanol to afford (R)-2-methyl-6-nitro-2,3-dihydroimidazo[2,1-b]oxazol-2-ylmethyl 4-(4-chlorobenzyl)piperazine-1-carboxylate (0.46 g, yield 28%) as a light yellow solid.

Melting point 161-163° C.

Example 120

Preparation of (R)-2-methyl-6-nitro-2,3-dihydroimidazo[2,1-b]oxazol-2-ylmethyl 4-(4-trifluoromethylbenzylideneamino)piperazine-1-carboxylate To the solution of (R)-3-(2-chloro-4-nitroimidazol-1-yl)-2-hydroxy-2-methylpropyl 4-(4-trifluoromethylbenzylideneamino)piperazine-1-carboxylate prepared in Example 103 (4.03 g, 7.77 mmol) in DMF (20 ml), sodium hydride (0.37 g, 9.32 mmol) was added followed by stirring for 1 hour with cooling on ice-bath. To the reaction mixture, ice water was added, and the precipitates were filtered off, washed with water and recrystallized from acetonitrile-isopropanol to afford (R)-2-methyl-6-nitro-2,3-dihydroimidazo[2,1-b]oxazol-2-ylmethyl 4-(4-trifluoromethylbenzylideneamino)piperazine-1-carboxylate (2.60 g, yield 69%) as a white solid. Melting point 176-178° C.

Example 121

Preparation of (R)-2-methyl-6-nitro-2,3-dihydroimidazo[2,1-b]oxazol-2-ylmethyl 4-(4-trifluoromethylphenylamino)piperidine-1-carboxylate To the solution of (R)-3-(2-chloro-4-nitroimidazol-1-yl)-2-hydroxy-2-methylpropyl 4-(4-trifluoromethylphenylamino)piperidine-1-carboxylate prepared in Example 105 (1.44 g, 2.85 mmol) in DMF (10 ml), sodium hydride (0.14 g, 3.42 mmol) was added followed by stirring for 1 hour with cooling on ice-bath. To the reaction mixture, ice-water was added, and the solution was extracted with ethyl acetate. The organic phase was washed with water, dried over magnesium sulfate and then concentrated under reduced pressure. The residue was purified by silica gel column chromatography (ethyl acetate) and recrystallized from acetonitrile-isopropanol to afford (R)-2-methyl-6-nitro-2,3-dihydroimidazo[2,1-b]oxazol-2-ylmethyl 4-(4-trifluoromethylphenylamino)piperidine-1-carboxylate (0.42 g, yield 31%) as a white solid.

Melting point 137-140° C.

Example 122

Preparation of (R)-2-methyl-6-nitro-2,3-dihydroimidazo[2,1-b]oxazol-2-ylmethyl 4-(4-trifluoromethylphenoxy)piperidine-1-carboxylate To the solution of (R)-3-(2-chloro-4-nitroimidazol-1-yl)-2-hydroxy-2-methylpropyl 4-(4-trifluoromethylphenoxy)piperidine-1-carboxylate prepared in Example 104 (0.18 g, 0.36 mmol) in DMF (2 ml), sodium hydride (19 mg, 0.47 mmol) was added followed by stirring for 1.5 hours with cooling on ice-bath. To the reaction mixture, ice-water was added, and the solution was extracted with ethyl acetate. The organic phase was washed with water, dried over magnesium sulfate and then concentrated under reduced pressure. The residue was purified by silica gel column chromatography (methylene chloride/ethyl acetate=9/1) and recrystallized from isopropanol to afford (R)-2-methyl-6-nitro-2,3-dihydroimidazo[2,1-b]oxazol-2-ylmethyl 4-(4-trifluoromethylphenoxy)piperidine-1-carboxylate (0.08 g, yield 47%) as a white solid.

Melting point 165-166° C.

Example 123

Preparation of (R)-2-methyl-6-nitro-2,3-dihydroimidazo[2,1-b]oxazol-2-ylmethyl 4-(4-trifluoromethylphenyl)-1,2,3,6-tetrahydropyridine-1-carboxylate To the solution of (R)-3-(2-chloro-4-nitroimidazol-1-yl)-2-hydroxy-2-methylpropyl 4-(4-trifluoromethylphenyl)-1,2,3,6-tetrahydropyridine-1-carboxylate prepared in Example 106 (0.32 g, 0.65 mmol) in DMF (3 ml), sodium hydride (31 mg, 0.78 mmol) was added followed by stirring for 1.5 hours with cooling on ice-bath. To the reaction mixture, ice-water was added, and the solution was extracted with ethyl acetate. The organic phase was washed with water, dried over magnesium sulfate and then concentrated under reduced pressure. The residue was purified by silica gel column chromatography (methylene chloride/ethyl acetate=9/1) and recrystallized from isopropanol to afford (R)-2-methyl-6-nitro-2,3-dihydroimidazo[2,1-b]oxazol-2-ylmethyl 4-(4-trifluoromethylphenyl)-1,2,3,6-tetrahydropyridine-1-carboxylate (0.14 g, yield 49%) as a white solid.

Optical purity 98.4% e.e. $[\alpha]_D^{26}$=2.500 (c0.560, CHCl$_3$). Melting point 169-171° C.

Example 124

Preparation of (R)-2-methyl-6-nitro-2,3-dihydroimidazo[2,1-b]oxazol-2-ylmethyl 5-chloro-2,3-dihydroindole-1-carboxylate To the solution of (R)-3-(2-chloro-4-nitroimidazol-1-yl)-2-hydroxy-2-methylpropyl 5-chloro-2,3-dihydroindole-1-carboxylate prepared in Example 113 (0.60 g, 1.44 mmol) in DMF (6 ml), sodium hydride (70 mg, 1.73 mmol) was added followed by stirring 1 hour with cooling on ice-bath. To the reaction mixture, ice-water was added, and the precipitates were filtered off, washed with water and recrystallized from acetonitrile-isopropanol to afford (R)-2-methyl-6-nitro-2,3-dihydroimidazo[2,1-b]oxazol-2-ylmethyl 5-chloro-2,3-dihydroindole-1-carboxylate (0.30 g, yield 55%) as a white solid.

Melting point 189-191° C.

Example 125

Preparation of (R)-2-methyl-6-nitro-2,3-dihydroimidazo[2,1-b]oxazol-2-ylmethyl 5-chloro-1,3-dihydroisoindol-2-carboxylate To the solution of (R)-3-(2-chloro-4-nitroimidazol-1-yl)-2-hydroxy-2-methylpropyl 5-chloro-1,3-dihydro-isoindol-2-carboxylate prepared in Example 114 (0.13 g, 0.31 mmol) in DMF (2 ml), sodium hydride (15 mg, 0.37 mmol) was added followed by stirring for 1 hour with cooling on ice-bath. To the reaction mixture, ice-water was added, and the solution was extracted with ethyl acetate. The organic phase was washed with water, dried over magnesium sulfate and then concentrated under reduced pressure. The residue was purified by silica gel column chromatography (ethyl acetate) to afford (R)-2-methyl-6-nitro-2,3-dihydroimidazo[2,1-b]oxazol-2-ylmethyl 5-chloro-1,3-dihydroisoindole 2-carboxylate (7 mg, yield 6%) as a light yellow solid.

Melting point 182° C. (decomposition).

Example 126

Preparation of (R)-2-methyl-6-nitro-2,3-dihydroimidazo[2,1-b]oxazol-2-ylmethyl 6-chloro-3,4-dihydro-1H-isoquinoline-2-carboxylate To the solution of (R)-3-(2-chloro-4-nitroimidazol-1-yl)-2-hydroxy-2-methylpropyl 6-chloro-3,4-dihydro-1H-isoquinoline-2-carboxylate prepared in Example 115 (0.26 g, 0.61 mmol) in DMF (2 ml), sodium hydride (30 mg, 0.73 mmol) was added followed by stirring for 1 hour with cooling on ice-bath. To the reaction mixture, ice-water was added, and the solution was extracted with ethyl acetate. The organic phase was washed with water, dried over magnesium sulfate, concentrated under reduced pressure and recrystallized from isopropanol to afford (R)-2-methyl-6-nitro-2,3-dihydroimidazo[2,1-b]oxazol-2-ylmethyl 6-chloro-3,4-dihydro-1H-isoquinoline-2-carboxylate (0.12 g, 49%) as a light yellow solid.

Melting point 180-182° C.

Example 127

Preparation of (R)-2-methyl-6-nitro-2,3-dihydroimidazo[2,1-b]oxazol-2-ylmethyl 6-chloro-3,4-dihydro-2H-quinoline-1-carboxylate To the solution of (R)-3-(2-chloro-4-nitroimidazol-1-yl)-2-hydroxy-2-methylpropyl 6-chloro-3,4-dihydro-2H-quinoline-1-carboxylate prepared in Example 116 (1.84 g, 4.29 mmol) in DMF (10 ml), sodium hydride (0.21 g, 5.15 mmol) was added followed by stirring for 1 hour with cooling on ice-bath. To the reaction mixture, ice-water was added, the solution was extracted with ethyl acetate. The organic phase was washed with water, dried over magnesium sulfate and then concentrated under reduced pressure. The residue was purified by silica gel column chromatography (methylene chloride/ethyl acetate=9/1) and recrystallized from acetonitrile-isopropanol to afford (R)-2-methyl-6-nitro-2,3-dihydroimidazo[2,1-b]oxazol-2-ylmethyl 6-chloro-3,4-dihydro-2H-quinoline-1-carboxylate (0.68 g, yield 40%) as a white solid.

Melting point 172-174° C.

Example 128

Preparation of 2-methyl-6-nitro-2-(4-trifluoromethoxyphenoxymethyl)-2,3-dihydroimidazo[2,1-b]oxazole 4-Trifluoromethoxyphenol (198 mg, 1.11 mmol) was dissolved in DMF (5 ml). To the solution, sodium hydride (48 mg, 1.21 mmol) was added at room temperature, and the solution was stirred for 20 minutes at 80° C. To the resulting solution, 2-chloro-1-(2-methyloxiran-2-ylmethyl)-4-nitroimidazole prepared in Example 6 (220 mg, 1.01 mmol) was added with cooling on ice-bath, and the solution was stirred for 15 minutes at 80° C. The reaction mixture was poured into ice-water, and the mixture was extracted with ethyl acetate. The organic phase was washed with a saturated saline solution, dried over magnesium sulfate and then filtered. The resulting filtrate was concentrated under reduced pressure. The residue was purified by silica gel column chromatography (methylene chloride/ethyl acetate=10/1) and then crystallized from methylene chloride-diisopropyl ether to afford 2-methyl-6-nitro-2-(4-trifluoromethoxyphenoxymethyl)-2,3-dihydroimidazo[2,1-b]oxazole (170 mg, yield 47%) as a white powder.

Melting point 126.8-127.9° C. MS 358(M−1)$^+$

Example 129

Preparation of 2-methyl-6-nitro-2-{4-[4-(4-trifluoromethoxyphenoxy)piperidin-1-yl]phenoxymethyl}-2,3-dihydroimidazo[2,1-b]oxazole 4-[4-(4-Trifluoromethoxyphenoxy)piperidin]-1-ylphenol (244 mg, 0.69 mmol) was dissolved in DMF (10 ml). To the solution, sodium hydride (33 mg, 0.83 mmol) was added at room temperature, and the solution was stirred for 20 minutes at 80° C. To the solution, 2-chloro-1-(2-methyloxiran-2-ylmethyl)-4-nitroimidazole prepared in Example 6 (150 mg, 0.69 mmol) was added with cooling on ice-bath, and the solution was stirred at 80° C. for 20 minutes. To the reaction mixture, ice-water was added, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/ethyl acetate=10/1) and then crystallized from methylene chloride/ethyl acetate to afford 2-methyl-6-nitro-2-{4-[4-(4-trifluoromethoxyphenoxy)piperidin-1-yl]phenoxymethyl}-2,3-dihydroimidazo[2,1-b]oxazole (103 mg, yield 28%) as a white powder.

Melting point 165.4-166.3° C.

Example 130

Preparation of 2-methyl-6-nitro-2-{4-[4-(4-trifluoromethylphenyl)piperazin-1-yl]phenoxymethyl}-2,3-dihydroimidazo[2,1-b]oxazole 4-[4-(4-Trifluoromethylphenyl)piperazin-1-yl]phenol (296 mg, 0.92 mmol) was dissolved in DMF (10 ml). To the solution, sodium hydride (44 mg, 1.1 mmol) was added at room temperature, and the solution was stirred for 20 minutes at 80° C. To the solution, 2-chloro-1-(2-methyloxiran-2-ylmethyl)-4-nitroimidazole prepared in Example 6 (200 mg, 0.92 mmol) was added with cooling on ice-bath, and the solution was stirred for further 20 minutes at 80° C. To the reaction mixture, ice-water was added, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/ethyl acetate=10/1) and then crystallized from methylene chloride/ethyl acetate to afford 2-methyl-6-nitro-2-{4-[4-(4-trifluoromethylphenyl)piperazin-1-yl]phenoxymethyl}-2,3-dihydroimidazo[2,1-b]oxazole (178 mg, yield 38%) as a white powder.

Melting point 230.7-233.1° C.

Example 131

Preparation of tert-butyl 4-[4-(2-methyl-6-nitro-2,3-dihydroimidazo[2,1-b]oxazol-2-ylmethoxy)phenyl]-piperazine-1-carboxylate Tert-butyl 4-(4-hydroxyphenyl)piperazine-1-carboxylate (2.01 g, 7.23 mmol) was dissolved in DMF (20 ml). To the solution, sodium hydride (320 mg, 8 mmol) was added at room temperature, and the solution was stirred for 20 minutes at 70° C. To the solution, 2-chloro-1-(2-methyloxiran-2-ylmethyl)-4-nitroimidazole prepared in Example 6 (1.5 g, 7.23 mmol) was added with cooling on ice-bath, and the solution was stirred for further 20 minutes at 80° C. To the reaction mixture, ice-water was added, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/ethyl acetate=20/1) and then crystallized from methylene chloride/ethyl acetate to afford tert-butyl 4-[4-(2-methyl-6-nitro-2,3-dihydroimidazo[2,1-b]oxazol-2-ylmethoxy)phenyl]piperazine-1-carboxylate (1.5 g, yield 45%) as a white powder.

$^1$H-NMR (CDCl$_3$) δppm: 1.48 (9H, s), 1.77 (3H, s), 2.99-3.03 (4H, m), 3.55-3.59 (4H, m), 4.02 (1H, d, J=10.2 Hz), 4.04 (1H, d, J=10.1 Hz), 4.18 (1H, d, J=10.1 Hz), 4.49 (1H, d, J=10.2 Hz), 6.76-6.81 (2H, m), 6.84-6.89 (2H, m), 7.55 (1H, s). Melting point 212.0-214.5° C. MS 459(M$^+$).

Example 132

Preparation of tert-butyl 4-[4-(2-methyl-6-nitro-2,3-dihydroimidazo[2,1-b]oxazol-2-ylmethoxy)phenyl]-piperidine-1-carboxylate Tert-butyl 4-(4-hydroxyphenyl)piperidine-1-carboxylate (364 mg, 1.31 mmol) was dissolved in DMF (10 ml). To the solution, sodium hydride (58 mg, 1.44 mmol) was added at room temperature, and the solution was stirred for 20 minutes at 80° C. To the solution, 2-chloro-1-(2-methyloxiran-2-ylmethyl)-4-nitroimidazole prepared in Example 6 (300 mg, 1.38 mmol) was added with cooling on ice-bath followed by stirring for further 20 minutes at 80° C. To the reaction mixture, ice-water was added, and the solution was stirred vigorously. The precipitates were filtered off, washed with water and dissolved in methylene chloride. The organic phase was washed with a saturated saline solution, dried over magnesium sulfate and then filtered. The resulting filtrate was concentrated under reduced pressure. The residue was purified by silica gel column chromatography (methylene chloride/methanol=200/1) and then crystallized from methylene chloride-diisopropyl ether to afford tert-butyl 4-[4-(2-methyl-6-nitro-2,3-dihydroimidazo[2,1-b]oxazol-2-ylmethoxy)phenyl]piperidine-1-carboxylate (248 mg, yield 41%) as a white powder.

Melting point 207.8-209.1° C.

Example 133

Preparation of 3,4-dichlorobenzyl 4-[4-(2-methyl-6-nitro-2,3-dihydroimidazo[2,1-b]oxazol-2-ylmethoxy) phenyl]piperazine-1-carboxylate Tert-butyl 4-[4-(2-methyl-6-nitro-2,3-dihydroimidazo[2,1-b]oxazol-2-ylmethoxy)phenyl]-piperazine-1-carboxylate prepared in Example 131 (118 mg, 0.26 mmol) was dissolved in methylene chloride (5 ml). To the solution, trifluoroacetic acid (5 ml) was added, and the mixture was stirred at room temperature for 3 hours. The reaction mixture was concentrated under reduced pressure and added methylene chloride (2 ml) and triethylamine (2 ml). The solution was stirred at room temperature for 5 minutes and then concentrated under reduced pressure. The residue was dissolved in DMF (15 ml) and the solution was added a solution of 3,4-dichlorobenzyl alcohol (136 mg, 0.77 mmol) and 1,1'-carbonyldiimidazole (125 mg, 0.77 mmol) in DMF (5 ml) stirred at room temperature for 3 hours followed by stirring at room temperature overnight. The reaction mixture was poured into water and extracted with ethyl acetate. The organic phase was washed with a saturated saline solution, dried over magnesium sulfate and then filtered. The resulting filtrate was concentrated under reduced pressure. The residue was purified by silica gel column chromatography (methylene chloride/methanol=200/1) and crystallized from methylene chloride-isopropyl ether to afford 3,4-dichlorobenzyl 4-[4-(2-methyl-6-nitro-2,3-dihydroimidazo[2,1-b]oxazol-2-ylmethoxy)phenyl]piperazine-1-carboxylate (101 mg, yield 70%) as a light yellow powder.

$^1$H-NMR (CDCl$_3$) δppm: 1.77 (3H, s), 3.01-3.06 (4H, m), 3.62-3.67 (4H, m), 4.02 (1H, d, J=10.2 Hz), 4.04 (1H, d, J=10.2 Hz), 4.18 (1H, d, J=10.2 Hz), 4.49 (1H, d, J=10.2 Hz), 5.09 (2H, s), 6.76-6.81 (2H, m), 6.84-6.89 (2H, m), 7.18-7.22 (1H, m), 7.41-7.47 (2H, m), 7.55 (1H, s).

Example 134

Preparation of 2-methyl-6-nitro-2-{4-[4-(4-trifluoromethylbenzyl)piperazin-1-yl]phenoxymethyl}-2,3-dihydroimidazo[2,1-b]oxazole Tert-butyl 4-[4-(2-methyl-6-nitro-2,3-dihydroimidazo[2,1-b]oxazol-2-ylmethoxy)phenyl]-piperazine-1-carboxylate prepared in Example 131 (88 mg, 0.19 mmol) was dissolved in trifluoroacetic acid (5 ml), and the solution was stirred at room temperature for 5 hours. The reaction mixture was concentrated under reduced pressure and added methylene chloride (2 ml) and triethylamine (2 ml). The solution was stirred at room temperature for 5 minutes and then concentrated under reduced pressure. The residue was dissolved in dichloroethane and added 4-trifluoromethylbenzaldehyde (40 µl, 0.29 mmol) and sodium triacetoxyborohydride (82 mg, 0.38 mmol) with cooling on ice-bath followed by stirring at room temperature overnight. To the solution, a saturated sodium hydrogencarbonate solution and methylene chloride were added. The mixture was extracted with methylene chloride, and the organic phase was dried over magnesium sulfate and filtered. The resulting filtrate was concentrated under reduced pressure. The residue was purified by silica gel column chromatography (methylene chloride/methanol=200/1) and crystallized from methylene chloride-ethyl acetate to afford 2-methyl-6-nitro-2-{4-[4-(4-trifluoromethylbenzyl)piperazin-1-yl]phenoxymethyl}-2,3-dihydroimidazo[2,1-b]oxazole (53 mg, yield 53%) as a white powder.

Melting point 171.8-173.1° C.

Using tert-butyl 4-[4-(2-methyl-6-nitro-2,3-dihydroimidazo[2,1-b]oxazol-2-ylmethoxy)phenyl]-piperidine-1-carboxylate prepared in Example 132 gave the compound of Example 135 in the same manner as in Example 134.

Example 135

2-Methyl-6-nitro-2-{4-[1-(4-trifluoromethoxybenzyl)piperidin-4-yl]phenoxymethyl}-2,3-dihydroimidazo[2,1-b]oxazole Yield 45%, melting point 160.6-161.1° C.

Example 136

Preparation of (R)-2-methyl-6-nitro-2-(4-trifluoromethoxyphenoxymethyl)-2,3-dihydroimidazo[2,1-b]oxazole 4-Trifluoromethoxyphenol (1.1 g, 6.17 mmol) was dissolved in DMF (20 ml). To the solution, sodium hydride (260 mg, 6.45 mmol) was added at room temperature, and the solution was stirred for 15 minutes at 80° C. To the solution, (R)-2-chloro-1-(2-methyloxiran-2-ylmethyl)-4-nitroimidazole prepared in Example 12 (1.22 g, 5.61 mmol) was added with cooling on ice-bath, and the solution was stirred for further 2 hours at 80° C. The reaction mixture was poured into ice-water, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/ethyl acetate=10/1) and and then crystallized from methylene chloride-diisopropyl ether to afford (R)-2-methyl-6-nitro-2-(4-trifluoromethoxyphenoxymethyl)-2,3-dihydroimidazo[2,1-b]oxazole (1.03 g, yield 51%) as a white powder.

Optical purity >99% e.e. $[\alpha]_D^{28}$=7.67° (concentration: 1.030, CHCl$_3$) MS 359(M$^+$) Melting point 176.5-178.0° C.

Using corresponding starting materials gave compounds of Examples 137 to 139 in the same manner as in Example 136.

Example 137

(R)-2-Methyl-6-nitro-2-[4-(thiomorpholin-4-yl)phenoxymethyl]-2,3-dihydroimidazo[2,1-b]oxazole Yield 38%, melting point 227.5-229.0° C., MS 376(M$^+$).

Example 138

(R)-2-Methyl-6-nitro-2-[4-(imidazol-1-yl)phenoxymethyl]-2,3-dihydroimidazo[2,1-b]oxazole Yield 44%, melting point 172-175° C.

Example 139

(R)-2-Methyl-6-nitro-2-[4-(1,2,4-triazol-1-yl)phenoxymethyl]-2,3-dihydroimidazo[2,1-b]oxazole Yield 53%, melting point 236.0-238.7° C.

Using ethyl 1-(4-hydroxyphenyl)piperidine-4-carboxylate gave the compound of Example 140 in the same manner as in Example 136.

Example 140

Ethyl (R)-1-[4-(2-methyl-6-nitro-2,3-dihydroimidazo-[2,1-b]oxazol-2-ylmethoxy)phenyl]piperidine-4-carboxylate Yield 30%, melting point 208.2-211.5° C.

Example 141

Preparation of (R)-2-methyl-6-nitro-2-{4-[4-(4-trifluoromethoxyphenoxy)piperidin-1-yl]phenoxymethyl}-2,3-dihydroimidazo[2,1-b]oxazole 4-[4-(4-Trifluoromethoxyphenoxy)piperidin-1-yl]phenol (17.4 g, 49.0 mmol) was dissolved in DMF (150 ml). To the solution, sodium hydride (2.15 g, 53.8 mmol) was added at room temperature, and the solution was stirred for 20 minutes at 80° C. To the solution, (R)-2-chloro-1-(2-methyloxiran-2-ylmethyl)-4-nitroimidazole prepared in Example 12 (14.9 g, 68.6 mmol) was added with cooling on ice-bath, and the solution was stirred for further 20 minutes at 80° C. To the reaction mixture, ice-water was added, and the mixture was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/ethyl acetate=10/1) and then crystallized from methylene chloride/ethyl acetate to afford (R)-2-methyl-6-nitro-2-{4-[4-(4-trifluoromethoxyphenoxy)piperidin-1-yl]phenoxymethyl}-2,3-dihydroimidazo[2,1-b]oxazole (14.3 g, yield 55%) as a light yellow powder.

MS 535(M+1)$^+$ Optical purity 99.9% e.e. $[\alpha]_D^{28}$=−9.94° (concentration: 1.006, CHCl$_3$) Melting point 194.5-196° C. $^1$H-NMR (CDCl$_3$) δppm: 1.77 (3H, s), 1.87-2.00 (2H, m), 2.05-2.16 (2H, m), 2.95-3.05 (2H, m), 3.32-3.41 (2H, m), 4.02 (1H, d, J=10.2 Hz), 4.04 (1H, d, J=10.2 Hz), 4.18 (1H, d, J=10.2 Hz), 4.36-4.45 (1H, m), 4.49 (1H, d, J=10.2 Hz), 6.74-6.81 (2H, m), 6.87-6.94 (4H, m), 7.11-7.16 (2H, m), 7.55 (1H, s).

Example 142

Preparation of (R)-2-methyl-6-nitro-2-{4-[4-(4-trifluoromethoxyphenyl)piperazin-1-yl]phenoxymethyl}-2,3-dihydroimidazo[2,1-b]oxazole 4-[4-(4-Trifluoromethoxyphenyl)piperazin-1-yl]phenol (1.7 g, 5.02 mmol) was dissolved in DMF (20 ml). To the solution, sodium hydride (221 mg, 5.53 mmol) was added at room temperature, and the solution was stirred for 20 minutes at 80° C. To the solution, (R)-2-chloro-1-(2-methyloxiran-2-ylmethyl)-4-nitroimidazole prepared in Example 12 (1.2 g, 5.53 mmol) was added with cooling on ice-bath, and the solution was stirred for further 20 minutes at 80° C.

To the reaction mixture, ice-water was added, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/ethyl acetate=10/1) and then recrystallized from ethyl acetate to afford (R)-2-methyl-6-nitro-2-{4-[4-(4-trifluoromethoxyphenyl)piperazin-1-yl]phenoxymethyl}-2,3-dihydroimidazo[2,1-b]oxazole (1.02 g, yield 39%) as a light yellow powder.

MS 519($M^+$) Optical purity >99% e.e. $[\alpha]_D^{28}$=−18.02° (concentration: 1.160, $CHCl_3$) Melting point 262.5-265° C.

Example 143

Preparation of tert-butyl (R)-4-[4-(2-methyl-6-nitro-2,3-dihydroimidazo[2,1-b]oxazol-2-ylmethoxy)phenyl]-piperidine-1-carboxylate Tert-butyl 4-(4-hydroxyphenyl)piperidine-1-carboxylate (1.07 g, 3.86 mmol) was dissolved in DMF (10 ml). To the solution, sodium hydride (185 mg, 4.63 mmol) was added at room temperature, and the solution was stirred for 20 minutes at 80° C. To the solution, (R)-2-chloro-1-(2-methyloxiran-2-ylmethyl)-4-nitroimidazole prepared in Example 12 (923 mg, 4.24 mmol) was added with cooling on ice-bath, and the solution was stirred for further 20 minutes at 80° C. To the reaction mixture, ice-water was added, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/methanol=200/1) and then crystallized from ethyl acetate-diisopropyl ether to afford tert-butyl (R)-4-[4-(2-methyl-6-nitro-2,3-dihydroimidazo[2,1-b]oxazol-2-ylmethoxy)phenyl]piperidine-1-carboxylate (857 mg, yield 48%) as a white powder.

MS 458($M^+$) Optical purity >99% e.e. $[\alpha]_D^{28}$=−1.07° (concentration: 1.028, $CHCl_3$) Melting point 227.5-228.3° C. (decomposition).

Using corresponding starting materials gave the compound of Example 144 in the same manner as in Example 143.

Example 144

Tert-butyl (R)-4-[4-(2-methyl-6-nitro-2,3-dihydroimidazo[2,1-b]oxazol-2-ylmethoxy)phenyl]-1,2,3,6-tetrahydropyridine-1-carboxylate Melting point 183.0-189.0° C. (decomposition).

Example 145

Preparation of tert-butyl (R)-4-[4-(2-methyl-6-nitro-2,3-dihydroimidazo[2,1-b]oxazol-2-ylmethoxy)benzoyl]-piperazine-1-carboxylate Tert-butyl 4-(4-hydroxybenzoyl)piperazine-1-carboxylate (6.6 g, 21.5 mmol) was dissolved in DMF (50 ml). To the solution, sodium hydride (991 mg, 24.8 mmol) was added at room temperature, and the solution was stirred for 20 minutes at 80° C. To the solution, (R)-2-chloro-1-(2-methyloxiran-2-ylmethyl)-4-nitroimidazole prepared in Example 12 (5.16 mg, 23.7 mmol) was added with cooling on ice-bath, and the solution was stirred for further 20 minutes at 80° C. To the reaction mixture, ice-water was added, and the solution was stirred vigorously. The precipitates were filtered off, washed with water, dissolved in methylene chloride. The organic phase was washed with a saturated saline solution, dried over magnesium sulfate and then filtered. The resulting filtrate was concentrated under reduced pressure. The residue was purified by silica gel column chromatography (methylene chloride/methanol=100/1) and then crystallized from methylene chloride-diisopropyl ether to afford tert-butyl (R)-4-[4-(2-methyl-6-nitro-2,3-dihydroimidazo[2,1-b]oxazol-2-ylmethoxy)benzoyl]piperazine-1-carboxylate (7.35 g, yield 70%) as a white powder.

MS 488(M+1)$^+$ Melting point 222.5-224.0° C.

Example 146

Preparation of tert-butyl (R)-4-[2-chloro-4-(2-methyl-6-nitro-2,3-dihydroimidazo[2,1-b]oxazol-2-ylmethoxy)-phenyl]piperazine-1-carboxylate Tert-butyl 4-(2-chloro-4-hydroxyphenyl)-piperazine-1-carboxylate (2.7 g, 8.63 mmol) was dissolved in DMF (20 ml). To the solution, sodium hydride (397 mg, 9.92 mmol) was added at room temperature, and the solution was stirred for 20 minutes at 80° C. To the solution, (R)-2-chloro-1-(2-methyloxiran-2-ylmethyl)-4-nitroimidazole prepared in Example 12 (2.1 g, 9.50 mmol) was added with cooling on ice-bath, and the solution was stirred for further 20 minutes at 80° C. To the reaction mixture, ice-water was added, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/methanol=200/1) and then crystallized from methylene chloride-ethyl acetate to afford tert-butyl (R)-4-[2-chloro-4-(2-methyl-6-nitro-2,3-dihydroimidazo[2,1-b]oxazol-2-ylmethoxy)phenyl]piperazine-1-carboxylate (2.34 g, yield 55%) as a white powder.

MS 493($M^+$) Melting point 207.0-209.5° C.

Example 147

Preparation of tert-butyl (R)-4-[3-(2-methyl-6-nitro-2,3-dihydroimidazo[2,1-b]oxazol-2-ylmethoxy)phenyl]-piperazine-1-carboxylate Tert-butyl 4-(3-hydroxyphenyl)piperazine-1-carboxylate (3.23 g, 11.6 mmol) was dissolved in DMF (40 ml). To the solution, sodium hydride (557 mg, 13.9 mmol) was added at room temperature, and the solution was stirred for 20 minutes at 80° C. To the solution, (R)-2-chloro-1-(2-methyloxiran-2-ylmethyl)-4-nitroimidazole prepared in Example 12 (2.78 g, 12.8 mmol) was added with cooling on ice-bath, and the solution was stirred for further 20 minutes at 80° C. To the reaction mixture, ice-water was added, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/methanol=100/1) and then crystallized from methylene chloride-ethyl acetate to afford tert-butyl (R)-4-[3-(2-methyl-6-nitro-2,3-dihydroimidazo[2,1-d]oxazol-2-ylmethoxy)phenyl]piperazine-1-carboxylate (1.4 g, yield 26%) as a white powder.

MS 459(M$^+$) Melting point 179.5-182.0° C.

Example 148

Preparation of tert-butyl (R)-4-[4-(2-methyl-6-nitro-2,3-dihydroimidazo[2,1-b]oxazol-2-ylmethoxy)phenyl]-piperazine-1-carboxylate Tert-butyl 4-(4-hydroxyphenyl)piperazine-1-carboxylate (13.5 g, 48.8 mmol) was dissolved in DMF (100 ml). To the solution, sodium hydride (2.15 g, 53.7 mmol) was added at room temperature, and the solution was stirred for 20 minutes at 70° C. To the solution, (R)-2-chloro-1-(2-methyloxiran-2-ylmethyl)-4-nitroimidazole prepared in Example 12 (10.6 g, 48.8 mmol) was added with cooling on ice-bath, and the solution was stirred for further 20 minutes at 80° C. To the reaction mixture, ice-water was added, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/methanol=100/1) and then crystallized from methylene chloride-ethyl acetate to afford tert-butyl (R)-4-[4-(2-methyl-6-nitro-2,3-dihydroimidazo[2,1-b]oxazol-2-ylmethoxy)phenyl]piperazine-1-carboxylate (9.9 g, yield 44%) as a white powder.

Optical purity >99.5% e.e. $[\alpha]_D^{28}$=−10.85° (concentration: 1.014, CHCl$_3$) MS 459(M$^+$) Melting point 230-232° C. $^1$H-NMR (CDCl$_3$) δppm: 1.48 (9H, s), 1.76 (3H, s), 2.99-3.03 (4H, m), 3.54-3.59 (4H, m), 4.02 (1H, d, J=10.2 Hz), 4.04 (1H, d, J=10.1 Hz), 4.18 (1H, d, J=10.1 Hz), 4.49 (1H, d, J=10.2 Hz), 6.76-6.81 (2H, m), 6.85-6.89 (2H, m), 7.58 (1H, s).

Example 149

Preparation of (R)-[4-(2-methyl-6-nitro-2,3-dihydroimidazo[2,1-b]oxazol-2-ylmethoxy)phenyl]-piperazine dihydrochloride Tert-butyl (R)-4-[4-(2-methyl-6-nitro-2,3-dihydroimidazo[2,1-b]oxazol-2-ylmethoxy)phenyl]-piperazine-1-carboxylate prepared in Example 148 (300 mg, 0.65 mmol) was dissolved in trifluoroacetic acid (5 ml) followed by stirring at room temperature for 3 hours. The reaction mixture was concentrated under reduced pressure, and the residue was dissolved in methanol. To the solution, a saturated hydrogen chloride (5 ml) in ethyl acetate was added, and the precipitates were filtered off and dried under reduced pressure to afford (R)-[4-(2-methyl-6-nitro-2,3-dihydroimidazo[2,1-b]oxazol-2-ylmethoxy)phenyl]piperazine dihydrochloride (279 mg, yield 99%) as a light yellow powder.

MS 359(M$^+$) Melting point 212-220° C. (decomposition) $^1$H-NMR (DMSO-d$_6$) δppm: 1.67 (3H, s), 3.22-3.31 (8H, m), 4.18 (1H, d, J=10.9 Hz), 4.23 (2H, s), 4.37 (1H, d, J=10.9 Hz), 6.85 (2H, d, J=9.1 Hz), 7.00 (2H, d, J=9.1 Hz), 8.16 (1H, s), 9.37 (3H, br).

Example 150

Preparation of (R)-2-methyl-6-nitro-2-{4-[4-(4-trifluoromethylbenzyl)piperazin-1-yl]phenoxymethyl}-2,3-dihydroimidazo[2,1-b]oxazole A mixture of tert-butyl (R)-4-[4-(2-methyl-6-nitro-2,3-dihydroimidazo[2,1-b]oxazol-2-ylmethoxy)-phenyl]piperazine-1-carboxylate prepared in Example 148 (800 mg, 1.74 mmol) and trifluoroacetic acid (3 ml) was stirred at room temperature for 7 hours. The reaction mixture was concentrated under reduced pressure, and the residue was dissolved in methylene chloride (10 ml). To the solution, triethylamine (3 ml, 21.52 mmol) was added followed by stirring at room temperature for 5 minutes. The mixture was concentrated under reduced pressure, and the residue was dissolved in methanol (10 ml). To the solution, 4-trifluoromethylbenzaldehyde (910 mg, 5.23 mmol), sodium cyanotrihydroborate (328 mg, 5.23 mmol) and acetic acid (0.33 ml, 5.23 mmol) were added followed by stirring at room temperature overnight. To the reaction mixture, a saturated sodium hydrogencarbonate solution and methylene chloride were added, and the solution was stirred and then extracted with methylene chloride. The organic phase was dried over magnesium sulfate and filtered. The resulting filtrate was concentrated under reduced pressure. The residue was purified by silica gel column chromatography (methylene chloride/methanol=200/1) to afford (R)-2-methyl-6-nitro-2-{4-[4-(4-trifluoromethylbenzyl)piperazin-1-yl]phenoxymethyl}-2,3-dihydroimidazo[2,1-b]oxazole (667 mg, yield 74%) as a light yellow powder.

Melting point 205.5-207° C.

Example 151

Preparation of ethyl (R)-4-[4-(2-methyl-6-nitro-2,3-dihydroimidazo[2,1-b]oxazol-2-ylmethoxy)phenyl]-piperazine-1-carboxylate Tert-butyl (R)-4-[4-(2-methyl-6-nitro-2,3-dihydroimidazo[2,1-b]oxazol-2-ylmethoxy)phenyl]-piperazine-1-carboxylate prepared in Example 148 (300 mg, 0.65 mmol) was dissolved in methylene chloride (5 ml). To the solution, trifluoroacetic acid (5 ml) was added followed by stirring at room temperature for 3 hours. The reaction mixture was concentrated under reduced pressure and then added methylene chloride (5 ml), triethylamine (2 ml) and ethyl chloroformate (0.11 ml, 1.31 mmol) followed by stirring at room temperature for 1 hour. The reaction mixture was poured into water and extracted with methylene chloride. The organic phase was washed with a saturated saline solution, dried over magnesium sulfate and then filtered. The resulting filtrate was concentrated under reduced pressure. The residue was purified by silica gel column chromatography (methylene chloride/methanol=200/1) and crystallized from methylene chloride-isopropyl ether to afford ethyl (R)-4-[4-(2-methyl-6-nitro-2,3-dihydroimidazo[2,1-b]oxazol-2-ylmethoxy)phenyl]piperazine-1-carboxylate (182 mg, yield 65%) as a white powder.

$[\alpha]_D^{28}$=−9.86° (concentration: 1.014, CHCl$_3$). MS 431 (M$^+$) Melting point 210.5-212.0° C.

Example 152

Preparation of 4-chlorobenzyl (R)-4-[4-(2-methyl-6-nitro-2,3-dihydroimidazo[2,1-b]oxazol-2-ylmethoxy)-phenyl]piperazine-1-carboxylate Tert-butyl (R)-4-[4-(2-methyl-6-nitro-2,3-dihydroimidazo[2,1-b]oxazol-2-ylmethoxy)phenyl]-piperazine-1-carboxylate prepared in Example 148 (300 mg, 0.65 mmol) was dissolved in methylene chloride (5 ml). To the solution, trifluoroacetic acid (5 ml) was added followed by stirring at room temperature for 3 hours. The reaction mixture was concentrated under reduced pressure and then added methylene chloride (2 ml) and triethylamine (2 ml). After stirring at room temperature for 5 minutes, the solution was concentrated under reduced pressure, and the residue was dissolved in DMF (15 ml). To the solution, a mixture of 4-chlorobenzyl alcohol (186 mg, 1.31 mmol), 1,1'-carbonyldiimidazole (212 mg, 1.31 mmol) in DMF (5 ml) stirred at room temperature for 3 hours was added followed by stirring at room temperature overnight. The reaction mixture was poured into water, extracted from ethyl acetate, and the organic phase was washed with a saturated saline solution, dried over magnesium sulfate and then filtered. The resulting filtrate was concentrated under reduced pressure. The residue was purified by silica gel column chromatography (methylene chloride/methanol=200/1) and crystallized from methylene chloride-isopropyl ether to afford 4-chlorobenzyl (R)-4-[4-(2-methyl-6-nitro-2,3-dihydroimidazo[2,1-b]oxazol-2-ylmethoxy)phenyl]piperazine-1-carboxylate (313 mg, yield 91%) as a light yellow powder.

$[\alpha]_D^{28}=-10.84°$ (concentration: 1.006, $CHCl_3$) MS 527 ($M^+$) Melting point 184.5-187.5° C.

Using corresponding starting materials gave the compound of Example 153 in the same manner as in Example 152.

Example 153

5-Chlorobenzofuran-2-ylmethyl (R)-4-[4-(2-methyl-6-nitro-2,3-dihydroimidazo[2,1-b]oxazol-2-ylmethoxy)-phenyl]piperazine-1-carboxylate Yield 79%, melting point 195-197° C.

Using tert-butyl (R)-4-[4-(2-methyl-6-nitro-2,3-dihydroimidazo[2,1-b]oxazol-2-ylmethoxy)phenyl]-piperidine-1-carboxylate prepared in Example 143, tert-butyl (R)-4-[4-(2-methyl-6-nitro-2,3-dihydroimidazo-[2,1-b]oxazol-2-ylmethoxy)phenyl]-1,2,3,6-tetrahydropyridine-1-carboxylate prepared in Example 144, tert-butyl (R)-4-[4-(2-methyl-6-nitro-2,3-dihydroimidazo-[2,1-b]oxazol-2-ylmethoxy)benzoyl]piperazine-1-carboxylate prepared in Example 145, or tert-butyl (R)-4-[3-(2-methyl-6-nitro-2,3-dihydroimidazo[2,1-b]oxazol-2-ylmethoxy)phenyl]piperazine-1-carboxylate prepared in Example 147 gave compounds of Examples 154 to 158 in the same manner as in Example 152.

Example 154

4-Trifluoromethoxybenzyl (R)-4-[4-(2-methyl-6-nitro-2,3-dihydroimidazo[2,1-b]oxazol-2-ylmethoxy)phenyl]-piperidine-1-carboxylate Yield 54%, melting point 202.5-204° C.

Example 155

4-Trifluoromethoxybenzyl (R)-4-[4-(2-methyl-6-nitro-2,3-dihydroimidazo[2,1-b]oxazol-2-ylmethoxy)phenyl]-1,2,3,6-tetrahydropyridine-1-carboxylate Yield 67%, melting point 174.3-174.8° C.

Example 156

4-Trifluoromethoxybenzyl (R)-4-[4-(2-methyl-6-nitro-2,3-dihydroimidazo[2,1-b]oxazol-2-ylmethoxy)benzoyl]-piperazine-1-carboxylate Yield 86%, melting point 168.5-172° C.

Example 157

Ethyl (R)-4-[4-(2-methyl-6-nitro-2,3-dihydroimidazo-[2,1-b]oxazol-2-ylmethoxy)benzoyl]piperazine-1-carboxylate Yield 85%, melting point 132-135° C.

Example 158

4-Trifluoromethoxybenzyl (R)-4-[3-(2-methyl-6-nitro-2,3-dihydroimidazo[2,1-b]oxazol-2-ylmethoxy)phenyl]-piperazine-1-carboxylate Yield 50%, melting point 136.5-138° C.

Example 159

Preparation of (R)-2-methyl-6-nitro-2-{4-[4-(4-trifluoromethoxybenzyl)piperazin-1-yl]phenoxymethyl}-2,3-dihydroimidazo[2,1-b]oxazole Tert-butyl (R)-4-[4-(2-methyl-6-nitro-2,3-dihydroimidazo[2,1-b]oxazol-2-ylmethoxy)phenyl]-piperazine-1-carboxylate prepared in Example 148 (4.22 g, 9.60 mmol) was dissolved in methylene chloride (10 ml). To the solution, trifluoroacetic acid (30 ml) was added followed by stirring at room temperature for 5 hours. The reaction mixture was concentrated under reduced pressure and added methylene chloride (10 ml) and triethylamine (10 ml). The solution was stirred at room temperature for 5 minutes and then concentrated under reduced pressure. The residue was dissolved in dichloroethane. To the solution, 4-trifluoromethoxybenzaldehyde (1.64 ml, 11.5 mmol) and sodium triacetoxyborohydride (3.05 g, 14.4 mmol) were added with cooling on ice-bath followed by stirring at room temperature overnight. To the reaction mixture, a saturated sodium hydrogencarbonate solution and methylene chloride were added, and the solution was stirred and extracted with methylene chloride. The organic phase was dried over magnesium sulfate and then filtered. The resulting filtrate was concentrated under reduced pressure. The residue was purified by silica gel column chromatography (methylene chloride/methanol=200/1) and then crystallized from methylene chloride-ethyl acetate to afford (R)-2-methyl-6-nitro-2-{4-[4-(4-trifluoromethoxybenzyl)piperazin-1-yl]phenoxymethyl}-2,3-dihydroimidazo[2,1-b]oxazole (3.23 g, yield 63%) as a light yellow powder.

Optical purity >99.5% e.e. $[\alpha]_D^{28}=-8.25°$ (concentration: 1.018, $CHCl_3$) MS 533($M^+$) Melting point 213.5-217° C.

The compound of Example 159 was prepared also with the following Example 160.

Example 160

Preparation of (R)-2-methyl-6-nitro-2-{4-[4-(4-trifluoromethoxybenzyl)piperazin-1-yl]phenoxymethyl}-2,3-dihydroimidazo[2,1-b]oxazole 4-[4-(4-Trifluoromethoxybenzyl)piperazin-1-yl]phenol (3.36 g, 9.54 mmol) was dissolved in of DMF (20 ml). To the solution, sodium hydride (420 mg, 10.5 mmol) was added at room temperature, and the solution was stirred for 15 minutes at 80° C. To the reaction mixture, (R)-2-chloro-1-(2-methyloxiran-2-ylmethyl)-4-nitroimidazole prepared in Example 12 (2.18 g, 10.0 mmol) was added with cooling on ice-bath followed by stirring for further 15 minutes at 80° C. To the reaction mixture, ice-water was added, and the solution was stirred vigorously. The precipitates were filtered off, washed with water and dissolved in methylene chloride. The solution was washed with a saturated saline solution, dried over magnesium sulfate and then filtered. The resulting filtrate was concentrated under reduced pressure. The residue was purified by silica gel column chromatography (methylene chloride/methanol=100/1) and then crystallized from methylene chloride-ethyl acetate to afford (R)-2-methyl-6-nitro-2-{4-[4-(4-trifluoromethoxybenzyl)piperazin-1-yl]phenoxymethyl}-2,3-dihydroimidazo[2,1-b]oxazole (2.0 g, yield 40%) as a light yellow powder.

Using tert-butyl (R)-4-[4-(2-methyl-6-nitro-2,3-dihydroimidazo[2,1-b]oxazol-2-ylmethoxy)phenyl]-piperidine-1-carboxylate prepared in Example 143, gave tert-butyl (R)-4-[4-(2-methyl-6-nitro-2,3-dihydroimidazo[2,1-b]oxazol-2-ylmethoxy)phenyl]-1,2,3,6-tetrahydropyridine-1-carboxylate prepared in Example 144, or tert-butyl (R)-4-[4-(2-methyl-6-nitro-2,3-dihydroimidazo[2,1-b]oxazol-2-ylmethoxy)benzoyl]-piperazine-1-carboxylate prepared in Example 145 gave compounds of Examples 161-163 in the same manner as in Example 159.

Example 161

(R)-2-Methyl-6-nitro-2-{4-[1-(4-trifluoromethoxybenzyl)piperidin-4-yl]phenoxymethyl}-2,3-dihydroimidazo[2,1-b]oxazole Yield 45%, melting point 186-188° C.

Example 162

(R)-2-Methyl-6-nitro-2-{4-[1-(4-trifluoromethoxybenzyl)-1,2,3,6-tetrahydropyridin-4-yl]phenoxymethyl}-2,3-dihydroimidazo[2,1-b]oxazole Yield 61%, melting point 168-174° C.

Example 163

(R)-4-[4-(2-Methyl-6-nitro-2,3-dihydroimidazo[2,1-b]oxazol-2-ylmethoxy)benzoyl]-1-(4-trifluoromethoxybenzyl)piperazine Yield 83%, melting point 155-156° C.

Example 164

Preparation of (R)-4-[4-(2-methyl-6-nitro-2,3-dihydroimidazo[2,1-b]oxazol-2-ylmethoxy)phenyl]-piperazin-1-carboxylic acid 4-trifluoromethoxybenzylamide Tert-butyl (R)-4-[4-(2-methyl-6-nitro-2,3-dihydroimidazo[2,1-b]oxazol-2-ylmethoxy)phenyl]-piperazine-1-carboxylate prepared in Example 148 (120 mg, 0.26 mmol) was dissolved in methylene chloride (5 ml). To the solution, trifluoroacetic acid (5 ml) was added followed by stirring at room temperature for 3 hours. The reaction mixture was concentrated under reduced pressure, then added methylene chloride (2 ml) and triethylamine (2 ml). The solution was stirred at room temperature for 5 minutes and then concentrated under reduced pressure. The residue was dissolved in DMF (10 ml). To the solution, a mixture of 4-trifluoromethoxybenzylamine (125 mg, 0.65 mmol) and 1,1'-carbonyldiimidazole (110 mg, 0.68 mmol) in DMF (5 ml) stirred at room temperature for 3 hours was added followed by stirring at room temperature overnight. The reaction mixture was poured into water and extracted with ethyl acetate. The organic phase was washed with a saturated saline solution, dried over magnesium sulfate and then filtered. The resulting filtrate was concentrated under reduced pressure. The residue was purified by silica gel column chromatography (methylene chloride/methanol=200/1) and crystallized from methylene chloride-isopropyl ether to afford (R)-4-[4-(2-methyl-6-nitro-2,3-dihydroimidazo[2,1-b]oxazol-2-ylmethoxy)phenyl]piperazine-1-carboxylic acid 4-trifluoromethoxybenzylamide (48 mg, yield 32%) as a white powder.

MS 558(M−18)$^+$ Melting point 166.5-168.5° C.

Example 165

Preparation of (R)-2-methyl-6-nitro-2-{4-[4-(4-trifluoromethoxybenzoyl)piperazin-1-yl]phenoxymethyl}-2,3-dihydroimidazo[2,1-b]oxazole Tert-butyl (R)-4-[4-(2-methyl-6-nitro-2,3-dihydroimidazo[2,1-b]oxazol-2-ylmethoxy)phenyl]-piperazine-1-carboxylate prepared in Example 148 (300 mg, 0.65 mmol) was dissolved in methylene chloride (5 ml). To the solution, trifluoroacetic acid (5 ml) was added followed by stirring at room temperature for 5 hours. The reaction mixture was concentrated under reduced pressure and added methylene chloride (10 ml), triethylamine (2 ml) and 4-trifluoromethoxybenzoyl chloride (0.15 ml, 0.98 mmol). The reaction mixture was stirred at room temperature for 1 hour, then poured into water, and extracted with methylene chloride. The organic phase was washed with a saturated saline solution, dried over magnesium sulfate and then filtered. The resulting filtrate was concentrated under reduced pressure. The residue was purified by silica gel column chromatography (methylene chloride/ethyl acetate=10/1) and crystallized from methylene chloride-diisopropyl ether to afford (R)-2-methyl-6-nitro-2-{4-[4-(4-trifluoromethoxybenzoyl)piperazin-1-yl]phenoxymethyl}-2,3-dihydroimidazo[2,1-b]oxazole (263 mg, yield 74%) as a white powder.

MS 547(M$^+$) Melting point 201.5-203.2° C.

Example 166

Preparation of (R)-2-methyl-6-nitro-2-[4-(1-oxothiomorpholin-4-yl)phenoxymethyl]-2,3-dihydroimidazo[2,1-b]oxazole (R)-2-Methyl-6-nitro-2-[4-(thiomorpholin-4-yl)phenoxymethyl]-2,3-dihydroimidazo[2,1-b]oxazole prepared in Example 137 (85 mg, 0.23 mmol) was dissolved in methylene chloride (5 ml). To the solution, m-chloroperbenzoic acid (59 mg, 0.24 mmol) was added followed by stirring at room temperature for 20 minutes. The reaction mixture was diluted with methylene chloride. The solution was washed with a sodium thiosulfate solution, a saturated sodium hydrogencarbonate solution and a saturated saline solution, dried over magnesium sulfate and then filtered. The resulting filtrate was concentrated under reduced pressure. The residue was crystallized from methylene chloride-isopropyl ether to afford (R)-2-methyl-6-nitro-2-[4-(1-oxothiomorpholin-4-yl)phenoxymethyl]-2,3-dihydroimidazo[2,1-b]oxazole (59 mg, yield 67%) as a white powder.

MS 392 ($M^+$) Melting point 198-200° C.

Example 167

Preparation of N-methyl-N-(2-methyl-6-nitro-2,3-dihydroimidazo[2,1-b]oxazol-2-ylmethyl)-2-(4-trifluoromethoxyphenoxy)ethylamine A mixture of 2-chloro-1-(2-methyloxiran-2-ylmethyl)-4-nitroimidazole prepared in Example 6 (84 mg, 0.39 mmol), N-methyl-2-(4-trifluoromethoxyphenoxy)ethylamine (100 mg, 0.43 mmol) and DMF (1 ml) was stirred at 65-70° C. for 8 hours. The reaction mixture was allowed to return to room temperature, poured into water and extracted with ethyl acetate. The organic phase was washed with a saturated saline solution and dried over sodium sulfate. After filtration, the filtrate was concentrated under reduced pressure. The residue was purified by silica gel column chromatography (methylene chloride/ethyl acetate=20/1) to afford a yellow oil.

The yellow oil was dissolved in DMF (1 ml). To the solution, sodium hydride (11 mg, 0.28 mmol) was added followed by stirring at room temperature for 1 hour. To the reaction mixture, ice-water was added, and the solution was extracted with ethyl acetate. The organic phase was washed with a saturated saline solution, dried over magnesium sulfate and filtered. The resulting filtrate was concentrated under reduced pressure. The residue was purified by silica gel column chromatography (methylene chloride/ethyl acetate=10/1) and crystallized from methylene chloride-diisopropyl ether to afford N-methyl-N-(2-methyl-6-nitro-2,3-dihydroimidazo[2,1-b]oxazol-2-ylmethyl)-2-(4-trifluoromethoxyphenoxy)ethylamine (34 mg, yield 21%) as a white powder.

Melting point 86.4-89.2° C.

Example 168

Preparation of tert-butyl N-methyl-N-{2-[N-methyl-(2-methyl-6-nitro-2,3-dihydroimidazo[2,1-b]oxazol-2-ylmethyl)amino]ethyl}carbamate A mixture of 2-chloro-4-nitro-1H-imidazole (5.97 g, 27.43 mmol), tert-butyl N-methyl-{2-[N-methyl-(2-methyloxiran-2-ylmethyl)amino]ethyl}carbamate (10.53 g, 40.76 mmol), triethylamine (0.76 ml, 5.49 mmol) and 1-propanol (60 ml) was stirred under reflux for 5 hours. The reaction mixture was allowed to return to room temperature and concentrated under reduced pressure. To the residue, water was added, and the solution was extracted with methylene chloride. The organic phase was washed with a saturated saline solution and dried over sodium sulfate. After filtration, the filtrate was concentrated under reduced pressure. The residue was purified by silica gel column chromatography (methylene chloride/methanol=20/1) to afford a yellow oil.

The yellow oil was dissolved in 1,4-dioxane (200 ml). To the solution, sodium hydride (500 mg, 12.5 mmol) was added followed by stirring under reflux overnight. The reaction mixture was allowed to return to room temperature and concentrated under reduced pressure. To the residue, ice-water was added, and the solution was extracted with methylene chloride. The organic phase was washed with a saturated saline solution, dried over sodium sulfate and then filtered. The filtrate was concentrated under reduced pressure. The residue was purified by silica gel column chromatography (methylene chloride/methanol=20/1) to afford tert-butyl N-methyl-N-{2-[N-methyl-(2-methyl-6-nitro-2,3-dihydroimidazo[2,1-b]oxazol-2-ylmethyl)amino]ethyl}carbamate (1.94 g, yield 13%) as a white powder.

$^1$H-NMR (CDCl$_3$) δppm: 1.45 (9H, s), 1.58 (3H, s), 2.38 (3H, s), 2.57-2.69 (3H, m), 2.79 (3H, s), 2.89 (1H, d, J=14.9 Hz), 3.15-3.25 (2H, bm), 3.85 (1H, d, J=14.9 Hz), 4.33 (1H, br), 7.52 (1H, s).

Example 169

Preparation of (S)—N-methyl-N-(2-methyl-6-nitro-2,3-dihydroimidazo[2,1-b]oxazol-2-ylmethyl)-2-{4-[4-(trifluoromethyl)phenyl]piperazin-1-yl}ethylamine (R)-2-Chloro-1-(2-methyloxiran-2-ylmethyl)-4-nitroimidazole prepared in Example 12 (523 mg, 2.41 mmol) and N-methyl-2-[4-(4-trifluoromethylphenyl)piperazin-1-yl]ethylamine (900 mg, 3.13 mmol) were added to DMF (15 ml) followed by stirring at 70-80° C. for 5 hours. The reaction mixture was allowed to return to room temperature, poured into water and extracted with ethyl acetate. The organic phase was washed with a saturated saline solution and dried over sodium sulfate. After filtration, the filtrate was concentrated under reduced pressure. The residue was purified by silica gel column chromatography (methylene chloride/ethyl acetate=20/1) to afford a yellow oil.

The yellow oil was dissolved in DMF (15 ml). To the solution, sodium hydride (115 mg, 2.89 mmol) was added followed by stirring at room temperature for 1 hour. To the reaction mixture, ice-water was added, and the solution was extracted with ethyl acetate. The organic phase was washed with a saturated saline solution, dried over magnesium sulfate and then filtered. The resulting filtrate was concentrated under reduced pressure. The residue was purified by silica gel column chromatography (methylene chloride/ethyl acetate=10/1) and crystallized from methylene chloride-diisopropyl ether to afford (S)—N-methyl-N-(2-methyl-6-nitro-2,3-dihydroimidazo[2,1-b]oxazol-2-ylmethyl)-2-{4-[4-(trifluoromethyl)phenyl]piperazin-1-yl}ethylamine (173 mg, yield 15%) as a white powder.

MS 468($M^+$) Melting point 148.0-150.5° C.

Using corresponding starting materials gave compounds of Examples 170 to 177 in the same manner as in Example 169.

Example 170

(S)—N-Methyl-N-(2-methyl-6-nitro-2,3-dihydroimidazo-[2,1-b]oxazol-2-ylmethyl)-2-(4-trifluoromethylphenoxy)ethylamine White powder, yield 12% MS 399(M−H)⁺ Melting point 123.0-126.0° C.

Example 171

(S)—N-Methyl-N-(2-methyl-6-nitro-2,3-dihydroimidazo[2,1-b]oxazol-2-ylmethyl)-2-(4-trifluoromethoxyphenoxy)ethylamine White powder, yield 45% MS 416(M⁺) Melting point 112.5-115.0° C.

Example 172

(S)—N,N'-Dimethyl-N-(2-methyl-6-nitro-2,3-dihydroimidazo[2,1-b]oxazol-2-ylmethyl)-N'-(4-trifluoromethylphenyl)-1,2-ethylenediamine White powder, yield 24% MS 413(M⁺) Melting point 135.5-137.5° C.

Example 173

Tert-butyl (S)-4-[2-(N-methyl-2-methyl-6-nitro-2,3-dihydroimidazo[2,1-b]oxazol-2-ylmethylamino)ethyl]-piperazine-1-carboxylate White powder, yield 30% MS 425(M+H)⁺ Melting point 149.5-151.8° C.

Example 174

(S)—N-Benzyl-N-[2-(4-trifluoromethoxyphenoxy)ethyl]-2-methyl-6-nitro-2,3-dihydroimidazo[2,1-b]oxazol-2-ylmethylamine White powder, yield 25% Melting point 96.5-97° C.

Example 175

(S)—N-Methyl-N-[3-(4-trifluoromethoxyphenoxy)propyl]-2-methyl-6-nitro-2,3-dihydroimidazo[2,1-b]oxazol-2-ylmethylamine White powder, yield 50% Melting point 92-95° C.

Example 176

(S)—N-Methyl-N-[2-(4-chlorophenoxy)ethyl]-2-methyl-6-nitro-2,3-dihydroimidazo[2,1-b]oxazol-2-ylmethylamine White powder, yield 27% Melting point 130.5-132° C.

Example 177

(S)—N-Methyl-N-(2-methyl-6-nitro-2,3-dihydroimidazo-[2,1-b]oxazol-2-ylmethyl)-2-[4-(4-trifluoromethylphenoxy)piperidin-1-yl]ethylamine Light brown powder, yield 26% $^1$H-NMR (CDCl$_3$) δppm: 1.58 (3H, s), 1.70-1.85 (2H, m), 1.98 (2H, br), 2.37 (3H, s), 2.25-2.50 (4H, m), 2.50-2.80 (5H, m), 2.90 (1H, d, J=14.9 Hz), 3.85 (1H, d, J=9.5 Hz), 4.37 (1H, m), 4.52 (1H, d, J=14.9 Hz), 7.42 (2H, d, J=8.7 Hz), 7.52 (1H, s), 7.53 (2H, d, J=8.7 Hz).

Example 178

Preparation of N-(2-ethoxycarbonylphenyl)-2-methyl-6-nitro-2,3-dihydroimidazo[2,1-b]oxazol-2-ylmethylamine A mixture of 2-chloro-4-nitro-1H-imidazole (891 mg, 6.04 mmol), 1-(2-methyloxiran-2-ylmethyl)-1H-benzo[d][1,3]oxazin-2,4-dione (1.41 g, 6.04 mmol), sodium acetate (545 mg, 6.64 mmol) and ethanol (10 ml) was stirred under reflux for 10 hours. The reaction mixture was allowed to return to room temperature, and concentrated under reduced pressure. To the residue, water was added, and the solution was extracted with methylene chloride. The organic phase was washed with a saturated saline solution and dried over sodium sulfate. After filtration, the filtrate was concentrated under reduced pressure, and the residue was dissolved in 1,4-dioxane (20 ml). To the solution, sodium hydride (219 mg, 5.48 mmol) was added followed by stirring under reflux for 5 hours. The reaction mixture was allowed to return to room temperature and concentrated under reduced pressure. To the residue, ice-water was added, and the precipitates were filtered off, which were purified by silica gel column chromatography (methylene chloride/ethyl acetate=20/1) to afford N-(2-ethoxycarbonylphenyl)-2-methyl-6-nitro-2,3-dihydroimidazo[2,1-b]oxazol-2-ylmethylamine (1.15 g, yield 55%) as a white powder.

Melting point 162.5-163.2° C.

Example 179

Preparation of (S)-1-[2-hydroxy-3-(N-methyl-benzylamino)-2-methylpropyl]-2-chloro-4-nitroimidazole A mixture of (R)-2-chloro-1-(2-methyloxiran-2-ylmethyl)-4-nitroimidazole prepared in Example 12 (500 mg, 2.3 mmol), N-methylbenzylamine (334 mg, 2.76 mmol) and DMF (2.5 ml) was stirred at 60° C. for 9 hours. The reaction mixture was allowed to return to room temperature and added water followed by extraction with ethyl acetate twice. The organic phases were combined, washed with water three times, and dried over sodium sulfate. After filtration, the filtrate was concentrated under reduced pressure. The residue was purified by silica gel column chromatography (n-hexane/ethyl acetate=1/1) to afford (S)-1-[2-hydroxy-3-(N-methyl-N-benzylamino)-2-methylpropyl]-2-chloro-4-nitroimidazole (712 mg, yield 91%) as a yellow oil.

$^1$H-NMR (CDCl$_3$) δppm: 1.13 (3H, s), 2.37-2.57 (5H, m), 3.51 (1H, d, J=12.9 Hz), 3.72 (1H, d, J=12.9 Hz), 3.85 (2H, s), 7.16-7.39 (5H, m), 7.87 (1H, s).

Using corresponding starting materials gave compounds of Examples 180 to 187 in the same manner as in Example 179.

Example 180

(S)-1-{2-Hydroxy-3-[N-methyl-(3-chlorobenzyl)]amino-2-methyl}propyl-2-chloro-4-nitroimidazole Yield 98% $^1$H-NMR (CDCl$_3$) δppm: 1.15 (3H, s), 2.35-2.57 (5H, m), 3.53 (1H, d, J=13.3 Hz), 3.67 (1H, d, J=13.3 Hz), 3.92 (2H, s), 7.10-7.31 (4H, m), 7.95 (1H, s).

Example 181

(S)-1-{2-Hydroxy-3-(N-methyl-4-chlorobenzylamino)-2-methylpropyl]-2-chloro-4-nitroimidazole Yield 86% $^1$H-NMR (CDCl$_3$) δppm: 1.13 (3H, s), 2.33-2.59 (5H, m), 3.53 (1H, d, J=13.2 Hz), 3.68 (1H, d, J=13.2 Hz), 3.92 (2H, s), 7.19 (2H, d, J=8.4 Hz), 7.31 (2H, d, J=8.4 Hz), 7.96 (1H, s).

Example 182

(S)-1-[2-Hydroxy-3-(N-methyl-4-trifluoromethoxybenzylamino)-2-methylpropyl]-2-chloro-4-nitroimidazole Yield 98% $^1$H-NMR (CDCl$_3$) δppm: 1.13 (3H, s), 2.37 (3H, s), 2.47 (1H, d, J=13.9 Hz), 2.58 (1H, d, J=13.9 Hz), 3.58 (1H, d, J=13.3 Hz), 3.72 (1H, d, J=13.3 Hz), 3.94 (2H, s), 7.19 (2H, d, J=8.6 Hz), 7.31 (2H, d, J=8.6 Hz), 7.99 (1H, s).

Example 183

(S)-1-[2-Hydroxy-3-(N-methyl-4-trifluoromethylbenzylamino)-2-methylpropyl]-2-chloro-4-nitroimidazole Yield 100% $^1$H-NMR (CDCl$_3$) δppm: 1.15 (3H, s), 2.38 (3H, s), 2.50 (1H, d, J=13.9 Hz), 2.60 (1H, d, J=13.9 Hz), 3.65 (1H, d, J=13.6 Hz), 3.79 (1H, d, J=13.6 Hz), 3.97 (2H, s), 7.41 (2H, d, J=8.2 Hz), 7.61 (2H, d, J=8.2 Hz), 8.00 (1H, s).

Example 184

(S)-1-[2-Hydroxy-3-(N-methyl-4-methoxybenzylamino)-2-methylpropyl]-2-chloro-4-nitroimidazole Yield 85% $^1$H-NMR (CDCl$_3$) δppm: 1.12 (3H, s), 2.36-2.50 (5H, m), 3.45 (1H, d, J=12.8 Hz), 3.64 (1H, d, J=12.8 Hz), 3.80 (3H, s), 3.84 (2H, s), 6.84 (2H, dd, J=1.9 Hz, 8.6 Hz), 7.13 (2H, dd, J=1.9 Hz, 8.6 Hz), 7.89 (1H, s).

Example 185

(S)-1-[2-Hydroxy-3-(N-methyl-4-dimethylaminobenzylamino)-2-methylpropyl]-2-chloro-4-nitroimidazole Yield 94% $^1$H-NMR (CDCl$_3$) δppm: 1.11 (3H, s), 2.34-2.47 (5H, m), 2.93 (s, 6H), 3.39 (1H, d, J=12.8 Hz), 3.60 (1H, d, J=12.8 Hz), 3.81 (2H, s), 6.65 (2H, d, J=8.7 Hz), 7.03 (2H, d, J=8.7 Hz), 7.87 (1H, s).

Example 186

(S)-1-[2-Hydroxy-3-(N-methyl-phenylamino)-2-methylpropyl]-2-chloro-4-nitroimidazole Yield 92% $^1$H-NMR (CDCl$_3$) δppm: 1.24 (3H, s), 3.06 (3H, s), 3.40 (2H, s), 4.05 (1H, d, J=14.2 Hz), 4.13 (1H, d, J=14.2 Hz), 6.74-6.89 (3H, m), 7.17-7.34 (2H, m), 8.04 (1H, s).

Example 187

(S)-1-[2-Hydroxy-3-(N-methyl-4-chlorophenylamino)-2-methylpropyl]-2-chloro-4-nitroimidazole Yield 92% $^1$H-NMR (CDCl$_3$) δppm: 1.24 (3H, s), 3.04 (3H, s), 3.38 (2H, s), 4.08 (2H, s), 6.74 (2H, dd, J=2.1 Hz, 7.2 Hz), 7.19 (2H, dd, J=2.1 Hz, 7.2 Hz), 8.02 (1H, s).

Example 188

Preparation of (S)-2-(N-benzyl-N-methyl)aminomethyl-2-methyl-6-nitro-2,3-dihydroimidazo[2,1-b]oxazole To a mixture of (S)-1-[2-hydroxy-3-(N-methylbenzylamino)-2-methylpropyl]-2-chloro-4-nitroimidazole prepared in Example 179 (710 mg, 2.1 mmol) and DMF (2.1 ml), sodium hydride (101 mg, 2.51 mmol) was added followed by stirring for 2 hours with cooling on ice-bath. To the reaction mixture, ethylacetate (0.7 ml) and water (5 ml) were added in this order. The precipitates were filtered off and dissolved in isopropyl alcohol (10 ml) with stirring under reflux. To the solution, activated carbon(28 mg) was added followed by stirring under reflux for 20 minutes. After filtration, isopropyl ether (3 ml) was added to the solution, and the mixture was allowed to stand. The precipitates were collected to afford (S)-2-(N-benzyl-N-methyl)aminomethyl-2-methyl-6-nitro-2,3-dihydroimidazo[2,1-b]oxazole (248 mg, yield 39%) as a yellow powder.

Melting point 132.5-133° C.

Using corresponding starting materials gave compounds of Examples 189 to 196 in the same manner as in Example 188.

Example 189

(S)-2-[N-(4-Chlorobenzyl)-N-methylamino]methyl-2-methyl-6-nitro-2,3-dihydroimidazo[2,1-b]oxazole Yield 44%, melting point 129-129.5° C.

Example 190

(S)-2-[N-(3-Chlorobenzyl)-N-methylamino]methyl-2-methyl-6-nitro-2,3-dihydroimidazo[2,1-b]oxazole Yield 65%, melting point 177.5-178.5° C.

Example 191

(S)-2-[N-(4-Trifluoromethoxybenzyl)-N-methylamino]-methyl-2-methyl-6-nitro-2,3-dihydroimidazo[2,1-b]oxazole Yield 53%, melting point 145-146° C.

Example 192

(S)-2-[N-(4-Trifluoromethylbenzyl)-N-methylamino]-methyl-2-methyl-6-nitro-2,3-dihydroimidazo[2,1-b]oxazole Yield 49%, melting point 130-132° C.

Example 193

(S)-2-[N-(4-Methoxybenzyl)-N-methylamino]methyl-2-methyl-6-nitro-2,3-dihydroimidazo[2,1-b]oxazole Yield 59%, melting point 144-147° C.

Example 194

(S)-2-[N-(4-Dimethylaminobenzyl)-N-methylamino]methyl-2-methyl-6-nitro-2,3-dihydroimidazo[2,1-b]oxazole Yield 47%, melting point 168-169° C.

Example 195

(S)-2-(N-Phenyl-N-methylamino)methyl-2-methyl-6-nitro-2,3-dihydroimidazo[2,1-b]oxazole Yield 55%, melting point 147-148° C.

Example 196

(S)-2-[N-(4-Chlorophenyl)-N-methylamino]methyl-2-methyl-6-nitro-2,3-dihydroimidazo[2,1-b]oxazole Yield 34%, melting point 174-175° C.

Example 197

Preparation of 4-trifluoromethylbenzyl (S)-4-[2-(N-methyl-2-methyl-6-nitro-2,3-dihydroimidazo[2,1-b]oxazol-2-ylmethylamino)ethyl]piperazine-1-carboxylate Tert-butyl (S)-4-[2-(N-methyl-2-methyl-6-nitro-2,3-dihydroimidazo[2,1-b]oxazol-2-ylmethylamino)-ethyl]piperazine-1-carboxylate prepared in Example 173 (300 mg, 0.71 mmol) was dissolved in methylene chloride (5 ml). To the solution, trifluoroacetic acid (5 ml) was added followed by stirring at room temperature for 3 hours. The reaction mixture was concentrated under reduced pressure and added methylene chloride (2 ml) and triethylamine (2 ml). After stirring for 5 minutes at room temperature, the solution was concentrated under reduced pressure. The residue was dissolved in DMF (15 ml). To the solution, a mixture of 4-trifluoromethylbenzyl alcohol (373 mg, 2.12 mmol) and 1,1'-carbonyldiimidazole (344 mg, 2.12 mmol) in DMF (5 ml) stirred at room temperature for 3 hours was added followed by stirring at room temperature for 1 hour. The reaction mixture was poured into water and extracted with ethyl acetate. The organic phase was washed with a saturated saline solution and dried over magnesium sulfate. After filtration, the resulting filtrate was concentrated under reduced pressure. The residue was purified by silica gel column chromatography (methylene chloride/methanol=50/1) and crystallized from methylene chloride-isopropyl ether to afford 4-trifluoromethylbenzyl (S)-4-[2-(N-methyl-2-methyl-6-nitro-2,3-dihydroimidazo[2,1-b]oxazol-2-ylmethylamino)ethyl]piperazine-1-carboxylate (196 mg, yield 53%) as a white powder.

MS 509(M–$H_2O$)+ Melting point 77.2-76.9° C.

Example 198

Preparation of (S)-N-methyl-N-(2-methyl-6-nitro-2,3-dihydroimidazo[2,1-b]oxazol-2-ylmethyl)-2-[4-(4-trifluoromethylbenzyl)piperazin-1-yl]ethylamine Tert-butyl (S)-4-[2-(N-methyl-2-methyl-6-nitro-2,3-dihydroimidazo[2,1-b]oxazol-2-ylmethylamino)-ethyl]piperazine-1-carboxylate prepared in Example 173 (400 mg, 0.94 mmol) was dissolved in methylene chloride (5 ml). To the solution, trifluoroacetic acid (5 ml) was added followed by stirring at room temperature for 5 hours. The reaction mixture was concentrated under reduced pressure and added methylene chloride (2 ml) and triethylamine (2 ml). After stirring for 5 minutes at room temperature, the solution was concentrated under reduced pressure. The residue was dissolved in methanol (10 ml). To the solution, 4-(trifluoromethyl)benzaldehyde (0.4 ml, 2.83 mmol), sodium cyanotrihydroborate (178 mg, 2.83 mmol) and acetic acid (0.2 ml) were added followed by stirring at room temperature for 30 minutes. To the solution, a saturated sodium hydrogencarbonate solution and methylene chloride were added followed by stirring, and the mixture was extracted with methylene chloride. The organic phase was dried over magnesium sulfate. After filtration, the resulting filtrate was concentrated under reduced pressure. The residue was purified by silica gel column chromatography (methylene chloride/methanol=200/1) and crystallized from methylene chloride-isopropyl ether to afford (S)-N-methyl-N-(2-methyl-6-nitro-2,3-dihydroimidazo[2,1-b]oxazol-2-ylmethyl)-2-[4-(4-trifluoromethylbenzyl)piperazin-1-yl]ethylamine (307 mg, yield 68%) as a white powder.

MS 482(M+) Melting point 102.0-104.5° C.

Example 199

Preparation of ethyl (6-nitro-2,3-dihydroimidazo[2,1-b]oxazol-2-ylmethyl)carbamate 2,4-Dinitro-1H-imidazole (0.678 g, 3.92 mmol) and phenyl oxiran-2-ylmethylcarbamate (1.04 g, 5.87 mmol) were dissolved in ethanol (20 ml). To the solution, sodium acetate (0.386 g, 4.70 mmol) was added followed by stirring under reflux overnight. To the reaction mixture, a saturated sodium hydrogencarbonate solution and methylene chloride were added, and the solution was extracted with methylene chloride. The organic phase was dried over sodium sulfate. After filtration, the filtrate was concentrated under reduced pressure. The resulting residue was purified by silica gel column chromatography (methylene chloride/methanol=50/1) and treated with diisopropyl ether to afford ethyl (6-nitro-2,3-dihydroimidazo[2,1-b]oxazol-2-ylmethyl)carbamate (0.116 g, yield 11.6%) as a light brown solid.

$^1$H-NMR (DMSO-$d_6$) δppm: 1.15 (3H, t, J=7.1 Hz), 3.41-3.51 (2H, m), 3.93-4.11 (3H, m), 4.38 (1H, dd, J=8.6 Hz, 10.7 Hz), 5.31-5.47 (1H, m), 7.52 (1H, br), 8.13 (1H, s).

Example 200

Preparation of benzyl (2-methyl-6-nitro-2,3-dihydroimidazo[2,1-b]oxazol-2-ylmethyl)carbamate 2,4-Dinitro-1H-imidazole (3 g, 19 mmol) and benzyl (2-methyloxiran-2-ylmethyl)carbamate (4.31 g, 19 mmol) were dissolved in ethanol (20 ml). To the solution, sodium acetate (1.56 g, 19.0 mmol) was added followed by stirring at 70° C. overnight. To the reaction mixture, a saturated sodium hydrogencarbonate solution and methylene chloride were added, and the solution was extracted with methylene chloride. The organic phase was dried over sodium sulfate. After filtration, the filtrate was concentrated under reduced pressure. The resulting residue was purified by silica gel column chromatography (n-hexane/ethyl acetate=1/1, methylene chloride/methanol=50/1) and recrystallized from ethyl acetate-methylene chloride to afford benzyl (2-methyl-6-nitro-2,3-dihydroimidazo[2,1-b]oxazol-2-ylmethyl)carbamate (0.298 g, yield 4.7%) as a colorless solid.

Melting point 171.3-172.2° C. $^1$H-NMR (DMSO-$d_6$) δppm: 1.55 (3H, s), 3.46 (2H, d, J=6.3 Hz), 4.06 (1H, d, J=11.0 Hz), 4.25 (1H, d, J=11.0 Hz), 5.03 (2H, s), 7.19-7.41 (5H, m), 7.76 (1H, t, J=6.3 Hz), 8.13 (1H, s).

Example 201

Preparation of 2-methyl-6-nitro-2,3-dihydroimidazo[2,1-b]oxazol-2-ylmethylamine trifluoroacetate A mixture of benzyl (2-methyl-6-nitro-2,3-dihydroimidazo[2,1-b]oxazol-2-ylmethyl)carbamate prepared in Example 200 (190 mg, 0.57 mmol), trifluoroacetic acid (4 ml) and methylene chloride (5 ml) was stirred at room temperature overnight. The reaction mixture was concentrated under reduced pressure. To the residue was treated with diethyl ether to afford 2-methyl-6-nitro-2,3-dihydroimidazo[2,1-b]oxazol-2-ylmethylamine trifluoroacetate (120 mg, yield 67%) as a light yellow powder.

$^1$H-NMR (DMSO-$d_6$) δppm: 1.35 (3H, s), 3.23 (1H, d, J=9.6 Hz), 3.49 (1H, d, J=9.6 Hz), 3.82-3.98 (2H, m), 7.98 (1H, s), 12.22 (1H, s).

Using corresponding starting materials gave compounds of Examples 202 to 204 in the same manner as in Example 200.

Example 202

Benzyl N-methyl-(2-methyl-6-nitro-2,3-dihydroimidazo-[2,1-b]oxazol-2-ylmethyl)carbamate Yield 14%, melting point 150.3-151.6° C.

Example 203

Benzyl (6-nitro-2,3-dihydroimidazo[2,1-b]oxazol-2-ylmethyl)carbamate

Yield 11% $^1$H-NMR (DMSO-$d_6$) δppm: 3.45-3.59 (2H, m), 4.07 (1H, dd, J=6.6 Hz, 10.8 Hz), 4.39 (1H, dd, J=8.6 Hz, 10.8 Hz), 5.04 (2H, s), 5.32-5.50 (1H, m), 7.23-7.41 (5H, m), 7.71 (1H, br), 8.13 (1H, s).

Example 204

Tert-butyl (6-nitro-2,3-dihydroimidazo[2,1-b]oxazol-2-ylmethyl)carbamate

Yield 27% $^1$H-NMR (CDCl$_3$) δppm: 1.43 (9H, s), 3.65 (2H, dd, J=4.3 Hz, 6.2 Hz), 4.20 (1H, dd, 7.0 Hz, 10.5 Hz), 4.36 (1H, dd, J=8.6 Hz, 10.5 Hz), 5.20 (1H, t, J=6.2 Hz), 5.35-5.48 (1H, m), 7.56 (1H, s).

Example 205

Preparation of 4-chlorobenzyl (2-methyl-6-nitro-2,3-dihydroimidazo[2,1-b]oxazol-2-ylmethyl)carbamate 2,4-Dinitro-1H-imidazole (0.518 g, 3.28 mmol) and 4-chlorobenzyl (2-methyloxiran-2-ylmethyl)carbamate (2.097 g, 8.20 mmol) and sodium acetate (0.538 g, 6.56 mmol) in ethanol (6 ml) was stirred under reflux for 1 hour. To the solution, water was added and the precipitates were filtered off. The resulting solid was treated with diethyl ether to afford 4-chlorobenzyl (2-methyl-6-nitro-2,3-dihydroimidazo[2,1-b]oxazol-2-ylmethyl)carbamate (0.197 g, yield 16%) as a colorless solid.

Melting point 221.0-221.8° C.

Using benzyl N-methyl-(2-methyl-6-nitro-2,3-dihydroimidazo[2,1-b]oxazol-2-ylmethyl)carbamate prepared in Example 202 gave the compound of Example 206 in the same manner as in Example 201.

Example 206

N-Methyl-2-methyl-6-nitro-2,3-dihydroimidazo[2,1-b]oxazol-2-ylmethylamine trifluoroacetate Melting point 176.2-178.8° C.

Using corresponding starting materials gave compounds of Examples 207 to 211 in the same manner as in Example 205.

Example 207

4-Fluorobenzyl (2-methyl-6-nitro-2,3-dihydroimidazo[2,1-b]oxazol-2-ylmethyl)carbamate Yield 25%, melting point 200.4-202.1° C.

Example 208

Ethyl (2-methyl-6-nitro-2,3-dihydroimidazo[2,1-b]oxazol-2-ylmethyl)carbamate

Yield 26%, melting point 182.5-183.4° C.

Example 209

4-Trifluoromethoxybenzyl (2-methyl-6-nitro-2,3-dihydroimidazo[2,1-b]oxazol-2-ylmethyl)carbamate Yield 17%, melting point 182.3-184.4° C.

Example 210

4-Chlorobenzyl (6-nitro-2,3-dihydroimidazo[2,1-b]oxazol-2-ylmethyl)carbamate

Yield 17%, melting point 182.6-182.9° C.

Example 211

4-Fluorobenzyl (6-nitro-2,3-dihydroimidazo[2,1-b]oxazol-2-ylmethyl)carbamate

Yield 17%, melting point 164.6-165.1° C.

Example 212

Preparation of 4-fluorobenzyl [3-(2-chloro-4-nitroimidazol-1-yl)-2-hydroxy-2-methylpropyl]-N-methylcarbamate 2-Chloro-4-nitro-1H-imidazole (0.953 g, 6.46 mmol) and 4-fluorobenzyl N-methyl-(2-methyloxiran-2-ylmethyl)carbamate (1.964 g, 7.75 mmol) were dissolved in ethanol (20 ml). To the solution, sodium acetate (0.583 g, 7.11 mmol) was added followed by stirring under reflux overnight. The reaction mixture was concentrated under reduced pressure. To the residue, ethyl acetate and water were added, and the solution was extracted with ethyl acetate. The organic phase was dried over sodium sulfate. After filtration, the filtrate was concentrated under reduced pressure. The resulting residue was purified by silica gel column chromatography (n-hexane/ethyl acetate=1/1) to afford 4-fluorobenzyl [3-(2-chloro-4-nitroimidazol-1-yl)-2-hydroxy-2-methylpropyl]-N-methylcarbamate (1.683 g, yield 65%) as a colorless oil.

$^1$H-NMR (CDCl$_3$) δppm: 1.17 (3H, s), 3.06 (3H, s), 3.25 (1H, d, J=14.7 Hz), 3.51 (1H, d, J=14.7 Hz), 4.00 (2H, s), 5.12 (2H, s), 6.95-7.09 (2H, m), 7.27-7.41 (2H, m), 8.07 (1H, s).

Using 4-fluorobenzyl N-methyl-(oxiran-2-yl-methyl)carbamate gave the compound of Example 213 in the same manner as in Example 212.

Example 213

4-Fluorobenzyl [3-(2-chloro-4-nitroimidazol-1-yl)-2-hydroxypropyl]-N-methylcarbamate Yield 51% $^1$H-NMR (CDCl$_3$) δppm: 3.04 (3H, s), 3.27-3.55 (2H, m), 3.73-4.23 (4H, m), 5.11 (2H, s), 7.00-7.14 (2H, m), 7.27-7.41 (2H, m), 7.96 (1H, s).

Example 214

Preparation of 4-fluorobenzyl N-methyl-(2-methyl-6-nitro-2,3-dihydroimidazo[2,1-b]oxazol-2-ylmethyl)carbamate 4-Fluorobenzyl [3-(2-chloro-4-nitroimidazol-1-yl)-2-hydroxy-2-methylpropyl]-N-methylcarbamate prepared in Example 212 (1.683 g, 4.20 mmol) was dissolved in 1,4-dioxane (30 ml). To the solution, sodium hydride (0.185 g, 4.62 mmol) was added followed by stirring at room temperature for 1 hour and then stirred under reflux for 7 hours. The reaction mixture was concentrated under reduced pressure. To the residue, water was added, and the precipitates were filtered off and purified by silica gel column chromatography (n-hexane/acetone=2/1). The resulting solid was treated with a mixture of n-hexane and ethyl acetate to afford 4-fluorobenzyl N-methyl-(2-methyl-6-nitro-2,3-dihydroimidazo[2,1-b]oxazol-2-ylmethyl)carbamate (0.381 g, yield 25%) as a colorless solid.

Melting point 168.9-169.9° C.

Using 4-fluorobenzyl [3-(2-chloro-4-nitroimidazol-1-yl)-2-hydroxypropyl]-N-methylcarbamate prepared in Example 213 gave the compound of Example 215 in the same manner as in Example 214.

Example 215

4-Fluorobenzyl N-methyl-6-nitro-2,3-dihydroimidazo[2,1-b]oxazol-2-ylmethylcarbamate Yield 16%, melting point 124.5-128.1° C.

Using corresponding starting materials gave compounds of Examples 216 to 220 in the same manner as in Example 179.

Example 216

(S)-1-(2-Chloro-4-nitroimidazol-1-yl)-3-{[1-(4-chlorophenyl)piperidin-4-yl]-N-methylamino}-2-hydroxy-2-methylpropane Yellow oil, yield 98% $^1$H-NMR (CDCl$_3$) δppm: 1.13 (3H, s), 1.57-1.82 (4H, m), 2.38-2.71 (4H, m), 2.40 (3H, m), 3.65-3.71 (2H, m), 3.82 (1H, s), 3.89-4.01 (2H, m), 6.81-6.86 (2H, m), 7.16-7.22 (2H, m), 8.06 (1H, s).

Example 217

(S)-1-(2-Chloro-4-nitroimidazol-1-yl)-3-{[1-(4-trifluoromethoxyphenyl)piperidin-4-yl]-N-methylamino}-2-hydroxy-2-methylpropane Yellow oil, yield 91% $^1$H-NMR (CDCl$_3$) δppm: 1.13 (3H, s), 1.59-1.83 (4H, m), 2.41 (3H, s), 2.43-2.73 (5H, m), 3.66-3.73 (2H, m), 3.84 (1H, s), 3.93 (1H, d, J=14.2 Hz), 4.00 (1H, d, J=14.2 Hz), 6.86-6.91 (2H, m), 7.07-7.12 (2H, m), 8.06 (1H, s).

Example 218

(S)-1-(2-Chloro-4-nitroimidazol-1-yl)-3-{[1-(4-trifluoromethylphenyl)piperidin-4-yl]-N-methylamino}-2-hydroxy-2-methylpropane Yellow oil, yield 96% $^1$H-NMR (CDCl$_3$) δppm: 1.13 (3H, s), 1.54-1.70 (2H, m), 1.77-1.84 (2H, m), 2.40 (3H, s), 2.42-2.60 (3H, m), 2.72-2.82 (2H, m), 3.79 (1H, s), 3.84-3.89 (2H, m), 3.92 (1H, d, J=14.2 Hz), 3.99 (1H, d, J=14.2 Hz), 6.91 (2H, d, J=8.7 Hz), 7.46 (2H, d, J=8.7 Hz), 8.06 (1H, s)

Example 219

(S)-1-(2-Chloro-4-nitroimidazol-1-yl)-3-{[1-(4-cyanophenyl)piperidin-4-yl]-N-methylamino}-2-hydroxy-2-methylpropane Yellow oil, yield 89% $^1$H-NMR (CDCl$_3$) δppm: 1.13 (3H, s), 1.51-1.65 (2H, m), 1.77-1.84 (2H, m), 2.39 (3H, s), 2.42-2.62 (3H, m), 2.76-2.88 (2H, m), 3.75 (1H, s), 3.88-4.03 (4H, m), 6.81-6.88 (2H, m), 7.45-7.53 (2H, m), 8.05 (1H, s).

Example 220

(S)-1-(2-Chloro-4-nitroimidazol-1-yl)-3-{[1-(tert-butoxycarbonyl)piperidin-4-yl]-N-methylamino}-2-hydroxy-2-methylpropane Yellow oil $^1$H-NMR (CDCl$_3$) δppm: 1.11 (3H, s), 1.46 (9H, s), 1.50-1.80 (4H, m), 2.37 (3H, s), 2.40-2.75 (5H, m), 3.90 (1H, d, J=14.2 Hz), 3.99 (1H, d, J=14.2 Hz), 4.22 (2H, br), 8.05 (1H, s).

Using compounds prepared in Examples 216 to 220 gave compounds of Examples 221 to 225 in the same manner as in Example 188.

Example 221

(S)-2-{[1-(4-Chlorophenyl)piperidin-4-yl]-N-methylaminomethyl}-2-methyl-6-nitro-2,3-dihydroimidazo[2,1-b]oxazole White powder, yield 47% MS 406(M+1)$^+$ Melting point 179.2-182.1° C.

Example 222

(S)-2-{[1-(4-Trifluoromethoxyphenyl)piperidin-4-yl]-N-methylaminomethyl}-2-methyl-6-nitro-2,3-dihydroimidazo[2,1-b]oxazole Melting point 127.2-129.7° C.

Example 223

(S)-2-{[1-(4-Trifluoromethylphenyl)piperidin-4-yl]-N-methylaminomethyl}-2-methyl-6-nitro-2,3-dihydroimidazo[2,1-b]oxazole Melting point 131.5-133.6° C.

Example 224

(S)-2-{[1-(4-Cyanophenyl)piperidin-4-yl]-N-methylaminomethyl}-2-methyl-6-nitro-2,3-dihydroimidazo[2,1-b]oxazole Melting point 149-152° C.

Example 225

(S)-2-{[1-(Tert-butoxycarbonyl)piperidin-4-yl]-N-methylaminomethyl}-2-methyl-6-nitro-2,3-dihydroimidazo[2,1-b]oxazole Light yellow powder, yield 37% Melting point 138.5-140.3° C.

Example 226

Preparation of (S)-2-{[1-(4-trifluoromethylbenzyloxycarbonyl)piperidin-4-yl]-N-methylaminomethyl}-2-methyl-6-nitro-2,3-dihydroimidazo[2,1-b]oxazole (S)-2-{[1-(Tert-butoxycarbonyl)piperidin-4-yl]-N-methylaminomethyl}-2-methyl-6-nitro-2,3-dihydroimidazo[2,1-b]oxazole prepared in Example 225 (400 mg, 1.01 mmol) was dissolved in methylene chloride (1 ml). To the solution, trifluoroacetic acid (1 ml) was added followed by stirring at room temperature for 5 hours. The reaction mixture was concentrated under reduced pressure and added methylene (1 ml) chloride and triethylamine (2 ml). The solution was stirred at room temperature for 5 minutes and then concentrated under reduced pressure, and the residue was dissolved in DMF (8 ml). To the solution, a mixture of 4-(trifluoromethyl)benzyl alcohol (267 mg, 1.51 mmol) and 1,1'-carbonyldiimidazole (246 mg, 1.51 mmol) in DMF (2 ml) stirred at room temperature for 4 hours was added followed by stirring at room temperature overnight. The reaction mixture was poured into water and extracted with ethyl acetate. The organic phase was washed with a saturated saline solution, dried over magnesium sulfate and then filtered. The resulting filtrate was concentrated under reduced pressure. The residue was purified by silica gel column chromatography (methylene chloride/methanol=200/1) and crystallized from methylene chloride-isopropyl ether to afford (S)-2-{[1-(4-trifluoromethylbenzyloxycarbonyl)piperidin-4-yl]-N-methylaminomethyl}-2-methyl-6-nitro-2,3-dihydroimidazo[2,1-b]oxazole (341 mg, yield 68%) as a light yellow powder.

Melting point 110.6-113.1° C.

Using corresponding starting materials gave compounds of Examples 227 and 228 in the same manner as in Example 226.

Example 227

(S)-2-{[1-(4-Trifluoromethoxybenzyloxycarbonyl)piperidin-4-yl]-N-methylaminomethyl}-2-methyl-6-nitro-2,3-dihydroimidazo[2,1-b]oxazole Melting point 84.2-86.8° C.

Example 228

(S)-2-{[1-(4-Chlorobenzyloxycarbonyl)piperidin-4-yl]-N-methylaminomethyl}-2-methyl-6-nitro-2,3-dihydroimidazo[2,1-b]oxazole Melting point 116.2-116.6° C.

Example 229

Preparation of 2-methyl-6-nitro-2-[4-(4-trifluoromethylbenzyloxy)piperidin-1-ylmethyl]-2,3-dihydroimidazo[2,1-b]oxazole 2-Chloro-1-(2-methyloxiran-2-ylmethyl)-4-nitroimidazole prepared in Example 6 (122 mg, 0.56 mmol) and 4-[4-(trifluoromethyl)benzyloxy]piperidine (188 mg, 4.86 mol) were dissolved in DMF (10 ml) followed by stirring at 70-75° C. for 5 hours. The reaction mixture was allowed to return to room temperature, poured into water, extracted with ethyl acetate. The organic phase was washed with a saturated saline solution, and dried over magnesium sulfate. After filtration, the filtrate was concentrated under reduced pressure. The residue was purified by silica gel column chromatography (methylene chloride/methanol=50/1) to afford a yellow oil.

The yellow oil was dissolved in DMF (10 ml). To the solution, sodium hydride (134 mg, 3.36 mmol) was added with cooling on ice-bath, and the solution was stirred at room temperature for 1 hour. The reaction mixture was poured into water, extracted with ethyl acetate. The organic phase was washed with a saturated saline solution, dried over magnesium sulfate and then filtered. The filtrate was concentrated under reduced pressure. The residue was purified by silica gel column chromatography (methylene chloride/ethyl acetate=10/1) and crystallized from ethyl acetate-diisopropyl ether to afford 2-methyl-6-nitro-2-[4-(4-trifluoromethylbenzyloxy)piperidin-1-ylmethyl]-2,3-dihydroimidazo[2,1-b]oxazole (41 mg, yield 17%) as a white powder.

MS 440(M−1)$^{+1}$H-NMR (CDCl$_3$) δppm: 1.45-1.70 (2H, m), 1.60 (3H, s), 1.75-1.88 (2H, m), 2.26-2.40 (1H, m), 2.45-2.55 (2H, m), 2.72-2.95 (3H, m), 3.38 (1H, m), 3.89 (1H, d, J=9.6 Hz), 4.31 (1H, d, J=9.6 Hz), 4.54 (2H, s), 7.43 (2H, d, J=8.2 Hz), 7.53 (1H, s), 7.79 (2H, d, J=8.2 Hz).

Example 230

Preparation of 1-(2-chloro-4-nitroimidazol-1-yl)-2-methyl-3-[4-(4-trifluoromethylphenoxy)piperidin-1-yl]propan-2-ol To a solution of 2-chloro-1-[2-hydroxy-2-methyl-3-(4-methylbenzenesulfonyloxy)propyl]-4-nitroimidazole prepared in Example 5 (0.30 g, 0.77 mmol) and 4-(4-trifluoromethylphenoxy)piperidine (0.21 g, 0.85 mmol) in DMF (6 ml), sodium iodide (0.13 g, 0.77 mmol) and triethylamine (0.12 ml, 0.77 mmol) were added followed by stirring at 80° C. for 7 hours. To the reaction mixture, water was added, and the resulting solution was extracted with ethyl acetate. The organic phase was washed with water, dried over magnesium sulfate and then concentrated under reduced pressure. The residue was purified by silica gel column chromatography (methylene chloride/ethyl acetate=9/1) to afford 1-(2-chloro-4-nitroimidazol-1-yl)-2-methyl-3-[4-(4-trifluoromethylphenoxy)piperidin-1-yl]propan-2-ol (0.23 g, yield 63%) as a yellow oil.

$^1$H-NMR (CDCl$_3$) δppm: 1.14 (3H, s), 1.76-2.04 (4H, m), 2.36 (1H, d, J=14.0 Hz), 2.43-2.72 (3H, m), 2.76-3.00 (2H, m), 3.46-3.52 (1H, br), 3.98 (2H, s), 4.37-4.50 (1H, m), 6.91-7.00 (2H, m), 7.48-7.61 (2H, m), 8.05 (1H, s).

Using corresponding starting materials gave the compound of Example 231 in the same manner as in Example 230.

Example 231

1-(2-Chloro-4-nitroimidazol-1-yl)-2-methyl-3-[4-(4-trifluoromethoxyphenoxy)piperidin-1-yl]propan-2-ol Yield 61% $^1$H-NMR (CDCl$_3$) δppm: 1.14 (3H, s), 1.74-2.04 (4H, m), 2.35 (1H, d, J=13.9 Hz), 2.40 (1H, d, J=13.9 Hz), 2.43-2.70 (2H, m), 2.74-3.00 (2H, m), 3.98 (2H, s), 4.25-4.41 (1H, m), 6.86-6.92 (2H, m), 7.11-7.15 (2H, m), 8.05 (1H, s).

Example 232

Preparation of 1-(2-chloro-4-nitroimidazol-1-yl)-2-methyl-3-[4-(4-trifluoromethoxyphenylamino)piperidin-1-yl]propan-2-ol A solution of 2-chloro-1-(2-methyloxiran-2-ylmethyl)-4-nitroimidazole prepared in Example 6 (0.3 g, 1.38 mmol) and N-(piperidin-4-yl)-4-trifluoromethoxyaniline (0.43 g, 1.66 mmol) in DMF (8 ml) was stirred at 80° C. for 2 hours.

To the reaction mixture, water was added, and the solution was extracted with ethyl acetate, dried over magnesium sulfate and then concentrated under reduced pressure. The residue was purified by silica gel column chromatography (n-hexane/ethyl acetate=1/1) to afford 1-(2-chloro-4-nitroimidazol-1-yl)-2-methyl-3-[4-(4-trifluoromethoxyphenylamino)piperidin-1-yl]propan-2-ol (0.37 g, yield 56%) as a yellow oil.

$^1$H-NMR (CDCl$_3$) δppm: 1.13 (3H, s), 1.39-1.63 (2H, m), 1.96-2.09 (2H, m), 2.47 (1H, d, J=13.9 Hz), 2.43-2.63 (3H, m), 2.67-2.83 (1H, m), 2.87-3.02 (1H, m), 3.15-3.39 (1H, m), 3.41-3.72 (2H, m), 3.97 (2H, s), 6.46-6.59 (2H, m), 6.96-7.09 (2H, m), 8.05 (1H, s).

Example 233

Preparation of 2-methyl-6-nitro-2-[4-(4-trifluoromethylphenoxy)piperidin-1-ylmethyl]-2,3-dihydroimidazo[2,1-b]oxazole To a solution of 1-(2-chloro-4-nitroimidazol-1-yl)-2-methyl-3-[4-(4-trifluoromethylphenoxy)-piperidin-1-yl]propan-2-ol prepared in Example 230 (225 mg, 0.49 mmol) in DMF (2.5 ml), sodium hydride (23 mg, 0.59 mmol) was added followed by stirring for 1 hour with cooling on ice-bath. To the reaction mixture, ice-water and ethyl acetate were added. The precipitates were filtered off, washed with water, recrystallized from methylene chloride-diisopropyl ether and then washed with n-hexane to afford 2-methyl-6-nitro-2-[4-(4-trifluoromethylphenoxy)piperidin-1-ylmethyl]-2,3-dihydroimidazo[2,1-b]oxazole (80 mg, yield 39%) as a light yellow solid.

Melting point 113-114° C.

Using corresponding starting materials gave the compound of Example 234 in the same manner as in Example 233.

Example 234

2-Methyl-6-nitro-2-[4-(4-trifluoromethoxyphenoxy)-piperidin-1-ylmethyl]-2,3-dihydroimidazo[2,1-b]oxazole Melting point 117-119° C.

Example 235

Preparation of 2-[4-(4-trifluoromethoxyphenyl)-aminopiperidin-1-yl]methyl-2-methyl-6-nitro-2,3-dihydroimidazo[2,1-b]oxazole Using 1-(2-chloro-4-nitro-imidazol-1-yl)-2-methyl-3-[4-(4-trifluoromethoxyphenylamino)piperidin-1-yl]propan-2-ol prepared in Example 233 (369 mg, 0.77 mmol) gave 2-[4-(4-trifluoromethoxyphenylamino)piperidin-1-yl]methyl-2-methyl-6-nitro-2,3-dihydroimidazo[2,1-b]oxazole (25 mg, yield 7%) as a yellow powder in the same manner as in Example 232.

MS 441(M$^+$) $^1$H-NMR (CDCl$_3$) δppm: 1.11-1.40 (2H, m), 1.61 (3H, s), 1.85-2.01 (2H, m), 2.37 (1H, dt, J=2.7 Hz, 11.4 Hz), 2.46-2.59 (2H, m), 2.76-2.84 (1H, m), 2.87 (1H, d, J=14.9 Hz), 2.95-3.03 (1H, m), 3.10-3.25 (1H, m), 3.50 (1H, d, J=7.8 Hz), 3.90 (1H, d, J=9.7 Hz), 4.29 (1H, d, J=9.7 Hz), 6.46-6.52 (2H, m), 6.98-7.01 (2H, m), 7.50 (1H, s).

Example 236

Preparation of tert-butyl N-methyl-[1-(2-methyl-6-nitro-2,3-dihydroimidazo[2,1-b]oxazol-2-ylmethyl)piperidin-4-yl]carbamate 2-Chloro-4-nitro-1H-imidazole (1.08 g, 7.31 mmol), tert-butyl N-methyl-[1-(2-methyloxiran-2-yl-methyl)piperidin-4-yl]carbamate (2.08 g, 7.31 mmol) and sodium acetate (660 mg, 8.04 mmol) in 1-propanol (15 ml) were stirred under reflux overnight. The reaction mixture was concentrated under reduced pressure. The residue was added water, and the mixture was extracted with methylene chloride. The organic phase was dried over sodium sulfate and then filtered. The resulting filtrate was concentrated under reduced pressure. The residue was purified by silica gel column chromatography (methylene chloride/methanol=200/1), crystallized from methylene chloride-isopropyl ether to afford tert-butyl N-methyl-[1-(2-methyl-6-nitro-2,3-dihydroimidazo[2,1-b]oxazol-2-ylmethyl)piperidin-4-yl]carbamate (348 mg, yield 12%) as a white powder.

MS 396(M+1)$^+$Melting point 198.8-201.1° C.

Example 237

Preparation of benzyl N-methyl-[1-(2-methyl-6-nitro-2,3-dihydroimidazo[2,1-b]oxazol-2-ylmethyl)piperidin-4-yl]carbamate Tert-butyl N-methyl-{1-(2-methyl-6-nitro-2,3-dihydroimidazo[2,1-b]oxazol-2-ylmethyl)piperidin-4-yl}carbamate prepared in Example 236 (207 mg, 0.52 mmol) was dissolved in methylene chloride (5 ml). To the solution, trifluoroacetic acid (5 ml) was added followed by stirring at room temperature for 5 hours. The reaction mixture was concentrated under reduced pressure. To the residue, methylene chloride (5 ml), triethylamine (1 ml) and benzyl chlorocarbonate (0.15 ml, 1.05 mmol) were added followed by stirring at room temperature for 30 minutes. The reaction mixture was poured into water, extracted with methylene chloride. The organic phase was dried over sodium sulfate and then filtered. The resulting filtrate was concentrated under reduced pressure. The residue was purified by silica gel column chromatography (methylene chloride/methanol=200/1) and crystallized from ethyl acetate-isopropyl ether to afford benzyl N-methyl-[1-(2-methyl-6-nitro-2,3-dihydroimidazo[2,1-b]oxazol-2-ylmethyl)piperidin-4-yl]carbamate (184 mg, yield 82%) as a white powder.

MS 430(M+H)$^+$Melting point 138.7-139.2° C.

Using 4-chlorobenzyl chlorocarbonate gave the compound of Example 238 in the same manner as in Example 237. Also, using 4-chlorophenylacetyl chloride gave the compound of Example 239 in the same manner as in Example 237.

Example 238

4-Chlorobenzyl N-methyl-[1-(2-methyl-6-nitro-2,3-dihydroimidazo[2,1-b]oxazol-2-ylmethyl)piperidin-4-yl]carbamate Melting point 147.2-149.2° C.

Example 239

2-{4-[N-(4-Chlorophenylacetyl)-N-methyl]aminopiperidin-1-yl}methyl-2-methyl-6-nitro-2,3-dihydroimidazo[2,1-b]oxazole Melting point 206.8-208° C.

Example 240

Preparation of 2-methyl-2-{4-[N-methyl-N-(4-trifluoromethoxyphenyl)]aminopiperidin-1-yl}methyl-6-nitro-2,3-dihydroimidazo[2,1-b]oxazole To a solution of 2-[4-(4-trifluoromethoxyphenyl)aminopiperidin-1-yl]methyl-2-methyl-6-nitro-2,3-dihydroimidazo[2,1-b]oxazole prepared in Example 235 (60 mg, 0.14 mmol) in methanol (2 ml), a 37% formaldehyde solution (51 μl, 0.70 mmol) and sodium cyanotrihydroborate (26 mg, 0.42 mmol) were added followed by stirring at room temperature for further 30 minutes. To the reaction mixture, acetic acid (23 μl, 0.42 mmol) was added followed by stirring at room temperature for 1 hour with cooling on ice-bath. To the reaction mixture, a sodium hydrogencarbonate solution was added, and the mixture was extracted with methylene chloride. The organic phase was dried over magnesium sulfate and then concentrated under reduced pressure. The residue was purified by silica gel column chromatography (methylene chloride/ethyl acetate=1/1) and crystallized from diisopropyl ether to afford 2-methyl-2-{4-[N-methyl-N-(4-trifluoromethoxyphenyl)]aminopiperidin-1-yl}methyl-6-nitro-2,3-dihydroimidazo[2,1-b]oxazole (40 mg, yield 65%) as a light yellow solid.

Melting point 135-136° C.

Example 241

Preparation of 2-[4-(4-chlorobenzyl)oxypiperidin-1-yl]methyl-2-methyl-6-nitro-2,3-dihydroimidazo[2,1-b]oxazole A mixture of 2-chloro-4-nitro-1H-imidazole (1.5 g, 10.17 mmol), 4-(4-chlorobenzyloxy)-1-(2-methylbxiran-2-ylmethyl)piperidine (2.5 g, 8.45 mmol), sodium hydrogencarbonate (0.86 g, 10.24 mmol) and ethanol (15 ml) was stirred under reflux for 15 hours. The reaction mixture was allowed to return to room temperature and concentrated under reduced pressure. To the residue, water was added, and the solution was extracted with methylene chloride. The organic phase was dried over sodium sulfate and then concentrated under reduced pressure. The residue was purified by silica gel column chromatography (methylene chloride/ethyl acetate=10/1) to afford 2-[4-(4-chlorobenzyl)oxypiperidin-1-yl]methyl-2-methyl-6-nitro-2,3-dihydroimidazo[2,1-b]oxazole (662 mg, yield 16%) as a white powder.

Melting point 129-130° C.

Example 242

Preparation of 2-{4-[N-(4-chlorophenyl)-N-methyl]aminopiperidin-1-yl}methyl-2-methyl-6-nitro-2,3-dihydroimidazo[2,1-b]oxazole A mixture of 2-chloro-1-(2-methyloxiran-2-yl-methyl)-4-nitroimidazole prepared in Example 6 (350 mg, 1.61 mmol), 4-[N-(4-chlorophenyl)-N-methylamino]-piperidine (373 mg, 1.66 mmol) and DMF (15 ml) was stirred at 70° C. for 5 hours. To the reaction mixture, sodium hydride (77 mg, 1.93 mmol) was added followed by stirring for 1 hour with cooling on ice-bath. The reaction mixture was poured into ice-water and extracted with ethyl acetate twice. The organic phases were combined, washed with water three times, washed with a saturated saline solution, dried over sodium sulfate and then concentrated under reduced pressure. The residue was purified by silica gel column chromatography (methylene chloride/ethyl acetate=1/1) to afford 2-{4-[N-(4-chlorophenyl)-N-methyl]aminopiperidin-1-yl}methyl-2-methyl-6-nitro-2,3-dihydroimidazo[2,1-b]oxazole (307 mg, yield 47%) as a light yellow powder.

Melting point 186-187.8° C.

Using 4-(4-trifluoromethoxybenzyl)piperidine, 4-(4-trifluoromethylbenzyl)piperidine, 4-(4-chlorobenzyl)piperidine and 4-(chlorobenzoyl)piperidine gave compounds of Examples 243 to 246 in the same manner as in Example 242.

Example 243

2-Methyl-6-nitro-2-[4-(4-trifluoromethoxybenzyl)-piperidin-1-yl]methyl-2,3-dihydroimidazo[2,1-b]oxazole Melting point 143.5-145° C.

Example 244

2-Methyl-6-nitro-2-[4-(4-trifluoromethylbenzyl)-piperidin-1-yl]methyl-2,3-dihydroimidazo[2,1-b]oxazole Melting point 125-126° C.

Example 245

2-[4-(4-Chlorobenzyl)piperidin-1-yl]methyl-2-methyl-6-nitro-2,3-dihydroimidazo[2,1-b]oxazole Melting point 109-110.5° C.

Example 246

2-[4-(4-Chlorobenzoyl)piperidin-1-yl]methyl-2-methyl-6-nitro-2,3-dihydroimidazo[2,1-b]oxazole Melting point 165-167° C.

Example 247

Preparation of 2-methyl-6-nitro-2-[4-(4-trifluoromethylbenzoyl)piperidin-1-yl]methyl-2,3-dihydroimidazo[2,1-b]oxazole A mixture of 2-chloro-1-(2-methyloxiran-2-ylmethyl)-4-nitroimidazole prepared in Example 6 (80 mg, 0.37 mmol), 4-(4-trifluoromethylbenzoyl)piperidine (95 mg, 0.37 mmol), sodium acetate (150 mg, 1.83 mmol) and DMF (2 ml) was stirred at 80° C. overnight. The reaction mixture was poured into water, and extracted with ethyl acetate twice. The organic phases were combined, washed with water three times, washed with a saturated saline solution, dried over sodium sulfate and then concentrated under reduced pressure. The residue was purified by silica gel column chromatography (ethyl acetate/n-hexane=1/1) to afford 2-methyl-6-nitro-2-[4-(4-trifluoromethylbenzoyl)piperidin-1-yl]methyl-2,3-dihydroimidazo[2,1-b]oxazole (46 mg, yield 29%) as a white powder.

Melting point 172-174° C.

Using corresponding starting materials gave the compound of Example 248 in the same manner as in Example 247.

Example 248

2-Methyl-6-nitro-2-[4-(4-trifluoromethoxybenzoyl)-piperidin-1-yl]-2,3-dihydroimidazo[2,1-b]oxazole Melting point 165-167° C.

Example 249

Preparation of (S)-2-[4-(3,4-dichlorobenzyloxy)-piperidin-1-ylmethyl]-2-methyl-6-nitro-2,3-dihydroimidazo[2,1-b]oxazole (R)-2-Chloro-1-(2-methyloxiran-2-ylmethyl)-4-nitroimidazole prepared in Example 12 (396 mg, 1.82 mmol) and 4-(3,4-dichlorobenzyloxy)piperidine (614 mg, 2.36 mol) in DMF (15 ml) were stirred at 70-75° C. for 4 hours. The reaction mixture was allowed to return to room temperature, poured into water, extracted with ethyl acetate. The organic phase was washed with a saturated saline water, dried over magnesium sulfate and then filtered. The filtrate was concentrated under reduced pressure. The residue was purified by silica gel column chromatography (methylene chloride/methanol=50/1) to afford a yellow oil.

The yellow oil was dissolved in DMF (15 ml). To the solution, sodium hydride (87 mg, 2.18 mmol) was added with cooling on ice-bath followed by stirring at room temperature overnight. The reaction mixture was poured into water and extracted with ethyl acetate. The extract was washed with a saturated saline solution, dried over magnesium sulfate and then filtered. The filtrate was concentrated under reduced pressure. The residue was purified by silica gel column chromatography (methylene chloride/ethyl acetate=10/1) and crystallized from methylene chloride-diisopropyl ether to afford (S)-2-[4-(3,4-dichlorobenzyloxy)piperidin-1-ylmethyl]-2-methyl-6-nitro-2,3-dihydroimidazo[2,1-b]oxazole (431 mg, yield 44%) as a white powder.

MS 441(M$^+$) Melting point 132.0-136.0° C.

Example 250

Preparation of (S)-[1-(2-methyl-6-nitro-2,3-dihydroimidazo[2,1-b]oxazol-2-ylmethyl)piperidin-4-yl]-(4-trifluoromethoxyphenyl)methanone Using (R)-2-chloro-1-(2-methyloxiran-2-ylmethyl)-4-nitroimidazole prepared in Example 12 (1.0 g, 4.6 mmol) and 4-(4-trifluoromethoxybenzoyl)piperidine (1.3 g, 4.8 mmol) gave (S)-[1-(2-methyl-6-nitro-2,3-dihydroimidazo[2,1-b]oxazol-2-ylmethyl)piperidin-4-yl]-(4-trifluoromethoxyphenyl)methanone (771 mg, yield 37%) as a light yellow powder.

Melting point 113.0-115.0° C.

Example 251

Preparation of ethyl (S)-1-(2-methyl-6-nitro-2,3-dihydroimidazo[2,1-b]oxazol-2-ylmethyl)piperidin-4-carboxylate 2-Chloro-4-nitro-1H-imidazole (3.7 g, 25.1 mmol), ethyl (S)-1-(2-methyloxiran-2-ylmethyl)piperidine-4-carboxylate (4.8 g, 21.1 mmol) and sodium hydrogencarbonate (2.2 g, 25.1 mmol) in ethanol (25 ml) were stirred under reflux overnight. The reaction mixture was concentrated under reduced pressure. To the residue, water was added, and the solution was extracted with methylene chloride. The organic phase was washed with a saturated saline solution, dried over magnesium sulfate and then filtered. The resulting filtrate was concentrated under reduced pressure. The residue was purified by silica gel column chromatography (n-hexane/ethyl acetate=3/1) and crystallized from diethyl ether to afford ethyl (S)-1-(2-methyl-6-nitro-2,3-dihydroimidazo[2,1-b]oxazol-2-ylmethyl)piperidine-4-carboxylate (1.4 g, yield 20%) as a white powder.

Melting point 101.0-103.0° C.

Example 252

Preparation of (S)-2-methyl-6-nitro-2-[4-(4-trifluoromethoxyphenyl)-1,2,3,6-tetrahydropyridin-1-ylmethyl]-2,3-dihydroimidazo[2,1-b]oxazole 4-(4-Trifluoromethoxyphenyl)-1,2,3,6-tetrahydropyridine (0.985 g, 4.05 mmol) and (R)-2-chloro-1-(2-methyloxiran-2-ylmethyl)-4-nitroimidazole prepared in Example 12 (0.839 g, 3.86 mmol) were added to DMF (15 ml), and the solution was stirred at 60° C. for 8 hours. The reaction mixture was added water and extracted with ethyl acetate. The organic phases was washed with water and a saturated saline solution, dried over sodium sulfate and then filtered. The resulting filtrate was concentrated under reduced pressure. The residue was purified by silica gel column chromatography (n-hexane/ethyl acetate=4/1) to afford as oil. The oil was dissolved in DMF (20 ml), and sodium hydride (94 mg, 2.35 mmol) was added with cooling on ice-bath followed by stirring at room temperature overnight. To the reaction mixture, water was added, and the solution was extracted with ethyl acetate. The organic phase was washed with water and a saturated saline solution, dried over sodium sulfate and then filtered. The resulting filtrate was concentrated under reduced pressure. The residue was purified by silica gel column chromatography (n-hexane/ethyl acetate=1/1) to afford (S)-2-methyl-6-nitro-2-[4-(4-trifluoromethoxyphenyl)-1,2,3,6-tetrahydropyridin-1-ylmethyl]-2,3-dihydroimidazo[2,1-b]oxazole (0.192 g, yield 23%) as a light yellow solid.

$^1$H-NMR (CDCl$_3$) δppm: 1.68 (3H, s), 2.46-3.39 (8H, m), 3.95 (1H, d, J=10.2 Hz), 4.49 (1H, br), 5.98 (1H, s), 7.16 (2H, d, J=8.3 Hz), 7.35 (2H, d, J=8.3 Hz), 7.53 (1H, s).

Example 253

Preparation of (S)-1-(2-chloro-4-nitroimidazol-1-yl)-2-methyl-3-[4-(4-trifluoromethylphenoxy)piperidin-1-yl]propan-2-ol (R)-2-Chloro-1-(2-methyloxiran-2-ylmethyl)-4-nitroimidazole prepared in Example 12 (500 mg, 2.30 mmol) and 4-(4-trifluoromethylphenoxy)piperidine (730 mg, 3.0 mmol) in DMF (10 ml) were stirred at 70-75° C. for 5 hours. The reaction mixture was allowed to return to room temperature, poured into water, and extracted with ethyl acetate. The extract was washed with a saturated saline solution, dried over magnesium sulfate and then filtered. The filtrate was concentrated under reduced pressure, and the residue was purified by silica gel column chromatography (methylene chloride/methanol=50/1) to afford (S)-1-(2-chloro-4-nitroimidazol-1-yl)-2-methyl-3-[4-(4-trifluoromethylphenoxy)piperidin-1-yl]propan-2-ol (1.06 g, yield 99%) as a yellow oil.

$^1$H-NMR (CDCl$_3$) δppm: 1.14 (3H, s), 1.80-2.04 (4H, m), 2, 38 (1H, d, J=14.0 Hz), 2.48-2.68 (2H, m), 2.52 (1H, d, J=14.0 Hz), 2.77-2.95 (2H, m), 3.73 (1H, s), 4.01 (2H, s), 4.39-4.46 (1H, m), 6.93-6.97 (2H, m), 7.49-7.55 (2H, m), 8.08 (1H, s).

Example 254

Preparation of (S)-1-(2-chloro-4-nitroimidazol-1-yl)-2-methyl-3-[4-(4-trifluoromethylbenzyloxy)piperidin-1-yl]propan-2-ol (R)-2-Chloro-1-(2-methyloxiran-2-ylmethyl)-4-nitroimidazole prepared in Example 12 (700 mg, 3.22 mmol) and 4-(4-trifluoromethylbenzyloxy)piperidine (1.09 g, 4.86 mol) in DMF (10 ml) were stirred at 70-75° C. for 4 hours. The reaction mixture was allowed to return to room temperature, poured into water and extracted with ethyl acetate. The extract was washed with a saturated saline solution, dried over magnesium sulfate and then filtered. The filtrate was concentrated under reduced pressure, and the residue was purified by silica gel column chromatography (methylene chloride/methanol=50/1) to afford (S)-1-(2-chloro-4-nitroimidazol-1-yl)-2-methyl-3-[4-(4-trifluoromethylbenzyloxy)piperidin-1-yl]propan-2-ol (1.36 g, yield 87%) as a yellow oil.

$^1$H-NMR (CDCl$_3$) δppm: 1.12 (3H, s), 1.61-1.78 (2H, m), 1.88-1.96 (2H, m), 2.32 (1H, d, J=13.9 Hz), 2.35-2.56 (2H, m), 2.47 (1H, d, J=13.9 Hz), 2.72-2.81 (1H, m), 2.86-2.95 (1H, m), 3.44-3.51 (1H, m), 3.63 (1H, bs), 3.97 (2H, s), 4.59 (2H, s), 7.43-7.47 (2H, m), 7.58-7.62 (2H, m), 8.05 (1H, s).

Using corresponding starting materials gave compounds of Examples 255 to 260 shown in the following table in the same manner as in Example 254.

TABLE 13

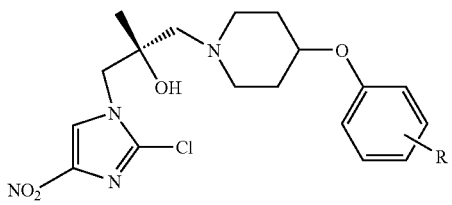

| Example | R | ¹H NMR(CDCl₃) δ | Yield (%) |
|---|---|---|---|
| 255 | 4-OCF₃ | 1.13(3H, s), 1.77-1.89(2H, m), 1.91-2.01(2H, m), 2.37(1H, d, J=13.9Hz), 2.45-2.67(2H, m), 2.51(1H, d, J=13.9Hz), 2.76-2.95(2H, m), 3.71(1H, s), 4.00(2H, s), 4.17-4.34(1H, m), 6.85-6.91(2H, m), 7.11-7.15(2H, m), 8.07(1H, s). | 99 |
| 256 | 4-Cl | 1.13(3H, s), 1.73-1.88(2H, m), 1.91-2.02(2H, m), 2.36(1H, d, J=13.9Hz), 2.44-2.63(2H, m), 2.50(1H, d, J=13.9Hz), 2.76-2.95(2H, m), 3.64(1H, s), 3.99(2H, s), 4.26-4.35(1H, m), 6.79-6.86(2H, m), 7.18-7.26(2H, m), 8.06(1H, s). | 99 |
| 257 | 4-CN | 1.14(3H, s), 1.81-1.92(2H, m), 1.95-2.03(2H, m), 2.36(1H, d, J=13.9Hz), 2.47-2.68(2H, m), 2.51(1H, d, J=13.9Hz), 2.77-2.94(2H, m), 3.53(1H, s), 4.00(2H, s), 4.40-4.47(1H, m), 6.90-6.96(2H, m), 7.53-7.60(2H, m), 8.06(1H, s). | 99 |
| 258 | 3-CF₃ | 1.14(3H, s), 1.81-1.91(2H, m), 1.94-2.02(2H, m), 2.37(1H, d, J=13.9Hz), 2.47-2.68(2H, m), 2.51(1H, d, J=13.9Hz), 2.77-2.97(2H, m), 3.61(1H, s), 3.99(2H, s), 4.38-4.44(1H, m), 7.04-7.12(2H, m), 7.18-7.22(1H, m), 7.35-7.42(1H, m), 8.07(1H, s). | 99 |

TABLE 14

| Example | R | ¹H NMR(CDCl₃) δ |
|---|---|---|
| 259 | OCF₃ | 1.12(3H, s), 1.66-1.76(2H, m), 1.86-1.95(2H, m), 2.32(1H, d, J=13.9Hz), 2.36-2.55(2H, m), 2.46(1H, d, J=13.9Hz), 2.72-2.82(1H, m), 2.85-2.96(1H, m), 3.42-3.49(1H, m), 3.69(1H, s), 4.00(2H, s), 4.52(2H, s), 7.17-7.21(2H, m), 7.35-7.39(2H, m), 8.06(1H, s). |
| 260 | Cl | 1.10(3H, s), 1.65-1.74(2H, m), 1.85-1.92(2H, m), 2.31(1H, d, J=13.9Hz), 2.38-2.54(2H, m), 2.46(1H, d, J=13.9Hz), 2.71-2.79(1H, m), 2.84-2.95(1H, m), 3.38-3.48(1H, m), 3.72(1H, s), 3.96(2H, s), 4.48(2H, s), 7.23-7.32(2H, m), 8.05(1H, s). |

Example 261

Preparation of (S)-1-(2-chloro-4-nitroimidazol-1-yl)-2-methyl-3-[4-(3-phenyl-2-propenyloxy)piperidin-1-yl]-propan-2-ol Using (R)-2-chloro-1-(2-methyloxiran-2-yl-methyl)-4-nitroimidazole prepared in Example 12 (0.198 g, 0.910 mmol) and 4-(3-phenyl-2-propenyloxy)piperidine (0.198 g, 0.910 mmol) gave (S)-1-(2-chloro-4-nitroimidazol-1-yl)-2-methyl-3-[4-(3-phenyl-2-propenyloxy)piperidin-1-yl]propan-2-ol (0.192 g, yield 49%) as a brown oil in the same manner as in Example 254.

¹H-NMR (CDCl₃) δppm: 1.12 (3H, s), 1.55-1.98 (4H, m), 2.28-2.94 (6H, m), 3.41-3.49 (1H, m), 3.62 (1H, br), 3.95 (2H, s), 4.16 (1H, d, J=6.0 Hz), 4.17 (1H, d, J=6.0 Hz), 6.28 (1H, ddd, J=6.0 Hz, 6.0 Hz, 15.9 Hz), 6.60 (1H, d, J=15.9 Hz), 7.21-7.42 (5H, m), 8.05 (1H, s).

Example 262

Preparation of (S)-1-(2-chloro-4-nitroimidazol-1-yl)-3-{4-[3-(4-chlorophenyl)-2-propenyloxy]piperidin-1-yl}-2-methylpropan-2-ol Using (R)-2-chloro-1-(2-methyloxiran-2-yl-methyl)-4-nitroimidazole prepared in Example 12 (0.217 g, 1.00 mmol)

and 4-[3-(4-chloro-phenyl)-2-propenyloxy]piperidine (0.250 g, 0.995 mmol) gave (S)-1-(2-chloro-4-nitroimidazol-1-yl)-3-{4-[3-(4-chlorophenyl)-2-propenyloxy]piperidin-1-yl}-2-methylpropan-2-ol (0.263 g, yield 56%) as a brown liquid in the same manner as in Example 254.

$^1$H-NMR (CDCl$_3$) δppm: 1.12 (3H, s), 1.55-2.01 (4H, m), 2.28-2.99 (6H, m), 3.40-3.51 (1H, m), 3.60 (1H, br), 3.96 (2H, s), 4.13-4.16 (2H, m), 6.20-6.31 (1H, m), 6.56 (1H, d, J=15.7 Hz), 7.19-7.34 (4H, m), 8.05 (1H, s).

Example 263

Preparation of (S)-2-{4-[3-(4-chlorophenyl)propoxy]-piperidin-1-ylmethyl}-2-methyl-6-nitro-2,3-dihydroimidazo[2,1-b]oxazole (R)-2-Chloro-1-(2-methyloxiran-2-ylmethyl)-4-nitroimidazole prepared in Example 12 (0.103 g, 0.473 mmol) and 4-[3-(4-chlorophenyl)propoxy]piperidine (0.109 g, 0.430 mmol) were dissolved in DMF (10 ml), and the solution was stirred at 60° C. for 4 hours. The reaction mixture was added water and extracted with ethyl acetate. The organic phase was combined, washed with water and a saturated saline solution, dried over sodium sulfate and then filtered. The resulting filtrate was concentrated under reduced pressure. The residue was purified by silica gel column chromatography (n-hexane/ethyl acetate=2/3) to afford an oil. The oil was dissolved in DMF (2 ml). To the solution, sodium hydride (15 mg, 0.375 mmol) was added with cooling on ice-bath followed by stirring at room temperature for 3 hours. To the reaction mixture, water was added, and the precipitates were filtered off, purified by silica gel column chromatography (methylene chloride/ethyl acetate=6/1) and then recrystallized from ethyl acetate/n-hexane=1/3 (6 ml) to afford (S)-2-{4-[3-(4-chlorophenyl)propoxy]-piperidin-1-ylmethyl}-2-methyl-6-nitro-2,3-dihydroimidazo[2,1-b]oxazole (36 mg, yield 19%) as a white powder.

Melting point 88.8-91.9° C.

Example 264

Preparation of (S)-1-(2-chloro-4-nitroimidazol-1-yl)-3-{4-[2-(4-chlorophenyl)ethoxy]piperidin-1-yl}-2-methylpropan-2-ol Using (R)-2-chloro-1-(2-methyloxiran-2-yl-methyl)-4-nitroimidazole prepared in Example 12 (0.076 g, 0.350 mmol) and 4-[2-(4-chlorophenyl)ethoxy]-piperidine (0.080 g, 0.334 mmol) gave (S)-1-(2-chloro-4-nitroimidazol-1-yl)-3-{4-[2-(4-chlorophenyl)ethoxy]-piperidin-1-yl}-2-methyl-propan-2-ol (0.109 g, yield 71%) as a light yellow oil in the same manner as in Example 254.

$^1$H-NMR (CDCl$_3$) δppm: 1.10 (3H, s), 1.51-1.72 (2H, m), 1.78-1.92 (2H, m), 2.24-2.50 (4H, m), 2.55-2.88 (4H, m), 3.29-3.39 (1H, m), 3.58-3.66 (3H, m), 3.94 (2H, s), 7.15 (2H, d, J=8.5 Hz), 7.24 (2H, d, J=8.5 Hz), 8.04 (1H, s).

Example 265

Preparation of (S)-1-(2-chloro-4-nitroimidazol-1-yl)-2-methyl-3-{4-[2-(4-trifluoromethylphenyl)ethoxy]-piperidin-1-yl}propan-2-ol Triphenyl-(4-trifluoromethylbenzyl)-phosphonium bromide (3.00 g, 5.98 mmol) was dissolved in DMSO (50 ml). To the solution, sodium hydride (0.239 g, 5.98 mmol) was added with cooling on ice-bath followed by stirring at room temperature for 1 hour. To the solution, a solution of benzyl 4-formyloxypiperidine-1-carboxylate (1.497 g, 5.69 mmol) in DMSO (10 ml) was added dropwise followed by stirring at 60° C. for 7 hours. The reaction mixture was added water and extracted with ethyl acetate twice. The organic phases were combined, washed with water and a saturated saline solution, dried over sodium sulfate and then filtered. The filtrate was concentrated under reduced pressure. The residue was purified by silica gel column chromatography (n-hexane/ethyl acetate=4/1) and then purified by silica gel column chromatography (methylene chloride/ethyl acetate=9/1) to afford benzyl 4-[2-(4-trifluoromethylphenyl)-vinyloxy]piperidin-1-carboxylate as a colorless oil.

The resulting benzyl 4-[2-(4-trifluoromethylphenyl)vinyloxy]piperidin-1-carboxylate was dissolved in ethanol (10 ml) and reduced by catalytic hydrogenation over 10% Pd/C (90 mg) at room temperature under atmospheric pressure. The reaction mixture was filtered through Celite. The filtrate was concentrated under reduced pressure to afford 4-[2-(trifluoromethylphenyl)ethoxy]piperidine as a brown liquid.

Using the resulting 4-[2-(trifluoromethylphenyl)ethoxy] piperidine and (R)-2-chloro-1-(2-methyloxiran-2-ylmethyl)-4-nitroimidazole prepared in Example 12 (0.184 g, 0.844 mmol) gave (S)-1-(2-chloro-4-nitroimidazol-1-yl)-2-methyl-3-{4-[2-(4-trifluoromethylphenyl)ethoxy]piperidin-1-yl}propan-2-ol (0.088 g, yield 3%) as a brown oil in the same manner as in Example 254.

$^1$H-NMR (CDCl$_3$) δppm: 1.10 (3H, s), 1.49-1.92 (4H, m), 2.24-2.81 (6H, m), 2.92 (2H, t, J=6.8 Hz), 3.30-3.35 (1H, m), 3.65 (2H, t, J=6.8 Hz), 3.94 (2H, s), 7.34 (2H, d, J=8.2 Hz), 7.54 (2H, d, J=8.2 Hz), 8.04 (1H, s).

Example 266

Preparation of (S)-1-(2-chloro-4-nitroimidazol-1-yl)-2-methyl-3-[4-(4-trifluoromethoxyphenylamino) piperidin-1-yl]propan-2-ol Using (R)-2-chloro-1-(2-methyloxiran-2-yl-methyl)-4-nitroimidazole prepared in Example 12 and N-(piperidin-4-yl)-4-trifluoromethoxyaniline gave (S)-1-(2-chloro-4-nitroimidazol-1-yl)-2-methyl-3-[4-(4-trifluoromethoxyphenylamino)piperidin-1-yl]propan-2-ol (1.36 g, yield 88%) as a yellow oil in the same manner as in Example 254.

$^1$H-NMR (CDCl$_3$) δppm: 1.13 (3H, s), 1.41-1.57 (2H, m), 2.03-2.08 (2H, m), 2.34 (1H, d, J=13.9 Hz), 2.49-2.59 (3H, m), 2.65-2.77 (2H, m), 3.08-2.16 (2H, m), 3.24-3.41 (1H, m), 3.97 (2H, s), 6.47-6.55 (2H, m), 6.98-7.04 (2H, m), 8.05 (1H, s).

Using corresponding starting materials gave compounds of Examples 267 to 269 shown in the following table in the same manner as in Example 266.

TABLE 15

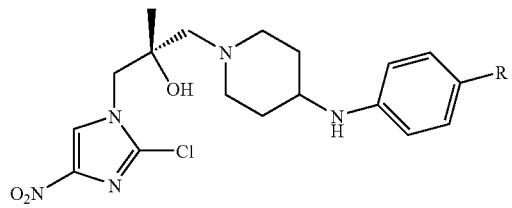

| Example | R | Yield (%) | ¹H NMR(CDCl₃) δ |
|---------|------|-----------|-----------------|
| 267 | Cl | 99 | 1.13(3H, s), 1.40-1.53(2H, m), 2.00-2.06(2H, m), 2.35(1H, d, J=13.9Hz), 2.45-2.59(3H, m), 2.71-3.01(2H, m), 3.18(1H, br), 3.48-3.58(2H, m), 3.97(2H, s), 6.47-6.54(2H, m), 7.07-7.14(2H, m), 8.05(1H, s). |
| 268 | CF₃ | 99 | 1.14(3H, s), 1.42-1.59(2H, m), 2.03-2.08(2H, m), 2.35(1H, d, J=13.9Hz), 2.49-2.60(2H, m), 2.50(1H, d, J=13.9Hz), 2.74-2.98(2H, m), 3.31-3.39(1H, m), 3.51(1H, s), 3.87(1H, d, J=9.3Hz) 3.97(2H, s), 6.58(2H, d, J=8.7Hz), 7.39(2H, d, J=8.7Hz), 8.05(1H, s). |
| 269 | CN | 99 | 1.13(3H, s), 1.40-1.53(2H, m), 2.00-2.06(2H, m), 2.35(1H, d, J=13.9Hz), 2.45-2.59(2H, m), 2.49(1H, d, J=13.9Hz), 2.71-3.01(2H, m), 3.18(1H, br), 3.48-3.58(2H, m), 3.97(2H, s), 6.51-6.57(2H, m), 7.38-7.44(2H, m), 8.05(1H, s). |

Example 270

Preparation of (S)-1-(4-piperidinopiperidin-1-yl)-3-(2-chloro-4-nitroimidazol-1-yl)-2-methyl-propan-2-ol (R)-2-Chloro-1-(2-methyloxiran-2-ylmethyl)-4-nitroimidazole prepared in Example 12 (0.500 g, 2.29 mmol) and 4-piperidinopiperidine (0.425 g, 2.53 mmol) were dissolved in DMF (5 ml), and the solution was stirred at 70° C. for 5 hours. The reaction mixture was added water and extracted with ethyl acetate twice. The organic phases were combined, washed with water and a saturated saline solution, dried over sodium sulfate and then filtered. The resulting filtrate was concentrated under reduced pressure. The residue was purified by silica gel column chromatography (n-hexane/ethyl acetate=3/2) using basic silica gel to afford (S)-1-(4-piperidinopiperidin-1-yl)-3-(2-chloro-4-nitroimidazol-1-yl)-2-methyl-propan-2-ol (0.656 g, yield 74%) as a brown oil.

¹H-NMR (CDCl₃) δppm: 1.11 (3H, s), 1.38-1.89 (10H, m), 2.18-2.55 (9H, m), 2.70-2.81 (1H, m), 2.89-3.01 (1H, m), 3.67 (1H, br), 3.94 (1H, s), 8.05 (1H, s).

Example 271

Preparation of (S)-1-(2-chloro-4-nitroimidazol-1-yl)-2-methyl-3-{[4-(4-trifluoromethoxyphenyl)sulfanyl]-piperidin-1-yl)propan-2-ol Using (R)-2-chloro-1-(2-methyloxiran-2-yl-methyl)-4-nitroimidazole prepared in Example 12 and 4-[4-(trifluoromethoxy)phenylsulfanyl]piperidine gave (S)-1-(2-chloro-4-nitroimidazol-1-yl)-2-methyl-3-{[4-(4-trifluoromethoxyphenyl)sulfanyl]piperidin-1-yl}propan-2-ol (3.4 g, yield 99%) as a yellow oil in the same manner as in Example 270.

¹H-NMR (CDCl₃) δppm: 1.11 (3H, s), 1.58-1.73 (2H, m), 1.91-1.99 (2H, m), 2.32 (1H, d, J=13.9 Hz), 2.41-2.50 (2H, m), 2.46 (1H, d, J=13.9 Hz), 2.75-3.09 (4H, m), 3.97 (2H, s), 7.11-7.17 (2H, m), 7.36-7.53 (2H, m), 8.04 (1H, s).

Example 272

Preparation of (S)-1-(2-chloro-4-nitroimidazol-1-yl)-2-methyl-3-[4-(4-trifluoromethoxybenzyl)piperidin-1-yl]propan-2-ol Using 4-(4-trifluoromethoxybenzyl)piperidine and (R)-2-chloro-1-(2-methyloxiran-2-ylmethyl)-4-nitroimidazole prepared in Example 12 gave (S)-1-(2-chloro-4-nitroimidazol-1-yl)-2-methyl-3-[4-(4-trifluoromethoxybenzyl)piperidin-1-yl]propan-2-ol (crude) as a yellow oil in the same manner as in Example 270.

¹H-NMR (CDCl₃) δppm: 1.10 (3H, m), 1.22-1.71 (5H, m), 2.26-2.55 (6H, m), 2.66-2.96 (3H, m), 3.94 (2H, s), 7.09-7.18 (4H, m), 8.06 (1H, s).

Using corresponding starting materials gave compounds of Examples 273 and 274 shown in the following table in the same manner as in Example 272.

TABLE 16

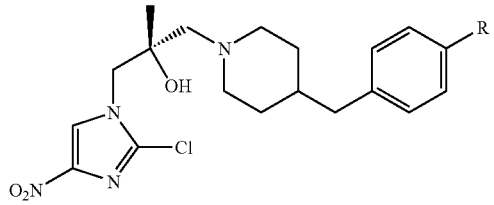

| Example | R | Yield (%) | ¹H NMR(CDCl₃) δ |
|---|---|---|---|
| 273 | 4-CF₃ | 56 | 1.10(3H, s), 1.14-1.38(2H, m), 1.47-1.64(3H, m), 2.29(1H, d, J=13.9Hz), 2.30-2.40(2H, m), 2.43(1H, d, J=13.9Hz), 2.60(2H, d, J=6.5Hz), 2.69(1H, d, J=11.7Hz), 2.90(1H, d, J=11.7Hz), 3.74(1H, br) 3.94(2H, s), 7.22-7.26(2H, m), 7.52-7.54(2H, m), 8.05(1H, s). |
| 274 | 4-Cl | 65 | 1.10(3H, s), 1.14-1.63(5H, m), 2.26-2.52(7H, m), 2.68(1H, d, J=11.5Hz), 2.90(1H, d, J=11.5Hz), 3.94(2H, s), 7.00-7.08(2H, m), 7.20-7.29(2H, m), 8.05(1H, s). |

Example 275

Preparation of (S)-1-(2-chloro-4-nitroimidazol-1-yl)-2-methyl-3-(4-phenyl-1,2,3,6-tetrahydropyridin-1-yl)propan-2-ol 4-Phenyl-1,2,3,6-tetrahydropyridine hydrochloride (0.495 g, 2.53 mmol) was added to a sodium hydroxide solution, and the solution was extracted with methylene chloride. The organic phase was dried over sodium sulfate and then filtered. The filtrate was concentrated under reduced pressure. To the residue, (R)-2-chloro-1-(2-methyloxiran-2-ylmethyl)-4-nitroimidazole prepared in Example 12 (0.5 g, 2.29 mmol) and DMF (5 ml) were added followed by stirring at 70° C. for 5 hours. The reaction mixture was poured into water and extracted with ethyl acetate twice. The organic phases were combined, washed with water and a saturated saline solution, dried over sodium sulfate and then filtered. The resulting filtrate was concentrated under reduced pressure, and the residue was purified by silica gel column chromatography (n-hexane/ethyl acetate=2/1) to afford (S)-1-(2-chloro-4-nitroimidazol-1-yl)-2-methyl-3-(4-phenyl-1,2,3,6-tetrahydropyridin-1-yl)propan-2-ol (0.492 g, yield 57%) as a yellow oil.

¹H-NMR (CDCl₃) δppm: 1.17 (3H, s), 2.47 (1H, d, J=13.9 Hz), 2.58-2.64 (3H, m), 2.78-3.00 (2H, m), 3.27-3.40 (2H, m), 3.62 (1H, br), 4.01 (2H, s), 6.02-6.05 (.1H, m), 7.23-7.41 (5H, m), 8.07 (1H, s).

Example 276

Preparation of (S)-1-(2-chloro-4-nitroimidazol-1-yl)-2-methyl-3-(4-phenylpiperidin-1-yl)propan-2-ol 4-Phenylpiperidine hydrochloride (0.522 g, 2.64 mmol) was added to a sodium hydroxide solution, and extracted with methylene chloride. The organic phase was dried over sodium sulfate and then filtered. The filtrate was concentrated under reduced pressure. To the residue, (R)-2-chloro-1-(2-methyloxiran-2-ylmethyl)-4-nitroimidazole prepared in Example 12 (0.5 g, 2.29 mmol) and DMF (5 ml) were added followed by stirring at 70° C. for 5 hours. The reaction mixture was poured into water and extracted with ethyl acetate twice. The organic phases were combined, washed with water and a saturated saline solution, dried over sodium sulfate and then filtered. The resulting filtrate was concentrated under reduced pressure. The residue was purified by silica gel column chromatography (n-hexane/ethyl acetate=2/1) to afford (S)-1-(2-chloro-4-nitroimidazol-1-yl)-2-methyl-3-(4-phenylpiperidin-1-yl)propan-2-ol (0.703 g, yield 81%) as a yellow oil.

¹H-NMR (CDCl₃) δppm: 1.14 (3H, s), 1.76-1.89 (4H, m), 2.36 (1H, d, J=13.9 Hz), 2.48-2.61 (4H, m), 2.75-2.89 (1H, m), 2.98-3.09 (1H, m), 3.75 (1H, br), 3.98 (2H, s), 7.18-7.35 (5H, m), 8.08 (1H, s).

Example 277

Preparation of (S)-1-(2-chloro-4-nitroimidazol-1-yl)-2-methyl-3-[4-(4-trifluoromethylphenyl)piperidin-1-yl]propan-2-ol (R)-2-Chloro-1-(2-methyloxiran-2-ylmethyl)-4-nitroimidazole prepared in Example 12 (0.329 g, 1.51 mmol) and 4-(4-trifluoromethylphenyl)piperidine (0.40 g, 1.66 mmol) were dissolved in DMF (5 ml) followed by stirring at 70° C. for 3 hours. The reaction mixture was poured into water and extracted with ethyl acetate twice. The organic phases were combined, washed with water and a saturated saline solution, dried over sodium sulfate and then filtered. The resulting filtrate was concentrated under reduced pressure. The residue was purified by silica gel column chromatography (n-hexane/ethyl acetate=2/1) to afford (S)-1-(2-chloro-4-nitroimidazol-1-yl)-2-methyl-3-[4-(4-trifluoromethylphenyl)piperidin-1-yl]propan-2-ol (0.361 g, yield 54%) as a brown oil.

¹H-NMR (CDCl₃) δppm: 1.13 (3H, s) 1.71-1.93 (4H, m), 2.36 (1H, d, J=14.0 Hz), 2.48-2.65 (4H, m), 2.77-2.90 (1H, m), 3.01-3.14 (1H, m), 3.64 (1H, br), 3.99 (2H, s), 7.32 (2H, d, J=8.1 Hz), 7.57 (2H, d, J=8.1 Hz), 8.07 (1H, s).

Example 278

Preparation of tert-butyl (S)-{1-[3-(2-chloro-4-nitroimidazol-1-yl)-2-hydroxy-2-methylpropyl]piperidin-4-yl}carbamate Using (R)-2-chloro-1-(2-methyloxiran-2-yl-methyl)-4-nitroimidazole prepared in Example 12 and tert-butyl piperidin-4-ylcarbamate gave tert-butyl (S)-{1-[3-(2-chloro-4-nitroimidazol-1-yl)-2-hydroxy-2-methylpropyl]piperidin-4-yl}carbamate (yield 92%) a yellow oil in the same manner as in Example 277.

$^1$H-NMR (CDCl$_3$) δppm: 1.11 (3H, s), 1.32-1.51 (2H, m), 1.44 (9H, m), 1.90-1.96 (2H, m), 2.32 (1H, d, J=13.9 Hz), 2.39-2.55 (2H, m), 2.46 (1H, d, J=13.9 Hz), 2.67-2.96 (3H, m), 3.44 (1H, br), 3.59 (1H, s), 3.96 (2H, s), 8.05 (1H, s).

Example 279

Preparation of tert-butyl (S)-{1-[3-(2-chloro-4-nitroimidazol-1-yl)-2-hydroxy-2-methyl-propyl]-piperidin-4-yl}-N-[2-(4-trifluoromethylphenyl)-ethyl] carbamate Using (R)-2-chloro-1-(2-methyloxiran-2-yl-methyl)-4-nitroimidazole prepared in Example 12 (0.332 g, 0.891 mmol) and tert-butyl piperidin-4-yl-N-[2-(4-trifluoromethylphenyl) ethyl]carbamate (0.194 g, 0.891 mmol) gave tert-butyl (S)-{1-[3-(2-chloro-4-nitroimidazol-1-yl)-2-hydroxy-2-methyl-propyl]piperidin-4-yl}-N-[2-(4-trifluoromethylphenyl)-ethyl]carbamate (0.370 g, yield 70%) as a light yellow oil in the same manner as in Example 277.

$^1$H-NMR (CDCl$_3$) δppm: 1.12 (3H, s), 1.49 (9H, s), 1.55-1.80 (4H, m), 2.17-2.57 (4H, m), 2.70-2.98 (4H, m), 3.21-3.30 (2H, m), 3.50 (1H, s), 3.95 (2H, s), 7.31 (2H, d, J=8.2 Hz), 7.57 (2H, d, J=8.2 Hz), 8.05 (1H, s).

Example 280

Preparation of (S)-2-methyl-6-nitro-2-[4-(4-trifluoromethylphenoxy)piperidin-1-ylmethyl]-2,3-dihydroimidazo-[2,1-b]oxazole (S)-1-(2-Chloro-4-nitroimidazol-1-yl)-2-methyl-3-[4-(4-trifluoromethylphenoxy)piperidin-1-yl]propan-2-ol prepared in Example 253 (1.06 g, 2.3 mmol) was dissolved in DMF (15 ml). To the solution, sodium hydride (110 mg, 2.76 mmol) was added with cooling on ice-bath followed by stirring at room temperature overnight. The reaction mixture was poured into water and extracted with ethyl acetate. The organic phase was washed with a saturated saline solution, dried over magnesium sulfate and then filtered. The filtrate was concentrated under reduced pressure. The residue was purified by silica gel column chromatography (methylene chloride/ethyl acetate=5/1) and crystallized from methylene chloride-diisopropyl ether to afford (S)-2-methyl-6-nitro-2-[4-(4-trifluoromethylphenoxy)piperidin-1-ylmethyl]-2,3-dihydroimidazo[2,1-b]oxazole (431 mg, yield 44%) as a white powder.

MS 427(M+1)$^+$Optical purity 97.8% e.e. [α]$_D^{27}$=−2.07° (concentration: 1.064, CHCl$_3$) $^1$H-NMR (CDCl$_3$) δppm: 1.61 (3H, s), 1.67-1.92 (4H, m), 2.41-2.51 (1H, m), 2.57 (1H, d, J=14.9 Hz), 2.58-2.67 (1H, m), 2.88 (1H, d, J=14.9 Hz), 2.74-2.98 (2H, m), 3.91 (1H, d, J=9.7 Hz), 4.31 (1H, d, J=9.7 Hz), 4.28-4.36 (1H, m), 6.91 (2H, d, J=8.7 Hz), 7.51 (2H, d, J=8.7 Hz), 7.54 (1H, s).

Example 281

Preparation of (S)-2-methyl-6-nitro-2-[4-(4-trifluoromethylbenzyloxy)piperidin-1-ylmethyl]-2,3-dihydroimidazo[2,1-b]oxazole (S)-1-(2-Chloro-4-nitroimidazol-1-yl)-2-methyl-3-[4-(4-trifluoromethylbenzyloxy)piperidin-1-yl]propan-2-ol prepared in Example 254 (1.36 g, 2.8 mmol) was dissolved in DMF (15 ml). To the solution, sodium hydride (134 mg, 3.36 mmol) was added with cooling on ice-bath followed by stirring at room temperature overnight. The reaction mixture was poured into water and extracted with ethyl acetate. The organic phase was washed with a saturated saline solution, dried over magnesium sulfate and then filtered. The filtrate was concentrated under reduced pressure, and the residue was purified by silica gel column chromatography (methylene chloride/ethyl acetate=10/1) and crystallized from methylene chloride-diisopropyl ether to afford (S)-2-methyl-6-nitro-2-[4-(4-trifluoromethylbenzyloxy)piperidin-1-ylmethyl]-2,3-dihydroimidazo[2,1-b]oxazole (431 mg, yield 44%) as a white powder.

MS 440(M−1)$^+$Melting point 91-92° C. Optical purity 99.6% e.e. [α]$_D^{27}$=−8.630 (concentration: 1.066, CHCl$_3$) $^1$H-NMR (CDCl$_3$) δppm: 1.44-1.66 (2H, m), 1.60 (3H, s), 1.71-1.85 (2H, m), 2.28-2.38 (1H, m), 2.44-2.56 (1H, m), 2.52 (1H, d, J=14.9 Hz), 2.72-2.81 (1H, m), 2.84 (1H, d, J=14.9 Hz), 2.87-2.94 (1H, m), 3.33-3.41 (1H, m), 3.88 (1H, d, J=9.6 Hz), 4.31 (1H, d, J=9.6 Hz), 4.54 (2H, s), 7.41-7.44 (2H, m), 7.52 (1H, s), 7.56-7.60 (2H, m).

Example 282

Preparation of (S)-2-[4-(4-trifluoromethoxyphenyl) aminopiperidin-1-yl]methyl-2-methyl-6-nitro-2,3-dihydroimidazo[2,1-b]oxazole Using (S)-1-(2-chloro-4-nitroimidazol-1-yl)-2-methyl-3-[4-(4-trifluoromethoxyphenylamino)piperidin-1-yl]propan-2-ol prepared in Example 266 gave (S)-2-[4-(4-trifluoromethoxyphenyl)aminopiperidin-1-yl]methyl-2-methyl-6-nitro-2,3-dihydroimidazo[2,1-b]oxazole (yield 73%) as a white powder in the same manner as in Example 281.

Melting point 107.5-109.0° C. MS 441(M$^+$) Optical purity 99.8% e.e. [α]$_D^{27}$=19.19° (concentration: 1.006, CHCl$_3$).

Example 283

Preparation of tert-butyl (S)-[1-(2-methyl-6-nitro-2, 3-dihydroimidazo[2,1-b]oxazol-2-ylmethyl)piperidin-4-yl]carbamate Using tert-butyl(S)-{1-[3-(2-chloro-4-nitroimidazol-1-yl)-2-hydroxy-2-methylpropyl]piperidin-4-yl}carbamate prepared in Example 278 gave tert-butyl(S)-[1-(2-methyl-6-nitro-2,3-dihydroimidazo[2,1-b]oxazol-2-ylmethyl) piperidin-4-yl]carbamate (yield 49%) as a white powder in the same manner as in Example 281.

MS 381(M$^+$) Melting point 158.5-160.7° C.

Example 284

Preparation of tert-butyl (S)-[1-(2-methyl-6-nitro-2, 3-dihydroimidazo[2,1-b]oxazol-2-ylmethyl)piperidin-4-yl]-N-[2-(4-trifluoromethylphenyl)ethyl]carbamate Using tert-butyl (S)-{1-[3-(2-chloro-4-nitroimidazol-1-yl)-2-hydroxy-2-methyl-propyl]piperidin-4-yl}-N-[2-(4-trifluoromethylphenyl)ethyl]carbamate prepared in Example 279 (0.37 g, 0.627 mmol) gave tert-butyl (S)-[1-(2-methyl- 6-nitro-2,3-dihydroimidazo[2,1-b]oxazol-2-ylmethyl)piperidin-4-yl]-N-[2-(4-trifluoromethylphenyl)ethyl]carbamate (0.211 g, yield 63%) as a light yellow powder in the same manner as in Example 281.

Melting point 206.8-208.6° C.

Example 285

Preparation of (S)-2-methyl-6-nitro-2-{4-[4-(trifluoromethoxyphenyl)sulfanyl]piperidin-1-ylmethyl)-2,3-dihydroimidazo[2,1-b]oxazole Using (S)-1-(2-chloro-4-nitro-imidazol-1-yl)-2-methyl-3-{[4-(4-trifluoromethoxyphenyl)sulfanyl]-piperidin-1-yl}propan-2-ol prepared in Example 271 gave (S)-2-methyl-6-nitro-2-{4-[4-(trifluoromethoxyphenyl)sulfanyl]piperidin-1-ylmethyl}-2,3-dihydroimidazo[2,1-b]oxazole (yield 62%) as a white powder in the same manner as in Example 281.

MS 458(M$^+$) Melting point 133.0-137.4° C.

Example 286

Preparation of (S)-2-methyl-6-nitro-2-[4-(4-trifluoromethoxybenzyl)piperidin-1-yl]methyl-2,3-dihydroimidazo-[2,1-b]oxazole Using (S)-1-(2-chloro-4-nitro-imidazol-1-yl)-2-methyl-3-[4-(4-trifluoromethoxybenzyl)piperidin-1-yl]propan-2-ol prepared in Example 272 gave (S)-2-methyl-6-nitro-2-[4-(4-trifluoromethoxybenzyl)piperidin-1-yl]methyl-2,3-dihydroimidazo[2,1-b]oxazole (yield 55%) as a white powder in the same manner as in Example 281.

Melting point 111.0-112.5° C. MS: 440(M$^+$) Optical purity 99.0% e.e. $[\alpha]_D^{27}$=5.38° (concentration: 1.004, CHCl$_3$).

Example 287

Preparation of (S)-2-methyl-6-nitro-2-(4-phenyl-1,2,3,6-tetrahydropyridin-1-ylmethyl)-2,3-dihydroimidazo[2,1-b]oxazole (S)-1-(2-Chloro-4-nitro-imidazol-1-yl)-2-methyl-3-(4-phenyl-1,2,3,6-tetrahydropyridin-1-yl)propan-2-ol prepared in Example 275 (0.492 g, 1.31 mmol) was dissolved in DMF (8 ml). To the solution, sodium hydride (63 mg, 1.57 mmol) was added with cooling on ice-bath followed by stirring at room temperature for 3 hours. To the reaction mixture, water was added. After extraction with ethyl acetate, the organic phase was washed with water and a saturated saline solution, dried over sodium sulfate and then filtered. The resulting filtrate was concentrated under reduced pressure, and the residue was purified by silica gel column chromatography (n-hexane/acetone=4/1) and recrystallized from methylene chloride-ethyl acetate to afford (S)-2-methyl-6-nitro-2-(4-phenyl-1,2,3,6-tetrahydropyridin-1-ylmethyl)-2,3-dihydroimidazo[2,1-b]oxazole (0.059 g, yield 13%) as a light yellow solid.

Melting point 200.1-201° C.

Example 288

Preparation of (S)-2-methyl-6-nitro-2-(4-phenylpiperidin-1-ylmethyl)-2,3-dihydroimidazo[2,1-b]oxazole (S)-1-(2-Chloro-4-nitro-imidazol-1-yl)-2-methyl-3-(4-phenylpiperidin-1-yl)propan-2-ol prepared in Example 276 (0.703 g, 1.86 mmol) was dissolved in DMF (5 ml). To the solution, sodium hydride (89 mg, 2.23 mmol) was added with cooling on ice-bath followed by stirring at room temperature for 3 hours. To the reaction mixture, water was added. The precipitates were filtered off, purified by silica gel column chromatography (n-hexane/acetone=3/1) and recrystallized from ethyl acetate to afford (S)-2-methyl-6-nitro-2-(4-phenylpiperidin-1-ylmethyl)-2,3-dihydroimidazo[2,1-b]oxazole (0.230 g, yield 36%) as a white powder.

Melting point 158.8-163.9° C.

Using corresponding starting materials gave compounds of Examples 289 to 294 in the same manner as in Example 288.

Example 289

(S)-1'-(2-Methyl-6-nitro-2,3-dihydroimidazo[2,1-b]oxazol-2-ylmethyl)-[1,4']bipiperidinyl Melting point 163.4-164.9° C.

Example 290

(S)-2-Methyl-6-nitro-2-[4-(4-trifluoromethylphenyl)-piperidin-1-ylmethyl]-2,3-dihydroimidazo[2,1-b]oxazole Melting point 138.7-139.9° C.

Example 291

(S)-2-Methyl-6-nitro-2-[4-(3-phenyl-2-propenyloxy)-piperidin-1-ylmethyl]-2,3-dihydroimidazo[2,1-b]oxazole Melting point 91.3-92.7° C.

Example 292

(S)-2-{4-[3-(4-Chlorophenyl)-2-propenyloxy]piperidin-1-ylmethyl}-2-methyl-6-nitro-2,3-dihydroimidazo[2,1-b]oxazole Melting point 140.6-142.8° C.

Example 293

(S)-2-Methyl-6-nitro-2-{4-[2-(4-trifluoromethylphenyl)-ethoxy]piperidin-1-ylmethyl}-2,3-dihydroimidazo[2,1-b]oxazole Melting point 84.6-86.8° C.

Example 294

(S)-2-{4-[2-(4-Chlorophenyl)ethoxy]piperidin-1-ylmethyl}-2-methyl-6-nitro-2,3-dihydroimidazo[2,1-b]oxazole Melting point 92.5-94° C.

Example 295

Preparation of (S)-[1-(2-methyl-6-nitro-2,3-dihydroimidazo[2,1-b]oxazol-2-ylmethyl)piperidin-4-yl]-N-methyl-4-trifluoromethoxyaniline (S)-2-[4-(4-Trifluoromethoxyphenyl)aminopiperidin-1-yl]methyl-2-methyl-6-nitro-2,3-dihydroimidazo[2,1-b]oxazole prepared in Example 282 (400 mg, 0.90 mmol) was dissolved in methanol (10 ml). To the solution, a 37% formaldehyde solution (0.13 ml, 4.52 mmol), sodium cyanotrihydroborate (170 mg, 2.71 mmol) and acetic acid (0.17 ml, 2.71 mmol) were added followed by stirring at room temperature for 30 minutes. The reaction mixture was poured into a saturated sodium hydrogencarbonate solution and extracted with methylene chloride. The organic phase was dried over magnesium sulfate and then filtered. The resulting filtrate was concentrated under reduced pressure. The residue was purified by silica gel column chromatography (methylene chloride/methanol=100/1) and recrystallized from methylene chloride-diisopropyl ether to afford (S)-N-[1-(2-methyl-6-nitro-2,3-dihydroimidazo[2,1-b]oxazol-2-ylmethyl)piperidin-4-yl]-N-methyl-4-trifluoromethoxyaniline (309 mg, yield 78%) as a light yellow crystals.

Optical purity 99.9% e.e. $[\alpha]_d^{17}$=7.77 (concentration: 1.042, CHCl$_3$) MS 455(M$^+$) Melting point 133.2-134.4° C.

Example 296

Preparation of (S)-N-[1-(2-methyl-6-nitro-2,3-dihydroimidazo[2,1-b]oxazol-2-ylmethyl)piperidin-4-yl]-N-(4-trifluoromethoxyphenyl)acetamide (S)-2-[4-(4-Trifluoromethoxyphenyl)aminopiperidin-1-yl]methyl-2-methyl-6-nitro-2,3-dihydroimidazo[2,1-b]oxazole prepared in Example 282 (153 mg, 0.35 mmol) was dissolved in methylene chloride (5 ml). To the solution, triethylamine (30 µl) and acetyl chloride (30 µl) were added followed by stirring at room temperature for 1.5 hours. The reaction mixture was poured into water and extracted with methylene chloride. The organic phase was dried over magnesium sulfate and then filtered. The resulting filtrate was concentrated under reduced pressure. The residue was purified by silica gel column chromatography (methylene chloride/methanol=100/1) and crystallized from methylene chloride-diisopropyl ether to afford (S)-N-[1-(2-methyl-6-nitro-2,3-dihydroimidazo[2,1-b]oxazol-2-ylmethyl)piperidin-4-yl]-N-(4-trifluoromethoxyphenyl)acetamide (82 mg, yield 49%) as a white powder.

MS 484(M+1)$^+$ Melting point 137.0-138.7° C.

Example 297

Preparation of (S)-2-{4-N-[(4-trifluoromethylphenyl)-acetyl]aminopiperidin-1-yl}methyl-2-methyl-6-nitro-2,3-dihydroimidazo[2,1-b]oxazole Tert-butyl (S)-[1-(2-methyl-6-nitro-2,3-dihydroimidazo[2,1-b]oxazol-2-ylmethyl)piperidin-4-yl]carbamate prepared in Example 283 (0.1 g, 0.262 mmol) was dissolved in ethanol (4 ml). To the solution, 6 N hydrochloric acid (3 ml) was added followed by stirring at room temperature for 5 hours. The reaction mixture was concentrated under reduced pressure. To the residue, methylene (4 ml) chloride and triethylamine (4 ml) were added. The resulting mixture was stirred at room temperature for 5 minutes and then concentrated. To the residue, toluene (10 ml) was added. The solution was concentrated to remove water azeotropically. To the residue, 4-trifluoromethylphenylacetic acid (0.064 g, 0.315 mmol), methylene chloride (4 ml), triethylamine (0.06 ml, 0.393 mmol) and 1-ethyl-3-(3-dimethylaminopropyl)carbodiimide hydrochloride (WSCD) (0.065 g, 0.341 mmol) were added followed by stirring at room temperature overnight. To the reaction mixture, water was added, and the mixture was extracted with methylene chloride twice. The organic phases were combined, washed with water and a saturated saline solution, dried over sodium sulfate and then filtered. The resulting filtrate was concentrated under reduced pressure, and the residue was purified by silica gel column chromatography (n-hexane/acetone=3/2) and recrystallized from ethyl acetate (3 ml) to afford (S)-2-{4-N-[(4-trifluoromethylphenyl)acetyl]aminopiperidin-1-yl}methyl-2-methyl-6-nitro-2,3-dihydroimidazo[2,1-b]oxazole (32 mg, yield 26%) as a white powder.

Melting point 152.7-154.3° C.

Example 298

Preparation of 4-trifluoromethylbenzyl (S)-[1-(2-methyl-6-nitro-2,3-dihydroimidazo[2,1-b]oxazol-2-ylmethyl)piperidin-4-yl]carbamate Tert-butyl (S)-[1-(2-methyl-6-nitro-2,3-dihydroimidazo[2,1-b]oxazol-2-ylmethyl)piperidin-4-yl]carbamate prepared in Example 283 (0.300 g, 0.787 mmol) was dissolved in methylene chloride (4 ml). To the solution, trifluoroacetic acid (2 ml) was added followed by stirring at room temperature for 2 hours. The reaction mixture was concentrated under reduced pressure, and added methylene chloride (4 ml) and triethylamine (4 ml). The mixture was stirred at room temperature for 5 minutes and concentrated under reduced pressure. The residue was dissolved in DMF (6 ml). To the solution, a mixture of 4-(trifluoromethyl)benzyl alcohol (0.166 g, 0.944 mmol) in DMF (4 ml) and 1,1'-carbonyldiimidazole (0.153 g, 0.944 mmol) stirred at room temperature for 4 hours was added followed by stirring at room temperature overnight and then at 65° C. for 8 hours. To the reaction mixture, water was added, and the solution was extracted with ethyl acetate twice. The organic phases were combined, washed with water and a saturated saline solution, dried over sodium sulfate and then filtered. The resulting filtrate was concentrated under reduced pressure. The residue was purified by silica gel column chromatography (n-hexane/acetone=2/1) and recrystallized from ethyl acetate to afford 4-trifluoromethylbenzyl (S)-[1-(2-methyl-6-nitro-2,3-dihydroimidazo[2,1-b]oxazol-2-ylmethyl)piperidin-4-yl]carbamate (0.107 g, yield 28%) as a light yellow powder.

Melting point 141.2-144° C.

Using corresponding starting materials gave compounds of Examples 299 and 300 in the same manner as in Example 298.

Example 299

1-(4-Trifluoromethylphenyl)piperidin-4-yl (S)-[1-(2-methyl-6-nitro-2,3-dihydroimidazo[2,1-b]oxazol-2-ylmethyl)piperidin-4-yl]carbamate Melting point 134.4-136.9° C.

Example 300

4-Trifluoromethoxybenzyl (S)-[1-(2-methyl-6-nitro-2,3-dihydroimidazo[2,1-b]oxazol-2-ylmethyl)piperidin-4-yl]carbamate Melting point 156.2-158.5° C.

Example 301

Preparation of (S)-N-[1-(2-methyl-6-nitro-2,3-dihydroimidazo[2,1-b]oxazol-2-ylmethyl)piperidin-4-yl]-4-trifluoromethylbenzylamine Tert-butyl (S)-[1-(2-methyl-6-nitro-2,3-dihydroimidazo[2,1-b]oxazol-2-ylmethyl)piperidin-4-yl]carbamate prepared in Example 283 (0.300 g, 0.787 mmol) was dissolved in methylene chloride (4 ml). To the solution, trifluoroacetic acid (2 ml) was added followed by stirring at room temperature for 1 hour. The reaction mixture was concentrated under reduced pressure and added methylene chloride (4 ml) and triethylamine (4 ml). The mixture was stirred at room temperature for 20 minutes and then concentrated under reduced pressure. The residue was dissolved in methanol (5 ml). To the solution, 4-trifluoromethylbenzaldehyde (0.164 g, 0.945 mmol), sodium cyanotrihydroborate (0.099 g, 1.57 mmol) and acetic acid (0.09 ml, 1.57 mmol) were added followed by stirring at room temperature for 4 hours. The reaction mixture was concentrated under reduced pressure. To the residue, water was added, and the solution was extracted with methylene chloride. The organic phases were combined, washed with a saturated saline solution, dried over sodium sulfate and then filtered. The resulting filtrate was concentrated under reduced pressure. The residue was purified by silica gel column chromatography (methylene chloride/methanol=20/1) and recrystallized from isopropyl alcohol to afford (S)-N-[1-(2-methyl-6-nitro-2,3-dihydroimidazo[2,1-b]oxazol-2-ylmethyl)piperidin-4-yl]-4-trifluoromethylbenzylamine (0.078 g, yield 22%) as a light yellow powder.

Melting point 148.6-152.9° C.

Example 302

Preparation of (S)-1-[1-(2-methyl-6-nitro-2,3-dihydroimidazo[2,1-b]oxazol-2-ylmethyl)piperidin-4-yl]-3-(4-trifluoromethylphenyl)urea Tert-butyl (S)-[1-(2-methyl-6-nitro-2,3-dihydroimidazo[2,1-b]oxazol-2-ylmethyl)piperidin-4-yl]carbamate prepared in Example 283 (0.300 g, 0.787 mmol) was dissolved in methylene chloride (4 ml). To the solution, trifluoroacetic acid (2 ml) was added followed by stirring at room temperature for 2 hours. The reaction mixture was concentrated under reduced pressure and added methylene chloride (4 ml) and triethylamine (4 ml). The mixture was stirred at room temperature for 5 minutes and concentrated under reduced pressure. The residue was called "residue 1".

On the other hand, 4-(trifluoromethyl)aniline (0.139 g, 0.865 mmol) and pyridine (0.07 ml, 0.865 mmol) was dissolved in THF (4 ml). To the solution, Phenyl chloroformate (0.108 ml, 0.865 mmol) was added with cooling on ice-bath followed by stirring at room temperature for 1 hour. The reaction mixture was added water and extracted with ethyl acetate. The organic phase was washed with water, 10% hydrochloric acid and a saturated saline solution, dried over sodium sulfate and then filtered. The resulting filtrate was concentrated under reduced pressure.

The resulting residue was dissolved in dimethylsulfoxide (6 ml). To the solution, the "residue 1" was added followed by stirring at room temperature overnight. To the reaction mixture, water was added, and the solution was extracted with ethyl acetate twice. The organic phases were combined, washed with water, a saturated sodium hydrogencarbonate solution and a saturated saline solution, dried over sodium sulfate and then filtered. The filtrate was concentrated under reduced pressure, and the resulting residue was purified by silica gel column chromatography (n-hexane/acetone=2/1) and recrystallized from isopropyl alcohol-n-hexane (1:1) (6 ml) to afford (S)-1-[1-(2-methyl-6-nitro-2,3-dihydroimidazo[2,1-b]oxazol-2-ylmethyl)piperidin-4-yl]-3-(4-trifluoromethylphenyl)urea (0.064 g, yield 17%) as a light yellow powder.

Melting point 136.8-139.9° C.

Example 303

Preparation of (S)-2-[4-N-(4-trifluoromethylbenzoyl)-aminopiperidin-1-yl]methyl-2-methyl-6-nitro-2,3-dihydroimidazo[2,1-b]oxazole Tert-butyl (S)-[1-(2-methyl-6-nitro-2,3-dihydroimidazo[2,1-b]oxazol-2-ylmethyl)piperidin-4-yl]carbamate prepared in Example 283 (360 mg, 0.92 mmol) was dissolved in methylene chloride (5 ml). To the solution, trifluoroacetic acid (5 ml) was added followed by stirring at room temperature for 5 hours. The reaction mixture was concentrated under reduced pressure and added methylene chloride (10 ml) and triethylamine (2 ml). To the solution, 4-trifluoromethylbenzoyl chloride (0.3 ml, 1.85 mmol) was added followed by stirring at room temperature for 1 hour. The reaction mixture was poured into water and extracted with methylene chloride. The organic phase was washed with a saturated saline solution, dried over magnesium sulfate and then filtered. The resulting filtrate was concentrated under reduced pressure. The residue was purified by silica gel column chromatography (methylene chloride/methanol=20/1) and crystallized from ethyl acetate-diisopropyl ether to afford (S)-2-[4-N-(4-trifluoromethylbenzoyl)aminopiperidin-1-yl]methyl-2-methyl-6-nitro-2,3-dihydroimidazo[2,1-b]oxazole (232 mg, yield 55%) as a white powder.

MS 454(M+H)$^+$ Melting point 170.5-171.7° C.

Example 304

Preparation of (S)-N-[1-(2-methyl-6-nitro-2,3-dihydroimidazo[2,1-b]oxazol-2-ylmethyl)piperidin-4-yl]-2-(4-trifluoromethylphenyl)ethylamine Tert-butyl (S)-[1-(2-methyl-6-nitro-2,3-dihydroimidazo[2,1-b]oxazol-2-ylmethyl)piperidin-4-yl]-N-[2-(4-trifluoromethylphenyl)ethyl]carbamate prepared in Example 284 (0.196 g, 0.354 mmol) was dissolved in methylene chloride (2 ml). To the solution, trifluoroacetic acid (1 ml) was added followed by stirring at room temperature for 4 hours. To the reaction mixture, a saturated sodium hydrogencarbonate solution was added, and the solution was extracted with methylene chloride twice. The organic phases were combined, dried over sodium sulfate and then filtered. The filtrate was concentrated under reduced pressure, and the resulting residue was purified by silica gel column chromatography (methylene chloride/ethyl acetate=10/1) and treated with isopropyl ether to afford (S)-N-[1-(2-methyl-6-nitro-2,3-dihydroimidazo[2,1-b]oxazol-2-ylmethyl)piperidin-4-yl]-2-(4-trifluoromethylphenyl)ethylamine (0.020 g, yield 12%) as a light yellow powder.

Melting point 80.7-84.2° C.

Example 305

Preparation of (S)-2-methyl-6-nitro-2-{4-[4-(trifluoromethoxy)benzenesulfinyl]piperidin-1-ylmethyl}-2,3-dihydroimidazo[2,1-b]oxazole (S)-2-Methyl-6-nitro-2-{4-[4-(trifluoromethoxyphenyl)sulfanyl]piperidin-1-ylmethyl}-2,3-dihydroimidazo[2,1-b]oxazole prepared in Example 285 (300 mg, 0.65 mmol) was dissolved in methylene chloride (5 ml). To the solution, m-chloroperbenzoic acid (169 mg, 0.69 mmol) was added followed by stirring at room temperature for 30 minutes. The reaction mixture was diluted with methylene chloride. The solution was washed with a sodium thiosulfate solution, a saturated sodium hydrogencarbonate solution and a saturated saline solution, dried over sodium sulfate and then filtered. The resulting filtrate was concentrated under reduced pressure. The residue was purified by silica gel column chromatography (methylene chloride/methanol=50/1) and crystallized from ethyl acetate-isopropyl ether to afford (S)-2-methyl-6-nitro-2-{4-[4-(trifluoromethoxy)benzenesulfinyl]piperidin-1-ylmethyl}-2,3-dihydroimidazo[2,1-b]oxazole (219 mg, yield 71%) as a white powder.

MS 475(M+H)$^+$ Melting point 107-109° C.

Example 306

Preparation of 2-(4-tert-butoxycarbonylpiperazin-1-yl)methyl-2-methyl-6-nitro-2,3-dihydroimidazo[2,1-b]oxazole 2-Chloro-4-nitro-1H-imidazole (3.19 g, 21.6 mmol) and tert-butyl 4-(2-methyloxiran-2-ylmethyl)-piperazine-1-carboxylate (5.53 g, 21.6 mmol) and sodium acetate (1.95 g, 23.8 mmol) were dissolved in 1-propanol (50 ml) followed by stirring under reflux for 48 hours. The reaction mixture was diluted with methylene chloride. The solution was washed with water and a saturated saline solution, dried over sodium sulfate and then filtered. The filtrate was concentrated under reduced pressure. The residue was purified by silica gel column chromatography (methylene chloride/methanol=100/1) and treated with methylene chloride-diisopropyl ether to afford 2-(4-tert-butoxycarbonylpiperazin-1-yl)methyl-2-methyl-6-nitro-2,3-dihydroimidazo[2,1-b]oxazole (1.85 g, yield 23%) as a white powder.

$^1$H-NMR (CDCl$_3$) δppm: 1.43 (9H, s), 1.62 (3H, s), 2.45-2.68 (5H, m), 2.87 (1H, d, J=14.9 Hz), 3.30 (4H, br), 3.93 (1H, d, J=9.7 Hz), 4.30 (1H, d, J=9.7 Hz), 7.54 (1H, s).

Using corresponding starting materials gave the compound of Example 307 in the same manner as in Example 306.

Example 307

2-[4-(4-Cyanophenyl)piperazin-1-yl]methyl-2-methyl-6-nitro-2,3-dihydroimidazo[2,1-b]oxazole Yield 18% $^1$H-NMR (CDCl$_3$) δppm: 1.67 (3H, s), 2.60-2.80 (3H, m), 2.80-3.00 (3H, m), 3.22 (4H, br), 3.97 (1H, d, J=9.8 Hz), 4.35-4.50 (1H, m), 6.78-6.85 (2H, m), 7.46-7.51 (2H, m), 7.55 (1H, s).

Example 308

Preparation of 2-[4-(4-trifluoromethylphenyl)piperazin-1-yl]methyl-2-methyl-6-nitro-2,3-dihydroimidazo[2,1-b]oxazole To a solution of 2-chloro-4-nitro-1H-imidazole (1.59 g, 10.8 mmol) and 1-(2-methyloxiran-2-ylmethyl)-4-(4-trifluoromethylphenyl)piperazine (3.23 g, 10.8 mmol) in 1-propanol (20 ml), sodium hydrogencarbonate (1.95 g, 23.8 mmol) was added followed by stirring under reflux overnight. The reaction mixture was concentrated under reduced pressure. The residue was added water, and the solution was extracted with methylene chloride. The organic phase was dried over sodium sulfate and then filtered. The filtrate was concentrated under reduced pressure. The residue was purified by silica gel column chromatography (methylene chloride/methanol=100/1) and crystallized from methylene chloride-isopropyl ether to afford 2-[4-(4-trifluoromethylphenyl)piperazin-1-yl]methyl-2-methyl-6-nitro-2,3-dihydroimidazo[2,1-b]oxazole (1.34 g, yield 29%) as a a light yellow powder.

MS 411(M$^+$) Melting point 159-160° C.

Also, the above purification by silica gel column chromatography gives an intermediate, 2-chloro-1-{3-[4-(4-trifluoromethylphenyl)piperazin-1-yl]-2-hydroxy-2-methyl}propyl-4-nitroimidazole (697 mg, yield 15%) as a yellow oil.

$^1$H-NMR (CDCl$_3$) δppm: 1.17 (3H, s), 2.32-2.91 (6H, s), 3.26-3.31 (4H, m), 4.03 (2H, s), 6.71 (1H, s), 6.89-6.93 (2H, m), 7.45-7.51 (2H, m), 8.06 (1H, s).

Using corresponding starting materials gave compounds of Examples 309 to 311 in the same manner as in Example 308.

Example 309

2-[4-(Biphenyl-4-yl)piperazin-1-yl]methyl-2-methyl-6-nitro-2,3-dihydroimidazo[2,1-b]oxazole Yield 32%, melting point 223-227.8° C.

Example 310

2-[4-(4-Chlorophenyl)piperazin-1-yl]methyl-2-methyl-6-nitro-2,3-dihydroimidazo[2,1-b]oxazole Yield 14%, melting point 196.6-197.3° C.

Example 311

2-[4-(4-Trifluoromethoxyphenyl)piperazin-1-yl] methyl-2-methyl-6-nitro-2,3-dihydroimidazo[2,1-b] oxazole Yield 18% $^1$H-NMR (CDCl$_3$) δppm: 1.61 (3H, s), 2.61 (1H, d, J=14.8 Hz), 2.65-2.73 (2H, m), 2.82-2.95 (2H, m), 2.93 (1H, d, J=14.8 Hz), 2.99-3.09 (4H, m), 3.94 (1H, d, J=9.7 Hz), 4.34 (1H, d, J=9.7 Hz), 6.78-6.86 (2H, m), 7.06-7.11 (2H, m), 7.53 (1H, s).

Example 312

Preparation of 1-[3-(4-tert-butoxycarbonylpiperazin-1-yl)-2-hydroxy-2-methyl]propyl-2-chloro-4-nitroimidazole 2-Chloro-4-nitro-1H-imidazole (863 mg, 5.85 mmol) and tert-butyl 4-(2-methyloxiran-2-ylmethyl)-piperazine-1-carboxylate (1.5 g, 5.85 mmol) was dissolved in 1-propanol (10 ml) followed by stirring under reflux for 6 hours. The reaction mixture was allowed to return to room temperature and concentrated under reduced pressure. The residue was purified by silica gel column chromatography (methylene chloride/methanol=100/1) to afford 1-[3-(4-tert-butoxycarbonylpiperazin-1-yl)-2-hydroxy-2-methyl]propyl-2-chloro-4-nitroimidazole (705 mg, yield 29.8%) as a white powder.
$^1$H-NMR (CDCl$_3$) δppm: 1.15 (3H, s), 1.45 (9H, s), 2.35 (1H, d, J=13.9 Hz), 2.45-2.65 (5H, m), 3.25 (1H, s), 3.42 (4H, t, J=4.3 Hz), 4.00 (2H, s), 8.05 (1H, s).

Using 2-chloro-4-nitro-1H-imidazole and tert-butyl 4-(oxiran-2-ylmethyl)piperazine-1-carboxylate, tert-butyl 4-[2-(2-methyloxiran-2-yl)ethyl]piperazine-1-carboxylate or benzyl 4-(2-methyloxiran-2-ylmethyl)-piperazine-1-carboxylate gave compounds of Examples 313 to 315 in the same manner as in Example 312.

Example 313

Tert-butyl 4-[3-(2-chloro-4-nitroimidazol-1-yl)-2-hydroxypropyl]piperazine-1-carboxylate Light yellow powder, yield 43% $^1$H-NMR (CDCl$_3$) δppm: 1.46 (9H, s), 2.16-2.50 (4H, m), 2.55-2.70 (2H, m), 3.40-3.51 (4H, m), 3.64 (1H, s), 3.91-4.09 (2H, m), 4.17 (1H, dd, J=2.0 Hz, 13.5 Hz), 8.00 (1H, s).

Example 314

Tert-butyl 4-[4-(2-chloro-4-nitroimidazol-1-yl)-3-hydroxy-3-methylbutyl]piperazine-1-carboxylate White powder, yield 17% $^1$H-NMR (CDCl$_3$) δppm: 1.23 (3H, s), 1.40-1.74 (11H, m), 2.23-2.58 (5H, m), 2.81-2.95 (1H, m), 3.26-3.51 (4H, m), 3.91 (1H, d, J=14.0 Hz), 3.99 (1H, d, J=14.0 Hz), 6.94 (1H, s), 8.07 (1H, s).

Example 315

Benzyl 4-[3-(2-chloro-4-nitroimidazol-1-yl)-2-hydroxy-2-methylpropyl]piperazine-1-carboxylate Light yellow oil, yield 81% $^1$H-NMR (CDCl$_3$) δppm: 1.14 (3H, s), 2.35-2.76 (6H, m), 3.43-3.61 (4H, m), 4.01 (2H, s), 5.13 (2H, s), 7.28-7.43 (5H, m), 8.04 (1H, s).

Example 316

Preparation of isobutyl 4-[3-(2-chloro-4-nitroimidazol-1-yl)-2-hydroxy-2-methylpropyl]piperazine-1-carboxylate A mixture of 1-[3-(4-tert-butoxycarbonyl-piperazin-1-yl)-2-hydroxy-2-methyl]propyl-2-chloro-4-nitroimidazole prepared in Example 312 (150 mg, 0.37 mmol) and trifluoroacetic acid (5 ml) was stirred at room temperature for 5 hours. The reaction mixture was concentrated under reduced pressure. The residue was dissolved in methylene chloride (5 ml). To the solution, triethylamine (0.23 ml, 1.63 mmol) and isobutyl chloroformate (112 mg, 0.82 mmol) were added in this order followed by stirring at room temperature for 30 minutes. The reaction mixture was washed with water, a saturated sodium hydrogencarbonate solution and a saturated saline solution in this order, dried over magnesium sulfate and then filtered. The filtrate was concentrated under reduced pressure to afford isobutyl 4-[3-(2-chloro-4-nitroimidazol-1-yl)-2-hydroxy-2-methylpropyl]piperazine-1-carboxylate, which was used in the next step without purification.
$^1$H-NMR (CDCl$_3$) δppm: 0.93 (6H, d, J=6.7 Hz), 1.14 (3H, s), 1.82-2.00 (1H, m), 2.39 (1H, d, J=13.9 Hz), 2.47-2.73 (5H, m), 3.11 (1H, d, J=7.3 Hz), 3.17 (1H, d, J=7.3 Hz), 3.41-3.55 (4H, m), 3.87 (2H, s), 4.04 (1H, s), 8.10 (1H, s).

Example 317

Preparation of benzyl 4-(2-methyl-6-nitro-2,3-dihydroimidazo[2,1-b]oxazol-2-ylmethyl)piperazine-1-carboxylate To a mixture of benzyl 4-[3-(2-chloro-4-nitroimidazol-1-yl)-2-hydroxy-2-methylpropyl]-piperazine-1-carboxylate prepared in Example 315 (55.22 g, 126.11 mmol) and 1,4-dioxane (550 ml), sodium hydride (6.05 g, 151.25 mmol) was added followed by stirring under reflux for 14 hours. The reaction mixture was allowed to return to room temperature and concentrated under reduced pressure. To the residue, water was added, and the solution was extracted with methylene chloride twice. The organic phases were washed with a saturated saline solution, dried over magnesium sulfate and then filtered. The filtrate was concentrated under reduced pressure, and the residue was purified by silica gel column chromatography (ethyl acetate) to afford benzyl 4-(2-methyl-6-nitro-2,3-dihydroimidazo[2,1-b]oxazol-2-ylmethyl)piperazine-1-carboxylate (26.54 g, yield 52%) as a white powder.

Melting point 130.5-132.1° C. $^1$H-NMR (CDCl$_3$) δppm: 1.61 (3H, s), 2.38-2.69 (5H, m), 2.86 (1H, d, J=14.8 Hz), 3.10-3.50 (4H, m), 3.92 (1H, d, J=9.9 Hz), 4.33 (1H, d, J=9.9 Hz), 5.11 (2H, s), 7.23-7.38 (5H, m), 7.53 (1H, s).

Using corresponding starting materials gave compounds of Examples 318 to 320 in the same manner as in Example 317.

Example 318

Isobutyl 4-(2-methyl-6-nitro-2,3-dihydroimidazo[2,1-b]oxazol-2-ylmethyl)piperazine-1-carboxylate Light yellow powder, yield 39%, melting point 176.5-177.3° C.

Example 319

Tert-butyl 4-(6-nitro-2,3-dihydroimidazo[2,1-b]oxazol-2-ylmethyl)piperazine-1-carboxylate White powder, yield 45%. Melting point 185-188° C. (decomposition) $^1$H-NMR (CDCl$_3$) δppm: 1.45 (9H, s), 2.48-2.58 (4H, m), 2.85 (2H, d, J=5.1 Hz), 3.31-3.45 (4H, m), 4.20 (1H, dd, J=6.9 Hz, 10.3 Hz), 4.34 (1H, dd, J=8.4 Hz, 10.3 Hz), 5.35-5.48 (1H, m), 7.55 (1H, s).

Example 320

Tert-butyl 4-[2-(2-methyl-6-nitro-2,3-dihydroimidazo-[2,1-b]oxazol-2-yl)ethyl]piperazine-1-carboxylate Light yellow powder, yield 70%, melting point 190-191° C. (decomposition).

Example 321

Preparation of tert-butyl 4-[3-(2-methyl-6-nitro-2,3-dihydroimidazo[2,1-b]oxazol-2-yl)propyl]piperazine-1-carboxylate A mixture of 3-(2-methyl-6-nitro-2,3-dihydroimidazo[2,1-b]oxazol-2-yl)propyl methane-sulfonate (2 g, 6.6 mmol), tert-butyl piperazine-1-carboxylate (1.4 g, 7.5 mmol), triethylamine (1.3 g, 12.85 mmol), potassium iodide (1.8 g, 10.8 mmol) and DMF (15 ml) was stirred at 60° C. overnight. The reaction mixture was allowed to return to room temperature and then added water, and the resulting solution was extracted with ethyl acetate three times. The organic phases were combined, washed with water twice and then with a saturated saline solution, dried over sodium sulfate and then filtered. The filtrate was concentrated under reduced pressure, and the residue was purified by silica gel column chromatography (methylene chloride/methanol=20/1) to afford tert-butyl 4-[3-(2-methyl-6-nitro-2,3-dihydroimidazo[2,1-b]oxazol-2-yl)propyl]piperazine-1-carboxylate (1.9 g, yield 73%) as a white powder.

Melting point 166-167° C.

Example 322

Preparation of 2-methyl-6-nitro-2-(piperazin-1-ylmethyl)-2,3-dihydroimidazo[2,1-b]oxazole dihydrochloride 2-(4-Tert-butoxycarbonylpiperazin-1-yl)methyl-2-methyl-6-nitro-2,3-dihydroimidazo[2,1-b]oxazole prepared in Example 306 (1.19 g, 3.24 mmol) was dissolved in trifluoroacetic acid (30 ml) followed by stirring at room temperature for 3 hours. The reaction mixture was concentrated under reduced pressure. The residue was dissolved in methanol (30 ml) and added a solution of hydrogen chloride in ethyl acetate slowly followed by stirring for 30 minutes with cooling on ice-bath. The precipitates were filtered off to afford 2-methyl-6-nitro-2-(piperazin-1-ylmethyl)-2,3-dihydroimidazo[2,1-b]oxazole dihydrochloride (1.06 g, yield 96%) as a yellow powder.

$^1$H-NMR (DMSO-$d_6$) δppm: 1.68 (3H, s), 3.00-3.59 (6H, m), 4.14 (1H, d, J=11.1 Hz), 4.36 (1H, d, J=11.1 Hz), 4.50-6.12 (4H, br), 8.17 (1H, s), 9.62 (2H, br).

Example 323

Preparation of 2-[4-(biphenyl-4-ylmethyl)piperazin-1-ylmethyl]-6-nitro-2,3-dihydroimidazo[2,1-b]oxazole A mixture of tert-butyl 4-(6-nitro-2,3-dihydroimidazo[2,1-b]oxazol-2-ylmethyl)piperazine-1-carboxylate prepared in Example 319 (400 mg, 1.13 mmol) and trifluoroacetic acid (10 ml) was stirred at room temperature for 4 hours. The reaction mixture was concentrated. The residue was dissolved in methylene chloride (10 ml) and neutralized with triethylamine (2 ml, 14.35 mmol). The resulting solution was concentrated under reduced pressure, and the residue was dissolved in methanol (10 ml). To the solution, 4-phenylbenzaldehyde (515 mg, 2.83 mmol), sodium cyanotrihydroborate (214 mg, 3.41 mmol) and acetic acid (0.21 mg, 3.67 mmol) were added in this order followed by stirring at room temperature overnight. The reaction mixture was concentrated. To the residue, water was added, and the solution was extracted with methylene chloride twice. The organic phases were combined, washed with a saturated sodium hydrogen-carbonate solution and a saturated saline solution in this order, dried over magnesium sulfate and then filtered. The filtrate was concentrated under reduced pressure. The residue was purified by silica gel column chromatography (methylene chloride/methanol=20/1) to afford 2-[4-(biphenyl-4-ylmethyl)piperazin-1-ylmethyl]-6-nitro-2,3-dihydroimidazo[2,1-b]oxazole (188 mg, yield 40%) as a white powder.

Melting point 183-185° C. (decomposition)

Using corresponding starting materials gave compounds of Examples 324 to 329 in the same manner as in Example 323.

Example 324

2-{2-[4-(4-Trifluoromethylbenzyl)piperazin-1-yl]ethyl}-2-methyl-6-nitro-2,3-dihydroimidazo[2,1-b]oxazole White powder, yield 36%, melting point 148-149° C.

Example 325

2-Methyl-6-nitro-2-{3-[4-(4-trifluoromethylbenzyl)-piperazin-1-yl]propyl}-2,3-dihydroimidazo[2,1-b]oxazole White powder, yield 57%. Melting point 154-156° C.

Example 326

2-{2-[4-(Biphenyl-4-ylmethyl)piperazin-1-yl]ethyl}-2-methyl-6-nitro-2,3-dihydroimidazo[2,1-b]oxazole White powder, yield 53%. Melting point 181-182° C.

Example 327

2-{3-[4-(Biphenyl-4-ylmethyl)piperazin-1-yl]propyl}-2-methyl-6-nitro-2,3-dihydroimidazo[2,1-b]oxazole White powder, yield 65%. Melting point 176-178° C.

Example 328

4-(N,N-Dimethylamino)-4'-[4-(2-methyl-6-nitro-2,3-dihydroimidazo[2,1-b]oxazol-2-ylmethyl)piperazin-1-ylmethyl]biphenyl White powder, yield 68% $^1$H-NMR (CDCl$_3$) δppm: 1.58 (3H, s), 2.36 (4H, br), 2.50-2.60 (2H, m), 2.54 (1H, d, J=14.8 Hz), 2.67-2.76 (2H, m), 2.84 (1H, d, J=14.8 Hz), 2.99 (6H, s), 3.41 (1H, d, J=12.9 Hz), 3.48 (1H, d, J=12.9 Hz), 3.87

(1H, d, J=9.7 Hz), 4.30 (1H, d, J=9.7 Hz), 6.76-6.82 (2H, m), 7.25-7.29 (2H, m), 7.46-7.51 (4H, m), 7.53 (1H, s).

Example 329

2-Methyl-6-nitro-2-[4-(2-phenyl-1H-imidazol-4-ylmethyl)piperazin-1-ylmethyl]-2,3-dihydroimidazo[2,1-b]oxazole White powder, yield 93% $^1$H-NMR (DMSO-$d_6$) δppm: 1.52 (3H, s), 2.10-2.64 (6H, m), 2.67 (1H, d, J=15.4 Hz), 2.74 (1H, d, J=15.4 Hz), 3, 10-3.70 (4H, br), 4.04 (1H, d, J=10.7 Hz), 4.21 (1H, d, J=10.7 Hz), 6.97 (1H, br), 7.27-7.34 (1H, m), 7.38-7.45 (2H, m), 7.88-7.93 (2H, m), 8.12 (1H, s).

Example 330

Preparation of 2-(3,4-dichlorophenyl)-1-[4-(2-methyl-6-nitro-2,3-dihydroimidazo[2,1-b]oxazol-2-ylmethyl)-piperazin-1-yl]ethanone A mixture of 3,4-(dichlorophenyl)acetic acid (418 mg, 2.04 mmol) and thionyl chloride (3 ml) was stirred under reflux for 6 hours. The reaction mixture was concentrated under reduced pressure to afford a corresponding acid chloride.

On the other hand, a mixture of 2-(4-tert-butoxycarbonylpiperazin-1-yl)methyl-2-methyl-6-nitro-2,3-dihydroimidazo[2,1-b]oxazole prepared in Example 306 (300 mg, 0.816 mmol) and trifluoroacetic acid (6 ml) was stirred at room temperature for 6 hours. The reaction mixture was concentrated under reduced pressure. The residue was dissolved in methylene chloride (10 ml) and added triethylamine (2 ml, 14.35 mmol). To the solution, a solution of the acid chloride obtained above in methylene chloride (5 ml) was added with cooling on ice-bath followed by stirring at room temperature for 30 minutes. The reaction mixture was washed with a saturated sodium hydrogencarbonate solution, water and a saturated saline solution in this order, dried over sodium sulfate and then filtered. The filtrate was concentrated under reduced pressure, and the residue was purified by silica gel column chromatography (methylene chloride/methanol=100/1) to afford 2-(3,4-dichlorophenyl)-1-[4-(2-methyl-6-nitro-2,3-dihydroimidazo[2,1-b]oxazol-2-ylmethyl)piperazin-1-yl]ethanone (255 mg, yield 69%) as a white powder.

Melting point 189-191° C.

Using corresponding starting materials gave compounds of Examples 331 and 332 in the same manner as in Example 330.

Example 331

1-[4-(2-Methyl-6-nitro-2,3-dihydroimidazo[2,1-b]oxazol-2-ylmethyl)piperazin-1-yl]-2-(4-trifluoromethylphenyl)ethanone Melting point 168-171.4° C.

Example 332

2-(3,4-Dichlorophenoxy)-1-[4-(2-methyl-6-nitro-2,3-dihydroimidazo[2,1-b]oxazol-2-ylmethyl)piperazin-1-yl]ethanone Melting point 209-211° C.

Example 333

Preparation of 2-[4-(2-methyl-6-nitro-2,3-dihydroimidazo[2,1-b]oxazol-2-ylmethyl)piperazin-1-yl]-N-(4-trifluoromethylphenyl)acetamide A mixture of 2-(4-tert-butoxycarbonylpiperazin-1-yl)methyl-2-methyl-6-nitro-2,3-dihydroimidazo[2,1-b]oxazole prepared in Example 306 (500 mg, 1.36 mmol) and trifluoroacetic acid (15 ml) was stirred at room temperature overnight. The reaction mixture was concentrated under reduced pressure. The residue was dissolved in methylene chloride (10 ml) and added triethylamine (2 ml, 14.35 mmol). The solution was concentrated under reduced pressure, and the residue was dissolved in DMF (10 ml). To the solution, 2-bromo-N-(4-trifluoromethylphenyl)acetamide (423 mg, 1.5 mmol), potassium carbonate (207 mg, 1.5 mmol), and sodium iodide (204 mg, 1.36 mmol) were added followed by stirring at room temperature for 5 hours. To the reaction mixture, water was added, and the solution was extracted with ethyl acetate twice. The organic phases were combined, washed with water three times and a saturated saline solution, dried over sodium sulfate and then filtered. The filtrate was concentrated under reduced pressure, and the residue was purified by silica gel column chromatography (methylene chloride/methanol=100/1) to afford 2-[4-(2-methyl-6-nitro-2,3-dihydroimidazo[2,1-b]oxazol-2-ylmethyl)piperazin-1-yl]-N-(4-trifluoromethylphenyl)acetamide (389 mg, yield 61%) as a white powder.

$^1$H-NMR (CDCl$_3$) δppm: 1.62 (3H, s), 2.53-2.84 (9H, m), 2.88 (1H, d, J=14.8 Hz), 3.06 (1H, d, J=16.7 Hz), 3.14 (1H, d, J=16.7 Hz), 3.93 (1H, d, J=9.7 Hz), 4.30 (1H, d, J=9.7 Hz), 7.55 (1H, s), 7.55-7.59 (2H, m), 7.65-7.71 (2H, m), 9.20 (1H, s).

Using corresponding starting materials gave compounds of Examples 334 to 336 in the same manner as in Example 333.

Example 334

Ethyl[4-(2-Methyl-6-nitro-2,3-dihydroimidazo[2,1-b]oxazol-2-ylmethyl)piperazin-1-yl]acetate $^1$H-NMR (CDCl$_3$) δppm: 1.25 (3H, t, J=7.1 Hz), 1.60 (3H, s), 2.45-2.64 (6H, m), 2.55 (1H, d, J=14.8 Hz), 2.72-2.81 (2H, m), 2.87 (1H, d, J=14.8 Hz), 3.14 (2H, s), 3.90 (1H, d, J=9.7 Hz), 4.16 (2H, q, J=7.1 Hz), 4.31 (1H, d, J=9.7 Hz), 7.57 (1H, s)

Example 335

3-{3-[4-(2-Methyl-6-nitro-2,3-dihydroimidazo[2,1-b]oxazol-2-ylmethyl)piperazin-1-yl]propyl}-3H-benzoxazol-2-one Melting point 123-126° C.

Example 336

1-(4-Chlorophenyl)-2-[4-(2-methyl-6-nitro-2,3-dihydroimidazo[2,1-b]oxazol-2-ylmethyl)piperazin-1-yl]ethanone $^1$H-NMR (CDCl$_3$) δppm: 1.60 (3H, s), 2.47 (4H, br), 2.53 (1H, d, J=14.9 Hz), 2.57-2.65 (2H, m), 2.74-2.84 (2H, m), 2.87 (1H, d, J=14.9 Hz), 3.64 (1H, d, J=16.7 Hz), 3.75 (1H, d, J=16.7 Hz), 3.90 (1H, d, J=9.7 Hz), 4.30 (1H, d, J=9.7 Hz), 7.42 (2H, d, J=8.6 Hz), 7.54 (1H, s), 7.92 (2H, d, J=8.6 Hz).

Example 337

Preparation of benzyl 4-(2-methyl-6-nitro-2,3-dihydroimidazo[2,1-b]oxazol-2-ylmethyl)piperazine-1-carboxylate A mixture of 2-(4-tert-butoxycarbonylpiperazin-1-yl)methyl-2-methyl-6-nitro-2,3-dihydroimidazo[2,1-b]oxazole prepared in Example 306 (130 mg, 0.35 mmol), trifluoroacetic acid (3 ml) and methylene chloride (5 ml) was stirred at room temperature for 1 hour. The reaction mixture was concentrated under reduced pressure. The residue was dissolved in methylene chloride (5 ml) and added triethylamine (107.5 mg, 1.06 mmol). To the solution, benzyl chloroformate (120 mg, 0.71 mmol) was added with cooling on ice-bath followed by stirring at room temperature for 1 hour. The reaction mixture was washed with water, a saturated sodium hydrogencarbonate solution and a saturated saline solution in this order, dried over sodium sulfate and then filtered. The filtrate was concentrated under reduced pressure. The residue was purified by silica gel column chromatography (methylene chloride/methanol=20/1) to afford a yellow oil. The oil was dissolved in ethyl acetate (5 ml). To the solution, a saturated hydrochloride solution in ethyl acetate was added, and the precipitates were filtered off to afford benzyl 4-(2-methyl-6-nitro-2,3-dihydroimidazo[2,1-b]oxazol-2-ylmethyl)piperazin-1-carboxylate hydrochloride (46.8 mg, yield 30%) as a white powder.

Melting point 130.5-132.1° C.

Using corresponding starting materials gave compounds of Examples 338 to 340 in the same manner as in Example 337.

Example 338

Phenyl 4-(2-methyl-6-nitro-2,3-dihydroimidazo[2,1-b]oxazol-2-ylmethyl)piperazine-1-carboxylate Melting point 81-85° C.

Example 339

Isopropyl 4-(2-methyl-6-nitro-2,3-dihydroimidazo[2,1-b]oxazol-2-ylmethyl)piperazine-1-carboxylate Melting point 158.3-159.8° C.

Example 340 n-Octyl 4-(2-methyl-6-nitro-2,3-dihydroimidazo[2,1-b]oxazol-2-ylmethyl)piperazine-1-carboxylate Melting point 138-139.4° C.

Example 341

Preparation of 4-trifluoromethylbenzyl 4-(6-nitro-2,3-dihydroimidazo[2,1-b]oxazol-2-ylmethyl)piperazine-1-carboxylate To the solution of tert-butyl 4-(6-nitro-2,3-dihydroimidazo[2,1-b]oxazol-2-ylmethyl)piperazine-1-carboxylate prepared in Example 319 (400 mg, 1.13 mmol) in methylene chloride (2 ml), trifluoroacetic acid (1 ml) was added followed by stirring at room temperature for 1 hour. The reaction mixture was concentrated under reduced pressure, and the residue was dissolved in DMF (1 ml) and neutralized with triethylamine (1 ml).

To the solution, a mixture of 4-trifluoromethylbenzyl alcohol (297 mg, 1.69 mmol), 1,1'-carbonyldiimidazole (274 mg, 1.69 mmol) and DMF (1 ml) stirred at room temperature for 1 hour was added followed by stirring at room temperature for 3 hours. The reaction mixture was diluted with water and extracted with ethyl acetate twice. The organic phases were combined, washed with water twice and then with a saturated saline solution, dried over sodium sulfate and then filtered. The filtrate was concentrated under reduced pressure. The residue was purified by silica gel column chromatography (methylene chloride/methanol=20/1) to afford 4-trifluoromethylbenzyl 4-(6-nitro-2,3-dihydroimidazo[2,1-b]oxazol-2-ylmethyl)piperazine-1-carboxylate (322 mg, yield 63%) as a light yellow powder.

Melting point 120-122° C.

Using corresponding starting materials gave compounds of Examples 342 and 343 in the same manner as in Example 341.

Example 342

4-Trifluoromethylbenzyl 4-[2-(2-methyl-6-nitro-2,3-dihydroimidazo[2,1-b]oxazol-2-yl)ethyl]piperazine-1-carboxylate Light yellow powder, yield 68%, melting point 139-140° C.

Example 343

4-Trifluoromethylbenzyl 4-[3-(2-methyl-6-nitro-2,3-dihydroimidazo[2,1-b]oxazol-2-yl)propyl]piperazine-1-carboxylate Light yellow powder, yield 57%, melting point 130-133° C.

Example 344

Preparation of 3-(4-trifluoromethylphenyl)-2-propynyl 4-(2-methyl-6-nitro-2,3-dihydroimidazo[2,1-b]oxazol-2-ylmethyl)piperazine-1-carboxylate maleate A mixture of 2-(4-tert-butoxycarbonyl-piperazin-1-yl)methyl-2-methyl-6-nitro-2,3-dihydroimidazo[2,1-b]oxazole prepared in Example 306 (220 mg, 0.6 mmol), trifluoroacetic acid (1 ml) and methylene chloride (2 ml) was stirred at room temperature for 2 hours. The reaction mixture was concentrated under reduced pressure. The residue was dissolved in methylene (2 ml) chloride and neutralized with triethylamine (1 ml, 7.17 mmol). The resulting solution was concentrated under reduced pressure, and the residue was dissolved in DMF (2 ml).

To the solution, a mixture of 3-(4-trifluoromethylphenyl)-2-propyn-1-ol (110 ml, 0.55 mmol), 1,1'-carbonyldiimidazole (90 mg, 0.55 mmol) and DMF (2 ml) stirred at room temperature for 2 hours was added followed by stirring at room temperature overnight. The reaction mixture was diluted with water and extracted with ethyl acetate twice. The organic phases were combined, washed with water twice and then with a saturated saline solution, dried over sodium sulfate and then filtered. The filtrate was concentrated under reduced pressure. The residue was purified by silica gel column chromatography (methylene chloride/ethyl acetate=5/1).

The resulting free form was dissolved in ethanol (5 ml) and added a solution of maleic acid (96 mg, 0.83 mmol) in ethanol (5 ml). The precipitates were filtered off to afford 3-(4-trifluoromethylphenyl)-2-propynyl 4-(2-methyl-6-nitro-2,3-dihydroimidazo[2,1-b]oxazol-2-ylmethyl)piperazine-1-carboxylate maleate (227 mg, yield 68%) as a white powder.

Melting point 166° C. (decomposition)

Example 345

Preparation of 4-methylsulfanylbenzyl 4-(2-methyl-6-nitro-2,3-dihydroimidazo[2,1-b]oxazol-2-ylmethyl)-piperazine-1-carboxylate A mixture of 2-(4-tert-butoxycarbonylpiperazin-1-yl)methyl-2-methyl-6-nitro-2,3-dihydroimidazo[2,1-b]oxazole prepared in Example 306 (900 mg, 2.4 mmol) and trifluoroacetic acid (20 ml) was stirred at room temperature for 2 hours. The reaction mixture was concentrated under reduced pressure. The residue was dissolved in methylene (20 ml) chloride and neutralized with triethylamine (6 ml, 43.05 mmol). The resulting mixture was concentrated under reduced pressure, and the residue was dissolved in DMF (5 ml).

To the solution, a mixture of 4-methylsulfanylbenzyl alcohol (470 mg, 3 mmol), 1,1'-carbonyldiimidazole (500 mg, 3.1 mmol) and DMF (10 ml) stirred at room temperature for 3 hours was added followed by stirring at room temperature overnight. To the reaction mixture, water was added, and the mixture was extracted with ethyl acetate twice. The organic phases were combined, washed with water twice, and then with a saturated saline solution, dried over sodium sulfate and then filtered. The filtrate was concentrated under reduced pressure. The residue was purified by silica gel column chromatography (methylene chloride/methanol=20/1) to afford 4-methylsulfanylbenzyl 4-(2-methyl-6-nitro-2,3-dihydroimidazo[2,1-b]oxazol-2-ylmethyl)piperazine-1-carboxylate (860 mg, yield 79%) as a white powder.

Melting point 118-120° C.

Example 346

Preparation of 4-methanesulfinylbenzyl 4-(2-methyl-6-nitro-2,3-dihydroimidazo[2,1-b]oxazol-2-ylmethyl)-piperazine-1-carboxylate To a mixture of 4-methylsulfanylbenzyl 4-(2-methyl-6-nitro-2,3-dihydroimidazo[2,1-b]oxazol-2-ylmethyl)piperazine-1-carboxylate prepared in Example 345 (300 mg, 0.67 mmol) and methylene chloride (10 ml), m-chloroperbenzoic acid (210 mg, 0.85 mmol) was added followed by stirring for 2 hours with cooling on ice-bath. The reaction mixture was washed with a saturated sodium sulfite solution, a saturated sodium hydrogencarbonate solution, and a saturated saline solution in this order, dried over sodium sulfate and then filtered. The filtrate was concentrated under reduced pressure, and the residue was recrystallized from isopropyl alcohol-ether to afford 4-methanesulfinylbenzyl 4-(2-methyl-6-nitro-2,3-dihydroimidazo[2,1-b]oxazol-2-ylmethyl) piperazine-1-carboxylate (203 mg, yield 65%) as a white powder.

Melting point 117-121° C.

Example 347

Preparation of 4-hydroxybenzyl 4-(2-methyl-6-nitro-2,3-dihydroimidazo[2,1-b]oxazol-2-ylmethyl) piperazine-1-carboxylate To a mixture of 4-(tert-butyldimethylsilanyloxy)benzyl 4-(2-methyl-6-nitro-2,3-dihydroimidazo[2,1-b]oxazol-2-ylmethyl)piperazine-1-carboxylate (400 mg, 0.75 mmol) and THF(10 ml), a 1M solution of tetrabutylammonium fluoride in THF (0.8 ml, 0.8 mmol) was added followed by stirring for 20 minutes with cooling on ice-bath. To the reaction mixture, ethyl acetate was added, and the solution was washed with a saturated ammonium chloride solution, water and a saturated saline solution in this order, dried over magnesium sulfate and then filtered. The filtrate was concentrated under reduced pressure. To the residue, diethyl ether was added, and the precipitates were filtered off to afford 4-hydroxybenzyl 4-(2-methyl-6-nitro-2,3-dihydroimidazo[2,1-b]oxazol-2-ylmethyl)piperazine-1-carboxylate (95 mg, yield 30%) as a light yellow powder.

$^1$H-NMR (CDCl$_3$) δppm: 1.59 (3H, s), 2.30-2.70 (4H, m), 2.56 (1H, d, J=15.0 Hz), 2.86 (1H, d, J=15.0 Hz), 3.10-3.55 (4H, m), 3.91 (1H, d, J=10.0 Hz), 4.28 (1H, d, J=10.0 Hz), 5.03 (2H, s), 5.30 (1H, brs), 6.84 (2H, d, J=8.0 Hz), 7.24 (2H, d, J=8.0 Hz), 7.53 (1H, s).

Example 348

Preparation of 4-acetylbenzyl 4-(2-methyl-6-nitro-2,3-dihydroimidazo[2,1-b]oxazol-2-ylmethyl)piperazine-1-carboxylate A mixture of 4-(1,1-dimethoxyethyl)benzyl 4-(2-methyl-6-nitro-2,3-dihydroimidazo[2,1-b]oxazol-2-ylmethyl)piperazine-1-carboxylate (600 mg, 1.23 mmol), 1 N hydrochloric acid (10 ml, 10 mmol) and THF (15 ml) was stirred at room temperature for 2 hours, then neutralized with a saturated sodium hydrogencarbonate solution, and the resulting mixture was extracted with ethyl acetate. The oranic phase was washed with water and then with a saturated saline solution, dried over magnesium sulfate and then filtered. The filtrate was concentrated under reduced pressure. To the residue, diethyl ether was added, and the precipitates were filtered off to afford 4-acetylbenzyl 4-(2-methyl-6-nitro-2,3-dihydroimidazo[2,1-b]oxazol-2-ylmethyl)piperazine-1-carboxylate (558 mg, yield 99%) as a white powder.

Melting point 101-102° C.

Example 349

Preparation of 4-benzoylbenzyl 4-(2-methyl-6-nitro-2,3-dihydroimidazo[2,1-b]oxazol-2-ylmethyl)piperazine-1-carboxylate Using 4-[dimethoxy(phenyl)methyl]benzyl 4-(2-methyl-6-nitro-2,3-dihydroimidazo[2,1-b]oxazol-2-ylmethyl)piperazine-1-carboxylate (800 mg, 1.45 mmol) gave 4-benzoylbenzyl 4-(2-methyl-6-nitro-2,3-dihydroimidazo[2,1-b] oxazol-2-ylmethyl)piperazine-1-carboxylate (630 mg, yield 86%) as a white powder in the same manner as in Example 348.

Melting point 105-107° C.

Example 350

Preparation of 4-aminobenzyl 4-(2-methyl-6-nitro-2,3-dihydroimidazo[2,1-b]oxazol-2-ylmethyl)piperazine-1-carboxylate A mixture of 4-(tert-butoxycarbonylamino)-benzyl 4-(2-methyl-6-nitro-2,3-dihydroimidazo[2,1-b]oxazol-2-ylmethyl)piperazine-1-carboxylate (340 mg, 0.66 mmol), trifluoroacetic acid (2 ml) and methylene chloride (10 ml) was stirred at room temperature for 2 hours, and then neutralized with a saturated sodium hydrogencarbonate solution. The organic phase was washed with water and a saturated saline solution in this order, dried over magnesium sulfate and then filtered. The filtrate was concentrated under reduced pressure. To the residue, diethyl ether was added, and the precipitates were filtered off to afford 4-aminobenzyl 4-(2-methyl-6-nitro-2,3-dihydroimidazo[2,1-b]oxazol-2-ylmethyl)piperazine-1-carboxylate (100 mg, yield 37%) as a light yellow powder.

$^1$H-NMR (CDCl$_3$) δppm: 1.61 (3H, s), 2.35-2.70 (4H, m), 2.56 (1H, d, J=15.0 Hz), 2.85 (1H, d, J=15.0 Hz), 3.05-3.55 (4H, m), 3.69 (2H, brs), 3.91 (1H, d, J=10.0 Hz), 4.28 (1H, d, J=10.0 Hz), 4.98 (2H, s), 6.55 (2H, d, J=8.0 Hz), 7.14 (2H, d, J=8.0 Hz), 7.53 (1H, s)

Example 351

Preparation of 4-(2-methyl-6-nitro-2,3-dihydroimidazo-[2,1-b]oxazol-2-ylmethyl)piperazine-1-carboxylic acid phenylamide hydrochloride A mixture of 2-(4-tert-butoxycarbonylpiperazin-1-yl)methyl-2-methyl-6-nitro-2,3-dihydroimidazo[2,1-b]oxazole prepared in Example 306 (130 mg, 0.35 mmol) and trifluoroacetic acid (3 ml) was stirred at room temperature overnight. The reaction mixture was concentrated under reduced pressure, and the residue was dissolved in methylene chloride (3 ml), then neutralized with triethylamine (2 ml, 14.35 mmol). To the solution, phenylisocyanate (63 mg, 0.53 mmol) was added followed by stirring at room temperature for 30 minutes, and then diluted with water. The solution was extracted with methylene chloride, and the organic phase was dried over magnesium sulfate and then filtered. The filtrate was concentrated under reduced pressure. The residue was purified by silica gel column chromatography (methylene chloride/methanol=50/1) to afford an amorphous form.

The amorphous form was dissolved in ethyl acetate. To the solution, a saturated hydrochloric acid solution in ethyl acetate was added, and the resulting precipitates were filtered off to afford 4-(2-methyl-6-nitro-2,3-dihydroimidazo[2,1-b]oxazol-2-ylmethyl)piperazine-1-carboxylic acid phenylamide hydrochloride (124 mg, yield 55%) as a light yellow powder.

$^1$H-NMR (DMSO-d$_6$) δppm: 1.55 (3H, s), 2.50-2.56 (4H, m), 2.75 (2H, s), 3.21-3.40 (4H, m), 4.05 (1H, d, J=10.7 Hz), 4.24 (1H, d, J=10.7 Hz), 6.92-6.99 (1H, m), 7.21-7.28 (2H, m), 7.44-7.48 (2H, m), 8.13 (1H, s), 8.59 (1H, s)

Example 352

Preparation of 4-(2-methyl-6-nitro-2,3-dihydroimidazo-[2,1-b]oxazol-2-ylmethyl)piperazine-1-carboxylic acid isopropylamide A mixture of tert-butyl 4-(2-methyl-6-nitro-2,3-dihydroimidazo[2,1-b]oxazol-2-ylmethyl)piperazine-1-carboxylate prepared in Example 306 (140 mg, 0.38 mmol) and trifluoroacetic acid (3 ml) was stirred at room temperature overnight. The reaction mixture was concentrated under reduced pressure, and the residue was dissolved in methylene chloride (3 ml), then neutralized with triethylamine (2 ml, 14.35 mmol). To the solution, isopropylisocyanate (75 μl, 0.76 mmol) was added followed by stirring at room temperature for 1 hour, then diluted with water. The solution was extracted with methylene chloride. The organic phase was dried over magnesium sulfate and then filtered. The filtrate was concentrated under reduced pressure. The residue was purified by silica gel column chromatography (methylene chloride/methanol=50/1) to afford 4-(2-methyl-6-nitro-2,3-dihydroimidazo[2,1-b]oxazol-2-ylmethyl)piperazine-1-carboxylic acid isopropylamide (90 mg, yield 67%) as a white powder.

Melting point 175-176.3° C.

Using corresponding starting materials gave compounds of Examples 353 and 354 in the same manner as in Example 352.

Example 353

4-(2-Methyl-6-nitro-2,3-dihydroimidazo[2,1-b]oxazol-2-ylmethyl)piperazine-1-carboxylic acid (3-chlorophenyl)-amide $^1$H-NMR (DMSO-d$_6$) δppm: 1.56 (3H, s), 2.50-2.56 (4H, m), 2.77 (2H, s), 3.21-3.40 (4H, m), 4.08 (1H, d, J=10.7 Hz), 4.26 (1H, d, J=10.7 Hz), 6.95 (1H, bd, J=8.0 Hz), 7.23 (1H, t, J=8.0 Hz), 7.36 (1H, bd, J=8.0 Hz), 7.61 (1H, t, J=2.0 Hz), 8.13 (1H, s), 8.61 (1H, s)

Example 354

4-(2-Methyl-6-nitro-2,3-dihydroimidazo[2,1-b]oxazol-2-ylmethyl)piperazine-1-carboxylic acid cyclohexylamide Melting point 216.5-218.5° C.

Example 355

Preparation of 4-(2-methyl-6-nitro-2,3-dihydroimidazo-[2,1-b]oxazol-2-ylmethyl)piperazine-1-carbothioic acid (4-chlorophenyl)amide 2-Methyl-6-nitro-2-(piperazin-1-ylmethyl)-2,3-dihydroimidazo[2,1-b]oxazole dihydrochloride prepared in Example 322 (196 mg, 0.73 mmol) was suspended in methylene chloride (10 ml), then neutralized with triethylamine (0.27 ml, 1.94 mmol). To the solution, 4-chlorophenyl isothiocyanate (140 mg, 0.83 mmol) was added followed by stirring at room temperature for 1 hour. The reaction mixture was washed with water, a saturated sodium hydrogencarbonate solution and a saturated saline solution in this order, dried over sodiumسulfate and then filtered. The filtrate was concentrated under reduced pressure. The residue was purified by silica gel column chromatography (methylene chloride/methanol=30/1) to afford 4-(2-methyl-6-nitro-2,3-dihydroimidazo[2,1-b]oxazol-2-ylmethyl)piperazine-1-carbothioic acid (4-chlorophenyl)amide (128 mg, yield 40%) as a light brown powder.

Melting point 204-206° C. (decomposition)

Using corresponding starting materials gave compounds of Examples 356 and 357 in the same manner as in Example 355.

Example 356

4-(2-Methyl-6-nitro-2,3-dihydroimidazo[2,1-b]oxazol-2-ylmethyl)piperazine-1-carbothioic acid phenylamide Melting point 164-165° C. (decomposition)

Example 357

4-(2-Methyl-6-nitro-2,3-dihydroimidazo[2,1-b]oxazol-2-ylmethyl)piperazine-1-carbothioic acid (4-methoxyphenyl)amide Melting point 189-191° C. (decomposition).

Example 358

Preparation of 2-[4-(2-methyl-6-nitro-2,3-dihydroimidazo[2,1-b]oxazol-2-ylmethyl)piperazin-1-yl]benzoxazole 2-(4-tert-Butoxycarbonylpiperazin-1-yl)methyl-2-methyl-6-nitro-2,3-dihydroimidazo[2,1-b]oxazole prepared in Example 306 (500 mg, 1.36 mmol) was dissolved in trifluoroacetic acid (10 ml) followed by stirring at room temperature for 3 hours. The reaction mixture was concentrated under reduced pressure, and added methylene chloride (1 ml) and triethylamine (1 ml). The solution was stirred at room temperature for 5 minutes, and then concentrated under reduced pressure. The residue was dissolved in methylene chloride. To the solution, 2-chlorobenzoxazole (0.19 ml, 1.63 mmol) and triethylamine (0.23 ml, 1.63 mmol) were added followed by stirring at room temperature for 1 hour. The reaction mixture was poured into water, and extracted with methylene chloride. The organic phase was washed with a saturated saline solution, dried over magnesium sulfate and then filtered. The filtrate was concentrated under reduced pressure, and the residue was purified by silica gel column chromatography (methylene chloride/methanol=100/1) and crystallized from methylene chloride-diisopropyl ether to afford 2-[4-(2-methyl-6-nitro-2,3-dihydroimidazo[2,1-b]oxazol-2-ylmethyl)piperazin-1-yl]benzoxazole (325 mg, yield 62%) as a white powder.

MS 384(M$^+$) Melting point 228.0-229.5° C.

Using corresponding starting materials gave compounds of Examples 359 to 361 in the same manner as in Example 358.

Example 359

2-[4-(6-Nitro-2,3-dihydroimidazo[2,1-b]oxazol-2-ylmethyl)piperazin-1-yl]benzoxazole White powder, yield 74% MS 370(M$^+$) Melting point 206-209° C. (decomposition).

Example 360

2-{4-[2-(2-Methyl-6-nitro-2,3-dihydroimidazo[2,1-b]oxazol-2-yl)ethyl]piperazin-1-yl}benzoxazole White powder, yield 73% MS 398(M$^+$) Melting point 187.6-189.6° C.

Example 361

2-{4-[3-(2-Methyl-6-nitro-2,3-dihydroimidazo[2,1-b]oxazol-2-yl)propyl]piperazin-1-yl}benzoxazole White powder, yield 90% MS 412(M$^+$) Melting point 172.0-174.4° C.

Example 362

Preparation of tert-butyl (S)-4-[3-(2-chloro-4-nitroimidazol-1-yl)-2-hydroxypropyl]piperazine-1-carboxylate (R)-2-Chloro-1-[2-hydroxy-3-(4-methylbenzene-sulfonyloxy)propyl]-4-nitroimidazole prepared in Example 8 (16.86 g, 44.86 mmol) and tert-butyl piperazine-1-carboxylate (8.36 g, 44.89 mmol) were dissolved in acetonitrile (100 ml). To the solution, triethylamine (6.3 ml, 45.2 mmol) was added followed by stirring under reflux for 6 hours. The reaction mixture was allowed to return to room temperature, and concentrated under reduced pressure. To the residue, water (100 ml) was added and extracted with ethyl acetate (100 ml) twice. The organic phases were combined, washed with water (100 ml) and a saturated saline solution (100 ml) in this order, dried over sodium sulfate and then filtered. The filtrate was concentrated under reduced pressure, and the residue was purified by silica gel column chromatography (methylene chloride/methanol=40/1) and then recrystallized from ethyl acetate/n-hexane to afford tert-butyl (S)-4-[3-(2-chloro-4-nitroimidazol-1-yl)-2-hydroxypropyl]piperazine-1-carboxylate (11.61 g, yield 66%) as a light yellow powder.

$^1$H-NMR (CDCl$_3$) δppm: 1.46 (9H, s), 2.21-2.50 (4H, m), 2.54-2.70 (2H, m), 3.39-3.48 (4H, m), 3.65 (1H, s), 3.89-4.10 (2H, m), 4.20 (1H, dd, J=1.9 Hz, 13.5 Hz), 8.00 (1H, s).

Example 363

Preparation of tert-butyl (S)-4-[3-(2-chloro-4-nitroimidazol-1-yl)-2-hydroxypropyl]piperazine-1-carboxylate (alternative synthesis of the compound of Example 362)

A mixture of (R)-2-chloro-1-(oxiran-2-ylmethyl)-4-nitroimidazole prepared in Example 9 (1 g, 4.91 mmol), tert-butyl piperazine-1-carboxylate (1.01 g, 5.40 mmol) and DMF (3 ml) was stirred at 70° C. for 6 hours. The reaction mixture was allowed to return to room temperature and added water (7 ml). The precipitates were filtered off, and purified by silica gel column chromatography (methylene chloride/methanol=40/1) to afford tert-butyl (S)-4-[3-(2-chloro-4-nitroimidazol-1-yl)-2-hydroxypropyl]piperazine-1-carboxylate (967 mg, 51%) as a light yellow powder.

Example 364

Preparation of tert-butyl (R)-4-[3-(2-chloro-4-nitroimidazol-1-yl)-2-hydroxypropyl]piperazine-1-carboxylate A mixture of 2-chloro-4-nitro-1H-imidazole (6.1 g, 41.35 mmol), (S)-(+)-glycidyl tosylate (12.27 g, 53.75 mmol) and sodium hydrogencarbonate (7.3 g, 86.89 mmol) in ethanol (30 ml) was stirred under reflux for 9 hours. The reaction mixture was allowed to return to room temperature, then diluted with water, and the solution was extracted with methylene chloride twice. The extract was washed with a saturated saline solution, dried over magnesium sulfate and then filtered. The filtrate was concentrated to afford a foam. The resulting foam was dissolved in DMF (60 ml). To the solution, tert-butyl piperazine-1-carboxylate (8.47 g, 45.48 mmol), triethylamine (6.92 ml, 49.64 mmol) and sodium iodide (6.82 g, 45.5 mmol) were added followed by stirring at room temperature for 24 hours. The reaction mixture was poured into water, and extracted with ethyl acetate twice. The organic phases were combined, washed with water three times, dried over magnesium sulfate and then filtered. The filtrate was concentrated under reduced pressure. The resulting residue was purified by silica gel column chromatography (ethyl acetate) to afford tert-butyl (R)-4-[3-(2-chloro-4-nitroimidazol-1-yl)-2-hydroxypropyl]piperazin-1-carboxylate (6.43 g, yield 40%) as a light yellow oil.

$^1$H-NMR (CDCl$_3$) δppm: 1.48 (9H, s), 2.16-2.50 (4H, m), 2.55-2.69 (2H, m), 3.37-3.50 (4H, m), 3.65 (1H, s), 3.90-4.25 (3H, m), 8.00 (1H, s).

Example 365

Preparation of tert-butyl (S)-4-[3-(2-chloro-4-nitroimidazol-1-yl)-2-hydroxy-2-methylpropyl]-piperazine-1-carboxylate A mixture of (R)-2-chloro-1-(2-methyloxiran-2-ylmethyl)-4-nitroimidazole prepared in Example 12 (7.00 g, 32.2 mmol) and tert-butyl piperazine-1-carboxylate (6.29 g, 33.8 mmol) and DMF (70 ml) was stirred at 70° C. for 8 hours. The reaction mixture was allowed to return to room temperature, then diluted with water, and then the solution was extracted with ethyl acetate twice. The organic phases were combined, washed with water three times, dried over sodium sulfate and then filtered. The filtrate was concentrated under reduced pressure. To the residue, diethyl ether was added. The precipitates were filtered off, and dried at room temperature under reduced pressure to afford tert-butyl (S)-4-[3-(2-chloro-4-nitroimidazol-1-yl)-2-hydroxy-2-methylpropyl]piperazin-1-carboxylate (10.25 g, yield 79%) as a light yellow powder.

Optical purity >98.4% e.e. [α]$_D^{27}$=25.488 (concentration: 1.024, CHCl$_3$) $^1$H-NMR (CDCl$_3$) δppm: 1.14 (3H, s), 1.46 (9H, s), 2.34 (1H, d, J=13.9 Hz), 2.47-2.67 (5H, m), 3.26 (1H, s), 3.44 (4H, t, J=4.4 Hz), 3.99 (2H, s), 8.04 (1H, s).

Example 366

Preparation of tert-butyl (S)-4-[3-(2-chloro-4-nitroimidazol-1-yl)-2-hydroxy-2-methylpropyl]-piperazine-1-carboxylate (alternative synthesis of the compound of Example 365)

To the solution of 2-Chloro-4-nitro-1H-imidazole (89.4 g, 606 mmol) and tert-butyl (S)-4-(2-methyloxiran-2-ylmethyl)piperazine-1-carboxylate (119 g, 466 mmol) in ethanol (475 ml), sodium hydrogen-carbonate (58.7 g, 699 mmol) was added followed by stirring under reflux for 6 hours. The reaction mixture was concentrated under reduced pressure, and the residue was added water. The mixture was extracted with ethyl acetate, and the extract was dried over sodium sulfate and then filtered. The filtrate was concentrated under reduced pressure. The residue was dispersed into ethyl acetate, and filtered off to afford a solid. The filtrate was concentrated, and the residue was purified by silica gel column chromatography (n-hexane/acetone=3/1) to afford a solid. The solids were combined and dried under reduced pressure to afford tert-butyl (S)-4-[3-(2-chloro-4-nitroimidazol-1-yl)-2-hydroxy-2-methylpropyl]-piperazine-1-carboxylate (84.7 g, yield 45%) as a white powder.

Example 367

Preparation of (R)-4-[3-(2-chloro-4-nitroimidazol-1-yl)-2-hydroxy-2-methylpropyl]piperazine-1-carboxylate A mixture of (S)-2-chloro-1-(2-methyloxiran-2-ylmethyl)-4-nitroimidazole prepared in Example 18 (440 mg, 2.02 mmol), tert-butyl piperazine-1-carboxylate (414 mg, 2.22 mmol) and DMF (4 ml) was stirred at 55-60° C. for 9 hours. The reaction mixture was allowed to return to room temperature, then diluted with water (24 ml), and the solution was extracted with ethyl acetate (10 ml) twice. The organic phases were combined, washed with water (20 ml) three times and a saturated saline solution (10 ml), dried over sodium sulfate and then filtered. The filtrate was concentrated under reduced pressure, and the residue treated with diethyl ether to afford tert-butyl (R)-4-[3-(2-chloro-4-nitroimidazol-1-yl)-2-hydroxy-2-methylpropyl]piperazine-1-carboxylate (662 mg, yield 81%) as a light yellow powder.

$^1$H-NMR (CDCl$_3$) δppm: 1.15 (3H, s), 1.45 (9H, s), 2.34 (1H, d, J=13.9 Hz), 2.48-2.67 (5H, m), 3.27 (1H, s), 3.44 (4H, t, J=4.4 Hz), 3.99 (2H, s), 8.04 (1H, s).

Using 2-chloro-4-nitro-1H-imidazole and tert-butyl (R)-4-(2-methyloxiran-2-ylmethyl)piperazine-1-carboxylate gave the compound of Example 368 in the same manner as in Example 366.

Example 368

Tert-butyl (R)-4-[3-(2-chloro-4-nitroimidazol-1-yl)-2-hydroxy-2-methylpropyl]piperazine-1-carboxylate (alternative synthesis of the compound of Example 367)

White powder, yield 20%.

Example 369

Preparation of (S)-1-(2-chloro-4-nitroimidazol-1-yl)-2-methyl-3-[4-(4-trifluoromethoxyphenyl)piperazin-1-yl]propan-2-ol To a suspension of (S)-1-(2-methyloxiran-2-ylmethyl)-4-(4-trifluoromethoxyphenyl)piperazine (0.43 g, 1.37 mmol) and 2-chloro-4-nitro-1H-imidazole (0.22 g, 1.51 mmol) in acetonitrile (4 ml), sodium hydrogencarbonate (0.17 g, 2.06 mmol) was added followed by stirring under reflux for 9 hours. To the reaction mixture, water was added, and the mixture was extracted with ethyl acetate. The organic phase was dried over magnesium sulfate and concentrated under reduced pressure. The residue was purified by silica gel column chromatography (n-hexane/ethyl acetate=3/1) to afford (S)-1-(2-chloro-4-nitroimidazol-1-yl)-2-methyl-3-[4-(4-trifluoromethoxyphenyl)piperazin-1-yl]propan-2-ol (0.20 g, yield 31%) as a light yellow oil.

$^1$H-NMR (CDCl$_3$) δppm: 1.18 (3H, s), 2.41 (1H, d, J=13.8 Hz), 2.56 (1H, d, J=13.8 Hz), 2.67-2.80 (2H, m), 2.85-2.96 (2H, m), 3.13-3.25 (4H, m), 4.03 (2H, s), 6.83-6.93 (2H, m), 7.07-7.17 (2H, m), 8.07 (1H, s).

Example 370

Preparation of (S)-1-(2-chloro-4-nitroimidazol-1-yl)-2-methyl-3-[4-(4-chlorophenyl)piperazin-1-yl]propan-2-ol (R)-2-Chloro-1-(2-methyloxiran-2-ylmethyl)-4-nitroimidazole prepared in Example 12 (20 g, 91.9 mmol) and 1-(4-chlorophenyl)piperazine (20.8 g, 0.11 mol) were added to DMF (200 ml) followed by stirring at 70-75° C. for 5 hours. The reaction mixture was allowed to return to room temperature, poured into water, and extracted with ethyl acetate. The organic phase was washed with a saturated saline solution, dried over sodium sulfate and then filtered. The filtrate was concentrated under reduced pressure. The residue was purified by silica gel column chromatography (methylene chloride/ethyl acetate=20/1) to afford (S)-1-(2-chloro-4-nitroimidazol-1-yl)-2-methyl-3-[4-(4-chlorophenyl)piperazin-1-yl]propan-2-ol (33.0 g, yield 87%) as a yellow amorphous form.

$^1$H-NMR (CDCl$_3$) δppm: 1.53 (3H, s), 2.42 (1H, d, J=13.9 Hz), 2.55 (1H, d, J=13.9 Hz), 2.67-2.76 (2H, m), 2.81-2.90 (2H, m), 3.13-3.17 (4H, m), 3.43 (1H, s), 4.03 (2H, s), 6.78-6.85 (2H, m), 7.16-7.23 (2H, m), 8.06 (1H, s).

Using corresponding starting materials gave compounds of Examples 371 to 384 shown in the following table in the same manner as in Example 370.

TABLE 17

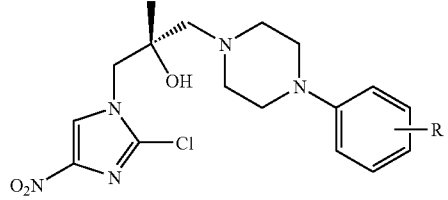

| Example | R | Yield (%) | $^1$H NMR(CDCl$_3$) δ |
|---|---|---|---|
| 371 | 4-CF$_3$ | 82 | 1.18(3H, s), 2.41(1H, d, J=13.9Hz), 2.56(1H, d, J=13.9Hz), 2.68-2.79(2H, m), 2.82-2.91(2H, m), 3.26-3.31(5H, m), 4.03(2H, s), 6.91(2H, d, J=8.7Hz), 7.49(2H, d, J=8.7Hz), 8.06(1H, s), |
| 372 | 4-H | 92 | 1.17(3H, s), 2.40(1H, d, J=13.9Hz), 2.55(1H, d, J=13.9Hz), 2.69-2.78(2H, m), 2.83-2.91(2H, m), 3.18-3.22(4H, m), 3.42(1H, s), 4.01(2H, s), 6.85-6.93(3H, m), 7.24-7.31(2H, m), 8.06(1H, s). |
| 373 | 4-F | 43 | 1.16(3H, s), 2.41(1H, d, J=13.9Hz), 2.55(1H, d, J=13.9Hz), 2.69-2.77(2H, m), 2.82-2.91(2H, m), 3.10-3.14(4H, m), 3.41(1H, s), 4.01(2H, s), 6.83-7.00(4H, m), 8.06(1H, s). |
| 374 | 4-OMe | 99 | 1.15(3H, s), 2.42(1H, d, J=13.9Hz), 2.55(1H, d, J=13.9Hz), 2.69-2.78(2H, m), 2.82-2.91(2H, m), 3.07-3.11(4H, m), 3.77(3H, s), 4.02(2H, s), 6.81-6.91(4H, m), 8.07(1H, s). |
| 375 | 4-COOEt | 100 | 1.17(3H, s), 1.37(3H, t, J=7.1Hz), 2.42(1H, d, J=13.9Hz), 2.55(1H, d, J=13.9Hz), 2.68-2.76(2H, m), 2.81-2.89(2H, m), 3.31-3.35(4H, m), 3.40(1H, s), 4.04(2H, s), 4.33(2H, q, J=7.1Hz), 6.83-6.87(2H, m), 7.90-7.95(2H, m), 8.06(1H, s). |
| 376 | 4-Me | 86 | 1.15(3H, s), 2.27(3H, s), 2.41(1H, d, J=13.9Hz), 2.55(1H, d, J=13.9Hz), 2.68-2.77(2H, m), 2.82-2.90(2H, m), 3.12-3.16(4H, m), 3.47(1H, s), 4.01(2H, s), 6.81-6.85(2H, m), 7.06-7.09(2H, m), 8.06(1H, s). |
| 377 | 4-CN | 99 | 1.18(3H, s), 2.43(1H, d, J=13.9Hz), 2.56(1H, d, J=13.9Hz), 2.66-2.75(2H, m), 2.81-2.90(2H, m), 3.31-3.35(4H, m), 3.51(1H, s), 4.03(1H, d, J=14.3Hz), 4.09(1H, d, J=14.3Hz), 6.82-6.88(2H, m), 7.46-7.52(2H, m), 8.07(1H, s). |
| 378 | 3,4-di-Cl | 99 | 1.17(3H, s), 2.41(1H, d, J=13.9Hz), 2.55(1H, d, J=13.9Hz), 2.68-2.76(2H, m), 2.80-2.89(2H, m), 3.15-3.19(4H, m), 3.40(1H, s), 4.03(2H, s), 6.72(1H, dd, J=8.9, 2.9Hz), 6.94(1H, d, J=2.9Hz), 7.28(1H, d, J=8.9Hz), 8.05(1H, s). |
| 379 | 3-CF$_3$ | 99 | 1.17(3H, s), 2.42(1H, d, J=13.9Hz), 2.56(1H, d, J=13.9Hz), 2.69-2.78(2H, m), 2.83-2.93(2H, m), 3.22-3.27(4H, m), 3.36(1H, s), 4.03(2H, s), 7.03-7.11(3H, m), 7.32-7.39(1H, m), 8.06(1H, s). |
| 380 | 2-CF$_3$ | 99 | 1.16(3H, s), 2.44(1H, d, J=14.0Hz), 2.57(1H, d, J=14.0Hz), 2.67-2.78(2H, m), 2.81-2.91(2H, m), 2.93-2.96(4H, m), 3.81(1H, s), 4.05(2H, s), 7.21-7.27(1H, m), |

TABLE 17-continued

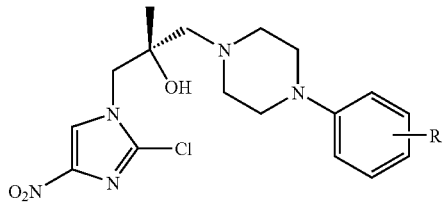

| Example | R | Yield (%) | ¹H NMR(CDCl₃) δ |
|---|---|---|---|
| 381 | 4-Cl-3-CF₃ | 99 | 7.35-7.39(1H, m), 7.50-7.57(1H, m), 7.60-7.64(1H, m), 8.11(1H, s).<br>1.18(3H, s), 2.42(1H, d, J=13.9Hz), 2.56(1H, d, J=13.9Hz), 2.68-2.77(2H, m), 2.83-2.92(2H, m), 3.19-3.24(4H, m), 3.40(1H, s), 4.04(2H, s), 6.95(1H, dd, J=8.9, 2.9Hz), 7.16(1H, d, J=2.9Hz), 7.34(1H, d, J=8.9Hz), 8.06(1H, s). |
| 382 | 4-COOᵗBu | 99 | 1.17(3H, s), 1.57(9H, s), 2.42(1H, d, J=13.9Hz), 2.55(1H, d, J=13.9Hz), 2.67-2.76(2H, m), 2.81-2.90(2H, m), 3.29-3.33(4H, m), 3.51(1H, s), 4.04(2H, s), 6.84(2H, d, J=9.0Hz), 7.87(2H, d, J=9.0Hz), 8.07(1H, s). |
| 383 | 2-F | 99 | 1.16(3H, s), 2.42(1H, d, J=13.9Hz), 2.57(1H, d, J=13.9Hz), 2.71-2.80(2H, m), 2.85-2.96(2H, m), 3.10-3.14(4H, m), 3.56(1H, s), 4.02(2H, s), 6.91-7.10(4H, m), 8.07(1H, s). |
| 384 | 4-NMe₂ | 82 | 1.14(3H, s), 2.40(1H, d, J=13.9Hz), 2.54(1H, d, J=13.9Hz), 2.70-2.77(2H, m), 2.81-2.91(8H, m), 3.05-3.09(4H, m), 3.66(1H, s), 4.01(2H, s), 6.72-6.76(2H, m), 6.86-6.91(2H, m), 8.07(1H, s). |

Using corresponding starting materials gave compounds of Examples 385 and 386 in the same manner as in Example 370.

Example 385

(S)-1(2-Chloro-4-nitroimidazol-1-yl)-2-methyl-3-[4-(4-pyridyl)piperazin-1-yl]propan-2-ol Yield 100% ¹H-NMR (CDCl₃) δppm: 1.18 (3H, s), 2.44 (1H, d, J=13.9 Hz), 2.56 (1H, d, J=13.9 Hz), 2.63-2.73 (2H, m), 2.77-2.91 (2H, m), 3.31-3.35 (4H, m), 3.54 (1H, s), 4.03-4.12 (2H, m), 6.63-6.66 (2H, m), 8.09 (1H, s), 8.23-8.27 (2H, m).

Example 386

(S)-1(2-Chloro-4-nitroimidazol-1-yl)-2-methyl-3-[4-(3-pyridyl)piperazin-1-yl]propan-2-ol Yield 81% ¹H-NMR (CDCl₃) δppm: 1.17 (3H, s), 2.44 (1H, d, J=13.9 Hz), 2.57 (1H, d, J=13.9 Hz), 2.67-2.79 (2H, m), 2.84-2.93 (2H, m), 3.20-3.25 (4H, m), 3.85 (1H, bs), 4.06 (2H, s), 7.16-7.19 (2H, m), 8.07-8.11 (2H, m), 8.26-8.28 (1H, m).

Using (R)-2-chloro-4-nitro-1-(oxiran-2-ylmethyl)imidazole prepared in Example 9 gave compounds of Examples 387 to 389 in the same manner as in Example 370.

Example 387

(S)-1-(2-Chloro-4-nitroimidazol-1-yl)-3-[4-(4-fluorophenyl)piperazin-1-yl]propan-2-ol Yield 86% ¹H-NMR (CDCl₃) δppm: 2.27-2.36 (1H, m), 2.49-2.63 (3H, m), 2.78-2.88 (2H, m), 2.97-3.18 (4H, m), 3.74 (1H, br), 3.96-4.08 (2H, m), 4.18-4.24 (1H, m), 6.84-7.01 (4H, m), 8.02 (1H, s).

Example 388

(S)-1-(2-Chloro-4-nitroimidazol-1-yl)-3-[4-(4-trifluoromethylphenyl)piperazin-1-yl]propan-2-ol Yield 49% ¹H-NMR (CDCl₃) δppm: 2.27-2.36 (1H, m), 2.49-2.63 (3H, m), 2.78-2.87 (2H, m), 3.28-3.31 (4H, m), 3.62 (1H, br), 3.95-4.11 (2H, m), 4.19-4.25 (1H, m), 6.92 (2H, d, J=8.6 Hz), 7.49 (2H, d, J=8.6 Hz), 8.02 (1H, s).

Example 389

(S)-1-(2-Chloro-4-nitroimidazol-1-yl)-3-[4-(4-cyanophenyl)piperazin-1-yl]propan-2-ol Yield 100% ¹H-NMR (CDCl₃) δppm: 2.28-2.37 (1H, m), 2.49-2.63 (3H, m), 2.76-2.85 (2H, m), 3.28-3.36 (4H, m), 3.58 (1H, br), 3.96-4.12 (2H, m), 4.19-4.25 (1H, m), 6.87 (2H, d, J=8.9 Hz), 7.51 (2H, d, J=8.9 Hz), 8.01 (1H, s)

Example 390

Preparation of 4-trifluoromethoxybenzyl (S)-4-[3-(2-chloro-4-nitroimidazol-1-yl)-2-hydroxy-2-methylpropyl]-piperazine-1-carboxylate A mixture of (R)-2-chloro-1-(2-methyloxiran-2-ylmethyl)-4-nitroimidazole prepared in Example 12 (15 g, 68.93 mmol) and 4-trifluoromethoxybenzyl piperazine-1-carboxylate (25.17 g, 82.72 mmol) in DMF (75 ml) was stirred at 65-70° C. for 20 hours. The reaction mixture was allowed to return to room temperature and poured into water (475 ml), and extracted with ethyl acetate (150 ml). The aqueous layer was extracted with ethyl acetate (150 ml) again. The organic phases were combined, washed with water (400 ml) 3 times and a saturated saline solution (100 ml), dried over sodium sulfate and then filtered. The filtrate was concentrated under reduced pressure. The residue was purified by silica gel column chromatography (ethyl acetate/n-hexane=1/2) to afford 4-trifluoromethoxybenzyl (S)-4-[3-(2-chloro-4-nitroimidazol-1-yl)-2-hydroxy-2-methylpropyl]-piperazine-1-carboxylate (29.98 g, yield 83%) as a yellow oil.

$^1$H-NMR (CDCl$_3$) δppm: 1.15 (3H, s), 2.36 (1H, d, J=14.0 Hz), 2.42-2.75 (5H, m), 3.18 (1H, s), 3.42-3.58 (4H, m), 4.00 (2H, s), 5.12 (2H, s), 7.21 (2H, d, J=8.6 Hz), 7.38 (2H, d, J=8.6 Hz), 8.03 (1H, s).

Example 391

Preparation of 3-(4-trifluoromethylphenyl)-2-propenyl (S)-4-[3-(2-chloro-4-nitroimidazol-1-yl)-2-hydroxy-2-methylpropyl]piperazine-1-carboxylate A mixture of (R)-2-chloro-1-(2-methyloxiran-2-ylmethyl)-4-nitroimidazole prepared in Example 12 (4.24 g, 19.48 mmol) and 3-(4-trifluoromethylphenyl)-2-propenyl piperazine-1-carboxylate (6.73 g, 21.41 mmol) in DMF (21 ml) were stirred at 50-55° C. for 24 hours. The reaction mixture was allowed to return to room temperature and poured into water (90 ml), and extracted with ethyl acetate (60 ml). The aqueous layer was extracted with ethyl acetate (60 ml) again. The organic phases were combined, washed with water (90 ml) 3 times and a saturated saline solution (60 ml), dried over sodium sulfate and then filtered. The filtrate was concentrated under reduced pressure, and the residue was purified by silica gel column chromatography (ethyl acetate/n-hexane=1/1) to afford 3-(4-trifluoromethylphenyl)-2-propenyl (S)-4-[3-(2-chloro-4-nitroimidazol-1-yl)-2-hydroxy-2-methylpropyl]piperazine-1-carboxylate (9.29 g, yield 90%) as a yellow oil.

$^1$H-NMR (CDCl$_3$) δppm: 1.16 (3H, s), 2.36 (1H, d, J=14.0 Hz), 2.43-2.76 (5H, m), 3.17 (1H, s), 3.48-3.67 (4H, m), 4.00 (2H, s), 4.78 (2H, dd, J=1.0 Hz, 6.1 Hz), 6.33-6.48 (1H, m), 6.66 (1H, d, J=15.9 Hz), 7.48 (2H, d, J=8.3 Hz), 7.58 (2H, d, J=8.3 Hz), 8.04 (1H, s).

Using corresponding starting materials gave the compound of Example 392 in the same manner as in Example 391.

Example 392

3-(4-Trifluoromethoxyphenyl)-2-propenyl (S)-4-[3-(2-chloro-4-nitroimidazol-1-yl)-2-hydroxy-2-methylpropyl]-piperazine-1-carboxylate $^1$H-NMR (CDCl$_3$) δppm: 1.15 (3H, s), 2.36 (1H, d, J=13.9 Hz), 2.51 (1H, d, J=13.9 Hz), 2.48-2.63 (2H, m), 2.63-2.78 (2H, m), 3.17 (1H, s), 3.39-3.63 (4H, m), 4.00 (2H, s), 4.75 (2H, dd, J=1.1 Hz, 6.3 Hz), 6.28 (1H, dt, J=6.3 Hz, 15.9 Hz), 6.62 (1H, d, J=15.9 Hz), 7.15-7.18 (2H, m), 7.38-7.42 (2H, m), 8.03 (1H, s).

Example 393

Preparation of tert-butyl (S)-4-(2-methyl-6-nitro-2,3-dihydroimidazo[2,1-b]oxazol-2-ylmethyl)piperazine-1-carboxylate Tert-butyl (S)-4-[3-(2-chloro-4-nitroimidazol-1-yl)-2-hydroxy-2-methylpropyl]-piperazine-1-carboxylate prepared in Example 365 (10.25 g, 25.4 mmol) was dissolved in DMF (30 ml). To the solution, sodium hydride (1.12 g, 27.9 mmol) was added followed by stirring for 2 hours with cooling on ice-bath. To the reaction mixture, ethyl acetate (10 ml) and water (70 ml) were added. The precipitates were filtered off, and washed with water. The crude solids were recrystallized from ethyl acetate (70 ml) to afford tert-butyl (S)-4-(2-methyl-6-nitro-2,3-dihydroimidazo[2,1-b]oxazol-2-ylmethyl)piperazine-1-carboxylate (6.62 g, yield 71%) as a light yellow powder.

Optical purity >99.5% e.e. [α]$_D^{27}$=−20.953° (concentration: 0.492, CHCl$_3$) $^1$H-NMR (CDCl$_3$) δppm: 1.44 (9H, s), 1.62 (3H, s), 2.45-2.66 (5H, m), 2.87 (1H, d, J=14.9 Hz), 3.29 (4H, br), 3.92 (1H, d, J=9.7 Hz), 4.30 (1H, d, J=9.7 Hz), 7.53 (1H, s).

Example 394

Preparation of tert-butyl (S)-4-(6-nitro-2,3-dihydroimidazo[2,1-b]oxazol-2-ylmethyl)piperazine-1-carboxylate Using tert-butyl (S)-4-[3-(2-chloro-4-nitroimidazol-1-yl)-2-hydroxypropyl]piperazine-1-carboxylate prepared in Example 363 (11 g, 28.22 mmol) gave tert-butyl (S)-4-(6-nitro-2,3-dihydroimidazo[2,1-b]oxazol-2-ylmethyl)piperazine-1-carboxylate (7.5 g, yield 75%) as a light yellow powder in the same manner as in Example 393.

Optical purity 96.6% e.e. [α]$_D^{22}$=−11.91° (concentration: 1.016, CHCl$_3$) $^1$H-NMR (CDCl$_3$) δppm: 1.45 (9H, s), 2.49-2.59 (4H, m), 2.85 (2H, d, J=5.2 Hz), 3.33-3.44 (4H, m), 4.19 (1H, dd, J=6.9 Hz, 10.2 Hz), 4.35 (1H, dd, J=6.9 Hz, 10.2 Hz), 5.36-5.49 (1H, m), 7.55 (1H, s).

Example 395

Preparation of tert-butyl (R)-4-(6-nitro-2,3-dihydroimidazo[2,1-b]oxazol-2-ylmethyl)piperazine-1-carboxylate Tert-butyl (R)-4-[3-(2-chloro-4-nitroimidazol-1-yl)-2-hydroxypropyl]piperazine-1-carboxylate prepared in Example 364 (6.43 g, 16.49 mmol) was dissolved in 1,4-dioxane (35 ml). To the solution, sodium hydride (730 mg, 18.25 mmol) was added with cooling on ice-bath, and the resulting solution was stirred at room temperature overnight and then stirred under reflux for 24 hours. The reaction mixture was allowed to return to room temperature and concentrated under reduced pressure. To the residue, water was added slowly, the mixture was extracted with methylene chloride twice, dried over sodium sulfate and then filtered. The filtrate was concentrated under reduced pressure. The residue was purified by silica gel column chromatography (ethyl acetate) to afford tert-butyl (R)-4-(6-nitro-2,3-dihydroimidazo[2,1-b]oxazol-2-ylmethyl)piperazine-1-carboxylate (1.23 g, yield 21%) as a white powder.

Optical purity >99% e.e. [α]$_D^{27}$=11.635° (concentration: 1.004, CHCl$_3$) $^1$H-NMR (CDCl$_3$) δppm: 1.45 (9H, s), 2.50-2.61 (4H, m), 2.85 (2H, d, J=5.3 Hz), 3.31-3.50 (4H, m), 4.18 (1H, dd, J=6.9 Hz, 10.2 Hz), 4.35 (1H, dd, J=8.4 Hz, 10.2 Hz), 5.35-5.50 (1H, m), 7.55 (1H, s).

Example 396

Preparation of tert-butyl (R)-4-(2-methyl-6-nitro-2,3-dihydroimidazo[2,1-b]oxazol-2-ylmethyl)piperazine-1-carboxylate Tert-butyl (R)-4-[3-(2-chloro-4-nitroimidazol-1-yl)-2-hydroxy-2-methylpropyl]-piperazine-1-carboxylate prepared in Example 368 (376 mg, 0.93 mmol) was dissolved in 1,4-dioxane (10 ml). To the solution, sodium hydride (45 mg, 1.12 mmol) was added with cooling on ice-bath, and the resulting solution was stirred at room temperature for 30 minutes and then stirred under reflux for 24 hours. The reaction mixture was allowed to return to room temperature and concentrated under reduced pressure. To the residue, water was added slowly, and the solution was extracted with ethyl acetate twice. The organic phase was dried over sodium sulfate and then filtered. The filtrate was concentrated under reduced pressure. The residue was purified by silica gel column chromatography (n-hexane/acetone=3/1) to afford tert-butyl (R)-4-(2-methyl-6-nitro-2,3-dihydroimidazo[2,1-b]oxazol-2-ylmethyl)piperazin-1-carboxylate (239 mg, yield 70%) as a white powder.

Optical purity 99.2% e.e. $[\alpha]_D^{27}$=21.073° (concentration: 0.522, CHCl$_3$) $^1$H-NMR (CDCl$_3$) δppm: 1.45 (9H, s), 1.61 (3H, s), 2.45-2.64 (5H, m), 2.87 (1H, d, J=14.9 Hz), 3.29 (4H, br), 3.92 (1H, d, J=9.7 Hz), 4.33 (1H, d, J=9.7 Hz), 7.52 (1H, s).

Example 397

Preparation of (S)-2-[4-(4-trifluoromethoxyphenyl)-piperazin-1-ylmethyl]-2-methyl-6-nitro-2,3-dihydroimidazo[2,1-b]oxazole To a solution of (S)-1-(2-chloro-4-nitroimidazol-1-yl)-2-methyl-3-[4-(4-trifluoromethoxyphenyl)piperazin-1-yl]propan-2-ol prepared in Example 369 (5.85 g, 12.61 mmol) in THF (150 ml), sodium hydride (0.66 g, 18.92 mmol) was added with cooling on ice-bath followed by stirring under reflux for 6 hours. The reaction mixture was concentrated under reduced pressure, and the residue was added water and ethyl acetate. The precipitates were filtered off, purified by silica gel column chromatography (n-hexane/ethyl acetate=1/1) and recrystallized from isopropanol to afford (S)-2-[4-(4-trifluoromethoxyphenyl)piperazin-1-yl]methyl-2-methyl-6-nitro-2,3-dihydroimidazo[2,1-b]oxazole (2.58 g, yield 48%) as a light yellow solid.

Optical purity 99.8% e.e. $[\alpha]_D^{26}$=8.80° (concentration: 1.000, CHCl$_3$) Melting point 129-130° C.

Example 398

Preparation of (S)-2-[4-(4-chlorophenyl)piperazin-1-ylmethyl]-2-methyl-6-nitro-2,3-dihydroimidazo[2,1-b]oxazole (S)-1-(2-Chloro-4-nitroimidazol-1-yl)-2-methyl-3-[4-(4-chlorophenyl)piperazin-1-yl]propan-2-ol prepared in Example 370 (33.0 g, 79.7 mmol) was dissolved in DMF (300 ml). To the solution, sodium hydride (3.7 g, 91.6 mmol) was added with cooling on ice-bath followed by stirring at room temperature overnight. To the reaction mixture, ice-water and ethyl acetate were added, and the solution was vigorously stirred. The precipitates were filtered off, washed with water and ethyl acetate, and dried under reduced pressure to afford 23.2 g of a crude light yellow powder. The crude powder was combined with another crude powder synthesized in the same manner (50 g), and the mixture was purified by silica gel column chromatography (methylene chloride/ethyl acetate=50/1) and crystallized from methylene chloride-ethyl acetate to afford (S)-2-[4-(4-chlorophenyl)piperazin-1-ylmethyl]-2-methyl-6-nitro-2,3-dihydroimidazo[2,1-b]oxazole (45 g, yield 90%) as a white powder.

Optical purity 99.6% e.e. $[\alpha]_D^{22}$=−10.20° (concentration: 0.5, CHCl$_3$) Melting point 218-219.6° C.

Using corresponding starting materials gave compounds of Examples 399 to 403 in the same manner as in Example 398.

Example 399

(S)-2-[4-(4-Fluorophenyl)piperazin-1-ylmethyl]-6-nitro-2,3-dihydroimidazo[2,1-b]oxazole Yield 42%, $[\alpha]_D^{28}$=2.10° (concentration: 0.5, CHCl$_3$) Melting point 178.5-179.5° C.

Example 400

(S)-2-[4-(3-Pyridyl)piperazin-1-ylmethyl]-2-methyl-6-nitro-2,3-dihydroimidazo[2,1-b]oxazole Yield 42%, melting point 145-147.7° C.

Example 401

(S)-2-[4-(4-Pyridyl)piperazin-1-ylmethyl]-2-methyl-6-nitro-2,3-dihydroimidazo[2,1-b]oxazole Yield 3% $^1$H-NMR (CDCl$_3$) δppm: 1.65 (3H, s), 2.62 (1H, d, J=14.8 Hz), 2.64-2.71 (2H, m), 2.79-2.89 (2H, m), 2.92 (1H, d, J=14.8 Hz), 3.15-3.30 (4H, m), 3.95 (1H, d, J=9.7 Hz), 4.33 (1H, d, J=9.7 Hz), 6.60 (2H, d, J=6.2 Hz), 7.53 (1H, s), 8.26 (2H, d, J=6.2 Hz)

Example 402

(S)-2-[4-(4-Trifluoromethylphenyl)piperazin-1-ylmethyl]-6-nitro-2,3-dihydroimidazo[2,1-b]oxazole Melting point 175.8-176.6° C.

Example 403

(S)-2-[4-(4-Cyanophenyl)piperazin-1-ylmethyl]-6-nitro-2,3-dihydroimidazo[2,1-b]oxazole Melting point 211-211.5° C.

Example 404

Preparation of (S)-2-[4-(4-chlorophenyl)piperazin-1-ylmethyl]-6-nitro-2,3-dihydroimidazo[2,1-b]oxazole 1-(4-Chlorophenyl)piperazine dihydrochloride (1.31 g, 4.86 mmol) was added to a sodium hydroxide solution, and the resulting mixture was extracted with methylene chloride. The extract was dried over sodium sulfate and then filtered. The filtrate was concentrated under reduced pressure to afford 1-(4-chlorophenyl)piperazine.

Then, a mixture of 1-(4-chlorophenyl)-piperazine obtained, (R)-2-chloro-1-(oxiran-2-ylmethyl)-4-nitroimidazole prepared in Example 9 (763 mg, 3.75 mmol) and DMF (5 ml) was stirred at 70° C. for 6 hours. To the solution, sodium hydride (219 mg, 5.48 mmol) was added with cooling on ice-bath followed by stirring at room temperature for 2 hours. To the reaction mixture, ice-water was added, and precipitates were filtered off. The resulting solids were recrystallized from acetone/water to afford (S)-2-[4-(4-chlorophenyl)piperazin-1-ylmethyl]-6-nitro-2,3-dihydroimidazo[2,1-b]oxazole (250 mg, yield 18%) as a light yellow powder.

Melting point 183-183.5° C.

Example 405

Preparation of 4-trifluoromethoxybenzyl (S)-4-(2-methyl-6-nitro-2,3-dihydroimidazo[2,1-b]oxazol-2-ylmethyl)piperazine-1-carboxylate 4-Trifluoromethoxybenzyl (S)-4-[3-(2-chloro-4-nitroimidazol-1-yl)-2-hydroxy-2-methylpropyl]-piperazine-1-carboxylate prepared in Example 390 (4.3 g, 8.24 mmol) was dissolved in DMF (13 ml). To the solution, sodium hydride (430 mg, 10.7 mmol) was added followed by stirring at the same temperature for 2 hours with cooling on ice-bath. To the reaction mixture, ethyl acetate (4.3 ml) and water (30 ml) were added in this order, and the solution was stirred for 30 minutes. The precipitates were filtered off and washed with water. The solids obtained were recrystallized from ethyl acetate/isopropyl ether and then recrystallized from isopropyl alcohol to afford 4-trifluoromethoxybenzyl (S)-4-(2-methyl-6-nitro-2,3-dihydroimidazo[2,1-b]oxazol-2-ylmethyl)piperazine-1-carboxylate (3.15 g, yield 79%) as a white powder.

Melting point 139.5-140.5° C. Optical purity >99.5% e.e. $[\alpha]_D^{27}$=18.04° (concentration: 1.020, $CHCl_3$) $^1$H-NMR ($CDCl_3$) δppm: 1.60 (3H, s), 2.39-2.75 (5H, m), 2.87 (1H, d, J=14.9 Hz), 3.14-3.56 (4H, m), 3.93 (1H, d, 9.7 Hz), 4.29 (1H, d, J=9.7 Hz), 5.10 (2H, s), 7.19 (2H, d, J=8.6 Hz), 7.36 (2H, d, J=8.6 Hz), 7.54 (1H, s)

Example 406

Preparation of 3-(4-trifluoromethylphenyl)-2-propenyl (S)-4-(2-methyl-6-nitro-2,3-dihydroimidazo[2,1-b]oxazol-2-ylmethyl)piperazine-1-carboxylate 3-(4-Trifluoromethylphenyl)-2-propenyl (S)-4-[3-(2-chloro-4-nitroimidazol-1-yl)-2-hydroxy-2-methyl-propyl]piperazine-1-carboxylate prepared in Example 391 (13.2 g, 24.81 mmol) was dissolved in DMF (40 ml). To the solution, sodium hydride (1.19 g, 29.78 mmol) was added followed by stirring for 1.5 hours with cooling on ice-bath. To the reaction mixture, ethyl acetate (13 ml) and water (92 ml) were added in this order followed by stirring for 30 minutes. The precipitates were filtered off, washed with water and purified by silica gel column chromatography (ethyl acetate) to afford 3-(4-trifluoromethylphenyl)-2-propenyl (S)-4-(2-methyl-6-nitro-2,3-dihydroimidazo[2,1-b]oxazol-2-ylmethyl)piperazine-1-carboxylate (10.17 g, yield 83%) as a light yellow powder.

Melting point 132-133° C. Optical purity 99.0% e.e. $[\alpha]_D^{27}$=−21.73° (concentration: 0.866, $CHCl_3$) $^1$H-NMR ($CDCl_3$) δppm: 1.62 (3H, s), 2.48-2.75 (5H, m), 2.88 (1H, d, J=14.9 Hz), 3.15-3.57 (4H, m), 3.94 (1H, d, J=9.7 Hz), 4.29 (1H, d, J=9.7 Hz), 4.75 (2H, d, J=1.15 Hz, 6.0 Hz), 6.29-6.42 (1H, m), 6.64 (1H, d, J=15.9 Hz), 7.47 (2H, d, J=8.4 Hz), 7.52-7.62 (3H, m).

Using corresponding starting materials gave the compound of Example 407 in the same manner as in Example 406.

Example 407

3-(4-Trifluoromethoxyphenyl)-2-propenyl (S)-4-(2-methyl-6-nitro-2,3-dihydroimidazo[2,1-b]oxazol-2-ylmethyl)piperazine-1-carboxylate Melting point 91-93° C. $[\alpha]_D^{27}$=−21.88° (concentration: 0.786, $CHCl_3$) $^1$H-NMR ($CDCl_3$) δppm: 1.54 (3H, s), 2.38-2.71 (5H, m), 2.84 (1H, d, J=14.9 Hz), 3.13-3.54 (4H, m), 3.92 (1H, d, J=9.7 Hz), 4.29 (1H, d, J=9.7 Hz), 4.73 (2H, dd, J=1.2 Hz, 6.2 Hz), 6.15-6.33 (1H, m), 6.60 (1H, d, J=16.0 Hz), 7.16 (2H, d, J=8.7 Hz), 7.40 (2H, d, J=8.7 Hz), 7.53 (1H, s).

Example 408

Preparation of (S)-2-methyl-6-nitro-2-(piperazin-1-ylmethyl)-2,3-dihydroimidazo[2,1-b]oxazole dihydrochloride Tert-butyl (S)-4-(2-methyl-6-nitro-2,3-dihydroimidazo[2,1-b]oxazol-2-ylmethyl)piperazine-1-carboxylate prepared in Example 393 (1.46 g, 3.98 mmol) was dissolved in trifluoroacetic acid (30 ml) followed by stirring at room temperature for 3 hours. The reaction mixture was concentrated under reduced pressure. The residue was dissolved in methanol (30 ml). To the solution, a solution of a saturated hydrogen chloride in ethyl acetate was added followed by stirring for 30 minutes with cooling on ice-bath. The precipitates were filtered off to afford (S)-2-methyl-6-nitro-2-(piperazin-1-ylmethyl)-2,3-dihydroimidazo[2,1-b]oxazole dihydrochloride (994 mg, yield 73%) as a yellow powder.

$^1$H-NMR (DMSO-$d_6$) δppm: 1.63 (3H, s), 2.80-3.36 (6H, m), 4.11 (1H, d, J=11.0 Hz), 4.25-4.98 (5H, m), 8.15 (1H, s), 9.31 (2H, br).

Example 409

Preparation of (S)-6-nitro-2-[4-(4-trifluoromethylbenzyl)piperazin-1-ylmethyl]-2,3-dihydroimidazo[2,1-b]oxazole A mixture of tert-butyl (S)-4-(6-nitro-2,3-dihydroimidazo[2,1-b]oxazol-2-ylmethyl)piperazine-1-carboxylate prepared in Example 394 (100 mg, 0.27 mmol) and trifluoroacetic acid (2 ml) was stirred at room temperature for 3 hours. The reaction mixture was concentrated under reduced pressure. The residue was dissolved in methylene chloride (5 ml) and neutralized with triethylamine (1 ml, 7.17 mmol), and then the solution was concentrated under reduced pressure. The residue was dissolved in methanol (5 ml), and the solution was added 4-trifluoromethylbenzaldehyde (148 mg, 0.85 mmol), sodium cyanotrihydroborate (53 mg, 0.85 mmol), and acetic acid (49 μl, 0.85 mmol) in this order followed by stirring at room temperature for 18 hours. The reaction mixture was concentrated under reduced pressure. To the residue, a saturated sodium hydrogencarbonate solution was added, and the solution was extracted with methylene chloride twice. The organic phases were combined, washed with a saturated sodium hydrogencarbonate solution and a saturated saline solution in this order, dried over magnesium sulfate and then filtered. The filtrate was concentrated under reduced pressure, and the residue was purified by silica gel column chromatography (methylene chloride/ethyl acetate=1/1) to afford (S)-6-nitro-2-[4-(4-trifluoromethylbenzyl)piperazin-1-ylmethyl]-2,3-dihydroimidazo[2,1-b]oxazole (53 mg, yield 46%) as a light yellow powder.

Melting point 149-150° C.

Example 410

Preparation of (S)-2-[4-(biphenyl-4-ylmethyl)piperazin-1-ylmethyl]-6-nitro-2,3-dihydroimidazo[2,1-b]oxazole A mixture of tert-butyl (S)-4-(6-nitro-2,3-dihydroimidazo[2,1-b]oxazol-2-ylmethyl)piperazine-1-carboxylate prepared in Example 394 (7.2 g, 20.26 mmol), trifluoroacetic acid (24 ml) and methylene chloride (72 ml) was stirred at room temperature for 2 hours. The reaction mixture was concentrated under reduced pressure, and the residue was dissolved in methylene chloride (100 ml), then neutralized with triethylamine (20 ml, 143.49 mmol). The solution was concentrated under reduced pressure, and the residue was dissolved in methanol (72 ml). To the solution, 4-phenylbenzaldehyde (7.38 g, 40.52 mmol), sodium cyanotrihydroborate (3.82 g, 60.78 mmol), and acetic acid (3.48 ml, 60.78 mmol) were added in this order followed by stirring at room temperature for 24 hours. The precipitates were filtered off, washed with methanol, and purified by silica gel column chromatography (methylene chloride/methanol=10/1) to afford (S)-2-[4-(biphenyl-4-ylmethyl)piperazin-1-ylmethyl]-6-nitro-2,3-dihydroimidazo[2,1-b]oxazole (5.52 g, yield 65%) as a yellow powder.

Optical purity >99.0% e.e. $[\alpha]_D^{28}$=−28.261° (concentration: 0.046, DMSO) Melting point 207-208° C.

Example 411

Preparation of (R)-2-[4-(biphenyl-4-ylmethyl)piperazin-1-ylmethyl]-6-nitro-2,3-dihydroimidazo[2,1-b]oxazole A mixture of tert-butyl (R)-4-(6-nitro-2,3-dihydroimidazo[2,1-b]oxazol-2-ylmethyl)piperazine-1-carboxylate prepared in Example 395 (101.5 mg, 0.29 mmol) and trifluoroacetic acid (2 ml) was stirred at room temperature for 3 hours. The reaction mixture was concentrated under reduced pressure. The residue was dissolved in methylene chloride (5 ml) and neutralized with triethylamine (2 ml, 14.35 mmol), and then the solution was concentrated under reduced pressure. The residue was dissolved in methanol (5 ml). To the solution, 4-phenylbenzaldehyde (156 mg, 0.86 mmol), sodium cyanotrihydroborate (53 mg, 0.84 mmol) and acetic acid (0.05 ml, 0.87 mmol) were added in this order followed by stirring at room temperature overnight. The reaction mixture was concentrated under reduced pressure. To the residue, a saturated sodium hydrogencarbonate solution was added, and the solution was extracted with methylene chloride twice. The organic phases were combined, washed with a saturated sodium hydrogencarbonate solution and a saturated saline solution in this order, dried over magnesium sulfate and then filtered. The filtrate was concentrated under reduced pressure, and the residue was purified by silica gel column chromatography (ethyl acetate) to afford (R)-2-[4-(biphenyl-4-ylmethyl)piperazin-1-ylmethyl]-6-nitro-2,3-dihydroimidazo[2,1-b]oxazole (56 mg, yield 46%) as a white powder.

$[\alpha]_D^{28}$=28.261° (concentration: 0.046, DMSO). Melting point 224-225° C.

Using corresponding starting materials gave the compound of Example 412 in the same manner as in Example 411.

Example 412

(R)-6-Nitro-2-[4-(4-trifluoromethylbenzyl)piperazin-1-ylmethyl]-2,3-dihydroimidazo[2,1-b]oxazole Yield 48%, melting point 141-143° C.

Example 413

Preparation of (S)-2-methyl-6-nitro-2-[4-(4'-trifluoromethylbiphenyl-4-ylmethyl)piperazin-1-ylmethyl]-2,3-dihydroimidazo[2,1-b]oxazole A mixture of tert-butyl (S)-4-(2-methyl-6-nitro-2,3-dihydroimidazo[2,1-b]oxazol-2-ylmethyl)-piperazine-1-carboxylate prepared in Example 393 (1.7 g, 4.6 mmol), trifluoroacetic acid (10 ml) and methylene chloride (30 ml) was stirred at room temperature for 3 hours. The reaction mixture was concentrated under reduced pressure. The residue was dissolved in methanol (30 ml). To the solution, 4'-trifluoromethylbiphenyl-4-carboaldehyde (2.3 g, 9.19 mmol), sodium cyanotrihydroborate (580 mg, 9.23 mmol) and acetic acid (0.55 ml, 9.62 mmol) were added in this order followed by stirring at room temperature overnight. The reaction mixture was concentrated under reduced pressure. To the residue, a saturated sodium hydrogencarbonate solution was added, and the solution was extracted with methylene chloride twice. The organic phases were combined, washed with a saturated sodium hydrogencarbonate solution and a saturated saline solution in this order, dried over magnesium sulfate and then filtered. The filtrate was concentrated under reduced pressure, and the residue was purified by silica gel column chromatography (methylene chloride/methanol=50/1) to afford (S)-2-methyl-6-nitro-2-[4-(4'-trifluoromethylbiphenyl-4-ylmethyl)piperazin-1-ylmethyl]-2,3-dihydroimidazo[2,1-b]oxazole (1.47 g, yield 63%) as a white powder.

$[\alpha]_D^{28}$=1.831° (concentration: 0.71, CHCl$_3$) $^1$H-NMR (CDCl$_3$) δppm: 1.60 (3H, s), 2.20-2.45 (4H, m), 2.45-2.65 (4H, m), 2.50 (1H, d, J=15.0 Hz), 2.86 (1H, d, J=15.0 Hz), 3.48 (2H, s), 3.89 (1H, d, J=10.0 Hz), 4.31 (1H, d, J=10.0 Hz), 7.37 (2H, d, J=8.0 Hz), 7.50-7.56 (3H, m), 7.68 (4H, s).

Using corresponding starting materials gave compounds of Examples 414 to 417 in the same manner as in Example 413.

Example 414

(S)-2-Methyl-6-nitro-2-[4-(4-trifluoromethylbenzyl)-piperazin-1-ylmethyl]-2,3-dihydroimidazo[2,1-b]oxazole Melting point 110-112° C.

Example 415

(S)-2-[4-(Biphenyl-4-ylmethyl)piperazin-1-ylmethyl]-2-methyl-6-nitro-2,3-dihydroimidazo[2,1-b]oxazole Melting point 182-184° C.

Example 416

(S)-2-Methyl-6-nitro-2-[4-(4-trifluoromethoxybenzyl)-piperazin-1-ylmethyl]-2,3-dihydroimidazo[2,1-b]oxazole Melting point 137-138° C.

Example 417

(S)-2-{4-[2-(4-Chlorophenyl)-4-methylthiazol-5-ylmethyl]piperazin-1-ylmethyl}-2-methyl-6-nitro-2,3-dihydroimidazo[2,1-b]oxazole Melting point 174.3-175.5° C.

Example 418

Preparation of (R)-2-[4-(biphenyl-4-ylmethyl)piperazin-1-ylmethyl]-2-methyl-6-nitro-2,3-dihydroimidazo[2,1-b]oxazole A mixture of tert-butyl (R)-4-(2-methyl-6-nitro-2,3-dihydroimidazo[2,1-b]oxazol-2-ylmethyl)-piperazine-1-carboxylate prepared in Example 396 (100 mg, 0.27 mmol) and trifluoroacetic acid (2 ml) was stirred at room temperature for 3 hours. The reaction mixture was concentrated under reduced pressure. The residue was dissolved in methylene chloride (5 ml) and neutralized with triethylamine (1 ml, 7.17 mmol), and then the solution was concentrated under reduced pressure. The residue was dissolved in methanol (5 ml). To the solution, 4-phenylbenzaldehyde (149 mg, 0.82 mmol), sodium cyanotrihydroborate (51 mg, 0.82 mmol) and acetic acid (48 μl, 0.82 mmol) were added in this order followed by stirring at room temperature for 15 hours. The reaction mixture was concentrated under reduced pressure, and the residue was added a saturated sodium hydrogencarbonate solution. The precipitates were filtered off and purified by silica gel column chromatography (ethyl acetate) to afford (R)-2-(biphenyl-4-ylmethyl)piperazin-1-ylmethyl)-2-methyl-6-nitro-2,3-dihydroimidazo[2,1-b]oxazole (67 mg, yield 57%) as a light yellow powder.

Melting point 112-114° C.

Using corresponding starting materials gave the compound of Example 419 in the same manner as in Example 418.

Example 419

(R)-2-Methyl-6-nitro-2-[4-(4-trifluoromethylbenzyl)-piperazin-1-ylmethyl]-2,3-dihydroimidazo[2,1-b]oxazole Melting point 93-95° C.

Example 420

Preparation of (S)-2-chloro-1-[4-(2-methyl-6-nitro-2,3-dihydroimidazo[2,1-b]oxazol-2-ylmethyl)piperazin-1-yl]ethanone A mixture of tert-butyl (S)-4-(2-methyl-6-nitro-2,3-dihydroimidazo[2,1-b]oxazol-2-ylmethyl)-piperazine-1-carboxylate prepared in Example 393 (1.5 g, 4.1 mmol) and trifluoroacetic acid (20 ml) was stirred at room temperature for 3 hours. The reaction mixture was concentrated under reduced pressure. The residue was dissolved in methylene chloride (20 ml), and the solution was added triethylamine (3 ml) and 4-dimethylaminopyridine (100 mg, 0.82 mmol) in this order. To the mixture, a solution of chloroacetyl chloride (0.49 ml, 6.2 mmol) in methylene chloride (2 ml) was added slowly with cooling on ice-bath followed by stirring at room temperature overnight. The reaction mixture was washed with water twice, a saturated sodium hydrogencarbonate solution and a saturated saline solution in this order, dried over magnesium sulfate and then filtered. The filtrate was concentrated under reduced pressure, and the residue was purified by silica gel column chromatography (methylene chloride/methanol=100/1) to afford (S)-2-chloro-1-[4-(2-methyl-6-nitro-2,3-dihydroimidazo[2,1-b]oxazol-2-ylmethyl)piperazin-1-yl]ethanone (600 mg, yield 43%) as a light brown powder.

$^1$H-NMR (CDCl$_3$) δppm: 1.64 (3H, s), 2.50-2.70 (3H, m), 2.61 (1H, d, J=15.0 Hz), 2.70-2.90 (1H, m), 2.89 (1H, d, J=15.0 Hz), 3.15-3.55 (3H, m), 3.60-3.75 (1H, m), 3.97 (1H, d, J=10.0 Hz), 4.03 (2H, s), 4.30 (1H, d, J=10.0 Hz), 7.55 (1H, s).

Example 421

Preparation of (S)-2-(4-chlorophenoxy)-1-[4-(2-methyl-6-nitro-2,3-dihydroimidazo[2,1-b]oxazol-2-ylmethyl)-piperazin-1-yl]ethanone A mixture of (S)-2-chloro-1-[4-(2-methyl-6-nitro-2,3-dihydroimidazo[2,1-b]oxazol-2-ylmethyl)-piperazin-1-yl]ethanone prepared in Example 420 (300 mg, 0.87 mmol), 4-chlorophenol (170 mg, 1.32 mmol), potassium carbonate (180 mg, 1.3 mmol) and DMF (5 ml) was stirred at 60° C. for 3 hours. The reaction mixture was allowed to return to room temperature, then diluted with water. The solution was extracted with ethyl acetate twice. The organic phases were combined, washed with a sodium hydroxide solution, water and a saturated saline solution in this order, dried over magnesium sulfate and then filtered. The filtrate was concentrated under reduced pressure, and the residue was recrystallized from ethanol to afford (S)-2-(4-chlorophenoxy)-1-[4-(2-methyl-6-nitro-2,3-dihydroimidazo[2,1-b]oxazol-2-ylmethyl)piperazin-1-yl]ethanone (260 mg, yield 68%) as a light brown powder.

Melting point 179-180° C.

Example 422

Preparation of (S)-2-(4-chlorophenylsulfanyl)-1-[4-(2-methyl-6-nitro-2,3-dihydroimidazo[2,1-b]oxazol-2-ylmethyl)piperazin-1-yl]ethanone Using a mixture of (S)-2-chloro-1-[4-(2-methyl-6-nitro-2,3-dihydroimidazo[2,1-b]oxazol-2-ylmethyl)piperazin-1-yl]ethanone prepared in Example 420 (300 mg, 0.87 mmol) and 4-chlorothiophenol (190 mg, 1.32 mmol) gave (S)-2-(4-chlorophenylsulfanyl)-1-[4-(2-methyl-6-nitro-2,3-dihydroimidazo[2,1-b]oxazol-2-ylmethyl)piperazin-1-yl]ethanone (80 mg, yield 20%) as a white powder in the same manner as in Example 421.

Melting point 142-145° C.

Example 423

Preparation of (S)-(4-chlorophenyl)-[4-(2-methyl-6-nitro-2,3-dihydroimidazo[2,1-b]oxazol-2-ylmethyl)-piperazin-1-yl]methanone A mixture of tert-butyl (S)-4-(2-methyl-6-nitro-2,3-dihydroimidazo[2,1-b]oxazol-2-ylmethyl)-piperazine-1-carboxylate prepared in Example 393 (300 mg, 0.82 mmol) and trifluoroacetic acid (6 ml) was stirred at room temperature for 3 hours. The reaction mixture was concentrated under reduced pressure. The residue was dissolved in methylene chloride (15 ml), and the solution was added triethylamine (2 ml, 14.35 mmol). To the solution, 4-chlorobenzoyl chloride (150.7 mg, 0.86 mmol) was added with cooling on ice-bath followed by stirring at room temperature for 1 hour. The reaction mixture was washed with a saturated sodium hydrogencarbonate solution, water and a saturated saline solution in this order, dried over sodium sulfate and then filtered. The filtrate was concentrated under reduced pressure, and the residue was treated with diethyl ether-ethyl acetate to afford (S)-(4-chlorophenyl)-[4-(2-methyl-6-nitro-2,3-dihydroimidazo[2,1-b]oxazol-2-ylmethyl)piperazin-1-yl]methanone (282 mg, yield 85%) as a yellow powder.

Melting point 173-174° C.

Using corresponding starting materials gave the compound of Example 424 in the same manner as in Example 423.

Example 424

(Biphenyl-4-yl)-[4-(2-methyl-6-nitro-2,3-dihydroimidazo[2,1-b]oxazol-2-ylmethyl)piperazin-1-yl]methanone Melting point 116-118° C.

Example 425

Preparation of [4-(2-methyl-6-nitro-2,3-dihydroimidazo-[2,1-b]oxazol-2-ylmethyl)piperazin-1-yl]phenylmethanone A mixture of 2-(4-tert-butoxycarbonylpiperazin-1-yl)methyl-2-methyl-6-nitro-2,3-dihydroimidazo[2,1-b]oxazole prepared in Example 306 (142 mg, 0.39 mmol), trifluoroacetic acid (1 ml) and methylene chloride (1 ml) was stirred at room temperature for 1 hour. The reaction mixture was concentrated under reduced pressure, and the residue was dissolved in methylene chloride (2 ml). To the mixture, triethylamine (2 ml, 14.35 mmol) was added. To the solution, benzoyl chloride (54 µl, 0.46 mmol) was added with cooling on ice-bath followed by stirring at room temperature for 1 hour. The reaction mixture was diluted with methylene chloride, washed with a saturated sodium hydrogencarbonate solution, water and a saturated saline solution in this order, dried over sodium sulfate and then filtered. The filtrate was concentrated under reduced pressure, and the residue was treated with diethyl ether to afford [4-(2-methyl-6-nitro-2,3-dihydroimidazo[2,1-b]oxazol-2-ylmethyl)piperazin-1-yl]phenylmethanone (72 mg, yield 50%) as a yellow powder.

Melting point 145-148.7° C.

Using corresponding starting materials gave compounds of Examples 426 to 433 in the same manner as in Example 425.

Example 426

(4-Chlorophenyl)-[4-(2-methyl-6-nitro-2,3-dihydroimidazo[2,1-b]oxazol-2-ylmethyl)piperazin-1-yl]methanone Melting point 150.0-155.2° C.

Example 427

[4-(2-Methyl-6-nitro-2,3-dihydroimidazo[2,1-b]oxazol-2-ylmethyl)piperazin-1-yl](pyridin-4-yl)methanone $^1$H-NMR (CDCl$_3$) δppm: 1.62 (3H, s), 2.25-2.75 (4H, m), 2.61 (1H, d, J=14.9 Hz), 2.88 (1H, d, J=14.9 Hz), 3.00-3.93 (4H, br), 3.95 (1H, d, J=9.8 Hz), 4.30 (1H, d, J=9.8 Hz), 7.26-7.55 (2H, m), 7.59 (1H, s), 8.67-8.72 (2H, m).

Example 428

1-[4-(2-Methyl-6-nitro-2,3-dihydroimidazo[2,1-b]oxazol-2-ylmethyl)piperazin-1-yl]-2-phenylethanone Melting point 175.2-175.9° C.

Example 429

1-[4-(2-Methyl-6-nitro-2,3-dihydroimidazo[2,1-b]oxazol-2-ylmethyl)piperazin-1-yl]-3-phenylpropan-1-one Melting point 166.8-169.1° C.

Example 430

1-[4-(2-Methyl-6-nitro-2,3-dihydroimidazo[2,1-b]oxazol-2-ylmethyl)piperazin-1-yl]-2-phenoxyethanone Melting point 158-160.6° C.

Example 431

2-(4-Chlorophenyl)-1-[4-(2-methyl-6-nitro-2,3-dihydroimidazo[2,1-b]oxazol-2-ylmethyl)piperazin-1-yl]ethanone Melting point 184-187° C.

Example 432

(Biphenyl-4-yl)-[4-(2-methyl-6-nitro-2,3-dihydroimidazo[2,1-b]oxazol-2-ylmethyl)piperazin-1-yl]methanone $^1$H-NMR (CDCl$_3$) δppm: 1.63 (3H, s), 2.45-2.80 (4H, m), 2.62 (1H, d, J=14.9 Hz), 2.90 (1H, d, J=14.9 Hz), 3.28-3.81 (4H, br), 3.95 (1H, d, J=9.8 Hz), 4.31 (1H, d, J=9.8 Hz), 7.34-7.50 (5H, m), 7.55 (1H, s), 7.56-7.63 (4H, m).

Example 433

[4-(2-Methyl-6-nitro-2,3-dihydroimidazo[2,1-b]oxazol-2-ylmethyl)piperazin-1-yl]-(4-trifluoromethylphenyl)-methanone Melting point 161-162° C.

Example 434

Preparation of (S)-[4-(2-methyl-6-nitro-2,3-dihydroimidazo[2,1-b]oxazol-2-ylmethyl)piperazin-1-yl]-(4-trifluoromethylphenyl)methanone (S)-2-Methyl-6-nitro-2-(piperazin-1-ylmethyl)-2,3-dihydroimidazo[2,1-b]oxazole dihydrochloride prepared in Example 408 (2.36 mg, 0.882 mmol) was suspended in methylene chloride (10 ml). To the suspension, triethylamine (1 ml, 7.17 mmol) was added. To the solution, 4-(trifluoromethyl)benzoyl chloride (193 mg, 0.926 mmol) was added with cooling on ice-bath followed by stirring at room temperature for 1 hour. The reaction mixture was washed with a saturated sodium hydrogencarbonate solution, water and a saturated saline solution in this order, dried over sodium sulfate and then filtered. The filtrate was concentrated under reduced pressure, and the residue was purified by silica gel column chromatography (methylene chloride/methanol=50/1) to afford (S)-[4-(2-methyl-6-nitro-2,3-dihydroimidazo[2,1-b]oxazol-2-ylmethyl)piperazin-1-yl]-(4-trifluoromethylphenyl)methanone (264 mg, yield 68%) as a white powder.

Melting point 183-184° C.

Using corresponding starting materials gave compounds of Example 435 to 438 in the same manner as in Example 434. (Compounds in Examples 435 to 437 were prepared with 2-methyl-6-nitro-2-(piperazin-1-ylmethyl)-2,3-dihydroimidazo[2,1-b]oxazole dihydrochloride prepared in Example 322)

Example 435

[4-(2-Methyl-6-nitro-2,3-dihydroimidazo[2,1-b]oxazol-2-ylmethyl)piperazin-1-yl]-(4-methoxyphenyl)methanone Melting point 135-137° C.

Example 436

[4-(2-Methyl-6-nitro-2,3-dihydroimidazo[2,1-b]oxazol-2-ylmethyl)piperazin-1-yl]-(4-methylphenyl)methanone Melting point 121-122° C.

Example 437

[4-(2-Methyl-6-nitro-2,3-dihydroimidazo[2,1-b]oxazol-2-ylmethyl)piperazin-1-yl]-(3-trifluoromethylphenyl)-methanone Melting point 122-124° C.

Example 438

(S)-2-(4-Chlorophenyl)-1-[4-(2-methyl-6-nitro-2,3-dihydroimidazo[2,1-b]oxazol-2-ylmethyl)piperazin-1-yl]ethanone Melting point 189-190° C.

Example 439

Preparation of (S)-2-(3,4-dichlorophenoxy)-1-[4-(2-methyl-6-nitro-2,3-dihydroimidazo[2,1-b]oxazol-2-ylmethyl)piperazin-1-yl]ethanone A mixture of 3,4-(dichlorophenoxy)acetic acid (234 mg, 1.06 mmol) and thionyl chloride (5 ml) was stirred under reflux for 30 minutes. The reaction mixture was concentrated under reduced pressure to afford corresponding acid chloride. It was dissolved in methylene chloride (5 ml).

The solution was added to a mixture of (S)-2-methyl-6-nitro-2-(piperazin-1-ylmethyl)-2,3-dihydroimidazo[2,1-b]oxazole dihydrochloride prepared in Example 408 (236 mg, 0.88 mmol), methylene chloride (10 ml), and triethylamine (1 ml, 7.17 mmol) with cooling on ice-bath followed by stirring at room temperature for 1 hour. The reaction mixture was washed with a saturated sodium hydrogencarbonate solution, water and a saturated saline solution in this order, dried over sodium sulfate and then filtered. The filtrate was concentrated under reduced pressure. The residue was purified by silica gel column chromatography (methylene chloride/methanol=50/1) to afford (S)-2-(3,4-dichlorophenoxy)-1-[4-(2-methyl-6-nitro-2,3-dihydroimidazo[2,1-b]oxazol-2-ylmethyl)-piperazin-1-yl]ethanone (183 mg, yield 44%) as a white powder.

Melting point 164-166° C.

Using corresponding starting materials gave the compound of Example 440 in the same manner as in Example 439.

Example 440

(S)-1-[4-(2-Methyl-6-nitro-2,3-dihydroimidazo[2,1-b]oxazol-2-ylmethyl)piperazin-1-yl]-4-(4-trifluoromethylphenyl)butan-1-one Melting point 145-146° C.

Example 441

Preparation of (S)-3-(4-chlorophenyl)-1-[4-(2-methyl-6-nitro-2,3-dihydroimidazo[2,1-b]oxazol-2-ylmethyl)-piperazin-1-yl]propenone A mixture of 4-chlorocinnamic acid (300 mg, 1.64 mmol), 1-hydroxybenzotriazole (HOBT) (240 mg, 1.77 mmol), WSCD (350 mg, 1.83 mmol) and methylene chloride (10 ml) stirred at room temperature for 30 minutes was added a mixture of (S)-2-methyl-6-nitro-2-(piperazin-1-ylmethyl)-2,3-dihydroimidazo[2,1-b]oxazole dihydrochloride prepared in Example 408 (434 mg, 1.64 mmol), methylene chloride (10 ml), and triethylamine (3.3 ml, 2.37 mmol) with cooling on ice-bath followed by stirring at room temperature for 3 hours. The reaction mixture was washed with a saturated sodium hydrogencarbonate solution, water and a saturated saline solution in this order, dried over sodium sulfate and then filtered. The filtrate was concentrated under reduced pressure. The residue was purified by silica gel column chromatography (ethyl acetate) to afford (S)-3-(4-chlorophenyl)-1-[4-(2-methyl-6-nitro-2,3-dihydroimidazo[2,1-b]oxazol-2-ylmethyl)piperazin-1-yl]propenone (180 mg, yield 26%) as a white powder.

Melting point 220-222° C.

Using corresponding starting materials gave compounds of Examples 442 to 445 in the same manner as in Example 441.

Example 442

(S)-3-(Chlorophenyl)-1-[4-(2-methyl-6-nitro-2,3-dihydroimidazo[2,1-b]oxazol-2-ylmethyl)piperazin-1-yl]propan-1-one Melting point 177-178° C.

Example 443

(S)-4-(4-Chlorophenyl)-1-[4-(2-methyl-6-nitro-2,3-dihydroimidazo[2,1-b]oxazol-2-ylmethyl)piperazin-1-yl]butan-1-one Melting point 146-147° C.

Example 444

(S)-3-(3,4-Dichlorophenyl)-1-[4-(2-methyl-6-nitro-2,3-dihydroimidazo[2,1-b]oxazol-2-ylmethyl)piperazin-1-yl]propenone Melting point 213-215° C.

Example 445

(S)-5-(4-Chlorophenyl)-1-[4-(2-methyl-6-nitro-2,3-dihydroimidazo[2,1-b]oxazol-2-ylmethyl)piperazin-1-yl]pentan-1-one Melting point 108-111° C.

Example 446

Preparation of 1-[4-(2-methyl-6-nitro-2,3-dihydroimidazo[2,1-b]oxazol-2-ylmethyl)piperazin-1-yl]-2-(4-tolyl)ethanone A mixture of 2-Methyl-6-nitro-2-(piperazin-1-ylmethyl)-2,3-dihydroimidazo[2,1-b]oxazole dihydrochloride prepared in Example 322 (240 mg, 0.79 mmol), DMF (5 ml) and triethylamine (0.22 ml, 1.58 mmol) was added p-tolylacetic acid (140 mg, 0.93 mmol) and WSCD (180 mg, 0.93 mmol) in this order followed by stirring at room temperature for 1 hour. The reaction mixture was diluted with ethyl acetate, washed with water twice, a saturated sodium hydrogencarbonate solution and a saturated saline solution in this order, dried over sodium sulfate and then filtered. The filtrate was concentrated under reduced pressure, and the residue was treated with diethylether to afford 1-[4-(2-methyl-6-nitro-2,3-dihydroimidazo[2,1-b]oxazol-2-ylmethyl)piperazin-1-yl]-2-(4-tolyl)ethanone (172 mg, yield 64%) as a white powder.

Melting point 213-214° C.

Using corresponding starting materials gave the compound of Example 447 in the same manner as in Example 446.

Example 447

(4-Dimethylaminophenyl)-[4-(2-methyl-6-nitro-2,3-dihydroimidazo[2,1-b]oxazol-2-ylmethyl)piperazin-1-yl]methanone Melting point 204-207° C.

Example 448

Preparation of (S)-2-{4-[3-(4-Chlorophenyl)propane-1-sulfonyl]piperazin-1-ylmethyl}-2-methyl-6-nitro-2,3-dihydroimidazo[2,1-b]oxazole A mixture of tert-butyl (S)-4-(2-methyl-6-nitro-2,3-dihydroimidazo[2,1-b]oxazol-2-ylmethyl)-piperazine-1-carboxylate prepared in Example 393 (300 mg, 0.82 mmol) and trifluoroacetic acid (10 ml) was stirred at room temperature for 1 hour. The reaction mixture was concentrated under reduced pressure, and the residue was dissolved in methylene chloride (10 ml). To the solution, triethylamine (3 ml, 21.52 mmol) was added followed by stirring at room temperature for 10 minutes, and then 3-(4-chlorophenyl)propane-1-sulfonyl chloride (300 mg, 1.19 mmol) was added followed by stirring at room temperature for 3 days. The reaction mixture was washed with water and a saturated saline solution, dried over sodium sulfate and then filtered. The filtrate was concentrated under reduced pressure. The residue was purified by silica gel column chromatography (methylene chloride/methanol=50/1) to afford (S)-2-{4-[3-(4-chlorophenyl)propane-1-sulfonyl]piperazin-1-ylmethyl}-2-methyl-6-nitro-2,3-dihydroimidazo[2,1-b]oxazole (330 mg, yield 84%) as a white powder.

Melting point 150-151° C.

Using 2-(4-tert-butoxycarbonylpiperazin-1-ylmethyl)-2-methyl-6-nitro-2,3-dihydroimidazo[2,1-b]oxazole prepared in Example 306 gave compounds of Examples 449 and 450 in the same manner as in Example 448.

Example 449

2-[4-(4-Chlorobenzenesulfonyl)piperazin-1-ylmethyl]-2-methyl-6-nitro-2,3-dihydroimidazo[2,1-b]oxazole Melting point 202-204° C.

Example 450

2-[4-(4-Chlorophenylmethanesulfonyl)piperazin-1-ylmethyl]-2-methyl-6-nitro-2,3-dihydroimidazo[2,1-b]oxazole Melting point 215-217° C.

Example 451

Preparation of (S)-2-f4-[2-(4-chlorophenyl)ethanesulfonyl]piperazin-1-ylmethyl}-2-methyl-6-nitro-2,3-dihydroimidazo[2,1-b]oxazole A mixture of (S)-2-methyl-6-nitro-2-(piperazin-1-ylmethyl)-2,3-dihydroimidazo[2,1-b]oxazole dihydrochloride prepared in Example 408 (236 mg, 0.88 mmol) and DMF (3 ml) was added potassium carbonate (500 mg, 3.62 mmol) and 2-(4-chlorophenyl)ethanesulfonyl chloride (240 mg, 1 mmol) in this order followed by stirring at room temperature overnight. To the reaction mixture, water was added, and the solution was extracted with ethyl acetate. The organic phase was washed with water three times and saturated saline solution, dried over sodium sulfate and then filtered. The filtrate was concentrated under reduced pressure. The residue was purified by silica gel column chromatography (methylene chloride/methanol=50/1) to afford (S)-2-{4-[2-(4-chlorophenyl)ethanesulfonyl]piperazin-1-ylmethyl}-2- methyl-6-nitro-2,3-dihydroimidazo[2,1-b]oxazole (100 mg, yield 26%) as a white powder.

Melting point 192-193° C.

Using (S)-2-methyl-6-nitro-2-(piperazin-1-ylmethyl)-2,3-dihydroimidazo[2,1-b]oxazole dihydrochloride prepared in Example 408 gave compounds of Examples 452 to 454 in the same manner as in Example 451. Also, using 2-methyl-6-nitro-2-(piperazin-1-ylmethyl)-2,3-dihydroimidazo[2,1-b]oxazole dihydrochloride prepared in Example 322 gave the compound of Example 455 in the same manner as in Example 451.

Example 452

(S)-2-[4-(4-Chlorobenzenesulfonyl)piperazin-1-ylmethyl]-2-methyl-6-nitro-2,3-dihydroimidazo[2,1-b]oxazole Melting point 216-218° C.

Example 453

(S)-2-[4-(4-Chlorophenylmethanesulfonyl)piperazin-1-ylmethyl]-2-methyl-6-nitro-2,3-dihydroimidazo[2,1-b]oxazole Melting point 204-206° C.

Example 454

(S)-2-{4-[4-(4-Chlorophenyl)butane-1-sulfonyl]-piperazin-1-ylmethyl}-2-methyl-6-nitro-2,3-dihydroimidazo[2,1-b]oxazole Melting point 176-177° C.

Example 455

2-{4-[2-(4-Chlorophenyl)ethanesulfonyl]piperazin-1-ylmethyl}-2-methyl-6-nitro-2,3-dihydroimidazo[2,1-b]oxazole Melting point 182-184° C.

Example 456

Preparation of 4-trifluoromethylbenzyl (S)-4-(6-nitro-2,3-dihydroimidazo[2,1-b]oxazol-2-ylmethyl) piperazine-1-carboxylate A mixture of tert-butyl (S)-4-(6-nitro-2,3-dihydroimidazo[2,1-b]oxazol-2-ylmethyl)piperazine-1-carboxylate prepared in Example 394 (300 mg, 0.84 mmol) and methylene chloride (2 ml) was added trifluoroacetic acid (1 ml) followed by stirring at room temperature for 1 hour. The reaction mixture was concentrated under reduced pressure, and the residue was dissolved in DMF (1 ml) and neutralized with triethylamine (1 ml).

To the solution, a mixture of 4-(trifluoromethyl)benzyl alcohol (297 mg, 1.69 mmol), DMF (1 ml), and 1,1'-carbonyldiimidazole (274 mg, 1.69 mmol) stirred at room temperature for 1 hour was added followed by stirring at room temperature for 3 hours. To the reaction mixture, water was added, and the solution was extracted with ethyl acetate twice. The organic phases were combined, washed with water twice and a saturated saline solution, dried over sodium sulfate and then filtered. The filtrate was concentrated under reduced pressure, and the residue was purified by silica gel column chromatography (methylene chloride/methanol=20/1) to afford 4-trifluoromethylbenzyl (S)-4-(6-nitro-2,3-dihydroimidazo[2,1-b]oxazol-2-ylmethyl)piperazine-1-carboxylate (273 mg, yield 71%) as a white powder.

$[\alpha]_D^{28}$=-14.851° (concentration: 0.404, CHCl$_3$) Melting point 125-125.5° C.

Example 457

Preparation of 4-trifluoromethylbenzyl (S)-4-(2-methyl-6-nitro-2,3-dihydroimidazo[2,1-b]oxazol-2-ylmethyl)-piperazine-1-carboxylate A mixture of tert-butyl (S)-4-(2-methyl-6-nitro-2,3-dihydroimidazo[2,1-b]oxazol-2-ylmethyl)piperazine-1-carboxylate prepared in Example 393 (1.87 g, 5.09 mmol) and methylene chloride (20 ml) was added trifluoroacetic acid (20 ml) followed by stirring for 5 minutes, and then concentrated under reduced pressure. The residue was dissolved in DMF (20 ml). To the solution, a mixture of 1,1'-carbonyldiimidazole (1.76 g, 10.9 mmol), 4-(trifluoromethyl)benzyl alcohol (1.92 g, 10.9 mmol) and DMF (20 ml) stirred at room temperature for 3 hours was added followed by stirring at room temperature overnight. The reaction mixture was extracted with ethyl acetate. The organic phases were combined, washed with water and a saturated saline solution, dried over sodium sulfate and then filtered. The resulting filtrate was concentrated under reduced pressure, and the residue was purified by silica gel column chromatography (n-hexane/acetone=3/1), recrystallized from isopropyl alcohol. The resulting solids were filtered off and then dried under reduced pressure to afford 4-trifluoromethylbenzyl (S)-4-(2-methyl-6-nitro-2,3-dihydroimidazo[2,1-b]oxazol-2-ylmethyl)piperazine-1-carboxylate (1.48 g, yield 53%) as a light yellow powder.

Melting point 140.4-141.6° C. Optical purity 99.9% e.e. $^1$H-NMR (CDCl$_3$) δppm: 1.62 (3H, s), 2.52-2.69 (5H, m), 2.88 (1H, d, J=14.9 Hz), 3.43 (4H, br), 3.93 (1H, d, J=9.7 Hz), 4.28 (1H, d, J=9.7 Hz), 5.16 (2H, s), 7.44 (2H, d, J=8.1 Hz), 7.53 (1H, s), 7.61 (2H, d, J=8.1 Hz).

Example 458

Preparation of 1,3,3-trimethyl-2-oxo-2,3-dihydro-1H-indol-5-ylmethyl (S)-4-(2-methyl-6-nitro-2,3-dihydroimidazo[2,1-b]oxazol-2-ylmethyl)piperazine-1-carboxylate To a mixture of 3,3-dimethyl-2-oxo-2,3-dihydro-1H-indol-5-ylmethyl (S)-4-(2-methyl-6-nitro-2,3-dihydroimidazo[2,1-b]oxazol-2-ylmethyl)piperazine-1-carboxylate (300 mg, 0.62 mmol) and DMF (3 ml), sodium hydride (27 mg, 0.68 mmol) was added followed by stirring for 30 minutes with cooling on ice-bath. To the reaction mixture, methyl iodide (97 mg, 0.68 mmol) was added followed by stirring at room temperature for 2 hours. To the reaction mixture, water was added, and the mixture was extracted with ethyl acetate twice. The organic phases were combined, washed with water twice and a saturated saline solution, dried over sodium sulfate and then filtered. The filtrate was concentrated under reduced pressure, and the residue was purified by silica gel column chromatography (ethyl acetate) to afford 1,3,3-trimethyl-2-oxo-2,3-dihydro-1H-indol-5-ylmethyl (S)-4-(2-methyl-6-nitro-2,3-dihydroimidazo[2,1-b]oxazol-2-ylmethyl)piperazine-1-carboxylate (140 mg, 45%) as a light yellow powder.

Melting point 80-100° C. (decomposition).

Using corresponding starting materials gave the compound of Example 459 in the same manner as in Example 458.

Example 459

1-Methyl-2-oxo-1,2,3,4-tetrahydroquinolin-6-ylmethyl (S)-4-(2-methyl-6-nitro-2,3-dihydroimidazo[2,1-b]oxazol-2-ylmethyl)piperazine-1-carboxylate Melting point 189-190° C.

Example 460

Preparation of 3,5-dichlorobenzyl (S)-4-(2-methyl-6-nitro-2,3-dihydroimidazo[2,1-b]oxazol-2-ylmethyl)-piperazine-1-carboxylate To a mixture of (S)-2-methyl-6-nitro-2-(piperazin-1-ylmethyl)-2,3-dihydroimidazo[2,1-b]oxazole dihydrochloride prepared in Example 408 (300 mg, 0.88 mmol) and DMF (3 ml), triethylamine (270 mg, 2.67 mmol) was added for neutralization. To the solution, a mixture of 3,5-dichlorobenzyl alcohol (180 mg, 1.02 mmol), DMF (3 ml) and 1,1'-carbonyldiimidazole (180 mg, 1.11 mmol) stirred at room temperature for 2 hours was added followed by stirring at room temperature overnight. To the reaction mixture, water was added, and the mixture was extracted with ethyl acetate twice. The organic phases were combined, washed with water twice and a saturated saline solution, dried over sodium sulfate and then filtered. The filtrate was concentrated under reduced pressure, and the residue was purified by silica gel column chromatography (ethyl acetate) to afford 3,5-dichlorobenzyl (S)-4-(2-methyl-6-nitro-2,3-dihydroimidazo[2,1-b]oxazol-2-ylmethyl)piperazine-1-carboxylate (220 mg, yield 53%) as a white powder.

Melting point 129-130° C.

Example 461

Preparation of 3-(3-trifluoromethylphenyl)-2-propenyl (S)-4-(2-methyl-6-nitro-2,3-dihydroimidazo[2,1-b]oxazol-2-ylmethyl)piperazine-1-carboxylate maleate Using tert-butyl (S)-4-(2-methyl-6-nitro-2,3-dihydroimidazo[2,1-b]oxazol-2-ylmethyl)piperazine-1-carboxylate prepared in Example 393 (1.09 g, 2.97 mmol) gave 3-(3-trifluoromethylphenyl)-2-propenyl (S)-4-(2-methyl-6-nitro-2,3-dihydroimidazo[2,1-b]oxazol-2-ylmethyl)piperazine-1-carboxylate maleate (945 mg, 63%) as a white powder in the same manner as in Example 344.

Melting point 136-138° C.

Using corresponding starting materials gave compounds of Examples 462 to 465 in the same manner as in Example 461.

Example 462

[(E)-3-Methyl-3-(3-trifluoromethylphenyl)]-2-propenyl (S)-4-(2-methyl-6-nitro-2,3-dihydroimidazo[2,1-b]oxazol-2-ylmethyl)piperazine-1-carboxylate maleate Melting point 142-143° C.

Example 463

3-(3-Chlorophenyl)-2-propenyl (S)-4-(2-methyl-6-nitro-2,3-dihydroimidazo[2,1-b]oxazol-2-ylmethyl)piperazine-1-carboxylate maleate Melting point 150-151° C.

Example 464

3-(2,4,6-Trifluorophenyl)-2-propenyl (S)-4-(2-methyl-6-nitro-2,3-dihydroimidazo[2,1-b]oxazol-2-ylmethyl)-piperazine-1-carboxylate maleate Melting point 158-159° C.

Example 465

[(Z)-3-Methyl-3-(3-trifluoromethylphenyl)]-2-propenyl (S)-4-(2-methyl-6-nitro-2,3-dihydroimidazo[2,1-b]oxazol-2-ylmethyl)piperazine-1-carboxylate maleate Melting point 124-125° C.

Example 466

Preparation of 4-fluorobenzyl (R)-4-(2-methyl-6-nitro-2,3-dihydroimidazo[2,1-b]oxazol-2-ylmethyl)piperazine-1-carboxylate Using tert-butyl (R)-4-(2-methyl-6-nitro-2,3-dihydroimidazo[2,1-b]oxazol-2-ylmethyl)piperazine-1-carboxylate prepared in Example 396 (106 mg, 0.29 mmol) gave 4-fluorobenzyl (R)-4-(2-methyl-6-nitro-2,3-dihydroimidazo[2,1-b]oxazol-2-ylmethyl)piperazine-1-carboxylate (79 mg, yield 66%) as a white powder in the same manner as in Example 457.

$[\alpha]_D^{28}$=19.70° (concentration: 1.066, $CHCl_3$) Melting point 167-169° C.

Example 467

Preparation of (S)-4-(2-methyl-6-nitro-2,3-dihydroimidazo[2,1-b]oxazol-2-ylmethyl)piperazine-1-carboxylic acid[3-(4-trifluoromethylphenyl)-2-propenyl]amide A mixture of tert-butyl (S)-4-(2-methyl-6-nitro-2,3-dihydroimidazo[2,1-b]oxazol-2-ylmethyl)piperazine-1-carboxylate prepared in Example 393 (926 mg, 2.52 mmol), trifluoroacetic acid (10 ml) and methylene chloride (3 ml) was stirred at room temperature for 5 hours. The reaction mixture was concentrated under reduced pressure, and the residue was dissolved in DMF (3 ml) and neutralized with triethylamine (2 ml, 14.35 mmol). To the solution, a mixture of 3-(4-trifluoromethylphenyl)-2-propenylamine (761 mg, 3.78 mmol), 1,1'-carbonyldiimidazole (613 mg, 3.78 mmol) and DMF (3 ml) stirred at room temperature overnight was added followed by stirring at room temperature overnight. To the reaction mixture, water was added followed by extraction with ethyl acetate. The extract was washed with water three times and a saturated saline solution, dried over magnesium sulfate and then filtered. The filtrate was concentrated under reduced pressure, and the residue was purified by silica gel column chromatography (methylene chloride/methanol=20/1) to afford (S)-4-(2-methyl-6-nitro-2,3- dihydroimidazo[2,1-b]oxazol-2-ylmethyl)piperazine-1-carboxylic acid[3-(4-trifluoromethylphenyl)-2-propenyl]amide (1.2 g, yield 96%) as a light yellow powder.

Melting point 105-107° C.

Using 2-(4-tert-butoxycarbonylpiperazin-1-yl)methyl-2-methyl-6-nitro-2,3-dihydroimidazo[2,1-b]oxazole prepared in Example 306 gave compounds of Examples 468 to 470 in the same manner as in Example 467.

Example 468

4-(2-Methyl-6-nitro-2,3-dihydroimidazo[2,1-b]oxazol-2-ylmethyl)piperazine-1-carboxylic acid (4-trifluoromethylbenzyl)amide Melting point 201-202.5° C.

Example 469

4-(2-Methyl-6-nitro-2,3-dihydroimidazo[2,1-b]oxazol-2-ylmethyl)piperazine-1-carboxylic acid (4-trifluoromethylphenyl)amide Melting point 216-217° C.

Example 470

4-(2-Methyl-6-nitro-2,3-dihydroimidazo[2,1-b]oxazol-2-ylmethyl)piperazine-1-carboxylic acid (4-chloro-3-trifluoromethylphenyl)amide Melting point 222-224° C.

Example 471

Preparation of (S)-4-(2-methyl-6-nitro-2,3-dihydroimidazo[2,1-b]oxazol-2-ylmethyl)piperazine-1-carboxylic acid cyclohexylamide (S)-2-Methyl-6-nitro-2-(piperazin-1-ylmethyl)-2,3-dihydroimidazo[2,1-b]oxazole dihydrochloride prepared in Example 408 (236 mg, 0.88 mmol) was dissoloved in a mixture of methylene chloride (15 ml) and triethylamine (2 ml, 14.35 mmol). To the solution, cyclohexyl isocyanate (120 mg, 0.96 mmol) was added followed by stirring at room temperature for 1 hour. The reaction mixture was washed with water and a saturated saline solution, dried over sodium sulfate and then filtered. The filtrate was concentrated under reduced pressure, and the residue was purified by silica gel column chromatography (methylene chloride/methanol=20/1) to afford (S)-4-(2-methyl-6-nitro-2,3-dihydroimidazo[2,1-b]oxazol-2-ylmethyl)piperazine-1-carboxylic acid cyclohexylamide (164 mg, 47%) as a light yellow powder.

Melting point 98-101° C.

Using 2-methyl-6-nitro-2-(piperazin-1-ylmethyl)-2,3-dihydroimidazo[2,1-b]oxazole dihydrochloride prepared in Example 322 gave compounds of Examples 472 to 476 in the same manner as in Example 471.

Example 472

4-(2-Methyl-6-nitro-2,3-dihydroimidazo[2,1-b]oxazol-2-ylmethyl)piperazine-1-carboxylic acid (4-methoxyphenyl)amide Melting point 167-168° C.

Example 473

4-(2-Methyl-6-nitro-2,3-dihydroimidazo[2,1-b]oxazol-2-ylmethyl)piperazine-1-carboxylic acid (4-chlorophenyl)-amide Melting point 185-188° C. (decomposition).

Example 474

4-(2-Methyl-6-nitro-2,3-dihydroimidazo[2,1-b]oxazol-2-ylmethyl)piperazine-1-carboxylic acid (3-trifluoromethylphenyl)amide Melting point 183-184° C.

Example 475

4-(2-Methyl-6-nitro-2,3-dihydroimidazo[2,1-b]oxazol-2-ylmethyl)piperazine-1-carboxylic acid (3,4-dichlorophenyl)amide Melting point 212-214° C. (decomposition).

Example 476

4-(2-Methyl-6-nitro-2,3-dihydroimidazo[2,1-b]oxazol-2-ylmethyl)piperazine-1-carboxylic acid (4-methylphenyl)-amide Melting point 202-203° C. (decomposition).

Example 477

Preparation of (S)-4-(2-methyl-6-nitro-2,3-dihydroimidazo[2,1-b]oxazol-2-ylmethyl)piperazine-1-carboxylic acid (4-trifluoromethylphenyl)amide (S)-2-Methyl-6-nitro-2-(piperazin-1-ylmethyl)-2,3-dihydroimidazo[2,1-b]oxazole dihydrochloride prepared in Example 408 (236 mg, 0.88 mmol) was dissolved in a mixture of methylene chloride (5 ml) and triethylamine (2 ml, 14.35 mmol). To the solution, a mixture of 4-aminobenzotrifluoride (142 mg, 0.882 mmol), 1,1'-carbonyldiimidazole (143 mg, 0.882 mmol) and DMF (6 ml) stirred at room temperature overnight was added followed by stirring at room temperature for 6 hours. To the reaction mixture, water was added, and the mixture was extracted with ethyl acetate. The organic phase was washed with water three times and a saturated saline solution, dried over sodium sulfate and then filtered. The filtrate was concentrated under reduced pressure, and the residue was purified by silica gel column chromatography (methylene chloride/methanol=30/1) to afford (S)-4-(2-methyl-6-nitro-2,3-dihydroimidazo[2,1-b]oxazol-2-ylmethyl)piperazine-1-carboxylic acid (4-trifluoromethylphenyl)amide (90 mg, yield 23%) as a white powder.

Melting point 150-152.5° C.

Using corresponding starting materials gave compounds of Examples 478 to 481 in the same manner as in Example 477.

Example 478

(S)-4-(2-Methyl-6-nitro-2,3-dihydroimidazo[2,1-b]oxazol-2-ylmethyl)piperazine-1-carboxylic acid (4-methoxyphenyl)amide Melting point 185.5-187.5° C.

Example 479

(S)-4-(2-Methyl-6-nitro-2,3-dihydroimidazo[2,1-b]oxazol-2-ylmethyl)piperazine-1-carboxylic acid (4-trifluoromethylbenzyl)amide Melting point 101-103.6° C.

Example 480

(S)-4-(2-Methyl-6-nitro-2,3-dihydroimidazo[2,1-b]oxazol-2-ylmethyl)piperazine-1-carboxylic acid (4-chlorophenyl)amide Melting point 156-159° C. (decomposition).

Example 481

(S)-4-(2-Methyl-6-nitro-2,3-dihydroimidazo[2,1-b]oxazol-2-ylmethyl)piperazine-1-carboxylic acid (4-methylphenyl)amide Melting point 207-210° C. (decomposition).

Example 482

Preparation of (S)-4-(2-methyl-6-nitro-2,3-dihydroimidazo[2,1-b]oxazol-2-ylmethyl)piperazine-1-carboxylic acid N-methyl-N-(4-trifluoromethylphenyl)amide A mixture of (S)-4-(2-methyl-6-nitro-2,3-dihydroimidazo[2,1-b]oxazol-2-ylmethyl)piperazine-1-carboxylic acid (4-trifluoromethylphenyl)amide prepared in Example 477 (200 mg, 0.44 mmol), DMF (4 ml), and sodium hydride (26 mg, 0.66 mmol) was stirred at room temperature for 1.5 hours. To the mixture, methyl iodide (0.5 ml, 0.76 mmol) was added followed by stirring at room temperature overnight. To the reaction mixture, water was added, and the mixture was extracted with ethyl acetate. The organic phase was washed with water three times and a saturated saline solution, dried over sodium sulfate and then filtered. The filtrate was concentrated under reduced pressure, and the residue was purified by silica gel column chromatography (methylene chloride/methanol=50/1) to afford (S)-4-(2-methyl-6-nitro-2,3-dihydroimidazo[2,1-b]oxazol-2-ylmethyl)piperazine-1-carboxylic acid N-methyl-N-(4-trifluoromethylphenyl)amide (35 mg, yield 17%) as a white powder.
Melting point 100.4-102.4° C.

Example 483

Preparation of (S)-[4-(2-methyl-6-nitro-2,3-dihydroimidazo[2,1-b]oxazol-2-ylmethyl)piperazin-1-yl]-[4-(4-trifluoromethylphenyl)piperidin-1-yl]methanone A mixture of tert-butyl (S)-4-(2-methyl-6-nitro-2,3-dihydroimidazo[2,1-b]oxazol-2-ylmethyl)-piperazine-1-carboxylate prepared in Example 393 (1.17 g, 3.32 mmol), trifluoroacetic acid (5 ml) and methylene chloride (10 ml) was stirred at room temperature for 2 hours. The reaction mixture was concentrated under reduced pressure, and the residue was dissolved in methylene chloride (10 ml). To the resulting solution, triethylamine (5 ml, 35.87 mmol) was added followed by stirring at room temperature for 10 minutes. The solution was concentrated under reduced pressure, the residue was dissolved in DMF (15 ml). To the mixture, potassium carbonate (920 mg, 6.64 mmol) and a solution of 4-(4-trifluoromethylphenyl)-piperidine-1-carbonylchloride (1.07 g, 3.65 mmol) in DMF (10 ml) was added slowly with cooling on ice-bath followed by stirring at room temperature overnight. To the reaction mixture, water was added followed by extraction with ethyl acetate. The extract was washed with water three times and a saturated saline solution, dried over sodium sulfate and then filtered. The filtrate was concentrated under reduced pressure, and the residue was purified by silica gel column chromatography (methylene chloride/methanol=30/1) to afford (S)-[4-(2-methyl-6-nitro-2,3-dihydroimidazo[2,1-b]oxazol-2-ylmethyl)piperazin-1-yl]-[4-(4-trifluoromethylphenyl)piperidin-1-yl]methanone (575 mg, yield 33%) as a white powder.

Melting point 179.1-181.9° C.

Example 484

Preparation of (S)-[4-(4-chlorophenyl)-1,2,3,6-tetrahydropyridin-1-yl]-[4-(2-methyl-6-nitro-2,3-dihydroimidazo[2,1-b]oxazol-2-ylmethyl)piperazin-1-yl]methanone A mixture of (S)-2-methyl-6-nitro-2-(piperazin-1-ylmethyl)-2,3-dihydroimidazo[2,1-b]oxazole dihydrochloride prepared in Example 408 (401 mg, 1.5 mmol), DMF (8 ml) and potassium carbonate (750 mg, 5.4 mmol) was stirred at room temperature for 10 minutes. To the reaction mixture, a solution of 4-(4-chlorophenyl)-1,2,3,6-tetrahydropyridine-1-carbonylchloride (400 mg, 1.56 mmol) in DMF (3 ml) was added slowly with cooling on ice-bath followed by stirring at room temperature overnight. To the reaction mixture, water was added, and the solution was extracted with ethyl acetate. The organic phase was washed with water three times and a saturated saline solution, dried over sodium sulfate and then filtered. The filtrate was concentrated under reduced pressure, and the residue was recrystallized from ethanol to afford (S)-[4-(4-chlorophenyl)-1,2,3,6-tetrahydropyridin-1-yl]-[4-(2-methyl-6-nitro-2,3-dihydroimidazo[2,1-b]oxazol-2-ylmethyl)piperazin-1-yl]methanone (380 mg, yield 53%) as a light yellow powder.
Melting point 161-162° C.

Using (S)-2-methyl-6-nitro-2-(piperazin-1-ylmethyl)-2,3-dihydroimidazo[2,1-b]oxazole dihydrochloride prepared in Example 408 gave compounds of Examples 485 and 486 in the same manner as in Example 484. Also, using 2-methyl-6-nitro-2-(piperazin-1-ylmethyl)-2,3-dihydroimidazo[2,1-b]oxazole dihydrochloride prepared in Example 322 gave the compound of Example 487 in the same manner as in Example 484.

Example 485

(S)-[4-(4-Chlorophenyl)pyridin-1-yl]-[4-(2-methyl-6-nitro-2,3-dihydroimidazo[2,1-b]oxazol-2-ylmethyl)-piperazin-1-yl]methanone Melting point 156-159° C.

Example 486

(S)-[4-(2-Methyl-6-nitro-2,3-dihydroimidazo[2,1-b]oxazol-2-ylmethyl)piperazin-1-yl]-[4-(4-trifluoromethylphenyl)-1,2,3,6-tetrahydropyridin-1-yl]methanone Melting point 168.4-171.7° C.

Example 487

[4-(4-Chlorophenyl)piperidin-1-yl]-[4-(2-methyl-6-nitro-2,3-dihydroimidazo[2,1-b]oxazol-2-ylmethyl)-piperazin-1-yl]methanone Melting point 186-187° C.

Example 488

Preparation of (S)-4-[4-(2-methyl-6-nitro-2,3-dihydroimidazo[2,1-b]oxazol-2-ylmethyl)piperazin-1-yl]benzoic acid Tert-butyl (S)-4-[4-(2-methyl-6-nitro-2,3-dihydroimidazo[2,1-b]oxazol-2-ylmethyl)piperazin-1-yl]benzoate (300 mg, 0.68 mmol) in triluoroacetic acid (10 ml) was stirred at room temperature for 5 hours. The reaction mixture was concentrated under reduced pressure, neutralized with triethylamine, and concentrated under reduced pressure. The residue was purified by silica gel column chromatography (methylene chloride/methanol=20/1), crystallized from methanol-diisopropyl ether to afford (S)-4-[4-(2-methyl-6-nitro-2,3-dihydroimidazo[2,1-b]oxazol-2-ylmethyl)piperazin-1-yl]benzoic acid (186 mg, yield 71%) as a white powder.
MS 387(M+) Melting point 248-252° C.

Example 489

Preparation of (S)-2-[4-(2,6-diphenylpyrimidin-4-yl)piperazin-1-ylmethyl]-2-methyl-6-nitro-2,3-dihydroimidazo[2,1-b]oxazole Tert-butyl (S)-4-(2-methyl-6-nitro-2,3-dihydroimidazo[2,1-b]oxazol-2-ylmethyl)piperazine-1-carboxylate prepared in Example 393 (500 mg, 1.36 mmol) was dissolved in methylene chloride (2 ml). To the solution, trifluoroacetic acid (10 ml) was added followed by stirring at room temperature for 3 hours. The reaction mixture was concentrated under reduced pressure, and added methylene chloride (4 ml) and triethylamine (4 ml). The reaction mixture was stirred at room temperature for 5 minutes and then concentrated under reduced pressure, and the residue was dissolved in DMF (5 ml). To the solution, 4-chloro-2,6-diphenylpyrimidine (400 mg, 1.50 mmol) and DBU (0.2 ml, 1.36 mmol) were added followed by stirring at 100° C. for 5 hours. The reaction mixture was allowed to return to room temperature, poured into water, and then the mixture was extracted with ethyl acetate. The organic phase was washed with a saturated saline solution, dried over magnesium sulfate and then filtered. The filtrate was concentrated under reduced pressure, and the residue was purified by silica gel column chromatography (methylene chloride/methanol=100/1) and crystallized from methylene chloride-diisopropyl ether to afford (S)-2-[4-(2,6-diphenylpyrimidin-4-yl)piperazin-1-ylmethyl]-2-methyl-6-nitro-2,3-dihydroimidazo[2,1-b]oxazole (113 mg, yield 17%) as a white powder.

MS 498(M+H)+Melting point 202.5-205.4° C.

Using corresponding starting materials gave the compound of Example 490 in the same manner as in Example 489.

Example 490

(S)-2-[4-(4,6-Diphenylpyrimidin-2-yl)piperazin-1-ylmethyl]-2-methyl-6-nitro-2,3-dihydroimidazo[2,1-b]oxazole Yield 7%, melting point 201.2-205.4° C.

Example 491

Preparation of tert-butyl{4-[3-(2-chloro-4-nitroimidazol-1-yl)-2-hydroxy-2-methylpropyl]piperazin-1-yl}carbamate 2-Chloro-4-nitro-1H-imidazole (2.05 g, 13.9 mmol), tert-butyl 4-(2-methyloxiran-2-ylmethyl)-piperazin-1-yl)carbamate (3.14 g, 11.6 mmol) and sodium hydrogencarbonate (1.46 g, 17.4 mmol) in 1-propanol (13 ml) were stirred under heating for 6 hours. The reaction mixture was extracted with ethyl acetate twice. The organic phases were combined, washed with a saturated saline solution, dried over sodium sulfate and then filtered. The resulting filtrate was concentrated under reduced pressure, and the residue was purified by silica gel column chromatography (n-hexane/acetone=2/1) to afford tert-butyl{4-[3-(2-chloro-4-nitroimidazol-1-yl)-2-hydroxy-2-methylpropyl]piperazin-1-yl}carbamate (1.55 g, yield 32%) as a white powder.
$^1$H-NMR (CDCl$_3$) δppm: 1.12 (3H, s), 1.46 (9H, s), 2.36 (1H, d, J=13.9 Hz), 2.50 (1H, d, J=13.9 Hz), 2.64-2.84 (8H, m), 3.32 (1H, s), 3.96 (2H, s), 5.46 (1H, br), 8.03 (1H, s).

Example 492

Preparation of tert-butyl{4-[3-(2-chloro-4-nitroimidazol-1-yl)-2-hydroxy-2-methylpropyl]piperazin-1-yl}carbamate (alternative synthesis of the compound of Example 491)

Using 2-chloro-1-(2-methyloxiran-2-ylmethyl)-4-nitroimidazole prepared in Example 6 (4.36 g, 20.0 mmol) and tert-butyl piperazin-1-ylcarbamate (4.44 g, 22.0 mmol) gave tert-butyl{4-[3-(2-chloro-4-nitroimidazol-1-yl)-2-hydroxy-2-methylpropyl]piperazin-1-yl}carbamate (6.08 g, yield 72%) as a white powder in the same manner as in Example 365.

Example 493

Preparation of tert-butyl[4-(2-methyl-6-nitro-2,3-dihydroimidazo[2,1-b]oxazol-2-ylmethyl)piperazin-1-yl]carbamate Using tert-butyl{4-[3-(2-chloro-4-nitroimidazol-1-yl)-2-hydroxy-2-methylpropyl]piperazin-1-yl}carbamate prepared in Example 492 (6.87 g, 16.4 mmol) gave tert-butyl [4-(2-methyl-6-nitro-2,3-dihydroimidazo[2,1-b]oxazol-2-ylmethyl)piperazin-1-yl]carbamate (2.71 g, yield 43%) as a white powder in the same manner as in Example 393.
$^1$H-NMR (CDCl$_3$) δppm: 1.43 (9H, s), 1.60 (3H, s), 2.36 (1H, d, J=14.0 Hz), 2.52-2.90 (9H, m), 3.90 (1H, d, J=9.7 Hz), 4.27 (1H, d, J=9.7 Hz), 5.35 (1H, br), 7.53 (1H, s).

Example 494

Preparation of benzyl[4-(2-methyl-6-nitro-2,3-dihydroimidazo[2,1-b]oxazol-2-ylmethyl)piperazin-1-yl]carbamate A mixture of tert-butyl[4-(2-methyl-6-nitro-2,3-dihydroimidazo[2,1-b]oxazol-2-ylmethyl)piperazin-1-yl]carbamate prepared in Example 493-(150 mg, 0.39 mmol) and trifluoroacetic acid (4 ml) was stirred at room temperature for 3 hours. The reaction mixture was concentrated under reduced pressure. The residue was dissolved in methylene chloride (4 ml) and neutralized with triethylamine (4 ml, 28.7 mmol). Subsequently, to the solution, benzyl chloroformate (100 mg, 0.59 mmol) was added with cooling on ice-bath followed by stirring at room temperature for 2 hours. To the reaction mixture, a saturated sodium hydrogencarbonate solution was added. The mixture was extracted with methylene chloride. The extract was washed with water and a saturated saline solution, dried over sodium sulfate and then filtered. The filtrate was concentrated under reduced pressure, and the residue was purified by silica gel column chromatography (n-hexane/acetone=1/1) to afford benzyl[4-(2-methyl-6-nitro-2,3-dihydroimidazo[2,1-b]oxazol-2-ylmethyl)piperazin-1-yl]carbamate (6.5 mg, yield 4%) as a light yellow powder.

$^1$H-NMR (CDCl$_3$) δppm: 1.60 (3H, s), 2.53-2.90 (10H, m), 3.89 (1H, d, J=9.6 Hz), 4.27 (1H, d, J=9.6 Hz), 5.11 (2H, s), 5.88 (1H, br), 7.25-7.34 (5H, m), 7.52 (1H, s).

Example 495

Preparation of N-[4-(2-methyl-6-nitro-2,3-dihydroimidazo[2,1-b]oxazol-2-ylmethyl)piperazin-1-yl]-N-(4-trifluoromethoxybenzylidene)amine A mixture of tert-butyl[4-(2-methyl-6-nitro-2,3-dihydroimidazo[2,1-b]oxazol-2-ylmethyl)piperazin-1-yl]carbamate prepared in Example 493 (40 mg, 0.11 mmol), 4-trifluoromethoxybenzaldehyde (24 mg, 0.13 mmol), trifluoroacetic acid (0.08 ml) and methylene chloride (1 ml) was stirred at room temperature for 3 hours. The mixture was added a saturated sodium hydrogencarbonate solution for neutralization followed by extraction with methylene chloride. The solution was washed with water and a saturated saline solution, dried over sodium sulfate and then filtered. The filtrate was concentrated under reduced pressure, and the residue was purified by silica gel column chromatography (methylene chloride/ethyl acetate=3/1) to afford N-[4-(2-methyl-6-nitro-2,3-dihydroimidazo[2,1-b]oxazol-2-ylmethyl)piperazin-1-yl]-N-(4-trifluoromethoxybenzylidene)amine (19 mg, yield 40%) as a white powder.

Melting point 189.2-190.9° C.

Example 496

Preparation of (S)-1-(2-chloro-4-nitroimidazol-1-yl)-2-methyl-3-{4-[(4-trifluoromethylbenzylidene)amino]-piperazin-1-yl}propan-2-ol A mixture of (R)-2-chloro-1-(2-methyloxiran-2-ylmethyl)-4-nitroimidazole prepared in Example 12 (218 mg, 1 mmol), N-(piperazin-1-yl)-N-(4-trifluoromethylbenzylidene)amine (283 mg, 1.1 mmol) and DMF (2 ml) was stirred at 70-80° C. for 7 hours. The reaction mixture was allowed to return to room temperature and then added water, and the resulting solution was extracted with ethyl acetate twice. The organic phases were combined, washed with water 3 times and a saturated saline solution, dried over sodium sulfate and then filtered. The filtrate was concentrated under reduced pressure, and the residue was purified by silica gel column chromatography (n-hexane/acetone=1/1) to afford (S)-1-(2-chloro-4-nitroimidazol-1-yl)-2-methyl-3-{4-[(4-trifluoromethylbenzylidene)amino]piperazin-1-yl}propan-2-ol (402 mg, yield 85%) as a light yellow powder.

$[α]_D^{27}$=19.01° (concentration: 1.010, CHCl$_3$) $^1$H-NMR (CDCl$_3$) δppm: 1.18 (3H, s), 2.42 (1H, d, J=13.9 Hz), 2.57 (1H, d, J=13.9 Hz), 2.71-2.95 (4H, m), 3.10-3.33 (5H, m), 4.02 (2H, s), 7.51 (1H, s), 7.58 (2H, d, J=8.4 Hz), 7.68 (2H, d, J=8.4 Hz), 8.05 (1H, s).

Example 497

Preparation of tert-butyl (S)-{4-[3-(2-chloro-4-nitroimidazol-1-yl)-2-hydroxy-2-methylpropyl]piperazin-1-yl}carbamate Using (R)-2-chloro-1-(2-methyloxiran-2-ylmethyl)-4-nitroimidazole prepared in Example 12 (29.8 g, 137 mmol) and tert-butyl piperazin-1-ylcarbamate (28.9 g, 144 mmol) gave tert-butyl (S)-{4-[3-(2-chloro-4-nitroimidazol-1-yl)-2-hydroxy-2-methylpropyl]piperazin-1-yl}carbamate (36.68 g, yield 64%) as a white powder in the same manner as in Example 496.

$[α]_D^{27}$=17.793° (concentration: 1.006, CHCl$_3$) $^1$H-NMR (CDCl$_3$) δppm: 1.12 (3H, s), 1.45 (9H, s), 2.36 (1H, d, J=14.0 Hz), 2.50 (1H, d, J=14.0 Hz), 2.64-2.84 (8H, m), 3.32 (1H, s), 3.97 (2H, s), 5.47 (1H, br), 8.04 (1H, s).

Using corresponding starting materials gave compounds of Examples 498 to 500 in the same manner as in Example 497.

Example 498

(S)-1-(2-Chloro-4-nitroimidazol-1-yl)-2-methyl-3-{4-[(4-trifluoromethoxybenzylidene)amino]piperazin-1-yl}propan-2-ol $[α]_D^{27}$=12.326° (concentration: 1.006, CHCl$_3$) $^1$H-NMR (CDCl$_3$) δppm: 1.17 (3H, s), 2.41 (1H, d, J=13.9 Hz), 2.56 (1H, d, J=13.9 Hz), 2.71-2.95 (4H, m), 3.14-3.29 (5H, m), 4.01 (2H, s), 7.19 (2H, d, J=8.0 Hz), 7.50 (1H, s), 7.62 (2H, d, J=8.0 Hz), 8.05 (1H, s).

Example 499

(S)-1-(2-Chloro-4-nitroimidazol-1-yl)-2-methyl-3-{4-[(5-trifluoromethylbenzofuran)-2-ylmethylene)amino]-piperazin-1-yl}propan-2-ol $^1$H-NMR (CDCl$_3$) δppm: 1.18 (3H, s), 2.43 (1H, d, J=14.0 Hz), 2.58 (1H, d, J=14.0 Hz), 2.73-2.82 (2H, m), 2.86-2.95 (2H, m), 3.17 (1H, s), 3.31 (4H, s), 4.03 (2H, s), 6.82 (1H, s), 7.46 (1H, s), 7.52 (1H, d, J=8.7 Hz), 7.59 (1H, d, J=8.7 Hz), 7.83 (1H, s), 8.05 (1H, s).

Example 500

(S)-1-{4-[(5-Chlorobenzofuran)-2-ylmethylene)amino]-piperazin-1-yl}-3-(2-chloro-4-nitroimidazol-1-yl)-2-methylpropan-2-ol $^1$H-NMR (CDCl$_3$) δppm: 1.18 (3H, s), 2.42 (1H, d, J=14.0 Hz), 2.57 (1H, d, J=14.0 Hz), 2.71-3.00 (4H, m), 3.17 (1H, s), 3.23-3.38 (4H, m), 4.02 (2H, s), 6.71 (1H, s), 7.22 (1H, dd, J=2.1 Hz, 8.7 Hz), 7.33-7.43 (2H, m), 7.50 (1H, d, J=2.1 Hz), 8.05 (1H, s).

Example 501

Preparation of (S)-1-(2-chloro-4-nitroimidazol-1-yl)-2-methyl-3-[4-(4-trifluoromethylphenylamino)piperazin-1-yl]propan-2-ol Using (R)-2-chloro-1-(2-methyloxiran-2-ylmethyl)-4-nitroimidazole prepared in Example 12 (0.610 g, 2.82 mmol) and N-(piperazin-1-yl)-4-trifluoromethylaniline (0.760 g, 3.09 mmol) gave (S)-1-(2-chloro-4-nitroimidazol-1-yl)-2-methyl-3-[4-(4-trifluoromethylphenylamino)piperazin-1-yl]propan-2-ol (1.125 g, yield 86%) as a colorless solid in the same manner as in Example 496.

$^1$H-NMR (CDCl$_3$) δppm: 1.15 (3H, s), 2.39 (1H, d, J=14.0 Hz), 2.54 (1H, d, J=14.0 Hz), 2.60-2.95 (8H, m), 3.25 (1H, s), 3.99 (2H, s), 4.67 (1H, s), 6.90 (2H, d, J=8.6 Hz), 7.43 (2H, d, J=8.6 Hz), 8.04 (1H, s).

Example 502

Preparation of (S)-N-[4-(2-methyl-6-nitro-2,3-dihydroimidazo[2,1-b]oxazol-2-ylmethyl)piperazin-1-yl]-4-trifluoromethylaniline Using (S)-1-(2-chloro-4-nitroimidazol-1-yl)-2-methyl-3-[4-(4-trifluoromethylphenylamino)piperazin-1-yl]propan-2-ol prepared in Example 501 (1.125 g, 2.43 mmol) gave (S)-N-[4-(2-methyl-6-nitro-2,3-dihydroimidazo[2,1-b]oxazol-2-ylmethyl)piperazin-1-yl]-4-trifluoromethylaniline (0.715 g, yield 69%) as a white solid in the same manner as in Example 493.

Melting point 192.1-195.3° C.

Example 503

Preparation of tert-butyl (S)-[4-(2-methyl-6-nitro-2,3-dihydroimidazo[2,1-b]oxazol-2-ylmethyl)piperazin-1-yl]carbamate Using tert-butyl (S)-{4-[3-(2-chloro-4-nitroimidazol-1-yl)-2-hydroxy-2-methylpropyl]piperazin-1-yl}carbamate prepared in Example 497 (36.68 g) gave tert-butyl (S)-[4-(2-methyl-6-nitro-2,3-dihydroimidazo[2,1-b]oxazol-2-ylmethyl)piperazin-1-yl]carbamate (19.51 g, yield 58%) as a white powder in the same manner as in Example 493.

Optical purity >99.5% e.e.

$[α]_D^{27}$ 9.84° (concentration: 1.016, CHCl$_3$) $^1$H-NMR (CDCl$_3$) δppm: 1.43 (9H, s), 1.60 (3H, s), 2.35 (1H, d, J=14.0 Hz), 2.52-2.92 (9H, m), 3.89 (1H, d, J=9.7 Hz), 4.27 (1H, d, J=9.7 Hz), 5.35 (1H, s), 7.53 (1H, s)

Example 504

Preparation of (S)-N-[4-(2-methyl-6-nitro-2,3-dihydroimidazo[2,1-b]oxazol-2-ylmethyl)piperazin-1-yl]-N-(4-trifluoromethylbenzylidene)amine To a mixture of (S)-1-(2-chloro-4-nitroimidazol-1-yl)-2-methyl-3-{4-[(4-trifluoromethylbenzylidene)amino]piperazin-1-yl}propan-2-ol prepared in Example 496 (847 mg, 0.85 mmol) and DMF (4 ml), sodium hydride (69 mg, 1.73 mmol) was added followed by stirring for 2.5 hours with cooling on ice-bath. To the reaction mixture, water was added, and the precipitates were filtered off. The resulting solid was washed with methanol and recrystallized from acetone/water to afford (S)-N-[4-(2-methyl-6-nitro-2,3-dihydroimidazo[2,1-b]oxazol-2-ylmethyl)piperazin-1-yl]-N-(4-trifluoromethylbenzylidene)amine (248 mg, yield 69%) as a light yellow powder.

Melting point 201-202.3° C. (decomposition) Optical purity >99.5% e.e. $[α]_D^{27}$=−64.64° (concentration: 1.018, CHCl$_3$) $^1$H-NMR (CDCl$_3$) δppm: 1.64 (3H, s), 2.55-2.79 (3H, m), 2.80-3.20 (7H, m), 3.94 (1H, d, J=9.7 Hz), 4.33 (1H, d, J=9.7 Hz), 7.44 (1H, s), 7.48-7.67 (5H, m).

Using corresponding starting materials gave compounds of Examples 505 to 507 in the same manner as in Example 504.

Example 505

(S)-N-[4-(2-Methyl-6-nitro-2,3-dihydroimidazo[2,1-b]oxazol-2-ylmethyl)piperazin-1-yl]-N-(4-trifluoromethylbenzylidene)amine Melting point 188.4-191.2° C. Optical purity >99.0% e.e. $[α]_D^{27}$=−58.30° (concentration: 1.024, CHCl$_3$) $^1$H-NMR (CDCl$_3$) δppm: 1.64 (3H, s), 2.55-2.77 (3H, m), 2.82-3.18 (7H, m), 3.94 (1H, d, J=9.7 Hz), 4.33 (1H, d, J=9.7 Hz), 7.16 (2H, d, J=8.2 Hz), 7.43 (1H, s), 7.55 (1H, s), 7.58 (2H, d, J=8.2 Hz).

Example 506

(S)-N-[4-(2-Methyl-6-nitro-2,3-dihydroimidazo[2,1-b]oxazol-2-ylmethyl)piperazin-1-yl]-N-(5-trifluoromethylbenzofuran-2-ylmethylene)amine Melting point 190.2-191.8° C. Optical purity 99.8% e.e. $[α]_D^{27}$=−81.050 (c=0.992, CHCl$_3$) $^1$H-NMR (CDCl$_3$) δppm: 1.64 (3H, s), 2.59-2.77 (3H, m), 2.86-3.00 (3H, m), 3.05-3.26 (4H, m), 3.96 (1H, d, J=9.7 Hz), 4.33 (1H, d, J=9.7 Hz), 6.79 (1H, s), 7.39 (1H, s), 7.41-7.57 (3H, m), 7.82 (1H, s).

Example 507

(S)-N-(5-Chlorobenzofuran-2-ylmethylene)-N-[4-(2-methyl-6-nitro-2,3-dihydroimidazo[2,1-b]oxazol-2-ylmethyl)piperazin-1-yl]amine Optical purity>99.0% e.e.

$[α]D$=−84.48° (concentration: 1.018, CHCl$_3$) Melting point 213.8-215.7° C. $^1$H-NMR (CDCl$_3$) δppm: 1.63 (3H, s), 2.57-2.76 (3H, m), 2.81-2.95 (3H, m), 3.00-3.24 (4H, m), 3.94 (1H, d, J =9.7 Hz), 4.32 (1H, d, J=9.7 Hz), 6.67 (1H, s), 7.17-7.23 (1H, m), 7.30-7.43 (2H, m), 7.48 (1H, d, J=2, 1 Hz), 7.53 (s, 1H).

Example 508

Preparation of (S)-N-(5-chlorobenzofuran-2-ylmethylene)-N-[4-(2-methyl-6-nitro-2,3-dihydroimidazo[2,1-b]oxazol-2-ylmethyl)piperazin-1-yl]amine (alternative synthesis of the compound of Example 507)

To a mixture of tert-butyl (S)-[4-(2-methyl-6-nitro-2,3-dihydroimidazo[2,1-b]oxazol-2-ylmethyl)piperazin-1-yl]carbamate prepared in Example 503 (0.20 g, 0.523 mmol) and 5-chlorobenzofuran-2-carbaldehyde (0.113 g, 0.628 mmol) and methylene chloride (4 ml), trifluoroacetic acid (0.4 ml) was added followed by stirring at room temperature for 2 hours. To the reaction mixture, a saturated sodium hydrogencarbonate solution was added followed by extraction with methylene chloride. The organic phase was washed with a saturated saline solution, dried over sodium sulfate and then filtered. The resulting filtrate was concentrated under reduced pressure, and the residue was purified by silica gel column chromatography (methylene chloride/ethyl acetate=4/1) to afford (S)-N-(5-chlorobenzofuran-2-ylmethylene)-N-[4-(2-methyl-6-nitro-2,3-dihydroimidazo[2,1-b]oxazol-2-ylmethyl)piperazin-1-yl]amine (0.137 g, yield 59%) as a light yellow powder.

Example 509

Preparation of (S)-N-[1-(4-chlorophenyl)ethylidene]-N-[4-(2-methyl-6-nitro-2,3-dihydroimidazo[2,1-b]oxazol-2-ylmethyl)piperazin-1-yl]amine A mixture of tert-butyl (S)-[4-(2-methyl-6-nitro-2,3-dihydroimidazo[2,1-b]oxazol-2-ylmethyl)-piperazin-1-yl]carbamate prepared in Example 503 (200 mg, 0.52 mmol), trifluoroacetic acid (2 ml) and methylene chloride (4 ml) was stirred at room temperature for 30 minutes. The reaction mixture was concentrated under reduced pressure, and the residue was dissolved in methylene chloride (4 ml) and then neutralized with triethylamine (4 ml, 28.7 mmol). To the neutralized solution, a solution of 4-chloroacetophenone (97 mg, 0.63 mmol) in ethanol (4 ml) was added followed by stirring under reflux for 4 hours. The reaction mixture was allowed to return to room temperature and concentrated under reduced pressure. The residue was purified by silica gel column chromatography (n-hexane/acetone=3/1) to afford (S)-N-[1-(4-chlorophenyl)ethylidene]-N-[4-(2-methyl-6-nitro-2,3-dihydroimidazo[2,1-b]oxazol-2-ylmethyl)piperazin-1-yl]amine (39 mg, yield 18%) as a light yellow powder.

Melting point 164.6-166.5° C.

Using corresponding starting materials gave compounds of Examples 510 to 513 in the same manner as in Example 509.

Example 510

(S)-N-[4-(2-Methyl-6-nitro-2,3-dihydroimidazo[2,1-b]oxazol-2-ylmethyl)piperazin-1-yl]-N-[1-(4-trifluoro-methylphenyl)ethylidene]amine Melting point 167.9-169.4° C.

Example 511

(S)-N-[4-(2-Methyl-6-nitro-2,3-dihydroimidazo[2,1-b]oxazol-2-ylmethyl)piperazin-1-yl]-N-[1-(4-trifluoro-methoxyphenyl)ethylidene]amine Melting point 177.8-180.1° C.

Example 512

(S)-N-Cyclohexylidene-N-[4-(2-methyl-6-nitro-2,3-dihydroimidazo[2,1-b]oxazol-2-ylmethyl)piperazin-1-yl]amine Melting point 178.6-179.3° C.

Example 513

N-(2-Benzylideneheptylidene)-N-[4-(2-methyl-6-nitro-2,3-dihydroimidazo[2,1-b]oxazol-2-ylmethyl)piperazin-1-yl]amine Melting point 166.6-169.6° C.

Example 514

Preparation of (S)-N-[4-(2-methyl-6-nitro-2,3-dihydro-imidazo[2,1-b]oxazol-2-ylmethyl)piperazin-1-yl]-N-(4-trifluoromethylbenzyl)amine To a mixture of (S)-N-[4-(2-methyl-6-nitro-2,3-dihydroimidazo[2,1-b]oxazol-2-ylmethyl)piperazin-1-yl]-N-(4-trifluoromethylbenzylidene)amine prepared in Example 504 (100 mg, 0.23 mmol) and THF (4 ml), sodium borohydride (13 mg, 0.34 mmol) was added with cooling on ice-bath followed by stirring at room temperature for 30 minutes. To the reaction mixture, methanol (1 ml) was added, and the solution was concentrated under reduced pressure. The residue was purified by silica gel column chromatography (n-hexane/ethyl acetate=2/1) to afford (S)-N-[4-(2-methyl-6-nitro-2,3-dihydroimidazo[2,1-b]oxazol-2-ylmethyl)piperazin-1-yl]-N-(4-trifluoromethylbenzyl)amine (32 mg, yield 31%) as a light yellow powder.

Melting point 131.3-135.5° C.

Example 515

Preparation of (S)-[4-(2-methyl-6-nitro-2,3-dihydro-imidazo[2,1-b]oxazol-2-ylmethyl)piperazin-1-yl]amine dihydrochloride A mixture of tert-butyl (S)-[4-(2-methyl-6-nitro-2,3-dihydroimidazo[2,1-b]oxazol-2-ylmethyl)-piperazin-1-yl]carbamate prepared in Example 503 (300 mg, 0.78 mmol), concentrated hydrochloric acid (2 ml) and methanol (4 ml) was stirred at 50° C. for 30 minutes. The reaction mixture was allowed to return to room temperature and concentrated under reduced pressure. The residue was recrystallized from methanol/ether to afford (S)-[4-(2-methyl-6-nitro-2,3-dihydroimidazo[2,1-b]oxazol-2-ylmethyl)piperazin-1-yl]amine dihydrochloride (265 mg, yield 91%) as a yellow powder.

Melting point 176° C. (decomposition)

Example 516

Preparation of 3-[3-(2-chloro-4-nitroimidazol-1-yl)-2-hydroxy-2-methylpropyl]-5-(4-trifluoromethoxyphenyl)-3H-[1,3,4]oxadiazol-2-one To a suspension of 2-chloro-4-nitro-1H-imidazole (2.21 g, 14.98 mmol) and 3-(2-methyloxiran-2-ylmethyl)-5-(4-trifluoromethoxyphenyl)-3H-[1,3,4]oxadiazol-2-one (2.37 g, 7.49 mmol) in ethanol (25 ml), sodium hydrogencarbonate (1.32 g, 15.73 mmol) was added followed by stirring under reflux for 8 hours. To the reaction mixture, water was added, and the mixture was extracted with methylene chloride. The organic phase was dried over magnesium sulfate, and concentrated under reduced pressure to afford 3-[3-(2-chloro-4-nitroimidazol-1-yl)-2-hydroxy-2-methylpropyl]-5-(4-trifluoromethoxyphenyl)-3H-[1,3,4]oxadiazol-2-one (3.27 g, yield 94%) as a light yellow amorphous form.

$^1$H-NMR (DMSO-$d_6$) δppm: 1.53 (3H, s), 3.67 (1H, d, J=8.8 Hz), 3.81 (1H, d, J=8.8 Hz), 4.49 (2H, s), 7.42-7.66 (2H, m), 7.86-8.09 (2H, m), 8.54 (1H, s), 10.98 (1H, br).

Using corresponding starting materials gave compounds of Examples 517 to 523 shown in the following table in the same manner as in Example 516.

Example 524

Preparation of 3-(2-methyl-6-nitro-2,3-dihydroimidazo-[2,1-b]oxazol-2-ylmethyl)-5-(4-trifluoromethoxyphenyl)-3H-[1,3,4]oxadiazol-2-one To a solution of 3-[3-(2-chloro-4-nitroimidazol-1-yl)-2-hydroxy-2-methylpropyl]-5-(4-trifluoromethoxyphenyl)-3H-[1,3,4]oxadiazol-2-one prepared in Example 516 (3.27 g, 7.05 mmol) in 1,4-dioxane (70 ml), sodium hydride (0.37 g, 9.17 mmol) was added with cooling on ice-bath followed by stirring under reflux for 3 hours. The reaction mixture was concentrated under reduced-pressure. To the solution, water was added with cooling on ice-bath, and the mixture was extracted with ethyl acetate. The extract was dried over magnesium sulfate, and then concentrated under reduced pressure. The residue was purified by silica gel column chromatography (methylene chloride/ethyl acetate=4/1) and recrystallized from acetonitrile-ethanol to afford 3-(2-methyl-6-nitro-2,3-dihydroimidazo[2,1-b]oxazol-2-ylmethyl)-5-(4-trifluoromethoxyphenyl)-3H-[1,3,4]oxadiazol-2-one (1.43 g, yield 48%) as a white solid.

Melting point 190-191° C.

TABLE 18

| Example | R | | $^1$H NMR δ | Yield (%) |
|---|---|---|---|---|
| 517 |  | CDCl$_3$ | 1.59(3H, s), 3.78(1H, d, J=8.5Hz), 3.86(1H, d, J=8.5Hz), 4.29(1H, d, J=15.1Hz), 4.57(1H, d, J=15.1Hz), 7.61(2H, d, J=8.1Hz), 7.79(2H, d, J=8.1Hz), 8.06(1H, s), 9.17(1H, br). | 70 |
| 518 | 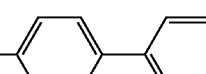 | CDCl$_3$ | 1.61(3H, s), 3.79(1H, d, J=8.5Hz), 3.85(1H, d, J=8.5Hz), 4.27(1H, d, J=15.0Hz), 4.56(1H, d, J=15.0Hz), 7.33-7.63(7H, m), 7.78(2H, d, J=8.4Hz), 8.06(1H, s), 9.02(1H, br). | 82 |
| 519 | 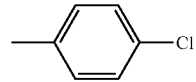 | CDCl$_3$ | 1.62(3H, s), 3.75(1H, d, J=8.5Hz), 3.83(1H, d, J=8.5Hz), 4.27(1H, d, J=15.0Hz), 4.54(1H, d, J=15.0Hz), 7.34(2H, dd, J=1.8Hz), 8.6Hz), 7.63(2H, dd, J=1.8Hz), 8.6Hz), 8.03(1H, s), 9.05(1H, br). | 57 |
| 520 | 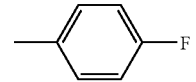 | DMSO-$d_6$ | 1.51(3H, s), 3.66(1H, d, J=8.8Hz), 3.79(1H, d, J=8.8Hz), 4.48(2H, s), 7.24-7.41(2H, m), 7.84-7.96(2H, m), 8.52(1H, s). | 64 |
| 521 | 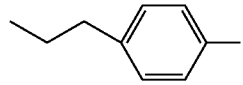 | CDCl$_3$ | 1.56(3H, s), 2.41-2.53(2H, m), 2.81-3.00(2H, m), 3.56(1H, d, J=8.5Hz), 3.63(1H, d, J=8.5Hz), 4.22(1H, d, J=15.0Hz), 4.42(1H, d, J=15.0Hz), 7.12(2H, d, J=8.4Hz), 7.26(2H, d, J=8.4Hz), 7.55(1H, br), 7.97(1H, s). | 92 |
| 522 | 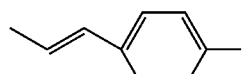 | DMSO-$d_6$ | 1.53(3H, s), 3.63(1H, d, J=8.8Hz), 3.77(1H, d, J=8.8Hz), 4.43(1H, d, J=15.0Hz), 4.51(1H, d, J=15.0Hz), 6.58(1H, d, J=15.9Hz), 7.43-7.55(3H, m), 7.64(2H, d, J=8.5Hz), 7.51(1H, s). | 89 |
| 523 | 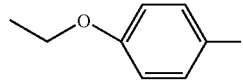 | CDCl$_3$ | 1.56(3H, s), 3.72(2H, s), 4.25(1H, d, J=15.1Hz), 4.44(1H, d, J=15.1Hz), 4.59(2H, s), 6.85(2H, dd, J=2.3Hz, 6.8Hz), 7.29(2H, dd, J=2.3Hz 6.8Hz), 7.98(1H, s), 8.49(1H, br). | 98 |

Using corresponding starting materials gave compounds of Examples 525 to 531 in the same manner as in Example 524.

Example 525

3-(2-Methyl-6-nitro-2,3-dihydroimidazo[2,1-b]oxazol-2-ylmethyl)-5-(4-trifluoromethylphenyl)-3H-[1,3,4]-oxadiazol-2-one Melting point 230-231° C.

Example 526

3-(2-Methyl-6-nitro-2,3-dihydroimidazo[2,1-b]oxazol-2-ylmethyl)-5-(biphenyl-4-yl)-3H-[1,3,4]oxadiazol-2-one Melting point 248-249° C.

Example 527

3-(2-Methyl-6-nitro-2,3-dihydroimidazo[2,1-b]oxazol-2-ylmethyl)-5-(4-chlorophenyl)-3H-[1,3,4]oxadiazol-2-one Melting point 221-222° C.

Example 528

3-(2-Methyl-6-nitro-2,3-dihydroimidazo[2,1-b]oxazol-2-ylmethyl)-5-(4-fluorophenyl)-3H-[1,3,4]oxadiazol-2-one Melting point 188-191° C.

Example 529

3-(2-Methyl-6-nitro-2,3-dihydroimidazo[2,1-b]oxazol-2-ylmethyl)-5-[2-(4-chlorophenyl)vinyl]-3H-[1,3,4]-oxadiazol-2-one Melting point 249-252° C.

Example 530

3-(2-Methyl-6-nitro-2,3-dihydroimidazo[2,1-b]oxazol-2-ylmethyl)-5-[2-(4-chlorophenyl)ethyl]-3H-[1,3,4]-oxadiazol-2-one Melting point 139-140° C.

Example 531

3-(2-Methyl-6-nitro-2,3-dihydroimidazo[2,1-b]oxazol-2-ylmethyl)-5-(4-chlorophenoxymethyl)-3H-[1,3,4]-oxadiazol-2-one Melting point 64-66° C.

Example 532

Preparation of 3-(2-methyl-6-nitro-2,3-dihydroimidazo-[2,1-b]oxazol-2-ylmethyl)-5-phenyl-3H-[1,3,4] oxadiazol-2-one A mixture of 2-chloro-4-nitro-1H-imidazole (170 mg, 1.15 mmol), 3-(2-methyloxiran-2-ylmethyl)-5-phenyl-3H-[1,3,4]oxadiazol-2-one (310 mg, 0.9 mmol), sodium hydrogencarbonate (120 mg, 1.43 mmol) and ethanol (2 ml) was stirred under reflux for 2.5 hours. The reaction mixture was allowed to return to room temperature, then diluted with water. The solution was extracted with methylene chloride. The organic phase was dried over magnesium sulfate and then filtered. The filtrate was concentrated under reduced pressure, the residue was dissolved in 1,4-dioxane (10 ml). To the solution, sodium hydride (55 mg, 1.38 mmol) was added followed by stirring at room temperature for 1 hour and then stirring under reflux for 1.5 hours. The reaction mixture was allowed to return to room temperature. To the solution, water was added, and the mixture was extracted with methylene chloride. The organic phase was dried over magnesium sulfate and then filtered. The filtrate was concentrated under reduced pressure, and the residue was recrystallized from ethanol to afford 3-(2-methyl-6-nitro-2,3-dihydro-imidazo[2,1-b]oxazol-2-ylmethyl)-5-phenyl-3H-[1,3,4]-oxadiazol-2-one (127 mg, yield 32%) as a light brown powder.

Melting point 225-227° C.

Example 533

Preparation of 5-(4-chlorobenzyl)-3-(2-methyl-6-nitro-2,3-dihydroimidazo[2,1-b]oxazol-2-ylmethyl)-3H-[1,3,4]oxadiazol-2-one A mixture of 2-methyloxiran-2-ylmethyl 4-methylbenzenesulfonate (3.98 g, 18.9 mmol), 5-(4-chlorobenzyl)-3H-[1,3,4]oxadiazol-2-one (5.5 g, 26.11 mmol), potassium carbonate (3.4 g, 24.6 mmol), sodium iodide (3.4 g, 22.68 mmol) and DMF (40 ml) was stirred at room temperature for 21 hours. To the reaction mixture, water was added, and the mixture was extracted with ethyl acetate twice. The organic phases were combined, washed with water three times, dried over magnesium sulfate and then filtered. The filtrate was concentrated under reduced pressure to afford a yellow oil (5.47 g).

A mixture of 2.3 g of the yellow oil (11.02 mmol), 2,4-dinitro-1H-imidazole (2.26 g, 14.3 mmol), sodium acetate (1.81 g, 22.07 mmol) and ethanol (22 ml) was stirred under reflux for 8 hours. The reaction mixture was allowed to return to room temperature. To the solution, water was added, and the mixture was extracted with ethyl acetate. The organic phase was washed with a saturated sodium hydrogencarbonate solution, dried over magnesium sulfate and then filtered. The filtrate was concentrated under reduced pressure, and the residue was purified by silica gel column chromatography (methylene chloride/ethyl acetate=3/1) to afford 5-(4-chlorobenzyl)-3-(2-methyl-6-nitro-2,3-dihydroimidazo[2,1-b]oxazol-2-ylmethyl)-3H-[1,3,4]oxadiazol-2-one (240 mg, 9%) as a white solid.

Melting point 151-153° C.

Example 534

Preparation of 5-(4-bromophenyl)-3-(2-methyl-6-nitro-2,3-dihydroimidazo[2,1-b]oxazol-2-ylmethyl)-3H-[1,3,4]-oxadiazol-2-one A mixture of 2-methyl-6-nitro-2,3-dihydro-imidazo[2,1-b]oxazol-2-ylmethyl methanesulfonate prepared in Example 41 (1.02 g, 3.67 mmol), 5-(4-bromophenyl)-3H-[1,3,4]oxadiazol-2-one (680 mg, 2.82 mmol), potassium carbonate (580 mg, 4.2 mmol), sodium iodide (890 mg, 5.94 mmol) and DMF (15 ml) was stirred at 100° C. for 3 hours. The reaction mixture was allowed to return to room temperature. To the solution, water was added, and the resulting solution was extracted with ethyl acetate twice. The organic phases were combined, washed with water three times, dried over magnesium sulfate and then filtered. The filtrate was concentrated under reduced pressure, and the residue was purified by silica gel column chromatography (methylene chloride/ethyl acetate=9/1) to afford 5-(4-bromophenyl)-3-(2-methyl-6-nitro-2,3-dihydro-imidazo[2,1-b]oxazol-2-ylmethyl)-3H-[1,3,4]oxadiazol-2-one (17.4 mg, yield 2%) as a light yellow powder.

Melting point 231-233° C.

Example 535

Preparation of 5-(4-bromophenyl)-3-(6-nitro-2,3-dihydroimidazo[2,1-b]oxazol-2-ylmethyl)-3H-[1,3,4]-oxadiazol-2-one Using 6-nitro-2,3-dihydroimidazo[2,1-b]oxazol-2-ylmethyl methanesulfonate prepared in Example 40 (3.28 g, 12.46 mmol) and 5-(4-bromophenyl)-3H-[1,3,4]oxadiazol-2-one (1.5 g, 6.22 mmol) gave 5-(4-bromophenyl)-3-(6-nitro-2,3-dihydroimidazo[2,1-b]oxazol-2-ylmethyl)-3H-[1,3,4]oxadiazol-2-one (312 mg, yield 12%) as a light brown powder in the same manner as in Example 534.

Melting point 264° C. (decomposition).

Using corresponding starting materials gave the compound of Example 536 in the same manner as in Example 535.

Example 536

3-(6-Nitro-2,3-dihydroimidazo[2,1-b]oxazol-2-ylmethyl)-5-(4-trifluoromethoxyphenyl)-3H-[1,3,4]oxadiazol-2-one Melting point 204-207° C.

Example 537

Preparation of 3-[2-(2-methyl-6-nitro-2,3-dihydroimidazo[2,1-b]oxazol-2-yl)ethyl]-5-(pyridin-4-yl)-3H-[1,3,4]oxadiazol-2-one A mixture of 5-(pyridin-4-yl)-3H-[1,3,4]-oxadiazol-2-one (150 mg, 0.92 mmol), sodium hydride (41 mg, 1.03 mmol) and DMF (1.5 ml) was stirred at room temperature for 1 hour. To the reaction mixture, 2-(2-methyl-6-nitro-2,3-dihydroimidazo[2,1-b]oxazol-2-yl)ethyl methanesulfonate prepared in Example 42 (200 mg, 0.69 mmol) and sodium iodide (140 mg, 0.93 mmol) were added in this order followed by stirring at 50-60° C. for 6 hours. The reaction mixture was allowed to return to room temperature. To the solution, water was added, and the resulting solution was extracted with ethyl acetate twice. The organic phases were combined, washed with water three times, dried over magnesium sulfate and then filtered. The filtrate was concentrated under reduced pressure, and the residue was purified by silica gel column chromatography (methylene chloride/ethyl acetate=25/1) to afford 3-[2-(2-methyl-6-nitro-2,3-dihydroimidazo[2,1-b]oxazol-2-yl)ethyl]-5-(pyridin-4-yl)-3H-[1,3,4]oxadiazol-2-one (137 mg, yield 56%) as a white powder.

Melting point 147-149° C.

Using corresponding starting materials gave the compound of Example 538 in the same manner as in Example 537.

Example 538

3-[2-(2-Methyl-6-nitro-2,3-dihydroimidazo[2,1-b]oxazol-2-yl)ethyl]-5-(pyrazin-2-yl)-3H-[1,3,4]oxadiazol-2-one Melting point 209-212° C.

Example 539

Preparation of (R)-3-[3-(2-chloro-4-nitroimidazol-1-yl)-2-hydroxy-2-methylpropyl]-5-(4-trifluoromethoxyphenyl)-3H-[1,3,4]oxadiazol-2-one To a solution of 5-(4-trifluoromethoxy-phenyl)-3H-[1,3,4]oxadiazol-2-one (0.68 g, 2.76 mmol) and (R)-2-chloro-1-(2-methyloxiran-2-ylmethyl)-4-nitroimidazole prepared in Example 12 (0.50 g, 2.30 mmol) in DMF (5 ml), potassium carbonate (0.38 g, 2.76 mmol) was added followed by stirring at room temperature for 16 hours, and then water was added. The solution was extracted with ethyl acetate, dried over magnesium sulfate, and then concentrated under reduced pressure. The residue was purified by silica gel column chromatography (methylene chloride/ethyl acetate=4/1) to afford (R)-3-[3-(2-chloro-4-nitroimidazol-1-yl)-2-hydroxy-2-methylpropyl]-5-(4-trifluoromethoxyphenyl)-3H-[1,3,4]oxadiazol-2-one (1.06 g, quantitative yield) as a white amorphous form.

$^1$H-NMR (DMSO-$d_6$) δppm: 1.53 (3H, s), 3.67 (1H, d, J=8.8 Hz), 3.81 (1H, d, J=8.8 Hz), 4.49 (2H, s), 7.42-7.66 (2H, m), 7.86-8.09 (2H, m), 8.54 (1H, s), 10.98 (1H, br).

Example 540

Preparation of (R)-3-(2-methyl-6-nitro-2,3-dihydroimidazo[2,1-b]oxazol-2-ylmethyl)-5-(4-trifluoromethoxy-phenyl)-3H-[1,3,4]oxadiazol-2-one To a solution of (R)-3-[3-(2-chloro-4-nitroimidazol-1-yl)-2-hydroxy-2-methylpropyl]-5-(4-trifluoromethoxyphenyl)-3H-[1,3,4]oxadiazol-2-one prepared in Example 539 (0.87 g, 1.88 mmol) in 1,4-dioxane (18 ml), sodium hydride (98 mg, 2.44 mmol) was added with cooling on ice-bath. The mixture was stirred under reflux for 5 hours, concentrated under reduced pressure, then water was added with cooling on ice-bath. The solution was extracted with ethyl acetate, and the organic phase was dried over magnesium sulfate and then concentrated under reduced pressure. The residue was purified by silica gel column chromatography (methylene chloride/ethyl acetate 9/1), and recrystallized from acetonitrile/isopropanol to afford (R)-3-(2-methyl-6-nitro-2,3-dihydroimidazo[2,1-b]oxazol-2-ylmethyl)-5-(4-trifluoromethoxyphenyl)-3H-[1,3,4]oxadiazol-2-one (0.32 g, yield 40%) as a white powder.

Optical purity 98.2% e.e. $[\alpha]_D^{26}=-12.43°$ (concentration: 0.668, CHCl$_3$) Melting point 146-148° C.

Example 541

Preparation of 3-[3-(2-chloro-4-nitroimidazol-1-yl)-2-hydroxy-2-methylpropyl]-3H-benzoxazol-2-one To a suspension of 2-chloro-4-nitro-1H-imidazole (503 mg, 3.41 mmol), 3-(2-methyloxiran-2-yl-methyl)-3H-benzoxazol-2-one (700 mg, 3.41 mmol) in ethanol (7 ml), sodium acetate (336 mg, 4.1 mmol) was added followed by stirring under reflux for 8 hours. The reaction mixture was allowed to return to room temperature. To a mixture, water was added, and the resulting solution was extracted with methylene chloride. The organic phase was dried over magnesium sulfate and then filtered. The filtrate was concentrated under reduced pressure, and the residue was purified by silica gel column chromatography (methylene chloride/methanol=30/1) to afford 3-[3-(2-chloro-4-nitroimidazol-1-yl)-2-hydroxy-2-methylpropyl]-3H-benzoxazol-2-one (616 mg, yield 51%) as a light yellow powder.

$^1$H-NMR (CDCl$_3$) δppm: 1.31 (3H, s), 3.04 (1H, s), 3.87 (1H, d, J=14.7 Hz), 3.98 (1H, d, J=14.7 Hz), 4.13 (1H, d, J=12.5 Hz), 10 4.24 (1H, d, J=14.5 Hz), 7.08-7.31 (4H, m), 8.04 (1H, s).

Using corresponding starting materials gave compounds of Examples 542 and 543 shown in the following table in the same manner as in Example 541.

Example 541 (615 mg, 1.74 mmol), sodium hydride (76.6 mg, 1.91 mmol), 1,4-dioxane (15 ml) was stirred under reflux for 1 hour. The reaction mixture was allowed to return to room temperature. To the solution, water was added and the solution was extracted with methylene chloride. The organic phase was dried over sodium sulfate and then filtered. The filtrate was concentrated under reduced pressure, and the residue was purified by silica gel column chromatography (methylene chloride/methanol=30/1) to afford 3-(2-methyl-6-nitro-2,3-dihydroimidazo[2,1-b]oxazol-2-ylmethyl)-3H-benzoxazol-2-one (209 mg, yield 38%) as a white powder.

Melting point 222.7-224.3° C.

Using corresponding starting materials gave compounds of Examples 545 and 546 in the same manner as in Example 544.

Example 545

5-Chloro-3-(2-methyl-6-nitro-2,3-dihydroimidazo[2,1-b]oxazol-2-ylmethyl)-3H-benzoxazol-2-one Melting point 207.6-207.9° C.

Example 546

5-Fluoro-3-(2-methyl-6-nitro-2,3-dihydroimidazo[2,1-b]oxazol-2-ylmethyl)-3H-benzoxazol-2-one Melting point 246.2-246.8° C.

TABLE 19

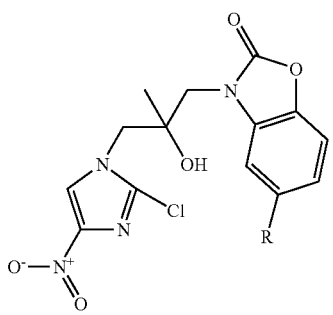

| Example | R | | $^1$H NMR δ | Yield (%) |
|---|---|---|---|---|
| 542 | Cl | CDCl$_3$ | 1.32(3H, s), 3.14(1H, s), 3.87(1H, d, J=14.7Hz), 3.95(1H, d, J=14.7Hz), 4.11(1H, d, J=14.4Hz), 4.25(1H, d, J=14.4Hz), 7.10-7.23(3H, m), 8.03(1H, s). | 35 |
| 543 | F | CDCl$_3$ | 1.11(3H, s), 2.66(1H, s), 3.86(1H, d, J=14.5Hz), 3.94(1H, d, J=14.5Hz), 4.16(1H, d, J=14.3Hz), 4.24(1H, d, J=14.3Hz), 6.89-7.00(1H, m), 7.29(1H, dd, J=2.7Hz, 8.8Hz), 7.37(1H, dd, J=4.4Hz, 8.8Hz), 8.01(1H, s). | 33 |

Example 544

Preparation of 3-(2-methyl-6-nitro-2,3-dihydroimidazo-[2,1-b]oxazol-2-ylmethyl)-3H-benzoxazol-2-one A mixture of 3-[3-(2-chloro-4-nitroimidazol-1-yl)-2-hydroxy-2-methylpropyl]-3H-benzoxazol-2-one prepared in

Example 547

Preparation of 5-bromo-3-(2-methyl-6-nitro-2,3-dihydro-imidazo[2,1-b]oxazol-2-ylmethyl)-3H-benzoxazol-2-one A mixture of 2-chloro-4-nitro-1H-imidazole (3.22 g, 21.8 mmol), 5-bromo-3-(2-methyloxiran-2-ylmethyl)-3H-benzoxazol-2-one (6.2 g, 21.8 mmol); sodium acetate (1.97 g, 24 mmol) and ethanol (50 ml) was stirred under reflux for 8 hours. The reaction mixture was allowed to return to room temperature and concentrated under reduced pressure. To the residue, water was added, and the resulting solution was extracted with methylene chloride. The organic phase was dried over magnesium sulfate and then filtered. The filtrate was concentrated under reduced pressure, and the residue was dissolved in 1,4-dioxane (60 ml). To the solution, sodium hydride (528 mg, 13.21 mmol) was added followed by stirring at 70-80° C. for 17 hours. The reaction mixture was allowed to return to room temperature and concentrated under reduced pressure. To the residue, water was added, extracted with methylene chloride. The organic phase was dried over magnesium sulfate and then filtered. The filtrate was concentrated under reduced pressure, and the residue was purified by silica gel column chromatography (methylene chloride/methanol=30/1) to afford 5-bromo-3-(2-methyl-6-nitro-2,3-dihydroimidazo[2,1-b]oxazol-2-ylmethyl)-3H-benzoxazol-2-one (1.82 g, yield 37%) as a white powder.

Melting point 243-245.5° C.

Example 548

Preparation of 5-(2-chloro-4-nitroimidazol-1-ylmethyl)-3-(4-hydroxybiphenyl-3-yl)-5-methyloxazolidin-2-one A mixture of 2-chloro-4-nitro-1H-imidazole (1.3 g, 8.78 mmol), 5-phenyl-3-(2-methyloxiran-2-yl-methyl)-3H-benzoxazol-2-one (2.47 g, 8.78 mmol), sodium acetate (792 mg, 9.66 mmol) and ethanol (30 ml) was stirred under reflux for 10 hours. The reaction mixture was allowed to return to room temperature and concentrated under reduced pressure. To the residue, water was added, and the resulting solution was extracted with methylene chloride. The organic phase was dried over magnesium sulfate and then filtered. The filtrate was concentrated under reduced pressure, and the residue was purified by silica gel column chromatography (methylene chloride/methanol=10/1) to afford 5-(2-chloro-4-nitroimidazol-1-ylmethyl)-3-(4-hydroxybiphenyl-3-yl)-5-methyloxazolidin-2-one (1.82 g, yield 61%) as a white powder.

$^1$H-NMR (DMSO-$d_6$) δppm: 1.55 (3H, s), 3.85 (1H, d, J=9.5 Hz), 3.98 (1H, d, J=9.5 Hz), 4.46 (1H, d, J=14.9 Hz), 4.56 (1H, d, J=14.9 Hz), 6.99 (1H, d, J=8.4 Hz), 7.27 (1H, t, J=7.3 Hz), 7.36-7.57 (6H, m), 8.52 (1H, s), 10.06 (1H, s).

Example 549

Preparation of 3-(2-methyl-6-nitro-2,3-dihydroimidazo-[2,1-b]oxazol-2-ylmethyl)-5-phenyl-3H-benzoxazol-2-one A mixture of 5-(2-chloro-4-nitroimidazol-1-ylmethyl)-3-(4-hydroxybiphenyl-3-yl)-5-methyloxazolidin-2-one prepared in Example 548 (1.23 g, 2.88 mmol), sodium hydride (127 mg, 3.16 mmol) and DMF (10 ml) was stirred at 100° C. for 4 hours. The reaction mixture was allowed to return to room temperature and concentrated under reduced pressure. To the residue, water was added, and the solution was extracted with methylene chloride. The organic phase was washed with water and a saturated saline solution, dried over magnesium sulfate and then filtered. The filtrate was concentrated under reduced pressure, and the residue was purified by silica gel column chromatography (methylene chloride/methanol=20/1) to afford 3-(2-methyl-6-nitro-2,3-dihydroimidazo[2,1-b]oxazol-2-ylmethyl)-5-phenyl-3H-benzoxazol-2-one (172 mg, yield 15%) as a yellowish brown powder.

Melting point 254-254.6° C.

Example 550

Preparation of 3-[2-(2-methyl-6-nitro-2,3-dihydroimidazo[2,1-b]oxazol-2-yl)ethyl]-3H-benzoxazol-2-one A mixture of 2-benzoxazolinone (240 mg, 1.8 mmol), sodium hydride (67 mg, 1.95 mmol) and DMF (10 ml) was stirred at room temperature for 30 minutes. To the reaction mixture, 2-(2-methyl-6-nitro-2,3-dihydro-imidazo[2,1-b]oxazol-2-yl)ethyl methanesulfonate prepared in Example 42 (500 mg, 1.7 mmol) was added followed by stirring at 50-60° C. for 4 hours. The reaction mixture was allowed to return to room temperature and poured into ice-water. The precipitates were filtered off and recrystallized from ethanol to afford 3-[2-(2-methyl-6-nitro-2,3-dihydroimidazo[2,1-b]oxazol-2-yl)ethyl]-3H-benzoxazol-2-one (320 mg, yield 56%) as a light brown powder.

Melting point 193-195° C.

Example 551

Preparation of 3-[5-(2-chloro-4-nitroimidazol-1-yl)-4-hydroxy-4-methylpentyl]-3H-benzoxazol-2-one Using 3-[3-(2-methyloxiran-2-yl)propyl]-3H-benzoxazol-2-one (3.8 g, 16.3 mmol) gave 3-[5-(2-chloro-4-nitroimidazol-1-yl)-4-hydroxy-4-methylpentyl]-3H-benzoxazol-2-one (3.5 g, 68%) as a white powder in the same manner as in Example 541.

$^1$H-NMR (CDCl$_3$) δppm: 1.20 (3H, s), 1.49-1.70 (2H, m), 1.88-2.07 (2H, m), 2.68 (1H, s), 3.81-3.93 (2H, m), 4.00 (2H, s), 6.98 (1H, d, J=7.3 Hz), 7.09-7.26 (3H, m), 8.00 (1H, s).

Example 552

Preparation of 3-[6-(2-chloro-4-nitroimidazol-1-yl)-5-hydroxy-5-methylhexyl]-3H-benzoxazol-2-one Using 3-[4-(2-methyloxiran-2-yl)butyl]-3H-benzoxazol-2-one (1.2 g, 4.86 mmol) gave 3-[6-(2-chloro-4-nitroimidazol-1-yl)-5-hydroxy-5-methylhexyl]-3H-benzoxazol-2-one (1.2 g, 62%) as a white powder in the same manner as in Example 541.

$^1$H-NMR (CDCl$_3$) δppm: 1.16 (3H, s), 1.38-1.58 (4H, m), 1.67-1.86 (2H, m), 2.15 (1H, s), 3.87 (2H, t, J=6.6 Hz), 3.98 (2H, s), 6.98 (1H, d, J=7.8 Hz), 7.08-7.26 (3H, m), 8.01 (1H, s).

Example 553

Preparation of 3-[3-(2-methyl-6-nitro-2,3-dihydroimidazo[2,1-b]oxazol-2-yl)propyl]-3H-benzoxazol-2-one Using 3-[5-(2-chloro-4-nitroimidazol-1-yl)-4-hydroxy-4-methylpentyl]-3H-benzoxazol-2-one prepared in Example 551 (3.5 g, 9.2 mmol) gave 3-[3-(2-methyl-6-nitro-2,3-dihydroimidazo[2,1-b]oxazol-2-yl)propyl]-3H-benzoxazol- 2-one (2.4 g, yield 76%) as a light yellow powder in the same manner as in Example 544.

Melting point 180-181° C.

Example 554

Preparation of 3-[4-(2-methyl-6-nitro-2,3-dihydro-imidazo[2,1-b]oxazol-2-yl)butyl]-3H-benzoxazol-2-one Using 3-[6-(2-chloro-4-nitroimidazol-1-yl)-5-hydroxy-5-methylhexyl]-3H-benzoxazol-2-one prepared in Example 552 (1.2 g, 3 mmol) gave 3-[4-(2-methyl-6-nitro-2,3-dihydroimidazo[2,1-b]oxazol-2-yl)butyl]-3H-benzoxazol-2-one (780 mg, yield 72%) as a light yellow powder in the same manner as in Example 544.

Melting point 155-158° C.

Example 555

Preparation of 1-[3-(2-chloro-4-nitroimidazol-1-yl)-2-hydroxy-2-methylpropyl]-3-methyl-1,3-dihydro-benzimidazol-2-one Using 1-methyl-3-(2-methyloxiran-2-ylmethyl)-1,3-dihydrobenzimidazol-2-one (1.41 g, 6.46 mmol) gave 1-[3-(2-chloro-4-nitroimidazol-1-yl)-2-hydroxy-2-methylpropyl]-3-methyl-1,3-dihydrobenzimidazol-2-one (1.23 g, yield 63%) as a white powder in the same manner as in Example 541.

$^1$H-NMR (CDCl$_3$) δppm: 1.23 (3H, s), 3.47 (3H, s), 3.94 (1H, d, J=12.4 Hz), 4.03 (1H, d, J=12.4 Hz), 4.06 (1H, d, J=11.9 Hz), 4.17 (1H, d, J=11.9 Hz), 4.79 (1H, s), 7.00-7.21 (4H, m), 8.09 (1H, s).

Using corresponding starting materials gave compounds of Examples 556 to 565 shown in the following table in the same manner as in Example 555.

TABLE 20

| Example | R | R' | $^1$H NMR δ | Yield (%) |
|---|---|---|---|---|
| 556 | (tetrahydropyran-4-yl-oxycarbonyl-tert-butyl group) | H | 1.23(3H, s), 1.51(9H, s), 1.75-1.89(2H, m), 2.17(2H, s), 2.20-2.41(2H, m), 2.75-2.91(2H, m), 3.90(1H, d, J=14.2Hz), 4.16(1H, d, J=14.2Hz), 4.25-4.50(3H, m), 7.00-7.23(4H, m), 8.09(1H, s). | 78 |
| 557 | Me | 6-Cl | 1.24(3H, s), 3.45(3H, s), 3.94(2H, s), 4.06(1H, d, J=14.4Hz), 4.18(1H, d, J=14.4Hz), 6.96(1H, d, J=8.4Hz), 7.06(1H, d, J=1.9Hz), 7.16(1H, dd, J=1.9Hz, 8.4Hz), 8.08(1H, s) | 69 |
| 558 | Me | 6-CF$_3$ | 1.26(3H, s), 3.51(3H, s), 3.95(1H, d, J=8.5Hz). 4.03(1H, d, J=8.5Hz), 4.14(1H, d, J=14.3Hz), 4.21(1H, d, J=14.3Hz), 7.13(1H, d, J=8.3Hz), 7.31(1H, s), 7.48(1H, d, J=8.3Hz), 8.07(1H, s). | 61 |
| 559 | Me | 5-Cl | 1.23(3H, s), 3.47(3H, s), 3.91(1H, d, J=14.8Hz), 3.99(1H, d, J=14.8Hz), 4.05(1H, d, J=14.0Hz), 4.17(1H, d, J=14.0Hz), 6.97(1H, d, J=8.4Hz), 7.06(1H, d, J=1.9Hz), 7.14(1H, dd, J=1.9Hz, 8.4Hz), 8.07(1H, s). | 56 |
| 560 | Me | 6-F | 1.24(3H, s), 3.46(3H, s), 3.90(1H, d, J=14.8Hz), 3.97(1H, d, J=14.8Hz), 4.06(1H, d, J=14.3Hz), 4.17(1H, d, J=14.3Hz), 6.79-7.00(3H, m), 8.08(1H, s). | 63 |
| 561 | Et | 6-Cl | 1.21(3H, s), 1.36(3H, t, J=7.2Hz), 3.84-4.20(6H, m), 6.98(1H, d, J=8.4Hz), 7.06(1H, d, J=1.8Hz), 7.15(1H, dd, J=1.8Hz, 8.4Hz), 8.08(1H, s). | 77 |
| 562 | isopropyl | 6-Cl | 1.24(3H, s), 1.55(6H, d, J=7.0Hz), 3.93(2H, s), 4.06(1H, d, J=14.3Hz), 4.17(1H, d, J=14.3Hz), 4.55-4.75(1H, m), 7.05(1H, s), 7.18(2H, s), 8.09(1H, s). | 69 |
| 563 | Me | 6-NMe$_2$ | 1.23(3H, s), 2.96(6H, s), 3.42(3H, s), 3.89(1H, d, J=14.8Hz), 3.99(1H, d, J=14.8Hz), 4.05(1H, d, J=14.3Hz), 4.16(1H, d, J=14.3Hz), 6.39(1H, d, J=2.2Hz), 6.60(1H, dd, J=2.2Hz, 8.6Hz), 6.92(1H, d, J=8.6Hz), 8.10(1H, s). | Crude |

TABLE 20-continued

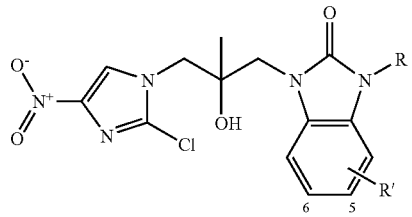

| Example | R | R' | $^1$H NMR δ | Yield (%) |
|---|---|---|---|---|
| 564 | n-hexyl | 6-Cl | 0.87(3H, t, J=6.9Hz), 1.16-1.39(9H, m), 1.64-1.82(2H, m), 3.80-3.93(4H, m), 4.05(1H, d, J=14.3Hz), 4.17(1H, d, J=14.3Hz), 6.97(1H, d, J=8.4Hz), 7.06(1H, d, J=1.8Hz), 7.14(1H, dd, J=1.8Hz, 8.4Hz), 8.08(1H, s). | 55 |
| 565 | Me | 6-CO$_2$Et | 1.25(3H, s), 1.42(3H, t, J=7.1Hz), 3.50(3H, s), 3.93-4.11(3H, m), 4.20(1H, d, J=14.3Hz), 4.40(2H, q, J=7.1Hz), 7.07(1H, d, J=8.3Hz), 7.75(1H, d, J=1.5Hz), 7.94(1H, dd, J=1.5Hz, 8.3Hz), 8.07(1H, s). | 48 |

Example 566

Preparation of 1-methyl-3-(2-methyl-6-nitro-2,3-dihydroimidazo[2,1-b]oxazol-2-ylmethyl)-1,3-dihydrobenzimidazol-2-one Using 1-[3-(2-chloro-4-nitroimidazol-1-yl)-2-hydroxy-2-methylpropyl]-3-methyl-1,3-dihydro-benzimidazol-2-one prepared in Example 555 (1.23 g, 3.37 mmol) gave 1-methyl-3-(2-methyl-6-nitro-2,3-dihydroimidazo[2,1-b]oxazol-2-ylmethyl)-1,3-dihydrobenzimidazol-2-one (563 mg, yield 51%) as a white powder in the same manner as in Example 544.

Melting point 203.2-204.4° C.

Using corresponding starting materials gave compounds of Examples 567 to 576 in the same manner as in Example 566.

Example 567

1-(1-Tert-butoxycarbonylpiperidin-4-yl)-3-(2-methyl-6-nitro-2,3-dihydroimidazo[2,1-b]oxazol-2-ylmethyl)-1,3-dihydrobenzimidazol-2-one Melting point 218-219.1° C.

Example 568

5-Chloro-1-methyl-3-(2-methyl-6-nitro-2,3-dihydroimidazo[2,1-b]oxazol-2-ylmethyl)-1,3-dihydro-benzimidazol-2-one Melting point 261.9-265.4° C. (decomposition)

Example 569

1-Methyl-3-(2-methyl-6-nitro-2,3-dihydroimidazo[2,1-b]oxazol-2-ylmethyl)-5-trifluoromethyl-1,3-dihydrobenzimidazol-2-one Melting point 232.4-234.7° C.

Example 570

6-Chloro-1-methyl-3-(2-methyl-6-nitro-2,3-dihydroimidazo[2,1-b]oxazol-2-ylmethyl)-1,3-dihydro-benzimidazol-2-one Melting point 261.3-263.3° C.

Example 571

5-Fluoro-1-methyl-3-(2-methyl-6-nitro-2,3-dihydroimidazo[2,1-b]oxazol-2-ylmethyl)-1,3-dihydro-benzimidazol-2-one Melting point 244.2-249.8° C. (decomposition).

Example 572

5-Chloro-1-ethyl-3-(2-methyl-6-nitro-2,3-dihydroimidazo[2,1-b]oxazol-2-ylmethyl)-1,3-dihydro-benzimidazol-2-one Melting point 240.9-245.6° C.

Example 573

5-Chloro-1-isopropyl-3-(2-methyl-6-nitro-2,3-dihydro-imidazo[2,1-b]oxazol-2-ylmethyl)-1,3-dihydro-benzimidazol-2-one Melting point 240.5-244.8° C.

Example 574

5-Dimethylamino-1-methyl-3-(2-methyl-6-nitro-2,3-dihydroimidazo[2,1-b]oxazol-2-ylmethyl)-1,3-dihydrobenzimidazol-2-one Melting point 264.6-268.3° C. (decomposition).

Example 575

5-Chloro-1-(n-hexyl)-3-(2-methyl-6-nitro-2,3-dihydro-imidazo[2,1-b]oxazol-2-ylmethyl)-1,3-dihydro-benzimidazol-2-one Melting point 168.1-169.3° C.

Example 576

5-Ethoxycarbonyl-1-methyl-3-(2-methyl-6-nitro-2,3-dihydroimidazo[2,1-b]oxazol-2-ylmethyl)-1,3-dihydrobenzimidazol-2-one Melting point 265.8-266.7° C.

Example 577

Preparation of 1-(2-methyl-6-nitro-2,3-dihydroimidazo-[2,1-b]oxazol-2-ylmethyl)-3-phenyl-1,3-dihydro-benzimidazol-2-one Using 1-(2-methyloxiran-2-ylmethyl)-3-phenyl-1,3-dihydrobenzimidazol-2-one (758 mg, 2.7 mmol) gave 1-(2-methyl-6-nitro-2,3-dihydroimidazo[2,1-b]oxazol-2-ylmethyl)-3-phenyl-1,3-dihydrobenzimidazol-2-one (70 mg, yield 13%) as a white powder in the same manner as in Example 200.

Melting point 234.5-234.7° C.

Using corresponding starting materials gave the compound of Example 578 in the same manner as in Example 577.

Example 578

1-(4-Fluorophenyl)-3-(2-methyl-6-nitro-2,3-dihydro-imidazo[2,1-b]oxazol-2-ylmethyl)-1,3-dihydro-benzimidazol-2-one Melting point 254.1-254.7° C.

Example 579

Preparation of 1-(2-methyl-6-nitro-2,3-dihydroimidazo-[2,1-b]oxazol-2-ylmethyl)-(3-piperidin-4-yl)-1,3-dihydrobenzimidazol-2-one A mixture of 1-(1-tert-butoxycarbonyl-piperidin-4-yl)-3-(2-methyl-6-nitro-2,3-dihydroimidazo-[2,1-b]oxazol-2-yl-methyl)-1,3-dihydrobenzimidazol-2-one prepared in Example 567 (371 mg, 0.74 mmol), trifluoroacetic acid (1 ml) and methylene chloride (10 ml) was stirred at room temperature for 2 hours. The reaction mixture was concentrated under reduced pressure. To the residue, a saturated sodium hydrogencarbonate solution, and the precipitates were filtered off. The precipitates were washed with water several times to afford 1-(2-methyl-6-nitro-2,3-dihydroimidazo[2,1-b]oxazol-2-ylmethyl)-(3-piperidin-4-yl)-1,3-dihydrobenzimidazol-2-one (255 mg, yield 86%) as a light yellow powder.

Melting point 192.3-198.8° C. (decomposition).

Example 580

Preparation of benzyl 4-[3-(2-methyl-6-nitro-2,3-dihydroimidazo[2,1-b]oxazol-2-ylmethyl)-2-oxo-2,3-dihydrobenzimidazol-1-yl]piperidine-1-carboxylate To a mixture of 1-(2-methyl-6-nitro-2,3-dihydroimidazo[2,1-b]oxazol-2-ylmethyl)-(3-piperidin-4-yl)-1,3-dihydrobenzimidazol-2-one prepared in Example 579 (90 mg, 0.23 mmol) and methylene chloride (5 ml), triethylamine (75 mg, 0.74 mmol) and benzyl chloroformate (126 mg, 0.74 mmol) were added in this order with cooling on ice-bath followed by stirring at room temperature for 3 hours. The reaction mixture was washed with water, a saturated sodium hydrogencarbonate solution and a saturated saline solution in this order, dried over magnesium sulfate and then filtered. The filtrate was concentrated under reduced pressure, and the residue was purified by silica gel column chromatography (n-hexane/acetone=1/1) to afford benzyl 4-[3-(2-methyl-6-nitro-2,3-dihydroimidazo[2,1-b]oxazol-2-ylmethyl)-2-oxo-2,3-dihydrobenzimidazol-1-yl]piperidine-1-carboxylate (25 mg, yield 21%) as a white powder.

Melting point 181.7-184.6° C.

Example 581

Preparation of 1-benzyl-3-[3-(2-chloro-4-nitroimidazol-1-yl)-2-hydroxy-2-methylpropyl]imidazolidin-2-one Using 1-benzyl-3-(2-methyloxiran-2-ylmethyl)-imidazolidin-2-one (680 mg, 2.76 mmol) gave 1-benzyl-3-[3-(2-chloro-4-nitroimidazol-1-yl)-2-hydroxy-2-methylpropyl]imidazolidin-2-one (580 mg, yield 59%) as a white powder in the same manner as in Example 541.

$^1$H-NMR (CDCl$_3$) δppm: 1.18 (3H, s), 3.17-3.54 (6H, m), 4.07 (2H, s), 4.37 (2H, s), 7.17-7.40 (5H, m), 8.13 (1H, s).

Using corresponding starting materials gave compounds of Examples 582 to 587 shown in the following table in the same manner as in Example 581.

TABLE 21

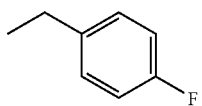

| Example | R (solvent) | ¹H NMR δ | Yield (%) |
|---|---|---|---|
| 582 | 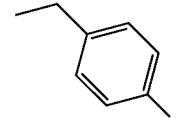<br>CDCl₃ | 1.19(3H, s), 3.16-3.52(6H, m), 4.06(2H, s), 4.33(2H, s), 6.93-7.09(2H, m), 7.18-7.30(2H, m), 8.13(1H, s). | 43 |
| 583 | 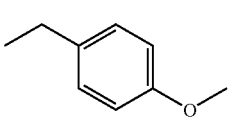<br>CDCl₃ | 1.19(3H, s), 3.16-3.55(6H, m), 4.05(2H, s), 4.31(2H, s), 7.14(2H, dd, J=2.0Hz, 8.6Hz), 7.46(2H, dd, J=2.0Hz, 8.6Hz), 8.13(1H, s). | 64 |
| 584 | 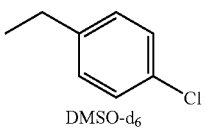<br>DMSO-d₆ | 1.03(3H, s), 3.02-3.27(4H, m), 3.39-3.55(2H, m), 3.73(3H, s), 4.03(2H, s), 4.29(2H, s), 6.90(2H, d, J=8.6Hz), 7.17(2H, d, J=8.6Hz), 8.48(1H, s). | 69 |
| 585 | <br>DMSO-d₆ | 1.04(3H, s), 3.05-3.25(4H, m), 3.36-3.48(2H, m), 4.03(2H, s), 4.22(2H, s), 7.28(2H, d, J=8.3Hz), 7.41(2H, d, J=8.3Hz), 8.48(1H, s). | 60 |
| 586 | 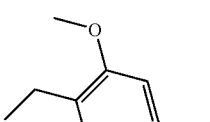<br>CDCl₃ | 1.16(3H, s), 1.59-1.84(4H, m), 2.00-2.18(2H, m), 2.89-3.02(2H, m), 3.09-3.50(8H, m), 3.61-3.80(1H, m), 4.00(1H, d, J=14.3Hz), 4.09(1H, d, J=14.3Hz), 7.18-7.36(5H, m), 8.12(1H, s). | Crude |
| 587 | <br>DMSO-d₆ | 1.03(3H, s), 3.05-3.23(4H, m), 3.30-3.50(2H, m), 3.75(3H, s), 3.77(3H, s), 4.02(2H, s), 4.20(2H, s), 6.47(1H, dd, J=2.2Hz, 8.3Hz), 6.56(1H, d, J=2.2Hz), 7.06(1H, d, J=8.3Hz), 8.48(1H, s). | 58 |

Example 588

Preparation of 1-benzyl-3-(2-methyl-6-nitro-2,3-dihydroimidazo[2,1-b]oxazol-2-ylmethyl)imidazolidin-2-one Using 1-benzyl-3-[3-(2-chloro-4-nitro-imidazol-1-yl)-2-hydroxy-2-methylpropyl]imidazolidin-2-one prepared in Example 581 (580 mg, 1.47 mmol) gave 1-benzyl-3-(2-methyl-6-nitro-2,3-dihydroimidazo[2,1-b]oxazol-2-ylmethyl)imidazolidin-2-one (395 mg, yield 75%) as a white powder in the same manner as in Example 544.

Melting point 180.2-180.9° C.

Using corresponding starting materials gave compounds of Examples 589 to 594 in the same manner as in Example 588.

Example 589

1-(4-Fluorobenzyl)-3-(2-methyl-6-nitro-2,3-dihydroimidazo[2,1-b]oxazol-2-ylmethyl)imidazolidin-2-one Melting point 182.5-183.3° C.

Example 590

1-(4-Bromobenzyl)-3-(2-methyl-6-nitro-2,3-dihydroimidazo[2,1-b]oxazol-2-ylmethyl)imidazolidin-2-one Melting point 205.7-208.1° C.

Example 591

1-(4-Methoxybenzyl)-3-(2-methyl-6-nitro-2,3-dihydro-imidazo[2,1-b]oxazol-2-ylmethyl)imidazolidin-2-one Melting point 158.6-160.5° C.

Example 592

1-(4-Chlorobenzyl)-3-(2-methyl-6. -nitro-2,3-dihydro-imidazo[2,1-b]oxazol-2-ylmethyl)imidazolidin-2-one Melting point 208.7-209.8° C.

Example 593

1-(1-Benzylpiperidin-4-yl)-3-(2-methyl-6-nitro-2,3-dihydroimidazo[2,1-b]oxazol-2-ylmethyl)imidazolidin-2-one $^1$H-NMR (CDCl$_3$) δppm: 1.41-1.72 (7H, m), 1.97-2.10 (2H, m), 2.88-2.95 (2H, m), 3.08-3.30 (4H, m), 3.43-3.70 (4H, m), 3.81 (1H, d, J=15.0 Hz), 3.91 (1H, d, J=10.3 Hz), 4.51 (1H, d, J=10.3 Hz), 7.13-7.31 (5H, m), 7.47 (1H, s)

Example 594

1-(2,4-Dimethoxybenzyl)-3-(2-methyl-6-nitro-2,3-dihydroimidazo[2,1-b]oxazol-2-ylmethyl)imidazolidin-2-one Melting point 175-175.4° C.

Example 595

Preparation of 1-(2-methyl-6-nitro-2,3-dihydroimidazo-[2,1-b]oxazol-2-ylmethyl)-3-phenylimidazolidin-2-one Using 1-(2-methyloxiran-2-ylmethyl)-3-phenylimidazolidin-2-one (300 mg, 1.29 mmol) gave 1-(2-methyl-6-nitro-2,3-dihydroimidazo[2,1-b]oxazol-2-ylmethyl)-3-phenylimidazolidin-2-one (59 mg, yield 26%) as a white powder in the same manner as in Example 200.

Melting point 194.8-197.4° C.

Example 596

Preparation of 1-(2-methyl-6-nitro-2,3-dihydroimidazo-[2,1-b]oxazol-2-ylmethyl)imidazolidin-2-one A mixture of 1-(2,4-dimethoxybenzyl)-3-(2-methyl-6-nitro-2,3-dihydroimidazo[2,1-b]oxazol-2-ylmethyl)imidazolidin-2-one prepared in Example 594 (100 mg, 0.24 mmol), trifluoroacetic acid (2 ml) and methylene chloride (2 ml) was stirred at room temperature for 1 hour. To the reaction mixture, a saturated sodium hydrogencarbonate solution was added for neutralization. The resulting solution was extracted with methylene chloride. The organic phase was dried over sodium sulfate and then filtered. The filtrate was concentrated under reduced pressure, and the residue was treated with diethyl ether to afford 1-(2-methyl-6-nitro-2,3-dihydroimidazo[2,1-b]oxazol-2-ylmethyl)imidazolidin-2-one (50 mg, yield 78%) as a white powder.

Melting point 224.8-229.1° C. (decomposition).

Example 597

Preparation of 3-(2-methyl-6-nitro-2,3-dihydroimidazo-[2,1-b]oxazol-2-ylmethyl)oxazolidin-2-one A mixture of 3-(2-methyloxiran-2-ylmethyl)-oxazolidin-2-one (2.87 g, 18.23 mmol), 2-chloro-4-nitro-1H-imidazole (2.7 g, 18.23 mmol), sodium acetate (1.64 g, 20.05 mmol) and ethanol (30 ml) was stirred under reflux for 10 hours. The reaction mixture was allowed to return to room temperature and concentrated under reduced pressure. To the residue, methylene chloride was added, and the resulting solution was washed with water, a saturated sodium hydrogencarbonate solution and a saturated saline solution in this order, dried over magnesium sulfate and then filtered. The filtrate was concentrated under reduced pressure, and the residue was dissolved in 1,4-dioxane (50 ml). To the solution, sodium hydride (610 mg, 15.25 mmol) was added followed by stirring under reflux overnight. The reaction mixture was allowed to return to room temperature and concentrated under reduced pressure. To the residue, water was added, and the solution was extracted with methylene chloride. The organic phase was dried over magnesium sulfate and then filtered. The filtrate was concentrated under reduced pressure, and the residue was purified by silica gel column chromatography (methylene chloride/methanol=20/1) to afford 3-(2-methyl-6-nitro-2,3-dihydroimidazo[2,1-b]oxazol-2-ylmethyl)oxazolidin-2-one (1.54 g, yield 40%) as a white powder.

$^1$H-NMR (DMSO-d$_6$) δppm: 1.59 (3H, s), 3.46-3.71 (4H, m), 4.11-4.30 (4H, m), 8.15 (1H, s).

Example 598

Preparation of 5-azidomethyl-3-[3-(2-chloro-4-nitroimidazol-1-yl)-2-hydroxy-2-methylpropyl]-oxazolidin-2-one A mixture of 2-chloro-4-nitro-1H-imidazole (350 mg, 2.37 mmol), 5-azidomethyl-3-(2-methyloxiran-2-ylmethyl)oxazolidin-2-one (500 mg, 2.37 mmol), sodium acetate (214 mg, 2.61 mmol) and ethanol (5 ml) was stirred at 70° C. for 8 hours. The reaction mixture was allowed to return to room temperature and concentrated under reduced pressure. To the residue, water was added, and the solution was extracted with methylene chloride. The organic phase was dried over sodium sulfate and then filtered. The filtrate was concentrated under reduced pressure, and the residue was purified by silica gel column chromatography (n-hexane/ethyl acetate=1/2) to afford 5-azidomethyl-3-[3-(2-chloro-4-nitroimidazol-1-yl)-2-hydroxy-2-methylpropyl]oxazolidin-2-one (640 mg, yield 75%) as a light yellow oil.

$^1$H-NMR (CDCl$_3$) δppm: 1.23 (3H, s), 3.17-3.35 (2H, m), 3.43-3.61 (2H, m), 3.67-3.84 (2H, m), 4.01-4.16 (2H, m), 4.68-4.81 (1H, m), 8.04 (1H, s).

Example 599

Preparation of 5-azidomethyl-3-(2-methyl-6-nitro-2,3-dihydroimidazo[2,1-b]oxazol-2-ylmethyl)oxazolidin-2-one 5-Azidomethyl-3-[3-(2-chloro-4-nitroimidazol-1-yl)-2-hydroxy-2-methylpropyl]oxazolidin-2-one prepared in Example 598 (1 g, 2.78 mmol) was dissolved in 1,4-dioxane (10 ml). To the solution, sodium hydride (130 mg, 3.25 mmol) was added followed by stirring at 80° C. for 4 hours.

The reaction mixture was allowed to return to room temperature and added water. The resulting solution was concentrated under reduced pressure. To the residue, water was added, and the solution was extracted with methylene chloride. The organic phase was dried over sodium sulfate and then filtered. The filtrate was concentrated under reduced pressure, and the residue was purified by silica gel column chromatography (methylene chloride/ethyl acetate=20/1) to afford 5-azidomethyl-3-(2-methyl-6-nitro-2,13-dihydroimidazo[2,1-b]oxazol-2-ylmethyl)oxazolidin-2-one (46 mg, yield 5%) as a light brown powder.

MS 323 (M$^+$)

Example 600

Preparation of 1-[3-(2-chloro-4-nitroimidazol-1-yl)-2-hydroxy-2-methylpropyl]-1,4-dihydrobenzo[d][1,3]oxazin-2-one Using 1-(2-methyloxiran-2-ylmethyl)-1,4-dihydrobenzo[d][1,3]oxazin-2-one (5.13 g, 23.04 mmol) gave 1-[3-(2-chloro-4-nitroimidazol-1-yl)-2-hydroxy-2-methylpropyl]-1,4-dihydrobenzo[d][1,3]oxazin-2-one (1.54 g, yield 36%) as a light yellow oil in the same manner as in Example 541.

$^1$H-NMR (CDCl$_3$) δppm: 1.23 (3H, s), 3.96 (1H, br), 4.04-4.20 (4H, m), 5.28 (2H, s), 7.00-7.07 (1H, m), 7.11-7.24 (2H, m), 7.30-7.43 (1H, m), 8.07 (1H, s).

Example 601

Preparation of 1-(2-methyl-6-nitro-2,3-dihydroimidazo-[2,1-b]oxazol-2-ylmethyl)-1,4-dihydrobenzo[d][1,3]-oxazin-2-one Using 1-[3-(2-chloro-4-nitroimidazol-1-yl)-2-hydroxy-2-methylpropyl]-1,4-dihydrobenzo[d][1,3]oxazin-2-one prepared in Example 600 (1.54 g, 4.20 mmol) gave 1-(2-methyl-6-nitro-2,3-dihydroimidazo[2,1-b]oxazol-2-ylmethyl-1,4-dihydrobenzo[d][1,3]oxazin-2-one (0.58 g, yield 42%) as a light tan solid in the same manner as in Example 544.

Melting point 230-231° C.

Example 602

Preparation of 1-[3-(2-chloro-4-nitroimidazol-1-yl)-2-hydroxy-2-methylpropyl]-3,3-difluoro-1,3-dihydroindol-2-one Using 3,3-difluoro-1-(2-methyloxiran-2-yl-methyl)-1,3-dihydroindol-2-one (1.14 g, 4.76 mmol) gave 1-[3-(2-chloro-4-nitroimidazol-1-yl)-2-hydroxy-2-methylpropyl]-3,3-difluoro-1,3-dihydroindol-2-one (968 mg, yield 53%) as a white powder in the same manner as in Example 541.

$^1$H-NMR (DMSO-d$_6$) δppm: 1.09 (3H, s), 3.73 (1H, d, J=14.5 Hz), 3.87 (1H, d, J=14.5 Hz), 4.13 (1H, d, J=14.4 Hz), 4.21 (1H, d, J=14.4 Hz), 5.39 (1H, s), 7.20-7.26 (1H, m), 7.33-7.37 (1H, m), 7.57-7.64 (1H, m), 7.67-7.71. (1H, m).

Using corresponding starting materials gave compounds of Examples 603 and 604 shown in the following table in the same manner as in Example 602.

TABLE 22

| Example | R | $^1$H NMR(CDCl$_3$) δ |
|---|---|---|
| 603 | Me | 1.21(3H, s), 1.38(6H, s), 3.77(1H, d, J=14.8Hz), 3.87(1H, d, J=14.8Hz), 4.05(1H, d, J=14.3Hz), 4.15(1H, d, J=14.3Hz), 6.91(1H, d, J=7.7Hz), 7.02-7.31(3H, m), 8.07(1H, s). |
| 604 | H | 1.24(3H, s), 3.64(2H, s), 3.79(1H, d, J=14.8Hz), 3.89(1H, d, J=14.8Hz), 4.09(1H, d, J=14.3Hz), 4.19(1H, d, J=14.3Hz), 6.93(1H, d, J=7.7Hz), 7.12(1H, d, J=7.5Hz), 7.25-7.35(2H, m), 8.07(1H, s). |

Example 605

Preparation of 3,3-difluoro-1-(2-methyl-6-nitro-2,3-dihydroimidazo[2,1-b]oxazol-2-ylmethyl)-1,3-dihydroindol-2-one Using 1-[3-(2-chloro-4-nitroimidazol-1-yl)-2-hydroxy-2-methylpropyl]-3,3-difluoro-1,3-dihydroindol-2-one prepared in Example 602 (903 mg, 2.34 mmol) gave 3,3-difluoro-1-(2-methyl-6-nitro-2,3-dihydroimidazo[2,1-b]oxazol-2-ylmethyl)-1,3-dihydroindol-2-one (77 mg, yield 9%) as a white powder in the same manner as in Example 544.

Melting point 202-206° C.

Using corresponding starting materials gave the compound of Example 606 in the same manner as in Example 605.

Example 606

3,3-Dimethyl-1-(2-methyl-6-nitro-2,3-dihydroimidazo-[2,1-b]oxazol-2-ylmethyl)-1,3-dihydroindol-2-one $^1$H-NMR (DMSO-d$_6$) δppm: 1.25 (3H, s), 1.37 (3H, s), 1.78 (3H, s), 3.96 (1H, d, J=15.1 Hz), 4.00 (1H, d, J=10.7 Hz), 4.22 (1H, d, J=15.1 Hz), 4.57 (1H, d, J=10.7 Hz), 7.04-7.17 (3H, m), 7.24-7.31 (1H, m), 7.44 (1H, s).

Example 607

Preparation of 1-(2-chloro-4-nitroimidazol-1-yl)-4-(1-ethyl-1H-tetrazol-5-yl)-2-methylbutan-2-ol Using 1-ethyl-5-[2-(2-methyloxiran-2-yl)-ethyl]-1H-tetrazol (1.04 g, 5.59 mmol) gave 1-(2-chloro-4-nitroimidazol-1-yl)-4-(1-ethyl-1H-tetrazol-5-yl)-2-methylbutan-2-ol (1.15 g, yield 69%) as a light yellow oil in the same manner as in Example 541.

$^1$H-NMR (CDCl$_3$) δppm: 1.29 (3H, s), 1.56 (3H, t, J=7.3 Hz), 2.04-2.22 (2H, m), 2.91-3.11 (2H, m), 4.10 (2H, s), 4.24 (1H, br), 4.34 (2H, q, J=7.3 Hz), 8.09 (1H, s).

Using corresponding starting materials gave compounds of Examples 608 and 609 shown in the following table in the same manner as in Example 607.

TABLE 23

[Structure: imidazole with nitro, Cl, and tetrazole-phenyl-R substituent via hydroxymethylbutyl chain]

| Example | R | ¹HNMR(CDCl₃) δ | Yield (%) |
|---|---|---|---|
| 608 | H | 1.26(3H, s), 2.02-2.08(2H, m), 2.96-3.17(2H, m), 3.80(1H, s), 4.04(2H, s), 7.42-7.46(2H, m), 7.60-7.62(3H, m), 8.03(1H, s). | 60 |
| 609 | Cl | 1.26(3H, s), 2.08-2.12(2H, m), 2.96-3.15(2H, m), 3.85(1H, s), 4.07(s, 2H), 7.40-7.44(2H, m), 7.56-7.61(2H, m), 8.04(1H, s). | 66 |

Example 610

Preparation of 2-[2-(1-ethyl-1H-tetrazol-5-yl)ethyl]-2-methyl-6-nitro-2,3-dihydroimidazo[2,1-b]oxazole Using 1-(2-chloro-4-nitroimidazol-1-yl)-4-(1-ethyl-1H-tetrazol-5-yl)-2-methylbutan-2-ol prepared in Example 607 (1.15 g, 3.49 mmol) gave 2-[2-(1-ethyl-1H-tetrazol-5-yl)ethyl]-2-methyl-6-nitro-2,3-dihydroimidazo[2,1-b]oxazole (68 mg, yield 7%) as a light yellow powder in the same manner as in Example 544.

Melting point 135-137° C.

Using corresponding starting materials gave compounds of Examples 611 and 612 in the same manner as in Example 610.

Example 611

2-Methyl-6-nitro-2-[2-(1-phenyl-1H-tetrazol-5-yl)ethyl]-2,3-dihydroimidazo[2,1-b]oxazole Melting point 158-159° C.

Example 612

2-{2-[1-(4-Chlorophenyl)-1H-tetrazol-5-yl]ethyl}-2-methyl-6-nitro-2,3-dihydroimidazo[2,1-b]oxazole Melting point 198-200° C.

Example 613

Preparation of 3-[2-(2-methyl-6-nitro-2,3-dihydroimidazo[2,1-b]oxazol-2-yl)ethyl]-5-(4-trifluoromethyl-benzylidene)thiazolidine-2,4-dione Using 2-(2-methyl-6-nitro-2,3-dihydroimidazo-[2,1-b]oxazol-2-yl)ethyl methanesulfonate prepared in Example 42 (280 mg, 0.96 mmol) and 5-(4-trifluoro-methylbenzylidene)thiazolidine-2,4-dione (320 mg, 1.17 mmol) gave 3-[2-(2-methyl-6-nitro-2,3-dihydroimidazo[2,1-b]oxazol-2-yl)ethyl]-5-(4-trifluoromethylbenzylidene)thiazolidine-2,4-dione (260 mg, yield 58%) as a light yellow powder in the same manner as in Example 537.

Melting point 257-258.5° C.

Example 614

Preparation of 1-[3-(2-chloro-4-nitroimidazol-1-yl)-2-hydroxy-2-methylpropyl]pyrrolidine-2,5-dione Using 1-(2-methyloxiran-2-ylmethyl)-pyrrolidine-2,5-dione (1.96 g, 11 mmol) gave 1-[3-(2-chloro-4-nitroimidazol-1-yl)-2-hydroxy-2-methylpropyl]pyrrolidine-2,5-dione (589 mg, yield 16%) as a white powder in the same manner as in Example 541.

¹H-NMR (DMSO-d₆) δppm: 0.96 (3H, s), 2.68 (4H, s), 3.48 (2H, s), 4.02 (2H, s), 5.19 (1H, s), 8.34 (1H, s).

Using corresponding starting materials gave compounds of Examples 615 and 616 shown in the following table in the same manner as in Example 614.

TABLE 24

[Structure: nitroimidazole with chloro and 2-hydroxy-2-methylpropyl-R substituent]

| Example | R | ¹H NMR δ(CDCl₃) | Yield (%) |
|---|---|---|---|
| 615 | [phthalimide group] | 1.21(3H, s), 3.48(1H, s), 3.79(1H, d, J=14.6Hz), 3.90(1H, d, J=14.6Hz), 4.01(1H, d, J=14.9Hz), 4.16(1H, d, J=14.9Hz), 7.75-7.93(4H, m), 8.06(1H, s). | 71 |

TABLE 24-continued

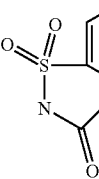

| Example | R | $^1$H NMR δ(CDCl$_3$) | Yield (%) |
|---|---|---|---|
| 616 | ![structure with SO2-N-C=O benzo ring] | 1.21(3H, s), 4.09(1H, d, J=14.4Hz), 4.18(1H, d, J=14.4Hz), 4.05(1H, d, J=14.3Hz), 4.15(1H, d, J=14.3Hz), 4.42(1H, d, J=14.0Hz), 4.49(1H, d, J=14.0Hz), 7.60-7.74(2H, m), 7.81-8.12(2H, m). | 55 |

Example 617

Preparation of 1-(2-methyl-6-nitro-2,3-dihydroimidazo-[2,1-b]oxazol-2-ylmethyl)pyrrolidine-2,5-dione Using 1-[3-(2-chloro-4-nitroimidazol-1-yl)-2-hydroxy-2-methylpropyl]pyrrolidine-2,5-dione prepared in Example 614 (589 mg, 1.86 mmol) gave 1-(2-methyl-6-nitro-2,3-dihydroimidazo[2,1-b]oxazol-2-ylmethyl)pyrrolidine-2,5-dione (232 mg, yield 34%) as a white powder in the same manner as in Example 544.

Melting point 202.5-203.4° C.

Using corresponding starting materials gave compounds of Examples 618 and 619 in the same manner as in Example 617.

Example 618

2-(2-Methyl-6-nitro-2,3-dihydroimidazo[2,1-b]oxazol-2-ylmethyl)isoindole-1,3-dione Melting point 264.6-268.3° C.

Example 619

2-(2-Methyl-6-nitro-2,3-dihydroimidazo[2,1-b]oxazol-2-ylmethyl)-1,1-dioxo-1,2-dihydro[d]benzothiazol-3-one Melting point 243-245° C. (decomposition).

Example 620

Preparation of 1-(2-chloro-4-nitroimidazol-1-yl)-2-(pyridin-3-yl)-propan-2-ol

Using 3-(2-methyloxiran-2-yl)pyridine (7.4 g, 54.75 mmol) gave 1-(2-chloro-4-nitroimidazol-1-yl)-2-(pyridin-3-yl)propan-2-ol (3.3 g, yield 24%) as a white powder in the same manner as in Example 541.

$^1$H-NMR (CDCl$_3$) δppm: 1.65 (3H, s), 4.19 (1H, d, J=14.2 Hz), 4.27 (1H, d, J=14.2 Hz), 5.82 (1H, s), 7.24-7.30 (1H, m), 7.68-7.72 (1H, m), 8.50-8.53 (1H, m), 8.68 (1H, d, J=2.3 Hz).

Example 621

Preparation of 2-methyl-6-nitro-2-(pyridin-3-yl)-2,3-dihydroimidazo[2,1-b]oxazole Using 1-(2-chloro-4-nitroimidazol-1-yl)-2-(pyridin-3-yl)propan-2-ol prepared in Example 620 (3.3 g, 11.7 mmol) gave 2-methyl-6-nitro-2-(pyridin-3-yl)-2,3-dihydroimidazo[2,1-b]oxazole (1.8 g, yield 63%) as a light brown powder in the same manner as in Example 544.

Melting point 212-214° C.

Example 622

Preparation of 2-methyl-6-nitro-2-(1-oxypyridin-3-yl)-2,3-dihydroimidazo[2,1-b]oxazole To a mixture of 2-methyl-6-nitro-2-(pyridin-3-yl)-2,3-dihydroimidazo[2,1-b]oxazole prepared in Example 621 (800 mg, 3.3 mmol) and methylene chloride (25 ml), m-chloroperbenzoic acid (1 g, 4.06 mmol) was added with cooling on ice-bath followed by stirring at room temperature overnight. The reaction mixture was filtered, and the filtrate was washed with a 20% aqueous sodium sulfite solution, a saturated sodium hydrogencarbonate solution and a saturated saline solution in this order, dried over magnesium sulfate and then filtered. The filtrate was concentrated under reduced pressure to afford 2-methyl-6-nitro-2-(1-oxypyridin-3-yl)-2,3-dihydroimidazo[2,1-b]oxazole (330 mg, 39%) as a white powder.

$^1$H-NMR (DMSO-d$_6$) δppm: 1.92 (3H, s), 4.51 (2H, s), 7.42-7.53 (2H, m), 8.14 (1H, s), 8.20-8.24 (1H, m), 8.42 (1H, s).

Example 623

Preparation of 1-(2-methyl-6-nitro-2,3-dihydroimidazo-[2,1-b]oxazol-2-ylmethyl)pieridin-4-one Using 1-(2-methyloxiran-2-ylmethyl)piperidin-4-one (2.2 g, 13 mmol) gave 1-(2-methyl-6-nitro-2,3-dihydroimidazo[2,1-b]oxazol-2-ylmethyl)piperidin-4-one (50 mg, yield 1%) as a light yellow powder in the same manner as in Example 597.

Melting point 124-126° C.

Example 624

Preparation of 4-[3-(2-chloro-4-nitroimidazol-1-yl)-2-hydroxy-2-methylpropyl]-1-(4-trifluoromethylbenzyl)-piperazin-2-one Using 4-(2-methyloxiran-2-ylmethyl)-1-(4-trifluoromethylbenzyl)piperazin-2-one (1.6 g, 4.9 mmol) gave 4-[3-(2-chloro-4-nitroimidazol-1-yl)-2-hydroxy-2-methylpropyl]-1-(4-trifluoromethylbenzyl)piperazin-2-one (1 g, yield 43%) as a light yellow powder in the same manner as in Example 541.

$^1$H-NMR (CDCl$_3$) δppm: 1.18 (3H, s), 2.45 (1H, d, J=13.9 Hz), 2.57 (1H, d, J=13.9 Hz), 2.72-2.98 (2H, m), 3.19-3.44 (3H, m), 3.55 (1H, d, J=16.5 Hz), 4.00 (1H, d, J=14.3 Hz), 4.10 (1H, d, J=14.3 Hz), 4.64 (2H, s), 7.37 (2H, d, J=8.2 Hz), 7.61 (2H, d, J=8.2 Hz), 8.02 (1H, s).

Using corresponding starting materials gave the compound of Example 625 in the same manner as in Example 624.

Example 625

1-Tert-butyl-4-[3-(2-chloro-4-nitroimidazol-1-yl)-2-hydroxy-2-methylpropyl]piperazin-2-one $^1$H-NMR (CDCl$_3$) δppm: 1.16 (3H, s), 1.44 (9H, s), 2.41 (1H, d, J=13.8 Hz), 2.51 (1H, d, J=13.8 Hz), 2.65-2.88 (3H, m), 2.93-3.09 (1H, m), 3.12-3.28 (2H, m), 3.99 (1H, d, J=14.3 Hz), 4.08 (1H, d, J=14.3 Hz), 8.05 (1H, s).

Example 626

Preparation of 4-(2-methyl-6-nitro-2,3-dihydroimidazo-[2,1-b]oxazol-2-ylmethyl)-1-(4-trifluoromethylbenzyl)-piperazin-2-one Using 4-[3-(2-chloro-4-nitroimidazol-1-yl)-2-hydroxy-2-methylpropyl]-1-(4-trifluoromethylbenzyl)-piperazin-2-one prepared in Example 624 (1 g, 2.1 mmol) gave 4-(2-methyl-6-nitro-2,3-dihydroimidazo[2,1-b]oxazol-2-ylmethyl)-1-(4-trifluoromethylbenzyl)piperazin-2-one (206 mg, yield 22%) as a light yellow powder in the same manner as in Example 544.

Melting point 88-93° C.

Using corresponding starting materials gave the compound of Example 627 in the same manner as in Example 626.

Example 627

1-Tert-butyl-4-(2-methyl-6-nitro-2,3-dihydroimidazo-[2,1-b]oxazol-2-ylmethyl)piperazin-2-one Melting point 193-194° C.

Example 628

Preparation of 1-tert-butyl-4-[2-(2-methyl-6-nitro-2,3-dihydroimidazo[2,1-b]oxazol-2-yl)ethyl]piperazin-2-one A mixture of 2-(2-methyl-6-nitro-2,3-dihydroimidazo[2,1-b]oxazol-2-yl)ethyl methanesulfonate prepared in Example 42 (290 mg, 1 mmol), 1-tert-butylpiperazin-2-one hydrochloride (200 mg, 1.28 mmol), triethylamine (242 mg, 2.39 mmol), potassium iodide (250 mg, 1.5 mmol) and DMF (3 ml) was stirred at 70° C. for 4 hours. The reaction mixture was allowed to return to room temperature. To the solution, water was added, and the resulting solution was extracted with ethyl acetate twice. The organic phases were combined, washed with water twice and a saturated saline solution, dried over magnesium sulfate and then filtered. The filtrate was concentrated under reduced pressure, and the residue was purified by silica gel column chromatography (methylene chloride/methanol=20/1) to afford 1-tert-butyl-4-[2-(2-methyl-6-nitro-2,3-dihydroimidazo[2,1-b]oxazol-2-yl)ethyl]piperazin-2-one (27 mg, yield 8%) as a white powder.

Melting point 153-154° C.

Using corresponding starting materials gave the compound of Example 629 in the same manner as in Example 628.

Example 629

4-[2-(2-Methyl-6-nitro-2,3-dihydroimidazo[2,1-b]oxazol-2-yl)ethyl]-1-phenylpiperazin-2-one Melting point 199-202° C. (decomposition).

Example 630

Preparation of 1-tert-butyl-4-[3-(2-methyl-6-nitro-2,3-dihydroimidazo[2,1-b]oxazol-2-yl)propyl]piperazin-2-one Using 3-(2-methyl-6-nitro-2,3-dihydroimidazo-[2,1-b]oxazol-2-yl)propyl methanesulfonate prepared in Example 39 (300 mg, 0.98 mmol) gave 1-tert-butyl-4-[3-(2-methyl-6-nitro-2,3-dihydroimidazo[2,1-b]oxazol-2-yl)propyl]piperazin-2-one (150 mg, yield 42%) as a white powder in the same manner as in Example 628.

Melting point 147-149° C. (decomposition).

Example 631

Preparation of 1-(benzimidazol-1-yl)-3-(2-chloro-4-nitroimidazol-1-yl)-2-methylpropan-2-ol Using 1-(2-methyloxiran-2-ylmethyl)-1H-benzimidazole (350 mg, 1.86 mmol) gave 1-(benzimidazol-1-yl)-3-(2-chloro-4-nitroimidazol-1-yl)-2-methylpropan-2-ol (135 mg, yield 22%) as a white powder in the same manner as in Example 541.

$^1$H-NMR (DMSO-d$_6$) δppm: 0.99 (3H, s), 4.06 (1H, d, J=14.2 Hz), 4.23-4.45 (3H, m), 5.44 (1H, s), 7.14-7.32 (2H, m), 7.57-7.77 (2H, m), 8.15 (1H, s), 8.36 (1H, s).

Using corresponding starting materials gave the compound of Example 632 in the same manner as in Example 631.

Example 632

1-(Imidazol-1-yl)-3-(2-chloro-4-nitroimidazol-1-yl)-2-methylpropan-2-ol $^1$H-NMR (CDCl$_3$) δppm: 1.19 (3H, s), 3.86-4.05 (3H, m), 4.13 (1H, d, J=14.2 Hz), 6.87 (1H, s), 6.89 (1H, s), 7.47 (1H, s), 8.08 (1H, s).

Example 633

Preparation of 1-(2-methyl-6-nitro-2,3-dihydroimidazo-[2,1-b]oxazol-2-ylmethyl)-1H-benzimidazole Using 1-(benzimidazol-1-yl)-3-(2-chloro-4-nitroimidazol-1-yl)-2-methylpropan-2-ol prepared in Example 631 (135 mg, 0.4 mmol) gave 1-(2-methyl-6-nitro-2,3-dihydroimidazo[2,1-b]oxazol-2-ylmethyl)-1H-benzimidazole (72 mg, yield 60%) as a white powder in the same manner as in Example 544.

Melting point 250.3-251.9° C. (decomposition).

Using corresponding starting materials gave the compound of Example 634 in the same manner as in Example 633.

Example 634

1-(2-Methyl-6-nitro-2,3-dihydroimidazo[2,1-b]oxazol-2-ylmethyl)imidazole

Melting point 245.5-247.8° C.

Example 635

Preparation of (S)-1-(2-chloro-4-nitroimidazol-1-yl)-3-(3,4-dihydro-2H-quinolin-1-yl)-2-methylpropan-2-ol A mixture of (R)-2-chloro-1-(2-methyloxiran-2-ylmethyl)-4-nitroimidazole prepared in Example 12 (100 mg, 0.46 mmol), 1,2,3,4-tetrahydroquinoline (122 mg, 0.92 mmol) and DMF (1 ml) was stirred at 80° C. for 8 hours. The reaction mixture was allowed to return to room temperature. To the solution, water was added, and the resulting solution was extracted with ethyl acetate twice. The organic phases were combined, washed with water twice and a saturated saline solution, dried over magnesium sulfate and then filtered. The filtrate was concentrated under reduced pressure, and the residue was purified by silica gel column chromatography (n-hexane/ethyl acetate=1/1) to afford (S)-1-(2-chloro-4-nitroimidazol-1-yl)-3-(3,4-dihydro-2H-quinolin-1-yl)-2-methylpropan-2-ol (134 mg, yield 83%) as an orange oil.

$^1$H-NMR (CDCl$_3$) δppm: 1.24 (3H, s), 1.94-2.04 (2H, m), 2.39 (1H, m), 2.79-2.85 (2H, m), 3.27-3.42 (4H, m), 6.66-6.72 (2H, m), 6.97-7.08 (2H, m), 8.04 (1H, s).

Using corresponding starting materials gave compounds of Examples 636 to 638 shown in the following table in the same manner as in Example 635.

TABLE 25

| Example | R | $^1$H NMR δ(CDCl$_3$) | Yield (%) |
|---|---|---|---|
| 636 | (1,2,3,4-tetrahydroisoquinolin-2-yl) | 1.18(3H, s), 2.51(1H, d, J=13.9Hz), 2.66(1H, d, J=13.9Hz), 2.82-2.98(4H, m), 3.76(1H, d, J=14.9Hz), 3.88(1H, d, J=14.9Hz), 4.03(2H, s), 7.00(1H, dd, J=2.3Hz, 7.7Hz), 7.06-7.20(3H, m), 8.01(1H, s). | 87 |
| 637 | (isoindolin-2-yl) | 1.20(3H, s), 2.55(1H, d, J=13.8Hz), 2.71(1H, d, J=13.8Hz), 3.81(1H, d, J=14.8Hz), 3.91(1H, d, J=14.8Hz), 4.05(4H, s), 7.10-7.23(4H, m), 8.00(1H, s). | 93 |
| 638 | (1,4-dioxa-8-azaspiro[4.5]decan-8-yl) | 1.11(3H, s), 1.67-1.78(4H, m), 2.37(1H, d, J=14.0Hz), 2.51(1H, d, J=14.0Hz), 2.57-2.82(4H, m), 3.69(1H, s), 3.95(4H, s), 3.99(2H, s), 8.06(1H, s). | 100 |

Example 639

Preparation of (S)-1-(2-methyl-6-nitro-2,3-dihydroimidazo[2,1-b]oxazol-2-ylmethyl)-1,2,3,4-tetrahydro-quinoline Using (S)-1-(2-chloro-4-nitroimidazol-1-yl)-3-(3,4-dihydro-2H-quinolin-1-yl)-2-methylpropan-2-ol prepared in Example 635 (134 mg, 0.38 mmol) gave (S)-1-(2-methyl-6-nitro-2,3-dihydroimidazo[2,1-b]oxazol-2-ylmethyl)-1,2,3,4-tetrahydroquinoline (64 mg, 54%) as a white powder in the same manner as in Example 393.

Melting point 168-172° C.

Using corresponding starting materials gave compounds of Examples 640 to 642 in the same manner as in Example 639.

Example 640

(S)-2-(2-Methyl-6-nitro-2,3-dihydroimidazo[2,1-b]oxazol-2-ylmethyl)-1,2,3,4-tetrahydroisoquinoline Melting point 153-155.3° C.

Example 641

(S)-2-(2-Methyl-6-nitro-2,3-dihydroimidazo[2,1-b]oxazol-2-ylmethyl)-2,3-dihydro-1H-isoindole $^1$H-NMR (CDCl$_3$) δppm: 1.68 (3H, s), 3.01 (1H, d, J=14.5 Hz), 3.24 (1H, d, J=14.5 Hz), 3.92 (1H, d, J=9.6 Hz), 4.08 (4H, s), 4.50 (1H, d, J=9.6 Hz), 7.13-7.21 (4H, m), 7.50 (1H, s).

Example 642

(S)-8-(2-Methyl-6-nitro-2,3-dihydroimidazo[2,1-b]oxazol-2-ylmethyl)-1,4-dioxa-8-azaspiro[4,5]decane Melting point 166.5-168.2° C.

Example 643

Preparation of (2S)-methyl-6-nitro-2-[(2S)-(4-trifluoromethoxyphenoxymethyl)pyrrolidin-1-ylmethyl]-2,3-dihydroimidazo[2,1-b]oxazole A mixture of (R)-2-chloro-1-(2-methyloxiran-2-ylmethyl)-4-nitroimidazole prepared in Example 12 (645 mg, 2.97 mmol), (S)-2-(4-trifluoromethoxyphenoxymethyl)pyrrolidine (930 mg, 3.56 mmol) and DMF (15 ml) was stirred at 80° C. for 8 hours. To the reaction mixture, sodium hydride (154 mg, 3.86 mmol) was added followed by stirring for 1 hour with cooling on ice-bath. The reaction mixture was poured into ice-water, and the mixture was extracted with ethyl acetate twice. The organic phases were combined, washed with water twice and a saturated saline solution, dried over magnesium sulfate and then filtered. The filtrate was concentrated under reduced pressure, and the residue was purified by silica gel column chromatography (methylene chloride) and recrystallized from methylene chloride-isopropyl ether to afford (2S)-methyl-6-nitro-2-[(2S)-(4-trifluoromethoxyphenoxymethyl)pyrrolidin-1-ylmethyl]-2,3-dihydroimidazo[2,1-b]oxazole (505 mg, yield 41%) as a white powder.

$^1$H-NMR (CDCl$_3$) δppm: 1.42-1.52 (1H, m), 1.59 (3H, s), 1.61-1.79 (2H, m), 1.87-1.99 (1H, m), 2.50-2.61 (1H, m), 3.03-3.17 (2H, m), 3.06 (1H, d, J=14.7 Hz), 3.20 (1H, d, J=14.7 Hz), 3.72-3.79 (2H, m), 3.92 (1H, dd, J=9.2 Hz, 3.7 Hz), 4.58 (1H, d, J=9.5 Hz), 6.80-6.88 (2H, m), 7.15-7.19 (1H, m), 7.42 (1H, s).

Example 644

Preparation of tert-butyl 4-[3-(2-chloro-4-nitro-imidazol-1-yl)-2-hydroxy-2-methylpropyl]homopiperazine-1-carboxylate A mixture of 2-chloro-4-nitro-1H-imidazole (8.39 g, 56.88 mmol), tert-butyl 4-(2-methyloxiran-2-ylmethyl)homopiperazine-1-carboxylate (15.38 g, 56.88 mmol) and sodium acetate (5.13 g, 62.57 mmol) in 1-propanol (100 ml) was stirred under reflux for 10 hours. The reaction mixture was allowed to return to room temperature and then concentrated under reduced pressure. The residue was dissolved in methylene chloride. The solution was washed with water, dried over sodium sulfate and then filtered. The filtrate was concentrated under reduced pressure, and the residue was purified by silica gel column chromatography (methylene chloride/ethyl acetate=5/1) to afford tert-butyl 4-[3-(2-chloro-4-nitroimidazol-1-yl)-2-hydroxy-2-methylpropyl]homopiperazine-1-carboxylate (6.25 g, yield 27%) as a reddish yellow oil.

$^1$H-NMR (CDCl$_3$) δppm: 1.14 (3H, s), 1.48 (9H, s), 1.69-1.90 (2H, m), 2.40-2.55 (1H, m), 2.66 (1H, d, J=14.1 Hz), 2.75-2.98 (5H, m), 3.30-3.59 (4H, m), 3.96 (2H, s), 8.06 (1H, s).

Example 645

Preparation of tert-butyl 4-(2-methyl-6-nitro-2,3-dihydroimidazo[2,1-b]oxazol-2-ylmethyl)homopiperazin-1-carboxylate Using tert-butyl 4-[3-(2-chloro-4-nitro-imidazol-1-yl)-2-hydroxy-2-methylpropyl]homopiperazine-1-carboxylate prepared in Example 644 (6.25 g, 14.96 mmol) gave tert-butyl 4-(2-methyl-6-nitro-2,3-dihydroimidazo[2,1-b]oxazol-2-ylmethyl)homopiperazine-1-carboxylate (3.07 g, yield 54%) as a white powder in the same manner as in Example 544.

$^1$H-NMR (CDCl$_3$) δppm: 1.47 (9H, s), 1.59 (3H, s), 1.68-1.79 (2H, m), 2.63-2.90 (5H, m), 3.06 (1H, d, J=15.1 Hz), 3.25-3.50 (4H, m), 3.91 (1H, d, J=9.7 Hz), 4.33 (1H, d, J=9.7 Hz), 7.54 (1H, s).

Example 646

Preparation of benzyl 4-(2-methyl-6-nitro-2,3-dihydroimidazo[2,1-b]oxazol-2-ylmethyl)homopiperazine-1-carboxylate hydrochloride A mixture of tert-butyl 4-(2-methyl-6-nitro-2,3-dihydroimidazo[2,1-b]oxazol-2-ylmethyl)-homopiperazine-1-carboxylate prepared in Example 645 (250 mg, 0.655 mmol) and trifluoroacetic acid (10 ml) was stirred at room temperature overnight. The reaction mixture was concentrated under reduced pressure, the residue was dissolved in methylene chloride (10 ml). To the solution, triethylamine (0.27 ml, 1.96 mmol) and benzyl chloroformate (0.19 ml, 1.31 mmol) were added followed by stirring at room temperature for 3 hours. To the reaction mixture, water was added, and the mixture was extracted with methylene chloride. The organic phase was dried over magnesium sulfate and then filtered. The filtrate was concentrated under reduced pressure, and the residue was purified by silica gel column chromatography (methylene chloride/ethyl acetate=1/1) to afford a light yellow oil. The resulting oil was dissolved in ethyl acetate. To the solution, a saturated hydrochloric acid/ethyl acetate solution was added, and the precipitates were filtered off to afford benzyl 4-(2-methyl-6-nitro-2,3-dihydroimidazo[2,1-b]oxazol-2-ylmethyl)homopiperazine-1-carboxylate hydrochloride (246 mg, yield 83%) as a white powder.

Melting point 115-117° C.

Example 647

Preparation of 2-[4-(biphenyl-4-ylmethyl)homopiperazin-1-ylmethyl]-2-methyl-6-nitro-2,3-dihydroimidazo[2,1-b]oxazole A mixture of tert-butyl 4-(2-methyl-6-nitro-2,3-dihydroimidazo[2,1-b]oxazol-2-ylmethyl)-homopiperazin-1-carboxylate prepared in Example 645 (346 mg, 0.91 mmol) and trifluoroacetic acid (10 ml) was stirred at room temperature overnight. The reaction mixture was concentrated under reduced pressure, and the residue was dissolved in methylene chloride (10 ml). To the solution, triethylamine (0.27 ml, 1.96 mmol) was added. The solution was concentrated under reduced pressure, and the residue was dissolved in methanol (10 ml). To the solution, 4-phenylbenzaldehyde (496 mg, 2.72 mmol), sodium cyanotrihydroborate (171 mg, 2.72 mmol) and acetic acid (0.17 ml, 2.72 mmol) were added in this order followed by stirring at room temperature overnight. The reaction mixture was poured into a saturated sodium hydrogencarbonate solution, then extracted with methylene chloride. The organic phase was dried over magnesium sulfate and then filtered. The filtrate was concentrated under reduced pressure, and the residue was purified by silica gel column chromatography (methylene chloride/ethyl acetate=5/1) to afford 2-[4-(biphenyl-4-ylmethyl)homopiperazin-1-ylmethyl]-2-methyl-6-nitro-2,3-dihydroimidazo[2,1-b]oxazole (251 mg, yield 62%) as a white powder.

Melting point 138-142.2° C.

Example 648

Preparation of 1'-tert-butoxycarbonyl-2,3-dihydro-6-nitrospiro[imidazo[2,1-b]oxazol-2,4'-piperidine]

2,4-Dinitro-1H-imidazole (1.0 g, 6.3 mmol), tert-butyl 1-oxa-6-azaspiro[2,5]octane-6-carboxylate (2.0 g, 9.5 mmol) and sodium acetate (612 mg, 7.5 mmol) in ethanol (7 ml) were stirred under reflux for 10 hours. The reaction mixture was concentrated under reduced pressure. To the residue, a saturated sodium hydrogencarbonate solution and methylene chloride were added followed by stirring vigorously, and then the mixture was extracted with methylene chloride. The organic phase was dried over sodium sulfate and then filtered. The resulting filtrate was concentrated under reduced pressure, and the residue was crystallized from methylene chloride-diisopropyl ether to afford 1'-tert-butoxycarbonyl-2,3-dihydro-6-nitrospiro[imidazo[2,1-b]oxazole-2,4'-piperidine] (586 mg, yield 29%) as a white powder.

Melting point 230-232° C.

Example 649

Preparation of tert-butyl 4-(2-chloro-4-nitroimidazol-1-ylmethyl)-4-hydroxypiperidine-1-carboxylate 2-Chloro-4-nitro-1H-imidazole (3.1 g, 21.0 mmol), tert-butyl 1-oxa-6-azaspiro[2,5]octane-6-carboxylate (4.4 g, 21.0 mmol) and sodium hydrogen-carbonate (1.94 g, 23.1 mmol) in ethanol (20 ml) were stirred under reflux for 6 hours. The reaction mixture was concentrated under reduced pressure, and the residue was added water. The resulting solution was extracted with methylene chloride. The organic phase was dried over magnesium sulfate and then filtered. The resulting filtrate was concentrated under reduced pressure, and the residue was purified by silica gel column chromatography (methylene chloride/methanol=100/1) to afford tert-butyl 4-(2-chloro-4-nitroimidazol-1-ylmethyl)-4-hydroxypiperidine-1-carboxylate (5.4 g, yield 72%) as a yellow oil.

$^1$H-NMR (CDCl$_3$) δppm: 1.45-1.71 (5H, m), 1.46 (9H, s), 3.03-3.14 (2H, m), 3.90-4.03 (2H, m), 4.02 (2H, s), 7.91 (1H, s).

Example 650

Preparation of tert-butyl 4-{2-[4-(2-chloro-4-nitroimidazol-1-ylmethyl)-4-hydroxypiperidin-1-yl]-2-oxoethyl}piperazine-1-carboxylate 2-Chloro-4-nitro-1H-imidazole (1.29 g, 8.76 mmol), tert-butyl 4-{2-(1-oxa-6-azaspiro[2,5]octan-6-yl)-2-oxoethyl}piperazine-1-carboxylate (2.97 g, 8.76 mmol) and sodium hydrogencarbonate (809 mg, 9.64 mmol) in ethanol (10 ml) was stirred under reflux for 5 hours. The reaction mixture was concentrated under reduced pressure, and a saturated sodium hydrogencarbonate solution was added. The solution was extracted with methylene chloride. The organic phase was dried over magnesium sulfate and then filtered. The resulting filtrate was concentrated under reduced pressure, and the residue was purified by silica gel column chromatography (methylene chloride/methanol=100/1) to afford tert-butyl 4-{2-[4-(2-chloro-4-nitroimidazol-1-ylmethyl)-4-hydroxypiperidin-1-yl]-2-oxoethyl}piperazine-1-carboxylate (2.58 g, yield 61%) as a yellow oil.

$^1$H-NMR (CDCl$_3$) δppm: 1.45 (9H, s), 1.53-1.71 (4H, m), 2.44 (4H, br), 2.96-3.04 (1H, m), 3.10-3.27 (2H, m), 3.35-3.48 (4H, m), 3.90-3.96 (2H, m), 4.05 (2H, s), 4.32-4.37 (2H, m), 8.04 (1H, s).

Using 6-(4-trifluoromethylphenyl)-1-oxa-6-azaspiro[2,5] octane gave the compound of Example 651 in the same manner as in Example 650.

Example 651

4-(2-Chloro-4-nitroimidazol-1-ylmethyl)-1-(4-trifluoromethylphenyl)piperidin-4-ol Light pink powder, yield 54%
$^1$H-NMR (CDCl$_3$) δppm: 1.60-1.66 (2H, m), 1.82-1.93 (3H, m), 3.10-3.22 (2H, m), 3.62-3.67 (2H, m), 4.07 (2H, s), 6.95 (2H, d, J=8.7 Hz), 7.50 (2H, d, J=8.7 Hz), 7.99 (1H, s).

Example 652

Preparation of 1'-tert-butoxycarbonyl-2,3-dihydro-6-nitrospiro[imidazo[2,1-b]oxazole-2,4'-piperidine]-(alternative synthesis method of the compound of Example 648)

Tert-butyl 4-(2-chloro-4-nitroimidazol-1-ylmethyl)-4-hydroxypiperidine-1-carboxylate prepared in Example 649 (26.7 g, 74.0 mmol) was dissolved in 1,4-dioxane (200 ml). To the solution, sodium hydride (3.6 g, 88.8 mmol) was added with cooling on ice-bath followed by stirring under reflux for 8 hours. The reaction mixture was concentrated under reduced pressure. To the residue, ice-water and methylene chloride were added followed by stirring vigorously. The precipitates were filtered off, washed with water and methanol, dried under reduced pressure to afford a solid (16.4 g). Then, the filtrate was extracted with methylene chloride. The organic phase was dried over magnesium sulfate and then filtered. The organic phase was concentrated under reduced pressure. The residue was crystallized with methanol to afford a solid (2.7 g). The solids were combined to afford 1'-tert-butoxycarbonyl-2,3-dihydro-6-nitrospiro [imidazo(2,1-b]oxazole-2,4'-piperidine] (19.1 g, yield 79%) as a white powder.

Melting point 230-232° C.

Example 653

Preparation of tert-butyl 4-[2-(2,3-dihydro-6-nitro-spiro[imidazo[2,1-b]oxazol-2,4'-piperidine]-1'-yl)-2-oxoethyl]piperazine-1-carboxylate Tert-butyl 4-{2-[4-(2-chloro-4-nitroimidazol-1-ylmethyl)-4-hydroxypiperidin-1-yl]-2-oxoethyl}-piperazine carboxylate prepared in Example 650 (2.58 g, 5.3 mmol) was dissolved in dioxane (30 ml). To the solution, sodium hydride (254 mg, 6.36 mmol) was added with cooling on ice-bath followed by stirring under reflux overnight. The reaction mixture was concentrated under reduced pressure. To the residue, ice-water and ethyl acetate were added followed by stirring vigorously. The precipitates were filtered off, washed with water and ethyl acetate, and then dried under reduced pressure to afford tert-butyl 4-[2-(2,3-dihydro-6-nitrospiro[imidazo[2,1-b]oxazol-2,4'-piperidine]-1'-yl)-2-oxoethyl]piperazine-1-carboxylate (996 mg, yield 42%) as a white powder.

Melting point 211.0-213.0° C.

Using corresponding starting materials gave the compound of Example 654 in the same manner as in Example 653.

Example 654

2,3-Dihydro-6-nitro-1'-(4-trifluoromethylphenyl) spiro[imidazo[2,1-b]oxazole-2,4'-piperidine]

White powder, yield 79% MS: 368($M^+$) Melting point 249.2-250.1° C.

Example 655

Preparation of 2,3-dihydro-6-nitrospiro[imidazo[2,1-b]oxazole-2,4'-piperidine]trifluoroacetate 1'-Tert-butoxycarbonyl-2,3-dihydro-6-nitrospiro[imidazo [2,1-b]oxazole-2,4'-piperidine] prepared in Example 652 (42 g, 0.13 mol) was suspended in methylene chloride (100 ml). To the suspension, trifluoroacetic acid (60 ml) was added slowly with cooling on ice-bath followed by stirring at room temperature overnight. The reaction mixture was concentrated under reduced pressure, and the residue was crystallized with methanol. The solids were filtered off, washed with methanol and ethyl acetate, and then dried under reduced pressure to afford 2,3-dihydro-6-nitrospiro[imidazo [2,1-b]oxazole-2,4'-piperidine]trifluoroacetate (43.6 g, yield 99%) as a light brown powder.

MS: 224($M^+$) Melting point 196-198° C. (decomposition) $^1$H-NMR (DMSO-$d_6$) δppm: 2.06-2.32 (4H, m), 3.12-3.35 (4H, m), 4.24 (2H, s), 8.21 (1H, s), 8.88 (2H, bs).

Example 656

Preparation of 1'-acetyl-2,3-dihydro-6-nitrospiro-[imidazo[2,1-b]oxazole-2,4'-piperidine]

2,3-Dihydro-6-nitrospiro[imidazo[2,1-b]oxazole-2,4'-piperidine]trifluoroacetate prepared in Example 655 (85.5 mg, 0.25 mmol) was suspended in methylene chloride (5 ml). To the suspension, triethylamine (74 μl) and acetyl chloride (20 μl) were added followed by stirring at room temperature for 1 hour. The reaction mixture was concentrated under reduced pressure. To the residue, methanol and water were added followed by stirring vigorously. The precipitates were filtered off, washed with water and isopropyl ether, and then dried under reduced pressure to afford 1'-acetyl-2,3-dihydro-6-nitrospiro[imidazo[2,1-b]oxazole-2,4'-piperidine] (37.8 mg, yield 56%) as a white powder.

MS: 266($M^+$) Melting point 232.0-234.0° C.

Example 657

Preparation of 1'-(4-trifluoromethylphenylacetyl)-2, 3-dihydro-6-nitrospiro[imidazo[2,1-b]oxazole-2,41-piperidine]

2,3-Dihydro-6-nitrospiro[imidazo[2,1-b]oxazole-2,4'-piperidine]trifluoroacetate prepared in Example 655 (300 mg, 0.89 mmol) was suspended in methylene chloride (5 ml). To the suspension, triethylamine (0.4 ml, 2.66 mmol) and (α,α,α-trifluoro-p-tolyl)acetyl chloride (2.7 ml, 1.33 mmol) were added followed by stirring at room temperature for 1 hour. The reaction mixture was poured into a saturated sodium hydrogencarbonate solution, and the mixture was extracted with methylene chloride. The organic phase was dried over magnesium sulfate and then filtered. The resulting filtrate was concentrated under reduced pressure, and the residue was purified by silica gel column chromatography (methylene chloride/methanol=200/1) and crystallized from methylene chloride-isopropyl ether to afford 1'-(4-trifluoromethyl-phenylacetyl)-2,3-dihydro-6-nitrospiro[imidazo [2,1-b]oxazole-2,4'-piperidine] (143 mg, yield 39%) as a white powder.

MS: 410($M^+$) Melting point 185.0-187.0° C.

Example 658

Preparation of 1'-(3,4-dichlorophenoxyacetyl)-2,3-dihydro-6-nitrospiro[imidazo[2,1-b]oxazole-2,4'-piperidine]

2,3-Dihydro-6-nitrospiro[imidazo[2,1-b]oxazole-2,4'-piperidine]trifluoroacetate prepared in Example 655 (300 mg, 0.89 mmol), (3,4-dichlorophenyl)-acetic acid (294 mg, 1.24 mmol) and WSCD (255 mg, 1.24 mmol) in DMF (5 ml) were stirred at room temperature for 1.5 hours. To the reaction mixture, water and diethyl ether was added followed by stirring vigorously. The precipitates were filtered off, washed with water and diethyl ether, and then dried under reduced pressure to afford 1'-(3,4-dichlorophenoxyacetyl)-2,3-dihydro-6-nitrospiro[imidazo[2,1-b]oxazole-2, 4'-piperidine] (96 mg, yield 25%) as a white powder.

Melting point 218.0-220.0° C.

Example 659

Preparation of 2,3-dihydro-1'-methyl-6-nitrospiro-[imidazo[2,1-b]oxazole-2,4'-piperidine]

2,3-Dihydro-6-nitrospiro[imidazo[2,1-b]oxazole-2,4'-piperidine] (250 mg, 1.12 mmol) obtained by neutrlization of 2,3-dihydro-6-nitrospiro[imidazo[2,1-b]oxazole-2,4'-piperidine]trifluoroacetate prepared in Example 655 was suspended in methanol (5 ml). To the suspension, a 37% formaldehyde solution (0.25 ml, 3.35 mmol), sodium cyanotrihydroborate (210 mg, 3.35 mmol) and acetic acid (0.19 ml, 3.35 mmol) were added followed by stirring at room temperature for 3 hours. The reaction mixture was poured into a saturated sodium hydrogencarbonate solution, and the mixture was extracted with methylene chloride. The organic phase was dried over sodium sulfate and then filtered. The resulting filtrate was concentrated under reduced pressure. The residue was crystallized from methylene chloride-diisopropyl ether to afford 2,3-dihydro-1-methyl-6-nitrospiro[imidazo[2,1-bloxazole-2,4'-piperidine] (160 mg, yield 60%) as a white powder.

MS: 238(M+) Melting point 237.0-239.0° C. (decomposition).

Example 660

Preparation of 1'-benzenesulfonyl-2,3-dihydro-6-nitrospiro[imidazo[2,1-b]oxazole-2,4'-piperidine]

2,3-Dihydro-6-nitrospiro[imidazo[2,1-b]oxazole-2,4'-piperidine]trifluoroacetate prepared in Example 655 (197 mg, 0.88 mmol) was suspended in methylene chloride (5 ml). To the suspension, triethylamine (0.36 ml, 2.64 mmol) and benzenesulfonyl chloride (0.28 ml, 2.10 mmol) were added followed by stirring at room temperature for 30 minutes. To the reaction mixture, diisopropyl ether and water were added followed by stirring vigorously. The precipitates were filtered off, washed with water and diisopropyl ether, and then dried under reduced pressure to afford 1'-benzenesulfonyl-2,3-dihydro-6-nitrospiro[imidazo[2,1-b]oxazole-2,4'-piperidine] (210 mg, yield 66%) as a white powder.

MS: 364(M+) $^1$H-NMR (DMSO-$d_6$) δppm: 1.99-2.18 (4H, m), 2.49-2.63 (2H, m), 3.40-3.54 (2H, m), 4.10 (2H, s), 7.65-7.81 (5H, m), 8.21 (1H, s).

Using corresponding starting materials gave the compound of Example 661 in the same manner as in Example 660.

Example 661

1'-Methanesulfonyl-2,3-dihydro-6-nitrospiro[imidazo-[2,1-b]oxazole-2,4'-piperidine]

$^1$H-NMR (DMSO-$d_6$) δppm: 1.98-2.22 (4H, m), 2.94 (3H, s), 3.04-3.13 (2H, m), 3.43-3.51 (2H, m), 4.16 (2H, s), 8.17 (1H, s).

Example 662

Preparation of 1'-benzyloxycarbonyl-2,3-dihydro-6-nitrospiro[imidazo[2,1-b]oxazole-2,4'-piperidine]

2,3-Dihydro-6-nitrospiro[imidazo[2,1-b]oxazole-2,4'-piperidine]trifluoroacetate prepared in Example 655 (250 mg, 0.74 mmol) was suspended in methylene chloride (5 ml). To the suspension, triethylamine (0.40 ml, 2.96 mmol) and benzyl chloroformate (0.32 ml, 2.22 mmol) were added followed by stirring at room temperature for 30 minutes. The reaction mixture was concentrated under reduced pressure, and the residue was purified by silica gel column chromatography (methylene chloride/methanol=200/1) and crystallized from methylene chloride-isopropyl ether to afford 1'-benzyloxycarbonyl-2,3-dihydro-6-nitrospiro[imidazo[2,1-b]oxazole-2,41-piperidine] (224 mg, yield 84%) as a white powder.

Melting point 175.0-177.0° C.

Example 663

Preparation of 1'-(4-trifluoromethylbenzyloxycarbonyl)-2,3-dihydro-6-nitrospiro[imidazo[2,1-b]oxazole-2,4'-piperidine]

2,3-Dihydro-6-nitrospiro[imidazo[2,1-b]oxazole-2,4'-piperidine]trifluoroacetate prepared in Example 655 (33 g, 97.6 mmol) was suspended in DMF (200 ml). To the suspension, triethylamine (20 ml, 0.15 mol) was added followed by stirring. To the solution, a mixture of 4-trifluoromethylbenzyl alcohol (25.8 g, 0.15 mol), 1,1$^1$-carbonyldiimidazole (23.7 g, 0.15 mol) and DMF (100 ml) stirred at room temperature for 3 hours was added followed by stirring at 70° C. for 2 hours. The reaction mixture was concentrated under reduced pressure. To the residue, water was added, and the precipitates were filtered off. The precipitates were purified by silica gel column chromatography (methylene chloride/ethyl acetate=10/1) and recrystallized from ethyl acetate-isopropyl ether to afford 1'-(4-trifluoromethylbenzyloxycarbonyl)-2,3-dihydro-6-nitrospiro[imidazo[2,1-b]oxazole-2,4'-piperidine] (37.2 g, yield 90%) as a white powder.

Melting point 189-190° C.

Using corresponding starting materials gave compounds of Examples 664 and 665 in the same manner as in Example 663.

Example 664

1'-[(4-Trifluoromethoxy)benzyloxycarbonyl]-2,3-dihydro-6-nitrospiro[imidazo[2,1-b]oxazole-2,4'-piperidine]

$^1$H-NMR (CDCl$_3$) δppm: 1.80-1.93 (2H, m), 2.13-2.19 (2H, m), 3.32-3.42 (2H, m), 4.00-4.20 (2H, m), 4.03 (2H, s), 5.14 (2H, s), 7.20-7.23 (2H, m), 7.38-7.46 (2H, m), 7.54 (1H, s).

Example 665

1'-(4-Formylaminobenzyloxycarbonyl)-2,3-dihydro-6-nitrospiro[imidazo[2,1-b]oxazole-2,4'-piperidine]

$^1$H-NMR (DMSO-$d_6$) δppm: 1.85-2.10 (4H, m), 3.15-3.40 (2H, m), 3.65-3.85 (2H, m), 4.16 (2H, s), 5.03 (2H, s), 7.33 (2H, d, J=8.5 Hz), 7.58 (2H, d, J=8.5 Hz), 8.15 (1H, s), 8.27 (1H, s)

Example 667

Preparation of 2,3-dihydro-6-nitrospiro[imidazo[2,1-b]oxazole-2,4'-piperidine]-1'-carboxylic acid phenylamide 2,3-Dihydro-6-nitrospiro[imidazo[2,1-b]oxazole-2,4'-piperidine]trifluoroacetate prepared in Example 655 (100 mg, 0.30 mmol) was suspended in DMF (5 ml). To the suspension, triethylamine (43 μl, 0.31 mmol) and phenylisocyanate (34 μl, 0.31 mmol) were added followed by stirring at room temperature for 30 minutes. To the reaction mixture, water was added followed by stirring, and the precipitates were filtered off. The precipitates were purified by silica gel column chromatography (methylene chloride/methanol=100/1) and recrystallized from ethyl acetate, filtered off to afford 2,3-dihydro-6-nitrospiro[imidazo[2,1-b]oxazole-2,4'-piperidine]-1'-carboxylic acid phenylamide (90 mg, yield 88%) as a white powder.

MS; 343($M^+$) Melting point 229-232° C. (decomposition)

Using pyridine 4-isocyanate or benzyl isocyanate gave compounds of Examples 668 and 669 in the same manner as in Example 667.

Example 668

2,3-Dihydro-6-nitrospiro[imidazo[2,1-b]oxazole-2,4'-piperidine]-1'-carboxylic acid 4-pyridinamide Melting point 217-219° C.

Example 669

2,3-Dihydro-6-nitrospiro[imidazo[2,1-b]oxazole-2,4'-piperidine]-1'-carboxylic acid benzylamide Melting point 244-247° C. (decomposition).

Example 670

Preparation of tert-butyl 4-(2,3-dihydro-6-nitrospiro[imidazo[2,1-b]oxazole-2,4'-piperidine]-1'-ylcarbonyl)piperazine-1-carboxylate Triphosgene (227 mg, 0.77 mmol) was dissolved in toluene (10 ml). To the solution, tert-butyl piperazine-1-carboxylate (425 mg, 2.28 mmol) and diisopropylethylamine (0.4 ml, 2.28 mmol) were added followed by stirring for 1 hour with cooling on ice-bath. To the solution, 2,3-dihydro-6-nitrospiro[imidazo[2,1-b]oxazole-2,4'-piperidine]trifluoroacetate prepared in Example 655 (700 mg, 2.07 mmol) was added. The solution was stirred at room temperature for 1 hour and then stirred under reflux for 1 hour. The reaction mixture was poured into water, and the mixture was extracted with ethyl acetate. The organic phase was washed with a saturated saline solution, dried over magnesium sulfate and then filtered. The resulting filtrate was concentrated under reduced pressure. The residue was purified by silica gel column chromatography (methylene chloride/acetone=10/1) and then crystallized from methylene chloride-diisopropyl ether to afford tert-butyl 4-(2,3-dihydro-6-nitrospiro[imidazo[2,1-b]oxazole-2,4'-piperidine]-1'-ylcarbonyl)piperazine-1-carboxylate (342 mg, yield 38%) as a white powder.

Melting point 260.0-265.0° C. (decomposition). $^1$H-NMR (CDCl$_3$) δppm: 1.47 (9H, s), 1.90-2.02 (2H, m), 2.10-2.16 (2H, m), 3.23-3.47 (10H, m), 3.60-3.66 (2H, m), 3.96 (2H, s), 7.54 (1H, s).

Using 4-trifluoromethylbenzyl piperazine-1-carboxylate or 1-(4-trifluoromethylbenzyl)piperazine gave compounds of Examples 671 and 672 in the same manner as in Example 670.

Example 671

4-Trifluoromethylbenzyl 4-(2,3-dihydro-6-nitrospiro[imidazo[2,1-b]oxazole-2,4'-piperidin]-1'-ylcarbonyl)piperazine-1-carboxylate Melting point 221-223° C.

Example 672

1-(2,3-Dihydro-6-nitrospiro[imidazo[2,1-b]oxazole-2,4'-piperidin]-1'-ylcarbonyl)-4-(4-trifluoromethylbenzyl)piperazine Melting point 226-230° C. (decomposition)

Example 673

Preparation of 2,3-dihydro-6-nitrospiro[imidazo[2,1-b]oxazole-2,4'-piperidin]-1'-carboxylic acid 4-(dimethylamino)phenylamide 2,3-Dihydro-6-nitrospiro[imidazo[2,1-b]oxazole-2,4'-piperidine]trifluoroacetate prepared in Example 655 (200 mg, 0.59 mmol) was suspended in DMF (5 ml). To the suspension, triethylamine (0.1 ml, 0.72 mmol) was added followed by stirring. To the solution, a mixture of N,N-dimethyl-p-phenylenediamine (132 mg, 0.98 mmol), 1,1'-carbonyldiimidazole (82.7 mg, 1.02 mmol) and DMF (5 ml) stirred at room temperature for 3 hours was added followed by stirring at room temperature for 30 minutes. To the reaction mixture, water was added followed by stirring, and the precipitates were filtered off. The precipitates were purified by silica gel column chromatography (methylene chloride/methanol=100/1) and crystallized from ethyl acetate to afford 2,3-dihydro-6-nitrospiro[imidazo[2,1-b]oxazole-2,4'-piperidine]-1'-carboxylic acid 4-(dimethylamino)phenylamide (181 mg, yield 79%) as a white powder.

MS 386($M^+$) Melting point 244-247° C. (decomposition)

Using 4-trifluoromethylbenzylamine or 4-trifluoromethoxybenzylamine gave compounds of Examples 674 and 675 in the same manner as in Example 673.

Example 674

2,3-Dihydro-6-nitrospiro[imidazo[2,1-b]oxazole-2,4'-piperidine]-1'-carboxylic acid 4-trifluoromethylbenzylamide Melting point 215-217° C.

Example 675

2,3-Dihydro-6-nitrospiro[imidazo[2,1-b]oxazole-2,4'-piperidine]-1'-carboxylic acid 4-trifluoromethoxybenzylamide Melting point 223-225° C.

Example 676

Preparation of 2,3-dihydro-6-nitrospiro[imidazo[2,1-b]oxazole-2,4'-piperidine]-1'-carbothioic acid 4-chlorophenylamide 2,3-Dihydro-6-nitrospiro[imidazo[2,1-b]oxazole-2,4'-piperidine]trifluoroacetate prepared in Example 655 (200 mg, 0.59 mmol) was suspended in DMF (5 ml). To the suspension, triethylamine (0.24 ml, 1.77 mmol) and 4-chlorophenyl isothiocyanate(200 mg, 1.18 mmol) were added followed by stirring at room temperature for 30 minutes. To the reaction mixture, water was added followed by stirring, and the precipitates were filtered off, purified by silica gel column chromatography (methylene chloride/methanol=100/1) and crystallized from methylene chloride-diisopropyl ether to afford 2,3-dihydro-6-nitrospiro[imidazo[2,1-b]oxazole-2,4'-piperidine]-1'-carbothioic acid 4-chlorophenylamide (222 mg, yield 87%) as a white powder.

$^1$H-NMR (DMSO-$d_6$) δppm: 2.02-2.19 (4H, m), 3.59-3.69 (2H, m), 4.19 (2H, s), 4.40-4.54 (2H, m), 7.30-7.37 (4H, m), 8.18 (1H, s), 9.48 (1H, s).

Example 677

Preparation of 4-[(2,3-dihydro-6-nitrospiro[imidazo-[2,1-b]oxazole-2,4'-piperidin])-1'-ylcarbonyl]aminobenzoic acid Tert-butyl 4-[(2,3-dihydro-6-nitrospiro[imidazo[2,1-b]oxazole-2,4'-piperidin])-1'-ylcarbonyl]aminobenzoate (150 mg, 0.68 mmol) was dissolved in methylene chloride (1 ml). To the solution, trifluoroacetic acid (5 ml) was added followed by stirring at room temperature overnight. The reaction mixture was concentrated under reduced pressure. The residue was crystallized from methanolethyl acetate to afford 4-[(2,3-dihydro-6-nitrospiro[imidazo[2,1-b]oxazole-2,4'-piperidin])-1'-ylcarbonyl]aminobenzoic acid (59 mg, yield 45%) as a white powder.

Melting point>300° C. $^1$H-NMR (DMSO-$d_6$) δppm: 1.92-2.12 (4H, m), 3.32-3.39 (2H, m), 3.86-3.95 (2H, m), 4.17 (2H, s), 7.45 (2H, d, J=8.8 Hz), 7.82 (2H, d, J=8.8 Hz), 8.17 (1H, s), 8.97 (1H, s), 12.54 (1H, s).

Example 678

Preparation of 2-[(2,3-dihydro-6-nitrospiro[imidazo-[2,1-b]oxazole-2,4'-piperidin])-1'-yl]benzothiazole 2,3-Dihydro-6-nitrospiro[imidazo[2,1-b]oxazole-2,4'-piperidine]trifluoroacetate prepared in Example 655 (84 mg, 0.25 mmol) was suspended in DMF (3 ml). To the suspension, triethylamine (76 μl, 0.55 mmol) and 2-chlorobenzothiazole (40 μl, 0.30 mmol) were added followed by stirring at 80° C. for 1 hour. The reaction mixture was concentrated under reduced pressure. To the residue, water was added, and the precipitate was filtered off, crystallized from methylene chloride-methanol to afford 2-[(2,3-dihydro-6-nitrospiro[imidazo[2,1-b]oxazole-2,4'-piperidine])-1'-yl]benzothiazole (55 mg, yield 62%) as a white powder.

MS; 357($M^+$) $^1$H-NMR (DMSO-$d_6$) δppm: 2.05-2.23 (4H, m), 3.52-3.63 (2H, m), 3.89-3.97 (2H, m), 4.18 (2H, s), 7.05-7.12 (1H, m), 7.26-7.32 (1H, m), 7.46-7.49 (1H, m), 7.76-7.80 (1H, m), 8.18 (1H, s).

Using 5-chloro-1-phenyl-1H-tetrazole gave the compound of Example 679 in the same manner as in Example 678.

Example 679

5-[(2,3-Dihydro-6-nitrospiro[imidazo[2,1-b]oxazole-2,4'-piperidin])-1'-yl]-1-phenyl-1H-tetrazole $^1$H-NMR (DMSO-$d_6$) δppm: 2.05-2.09. (4H, m), 3.24-3.40 (4H, m), 4.14 (2H, s), 7.59-7.72 (5H, m), 8.15 (1H, s).

Example 680

Preparation of tert-butyl 4-[(2,3-dihydro-6-nitrospiro[imidazo[2,1-b]oxazole-2,4'-piperidin])-1'-ylacetyl]piperazine-1-carboxylate 2,3-Dihydro-6-nitrospiro[imidazo[2,1-b]oxazole-2,4'-piperidine]trifluoroacetate prepared in Example 655 (700 mg, 2.07 mmol) was suspended in DMF (20 ml). To the suspension, tert-butyl 4-(chloroacetyl)piperazine-1-carboxylate (599 mg, 2.28 mmol), N,N-diisopropylethylamine (0.8 ml, 4.57 mmol) and sodium iodide (310 mg, 2.07 mmol) were added followed by stirring at 100° C. for 3 hours. The reaction mixture was allowed to return to room temperature. To the solution, ethyl acetate and water were added followed by stirring vigorously. The precipitates were filtered off, washed with water and ethyl acetate, and then dried under reduced pressure to afford tert-butyl 4-[(2,3-dihydro-6-nitrospiro[imidazo[2,1-b]oxazole-2,4'-piperidin])-1'-ylacetyl]piperazine-1-carboxylate (688 mg, yield 74%) as a white powder.

Melting point >300° C. $^1$H-NMR (DMSO-$d_6$) δppm: 1.41 (9H, s), 1.95-2.01 (4H, m), 2.43-2.64 (4H, m), 3.21 (2H, s), 3.26-3.42 (6H, m), 3.50-3.52 (2H, m), 4.12 (2H, s), 8.14 (1H, s).

Using 2-chloro-N-(4-trifluoromethylphenyl)-acetamide or 3-(3-chloropropyl)-3H-benzoxazol-2-one gave compounds of Examples 681 and 682 in the same manner as in Example 680.

Example 681

(2,3-Dihydro-6-nitrospiro[imidazo[2,1-b]oxazole-2,4'-piperidin])-1'-ylacetic acid (4-trifluoromethylphenyl)-amide Melting point 273-275° C. (decomposition).

Example 682

3-[3-(2,3-Dihydro-6-nitrospiro(imidazo[2,1-b]oxazole-2,4'-piperidin])-1'-yl]propyl-3H-benzoxazol-2-one Melting point 190-192° C.

Example 683

Preparation of tert-butyl 4-[2-(2,3-dihydro-6-nitrospiro[imidazo[2,1-b]oxazole-2,4'-piperidin])-1'-ylethyl]piperazine-1-carboxylate 2,3-Dihydro-6-nitrospiro[imidazo[2,1-b]oxazole-2,4'-piperidine]trifluoroacetate prepared in Example 655 (200 mg, 0.59 mmol) was suspended in DMF (5 ml). To the suspension, tert-butyl 4-(2-chloroethyl)piperazine-1-carboxylate (150 mg, 0.60 mmol), triethylamine (0.25 ml, 1.79 mmol) and sodium iodide (108 mg, 0.72 mmol) were added followed by stirring at 50° C. for 5 hours. The reaction mixture was allowed to return to room temperature. To the solution, ethyl acetate and water were added followed by stirring vigorously. The precipitates were filtered off, washed with water and ethyl acetate, and then dried under reduced pressure to afford tert-butyl 4-[2-(2,3-dihydro-6-nitrospiro[imidazo[2,1-b]oxazole-2,4'-piperidin])-1'-ylethyl]piperazine-1-carboxylate (80 mg, yield 31%) as a white powder.
Melting point 214-215° C.

Example 684

Preparation of 4-trifluromethylbenzyl 4-[2-(2,3-dihydro-6-nitrospiro[imidazo[2,1-b]oxazole-2,4'-piperidin]-1'-yl)-2-oxoethyl]piperazine-1-carboxylate Tert-butyl 4-[2-(2,3-dihydro-6-nitrospiro[imidazo[2,1-b]oxazol-2,4'-piperidin]-1'-yl)-2-oxoethyl]piperazine-1-carboxylate prepared in Example 653 (300 mg, 0.67 mmol) was dissolved in methylene chloride (5 ml) To the solution, trifluoroacetic acid (5 ml) was added followed by stirring at room temperature for 6 hours. The reaction mixture was concentrated under reduced pressure. To the residue, methylene chloride (1 ml) and triethylamine (1 ml) were added. The reaction mixture was stirred at room temperature for 5 minutes and concentrated under reduced pressure, and the residue was dissolved in DMF (15 ml). To the solution, a mixture of 4-trifluoromethylbenzyl alcohol (293 mg, 1.67 mmol), 1,1'-carbonyldiimidazole (270 mg, 1.67 mmol) and DMF (5 ml) stirred at room temperature for 3 hours was added followed by stirring at room temperature overnight. The reaction mixture was poured into water and extracted with ethyl acetate, and the organic phase was washed with a saturated saline solution and dried over magnesium sulfate. After filtration, the resulting filtrate was concentrated under reduced pressure. The residue was purified by silica gel column chromatography (methylene chloride/methanol=200/1) and crystallized from methylene chloride-isopropyl ether to afford 4-trifluromethylbenzyl 4-[2-(2,3-dihydro-6-nitrospiro[imidazo[2,1-b]oxazole-2,4'-piperidin]-1'-yl)-2-oxoethyl]piperazine-1-carboxylate (324 mg, yield 88%) as a light pink powder.
MS 553(M+H)$^+$ Melting point 139.0-141.0° C.

Using corresponding starting materials gave the compound of Example 685 in the same manner as in Example 684.

Example 685

4-Trifluoromethoxybenzyl 4-[2-(2,3-dihydro-6-nitrospiro[imidazo[2,1-b]oxazole-2,4'-piperidin]-1'-yl)-2-oxoethyl]piperazine-1-carboxylate Melting point 137-139° C.
Using tert-butyl 4-[2-(2,3-dihydro-6-nitrospiro[imidazo[2,1-b]oxazole-2,4'-piperidin])-1'-ylethyl]piperazine-1-carboxylate prepared in Example 683 gave compounds of Examples 686 to 689 in the same manner as in Example 684.

Example 686

4-Chlorobenzyl 4-[2-(2,3-dihydro-6-nitrospiro[imidazo-[2,1-b]oxazole-2,4'-piperidin])-1'-ylethyl]piperazine-1-carboxylate Melting point 178-179° C.

Example 687

4-Trifluoromethylbenzyl 4-[2-(2,3-dihydro-6-nitrospiro[imidazo[2,1-b]oxazole-2,4'-piperidin])-1'-ylethyl]piperazine-1-carboxylate Melting point 174-175° C.

Example 688

4-Trifluoromethoxybenzyl 4-[2-(2,3-dihydro-6-nitrospiro[imidazo[2,1-b]oxazole-2,4'-piperidin])-1'-ylethyl]piperazine-1-carboxylate Melting point 176-177° C.

Example 689

Biphenyl-4-ylmethyl 4-[2-(2,3-dihydro-6-nitrospiro[imidazo[2,1-b]oxazole-2,4'-piperidin])-1'-ylethyl]piperazine-1-carboxylate $^1$H-NMR (CDCl$_3$) δppm: 1.90-2.05 (2H, m), 2.15-2.20 (2H, m), 2.40-2.80 (12H, m), 3.45-3.60 (4H, m), 3.99 (2H, s), 5.17 (2H, s), 7.31-7.62 (10H, m).
Using tert-butyl 4-[(2,3-dihydro-6-nitrospiro[imidazo[2,1-b]oxazole-2,4'-piperidin]-1'-ylacetyl)piperazine-1-carboxylate prepared in Example 680 gave the compound of Example 690 in the same manner as in Example 684.

Example 690

4-Trifluoromethylbenzyl 4-(2,3-dihydro-6-nitrospiro[imidazo[2,1-b]oxazole-2,4'-piperidin])-1'-ylacetyl]piperazine-1-carboxylate Melting point 137-139° C.

Example 691

Preparation of 1-(2,3-dihydro-6-nitrospiro[imidazo[2,1-b]oxazole-2,4'-piperidin])-1'-yl)-2-[4-(4-trifluoro-methylbenzyl)piperazin-1-yl]ethanone Tert-butyl 4-[2-(2,3-dihydro-6-nitrospiro[imidazo[2,1-b]oxazole-2,4'-piperidine]-1'-yl)-2-oxoethyl]piperazine-1-carboxylate prepared in Example 653 (300 mg, 0.67 mmol) was dissolved in methylene chloride (5 ml). To the solution, trifluoroacetic acid (10 ml) was added followed by stirring at room temperature for 6 hours. The reaction mixture was concentrated under reduced pressure. To the solution, methylene chloride (1 ml) and triethylamine (1 ml) were added followed by stirring at room temperature for 5 minutes. The solution was concentrated under reduced pressure and the residue was dissolved in methanol (10 ml). To the solution, 4-trifluoromethylbenzaldehyde (0.23 ml, 1.67 mmol), sodium cyanotrihydroborate (105 mg, 1.67 mmol) and acetic acid (0.1 ml) were added with cooling on ice-bath followed by stirring at room temperature overnight. To the solution, a saturated aqueous sodium hydrogencarbonate solution and methylene chloride were added followed by stirring. The organic phase was dried over magnesium sulfate and then filtered. The resulting filtrate was concentrated under reduced pressure. The residue was purified by silica gel column chromatography (methylene chloride/methanol=50/1) and crystallized from methylene chloride-diisopropyl ether to afford 1-(2,3-dihydro-6-nitrospiro[imidazo[2,1-b]

oxazole-2,4'-piperidin])-1'-yl)-2-[4-(4-trifluoromethylbenzyl)piperazin-1-yl]ethanone (226 mg, yield 67%) as a white powder.

MS 508(M)⁺ Melting point 145-147° C.

Using corresponding starting materials gave the compound of Example 692 in the same manner as in Example 691.

Example 692

1-(2,3-Dihydro-6-nitrospiro[imidazo[2,1-b]oxazole-2,4'-piperidin]-1'-yl)-2-[(4-phenylbenzyl)piperazin-1-yl]ethanone Melting point 187-188° C.

Using tert-butyl 4-(2,3-dihydro-6-nitrospiro[imidazo[2,1-b]oxazole-2,4'-piperidin]-1'-ylacetyl)piperazine-1-carboxylate prepared in Example 680 gave compounds of Examples 693 and 694 in the same manner as in Example 691.

Example 693

1-(2,3-Dihydro-6-nitrospiro[imidazo[2,1-b]oxazole-2,4'-piperidin]-1'-ylacetyl)-4-(4-trifluoromethyl-benzyl)piperazine Melting point 195-197° C. (decomposition)

Example 694

1-(2,3-Dihydro-6-nitrospiro[imidazo[2,1-b]oxazole-2,41-piperidin]-1'-ylacetyl)-4-(4-phenylbenzyl)piperazine Melting point 226-227° C. (decomposition).

Example 695

Preparation of 4-[(2,3-dihydro-6-nitrospiro[imidazo-[2,1-b]oxazole-2,4'-piperidin]-1'-yl)-2-oxoethyl]-piperazine-1-carboxylic acid (4-trifluoromethylphenyl)amide Tert-butyl 4-[2-(2,3-dihydro-6-nitrospiro[imidazo[2,1-b]oxazole-2,4'-piperidine]-1'-yl)-2-oxoethyl]piperazine-1-carboxylate prepared in Example 653 (300 mg, 0.67 mmol) was dissolved in methylene chloride (5 ml). To the solution, trifluoroacetic acid (10 ml) was added followed by stirring at room temperature for 4 hours. The reaction mixture was concentrated under reduced pressure. To the solution, methylene chloride (1 ml) and triethylamine (1 ml) were added followed by stirring at room temperature for 5 minutes. The solution was concentrated under reduced pressure, and the residue was dissolved in DMF (10 ml). To the solution, a mixture of 4-aminobenzotrifluoride (0.17 ml, 1.33 mmol) and 1,1'-carbonyldiimidazole (220 mg, 1.33 mmol) and DMF (5 ml) stirred at room temperature for 3 hours was added followed by stirring at room temperature for 2 hours. The reaction mixture was poured into water and extracted with ethyl acetate, and the organic phase was washed with a saturated saline solution, dried over magnesium sulfate and then filtered. The resulting filtrate was concentrated under reduced pressure, and the residue was purified by silica gel column chromatography (methylene chloride/methanol=200/1) and crystallized from methylene chloride-isopropyl ether to afford 4-[(2,3-dihydro-6-nitrospiro[imidazo[2,1-b]oxazole-2,4'-piperidin]-1'-yl)-2-oxoethyl]piperazine-1-carboxylic acid (4-trifluoromethylphenyl)amide (213 mg, yield 59%) as a white powder.

Melting point 153.0-155.0° C.

Example 696

Preparation of 2-{4-[2-(2,3-dihydro-6-nitrospiro[imidazo[2,1-b]oxazole-2,4'-piperidin]-1'-yl)-2-oxoethyl]piperazin-1-yl}-N-(4-trifluoromethylphenyl)acetamide Tert-butyl 4-[2-(2,3-dihydro-6-nitrospiro[imidazo[2,1-b]oxazol-2,4'-piperidin]-1'-yl)-2-oxoethyl]piperazine-1-carboxylate prepared in Example 653 (300 mg, 0.67 mmol) was dissolved in methylene chloride (5 ml). To the solution, trifluoroacetic acid (10 ml) was added followed by stirring at room temperature for 6 hours. The reaction mixture was concentrated under reduced pressure. To the residue, methylene chloride (1 ml) and triethylamine (1 ml) were added followed by stirring at room temperature for 5 minutes, and then the solution was concentrated under reduced pressure. The residue was dissolved in DMF (10 ml). To the solution, 2-bromo-N-(4-trifluoromethylphenyl)acetamide (207 mg, 0.73 mmol) and triethylamine (0.28 ml, 2.0 mmol) were added followed by stirring at 100° C. for 2 hours. The reaction mixture was poured into water and extracted with ethyl acetate. The organic phase was washed with a saturated saline solution, dried over magnesium sulfate and then filtered. The resulting filtrate was concentrated under reduced pressure, and the residue was purified by silica gel column chromatography (methylene chloride/methanol=100/1) and crystallized from methylene chloride-diisopropyl ether to afford 2-{4-[2-(2,3-dihydro-6-nitrospiro[imidazo[2,1-b]oxazole-2,4'-piperidin]-1'-yl)-2-oxoethyl]piperazin-1-yl}-N-[4-trifluoromethylphenyl]acetamide (275 mg, yield 75%) as a white powder.

MS 552(M+1)⁺ Melting point 133.0-135.0° C.

Example 697

Preparation of 2-[4-(benzoxazol-2-yl)piperazin-1-yl]-1-(2,3-dihydro-6-nitrospiro[imidazo[2,1-b]oxazole-2,41-piperidin]-1'-yl)ethanone Tert-butyl 4-[2-(2,3-dihydro-6-nitrospiro[imidazo[2,1-b]oxazole-2,4'-piperidine]-1'-yl)-2-oxoethyl]piperazine-1-carboxylate prepared in Example 653 (227 mg, 0.50 mmol) was dissolved in methylene chloride (5 ml). To the solution, trifluoroacetic acid (5 ml) was added followed by stirring at room temperature for 4 hours. The reaction mixture was concentrated under reduced pressure. To the residue, methylene chloride (1 ml) and triethylamine (1 ml) were added followed by stirring at room temperature for 5 minutes, and then the solution was concentrated under reduced pressure. The residue was dissolved in DMF (5 ml). To the solution, triethylamine (0.21 ml, 1.52 mmol) and 2-chlorobenzoxazole (86 μl, 0.76 mmol) were added followed by stirring at 80° C. for 2 hours. To the reaction mixture, water was added, and the mixture was extracted with methylene chloride. The organic phase was dried over magnesium sulfate and then filtered. The resulting filtrate was concentrated under reduced pressure. The residue was crystallized from methylene chloride-ethyl acetate to afford 2-[4-(benzoxazol-2-yl)piperazin-1-yl]-1-(2,3-dihydro-6-nitrospiro[imidazo[2,1-b]oxazole-2,4'-piperidin]-1'-yl)ethanone (99 mg, 42%) as a light yellow powder.

MS 467(M⁺) Melting point 260.0-263.0° C. (decomposition).

Compounds gave from appropriate starting materials in the same manner as in the above Examples 1 to 697 are shown in the following tables 26 to 77.

TABLE 26

| Example | R1 | R2 | R3 | R4 | R5 | R6 | R7 | mp(° C.) | |
|---|---|---|---|---|---|---|---|---|---|
| 698 | —H | —H | —H | —H | —CH$_3$ | —H | —H | 193-195 | |
| 699 | —H | —H | —H | —H | —CO$_2$C$_2$H$_5$ | —H | —H | 195-197.5 | |
| 700 | —H | —H | —H | —H | —OCH$_3$ | —H | —H | 189-190 | |
| 701 | —H | —H | —H | —H | —Cl | —Cl | —H | 182-183 | |
| 702 | —H | —H | —H | —H | —H | —H | —H | 185-186 | |
| 703 | —CH$_3$ | —H | —H | —H | —OCH$_3$ | —H | —H | 177.5-179 | |
| 704 | —CH$_3$ | —H | —H | —H | —F | —H | —H | 194-196 | |
| 705 | —CH$_3$ | —H | —H | —H | —CH$_3$ | —H | —H | 145-147 | |
| 706 | —CH$_3$ | —H | —H | —H | —H | —Cl | —H | 190.5-192 | |
| 707 | —CH$_3$ | —H | —H | —H | —H | —H | —Cl | 163-164 | |
| 708 | —CH$_3$ | —H | —H | —H | —H | —H | —OCH$_3$ | 177-180 | |
| 709 | —CH$_3$ | —H | —H | —H | —H | —CF$_3$ | —H | 182-183.5 | |
| 710 | —CH$_3$ | —H | —H | —OCH$_3$ | —OCH$_3$ | —OCH$_3$ | —H | 179-182 | |
| 711 | —CH$_3$ | —H | —H | —H | —H | —H | —F | 142-144 | |
| 712 | —CH$_3$ | —H | —H | —H | —Br | —H | —H | 197-199 | |
| 713 | —CH$_3$ | —H | —H | —H | —CONH$_2$ | —H | —H | 234-235 | dec |
| 714 | —CH$_3$ | —H | —H | —H | —CO$_2$C$_2$H$_5$ | —H | —H | 151-152 | |
| 715 | —CH$_3$ | —H | —H | —H | —COCH$_3$ | —H | —H | 196-199 | |
| 716 | —CH$_3$ | —H | —H | —H | —SO$_2$NH$_2$ | —H | —H | 218-220 | dec |
| 717 | —CH$_3$ | —H | —H | —H | —H | —CO$_2$C$_2$H$_5$ | —H | 112-114 | |
| 718 | —CH$_3$ | —H | —H | —H | —H | —H | —CO$_2$C$_2$H$_5$ | 132-134 | |
| 719 | —CH$_3$ | —CH$_3$ | —H | —H | —Br | —H | —H | 132-133 | |
| 720 | —CH$_3$ | —H | —H | —H | —CF$_3$ | —H | —H | 198.5-200 | |
| 721 | —CH$_3$ | —H | —H | —H | —OCF$_3$ | —H | —H | 163.5-164.8 | |
| 722 | —CH$_3$ | —CH$_3$ | —H | —H | —CF$_3$ | —H | —H | 129-130 | |
| 723 | —CH$_3$ | —CH$_3$ | —H | —H | —OCF$_3$ | —H | —H | 138-140 | |
| 724 | —CH$_3$ | —H | —H | —H | Morpholino- | —H | —H | 223-225 | |
| 725 | —CH$_3$ | —H | —H | —H | Morpholino- | —H | —H | 134-135 | |
| 726 | —CH$_3$ | —H | —H | —H | C$_6$H$_{13}$NHCO— | —H | —H | 197-198 | |

TABLE 27

| Example | n | R1 | R2 | mp (° C.) or 1H NMR |
|---|---|---|---|---|
| 727 | 1 | —H | —CH$_2$Ph | 143.5-145 |
| 728 | 1 | —H | -cyclo-C$_6$H$_{11}$ | 187-188.5 |
| 729 | 1 | —CH$_3$ | —CH$_2$Ph | 141-142 |
| 730 | 1 | —CH$_3$ | —(CH$_2$)$_2$Ph | 124-127 |
| 731 | 1 | —CH$_3$ | -cyclo-C$_6$H$_{11}$ | 176-178 |
| 732 | 1 | —CH$_3$ | -4-PYRIDYL | 151-153 (dec) |
| 733 | 1 | —CH$_3$ | —CH(CH$_3$)$_2$ | 163-165 |
| 734 | 1 | —CH$_3$ | —CH$_2$CO$_2$C$_2$H$_5$ | 142-143 |
| 735 | 1 | —CH$_3$ | —C$_6$H$_{13}$ | 129-130 |
| 736 | 1 | —CH$_3$ | —(CH$_2$)$_2$CO$_2$C$_2$H$_5$ | 94-96 |
| 737 | 1 | —CH$_3$ | —CH$_2$CH$_2$Cl | DMSO-d$_6$, 1.59(3H, s), 3.22-3.33(2H, m), 3.57(2H, t, J=6.0Hz), 4.07(2H, dd, J=11.1Hz, 27.6Hz), 4.27(2H, dd, J=7.6Hz, 9.9Hz), 6.47-6.59(1H, m), 8.13(1H, s) |
| 738 | 1 | —H | —C$_8$H$_{17}$ | DMSO-d6, 0.85(3H, t, J=6.9Hz), 1.00-1.45(12H, m), 2.90-2.98(2H, m), 4.06(1H, |

TABLE 27-continued

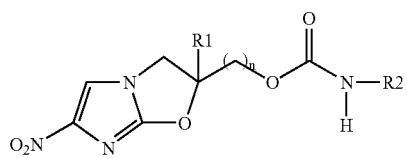

| Example | n | R1 | R2 | mp (° C.) or 1H NMR |
|---|---|---|---|---|
| | | | | dd, J=6.8Hz, 10.8Hz), 4.25-4.46(3H, m), |
| | | | | 5.48-5.66(1H, m), 7.28(1H, t, J=5.6Hz), |
| | | | | 8.13(1H, s) |
| 739 | 2 | —H | $C_8H_{17}$— | 86-88 |
| 740 | 2 | —$CH_3$ | Ph— | 131-133 |
| 741 | 2 | —$CH_3$ | $PhCH_2$— | 127-127.5 |
| 742 | 2 | —$CH_3$ | $PhCH_2CH_2$— | 124-125 |

TABLE 28

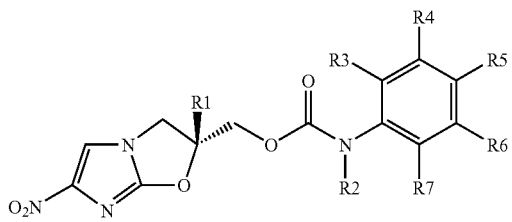

| Example | R1 | R2 | R3 | R4 | R5 | R6 | R7 | mp (° C.) |
|---|---|---|---|---|---|---|---|---|
| 743 | —$CH_3$ | —$CH_3$ | —H | —H | —H | —Cl | —H | 103-104 |
| 744 | —$CH_3$ | —$CH_2Ph$ | —H | —H | —Cl | —H | —H | 168-169 |
| 745 | —$CH_3$ | —$C_6H_{13}$ | —H | —H | —Cl | —H | —H | 98-100 |
| 746 | —$CH_3$ | —$CH_3$ | —H | —H | —Br | —H | —H | 147-150 |
| 747 | —$CH_3$ | —$CH_3$ | —H | —H | —$CF_3$ | —H | —H | 140-141 |
| 748 | —$CH_3$ | —$CH_3$ | —H | —H | —F | —H | —H | 111-113 |
| 749 | —$CH_3$ | —$C_4H_9$ | —H | —H | —Cl | —H | —H | 114-116 |
| 750 | —$CH_3$ | —$C_2H_5$ | —H | —H | —Cl | —H | —H | 87-89 |
| 751 | —$CH_3$ | —$CH_2CH(CH_3)_2$ | —H | —H | —Cl | —H | —H | 161-165 |
| 752 | —$CH_3$ | 4-$ClPhCH_2$— | —H | —H | —Cl | —H | —H | 175-178 |

TABLE 29

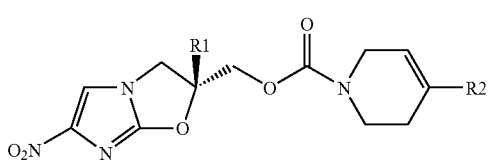

| Example | R1 | R2 | mp (° C.) |
|---|---|---|---|
| 753 | —$CH_3$ | 4-$CF_3$OPh— | 165-166 |
| 754 | —$CH_3$ | 4-$CH_3$OPh— | 155-157 |
| 755 | —$CH_3$ | 4-ClPh— | 157-158 |
| 756 | —$CH_3$ | 3-$CF_3$Ph— | 100-101 |
| 757 | —$CH_3$ | 4-BrPh— | 168-170 |
| 758 | —$CH_3$ | 4-FPh— | 151-154 |

TABLE 30

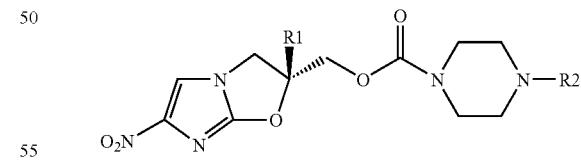

| Example | R1 | R2 | mp (° C.) |
|---|---|---|---|
| 759 | —$CH_3$ | 4-$CF_3$Ph— | 151-153 |
| 760 | —$CH_3$ | 4-ClPh— | 143-144 |
| 761 | —$CH_3$ | 3-ClPh— | 136-138 |
| 762 | —$CH_3$ | 3,4-$Cl_2$Ph— | 142-143 |
| 763 | —$CH_3$ | 4-$CH_3$OPh— | 163-164 |
| 764 | —$CH_3$ | 3-$CF_3$Ph— | 105-107 |
| 765 | —$CH_3$ | 4-FPh— | 139-140 |
| 766 | —$CH_3$ | 4-$CF_3$OPhCH$_2$OCO— | 166-167 |
| 767 | —$CH_3$ | 4-$CF_3$PhCH=CHCH$_2$OCO— | 186-188 |
| 768 | —$CH_3$ | 4-$CF_3$PhCH$_2$— | 205-206 |
| 769 | —$CH_3$ | 4-$CF_3$OPhCH$_2$— | 133-134 |

TABLE 31

[Structure: imidazo-oxazole with O₂N, R1, and CH₂-O-phenyl-piperazine-R2]

| Example | R1 | R2 | mp (° C.) or 1H NMR |
|---------|-----|-----|---------------------|
| 770 | —CH₃ | 4-ClPh— | 228.8-232.2 |
| 771 | —CH₃ | 4-CF₃OPh— | 236.2-237.4 |
| 772 | —CH₃ | 4-CF₃OPhCH₂— | CDCl₃; 1.76(3H, s), 3.03(4H, br), 3.62-3.67(4H, m), 4.01(1H, d, J=10.2Hz), 4.04(1H, d, J=10.2Hz), 4.18(1H, d, J=10.2Hz), 4.48(1H, d, J=10.2Hz), 5.15(2H, s), 6.76-6.80(2H, m), 6.85-6.89(2H, m), 7.19-7.23(2H, m), 7.38-7.42(2H, m), 7.54(1H, s) |
| 773 | —CH₃ | 4-ClPhCH₂— | 174.2-175 |
| 774 | —CH₃ | 4-CF₃OPhCH₂OCO— | 155.5-156.5 |
| 775 | —CH₃ | 4-CF₃PhCH=CHCH₂OCO— | 155-159.8 |

TABLE 32

[Structure: imidazo-oxazole with O₂N, R1, and CH₂-O-phenyl with R2,R3,R4,R5,R6]

| Example | R1 | R2 | R3 | R4 | R5 | R6 | mp (° C.) |
|---------|-----|-----|-----|-----|-----|-----|-----------|
| 776 | —CH₃ | —H | —H | —H | —H | —H | 151-153.5 |
| 777 | —CH₃ | —H | —H | —I | —H | —H | 220-221 |
| 778 | —CH₃ | —H | —H | —Cl | —H | —H | 185-186.5 |
| 779 | —CH₃ | —H | —H | Morpholino- | —H | —H | 233-240 dec |
| 780 | —CH₃ | —H | —H | Piperidino- | —H | —H | 217-218.5 dec |

TABLE 33

[Structure: imidazo-oxazole with O₂N, R1, and CH₂-O-phenyl(R2,R3)-piperazine-R4]

| Example | R1 | R2 | R3 | R4 | mp (° C.) or 1H NMR |
|---------|-----|-----|-----|-----|---------------------|
| 781 | —CH₃ | —H | —H | —CH₃ | 230-231.5 dec |
| 782 | —CH₃ | —H | —Cl | —CH₃ | 201-204.5 dec |
| 783 | —CH₃ | —H | —H | 4-CF₃Ph— | 258-259 dec |
| 784 | —CH₃ | —H | —H | 4-ClPhCH₂— | 207-208.4 |
| 785 | —CH₃ | —H | —H | 4-ClPh— | 251-257 dec |
| 786 | —CH₃ | —H | —H | CH₃CO— | 206-207.5 |
| 787 | —CH₃ | —H | —Cl | C₂H₅OCO— | 168.5-171 |
| 788 | —CH₃ | —Cl | —H | t-BuOCO— | 192-194.5 |
| 789 | —CH₃ | —Cl | —H | C₂H₅OCO— | 178.5-180.5 |
| 790 | —CH₃ | —Cl | —Cl | t-BuOCO— | 233-233.5 dec |
| 791 | —CH₃ | —Cl | —Cl | C₂H₅OCO— | 224.2-225.7 |
| 792 | —CH₃ | —H | —H | —CO₂CH₂CF₃ | 213-216 |
| 793 | —CH₃ | —H | —H | —CO₂C₄H₉ | 197.5-199 |
| 794 | —CH₃ | —H | —H | —CO₂(CH₂)₇CH₃ | 198-201 |

TABLE 33-continued

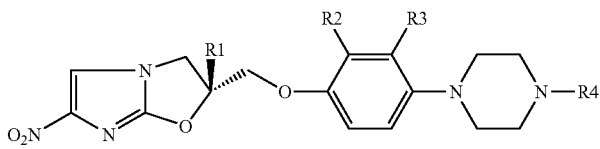

| Example | R1 | R2 | R3 | R4 | mp (° C.) or 1H NMR |
|---|---|---|---|---|---|
| 795 | —CH₃ | —H | —H | —CO₂(CH₂)₂OCH₃ | 176-179 |
| 796 | —CH₃ | —H | —Cl | 4-CF₃OPhCH₂OCO— | 153-155 |
| 797 | —CH₃ | —Cl | —H | 4-CF₃OPhCH₂OCO— | 176-176.8 |
| 798 | —CH₃ | —Cl | —Cl | 4-CF₃OPhCH₂OCO— | 196.5-197.5 |
| 799 | —CH₃ | —H | —H | 4-CF₃OPhCH2OCO— | 187-189 |
| 800 | —CH₃ | —H | —H | 4-CF₃PhCH₂OCO— | 180.5-182.5 |
| 801 | —CH₃ | —H | —H | 4-CF₃PhCH=CHCH₂OCO— | 185-187 |
| 802 | —CH₃ | —H | —H | 3,4-Cl₂PhCH₂OCO— | 171-171.5 |
| 803 | —CH₃ | —H | —H | 4-CF₃OPhNHCO— | 228-232 dec |
| 804 | —CH₃ | —H | —H | —CO₂(CH₂)₂N(CH₃)₂ | CDCl₃: 1.76(3H, s), 2.30(6H, s), 2.61(2H, t, J=5.8Hz), 2.99-3.04(4H, m), 3.60-3.64(4H, m), 4.03(1H, d, J=10.2Hz), 4.04(1H, d, J=10.1Hz), 4.18(1H, d, J=10.1Hz), 4.22(2H, t, J=5.8Hz), 4.49(1H, d, J=10.2Hz), 6.76-6.81(2H, m), 6.83-6.89(2H, m), 7.55(1H, s) |

TABLE 34

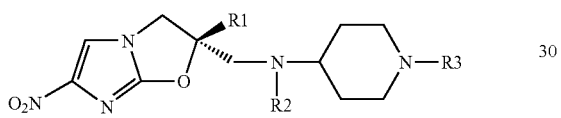

| Example | R1 | R2 | R3 | mp (° C.) |
|---|---|---|---|---|
| 805 | —CH₃ | —CH₃ | 4-CF₃OPh— | 127.2-129.7 |
| 806 | —CH₃ | —CH₃ | 4-CF₃Ph— | 131.5-133.6 |
| 807 | —CH₃ | —CH₃ | 4-NCPh— | 149-152 |
| 808 | —CH₃ | —CH₃ | 4-CF₃OPhCH₂OCO— | 84.2-86.8 |
| 809 | —CH₃ | —CH₃ | 4-ClPhCH₂OCO— | 116.2-116.6 |

TABLE 35

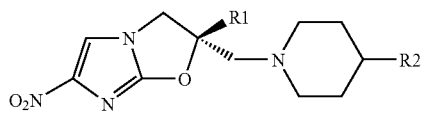

| Example | R1 | R2 | mp (° C.) or 1H NMR |
|---|---|---|---|
| 810 | —CH₃ | —OPh | 153.2-154.8 |
| 811 | —CH₃ | 4-CF₃PhNH— | CDCl₃; 1.16-1.42(2H, m), 1.61(3H, s), 1.87-2.01(2H, m), 2.31-2.60(3H, m), 2.78-3.02(4H, m), 3.24-3.30(1H, m), 3.82(1H, d, J=8.1Hz), 3.91(1H, d, J=9.7Hz), 4.29(1H, d, J=9.7Hz), 6.54(2H, d, J=8.6Hz), 6.98-7.36(2H, d, J=8.6Hz), 7.54(1H, s) |
| 812 | —CH₃ | 4-CF₃Ph— | 130-131.8 |
| 813 | —CH₃ | 4-CF₃PhCH₂— | 117.5-118.5 |
| 814 | —CH₃ | 4-ClPhCH₂— | 146.5-147.5 |
| 815 | —CH₃ | 4-ClPhCO— | 177-179 |
| 816 | —CH₃ | 4-CF₃PhCO— | 98-100 |
| 817 | —CH₃ | 4-CF₃OPhO— | 119.4-120.7 |
| 818 | —CH₃ | 4-ClPhO— | 141-144 |
| 819 | —CH₃ | 3-CF₃PhO— | 89-91.7 |
| 820 | —CH₃ | 4-NCPhO— | 171-174.7 |
| 821 | —CH₃ | 4-FPhO— | 124-128 |
| 822 | —CH₃ | 4-CF₃OPhCH₂O— | 113-115 |
| 823 | —CH₃ | 4-ClPhCH₂O— | 138-140 |

TABLE 35-continued

| Example | R1 | R2 | mp (° C.) or 1H NMR |
|---|---|---|---|
| 824 | —CH₃ | 4-PhPhCH₂O— | 115-116.5 |
| 825 | —CH₃ | PhCH₂CH₂O— | 79-81 |
| 826 | —CH₃ | 4-PyridylCH₂O— | 80.8-83.9 |
| 827 | —CH₃ | 3-PyridylCH₂O— | 77-79 |
| 828 | —CH₃ | 4-CF₃OPhCH₂OCO— | 101-102 |
| 829 | —CH₃ | 4-ClPhNHCO— | 153-155 |
| 830 | —CH₃ | 4-ClPhCH₂NHCO— | 161-164 |
| 831 | —CH₃ | 4-ClPhNH— | 159-161 |
| 832 | —CH₃ | 4-NCPhNH— | 148.5-150 |
| 833 | —CH₃ | 4-ClPhN(CH₃)— | 180.2-181.1 dec |
| 834 | —CH₃ | 4-NCPhN(CH₃)— | 188.5-191 |
| 835 | —CH₃ | 4-CF3PhN(CH₃)— | 161-164 |
| 836 | —CH₃ | (4-ClPh)₂N— | 178.5-180 |

TABLE 36

| Example | R1 | R2 | R3 | R4 | R5 | R6 | mp (° C.) or 1H NMR |
|---|---|---|---|---|---|---|---|
| 837 | —CH₃ | —H | —H | —CH(CH₃)₂ | —H | —H | 158.5-160 |
| 838 | —CH₃ | —H | —Cl | —Cl | —H | —H | 115-117.9 |
| 839 | —CH₃ | —H | —H | —CF₃ | —H | —H | 126-129.2 |
| 840 | —H | —H | —H | —CF₃ | —H | —H | 164-166 |
| 841 | —CH₃ | —H | —H | —OPh | —H | —H | 157-158.2 |
| 842 | —CH₃ | —H | —OCH₃ | —OCH₃ | —OCH₃ | —H | 148-151.9 |
| 843 | —CH₃ | —H | —H | —CO₂CH₃ | —H | —H | 151-152.5 |
| 844 | —CH₃ | —H | —H | -3-PYRIDYL | —H | —H | 140-143.8 |
| 845 | —CH₃ | —H | —Ph | —H | —H | —H | 94.6-96.5 |
| 846 | —CH₃ | —H | —H | -cyclo-C₆H₁₁ | —H | —H | 162-163.9 |
| 847 | —CH₃ | —Ph | —H | —H | —H | —H | 146.8-149 |
| 848 | —CH₃ | —H | —H | —CH=CHPh | —H | —H | 178.5-181.8 |
| 849 | —CH₃ | —H | —CF₃ | —H | —CF₃ | —H | 154-156.2 |
| 850 | —CH₃ | —H | —H | —H | —H | —H | CDCl₃, 1.59(3H, s), 2.34(4H, bs), 2.50-2.59(2H, m), 2.53(1H, d, J=14.8Hz), 2.67-2.76(2H, m), 2.85(1H, d, J=14.8Hz), 3.41(1H, d, J=12.9Hz), 3.47(1H, d, J=12.9Hz), 3.87(1H, d, J=9.6Hz), 4.30(1H, d, J=9.6Hz), 7.23-7.33(5H, m), 7.53(1H, s) |
| 851 | —CH₃ | —H | —H | —N(CH₃)₂ | —H | —H | CDCl₃ 1.58(3H, s), 2.30(4H, br), 2.49-2.57(2H, m), 2.52(1H, d, J=14.9Hz), 2.65-2.73(2H, m), 2.84(1H, d, J=14.9Hz), 2.93(6H, s), 3.34(2H, d, J=3.50Hz), 3.86(1H, d, J=9.6Hz), 4.30(1H, d, J=9.6Hz), 6.67(2H, d, J=8.7Hz), 7.11(2H, d, J=8.7Hz), 7.52(1H, s) |
| 852 | —CH₃ | —H | —H | —OCH₃ | —H | —H | CDCl₃, 1.59(3H, s), 2.31(4H, br), 2.50-2.58(2H, m), 2.53(1H, d, J=14.8Hz), 2.65-2.74(2H, m), 2.84(1H, d, J=14.8Hz), 3.35(1H, d, J=13.0Hz), 3.41(1H, d, J=13.0Hz), 3.79(3H, s), 3.88(1H, d, J=9.7Hz), 4.30(1H, d, J=9.7Hz), 6.83(2H, d, J=8.6Hz), 7.17(2H, d, J=8.6Hz), 7.52(1H, s) |
| 853 | —CH₃ | —H | —H | —CH₂Ph | —H | —H | CDCl₃ 1.61(3H, s), 2.30-2.73(9H, m), 2.84(1H, d, J=14.8Hz), 3.49(2H, s), 3.87(1H, d, J=9.7Hz), |

TABLE 36-continued

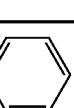

| Example | R1 | R2 | R3 | R4 | R5 | R6 | mp (° C.) or 1H NMR |
|---|---|---|---|---|---|---|---|
| | | | | | | | 3.95(2H, s), 4.30(1H, d, J=9.7Hz), 7.09-7.33(9H, m), 7.52(1H, s) |

TABLE 37

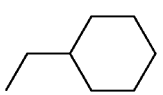

| Example | R1 | R2 | R3 | R4 | R5 | R6 | mp (° C.) or 1H NMR |
|---|---|---|---|---|---|---|---|
| 854 | —CH₃ | —H | —H | —Cl | —H | —H | 176.8-181.3 |
| 855 | —CH₃ | —H | —H | —Cl | —Cl | —H | 111.8-114.8 |
| 856 | —CH₃ | —H | —H | —OCH₃ | —H | —H | 183.3-186.6 |
| 857 | —CH₃ | —H | —H | —H | —H | —Cl | 123.5-125.3 |
| 858 | —CH₃ | —H | —H | —H | —H | —H | CDCl₃; 1.59(3H, s), 2.37(4H, bs), 2.51-2.61(2H, m), 2.54(1H, d, J=14.8Hz), 2.69-2.76(2H, m), 2.86(1H, d, J=14.8Hz), 3.44(1H, d, J=13.1Hz), 3.51(1H, d, J=13.1Hz), 3.88(1H, d, J=9.6Hz), 4.31(1H, d, J=9.6Hz), 7.29-7.36(3H, m), 7.39-7.47(2H, m), 7.51-7.60(4Hm), 7.53(1H, s) |
| 859 | —CH₃ | —H | —H | —CF₃ | —H | —H | CDCl₃; 1.60(3H, s), 2.37-2.75(9H, m), 2.87(1H, d, J=14.9Hz), 3.49(2H, s), 3.88(1H, d, J=9.6Hz), 4.30(1H, d, J=9.6Hz), 7.37(1H, d, J=8.0Hz), 7.53(1H, s), 7.54(1H, d, J=8.0Hz), 7.68(4H, s) |
| 860 | —CH₃ | —H | —H | —OCF₃ | —H | —H | CDCl₃; 1.60(3H, s), 2.38(4H, br), 2.55(1H, d, J=14.9Hz), 2.60(2H, br), 2.71-2.76(2H, m), 2.87(1H, d, J=14.9Hz), 3.50(2H, s), 3.89(1H, d, J=9.7Hz), 4.30(1H, d, J=9.7Hz), 7.27(2H, d, J=6.6Hz), 7.36(2H, d, J=8.1), 7.47-7.52(2H, m), 7.53(1H, s), 7.55-7.61(2H, m) |

TABLE 38

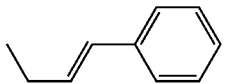

| Example | R1 | R2 | mp (° C.) |
|---|---|---|---|
| 861 | —CH₃ | 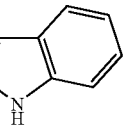 | 134-138.8 |
| 862 | —CH₃ | | 188.6-190.7 |
| 863 | —CH₃ | | 127-131.5 |

TABLE 38-continued

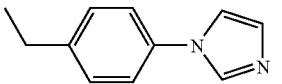

| Example | R1 | R2 | mp (° C.) |
|---|---|---|---|
| 864 | —CH₃ | | 156-158.6 |
| 865 | —CH₃ | | 102.8-104.9 |

TABLE 38-continued
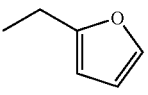
| Example | R1 | R2 | mp (° C.) |
|---|---|---|---|
| 866 | —CH₃ | 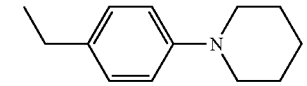 | 129-133 |
| 867 | —CH₃ | 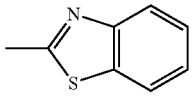 | 164.0-168.5 |
| 868 | —CH₃ | 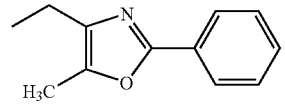 | 221.5-222.3 |
| 869 | —CH₃ | 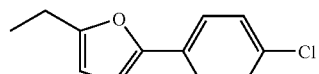 | 158-159.4 |
| 870 | —CH₃ | 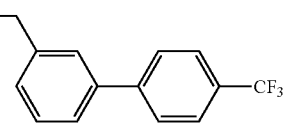 | 105-107 |
| 871 | —CH₃ | 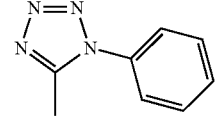 | 142-145.4 |
TABLE 39
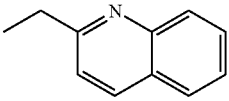
| Example | R1 | R2 | mp (° C.) |
|---|---|---|---|
| 872 | —CH₃ | 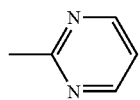 | 196-199.4 |
| 873 | —CH₃ | | 102-104 |
| 874 | —CH₃ | | 215.5-217 |
| 875 | —CH₃ | | 195-197.8 |
TABLE 40
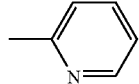
| Example | R1 | R2 | R3 | R4 | R5 | R6 | mp (° C.) or 1H NMR |
|---|---|---|---|---|---|---|---|
| 876 | —H | —H | —H | —CF₃ | —H | —H | 175.8-176.6 |
| 877 | —CH₃ | —H | —H | —H | —H | —H | 180.6-184.2 |
| 878 | —CH₃ | —H | —H | —F | —H | —H | 175-179.5 |
| 879 | —CH₃ | —H | —H | —OCH₃ | —H | —H | 172-172.5 |
| 880 | —CH₃ | —H | —H | —CO₂C₂H₅ | —H | —H | 175-179.2 |
| 881 | —CH₃ | —H | —H | —CH₃ | —H | —H | 185-185.5 |
| 882 | —CH₃ | —H | —H | —Cl | —Cl | —H | 177-177.3 |
| 883 | —CH₃ | —H | —H | —H | —CF₃ | —H | 171.6-173.6 |
| 884 | —CH₃ | —H | —H | —H | —H | —CF₃ | 179.5-180.3 |
| 885 | —CH₃ | —H | —H | —Cl | —CF₃ | —H | 170.5-171.2 |
| 886 | —CH₃ | —H | —H | —CO₂H | —H | —H | 248-252 |
| 887 | —CH₃ | —H | —H | —H | —H | —F | 191-192.2 |
| 888 | —CH₃ | —H | —H | —N(CH₃)₂ | —H | —H | 206-207 |
| 889 | —H | —H | —H | —F | —H | —H | 178.5-179.5 |
| 890 | —H | —H | —H | —CN | —H | —H | 211-211.5 |
| 891 | —H | —H | —H | —Cl | —H | —H | 183-183.5 |
| 892 | —CH₃ | —H | —H | —CF₃ | —H | —H | CDCl₃; 1.64(3H, s), 2.59-2.75(2H, m), 2.62(1H, d, J=15Hz), 2.80-2.95(2H, m), 2.93(1H, d, J=15Hz), 3.00-3.25(4H, m), 3.94(1H, d, |

TABLE 40-continued

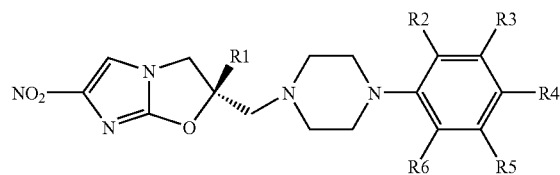

| Example | R1 | R2 | R3 | R4 | R5 | R6 | mp (° C.) or 1H NMR |
|---|---|---|---|---|---|---|---|
| | | | | | | | J=10Hz), 4.35(1H, d, J=10Hz), 6.86(2H, d, J=8Hz), 7.46(2H, d, J=8Hz), 7.53(1H, s) |
| 893 | —CH₃ | —H | —H | CO₂C(CH₃)₃ | —H | —H | 198.5-200.5 |

TABLE 41

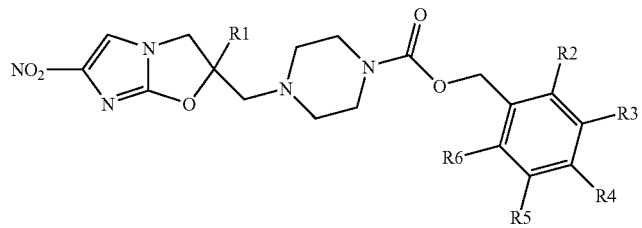

| Example | R1 | R2 | R3 | R4 | R5 | R6 | mp (° C.) |
|---|---|---|---|---|---|---|---|
| 894 | —CH₃ | —H | —H | —Cl | —H | —H | 144.2-145.6 |
| 895 | —CH₃ | —H | —H | —OCF₃ | —H | —H | 153-156.9 |
| 896 | —CH₃ | —H | —H | —Cl | —Cl | —H | 114.5-116.6 |
| 897 | —CH₃ | —H | —H | —H | —Cl | —H | 132.4-136.3 |
| 898 | —CH₃ | —H | —H | —H | —H | —Cl | 143.5-145 |
| 899 | —CH₃ | —H | —H | —Br | —H | —H | 151-152 |
| 900 | —CH₃ | —H | —H | —Ph | —H | —H | 134-135.2 |
| 901 | —CH₃ | —H | —H | —CO₂CH₃ | —H | —H | 127-130.5 |
| 902 | —CH₃ | —H | —H | —OCH₃ | —H | —H | 128-130 |
| 903 | —CH₃ | —H | —H | —OCH₂Ph | —H | —H | 128-131 |
| 904 | —CH₃ | —Cl | —H | —H | —H | —Cl | 142-145.5 |
| 905 | —CH₃ | —H | —Cl | —H | —Cl | —H | 132-135.3 |
| 906 | —CH₃ | —H | —H | —H | —CF₃ | —H | 117-118 |
| 907 | —CH₃ | —H | —H | —CH₃ | —H | —H | 117-118 |
| 908 | —CH₃ | —H | —H | —H | —OCH₃ | —H | 106-108 |
| 909 | —CH₃ | —H | —H | —H | —H | —CH₃ | 143-145 |
| 910 | —CH₃ | —H | —H | —H | —H | —OCH₃ | 127-130 |
| 911 | —CH₃ | —H | —H | —H | —H | —CF₃ | 144-145 |
| 912 | —CH₃ | —H | —H | —OC₄H₉ | —H | —H | 126-127 |
| 913 | —CH₃ | —H | —H | —NO₂ | —H | —H | 156-158 |
| 914 | —CH₃ | —H | —CF₃ | —H | —CF₃ | —H | 159-160 |
| 915 | —CH₃ | —H | —H | —CN | —H | —H | 125-129 |
| 916 | —CH₃ | —H | —H | —C(CH₃)₃ | —H | —H | 147-149 |
| 917 | —CH₃ | —H | —H | —H | —CH₃ | —H | 125-127 |
| 918 | —CH₃ | —H | —H | —CH₃ | —CH₃ | —H | 135-138 |
| 919 | —CH₃ | —H | —H | —OCH₃ | —OCH₃ | —H | 149-151 |
| 920 | —CH₃ | —H | —H | —H | —H | —F | 131-133 |
| 921 | —CH₃ | —H | —H | —C₂H₅ | —H | —H | 144-146 |
| 922 | —CH₃ | —H | —H | —SO₂CH₃ | —H | —H | 112-115 |
| 923 | —CH₃ | —H | —H | —CON(CH₃)₂ | —H | —H | 108-111 |
| 924 | —CH₃ | —H | —H | —CONHC₃H₇ | —H | —H | 124-126 |
| 925 | —CH₃ | —H | —H | —OCH(CH₃)₂ | —H | —H | 122-123 |
| 926 | —CH₃ | —H | —H | —OSO₂CH₃ | —H | —H | 100-104 |
| 927 | —CH₃ | —H | —H | —I | —H | —H | 132-134 |
| 928 | —CH₃ | —H | —H | —NHCOCH₃ | —H | —H | 105-109 |
| 929 | —CH₃ | —H | —H | —CONH₂ | —H | —H | 159-161 |
| 930 | —CH₃ | —H | —H | —F | —Cl | —H | 148-149 |

TABLE 42

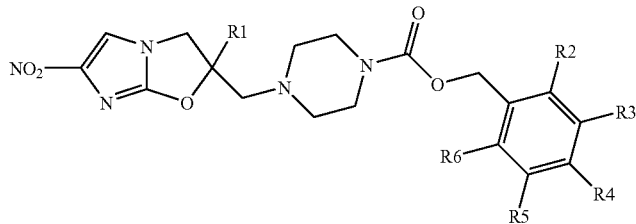

| Example | R1 | R2 | R3 | R4 | R5 | R6 | mp (° C.) or 1H NMR |
|---|---|---|---|---|---|---|---|
| 931 | —CH₃ | —H | —H | —F | —H | —H | CDCl₃ 1.62(3H, s), 2.38-2.70(4H, bm), 2.56(1H, d, J=14.9Hz), 2.87(1H, d, J=14.9Hz), 3.41(4H, bs), 3.92(1H, d, J=9.7Hz), 4.28(1H, d, J=9.7Hz), 5.06(2H, s), 6.99-7.07(2H, m), 7.28-7.34(2H, m), 7.53(1H, s) |
| 932 | —CH₃ | —H | —H | —CF₃ | —H | —H | CDCl₃ 1.62(3H, s), 2.45-2.75(4H, bm), 2.58(1H, d, J=14.9Hz), 2.86(1H, d, J=14.9Hz), 3.20-3.60(4H, br), 3.94(1H, d, J=9.8Hz), 4.29(1H, d, J=9.8Hz), 5.15(2H, s), 7.44(1H, d, J=8.0Hz), 7.54(1H, s), 7.61(1H, d, J=8.0Hz) |
| 933 | —CH₃ | —H | —H | —OH | —H | —H | CDCl₃ 1.59(3H, s), 2.30-2.70(4H, m), 2.56(1H, d, J=15Hz), 2.86(1H, d, J=15Hz), 3.10-3.55(4H, m), 3.91(1H, d, J=10Hz), 4.28(1H, d, J=10Hz), 5.03(2H, s), 5.30(1H, brs), 6.84(2H, d, J=8Hz), 7.24(2H, d, J=8Hz), 7.53(1H, s) |
| 934 | —CH₃ | —H | —H | —NH₂ | —H | —H | CDCl₃ 1.61(3H, s), 2.35-2.70(4H, m), 2.56(1H, d, J=15Hz), 2.85(1H, d, J=15Hz), 3.05-3.55(4H, m), 3.69(2H, brs), 3.91(1H, d, J=10Hz), 4.28(1H, d, J=10Hz), 4.98(2H, s), 6.55(2H, d, J=8Hz), 7.14(2H, d, J=8Hz), 7.53(1H, s) |
| 935 | —CH₃ | —H | —H | (CH₃)₃C(CH₃)₂Si— | —H | —H | 114-115 |
| 936 | —CH₃ | —H | —H | (CH₃)₃COCONH— | —H | —H | 124-127 |

TABLE 43

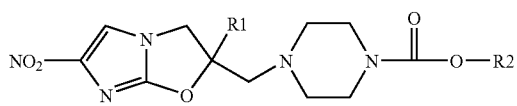

| Example | R1 | R2 | mp (° C.) |
|---|---|---|---|
| 937 | —CH₃ | —(CH₂)₂Ph | 143.5-144.6 |
| 938 | —CH₃ | 4-ClPh(CH₂)₂— | 118-119 |

TABLE 43-continued

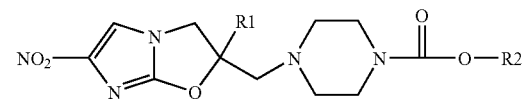

| Example | R1 | R2 | mp (° C.) |
|---|---|---|---|
| 939 | —CH₃ | 4-ClPhCH=CHCH₂— | 121-123.3 |
| 940 | —CH₃ | 4-CF₃PhCH=CHCH₂— | 121-122 |
| 941 | —CH₃ | 4-CF₃OPhCH=CHCH₂— | 127-128 |

TABLE 44

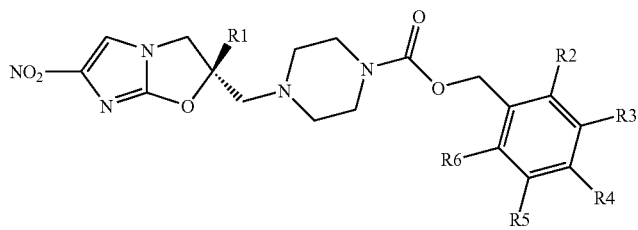

| Example | R1 | R2 | R3 | R4 | R5 | R6 | mp (° C.) or 1H NMR |
|---|---|---|---|---|---|---|---|
| 942 | —CH₃ | —H | —H | —H | —Cl | —H | 83-85 |
| 943 | —CH₃ | —H | —H | —F | —H | —H | 174-175 |
| 944 | —CH₃ | —H | —H | —H | —H | —CH₃ | 187-188.5 |
| 945 | —CH₃ | —H | —H | —H | —H | —H | 163.5-165.5 |
| 946 | —CH₃ | —H | —H | —Cl | —H | —H | 172.5-174 |
| 947 | —H | —H | —H | —OCF₃ | —H | —H | 128-129 |
| 948 | —CH₃ | —H | —H | —Cl | —Cl | —H | 97-98 |
| 949 | —CH₃ | —H | —H | —F | —F | —H | 115-116 |
| 950 | —CH₃ | —H | —H | —H | —F | —F | 101-103 |
| 951 | —CH₃ | —H | —F | —H | —F | —H | 85-87 |
| 952 | —CH₃ | —F | —F | —F | —F | —F | 143-144 |
| 953 | —CH₃ | —F | —H | —F | —H | —F | 92-95 |
| 954 | —CH₃ | —H | —F | —H | —H | —F | 144-146 |
| 955 | —CH₃ | —F | —H | —H | —H | —F | 169-170 |
| 956 | —CH₃ | —H | —H | —F | —H | —F | 178-182 |
| 957 | —CH₃ | —H | —H | —H | —F | —H | 112-115 |
| 958 | —CH₃ | —H | —H | —H | —CF₃ | —H | 78-80 |
| 959 | —CH₃ | —H | —H | —H | —H | —F | 175-176 |
| 960 | —CH₃ | —H | —H | —Br | —H | —H | 166-167 |
| 961 | —H | —H | —H | —F | —H | —H | 121.5-122 |
| 962 | —H | —H | —H | —Cl | —H | —H | 112.9-116.7 |
| 963 | —H | —H | —H | —Cl | —Cl | —H | 105.5-106 |
| 964 | —H | —H | —H | —H | —Cl | —H | 97.5-98 |
| 965 | —H | —H | —H | —H | —F | —H | 93-94 |
| 966 | —CH₃ | —H | —H | —OCHF₂ | —H | —H | 134-135 |
| 967 | —CH₃ | —H | —H | —F | —OCH₃ | —F | 71-74 |
| 968 | —CH₃ | —H | —H | —F | —OCHF₂ | —F | 84-86 |
| 969 | —CH₃ | —H | —H | —Cl | —OCHF₂ | —H | 85-87 |
| 970 | —CH₃ | —H | —H | —Cl | —H | —H | 180-181 |
| 971 | —CH₃ | —H | —H | —CF₃ | —H | —H | 185-187 |
| 972 | —CH₃ | —H | —H | —OCF₃ | —H | —H | 172-173 |
| 973 | —CH₃ | —H | —H | —OCH₂CF₃ | —H | —H | 76-80 |
| 974 | —CH₃ | —H | —H | —Cl | —OCH₂CF₃ | —H | 139-140 |

TABLE 45

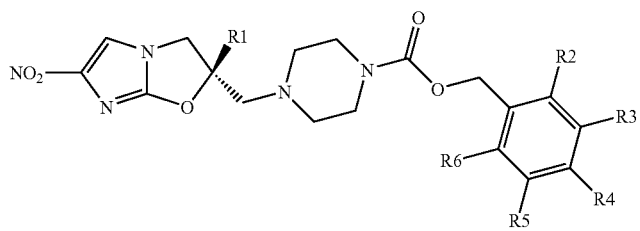

| Example | R1 | R2 | R3 | R4 | R5 | R6 | mp (° C.) or 1H NMR |
|---|---|---|---|---|---|---|---|
| 975 | —CH₃ | —H | —H | —OCH₂CF₃ | —Cl | —H | CDCl₃ 1.62(3H, s), 2.40-2.75(4H, m), 2.57(1H, d, J=15Hz), 2.87(1H, d, J=15Hz), 3.05-3.50(4H, m), 3.92(1H, d, J=10Hz), 4.28(1H, d, J=10Hz), 4.40(2H, q, J=8Hz), 5.02(2H, s), 6.40(2H, d, J=8Hz), 7.21(2H, dd, J=8.2Hz), 7.39(1H, d, J=2Hz), 7.53(1H, s) |
| 976 | —CH₃ | —H | —H | —OCHF₂ | —Cl | —H | CDCl₃ 1.62(3H, s), 2.40-2.70(4H, m), 2.59(1H, d, J=15Hz), 2.87(1H, d, J=15Hz), 3.10-3.55(4H, m), 3.96(1H, d, J=10Hz), 4.30(1H, d, J=10Hz), 5.13(2H, s), 6.53(1H, t, J=73Hz), 7.10-7.30(2H, m), 7.42(1H, s), 7.55(1H, s) |

TABLE 45-continued

[Structure: imidazo-oxazole with NO2, R1, piperazine carboxylate, benzyl with R2-R6]

| Example | R1 | R2 | R3 | R4 | R5 | R6 | mp (° C.) or 1H NMR |
|---------|-----|-----|-----|-----|-----|-----|---------------------|
| 977 | —CH₃ | —H | —H | —Br | —OCHF₂ | —F | CDCl₃ 1.62(3H, s), 2.40-2.65(4H, m), 2.59(1H, d, J=15Hz), 2.86(1H, d, J=15Hz), 3.00-3.50(4H, m), 3.96(1H, d, J=10Hz), 4.29(1H, d, J=10Hz), 5.14(2H, s), 6.59(1H, t, J=73Hz), 7.17(1H, m), 7.39(1H, m), 7.55(1H, s) |

TABLE 46

[Structure: imidazo-oxazole with NO2, R1, piperazine carboxylate, benzyl with R2-R6]

| Example | R1 | R2 | R3 | R4 | R5 | R6 | mp (° C.) |
|---------|-----|-----|-----|-----|-----|-----|-----------|
| 978 | —CH₃ | —H | —H | —CF₃ | —H | —H | 139.8 141.7 |
| 979 | —CH₃ | —H | —H | —H | —Cl | —H | 108-111 |
| 980 | —CH₃ | —H | —H | —H | —H | —CH₃ | 185-186 |
| 981 | —CH₃ | —H | —H | —Cl | —CF₃ | —H | 115-115.5 |
| 982 | —CH₃ | —H | —H | —CF₃ | —CH₃ | —H | 91-91.5 |
| 983 | —CH₃ | —H | —H | —SCF₃ | —H | —H | 136.5-137 |
| 984 | —CH₃ | —H | —H | —F | —Cl | —H | 72.5-73 |
| 985 | —CH₃ | —H | —H | —Cl | —H | —CH₃ | 178.5-179 |

TABLE 47

[Structure: imidazo-oxazole with NO2, R1, piperazine carboxylate-O-R2]

| Example | R1 | R2 | mp (° C.) |
|---------|-----|-----|-----------|
| 986 | —CH₃ | —CH₂-cyclo-C₆H₁₁ | 101-103 |
| 987 | —CH₃ | -cyclo-C₆H₁₁ | 189.6-191.6 |
| 988 | —CH₃ | —CH₂CF₃ | 123.5-124 |
| 989 | —CH₃ | —CH₂CH=C(CH₃)₂ | 138-138.5 |
| 990 | —CH₃ | (E)-3,4-Cl₂PhCH=CHCH₂— | 145-148 |
| 991 | —CH₃ | (E)-4-ClPhCH=CHCH₂— | 124-125 |
| 992 | —CH₃ | (E)-4-CF₃OPhCH=CHCH₂— | 60-61 |
| 993 | —H | (E)-4-ClPhCH=CHCH₂— | 113-114 |
| 994 | —H | (E)-4-ClPhC(CH₃)=CHCH₂— | 109-110 |
| 995 | —H | (Z)-4-ClPhC(CH₃)=CHCH₂— | 95-96 |
| 996 | —CH₃ | (E)-4-CF₃PhCH=CHCH₂— | 132-133 |
| 997 | —CH₃ | (Z)-4-CF₃PhCH=CHCH₂— | 138-140 |
| 998 | —CH₃ | (E)-3-CF₃-4-ClPhCH=CHCH₂— | 147-149 |
| 999 | —CH₃ | (E)-4-FPhCH=CHCH₂— | 155-156 |

TABLE 47-continued

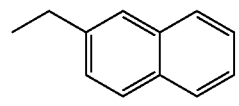

| Example | R1 | R2 | mp (° C.) |
|---|---|---|---|
| 1000 | —CH₃ | (E)-4-CF₃PhCH=C(CH₃)CH₂— | 122-123 |
| 1001 | —CH₃ | (4-CF₃Ph)₂C=CHCH₂— | 145-146 |
| 1002 | —CH₃ | 4-ClPh(CH₂)₂— | 150-151 |
| 1003 | —CH₃ | 4-ClPh(CH₂)₃— | 96-97 |
| 1004 | —CH₃ | 4-ClPh(CH₂)₄— | 78-82 |
| 1005 | —CH₃ | 4-ClPhO(CH₂)₂— | 138-139 |
| 1006 | —CH₃ | 4-CF₃OPh(CH₂)₃— | 46-48 |
| 1007 | —CH₃ | 4-CF₃Ph(CH₂)₃— | 118-120 |
| 1008 | —CH₃ | 4-CF₃PhO(CH₂)₂— | 104-108 |
| 1009 | —CH₃ | 4-CF₃OPhN(CH₃)(CH₂)₂— | 102-104 |
| 1010 | —CH₃ | (E)-4-ClPhC(CH₃)=CHCH2— | CDCl₃ 1.62(3H, s), 2.02-2.10(3H, m), 2.57(1H, d, J=14.9Hz), 2.40-2.73(4H, m), 2.87(1H, d, J=14.9Hz), 3.06-3.62(4H, m), 3.93(1H, d, J=9.7Hz), 4.29(1H, d, J=9.7Hz), 4.76(2H, m), 5.87(1H, dt, J=1.3Hz, 6.7Hz), 7.23-7.37(4H, m), 7.54(1H, s) |
| 1011 | —CH₃ | (Z)-4-ClPhC(CH₃)=CHCH₂— | CDCl₃ 1.62(3H, s), 2.02-2.10(3H, m), 2.58(1H, d, J=14.9Hz), 2.35-2.72(4H, m), 2.86(1H, d, J=14.9Hz), 3.04-3.56(4H, m), 3.94(1H, d, J=9.8Hz), 4.30(1H, d, J=9.8Hz), 4.46(2H, m), 5.66(1H, dt, J=1.4Hz, 7.0Hz), 7.04-7.12(2H, m), 7.23-7.35(2H, m), 7.53(1H, s) |

TABLE 48

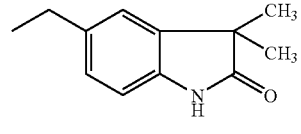

| Example | R1 | R2 | mp (° C.) |
|---|---|---|---|
| 1012 | —CH₃ | 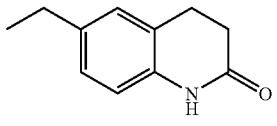 | 80-85 |
| 1013 | —CH₃ | 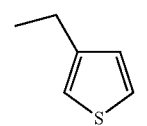 | 120-140 |
| 1014 | —CH₃ | 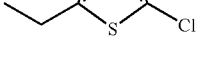 | 189-190 |
| 1015 | —CH₃ | 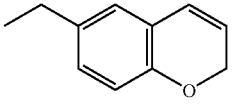 | 196.1-199.1 |

TABLE 48-continued

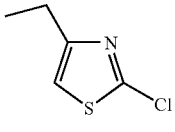

| Example | R1 | R2 | mp (° C.) |
|---|---|---|---|
| 1016 | —CH₃ | 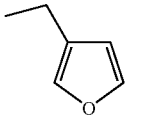 | 137.4-139.2 |
| 1017 | —CH₃ | | 71-76.4 |
| 1018 | —CH₃ | | 121.1-122.1 |
| 1019 | —CH₃ | | 177.1-178.9 |
| 1020 | —CH₃ | 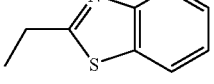 | 158.5-160.4 |

TABLE 49

| Example | R1 | R2 | mp (° C.) |
|---|---|---|---|
| 1021 | —CH₃ | 5-ethylfuran-2-yl-(4-chlorophenyl) | 193.4-195.9 |
| 1022 | —CH₃ | 4-ethylthiazol-2-yl-(4-chlorophenyl) | 203.6-204.9 |
| 1023 | —CH₃ | 2-ethylbenzoxazole | 89.7-91.8 |
| 1024 | —CH₃ | 4-methyl-5-ethylthiazol-2-yl-(4-chlorophenyl) | 185.2-187.5 |
| 1025 | —CH₃ | 2-ethyl-5-chlorobenzoxazole | 93.6-96.5 |
| 1026 | —CH₃ | 4-ethyloxazol-2-yl-(4-chlorophenyl) | 215.3-216.4 |

TABLE 49-continued

| Example | R1 | R2 | mp (° C.) |
|---|---|---|---|
| 1027 | —CH₃ | 3-ethyl-5-chlorobenzothiophene | 180.7-182.3 |
| 1028 | —CH₃ | 2-ethyl-5-chlorobenzothiophene | 170.2-170.6 |
| 1029 | —CH₃ | 2-ethyl-5-chlorobenzofuran | 134.3-135.7 |
| 1030 | —CH₃ | 5-ethyl-2-(4-chlorophenyl)-1,3,4-oxadiazole | 83.6-86.3 |
| 1031 | —CH₃ | 3-ethyl-1-(4-chlorophenyl)pyrazole | 191.8-192.9 |

TABLE 50

| Example | R1 | R2 | mp (° C.) or 1H NMR |
|---|---|---|---|
| 1032 | —CH₃ | 6-ethyl-3-methylbenzoxazol-2(3H)-one | 174.3-179.2 |
| 1033 | —CH₃ | 5-ethyl-1-phenyltetrazole | 108.9-113.1 |

TABLE 50-continued

| Example | R1 | R2 | mp (° C.) or 1H NMR |
|---|---|---|---|
| 1034 | —CH₃ | 5-ethyl-1-(4-chlorophenyl)tetrazole | 193.5-194.7 |
| 1035 | —H | 2-ethylbenzothiazole | 152-153.5 |
| 1036 | —H | 4-ethyl-2-(4-chlorophenyl)thiazole | 190.3-191.2 |
| 1037 | —H | 3-ethyl-5-chlorobenzothiophene | 177.5-180.9 |
| 1038 | —CH₃ | 5-butyl-1-(4-chlorophenyl)tetrazole | 127.5-128.1 |
| 1039 | —CH₃ | 2-ethyl-5-trifluoromethoxybenzothiophene | 140-141.5 |
| 1040 | —CH₃ | 1-ethyl-4-(4-trifluoromethoxyphenyl)-1,2,3,6-tetrahydropyridine | 114-117 |
| 1041 | —CH₃ | 1-propylpiperidine | CDCl₃ 1.40-1.62(5H, m), 1.80-1.93(2H, br), 2.46-2.64(13H, m), 2.87(1H, d, J=14.9Hz), 3.37(4H, br), 3.92(1H, d, J=9.7Hz), 4.20(2H, t, J=6.1), 7.53(1H, s) |

TABLE 51

| Example | R1 | R2 | mp (° C.) |
|---|---|---|---|
| 1042 | —CH₃ | 4-CF₃OPh— | 160.5-161.4 |
| 1043 | —CH₃ | 4-CF₃Ph— | 158.6-160.6 |
| 1044 | —CH₃ | 4-CH₃OPh— | 138.5-139.5 |
| 1045 | —CH₃ | Ph— | 163-163.5 |
| 1046 | —CH₃ | 4-FPh— | 159-160 |
| 1047 | —CH₃ | PhCH₂— | 141.5-142 |
| 1048 | —CH₃ | 4-ClPh— | 177-178 |
| 1049 | —CH₃ | 4-NCPh— | 158-159 |
| 1050 | —CH₃ | 4-ClPhCH₂— | 144-145 |
| 1051 | —CH₃ | 4-CF₃PhCH₂— | 95.5-97 |
| 1052 | —CH₃ | 4-CF₃OPhCH₂— | 143-143.5 |
| 1053 | —CH₃ | 4-CF₃PhCO— | 160.5-162.4 |
| 1054 | —CH₃ | 4-ClPhCO— | 218-220.3 |
| 1055 | —CH₃ | 4-CF₃OPhCO— | 169.8-172.7 |

TABLE 52

| Example | R1 | R2 | R3 | R4 | R5 | R6 | Mp (° C.) |
|---|---|---|---|---|---|---|---|
| 1056 | —H | —H | —H | —CF₃ | —H | —H | 215.3-217.8 |
| 1057 | —H | —H | —H | —Br | —H | —H | 219.2-221.3 |
| 1058 | —H | —F | —H | —Br | —H | —H | 198.8-200.5 |
| 1059 | —H | —H | —F | —Cl | —H | —H | 199-199.5 |

TABLE 52-continued

| Example | R1 | R2 | R3 | R4 | R5 | R6 | Mp (° C.) |
|---|---|---|---|---|---|---|---|
| 1060 | —H | —H | —H | —CN | —H | —H | 180.2-184.1 |
| 1061 | —H | —F | —F | —F | —H | —H | 188.5-189.2 |
| 1062 | —H | —H | —F | —F | —F | —H | 191.7-192.6 |
| 1063 | —H | —F | —H | —Cl | —H | —H | 202.8-203.3 |

TABLE 53

| Example | R1 | R2 | R3 | R4 | R5 | R6 | mp (° C.) |
|---|---|---|---|---|---|---|---|
| 1064 | —H | —H | —H | —Cl | —H | —H | 214.2-214.8 |
| 1065 | —H | —H | —Cl | —Cl | —H | —H | 204.1-205.7 |
| 1066 | —H | —H | —CF₃ | —H | —H | —H | 127.8-131.8 |
| 1067 | —H | —H | —H | —OCF₃ | —H | —H | 204.2-205.3 |
| 1068 | —H | —H | —H | —F | —H | —H | 199.2-200.2 |

TABLE 54

| Example | R1 | R2 | R3 | R4 | R5 | mp (° C.) |
|---|---|---|---|---|---|---|
| 1069 | —H | —H | —Cl | —H | —H | 164.6-165.9 |
| 1070 | —H | —H | —CF₃ | —H | —H | 194.9-196 |
| 1071 | —H | —H | —OCF₃ | —H | —H | 211.7-212.1 |
| 1072 | —H | —H | —H | —CF₃ | —H | 182.9-185.9 |

TABLE 55

| Example | R1 | R2 | R3 | R4 | R5 | R6 | mp (° C.) |
|---|---|---|---|---|---|---|---|
| 1073 | —H | —H | —H | —F | —H | —H | 202.5-203.1 |

TABLE 55-continued

| Example | R1 | R2 | R3 | R4 | R5 | R6 | mp (° C.) |
|---|---|---|---|---|---|---|---|
| 1074 | —H | —H | —H | —OCH₃ | —H | —H | 205.4-206.4 |
| 1075 | —H | —H | —H | —Cl | —H | —Cl | 162.7-164 |
| 1076 | —H | —H | —H | —Cl | —H | —H | 233.7-236.2 |
| 1077 | —H | —H | —H | -1-PYRRYL | —H | —H | 249.1-249.7 |
| 1078 | —H | —H | —H | —Ph | —H | —H | 211.6-212 |
| 1079 | —H | —H | —H | —OCH₂Ph | —H | —H | 202.2-203.9 |
| 1080 | —H | —H | —H | —Br | —H | —H | 224.4-226.2 |
| 1081 | —H | —H | —H | —OC₈H₁₇ | —H | —H | 156.8-158.3 |
| 1082 | —H | —H | —H | —CN | —H | —H | 197.8-198.7 |
| 1083 | —H | —H | —H | —OPh | —H | —H | 198.1-200.1 |
| 1084 | —H | —H | —F | —F | —F | —H | 193.8-196 |
| 1085 | —H | —CH₃ | —H | —CH₃ | —H | —CH₃ | 177.9-178.3 |
| 1086 | —H | —CH₃ | —H | —H | —H | —CH₃ | 175.7-178.2 |
| 1087 | —H | —H | —CF₃ | —H | —CF₃ | —H | 200.2-202.3 |
| 1088 | —H | —H | —H | —Cl | —F | —H | 197.2-199.2 |
| 1089 | —H | —H | —H | —Br | —H | —F | 206.1-207.4 |
| 1090 | —H | —H | —H | —F | —F | —F | 174-174.7 |
| 1091 | —H | —H | —H | —Cl | —H | —F | 202.8-203.7 |
| 1092 | —H | —H | —H | —C₄H₉ | —H | —H | 162.2-165.1 |
| 1093 | —H | —H | —H | —N(Ph)₂ | —H | —H | 182.6-186.4 |
| 1094 | —H | —H | —H | —H | —Cl | —Cl | 223.5-224.5 |
| 1095 | —H | —H | —H | —I | —H | —H | 217-221.1 |
| 1096 | —H | —H | —H | -1-(1,2,4-triazolyl) | —H | —H | 200.6-202.3 |

TABLE 56

| Example | R1 | R2 | R3 | R4 | R5 | R6 | MS |
|---|---|---|---|---|---|---|---|
| 1097 | —H | —H | —H | —H | —H | —H | 370 |
| 1098 | —H | —Cl | —H | —H | —H | —H | 404 |
| 1099 | —H | —H | —Cl | —H | —H | —H | 404 |
| 1100 | —H | —F | —H | —H | —H | —H | 388 |
| 1101 | —H | —H | —H | —CH(CH₃)₂ | —H | —H | 412 |
| 1102 | —H | —H | —H | —NO₂ | —H | —H | 415 |
| 1103 | —H | —CF₃ | —H | —H | —H | —H | 438 |
| 1104 | —H | —H | —CF₃ | —H | —H | —H | 438 |
| 1105 | —H | —H | —H | —C(CH₃)₃ | —H | —H | 426 |
| 1106 | —H | —H | —H | —OC₂H₅ | —H | —H | 414 |
| 1107 | —H | —Cl | —Cl | —H | —Cl | —H | 472 |
| 1108 | —H | —Cl | —Cl | —H | —H | —Cl | 472 |
| 1109 | —H | —H | —H | —H | —OPh | —H | 462 |
| 1110 | —H | —H | —F | —H | —H | —F | 406 |
| 1111 | —H | —F | —H | —F | —H | —H | 406 |
| 1112 | —H | —H | —H | —F | —F | —H | 406 |
| 1113 | —H | —H | —F | —H | —F | —H | 406 |
| 1114 | —H | —H | —H | —F | —F | —F | 424 |
| 1115 | —H | —H | —F | —H | —F | —F | 424 |
| 1116 | —H | —F | —H | —H | —F | —F | 424 |
| 1117 | —H | —H | —F | —F | —H | —F | 424 |
| 1118 | —H | —F | —H | —F | —H | —F | 424 |
| 1119 | —H | —OCF₃ | —H | —H | —H | —H | 454 |
| 1120 | —H | —H | —H | —C₂H₅ | —H | —H | 398 |
| 1121 | —H | —H | —H | —H | —Br | —H | 448 |

TABLE 56-continued

| Example | R1 | R2 | R3 | R4 | R5 | R6 | MS |
|---|---|---|---|---|---|---|---|
| 1122 | —H | —Br | —H | —H | —H | —H | 448 |
| 1123 | —H | —H | —H | —H | —F | —F | 406 |
| 1124 | —H | —Cl | —H | —H | —H | —Cl | 438 |
| 1125 | —H | —OC$_2$H$_5$ | —H | —H | —H | —H | 414 |
| 1126 | —H | —H | —H | —OC$_4$H$_9$ | —H | —H | 442 |
| 1127 | —H | —H | —H | —H | —H | —OCH$_2$Ph | 476 |
| 1128 | —H | —H | —H | —H | —NO$_2$ | —H | 415 |
| 1129 | —H | —H | —H | —H | —OCF$_3$ | —H | 454 |
| 1130 | —H | —H | —H | —Cl | —Cl | —H | 438 |
| 1131 | —H | —Cl | —H | —H | —Cl | —H | 438 |
| 1132 | —H | —H | —H | —H | —OCOCH$_3$ | —H | 428 |
| 1133 | —H | —NO$_2$ | —H | —H | —H | —H | 415 |
| 1134 | —H | —H | —H | —H | —F | —H | 388 |
| 1135 | —H | —H | —Cl | —H | —Cl | —H | 438 |
| 1136 | —H | —H | —H | —H | —CN | —H | 395 |
| 1137 | —H | —H | —OCH$_3$ | —H | —H | —H | 400 |
| 1138 | —H | —OCH$_3$ | —OCH$_3$ | —H | —H | —H | 430 |
| 1139 | —H | —OCH$_3$ | —H | —OCH$_3$ | —H | —H | 430 |
| 1140 | —H | —OCH$_3$ | —H | —H | —OCH$_3$ | —H | 430 |

TABLE 57

| Example | R1 | R2 | R3 | R4 | R5 | R6 | MS |
|---|---|---|---|---|---|---|---|
| 1141 | —H | —H | —H | —OCH$_3$ | —OCH$_3$ | —H | 430 |
| 1142 | —H | —H | —H | —OCH$_3$ | —OCH$_3$ | —OCH$_3$ | 460 |
| 1143 | —H | —H | —Cl | —H | —H | —NO$_2$ | 449 |
| 1144 | —H | —H | —H | —OCH$_3$ | —H | —NO$_2$ | 445 |
| 1145 | —H | —H | —OCH$_3$ | —H | —H | —NO$_2$ | 445 |
| 1146 | —H | —H | —H | —H | —Ph | —H | 446 |
| 1147 | —H | —NHSO$_2$CH$_3$ | —H | —H | —H | —H | 463 |
| 1148 | —H | —H | —H | —CH$_3$ | —H | —H | 384 |
| 1149 | —H | —H | —H | —CH$_3$ | —CH$_3$ | —H | 398 |
| 1150 | —H | —CH$_3$ | —H | —CH$_3$ | —H | —H | 398 |
| 1151 | —H | —H | —H | —H | —CH$_3$ | —H | 384 |
| 1152 | —H | —H | —CH$_3$ | —H | —H | —CH$_3$ | 398 |
| 1153 | —H | —H | —H | —H | —H | —CH$_3$ | 384 |
| 1154 | —H | —H | —H | —H | —CH$_3$ | —CH$_3$ | 398 |
| 1155 | —H | —H | —H | —OCOCH$_3$ | —H | —H | 428 |
| 1156 | —H | —H | —H | —OC$_3$H$_7$ | —H | —H | 428 |
| 1157 | —H | —H | —H | —NHCOCH$_3$ | —H | —H | 427 |
| 1158 | —H | —H | —CH$_3$ | —H | —CH$_3$ | —H | 398 |
| 1159 | —H | —H | —CH$_3$ | —CH$_3$ | —H | —CH$_3$ | 412 |
| 1160 | —H | —H | —H | —CO$_2$CH$_3$ | —H | —H | 428 |
| 1161 | —H | —H | —H | —CH=CHPh(trans) | —H | —H | 472 |
| 1162 | —H | —H | —H | —N(CH$_3$)$_2$ | —H | —H | 413 |
| 1163 | —H | —H | —Br | —H | —H | —OCH$_3$ | 478 |
| 1164 | —H | —H | —H | —F | —H | —Cl | 422 |
| 1165 | —H | —H | —Br | —H | —H | —F | 466 |
| 1166 | —H | —H | —OCH$_3$ | —H | —H | —F | 418 |
| 1167 | —H | —H | —H | —CH$_2$CH(CH$_3$)$_2$ | —H | —H | 426 |
| 1168 | —H | —Br | —H | —OCH$_3$ | —OCH$_3$ | —H | 508 |
| 1169 | —H | —F | —F | —F | —F | —F | 460 |

TABLE 57-continued

| Example | R1 | R2 | R3 | R4 | R5 | R6 | MS |
|---|---|---|---|---|---|---|---|
| 1170 | —H | —H | —H | —N(CH$_3$)$_2$ | —H | —OCH$_3$ | 443 |
| 1171 | —H | —H | —OCH$_2$Ph | —H | —OCH$_2$Ph | —H | 582 |
| 1172 | —H | —H | —H | —OCH$_2$Ph | —OCH$_2$Ph | —H | 582 |
| 1173 | —H | —H | —H | —H | —OC$_2$H$_5$ | —H | 414 |
| 1174 | —H | —H | —H | —H | —OCH$_2$Ph | —H | 476 |
| 1175 | —H | —H | —H | —OCH$_2$Ph | —OCH$_3$ | —H | 506 |
| 1176 | —H | —H | —H | —SC$_2$H$_5$ | —H | —H | 430 |
| 1177 | —H | —H | —H | —OCHF$_2$ | —H | —H | 436 |
| 1178 | —H | —H | —H | —OCH(CH$_3$)$_2$ | —H | —H | 428 |
| 1179 | —H | —H | —H | —OCH$_3$ | —Br | —H | 478 |
| 1180 | —H | —H | —H | —N(C$_2$H$_5$)$_2$ | —H | —H | 441 |
| 1181 | —H | —H | —H | —OCH$_3$ | —F | —H | 418 |
| 1182 | —H | —H | —H | —OCH$_3$ | —CH$_3$ | —H | 414 |
| 1183 | —H | —OCH$_3$ | —H | —H | —F | —H | 418 |
| 1184 | —H | —Cl | —H | —H | —NO$_2$ | —H | 449 |

TABLE 58

| Example | R1 | R2 | R3 | R4 | R5 | R6 | MS |
|---|---|---|---|---|---|---|---|
| 1185 | —H | —H | —H | —OC$_2$H$_5$ | —OC$_2$H$_5$ | —H | 458 |
| 1186 | —H | —H | —H | —OCOCH$_3$ | —OCH$_3$ | —H | 458 |
| 1187 | —H | —NO$_2$ | —H | —OCH$_3$ | —OCH$_3$ | —H | 475 |
| 1188 | —H | —H | —H | —SCH$_3$ | —H | —H | 416 |
| 1189 | —H | —H | —H | —Cl | —NO$_2$ | —H | 449 |
| 1190 | —H | —H | —H | —SO$_2$CH$_3$ | —H | —H | 448 |
| 1191 | —H | —H | —H | —OCH$_3$ | —OCH$_2$Ph | —H | 506 |
| 1192 | —H | —H | —H | —Cl | —CF$_3$ | —H | 472 |
| 1193 | —H | —I | —H | —H | —H | —H | 496 |
| 1194 | —H | —H | —H | —H | —SCF$_3$ | —H | 470 |
| 1195 | —H | —OCH$_3$ | —H | —OCH$_3$ | —OCH$_3$ | —H | 460 |
| 1196 | —H | —H | —OCH$_3$ | —H | —OCH$_3$ | —H | 430 |
| 1197 | —H | —CO$_2$CH$_3$ | —H | —H | —H | —H | 428 |
| 1198 | —H | —OCH$_3$ | —H | —H | —H | —OCH$_3$ | 430 |
| 1199 | —H | —OCH$_3$ | —H | —OCH$_3$ | —H | —OCH$_3$ | 460 |
| 1200 | —H | —OCHF$_2$ | —H | —H | —H | —H | 436 |
| 1201 | —H | —H | —Br | —OCH$_3$ | —OCH$_3$ | —H | 508 |
| 1202 | —H | —H | —CH$_3$ | —OCH$_3$ | —H | —CH$_3$ | 428 |
| 1203 | —H | —H | —H | —OH | —H | —H | 386 |
| 1204 | —H | —H | —OCH$_3$ | —OH | —OCH$_3$ | —H | 446 |
| 1205 | —H | —H | —H | —OH | —H | —OH | 402 |
| 1206 | —H | —H | —H | —H | —H | —OCH$_3$ | 400 |
| 1207 | —H | —F | —H | —H | —H | —F | 406 |
| 1208 | —H | —H | —H | -3-PYRIDYL | —H | —H | 447 |
| 1209 | —H | —H | —H | —OCH$_2$Ph | —Cl | —H | 510 |
| 1210 | —H | —H | —H | -2-THIENYL | —H | —H | 452 |
| 1211 | —H | —H | —OCH$_3$ | —OCH$_3$ | —OCH$_3$ | —H | 460 |
| 1212 | —H | —H | —H | -cyclo-C$_6$H$_{11}$ | —H | —H | 452 |
| 1213 | —H | —H | —H | CH$_2$=CHCH$_2$O— | —H | —H | 426 |
| 1214 | —H | —H | —H | Pyrrolidinyl- | —H | —H | 439 |
| 1215 | —H | EtOCOCH$_2$O— | —H | —H | —H | —H | 472 |
| 1216 | —H | —H | —H | —OCH$_3$ | cyclo-C$_5$H$_9$O— | —H | 484 |
| 1217 | —H | —H | CF$_3$CF$_2$O— | —H | —H | —H | 504 |

TABLE 58-continued

| Example | R1 | R2 | R3 | R4 | R5 | R6 | MS |
|---|---|---|---|---|---|---|---|
| 1218 | —H | —H | —H | Imidazolyl- | —H | —H | 436 |
| 1219 | —H | —H | —H | Piperidino- | —H | —H | 453 |
| 1220 | —H | —H | —H | 4-CF$_3$Ph— | —H | —H | 514 |
| 1221 | —H | —H | —H | 4-CH$_3$OPh— | —H | —H | 476 |
| 1222 | —H | —H | —H | (CH$_3$)$_2$N(CH$_2$)$_3$O— | —H | —H | 471 |
| 1223 | —H | —H | —H | Morpholino- | —NO$_2$ | —H | 500 |
| 1224 | —H | —H | —H | Piperidino- | —NO$_2$ | —H | 498 |
| 1225 | —H | —H | —H | 4-FPh— | —H | —H | 464 |
| 1226 | —H | —H | —H | 4-CH$_3$(CH$_2$)$_6$Ph— | —H | —H | 572 |
| 1227 | —H | —H | —H | 3,4-F$_2$Ph— | —H | —H | 482 |
| 1228 | —H | —H | —H | 4-CH$_3$(CH$_2$)$_3$Ph— | —H | —H | 502 |
| 1229 | —H | —H | —H | 3-Cl-4-FPh— | —H | —H | 498 |

TABLE 59

| Example | R1 | R2 | R3 | R4 | R5 | R6 | MS |
|---|---|---|---|---|---|---|---|
| 1230 | —H | —H | —H | 4-CF$_3$OPh— | —H | —H | 530 |
| 1231 | —H | —H | —H | 4-CH$_3$Ph— | —H | —H | 460 |
| 1232 | —H | —H | —H | 4-NCPh— | —H | —H | 471 |
| 1233 | —H | —H | —H | 3,4-(CH$_3$O)$_2$Ph— | —H | —H | 506 |
| 1234 | —H | —H | —OCH$_2$O— | —H | —H | —H | 414 |
| 1235 | —H | —H | —H | —OCH$_2$O— | —H | —Cl | 448 |
| 1236 | —H | —H | —H | —OCH$_2$O— | —H | —H | 414 |
| 1237 | —H | —H | —H | —OCH$_2$O— | —OCH$_3$ | —H | 444 |
| 1238 | —H | —NO$_2$ | —H | —OCH$_2$O— | —H | —H | 459 |
| 1239 | —H | —H | —H | 4-(4-methylpiperazin-1-yl)- | —F | —H | 486 |
| 1240 | —H | —H | 4-(4-methylpiperazine-1-carbonyl)-3-methylphenyl | —H | —H | —NO2 | 617 |
| 1241 | —H | —H | 4-(4-methylpiperazine-1-carbonyl)phenyl | —H | —H | —NO2 | 589 |

TABLE 59-continued

Structure: Core scaffold with NO₂-imidazo-oxazole-CH₃, piperazine, N=C(R1)-phenyl with R2, R3, R4, R5, R6 substituents

| Example | R1 | R2 | R3 | R4 | R5 | R6 | MS |
|---------|----|----|----|----|----|----|----|
| 1242 | —H | —H | 3-methyl-7-methoxy-1-methyl-quinolin-2(1H)-one | —H | —H | —OCH3 | 587 |
| 1243 | —H | —H | —H | 1-methyl-1,2,4-triazol-3-yl | —H | —H | 437 |
| 1244 | —H | —H | —H | 1-(1-acetylpiperidin-4-yl)-2-oxo-1,2,3,4-tetrahydroquinolin-6-yl | —H | —H | 626 |
| 1245 | —H | —H | —H | 4-(2-methoxyacetyl)morpholin | —H | —H | 513 |
| 1246 | —H | —H | —H | 2-methylbenzofuran-5-yl | —H | —H | 486 |

TABLE 60

Structure: NO₂-imidazo-oxazole-CH₃-piperazine-N=CH-CH=CH-R1

| Example | R1 | mp (° C.) or MS |
|---------|----|-----|
| 1247 | 5-CF₃-2-methylbenzofuran | 174.1-175.8 |
| 1248 | 5-OCF₃-2-methylbenzofuran | 201.9-203 |
| 1249 | 5-Cl-2-methylbenzofuran | 218.8-220.1 |
| 1250 | 6-CF₃-2-methylbenzofuran | 156-159.3 |
| 1251 | 2-furyl | 386 |
| 1252 | 5-methylbenzo[d][1,3]dioxol | 496 |

TABLE 60-continued
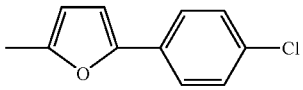
| Example | R1 | mp (° C.) or MS |
|---|---|---|
| 1253 | 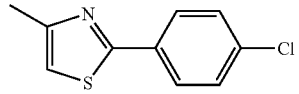 | 513 |
| 1254 | 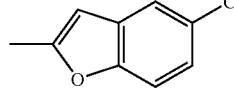 | 440 |
TABLE 61
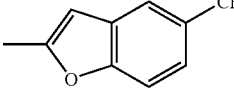
| Example | R1 | mp (° C.) |
|---|---|---|
| 1255 | 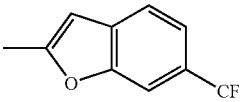 | 211.5-213.6 |
| 1256 | 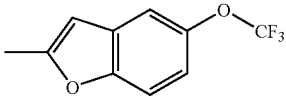 | 190.2-191.8 |
| 1257 | 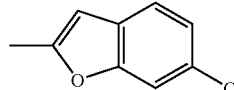 | 182-185.7 |
| 1258 | 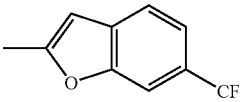 | 192.3-195.5 |
| 1259 | 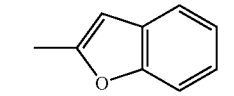 | 218.4-218.9 |
| 1260 | 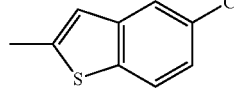 | 196-197.8 |
| 1261 | | 212.5-212.9 |
| 1262 | | 219.2-220 |
TABLE 61-continued
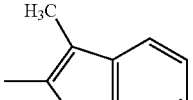
| Example | R1 | mp (° C.) |
|---|---|---|
| 1263 | | 209.4-210.4 |
TABLE 62
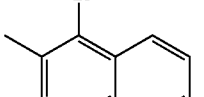
| Example | R1 | mp (° C.) or MS |
|---|---|---|
| 1264 | 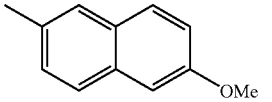 | 205.4-206.6 |
| 1265 | 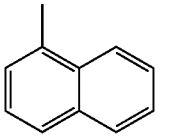 | 214.7-215.2 |
| 1266 | | 420 |
| 1267 | 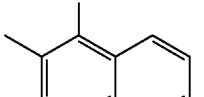 | 498 |
| 1268 | | 420 |
| 1269 | 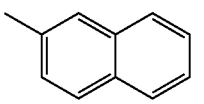 | 463 |
| 1270 | 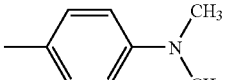 | 450 |

TABLE 63

[Structure: NO2-imidazo-oxazoline-CH3-CH2-piperazine-N=CH-R1]

| Example | R1 | mp (° C.) or MS |
|---|---|---|
| 1271 | 2-methylfluorene | 227.6-228.3 |
| 1272 | 6-methyl-2,3-dihydro-1,4-benzodioxine | 428 |
| 1273 | 1-methylpyrene | 494 |
| 1274 | methylcyclohexane | 376 |
| 1275 | 1-methylcyclohexene | 374 |

TABLE 64

[Structure: NO2-imidazo-oxazoline-CH3-CH2-piperazine-N=CH-R1]

| Example | R1 | mp (° C.) or MS |
|---|---|---|
| 1276 | 3-methylfuran | 360 |
| 1277 | 2,5-dimethylfuran | 374 |
| 1278 | 2-ethyl-5-methylfuran | 388 |
| 1279 | 5-(4-bromophenyl)-2-methylfuran | 230.6-232.6 |
| 1280 | 5-(4-chlorophenyl)-2-methylfuran | 470 |

TABLE 64-continued

[Structure: NO2-imidazo-oxazoline-CH3-CH2-piperazine-N=CH-R1]

| Example | R1 | mp (° C.) or MS |
|---|---|---|
| 1281 | 5-(4-nitrophenyl)-2-methylfuran | 481 |
| 1282 | 5-(2-chlorophenyl)-2-methylfuran | 470 |
| 1283 | 5-(2-trifluoromethylphenyl)-2-methylfuran | 504 |
| 1284 | 5-(2-chloro-5-trifluoromethylphenyl)-2-methylfuran | 538 |
| 1285 | 5-(2-nitrophenyl)-2-methylfuran | 481 |

TABLE 65

[Structure: NO2-imidazo-oxazoline-CH3-CH2-piperazine-N=CH-R1]

| Example | R1 | mp (° C.) or MS |
|---|---|---|
| 1286 | 5-nitro-2-methylfuran | 405 |
| 1287 | 2,5-dimethyl-3-methylfuran (trimethylfuran) | 388 |
| 1288 | 5-(3-nitrophenyl)-4-methylfuran | 481 |

TABLE 66

[Structure: NO2-substituted imidazo-oxazoline with CH3, piperazine, N=CH-R1]

| Example | R1 | mp (° C.) or MS |
|---------|----|--------------------|
| 1289 | 2-methylthiophene | 376 |
| 1290 | 4-bromo-5-methylthiophene | 217.8-218.5 |
| 1291 | 5-methyl-2,2'-bithiophene | 213.2-215.6 |
| 1292 | 5'-bromo-5-methyl-2,2'-bithiophene | 536 |
| 1293 | 5-methyl-2-nitrothiophene | 421 |
| 1294 | 2,3-dimethylthiophene | 390 |
| 1295 | 2-chloro-5-methylthiophene | 410 |
| 1296 | 2-ethyl-5-methylthiophene | 404 |
| 1297 | 5-methyl-2-(1-methyl-5-trifluoromethylpyrazol-3-yl)thiophene | 524 |
| 1298 | 5-methyl-2-(1-methyl-3-trifluoromethylpyrazol-5-yl)thiophene | 524 |
| 1299 | 5-methyl-2-(3-phenoxy)thiophene | 468 |

TABLE 67

[Structure: NO2-substituted imidazo-oxazoline with CH3, piperazine, N=CH-R1]

| Example | R1 | mp (° C.) or MS |
|---------|----|--------------------|
| 1300 | 3-methylthiophene | 376 |
| 1301 | 4-methyl-2-nitrothiophene | 421 |

TABLE 68

[Structure: NO2-substituted imidazo-oxazoline with CH3, piperazine, N=CH-R1]

| Example | R1 | mp (° C.) or MS |
|---------|----|--------------------|
| 1302 | 2-methylpyridine | 371 |
| 1303 | 3-methylpyridine | 371 |
| 1304 | 4-methylpyridine | 371 |
| 1305 | 6-methyl-3-phenylpyridine | 447 |
| 1306 | 6-methyl-3-(4-fluorophenyl)pyridine | 465 |
| 1307 | 6-methyl-3-(4-trifluoromethylphenyl)pyridine | 515 |
| 1308 | 6-methyl-3-(4-trifluoromethoxyphenyl)pyridine | 531 |
| 1309 | 6-methyl-3-(3,4-difluorophenyl)pyridine | 483 |

TABLE 68-continued
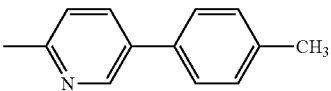
| Example | R1 | mp (° C.) or MS |
|---|---|---|
| 1310 | 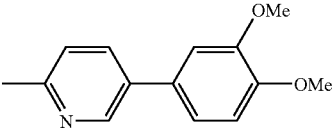 | 461 |
| 1311 | 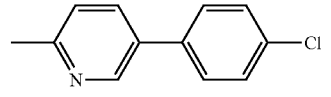 | 507 |
| 1312 | 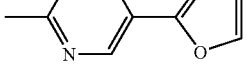 | 481 |
TABLE 69
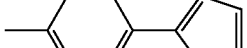
| Example | R1 | mp (° C.) or MS |
|---|---|---|
| 1313 | 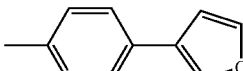 | 437 |
| 1314 | 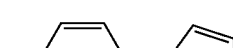 | 453 |
| 1315 | 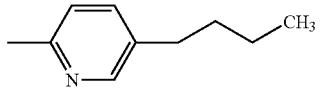 | 437 |
| 1316 | 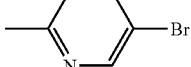 | 453 |
| 1317 | 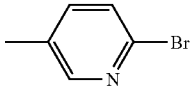 | 427 |
| 1318 | 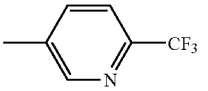 | 449 |
| 1319 | 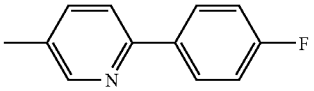 | 449 |
TABLE 69-continued
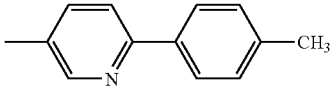
| Example | R1 | mp (° C.) or MS |
|---|---|---|
| 1320 | 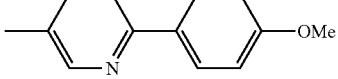 | 439 |
| 1321 | 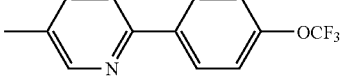 | 465 |
| 1322 | 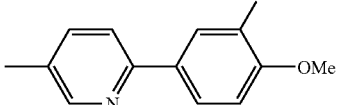 | 461 |
| 1323 | 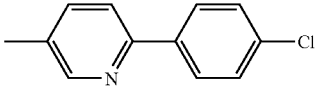 | 477 |
| 1324 |  | 531 |
TABLE 70
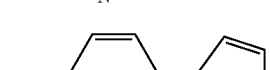
| Example | R1 | mp (° C.) or MS |
|---|---|---|
| 1325 | 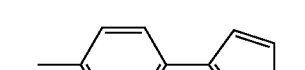 | 507 |
| 1326 | | 481 |
| 1327 | | 499 |
| 1328 | | 453 |
| 1329 | | 437 |

TABLE 70-continued

| Example | R1 | mp (° C.) or MS |
|---|---|---|
| 1330 | 2-methylthiazole | 377 |
| 1331 | 4-methyl-2-(biphenyl-4-yl)thiazole | 189.4-190.6 |
| 1332 | 6-methyl-3-(4-chlorobenzyl)pyridine | 498 |
| 1333 | 4-methyl-2-phenylthiazole | 453 |
| 1334 | 4-methyl-2-(4-methoxyphenyl)thiazole | 483 |
| 1335 | 5-methyl-2-(4-chlorophenyl)thiazole | 487 |
| 1336 | 4-methyl-2-(4-chlorophenyl)oxazole | 201.2-203.5 |

TABLE 71

| Example | R1 | mp (° C.) or MS |
|---|---|---|
| 1337 | 2,5-dimethyl-1-[3-(trifluoromethyl)phenyl]pyrrole | 531 |
| 1338 | 2-methyl-1-(2-nitrobenzyl)pyrrole | 494 |

TABLE 71-continued

| Example | R1 | mp (° C.) or MS |
|---|---|---|
| 1339 | 5-methyl-8-methoxy-1-methyl-3,4-dihydroquinolin-2(1H)-one | 483 |
| 1340 | 5-methyl-8-methoxy-1-methylquinolin-2(1H)-one | 481 |
| 1341 | 6-methyl-8-methoxy-1-methyl-3,4-dihydroquinolin-2(1H)-one | 469 |
| 1342 | 5-methyl-8-methoxyquinolin-2(1H)-one | 467 |
| 1343 | 5-methyl-8-benzyloxyquinolin-2(1H)-one | 543 |

TABLE 72

| Example | R1 | mp (° C.) or MS |
|---|---|---|
| 1344 | 5-methyl-8-methoxy-3,4-dihydroquinolin-2(1H)-one | 469 |

TABLE 72-continued

| Example | R1 | mp (° C.) or MS |
|---|---|---|
| 1345 | 2-methylquinoline | 220.6-220.9 |
| 1346 | 2-methylquinoline isomer | 421 |
| 1347 | 4-methylquinoline | 421 |
| 1348 | 3-methyl-1-tosyl-indole | 563 |
| 1349 | 1-benzyl-3-methyl-indole | 499 |
| 1350 | methyl 3-methyl-1H-indole-6-carboxylate | 467 |
| 1351 | 3-methyl-2-phenyl-1H-indole | 485 |

TABLE 73

| Example | R1 | mp (° C.) or MS |
|---|---|---|
| 1352 | methylbenzimidazole | 153.1-157.5 |
| 1353 | methyl-2-(thiophen-2-yl)-1H-benzimidazole | 492 |
| 1354 | methylimidazo[2,1-b]thiazole | 416 |
| 1355 | methyl-2-(2-methoxyphenyl)benzothiazole | 533 |
| 1356 | 2-methylimidazo[1,2-a]pyridine | 410 |
| 1357 | 9-ethyl-3-methylcarbazole | 487 |
| 1358 | 6-methylcoumarin | 188.6-190.6 |
| 1359 | 2,3-dimethylbenzothiophene | 440 |
| 1360 | 2,2,6-trimethylchroman | 454 |
| 1361 | 5-methyl-2,3-dihydrobenzofuran | 412 |

TABLE 74

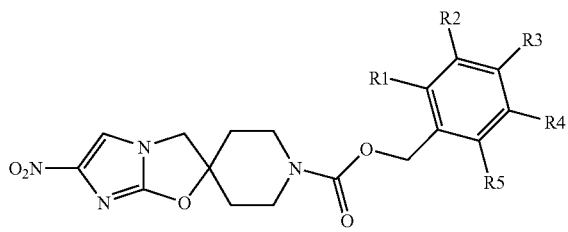

| Example | R1 | R2 | R3 | R4 | R5 | mp (° C.) |
|---|---|---|---|---|---|---|
| 1362 | —H | —H | —F | —H | —H | 187-188 |
| 1363 | —H | —H | —Cl | —H | —H | 183-184 |
| 1364 | —H | —OCH₃ | —OCH₃ | —OCH₃ | —H | 169-170 |
| 1365 | —H | —Cl | —Cl | —H | —H | 174-175 |
| 1366 | —Cl | —H | —H | —H | —Cl | 208-209 |
| 1367 | —F | —F | —H | —H | —H | 184-185 |
| 1368 | —H | —F | —F | —H | —H | 185-186 |
| 1369 | —H | —H | —CO₂CH₃ | —H | —H | 183-184.5 |
| 1370 | —H | —CO₂C₂H₅ | —H | —CO₂C₂H₅ | —H | 181-182 |
| 1371 | —H | —H | —OCH₃ | —H | —H | 175-176 |
| 1372 | —Cl | —H | —H | —H | —H | 173-174.5 |
| 1373 | —H | —Cl | —H | —H | —H | 173-174 |
| 1374 | —H | —CF₃ | —H | —H | —H | 184-186 |
| 1375 | —CF₃ | —H | —H | —H | —H | 188-190 |
| 1376 | —H | —H | —Ph | —H | —H | 187-188 |
| 1377 | —H | —CF₃ | —H | —CF₃ | —H | 183-184 |
| 1378 | —F | —F | —F | —F | —F | 235-237 |
| 1379 | —H | —H | —SCH₃ | —H | —H | 177-179 |
| 1380 | —H | —H | —C(CH₃)₃ | —H | —H | 201-202 |
| 1381 | —CH₃ | —H | —H | —H | —H | 183-185 |
| 1382 | —OCF₃ | —H | —H | —H | —H | 190-191 |
| 1383 | —H | —OCF₃ | —H | —H | —H | 188-189 |

TABLE 75

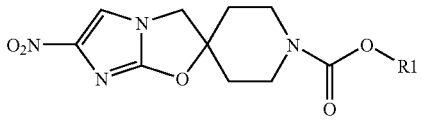

| Example | R1 | mp (° C.) |
|---|---|---|
| 1384 | (CH₃)₂CH— | 251-253 |
| 1385 | (CH₃)₂CHCH₂— | 233-235 |
| 1386 | C₈H₁₇— | 219-220 |
| 1387 | Ph(CH₂)₂— | 198-200 |
| 1388 | PhCH=CHCH₂— | 180-181 |
| 1389 | Ph(CH₂)₃— | 186-187.5 |
| 1390 | (Ph)₂CH— | 202-204 |
| 1391 | Ph— | 242-244 |
| 1392 | 2-NaphthylCH₂— | 173.5-174.5 |
| 1393 | 4-PyridylCH₂— | 163-164 |
| 1394 | 4-ClPh(CH₂)₂— | 198-200 |
| 1395 | (4-ClPh)₂CH— | 238-240 |
| 1396 | 4-CH₃Ph— | 230-231 |
| 1397 | 4-CH₃OPh— | 248-250 |
| 1398 | 2-BocNHPhCH₂— | 144-145 |
| 1399 | CH₃OCH₂CH₂— | 1.80-2.00(m, 2H), 2.15-2.25(m, 2H), 3.30-3.40(m, 5H), 3.68(t, 2H, J=4.5Hz), 3.95-4.20(m, 4H), 4.27(t, 2H, J=4.5Hz), 7.54(s, 1H) |
| 1400 | 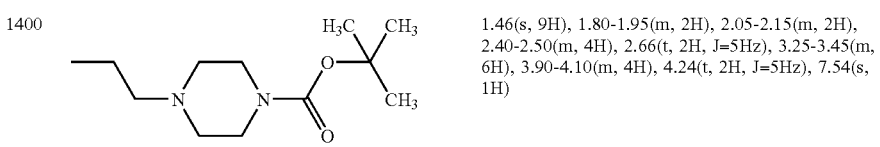 | 1.46(s, 9H), 1.80-1.95(m, 2H), 2.05-2.15(m, 2H), 2.40-2.50(m, 4H), 2.66(t, 2H, J=5Hz), 3.25-3.45(m, 6H), 3.90-4.10(m, 4H), 4.24(t, 2H, J=5Hz), 7.54(s, 1H) |

TABLE 75-continued

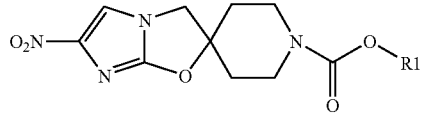

| Example | R1 | mp (° C.) |
|---|---|---|
| 1401 | 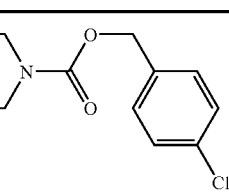 | 1.80-1.95(m, 2H), 2.05-2.25(m, 2H), 2.35-2.60(m, 4H), 2.63-2.81(m, 2H), 3.25-3.55(m, 6H), 3.85-4.25(m, 6H), 5.09(s, 2H), 7.20-7.40(m, 4H), 7.54(s, 1H) |

TABLE 76

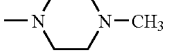

| Example | R1 | R2 | R3 | R4 | R5 | R6 | mp (° C.) |
|---|---|---|---|---|---|---|---|
| 1402 | —H | —H | —H | —Cl | —H | —H | 249-252 (dec.) |
| 1403 | —H | —H | —H | —F | —H | —H | 238-240 (dec.) |
| 1404 | —H | —H | —H | —CF₃ | —H | —H | 215-217 |
| 1405 | —H | —H | —H | —OCF₃ | —H | —H | 231-233 |
| 1406 | —H | —H | —H | —CH₃ | —H | —H | >300 |
| 1407 | —H | —H | —F | Morpholino- | —H | —H | 240-245 (dec.) |
| 1408 | —H | —H | —H | —CO₂C(CH₃)₃ | —H | —H | >300 |
| 1409 | —H | —H | —Cl | 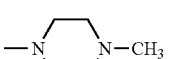 | —H | —H | 205-207 |
| 1410 | —H | —H | —H | 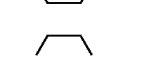 | —H | —H | 246-250 (dec.) |
| 1411 | —H | —H | —F | 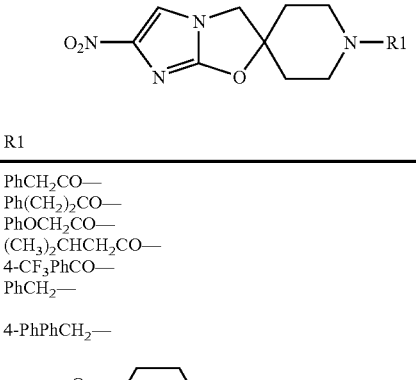 | —H | —H | 220-225 (dec.) |

TABLE 77

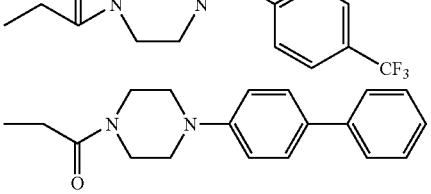

| Example | R1 | Mp (° C.) |
|---|---|---|
| 1412 | PhCO— | 178-180 |
| 1413 | PhCH₂CO— | 170-171 |
| 1414 | Ph(CH₂)₂CO— | 160.5-162 |
| 1415 | PhOCH₂CO— | 203-205 |
| 1416 | (CH₃)₂CHCH₂CO— | 214-215 |
| 1417 | 4-CF₃PhCO— | 165-166 |
| 1418 | PhCH₂— | 249-251 (dec.) |
| 1419 | 4-PhPhCH₂— | 262-264 (dec.) |
| 1420 | | 195-197 (dec.) |
| 1421 | | 226-227 (dec.) |

Example 1422

Production of (S)-1-(2-bromo-4-nitroimidazol-1-yl)-2-methyl-3-{4-[1-(4-trifluoromethoxyphenyl)piperidin-4-yl]piperazin-1-yl}propan-2-ol A mixture of (R)-2-bromo-4-nitro-1-(2-methyl-2-oxiranylmethyl)imidazole (485 mg, 1.75 mmol), 1-[1-(4-trifluoromethoxyphenyl)piperidin-4-yl]piperazine (720 mg, 2.19 mmol) and ethanol (10 ml) was stirred at 50° C. for 8 hours. The reaction mixture was concentrated, and the residue was purified by silica gel column chromatography (methylene chloride/methanol=20/1) to obtain (S)-1-(2-bromo-4-nitroimidazol-1-yl)-2-methyl-3-{4-[1-(4-trifluoromethoxyphenyl)piperidin-4-yl]piperazin-1-yl}propan-2-ol (792 mg, yield 77%) as a yellow amorphous form.

H-NMR(CDCl₃) δppm: 1.13 (3H, s), 1.50-1.75 (2H, m), 1.81-2.00 (2H, m), 2.35 (1H, d, J=13.9 Hz), 2.40-2.86 (12H, m), 3.57-3.76 (2H, m), 3.98 (2H, s), 6.89 (2H, d, J=8.5 Hz), 7.09 (2H, d, J=8.5 Hz), 8.12 (1H, s).

Following compounds were produced in the same manner.

Example 1423

Tert-butyl (S)-4-{4-[3-(2-chloro-4-nitroimidazol-1-yl)-2-hydroxy-2-methylpropyl]piperazin-1-yl}piperidine-1-carboxylate $^1$H-NMR (CDCl$_3$) δppm: 1.12 (3H, s), 1.29-1.48 (11H, m), 1.67-1.81 (2H, m), 2.34 (1H, d, J=13.8 Hz), 2.38-2.74 (12H, m), 3.97 (2H, s), 4.02-4.14 (2H, m), 8.05 (1H, s).

Example 1424

Tert-butyl (S)-4-{1-[3-(2-chloro-4-nitroimidazol-1-yl)-2-hydroxy-2-methylpropyl]piperidin-4-yl}piperazin-1-carboxylate $^1$H-NMR (CDCl$_3$) δppm: 1.11 (3H, s), 1.38-1.57 (11H, m), 1.69-1.86 (2H, m), 2.24-2.50 (9H, m), 2.67-2.79 (1H, m), 2.86-3.00 (1H, m), 3.31-3.43 (4H, m), 3.95 (2H, s), 8.04 (1H, s).

TABLE 78

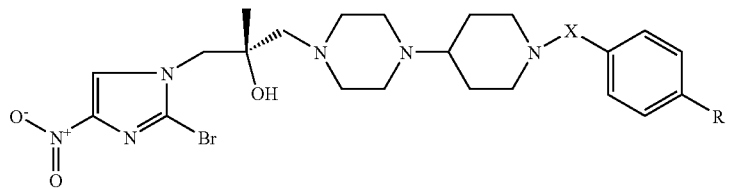

| Example | X | R | $^1$H-NMR(CDCl$_3$) δppm |
|---|---|---|---|
| 1425 | none | OCF$_3$ | 1.13(3H, s), 1.50-1.75(2H, m), 1.81-2.00(2H, m), 2.35(1H, d, J=13.9Hz), 2.40-2.86(12H, m), 3.57-3.76(2H, m), 3.98(2H, s), 6.89(2H, d, J=8.5Hz), 7.09(2H, d, J=8.5Hz), 8.12(1H, s). |
| 1426 | C=O | Cl | 1.13(3H, s), 1.31-1.56(2H, m), 1.70-2.00(2H, m), 2.36(1H, d, J=13.9Hz), 2.65-2.91(12H, m), 3.63-3.84(1H, m), 3.93(2H, s), 4.56-4.74(1H, m), 7.19-7.42(4H, m), 8.13(1H, s). |
| 1427 | C=O | OCF$_3$ | 1.14(3H, s), 1.35-1.60(2H, m), 1.74-2.00(2H, m), 2.36(1H, d, J=13.9Hz), 2.42-2.93(12H, m), 3.65-3.81(1H, m), 4.00(2H, s), 4.56-4.74(1H, m), 7.25(2H, d, J=8.7Hz), 7.44(2H, d, J=8.7Hz), 8.14(1H, s). |
| 1428 | CH$_2$ | Cl | 1.12(3H, s), 1.43-2.05(6H, m), 2.34(1H, d, J=13.9Hz), 2.37-2.95(12H, m), 3.47(2H, s), 3.97(2H, s), 7.12-7.30(4H, m), 8.12(1H, s). |
| 1429 | CH$_2$ | OCF$_3$ | 1.12(3H, s), 1.44-2.05(6H, m), 2.35(1H, d, J=14.0Hz), 2.42-2.93(12H, m), 3.48(2H, s), 3.98(2H, s), 7.15(2H, d, J=8.6Hz), 7.34(2H, d, J=8.6Hz), 8.12(1H, s). |

TABLE 79

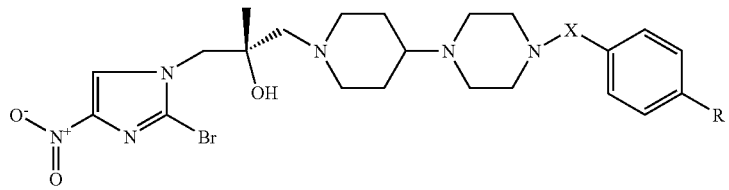

| Example | X | R | $^1$H-NMR(CDCl$_3$) δppm |
|---|---|---|---|
| 1430 | C=O | Cl | 1.12(3H, s), 1.43-1.81(4H, m), 2.10-2.62(9H, m), 2.71-3.07(2H, m), 3.31-3.45(4H, m), 3.96(2H, s), 7.24-7.40(4H, m), 8.10(1H, s). |
| 1431 | C=O | OCF$_3$ | 1.12(3H, s), 1.45-1.83(4H, m), 2.12-2.57(9H, m), 2.71-3.07(2H, m), 3.28-3.47(4H, m), 3.96(2H, s), 7.25(2H, d, J=8.6Hz), 7.45(2H, d, J=8.6Hz), 8.10(1H, s). |
| 1432 | CH$_2$ | OCF$_3$ | 1.11(3H, s), 1.50-1.98(4H, m), 2.24-3.10(15H, m), 3.54(2H, s), 3.98(2H, s), 7.16(2H, d, J=8.6Hz), 7.34(2H, d, J=8.6Hz), 8.12(1H, s). |
| 1433 | CH$_2$ | Cl | 1.11(3H, s), 1.40-1.83(4H, m), 2.25-3.02(15H, m), 3.46(2H, s), 3.95(2H, s), 7.14-7.29(4H, m), 8.12(1H, s). |
| 1434 | none | OCF$_3$ | 1.13(3H, s), 1.50-1.64(2H, m), 1.76-1.88(2H, m), 2.15-2.43(5H, m), 2.52-2.95(6H, m), 3.05-3.19(4H, m), 3.98(2H, s), 6.89(2H, d, J=8.7Hz), 7.11(2H, d, J=8.7Hz), 8.1(1H, s). |

TABLE 79-continued

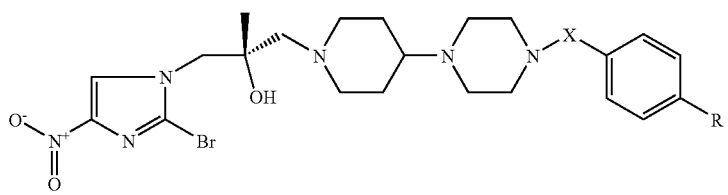

| Example | X | R | ¹H-NMR(CDCl₃) δppm |
|---|---|---|---|
| 1435 | none | Cl | 1.13(3H, s), 1.50-1.64(2H, m), 1.71-1.90(2H, m), 2.12-2.48(5H, m), 2.55-2.90(6H, m), 3.05-3.19(4H, m), 3.96(2H, s), 6.84(2H, d, J=8.7Hz), 7.18(2H, d, J=8.7Hz), 8.11(1H, s). |

TABLE 80

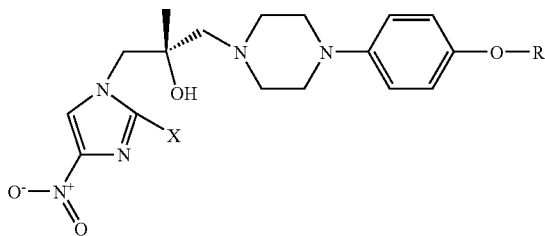

| Example | X | R | ¹H-NMR(CDCl₃) δppm |
|---|---|---|---|
| 1436 | Cl | 4-ClPh— | 1.17(3H, s), 2.41(1H, d, J=13.9Hz), 2.56(1H, d, J=13.9Hz), 2.63-2.73(2H, m), 2.76-2.92(2H, m), 3.08-3.18(4H, m), 3.40(1H, s), 4.01(2H, s), 6.80-6.96(6H, m), 7.14-7.24(2H, m), 8.06(1H, s). |
| 1437 | Br | 4-CF₃PhCH₂— | 1.16(3H, s), 2.39(1H, d, J=13.9Hz), 2.55(1H, d, J=13.9Hz), 2.65-2.78(2H, m), 2.84-2.92(2H, m), 3.02-3.14(4H, m), 3.46(1H, s), 4.01(2H, s), 5.08(2H, s), 6.89(4H, m), 7.48(2H, d, J=8.3Hz), 7.63(2H, d, J=8.3Hz), 8.12(1H, s). |
| 1438 | Br | 4-ClPhCH₂— | 1.16(3H, s), 2.39(1H, d, J=13.9Hz), 2.55(1H, d, J=13.9Hz), 2.63-2.78(2H, m), 2.80-2.96(2H, m), 3.04-3.12(4H, m), 3.47(1H, s), 4.01(2H, s), 4.98(2H, s), 6.88(4H, s), 7.35(4H, s), 8.12(1H, s). |
| 1439 | Cl | 4-CF₃OPhCH₂— | 1.16(3H, s), 2.40(1H, d, J=13.9Hz), 2.55(1H, d, J=13.9Hz), 2.65-2.76(2H, m), 2.78-2.92(2H, m), 3.04-3.12(4H, m), 3.45(1H, s), 4.00(2H, s), 5.0(2H, s), 6.89(4H, s), 7.22(2H, d, J=8.6Hz), 7.45(2H, d, J=8.6Hz), 8.06(1H, s). |
| 1440 | Cl | 4-CF₃OPh— | 1.18(3H, s), 2.41(1H, d, J=13.9Hz), 2.56(1H, d, J=13.9Hz), 2.65-2.76(2H, m), 2.78-2.88(2H, m), 3.06-3.20(4H, m), 3.39(1H, s), 4.02(2H, s), 6.84-7.00(6H, m), 7.14(2H, d, J=8.3Hz), 8.06(1H, s). |
| 1441 | Cl | 4-CF₃Ph— | 1.18(3H, s), 2.42(1H, d, J=13.9Hz), 2.57(1H, d, J=13.9Hz), 2.65-2.77(2H, m), 2.79-2.92(2H, m), 3.06-3.20(4H, m), 3.40(1H, s), 4.03(2H, s), 6.80-7.00(6H, m), 7.53(2H, d, J=8.6Hz), 8.07(1H, s). |

TABLE 81

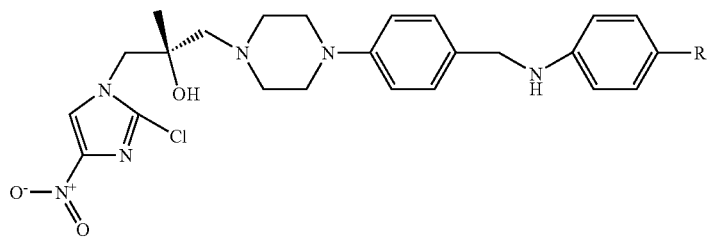

| Example | R | ¹H-NMR(CDCl₃) δppm |
|---|---|---|
| 1442 | Cl— | 1.17(3H, s), 2.40(1H, d, J=13.9Hz), 2.55(1H, d, J=13.9Hz), 2.65-2.92(4H, m), 3.08-3.24(4H, m), 3.40(2H, s), 4.00(2H, s), 4.20(2H, s), 6.54(2H, d, J=8.7Hz), 6.88(2H, d, J=8.7Hz), 7.09(2H, d, J=8.7Hz), 7.18-7.25(2H, m), 8.06(1H, s). |
| 1443 | CF₃O— | 1.16(3H, s), 2.41(1H, d, J=13.9Hz), 2.55(1H, d, J=13.9Hz), 2.65-2.92(4H, m), 3.08-3.25(4H, m), 3.44(2H, s), 4.02(2H, s), 4.21(2H, s), 6.57(2H, d, J=8.6Hz), 6.89(2H, d, J=8.6Hz), 7.01(2H, d, J=8.3Hz), 7.22(2H, d, J=8.3Hz), 8.06(1H, s). |

TABLE 82

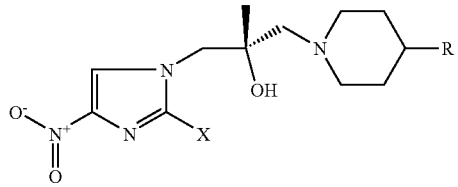

| Example | X | R | ¹N-NMR (CDCl₃) δppm |
|---|---|---|---|
| 1444 | Cl | | 1.15(3H, s), 1.51-1.86(4H, m), 2.27-2.57(3H, m), 2.75-2.92(2H, m), 3.00-3.16(2H, m), 3.56(1H, s), 4.17(2H, s), 6.90-7.02(4H, m), 7.10-7.25(2H, m), 7.56(2H, d, J=8.8Hz), 8.01(1H, s). |
| 1445 | Br | ![](N-methylpiperidine-O-phenyl-OCF₃) | 1.25(3H, s), 1.50-2.00(8H, m), 2.24-2.67(7H, m), 2.75-3.20(4H, m), 3.97(2H, s), 4.25-4.40(1H, m), 6.88(2H, d, J=8.8Hz), 7.13(2H, d, J=8.8Hz), 8.12(1H, s). |
| 1446 | Cl | | 1.14(3H, s), 1.76-1.93(4H, m), 2.24-2.52(5H, m), 2.74-2.86(1H, m), 2.95-3.07(1H, m), 3.98(2H, s), 7.17(2H, d, J=8.8Hz), 7.55(2H, d, J=8.8Hz), 8.05(1H, s). |
| 1447 | Cl | | 1.13(3H, s), 1.51-1.90(4H, m), 2.19-2.55(5H, m), 2.71-2.83(1H, m), 2.85-3.19(5H, m), 3.51-3.83(4H, m), 3.98(2H, s), 6.90(2H, d, J=8.3Hz), 7.13(2H, d, J=8.3Hz), 8.05(1H, s). |
| 1448 | Cl | -phenyl-Cl) | 1.15(3H, s), 1.39-1.83(5H, m), 2.33-2.62(3H, m), 3.00-3.15(2H, m), 3.49-3.61(2H, m), 4.17(2H, s), 6.97-7.05(4H, m), 7.21-7.24(2H, m), 7.53-7.58(2H, m), 8.08(1H, s) |

TABLE 82-continued

| Example | X | R | ¹N-NMR (CDCl₃) δppm |
|---|---|---|---|
| 1449 | Cl | (4-methylphenyl)-O-CH₂-(4-OCF₃-phenyl) | 1.14(3H, s), 1.61-1.81(5H, m), 2.34-2.57(3H, m), 2.77-2.84(2H, m), 3.01-3.06(2H, m), 3.99(2H, s), 5.04(2H, s), 6.89-6.95(2H, m), 7.11-7.25(4H, m), 7.43-7.48(2H, m), 8.09(1H, s) |
| 1450 | Cl | (4-methylphenyl)-O-CH₂-(4-CF₃-phenyl) | 1.14(3H, s), 1.45-1.80(5H, m), 2.38-2.60(3H, m), 2.78-2.90(2H, m), 3.01-3.06(2H, m), 3.98(2H, s), 5.11(2H, s), 6.89-6.93(2H, m), 7.12-7.18(2H, m), 7.52-7.55(2H, m), 7.62-7.65(2H, m), 8.08(1H, s) |
| 1451 | Cl | (4-methylphenyl)-O-CH₂-(4-Cl-phenyl) | 1.14(3H, s), 1.38-1.80(5H, m), 2.28-2.60(3H, m), 2.77-2.93(2H, m), 3.02-3.08(2H, m), 3.98(2H, s), 5.01(2H, s), 6.84-6.92(2H, m), 7.11-7.16(2H, m), 7.32-7.36(4H, m), 8.08(1H, s) |

TABLE 83

| Example | R1 | R2 | ¹H-NMR(CDCl₃) δppm |
|---|---|---|---|
| 1452 | piperazine-N-C(=O)-O-tBu | CH₃ | 1.13(3H, s), 1.48(9H, s), 2.42(3H, s), 2.43(2H, s), 3.03-3.13(4H, m), 3.42(1H, d, J=10.7Hz), 3.50-3.63(5H, m), 3.85(2H, s), 6.84(2H, d, J=7.1Hz), 7.11(2H, d, J=7.1Hz), 7.88(1H, s). |
| 1453 | piperazine-N-C(=O)-O-tBu | C₂H₅ | 1.06-1.11(6H, m), 1.48(9H, s), 2.41(1H, d, J=13.2Hz), 2.55(1H, d, J=13.2Hz), 2.64-2.68(2H, m), 3.10-3.13(4H, m), 3.42(1H, d, J=13.2Hz), 3.57-3.60(4H, m), 3.69(1H, d, J=13.2Hz), 3.79(2H, s), 6.83-6.86(2H, m), 7.09-7.12(2H, m), 7.84(1H, s). |

Example 1454

Production of (S)-2-methyl-6-nitro-2-{4-[1-(4-trifluoromethoxyphenyl)piperidin-4-yl]piperazin-1-ylmethyl}-2,3-dihydroimidazo[2,1-b]oxazole (S)-1-(2-bromo-4-nitroimidazol-1-yl)-2-methyl-3-{4-[1-(4-trifluoromethoxyphenyl)piperidin-4-yl]piperazin-1-yl}propan-2-ol (790 mg, 1.34 mmol) was dissolved in N,N-dimethylformamide (4 ml), sodium hydride (69 mg, 1.74 mmol) was added while cooling on ice, and the solution was stirred at the same temperature for 1 hour. To the reaction mixture, ethyl acetate (1.3 ml) and water (10 ml) were added in this order, and the precipitated crystals were filtered off and washed with water. The crystals were purified by silica gel column chromatography (methylene chloride/methanol=10/1) and recrystallized from ethyl acetate/isopropyl ether to obtain (S)-2-methyl-6-nitro-2-{4-[1-(4-trifluoromethoxyphenyl)piperidin-4-yl]piperazin-1-ylmethyl}-2,3-dihydroimidazo[2,1-b]oxazole (270 mg, yield 40%) as a white powder.

Melting point 180-181.5° C.

Following compounds were produced in the same manner.

Example 1455

(S)-2-{4-[4-(4-chlorophenyl)piperazin-1-yl]piperidin-1-ylmethyl}-2-methyl-6-nitro-2,3-dihydroimidazo[2,1-b]oxazole Yield 34% Melting point 226-228° C.

Example 1456

(S)-2-methyl-6-nitro-2-{4-[4-(4-trifluoromethoxyphenyl)piperazin-1-yl]piperidin-1-ylmethyl}-2,3-dihydroimidazo[2,1-b]oxazole Yield 23% Melting point 193-194° C.

Example 1457

(S)-2-{4-[4-(4-chlorobenzyl)piperazin-1-yl]piperidin-1-ylmethyl}-2-methyl-6-nitro-2,3-dihydroimidazo[2,1-b]oxazole Yield 25% Melting point 148-149° C.

Example 1458

(S)-2-methyl-6-nitro-2-{4-[4-(4-trifluoromethoxybenzyl)piperazin-1-yl]piperidin-1-ylmethyl}-2,3-dihydroimidazo[2,1-b]oxazole Yield 21% Melting point 142-143° C.

Example 1459

(S)-(4-chlorophenyl)-{4-[1-(2-methyl-6-nitro-2,3-dihydroimidazo[2,1-b]oxazol-2-ylmethyl)piperidin-4-yl]piperazin-1-yl}methanone Yield 29% Melting point 174-175° C.

Example 1460

(S)-{4-[1-(2-methyl-6-nitro-2,3-dihydroimidazo[2,1-b]oxazol-2-ylmethyl)piperidin-4-yl]piperazin-1-yl}-(4-trifluoromethoxyphenyl)methanone Yield 29% Melting point 137-138° C.

Example 1461

(S)-2-{4-[1-(4-chlorobenzyl)piperidin-4-yl]piperazin-1-ylmethyl}-2-methyl-6-nitro-2,3-dihydroimidazo[2,1-b]oxazole Yield 24% Melting point 168-169° C.

Example 1462

(S)-2-methyl-6-nitro-2-{4-[1-(4-trifluoromethoxybenzyl)piperidin-4-yl]piperazin-1-ylmethyl}-2,3-dihydroimidazo[2,1-b]oxazole Yield 27% Melting point 140-141° C.

Example 1463

(S)-(4-chlorophenyl)-{4-[4-(2-methyl-6-nitro-2,3-dihydroimidazo[2,1-b]oxazol-2-ylmethyl)piperazin-1-yl]piperidin-1-yl}methanone Yield 30% Melting point 218-220° C.

Example 1464

(S)-{4-[4-(2-methyl-6-nitro-2,3-dihydroimidazo[2,1-b]oxazol-2-ylmethyl)piperazin-1-yl]piperidin-1-yl}-(4-trifluoromethoxyphenyl)methanone Yield 27% Melting point 133-134° C.

Example 1465

(S)-1'-(2-methyl-6-nitro-2,3-dihydroimidazo[2,1-b]oxazol-2-ylmethyl)-4-(4-trifluoromethoxyphenoxy)-[1,4']bipiperidinyl Yield 41% Melting point 131-132° C.

Example 1466

Production of tert-butyl (S)-4-[4-(2-methyl-6-nitro-2,3-dihydroimidazo[2,1-b]oxazol-2-ylmethyl)piperazin-1-yl]piperidine-1-carboxylate A mixture of (R)-2-chloro-4-nitro-1-(2-methyl-2-oxiranylmethyl)imidazole (3 g, 13.79 mmol), tert-butyl 4-piperazin-1-yl-piperidine-1-carboxylate (3.9 g, 14.48 mmol), and ethanol (30 ml) was stirred at 50° C. for 9 hours. The reaction mixture was concentrated, and the residue was purified by silica gel column chromatography (methylene chloride/methanol=10/1) to obtain a yellow amorphous form. The amorphous form was dissolved in N,N-dimethylformamide (18 ml), sodium hydride (651 mg, 16.28 mmol) was added while cooling on ice, and the resultant solution was stirred at the same temperature for 1 hour. To the reaction mixture, ethyl acetate (6 ml) and water (42 ml) were added in this order, and the precipitated crystals were filtered off and washed with water. The filtrate was recrystallized from 2-propanol (20 ml)/water (60 ml) to obtain tert-butyl (S)-4-[4-(2-methyl-6-nitro-2,3-dihydroimidazo[2,1-b]oxazol-2-ylmethyl)piperazin-1-yl]piperidine-1-carboxylate (4.08 g, 66%) as a light yellow powder.

Melting point 181-182° C.

The following compound was produced in the same manner.

Example 1467

Tert-butyl (S)-4-[1-(2-methyl-6-nitro-2,3-dihydroimidazo[2,1-b]oxazol-2-ylmethyl)piperidin-4-yl]piperazine-1-carboxylate Yield 56% Melting point 184-185° C.

Example 1468

Production of 4-trifluoromethoxybenzyl (S)-4-[4-(2-methyl-6-nitro-2,3-dihydroimidazo[2,1-b]oxazol-2-ylmethyl)piperazin-1-yl]piperidine-1-carboxylate A mixture of 4-(trifluoromethoxy)benzyl alcohol (480 mg, 2.50 mmol), 1,1'-carbonylbis-1H-imidazole (405 mg, 2.50 mmol), and N,N-dimethyl-formamide (3 ml) was stirred at room temperature for 14 hours.

Meanwhile, tert-butyl (S)-4-[4-(2-methyl-6-nitro-2,3-dihydroimidazo[2,1-b]oxazol-2-ylmethyl)-piperazin-1-yl]piperidine-1-carboxylate (750 mg, 1.66 mmol) was dissolved in methylene chloride (5 ml), trifluoroacetic acid (5 ml) was added, and the resultant solution was stirred at room temperature for 14 hours. The reaction mixture was concentrated. To the residue, methanol (5 ml) and triethylamine (5 ml) were added, and the mixture was stirred at room temperature for 10 minutes and then concentrated. The residue was dissolved in N,N-dimethylformamide (5 ml). The solution was added to the above described N,N-dimethylformamide solution followed by stirring at 50° C. for 3 hours.

The reaction mixture was allowed to return to room temperature, poured in water (40 ml), and extracted with ethyl acetate (30 ml) twice. The organic phases were combined, washed with water (40 ml) twice followed by a saturated saline solution (30 ml), and then dried over sodium sulfate. After filtration, the filtrate was concentrated, and the residue was purified by silica gel column chromatography (methylene chloride/methanol=10/1) and then recrystallized from ethyl acetate/isopropyl ether to obtain 4-trifluoromethoxybenzyl (S)-4-[4-(2-methyl-6-nitro-2,3-dihydroimidazo[2,1-b]oxazol-2-ylmethyl)piperazin-1-yl]piperidine-1-carboxylate (545 mg, 58%) as a light brown powder.

Melting point 105-106° C.

The following compound was produced in the same manner.

Example 1469

4-Trifluoromethoxybenzyl (S)-4-[1-(2-methyl-6-nitro-2,3-dihydroimidazo[2,1-b]oxazol-2-ylmethyl)piperidin-4-yl]piperazin-1-carboxylate Yield 64% Melting point 110-111° C.

Example 1470

Production of (S)-2-methyl-6-nitro-2-[4-{1-[3-(4-trifluoromethoxyphenyl)-2-propenyl]piperidin-4-yl}piperazin-1-ylmethyl]-2,3-dihydroimidazo[2,1-b]oxazole Tert-butyl (S)-4-[4-(2-methyl-6-nitro-2,3-dihydroimidazo[2,1-b]oxazol-2-ylmethyl)piperazin-1-yl]piperidine-1-carboxylate (750 mg, 1.66 mmol) was dissolved in methylene chloride (5 ml), trifluoroacetic acid (5 ml) was added followed by stirring at room temperature for 1.5 hours. The reaction mixture was concentrated. To the residue, methylene chloride (5 ml) and triethylamine (5 ml) were added, and the mixture was stirred at room temperature for 10 minutes and then concentrated. The residue was dissolved in 1,2-dichloroethane (20 ml), 3-(4-trifluoromethoxyphenyl)propenal (396 mg, 1.83 mmol) and sodium triacetoxyborohydride (564 mg, 2.66 mmol) were added followed by stirring at room temperature for 3.5 hours. The reaction solution was washed with a saturated sodium hydrogencarbonate solution (15 ml), water (20 ml), and a saturated saline solution (20 ml) in this order, and then dried over sodium sulfate. After filtration, the filtrate was concentrated, and the residue was purified by silica gel column chromatography (methylene chloride/methanol=10/1) and then recrystallized from methanol/water to obtain (S)-2-methyl-6-nitro-2-[4-{1-[3-(4-trifluoromethoxyphenyl)-2-propenyl]piperidin-4-yl}piperazin-1-ylmethyl]-2,3-dihydroimidazo[2,1-b]oxazole (446 mg, 49%) as a light yellow powder.

Melting point 157-158° C.

Following compounds were produced in the same manner.

Example 1471

(S)-2-methyl-6-nitro-2-[4-{4-[3-(4-trifluoromethoxyphenyl)-2-propenyl]piperazin-1-yl}piperidin-1-ylmethyl]-2,3-dihydroimidazo[2,1-b]oxazole Melting point 174-175° C.

Example 1472

(S)-2-methyl-6-nitro-2-{4-[4-(4-trifluoromethoxyphenoxy)phenyl]piperazin-1-ylmethyl}-2,3-dihydroimidazo[2,1-b]oxazole 4-toluenesulfonate Melting point 146.1-148.6° C.

Example 1473

(S)-2-methyl-6-nitro-2-{4-[4-(4-trifluoromethoxyphenoxy)phenyl]piperazin-1-ylmethyl}-2,3-dihydroimidazo[2,1-b]oxazole hydrochloride Melting point 133-137° C.

TABLE 84

| Example | R1 | R2 | $^1$H-NMR(CDCl$_3$) δppm |
|---|---|---|---|
| 1474 | ![structure: -C(=O)O-C(CH3)2-CH3] | CH$_3$ | 1.48(9H, s), 1.55(3H, s), 2.36(3H, s), 2.61(1H, d, J=12.3Hz), 2.80(1H, d, J=12.3Hz), 3.03-3.15(4H, m), 3.41(1H, d, J=10.8Hz), 3.48-3.60(5H, m), 3.69(1H, d, J=8.1Hz), 4.08(1H, d, J=8.1Hz), 6.85(2H, d, J=7.1Hz), 7.06(1H, d, J=7.1Hz), 7.46(1H, s). |
| 1475 | ![structure: -C(=O)O-C(CH3)2-CH3] | C$_2$H$_5$ | 0.97(3H, t, J=7.1Hz), 1.49(9H, s), 1.53(3H, s), 2.54-2.78(3H, m), 2.93-2.96(1H, m), 3.10-3.13(4H, m), 3.39-3.43(1H, m), 3.57-3.67(6H, m), .396(1H, d, J=9.8Hz), 6.83-6.85(2H, m), 7.02-7.05(2H, m), 7.43(1H, s). |

TABLE 84-continued

| Example | R1 | R2 | $^1$H-NMR(CDCl$_3$) δppm |
|---|---|---|---|
| 1476 | H | CH$_3$ | 1.53(3H, s), 2.37(3H, s), 2.60(1H, d, J=12.2Hz), 2.78(1H, d, J=12.2Hz), 2.98-3.18(8H, m), 3.40(1H, d, J=10.8Hz), 3.55(1H, d, J=10.8Hz), 3.66(1H, d, J=8.1Hz), 4.04(1H, d, J=8.1Hz), 6.85(2H, d, J=7.1Hz), 7.06(2H, d, J=7.1Hz), 7.45(1H, s). |
| 1477 | H | C$_2$H$_5$ | 0.98(3H, t, J=7.1Hz), 1.53(3H, s), 2.55-2.75(3H, m), 2.93-2.95(1H, m), 3.15-3.18(4H, m), 3.24-3.28(4H, m), 3.37-3.43(1H, m), 3.62-3.67(2H, m), 3.94(1H, d, J=9.8Hz), 6.82-6.87(2H, m), 7.02-7.05(2H, m), 7.44(1H, s). |

TABLE 85

| Example | R1 | R2 | mp (° C.) |
|---|---|---|---|
| 1478 | —CH$_3$ | 4-ClPh— | 202.6-204.0 dec |
| 1479 | —CH$_3$ | 4-CF$_3$PhCH$_2$— | 172.0-174.2 |
| 1480 | —CH$_3$ | 4-ClPhCH$_2$— | 227.0-228.3 dec |
| 1481 | —CH$_3$ | 4-CF$_3$OPhCH$_2$— | 176-179.5 |
| 1482 | —CH$_3$ | 4-CF$_3$OPh— | 114.1-116.6 |
| 1483 | —CH$_3$ | 4-CF$_3$Ph— | 105-110 |

TABLE 86

| Example | R1 | R2 | R3 | mp (° C.) |
|---|---|---|---|---|
| 1484 | —CH$_3$ | —CH$_3$ | 4-ClPh— | 126.2-127.5 |
| 1485 | —CH$_3$ | —CH$_3$ | 4-CF$_3$OPh— | 103.0-106.6 |
| 1486 | —CH$_3$ | —H | 4-ClPh— | 209.8-210.3 dec |
| 1487 | —CH$_3$ | —H | 4-CF$_3$OPh— | 110.0-113.5 |

TABLE 87

| Example | R1 | R2 | mp (° C.) or $^1$H NMR |
|---|---|---|---|
| 1488 | —CH$_3$ | (4-methylphenyl 4-trifluoromethylphenyl ether group) | 110.6-111.7 |
| 1489 | —CH$_3$ | (N-(4-trifluoromethoxyphenyl)acetamide group) | $^1$H NMR(CDCl$_3$) δppm 1.56-1.71(7H, m), 2.16(3H, m), 2.57(1H, d, J=14.9Hz), 2.76-3.10(3H, m), 3.93(1H, d, J=9.8Hz), 4.36(1H, d, J=9.8Hz), 7.12(2H, d, J=8.5Hz), 7.55-7.68(3H, m), 9.04(1H, s). |

TABLE 87-continued

| Example | R1 | R2 | mp (° C.) or ¹H NMR |
|---|---|---|---|
| 1490 | —CH₃ | 1-acetyl-4-[4-(trifluoromethoxy)phenyl]piperazine | ¹H NMR(CDCl₃) δppm 1.48-1.68(4H, m), 1.75-1.95(1H, m), 2.19-2.56(4H, m), 2.75-3.19(9H, m), 3.53-3.77(4H, m), 3.88(1H, d, J=9.7Hz), 4.36(1H, d, J=9.7Hz), 6.89(2H, d, J=8.5Hz), 7.13(2H, d, J=8.5Hz), 7.68(1H, s). |
| 1491 | —CH₃ | 4-methylphenyl {[4-(trifluoromethoxy)phenyl]methyl} ether | 148.4-149.7 |
| 1492 | —CH₃ | 4-methylphenyl {[4-(trifluoromethyl)phenyl]methyl} ether | 160.4-161.8 |
| 1493 | —CH₃ | 4-methylphenyl [(4-chlorophenyl)methyl] ether | 164.4-167.3 dec |
| 1494 | —CH₃ | N-methyl-N-(4-methylphenyl)-4-(trifluoromethoxy)benzylamine | 140.2-142.8 |

TABLE 88

| Example | R1 | R2 | R3 | mp (° C.) or ¹H NMR |
|---|---|---|---|---|
| 1495 | —CH₃ | 4-{4-[(4-chlorobenzyl)]piperazin-1-yl}phenyl | —CH₃ | 143.1-145.8 |

TABLE 88-continued

| Example | R1 | R2 | R3 | mp (° C.) or ¹H NMR |
|---|---|---|---|---|
| 1496 | —CH₃ | 4-ethylphenyl-piperazine-N-CH₂-(4-chlorophenyl) | —C₂H₅ | ¹H NMR(CDCl₃) δ 0.97(3H, t, J=7.1Hz), 1.51(3H, s), 2.58-2.76(7H, m), 2.89(1H, d, J=14.9Hz), 3.17-3.20(4H, m), 3.38(1H, d, J=13.3Hz), 3.54-3.64(4H, m), 3.89(1H, d, J=9.8Hz), 6.82-6.85(2H, m), 7.01-7.04(2H, m), 7.27-7.30(4H, m), 7.41(1H, s). |
| 1497 | —CH₃ | 4-ethylphenyl-piperidin-4-yl-N(ethyl)-(4-chlorophenyl) | —CH₃ | 100.7-103.0 |

The following compounds were produced in the same manner as in Example 649.

TABLE 89

| Example | R | Solvent | ¹H-NMR δppm |
|---|---|---|---|
| 1498 | —Cl | DMSO-d₆ | 1.32-1.50(2H, m), 1.55-1.75(2H, m), 2.86-3.02(2H, m), 3.36-3.50(2H, m), 4.05(2H, s), 4.93(1H, s), 6.95(2H, d, J=8.9Hz), 7.21(2H, d, J=8.9Hz), 8.35(1H, s). |
| 1499 | —OCF₃ | DMSO-d₆ | 1.51-1.67(2H, m), 1.76-1.94(2H, m), 2.02(1H, s), 2.96-3.12(2H, m), 3.37-3.56(2H, m), 4.07(2H, s), 6.9(2H, d, J=8.9Hz), 7.12(2H, d, J=8.9Hz), 8.00(1H, s). |
| 1500 | —N(CH₃)-(4-OCF₃-phenyl) | CDCl₃ | 1.57-1.71(2H, m), 1.78-1.98(2H, m), 2.92-3.08(2H, m), 3.24(3H, s), 3.35-3.51(2H, m), 4.09(2H, s), 6.74(2H, d, J=8.9Hz), 6.88-7.10(6H, m), 8.02(1H, s). |
| 1501 | —O-(4-OCF₃-phenyl) | CDCl₃ | 1.55-1.69(2H, m), 1.80-1.98(2H, m), 2.92-3.08(2H, m), 3.33-3.49(2H, m), 4.09(2H, s), 6.82-6.98(6H, m), 7.14(2H, d, J=8.9Hz), 8.02(1H, s). |

TABLE 89-continued

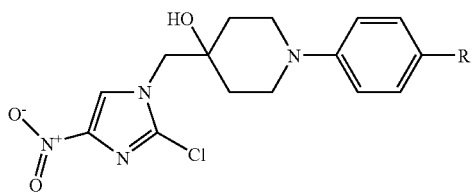

| Example | R | Solvent | ¹H-NMR δppm |
|---|---|---|---|
| 1502 | ![structure with N-methylpiperidine-O-phenyl-OCF3] | CDCl₃ | 1.53-1.67(2H, m), 1.80-2.16(6H, m), 2.84-3.06(4H, m), 3.24-3.45(4H, m), 4.11(2H, s), 4.33-4.47(1H, m), 6.80-6.92(6H, m), 7.14(2H, d, J=8.9Hz), 8.00(1H, s). |
| 1503 | ![structure with N-methylpiperazine-phenyl-OCF3] | CDCl₃ | 1.53-1.65(2H, m), 1.82-1.98(2H, m), 2.84-3.00(2H, m), 3.14-3.39(10H, m), 4.07(2H, s), 6.84-6.96(6H, m), 7.14(2H, d, J=8.6Hz), 8.01(1H, s). |

The following compounds were produced in the same manner as in Example 652.

TABLE 90

| Example | R1 | mp (° C.) |
|---|---|---|
| 1504 | —Cl | 242.0-245.0 |
| 1505 | —OCF₃ | 235.9-236.8 dec. |
| 1506 | ![H3C-N(CH3)-phenyl-OCF3] | 214.0-215.1 dec. |
| 1507 | ![MeO-phenyl-OCF3] | 227.3-229.4 |
| 1508 | ![N-methylpiperidine-O-phenyl-OCF3] | 237.6-238.4 |
| 1509 | ![N-methylpiperazine-phenyl-OCF3] | 254.2-256.8 |

The following compounds were produced in the same manner as in Example 128.

Example 1510

(R)-2-methyl-6-nitro-2-{4-[1-(4-trifluoromethoxy-benzyl)piperidin-4-yl]phenoxymethyl}-2,3-dihy-droimidazo[2,1-b]oxazole Melting point 186-188° C.

Example 1511

(R)-6-nitro-2-{4-[4-(4-trifluoromethoxyphenoxy)-piperidin-1-yl]phenoxymethyl}-2,3-dihydroimidazo [2,1-b]oxazole Melting point 157-160° C.

Example 1512

(R)-2-methyl-6-nitro-2-{4-[3-(4-trifluoromethox-yphenoxy)-8-azabicyclo[3.2.1]octan-8-yl]phe-noxymethyl}-2,3-dihydroimidazo[2,1-b]oxazole 4-toluenesulfonate Melting point 207.2. -208.0° C. (decomposition).

Example 1513

2-Methyl-6-nitro-2-[4-(4-trifluoromethoxyphenoxy)-benzyloxymethyl]-2,3-dihydroimidazo[2,1-b]ox-azole Melting point 107.9-109.3° C.

Example 1514

6-Nitro-2-{4-[4-(4-trifluoromethoxyphenoxy)piperi-din-1-yl]phenoxymethyl}-2,3-dihydroimidazo[2,1-b] oxazole Melting point 173.2-177.3° C.

Example 1515

2-Methyl-6-nitro-2-{4-[4-(4-chlorophenoxy)piperidin-1-yl]phenoxymethyl}-2,3-dihydroimidazo[2,1-b]oxazole Melting point 151.0-152.3° C.

Example 1516

(S)-2-methyl-6-nitro-2-{4-[4-(4-trifluoromethoxyphenoxy)piperidin-1-yl]phenoxymethyl}-2,3-dihydroimidazo[2,1-b]oxazole Melting point 199.0-200.5° C.

TABLE 91

| Example | R1 | R2 | mp (° C.) |
|---|---|---|---|
| 1517 | —CH₃ | —Cl | 183.8-184 |
| 1518 | —CH₃ | —CF₃ | 179.4-180.9 |
| 1519 | —CH₃ | —F | 190.2-192.8 |
| 1520 | —CH₃ | —OCH₃ | 193.3-194.5 |
| 1521 | —CH₃ | —CH₃ | 198.2-201.1 dec |
| 1522 | —CH₃ | —H | 194.5-197.5 |
| 1523 | —CH₃ | —CN | 196.2-198.5 dec |
| 1524 | —H | —OCF₃ | 157.0-160.0 |
| 1525 | —H | —Cl | 166.5-171.0 dec |

TABLE 92

| Example | R1 | R2 | R3 | R4 | R5 | R6 | MS (M + 1) |
|---|---|---|---|---|---|---|---|
| 1526 | —CH₃ | —OCH₃ | —H | —H | —H | —H | 481 |
| 1527 | —CH₃ | —H | —OCH₃ | —H | —H | —H | 481 |
| 1528 | —CH₃ | —H | —H | —OCH₃ | —H | —H | 481 |
| 1529 | —CH₃ | —H | —H | —H | —OCH₃ | —OCH₃ | 511 |
| 1530 | —CH₃ | —OCH₃ | —H | —H | —H | —OCH₃ | 511 |
| 1531 | —CH₃ | —H | —H | —OCH₃ | —OCH₃ | —H | 511 |
| 1532 | —CH₃ | —H | —OCH₃ | —H | —OCH₃ | —H | 511 |
| 1533 | —CH₃ | —H | —H | —H | —H | —H | 451 |
| 1534 | —CH₃ | —H | —H | —H | —H | —Cl | 485 |
| 1535 | —CH₃ | —H | —H | —H | —Cl | —H | 485 |
| 1536 | —CH₃ | —H | —H | —Cl | —H | —H | 485 |
| 1537 | —CH₃ | —Cl | —Cl | —H | —H | —H | 519 |
| 1538 | —CH₃ | —Cl | —H | —Cl | —H | —H | 519 |
| 1539 | —CH₃ | —Cl | —H | —H | —Cl | —H | 519 |
| 1540 | —CH₃ | —Cl | —H | —H | —H | —Cl | 519 |
| 1541 | —CH₃ | —H | —Cl | —Cl | —H | —H | 519 |
| 1542 | —CH₃ | —H | —Cl | —H | —Cl | —H | 519 |
| 1543 | —CH₃ | —H | —H | —H | —H | —CH₃ | 465 |
| 1544 | —CH₃ | —H | —H | —H | —CH₃ | —H | 465 |
| 1545 | —CH₃ | —H | —H | —CH₃ | —H | —H | 465 |
| 1546 | —CH₃ | —CH₃ | —CH₃ | —H | —H | —H | 479 |
| 1547 | —CH₃ | —CH₃ | —H | —CH₃ | —H | —H | 479 |
| 1548 | —CH₃ | —CH₃ | —H | —H | —CH₃ | —H | 479 |
| 1549 | —CH₃ | —CH₃ | —H | —H | —H | —CH₃ | 479 |
| 1550 | —CH₃ | —H | —CH₃ | —CH₃ | —H | —H | 479 |
| 1551 | —CH₃ | —H | —CH₃ | —H | —CH₃ | —H | 479 |
| 1552 | —CH₃ | —H | —H | —H | —H | —F | 469 |
| 1553 | —CH₃ | —H | —H | —H | —F | —H | 469 |

TABLE 92-continued

| Example | R1 | R2 | R3 | R4 | R5 | R6 | MS (M + 1) |
|---|---|---|---|---|---|---|---|
| 1554 | —$CH_3$ | —H | —H | —F | —H | —H | 469 |
| 1555 | —$CH_3$ | —F | —F | —H | —H | —H | 487 |
| 1556 | —$CH_3$ | —F | —H | —F | —H | —H | 487 |
| 1557 | —$CH_3$ | —F | —H | —H | —F | —H | 487 |
| 1558 | —$CH_3$ | —F | —H | —H | —H | —F | 487 |
| 1559 | —$CH_3$ | —H | —F | —F | —H | —H | 487 |
| 1560 | —$CH_3$ | —$CO_2C_2H_5$ | —H | —H | —H | —H | 523 |
| 1561 | —$CH_3$ | —H | —$CO_2C_2H_5$ | —H | —H | —H | 523 |
| 1562 | —$CH_3$ | —H | —H | —$CO_2C_2H_5$ | —H | —H | 523 |
| 1563 | —$CH_3$ | —CN | —H | —H | —H | —H | 476 |
| 1564 | —$CH_3$ | —H | —CN | —H | —H | —H | 476 |
| 1565 | —$CH_3$ | —H | —H | —CN | —H | —H | 476 |
| 1566 | —$CH_3$ | —H | —H | —H | —H | —$CF_3$ | 519 |
| 1567 | —$CH_3$ | —H | —H | —H | —$CF_3$ | —H | 519 |

TABLE 93

| Example | R1 | R2 | R3 | R4 | R5 | R6 | MS (M + 1) |
|---|---|---|---|---|---|---|---|
| 1568 | —$CH_3$ | —H | —H | —$CF_3$ | —H | —H | 519 |
| 1569 | —$CH_3$ | —H | —H | —H | —H | —$OCF_3$ | 535 |
| 1570 | —$CH_3$ | —H | —F | —H | —F | —H | 487 |
| 1571 | —$CH_3$ | —H | —H | —H | —$OCF_3$ | —H | 535 |
| 1572 | —$CH_3$ | —H | —H | —$OCF_3$ | —H | —H | 535 |
| 1573 | —$CH_3$ | —H | —H | —H | —H | —$OCH(CH_3)_2$ | 509 |
| 1574 | —$CH_3$ | —H | —H | —$CH_3$ | —H | —$CO_2C_2H_5$ | 537 |
| 1575 | —$CH_3$ | —H | —H | —$OCH_3$ | —H | —$CO_2CH_3$ | 539 |
| 1576 | —$CH_3$ | —H | —H | —Br | —H | —F | 547 |
| 1577 | —$CH_3$ | —H | —$CH_3$ | —H | —H | —F | 483 |
| 1578 | —$CH_3$ | —H | —H | —$C_3H_7$ | —H | —H | 493 |
| 1579 | —$CH_3$ | —H | —H | —Cl | —F | —H | 503 |
| 1580 | —$CH_3$ | —H | —H | —$NO_2$ | —H | —F | 514 |
| 1581 | —$CH_3$ | —H | —H | —$CH_2CH=CH_2$ | —H | —$OCH_3$ | 521 |
| 1582 | —$CH_3$ | —H | —H | —H | —$C_6H_5$ | —H | 527 |
| 1583 | —$CH_3$ | —H | —H | —H | —$N(C_2H_5)_2$ | —H | 522 |
| 1584 | —$CH_3$ | —H | —$CH=CHCH_3$(cis) | —H | —H | —$OC_2H_5$ | 535 |
| 1585 | —$CH_3$ | —H | —H | —$CH(CH_3)_2$ | —H | —H | 493 |
| 1586 | —$CH_3$ | —H | —H | —H | —$NHCONH_2$ | —H | 509 |
| 1587 | —$CH_3$ | —H | —H | —$CH_2CH_2COCH_3$ | —H | —H | 521 |
| 1588 | —$CH_3$ | —H | —H | —H | —$NHC_6H_5$ | —H | 542 |
| 1589 | —$CH_3$ | —H | —H | —$NH_2$ | —H | —Cl | 500 |
| 1590 | —$CH_3$ | —H | —H | —$CH_2CO_2CH_3$ | —H | —H | 523 |
| 1591 | —$CH_3$ | —H | —H | —$OCH_3$ | —H | —Cl | 515 |
| 1592 | —$CH_3$ | —H | —H | —H | —$CO_2CH_3$ | —H | 509 |
| 1593 | —$CH_3$ | —H | —H | —$COCH_3$ | —H | —$CONH_2$ | 536 |
| 1594 | —$CH_3$ | —H | —H | —$COC_2H_5$ | —H | —H | 507 |
| 1595 | —$CH_3$ | —H | —H | —$COCH_3$ | —H | —$CH_3$ | 507 |
| 1596 | —$CH_3$ | —H | —H | —$COCH_3$ | —OH | —H | 509 |
| 1597 | —$CH_3$ | —H | —H | —$NHCOCH_3$ | —H | —H | 508 |
| 1598 | —$CH_3$ | —H | —$CH_3$ | —$CH_3$ | —$CH_3$ | —H | 493 |
| 1599 | —$CH_3$ | —H | —H | —H | —H | —$CH_2C_6H_5$ | 541 |
| 1600 | —$CH_3$ | —H | —$OCH_3$ | —H | —H | —$CO_2CH_3$ | 539 |

TABLE 93-continued
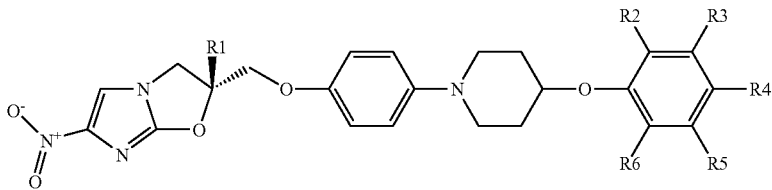
| Example | R1 | R2 | R3 | R4 | R5 | R6 | MS (M + 1) |
|---|---|---|---|---|---|---|---|
| 1601 | —CH$_3$ | —H | —H | —SCH$_3$ | —H | —H | 497 |
| 1602 | —CH$_3$ | —H | —H | —CHF$_2$ | —H | —H | 517 |
TABLE 94
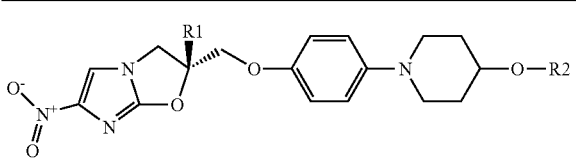
| Example | R1 | R2 | MS (M + 1) |
|---|---|---|---|
| 1603 | —CH$_3$ | | 495 |
| 1604 | —CH$_3$ | | 501 |
| 1605 | —CH$_3$ | | 507 |
| 1606 | —CH$_3$ | | 518 |
| 1607 | —CH$_3$ | | 518 |
| 1608 | —CH$_3$ | | 522 |
| 1609 | —CH$_3$ | | 519 |
TABLE 94-continued
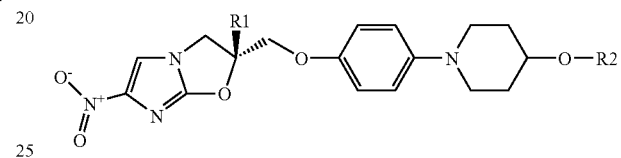
| Example | R1 | R2 | MS (M + 1) |
|---|---|---|---|
| 1610 | —CH$_3$ | | 531 |
| 1611 | —CH$_3$ | | 525 |
| 1612 | —CH$_3$ | | 502 |
TABLE 95
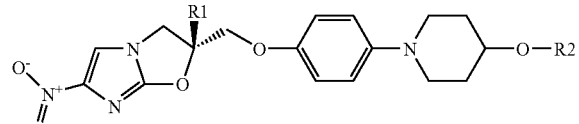
| Example | R1 | R2 | MS (M + 1) |
|---|---|---|---|
| 1613 | —CH$_3$ | | 502 |
| 1614 | —CH$_3$ | | 517 |

TABLE 95-continued
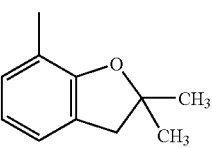
| Example | R1 | R2 | MS (M + 1) |
|---|---|---|---|
| 1615 | —CH₃ | 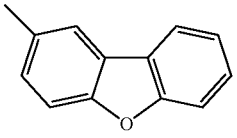 | 521 |
| 1616 | —CH₃ | 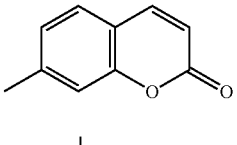 | 541 |
| 1617 | —CH₃ | 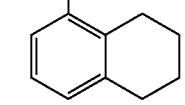 | 519 |
| 1618 | —CH₃ | 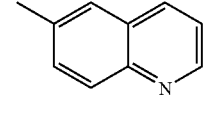 | 505 |
TABLE 95-continued
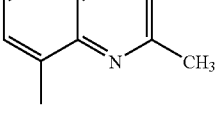
| Example | R1 | R2 | MS (M + 1) |
|---|---|---|---|
| 1619 | —CH₃ | 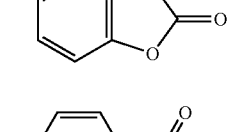 | 502 |
| 1620 | —CH₃ | 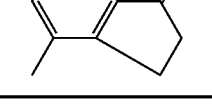 | 516 |
| 1621 | —CH₃ | 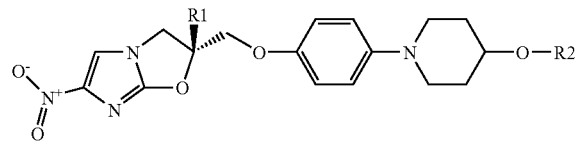 | 507 |
| 1622 | —CH₃ | 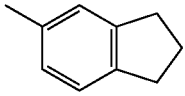 | 505 |
TABLE 96
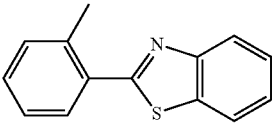
| Example | R1 | R2 | MS (M + 1) |
|---|---|---|---|
| 1623 | —CH₃ | 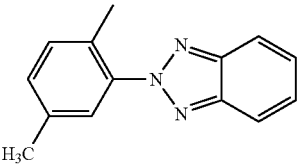 | 491 |
| 1624 | —CH₃ | | 584 |
| 1625 | —CH₃ | | 582 |

TABLE 96-continued
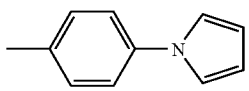
| Example | R1 | R2 | MS (M + 1) |
|---|---|---|---|
| 1626 | —CH₃ | 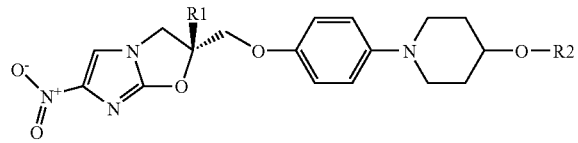 | 516 |
| 1627 | —CH₃ | 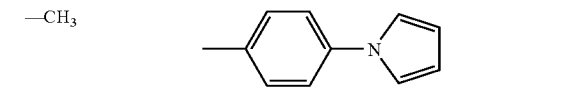 | 568 |
| 1628 | —CH₃ | 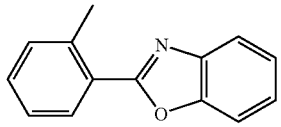 | 659 |
| 1629 | —CH₃ | 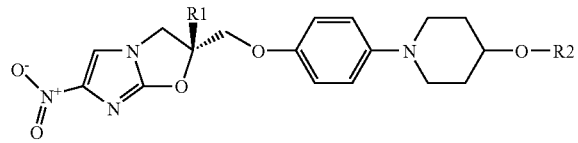 | 635 |
| 1630 | —CH₃ | 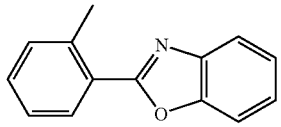 | 673 |
| 1631 | —CH₃ | 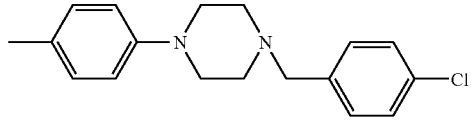 | 508 |
| 1632 | —CH₃ | 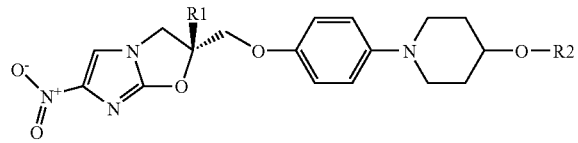 | 505 |

TABLE 97

Structure: imidazooxazole (nitro-substituted) with R1, -CH2-O-phenyl-N(piperidine)-O-R2

| Example | R1 | R2 | MS (M + 1) |
|---|---|---|---|
| 1633 | —CH₃ | 2-methylpyridine | 452 |
| 1634 | —CH₃ | 3-methylpyridine | 452 |
| 1635 | —CH₃ | 3-methylbenzo[d]isoxazole | 492 |
| 1636 | —CH₃ | 5-methylbenzo[c][1,2,5]oxadiazole | 493 |
| 1637 | —CH₃ | 3-methylquinoxaline | 503 |
| 1638 | —CH₃ | 4-methylcoumarin | — |

TABLE 98

Structure: imidazooxazole (O₂N-substituted) with R1, -CH2-O-phenyl(R2,R3)-N(piperazine)-N-R4

| Example | R1 | R2 | R3 | R4 | mp (° C.) or ¹H NMR |
|---|---|---|---|---|---|
| 1639 | —CH₃ | —H | —H | —CH₂C₆H₅ | 208-210.5 |
| 1640 | —CH₃ | —H | —H | 4-BrPhCH₂— | 213.5-215.4 |
| 1641 | —CH₃ | —H | —H | 4-BrPhCH₂OCO— | 185.4-188.5 |
| 1642 | —CH₃ | —H | —H | -cyclo-C₆H₁₁ | 255.4-257.9 dec |
| 1643 | —CH₃ | —H | —H | 4-CF₃PhCH=N— | 178.0-278.6 |
| 1644 | —CH₃ | —H | —H | 4-CF₃OPhOCO— | 226.5-226.8 |
| 1645 | —CH₃ | —H | —H | 4-CF₃PhCCCH₂OCO— | 186.4-187.7 |
| 1646 | —H | —H | —H | 4-CF₃OPh— | 232.0-234.5 |
| 1647 | —H | —H | —H | 4-CF₃OPhCH₂— | 171.4-172.9 |
| 1648 | —H | —H | —H | 4-ClPhCH₂— | 191.2-192.0 |
| 1649 | —H | —H | —H | (CH₃)₃COCO— | $^1$H NMR(CDCl₃) δ 1.48(9H, s), 2.99-3.04(4H, m), 3.55-3.60(4H, m), 4.22-4.37(2H, m), 4.39-4.49(2H, m), 5.56-5.63(1H, m), 6.79-6.91(4H, m), 7.63(1H, s). |

TABLE 99

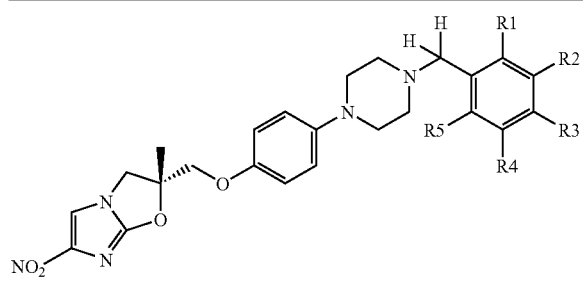

| Example | R1 | R2 | R3 | R4 | R5 | MS (M + 1) |
|---|---|---|---|---|---|---|
| 1650 | —H | —CF$_3$ | —H | —H | —H | 518 |
| 1651 | —H | —H | —NO$_2$ | —H | —H | 495 |
| 1652 | —H | —H | —CF$_3$ | —H | —H | 518 |
| 1653 | —H | —H | —CH$_3$ | —H | —H | 464 |
| 1654 | —H | —H | —CN | —H | —H | 475 |
| 1655 | —H | —H | —C$_6$H$_5$ | —H | —H | 526 |
| 1656 | —H | —H | —F | —H | —H | 468 |
| 1657 | —H | —Cl | —Cl | —H | —H | 518 |
| 1658 | —CF$_3$ | —H | —H | —H | —H | 518 |
| 1659 | —H | —H | —OCH$_3$ | —H | —H | 480 |
| 1660 | —H | —H | —SCH$_3$ | —H | —H | 496 |
| 1661 | —H | —H | —SO$_2$CH$_3$ | —H | —H | 528 |
| 1662 | —H | —H | —OCH$_2$C$_6$H$_5$ | —H | —H | 556 |
| 1663 | —H | —Cl | —H | —Cl | —H | 518 |
| 1664 | —F | —F | —F | —H | —H | 504 |
| 1665 | —H | —H | —OCOCH$_3$ | —H | —H | 508 |

TABLE 100

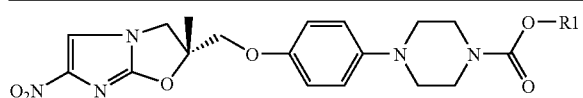

| Example | R1 | MS (M + 1) |
|---|---|---|
| 1666 | 4-CF$_3$OPh— | 564 |
| 1667 | 4-CH$_3$OPhCH$_2$— | 524 |
| 1668 | 4-CH$_3$PhCH$_2$— | 508 |
| 1669 | 4-CH$_3$O$_2$CPhCH$_2$— | 552 |
| 1670 | —CH$_2$C$_6$H$_5$ | 494 |
| 1671 | 4-CH$_3$SPhCH$_2$— | 540 |
| 1672 | 4-NO$_2$PhCH$_2$— | 539 |
| 1673 | 3,4,5-(CH$_3$O)$_3$PhCH$_2$— | 584 |
| 1674 | 2-CH$_3$CONHPhCH$_2$— | 551 |
| 1675 | 4-FPhCH$_2$— | 512 |
| 1676 | 4-CF$_3$OPhCH$_2$— | 578 |
| 1677 | 4-PhCH$_2$OPhCH$_2$— | 600 |
| 1678 | 4-CF$_3$SPhCH$_2$— | 594 |
| 1679 | 3-CF$_3$OPhCH$_2$— | 578 |
| 1680 | 2-CF$_3$OPhCH$_2$— | 578 |
| 1681 | C$_6$F$_5$CH$_2$— | 584 |
| 1682 | PhCH═CHCH$_2$— | 520 |
| 1683 | 4-ClPhCH═CHCH$_2$— | 554 |
| 1684 | 4-CF$_3$OPhCH═CHCH$_2$— | 604 |
| 1685 | —(CH$_2$)$_2$C$_6$H$_5$ | 508 |
| 1686 | Ph(CH$_2$)$_3$— | 522 |
| 1687 | PhCCCH$_2$— | 518 |
| 1688 | PhS(CH$_2$)$_2$— | 540 |
| 1689 | PhCH$_2$O(CH$_2$)$_2$— | 538 |
| 1690 | —CH$_2$CH$_2$CH═CH$_2$ | 458 |
| 1691 | —CH$_2$CH$_2$CN | 457 |
| 1692 | CH$_3$(CH$_2$)$_{15}$— | 628 |
| 1693 | CH$_3$CH$_2$OCH$_2$)$_2$O(CH$_2$)$_2$— | 520 |
| 1694 | —CH$_2$CH$_2$CCH | 456 |
| 1695 | CF$_3$CF$_2$CF$_2$CH$_2$— | 586 |
| 1696 | —CH$_2$-cyclo-C$_3$H$_5$ | 458 |

TABLE 101

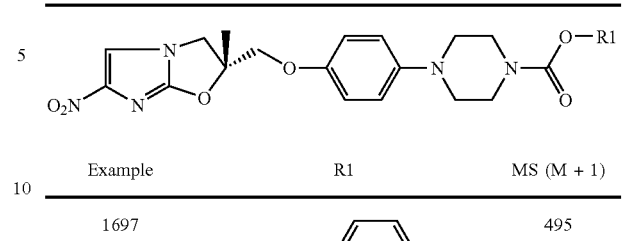

| Example | R1 | MS (M + 1) |
|---|---|---|
| 1697 | 3-ethylpyridyl | 495 |
| 1698 | 2-ethylpyridyl | 495 |
| 1699 | 2-ethylfuryl | 484 |
| 1700 | 5-chloro-3-ethylbenzothienyl | 584 |
| 1701 | 1-(4-chlorophenyl)-5-ethyltetrazolyl | 596 |
| 1702 | 2-ethyl-5-(trifluoromethoxy)benzothienyl | 634 |
| 1703 | 4-ethylpyridyl | 495 |
| 1704 | ethyladamantyl | 552 |
| 1705 | 4-propylpyridyl | 509 |
| 1706 | 3-ethylfuryl | 484 |

TABLE 102

| Example | R1 | MS (M + 1) |
|---|---|---|
| 1707 | 2-methylindane | 520 |
| 1708 | 5-ethyl-2-nitrofuran | 529 |
| 1709 | 6-ethylnaphthalene | 544 |

TABLE 103

| Example | R1 | MS (M + 1) |
|---|---|---|
| 1710 | —CH$_2$CH=CH$_2$ | 400 |
| 1711 | —C$_6$H$_{13}$ | 444 |
| 1712 | —CH$_2$CN | 399 |
| 1713 | —(CH$_2$)$_2$CH(CH$_3$)$_2$ | 430 |
| 1714 | —CH$_2$CON(CH$_3$)$_2$ | 445 |

TABLE 104

| Example | R1 | R2 | mp (° C.) or $^1$H NMR |
|---|---|---|---|
| 1715 | —CH$_3$ | 4-CF$_3$OPh— | 157.9-158.8 |
| 1716 | —CH$_3$ | 4-CF$_3$OPhCH$_2$— | 188.4—190.2 |
| 1717 | —CH$_3$ | 4-CF$_3$OPhCH$_2$OCO— | 112.1-115.4 |
| 1718 | —CH$_3$ | 4-CF$_3$OPhCO— | |
| 1719 | —CH$_3$ | 4-CF$_3$OPhNHCO— | |

TABLE 105

| Example | R1 | R2 | R3 | mp (° C.) |
|---|---|---|---|---|
| 1720 | —H | 4-CF$_3$OPh— | —CH$_3$ | 126.9-128.9 |
| 1721 | —H | 4-CF$_3$OPh— | —C$_2$H$_5$ | 102.1-103.1 |
| 1722 | —H | 4-ClPh— | —C$_2$H$_5$ | 121.7-123.6 |
| 1723 | —H | —C$_6$H$_5$ | —CH$_3$ | 169.5-171.0 |
| 1724 | —H | 4-CF$_3$OPhCH$_2$— | —CH$_3$ | 134.8-136.8 |
| 1725 | —H | 4-ClPhCH$_2$— | —CH$_3$ | 161.4-164.1 |
| 1726 | —H | 4-CF$_3$PhCH$_2$— | —CH$_3$ | 136.4-137.9 |
| 1727 | —H | 4-CF$_3$OPhCH$_2$— | —C$_2$H$_5$ | 119-120.5 |
| 1728 | —H | 4-CF$_3$PhCH$_2$— | —C$_2$H$_5$ | 134.3-135.7 |
| 1729 | —H | 4-ClPhCH$_2$— | —C$_2$H$_5$ | 135.8-137 |
| 1730 | —F | 4-CF$_3$OPhCH$_2$— | —CH$_3$ | 132.7-134.7 |
| 1731 | —H | 4-CF$_3$OPhCH$_2$— | 4-CF$_3$OPhCH$_2$— | 135.9-137 |
| 1732 | —H | 4-CF$_3$OPhCH$_2$— | —C$_6$H$_5$ | 198.9-200.8 |
| 1733 | —H | 4-CF$_3$PhCH$_2$— | —C$_6$H$_5$ | 192.7-194.7 |
| 1734 | —H | 4-ClPhCH$_2$— | —C$_6$H$_5$ | 195.1-196.1 |
| 1735 | —H | —C$_6$H$_5$ | —COCH$_3$ | 167.7-168.7 |
| 1736 | —H | 4-ClPh— | —COCH$_3$ | 220.0-223.5 |
| 1737 | —H | 4-CF$_3$Ph— | —COCH$_3$ | 223.1-224.6 |
| 1738 | —H | 4-CF$_3$OPh— | —COCH$_3$ | 243.6-244.9 |
| 1739 | —F | 4-ClPh— | —COCH$_3$ | 221.8-223.0 |
| 1740 | —F | 4-CF$_3$OPh— | —COCH$_3$ | 240.3-242.9 |
| 1741 | —H | —C$_6$H$_5$ | —CO$_2$CH$_3$ | 182.7-184.8 |
| 1742 | —H | 4-ClPh— | —CO$_2$CH$_3$ | 244.0-245.1 |
| 1743 | —H | 4-CF$_3$OPhCH$_2$— | —H | 151.4-154.3 |
| 1744 | —H | 4-CF$_3$OPhCH$_2$— | —CO$_2$C$_2$H$_5$ | 105.1-107.6 |
| 1745 | —H | 4-ClPh(CH$_2$)$_2$— | —CH$_3$ | 116.1-117.6 |
| 1746 | —H | 4-CF$_3$OPhO(CH$_2$)$_3$— | —H | 189.9-191.0 |
| 1747 | —H | 4-CF$_3$OPhCO— | —CH$_3$ | 143.3-145.9 |

TABLE 106

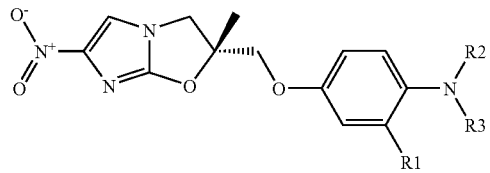

| Example | R1 | R2 | R3 | $^1$H NMR |
|---|---|---|---|---|
| 1748 | —H | 4-CF$_3$Ph— | —CH$_3$ | $^1$H NMR(CDCl$_3$) δ 1.80(3H, s), 3.28(3H, s), 4.06(1H, d, J=10.2Hz), 4.11(1H, d, J=10.2Hz), 4.26(1H, d, J=10.2Hz), 4.52(1H, d, J=10.2Hz), 6.70(2H, d, J=8.7Hz), 6.88(2H, d, J=8.8Hz), 7.13(2H, d, J=8.8Hz), 7.39(2H, d, J=8.7Hz), 7.57(1H, s). |
| 1749 | —H | 4-ClPh— | —CH$_3$ | $^1$H NMR(CDCl$_3$) δ 1.79(3H, s), 3.22(3H, s), 4.04(1H, d, J=10.4Hz), 4.08(1H, d, J=10.4Hz), 4.23(1H, d, J=10.1Hz), 4.50(1H, d, J=10.1Hz), 6.70-6.73(2H, m), 6.81-6.84(2H, m), 7.03-7.06(2H, m), 7.12-7.15(2H, m), 7.56(1H, s). |
| 1750 | —H | 4-CF$_3$Ph— | —C$_2$H$_5$ | $^1$H NMR(CDCl$_3$) δ 1.20(3H, d, J=7.1Hz), 1.81(3H, s), 3.71(2H, q, J=7.1Hz), 4.07(1H, d, J=10.2Hz), 4.11(1H, d, J=10.2Hz), 4.27(1H, d, J=10.2Hz), 4.52(1H, d, J=10.2Hz), 6.63-6.66(2H, m), 6.88-6.91(2H, m), 7.10-7.12(2H, m), 7.34-7.37(2H, m), 7.57(1H, s). |
| 1751 | —F | 4-ClPh— | —CH$_3$ | $^1$H NMR(CDCl$_3$) δ 1.80(3H, s), 3.20(3H, s), 4.06(1H, d, J=10.2Hz), 4.09(1H, d, J=10.1Hz), 4.25(1H, d, J=10.1Hz), 4.49(1H, d, J=10.2Hz), 6.54-6.57(2H, m), 6.64-6.71(2H, m), 7.09-7.19(3H, m), 7.57(1H, s). |
| 1752 | —H | 4-CF$_3$OPhCH$_2$— | —COCH$_3$ | $^1$H NMR(CDCl$_3$) δ 1.79(3H, s), 1.85(3H, s), 4.06(1H, d, J=10.2Hz), 4.08(1H, d, J=10.2Hz), 4.24(1H, d, J=10.2Hz), 4.48(1H, d, J=10.2Hz), 4.82(2H, s), 6.78-6.82(2H, m), 6.88-6.91(2H, m), 7.09-7.11(2H, m), 7.20-7.22(2H, m), 7.56(1H, s). |
| 1753 | —H | 4-CF$_3$OPhCO— | —CH$_3$ | $^1$H NMR(CDCl$_3$) δ 1.76(3H, s), 3.45(3H, s), 4.03(1H, d, J=10.1Hz), 4.04(1H, d, J=10.2Hz), 4.18(1H, d, J=10.1Hz), 4.46(1H, d, J=10.2Hz), 6.69-6.72(2H, m), 6.95-6.98(2H, m), 7.37-7.46(4H, m), 7.55(1H, s). |
| 1754 | —H | 4-ClPhCO— | —CH$_3$ | $^1$H NMR(CDCl$_3$) δ 1.77(3H, s), 3.43(3H, s), 4.03(1H, d, J=10.1Hz), 4.04(1H, d, J=10.2Hz), 4.18(1H, d, J=10.1Hz), 4.46(1H, d, J=10.2Hz), 6.69-6.72(2H, m), 6.94-6.97(2H, m), 7.13-7.23(4H, m), 7.55(1H, s). |
| 1755 | —H | 4-ClPhCO— | —H | $^1$H NMR(DMSO) δ 1.68(3H, s), 4.17-4.20(1H, m), 4.22-4.30(2H, m), 4.36-4.39(1H, m), 6.88-6.91(2H, m), 7.57-7.66(4H, m), 7.94-7.97(2H, m), 8.15(1H, s), 10.19(1H, brs). |

TABLE 107

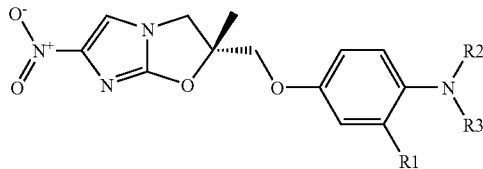

| Example | R1 | R2 | R3 | $^1$H NMR |
|---|---|---|---|---|
| 1756 | —H | 4-ClPhCO— | —H | $^1$H NMR(DMSO) δ 1.68(3H, s), 4.17-4.20(1H, m), 4.22-4.30(2H, m), 4.36-4.39(1H, m), 6.88-6.91(2H, m), 7.57-7.66(4H, m), 7.94-7.97(2H, m), 8.15(1H, s), 10.19(1H, brs). |
| 1757 | —H | 4-CF$_3$PhCO— | —H | $^1$H NMR(DMSO) δ 1.68(3H, s), 4.17-4.21(1H, m), 4.24-4.30(2H, m), 4.36-4.40(1H, |

TABLE 107-continued

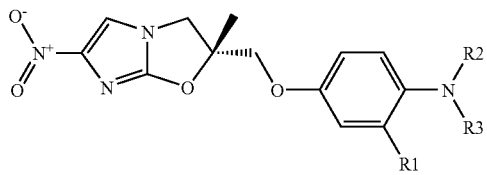

| Example | R1 | R2 | R3 | $^1$H NMR |
|---|---|---|---|---|
| | | | | m), 6.90-6.93(2H, m), 7.65-7.68(2H, m), 7.88-7.90(2H, m), 8.11-8.13(2H, m), 8.16(1H, s), 10.35(1H, brs). |
| 1758 | —H | 4-CF$_3$OPhCO— | —H | $^1$H NMR(DMSO) δ 1.68(3H, s), 4.17-4.20(1H, m), 4.24-4.31(2H, m), 4.36-4.40(1H, m), 6.89-6.92(2H, m), 7.49-7.52(2H, m), 7.63-7.66(2H, m), 8.04-8.06(2H, m), 8.16(1H, s), 10.23(1H, brs). |
| 1759 | —H | 4-ClPh— | —H | 142.6-144.7 |
| 1760 | —H | 4-CF$_3$OPh(CH$_2$)$_2$— | —H | |
| 1761 | —H | 4-CF$_3$OPh(CH$_2$)$_2$— | —CH$_3$ | |
| 1762 | —H | 4-CF$_3$OPhO(CH$_2$)$_3$— | —C$_2$H$_5$ | 107.6-109.2 |
| 1763 | —H | 4-CF$_3$OPhCOCH$_2$— | —H | |
| 1764 | —H | 4-CF$_3$OPhCOCH$_2$— | —CH$_3$ | |

TABLE 108

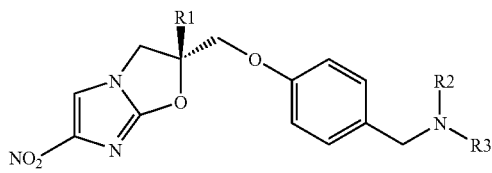

| Example | R1 | R2 | R3 | mp (° C.) or $^1$H NMR |
|---|---|---|---|---|
| 1765 | —CH$_3$ | —H | 4-ClPh— | 171.5-173.5 |
| 1766 | —CH$_3$ | —H | 4-CF$_3$Ph— | 172.2-174.9 |
| 1767 | —CH$_3$ | —CH$_3$ | 4-CF$_3$OPhCH$_2$— | 138.5-141.0 |
| 1768 | —CH$_3$ | —H | 4-CF$_3$OPh— | 165.1-167.2 |
| 1769 | —CH$_3$ | —COCH$_3$ | 4-CF$_3$OPh— | 128.4-130.8 |
| 1770 | —CH$_3$ | —CH$_3$ | 4-CF$_3$OPh— | 113.6-114.5 |
| 1771 | —CH$_3$ | —CH$_3$ | 4-CF$_3$Ph— | 168.2-170.7 |
| 1772 | —CH$_3$ | —COCH$_3$ | 4-CF$_3$Ph— | 132.8-133.9 |
| 1773 | —CH$_3$ | —CH$_3$ | 4-ClPh— | 160.9-163.4 |
| 1774 | —CH$_3$ | —CO$_2$C$_2$H$_5$ | 4-CF$_3$OPh— | $^1$H NMR(CDCl$_3$) δ 1.21(3H, t, d=7.1), 1.77(3H, s), 4.05(1H, d, J=10.3Hz), 4.06(1H, d, J=10.2Hz), 4.15-4.22(3H, m), 4.49(1H, d, J=10.3Hz), 4.78(2H, s), 6.74-6.78(2H, m), 7.07-7.13(6H, m), 7.55(1H, s). |
| 1775 | —CH$_3$ | —COCH$_3$ | 4-ClPh— | $^1$H NMR(CDCl$_3$) δ 1.78(3H, s), 1.86(3H, s), 4.03(1H, d, J=10.2Hz), 4.05(1H, d, J=10.1Hz), 4.21(1H, d, J=10.1Hz), 4.48(1H, d, J=10.2Hz), 4.78(2H, s), 6.71-6.74(2H, m), 6.87-6.89(2H, m), 7.08-7.11(2H, m), 7.28-7.32(2H, m), 7.55(1H, s). |

TABLE 109

| Example | R1 | R2 | mp (° C.) |
|---|---|---|---|
| 1776 | —CH₃ | -4-PYRIDYL | 228.2-229.8 dec |
| 1777 | —CH₃ | —CHO | 176.0-179.5 |
| 1778 | —CH₃ | 4-ClPhCO— | 186.2-188.5 |
| 1779 | —CH₃ | 4-CF₃PhCO— | 170.3-172.4 |
| 1780 | —CH₃ | 4-CF₃OPhCO— | 159.7-160.7 |

TABLE 110

| Example | R1 | R2 | mp (° C.) or ¹H NMR |
|---|---|---|---|
| 1781 | —CH₃ | 1-methylpiperidin-4-one | 177.4-184.3 |
| 1782 | —CH₃ | 3-methyloxazolidin-2-one | 196.3-197.8 |
| 1783 | —CH₃ | 8-methyl-1,4-dioxa-8-azaspiro[4.5]decane | 212.3-214.0 |
| 1784 | —CH₃ | 1-methyl-4-(4-chlorophenyl)piperidine | 251.9-253.0 |
| 1785 | —CH₃ | 1-methyl-4-(4-chlorophenyl)-1,2,3,6-tetrahydropyridine | 216.7-219.5 dec |
| 1786 | —CH₃ | 1-methyl-4-(4-trifluoromethoxyphenyl)piperidine | 248.1-248.2 |
| 1787 | —CH₃ | 1-ethyl-4-(4-trifluoromethoxyphenoxy)piperidine | 150.3-154.9 |
| 1788 | —CH₃ | 1-acetyl-4-(4-trifluoromethoxyphenoxy)piperidine | 150.8-151.2 |

TABLE 110-continued

[Structure: nitroimidazooxazole with R1 at stereocenter and CH2-O-phenyl-R2]

| Example | R1 | R2 | mp (° C.) or ¹H NMR |
|---|---|---|---|
| 1789 | —CH₃ | [1-methyl-4-hydroxy-4-(4-trifluoromethoxyphenyl)piperidine] | ¹H NMR(CDCl₃) δ 1.55(1H, s), 1.60(1H, s), 1.77(3H, s), 1.80-1.95(2H, m), 2.15-2.40(2H, m), 3.04-3.27(2H, m), 3.33-3.53(2H, m), 3.95-4.11(2H, m), 4.19(1H, d, J=10.2Hz), 4.50(1H, d, J=10.2Hz), 6.71-6.86(2H, m), 6.88-7.02(2H, m), 7.14-7.31(2H, m), 7.47-7.63(3H, m). |
| 1790 | —CH₃ | [1-methyl-4-phenyl-1,2,3,6-tetrahydropyridine] | ¹H NMR(DMSO) δ 1.67(3H, s), 2.61(2H, brs), 3.74(2H, d, J=2.9Hz), .17(1H, d, J=13.0Hz), 4.21(2H, s), 6.28(1H, s), 6.81(2H, d, J=9.1Hz), 6.94(2H, d, J=9.2Hz), 7.18-7.57(5H, m), 8.17(1H, s). |

TABLE 111

[Structure: nitroimidazooxazole with R1 at stereocenter and CH2-O-phenyl-R2]

| Example | R1 | R2 | mp (° C.) or ¹H NMR |
|---|---|---|---|
| 1791 | —CH₃ | [1-(4-chlorobenzyl)-4-methylpiperidine] | 202.0-203.5 |
| 1792 | —CH₃ | [1-benzyl-4-methylpiperidine] | 206.0 |
| 1793 | —CH₃ | [N-(4-trifluoromethoxyphenyl)acetamide] | 247.8-249.8 |
| 1794 | —CH₃ | [3-(dimethylamino)propoxy-4-trifluoromethoxyphenyl] | 97.7-99.7 |
| 1795 | —CH₃ | [ethylidene hydrazone of 4-trifluoromethylaniline] | 172.5-175.8 |
| 1796 | —CH₃ | [2-(methylamino)-5-chloropyridine] | 160.7-163.0 |

TABLE 111-continued

[Structure: imidazo-oxazole core with nitro group, R1 substituent, and CH2-O-phenyl-R2 group]

| Example | R1 | R2 | mp (° C.) or ¹H NMR |
|---------|-----|-----|---------------------|
| 1797 | —CH₃ | [structure: CH₃-CH=N-N(CH₃)-phenyl-CF₃] | ¹H NMR(CDCl₃) δ 1.81(3H, s), 3.44(3H, s), 4.06(1H, d, J=10.24Hz), 4.12(1H, d, J=10.0Hz), 4.27(1H, d, J=10.0Hz), 4.52(1H, d, J=10.2Hz), 6.83-6.91(2H, m), 7.39-7.45(2H, m), 7.51-7.56(3H, m), 7.57(1H, s), 7.62-7.68(2H, m) |

TABLE 112

[Structure: imidazo-oxazole core with nitro group, R1 substituent, and CH2-O-phenyl-R2 group]

| Example | R1 | R2 | mp (° C.) or ¹H NMR |
|---------|-----|-----|---------------------|
| 1798 | —CH₃ | [structure: CH₃-CH=N-NH-phenyl-OCF₃] | ¹H NMR(CDCl₃) δ 1.80(3H, s), 4.01-4.14(2H, m), 4.26(1H, d, J=10.0Hz), 4.51(1H, d, J=10.3Hz), 6.85(2H, d, J=8.6Hz), 7.03-7.09(4H, m), 7.53-7.60(4H, m), 7.66(1H, s) |
| 1799 | —CH₃ | [structure: CH₃-CH=N-NH-phenyl-Cl] | ¹H NMR(CDCl₃) δ 1.81(3H, s), 4.05(1H, d, J=10.3Hz), 4.11(1H, d, J=10.0Hz), 4.26(1H, d, J=10.0Hz), 4.51(1H, d, J=10.3Hz), 6.83-7.05(4H, m), 7.20-7.26(2H, m), 7.51-7.60(4H, m), 7.65(1H, s) |
| 1800 | —CH₃ | [structure: CH₃-CH=CH-CH₂-NH-phenyl-OCF₃] | |
| 1801 | —CH₃ | [structure: CH₃-CH=CH-CH₂-N(CH₃)-phenyl-OCF₃] | |
| 1802 | —CH₃ | [structure: CH₃-CH=N-piperazinyl-phenyl-CF₃] | |

TABLE 112-continued

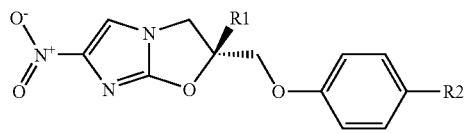

| Example | R1 | R2 | mp (° C.) or ¹H NMR |
|---|---|---|---|
| 1803 | —CH₃ |  | 209.1-212.9 |

TABLE 113

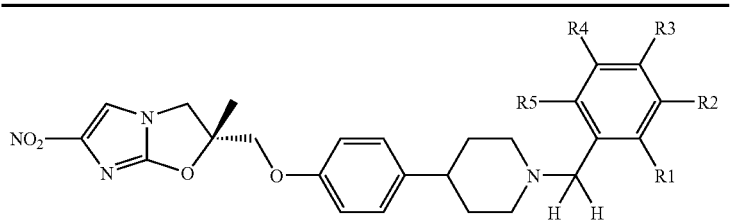

| Example | R1 | R2 | R3 | R4 | R5 | MS (M + 1) |
|---|---|---|---|---|---|---|
| 1804 | —H | —CF₃ | —H | —H | —H | 517 |
| 1805 | —H | —H | —NO₂ | —H | —H | 494 |
| 1806 | —H | —H | —CF₃ | —H | —H | 517 |
| 1807 | —H | —H | —CH₃ | —H | —H | 463 |
| 1808 | —H | —H | —CN | —H | —H | 474 |
| 1809 | —H | —H | —C₆H₅ | —H | —H | 525 |
| 1810 | —H | —H | —F | —H | —H | 467 |
| 1811 | —H | —Cl | —Cl | —H | —H | 517 |
| 1812 | —CF₃ | —H | —H | —H | —H | 517 |
| 1813 | —H | —H | —OCH₃ | —H | —H | 479 |
| 1814 | —H | —H | —SCH₃ | —H | —H | 495 |
| 1815 | —H | —H | —SO₂CH₃ | —H | —H | 527 |
| 1816 | —H | —H | —OCH₂C₆H₅ | —H | —H | 555 |
| 1817 | —H | —Cl | —H | —Cl | —H | 517 |
| 1818 | —F | —F | —F | —H | —H | 503 |
| 1819 | —H | —H | —OCOCH₃ | —H | —H | 507 |

TABLE 114

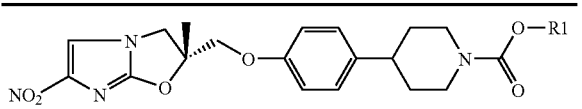

| Example | R1 | MS (M + 1) |
|---|---|---|
| 1820 | 4-CF₃OPh— | 563 |
| 1821 | 4-CH₃OOPhCH₂— | 523 |
| 1822 | 4-CH₃PhCH₂— | 507 |
| 1823 | 4-CH₃O₂CPhCH₂— | 551 |
| 1824 | —CH₂C₆H₅ | 493 |
| 1825 | 4-CH₃SPhCH₂— | 539 |
| 1826 | 4-NO₂PhCH₂— | 538 |
| 1827 | 3,4,5-(CH₃O)₃PhCH₂— | 583 |
| 1828 | 2-CH₃CONHPhCH₂— | 550 |
| 1829 | 4-FPhCH₂— | 511 |
| 1830 | 4-CF₃OPhCH₂— | 577 |
| 1831 | 4-PhCH₂OPhCH₂— | 599 |

TABLE 114-continued

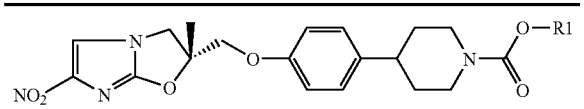

| Example | R1 | MS (M + 1) |
|---|---|---|
| 1832 | 4-CF₃SPhCH₂— | 593 |
| 1833 | 3-CF₃OPhCH₂— | 577 |
| 1834 | 2-CF₃OPhCH₂— | 577 |
| 1835 | C₆F₅CH₂— | 583 |
| 1836 | PhCH=CHCH₂— | 519 |
| 1837 | 4-ClPhCH=CHCH₂— | 553 |
| 1838 | 4-CF₃OPhCH=CHCH₂— | 603 |
| 1839 | —(CH₂)₂C₆H₅ | 507 |
| 1840 | Ph(CH₂)₃— | 521 |
| 1841 | PhCCCH₂— | 517 |
| 1842 | PhS(CH₂)₂— | 539 |
| 1843 | PhCH₂O(CH₂)₂— | 537 |

TABLE 114-continued
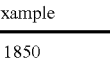
| Example | R1 | MS (M + 1) |
|---|---|---|
| 1844 | —CH₂CH₂CH═CH₂ | 457 |
| 1845 | —CH₂CH₂CN | 456 |
| 1846 | CH₃CH₂O(CH₂)₂O(CH₂)₂— | 519 |
| 1847 | —CH₂CH₂CCH | 455 |
| 1848 | CF₃CF₂CF₂CH₂— | 585 |
| 1849 | —CH₂-cyclo-C₃H₅ | 457 |
TABLE 115
| Example | R1 | MS (M + 1) |
|---|---|---|
| 1850 |  | 494 |
| 1851 |  | 494 |
| 1852 |  | 483 |
| 1853 |  | 583 |
| 1854 |  | 595 |
| 1855 | 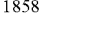 | 499 |
| 1856 |  | 494 |
| 1857 | 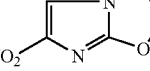 | 551 |
| 1858 | 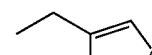 | 508 |
TABLE 115-continued
| Example | R1 | MS (M + 1) |
|---|---|---|
| 1859 |  | 483 |
| 1860 |  | 519 |
| 1861 |  | 528 |
TABLE 116
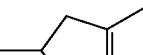
| Example | R1 | MS (M + 1) |
|---|---|---|
| 1862 |  | 543 |
TABLE 117
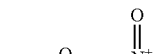
| Example | R1 | MS (M + 1) |
|---|---|---|
| 1863 | —CH₂CH═CH₂ | 399 |
| 1864 | —(CH₂)₂C₆H₅ | 463 |
| 1865 | —C₆H₁₃ | 443 |
| 1866 | —CH₂CN | 398 |
| 1867 | —CH₂CON(CH₃)₂ | 444 |
| 1868 | PhCOCH₂— | 477 |
TABLE 118
| Example | R1 | R2 | mp (° C.) |
|---|---|---|---|
| 1869 | —CH₃ | 4-CF₃PhCH₂— | 171.4-172.4 |
| 1870 | —CH₃ | 4-CF₃PhCH₂OCO— | 130.4-131.7 |
| 1871 | —CH₃ | 4-ClPhCH₂OCO— | 126.8-129.1 |

TABLE 118-continued

| Example | R1 | R2 | mp (° C.) |
|---|---|---|---|
| 1872 | —CH₃ | 4-CF₃OPhCH₂OCO— | 143.8-144.8 |
| 1873 | —CH₃ | 4-ClPhCH₂— | 183.0-187.2 |
| 1874 | —CH₃ | 4-CF₃OPhCH₂— | 174.3-176.5 |
| 1875 | —CH₃ | 4-CF₃Ph— | 156.7-157.7 |
| 1876 | —CH₃ | (CH₃)₃COCO— | 197.0-198.2 |
| 1877 | —CH₃ | 4-CF₃OPh— | 154.5-156.7 |

TABLE 119

| Example | R1 | R2 | mp (° C.) or ¹H NMR |
|---|---|---|---|
| 1878 | —CH₃ | 4-ClPhCH₂— | 214.3-216.1 |
| 1879 | —CH₃ | 4-CF₃Ph— | 158.5-160.1 |
| 1880 | —CH₃ | 4-CF₃OPh— | 161.7-164.4 |
| 1881 | —CH₃ | 4-ClPh— | 163.5-166.3 |
| 1882 | —CH₃ | 4-CF₃OPhCH₂— | ¹H NMR(CDCl₃) δ 1.76(3H, s), 4.02(1H, d, J=10.2Hz), 4.04(1H, d, J=10.2Hz), 4.18(1H, d, J=10.2Hz), 4.48(1H, d, J=10.2Hz), 5.00(2H, s), 6.77-6.81(2H, m), 6.85-6.90(2H, m), 7.21-7.23(2H, m), 7.42-7.45(2H, m), 7.54(1H, s). |
| 1883 | —CH₃ | 4-CF₃PhCH₂— | ¹H NMR(CDCl₃) δ 1.77(3H, s), 4.02(1H, d, J=10.2Hz), 4.04(1H, d, J=10.2Hz), 4.18(1H, d, J=10.2Hz), 4.49(1H, d, J=10.2Hz), 5.07(2H, s), 6.77-6.81(2H, m), 6.85-6.91(2H, m), 7.51-7.55(3H, m), 7.62-7.65(2H, m). |

Example 1884

Production of (R)-2-methyl-6-nitro-2-{4-[4-(4-trifluoromethoxyphenoxy)piperidin-1-yl]phenoxymethyl}-2,3-dihydroimidazo[2,1-b]oxazole 4-[4-(4-Trifluoromethoxyphenoxy)piperidin-1-yl]phenol (693 mg, 1.96 mmol) was dissolved in N,N'-dimethylformamide (3 ml), and sodium hydride (86 mg, 2.16 mmol) was added while cooling on ice followed by stirring at 70-75° C. for 20 minutes. The mixture was cooled on ice. To the solution, a solution prepared by dissolving (R)-2-bromo-4-nitro-1-(2-methyl-2-oxiranylmethyl)imidazole (720 mg, 2.75 mmol) in N,N'-dimethylformamide (3 ml) was added followed by stirring at 70-75° C. for 20 minutes. The reaction mixture was allowed to return to room temperature, ice water (25 ml) was added, and the resultant solution was extracted with methylene chloride (50 ml) three times. The organic phases were combined, washed with water 3 times, and dried over magnesium sulfate. After filtration, the filtrate was concentrated, and the residue was purified by silica gel column chromatography (methylene chloride/ethyl acetate=3/1). Recrystallization from ethyl acetate/isopropyl ether gave (R)-2-methyl-6-nitro-2-{4-[4-(4-trifluoromethoxyphenoxy)piperidin-1-yl]phenoxymethyl}-2,3-dihydroimidazo[2,1-b]oxazole (343 mg, 33%) as a light yellow powder.

Example 1885

(1) Production of 3-(4-trifluoromethylphenyl)-2-propenyl (S)-4-[3-(2-bromo-4-nitroimidazol-1-yl)-2-hydroxy-2-methylpropyl]piperazin-1-carboxylate A mixture of (R)-2-bromo-4-nitro-1-(2-methyl-2-oxiranylmethyl)imidazole (2.04 g, 7.78 mmol), 3-(4-trifluoromethylphenyl)-2-propenyl piperazine-1-carboxylate (2.69 g, 8.56 mmol) and N,N'-dimethylformamide (10 ml) was stirred at 50° C. for 20 hours. The reaction solution was allowed to return to room temperature, water was added, and the resultant solution was extracted with ethyl acetate (15 ml) twice. The organic phases were combined, washed with water three times, and dried over sodium sulfate. After filtration, the filtrate was concentrated, and the residue was purified by silica gel column chromatography (n-hexane/ethyl acetate=1/2) to obtain 3-(4-trifluoromethylphenyl)-2-propenyl (S)-4-[3-(2-bromo-4-nitroimidazol-1-yl)-2-hydroxy-2-methylpropyl]piperazin-1-carboxylate (3.77 g, 84%) as a yellow oil.

$^1$H-NMR (CDCl3) δ ppm: 1.16 (3H, s), 2.36 (1H, d, J=14.0 Hz), 2.43-2.76 (5H, m), 3.21 (1H, s), 3.41-3.57 (4H, m), 4.01 (2H, s), 4.78 (2H, dd, J=1.0 Hz, 6.1 Hz), 6.29-6.43 (1H, m), 6.66 (1H, d, J=16.0 Hz), 7.48 (2H, d, J=8.3 Hz), 7.58 (2H, d, J=8.3 Hz), 8.10 (1H, s).

(2) Production of 3-(4-trifluoromethylphenyl)-2-propenyl (S)-4-(2-methyl-6-nitro-2,3-dihydroimidazo-[2,1-b]oxazol-2-ylmethyl)piperazine-1-carboxylate 3-(4-Trifluoromethylphenyl)-2-propenyl (S)-4-[3-(2-bromo-4-nitroimidazol-1-yl)-2-hydroxy-2-methylpropyl]piperazine-1-carboxylate (3.5 g, 6.07 mmol) was dissolved in N,N'-dimethylformamide (10.5 ml), and sodium hydride (316 mg, 7.89 mmol) was added while cooling on ice followed by stirring at the same temperature for 1.5 hours. To the reaction solution, ethyl acetate (3.5 ml) and water (24.5 ml) were added followed by stirring for 30 minutes. The precipitated crystals were filtered off, washed with water, and purified by silica gel column chromatography (ethyl acetate). Recrystallization from 2-propanol/water gives a light yellow powder of 3-(4-trifluoromethylphenyl)-2-propenyl (S)-4-(2-methyl-6-nitro-2,3-dihydroimidazo[2,1-b]oxazol-2-ylmethyl)piperazine-1-carboxylate (2.07 g, 69%).

Test Example 1

Antimicrobial Assay (Agar Dilution Method)

The minimal inhibitory concentration of the 2,3-dihydro-6-nitroimidazo[2,1-b]oxazole compound obtained in Example 397 against *Mycobacterium tuberculosis* (*M. tuberculosis* H37Rv) was determined using a 7H11 medium (manufactured by BBL). The above strain had been cultured on a 7H9 medium (manufactured by BBL) in advance, the number of viable cells had been counted, and a cell suspension with the final viable cell count approximately 10$^6$ CFU/ml was prepared, using a cell suspension stored freezing at −80° C. 5 μl of the thus prepared cell suspension was inoculated onto the 7H11 agar medium containing the test compound and then cultured at 37° C. for 14 days. Thereafter, the culture was subjected to the test to determine the minimal inhibitory concentration.

The minimal inhibitory concentration of the compound against *M. tuberculosis* H37Rv was 0.024 μg/ml.

The invention claimed is:

1. A 2,3-dihydro-6-nitroimidazo[2,1-b]oxazole compound represented by the following general formula (1), optically active form thereof, or pharmaceutically acceptable salt thereof:

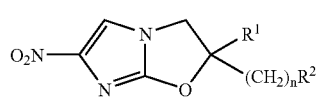

(1)

wherein R$^1$ represents a hydrogen atom or C1-6 alkyl group, n represents an integer of 0 to 6, and R$^2$ represents a group represented by general formula (A), (B), (C), (D), (E), (F) or (G) indicated below, and further, R$^1$ and —(CH$_2$)$_n$R$^2$ may bind to each other together with carbon atoms adjacent thereto through nitrogen atoms, so as to form a spiro ring represented by general formula (H) indicated below:

a group represented by the following general formula (A):

—OR$^3$ (A)

wherein R$^3$ represents:

A3) C1-6 alkoxy-C1-6 alkyl group;

A4) phenyl C1-6 alkyl group (which may be substituted on the phenyl ring by at least one group selected from the group consisting of a phenyl C1-6 alkoxy group, a halogen-substituted or unsubstituted C1-6 alkyl group, a halogen-substituted or unsubstituted C1-6 alkoxy group, and a phenoxy group which may have, as a substituent, at least one halogen-substituted or unsubstituted C1-6 alkoxy group on the phenyl ring);

A5) biphenylyl C1-6 alkyl group;

A6) phenyl C2-6 alkenyl group:

A7) C1-6 alkylsulfonyl group;

A8) benzenesulfonyl group which may be substituted by a C1-6 alkyl group;

A9) C1-6 alkanoyl group;

A10) a group represented by the following general formula (Aa):

(Aa)

wherein R$^4$ represents a C1-6 alkoxycarbonyl group; phenyl C1-6 alkoxycarbonyl group (which may be substituted on the phenyl ring by at least one group selected from the group consisting of a phenyl C1-6 alkoxy group, a halogen-substituted or unsubstituted C1-6 alkyl group, and a halogen-substituted or unsubstituted C1-6 alkoxy group); or phenyl C1-6 alkyl group (which may be substituted on the phenyl ring by at least one group selected from the group consisting of a phenyl C1-6 alkoxy group, a halogen-substituted or unsubstituted C1-6 alkyl group, and a halogen-substituted or unsubstituted C1-6 alkoxy group);

A11) biphenylyl C1-6 alkoxycarbonyl group;

A12) benzoxazolyl C1-6 alkyl group (which may be substituted on the benzoxazole ring by at least one oxo group as a substituent);

A13) benzoxazolyl group; or

A14) oxazolyl C1-6 alkyl group (which may be substituted on the oxazole ring by at least one group selected from the group consisting of a phenyl group and C1-6 alkyl group as a substituent), a group represented by the following general formula (B):

—SR$^5$ (B)

wherein R$^5$ represents a tetrazolyl group (which may be substituted on the tetrazole ring by a C1-6 alkyl group or phenyl group which may have a halogen atom as a substituent), or benzoxazolyl group, a group represented by the following general formula (C):

—COOR$^6$ (C)

wherein R$^6$ represents a C1-6 alkyl group, a carbamoyloxy group represented by the following general formula (D):

$$—OOCNR^7R^8 \quad (D)$$

wherein $R^7$ and $R^8$ each identically or differently represent any one of:

D1) hydrogen atom;
D2) C1-8 alkyl group;
D3) halogen-substituted C1-6 alkyl group;
D4) C1-6 alkoxycarbonyl-C1-6 alkyl group;
D5) C3-8 cycloalkyl group;
D6) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
D7) phenyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, a C1-6 alkanoyl group, a carboxyl group, a C1-6 alkoxycarbonyl group, a phenyl C1-6 alkoxycarbonyl group, a carbamoyl group, a C1-6 alkylcarbamoyl group, an aminosulfonyl group, and a morpholino group);
D8) naphthyl group;
D9) pyridyl group; and
D10) $R^7$ and $R^8$ may bind to each other together with nitrogen atoms adjacent thereto directly or through other hetero atoms or carbon atoms, so as to form a saturated heterocyclic group shown in any one of (D10-1) to (D10-3) indicated below, or benzene condensed heterocyclic group shown in any one of (D10-4) to (D10-7) indicated below:
(D10-1) piperazinyl group represented by the following general formula (Da):

wherein $R^9$ represents:
(Da1) hydrogen atom;
(Da2) C1-6 alkyl group;
(Da3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da4) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da5) C1-6 alkoxycarbonyl group;
(Da6) phenyl C1-6 alkoxycarbonyl group (which may be substituted on the phenyl ring by at least one group selected from the group consisting of a halogen atom, a halogen-substituted or unsubstituted C1-6 alkyl group and a halogen-substituted or unsubstituted C1-6 alkoxy group);
(Da7) phenyl C3-6 alkenyloxycarbonyl group (which may have at least one halogen-substituted or unsubstituted C1-6 alkyl group on the phenyl ring); or
(Da8) phenyl C1-6 alkylidene substituted amino group (which may be substituted on the phenyl ring by at least one halogen-substituted or unsubstituted C1-6 alkyl group as a substituent),
(D10-2) a group represented by the following general formula (Db):

wherein the dotted line represents that the bond may be a double bond, and $R^{10}$ represents:
(Db1) hydrogen atom;
(Db2) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Db3) phenoxy group (which may be substituted on the phenyl ring by at least one halogen-substituted or unsubstituted C1-6 alkyl group); or
(Db4) phenylamino group (which may be substituted on the phenyl ring by at least one halogen-substituted or unsubstituted C1-6 alkyl group),
(D10-3) morpholino group;
(D10-4) indolinyl group (which may be substituted on the indoline ring by at least one halogen atom as a substituent);
(D10-5) isoindolinyl group (which may be substituted on the isoindoline ring by at least one halogen atom as a substituent);
(D10-6) 1,2,3,4-tetrahydroquinolyl group, (which may be substituted on the 1,2,3,4-tetrahydroquinoline ring by at least one halogen atom as a substituent); and
(D10-7) 1,2,3,4-tetrahydroisoquinolyl group, (which may be substituted on the 1,2,3,4-tetrahydroisoquinoline ring by at least one halogen atom as a substituent),
a phenoxy group represented by the following general formula (E):

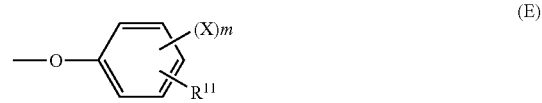

wherein X represents a halogen atom or amino substituted C1-6 alkyl group which may have a C1-6 alkyl group as a substituent, m represents an integer of 0 to 3, and $R^{11}$ represents:
E2) halogen-substituted or unsubstituted C1-6 alkyl group;
E3) halogen-substituted or unsubstituted C1-6 alkoxy group;
E4) a group represented by the following general formula (Ea):

$$—(W)o-NR^{12}R^{13} \quad (Ea)$$

wherein W represents a group —CO— or a C1-6 alkylene group, o represents an integer of 0 or 1, and $R^{12}$ and $R^{13}$ each identically or differently represent any one of:
(Ea1) hydrogen atom;
(Ea2) C1-6 alkyl group;
(Ea3) C1-6 alkanoyl group;
(Ea4) C1-6 alkoxycarbonyl group;
(Ea5) phenyl C1-6 alkyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group as a substituent), and the alkyl portion may be substituted by a C1-6 alkoxyimino group);
(Ea6) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Ea7) benzoyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group);
(Ea8) pyridyl group (which may be substituted on the pyridine ring by at least one halogen atom as a substituent);
(Ea9) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Ea10) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and
(Ea11) benzoyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group),
E5) imidazolyl group;
E6) triazolyl group;
E7) morpholino group;
E8) thiomorpholino group;
E9) s-oxide thiomorpholino group;
E10) piperidyl group represented by the following general formula (Eaa):

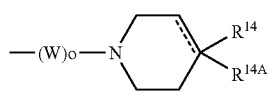
(Eaa)

wherein W and o are the same as above, $R^{14A}$ represents a hydrogen atom, hydroxyl group, C1-6 alkoxy group, or phenyl group (which may be substituted by halogen on the phenyl ring); the dotted line represents that the bond may be a double bond, and when the dotted line represents a double bond, it means that only $R^{14}$ is substituted; $R^{14}$ and $R^{14A}$ may bind to each other together with carbon atoms adjacent thereto to form a C1-4 alkylenedioxy group, and $R^{14}$ represents:
(Eaa1) hydrogen atom;
(Eaa2) C1-6 alkoxycarbonyl group;
(Eaa3) phenoxy group (which may be substituted on the phenyl ring by at least one group selected from the group consisting of a halogen atom; a halogen-substituted or unsubstituted C1-6 alkyl group; a halogen-substituted or unsubstituted C1-6 alkoxy group; a C1-4 alkylenedioxy group; a C1-6 alkoxycarbonyl group; a cyano group; a C2-6 alkenyl group; a nitro group; a phenyl group; an amino group which may have, as a substituent, a group selected from the group consisting of a phenyl group, a C1-6 alkyl group, a carbamoyl group and a C1-6 alkanoyl group; a C1-6 alkanoyl-substituted C1-6 alkyl group; a hydroxyl group; a C1-6 alkoxycarbonyl-substituted C1-6 alkyl group; a phenyl C1-6 alkyl group; a C1-6 alkanoyl group; a C1-6 alkylthio group; a 1,2,4-triazolyl group; an isoxazolyl group; an imidazolyl group; a benzothiazolyl group; a 2H-benzotriazolyl group; a pyrrolyl group; a benzoxazolyl group; a piperazinyl group (which may be substituted on the piperazine ring by at least one group selected from the group consisting of a C1-6 alkoxycarbonyl group and a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent); a piperidinyl group (which may be substituted on the piperidine ring by at least one group selected from the group consisting of an amino group (which may be substituted on the amino group by at least one group selected from the group consisting of a C1-6 alkyl group and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent); and a carbamoyl group));
(Eaa4) hydroxyl group;
(Eaa5) carboxy group;
(Eaa6) phenyl group (which may be substituted on the phenyl ring by at least one group selected from the group consisting of a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group as a substituent), a halogen atom, a halogen-substituted or unsubstituted C1-6 alkyl group, and a halogen-substituted or unsubstituted C1-6 alkoxy group as a substituent);
(Eaa7) C1-6 alkoxy group;
(Eaa8) C3-8 cycloalkyl-C1-6 alkoxy group;
(Eaa9) phenylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Eaa10) tetrahydropyranyloxy group;
(Eaa11) 1,3-dioxolanyl group;
(Eaa12) oxo group;
(Eaa13) naphthyloxy group (which may be substituted on the naphthalene ring by at least one C1-6 alkyl group as a substituent);
(Eaa14) 2,3-dihydrobenzofuryloxy group (which may be substituted on the 2,3-dihydrobenzofuran ring by at least one group selected from the group consisting of a C1-6 alkyl group and an oxo group);
(Eaa15) benzothiazolyloxy group (which may be substituted on the benzothiazole ring by at least one C1-6 alkyl group);
(Eaa16) 1,2,3,4-tetrahydronaphthyloxy group (which may be substituted on the 1,2,3,4-tetrahydronaphthalene ring by at least one oxo group as a substituent);
(Eaa17) 1,3-benzoxathiolanyloxy group (which may be substituted on the 1,3-benzoxathiolan ring by at least one oxo group as a substituent);
(Eaa18) isoquinolyloxy group;
(Eaa19) pyridyloxy group;
(Eaa20) quinolyloxy group (which may be substituted on the quinoline ring by at least one C1-6 alkyl group as a substituent);
(Eaa21) dibenzofuryloxy group;
(Eaa22) 2H-chromenyloxy group (which may be substituted on the 2H-chromen ring by at least one oxo group as a substituent);
(Eaa23) benzisoxazolyloxy group;
(Eaa24) quinoxalyloxy group;
(Eaa25) 2,3-dihydro-1H-indenyloxy group (which may be substituted on the 2,3-dihydro-1H-indene ring by at least one oxo group as a substituent);
(Eaa26) benzofurazanyloxy group; or
(Eaa27) phenyl C2-6 alkenyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group),
E11) a group represented by the following general formula (Eab):

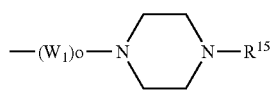

(Eab)

wherein o is the same as above, $W_1$ represents a C1-C6 alkylene group and $R^{15}$ represents:
(Eab1) hydrogen atom;
(Eab2) C1-6 alkyl group (wherein the alkyl group may be substituted by a morpholino group, benzoyl group, carbamoyl group which may have a C1-6 alkyl group as a substituent, or cyano group);
(Eab3) C3-8 cycloalkyl group;
(Eab4) phenyl C1-6 alkyl group (which may be substituted on the phenyl ring by at least one group selected from the group consisting of a halogen atom, a cyano group, a phenyl group, a nitro group, a C1-6 alkylthio group, a C1-6 alkylsulfonyl group, a phenyl C1-6 alkoxy group, a C2-6 alkanoyloxy group, a halogen-substituted or unsubstituted C1-6 alkyl group, a halogen-substituted or unsubstituted C1-6 alkoxy group, and a 1,2,3-thiadiazolyl group);
(Eab5) C2-6 alkenyl group;
(Eab6) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);
(Eab7) C1-6 alkanoyl group;
(Eab8) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab9) benzoyl group (which may be substituted on the benzene ring by at least one group selected from the group consisting of a halogen atom, a halogen-substituted or unsubstituted C1-6 alkyl group, and a halogen-substituted or unsubstituted C1-6 alkoxy group);
(Eab10) C1-20 alkoxycarbonyl group (which may be substituted on the alkoxy group by at least one group selected from the group consisting of a halogen atom, an amino group which may have a C1-6 alkyl group as a substituent, and a C1-6 alkoxy-substituted C1-6 alkoxy group);
(Eab11) phenyl C1-6 alkoxycarbonyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, a nitro group, a halogen-substituted or unsubstituted C1-6 alkylthio group, an amino group which may have a C1-6 alkanoyl group, a phenyl C1-6 alkoxy group, a C1-6 alkoxycarbonyl group, and a 1,2,3-thiadiazolyl group);
(Eab12) a phenyl C3-6 alkenyloxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab13) phenoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab14) phenyl C1-6 alkylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab15) phenylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eab16) benzofuryl-substituted C1-6 alkoxycarbonyl group which may be substituted by at least one halogen atom on the benzofuran ring;
(Eab17) benzothienyl C1-6 alkoxycarbonyl group (which may be substituted on the benzothiophene ring by at least one group selected from the group consisting of a halogen atom and a halogen-substituted or unsubstituted C1-6 alkoxy group as a substituent);

(Eab18) naphthyl-substituted C1-6 alkoxycarbonyl group;
(Eab19) pyridyl-substituted C1-6 alkoxycarbonyl group (which may be substituted on the pyridine ring by at least one halogen atom as a substituent);
(Eab20) furyl-substituted C1-6 alkoxycarbonyl group (which may be substituted on the furan ring by at least one nitro group as a substituent);
(Eab21) thienyl-substituted C1-6 alkoxycarbonyl group (which may have at least one halogen atom as a substituent on the thiophene ring);
(Eab22) thiazolyl-substituted C1-6 alkoxycarbonyl group (which may be substituted on the thiazole ring by at least one group selected from the group consisting of a C1-6 alkyl group and a phenyl group (which may be substituted on the phenyl ring by at least one halogen-substituted or unsubstituted C1-6 alkyl group));
(Eab23) tetrazolyl-substituted C1-6 alkoxycarbonyl group (which may be substituted on the tetrazole ring by at least one group selected from the group consisting of a C1-6 alkyl group and a phenyl group (which may have at least one halogen atom as a substituent on the phenyl ring) as a substituent);
(Eab24) 2,3-dihydro-1H-indenyloxycarbonyl group;
(Eab25) adamantane-substituted C1-6 alkoxycarbonyl group;
(Eab26) phenyl C3-6 alkynyloxycarbonyl group;
(Eab27) phenylthio C1-6 alkoxycarbonyl group;
(Eab28) phenyl C1-6 alkoxy-substituted C1-6 alkoxycarbonyl group;
(Eab29) C2-6 alkenyloxycarbonyl group;
(Eab30) C2-6 alkynyloxycarbonyl group;
(Eab31) C3-8 cycloalkyl-substituted C1-6 alkoxycarbonyl group; or
(Eab32) benzoyl-substituted C1-6 alkoxycarbonyl group,
E12) a group represented by the following general formula (Eb):

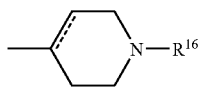
(Eb)

wherein the dotted line represents that the bond may be a double bond, and $R^{16}$ is defined as the same as $R^{15}$;
E13) a group represented by the following general formula (Ec):

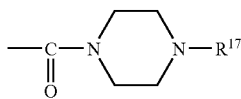
(Ec)

wherein $R^{17}$ represents:
(Ec1) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Ec2) C1-6 alkoxycarbonyl group; or
(Ec3) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group),
E14) pyridyl group;
E15) a group represented by the following general formula (Ee):

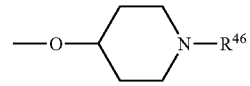
(Ee)

wherein $R^{46}$ represents a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group as a substituent); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or C1-6 alkoxycarbonyl group,
E16) phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
E17) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
E18) 8-azabicyclo[3,2,1]octyl group (which may be substituted on the 8-azabicyclo[3,2,1]octane ring by at least one phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent);
E19) a group represented by the following general formula (Ef):

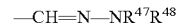
—CH=N—NR$^{47}$R$^{48}$ (Ef)

wherein $R^{47}$ and $R^{48}$ each identically or differently represent any one of a hydrogen atom, a C1-6 alkyl group, a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), or a pyridyl group (which may be substituted on the pyridine ring by at least one halogen-substituted or unsubstituted C1-6 alkyl group as a substituent); and further, $R^{47}$ and $R^{48}$ may bind to each other together with nitrogen atoms adjacent thereto directly or through other hetero atoms, so as to form a 5-7 membered saturated heterocyclic ring, which may be substituted on the heterocyclic ring by at least one phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent;

E20) phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

E21) amino substituted C2-6 alkenyl group (which may be substituted on the amino group by at least one group selected from the group consisting of a C1-6 alkyl group and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group)); or E22) oxazolidinyl group (which may be substituted on the oxazolidine ring by at least one oxo group as a substituent), a group represented by the following general formula (F):

—NR$^{19}$R$^{20}$  (F)

wherein R$^{19}$ and R$^{20}$ each identically or differently represent any one of:

F1) hydrogen atom;

F2) C1-6 alkyl group;

F3) phenyl C1-6 alkyl group (which may be substituted on the phenyl ring by at least one group selected from the group consisting of: a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a halogen atom; a halogen-substituted or unsubstituted C1-6 alkyl group; a halogen-substituted or unsubstituted C1-6 alkoxy group; an amino group which may have at least one group selected from the group consisting of a C1-6 alkyl group, and a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a piperazinyl group (which may be substituted on the piperazine ring by at least one phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent); and a piperidyl group (which may be substituted on the piperidine ring by at least one amino group which may have a group selected from the group consisting of a phenyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group) and a C1-6 alkyl group as a substituent));

F4) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

F5) amino C1-6 alkyl group (which may be substituted on the amino group by at least one group selected from the group consisting of a C1-6 alkyl group, a C1-6 alkoxycarbonyl group, and a phenyl group which may be substituted on the phenyl group by at least one group selected from a group consisting of a halogen atom and a halogen-substituted or unsubstituted C1-6 alkyl group);

F6) phenyl group (which may be substituted on the phenyl ring by at least one group selected from the group consisting of a halogen atom, a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), and a C1-6 alkoxycarbonyl group);

F7) C1-6 alkoxycarbonyl group;

F8) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

F9) a group represented by the following general formula (Fa):

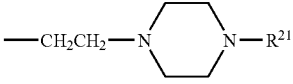

wherein R$^{21}$ represents a C1-6 alkoxycarbonyl group; phenyl C1-6 alkoxycarbonyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom and a halogen-substituted or unsubstituted C1-6 alkyl group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

F10) 1-substituted-4-piperidyl group represented by the following formula (Fb):

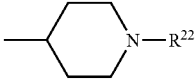

wherein R$^{22}$ represents a C1-6 alkoxycarbonyl group; phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

F11) piperidyl C1-6 alkyl group (which may have at least one phenoxy group (which may have at least one halogen-substituted or unsubstituted C1-6 alkyl group as a substituent) as a substituent);

F12) in addition, $R^{19}$ and $R^{20}$ may bind to each other together with nitrogen atoms adjacent thereto directly or through other hetero atoms or carbon atoms, so as to form a heterocyclic ring shown in any one of (F12-1) to (F12-10) indicated below:

(F12-1) a group represented by the following formula (Fc):

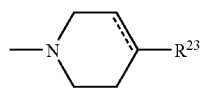  (Fc)

wherein the dotted line represents that the, bond may be a double bond, and $R^{23}$ represents:

(Fc1) C1-6 alkyl group;

(Fc2) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc3) phenyl group (which may be substituted on the phenyl ring by at least one group selected from the group consisting of: a halogen atom; a halogen-substituted or unsubstituted C1-6 alkyl group; a halogen-substituted or unsubstituted C1-6 alkoxy group; an amino group which may have, as a substituent, a group selected from the group consisting of a C1-6 alkyl group and a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and a piperidyl group (which may have, on the piperidine ring, as a substituent, at least one amino group that may have a group selected from the group consisting of a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) and a C1-6 alkyl group));

(Fc4) phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc5) biphenylyl C1-6 alkoxy group;

(Fc6) phenyl C3-6 alkenyloxy group which may be substituted on the phenyl ring by at least one halogen atom;

(Fc7) phenoxy group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Fc8) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc9) C1-6 alkoxycarbonyl group;

(Fc10) phenyl C1-6 alkoxycarbonyl group (which may be substituted on the phenyl ring by at least one halogen-substituted or unsubstituted C1-6 alkoxy group);

(Fc11) phenyl C1-6 alkylcarbamoyl group wherein at least one halogen may be substituted on the phenyl ring;

(Fc12) phenylcarbamoyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group);

(Fc13) phenylthio group (which may be substituted on the phenyl ring by at least one halogen-substituted or unsubstituted C1-6 alkoxy group);

(Fc14) phenyl sulfoxide (which may be substituted on the phenyl ring by at least one halogen-substituted or unsubstituted C1-6 alkoxy group);

(Fc15) pyridyl C1-6 alkoxy group; or (Fc16) a group represented by the following general formula (Fca):

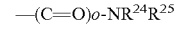  (Fca)

wherein o is the same as above, and each of $R^{24}$ and $R^{25}$ represents:

(Fca1) hydrogen atom;

(Fca2) C1-6 alkyl group;

(Fca3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca4) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Fca5) C1-6 alkanoyl group;

(Fca6) phenyl C2-6 alkanoyl group that may be substituted on the phenyl ring by at least one halogen atom;

(Fca7) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca8) C1-6 alkoxycarbonyl group;

(Fca9) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fca10) phenylcarbamoyl group (which may be substituted on the phenyl ring by at least one halogen-substituted or unsubstituted C1-6 alkyl group);

(Fca11) piperidyloxycarbonyl group (which may be substituted on the piperidine ring by at least one phenyl group (which may be substituted on the phenyl ring by at least one halogen-substituted or unsubstituted C1-6 alkyl group) as a substituent); or (Fca12) $R^{24}$ and $R^{25}$ may form a 5-6 membered saturated heterocyclic ring through nitrogen atoms adjacent thereto, which may be substituted on the heterocyclic ring by at least one group selected from the group consisting of a C1-6 alkoxycarbonyl group; a benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenoxy group (which may be substituted on the phenyl ring by at least one group selected from the group consisting of a halogen atom, a halogen-substituted or unsubstituted C1-6 alkyl group; and a halogen-substituted or unsubstituted C1-6 alkoxy group); a phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); a phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (F12-2) 4-substituted-1-piperazinyl group represented by the following general formula (Fd):

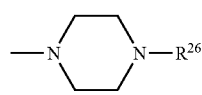

(Fd)

wherein $R^{26}$ represents:
(Fd1) hydrogen atom;
(Fd2) C1-6 alkyl group;
(Fd3) C3-8 cycloalkyl group;
(Fd4) C3-8 cycloalkyl C1-6 alkyl group;
(Fd5) C1-6 alkoxycarbonyl C1-6 alkyl group;
(Fd6) phenyl C2-6 alkenyl group;

(Fd7) phenyl C1-6 alkyl group (which may be substituted on the phenyl ring by 1 to 3 groups selected from the group consisting of: a halogen atom; a cyano group; a halogen-substituted or unsubstituted C1-6 alkyl group; C3-8 cycloalkyl group; a halogen-substituted or unsubstituted C1-6 alkoxy group; an amino group which may have a C1-6 alkyl group as a substituent; a C1-6 alkoxycarbonyl group; a phenoxy group; a phenyl C1-6 alkyl group; a phenyl C2-6 alkenyl group; a pyridyl group; an imidazolyl group; and a piperidyl group);

(Fd8) biphenylyl C1-6 alkyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and an amino group which may have a C1-6 alkyl group as a substituent);

(Fd9) naphthyl C1-6 alkyl group;

(Fd10) phenyl group (which may be substituted on the phenyl ring by at least one group selected from the group consisting of: a halogen atom; a cyano group; an amino group that may have a C1-6 alkyl group as a substituent; a halogen-substituted or unsubstituted C1-6 alkyl group; a halogen-substituted or unsubstituted C1-6 alkoxy group; a C1-6 alkoxycarbonyl group; a carboxyl group, a phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); an amino C1-6 alkyl group (which may have on the amino group at least one group selected from the group consisting of a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) and a C1-6 alkyl group)); and a phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group));

(Fd11) biphenylyl group (which may be substituted on the phenyl ring by at least one halogen-substituted or unsubstituted C1-6 alkyl groups);

(Fd12) amino group, amino group which is substituted by a C1-6 alkoxycarbonyl group, phenyl C1-6 alkylamino group (which may be substituted on the phenyl ring by at least one halogen-substituted or unsubstituted C1-6 alkyl group), or phenylamino group (which may be substituted on the phenyl ring by at least one group selected from the group consisting of a halogen-substituted or unsubstituted C1-6 alkyl group and a halogen atom);

(Fd13) benzoyl C1-6 alkyl group (which may have on the phenyl ring at least one halogen atom as a substituent);

(Fd14) phenylcarbamoyl C1-6 alkyl group (which may be substituted on the phenyl ring by at least one halogen-substituted or unsubstituted C1-6 alkyl group);

(Fd15) thiazolyl C1-6 alkyl group (which may be substituted on the thiazole ring by at least one group selected from the group consisting of a halogen-substituted or unsubstituted phenyl group and a C1-6 alkyl group);

(Fd16) oxazolyl C1-6 alkyl group (which may be substituted on the oxazole ring by at least one group selected from the group consisting of a halogen-substituted or unsubstituted phenyl group and a C1-6 alkyl group);

(Fd17) indolyl C1-6 alkyl group;

(Fd18) furyl C1-6 alkyl group (which may be substituted on the furan ring by at least one halogen-substituted or unsubstituted phenyl group);

(Fd19) imidazolyl C1-6 alkyl group (which may be substituted on the imidazole ring by a phenyl group);

(Fd20) quinolyl C1-6 alkyl group;

(Fd21) tetrazolyl group (which may be substituted on the tetrazole ring by a phenyl group);

(Fd22) pyrimidyl group which may be substituted by a phenyl group;

(Fd23) pyridyl group;

(Fd24) benzoxazolyl group;

(Fd25) benzothiazolyl group;

(Fd26) benzoxazolyl C1-6 alkyl group (which may have on the benzoxazole ring at least one oxo group as a substituent);

(Fd27) phenoxy C2-6 alkanoyl group which may be substituted on the phenyl ring by a halogen atom;

(Fd28) phenylthio C2-6 alkanoyl group which may be substituted on the phenyl ring by a halogen atom;

(Fd29) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fd30) benzoyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and an amino group which may have a C1-6 alkyl group as a substituent);

(Fd31) biphenylylcarbonyl group;

(Fd32) pyridylcarbonyl group;

(Fd33) phenyl C2-6 alkenylcarbonyl group wherein a halogen atom may be substituted on the phenyl ring;

(Fd34) phenyl C1-6 alkylsulfonyl group wherein a halogen atom may be substituted on the phenyl ring;

(Fd35) benzenesulfonyl group (which may be substituted on the benzene ring by at least one group selected from the group consisting of a halogen atom and a C1-6 alkyl group);

(Fd36) a group represented by the following general formula (Fda):

—COOR²⁷             (Fda)

wherein $R^{27}$ represents:

(Fda1) halogen-substituted or unsubstituted C1-8 alkyl group;

(Fda2) C3-8 cycloalkyl group;

(Fda3) C3-8 cycloalkyl-C1-6 alkyl group;

(Fda4) C1-6 alkoxy-C1-6 alkyl group;

(Fda5) amino-C1-6 alkyl group which may have a C1-6 alkyl group;

(Fda6) a group represented by the following general formula (Fdb):

wherein $R^{28}$, $R^{29}$, or $R^{30}$ represent a hydrogen atom, a C1-6 alkyl group, or a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), respectively;

(Fda7) phenyl C1-6 alkyl group (which may be substituted on the phenyl ring by 1 to 5 groups selected from the group consisting of: a halogen atom; a halogen-substituted or unsubstituted C1-6 alkyl group; a halogen-substituted or unsubstituted C1-6 alkoxy group; a halogen-substituted or unsubstituted C1-6 alkylthio group; a phenyl C1-6 alkoxy group; a hydroxy group; a C1-6 alkylsulfinyl group; a C1-6 alkylsulfonyl group; C1-6 alkylsulfonyloxy group; a cyano group; a C1-6 alkanoyl group; a benzoyl group; a phenyl C1-6 alkyl group which may have a C1-6 alkoxy group in the alkyl portion; an amino group; a nitro group; a carbamoyl group; a C1-6 alkanoylamino group; a C1-6 alkoxycarbonyl group; a C1-6 alkylaminocarbonyl group; a C1-6 alkoxycarbonylamino group; a tri-C1-6-alkylsiloxy group; a pyrrolyl group; a tetrahydropyranyloxy group; and an imidazolyl group);

(Fda8) biphenylyl C1-6 alkyl group;

(Fda9) benzhydryl group (which may be substituted on the benzene ring by at least one group selected from the group consisting of a halogen atom, a trifluoromethyl group, and a trifluoromethoxy group);

(Fda10) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fda11) phenyl C2-6 alkynyl group (which may be substituted on the phenyl ring by at least one halogen-substituted or unsubstituted C1-6 alkyl group as a substituent);

(Fda12) pyridyl C1-6 alkyl group;

(Fda13) a group represented by the following general formula (Edc):

wherein $R^{31}$ represents a phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (Fda14) piperidino C1-6 alkyl group (which may be substituted on the piperidine ring by a phenoxy group which may have at least one halogen-substituted or unsubstituted alkyl group as a substituent on the phenyl ring);

(Fda15) amino C1-6 alkyl group which may have, as a substituent, at least one group selected from the group consisting of a C1-6 alkyl group and a phenyl group which may have, as a substituent, a halogen-substituted or unsubstituted C1-6 alkoxy group on the phenyl ring;

(Fda16) 1,2,3,6-tetrahydropyridyl C1-6 alkyl group (which may be substituted on the 1,2,3,6-tetrahydropyridine ring by at least one phenyl group which may have, as a substituent, at least one halogen-substituted or unsubstituted C1-6 alkoxy group on the phenyl ring);

(Fda17) naphthyl C1-6 alkyl group;

(Fda18) fluorenyl C1-6 alkyl group;

(Fda19) pyridyl C1-6 alkyl group;

(Fda20) furyl C1-6 alkyl group (which may be substituted on the furan ring by a halogen-substituted or unsubstituted phenyl group);

(Fda21) thienyl C1-6 alkyl group;

(Fda22) oxazolyl C1-6 alkyl group (which may be substituted on the oxazole ring by a halogen atom or a halogen-substituted or unsubstituted phenyl group);

(Fda23) oxadiazolyl C1-6 alkyl group (which may be substituted on the oxadiazole ring by a halogen-substituted or unsubstituted phenyl group);

(Fda24) pyrazolyl C1-6 alkyl group (which may be substituted on the pyrazole ring by a halogen-substituted or unsubstituted phenyl group);

(Fda25) benzothienyl C1-6 alkyl group (which may be substituted on the benzothiophene ring by at least one group selected from the group consisting of a halogen atom and a halogen-substituted or unsubstituted C1-6 alkoxy group);

(Fda26) thienyl C1-6 alkyl group that may be substituted on the thiophene ring by a halogen atom;

(Fda27) benzothiazolyl C1-6 alkyl group;

(Fda28) benzofuryl C1-6 alkyl group which may be substituted on the benzofuran ring by a halogen atom;

(Fda29) indolinyl C1-6 alkyl group (which may be substituted on the indoline ring by at least one group selected from the group consisting of a C1-6 alkyl group and an oxo group);

(Fda30) benzoxazolyl C1-6 alkyl group (which may be substituted on the benzoxazole ring by at least one group selected from a group consisting of a halogen atom, a C1-6 alkyl group, and an oxo group);

(Fda31) chromenyl C1-6 alkyl group;

(Fda32) 1,2,3,4-tetrahydroquinolyl C1-6 alkyl group (which may be substituted on the quinoline ring by at least one group selected from the group consisting of a C1-6 alkyl group and an oxo group);

(Fda33) thiazolyl C1-6 alkyl group (which may be substituted on the thiazole ring by at least one group selected from the group consisting of a halogen atom, a halogen-substituted or unsubstituted phenyl group, and a C1-6 alkyl group); or (Fda34) tetrazolyl C1-6 alkyl group (which may be substituted on the tetrazole ring by a group selected from the group consisting of a halogen-substituted or unsubstituted phenyl group and a C1-6 alkyl group);

(Fd37) a group represented by the following general formula (Fe):

-Z-NR$^{32}$R$^{33}$             (Fe)

wherein Z represents —C=O or —C=S, and R$^{32}$ and R$^{33}$ each identically or differently represent any one of:

(Fe1) hydrogen atom;

(Fe2) C1-6 alkyl group;

(Fe3) C3-8 cycloalkyl group;

(Fe4) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fe5) phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fe6) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and (Fe7) R$^{32}$ and R$^{33}$ may bind to each other together with nitrogen atoms adjacent thereto through other carbon atoms, so as to form a piperidine ring or 1,2,3,6-tetrahydropyridine ring, which may be substituted on the piperidine or 1,2,3,6-tetrahydropyridine ring by a phenyl group, which may be substituted at least one group selected from the group consisting of a halogen atom and a halogen-substituted or unsubstituted C1-6 alkyl group, (Fd38) a group represented by the following general formula (Ff):

(Ff)

wherein R$^{34}$ represents a hydrogen atom or C1-6 lower alkyl group, and R$^{35}$ represents:

(Ff1) C3-8 cycloalkyl group;

(Ff2) C3-8 cycloalkenyl group;

(Ff3) a group represented by the following general formula (Ffa):

(Ffa)

wherein each of R$^{36}$, R$^{37}$, and R$^{38}$ represents: a hydrogen atom; C1-6 alkyl group; phenyl group (which may be substituted on the phenyl ring by at least one 1 to 5 groups selected from the group consisting of a halogen atom, a halogen-substituted or unsubstituted C1-6 alkyl group, a halogen-substituted or unsubstituted C1-6 alkoxy group, a C1-4 alkylenedioxy group, a C1-6 alkylsulfonyl group, a halogen-substituted or unsubstituted C1-6 alkylthio group, a nitro group, and an amino group which may have a C1-6 alkanoyl group as a substituent); benzofuryl group (which may be substituted on the benzofuran ring by at least one group selected from the group consisting of a halogen atom, a halogen-substituted or unsubstituted C1-6 alkyl group, and a halogen-substituted or unsubstituted C1-6 alkoxy group); biphenylyl group; furyl group (which may be substituted on the furan ring by a phenyl group which may have a halogen atom as a substituent); or thiazolyl group (which may be substituted on the thiazole ring by at least one phenyl group which may have a halogen atom as a substituent), (Ff4) phenyl group (which may be substituted on the phenyl ring by at least one group selected from the group consisting of: a halogen atom; a halogen-substituted or unsubstituted C1-6 alkyl group; a C3-8 cycloalkyl group; a hydroxyl group; a halogen-substituted or unsubstituted C1-8 alkoxy group; a C3-8 cycloalkoxy group; a C1-4 alkylenedioxy group; a cyano group; a nitro group; a phenyl C2-6 alkenyl group; a C2-6 alkanoyloxy group; an amino group which may have a C1-6 alkanoyl group as a substituent; a C1-6 alkylsulfonylamino group; a phenyl C1-6 alkoxy group; a phenoxy group; an amino group which has at least one C1-6 alkyl group as a substituent; an amino group which has at least one phenyl group as a substituent; an amino C1-6 alkoxy group which may have at least one C1-6 alkyl group as a substituent; a C1-6 alkoxycarbonyl group; a C1-6 alkoxycarbonyl C1-6 alkoxy group; a C1-6 alkylthio group; a pyrrolyl group; an imidazolyl group; a piperidyl group; a morpholino group; a pyrrolidinyl group; a thienyl group; a benzofuryl group; a piperazinyl group (which may be substituted on the piperazine ring by at least one group selected from the group consisting of a C1-6 alkyl group, a phenyl C1-6 alkyl group, and a benzoyl group which may have at least one C1-6 alkyl group as a substituent); a quinolyl group which may be substituted on the quinoline ring by at least one group selected from the group consisting of a C1-6 alkoxy group and an oxo group; a piperidylcarbonyl group which may be substituted on the piperidine ring by a carbostyril group; and a triazolyl group);

(Ff5) naphthyl group which may be substituted on the naphthalene ring by at least one group selected from the group consisting of a halogen atom, a halogen-substituted or unsubstituted C1-6 alkoxy group, and an amino group which may have a C1-6 alkyl group as a substituent;

(Ff6) biphenylyl group (which may be substituted on the biphenylyl ring by at least one group selected from the group consisting of a halogen atom, a halogen-substituted or unsubstituted C1-9 alkyl group, and a halogen-substituted or unsubstituted C1-6 alkoxy group);

(Ff7) fluorenyl group; pyrenyl group;

(Ff8) benzofuryl group (which may be substituted on the benzofuran ring by at least one group selected from the group consisting of a halogen atom, a halogen-substituted or unsubstituted C1-6 alkyl group, and a halogen-substituted or unsubstituted C1-6 alkoxy group);

(Ff9) benzothienyl group (which may be substituted on the benzothiophene ring by at least one group selected from the group consisting of a halogen atom, a halogen-substituted or unsubstituted C1-6 alkyl group, and a halogen-substituted or unsubstituted C1-6 alkoxy group);

(Ff10) pyridyl group (which may be substituted on the pyridine ring by at least one group selected from the group consisting of a halogen atom, a halogen-substituted or unsubstituted C1-6 alkyl group, a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), a furyl group, and a thienyl group);

(Ff11) furyl group (which may be substituted on the furan ring by 1 to 3 groups selected from the group consisting of a C1-6 alkyl group, a nitro group, and a phenyl group (which may be substituted on the phenyl ring-by at least one group selected from the group consisting of a halogen atom, a halogen-substituted or unsubstituted C1-6 alkyl group, a halogen-substituted or unsubstituted C1-6 alkoxy group, and a nitro group));

(Ff12) benzothiazole group (which may have, on the benzothiazole ring, at least one phenyl group that may have, as a substituent, a C1-6 alkoxy group on the phenyl ring);

(Ff13) thienyl group (which may have, on the thiophene ring, at least one group selected from the group consisting of a halogen atom, a nitro group, a C1-6 alkyl group, a pyrazolyl group which may be substituted on the pyrazole ring by at least one halogen-substituted or unsubstituted C1-6 alkyl group as a substituent, and a thienyl group which may have a halogen atom on the thiophene ring);

(Ff14) indolyl group (which may be substituted on the indole ring by at least one group selected from the group consisting of a phenylsulfonyl group which may have a C1-6 alkyl group as a substituent, a phenyl C1-6 alkyl group, a C1-6 alkoxycarbonyl group, and a phenyl group);

(Ff15) pyrrolyl group (which may be substituted on the pyrrole ring by at least one group selected from the group consisting of a phenyl group which may be substituted by at least one halogen-substituted or unsubstituted C1-6 alkyl group, and a C1-6 alkyl group);

(Ff16) coumaryl group;

(Ff17) benzimidazolyl group (which may be substituted on the benzimidazole ring by at least one thienyl group as a substituent);

(Ff18) oxazolyl group (which may be substituted on the oxazole ring by at least one phenyl group that may have a halogen atom as a substituent);

(Ff19) thiazolyl group (which may be substituted on the thiazole ring by at least one phenyl group, wherein at least one group selected from the group consisting of a halogen atom, a nitro group, and a phenyl group);

(Ff20) quinolyl group;

(Ff21) 3,4-dihydrocarbostyril group (which may be substituted on the 3,4-dihydrocarbostyril ring by at least one group selected from the group consisting of a C1-6 alkoxy group, a C1-6 alkyl group, and a phenyl C1-6 alkoxy group), or carbostyril group (which may be substituted on the carbostyril ring by at least one group selected from the group consisting of a C1-6 alkoxy group, a C1-6 alkyl group, and a phenyl C1-6 alkoxy group);
(Ff22) imidazo[2,1-b]thiazolyl group;
(Ff23) imidazo[2,1-a]pyridyl group;
(Ff24) chromanyl group (which may be substituted on the chroman ring by at least one C1-6 alkyl group); or
(Ff25) 2,3-dihydrobenzofuryl group, or
(Fd39) a group represented by the following general formula (Ffb):

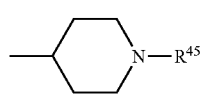

(Ffb)

wherein R⁴⁵ represents: a C1-6 alkoxycarbonyl group; phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); amino substituted C1-6 alkyl group which may have, on the amino group, a group selected from a group consisting of a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) and a C1-6 alkyl group as a substituent; benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group),
(F12-3) morpholino group;
(F12-4) imidazolyl group;
(F12-5) 1,4-dioxaazaspiro[4,5]decyl group (which may be substituted on the 1,4-dioxaazaspiro-[4,5]decane ring by at least one oxo group as a substituent);
(F12-6) homopiperazinyl group (which may be substituted on the homopiperazine ring by at least one group selected from the group consisting of a C1-6 alkoxycarbonyl group, a phenyl C1-6 alkoxycarbonyl group, and a phenyl-substituted or unsubstituted phenyl group as a substituent);
(F12-7) piperazinyl group (which may be substituted on the piperazine ring by at least one group selected from the group consisting of an oxo group, a C1-6 alkyl group, and a phenyl C1-6 alkyl group (which may be substituted on the phenyl ring by at least one halogen-substituted or unsubstituted C1-6 alkyl group));
(F12-8) piperidyl group (which may be substituted on the piperidine ring by at least one oxo group as a substituent);
(F12-9) pyrrolidinyl group (which may be substituted on the pyrrolidine ring by at least one phenoxy C1-6 alkyl group that may have a halogen-substituted or unsubstituted C1-6 alkoxy group as a substituent); and
(F12-10) isoindolinyl group,
F13) moreover, R¹⁹ and R²⁰ may bind to each other together with nitrogen atoms adjacent thereto directly or through hetero atoms, so as to form a cyclic imide or amide shown in any one of (F13-1) to (F13-11) indicated below:
(F13-1) succinimide group;
(F13-2) oxazolidinyl group (which may be substituted on the oxazolidine ring by at least one oxo group as a substituent);
(F13-3) benzo-1,3-oxazolidinyl group (which may be substituted on the benzo-1,3-oxazolidine ring by at least one group selected from the group consisting of an oxo group, a halogen atom, and a phenyl group as a substituent);
(F13-4) imidazolidinyl group (which may be substituted on the imidazolidine ring by at least one group selected from the group consisting of an oxo group, a phenyl C1-6 alkyl group (which may be substituted on the phenyl ring by 1 to 3 groups selected from the group consisting of a halogen atom and a C1-6 alkoxy group), and a phenyl group);
(F13-5) benzimidazolidinyl group (which may be substituted on the benzimidazolidine ring by at least one group selected from the group consisting of: an oxo group; a halogen atom; a halogen-substituted or unsubstituted C1-6 alkyl group; an amino group which may have a C1-6 alkyl group as a substituent; a C1-6 alkoxycarbonyl group; and a piperidyl group (which may be substituted on the piperidine ring by at least one group selected from the group consisting of a C1-6 alkyl group, a phenyl group wherein 1 to 3 halogen atoms may be substituted on the phenyl ring, a C1-6 alkoxycarbonyl group, and a phenyl C1-6 alkoxycarbonyl group as a substituent));
(F13-6) phthalimide group;
(F13-7) indolinyl group (which may have on the indoline ring at least one group selected from the group consisting of a C1-6 alkyl group, a halogen atom, and an oxo group as a substituent);
(F13-8) 2,3-dihydrobenzothiazolyl group (which may have at least one oxo group on the 2,3-dihydrobenzothiazole ring);
(F13-9) 1H-2,4-benzoxazinyl group (which may be substituted on the 1H-2,4-benzoxazine ring by at least one oxo group as a substituent);
(F13-10) a group represented by the following general formula (Fga):

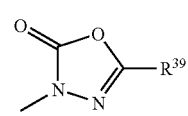

(Fga)

wherein R³⁹ represents: a hydrogen atom; a phenyl C1-6 alkyl group which may have, as a substituent, a halogen atom on the phenyl ring; phenoxy C1-6 alkyl group which may have, as a substituent, a halogen atom on the phenyl ring; phenyl C2-6 alkenyl group which may have, as a substituent, a halogen atom on the phenyl ring; phenyl group which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a phenyl group as a substituent; pyridyl group; or pyrazinyl group, and (F13-11) 1,3-thiazolidinyl group (which may be substituted on the 1,3-thiazolidine ring by at least one group selected from a group consisting of an oxo group and a phenyl C1-6 alkylidene group which may have a halogen-substituted or unsubstituted C1-6 alkyl group on the phenyl ring as a substituent), a group represented by the following general formula (G):

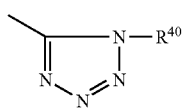

(G)

wherein $R^{40}$ represents a C1-6 alkyl group, or halogen-substituted or unsubstituted phenyl group, a Spiro ring group represented by the following general formula (H):

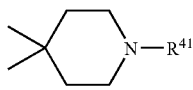

(H)

wherein $R^{41}$ represents:

H1) hydrogen atom;

H2) C1-6 alkyl group;

H3) phenyl C1-6 alkyl group that may have a phenyl group as a substituent on the phenyl ring;

H4) phenyl group (which may be substituted on the phenyl ring by at least one group selected from the group consisting of: a halogen atom; a halogen-substituted or unsubstituted C1-6 alkyl group; a halogen-substituted or unsubstituted C1-6 alkoxy group; an amino group (which may be substituted on the amino group by at least one group selected from the group consisting of a C1-6 alkyl group and a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group)); an phenoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and piperidyl group (which may be substituted on the piperidine ring by at least one group selected from the group consisting of phenoxy groups (which may be substituted on the phenyl ring by at least one group selected from the group consisting of a halogen atom, a halogen-substituted or unsubstituted C1-6 alkyl group, and a halogen-substituted or unsubstituted C1-6 alkoxy group) as a substituent));

H5) piperazinyl C1-6 alkyl group (which may be substituted on the piperazine ring by at least one group selected from the group consisting of a C1-6 alkoxycarbonyl group and a phenyl C1-6 alkoxycarbonyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, and a phenyl group);

H6) piperazinylcarbonyl C1-6 alkyl group (which may be substituted on the piperazine ring by at least one group selected from the group consisting of: a C1-6 alkoxycarbonyl group; a phenyl C1-6 alkoxycarbonyl group which may have, as a substituent, a halogen-substituted or unsubstituted C1-6 alkyl group on the phenyl ring; and a phenyl C1-6 alkyl group which may have, as a substituent, at least one group selected from the group consisting of a halogen-substituted or unsubstituted C1-6 alkyl group and a phenyl group on the phenyl ring);

H7) phenylcarbamoyl C1-6 alkyl group which may have at least one halogen-substituted or unsubstituted C1-6 alkyl group as a substituent on the phenyl ring;

H8) benzoxazolyl C1-6 alkyl group (which may have at least one oxo group as a substituent on the benzoxazole ring);

H9) benzothiazolyl group;

H10) tetrazolyl group (which may have at least one phenyl group as a substituent on the tetrazole ring);

H11) C1-6 alkylsulfonyl group;

H12) phenylsulfonyl group which may have at least one C1-6 alkyl group as a substituent on the phenyl ring;

H13) phenylthiocarbamoyl group which may be substituted on the phenyl ring by at least one halogen atom as a substituent;

H14) C1-8 alkoxycarbonyl group;

H15) phenyl C1-6 alkoxycarbonyl group (which may be substituted on the phenyl ring by at least one group selected from the group consisting of a halogen atom, a C1-6 alkoxycarbonyl group, an amino group which may have a C1-6 alkoxycarbonyl group as a substituent, a halogen-substituted or unsubstituted C1-6 alkyl group, a halogen-substituted or unsubstituted C1-6 alkoxy group, a nitro group, and a C1-6 alkylthio group);

H16) benzhydryloxycarbonyl group (which may be substituted on the phenyl ring by at least one halogen atom);

H17) C1-6 alkoxycarbonyl group which may have a phenyl-substituted or unsubstituted phenyl group;

H18) naphthyl C1-6 alkoxycarbonyl group;

H19) pyridyl C1-6 alkoxycarbonyl group;

H20) C1-6 alkoxy-substituted C1-6 alkoxycarbonyl group;

H21) piperazinyl C1-6 alkoxycarbonyl group (which may be substituted on the piperazine ring by at least one group selected from the group consisting of a C1-6 alkoxycarbonyl group and a phenyl C1-6 alkyl group (which may have at least one halogen atom as a substituent on the phenyl ring) as a substituent);

H22) phenoxycarbonyl group (which may be substituted on the phenyl ring by at least one group selected from the group consisting of a C1-6 alkyl group and a C1-6 alkoxy group);

H23) C1-6 alkanoyl group;

H24) benzoyl group (which may be substituted on the phenyl ring by at least one halogen-substituted or unsubstituted C1-6 alkyl group);

H25) phenyl C1-6 alkanoyl group (which may be substituted on the phenyl ring by at least one halogen-substituted or unsubstituted C1-6 alkyl group);

H26) phenoxy C1-6 alkanoyl group (wherein 1 to 3 halogen atoms may be substituted on the phenyl ring);

H27) piperazinyl C2-6 alkanoyl group (which may be substituted on the piperazine ring by at least one group selected from a group consisting of: a C1-6 alkanoyl group; a phenyl C1-6 alkyl group which may have, as a substituent, at least one group selected from the group consisting of a phenyl group, a halogen atom, a halogen-substituted or unsubstituted C1-6 alkyl group, and a halogen-substituted or unsubstituted C1-6 alkoxy group, on the phenyl ring; a phenyl C1-6 alkoxycarbonyl group which may have, as a substituent, at least one group selected from the group consisting of a halogen atom, a halogen-substituted or unsubstituted C1-6 alkyl group, and a halogen-substituted or unsubstituted C1-6 alkoxy group, on the phenyl ring; a phenylcarbamoyl C1-6 alkyl group which may have, as a substituent, at least one group selected from the group consisting of a halogen atom, a halogen-substituted or unsubstituted C1-6 alkyl group, and a halogen-substituted or unsubstituted C1-6 alkoxy group, on the phenyl ring; a phenylcarbamoyl group which may have, as a substituent, at least one group selected from the group consisting of a halogen atom, a halogen-substituted or unsubstituted C1-6 alkyl group, and a halogen-substituted or unsubstituted C1-6 alkoxy group, on the phenyl ring; and a benzoxazolyl group);

H28) phenylcarbamoyl group (which may be substituted on the phenyl ring by 1 to 3 groups selected from the group consisting of a halogen atom, an amino group which may have a C1-6 alkyl group as a substituent, a carboxyl group, a C1-6 alkoxycarbonyl group, a halogen-substituted or unsubstituted C1-6 alkyl group, a halogen-substituted or unsubstituted C1-6 alkoxy group, a piperazinyl group which may have a C1-6 alkyl group as a substituent on the piperazine ring, and a morpholino group);

H29) phenyl C1-6 alkylcarbamoyl group (which may be substituted on the phenyl ring by at least one group selected from the group consisting of a halogen-substituted or unsubstituted C1-6 alkyl group and a halogen-substituted or unsubstituted C1-6 alkoxy group); or H30) piperazinylcarbonyl group (which may be substituted on the piperazine ring by at least one group selected from the group consisting of a C1-6 alkoxycarbonyl group, a phenyl C1-6 alkoxycarbonyl group which may have at least one halogen-substituted or unsubstituted C1-6 alkyl group on the phenyl ring, and a phenyl C1-6 alkyl group which may have a halogen-substituted or unsubstituted C1-6 alkyl group on the phenyl ring), provided that, in the above general formula (1), when $R^1$ represents a hydrogen atom and $R^2$ represents a group represented by the above general formula (A), then $R^3$ cannot be an isopropyl group; when $R^1$ represents a hydrogen atom, $R^2$ represents a group represented by the above general formula (E), and m is 0, then $R^{11}$ cannot be a hydrogen atom; and further, when $R^1$ represents a hydrogen atom and $R^2$ represents a group represented by the above general formula (F), then it is not possible that $R^{19}$ represents a hydrogen atom and $R^{20}$ represents a tert-butoxycarbonyl group.

2. The 2,3-dihydro-6-nitroimidazo[2,1-b]oxazole compound represented by the following general formula (1'), optically active form thereof, or pharmaceutically acceptable salt thereof according to claim 1:

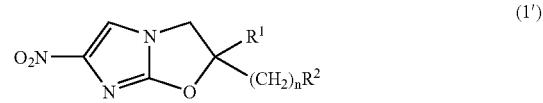

wherein $R^1$ represents a hydrogen atom or C1-6 alkyl group, n represents an integer of 0 to 6, and $R^2$ represents a group represented by general formula (A'), (B'), (C'), (D'), (E'), (F') or (G') indicated below, and further, $R^1$ and —(CH$_2$)$_n$R$^2$ may bind to each other together with carbon atoms adjacent thereto through nitrogen atoms, so as to form a spiro ring represented by general formula (H') indicated below:

a group represented by the following general formula (A'):

wherein $R^3$ represents:

A3) C1-6 alkoxy-C1-6 alkyl group

A4) phenyl C1-6 alkyl group (which may be substituted on the phenyl ring by at least one group selected from the group consisting of a benzyloxy group, a halogen-substituted or unsubstituted C1-6 alkyl group, and a halogen-substituted or unsubstituted C1-6 alkoxy group);

A5) biphenylyl C1-6 alkyl group;

A6) cinnamyl group:

A7) methanesulfonyl group;

A8) benzenesulfonyl group that may be substituted by a methyl group;

A9) C1-6 alkanoyl group;

A10) a group represented by the following general formula (Aa'):

wherein $R^4$ represents a C1-6 alkoxycarbonyl group, phenyl C1-6 alkoxycarbonyl group (which may be substituted on the phenyl ring by at least one group selected from the group consisting of a benzyloxy group, a halogen-substituted or unsubstituted C1-6 alkyl group, and a halogen-substituted or unsubstituted C1-6 alkoxy group), or phenyl C1-6 alkyl group (which may be substituted on the phenyl ring by at least one group selected from the group consisting of a benzyloxy group, a halogen-substituted or unsubstituted C1-6 alkyl group, and a halogen-substituted or unsubstituted C1-6 alkoxy group);

A11) biphenylyl C1-6 alkoxycarbonyl group;

A12) 2-(2-oxo-3-benzoxazolyl)ethyl group;

A13) 2-benzoxazolyl group; or

A14) 2-phenyl-5-methyl-4-oxazolylmethyl group, a group represented by the following general formula (B'):

wherein R⁵ represents a 5-(1H)-tetrazolyl group (wherein position 1 may be substituted by a C1-6 alkyl group, or halogen-substituted or unsubstituted phenyl group), or 2-benzoxazolyl group, a group represented by the following general formula (C'):

—COOR⁶                       (C')

wherein R⁶ represents a C1-6 alkyl group, a carbamoyloxy group represented by the following general formula (D'):

—OOCNR⁷R⁸                  (D')

wherein R⁷ and R⁸ each identically or differently represent any one of:
D1) hydrogen atom;
D2) C1-8 alkyl group;
D3) halogen-substituted C1-6 alkyl group;
D4) C1-6 alkoxycarbonyl-C1-6 alkyl group;
D5) C5-8 cycloalkyl group;
D6) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
D7) phenyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, a C1-6 alkanoyl group, a carboxyl group, a C1-6 alkoxycarbonyl group, a benzyloxycarbonyl group, a carbamoyl group, a C1-6 alkylcarbamoyl group, an aminosulfonyl group, and a morpholino group);
D8) 1-naphthyl group;
D9) 4-pyridyl group; and
D10) R⁷ and R⁸ may bind to each other together with nitrogen atoms adjacent thereto directly or through other hetero atoms or carbon atoms, so as to form a saturated heterocyclic group shown in any one of (D10-1) to (D10-3) indicated below, or benzene condensed heterocyclic group shown in any one of (D10-4) to (D10-7) indicated below:
(D10-1) a piperazinyl group represented by the following general formula (Da'):

wherein R⁹ represents:
(Da1) hydrogen atom;
(Da2) C1-6 alkyl group;
(Da3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da4) phenyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group);
(Da5) C1-6 alkoxycarbonyl group;

(Da6) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Da7) 4-trifluoromethylcinnamyloxycarbonyl group; or
(Da8) 4-trifluoromethylbenzylideneamino group,
(D10-2) a group represented by the following general formula (Db'):

wherein the dotted line represents that the bond may be a double bond, and R¹⁰ represents:
(Db1) hydrogen atom;
(Db2) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Db3) phenoxy group (which may be substituted on the phenyl ring by at least one halogen-substituted or unsubstituted C1-6 alkyl group); or
(Db4) phenylamino group (which may be substituted on the phenyl ring by at least one halogen-substituted or unsubstituted C1-6 alkyl group), and
(D10-3) a morpholino group;
(D10-4) halogen-substituted or unsubstituted 1-indolinyl group;
(D10-5) halogen-substituted or unsubstituted 2-isoindolinyl group;
(D10-6) halogen-substituted or unsubstituted 1,2,3,4-tetrahydro-1-quinolinyl group; and
(D10-7) halogen-substituted or unsubstituted 1,2,3,4-tetrahydro-2-isoquinolinyl group, a phenoxy group represented by the following general formula (E'):

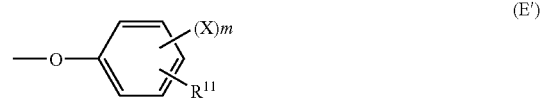

wherein X represents a halogen atom, m represents an integer of 0 to 3, and R¹¹ represents:
E2) halogen-substituted or unsubstituted C1-6 alkyl group;
E3) halogen-substituted or unsubstituted C1-6 alkoxy group;
E4) morpholino group;
E5) thiomorpholino group;
E6) S-oxide thiomorpholino group;
E7) 1-imidazolyl group;
E8) 1-triazolyl group;

E9) piperidinyl group represented by the following general formula (Ea'):

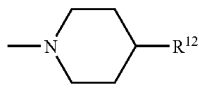

wherein $R^{12}$ represents:
(Ea1) hydrogen atom;
(Ea2) C1-6 alkoxycarbonyl group; or
(Ea3) phenoxy group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group), E10) a group represented by the following formula (Eb')

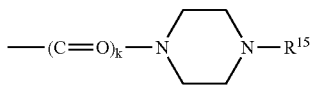

wherein k represents an integer of 0 or 1, and $R^{15}$ represents:
(Eb1) hydrogen atom;
(Eb2) C1-6 alkyl group;
(Eb3) phenyl C1-6 alkyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);
(Eb4) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);
(Eb5) C1-6 alkanoyl group;
(Eb6) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eb7) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eb8) C1-8 alkoxycarbonyl group (which may be substituted on the alkoxy group by at least one group selected from the group consisting of a halogen atom, a di(C1-6 alkyl)amino group, and a C1-6 alkoxy group);
(Eb9) phenyl C1-6 alkoxycarbonyl group (which may be substituted on the phenyl ring by at least one group selected from-the group consisting of a halogen atom, a halogen-substituted or unsubstituted C1-6 alkyl group, and a halogen-substituted or unsubstituted C1-6 alkoxy group);
(Eb10) phenyl C3-6 alkenyloxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eb11) phenoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eb12) phenyl C1-6 alkylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Eb13) phenylcarbamoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or
(Eb14) 2-benzofuranylmethyloxycarbonyl group which may be substituted by a halogen atom on the benzene ring, E11) a group represented by the following general formula (Ec'):

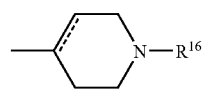

wherein the dotted line represents that the bond may be a double bond, and $R^{16}$ represents:
(Ec1) hydrogen atom;
(Ec2) C1-6 alkyl group;
(Ec3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Ec4) C1-8 alkoxycarbonyl group; or
(Ec5) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), a group represented by the following general formula (F'):

$$-NR^{19}R^{20} \quad (F')$$

wherein $R^{19}$ and $R^{20}$ each identically or differently represent any one of:
F1) hydrogen atom;
F2) C1-6 alkyl group;
F3) phenyl C1-6 alkyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a dimethylamino group);
F4) phenoxy C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

F5) N-methylamino C1-6 alkyl group (wherein, the position N may be substituted by a C1-6 alkoxycarbonyl group, or phenyl group that may be substituted on the phenyl ring by at least one group selected from the group consisting of a halogen atom and a halogen-substituted or unsubstituted C1-6 alkyl group);

F6) phenyl group (which may be substituted on the phenyl ring by at least one group selected from the group consisting of a halogen atom and a C1-6 alkoxycarbonyl group);

F7) C1-6 alkoxycarbonyl group;

F8) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

F9) 4-substituted-1-piperazinylethyl group represented by the following general formula (Fa'):

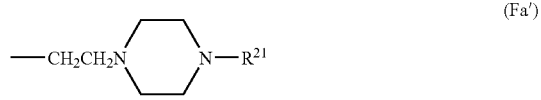

wherein $R^{21}$ represents a C1-6 alkoxycarbonyl group; phenyl C1-6 alkoxycarbonyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom and a halogen-substituted or unsubstituted C1-6 alkyl group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group), F10) 1-substituted-4-piperidinyl group represented by the following formula (Fb'):

wherein $R^{22}$ represents a C1-6 alkoxycarbonyl group; phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group), F11) 2-[4-(4-trifluoromethylphenoxy)-1-piperidinyl]ethyl group;

F12) in addition, $R^{19}$ and $R^{20}$ may bind to each other together with nitrogen atoms adjacent thereto directly or through other hetero atoms or carbon atoms, so as to form a heterocyclic ring shown in any one of (F12-1) to (F12-10) indicated below:

(F12-1) a group represented by the following formula (Fc'):

wherein the dotted line represents that the bond may be a double bond, and $R^{23}$ represents:

(Fc1) C1-6 alkyl group;

(Fc2) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc3) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc4) phenyl C1-6 alkoxy group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc5) 4-biphenylyl C1-6 alkoxy group;

(Fc6) phenyl C3-6 alkenyloxy group which may be substituted on the phenyl ring by a halogen atom;

(Fc7) phenoxy group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);

(Fc8) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fc9) C1-6 alkoxycarbonyl group;

(Fc10) phenyl C1-6 alkoxycarbonyl group (which may be substituted on the phenyl ring by at least one halogen-substituted or unsubstituted C1-6 alkoxy group);

(Fc11) phenyl C1-6 alkylcarbamoyl group wherein a halogen atom may be substituted on the phenyl ring;

(Fc12) phenylcarbamoyl group wherein a halogen atom may be substituted on the phenyl ring;

(Fc13) phenylthio group (which may be substituted on the phenyl ring by at least one halogen-substituted or unsubstituted C1-6 alkoxy group);

(Fc14) phenyl sulfoxide group (which may be substituted on the phenyl ring by at least one halogen-substituted or unsubstituted C1-6 alkoxy group);
(Fc15) pyridylmethoxy group; or
(Fc16) a group represented by the following general formula (Fca'):

$$-NR^{24}R^{25} \quad (Fca')$$

wherein each of $R^{24}$ and $R^{25}$ represents:
(Fca1) hydrogen atom;
(Fca2) C1-6 alkyl group;
(Fca3) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Fca4) phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group);
(Fca5) C1-6 alkanoyl group;
(Fca6) phenylacetyl group which may be substituted on the phenyl ring by a halogen atom;
(Fca7) benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Fca8) C1-6 alkoxycarbonyl group;
(Fca9) phenyl C1-6 alkoxycarbonyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);
(Fca10) phenylcarbamoyl group (which may be substituted by at least one halogen-substituted or unsubstituted C1-6 alkoxy group on the phenyl ring);
(Fca11) 1-(4-trifluoromethylphenyl)-4-piperidinyloxycarbonyl group; or
(Fca12) $R^{24}$ and $R^{25}$ may form a piperidine ring through nitrogen adjacent thereto,
(F12-2) 4-substituted-1-piperazinyl group represented by the following general formula (Fd'):

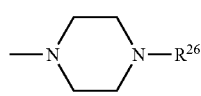

(Fd')

wherein $R^{26}$ represents:
(Fd1) hydrogen atom;
(Fd2) C1-6 alkyl group;
(Fd3) C5-8 cycloalkyl group;
(Fd4) C5-8 cycloalkyl-C1-6 alkyl group;
(Fd5) C1-6 alkoxycarbonyl-C1-6 alkyl group;
(Fd6) cinnamyl group;
(Fd7) phenyl C1-6 alkyl group (which may be substituted on the phenyl ring by 1 to 3 groups selected from the group consisting of a halogen atom; a cyano group; a halogen-substituted or unsubstituted C1-6 alkyl group; a cyclohexyl group; a halogen-substituted or unsubstituted C1-6 alkoxy group; a dimethylamino group; a C1-6 alkoxycarbonyl group; a phenoxy group; a phenyl C1-6 alkyl group; a styryl group; a 3-pyridyl group; a 1-imidazolyl group; and a 1-piperidino group);
(Fd8) biphenylylmethyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a dimethylamino group);
(Fd9) 1- or 2-naphthylmethyl group;
(Fd10) phenyl group (which may be substituted on the phenyl ring by at least one group selected from the group consisting of: a halogen atom; a cyano group; a dimethylamino group; a halogen-substituted or unsubstituted C1-6 alkyl group; a halogen-substituted or unsubstituted C1-6 alkoxy group; a C1-6 alkoxycarbonyl group, and a carboxyl group);
(Fd11) biphenylyl group (which may be substituted on the phenyl ring by at least one group selected from the group consisting of halogen-substituted or unsubstituted C1-6 alkyl groups);
(Fd12) amino group, amino group substituted by a C1-6 alkoxycarbonyl group, benzylamino group, trifluoromethylbenzylamino group, or phenylamino group (which may be substituted on the phenyl ring by at least one group selected from the group consisting of a halogen-substituted or unsubstituted C1-6 alkyl group and a halogen atom);
(Fd13) 4-chlorobenzoylmethyl group;
(Fd14) phenylcarbamoylmethyl group (which may be substituted on the phenyl ring by at least one halogen-substituted or unsubstituted C1-6 alkyl group);
(Fd15) 4- or 5-thiazolylmethyl group (which may be substituted on the thiazole ring by at least one group selected from the group consisting of a halogen-substituted or unsubstituted phenyl group and a C1-6 alkyl group);
(Fd16) 4-oxazolylmethyl group (which may be substituted on the oxazole ring by at least one group selected from the group consisting of a halogen-substituted or unsubstituted phenyl group and a C1-6 alkyl group);
(Fd17) 2-indolylmethyl group;
(Fd18) 2-furylmethyl group (which may be substituted on the furan ring by at least one halogen-substituted or unsubstituted phenyl group);
(Fd19) 4- or 5-imidazolylmethyl group (which may be substituted on the imidazole ring by a phenyl group);
(Fd20) 2-quinolylmethyl group;
(Fd21) 5-(1H)-tetrazolyl group (wherein the position-1 of the tetrazole ring may be substituted by a phenyl group);
(Fd22) 2- or 4-pyrimidyl group that may be substituted by a phenyl group;
(Fd23) 2-, 3-, or 4-pyridyl group;
(Fd24) 2-benzoxazolyl group;
(Fd25) 2-benzothiazolyl group;
(Fd26) 2-oxo-3-benzoxazolyl-C1-6 alkyl group;
(Fd27) phenoxy C2-6 alkanoyl group which may be substituted on the phenyl ring by a halogen atom;
(Fd28) phenylthio C2-6 alkanoyl group that may be substituted on the phenyl ring by a halogen atom;
(Fd29) phenyl C2-6 alkanoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fd30) benzoyl group (which may be substituted on the phenyl ring by at least one group selected from the group consisting of a halogen atom, a halogen-substituted or unsubstituted C1-6 alkyl group, a halogen-substituted or unsubstituted C1-6 alkoxy group, and a C1-6 alkylamino group);

(Fd31) 4-biphenylylcarbonyl group;

(Fd32) 2-, 3-, or 4-pyridylcarbonyl group;

(Fd33) cinnamoyl group wherein a halogen atom may be substituted on the phenyl ring;

(Fd34) phenyl C1-6 alkylsulfonyl group which may be substituted by a halogen atom on the phenyl ring;

(Fd35) benzenesulfonyl group (which may be substituted on the benzene ring by at least one group selected from the group consisting of a chlorine atom and a methyl group);

(Fd36) a group represented by the following general formula (Fda'):

wherein $R^{27}$ represents:

(Fda1) halogen-substituted or unsubstituted C1-8 alkyl group;

(Fda2) C5-8 cycloalkyl group;

(Fda3) C5-8 cycloalkyl-C1-6 alkyl group;

(Fda4) C1-6 alkoxy-C1-6 alkyl group;

(Fda5) C1-6 alkylamino-C1-6 alkyl group;

(Fda6) a group represented by the following general formula (Fdb'):

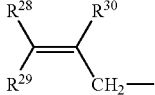

wherein $R^{28}$, $R^{29}$ and $R^{30}$ represent a hydrogen atom, a C1-6 alkyl group, or a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), respectively;

(Fda7) phenyl C1-6 alkyl group (which may be substituted on the phenyl ring by 1 to 5 groups selected from the group consisting of a halogen atom; a halogen-substituted or unsubstituted C1-6 alkyl group; a halogen-substituted or unsubstituted C1-6 alkoxy group; a halogen-substituted or unsubstituted C1-6 alkylthio group; a phenyl C1-6 alkoxy group; a hydroxy group; a methylsulfinyl group; a methanesulfonyl group; methanesulfonyloxy group; a cyano group; an acetyl group; a benzoyl group; an α,α-dimethoxybenzyl group, an amino group, a nitro group; a carbamoyl group; an acetylamino group; a C1-6 alkoxycarbonyl group; a C1-6 alkylaminocarbonyl group; a C1-6 alkoxycarbonylamino group; a tri-C1-6-alkylsiloxy group; a pyrrolyl group; a tetrahydropyranyloxy group; and an 1-imidazolyl group);

(Fda8) biphenylyl C1-6 alkyl group;

(Fda9) benzhydryl group (which may be substituted on the benzene ring by at least one group selected from the group consisting of a halogen atom, a trifluoromethyl group, and a trifluoromethoxy group);

(Fda10) phenoxy C1-6 alkyl group (which may be substituted on the phenyl ring by at least one group selected from a group consisting of a halogen atom, a halogen-substituted or unsubstituted C1-6 alkyl group, and a halogen-substituted or unsubstituted C1-6 alkoxy group);

(Fda11) 3-(4-trifluoromethyl)phenyl-2-propynyl group;

(Fda12) 2-, 3-, or 4-pyridylmethyl group;

(Fda13) a group represented by the following general formula (Fdc'):

wherein $R^{31}$ represents a phenyl group (which may be substituted on the phenyl ring by at least one group selected from the group consisting of a halogen atom, a cyano group, a halogen-substituted or unsubstituted C1-6 alkyl group, and a halogen-substituted or unsubstituted C1-6 alkoxy group); phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); or benzoyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), (Fda14) 1-piperidinoethyl group (wherein the position-4 of the piperidine ring may be substituted by a 4-trifluoromethylphenoxy group);

(Fda15) N-methyl-N-(4-trifluoromethoxy)-phenylaminoethyl group;

(Fda16) 4-(4-trifluoromethoxyphenyl)-1,2,3,6-tetrahydro-1-pyridinylethyl group;

(Fda17) 1- or 2-naphthylmethyl group;

(Fda18) 1-, 2-, 3-, 4-, or 9-fluorenylmethyl group;

(Fda19) 2-, 3-, or 4-pyridylmethyl group;

(Fda20) 2-furylmethyl group (wherein the position-4 of the furan ring may be substituted by a halogen-substituted or unsubstituted phenyl group);

(Fda21) 3-thienylmethyl group;

(Fda22) 4-oxazolylmethyl group (wherein the position-2 of the oxazoline ring may be substituted by a halogen atom or chlorophenyl group);

(Fda23) 4-thiazolylmethyl group which may be substituted by a halogen atom;

(Fda24) 5-oxadiazolylmethyl group wherein the position-2 of the oxadiazoline ring may be substituted by a halogen-substituted or unsubstituted phenyl group;

(Fda25) 3-pyrazolylmethyl group wherein the position-1 of the pyrazoline ring may be substituted by a halogen-substituted or unsubstituted phenyl group;

(Fda26) 2- or 3-benzothiophenylmethyl group (which may be substituted on the benzene ring by at least one group selected from the group consisting of a halogen atom and a halogen-substituted or unsubstituted C1-6 alkoxy group);

(Fda27) benzoxazol-2-ylmethyl group which may be substituted by a halogen atom on the benzene ring;

(Fda28) 2-thienylmethyl group which may be substituted by a halogen atom;

(Fda29) 2-benzothiazolylmethyl group;

(Fda30) 2-(5-chloro)benzofuranylmethyl group;

(Fda31) 3,3-dimethyl-2-oxo-5-indolinylmethyl group (wherein the position-1 of the indoline ring may be substituted by a C1-6 alkyl group);

(Fda32) 2-oxo-6-benzoxazolylmethyl group (wherein the position-1 of the benzoxazoline ring may be substituted by a C1-6 alkyl group);

(Fda33) 7-chromenylmethyl group;

(Fda34) 2-oxo-1,2,3,4-tetrahydro-6-quinolylmethyl group (wherein the position-1 of the quinoline ring may be substituted by a C1-6 alkyl group);

(Fda35) 5-thiazolylmethyl group (which may be substituted on the thiazole ring by at least one group selected from the group consisting of a halogen-substituted or unsubstituted phenyl group and a C1-6 alkyl group); or (Fda36) 5-(1H)-tetrazolyl C1-6 alkyl group (wherein the position-1 of the tetrazole ring may be substituted by a group selected from the group consisting of a halogen-substituted or unsubstituted phenyl group and a C1-6 alkyl group), (Fd37) a group represented by the following general formula (Fe'):

-Z-NR$^{32}$R$^{33}$         (Fe')

wherein Z represents —C═O or —C═S, and R$^{32}$ and R$^{33}$ each identically or differently represent any one of:

(Fe1) hydrogen atom;

(Fe2) C1-6 alkyl group;

(Fe3) C5-8 cycloalkyl group;

(Fe4) phenyl C1-6 alkyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fe5) phenyl C2-6 alkenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group);

(Fe6) phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group); and (Fe7) R$^{32}$ and R$^{33}$ may bind to each other together with nitrogen atoms adjacent thereto through other carbon atoms, so as to form a piperidine ring or 1,2,3,6-tetrahydropyridine ring, wherein the position-4 of the piperidine ring or 1,2,3,6-tetrahydropyridine ring may be substituted by a phenyl group, and the phenyl group may be substituted by at least one group selected from the group consisting of a halogen atom and a halogen-substituted or unsubstituted C1-6 alkyl group, or (Fd38) a group represented by the following general formula (Ff'):

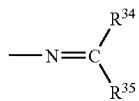

(Ff')

wherein R$^{34}$ represents a hydrogen atom or C1-6 lower alkyl group, and R$^{35}$ represents:

(Ff1) C5-8 cycloalkyl group;

(Ff2) C5-8 cycloalkenyl group;

(Ff3) a group represented by the following general formula (Ffa'):

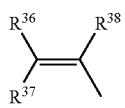

(Ffa')

wherein each of R$^{36}$, R$^{37}$ and R$^{38}$ represents: a hydrogen atom; C1-6 alkyl group; phenyl group (which may be substituted on the phenyl ring by at least one 1 to 5 groups selected from the group consisting of a halogen atom, a halogen-substituted or unsubstituted C1-6 alkyl group, a halogen-substituted or unsubstituted C1-6 alkoxy group, a methylenedioxy group, a methanesulfonyl group, a halogen-substituted or unsubstituted C1-6 alkylthio group, a nitro group, and an acetylamino group); 2-benzofuranyl group (which may be substituted on the benzene ring by at least one group selected from the group consisting of a halogen atom, a halogen-substituted or unsubstituted C1-6 alkyl group, and a halogen-substituted or unsubstituted C1-6 alkoxy group); 4-biphenylyl group; 2-furyl group which may be substituted by a 4-chlorophenyl group; or 2-(4-chlorophenyl)-4-thiazolyl group, (Ff4) phenyl group (which may be substituted on the phenyl ring by at least one group selected from the group consisting of: a halogen atom; a halogen-substituted or unsubstituted C1-6 alkyl group; a C5-8 cycloalkyl group; a hydroxy group; a halogen-substituted or unsubstituted C1-8 alkoxy group; a C5-8 cycloalkoxy group; a methylenedioxy group; an ethylenedioxy group; a cyano group; a nitro group; a cinnamyl group; a C1-6 alkanoyloxy group; a C1-6 alkanoylamino group; a methanesulfonylamino group; a phenyl C1-6 alkoxy group; a phenoxy group; a di(C1-6 alkyl)amino group; a diphenylamino group; a di(C1-6 alkyl)amino C1-6 alkoxy group; a methoxycarbonyl group; a C1-6 alkoxycarbonyl C1-6 alkoxy group; a C1-6 alkylthio group; a pyrrolyl group; a 1-imidazolyl group; a piperidino group; a morpholino group; pyrrolidinyl group; a 2-thienyl group; a 2-benzofuranyl group; a 4-piperazinyl group wherein the position-1 may be substituted by a group selected from the group consisting of a C1-6 alkyl group, a phenyl C1-6 alkyl group, a benzoyl group, and a C1-6 alkyl group substituted benzoyl group; a 2-oxo-3-quinolyl group which may be substituted on the benzene ring by a C1-6 alkoxy group; a 4-(carbostyril-1-yl)piperidinyl-1-carbonyl group; and a triazolyl group);

(Ff5) 1- or 2-naphthyl group substituted by a halogen atom, halogen-substituted or unsubstituted C1-6 alkoxy group, or dimethylamino group;

(Ff6) 3- or 4-biphenylyl group (which may be substituted on the biphenyl ring by at least one group selected from the group consisting of a halogen atom, a halogen-substituted or unsubstituted C1-9 alkyl group, and a halogen-substituted or unsubstituted C1-6 alkoxy group);

(Ff7) 2-fluorenyl group; 3-pyrenyl group;

(Ff8) 2-benzofuranyl group (which may be substituted on the benzene ring by at least one group selected from the group consisting of a halogen atom, a halogen-substituted or unsubstituted C1-6 alkyl group, and a halogen-substituted or unsubstituted C1-6 alkoxy group);

(Ff9) 2- or 3-benzothiophenyl group (which may be substituted on the benzene ring by at least one group selected from the group consisting of a halogen atom, a halogen-substituted or unsubstituted C1-6 alkyl group, and a halogen-substituted or unsubstituted C1-6 alkoxy group; or the position-3 or -2 of the thiophene ring may be substituted by a C1-6 alkyl group);

(Ff10) 2-, 3-, or 4-pyridyl group (which may be substituted on the pyridyl group by at least one group selected from the group consisting of a halogen atom, a halogen-substituted or unsubstituted C1-6 alkyl group, a phenyl group (which may be substituted on the phenyl ring by at least one group selected from the group consisting of a halogen atom, a halogen-substituted or unsubstituted C1-6 alkyl group, and a halogen-substituted or unsubstituted C1-6 alkoxy group), a 2-furyl group, a 3-furyl group, a 2-thienyl group, and a 3-thienyl group);

(Ff11) 2- or 3-furyl group (which may be substituted on the furan ring by 1 to 3 groups selected from the group consisting of a C1-6 alkyl group, a nitro group, and a phenyl group (which may be substituted on the phenyl ring by 1 to 3 groups selected from the group consisting of a halogen atom, a halogen-substituted or unsubstituted C1-6 alkyl group, a halogen-substituted or unsubstituted C1-6 alkoxy group, and a nitro group));

(Ff12) 2-(2-methoxyphenyl)benzothiazol-5-yl group;

(Ff13) 2-thienyl group; 3-thienyl group; 4-bromo-2-thienyl group; 5-chloro-2-thienyl group; 5-ethyl-2-thienyl group; 3-methyl-2-thienyl group; 5-nitro-2-thienyl group; 5-(1-methyl-3-trifluoromethyl-5-pyrazolyl)-2-thienyl group; 5-(1-methyl-5-trifluoro-methyl-3-pyrazolyl)-2-thienyl group; 2,2'-bithien-5-yl group; 5'-bromo-2,2'-bithien-5-yl group;

(Ff14) 1-(4-methylbenzenesulfonyl)indol-3-yl group; 1-benzylindol-3-yl group; 6-methoxy-carbonylindol-3-yl group; 2-phenylindol-3-yl group;

(Ff15) 1-(3-trifluoromethyl)phenyl-2,5-dimethyl-3-pyrrolyl group;

(Ff16) 6-coumaryl group;

(Ff17) 2-(2-thienyl)-5-benzimidazolyl group; 6-benzimidazolyl group;

(Ff18) 2-(4-chlorophenyl)-4-oxazolyl group;

(Ff19) 2-phenyl-4-thiazolyl group; 2-(4-chlorophenyl)-4-thiazolyl group; 2-(4-nitrophenyl)-4-thiazolyl group; 2-(4-biphenylyl)-4-thiazolyl group;

(Ff20) 2-thiazolyl group;

(Ff21) 2- or 4-quinolinyl group;

(Ff22) 8-methoxy-3,4-dihydrocarbostyril-5-yl group; 8-methoxy-1-methyl-3,4-dihydrocarbostyril-5-yl group; 8-benzyloxy-3,4-dihydrocarbostyril-5-yl group; 8-methoxycarbostyril-5-yl group; 8-methoxy-1-methylcarbostyril-5-yl group; 8-benzyloxycarbostyril-5-yl group; 8-methoxy-3,4-dihydrocarbostyril-6-yl group; 8-methoxy-1-methyl-3,4-dihydrocarbostyril-6-yl group; 8-benzyloxy-3,4-dihydrocarbostyril-6-yl group; 8-methoxycarbostyril-6-yl group; 8-methoxy-1-methyl-carbostyril-6-yl group; 8-benzyloxycarbostyril-6-yl group;

(Ff23) 6-imidazo[2,1-b]thiazolyl group;

(Ff24) 2-imidazo[2,1-a]pyridyl group;

(Ff25) 2,2-dimethyl-6-chromanyl group; or (Ff26) 2,3-dihydro-5-benzofuranyl group, (F12-3) morpholino group;

(F12-4) 1-imidazolyl group;

(F12-5) 1,4-dioxa-8-azaspiro[4,5]-8-decyl group;

(F12-6) 4-tert-butoxycarbonyl-1-homopiperazinyl group; 4-benzyloxycarbonyl-1-homopiperazinyl group; 4-(4-biphenylyl)-1-homopiperazinyl group, (F12-7) 1-tert-butyl-2-piperazinon-4-yl group; 1-(4-trifluoromethylbenzyl)-2-piperazinon-4-yl group, (F12-8) 4-oxo-1-piperidinyl group;

(F12-9) 2-(4-trifluoromethoxyphenoxymethyl)-pyrrolidin-1-yl group; and (F12-10) 2-isoindolinyl group, and F13) moreover, $R^{19}$ and $R^{20}$ may bind to each other together with nitrogen atoms adjacent thereto directly or through hetero atoms, so as to form a cyclic imide or amide shown in any one of (F13-1) to (F13-11) indicated below:

(F13-1) 2-succinimide group;

(F13-2) 2-oxooxazolin-3-yl group;

(F13-3) 2-oxobenzo-1,3-oxazolidin-3-yl group; 5-bromo-2-oxobenzo-1,3-oxazolidin-3-yl group; 5-chloro-2-oxobenzo-1,3-oxazolidin-3-yl group; 5-phenyl-2-oxobenzo-1,3-oxazolidin-3-yl group;

(F13-4) 2-oxoimidazolidin-1-yl group (wherein the position-3 of 2-oxoimidazolidin-1-yl group may be substituted by a phenyl C1-6 alkyl group (which may be substituted on the phenyl ring by 1 to 3 groups selected from the group consisting of a halogen atom and a methoxy group), or a phenyl group);

(F13-5) 2-oxobenzimidazolidin-1-yl group (which may be substituted on the benzene ring by a halogen atom, halogen-substituted or unsubstituted C1-6 alkyl group, dimethylamino group, or ethoxycarbonyl group; or the position-3 of the imidazolidine ring may be substituted by a 4-piperidinyl group, which may be substituted by a group selected from the group consisting of a C1-6 alkyl group, a phenyl group wherein 1 to 3 halogen atoms may be substituted on the phenyl ring, a tert-butoxycarbonyl group, and a benzyloxycarbonyl group);

(F13-6) phthalimid-2-yl group;

(F13-7) oxyindol-1-yl group, wherein the position-3 may be substituted by 2 methyl groups or fluorine atoms;

(F13-8) benzoic sulfimid-2-yl group;

(F13-9) 1H-2,4-benzoxazin-3(4H)-on-4-yl group;

(F13-10) a group represented by the following general formula (Fga'):

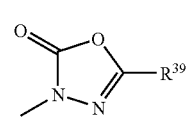

(Fga')

wherein $R^{39}$ represents: a hydrogen atom; halogen-substituted or unsubstituted phenyl C1-6 alkyl group;

halogen-substituted or unsubstituted phenoxymethyl group; halogen-substituted or unsubstituted styryl group; phenyl group which may be substituted by at least one group selected from a group consisting of a halogen atom, a halogen-substituted or unsubstituted C1-6 alkyl group, and a halogen-substituted or unsubstituted C1-6 alkoxy group; biphenylyl group; 4-pyridyl group; or 2-pyrazinyl group, and (F13-11) 5-(4-trifluoromethylbenzylidene)-1,3-thiazolidine-2,4-dion-3-yl group;

a group represented by the following general formula (G'):

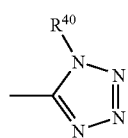

wherein $R^{40}$ represents a C1-6 alkyl group, or halogen-substituted or unsubstituted phenyl group, a spiro ring group represented by the following general formula (H'):

wherein $R^{41}$ represents:
H1) hydrogen atom;
H2) C1-6 alkyl group;
H3) phenyl C1-6 alkyl group or 4-biphenylyl C1-6 alkyl group;
H4) phenyl group (which may be substituted by a halogen-substituted or unsubstituted C1-6 alkyl group);
H5) 4-substituted-1-piperazinyl C1-6 alkyl group (wherein the substituent at the position-4 is a C1-6 alkoxycarbonyl group, 4-biphenylylmethoxycarbonyl group or benzyloxycarbonyl group, and the benzyloxycarbonyl group may be substituted by 1 to 3 groups selected from the group consisting of a halogen atom, a halogen-substituted or unsubstituted C1-6 alkyl group, and a halogen-substituted or unsubstituted C1-6 alkoxy group on the benzene ring);
H6) 4-substituted-1-piperazinylcarbonyl C1-6 alkyl group, wherein the position-4 is substituted with a C1-6 alkylcarbonyl group, 4-trifluoromethylbenzyloxycarbonyl group, 4-trifluoromethylbenzyl group, or biphenylylmethyl group;
H7) 4-trifluoromethylphenylcarbamoyl C1-6 alkyl group;
H8) 2-benzoxazolon-1-ylpropyl group;
H9) 2-benzothiazolyl group;
H10) 1-phenyl-5-tetrazolyl group;
H11) methanesulfonyl group;
H12) benzenesulfonyl or p-toluenesulfonyl group;
H13) phenylthiocarbamoyl group, wherein the position-4 of the phenyl ring may be substituted by a halogen atom;
H14) C1-8 alkoxycarbonyl group;
H15) phenyl C1-6 alkoxycarbonyl group (which may be substituted on the phenyl ring by at least one group selected from the group consisting of a halogen atom, a C1-6 alkoxycarbonyl group, a C1-6 alkoxycarbonylamino group, a halogen-substituted or unsubstituted C1-6 alkyl group, a halogen-substituted or unsubstituted C1-6 alkoxy group, a nitro group, and a methylthio group);
H16) benzhydryloxycarbonyl group (which may be substituted on the phenyl ring by 1 to 4 halogen atoms);
H17) 4-biphenylylmethoxcarbonyl group;
H18) naphthylmethoxycarbonyl group;
H19) pyridylmethoxycarbonyl group;
H20) methoxyethoxycarbonyl group;
H21) 2-(1-piperazinyl)ethoxycarbonyl group wherein the position-4 may be substituted by a C1-6 alkoxycarbonyl group, or halogen-substituted or unsubstituted phenyl C1-6 alkoxycarbonyl group;
H22) phenoxycarbonyl group (which may be substituted on the phenyl ring by at least one group selected from the group consisting of a C1-6 alkyl group and a C1-6 alkoxy group);
H23) C1-6 alkanoyl group;
H24) benzoyl group (which may be substituted on the phenyl ring by at least one halogen-substituted or unsubstituted C1-6 alkyl group);
H25) phenyl C2-6 alkanoyl group (which may be substituted on the phenyl ring by at least one halogen-substituted or unsubstituted C1-6 alkyl group);
H26) phenoxy C2-6 alkanoyl group (which may be substituted by 1 to 3 halogen atoms on the phenyl ring);
H27) 4-substituted-1-piperazinyl C2-6 alkanoyl group (wherein the substituent at the position-4 is a C1-6 alkanoyl group, phenyl C1-6 alkyl group, 4-biphenylylmethyl group, phenyl C1-6 alkoxycarbonyl group, phenylcarbamoylmethyl group, phenyl carbamoyl group, or 2-benzoxazolyl group; and the phenyl ring of each of these phenyl C1-6 alkyl group, phenyl C1-6 alkoxycarbonyl group, phenylcarbamoylmethyl group and phenyl carbamoyl group, may be substituted by 1 to 3 groups selected from the group consisting of a halogen atom, a halogen-substituted or unsubstituted C1-6 alkyl group, and a halogen-substituted or unsubstituted C1-6 alkoxy group);
H28) phenylcarbamoyl group (which may be substituted on the phenyl ring by 1 to 3 groups selected from the group consisting of a halogen atom, a dimethylamino group, a carboxyl group, a C1-6 alkoxycarbonyl group, a halogen-substituted or unsubstituted C1-6 alkyl group, a halogen-substituted or unsubstituted C1-6 alkoxy group, a 4-methyl-1-piperazinyl group, and a morpholino group);
H29) benzylcarbamoyl group (which may be substituted on the phenyl ring by at least one group selected from the group consisting of a halogen-substituted or unsubstituted C1-6 alkyl group and a halogen-substituted or unsubstituted C1-6 alkoxy group); or
H30) 4-substituted-1-piperazinylcarbonyl group, wherein the position-4 is substituted with a tert-butoxycarbonyl group, 4-trifluoromethylbenzyloxycarbonyl group, or 4-trifluoromethylbenzyl group, provided that, in the above general formula (1') when $R^1$ represents a hydrogen atom and $R^2$ represents a group represented by the above general formula (A'), then $R^3$ cannot be an isopropyl group; when $R^1$ represents a hydrogen atom, $R^2$ represents a group represented by the above general formula (E'), and m is 0, then $R^{11}$ cannot be a hydrogen atom; and further, when $R^1$ represents a hydrogen atom and $R^2$ represents a group represented by the above general formula (F'), then it is not possible that $R^{19}$ represents a hydrogen atom and $R^{20}$ represents a tert-butoxycarbonyl group.

3. The 2,3-dihydro-6-nitroimidazo[2,1-b]oxazole compound, optically active form thereof, or pharmaceutically acceptable salt thereof according to claim 1, wherein $R^2$ represents a group represented by general formula (A).

4. The 2,3-dihydro-6-nitroimidazo[2,1-b]oxazole compound, optically active form thereof, or pharmaceutically acceptable salt thereof according to claim 1, wherein $R^2$ represents a group represented by general formula (B).

5. The 2,3-dihydro-6-nitroimidazo[2,1-b]oxazole compound, optically active form thereof, or pharmaceutically acceptable salt thereof according to claim 1, wherein $R^2$ represents a group represented by general formula (C).

6. The 2,3-dihydro-6-nitroimidazo[2,1-b]oxazole compound, optically active form thereof, or pharmaceutically acceptable salt thereof according to claim 1, wherein $R^2$ represents a group represented by general formula (D).

7. The 2,3-dihydro-6-nitroimidazo[2,1-b]oxazole compound, optically active form thereof, or pharmaceutically acceptable salt thereof according to claim 1, wherein $R^2$ represents a group represented by general formula (E).

8. The 2,3-dihydro-6-nitroimidazo[2,1-b]oxazole compound, optically active form thereof, or pharmaceutically acceptable salt thereof according to claim 1, wherein $R^2$ represents a group represented by general formula (F).

9. The 2,3-dihydro-6-nitroimidazo[2,1-b]oxazole compound, optically active form thereof, or pharmaceutically acceptable salt thereof according to claim 1, wherein $R^2$ represents a group represented by general formula (G).

10. The 2,3-dihydro-6-nitroimidazo[2,1-b]oxazole compound, optically active form thereof, or pharmaceutically acceptable salt thereof according to claim 1, wherein $R^1$ and —(CH$_2$)$_n$R$^2$ may bind to each other together with carbon atoms adjacent thereto through nitrogen atoms, so as to form a spiro ring represented by general formula (H).

11. The 2,3-dihydro-6-nitroimidazo[2,1-b]oxazole compound, optically active form thereof, or pharmaceutically acceptable salt thereof according to any one of claims 3 to 10, wherein n is 0.

12. The 2,3-dihydro-6-nitroimidazo[2,1-b]oxazole compound, optically active form thereof, or pharmaceutically acceptable salt thereof according to any one of claims 3 to 10, wherein n represents an integer of 1 to 6.

13. The 2,3-dihydro-6-nitroimidazo[2,1-b]oxazole compound, optically active form thereof, or pharmaceutically acceptable salt thereof according to any one of claims 3 to 10, wherein $R^1$ represents a hydrogen atom.

14. The 2,3-dihydro-6-nitroimidazo[2,1-b]oxazole compound, optically active form thereof, or pharmaceutically acceptable salt thereof according to any one of claims 3 to 10, wherein $R^1$ represents a C1-6 alkyl group.

15. The 2,3-dihydro-6-nitroimidazo[2,1-b]oxazole compound, optically active form thereof, or pharmaceutically acceptable salt thereof according to claim 7, wherein $R^{11}$ represents any one of (E1) to (E3).

16. The 2,3-dihydro-6-nitroimidazo[2,1-b]oxazole compound, optically active form thereof, or pharmaceutically acceptable salt thereof according to claim 7, wherein $R^{11}$ represents (E4).

17. The 2,3-dihydro-6-nitroimidazo[2,1-b]oxazole compound, optically active form thereof, or pharmaceutically acceptable salt thereof according to claim 7, wherein $R^{11}$ represents any one of (E5) to (E9).

18. The 2,3-dihydro-6-nitroimidazo[2,1-b]oxazole compound, optically active form thereof, or pharmaceutically acceptable salt thereof according to claim 7, wherein $R^{11}$ represents (E10).

19. The 2,3-dihydro-6-nitroimidazo[2,1-b]oxazole compound, optically active form thereof, or pharmaceutically acceptable salt thereof according to claim 7, wherein $R^{11}$ represents (E11).

20. The 2,3-dihydro-6-nitroimidazo[2,1-b]oxazole compound, optically active form thereof, or pharmaceutically acceptable salt thereof according to claim 7, wherein $R^{11}$ represents (E12).

21. The 2,3-dihydro-6-nitroimidazo[2,1-b]oxazole compound, optically active form thereof, or pharmaceutically acceptable salt thereof according to claim 7, wherein $R^{11}$ represents (E13).

22. The 2,3-dihydro-6-nitroimidazo[2,1-b]oxazole compound, optically active form thereof, or pharmaceutically acceptable salt thereof according to claim 7, wherein $R^{11}$ represents any one of (E14) to (E17) and (E19) to (E22).

23. The 2,3-dihydro-6-nitroimidazo[2,1-b]oxazole compound, optically active form thereof, or pharmaceutically acceptable salt thereof according to claim 7, wherein $R^{11}$ represents (E18).

24. The 2,3-dihydro-6-nitroimidazo[2,1-b]oxazole compound, optically active form thereof, or pharmaceutically acceptable salt thereof according to claim 8, wherein $R^{19}$ and $R^{20}$ each identically or differently represent any one of (F1) to (F11).

25. The 2,3-dihydro-6-nitroimidazo[2,1-b]oxazole compound, optically active form thereof, or pharmaceutically acceptable salt thereof according to claim 8, wherein $R^{19}$ and $R^{20}$, together with nitrogen atoms adjacent thereto, form a heterocyclic ring shown in any one of (F12-3) to (F12-10) and (F13) directly or through other hetero atoms or carbon atoms.

26. The 2,3-dihydro-6-nitroimidazo[2,1-b]oxazole compound, optically active form thereof, or pharmaceutically acceptable salt thereof according to claim 8, wherein $R^{19}$ and $R^{20}$, together with nitrogen atoms adjacent thereto, form a heterocyclic ring shown in (F12-1) directly or through other hetero atoms or carbon atoms.

27. The 2,3-dihydro-6-nitroimidazo[2,1-b]oxazole compound, optically active form thereof, or pharmaceutically acceptable salt thereof according to claim 8, wherein $R^{19}$ and $R^{20}$, together with nitrogen atoms adjacent thereto, form a heterocyclic ring shown in (F12-2) directly or through other hetero atoms or carbon atoms.

28. The 2,3-dihydro-6-nitroimidazo[2,1-b]oxazole compound, optically active form thereof, or pharmaceutically acceptable salt thereof according to claim 18, wherein o is 0.

29. The 2,3-dihydro-6-nitroimidazo[2,1-b]oxazole compound, optically active form thereof, or pharmaceutically acceptable salt thereof according to claim 18, wherein o is 1, and W represents a group —CO—.

30. The 2,3-dihydro-6-nitroimidazo[2,1-b]oxazole compound, optically active form thereof, or pharmaceutically acceptable salt thereof according to claim 18, wherein o is 1, and W represents a C1-6 alkylene group.

31. The 2,3-dihydro-6-nitroimidazo[2,1-b]oxazole compound, optically active form thereof, or pharmaceutically acceptable salt thereof according to claim 18, wherein $R^{14}$ is any one of (Eaa1) to (Eaa2) and (Eaa4) to (Eaa27).

32. The 2,3-dihydro-6-nitroimidazo[2,1-b]oxazole compound, optically active form thereof, or pharmaceutically acceptable salt thereof according to claim 18, wherein $R^{14}$ is (Eaa3).

33. The 2,3-dihydro-6-nitroimidazo[2,1-b]oxazole compound, optically active form thereof, or pharmaceutically acceptable salt thereof according to claim 19, wherein o is 0.

34. The 2,3-dihydro-6-nitroimidazo[2,1-b]oxazole compound, optically active form thereof, or pharmaceutically acceptable salt thereof according to claim 19, wherein o is 1.

35. The 2,3-dihydro-6-nitroimidazo[2,1-b]oxazole compound, optically active form thereof, or pharmaceutically acceptable salt thereof according to claim 27, wherein $R^{26}$ is any one of (Fd1) to (Fd35), (Fd37) and (Fd39).

36. The 2,3-dihydro-6-nitroimidazo[2,1-b]oxazole compound, optically active form thereof, or pharmaceutically acceptable salt thereof according to claim 27, wherein $R^{26}$ is (Fd36).

37. The 2,3-dihydro-6-nitroimidazo[2,1-b]oxazole compound, optically active form thereof, or pharmaceutically acceptable salt thereof according to claim 27, wherein $R^{26}$ is (Fd38).

38. The 2,3-dihydro-6-nitroimidazo[2,1-b]oxazole compound, optically active form thereof, or pharmaceutically acceptable salt thereof according to claim 36, wherein $R^{27}$ is any one of (Fda1) to (Fda5) and (Fda7) to (Fda34).

39. The 2,3-dihydro-6-nitroimidazo[2,1-b]oxazole compound, optically active form thereof, or pharmaceutically acceptable salt thereof according to claim 36, wherein $R^{27}$ is (Fda6).

40. The 2,3-dihydro-6-nitroimidazo[2,1-b]oxazole compound, optically active form thereof, or pharmaceutically acceptable salt thereof according to claim 37, wherein $R^{35}$ is any one of (Ff1) to (Ff3), (Ff5) to (Ff7), and (Ff9) to (Ff26).

41. The 2,3-dihydro-6-nitroimidazo[2,1-b]oxazole compound, optically active form thereof, or pharmaceutically acceptable salt thereof according to claim 37, wherein $R^{35}$ is (Ff4).

42. The 2,3-dihydro-6-nitroimidazo[2,1-b]oxazole compound, optically active form thereof, or pharmaceutically acceptable salt thereof according to claim 37, wherein $R^{35}$ is (Ff8).

43. 3-(4-Trifluoromethylphenyl)-2-propenyl 4-(2-methyl-6-nitro-2,3-dihydroimidazo[2,1-b]oxazol-2-ylmethyl)piperazin-1-carboxylate, 3-(4-trifluoromethylphenyl)-2-propenyl (S)-4-(2-methyl-6-nitro-2,3-dihydroimidazo[2,1-b]oxazol-2-ylmethyl)-piperazin-1-carboxyate, 3-(4-trifluoromethylphenyl)-2-propenyl (R)-4-(2-methyl-6-nitro-2,3-dihydroimidazo[2,1-b]oxazol-2-ylmethyl)-piperazin-1-carboxylate, 2-methyl-6-nitro-2-{4-[4-(4-trifluoromethoxyphenoxy)-piperidin-1-yl]phenoxymethyl}-2,3-dihydroimidazo[2,1-b]oxazole, (S)-2-methyl-6-nitro-2-{4-[4-(4-trifluoromethoxyphenoxy)piperidin-1-yl]phenoxymethyl}-2,3-dihydroimidazo[2,1-b]oxazole, (R)-2-methyl-6-nitro-2-{4-[4-(4-trifluoromethoxyphenoxy)piperidin-1-yl]phenoxymethyl}-2,3-dihydroimidazo[2,1-b]oxazole, 6-nitro-2-{4-[4-(4-trifluoromethoxyphenoxy)piperidin-1-yl]phenoxymethyl}-2,3-dihydroimidazo[2,1-b]oxazole, (S)-6-nitro-2-{4-[4-(4-trifluoromethoxyphenoxy)-piperidin-1-yl]phenoxymethyl}-2,3-dihydroimidazo[2,1-b]oxazole, (R)-6-nitro-2-{4-[4-(4-trifluoromethoxyphenoxy)-piperidin-1-yl]phenoxymethyl}-2,3-dihydroimidazo[2,1-b]oxazole, 2-methyl-6-nitro-2-{4-[3-(4-trifluoromethoxyphenoxy)-8-azabicyclo[3.2.1]octan-8-yl]phenoxymethyl}-2,3-dihydroimidazo[2,1-b]oxazole, (S)-2-methyl-6-nitro-2-{4-[3-(4-trifluoromethoxyphenoxy)-8-azabicyclo[3.2.1]octan-8-yl]phenoxymethyl}-2,3-dihydroimidazo[2,1-b]oxazole, (R)-2-methyl-6-nitro-2-{4-[3-(4-trifluoromethoxyphenoxy)-8-azabicyclo[3.2.1]octan-8-yl]phenoxymethyl}-2,3-dihydroimidazo[2,1-b]oxazole, (R)-2-methyl-6-nitro-2-{4-[3-(4-trifluoromethoxyphenoxy)-8-azabicyclo[3.2.1]octan-8-yl]phenoxymethyl}-2,3-dihydroimidazo[2,1-b]oxazole 4-toluene sulfonate, 2-methyl-6-nitro-2-[4-(4-trifluoromethylbenzylideneamino)piperazin-1-ylmethyl]-2,3-dihydroimidazo[2,1-b]oxazole, (S)-2-methyl-6-nitro-2-[4-(4-trifluoromethylbenzylideneamino)piperazin-1-ylmethyl]-2,3-dihydroimidazo[2,1-b]oxazole, 2-[4-(5-chlorobenzofuran-2-ylmethyleneamino)piperazin-1-ylmethyl]-2-methyl-6-nitro-2,3-dihydroimidazo[2,1-b]oxazole, (S)-2-[4-(5-chlorobenzofuran-2-ylmethyleneamino)-piperazin-1-ylmethyl]-2-methyl-6-nitro-2,3-dihydroimidazo-[2,1-b]oxazole, (S)-2-[4-(5-trifluoromethylbenzofuran-2-ylmethyleneamino)piperazin-1-ylmethyl]-2-methyl-6-nitro-2,3-dihydroimidazo[2,1-b]oxazole, 2-methyl-6-nitro-2-{4-[4-(4-trifluoromethylbenzyl)-piperazin-1-yl]phenoxymethyl}-2,3-dihydroimidazo[2,1-b]oxazole, (S)-2-methyl-6-nitro-2-{4-[4-(4-trifluoromethylbenzyl)piperazin-1-yl]phenoxymethyl}-2,3-dihydroimidazo[2,1-b]oxazole, (R)-2-methyl-6-nitro-2-{4-[4-(4-trifluoromethylbenzyl)piperazin-1-yl]phenoxymethyl}-2,3-dihydroimidazo[2,1-b]oxazole, 2-methyl-6-nitro-2-{4-[4-(4-trifluoromethoxybenzyl)piperazin-1-yl]phenoxymethyl}-2,3-dihydroimidazo[2,1-b]oxazole, (S)-2-methyl-6-nitro-2-{4-[4-(4-trifluoromethoxybenzyl)piperazin-1-yl]phenoxymethyl}-2,3-dihydroimidazo[2,1-b]oxazole, (R)-2-methyl-6-nitro-2-{4-[4-(4-trifluoromethoxybenzyl)piperazin-1-yl]phenoxymethyl}-2,3-dihydroimidazo[2,1-b]oxazole, 2-methyl-6-nitro-2-[4-(4-trifluoromethylphenoxy)-piperidin-1-ylmethyl]-2,3-dihydroimidazo[2,1-b]oxazole, (S)-2-methyl-6-nitro-2-[4-(4-trifluoromethylphenoxy)-piperidin-1-ylmethyl]-2,3-dihydroimidazo[2,1-b]oxazole, (R)-2-methyl-6-nitro-2-[4-(4-trifluoromethylphenoxy)-piperidin-1-ylmethyl]-2,3-dihydroimidazo[2,1-b]oxazole, 2-[4-(4-trifluoromethoxyphenyl)piperazin-1-ylmethyl]-2-methyl-6-nitro-2,3-dihydroimidazo[2,1-b]oxazole, (S)-2-[4-(4-trifluoromethoxyphenyl)piperazin-1-ylmethyl]-2-methyl-6-nitro-2,3-dihydroimidazo[2,1-b]oxazole, (R)-2-[4-(4-trifluoromethoxyphenyl)piperazin-1-ylmethyl]-2-methyl-6-nitro-2,3-dihydroimidazo[2,1-b]oxazole, 2-[4-(4-chlorophenyl)piperazin-1-ylmethyl]-2-methyl-6-nitro-2,3-dihydroimidazo[2,1-b]oxazole, (S)-2-[4-(4-chlorophenyl)piperazin-1-ylmethyl]-2-methyl-6-nitro-2,3-dihydroimidazo[2,1-b]oxazole, (R)-2-[4-(4-chlorophenyl)piperazin-1-ylmethyl]-2-methyl-6-nitro-2,3-dihydroimidazo[2,1-b]oxazole, 2-methyl-6-nitro-2-[4-(4'-trifluoromethylbiphenyl-4-ylmethyl)piperazin-1-ylmethyl]-2,3-dihydroimidazo[2,1-b]oxazole, (S)-2-methyl-6-nitro-2-[4-(4'-trifluoromethylbiphenyl-4-ylmethyl)piperazin-1-ylmethyl]-2,3-dihydroimidazo-[2,1-b]oxazole, (R)-2-methyl-6-nitro-2-[4-(4'-trifluoromethylbiphenyl-4-ylmethyl)piperazin-1-ylmethyl]-2,3-dihydroimidazo[2,1-b]oxazole, 2-methyl-6-nitro-2-{4-[4-(4-trifluoromethylphenyl)-piperazin-1-yl]phenoxymethyl}-2,3-dihydroimidazo[2,1-b]oxazole, (S)-2-methyl-6-nitro-2-{4-[4-(4-trifluoromethylphenyl)-piperazin-1-yl]phenoxymethyl}-2,3-dihydroimidazo[2,1-b]oxazole, (R)-2-methyl-6-nitro-2-{4-[4-(4-trifluoromethylphenyl)-piperazin-1-yl]phenoxymethyl}-2,3-dihydroimidazo[2,1-b]oxazole, 2-methyl-6-nitro-2-{4-[4-(4-chlorobenzyl)piperazin-1-yl]phenoxymethyl}-2,3-dihydroimidazo[2,1-b]oxazole, (S)-2-methyl-6-nitro-2-{4-[4-(4-chlorobenzyl)piperazin-1-yl]phenoxymethyl}-2,3-dihydroimidazo[2,1-b]oxazole, (R)-2-methyl-6-nitro-2-{4-[4-(4-chlorobenzyl)piperazin-1-yl]phenoxymethyl}-2,3-dihydroimidazo[2,1-b]oxazole, 2-methyl-6-nitro-2-{4-[4-(4-chlorophenyl)piperazin-1-yl]phenoxymethyl}-2,3-dihydroimidazo[2,1-b]oxazole, (S)-2-methyl-6-nitro-2-{4-[4-(4-chlorophenyl)piperazin-1-yl]phenoxymethyl}-2,3-dihydroimidazo[2,1-b]oxazole, (R)-2-methyl-6-nitro-2-{4-[4-(4-chlorophenyl)piperazin-1-yl]phenoxymethyl}-2,3-dihydroimidazo[2,1-b]oxazole, 2-methyl-6-nitro-2-{4-[4-(4-trifluoromethoxy-benzyloxycarbonyl)piperazin-1-yl]phenoxymethyl}-2,3-dihydroimidazo[2,1-b]oxazole, (S)-2-methyl-6-nitro-2-{4-[4-(4-trifluoromethoxybenzyloxycarbonyl)piperazin-1-yl]phenoxymethyl}-2,3-dihydroimidazo[2,1-b]oxazole, (R)-2-methyl-6-nitro-2-{4-[4-(4-trifluoromethoxybenzyloxycarbonyl)piperazin-1-yl]phenoxymethyl}-2,3-dihydroimidazo[2,1-b]oxazole, 2-methyl-6-nitro-2-{4-[4-(3,4-dichlorobenzyloxycarbonyl)piperazin-1-yl]phenoxymethyl}-2,3-dihydroimidazo[2,1-b]oxazole, (S)-2-methyl-6-nitro-2-{4-[4-(3,4-dichlorobenzyloxycarbonyl)piperazin-1-yl]phenoxymethyl}-2,3-dihydroimidazo[2,1-b]oxazole, (R)-2-methyl-6-nitro-2-{4-[4-(3,4-dichlorobenzyloxycarbonyl)piperazin-1-yl]phenoxymethyl}-2,3-dihydroimidazo[2,1-b]oxazole, 2-methyl-6-nitro-2-[4-(4-trifluoromethoxyphenoxy)-piperidin-1-ylmethyl]-2,3-dihydroimidazo[2,1-b]oxazole, (S)-2-methyl-6-nitro-2-[4-(4-trifluoromethoxyphenoxy)-piperidin-1-ylmethyl]-2,3-dihydroimidazo[2,1-b]oxazole, (R)-2-methyl-6-nitro-2-[4-(4-trifluoromethoxyphenoxy)-piperidin-1-ylmethyl]-2,3-dihydroimidazo[2,1-b]oxazole, 2-methyl-6-nitro-2-[4-(4-trifluoromethylphenyl)-piperazin-1-ylmethyl]-2,3-dihydroimidazo[2,1-b]oxazole, (S)-2-methyl-6-nitro-2-[4-(4-trifluoromethylphenyl)-piperazin-1-ylmethyl]-2,3-dihydroimidazo[2,1-b]oxazole, (R)-2-methyl-6-nitro-2-[4-(4-trifluoromethylphenyl)-piperazin-1-ylmethyl]-2,3-dihydroimidazo[2,1-b]oxazole, 2-methyl-6-nitro-2-[4-(5-trifluoromethoxylbenzofuran-2-ylmethyleneamino)piperazin-1-ylmethyl]-2,3-dihydroimidazo[2,1-b]oxazole, (S)-2-methyl-6-nitro-2-[4-(5-trifluoromethoxylbenzofuran-2-ylmethyleneamino)piperazin-1-ylmethyl]-2,13-dihydroimidazo[2,1-b]oxazole, (R)-2-methyl-6-nitro-2-[4-(5-trifluoromethoxylbenzofuran-2-ylmethyleneamino)piperazin-1-ylmethyl]-2,3-dihydroimidazo[2,1-b]oxazole, 2-methyl-6-nitro-2-[4-(5-trifluoromethylbenzofuran-2-ylmethyleneamino)piperazin-1-ylmethyl]-2,3-dihydroimidazo[2,1-b]oxazole, (S)-2-methyl-6-nitro-2-[4-(5-trifluoromethylbenzofuran-2-ylmethyleneamino)piperazin-1-ylmethyl]-2,3-dihydroimidazo[2,1-b]oxazole, (R)-2-methyl-6-nitro-2-[4-(5-trifluoromethylbenzofuran-2-ylmethyleneamino)piperazin-1-ylmethyl]-2,3-dihydroimidazo[2,1-b]oxazole, 2-methyl-6-nitro-2-{4-[4-(4-chlorophenoxy)piperidin-1-yl]phenoxymethyl}-2,3-dihydroimidazo[2,1-b]oxazole, (S)-2-methyl-6-nitro-2-{4-[4-(4-chlorophenoxy)-piperidin-1-yl]phenoxymethyl}-2,3-dihydroimidazo[2,1-b]oxazole, (R)-2-methyl-6-nitro-2-{4-[4-(4-chlorophenoxy)-piperidin-1-yl]phenoxymethyl}-2,3-dihydroimidazo[2,1-b]oxazole, 2-methyl-6-nitro-2-{4-[4-(4-trifluoromethylphenoxy)-piperidin-1-yl]phenoxymethyl}-2,3-dihydroimidazo[2,1-b]oxazole, (S)-2-methyl-6-nitro-2-{4-[4-(4-trifluoromethylphenoxy)piperidin-1-yl]phenoxymethyl}-2,3-dihydroimidazo[2,1-b]oxazole, (R)-2-methyl-6-nitro-2-{4-[4-(4-trifluoromethylphenoxy)piperidin-1-yl]phenoxymethyl}-2,3-dihydroimidazo[2,1-b]oxazole, 2-methyl-6-nitro-2-{4-[1-(4-chlorobenzyl)piperidin-4-yl]phenoxymethyl}-2,3-dihydroimidazo[2,1-b]oxazole, (S)-2-methyl-6-nitro-2-{4-[1-(4-chlorobenzyl)piperidin-4-yl]phenoxymethyl}-2,3-dihydroimidazo[2,1-b]oxazole, or (R)-2-methyl-6-nitro-2-{4-[1-(4-chlorobenzyl)piperidin-4-yl]phenoxymethyl}-2,3-dihydroimidazo[2,1-b]oxazole.

44. A pharmaceutical composition which is an antitubercular agent comprising, as an active ingredient, the 2,3-dihydro-6-nitroimidazo[2,1-b]oxazole compound, optically active form thereof, or pharmacologically acceptable salt thereof according to claim 1.

45. A pharmaceutical composition which is an antitubercular agent comprising, as an active ingredient, at least one compound selected from the 2,3-dihydro-6-nitroimidazo[2,1-b]oxazole compounds according to claim 43.

46. A method for producing a compound represented by the following general formula (1a):

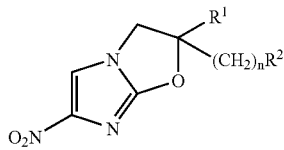

(1a)

wherein $R^1$, $R^2$ and n are defined as the same as in claim 1,
said production method comprising: the reaction of a 4-nitroimidazole compound represented by the following general formula (2):

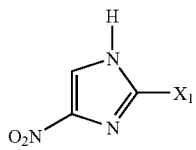

(2)

wherein $X_1$ represents a halogen atom or nitro group, with an epoxy compound represented by the following general formula (3a):

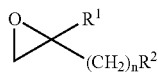

(3a)

wherein $R^1$, $R^2$ and n are defined as the same as in claim 1, so as to obtain a compound represented by the following general formula (4a):

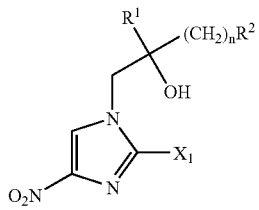

(4a)

wherein $R^1$, $R^2$ and n are defined as the same as in claim 1, and
$X_1$ represents a halogen atom or nitro group; and
the following ring closure of the obtained compound represented by the above general formula (4a).

47. A method for producing a compound represented by the following general formula (1b):

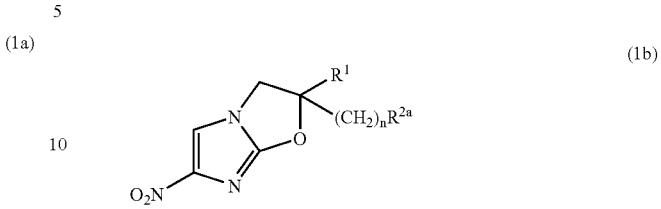

(1b)

wherein $R^1$ is as defined in claim 1, and $R^{2a}$ represents a group represented by the general formula (A), (B), (E) or (F) according to claim 1,
said production method comprising: the reaction of a compound represented by the following general formula (3b):

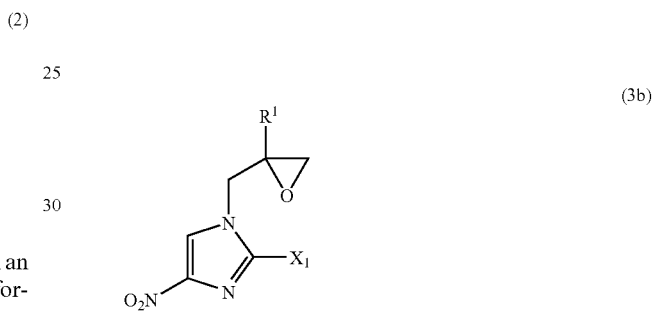

(3b)

wherein $R^1$ is as defined in claim 1, and $X_1$ represents a halogen atom or nitro group,
with a compound (5) represented by the following general formula $R^{2a}$ H(5) or a salt thereof,
wherein $R^{2a}$ represents the group represented by the general formula (A), (B), (E) or (F) according to claim 1, so as to obtain a compound represented by the following general formula (4b):

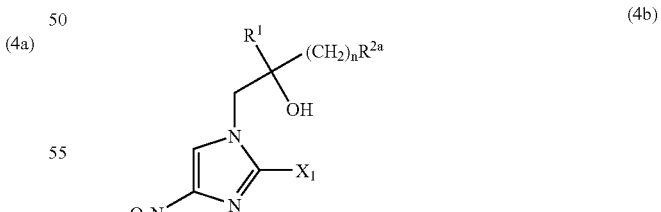

(4b)

wherein $R^1$ is as defined in claim 1, $R^{2a}$ represents the group represented by the general formula (A), (B), (E) or (F) according to claim 1, and $X_1$ represents a halogen atom or nitro group; and
the following ring closure of the obtained compound represented by the above general formula (4b).

48. A method for producing a compound represented by the following general formula (1c):

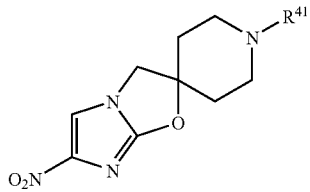
(1c)

wherein $R^{41}$ is as defined in claim 1, said production method comprising: the reaction of a compound represented by the following general formula (2):

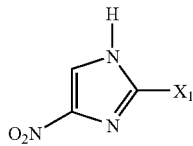
(2)

wherein $X_1$ represents a halogen atom or nitro group, with a compound represented by the following general formula (3c):

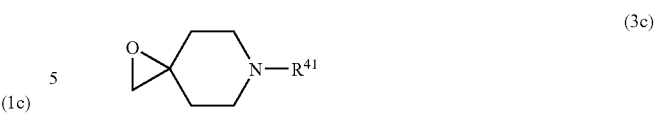
(3c)

wherein $R^{41}$ is as defined in claim 1, so as to obtain a compound represented by the following general formula (4c):

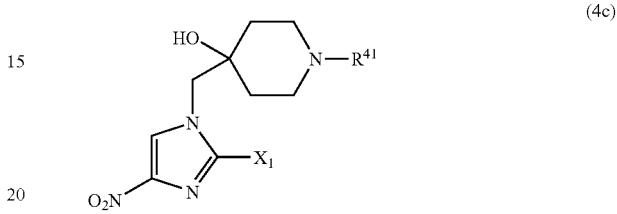
(4c)

wherein $R^{41}$ is as defined in claim 1, and $X_1$ represents a halogen atom or nitro group; and the following ring closure of the obtained compound represented by the above general formula (4c).

49. (R)-2-methyl-6-nitro-2-{4-[4-(4-trifluoromethoxyphenoxy)piperidin-1-yl]phenoxymethyl}-2,3-dihydroimidazo[2,1-b]oxazole.

50. A pharmaceutical composition which is an antitubercular agent comprising, as an active ingredient, the 2,3-dihydro-6-nitroimidazo[2,1-b]oxazole compound according to claim 49.

* * * * *

UNITED STATES PATENT AND TRADEMARK OFFICE
CERTIFICATE OF CORRECTION

PATENT NO. : 7,262,212 B2
APPLICATION NO. : 10/530429
DATED : August 28, 2007
INVENTOR(S) : Hidetsugu Tsubouchi et al.

It is certified that error appears in the above-identified patent and that said Letters Patent is hereby corrected as shown below:

Claim 1, col. 659, line 25, "the, bond" should read --the bond--.

Claim 1, col. 664, line 52, "(Edc)" should read --(Fdc)--.

Claim 1, col. 668, line 20, "ring-by" should read --ring by--.

Claim 1, col. 671, line 30, "a Spiro" should read --a spiro--.

Claim 2, col. 674, line 26, "group" should read --group;--.

Signed and Sealed this

Second Day of September, 2008

JON W. DUDAS
*Director of the United States Patent and Trademark Office*